(12) United States Patent
Berdini et al.

(10) Patent No.: US 11,001,575 B1
(45) Date of Patent: *May 11, 2021

(54) BENZOLACTAM COMPOUNDS AS PROTEIN KINASE INHIBITORS

(71) Applicant: OTSUKA PHARMACEUTICAL CO., LTD., Tokyo (JP)

(72) Inventors: Valerio Berdini, Cambridge (GB); Ildiko Maria Buck, London (GB); James Edward Harvey Day, Cambridge (GB); Charlotte Mary Griffiths-Jones, Cambridge (GB); Thomas Daniel Heightman, Harpenden (GB); Steven Howard, Cambridge (GB); Christopher William Murray, Cambridge (GB); David Norton, Cambridge (GB); Marc O'Reilly, Hereford (GB); Alison Jo-Anne Woolford, Cambridge (GB); Michael Liam Cooke, Nottingham (GB); David Cousin, Nottingham (GB); Stuart Thomas Onions, Nottingham (GB); Jonathan Martin Shannon, Nottingham (GB); John Paul Watts, Southwell (GB)

(73) Assignee: OTSUKA PHARMACEUTICAL CO., LTD., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/541,863

(22) Filed: Aug. 15, 2019

Related U.S. Application Data

(63) Continuation of application No. 15/767,775, filed as application No. PCT/IB2016/001507 on Oct. 20, 2016, now Pat. No. 10,457,669.

(30) Foreign Application Priority Data

Oct. 21, 2015 (GB) .................................. 1518676.0
Jun. 30, 2016 (GB) .................................. 1611351.6

(51) Int. Cl.
*C07D 405/14* (2006.01)
*A61K 31/55* (2006.01)
(Continued)

(52) U.S. Cl.
CPC .......... *C07D 405/14* (2013.01); *A61K 31/444* (2013.01); *A61K 31/506* (2013.01);
(Continued)

(58) Field of Classification Search
CPC .. C07D 405/14; C07D 497/08; C07D 487/04; C07D 417/14; C07D 471/08;
(Continued)

(56) References Cited

U.S. PATENT DOCUMENTS 5,958,934 A    9/1999 Berger et al.
10,457,669 B2  10/2019 Berdini et al.
(Continued)

FOREIGN PATENT DOCUMENTS

WO    9420085 A1    9/1994
WO    9501348 A2    1/1995
(Continued)

OTHER PUBLICATIONS

Search Report for Great Britain Patent Application No. GB1518676.0 dated Jun. 20, 2016.
(Continued)

*Primary Examiner* — John M Mauro
(74) *Attorney, Agent, or Firm* — Heslin Rothenberg Farley & Mesiti P.C.

(57) ABSTRACT

The invention provides a compound of formula (0):

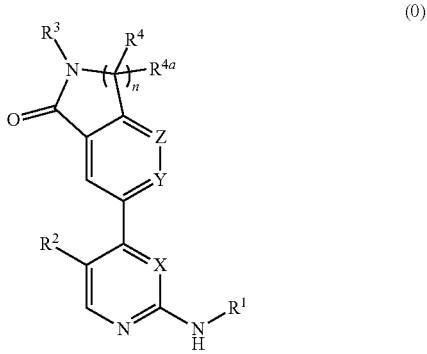

or a pharmaceutically acceptable salt, N-oxide or tautomer thereof; wherein:
n is 1 or 2;
X is CH or N;
Y is selected from CH and C—F;
Z is selected from C—$R^z$ and N;
$R^1$ is selected from:
  -(Alk$^1$)$_t$-Cyc$^1$; wherein t is 0 or 1;
  Optionally substituted $C_{1-6}$ acyclic hydrocarbon groups
$R^2$ is selected from hydrogen; halogen; and $C_{1-3}$ hydrocarbon groups optionally substituted with one or more fluorine atoms;
$R^3$ is hydrogen or a group L-$R^7$;
$R^4$ is selected from hydrogen; methoxy; and optionally substituted $C_{1-3}$ alkyl; and
$R^{4a}$ is selected from hydrogen and a $C_{1-3}$ alkyl group;
wherein $R^z$, Alk$^1$, Cyc$^1$, $L^1$ and $R^7$ are defined herein;
provided that the compound is other than 6-benzyl-3-{2-[(2-methylpyrimidin-4-yl)amino]pyridin-4-yl}-7,8-dihydro-1,6-naphthyridin-5(6H)-one and 3-{2-[(2-meth-
(Continued)

ylpyrimidin-4-yl)amino]pyridin-4-yl}-7,8-dihydro-1,6-naphthyridin-5(6H)-one and salts and tautomers thereof. The compounds are inhibitors of ERK1/2 kinases and will be useful in the treatment of ERK1/2-mediated conditions. The compounds are therefore useful in therapy, in particular in the treatment of cancer.

26 Claims, No Drawings

(51) Int. Cl.

| | |
|---|---|
| C07D 487/04 | (2006.01) |
| A61P 35/00 | (2006.01) |
| A61K 31/553 | (2006.01) |
| C07D 403/14 | (2006.01) |
| C07D 471/08 | (2006.01) |
| C07D 403/04 | (2006.01) |
| C07D 413/14 | (2006.01) |
| A61K 31/506 | (2006.01) |
| C07D 498/22 | (2006.01) |
| A61K 31/5377 | (2006.01) |
| C07D 417/14 | (2006.01) |
| C07D 409/14 | (2006.01) |
| C07D 513/04 | (2006.01) |
| A61K 31/444 | (2006.01) |
| C07D 401/14 | (2006.01) |
| C07D 471/04 | (2006.01) |
| C07D 497/08 | (2006.01) |
| A61K 31/541 | (2006.01) |

(52) U.S. Cl.
 CPC ........ *A61K 31/5377* (2013.01); *A61K 31/541* (2013.01); *A61K 31/55* (2013.01); *A61K 31/553* (2013.01); *A61P 35/00* (2018.01); *C07D 401/14* (2013.01); *C07D 403/04* (2013.01); *C07D 403/14* (2013.01); *C07D 409/14* (2013.01); *C07D 413/14* (2013.01); *C07D 417/14* (2013.01); *C07D 471/04* (2013.01); *C07D 471/08* (2013.01); *C07D 487/04* (2013.01); *C07D 497/08* (2013.01); *C07D 498/22* (2013.01); *C07D 513/04* (2013.01)

(58) Field of Classification Search
 CPC .. C07D 403/04; C07D 413/14; C07D 409/14; C07D 471/04; C07D 401/14; C07D 403/14; C07D 513/04; C07D 498/22; A61P 35/00; A61K 31/541; A61K 31/506; A61K 31/553; A61K 31/444; A61K 31/5377; A61K 31/55
 See application file for complete search history.

(56) References Cited

U.S. PATENT DOCUMENTS

| | | |
|---|---|---|
| 2006/0270686 A1 | 11/2006 | Kelly et al. |
| 2008/0280891 A1 | 11/2008 | Kelly et al. |
| 2010/0093698 A1 | 4/2010 | Bahmanyar et al. |
| 2010/0160303 A1 | 6/2010 | Liu et al. |
| 2010/0249092 A1 | 9/2010 | Singh et al. |
| 2010/0267712 A1 | 10/2010 | Heemskerk et al. |
| 2013/0065897 A1 | 3/2013 | Spicer et al. |
| 2013/0079306 A1 | 3/2013 | Uchida et al. |
| 2019/0047990 A1 | 2/2019 | Berdini et al. |

FOREIGN PATENT DOCUMENTS

| | | |
|---|---|---|
| WO | 9950249 A2 | 10/1999 |
| WO | 02102313 A2 | 12/2002 |
| WO | 2004099159 A1 | 11/2004 |
| WO | 2005020921 A2 | 3/2005 |
| WO | 2005113541 A1 | 12/2005 |
| WO | 2006113769 A1 | 10/2006 |
| WO | 2007070398 A1 | 6/2007 |
| WO | 2008003766 A2 | 1/2008 |
| WO | 2008008059 A1 | 1/2008 |
| WO | 2008124085 A2 | 10/2008 |
| WO | 2009017838 A2 | 2/2009 |
| WO | 2009039635 A1 | 4/2009 |
| WO | 2009092432 A1 | 7/2009 |
| WO | 2009158571 A1 | 12/2009 |
| WO | 2010020432 A2 | 2/2010 |
| WO | 2010057833 A1 | 5/2010 |
| WO | 2010131922 A2 | 11/2010 |
| WO | 2010151747 A1 | 12/2010 |
| WO | 2011008931 A2 | 1/2011 |
| WO | 2011080718 A1 | 7/2011 |
| WO | 2011087776 A1 | 7/2011 |
| WO | 2011090760 A1 | 7/2011 |
| WO | 2012016217 A1 | 2/2012 |
| WO | 2013000994 A1 | 1/2013 |
| WO | 2013130976 A1 | 9/2013 |
| WO | 2014040555 A1 | 3/2014 |
| WO | 2014055634 A1 | 4/2014 |
| WO | 2014124230 A2 | 8/2014 |
| WO | 2014130856 A2 | 8/2014 |
| WO | 2015030847 A1 | 3/2015 |
| WO | 2015048547 A2 | 4/2015 |
| WO | 2015108861 A1 | 7/2015 |
| WO | 2015154039 A2 | 10/2015 |
| WO | 2015157556 A1 | 10/2015 |
| WO | 2016025649 A1 | 2/2016 |
| WO | 2016106029 A1 | 6/2016 |
| WO | 2016162325 A1 | 10/2016 |
| WO | 2016205418 A1 | 12/2016 |
| WO | 2017080979 A1 | 5/2017 |
| WO | 2018019204 A1 | 2/2018 |

OTHER PUBLICATIONS

International Search Report for PCT/IB2016/001507 dated Dec. 13, 2016.
Sivaprakasam, Prasanna et al., "Discovery of New Acylaminopyridines as GSK-3 Inhibitors by a Structure Guided In-depth Exploration of Chemical Space Around a Pyrrolopyridinone Core," Bioorg. Med, Chem. Letts, 2015, 25, 9, 1856-1863.
Rowe Raymond C. et al., "Handbook of Pharmaceutical Excipients 6th Edition, Pharmaceutical Press," London, England (2009) excerpts p. 1-17.
Oslodkin Dmitry I. et al., "Glycogen Synthase Kinase 3 as an Anticancer Drug Target: Novel Experimental Findings and Trends in the Design of Inhibitors," Current Pharmaceutical Design, 2013, 19, 665-679.
CAS Registry Extracts, 32 pp. (2008-2014).
Reader, Michael et al., "6-Pyrimidin-Isoindole Derivative as ERK1/2 Inhibitor," U.S. Appl. No. 16/604,002, filed Oct. 9, 2019, 114 pp.

BENZOLACTAM COMPOUNDS AS PROTEIN KINASE INHIBITORS

CROSS REFERENCE TO RELATED APPLICATIONS

This application is a continuation of U.S. National Phase application Ser. No. 15/767,775 filed Apr. 12, 2018, which is a national stage filing under section 371 of International Application No. PCT/IB2016/001507, filed on Oct. 20, 2016, and published on Apr. 27, 2017 as WO 2017/068412, which claims priority to Great Britain Application No. 1611351.6, filed on Jun. 30, 2016 and Great Britain Application No. 1518676.0, filed on Oct. 21, 2015. The entire contents of WO 2017/068412 are hereby incorporated herein by reference.

The invention relates to new benzolactam compounds, to pharmaceutical compositions comprising the compounds and to the use of the compounds in the treatment of diseases such as cancer.

BACKGROUND OF THE INVENTION

MAPK Signalling and the Role of ERK1/2

The extracellular signal regulated kinases (ERK1/2) are ubiquitously expressed protein serine/threonine kinases that comprise a key component of the mitogen-activated protein kinase (MAPK) signalling pathway. The MAPK pathway is an evolutionary conserved cell signalling pathway that regulates a variety of cellular processes including cell cycle progression, cell migration, cell survival, differentiation, metabolism, proliferation and transcription. The ERK/MAPK signalling pathway responds to the extracellular stimulation of cell-surface receptor tyrosine kinases (RTKs). Upon activation of RTKs, the RAS GTPases (K-RAS, N-RAS and H-RAS) are converted from an inactive GDP-bound state to an active GTP-bound state. Activated RAS phosphorylates and thereby activates RAF (A-RAF, B-RAF and C-RAF), which in turn phosphorylates and activates the dual-specificity kinase MEK (MEK1/2). Subsequently, activated MEK phosphorylates and activates ERK1/2. Upon activation, ERK1/2 activates multiple nuclear and cytoplasmic substrates. There are currently >200 known ERK1/2 substrates, which include transcription factors, kinases, phosphatases and cytoskeletal proteins (Roskoski, Pharmacol. Res. 2012; 66: 105-143).

A number of isozymes of ERK have been identified (ERK1, ERK2, ERK3/4, ERK5, ERK7) but the two most widely studied isozymes are ERK1 and ERK2: see R. Roberts, *J. Exp. Pharm., The extracellular signal-regulated kinase (ERK) pathway: a potential therapeutic target in hypertension,* 2012: 4, 77-83, and Cargnello et al., *Microbiol. & Mol. Biol. Rev., Activation and Function of the MAPKs and Their Substrates, the MAPK-Activated Protein Kinases* 2011, 50-83.

Upregulation of ERK1/2 Signalling in Cancer

ERK1/2 activity is commonly upregulated in cancer, as a result of activating mutations within upstream components of the MAPK pathway. Approximately 30% of human cancers contain activating RAS mutations (Roberts and Der, Oncogene. 2007; 26: 3291-3310). K-RAS is the most frequently mutated isoform and is mutated in 22% of all tumours. KRAS mutations are particularly prevalent in pancreatic adenocarcinoma (70-90%), non-small cell carcinoma (10-20%) and colorectal cancer (25-35%) (Neuzillet et al., 2014. Pharmacol. Ther. 141; 160-171). N-RAS and H-RAS mutations occur in 8% and 3% of cancers, respectively (Prior et al., Cancer Res. 2012; 72 (10); 2457-2467). Notably, activating N-RAS mutations have been reported in 15-20% of melanoma cases. Furthermore, activating B-RAF mutations occur in 8% of all tumours and are particularly prevalent in melanoma (50-60%), papillary thyroid cancer (40-60%), colorectal cancer (5-10%) and non-small cell lung cancer (3-5%) (Neuzillet et al., 2014. Pharmacol. Ther. 141; 160-171). In addition to the occurrence of activating RAS and RAF mutations, the MAPK signalling pathway can also be up-regulated in cancer by the over-expression or mutational activation of upstream RTKS such as EGFR (Lynch et al., *N Engl J Med.* 2004; 350: 2129-2139), HER2 (Stephens et al., Nature. 2004; 431: 525-526) and FGFR (Ahmed et al, Biochim. Biophys. Acta Mol. Cell. Res. 2012; 1823: 850-860).

There are multiple mechanisms by which aberrant ERK1/2 signalling can contribute to cancer progression. Upon activation, ERK1/2 phosphorylates and activates a wide range of transcription factors that are involved in promoting cell proliferation and differentiation, such as c-Fos (Murphy et al., Nat. Cell Biol. 2002: 4 (8):556-64) and ELK-1 (Gille et al., EMBO J. 1995; 14 (5):951-62). In addition, ERK1/2 signalling is known to promote cell cycle progression via multiple mechanisms, including the induction of D-type cyclins and repression of the cyclin-dependent kinase inhibitor p27$^{KIP1}$ (Kawada et al., Oncogene. 1997; 15: 629-637, Lavoie et al., J. Biol. Chem. 1996; 271: 20608-20616). Furthermore, ERK1/2 signalling can promote cell survival by regulating a range of apoptotic proteins. Examples of such mechanisms include the ERK1/2-dependent repression of the pro-apoptotic BCL-2 family proteins BIM1 and BAD (She et al., J. Biol Chem. 2002; 277: 24039-24048. Ley et al., J. Biol. Chem. 2003; 278: 18811-18816) and the ERK1/2-dependent stabilisation of anti-apoptotic proteins such as MCL-1 (Domina et al., Oncogene. 2004; 23: 5301-5315).

Role of ERK1/2 in MAPK Inhibitor Resistance

A wide range of pre-clinical studies have demonstrated that the inhibition of the MAPK pathway suppresses the growth of cancer cell lines harbouring B-Raf or Ras mutations (Friday & Adjei, Clin. Cancer Res. 2008; 14: 342-346). The RAF inhibitors vemurafenib and dabrafenib, and the MEK inhibitor trametinib are clinically approved for the treatment of BRAF-mutant melanoma. These agents elicit profound anti-tumour responses in the majority of patients, although the duration of response is short-lived, due to the onset of acquired drug resistance (Chapman et al., N. Engl. J. Med. 2011; 364 2507-2516. Hauschild et al., Lancet. 2012; 380: 358-365. Solit and Rosen, N Engl J Med. 2011; 364 (8): 772-774. Flaherty et al., N. Engl. J. Med. 2012; 367: 1694-1703). Multiple mechanisms of acquired B-RAF inhibitor resistance have been identified. These include the upregulation or activation of alternative MEK activators such as C-RAF or COT1 (Villanueva et al, Cancer Cell. 2010; 18:683-95. Johannessen et al., Nature. 2010; 468: 968-72), the upregulation of RTK or NRAS signalling (Nazarian et al., Nature. 2010; 468:973-7), and the onset of MEK activating mutations (Wagle et al., J Clin Oncol. 2011; 29:3085-96). Mechanisms of MEK inhibitor-resistance include the occurrence of MEK mutations that reduce drug binding or enhance intrinsic MEK activity (Emery et al., Proc Natl. Acad. Sci. 2009; 106: 20411-20416. Wang et al., Cancer Res. 2011; 71: 5535-5545), and BRAF or KRAS amplification (Little et al., Biochem Soc. Trans. 2012; 40(1): 73-8). A common feature of RAF or MEK inhibitor resistance mechanisms is the re-activation of ERK1/2 signalling, which drives proliferation and survival of the cells in the presence of inhibitors. Based on this observation, it has been suggested that direct ERK1/2 inhibition may be an effective therapeutic approach to overcoming acquired RAF or MEK inhibitor resistance. There is pre-clinical evidence that the inhibition of ERK1/2 overcomes acquired RAF or MEK inhibitor resistance (Hatzivassiliou et al., Mol Cancer Ther. 2012; 11(5):1143-54. Morris et al., Cancer Discov. 2013; 3 (7):742-50)

Additional Diseases

In addition to oncology, abnormal ERK1/2 signalling has also been reported in other diseases including cardiovascular disease (Muslin, Clin. Sci. 2008; 115: 203-218), Alzheimer's disease (Giovannini et al., Neuroscience. 2008; 153: 618-633), polycystic kidney disease (Omori et al., J Am Soc Nephrol. 2006; 17:1604-1614), Asthma (Duan et al., J Immunol. 2004; 172: 7053-7059) and emphysema (Mercer et al., J. Biol. Chem. 2004; 279: 17690-17696).

The Invention

The present invention provides compounds which are useful in therapy, in particular in the treatment of cancer. The compounds are inhibitors of ERK1/2 kinases and will be useful in the treatment of ERK1/2-mediated conditions.

Accordingly, in a first aspect of the invention (Embodiment 0.1), there is provided a compound of formula (0):

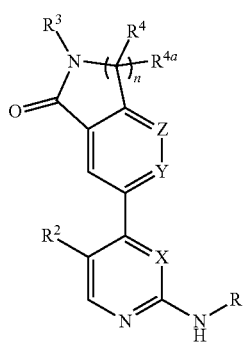

(0)

or a pharmaceutically acceptable salt, N-oxide or tautomer thereof; wherein:

n is 1 or 2;

X is CH or N;

Y is selected from CH and C—F;

Z is selected from C—$R^z$ and N;

$R^z$ is selected from hydrogen; halogen; methoxy; and $C_{1-3}$ alkyl optionally substituted with hydroxy or methoxy;

$R^1$ is selected from:
- -(Alk$^1$)$_t$-Cyc$^1$; wherein t is 0 or 1; and Alk$^1$ is a $C_{1-4}$ straight chain or branched alkylene group optionally substituted with 1 or 2 hydroxy groups; and
- $C_{1-6}$ acyclic hydrocarbon groups which are unsubstituted or substituted with 1, 2 or 3 substituents $R^5$ selected from hydroxy; oxo; fluorine; and cyano; and wherein 1 or 2 but not all of the carbon atoms of the hydrocarbon group can be replaced by O or N;

Cyc$^1$ is a cyclic group selected from (a) 3 to 9 membered non-aromatic monocyclic and bicyclic carbocyclic and heterocyclic groups containing 0, 1, 2, or 3 heteroatom ring members selected from O, N, S, S(O) and S(O)$_2$; (b) 5 to 6 membered monocyclic heteroaryl groups containing 1, 2 or 3 heteroatom ring members of which 1 is N and the others, when present, are selected from O, N and S; and (c) 3 to 7 membered monocyclic carbocyclic groups; wherein each cyclic group (a), (b) and (c) is unsubstituted or substituted with 1, 2 or 3 substituents $R^6$ selected from hydroxy; oxo; fluorine; amino; NH(Hyd$^1$); N(Hyd$^1$)$_2$; O-Hyd$^1$; —C(═O)-Hyd$^1$; —C(═O)—O-Hyd$^1$ and Hyd$^1$; where Hyd$^1$ is a $C_{1-4}$ non-aromatic hydrocarbon group optionally substituted with one or more substituents selected from fluorine, hydroxyl and methoxy;

$R^2$ is selected from hydrogen; halogen; and $C_{1-3}$ hydrocarbon groups optionally substituted with one or more fluorine atoms;

$R^3$ is hydrogen or a group $L^1$-$R^7$;

$R^4$ is selected from hydrogen; methoxy; and $C_{1-3}$ alkyl optionally substituted with hydroxy, amino, mono- or di-$C_{1-2}$ alkylamino, a cyclic amino group or methoxy; wherein the cyclic amino group is a saturated 4-7 membered heterocyclic group containing a nitrogen ring member and optionally a second heteroatom ring member selected from O, N and S, wherein the cyclic amino group is linked via a nitrogen ring member thereof to the $C_{1-2}$ alkyl, and wherein the cyclic amino group is optionally substituted with one or two methyl groups; provided that no more than one $R^4$ can be other than hydrogen or methyl;

$R^{4a}$ is selected from hydrogen and a $C_{1-3}$ alkyl group;

$L^1$ is selected from a bond; Alk$^2$, Alk$^2$-O and Alk$^2$-C(═O) wherein Alk$^2$ is a $C_{1-4}$ straight chain or branched alkylene group which is optionally substituted with one or more substituents selected from hydroxy, methoxy, amino, methylamino, dimethylamino and fluorine;

$R^7$ is selected from:
- hydrogen;
- CO$_2$H;
- NR$^8$R$^9$;
- a carbocyclic or heterocyclic group having from 3 to 12 ring members, of which 0, 1, 2 or 3 are heteroatom ring members selected from O, N and S and oxidised forms of S, the carbocyclic or heterocyclic group being optionally substituted with one or more substituents $R^{10}$; and
- an acyclic $C_{1-8}$ hydrocarbon group optionally substituted with one or more substituents selected from hydroxy; oxo; halogen; cyano; carboxy; amino; mono- or di-$C_{1-4}$ alkylamino; and carbocyclic and heterocyclic groups having from 3 to 12 ring members, of which 0, 1, 2 or 3 are heteroatom ring members selected from O, N and S and oxidised forms of S, the carbocyclic or heterocyclic group being optionally substituted with one or more substituents $R^{10}$; wherein one or two but not all of the carbon atoms of the acyclic $C_{1-8}$ hydrocarbon group may optionally be replaced by O, S, SO, SO$_2$ or NR$^1$;

$R^8$ is selected from hydrogen and a $C_{1-4}$ hydrocarbon group, the $C_{1-4}$ hydrocarbon group being optionally substituted with 1-2 substituents selected from hydroxy, amino, mono-$C_{1-4}$ alkylamino, di-$C_{1-4}$ alkylamino, and 4-7 membered saturated heterocyclic rings containing 1-2 heteroatom ring members selected from O and N, wherein the mono-$C_{1-4}$ alkylamino, di-$C_{1-4}$ alkylamino, and 4-7 membered saturated heterocyclic rings are each optionally substituted with 1-2 hydroxy or $C_{1-3}$ alkyl substituents;

$R^9$ is selected from:
- hydrogen;
- a carbocyclic or heterocyclic group having from 3 to 12 ring members, of which 0, 1, 2 or 3 are heteroatom ring members selected from O, N and S and oxidised forms of S, the carbocyclic or heterocyclic group being optionally substituted with one or more substituents $R^{10}$; and an acyclic $C_{1-8}$ hydrocarbon group optionally substituted with one or more substituents selected from hydroxy; oxo; halogen; cyano; carboxy; amino; mono- or di-$C_{1-4}$ alkylamino; and carbocyclic and heterocyclic groups having from 3 to 12 ring members, of which 0, 1, 2 or 3 are heteroatom ring members selected from O, N and S and oxidised forms of S, the carbocyclic or heterocyclic group being optionally substituted with one or more substituents $R^{10}$; wherein one or two but not all of the carbon atoms of the acyclic $C_{1-8}$ hydrocarbon group may optionally be replaced by O, S, SO, $SO_2$ or $NR^{11}$;

or $NR^8R^9$ forms a heterocyclic group having from 4 to 12 ring members wherein, in addition to the nitrogen atom of $NR^8R^9$, the heterocyclic group optionally contains 1 or 2 further heteroatom ring members selected from O, N and S and oxidised forms of S; and wherein the heterocyclic group is optionally substituted with one or more substituents $R^{10}$;

$R^{10}$ is selected from:
halogen; hydroxy; oxo; cyano;
$OR^{12}$ wherein $R^{12}$ is $C_{1-6}$ alkyl or $C_{3-6}$ cycloalkyl, each being optionally substituted with halogen;
an acyclic $C_{1-8}$ hydrocarbon group optionally substituted with one or more substituents selected from hydroxy; oxo; halogen; cyano; carboxy; amino; mono- or di-$C_{1-4}$ alkylamino; and carbocyclic and heterocyclic groups having 3 to 7 ring members of which 0, 1, 2, 3 or 4 are heteroatom ring members selected from N, O and S, wherein the carbocyclic and heterocyclic groups are optionally substituted with one or more substituents $R^{13}$ selected from hydroxy; halogen; cyano; amino; —NH(Hyd¹); —N(Hyd¹)$_2$; and —(O)$_v$-Hyd¹ where v is 0 or 1; wherein one or two but not all of the carbon atoms of the acyclic $C_{1-8}$ hydrocarbon group may optionally be replaced by O, S, SO, $SO_2$ or $NR^{11}$; and
carbocyclic and heterocyclic groups having 3 to 7 ring members of which 0, 1, 2, 3 or 4 are heteroatom ring members selected from N, O and S, wherein the carbocyclic and heterocyclic groups are optionally substituted with one or more substituents $R^{13}$; and
$R^{11}$ is selected from hydrogen and a $C_{1-4}$ hydrocarbon group; provided that the compound is other than 6-benzyl-3-{2-[(2-methylpyrimidin-4-yl)amino]pyridin-4-yl}-7,8-dihydro-1,6-naphthyridin-5(6H)-one and 3-{2-[(2-methylpyrimidin-4-yl)amino]pyridin-4-yl}-7,8-dihydro-1,6-naphthyridin-5(6H)-one and salts and tautomers thereof.

Particular aspects and embodiments of the invention are set out in Embodiments 0.2 to 1.179 below.

0.2 A compound according to Embodiment 0.1 wherein $Cyc^1$ is a cyclic group selected from (a) 3 to 9 membered non-aromatic monocyclic and bicyclic carbocyclic and heterocyclic groups containing 0, 1, 2, or 3 heteroatom ring members selected from O, N, S and $S(O)_2$; (b) 5 to 6 membered monocyclic heteroaryl groups containing 1, 2 or 3 heteroatom ring members of which 1 is N and the others, when present, are selected from O, N and S; and (c) 3 to 7 membered monocyclic carbocyclic groups; wherein each cyclic group (a), (b) and (c) is unsubstituted or substituted with 1, 2 or 3 substituents $R^6$ selected from hydroxy; oxo; fluorine; amino; NH(Hyd¹); N(Hyd¹)$_2$; O-Hyd¹; —C(=O)-Hyd¹; —C(=O)—O—Hyd¹ and Hyd¹; where Hyd¹ is a $C_{1-4}$ non-aromatic hydrocarbon group optionally substituted with one or more substituents selected from fluorine, hydroxyl and methoxy.

0.3 A compound according to Embodiment 0.1 or 0.2 wherein $R^{4a}$ is methyl.

0.4 A compound according to Embodiment 0.1 or 0.2 wherein $R^{4a}$ is hydrogen.

0.5 A compound according to any one of Embodiments 0.1 to 0.4 wherein $R^{10}$ is selected from:
halogen; hydroxy; oxo; cyano;
$OR^{12}$ wherein $R^{12}$ is $C_{1-6}$ alkyl or $C_{3-6}$ cycloalkyl, each being optionally substituted with halogen;
an acyclic $C_{1-8}$ hydrocarbon group optionally substituted with one or more substituents selected from hydroxy; oxo; halogen; cyano; carboxy; amino; mono- or di-$C_{1-4}$ alkylamino; and carbocyclic and heterocyclic groups having 3 to 7 ring members of which 0, 1, 2, 3 or 4 are heteroatom ring members selected from N, O and S, wherein the carbocyclic and heterocyclic groups are optionally substituted with one or more substituents $R^{13}$ selected from hydroxy; halogen; cyano and —(O)$_v$-Hyd¹ where v is 0 or 1; wherein one or two but not all of the carbon atoms of the acyclic $C_{1-8}$ hydrocarbon group may optionally be replaced by O, S, SO, $SO_2$ or $NR^{11}$; and
carbocyclic and heterocyclic groups having 3 to 7 ring members of which 0, 1, 2, 3 or 4 are heteroatom ring members selected from N, O and S, wherein the carbocyclic and heterocyclic groups are optionally substituted with one or more substituents $R^{13}$.

1.0 A compound of formula (1):

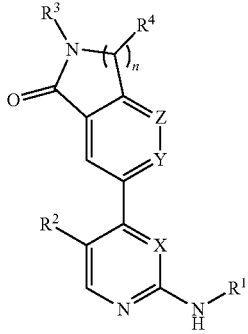

(1)

or a pharmaceutically acceptable salt or tautomer thereof; wherein:
n is 1 or 2;
X is CH or N;
Y is selected from CH and C—F;
Z is selected from C—$R^z$ and N;
$R^z$ is selected from hydrogen; halogen; methoxy; and $C_{1-3}$ alkyl optionally substituted with hydroxy or methoxy;
$R^1$ is selected from:
-(Alk¹)$_t$-Cyc¹; wherein t is 0 or 1; and Alk¹ is a $C_{1-4}$ straight chain or branched alkylene group optionally substituted with 1 or 2 hydroxy groups; and
$C_{1-6}$ acyclic hydrocarbon groups which are unsubstituted or substituted with 1, 2 or 3 substituents $R^5$ selected from hydroxy; oxo; fluorine; and cyano; and wherein 1 or 2 but not all of the carbon atoms of the hydrocarbon group can be replaced by O or N;
Cyc¹ is a cyclic group selected from (a) 3 to 9 membered non-aromatic monocyclic and bicyclic carbocyclic and heterocyclic groups containing 0, 1, 2, or 3 heteroatom ring members selected from O, N, S and $S(O)_2$; (b) 5 to 6 membered monocyclic heteroaryl groups containing 1, 2 or 3 heteroatom ring members of which 1 is N and the others, when present, are selected from O, N and S; and (c) 3 to 7 membered monocyclic carbocyclic groups; wherein each cyclic group (a), (b) and (c) is unsubstituted or substituted with 1, 2 or 3 substituents $R^6$ selected from hydroxy; oxo; fluorine; amino; NH(Hyd$^1$); N(Hyd$^1$)$_2$; O-Hyd$^1$; —C(=O)-Hyd$^1$; —C(=O)—O-Hyd$^1$ and Hyd$^1$;
  where Hyd$^1$ is a $C_{1-4}$ non-aromatic hydrocarbon group optionally substituted with one or more substituents selected from fluorine, hydroxyl and methoxy;
$R^2$ is selected from hydrogen; halogen; and $C_{1-3}$ hydrocarbon groups optionally substituted with one or more fluorine atoms;
$R^3$ is hydrogen or a group L-R$^7$;
$R^4$ is selected from hydrogen; methoxy; and $C_{1-3}$ alkyl optionally substituted with hydroxy, amino, mono- or di-$C_{1-2}$ alkylamino, a cyclic amino group or methoxy; wherein the cyclic amino group is a saturated 4-7 membered heterocyclic group containing a nitrogen ring member and optionally a second heteroatom ring member selected from O, N and S, wherein the cyclic amino group is linked via a nitrogen ring member thereof to the $C_{1-2}$ alkyl, and wherein the cyclic amino group is optionally substituted with one or two methyl groups; provided that no more than one $R^4$ can be other than hydrogen or methyl;
$L^1$ is selected from a bond; Alk$^2$, Alk$^2$-O and Alk$^2$-C(=O) wherein Alk$^2$ is a $C_{1-4}$ straight chain or branched alkylene group which is optionally substituted with one or more substituents selected from hydroxy, methoxy, amino, methylamino, dimethylamino and fluorine;
$R^7$ is selected from:
hydrogen;
$CO_2H$;
$NR^8R^9$;
a carbocyclic or heterocyclic group having from 3 to 12 ring members, of which 0, 1, 2 or 3 are heteroatom ring members selected from O, N and S and oxidised forms of S, the carbocyclic or heterocyclic group being optionally substituted with one or more substituents $R^{10}$; and
an acyclic $C_{1-8}$ hydrocarbon group optionally substituted with one or more substituents selected from hydroxy; oxo; halogen; cyano; carboxy; amino; mono- or di-$C_{1-4}$ alkylamino; and carbocyclic and heterocyclic groups having from 3 to 12 ring members, of which 0, 1, 2 or 3 are heteroatom ring members selected from O, N and S and oxidised forms of S, the carbocyclic or heterocyclic group being optionally substituted with one or more substituents $R^{10}$; wherein one or two but not all of the carbon atoms of the acyclic $C_{1-8}$ hydrocarbon group may optionally be replaced by O, S, SO, $SO_2$ or $NR^1$;
$R^3$ is selected from hydrogen and a $C_{1-4}$ hydrocarbon group, the $C_{1-4}$ hydrocarbon group being optionally substituted with 1-2 substituents selected from hydroxy, amino, mono-$C_{1-4}$ alkylamino, di-$C_{1-4}$ alkylamino, and 4-7 membered saturated heterocyclic rings containing 1-2 heteroatom ring members selected from O and N, wherein the mono-$C_{1-4}$ alkylamino, di-$C_{1-4}$ alkylamino, and 4-7 membered saturated heterocyclic rings are each optionally substituted with 1-2 hydroxy or $C_{1-3}$ alkyl substituents;
$R^9$ is selected from:
hydrogen;
a carbocyclic or heterocyclic group having from 3 to 12 ring members, of which 0, 1, 2 or 3 are heteroatom ring members selected from O, N and S and oxidised forms of S, the carbocyclic or heterocyclic group being optionally substituted with one or more substituents $R^{10}$; and an acyclic $C_{1-8}$ hydrocarbon group optionally substituted with one or more substituents selected from hydroxy; oxo; halogen; cyano; carboxy; amino; mono- or di-$C_{1-4}$ alkylamino; and carbocyclic and heterocyclic groups having from 3 to 12 ring members, of which 0, 1, 2 or 3 are heteroatom ring members selected from O, N and S and oxidised forms of S, the carbocyclic or heterocyclic group being optionally substituted with one or more substituents $R^{10}$; wherein one or two but not all of the carbon atoms of the acyclic $C_{1-8}$ hydrocarbon group may optionally be replaced by O, S, SO, $SO_2$ or $NR^1$;
or $NR^8R^9$ forms a heterocyclic group having from 4 to 12 ring members wherein, in addition to the nitrogen atom of $NR^8R^9$, the heterocyclic group optionally contains 1 or 2 further heteroatom ring members selected from O, N and S and oxidised forms of S; and wherein the heterocyclic group is optionally substituted with one or more substituents $R^{10}$;
$R^{10}$ is selected from:
halogen; hydroxy; oxo; cyano;
$OR^{12}$ wherein $R^{12}$ is $C_{1-6}$ alkyl or $C_{3-6}$ cycloalkyl, each being optionally substituted with halogen;
an acyclic $C_{1-8}$ hydrocarbon group optionally substituted with one or more substituents selected from hydroxy; oxo; halogen; cyano; carboxy; amino; mono- or di-$C_{1-4}$ alkylamino; and carbocyclic and heterocyclic groups having 3 to 7 ring members of which 0, 1, 2, 3 or 4 are heteroatom ring members selected from N, O and S, wherein the carbocyclic and heterocyclic groups are optionally substituted with one or more substituents $R^{13}$ selected from hydroxy; halogen; cyano; and —(O)$_v$-Hyd$^1$ where v is 0 or 1; wherein one or two but not all of the carbon atoms of the acyclic $C_{1-8}$ hydrocarbon group may optionally be replaced by O, S, SO, $SO_2$ or $NR^{11}$; and
carbocyclic and heterocyclic groups having 3 to 7 ring members of which 0, 1, 2, 3 or 4 are heteroatom ring members selected from N, O and S, wherein the carbocyclic and heterocyclic groups are optionally substituted with one or more substituents $R^{13}$; and
$R^{11}$ is selected from hydrogen and a $C_{1-4}$ hydrocarbon group; provided that the compound is other than 6-benzyl-3-{2-[(2-methylpyrimidin-4-yl)amino]pyridin-4-yl}-7,8-dihydro-1,6-naphthyridin-5(6H)-one and 3-{2-[(2-methylpyrimidin-4-yl)amino]pyridin-4-yl}-7,8-dihydro-1,6-naphthyridin-5(6H)-one and salts and tautomers thereof.

1.01 A compound according to any one of Embodiments 0.1 to 1.0 wherein $R^1$ is selected from:
  -(Alk$^1$)$_t$-Cyc$^1$; wherein t is 0 or 1; and Alk$^1$ is a $C_{1-4}$ straight chain or branched alkylene group optionally substituted with 1 or 2 hydroxy groups; and
  $C_{1-6}$ acyclic hydrocarbon groups which are unsubstituted or substituted with 1, 2 or 3 substituents $R^5$ selected from hydroxy; oxo; and fluorine; and wherein 1 or 2 but not all of the carbon atoms of the hydrocarbon group can be replaced by 0 or N;

1.02 A compound according to any one of Embodiments 0.1 to 1.01 wherein $R^6$ is selected from hydroxy; oxo; fluorine; O-Hyd$^1$; —C(=O)-Hyd$^1$; —C(=O)—O-Hyd$^1$ and Hyd$^1$; where Hyd$^1$ is a $C_{1-4}$ non-aromatic hydrocarbon group optionally substituted with one or more substituents selected from fluorine, hydroxyl and methoxy.

1.03 A compound according to any one of Embodiments 0.1 to 1.02 wherein $R^3$ is selected from hydrogen and a $C_{1-4}$ hydrocarbon group optionally substituted with hydroxy.

1.04 A compound according to any one of Embodiments 0.1 to 1.03 wherein, when $R^{10}$ is selected from:

halogen; hydroxy; oxo; cyano;
OR¹² wherein R¹² is C₁₋₆ alkyl or C₃₋₆ cycloalkyl, each being optionally substituted with halogen;
an acyclic C₁₋₈ hydrocarbon group optionally substituted with one or more substituents selected from hydroxy; oxo; halogen; cyano; carboxy; amino; mono- or di-C₁₋₄ alkylamino; and carbocyclic and heterocyclic groups having 3 to 6 ring members of which 0, 1 or 2 are heteroatom ring members selected from N, O and S, wherein the carbocyclic and heterocyclic groups are optionally substituted with one or more substituents R¹³ selected from hydroxy; halogen; cyano; and —(O)ᵥ-Hyd¹ where v is 0 or 1; wherein one or two but not all of the carbon atoms of the acyclic C₁₋₈ hydrocarbon group may optionally be replaced by O, S, SO, SO₂ or NR¹¹; and
carbocyclic and heterocyclic groups having 3 to 6 ring members of which 0, 1, 2 or 3 are heteroatom ring members selected from N, O and S, wherein the carbocyclic and heterocyclic groups are optionally substituted with one or more substituents R¹³; and R¹¹ is selected from hydrogen and a C₁₋₄ hydrocarbon group.

1.05 A compound according to Embodiment 1.04 wherein, when R¹⁰ is selected from:
halogen; hydroxy; oxo; cyano;
OR¹² wherein R¹² is C₁₋₆ alkyl or C₃₋₆ cycloalkyl, each being optionally substituted with halogen;
an acyclic C₁₋₈ hydrocarbon group optionally substituted with one or more substituents selected from hydroxy; oxo; halogen; cyano; carboxy; amino; mono- or di-C₁₋₄ alkylamino; and carbocyclic and heterocyclic groups having 3 to 6 ring members of which 0, 1 or 2 are heteroatom ring members selected from N, O and S, wherein the carbocyclic and heterocyclic groups are optionally substituted with one or more substituents R¹³ selected from hydroxy; halogen; cyano; and —(O)ᵥ-Hyd¹ where v is 0 or 1; wherein one or two but not all of the carbon atoms of the acyclic C₁₋₈ hydrocarbon group may optionally be replaced by O, S, SO, SO₂ or NR¹¹; and
carbocyclic and heterocyclic groups having 3 to 6 ring members of which 0, 1 or 2 are heteroatom ring members selected from N, O and S, wherein the carbocyclic and heterocyclic groups are optionally substituted with one or more substituents R¹³; and
R¹¹ is selected from hydrogen and a C₁₋₄ hydrocarbon group.

1.06 A compound according to any one of Embodiments 0.1 to 1.05 wherein, when Z is C—R$^z$, R$^z$ is selected from hydrogen; halogen; methoxy; and C₁₋₃ alkyl optionally substituted with hydroxyl.

1.1 A compound of formula (1):

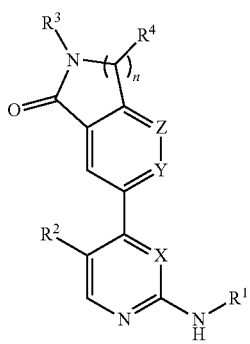

(1)

or a pharmaceutically acceptable salt or tautomer thereof;

wherein:
n is 1 or 2;
X is CH or N;
Y is selected from CH and C—F;
Z is selected from C—R$^z$ and N;
R$^z$ is selected from hydrogen; halogen; and C₁₋₃ alkyl optionally substituted with hydroxy or methoxy;
R¹ is selected from:
-(Alk¹)ₜ-Cyc¹; wherein t is 0 or 1; and Alk¹ is a C₁₋₄ straight chain or branched alkylene group optionally substituted with 1 or 2 hydroxy groups; and
C₁₋₆ acyclic hydrocarbon groups which are unsubstituted or substituted with 1, 2 or 3 substituents R⁵ selected from hydroxy; oxo; fluorine; and wherein 1 or 2 but not all of the carbon atoms of the hydrocarbon group can be replaced by 0 or N;
Cyc¹ is a cyclic group selected from (a) 3 to 9 membered non-aromatic monocyclic and bicyclic carbocyclic and heterocyclic groups containing 0, 1, 2, or 3 heteroatom ring members selected from O, N, S and S(O)₂; (b) 5 to 6 membered monocyclic heteroaryl groups containing 1, 2 or 3 heteroatom ring members of which 1 is N and the others, when present, are selected from O, N and S; and (c) 3 to 7 membered monocyclic carbocyclic groups; wherein each cyclic group (a), (b) and (c) is unsubstituted or substituted with 1, 2 or 3 substituents R⁶ selected from hydroxy; oxo; fluorine; O-Hyd¹; —C(=O)-Hyd¹; —C(=O)—O-Hyd¹ and Hyd¹; where Hyd¹ is a C₁₋₄ non-aromatic hydrocarbon group optionally substituted with one or more substituents selected from fluorine, hydroxyl and methoxy;
R² is selected from hydrogen; halogen; and C₁₋₃ hydrocarbon groups optionally substituted with one or more fluorine atoms;
R³ is hydrogen or a group L¹-R⁷;
R⁴ is selected from hydrogen and C₁₋₂ alkyl optionally substituted with hydroxy, amino, mono- or di-C₁₋₂ alkylamino, a cyclic amino group or methoxy; wherein the cyclic amino group is a saturated 4-7 membered heterocyclic group containing a nitrogen ring member and optionally a second heteroatom ring member selected from O, N and S, wherein the cyclic amino group is linked via a nitrogen ring member thereof to the C₁₋₂ alkyl, and wherein the cyclic amino group is optionally substituted with one or two methyl groups; provided that no more than one R⁴ can be other than hydrogen or methyl;
L¹ is selected from a bond; Alk², Alk²-O and Alk²-C(=O) wherein Alk² is a C₁₋₄ straight chain or branched alkylene group which is optionally substituted with one or more substituents selected from hydroxy, methoxy, amino, methylamino, dimethylamino and fluorine;
R⁷ is selected from:
hydrogen;
CO₂H;
NR⁸R⁹;
a carbocyclic or heterocyclic group having from 3 to 12 ring members, of which 0, 1, 2 or 3 are heteroatom ring members selected from O, N and S and oxidised forms of S, the carbocyclic or heterocyclic group being optionally substituted with one or more substituents R¹⁰; and
an acyclic C₁₋₈ hydrocarbon group optionally substituted with one or more substituents selected from hydroxy; oxo; halogen; cyano; carboxy; amino; mono- or di-C₁₋₄ alkylamino; and carbocyclic and heterocyclic groups having from 3 to 12 ring members, of which 0, 1, 2 or 3 are heteroatom ring members selected from O, N and S and oxidised forms of S, the carbocyclic or heterocyclic group being optionally substituted with one or more substituents $R^{10}$; wherein one or two but not all of the carbon atoms of the acyclic $C_{1-8}$ hydrocarbon group may optionally be replaced by O, S, SO, $SO_2$ or $NR^{11}$;

$R^3$ is selected from hydrogen and a $C_{1-4}$ hydrocarbon group optionally substituted with hydroxy;

$R^9$ is selected from:

hydrogen;

a carbocyclic or heterocyclic group having from 3 to 12 ring members, of which 0, 1, 2 or 3 are heteroatom ring members selected from O, N and S and oxidised forms of S, the carbocyclic or heterocyclic group being optionally substituted with one or more substituents $R^{10}$; and an acyclic $C_{1-8}$ hydrocarbon group optionally substituted with one or more substituents selected from hydroxy; oxo; halogen; cyano; carboxy; amino; mono- or di-$C_{1-4}$ alkylamino; and carbocyclic and heterocyclic groups having from 3 to 12 ring members, of which 0, 1, 2 or 3 are heteroatom ring members selected from O, N and S and oxidised forms of S, the carbocyclic or heterocyclic group being optionally substituted with one or more substituents $R^{10}$; wherein one or two but not all of the carbon atoms of the acyclic $C_{1-8}$ hydrocarbon group may optionally be replaced by O, S, SO, $SO_2$ or $NR^{11}$;

or $NR^8R^9$ forms a heterocyclic group having from 4 to 12 ring members wherein, in addition to the nitrogen atom of $NR^8R^9$, the heterocyclic group optionally contains 1 or 2 further heteroatom ring members selected from O, N and S and oxidised forms of S; and wherein the heterocyclic group is optionally substituted with one or more substituents $R^{10}$;

$R^{10}$ is selected from:

halogen; hydroxy; oxo; cyano;

$OR^{12}$ wherein $R^{12}$ is $C_{1-6}$ alkyl or $C_{3-6}$ cycloalkyl, each being optionally substituted with halogen;

an acyclic $C_{1-8}$ hydrocarbon group optionally substituted with one or more substituents selected from hydroxy; oxo; halogen; cyano; carboxy; amino; mono- or di-$C_{1-4}$ alkylamino; and carbocyclic and heterocyclic groups having 3 to 6 ring members of which 0, 1 or 2 are heteroatom ring members selected from N, O and S, wherein the carbocyclic and heterocyclic groups are optionally substituted with one or more substituents $R^{13}$ selected from hydroxy; halogen; cyano; and —(O)$_v$-Hyd$^1$ where v is 0 or 1; wherein one or two but not all of the carbon atoms of the acyclic $C_{1-8}$ hydrocarbon group may optionally be replaced by O, S, SO, $SO_2$ or $NR^{11}$; and carbocyclic and heterocyclic groups having 3 to 6 ring members of which 0, 1 or 2 are heteroatom ring members selected from N, O and S, wherein the carbocyclic and heterocyclic groups are optionally substituted with one or more substituents $R^{13}$; and $R^{11}$ is selected from hydrogen and a $C_{1-4}$ hydrocarbon group; provided that the compound is other than 6-benzyl-3-{2-[(2-methylpyrimidin-4-yl)amino]pyridin-4-yl}-7,8-dihydro-1,6-naphthyridin-5(6H)-one and 3-{2-[(2-methylpyrimidin-4-yl)amino]pyridin-4-yl}-7,8-dihydro-1,6-naphthyridin-5(6H)-one and salts and tautomers thereof.

1.2 A compound according to any one of Embodiments 0.1 to 1.1 wherein X is N.

1.2A A compound according to any one of Embodiments 0.1 to 1.1 wherein X is CH.

1.3 A compound according to any one of Embodiments 0.1 to 1.2 wherein Y is CH.

1.4 A compound according to any one of Embodiments 0.1 to 1.1 having the general formula (2):

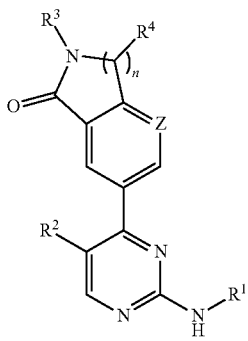

(2)

or a pharmaceutically acceptable salt or tautomer thereof; wherein $R^1$, $R^2$, $R^3$, $R^4$, Z and n are as defined in any one of Embodiment 0.1 to 1.1.

1.5 A compound according to any one of Embodiments 0.1 to 1.4 wherein n is 1.

1.6 A compound according to any one of Embodiments 0.1 to 1.4 wherein n is 2.

1.7 A compound according to any one of Embodiments 0.1 to 1.1 having the general formula (3):

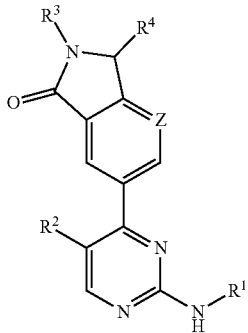

(3)

or a pharmaceutically acceptable salt or tautomer thereof; wherein $R^1$, $R^2$, $R^3$, $R^4$ and Z are as defined in any one of Embodiments 0.1 to 1.1.

1.7A A compound according to Embodiment 1.7 wherein the compound has the structure (3A):

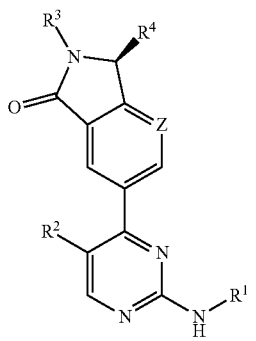

(3A)

1.7B A compound according to Embodiment 1.7 wherein the compound has the structure (3B):

(3B)

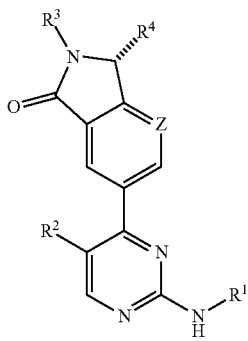

1.8 A compound according to any one of Embodiments 0.1 to 1.7 wherein $R^1$ is selected from:
-$(Alk^1)_t$-$Cyc^1$; wherein t is 0 or 1; and $Alk^1$ is a $C_{1-2}$ straight chain or branched alkylene group optionally substituted with 1 or 2 hydroxy groups; and
$C_{1-6}$ acyclic hydrocarbon groups which are unsubstituted or substituted with 1, 2 or 3 substituents $R^5$ selected from hydroxy; oxo; fluorine; and wherein 1 or 2 but not all of the carbon atoms of the hydrocarbon group can be replaced by O or N.

1.9 A compound according to any one of Embodiments 0.1 to 1.7 wherein $R^1$ is selected from:
-$(Alk^1)_t$-$Cyc^1$; wherein t is 0; and
$C_{1-6}$ acyclic hydrocarbon groups which are unsubstituted or substituted with 1, 2 or 3 substituents $R^5$ selected from hydroxy; oxo; fluorine; and wherein 1 or 2 but not all of the carbon atoms of the hydrocarbon group can be replaced by O or N.

1.10 A compound according to any one of Embodiments 0.1 to 1.7 wherein $R^1$ is selected from:
-$(Alk^1)_t$-$Cyc^1$; wherein t is 0; and
$C_{1-6}$ acyclic hydrocarbon groups which are unsubstituted or substituted with 1 or 2 hydroxy substituents; and wherein 1 but not all of the carbon atoms of the hydrocarbon group can be replaced by O.

1.11 A compound according to any one of Embodiments 0.1 to 1.7 wherein $R^1$ is selected from:
-$(Alk^1)_t$-$Cyc^1$; wherein t is 0; and
$C_{3-6}$ acyclic hydrocarbon groups which are unsubstituted or substituted with 1 or 2 hydroxy substituents; and wherein 1 but not all of the carbon atoms of the hydrocarbon group can be replaced by O.

1.12 A compound according to any one of Embodiments 0.1 to 1.7 wherein $R^1$ is selected from:
-$(Alk^1)_t$-$Cyc^1$; wherein t is 0; and
$C_{3-5}$ acyclic hydrocarbon groups which are unsubstituted or substituted with 1 or 2 hydroxy substituents; and wherein 1 but not all of the carbon atoms of the hydrocarbon group can be replaced by O.

1.13 A compound according to any one of Embodiments 0.1 to 1.7 wherein $R^1$ is selected from $C_{1-6}$ acyclic hydrocarbon groups which are unsubstituted or substituted with 1, 2 or 3 substituents $R^5$ selected from hydroxy; oxo; fluorine; and wherein 1 or 2 but not all of the carbon atoms of the hydrocarbon group can be replaced by O or N.

1.14 A compound according to Embodiment 1.13 wherein $R^1$ is selected from $C_{2-6}$ acyclic hydrocarbon groups which are unsubstituted or substituted with 1, 2 or 3 substituents $R^5$ selected from hydroxy; oxo; fluorine; and wherein 1 or 2 but not all of the carbon atoms of the hydrocarbon group can be replaced by O or N.

1.15 A compound according to Embodiment 1.14 wherein $R^1$ is selected from $C_{3-6}$ acyclic hydrocarbon groups which are unsubstituted or substituted with 1, 2 or 3 substituents $R^5$ selected from hydroxy; oxo; fluorine; and wherein 1 or 2 but not all of the carbon atoms of the hydrocarbon group can be replaced by O or N.

1.16 A compound according to Embodiment 1.15 wherein $R^1$ is selected from $C_{3-5}$ acyclic hydrocarbon groups which are unsubstituted or substituted with 1, 2 or 3 substituents $R^5$ selected from hydroxy; oxo; fluorine; and wherein 1 or 2 but not all of the carbon atoms of the hydrocarbon group can be replaced by O or N.

1.17 A compound according to Embodiment 1.16 wherein $R^1$ is selected from $C_{3-4}$ acyclic hydrocarbon groups which are unsubstituted or substituted with 1, 2 or 3 substituents $R^5$ selected from hydroxy; oxo; fluorine; and wherein 1 or 2 but not all of the carbon atoms of the hydrocarbon group can be replaced by O or N.

1.17A A compound according to any one of Embodiments 1.8, 1.9, 1.13, 1.14, 1.15, 1.16 and 1.17 wherein there are 0, 1 or 2 substituents $R^5$ present in $R^1$.

1.17B A compound according to any one of Embodiments 1.8, 1.9, 1.13, 1.14, 1.15, 1.16 and 1.17 wherein there are 0 substituents $R^5$ present in $R^1$.

1.17B A compound according to any one of Embodiments 1.8, 1.9, 1.13, 1.14, 1.15, 1.16 and 1.17 wherein there is 1 substituent $R^5$ present in $R^1$.

1.17C A compound according to any one of Embodiments 1.8, 1.9, 1.13, 1.14, 1.15, 1.16 and 1.17 wherein there are 2 substituents $R^5$ present in $R^1$.

1.18 A compound according to any one of Embodiments 0.1 to 1.17A wherein, when $R^1$ consists of or comprises an unsubstituted or substituted hydrocarbon group, the hydrocarbon group is selected from unsubstituted or substituted alkyl and alkenyl groups.

1.19 A compound according to Embodiment 1.18 wherein the hydrocarbon group is selected from unsubstituted or substituted alkyl groups.

1.20 A compound according to anyone of Embodiments 1.13 to 1.19 wherein the acyclic hydrocarbon groups are unsubstituted or substituted with 1 or 2 substituents $R^5$ selected from hydroxy; oxo; fluorine; and wherein 1 or 2 but not all of the carbon atoms of the hydrocarbon group can be replaced by O or N.

1.21 A compound according to Embodiment 1.20 wherein the acyclic hydrocarbon groups are unsubstituted or substituted with 1 or 2 substituents $R^5$ selected from hydroxy; oxo; and fluorine; and wherein 1 but not all of the carbon atoms of the hydrocarbon group can be replaced by O.

1.22 A compound according to Embodiment 1.21 wherein the acyclic hydrocarbon groups are unsubstituted or substituted with 1 or 2 substituents $R^5$ selected from hydroxy; and wherein 1 but not all of the carbon atoms of the hydrocarbon group can be replaced by O.

1.23 A compound according to any one of Embodiments 0.1 to 1.7 wherein $R^1$ is selected from $Cyc^1$; isopropyl; tert-butyl; 1,3-dihydroxy-prop-2-yl; 2,3-dihydroxy-prop-1-yl and 2-methoxyethyl.

1.24 A compound according to any one of Embodiments 0.1 to 1.7 wherein $R^1$ is selected from -$(Alk^1)_t$-$Cyc^1$; wherein t is 0 or 1; and $Alk^1$ is a $C_{1-4}$ straight chain or branched alkylene group optionally substituted with 1 or 2 hydroxy groups.

1.25 A compound according to Embodiment 1.24 wherein $R^1$ is selected from -$(Alk^1)_t$-$Cyc^1$; wherein t is 0 or 1; and $Alk^1$ is a $CH_2$, $CH(CH_3)$ or $CH_2CH_2$ group.

1.26 A compound according to Embodiment 1.25 wherein t is 0 and therefore $R^1$ is $Cyc^1$.

1.26A A compound according to any one of Embodiments 0.1 to 1.7 wherein t is 0 and therefore $R^1$ is $Cyc^1$.

1.27 A compound according to any one of Embodiments 0.1 to 1.12 and 1.23 to 1.26 wherein $Cyc^1$ is a cyclic group selected from:
  (a-i) 3 to 9 membered monocyclic and bicyclic non-aromatic carbocyclic groups (e.g. cycloalkyl groups);
  (a-ii) 4 to 9 membered non-aromatic (e.g. saturated) monocyclic and bicyclic heterocyclic groups containing 1 or 2 heteroatom ring members selected from O, N, S and $S(O)_2$;
  (b) 5 to 6 membered monocyclic heteroaryl groups containing 1 or 2 heteroatom ring members of which 1 is N and the others, when present, are selected from O, N and S; and
  (c) phenyl groups;
  wherein each cyclic group (a-i), (a-ii), (b) and (c) is unsubstituted or substituted with 1, 2 or 3 substituents $R^6$ selected from hydroxy; oxo; fluorine; O-$Hyd^1$; —C(=O)-$Hyd^1$; —C(=O)—O—$Hyd^1$ and $Hyd^1$; where $Hyd^1$ is a $C_{1-4}$ non-aromatic hydrocarbon group optionally substituted with one or more substituents selected from fluorine, hydroxyl and methoxy.

1.27A A compound according to any one of Embodiments 0.1 to 1.12 and 1.23 to 1.26 wherein $Cyc^1$ is a cyclic group selected from:
  (a-i) 3 to 9 membered monocyclic and bicyclic non-aromatic carbocyclic groups (e.g. cycloalkyl groups);
  (a-ii) 4 to 9 membered non-aromatic (e.g. saturated) monocyclic and bicyclic heterocyclic groups containing 1 or 2 heteroatom ring members selected from O, N, S and $S(O)_2$;
  (b) 5 to 6 membered monocyclic heteroaryl groups containing 1, 2 or 3 heteroatom ring members of which 1 is N and the others, when present, are selected from O, N and S; and
  (c) phenyl groups;
  wherein each cyclic group (a-i), (a-ii), (b) and (c) is unsubstituted or substituted with 1, 2 or 3 substituents $R^6$ selected from hydroxy; oxo; fluorine; $N(Hyd^1)_2$; O-$Hyd^1$; —C(=O)-$Hyd^1$; —C(=O)—O—$Hyd^1$ and $Hyd^1$; where $Hyd^1$ is a $C_{1-4}$ non-aromatic hydrocarbon group optionally substituted with one or more substituents selected from fluorine, hydroxyl and methoxy.

1.27B A compound according to any one of Embodiments 0.1 to 1.12 and 1.23 to 1.26 wherein $Cyc^1$ is a cyclic group selected from:
  (a-i) 3 to 9 membered monocyclic and bicyclic non-aromatic carbocyclic groups (e.g. cycloalkyl groups);
  (a-ii) 4 to 9 membered non-aromatic (e.g. saturated) monocyclic and bicyclic heterocyclic groups containing 1 or 2 heteroatom ring members selected from O, N, S and $S(O)_2$;
  (b) 5 to 6 membered monocyclic heteroaryl groups containing 1, 2 or 3 heteroatom ring members of which 1 is N and the others, when present, are selected from O, N and S; and
  (c) phenyl groups;
  wherein each cyclic group (a-i), (a-ii), (b) and (c) is unsubstituted or substituted with 1, 2 or 3 substituents $R^6$ selected from hydroxy; oxo; fluorine; $N(Hyd^1)_2$; O-$Hyd^1$; —C(=O)-$Hyd^1$; —C(=O)—O—$Hyd^1$ and $Hyd^1$; where $Hyd^1$ is a $C_{1-4}$ non-aromatic hydrocarbon group optionally substituted with one or more substituents selected from fluorine, hydroxyl and methoxy.

1.27C A compound according to any one of Embodiments 0.1 to 1.12 and 1.23 to 1.26 wherein $Cyc^1$ is a cyclic group selected from:
  (a-i) 3-, 4-, 5-, or 6-membered monocyclic non-aromatic carbocyclic groups (e.g. $C_{3-6}$ cycloalkyl groups);
  (a-ii) 4-, 5-, 6-, or 7-membered non-aromatic (e.g. saturated) monocyclic and 7-membered bicyclic heterocyclic groups containing 1 or 2 heteroatom ring members selected from O, N, S and $S(O)_2$;
  (b) 5- or 6-membered monocyclic heteroaryl groups containing 1, 2 or 3 heteroatom ring members of which 1 is N and the others, when present, are selected from O, N and S; and
  (c) phenyl groups;
  wherein each cyclic group (a-i), (a-ii), (b) and (c) is unsubstituted or substituted with 1, 2 or 3 substituents $R^6$ selected from hydroxy; oxo; fluorine; $N(Hyd^1)_2$; O-$Hyd^1$; —C(=O)-$Hyd^1$; —C(=O)—O—$Hyd^1$ and $Hyd^1$; where $Hyd^1$ is a $C_{1-4}$ non-aromatic hydrocarbon group optionally substituted with one or more substituents selected from fluorine, hydroxyl and methoxy.

1.27D A compound according to any one of Embodiments 0.1 to 1.12 and 1.23 to 1.26 wherein $Cyc^1$ is a cyclic group selected from:
  (a-i) 3-, 4-, 5-, or 6-membered monocyclic non-aromatic carbocyclic groups (e.g. $C_{3-6}$ cycloalkyl groups) unsubstituted or substituted with 1, 2 or 3 substituents $R^6$ selected from hydroxy; oxo; fluorine; $N(Hyd^1)_2$ (e.g. —$NMe_2$); O-$Hyd^1$ (e.g. methoxy); —C(=O)-$Hyd^1$ (e.g. —C(=O)-methyl); —C(=O)—O—$Hyd^1$ (e.g. —C(=O)—O—$^tBu$) and $Hyd^1$ (e.g. methyl, iso-propyl); where $Hyd^1$ is a $C_{1-4}$ non-aromatic hydrocarbon group optionally substituted with one or more substituents selected from hydroxyl;
  (a-ii) 4-, 5-, 6-, or 7-membered non-aromatic (e.g. saturated) monocyclic and 7-membered bicyclic heterocyclic groups containing 1 or 2 heteroatom ring members selected from O, N, S and $S(O)_2$ unsubstituted or substituted with 1, 2 or 3 substituents $R^6$ selected from oxo; O-$Hyd^1$ (e.g. methoxy); and $Hyd^1$ (e.g. methyl, ethyl); where $Hyd^1$ is a $C_{1-4}$ non-aromatic hydrocarbon group;
  (b) 5- or 6-membered monocyclic heteroaryl groups containing 1, 2 or 3 heteroatom ring members of which 1 is N and the others, when present, are selected from O, N and S; and
  (c) unsubstituted phenyl groups.

1.28 A compound according to Embodiment 1.27 wherein $Cyc^1$ is a cyclic group selected from:
  (a-i) 3 to 7 membered monocyclic non-aromatic carbocyclic groups (e.g. cycloalkyl groups);
  (a-ii) 4 to 7 membered non-aromatic (e.g. saturated) monocyclic heterocyclic groups and 7 to 9 membered bicyclic heterocyclic groups, wherein the heterocyclic groups contain 1 or 2 heteroatom ring members selected from O, N, S and $S(O)_2$;
  (b) 5 to 6 membered monocyclic heteroaryl groups containing 1 or 2 heteroatom ring members of which 1 is N and the others, when present, are selected from O, N and S; and
  (c) phenyl groups;
  wherein each cyclic group (a-i), (a-ii), (b) and (c) is unsubstituted or substituted with 1, 2 or 3 substituents $R^6$ selected from hydroxy; oxo; fluorine; O-$Hyd^1$; —C(=O)-$Hyd^1$; —C(=O)—O—$Hyd^1$ and $Hyd^1$; where $Hyd^1$ is a $C_{1-4}$ non-aromatic hydrocarbon group optionally substituted with one or more substituents selected from fluorine, hydroxyl and methoxy.

1.28A A compound according to any one of Embodiments 0.1 to 1.12 and 1.23 to 1.26 wherein $Cyc^1$ is a cyclic group selected from:

(a-ii) 4 to 7 membered non-aromatic (e.g. saturated) monocyclic heterocyclic groups, wherein the heterocyclic groups contain 1 or 2 heteroatom ring members selected from O, N, S and $S(O)_2$; and (b) 5 to 6 membered monocyclic heteroaryl groups containing 1, 2 or 3 heteroatom ring members of which 1 is N and the others, when present, are selected from O, N and S;

wherein each cyclic group (a-ii) and (b) is unsubstituted or substituted with 1, 2 or 3 substituents $R^6$ selected from hydroxy; oxo; fluorine; O-$Hyd^1$; —C(=O)-$Hyd^1$; —C(=O)—O-$Hyd^1$ and $Hyd^1$; where $Hyd^1$ is a $C_{1-4}$ non-aromatic hydrocarbon group optionally substituted with one or more substituents selected from fluorine, hydroxyl and methoxy.

1.28B A compound according to Embodiment 1.28A wherein $Cyc^1$ is a cyclic group selected from:

(a-ii) 4 to 7 membered saturated monocyclic heterocyclic groups, wherein the heterocyclic groups contain 1 oxygen heteroatom ring member; and (b) 5 to 6 membered monocyclic heteroaryl groups containing 1 or 2 nitrogen heteroatom ring members and optionally a further heteroatom ring member selected from O, N, and S;

wherein each cyclic group (a-ii) and (b) is unsubstituted or substituted with 1, 2 or 3 substituents $R^6$ selected from hydroxy; oxo; fluorine; O-$Hyd^1$; —C(=O)-$Hyd^1$; —C(=O)—O-$Hyd^1$ and $Hyd^1$; where $Hyd^1$ is a $C_{1-4}$ non-aromatic hydrocarbon group optionally substituted with one or more substituents selected from fluorine, hydroxyl and methoxy.

1.28C A compound according to Embodiment 1.28B wherein $Cyc^1$ is a cyclic group selected from:

(a-ii) 5 to 6 membered saturated monocyclic heterocyclic groups, wherein the heterocyclic groups contain 1 oxygen heteroatom ring member;

(b-i) 5 membered monocyclic heteroaryl groups containing 2 or 3 nitrogen heteroatom ring members; and (b-ii) 6 membered monocyclic heteroaryl groups containing 1 or 2 nitrogen heteroatom ring members;

wherein each cyclic group (a-ii), (b-i) and (b-ii) is unsubstituted or substituted with 1, 2 or 3 substituents $R^6$ selected from hydroxy; oxo; fluorine; O-$Hyd^1$; —C(=O)-$Hyd^1$; —C(=O)—O-$Hyd^1$ and $Hyd^1$; where $Hyd^1$ is a $C_{1-4}$ non-aromatic hydrocarbon group optionally substituted with one or more substituents selected from fluorine, hydroxyl and methoxy.

1.28D A compound according to Embodiment 1.28B wherein $Cyc^1$ is a cyclic group selected from:

(a-ii) 4 to 7 membered saturated monocyclic heterocyclic groups, wherein the heterocyclic groups contain 1 oxygen heteroatom ring member; wherein each cyclic group (a-ii) is unsubstituted or substituted with 1, 2 or 3 substituents $R^6$ selected from hydroxy; oxo; fluorine; O-$Hyd^1$; —C(=O)-$Hyd^1$; —C(=O)—O-$Hyd^1$ and $Hyd^1$; where $Hyd^1$ is a $C_{1-4}$ non-aromatic hydrocarbon group optionally substituted with one or more substituents selected from fluorine, hydroxyl and methoxy.

1.28E A compound according to Embodiment 1.28D wherein $Cyc^1$ is a cyclic group selected from:

(a-ii) 4 to 7 membered saturated monocyclic heterocyclic groups, wherein the heterocyclic groups contain 1 oxygen heteroatom ring member; wherein each cyclic group (a-ii) and (b) is unsubstituted or substituted with 1, 2 or 3 substituents $R^6$ selected from oxo; fluorine; and $Hyd^1$; where $Hyd^1$ is a $C_{1-4}$ non-aromatic hydrocarbon group optionally substituted with one or more substituents selected from fluorine, hydroxyl and methoxy.

1.28F A compound according to Embodiment 1.28B wherein $Cyc^1$ is a cyclic group selected from:

(b) 5 to 6 membered monocyclic heteroaryl groups containing 1 or 2 nitrogen heteroatom ring members and optionally a further heteroatom ring member selected from O, N, and S;

wherein each cyclic group (b) is unsubstituted or substituted with 1, 2 or 3 substituents $R^6$ selected from fluorine; O-$Hyd^1$; and $Hyd^1$; where $Hyd^1$ is a $C_{1-4}$ non-aromatic hydrocarbon group optionally substituted with one or more substituents selected from fluorine, hydroxyl and methoxy.

1.28G A compound according to Embodiment 1.28B wherein $Cyc^1$ is a cyclic group selected from:

(b) 6 membered monocyclic heteroaryl groups containing 1 or 2 nitrogen heteroatom ring members;

wherein each cyclic group (b) is unsubstituted or substituted with 1, 2 or 3 substituents $R^6$ selected from hydroxy; oxo; fluorine; O-$Hyd^1$; —C(=O)-$Hyd^1$; —C(=O)—O-$Hyd^1$ and $Hyd^1$; where $Hyd^1$ is a $C_{1-4}$ non-aromatic hydrocarbon group optionally substituted with one or more substituents selected from fluorine, hydroxyl and methoxy.

1.28H A compound according to Embodiment 1.28G wherein $Cyc^1$ is a cyclic group selected from:

(b) 6 membered monocyclic heteroaryl groups containing 1 or 2 nitrogen heteroatom ring members;

wherein each cyclic group (b) is unsubstituted or substituted with 1, 2 or 3 substituents $R^6$ selected from O-$Hyd^1$; and $Hyd^1$; where $Hyd^1$ is a $C_{1-4}$ non-aromatic hydrocarbon group optionally substituted with one or more substituents selected from fluorine, hydroxyl and methoxy.

1.29 A compound according to Embodiment 1.28 wherein $Cyc^1$ is a cyclic group selected from:

(a-i) 3 to 7 membered monocyclic non-aromatic carbocyclic groups (e.g. cycloalkyl groups) which are unsubstituted or substituted as defined in Embodiment 1.27.

1.30 A compound according to Embodiment 1.29 wherein $Cyc^1$ is a cyclic group selected from:

(a-i) 4 to 6 membered monocyclic non-aromatic carbocyclic groups (e.g. cycloalkyl groups) which are unsubstituted or substituted as defined in Embodiment 1.27.

1.31 A compound according to Embodiment 1.30 wherein the 4 to 6 membered monocyclic non-aromatic carbocyclic group is a 4 to 6 membered cycloalkyl group which is unsubstituted or substituted as defined in Embodiment 1.27.

1.32 A compound according to Embodiment 1.30 wherein the 4 to 6 membered cycloalkyl group is selected from cyclobutyl and cyclohexyl groups which are unsubstituted or substituted as defined in Embodiment 1.27.

1.32A A compound according to any one of Embodiments 0.1 to 1.12 and 1.23 to 1.32 wherein 0, 1 or 2 substituents $R^6$ are present in $R^1$.

1.32B A compound according to any one of Embodiments 0.1 to 1.12 and 1.23 to 1.32 wherein 0 substituents $R^6$ are present in $R^1$.

1.32C A compound according to any one of Embodiments 0.1 to 1.12 and 1.23 to 1.32 wherein 1 substituent $R^6$ is present in $R^1$.

1.32D A compound according to any one of Embodiments 0.1 to 1.12 and 1.23 to 1.32 wherein 2 substituents $R^6$ are present in $R^1$.

1.33 A compound according to any one of Embodiments 1.28 to 1.32 wherein the carbocyclic groups are unsubstituted or substituted with 1 or 2 substituents $R^6$ selected from hydroxy; oxo; fluorine; O-$Hyd^1$; and $Hyd^1$.

1.34 A compound according to Embodiment 1.33 wherein the carbocyclic groups are unsubstituted or substituted with 1 or 2 substituents $R^6$ selected from hydroxy; methoxy; and methyl; for example wherein the carbocyclic groups are unsubstituted or substituted with 1 substituent $R^6$ selected from hydroxy and methoxy.

1.35 A compound according to Embodiment 1.27 wherein $Cyc^1$ is a cyclic group selected from:

(a-ii) 4 to 7 membered non-aromatic (e.g. saturated) monocyclic heterocyclic groups and 7 to 9 membered bicyclic heterocyclic groups, wherein the heterocyclic groups contain 1 or 2 heteroatom ring members selected from O, N, S and $S(O)_2$ and are unsubstituted or substituted as defined in Embodiment 1.27.

1.36 A compound according to Embodiment 1.35 wherein $Cyc^1$ is a cyclic group selected from:

(a-ii) 4 to 7 membered non-aromatic (e.g. saturated) monocyclic heterocyclic groups wherein the heterocyclic groups contain 1 or 2 heteroatom ring members selected from O, N, S and $S(O)_2$ and are unsubstituted or substituted as defined in Embodiment 1.27 or Embodiment 1.28.

1.36A A compound according to Embodiment 1.36 wherein $Cyc^1$ is a cyclic group selected from:

(a-ii) 4 to 7 membered saturated monocyclic heterocyclic groups wherein the heterocyclic groups contain 1 or 2 heteroatom ring members selected from O and N and are unsubstituted or substituted as defined in Embodiment 1.27 or Embodiment 1.28.

1.36B A compound according to Embodiment 1.36 wherein $Cyc^1$ is a cyclic group selected from:

(a-ii) 4 to 7 membered saturated monocyclic heterocyclic groups wherein the heterocyclic groups contain 1 heteroatom ring member selected from O and N and are unsubstituted or substituted as defined in Embodiment 1.27 or Embodiment 1.28.

1.36C A compound according to Embodiment 1.36 wherein $Cyc^1$ is a cyclic group selected from oxetane, tetrahydrofuran, oxan, oxaspiro[3.3]heptane, azetidine, pyrrolidine and piperidine groups.

1.37 A compound according to Embodiment 1.36 wherein $Cyc^1$ is a cyclic group selected from:

(a-ii) 4 to 6 membered non-aromatic (e.g. saturated) monocyclic heterocyclic groups wherein the heterocyclic groups contain 1 or 2 heteroatom ring members selected from O, N, S and $S(O)_2$ and are unsubstituted or substituted as defined in Embodiment 1.27.

1.38 A compound according to Embodiment 1.37 wherein $Cyc^1$ is a cyclic group selected from:

(a-ii) 4 to 6 membered saturated non-aromatic monocyclic heterocyclic groups wherein the heterocyclic groups contain 1 or 2 heteroatom ring members selected from O, N and S and are unsubstituted or substituted as defined in Embodiment 1.27.

1.39 A compound according to Embodiment 1.38 wherein $Cyc^1$ is a cyclic group selected from:

(a-ii) 4 to 6 membered saturated non-aromatic monocyclic heterocyclic groups wherein the heterocyclic groups contain 1 heteroatom ring member selected from O and N and are unsubstituted or substituted as defined in Embodiment 1.27.

1.40 A compound according to Embodiment 1.39 wherein $Cyc^1$ is a cyclic group selected from oxetane, tetrahydrofuran, oxan, azetidine, pyrrolidine and piperidine groups, each of which is unsubstituted or substituted as defined in Embodiment 1.27.

1.41 A compound according to Embodiment 1.40 wherein $Cyc^1$ is a cyclic group selected from oxetane, tetrahydrofuran, oxan, azetidine and piperidine groups, each of which is unsubstituted or substituted as defined in Embodiment 1.27.

1.42 A compound according to Embodiment 1.40 wherein $Cyc^1$ is an oxan group which is unsubstituted or substituted as defined in Embodiment 1.27.

1.43 A compound according to any one of Embodiments 1.36 to 1.42 wherein the heterocyclic groups are unsubstituted or substituted with with 1 or 2 substituents $R^6$ selected from hydroxy; oxo; fluorine; O-$Hyd^1$; —C(=O)-$Hyd^1$ and $Hyd^1$; where $Hyd^1$ is a $C_{1-4}$ non-aromatic hydrocarbon group (e.g. an alkyl, alkenyl, alkynyl, cycloalkyl or cycloalkylalkyl group) optionally substituted with one or more substituents selected from fluorine, hydroxyl and methoxy.

1.44 A compound according to Embodiment 1.43 wherein the heterocyclic groups are unsubstituted or substituted with with 1 or 2 substituents $R^6$ selected from hydroxy; fluorine; O-$Hyd^1$; —C(=O)-$Hyd^1$; —C(=O)—O-$Hyd^1$ and $Hyd^1$; where $Hyd^1$ is a saturated $C_{1-4}$ hydrocarbon group (e.g. an alkyl, cycloalkyl or cycloalkylalkyl group).

1.45 A compound according to Embodiment 1.44 wherein the heterocyclic groups are unsubstituted or substituted with with 1 or 2 substituents $R^6$ selected from —C(=O)-$Hyd^1$; —C(=O)—O-$Hyd^1$ and $Hyd^1$; where $Hyd^1$ is a saturated $C_{1-4}$ hydrocarbon group (e.g. an alkyl, cycloalkyl or cycloalkylalkyl group).

1.46 A compound according to Embodiment 1.45 wherein the heterocyclic groups are unsubstituted or substituted with with 1 or 2 substituents $R^6$ selected from $C_{1-4}$ alkyl such as methyl; $C_{1-4}$ alkanoyl such as acetyl; and $C_{1-4}$ alkoxycarbonyl such as tert-butoxycarbonyl.

1.47 A compound according to Embodiment 1.46 wherein the heterocyclic groups are unsubstituted or substituted with with 1 or 2 $C_{1-4}$ alkyl (e.g. methyl) group substituents $R^6$ or by a single substituent selected from $C_{1-4}$ alkanoyl (e.g. acetyl); and $C_{1-4}$ alkoxycarbonyl (e.g. tert-butoxycarbonyl).

1.48 A compound according to Embodiment 1.47 wherein the heterocyclic groups are unsubstituted or substituted with with 1 or 2 methyl group substituents $R^6$.

1.49 A compound according to Embodiment 1.47 wherein the heterocyclic groups are unsubstituted.

1.50 A compound according to Embodiment 1.27 wherein $Cyc^1$ is a cyclic group selected from:

(a-ii) 7 to 9 membered bicyclic heterocyclic groups, wherein the heterocyclic groups contain 1 or 2 heteroatom ring members selected from O, N, S and $S(O)_2$ and are unsubstituted or substituted as defined in Embodiment 1.27.

1.51 A compound according to Embodiment 1.50 wherein $Cyc^1$ is a cyclic group selected from:

(a-ii) 7 to 9 membered bicyclic heterocyclic groups, wherein the heterocyclic groups contain 1 heteroatom ring member selected from O and N and are unsubstituted or substituted as defined in Embodiment 1.27.

1.52 A compound according to Embodiment 1.51 wherein $Cyc^1$ is a cyclic group selected from:

(a-ii) 7 to 9 membered bicyclic heterocyclic groups, wherein the heterocyclic groups are bridged bicyclic or spiro-bicyclic groups containing 1 heteroatom ring member selected from O and N and are unsubstituted or substituted as defined in Embodiment 1.27.

1.53 A compound according to Embodiment 1.52 wherein $Cyc^1$ is a 7 to 9 membered bridged bicyclic heterocyclic group containing 1 heteroatom ring member selected from O and N, the heterocyclic group being unsubstituted or substituted as defined in Embodiment 1.27.

1.54 A compound according to Embodiment 1.53 wherein the heterocyclic group is an oxabicyclo[3.2.1]octane group.

1.55 A compound according to Embodiment 1.52 wherein $Cyc^1$ is a 7 to 9 membered spiro-bicyclic heterocyclic group containing 1 heteroatom ring member selected from O and N, the heterocyclic group being unsubstituted or substituted as defined in Embodiment 1.27.

1.56 A compound according to Embodiment 1.55 wherein the heterocyclic group is an oxaspiro[3.3]heptane group.

1.57 A compound according to Embodiment 1.27 wherein $Cyc^1$ is a cyclic group selected from:
  (b) 5 to 6 membered monocyclic heteroaryl groups containing 1 or 2 heteroatom ring members of which 1 is N and the others, when present, are selected from O, N and S; and
  (c) phenyl groups;
wherein the heteroaryl groups and phenyl groups are unsubstituted or substituted as defined in Embodiment 1.27.

1.58 A compound according to Embodiment 1.57 wherein $Cyc^1$ is a cyclic group selected from:
  (b) 5 to 6 membered monocyclic heteroaryl groups containing 1 or 2 heteroatom ring members of which 1 is N and the others, when present, are selected from O, N and S;
wherein the heteroaryl groups are unsubstituted or substituted as defined in Embodiment 1.27.

1.59 A compound according to Embodiment 1.58 wherein the 5 to 6 membered monocyclic heteroaryl groups are selected from pyrazole and pyridine, each being unsubstituted or substituted as defined in Embodiment 1.27.

1.60 A compound according to any one of Embodiments 1.57 to 1.59 wherein the heteroaryl group is unsubstituted or substituted with 1 or 2 substituents $R^6$ selected from hydroxy; O-$Hyd^1$; —C(=O)-$Hyd^1$; —C(=O)—O-$Hyd^1$ and $Hyd^1$; where $Hyd^1$ is a $C_{1-4}$ non-aromatic hydrocarbon group (e.g. an alkyl, alkenyl, alkynyl, cycloalkyl or cycloalkylalkyl group) optionally substituted with one or more substituents selected from fluorine, hydroxyl and methoxy.

1.61 A compound according to Embodiment 1.60 wherein the heteroaryl group is unsubstituted or substituted with 1 or 2 substituents $R^6$ selected from hydroxy; O-$Hyd^1$; —C(=O)-$Hyd^1$; and $Hyd^1$; where $Hyd^1$ is a saturated $C_{1-4}$ hydrocarbon group (e.g. an alkyl, cycloalkyl or cycloalkylalkyl group) optionally substituted with one or more substituents selected from hydroxyl and methoxy.

1.62 A compound according to Embodiment 1.61 wherein the heteroaryl group is unsubstituted or substituted with 1 or 2 substituents $R^6$ selected from O-$Hyd^1$; and $Hyd^1$; where $Hyd^1$ is a saturated $C_{1-4}$ hydrocarbon group (e.g. an alkyl, cycloalkyl or cycloalkylalkyl group).

1.63 A compound according to Embodiment 1.61 wherein the heteroaryl group is unsubstituted or substituted with 1 or 2 substituents $R^6$ selected from $Hyd^1$; where $Hyd^1$ is a saturated $C_{1-4}$ hydrocarbon group (e.g. an alkyl, cycloalkyl or cycloalkylalkyl group).

1.64 A compound according to Embodiment 1.61 wherein the heteroaryl group is unsubstituted or substituted with 1 or 2 $C_{1-4}$ alkyl (e.g. methyl) group substituents $R^6$.

1.65 A compound according to Embodiment 1.27 wherein $Cyc^1$ is a cyclic group selected from:
  (c) phenyl groups;
wherein the phenyl groups are unsubstituted or substituted as defined in Embodiment 1.27.

1.66 A compound according to Embodiment 1.65 wherein the phenyl groups are unsubstituted.

1.67 A compound according to any one of Embodiments 0.1 to 1.13, 1.23 to 1.32, 1.35 to 1.41, 1.50 to 1.59 and 1.65 wherein 0, 1 or 2 substituents $R^6$ are present and are selected from hydroxy; oxo; fluorine; O-$Hyd^1$; —C(=O)-$Hyd^1$; —C(=O)—O-$Hyd^1$ and $Hyd^1$; where $Hyd^1$ is a $C_{1-4}$ non-aromatic hydrocarbon group (e.g. an alkyl, alkenyl, alkynyl, cycloalkyl or cycloalkylalkyl group) optionally substituted with one or more substituents selected from fluorine, hydroxyl and methoxy.

1.67A A compound according to any one of Embodiments 0.1 to 1.13, 1.23 to 1.32, 1.35 to 1.41, 1.50 to 1.59 and 1.65 wherein 0, 1 or 2 substituents $R^6$ are present and are selected from hydroxy; oxo; fluorine; amino; NH($Hyd^1$); N($Hyd^1$)$_2$; O-$Hyd^1$; —C(=O)-$Hyd^1$; —C(=O)—O-$Hyd^1$ and $Hyd^1$; where $Hyd^1$ is a $C_{1-4}$ non-aromatic hydrocarbon group optionally substituted with one or more substituents selected from fluorine, hydroxyl and methoxy.

1.67B A compound according to any one of Embodiments 0.1 to 1.13, 1.23 to 1.32, 1.35 to 1.41, 1.50 to 1.59 and 1.65 wherein 0, 1 or 2 substituents $R^6$ are present and are selected from hydroxy; oxo; fluorine; N($Hyd^1$)$_2$ (e.g. —NMe$_2$); O-$Hyd^1$ (e.g. methoxy); —C(=O)-$Hyd^1$ (e.g. —C(=O)-methyl); —C(=O)—O-$Hyd^1$ (e.g. —C(=O)—O—$^t$Bu) and $Hyd^1$ (e.g. methyl, ethyl, iso-propyl); where $Hyd^1$ is a $C_{1-4}$ non-aromatic hydrocarbon group optionally substituted with one or more substituents selected from fluorine, hydroxyl and methoxy.

1.68 A compound according to Embodiment 1.67 wherein 0, 1 or 2 substituents $R^6$ are present and selected from hydroxy; fluorine; O-$Hyd^1$; —C(=O)-$Hyd^1$; —C(=O)—O-$Hyd^1$ and $Hyd^1$; where $Hyd^1$ is a $C_{1-4}$ non-aromatic hydrocarbon group (e.g. an alkyl, alkenyl, alkynyl, cycloalkyl or cycloalkylalkyl group) optionally substituted with one or more substituents selected from fluorine, hydroxyl and methoxy.

1.69 A compound according to Embodiment 1.68 wherein 0, 1 or 2 substituents $R^6$ are present and selected from hydroxy; O-$Hyd^1$; —C(=O)-$Hyd^1$; —C(=O)—O-$Hyd^1$ and $Hyd^1$; where $Hyd^1$ is a $C_{1-4}$ non-aromatic hydrocarbon group (e.g. an alkyl, alkenyl, alkynyl, cycloalkyl or cycloalkylalkyl group) optionally substituted with one or more substituents selected from hydroxyl and methoxy.

1.70 A compound according to Embodiment 1.69 wherein 0, 1 or 2 substituents $R^6$ are present and selected from hydroxy; O-$Hyd^1$; —C(=O)-$Hyd^1$; —C(=O)—O-$Hyd^1$ and $Hyd^1$; where $Hyd^1$ is a saturated $C_{1-4}$ hydrocarbon group (e.g. an alkyl, cycloalkyl or cycloalkylalkyl group) optionally substituted with one or more substituents selected from hydroxyl and methoxy.

1.71 A compound according to Embodiment 1.70 wherein 0, 1 or 2 substituents $R^6$ are present and selected from hydroxy; O-$Hyd^1$; —C(=O)-$Hyd^1$; —C(=O)—O-$Hyd^1$ and $Hyd^1$; where $Hyd^1$ is a saturated $C_{1-4}$ hydrocarbon group (e.g. a saturated $C_{1-3}$ hydrocarbon group such as an alkyl or cyclopropyl group).

1.72 A compound according to Embodiment 1.71 wherein 0, 1 or 2 substituents $R^6$ are present and selected from hydroxy; methyl; methoxy; acetyl; and tert-butoxycarbonyl.

1.73 A compound according to any one of Embodiments 1.7, 1.42 to 1.49 and 1.67 to 1.72 having the general formula (4):

(4)

or a pharmaceutically acceptable salt or tautomer thereof; wherein $R^1$, $R^2$, $R^3$, $R^4$ and Z are as defined in any one of Embodiments 1.0, 1.7, 1.42 to 1.49 and 1.67 to 1.72; and v is 0, 1, 2 or 3.

1.73A A compound according to Embodiment 1.73 having the structure (4A):

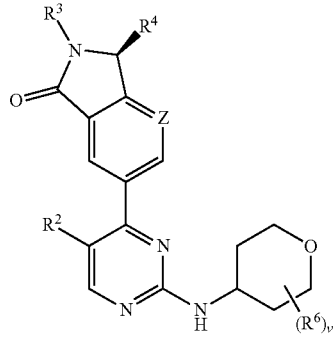

(4A)

1.73B A compound according to Embodiment 1.73 having the structure (4B):

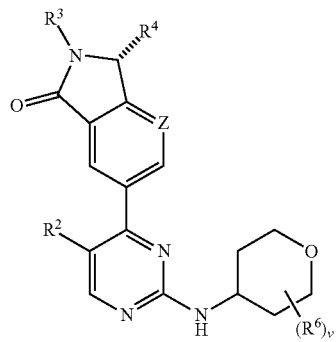

(4B)

1.74 A compound according to any one of Embodiments 1.73 to 1.73B wherein v is 0, 1 or 2.

1.75 A compound according to any one of Embodiments 1.73 to 1.73B wherein v is 0 or 1.

1.76 A compound according to any one of Embodiments 1.73 to 1.731B wherein v is 0.

1.77 A compound according to any one of Embodiments 1.73 to 1.731B wherein v is 1.

1.78 A compound according to any one of Embodiments 1.73 to 1.731B wherein v is 2.

1.79 A compound according to any one of Embodiments 1.73 to 1.731B wherein v is 3.

1.80 A compound according to any one of Embodiments 0.1 to 1.79 wherein $R^1$ is selected from groups AA to ACY in Table 1 below, where * marks the point of connection to the N atom.

1.80A A compound according to any one of Embodiments 0.1 to 1.79 wherein $R^1$ is selected from groups AA to ABI in Table 1 below, where * marks the point of connection to the Na tom.

TABLE 1

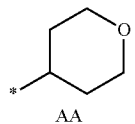

AA

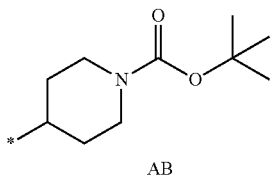 [SMILES: *C1CCN(C(=O)OC(C)(C)C)CC1]

AB

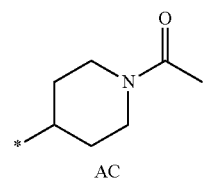 [SMILES: *C1CCN(C(C)=O)CC1]

AC

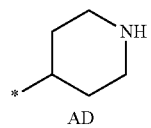

AD

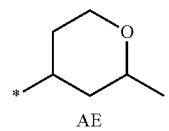

AE

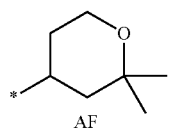

AF

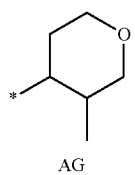

AG

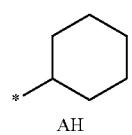

AH

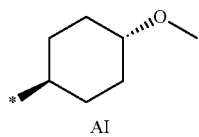

AI

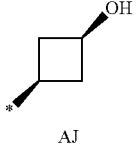 [SMILES: *[C@H]1C[C@@H](O)C1]

AJ

TABLE 1-continued
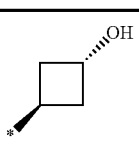
AK
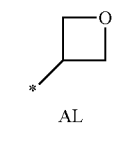
AL
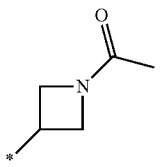
AM
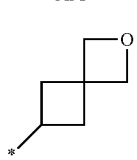
AN
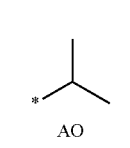
AO
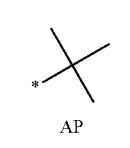
AP
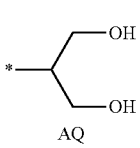
AQ
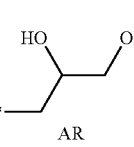
AR
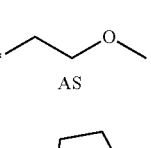
AS
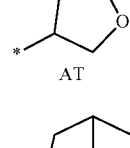
AT
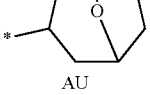
AU
TABLE 1-continued
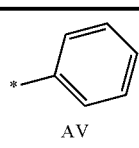
AV
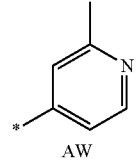
AW
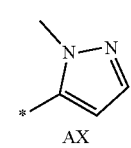
AX
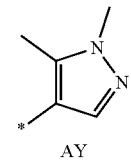
AY
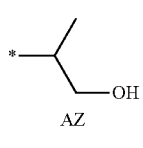
AZ
AAA
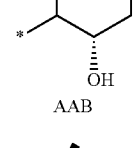
AAB
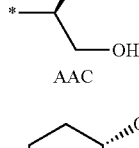
AAC
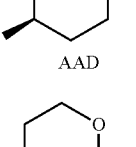
AAD
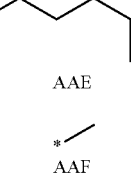
AAE
AAF TABLE 1-continued
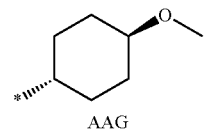
AAG
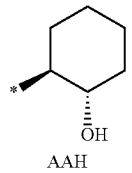 [SMILES: *[C@H]1CCCC[C@@H]1O ; "AAH"]
AAH
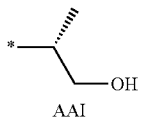
AAI
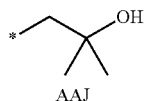
AAJ
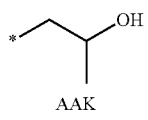
AAK
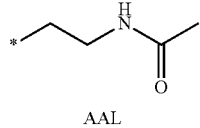 [SMILES: *CCNC(C)=O]
AAL
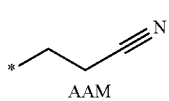
AAM
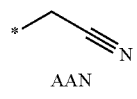
AAN
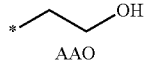
AAO
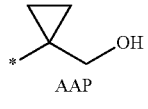
AAP
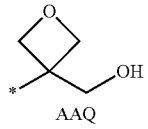
AAQ
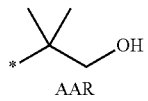
AAR
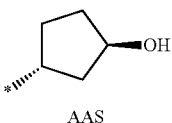 [SMILES: *[C@@H]1CC[C@@H](O)C1]
AAS
TABLE 1-continued
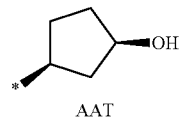
AAT
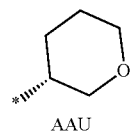
AAU
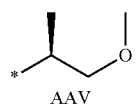
AAV
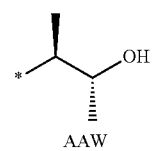
AAW
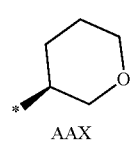
AAX
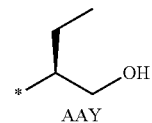
AAY
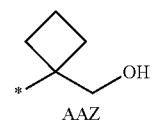
AAZ
ABA
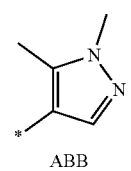 [SMILES: *c1cnn(C)c1C]
ABB
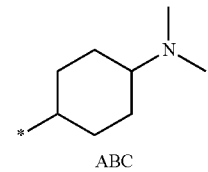
ABC
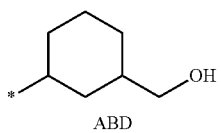 [SMILES: *C1CCCC(CO)C1]
ABD TABLE 1-continued
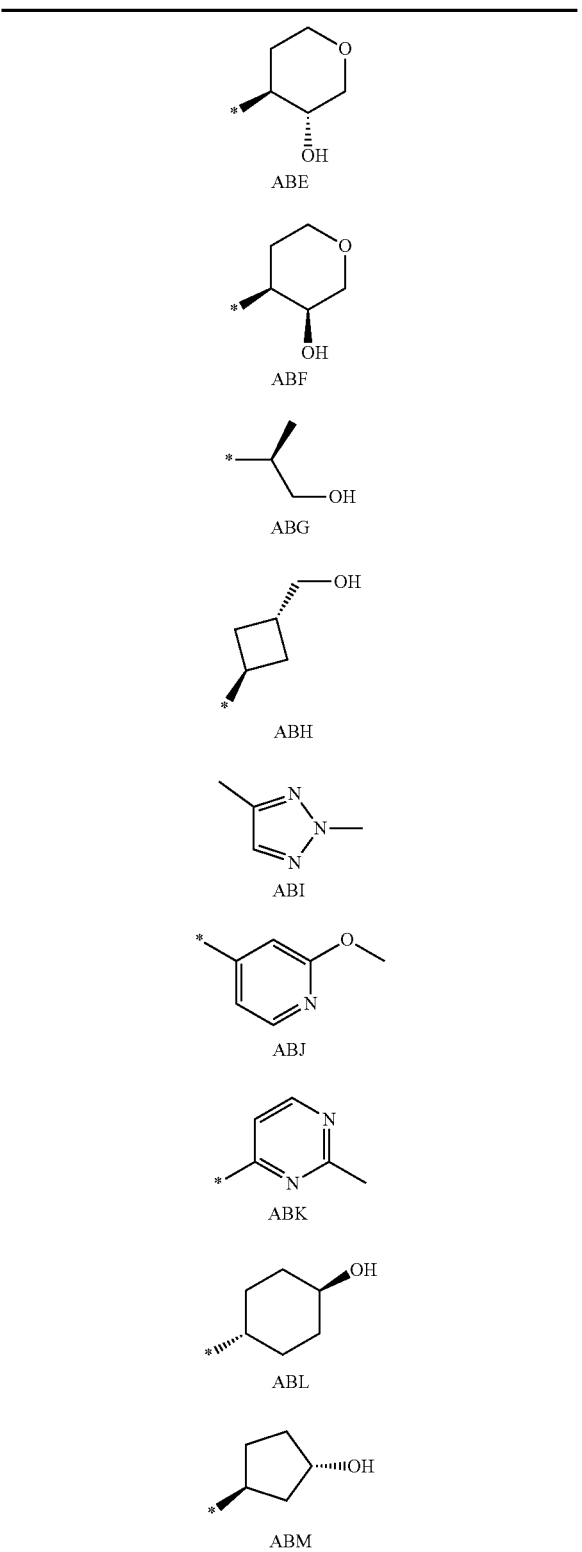
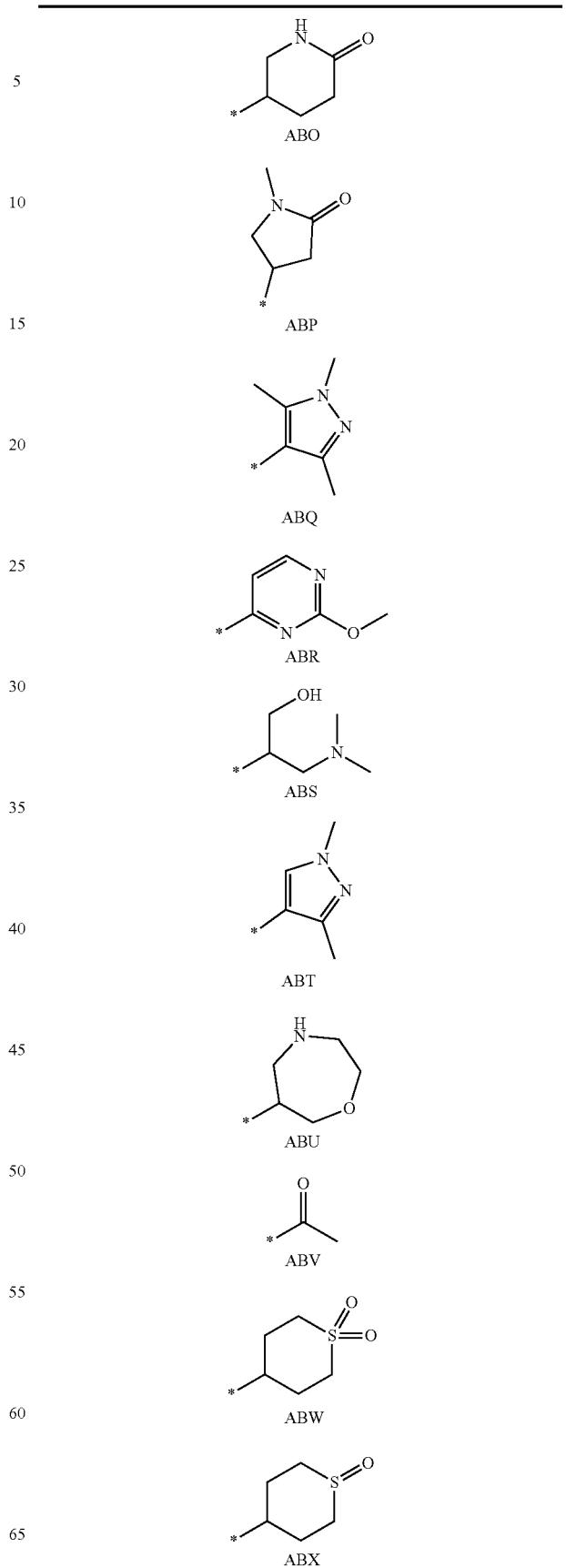

TABLE 1-continued
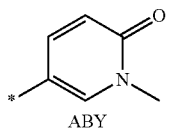
ABY
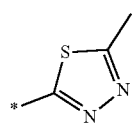
ABZ
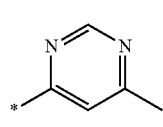
ACA
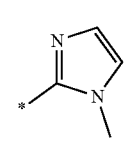
ACB
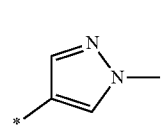
ACC
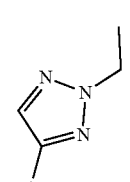
ACD
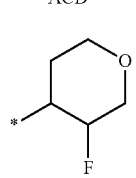
ACE
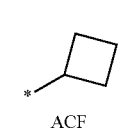
ACF
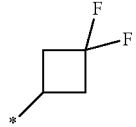
ACG
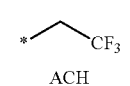
ACH
TABLE 1-continued
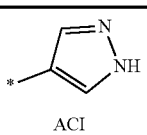
ACI
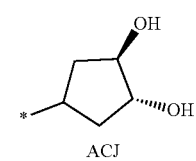 [SMILES: *C1C[C@@H](O)[C@H](O)C1]
ACJ
H—*
ACK
ACL
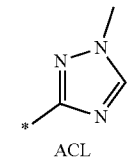
ACM
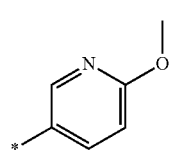
ACN
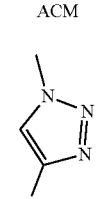
ACO
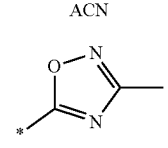
ACP
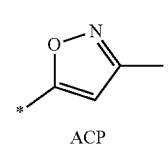
ACQ
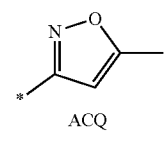
ACR
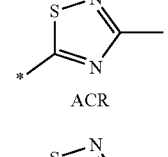
ACS TABLE 1-continued

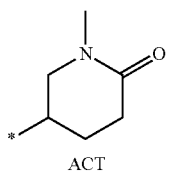 [SMILES: *C1CCC(=O)N(C)C1]

ACT

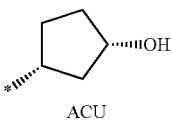

ACU

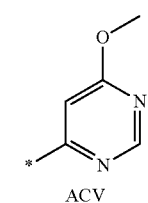 [SMILES: *c1cc(OC)ncn1]

ACV

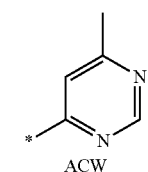 [SMILES: *c1cc(C)ncn1]

ACW

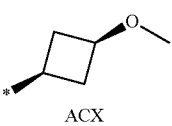

ACX

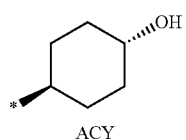 [SMILES: *[C@H]1CC[C@H](O)CC1]

ACY 1.81 A compound according to Embodiment 1.80A wherein $R^1$ is selected from groups AA, AE, AF, AG and AY in Table 1.

1.81A A compound according to Embodiment 1.80A wherein $R^1$ is selected from groups AA, AE, AF, AG, AY, AAC, AAF and ABI in Table 1.

1.81 BA compound according to Embodiment 1.80 wherein $R^1$ is selected from groups AA, ABJ and ABK in Table 1.

1.82 A compound according to Embodiment 1.81 wherein $R^1$ is group AA in Table 1.

1.82A A compound according to Embodiment 1.81A wherein $R^1$ is group ABI in Table 1.

1.82B A compound according to Embodiment 1.81B wherein $R^1$ is group ABJ in Table 1.

1.82C A compound according to Embodiment 1.81B wherein $R^1$ is group ABK in Table 1.

1.83 A compound according to any one of Embodiments 0.1 to 1.82 wherein $R^2$ is selected from hydrogen; fluorine; chlorine; and $C_{1-3}$ hydrocarbon groups optionally substituted with one or more fluorine atoms.

1.83A A compound according to any one of Embodiments 0.1 to 1.82 wherein $R^2$ is selected from hydrogen; fluorine; chlorine; bromine; and $C_{1-3}$ hydrocarbon groups optionally substituted with one or more fluorine atoms.

1.84 A compound according to Embodiment 1.83 wherein $R^2$ is selected from hydrogen; fluorine; chlorine; $C_{1-3}$ alkyl; $C_{2-3}$ alkenyl; cyclopropyl; and trifluoromethyl.

1.84A A compound according to Embodiment 1.83 wherein $R^2$ is selected from hydrogen; fluorine; chlorine; bromine; $C_{1-3}$ alkyl; $C_{2-3}$ alkenyl; cyclopropyl; and trifluoromethyl.

1.85 A compound according to Embodiment 1.84 wherein $R^2$ is selected from hydrogen; fluorine; chlorine; methyl; ethyl; isopropyl; vinyl; isopropenyl; cyclopropyl; and trifluoromethyl.

1.85A A compound according to Embodiment 1.84A wherein $R^2$ is selected from hydrogen; fluorine; chlorine; bromine; methyl; ethyl; isopropyl; vinyl; isopropenyl; cyclopropyl; and trifluoromethyl.

1.86 A compound according to Embodiment 1.84 wherein $R^2$ is selected from fluorine; chlorine; ethyl; isopropyl; vinyl; isopropenyl; cyclopropyl; and trifluoromethyl.

1.86A A compound according to Embodiment 1.84A wherein $R^2$ is selected from fluorine; chlorine; bromine; ethyl; isopropyl; vinyl; isopropenyl; cyclopropyl; and trifluoromethyl.

1.87 A compound according to Embodiment 1.84 wherein $R^2$ is selected from chlorine; isopropyl; vinyl; isopropenyl; and cyclopropyl.

1.87A A compound according to Embodiment 1.84A wherein $R^2$ is selected from chlorine; bromine; isopropyl; vinyl; isopropenyl; and cyclopropyl.

1.88 A compound according to Embodiment 1.84 wherein $R^2$ is chlorine.

1.88A A compound according to Embodiment 1.84A wherein $R^2$ is bromine.

1.89 A compound according to Embodiment 1.88 having the general formula (5):

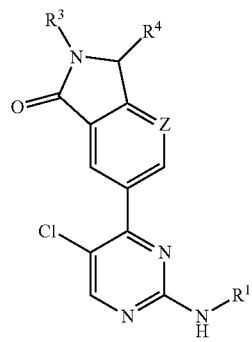

(5)

or a pharmaceutically acceptable salt or tautomer thereof.

1.89A A compound according to Embodiment 1.89 having the structure (5A):

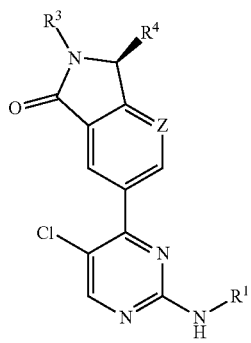

(5A)

1.89B A compound according to Embodiment 1.89 having the structure (5B):

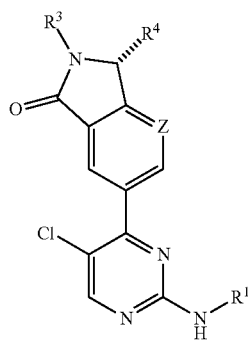

(5B)

1.90 A compound according to any one of Embodiments 0.1 to 1.89B wherein Z is CR$^z$.

1.91 A compound according to Embodiment 1.90 wherein R$^z$ is selected from hydrogen, fluorine, chlorine, methyl, hydroxymethyl and methoxymethyl.

1.92 A compound according to Embodiment 1.91 wherein R$^z$ is selected from hydrogen and fluorine.

1.93 A compound according to Embodiment 1.92 wherein R$^z$ is hydrogen.

1.94 A compound according to any one of Embodiments 0.1 to 1.89 wherein Z is N.

1.95 A compound according to any one of Embodiments 0.1 to 1.94 wherein R$^4$ is selected from hydrogen and C$_{1-2}$ alkyl optionally substituted with hydroxy, amino, methylamino, dimethylamino, a cyclic amino group or methoxy; wherein the cyclic amino group is selected from azetidine, pyrrolidine, piperidine, piperazine, N-methyl-piperazine, morpholine and thiomorpholine.

1.96 A compound according to Embodiment 1.95 wherein R$^4$ is selected from hydrogen, methyl, —CH$_2$OH, —CH$_2$NH$_2$; —(CH$_2$)$_2$OH; —(CH$_2$)$_2$OCH$_3$; and —(CH$_2$)$_2$NH$_2$.

1.97 A compound according to Embodiment 1.95 wherein R$^4$ is selected from hydrogen, methyl, —CH$_2$OH and —(CH$_2$)$_2$OH.

1.98 A compound according to Embodiment 1.97 wherein R$^4$ is hydrogen.

1.99 A compound according to Embodiment 1.97 wherein wherein R$^4$ is methyl.

1.100 A compound according to Embodiment 1.97 wherein R$^4$ is —CH$_2$OH.

1.101 A compound according to any one of Embodiments 0.1 to 1.100 wherein R$^3$ is hydrogen.

1.102 A compound according to any one of Embodiments 0.1 to 1.100 wherein R$^3$ is a group L$^1$-R$^7$; and L$^1$ is selected from a bond; Alk$^2$, Alk$^2$-O and Alk$^2$-C(=O) wherein Alk$^2$ is a C$_{1-4}$ straight chain or branched alkylene group which is optionally substituted with one or more hydroxy or fluorine substituents.

1.103 A compound according to Embodiment 1.102 wherein L$^1$ is a bond.

1.104 A compound according to Embodiment 1.102 wherein L$^1$ is a group Alk$^2$.

1.105 A compound according to Embodiment 1.102 wherein L$^1$ is a group Alk$^2$-.

1.106 A compound according to Embodiment 1.102 wherein L is Alk$^2$-C(=O).

1.106A A compound according to any one of Embodiments 0.1 to 1.102 and 1.104 to 1.106 wherein Alk$^2$ is selected from a C$_{1-4}$ straight chain or branched alkylene group optionally substituted with one or more hydroxyl substituents.

1.107 A compound according to any one of Embodiments 0.1 to 1.102 and 1.104 to 1.106 wherein Alk$^2$ is selected from a C$_{1-4}$ straight chain or branched alkylene group.

1.107A A compound according to Embodiment 1.106A wherein Alk$^2$ is selected from a C$_{1-3}$ straight or branched alkylene group optionally substituted with one or more hydroxyl substituents.

1.108 A compound according to Embodiment 1.107 wherein Alk$^2$ is selected from a C$_{1-3}$ straight chain or branched alkylene group.

1.108A A compound according to Embodiment 1.107A wherein Alk$^2$ is selected from CH$_2$, CH(CH$_3$), CH(CH$_2$OH) and CH(CH$_2$CH$_3$), 1.109 A compound according to Embodiment 1.108 wherein Alk$^2$ is selected from CH$_2$, CH$_2$CH$_2$, CH(CH$_3$) and C(CH$_3$)$_2$.

1.109A A compound according to Embodiment 1.109 wherein Alk$^2$ is selected from CH$_2$ and CH(CH$_3$).

1.110 A compound according to Embodiment 1.109 wherein Alk$^2$ is CH$_2$.

1.110A A compound according to Embodiment 1.109 wherein Alk$^2$ is CH(CH$_3$).

1.110B A compound according to Embodiment 1.108A wherein Alk$^2$ is CH(CH$_2$OH).

1.111 A compound according to any one of Embodiments 1.106 to 1.110 having the general formula (6):

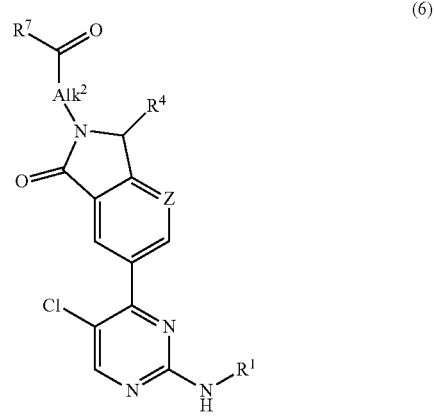

(6)

or a pharmaceutically acceptable salt or tautomer thereof.

1.111A A compound according to Embodiment 1.111 having the structure (6A):

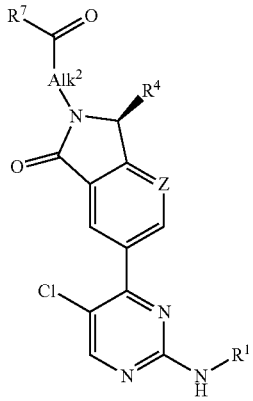

1.111B A compound according to Embodiment 1.111 having the structure (6B):

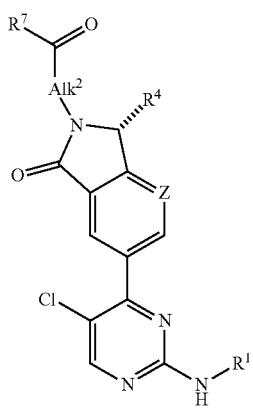

1.112 A compound according to Embodiment 1.111 having the general formula (7):

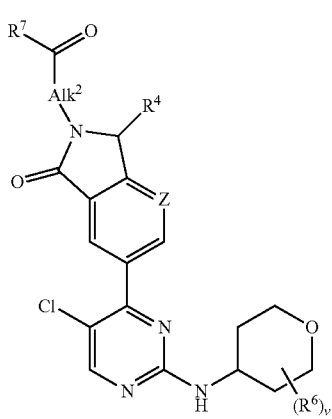

or a pharmaceutically acceptable salt or tautomer thereof.

1.112A A compound according to Embodiment 1.112 having the formula (7A):

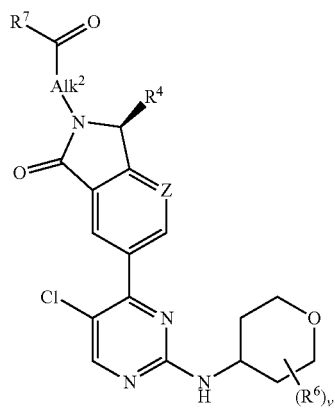

1.112B A compound according to Embodiment 1.112 having the formula (7B):

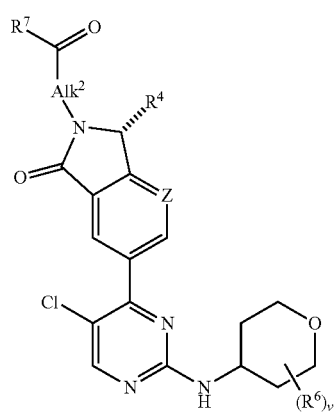

1.112C A compound according to any one of Embodiments 1.111 to 1.112B wherein the moiety:

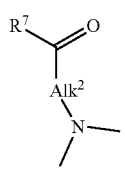

has the structure:

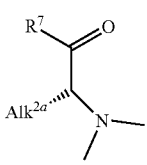

where $Alk^{2a}$ ia the residue of $Alk^2$.

1.112D A compound according to any one of Embodiments 1.111 to 1.112B wherein the moiety:

has the structure:

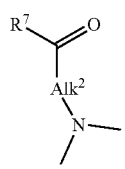

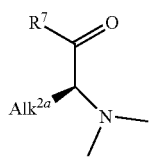

where Alk$^{2a}$ ia the residue of Alk$^2$.

1.112E A compound according to Embodiment 1.112C or 1.112D wherein Alk$^{2a}$ is selected from hydrogen and C$_{1-3}$ alkyl optionally substituted with hydroxy.

1.112F A compound according to Embodiment 1.112E wherein Alk$^{2a}$ is selected from hydrogen and methyl.

1.112G A compound according to Embodiment 1.112F wherein Alk$^{2a}$ is hydrogen.

1.112H A compound according to Embodiment 1.112E wherein Alk$^{2a}$ is methyl.

1.113 A compound according to any one of Embodiments 0.1 to 1.100 and 1.102 to 1.112H wherein R$^7$ is selected from:
  NR$^8$R$^9$;
  a carbocyclic or heterocyclic group having from 3 to 12 ring members, of which 0, 1, 2 or 3 are heteroatom ring members selected from O, N and S and oxidised forms of S, wherein the carbocyclic or heterocyclic group is attached through a carbon ring member thereof to L$^1$, and wherein the carbocyclic or heterocyclic group is optionally substituted with one or more substituents R$^{10}$; and
  an acyclic C$_{1-3}$ hydrocarbon group optionally substituted with one or more substituents selected from hydroxy; oxo; halogen; cyano; carboxy; amino; mono- or di-C$_{1-4}$ alkylamino; and carbocyclic and heterocyclic groups having from 3 to 12 ring members, of which 0, 1, 2 or 3 are heteroatom ring members selected from O, N and S and oxidised forms of S, the carbocyclic or heterocyclic group being optionally substituted with one or more substituents R$^{10}$; wherein one or two but not all of the carbon atoms of the acyclic C$_{1-3}$ hydrocarbon group may optionally be replaced by O, S, SO, SO$_2$ or NR$^{11}$.

1.114 A compound according to Embodiment 1.113 wherein R$^7$ is a carbocyclic or heterocyclic group having from 3 to 12 ring members, of which 0, 1, 2 or 3 are heteroatom ring members selected from O, N and S and oxidised forms of S, wherein the carbocyclic or heterocyclic group is attached through a carbon ring member thereof to L$^1$, and wherein the carbocyclic or heterocyclic group is optionally substituted with one or more substituents R$^{10}$.

1.115 A compound according to Embodiment 1.114 wherein R$^7$ is a monocyclic carbocyclic or heterocyclic group having from 3 to 7 ring members, of which 0, 1, 2 or 3 are heteroatom ring members selected from O, N and S and oxidised forms of S, wherein the carbocyclic or heterocyclic group is attached through a carbon ring member thereof to L$^1$, and wherein the carbocyclic or heterocyclic group is optionally substituted with one or more substituents R$^{10}$.

1.116 A compound according to Embodiment 1.115 wherein R$^7$ is a monocyclic carbocyclic or heterocyclic group selected from:
  C$_{3-6}$ cycloalkyl groups;
  phenyl groups;
  4-7 membered non-aromatic heterocyclic groups containing 1, 2 or 3 heteroatom ring members selected from O, N and S and oxidised forms of S; and
  5-6 membered heteroaryl groups containing 1, 2 or 3 heteroatom ring members selected from O, N and S;
  each of the monocyclic carbocyclic and heterocyclic groups being optionally substituted with one or more substituents R$^{10}$.

1.117 A compound according to Embodiment 1.116 wherein R$^7$ is a monocyclic carbocyclic or heterocyclic group selected from:
  C$_{3-6}$ cycloalkyl groups;
  phenyl groups;
  4-7 membered non-aromatic heterocyclic groups containing 1, 2 or 3 heteroatom ring members selected from O, N and S and oxidised forms of S; and
  5-6 membered heteroaryl groups containing 1, 2 or 3 heteroatom ring members selected from O, N and S;
  each of the monocyclic carbocyclic and heterocyclic groups being optionally substituted with one or more substituents R$^{10}$.

1.118 A compound according to Embodiment 1.117 wherein R$^7$ is a monocyclic carbocyclic or heterocyclic group selected from:
  C$_{3-6}$ cycloalkyl groups;
  4-6 membered non-aromatic heterocyclic groups containing 1, 2 or 3 heteroatom ring members selected from O, N and S and oxidised forms of S; and
  5 membered heteroaryl groups containing 1, 2 or 3 heteroatom ring members selected from O, N and S;
  each of the monocyclic carbocyclic and heterocyclic groups being optionally substituted with one or more substituents R$^{10}$.

1.119 A compound according to Embodiment 1.118 wherein R$^7$ is a monocyclic carbocyclic or heterocyclic group selected from:
  C$_{3-5}$ cycloalkyl groups;
  4-6 membered non-aromatic heterocyclic groups containing 1, 2 or 3 heteroatom ring members selected from O, N and S and oxidised forms of S; and
  5 membered heteroaryl groups containing 1, 2 or 3 heteroatom ring members selected from O and N;
  each of the monocyclic carbocyclic and heterocyclic groups being optionally substituted with one or more substituents R$^{10}$.

1.120 A compound according to Embodiment 1.119 wherein R$^7$ is a monocyclic carbocyclic or heterocyclic group selected from cyclopropyl; cyclopentane; oxetane; tetrahydrofuran; pyrrolidine; pyrrolidone; piperidone; isoxazole; oxadiazole and triazole; each of the monocyclic carbocyclic and heterocyclic groups being optionally substituted with one or more substituents R$^{10}$.

1.121 A compound according to Embodiment 1.113 wherein R$^7$ is an acyclic C$_{1-3}$ hydrocarbon group optionally substituted with one or more substituents selected from hydroxy; oxo; halogen; cyano; carboxy; amino; mono- or di-C$_{1-4}$ alkylamino; and carbocyclic and heterocyclic groups having from 3 to 12 ring members, of which 0, 1, 2 or 3 are heteroatom ring members selected from O, N and S and oxidised forms of S, the carbocyclic or heterocyclic group being optionally substituted with one or more substituents $R^{10}$; wherein one or two but not all of the carbon atoms of the acyclic $C_{1-3}$ hydrocarbon group may optionally be replaced by O, S, SO, $SO_2$ or $NR^{11}$.

1.122 A compound according to Embodiment 1.121 wherein $R^7$ is an acyclic $C_{1-4}$ hydrocarbon group optionally substituted with one or more substituents selected from hydroxy; oxo; halogen; amino; mono- or di-$C_{1-4}$alkylamino; and carbocyclic and heterocyclic groups having from 3 to 7 ring members, of which 0, 1, 2 or 3 are heteroatom ring members selected from O, N and S and oxidised forms of S, the carbocyclic or heterocyclic group being optionally substituted with one or more substituents $R^{10}$; wherein one but not all of the carbon atoms of the acyclic $C_{1-4}$ hydrocarbon group may optionally be replaced by O, S, SO, $SO_2$ or $NR^{11}$.

1.123 A compound according to Embodiment 1.122 wherein $R^7$ is an acyclic $C_{1-4}$ hydrocarbon group optionally substituted with one or more substituents selected from hydroxy; oxo; fluorine; amino; mono- or di-$C_{1-4}$ alkylamino; and carbocyclic and heterocyclic groups having from 3 to 7 ring members, of which 0, 1, 2 or 3 are heteroatom ring members selected from O, N and S and oxidised forms of S, the carbocyclic or heterocyclic group being optionally substituted with one or more substituents $R^{10}$; wherein one but not all of the carbon atoms of the acyclic $C_{1-4}$ hydrocarbon group may optionally be replaced by O or $NR^{11}$.

1.124 A compound according to Embodiment 1.123 wherein $R^1$ is an acyclic $C_{1-4}$ hydrocarbon group optionally substituted with one or more substituents selected from hydroxy; amino; mono- or di-$C_{1-4}$ alkylamino; and carbocyclic and heterocyclic groups having from 3 to 6 ring members, of which 0, 1, 2 or 3 are heteroatom ring members selected from O and N, the carbocyclic or heterocyclic group being optionally substituted with one or more substituents $R^{10}$; wherein one but not all of the carbon atoms of the acyclic $C_{1-4}$ hydrocarbon group may optionally be replaced by O or $NR^{11}$.

1.125 A compound according to Embodiment 1.123 wherein $R^7$ is an acyclic $C_{1-4}$ hydrocarbon group; wherein one but not all of the carbon atoms of the acyclic $C_{1-4}$ hydrocarbon group may optionally be replaced by O.

1.126 A compound according to Embodiment 1.113 wherein $R^7$ is a group $NR^8R^9$.

1.127 A compound according to Embodiment 1.1.26 wherein $R^3$ is selected from hydrogen; $C_{1-4}$ alkyl; cyclobutyl; cyclopropylmethyl and hydroxy-$C_{2-4}$-alkyl.

1.128 A compound according to Embodiment 1.127 wherein $R^3$ is selected from hydrogen; methyl; ethyl; propyl; isopropyl; cyclopropyl; hydroxyethyl; and hydroxypropyl.

1.129 A compound according to Embodiment 1.128 wherein $R^8$ is selected from hydrogen; methyl; ethyl; and hydroxyethyl.

1.130 A compound according to Embodiment 1.129 wherein $R^8$ is selected from hydrogen and methyl.

1.131 A compound according to Embodiment 1.130 wherein $R^8$ is hydrogen.

1.132 A compound according to Embodiment 1.130 wherein $R^8$ is methyl.

1.133 A compound according to anyone of Embodiments 1.126 to 1.131 wherein $R^9$ is selected from:
hydrogen;
a carbocyclic or heterocyclic group having from 3 to 10 ring members, of which 0, 1 or 2 are heteroatom ring members selected from O, N and S and oxidised forms of S, the carbocyclic or heterocyclic group being optionally substituted with one or more substituents $R^{10}$; and
an acyclic $C_{1-3}$ hydrocarbon group optionally substituted with one or more substituents selected from hydroxy; oxo; halogen; carboxy; amino; mono- or di-$C_{1-4}$ alkylamino; and
carbocyclic and heterocyclic groups having from 3 to 10 ring members, of which 0, 1 or 2 are heteroatom ring members selected from O, N and S and oxidised forms of S, the carbocyclic or heterocyclic group being optionally substituted with one or more substituents $R^1$; wherein one or two but not all of the carbon atoms of the acyclic $C_{1-8}$ hydrocarbon group may optionally be replaced by 0, S, $SO_2$ or $NR^{11}$.

1.133A A compound according to Embodiment 1.133 wherein $R^9$ is an acyclic $C_{1-8}$ hydrocarbon group optionally substituted with one or more substituents selected from hydroxy; and carbocyclic and heterocyclic groups having from 3 to 10 ring members, of which 0, 1 or 2 are heteroatom ring members selected from O, N and S and oxidised forms of S, the carbocyclic or heterocyclic group being optionally substituted with one or more substituents $R^{10}$;
wherein one or two but not all of the carbon atoms of the acyclic $C_{1-3}$ hydrocarbon group may optionally be replaced by 0, S, $SO_2$ or $NR^{11}$.

1.133B A compound according to Embodiment 1.133A wherein $R^9$ is an acyclic $C_{1-8}$ hydrocarbon group optionally substituted with one or more substituents selected from hydroxy; and carbocyclic and heterocyclic groups having from 3 to 10 ring members, of which 0, 1 or 2 are heteroatom ring members selected from O, N and S and oxidised forms of S, the carbocyclic or heterocyclic group being optionally substituted with one or more substituents $R^{10}$.

1.133C A compound according to Embodiment 1.133B wherein $R^9$ is an acyclic $C_{1-3}$ hydrocarbon group optionally substituted with one or more substituents selected from hydroxy; and carbocyclic and heterocyclic groups having from 3 to 10 ring members, of which 0, 1 or 2 are heteroatom ring members selected from O, N and S and oxidised forms of S, the carbocyclic or heterocyclic group being optionally substituted with one or more substituents $R^{10}$.

1.134 A compound according to Embodiment 1.131 or Embodiment 1.132 wherein $R^9$ is selected from:
hydrogen;
a carbocyclic or heterocyclic group having from 3 to 10 ring members, of which 0, 1 or 2 are heteroatom ring members selected from O and N, the carbocyclic or heterocyclic group being optionally substituted with one or more substituents $R^{10}$; and
an acyclic $C_{1-3}$ hydrocarbon group optionally substituted with one or more substituents selected from hydroxy; oxo; halogen; carboxy; amino; mono- or di-$C_{1-4}$ alkylamino; and carbocyclic and heterocyclic groups having from 3 to 10 ring members, of which 0 or 1 are heteroatom ring members selected from O and N, the carbocyclic or heterocyclic group being optionally substituted with one or more substituents $R^{10}$; wherein one or two but not all of the carbon atoms of the acyclic $C_{1-8}$ hydrocarbon group may optionally be replaced by O, S, $SO_2$ or $NR^{11}$.

1.135 A compound according to Embodiment 1.134 wherein $R^9$ is selected from:
hydrogen;
a carbocyclic group having from 3 to 10 ring members, the carbocyclic group being optionally substituted with one or more substituents $R^{10}$; and
a heterocyclic group having from 4 to 10 ring members, of which 1 or 2 are heteroatom ring members selected from O and N, the heterocyclic group being optionally substituted with one or more substituents $R^{10}$; and an acyclic $C_{1-8}$ hydrocarbon group optionally substituted with one or more substituents selected from hydroxy; oxo; halogen; carboxy; amino; mono- or di-$C_{1-4}$ alkylamino; and carbocyclic and heterocyclic groups having from 3 to 10 ring members, of which 0 or 1 are heteroatom ring members selected from O and N, the carbocyclic or heterocyclic group being optionally substituted with one or more substituents $R^{10}$; wherein one or two but not all of the carbon atoms of the acyclic $C_{1-8}$ hydrocarbon group may optionally be replaced by O, S, $SO_2$ or $NR^{11}$.

1.136 A compound according to Embodiment 1.135 wherein $R^9$ is selected from:

hydrogen;

a carbocyclic group having from 3 to 10 ring members, the carbocyclic group being optionally substituted with one or more substituents $R^{10}$;

a heterocyclic group having from 4 to 10 ring members, of which 1 or 2 are heteroatom ring members selected from O and N, the heterocyclic group being optionally substituted with one or more substituents $R^{10}$; and an acyclic $C_{1-8}$ hydrocarbon group optionally substituted with one or more substituents selected from hydroxy; oxo; halogen; carboxy; amino; mono- or di-$C_{1-4}$ alkylamino; and carbocyclic and heterocyclic groups having from 3 to 10 ring members, of which 0 or 1 are heteroatom ring members selected from O and N, the carbocyclic or heterocyclic group being optionally substituted with one or more substituents $R^{10}$; wherein one or two but not all of the carbon atoms of the acyclic $C_{1-8}$ hydrocarbon group may optionally be replaced by O, S, $SO_2$ or $NR^{11}$.

1.137 A compound according to Embodiment 1.136 wherein $R^9$ is selected from:

hydrogen;

a monocyclic carbocyclic group having from 3 to 6 ring members, the monocyclic carbocyclic group being optionally substituted with one or more substituents $R^{10}$;

a bicyclic carbocyclic group having from 7 to 10 ring members, the bicyclic carbocyclic group being optionally substituted with one or more substituents $R^{10}$;

a monocyclic heterocyclic group having from 4 to 7 ring members, of which 1 is a heteroatom ring member selected from O and N, the heterocyclic group being optionally substituted with one or more substituents $R^{10}$; and an acyclic $C_{1-8}$ hydrocarbon group optionally substituted with one or more substituents selected from hydroxy; oxo; halogen; amino; mono- or di-$C_{1-4}$ alkylamino; and carbocyclic and heterocyclic groups having from 3 to 10 ring members, of which 0 or 1 are heteroatom ring members selected from O and N, the carbocyclic or heterocyclic group being optionally substituted with one or more substituents $R^{10}$; wherein one or two but not all of the carbon atoms of the acyclic $C_{1-8}$ hydrocarbon group may optionally be replaced by O, S, $SO_2$ or $NR^{11}$.

1.138 A compound according to Embodiment 1.137 wherein $R^9$ is selected from:

hydrogen;

a monocyclic non-aromatic carbocyclic group having from 3 to 6 ring members, the monocyclic non-aromatic carbocyclic group being optionally substituted with one or more substituents $R^{10}$;

a bicyclic carbocyclic group having from 7 to 10 ring members, the bicyclic carbocyclic group being non-aromatic or containing no more than one aromatic ring; the bicyclic carbocyclic group being optionally substituted with one or more substituents $R^{10}$;

a monocyclic heterocyclic group having from 4 to 7 ring members, of which 1 is a heteroatom ring member selected from O and N, the heterocyclic group being optionally substituted with one or more substituents $R^{10}$; and an acyclic $C_{1-8}$ hydrocarbon group optionally substituted with one or more substituents selected from hydroxy; oxo; halogen; amino; mono- or di-$C_{1-4}$ alkylamino; and carbocyclic and heterocyclic groups having from 3 to 10 ring members, of which 0 or 1 are heteroatom ring members selected from O and N, the carbocyclic or heterocyclic group being optionally substituted with one or more substituents $R^{10}$; wherein one or two but not all of the carbon atoms of the acyclic $C_{1-8}$ hydrocarbon group may optionally be replaced by O, S, $SO_2$ or $NR^{11}$.

1.138A A compound according to Embodiment 1.138 wherein $R^9$ is an acyclic $C_{1-8}$ hydrocarbon group optionally substituted with one or more substituents selected from hydroxy; and carbocyclic and heterocyclic groups having from 3 to 10 ring members, of which 0 or 1 are heteroatom ring members selected from O and N, the carbocyclic or heterocyclic group being optionally substituted with one or more substituents $R^{10}$; wherein one or two but not all of the carbon atoms of the acyclic $C_{1-3}$ hydrocarbon group may optionally be replaced by O, S, $SO_2$ or $NR^{11}$.

1.138B A compound according to Embodiment 1.138A wherein $R^9$ is an acyclic $C_{1-3}$ hydrocarbon group optionally substituted with one or more substituents selected from hydroxy; and carbocyclic and heterocyclic groups having from 3 to 10 ring members, of which 0 or 1 are heteroatom ring members selected from O and N, the carbocyclic or heterocyclic group being optionally substituted with one or more substituents $R^{10}$.

1.138C A compound according to Embodiment 1.138B wherein $R^9$ is an acyclic $C_{1-3}$ hydrocarbon group optionally substituted with one or more substituents selected from hydroxy; and carbocyclic and heterocyclic groups having from 3 to 10 ring members, of which 0 or 1 are heteroatom ring members selected from O and N, the carbocyclic or heterocyclic group being optionally substituted with one or more substituents $R^{10}$.

1.139 A compound according to Embodiment 1.138 wherein $R^9$ is selected from:

hydrogen;

a monocyclic saturated carbocyclic group having from 3 to 6 ring members, the monocyclic saturated carbocyclic group being optionally substituted with one or more substituents $R^{10}$;

a bicyclic carbocyclic group having from 9 or 10 ring members, the bicyclic carbocyclic group containing an aromatic ring and a non-aromatic ring; the bicyclic carbocyclic group being optionally substituted with one or more substituents $R^{10}$;

a monocyclic heterocyclic group having from 4 to 6 ring members, of which 1 is a heteroatom ring member selected from 0, the heterocyclic group being optionally substituted with one or more substituents $R^{10}$; and an acyclic saturated $C_{1-3}$ hydrocarbon group optionally substituted with one or more substituents selected from hydroxy; halogen; amino; mono- or di-$C_{1-4}$ alkylamino; phenyl; and monocyclic heterocyclic groups having from 4 to 6 ring members, of which 1 is a heteroatom ring member selected from O and N, the phenyl or heterocyclic group being optionally substituted with one or more substituents $R^{10}$; wherein one but not all of the carbon atoms of the acyclic $C_{1-3}$ hydrocarbon group may optionally be replaced by 0, S, $SO_2$ or $NR^{11}$.

1.139A A compound according to Embodiment 1.139 wherein $R^9$ is an acyclic saturated $C_{1-3}$ hydrocarbon group optionally substituted with one or more substituents selected from hydroxy; phenyl; and monocyclic heterocyclic groups having from 4 to 6 ring members, of which 1 is a heteroatom ring member selected from O and N, the phenyl or heterocyclic group being optionally substituted with one or more substituents $R^{10}$; wherein one but not all of the carbon atoms of the acyclic $C_{1-8}$ hydrocarbon group may optionally be replaced by O, S, $SO_2$ or $NR^{11}$.

1.139B A compound according to Embodiment 1.139A wherein $R^9$ is an acyclic saturated $C_{1-3}$ hydrocarbon group optionally substituted with one or more substituents selected from hydroxy; phenyl; and monocyclic heterocyclic groups having from 4 to 6 ring members, of which 1 is a heteroatom ring member selected from O and N, the phenyl or heterocyclic group being optionally substituted with one or more substituents $R^{10}$.

1.139C A compound according to Embodiment 1.139B wherein $R^9$ is an acyclic saturated $C_{1-3}$ hydrocarbon group optionally substituted with one or more substituents selected from hydroxy; phenyl; and pyridyl, the phenyl or pyridyl group being optionally substituted with one or more substituents $R^{10}$.

1.139D A compound according to Embodiment 1.139C wherein $R^9$ is an acyclic saturated $C_{1-3}$ hydrocarbon group optionally substituted with one or more substituents selected from hydroxy; and phenyl, the phenyl group being optionally substituted with one or more substituents $R^{10}$.

1.139E A compound according to Embodiment 1.139C wherein $R^9$ is an acyclic saturated $C_{1-3}$ hydrocarbon group optionally substituted with one or more substituents selected from hydroxy; and phenyl, the phenyl group being optionally substituted with one or more substituents $R^{10}$ wherein $R^{10}$ is selected from: fluorine; chlorine; hydroxy; oxo; cyano; and $OR^{12}$ wherein $R^{12}$ is methyl, ethyl, propyl, iso-propyl or cyclopropyl, each being optionally substituted with fluorine.

1.139F A compound according to Embodiment 1.139C wherein $R^9$ is an acyclic saturated $C_{1-3}$ hydrocarbon group optionally substituted with one or more substituents selected from hydroxy; and phenyl, the phenyl group being optionally substituted with one or two substituents $R^{10}$ wherein $R^{10}$ is selected from: fluorine and $OR^{12}$ wherein $R^{12}$ is methyl, ethyl, propyl, iso-propyl or cyclopropyl, each being optionally substituted with fluorine.

1.139G A compound according to Embodiment 1.139C wherein $R^9$ is an acyclic saturated $C_{1-3}$ hydrocarbon group optionally substituted with one or more substituents selected from hydroxy; and phenyl, the phenyl group being optionally substituted with one or two substituents $R^{10}$ wherein $R^{10}$ is selected from: fluorine and $OR^{12}$ wherein $R^{12}$ is methyl, ethyl, propyl, iso-propyl or cyclopropyl, each being unsubstituted.

1.139H A compound according to Embodiment 1.139C wherein $R^9$ is an acyclic saturated $C_{1-3}$ hydrocarbon group optionally substituted with one or more substituents selected from hydroxy; and phenyl, the phenyl group being optionally substituted with one or two substituents $R^{10}$ wherein $R^{10}$ is selected from: fluorine and $OR^{12}$ wherein $R^{12}$ is unsubstituted methyl.

1.139J A compound according to any one of Embodiments 1.133 to 1.139H wherein $R^9$ is an acyclic saturated hydrocarbon group substituted with a carbocyclic or heterocyclic group and optionally a hydroxyl group, wherein the acyclic saturated hydrocarbon group has the structure:

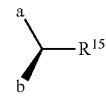

wherein $R^{15}$ is $C_{1-3}$ alkyl or hydroxy-$C_{1-3}$ alkyl; "a" denotes the point of attachment to the carbocyclic or heterocyclic group and "b" denotes the point of attachment to the nitrogen atom of $NR^8R^9$.

1.139K A compound according to any one of Embodiments 1.133 to 1.139H wherein $R^9$ is an acyclic saturated hydrocarbon group substituted with a carbocyclic or heterocyclic group and optionally a hydroxyl group, wherein the acyclic saturated hydrocarbon group has the structure:

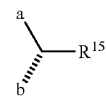

wherein $R^{15}$ is $C_{1-3}$ alkyl or hydroxy-$C_{1-3}$ alkyl; "a" denotes the point of attachment to the carbocyclic or heterocyclic group and "b" denotes the point of attachment to the nitrogen atom of $NR^8R^9$.

1.140 A compound according to Embodiment 1.139 wherein $R^9$ is selected from:
  hydrogen;
  cyclopropyl, cyclobutyl, cyclopentyl and cyclohexyl groups each being optionally substituted with one or more substituents $R^{10}$;
  indane and tetrahydronaphathalene, each being optionally substituted with one or more substituents $R^{10}$;
  oxetane and oxanyl, each being optionally substituted with one or more substituents $R^{10}$; and
  an acyclic saturated $C_{1-6}$ hydrocarbon group optionally substituted with one or more substituents selected from hydroxy; halogen; amino; mono- or di-$C_{1-4}$ alkylamino; phenyl; and oxetane; the phenyl or oxetane group being optionally substituted with one or more substituents $R^{10}$.

1.140A A compound according to any one of Embodiments 0.1 to 1.132 wherein $R^9$ is selected from groups HA to SX in Table 3 below, where * marks the point of connection to the N atom.

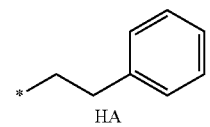
HA

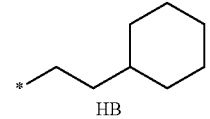
HB

-continued
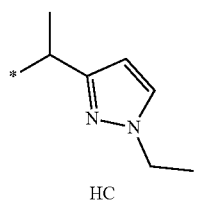
HC
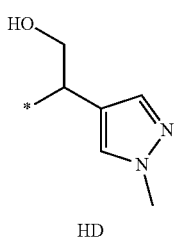
HD
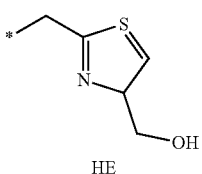
HE
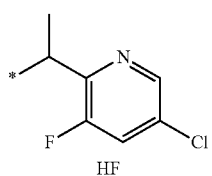
HF
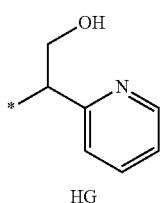 [SMILES: *C(CO)c1ccccn1]
HG
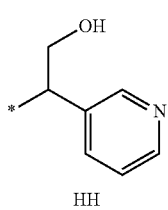
HH
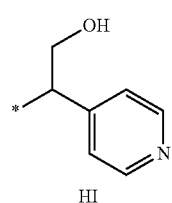
HI
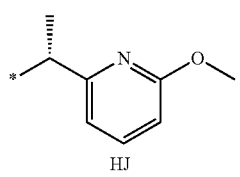
HJ
-continued
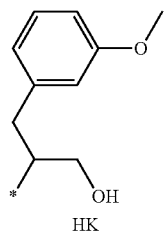
HK
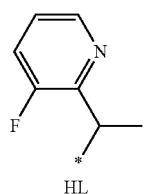
HL
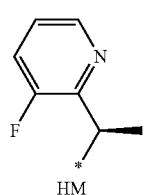
HM
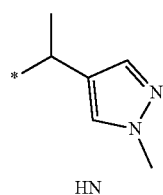
HN
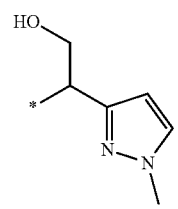
HO
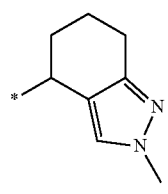
HP
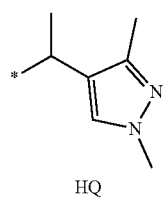
HQ -continued
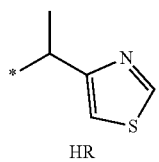
HR
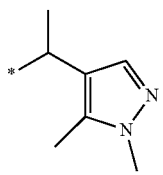
HS
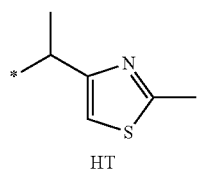
HT
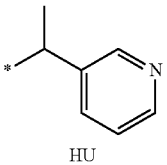
HU
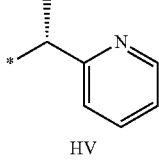
HV
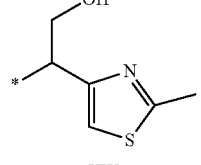
HW
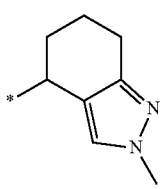
HX
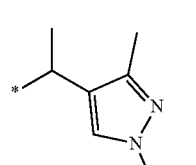
HY
-continued
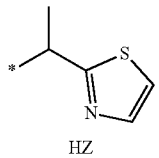
HZ
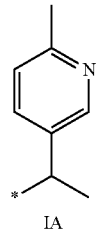
IA
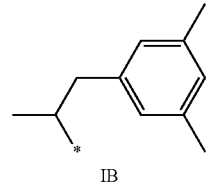
IB
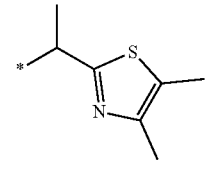
IC
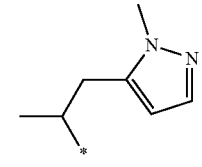
ID
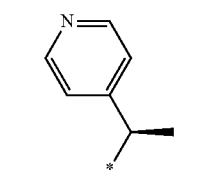
IE
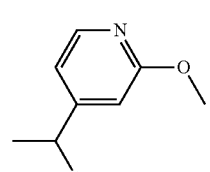
IF
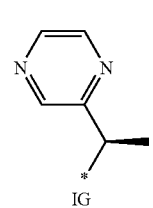
IG 51
-continued
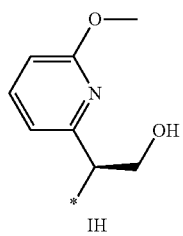
IH
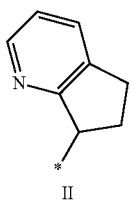
II
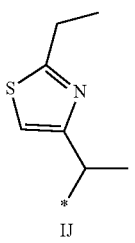 [SMILES: *C(C)c1csc(CC)n1]
IJ
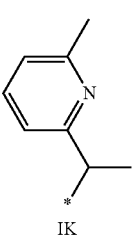
IK
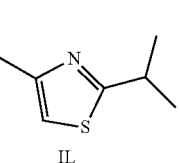
IL
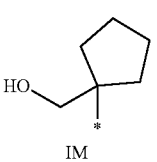
IM
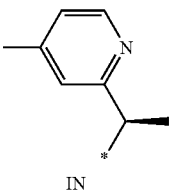
IN
52
-continued
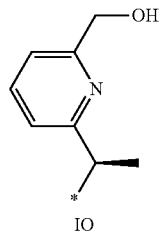
IO
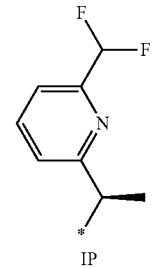
IP
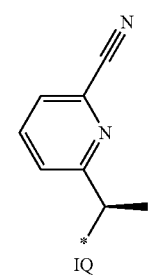
IQ
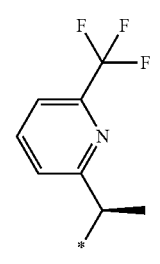
IR
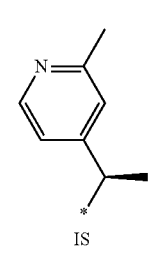
IS
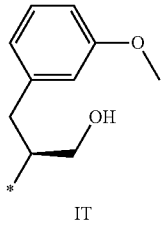
IT 53
-continued
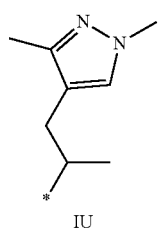
IU
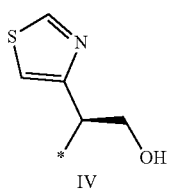
IV
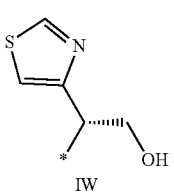
IW
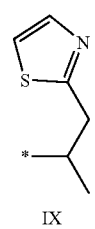
IX
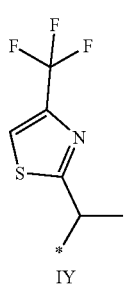
IY
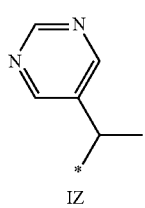
IZ
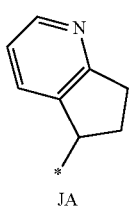 [SMILES: *C1CCc2ncccc21]
JA
54
-continued
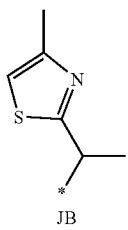
JB
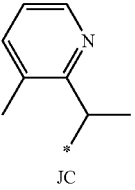 [SMILES: *C(C)c1ncccc1C]
JC
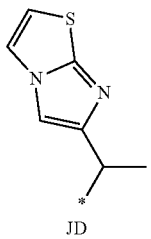
JD
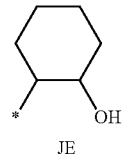
JE
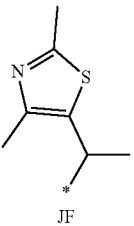 [SMILES: *C(C)c1sc(C)nc1C]
JF
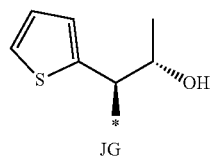 [SMILES: *[C@@H](c1cccs1)[C@H](C)O]
JG
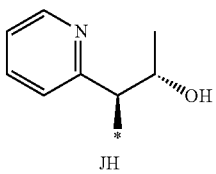 [SMILES: *[C@@H](c1ccccn1)[C@H](C)O]
JH
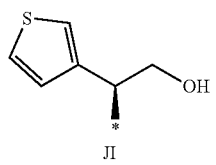 [SMILES: *[C@H](CO)c1ccsc1]
JI -continued
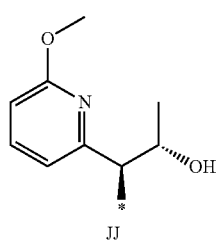 [SMILES: *[C@@H](c1cccc(OC)n1)[C@H](C)O]
JJ
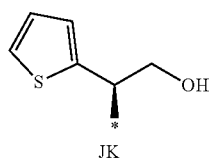 [SMILES: *[C@H](CO)c1cccs1]
JK
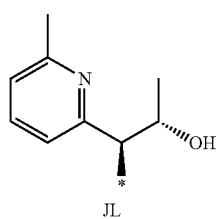 [SMILES: *[C@@H](c1cccc(C)n1)[C@H](C)O]
JL
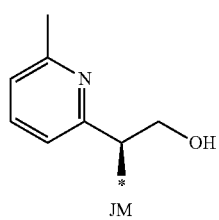 [SMILES: *[C@H](CO)c1cccc(C)n1]
JM
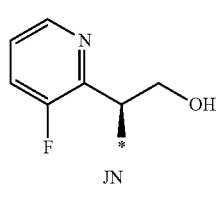 [SMILES: *[C@H](CO)c1ncccc1F]
JN
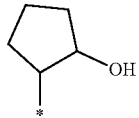
JO
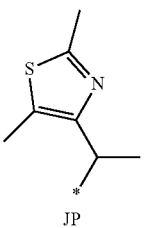 [SMILES: *C(C)c1nc(C)sc1C]
JP
-continued
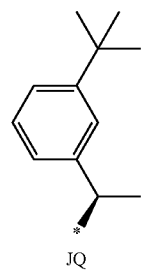 [SMILES: *[C@H](C)c1cccc(C(C)(C)C)c1]
JQ
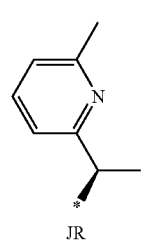 [SMILES: *[C@H](C)c1cccc(C)n1]
JR
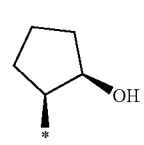
JS
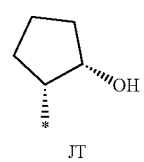 [SMILES: *[C@@H]1CCC[C@@H]1O]
JT
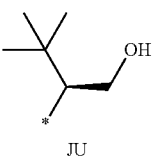 [SMILES: *[C@H](CO)C(C)(C)C]
JU
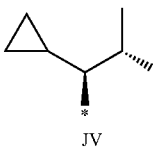
JV
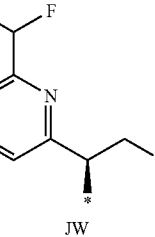
JW 57
-continued
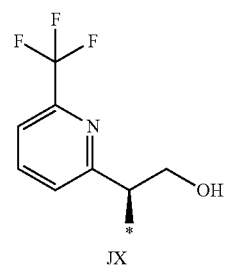 [SMILES: *[C@H](CO)c1cccc(C(F)(F)F)n1]
JX
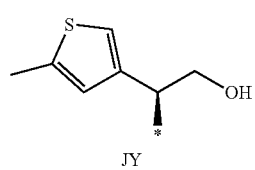 [SMILES: *[C@H](CO)c1csc(C)c1]
JY
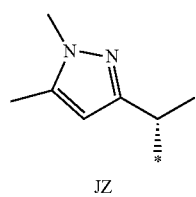 [SMILES: *[C@@H](C)c1cc(C)n(C)n1]
JZ
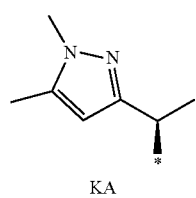 [SMILES: *[C@H](C)c1cc(C)n(C)n1 ; "KA"]
KA
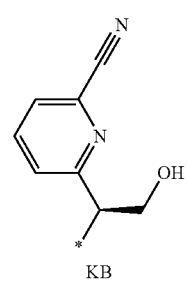
KB
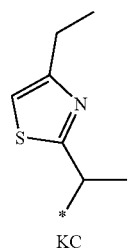
KC
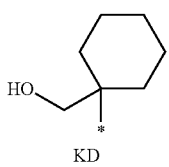
KD
58
-continued
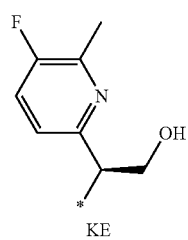
KE
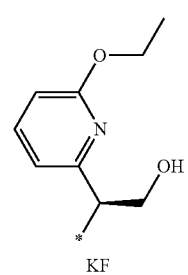
KF
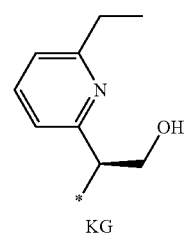 [SMILES: *[C@H](CO)c1cccc(CC)n1]
KG
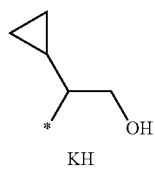
KH
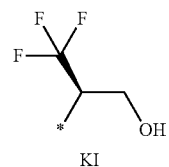
KI
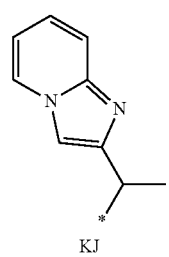 [SMILES: *C(C)c1cn2ccccc2n1]
KJ -continued
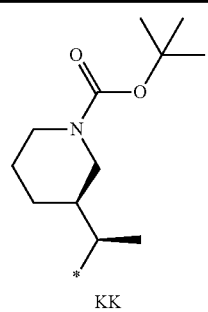
KK
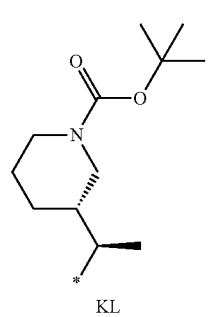
KL
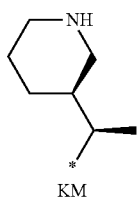
KM
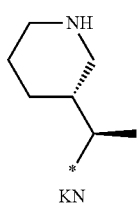
KN
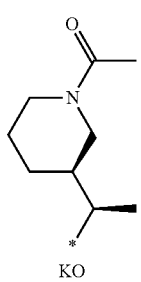
KO
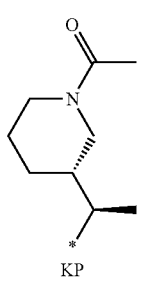
KP
-continued
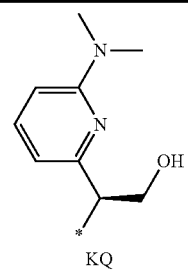
KQ
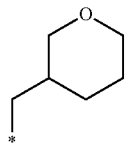
KR
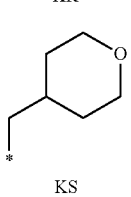
KS
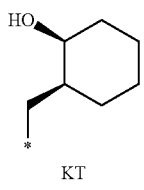
KT
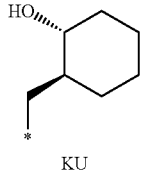
KU
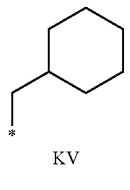
KV
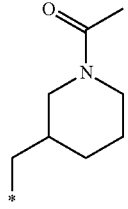
KW
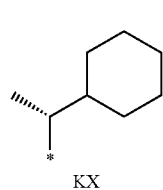
KX -continued
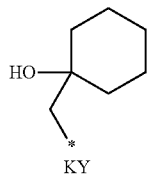
KY
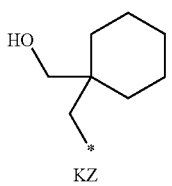 [SMILES: *CC1(CO)CCCCC1]
KZ
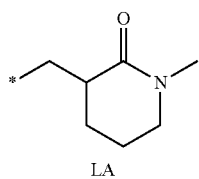
LA
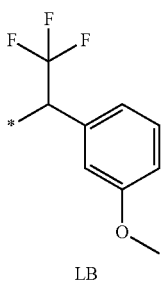
LB
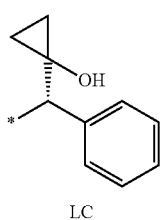 [SMILES: *[C@@H](c1ccccc1)C1(O)CC1]
LC
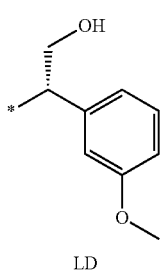 [SMILES: *[C@H](CO)c1cccc(OC)c1]
LD
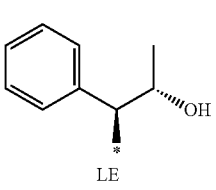
LE
-continued
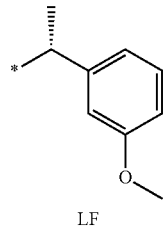
LF
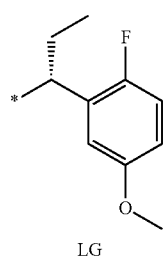
LG
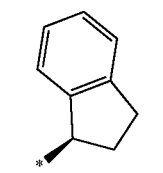
LH
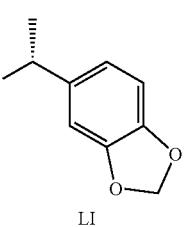
LI
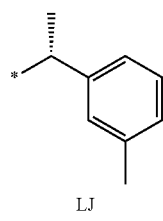
LJ
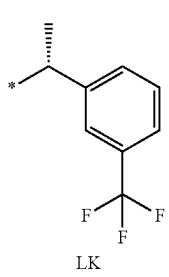
LK -continued
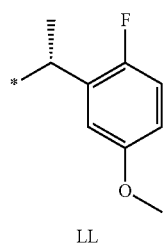 [SMILES: *[C@H](C)c1cc(OC)ccc1F]
LL
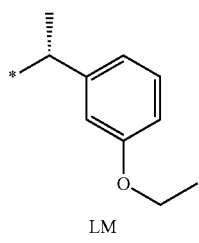
LM
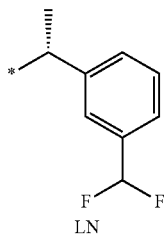
LN
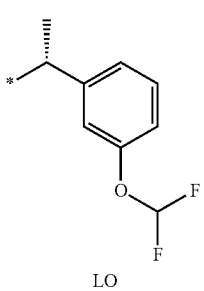 [SMILES: *[C@H](C)c1cccc(OC(F)F)c1 ; "LO"]
LO
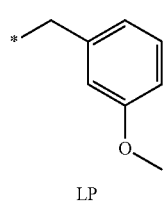
LP
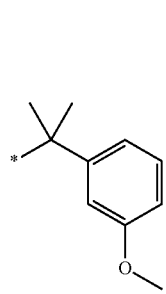
LQ
-continued
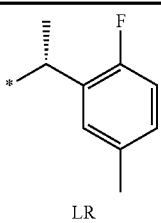
LR
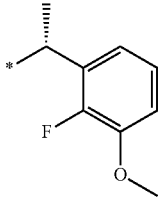
LS
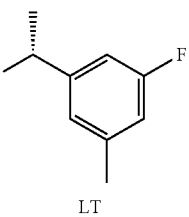
LT
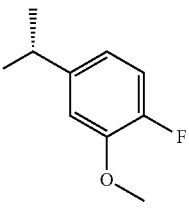
LU
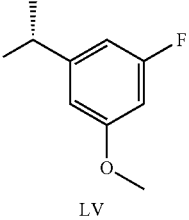
LV
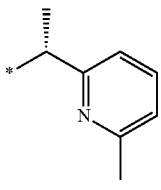
LW
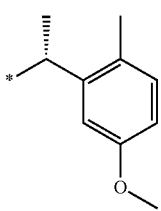
LX

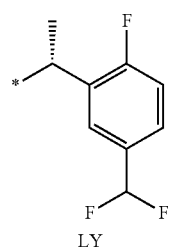
LY
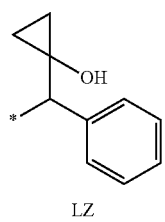 [SMILES: *C(c1ccccc1)C1(O)CC1]
LZ
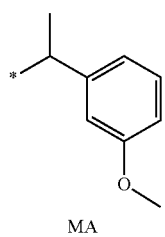
MA
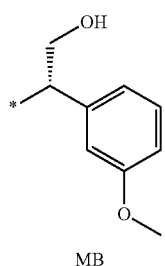 [SMILES: *[C@H](CO)c1cccc(OC)c1]
MB
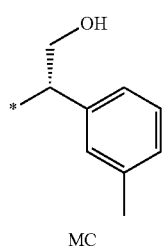 [SMILES: *[C@H](CO)c1cccc(C)c1]
MC
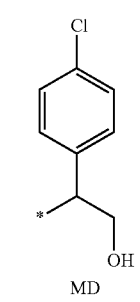
MD
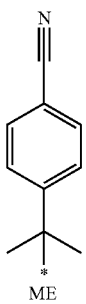
ME
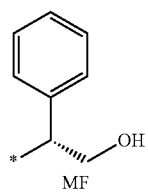
MF
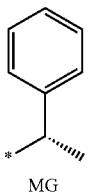
MG
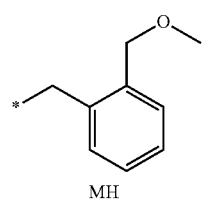
MH
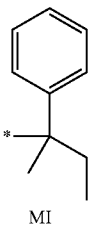
MI
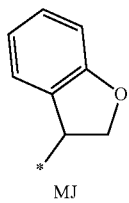
MJ
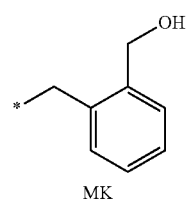
MK -continued
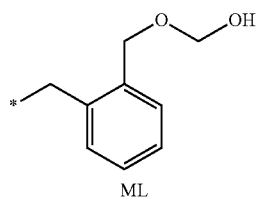
ML
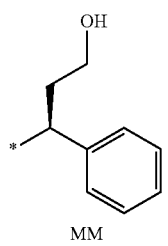
MM
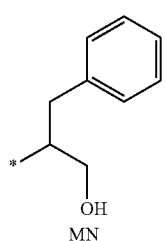
MN
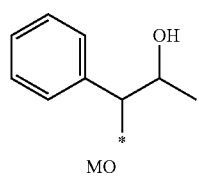 [SMILES: *C(c1ccccc1)C(C)O]
MO
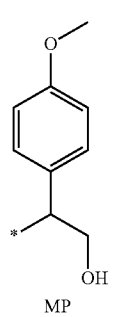
MP
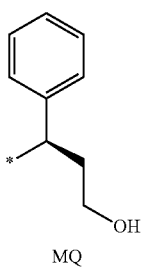
MQ
-continued
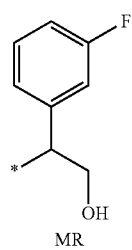
MR
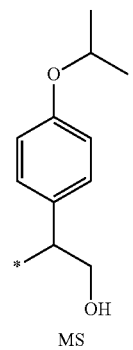 [SMILES: *C(CO)c1ccc(OC(C)C)cc1]
MS
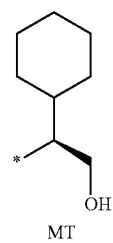
MT
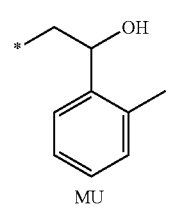
MU
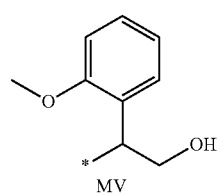
MV
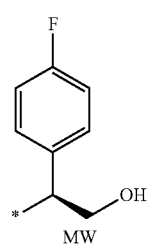
MW -continued
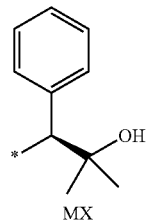
MX
MY
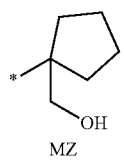
MZ
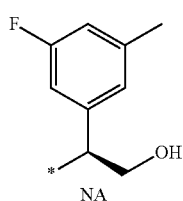
NA
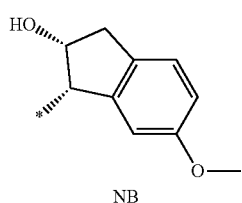 [SMILES: *[C@H]1c2cc(OC)ccc2C[C@H]1O ; "NB"]
NB
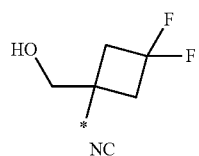
NC
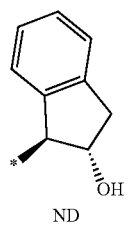
ND
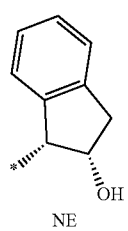
NE
-continued
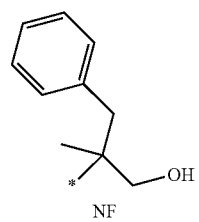
NF
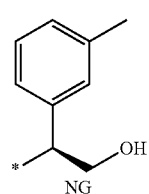 [SMILES: *[C@H](CO)c1cccc(C)c1]
NG
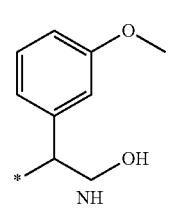
NH
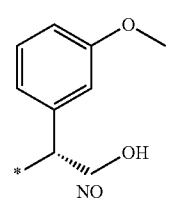
NO
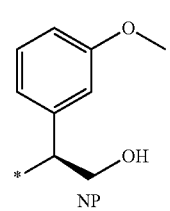
NP
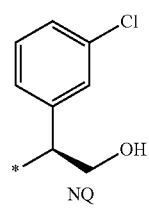
NQ
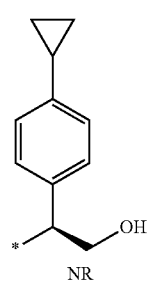 [SMILES: *[C@H](CO)c1ccc(C2CC2)cc1]
NR 71
-continued
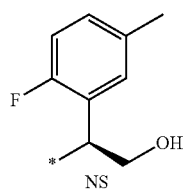
NS
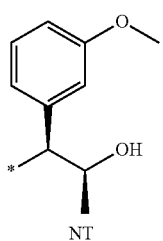
NT
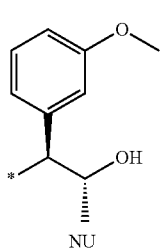
NU
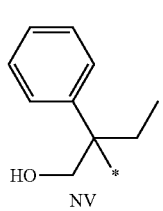
NV
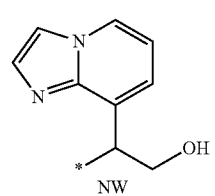
NW
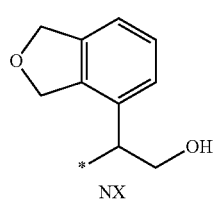 [SMILES: *C(CO)c1cccc2c1COC2]
NX
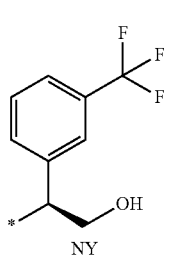
NY
72
-continued
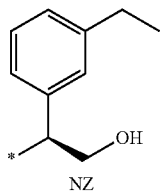 [SMILES: *[C@H](CO)c1cccc(CC)c1]
NZ
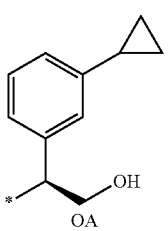
OA
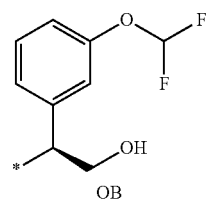
OB
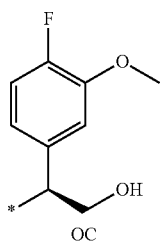
OC
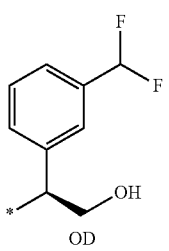
OD
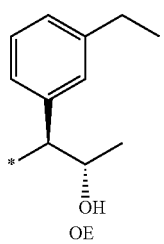
OE
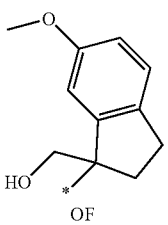
OF -continued
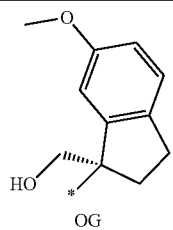
OG
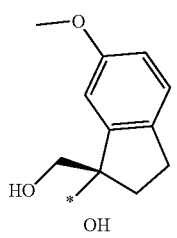
OH
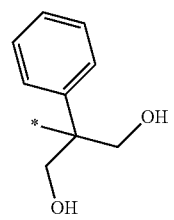
OI
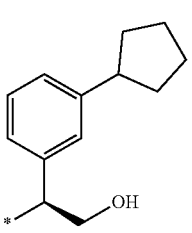
OJ
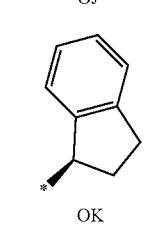
OK
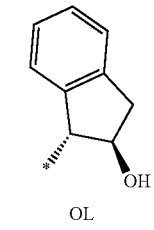
OL
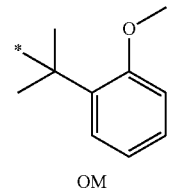 [SMILES: *C(C)(C)c1ccccc1OC]
OM
-continued
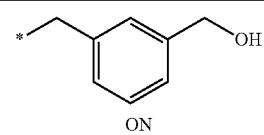
ON
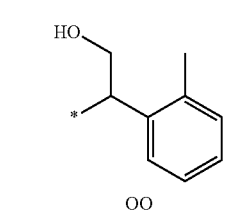
OO
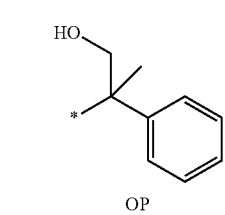
OP
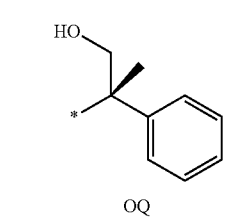 [SMILES: *[C@](C)(CO)c1ccccc1]
OQ
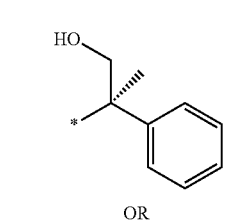 [SMILES: *[C@@](C)(CO)c1ccccc1]
OR
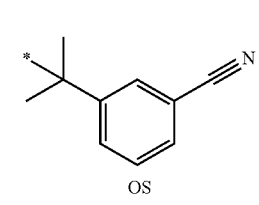
OS
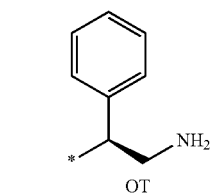
OT
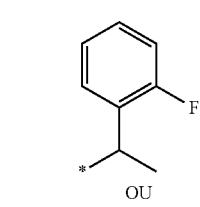
OU

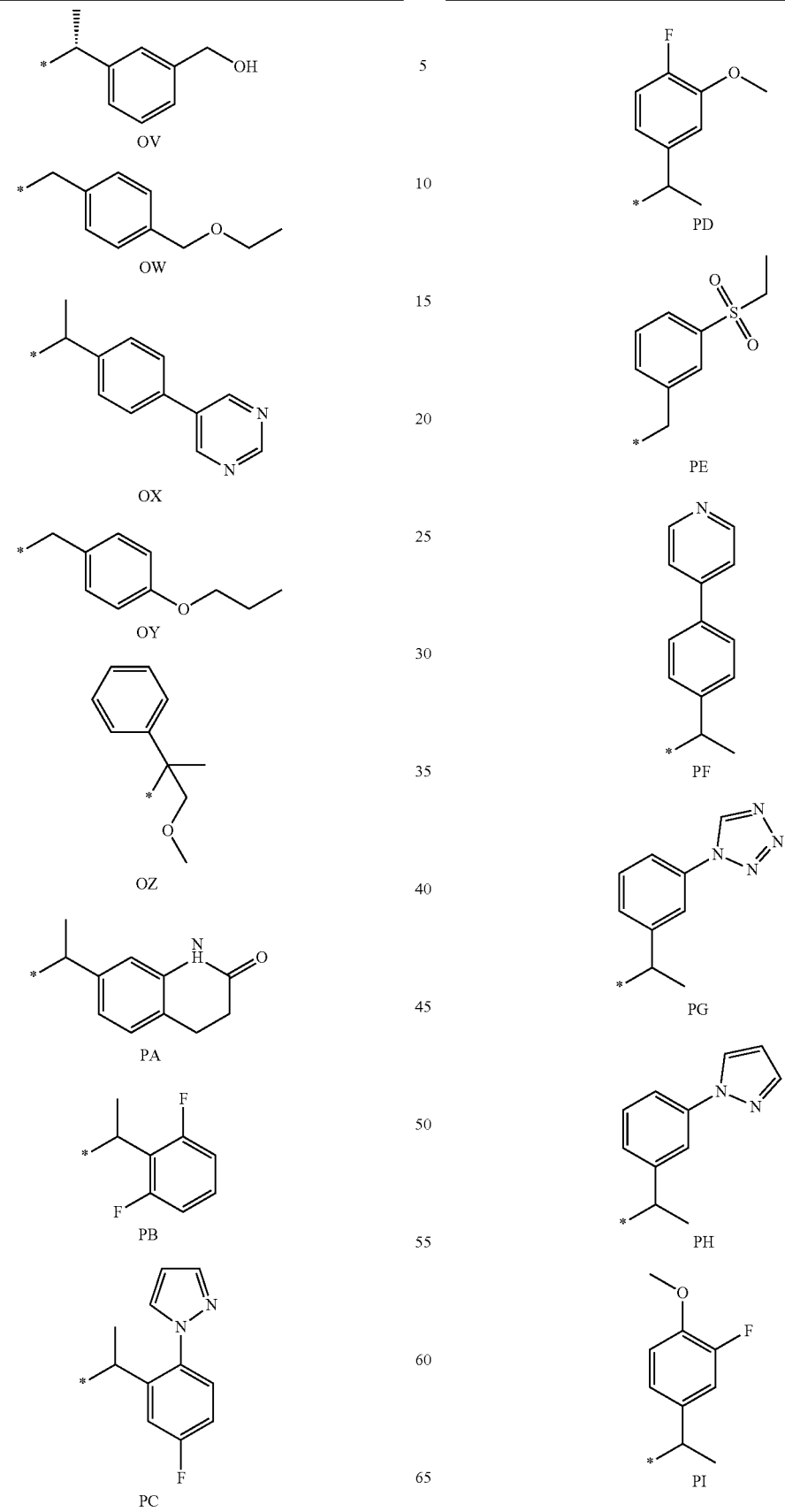

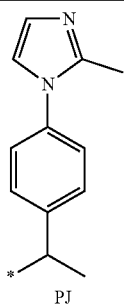
PJ
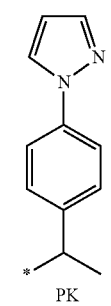
PK
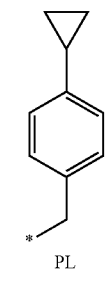
PL
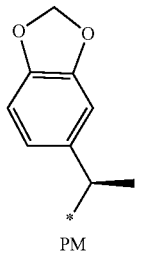 [SMILES: *[C@H](C)c1ccc2c(c1)OCO2]
PM
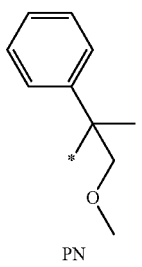 [SMILES: *C(C)(COC)c1ccccc1 ; "PN"]
PN
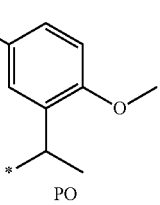
PO
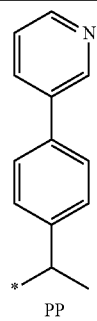
PP
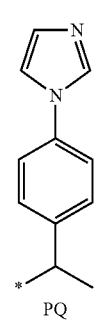
PQ
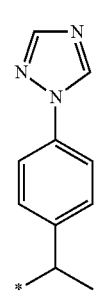
PR
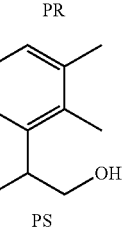
PS
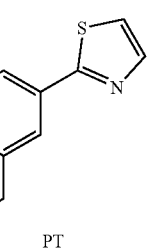
PT
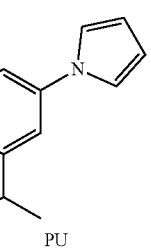
PU

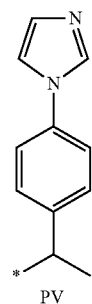
PV
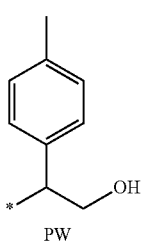
PW
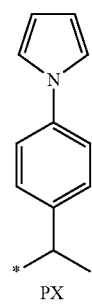
PX
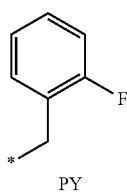
PY
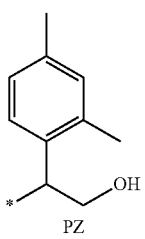
PZ
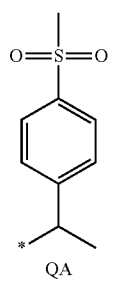
QA
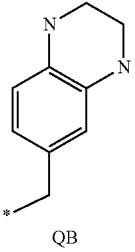
QB
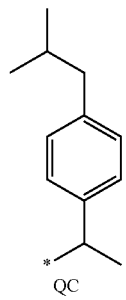
QC
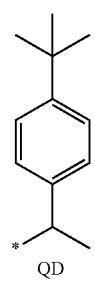
QD
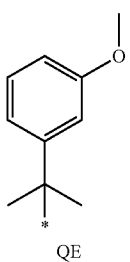
QE
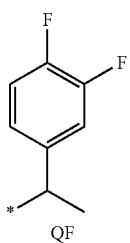
QF

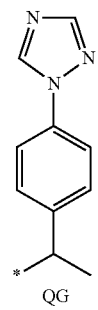
QG
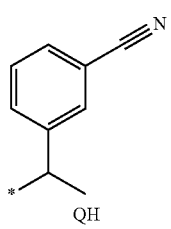
QH
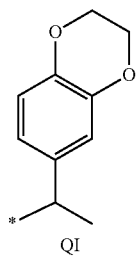
QI
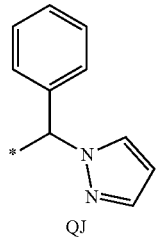
QJ
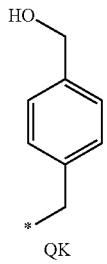
QK
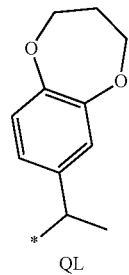
QL
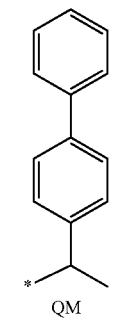
QM
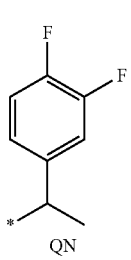
QN
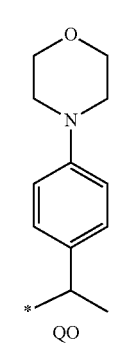
QO
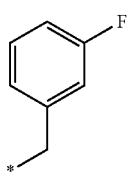
QP
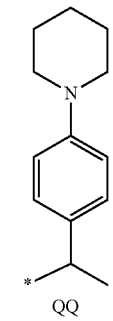
QQ
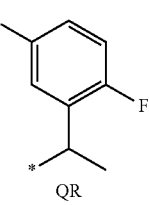
QR

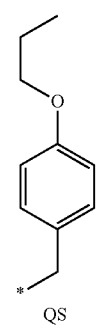
QS
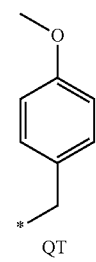
QT
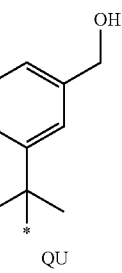
QU
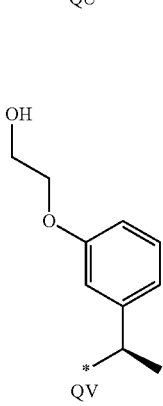
QV
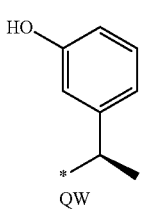
QW
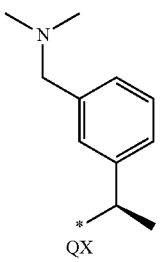
QX
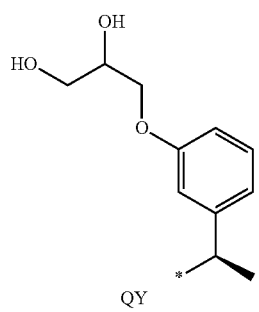
QY
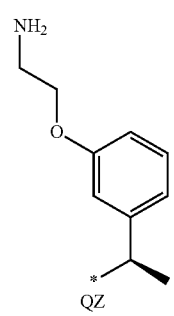
QZ
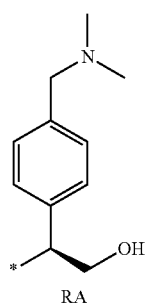
RA
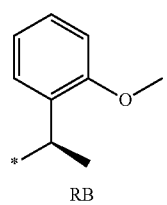 [SMILES: *[C@H](C)c1ccccc1OC]
RB
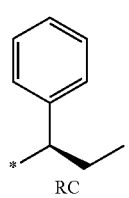
RC 85
-continued
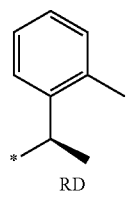
RD
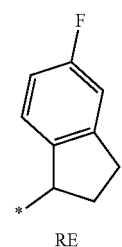 [SMILES: *C1CCc2cc(F)ccc21]
RE
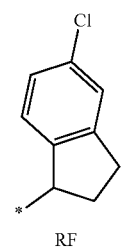
RF
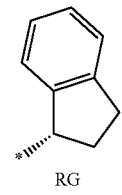
RG
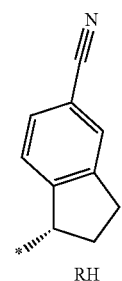
RH
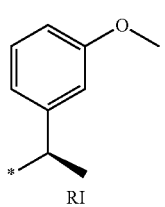
RI
86
-continued
RJ
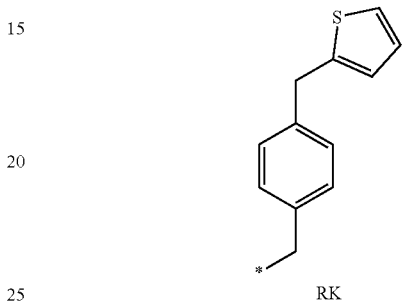
RK
RL
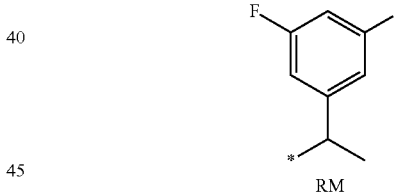
RM
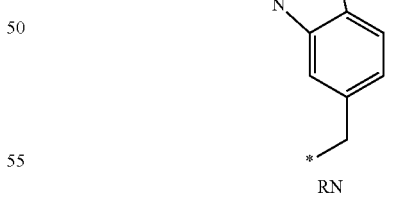
RN
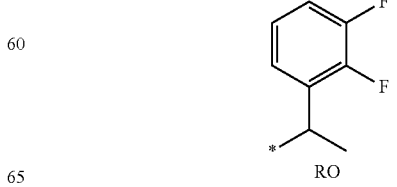
RO

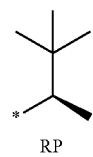 [SMILES: *[C@H](C)C(C)(C)C]
RP
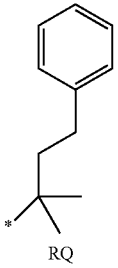
RQ
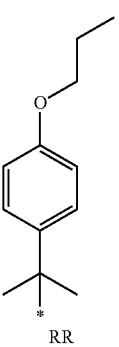
RR
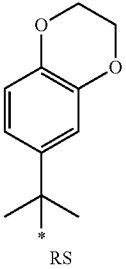
RS
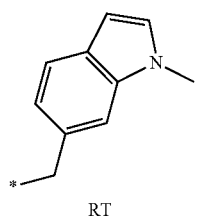
RT
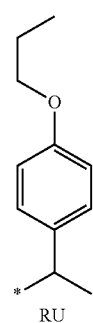
RU
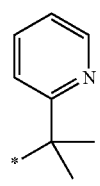
RV
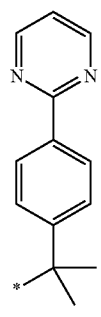
RW
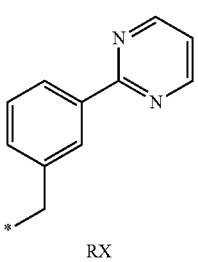
RX
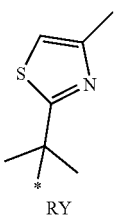
RY
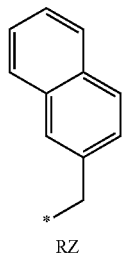
RZ
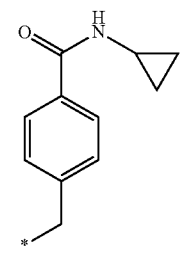
SA

89
-continued
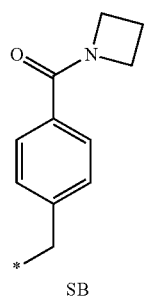
SB
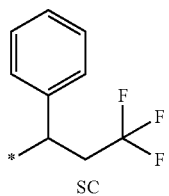
SC
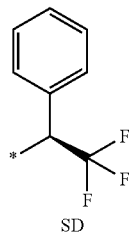
SD
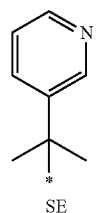 [SMILES: *C(C)(C)c1cccnc1]
SE
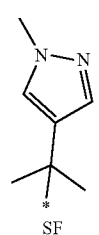
SF
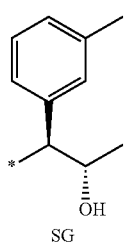
SG
90
-continued
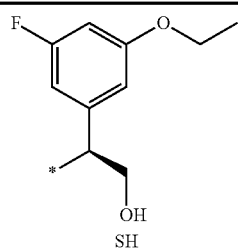
SH
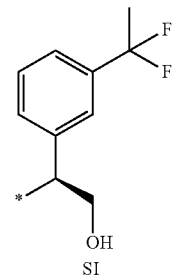
SI
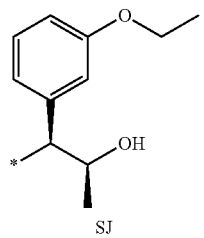
SJ
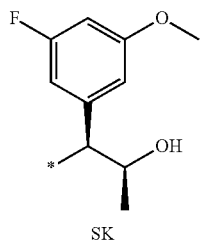
SK
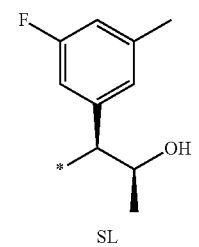 [SMILES: *[C@@H](c1cc(C)cc(F)c1)[C@H](C)O]
SL
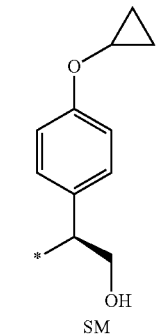
SM -continued

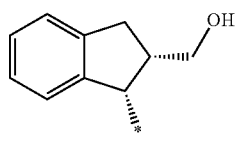
SN

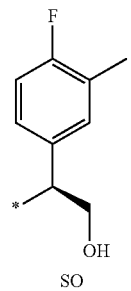
SO

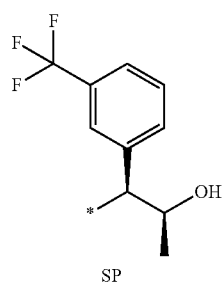 [SMILES: *[C@@H](c1cccc(C(F)(F)F)c1)[C@H](C)O ; "SP"]
SP

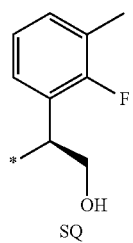
SQ

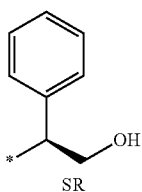
SR

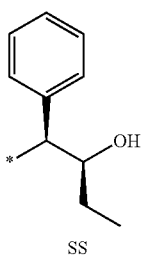
SS

-continued

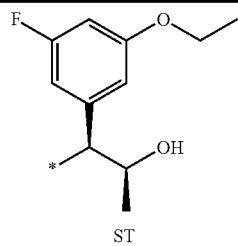
ST

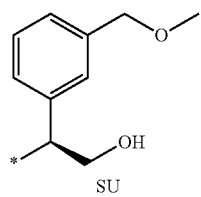
SU

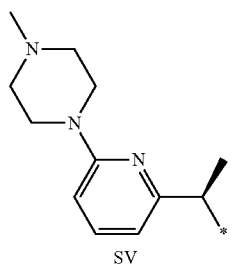
SV

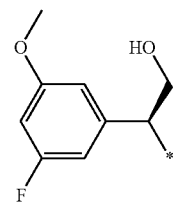
SW

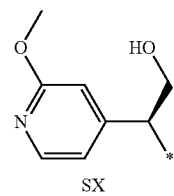
SX 1.140B A compound according to Embodiment 1.140A wherein $R^9$ is selected from groups IH, KQ, NG and NP in Table 3, where * marks the point of connection to the N atom.

1.140C A compound according to Embodiment 1.140A wherein $R^9$ is selected from groups SV, SW and SX in Table 3, where * marks the point of connection to the N atom.

1.140D A compound according to Embodiment 1.140B wherein $R^9$ is group NG in Table 3, where * marks the point of connection to the N atom.

1.140E A compound according to Embodiment 1.140B wherein $R^9$ is group SW in Table 3, where * marks the point of connection to the N atom.

1.141 A compound according to Embodiment 1.126 wherein $NR^8R^9$ forms a heterocyclic group having from 4 to 12 ring members wherein, in addition to the nitrogen atom of $NR^8R^9$, the heterocyclic group optionally contains 1 or 2 further heteroatom ring members selected from O, N and S and oxidised forms of S; and wherein the heterocyclic group is optionally substituted with one or more substituents $R^{10}$.

1.142 A compound according to Embodiment 1.141 wherein $NR^8R^9$ forms a heterocyclic group having from 4 to 11 ring members wherein, in addition to the nitrogen atom of $NR^8R^9$, the heterocyclic group optionally contains 1 or 2 further heteroatom ring members selected from O and N; and wherein the heterocyclic group is optionally substituted with one or more substituents $R^{10}$.

1.143 A compound according to Embodiment 1.142 wherein $NR^8R^9$ forms a heterocyclic group selected from:
monocyclic heterocyclic groups having from 4 to 7 ring members wherein, in addition to the nitrogen atom of $NR^8R^9$, the heterocyclic group optionally contains 1 or 2 further heteroatom ring members selected from O and N; and wherein the heterocyclic group is optionally substituted with one or more substituents $R^{10}$;
non-aromatic bicyclic heterocyclic groups having from 7 to 10 ring members wherein, in addition to the nitrogen atom of $NR^8R^9$, the heterocyclic group optionally contains 1 or 2 further heteroatom ring members selected from O and N; and wherein the heterocyclic group is optionally substituted with one or more substituents $R^{10}$; and
bicyclic heterocyclic groups having from 7 to 11 ring members, one ring of the bicyclic heterocyclic group being aromatic and the other ring being non-aromatic; wherein, in addition to the nitrogen atom of $NR^8R^9$, the heterocyclic group optionally contains 1 or 2 further heteroatom ring members selected from O and N; and wherein the heterocyclic group is optionally substituted with one or more substituents $R^{10}$.

1.144 A compound according to Embodiment 1.143 wherein $NR^8R^9$ forms a heterocyclic group selected from:
monocyclic heterocyclic groups having from 4 to 7 ring members wherein, in addition to the nitrogen atom of $NR^8R^9$, the heterocyclic group optionally contains 1 or 2 further heteroatom ring members selected from O and N; and wherein the heterocyclic group is optionally substituted with one or more substituents $R^{10}$.

1.145 A compound according to Embodiment 1.143 or Embodiment 1.144 wherein the monocyclic heterocyclic group is non-aromatic.

1.146 A compound according to Embodiment 1.145 wherein the monocyclic heterocyclic group is selected from azetidine, pyrrolidine, piperidine, azepane, morpholine and piperazine, the heterocyclic group being optionally substituted with one or more substituents $R^{10}$.

1.147 A compound according to Embodiment 1.143 wherein $NR^8R^9$ forms a heterocyclic group selected from:
non-aromatic bicyclic heterocyclic groups having from 7 to 10 ring members wherein, in addition to the nitrogen atom of $NR^8R^9$, the heterocyclic group optionally contains 1 or 2 further heteroatom ring members selected from O and N; and wherein the heterocyclic group is optionally substituted with one or more substituents $R^{10}$.

1.148 A compound according to Embodiment 1.147 wherein $NR^8R^9$ forms a heterocyclic group selected from:
non-aromatic fused bicyclic, spirobicyclic and bridge bicyclic heterocyclic groups having from 7 to 10 ring members wherein, in addition to the nitrogen atom of $NR^8R^9$, the heterocyclic group optionally contains 1 or 2 further heteroatom ring members selected from O and N; and wherein the heterocyclic group is optionally substituted with one or more substituents $R^{10}$.

1.149 A compound according to Embodiment 1.148 wherein $NR^8R^9$ forms a heterocyclic group selected from:
non-aromatic fused bicyclic, spirobicyclic and bridge bicyclic heterocyclic groups having from 7 to 10 ring members wherein, in addition to the nitrogen atom of $NR^8R^9$, the heterocyclic group optionally contains no further heteroatom ring members; and wherein the heterocyclic group is optionally substituted with one or more substituents $R^{10}$.

1.150 A compound according to Embodiment 1.149 wherein $NR^8R^9$ forms a non-aromatic heterocyclic group selected from 5.5 fused bicyclic heterocyclic rings; 5.6 fused bicyclic heterocyclic rings; spirocyclopropylpiperidine; azabicyclo-heptanes; and azabicyclooctanes; and
wherein the heterocyclic group is optionally substituted with one or more substituents $R^{10}$.

1.151 A compound according to Embodiment 1.141 wherein $NR^8R^9$ forms a heterocyclic group selected from:
fused bicyclic heterocyclic groups having from 7 to 11 ring members, one ring of the fused bicyclic heterocyclic group being aromatic and the other ring being non-aromatic;
wherein, in addition to the nitrogen atom of $NR^8R^9$, the heterocyclic group optionally contains 1 or 2 further heteroatom ring members selected from O and N; and wherein the heterocyclic group is optionally substituted with one or more substituents $R^{10}$.

1.151A A compound according to Embodiment 1.141 wherein $NR^8R^9$ forms a heterocyclic group selected from:
fused bicyclic heterocyclic groups having from 7 to 12 ring members, one ring of the fused bicyclic heterocyclic group being aromatic and the other ring being non-aromatic; wherein, in addition to the nitrogen atom of $NR^8R^9$, the heterocyclic group optionally contains 1 or 2 further heteroatom ring members selected from O and N; and wherein the heterocyclic group is optionally substituted with one or more substituents $R^{10}$.

1.152 A compound according to Embodiment 1.151 or Embodiment 1.51A wherein the aromatic ring of the fused bicyclic heterocyclic ring is a 5 or 6 membered ring containing 0, 1 or 2 heteroatom ring members selected from N and O.

1.153 A compound according to Embodiment 1.152 wherein the aromatic ring of the fused bicyclic heterocyclic ring is a 5 or 6 membered ring containing 0, 1 or 2 nitrogen ring members; for example wherein the aromatic ring is selected from benzene, pyrrole, pyridine and pyrimidine rings.

1.154 A compound according to any one of Embodiments 1.151 to 1.153 wherein the non-aromatic ring is selected from 5, 6 and 7-membered rings and bridged bicyclic rings, provided that the total number of ring members in the heterocyclic group does not exceed 11.

1.154 A compound according to any one of Embodiments 1.151 to 1.153 wherein the non-aromatic ring is selected from 5, 6 and 7-membered rings, provided that the total number of ring members in the heterocyclic group does not exceed 11.

1.155 A compound according to any one of Embodiments 1.151 to 1.154 wherein the nitrogen atom of $NR^8R^9$ is located in the non-aromatic ring.

1.156 A compound according to any one of Embodiments 1.151 to 1.154 wherein the non-aromatic ring is selected from 5, 6 and 7-membered rings containing a single nitrogen heteroatom ring member and 6- and 7-membered rings containing one nitrogen and one oxygen heteroatom ring member.

1.157 A compound according to Embodiment 1.151 wherein $NR^8R^9$ forms a heterocyclic group selected from tetrahydroisoquinoline; tetrahydroquinoline; dihydroindole; dihydroisoindole; tetrahydrobenzazepine; pyrimidinopiperidine; benzomorpholine and benzo-homomorpholine; and wherein the heterocyclic group is optionally substituted with one or more substituents $R^{10}$.

1.157AA compound according to Embodiment 1.141 wherein $NR^8R^9$ forms a heterocyclic group selected from tetrahydroisoquinoline; tetrahydroquinoline; tetrahydronapthyridine; dihydroindole; dihydroisoindole; tetrahydrobenzazepine; pyrimidinopiperidine; benzomorpholine; benzo-homomorpholine; azatricyclododecatrienyl; and tetrahydro-oxopyrimidoazepine wherein the heterocyclic group is optionally substituted with one or more substituents $R^{10}$.

1.158 A compound according to Embodiment 1.157 wherein $NR^8R^9$ forms a heterocyclic group selected from tetrahydroisoquinoline and tetrahydrobenzazepine; and wherein the heterocyclic group is optionally substituted with one or more substituents $R^{10}$.

1.159 A compound according to Embodiment 1.158 wherein $NR^8R^9$ forms a tetrahydroisoquinoline group which is optionally substituted with one or more substituents $R^{10}$.

1.160 A compound according to Embodiment 1.158 wherein $NR^8R^9$ forms a tetrahydrobenzazepine group which is optionally substituted with one or more substituents $R^{10}$.

1.161 A compound according to anyone of Embodiments 1.126 to 1.160 having the formula (8):

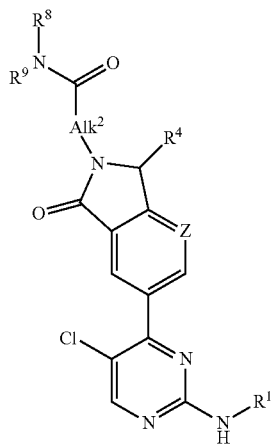

(8)

or a pharmaceutically acceptable salt or tautomer thereof, wherein $R^1$, $R^4$, $R^8$, $R^9$, $Alk^2$ and Z are as defined in any of the preceding Embodiments.

1.161A A compound according to Embodiment 1.161 wherein the compound has the structure (8A):

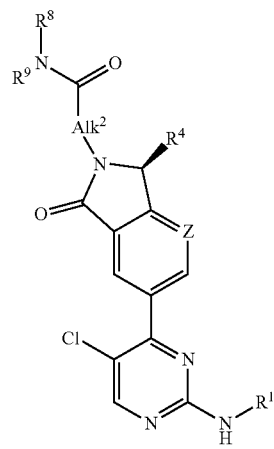

(8A)

1.161B A compound according to Embodiment 1.161 wherein the compound has the structure (8B):

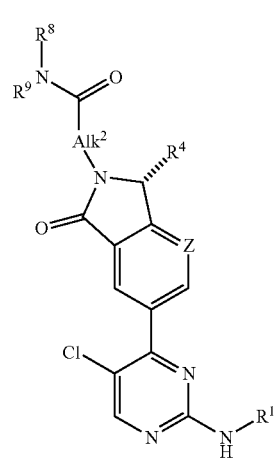

(8B)

1.162 A compound according to anyone of Embodiments 1.126 to 1.160 having the formula (9):

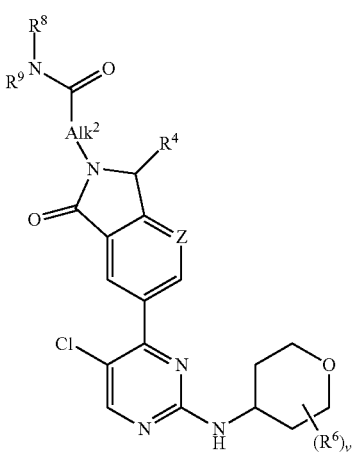

(9)

or a pharmaceutically acceptable salt or tautomer thereof, wherein $R^4$, $R^6$, $R^8$, $R^9$, $Alk^2$, Z and v are as defined in any of the preceding Embodiments.

1.162A A compound according to Embodiment 1.162 wherein the compound has the structure (9A):

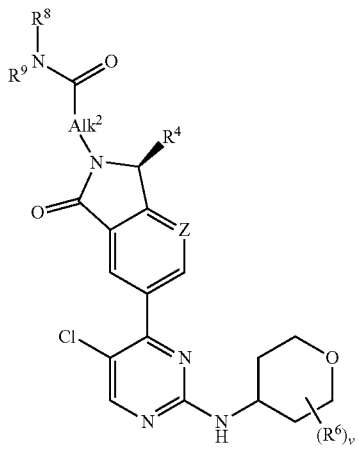

(9A)

1.162B A compound according to Embodiment 1.162 wherein the compound has the structure (9B):

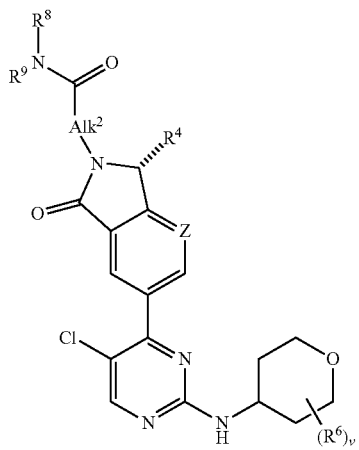

(9B)

1.162C A compound according to any one of Embodiments 1.161 to 1.162B wherein the moiety:

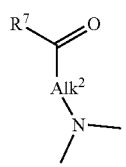

has the structure:

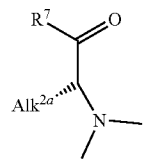

where $Alk^{2a}$ ia the residue of $Alk^2$.

1.162D A compound according to any one of Embodiments 1.161 to 1.162B wherein the moiety:

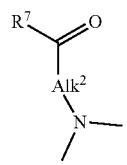

has the structure:

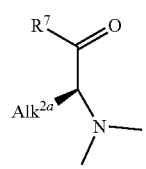

where $Alk^{2a}$ ia the residue of $Alk^2$.

1.163 A compound according to any one of Embodiments 0.1 to 1.100 and 1.102 to 1.162D wherein $R^{10}$ is selected from:
halogen; hydroxy; oxo; cyano;
$OR^{12}$ wherein $R^{12}$ is $C_{1-6}$ alkyl or $C_{3-6}$ cycloalkyl, each being optionally substituted with halogen;
an acyclic $C_{1-8}$ hydrocarbon group optionally substituted with one or more substituents selected from hydroxy; oxo; halogen; cyano; carboxy; amino; mono- or di-$C_{1-4}$ alkylamino; and carbocyclic and heterocyclic groups having 3 to 6 ring members of which 0, 1 or 2 are heteroatom ring members selected from N, O and S, wherein the carbocyclic and heterocyclic groups are optionally substituted with one or more substituents $R^{13}$ selected from hydroxy; halogen; cyano; and —(O)$_v$-Hyd$^1$ where v is 0 or 1; wherein one or two but not all of the carbon atoms of the acyclic $C_{1-8}$ hydrocarbon group may optionally be replaced by O, S, SO, $SO_2$ or $NR^{11}$; and
carbocyclic and heterocyclic groups having 3 to 6 ring members of which 0, 1 or 2 are heteroatom ring members selected from N, O and S, wherein the carbocyclic and heterocyclic groups are optionally substituted with one or more substituents $R^{13}$; and
$R^{11}$ is selected from hydrogen and a $C_{1-4}$ hydrocarbon group.

1.164 A compound according to Embodiment 1.163 wherein $R^{10}$ is selected from:
halogen; hydroxy; oxo; cyano;
$OR^{12}$ wherein $R^{12}$ is $C_{1-6}$ alkyl or $C_{3-6}$ cycloalkyl, each being optionally substituted with halogen;
an acyclic $C_{1-8}$ hydrocarbon group (e.g. an alkyl, alkenyl or alkynyl group) optionally substituted with one or more substituents selected from hydroxy; oxo; halogen; cyano; carboxy; amino; mono- or di-$C_{1-4}$ alkylamino; wherein one or two but not all of the carbon atoms of the acyclic $C_{1-8}$ hydrocarbon group may optionally be replaced by O, S, SO, $SO_2$ or $NR^{11}$; and aryl and heteroaryl groups having 5 or 6 ring members of which 0, 1 or 2 are heteroatom ring members selected from N, O and S, wherein the aryl and heteroaryl groups are optionally substituted with one or more substituents selected from hydroxy; halogen; halogen; cyano; and —$(O)_v$-$Hyd^1$ where v is 0 or 1; and $R^{11}$ is selected from hydrogen and a $C_{1-4}$ hydrocarbon group (e.g. an alkyl, alkenyl, alkynyl, cycloalkyl, alkylcycloalkyl or cycloalkyl group).

1.165 A compound according to Embodiment 1.164 wherein $R^{10}$ is selected from:

fluorine; chlorine; hydroxy; oxo; cyano; methoxy; ethoxy; trifluoromethoxy; difluoromethoxy;

an acyclic $C_{1-6}$ hydrocarbon group (e.g. an alkyl, alkenyl or alkynyl group) optionally substituted with one or more substituents selected from hydroxy; oxo; fluorine; amino; mono- or di-$C_{1-2}$ alkylamino; wherein one but not all of the carbon atoms of the acyclic $C_{1-6}$ hydrocarbon group may optionally be replaced by O, $SO_2$ or $NR^{11}$; and aryl and heteroaryl groups having 5 or 6 ring members of which 0, 1 or 2 are heteroatom ring members selected from N, O and S, wherein the aryl and heteroaryl groups are optionally substituted with one or more substituents selected from hydroxy; fluorine; chlorine; and —$(O)_v$-$Hyd^1$ where v is 0 or 1; and $R^{11}$ is selected from hydrogen and a $C_{1-2}$ alkyl group.

1.166 A compound according to Embodiment 1.165 wherein $R^{10}$ is selected from:

fluorine; chlorine; hydroxy; oxo; cyano; methoxy; ethoxy; trifluoromethoxy; difluoromethoxy;

a $C_{1-4}$ hydrocarbon group (e.g. an alkyl, alkenyl, alkynyl, cyclopropyl, methylcyclopropyl or cyclopropylmethyl group) optionally substituted with one or more substituents selected from hydroxy; oxo; fluorine; amino; mono- or di-$C_{1-2}$ alkylamino; wherein one but not all of the carbon atoms of the $C_{1-4}$ alkyl group may optionally be replaced by O;

phenyl optionally substituted with one or more substituents selected from hydroxy; fluorine; chlorine; and —$(O)_v$-$Hyd^1$ where v is 0 or 1;

heteroaryl groups having 5 or 6 ring members of which 1 or 2 are heteroatom ring members selected from N, O and S, wherein the heteroaryl groups are optionally substituted with one or more substituents selected from hydroxy; fluorine; chlorine; and —$(O)_v$-$Hyd^1$ where v is 0 or 1.

1.167 A compound according to Embodiment 1.166 wherein $R^{10}$ is selected from:

fluorine; chlorine; hydroxy; oxo; cyano; methoxy; ethoxy; trifluoromethoxy; difluoromethoxy;

a saturated $C_{1-4}$ hydrocarbon group (e.g. $C_{1-4}$ alkyl, cyclopropyl, cyclobutyl, cyclopropylmethyl or methylcyclopropyl) optionally substituted with one or more substituents selected from hydroxy and fluorine; wherein one but not all of the carbon atoms of the $C_{1-4}$ hydrocarbon group may optionally be replaced by O;

phenyl optionally substituted with one or more substituents selected from hydroxy; fluorine; chlorine; and —$(O)_v$-$Hyd^1$ where v is 0 or 1;

heteroaryl groups having 5 or 6 ring members of which 1 or 2 are heteroatom ring members selected from N, O and S, wherein the heteroaryl groups are optionally substituted with one or more substituents selected from hydroxy; fluorine; chlorine; and —$(O)_v$-$Hyd^1$ where v is 0 or 1.

1.168 A compound according to Embodiment 1.167 wherein $R^{10}$ is selected from:

fluorine; chlorine; hydroxy; oxo; cyano; methoxy; ethoxy; trifluoromethoxy; difluoromethoxy;

a saturated $C_{1-4}$ hydrocarbon group (e.g. $C_{1-4}$ alkyl, cyclopropyl, cyclobutyl, cyclopropylmethyl or methylcyclopropyl) optionally substituted with one or more substituents selected from hydroxy and fluorine; wherein one but not all of the carbon atoms of the $C_{1-4}$ hydrocarbon group may optionally be replaced by O;

phenyl optionally substituted with one or more substituents selected from hydroxy; fluorine; chlorine; and —$(O)_v$-$Hyd^1$ where v is 0 or 1;

heteroaryl groups having 5 ring members of which 1 or 2 are heteroatom ring members selected from N, O and S, wherein the heteroaryl groups are optionally substituted with one or more substituents selected from —$(O)_v$-$Hyd^1$ where v is 0.

1.169 A compound according to Embodiment 1.168 wherein $R^{10}$ is selected from oxo; fluorine; chlorine; cyano; methyl; ethyl; isopropyl; tert-butyl; hydroxymethyl; trifluoromethyl; methoxy; trifluoromethoxy; difluoromethoxy; phenyl; and thiazolyl.

1.169A A compound according to Embodiment 1.163 wherein $R^{10}$ is selected from fluorine, methyl, methoxy and dimethylamino.

1.169B A compound according to any one of Embodiments 0.1 to 1.100 and 1.102 to 1.169 wherein there are 0, 1, 2, 3 or 4 substituents $R^{10}$ present in $R^7$.

1.169C A compound according to any one of Embodiments 0.1 to 1.100 and 1.102 to 1.169 wherein there are 0, 1, 2 or 3 substituents $R^{10}$ present in $R^7$.

1.169D A compound according to any one of Embodiments 0.1 to 1.100 and 1.102 to 1.169 wherein there are 0, 1 or 2 substituents $R^{10}$ present in $R^7$.

1.169E A compound according to any one of Embodiments 0.1 to 1.100 and 1.102 to 1.169 wherein there are 1 or 2 substituents $R^{10}$ present in $R^7$.

1.169F A compound according to any one of Embodiments 0.1 to 1.100 and 1.102 to 1.169 wherein there are 0 substituents $R^{10}$ present in $R^7$.

1.169G A compound according to any one of Embodiments 0.1 to 1.100 and 1.102 to 1.169 wherein there is 1 substituent $R^{10}$ present in $R^7$.

1.169H A compound according to any one of Embodiments 0.1 to 1.100 and 1.102 to 1.169 wherein there are 2 substituents $R^{10}$ present in $R^7$.

1.169J A compound of formula (0):

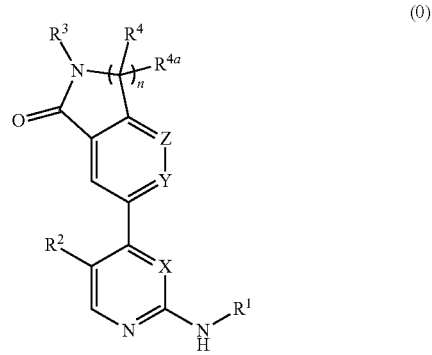

or a pharmaceutically acceptable salt, N-oxide or tautomer thereof; wherein:

n is 1 or 2;

X is CH or N;

Y is selected from CH and C—F;

Z is selected from C—$R^z$ and N;

$R^z$ is selected from hydrogen; fluorine; methoxy; and $C_{1-2}$ alkyl optionally substituted with hydroxy or methoxy;

$R^1$ is selected from:

-$(Alk^1)_t$-$Cyc^1$; wherein t is 0 or 1; and $Alk^1$ is a methylene group; and $C_{1-6}$ acyclic hydrocarbon groups which are unsubstituted or substituted with 1, 2 or 3 substituents $R^5$ selected from hydroxy; oxo; and cyano; and wherein 1 but not all of the carbon atoms of the hydrocarbon group can be replaced by O (for example to form an alkoxyalkyl group such as methoxyethyl or methoxypropyl;

$Cyc^1$ is a cyclic group selected from (a) 3 to 8 membered non-aromatic monocyclic and bicyclic carbocyclic and heterocyclic groups containing 0 or 1 heteroatom ring members selected from O, N, S, S(O) and S(O)$_2$; (b) 5 to 6 membered monocyclic heteroaryl groups containing 1, 2 or 3 heteroatom ring members of which 1 is N and the others, when present, are selected from O, N and S; and (c) phenyl; (a), (b) and (c) is unsubstituted or substituted with 1, 2 or 3 substituents $R^6$ selected from hydroxy; oxo; fluorine; amino; N(Hyd$^1$)$_2$; O-Hyd$^1$; —C(=O)-Hyd$^1$; —C(=O)—O-Hyd$^1$ and Hyd$^1$; where Hyd$^1$ is a $C_{1-3}$ non-aromatic hydrocarbon group optionally substituted with one or more substituents selected from fluorine, hydroxyl and methoxy;

$R^2$ is selected from hydrogen; fluorine, chlorine, bromine, methyl, trifluoromethyl, ethyl, 1-hydroxyethyl, cyclopropyl, iso-propyl, vinyl and allyl groups $R^3$ is hydrogen or a group $L^1$-$R^7$;

$R^4$ is selected from hydrogen; methoxy; and $C_{1-3}$ alkyl optionally substituted with hydroxy, amino, di-$C_{1-2}$ alkylamino, or methoxyl;

$R^{4a}$ is selected from hydrogen and methyl;

$L^1$ is selected from a bond; $Alk^2$ and $Alk^2$-C(=O); wherein $Alk^2$ is a $C_{1-4}$ straight chain or branched alkylene group which is optionally substituted with one or more substituents selected from hydroxy, methoxy, amino, methylamino, (dimethyl)amino and fluorine;

$R^7$ is selected from:

hydrogen;

CO$_2$H;

NR$^8$R$^9$;

a heterocyclic group having from 5 to 12 ring members, of which 1, 2 or 3 are heteroatom ring members selected from O and N, the carbocyclic or heterocyclic group being optionally substituted with one or more substituents R$^{10}$; and an acyclic $C_{1-8}$ hydrocarbon group optionally substituted with one or more substituents selected from hydroxy; oxo; mono- or di-$C_{1-4}$ alkylamino; and carbocyclic and heterocyclic groups having from 3 to 10 ring members, of which 0, 1, 2 or 3 are heteroatom ring members selected from O and N, the carbocyclic or heterocyclic group being optionally substituted with one or more substituents R$^{10}$; wherein one but not all of the carbon atoms of the acyclic $C_{1-8}$ hydrocarbon group may optionally be replaced by O or NR$^{11}$ (for example to form a $C_{1-4}$ alkoxy group such as methoxy or tert-butyloxy; or an alkoxyalkyl group such as methoxymethyl; or a group CH$_2$O; or a group O—CH(CH$_3$)$_2$);

$R^8$ is selected from hydrogen, methyl, ethyl, hydroxyethyl, aminoethyl and (dimethylamino)ethyl;

$R^9$ is selected from:

hydrogen;

a carbocyclic or heterocyclic group having from 3 to 10 ring members, of which 0, 1 or 2 are heteroatom ring members selected from O and N and oxidised forms of S, the carbocyclic or heterocyclic group being optionally substituted with one or more substituents R$^{10}$; and an acyclic $C_{1-6}$ hydrocarbon group optionally substituted with one or more substituents selected from hydroxy; fluorine; mono- or di-$C_{1-4}$ alkylamino; and carbocyclic and heterocyclic groups having from 3 to 11 ring members, of which 0, 1, 2 or 3 are heteroatom ring members selected from O, N and S, the carbocyclic or heterocyclic group being optionally substituted with one or more substituents R$^{10}$; wherein one or two but not all of the carbon atoms of the acyclic $C_{1-6}$ hydrocarbon group may optionally be replaced by O (for example to give an O-ether linkage between the acyclic hydrocarbon group and an attached carbocylic group substituent; or to give an alkoxy substituent such as methoxy on the acyclic hydrocarbon group);

or NR$^8$R$^9$ forms a heterocyclic group having from 5 to 12 ring members wherein, in addition to the nitrogen atom of NR$^8$R$^9$, the heterocyclic group optionally contains 1 or 2 further heteroatom ring members selected from O and N; and wherein the heterocyclic group is optionally substituted with one or more substituents R$^{10}$;

R$^{10}$ is selected from:

fluorine; chlorine; hydroxy; oxo; cyano;

OR$^{12}$ wherein R$^{12}$ is methyl, ethyl, propyl, iso-propyl or cyclopropyl, each being optionally substituted with fluorine;

an acyclic $C_{1-8}$ hydrocarbon group optionally substituted with one or more substituents selected from hydroxy; oxo; fluorine; amino; dimethylamino; and carbocyclic and heterocyclic groups having 3 to 7 ring members of which 0, 1, 2, 3 or 4 are heteroatom ring members selected from N, O and S, wherein the carbocyclic and heterocyclic groups are optionally substituted with one or more substituents R$^{13}$ selected from hydroxy; halogen; —N(Hyd$^1$)$_2$; and —(O)$_v$-Hyd$^1$ where v is 0 or 1; wherein one or two but not all of the carbon atoms of the acyclic $C_{1-8}$ hydrocarbon group may optionally be replaced by 0 (for example to give an alkoxy alkyl group such as methoxymethyl or ethoxymethyl; a hydroxyalkoxy group such as hydroxyethoxy; or a group C(=O)O—$C_{1-4}$ alkyl such as) SO$_2$ (for example to give a $C_{1-3}$ alkyl sulphonyl group such as ethylsulphonyl), or NR$^{11}$ (for example to give an alkylamino group such as methylamino, ethylamino, dimethylamino or methyl(ethyl)amino, or an alkylaminoalkyl group such as methylaminomethyl or dimethylaminomethyl; or an aminoalkoxy group such as aminoethoxy or dimethylaminoethoxy; or hydroxalkylamino group such as hydroxyethyl(methyl)amino; or an amide group such as C(=O)NH); and carbocyclic and heterocyclic groups having 3 to 7 ring members of which 0, 1, 2, 3 or 4 are heteroatom ring members selected from N, O and S, wherein the carbocyclic and heterocyclic groups are optionally substituted with one or more substituents R$^{13}$; and R$^{11}$ is selected from hydrogen and a $C_{1-4}$ hydrocarbon group;

provided that the compound is other than 6-benzyl-3-{2-[(2-methylpyrimidin-4-yl)amino]pyridin-4-yl}-7,8-dihydro-1,6-naphthyridin-5(6H)-one and 3-{2-[(2-methylpyrimidin-4-yl)amino]pyridin-4-yl}-7,8-dihydro-1,6-naphthyridin-5(6H)-one and salts and tautomers thereof.

1.170 A compound according to any one of Embodiments 0.1 to 1.100 or Embodiment 1.169J wherein R$^3$ is selected from groups BA to GBB in Table 2 below, where * marks the point of connection to the N atom.

TABLE 2
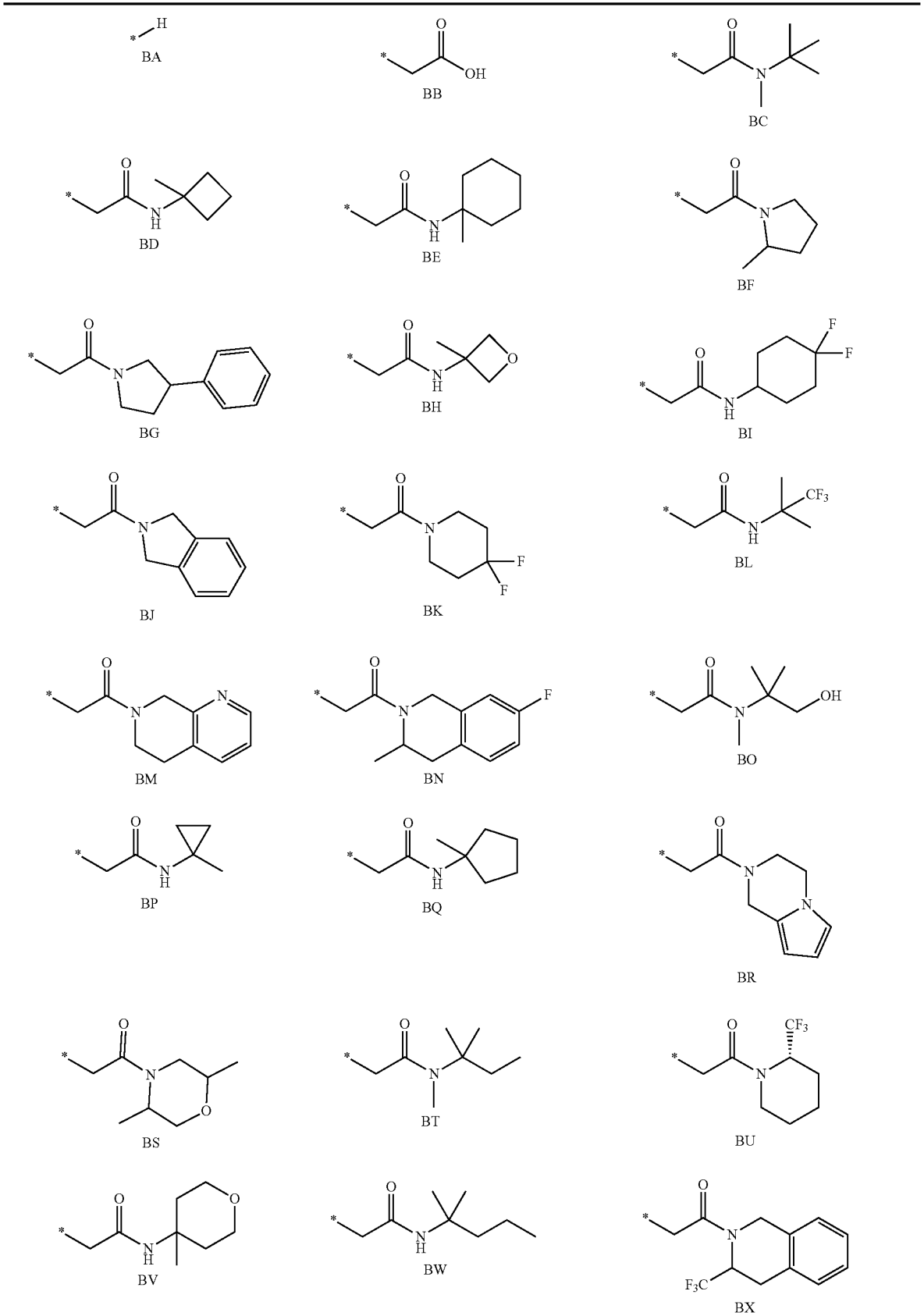

TABLE 2-continued
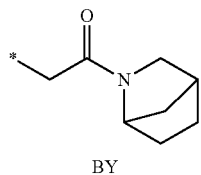 [SMILES: *CC(=O)N1CC2CCC1C2 ; "BY"]
BY
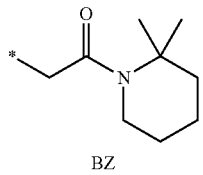
BZ
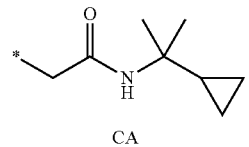 [SMILES: *CC(=O)NC(C)(C)C1CC1 ; "CA"]
CA
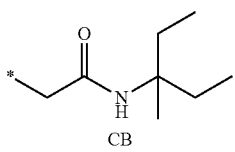
CB
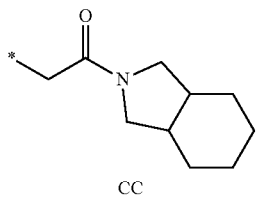 [SMILES: *CC(=O)N1CC2CCCCC2C1 ; "CC"]
CC
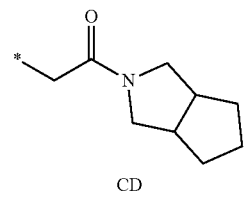 [SMILES: *CC(=O)N1CC2CCCC2C1 ; "CD"]
CD
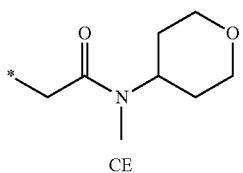 [SMILES: *CC(=O)N(C)C1CCOCC1]
CE
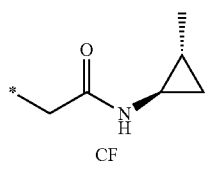
CF
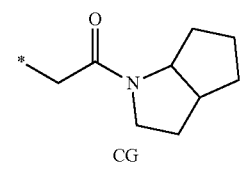
CG
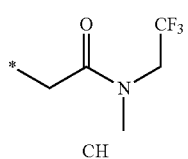
CH
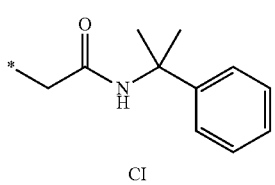 [SMILES: *CC(=O)NC(C)(C)c1ccccc1 ; "CI"]
CI
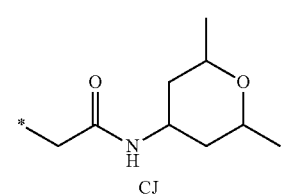
CJ
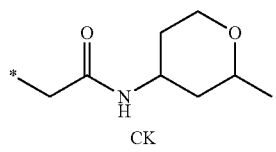
CK
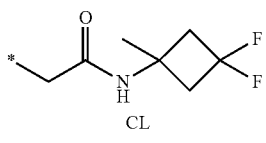
CL
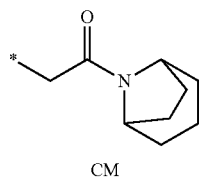 [SMILES: *CC(=O)N1C2CCCC1CC2]
CM
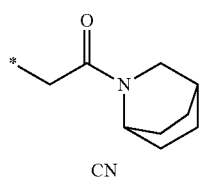 [SMILES: *CC(=O)N1CC2CCC1CC2 ; "CN"]
CN
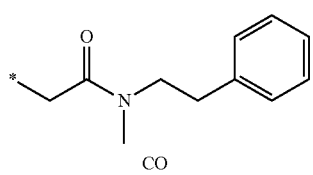
CO
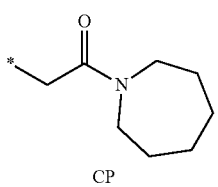 [SMILES: *CC(=O)N1CCCCCC1 ; "CP"]
CP
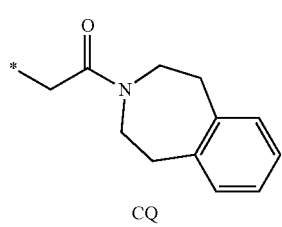
CQ
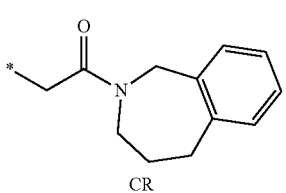
CR
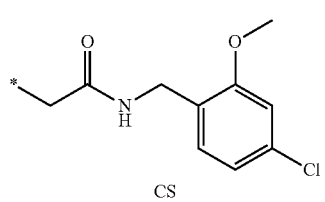 [SMILES: *CC(=O)NCc1ccc(Cl)cc1OC ; "CS"]
CS
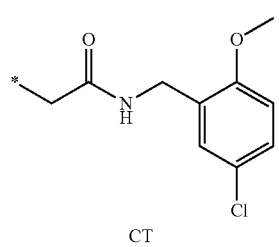 [SMILES: *CC(=O)NCc1cc(Cl)ccc1OC ; "CT"]
CT
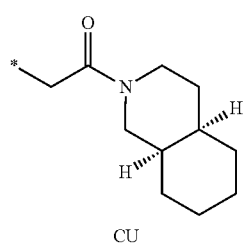 [SMILES: *CC(=O)N1CC[C@H]2CCCC[C@H]2C1 ; "CU"]
CU
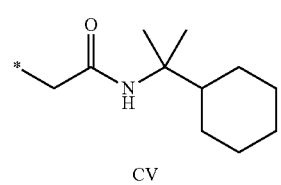 [SMILES: *CC(=O)NC(C)(C)C1CCCCC1 ; "CV"]
CV TABLE 2-continued
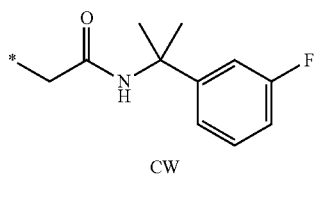 [SMILES: *CC(=O)NC(C)(C)c1cccc(F)c1 ; "CW"]
CW
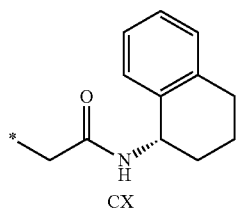
CX
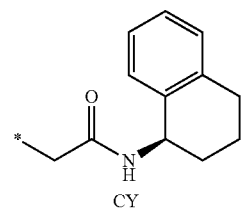
CY
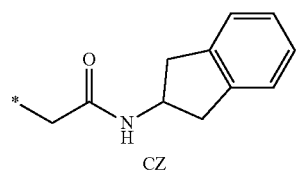
CZ
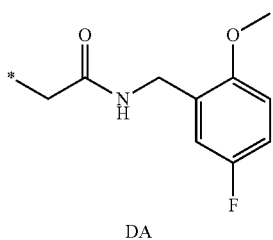 [SMILES: *CC(=O)NCc1cc(F)ccc1OC ; "DA"]
DA
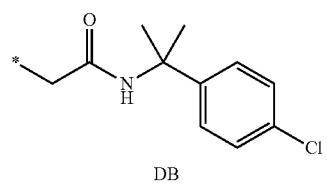 [SMILES: *CC(=O)NC(C)(C)c1ccc(Cl)cc1 ; "DB"]
DB
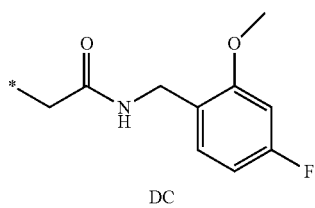 [SMILES: *CC(=O)NCc1ccc(F)cc1OC ; "DC"]
DC
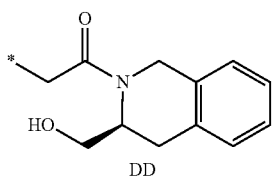
DD
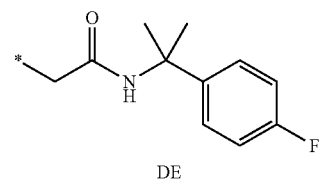 [SMILES: *CC(=O)NC(C)(C)c1ccc(F)cc1 ; "DE"]
DE
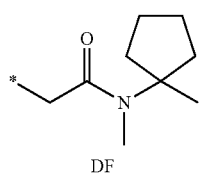
DF
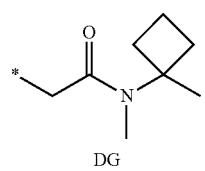
DG
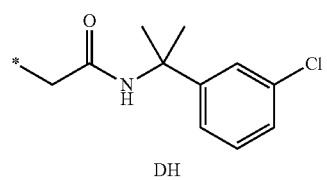
DH
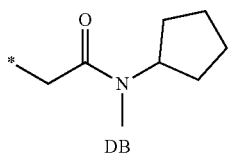
DB
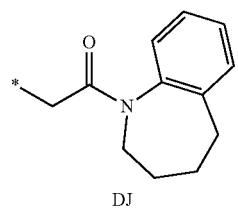
DJ
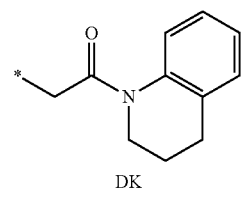
DK
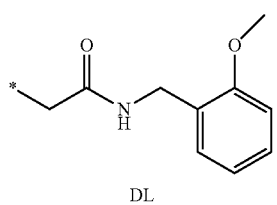 [SMILES: *CC(=O)NCc1ccccc1OC ; "DL"]
DL
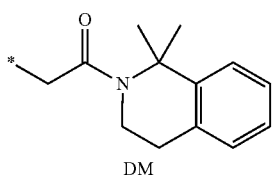
DM
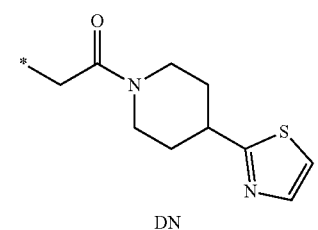 [SMILES: *CC(=O)N1CCC(c2nccs2)CC1 ; "DN"]
DN
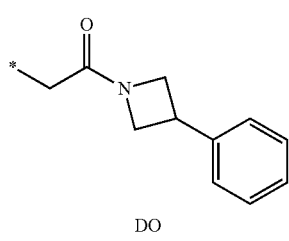 [SMILES: *CC(=O)N1CC(c2ccccc2)C1 ; "DO"]
DO
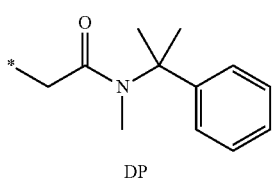
DP
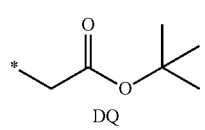
DQ TABLE 2-continued
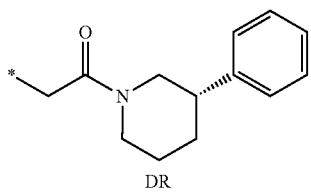
DR
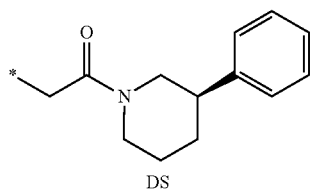
DS
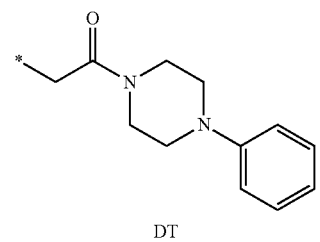 [SMILES: *CC(=O)N1CCN(c2ccccc2)CC1 ; "DT"]
DT
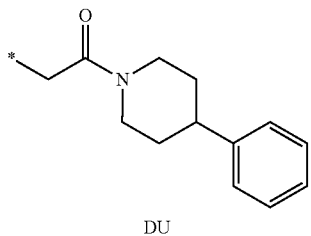
DU
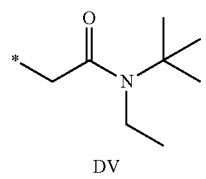 [SMILES: *CC(=O)N(CC)C(C)(C)C ; "DV"]
DV
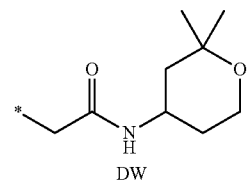
DW
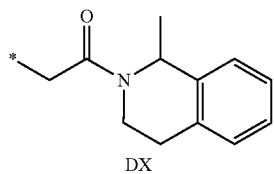
DX
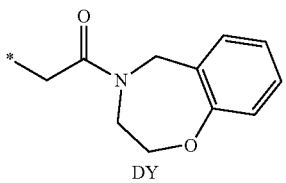
DY
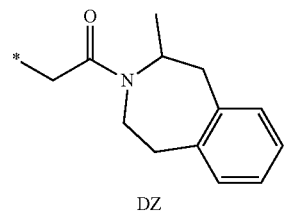
DZ
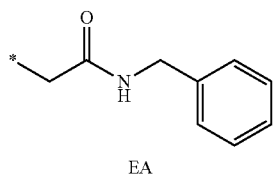 [SMILES: *CC(=O)NCc1ccccc1 ; "EA"]
EA
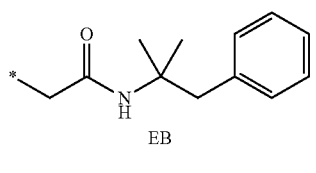
EB
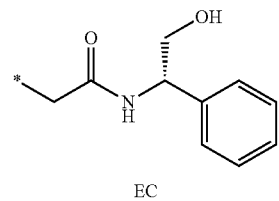 [SMILES: *CC(=O)N[C@H](CO)c1ccccc1]
EC
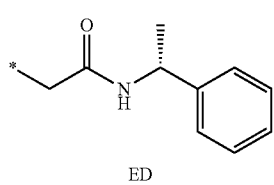 [SMILES: *CC(=O)N[C@H](C)c1ccccc1 ; "ED"]
ED
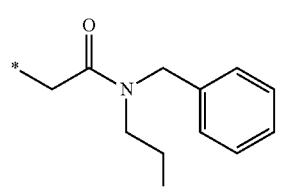
EE
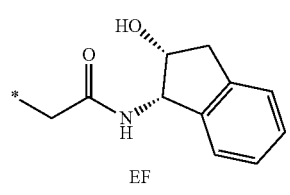 [SMILES: *CC(=O)N[C@H]1c2ccccc2C[C@H]1O]
EF
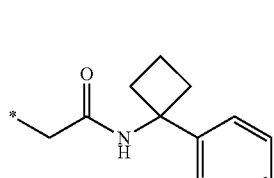
EG
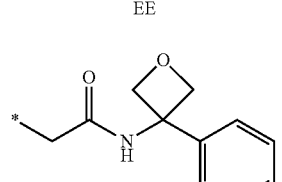
EH
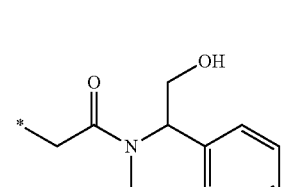
EI
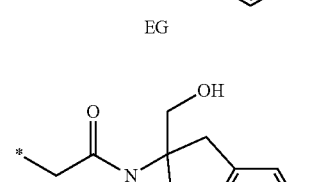
EJ
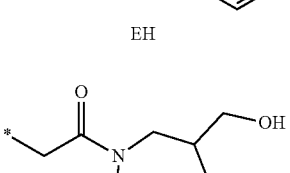
EK
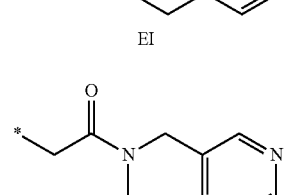
EL TABLE 2-continued
| | | |
|---|---|---|
| 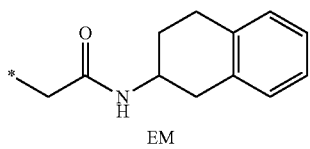 EM | 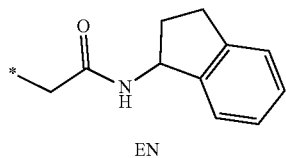 [SMILES: *CC(=O)NC1CCc2ccccc21] EN | 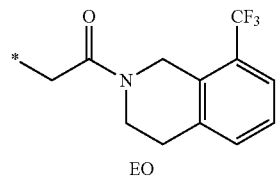 [SMILES: *CC(=O)N1CCc2cccc(C(F)(F)F)c2C1] EO |
| 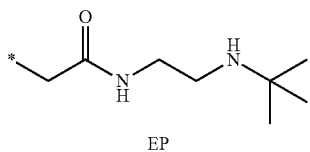 [SMILES: *CC(=O)NCCNC(C)(C)C ; "EP"] EP | 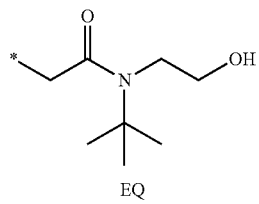 [SMILES: *CC(=O)N(CCO)C(C)(C)C] EQ | 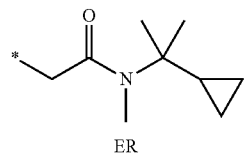 [SMILES: *CC(=O)N(C)C(C)(C)C1CC1] ER |
| 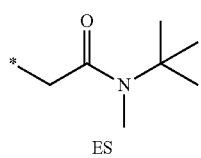 ES | 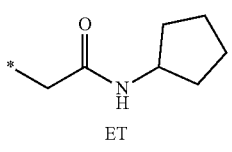 [SMILES: *CC(=O)NC1CCCC1] ET | 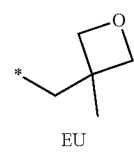 [SMILES: *CC1(C)COC1] EU |
| 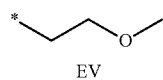 EV | 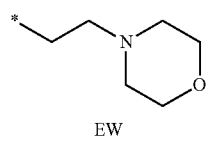 EW | 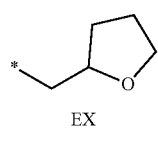 [SMILES: *CC1CCCO1] EX |
| 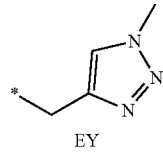 [SMILES: *Cc1cn(C)nn1] EY | 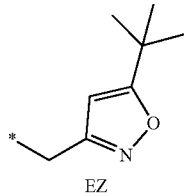 [SMILES: *Cc1cc(C(C)(C)C)on1] EZ | 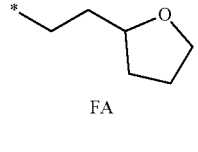 FA |
| 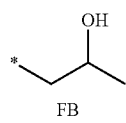 FB | 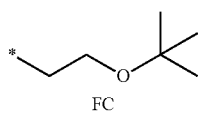 FC | 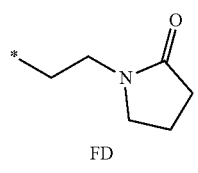 [SMILES: *CCN1CCCC1=O ; "FD"] FD |
| 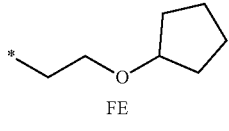 [SMILES: *CCOC1CCCC1] FE | 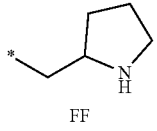 FF | 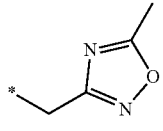 FG |
| 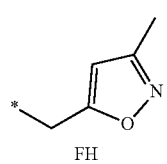 FH | 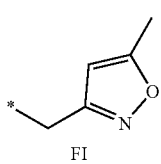 FI | 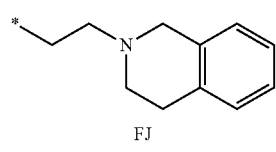 [SMILES: *CCN1CCc2ccccc2C1] FJ |
| 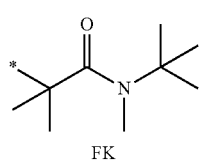 FK | 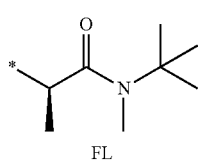 FL | 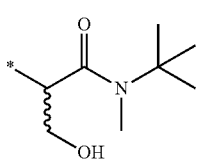 FM |

TABLE 2-continued
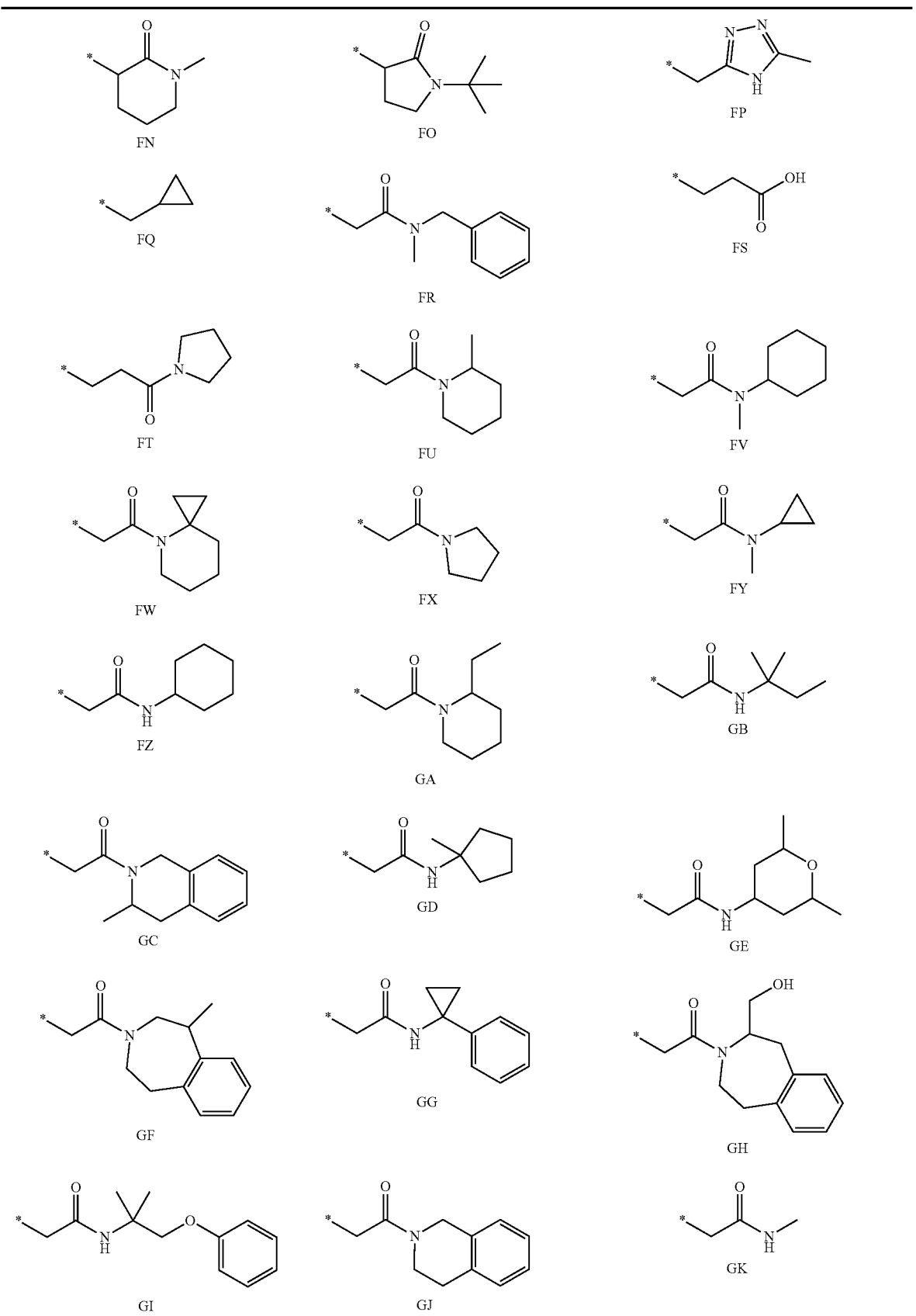

TABLE 2-continued
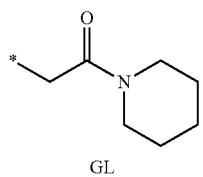
GL
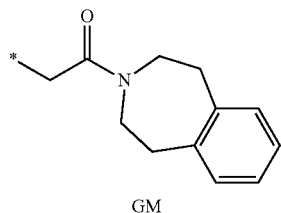 [SMILES: *CC(=O)N1CCc2ccccc2CC1]
GM
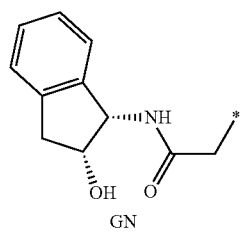 [SMILES: *CC(=O)N[C@H]1c2ccccc2C[C@H]1O]
GN
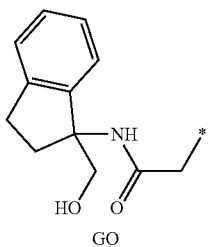 [SMILES: *CC(=O)NC1(CO)CCc2ccccc21]
GO
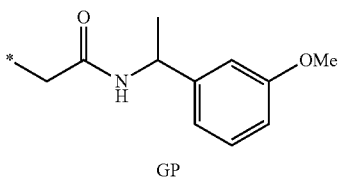 [SMILES: *CC(=O)NC(C)c1cccc(OC)c1]
GP
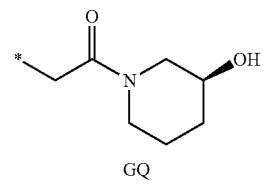 [SMILES: *CC(=O)N1CCC[C@H](O)C1]
GQ
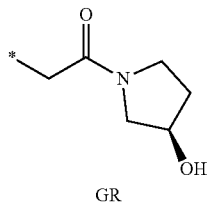 [SMILES: *CC(=O)N1CC[C@@H](O)C1 ; "GR"]
GR
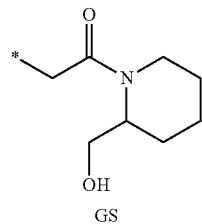 [SMILES: *CC(=O)N1CCCCC1CO]
GS
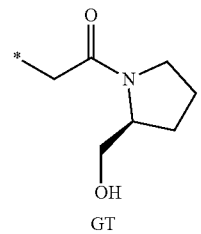 [SMILES: *CC(=O)N1CCC[C@H]1CO]
GT
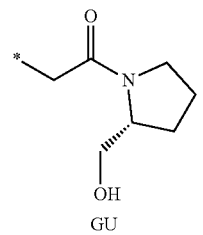 [SMILES: *CC(=O)N1CCC[C@@H]1CO]
GU
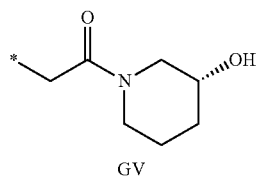 [SMILES: *CC(=O)N1CCC[C@@H](O)C1]
GV
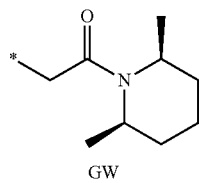 [SMILES: *CC(=O)N1[C@H](C)CCC[C@@H]1C]
GW
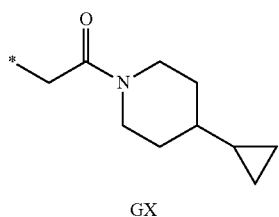 [SMILES: *CC(=O)N1CCC(C2CC2)CC1]
GX
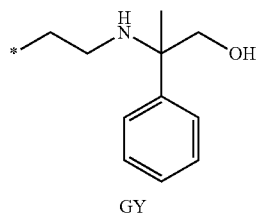 [SMILES: *CCNC(C)(CO)c1ccccc1]
GY
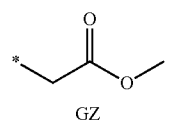 [SMILES: *CC(=O)OC]
GZ
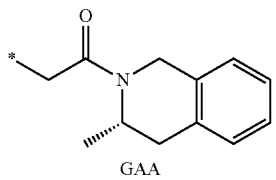 [SMILES: *CC(=O)N1Cc2ccccc2C[C@@H]1C]
GAA
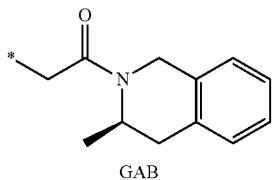 [SMILES: *CC(=O)N1Cc2ccccc2C[C@H]1C]
GAB
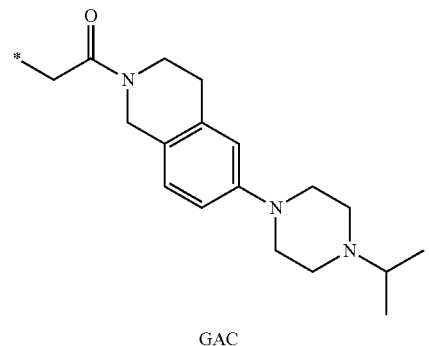 [SMILES: *CC(=O)N1CCc2cc(N3CCN(C(C)C)CC3)ccc2C1]
GAC TABLE 2-continued
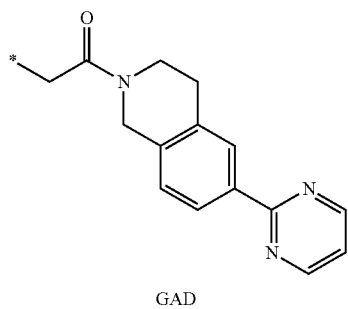 [SMILES: *CC(=O)N1CCc2cc(-c3ncccn3)ccc2C1]
GAD
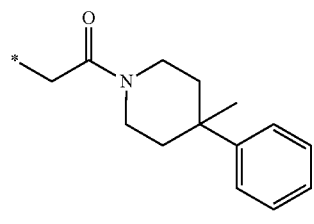
GAE
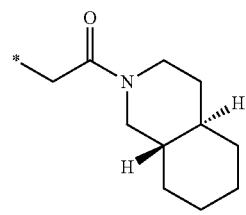
GAF
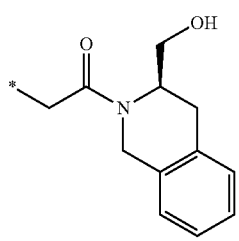
GAG
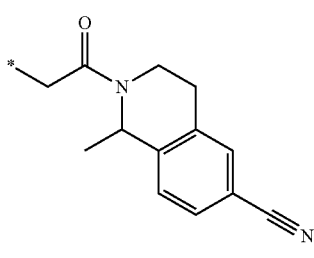
GAH
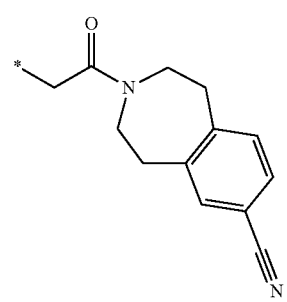
GAI
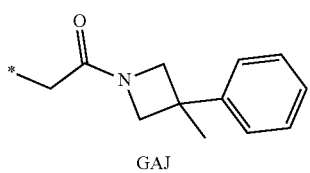 [SMILES: *CC(=O)N1CC(C)(c2ccccc2)C1]
GAJ
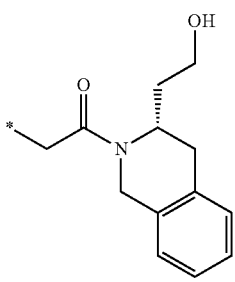
GAK
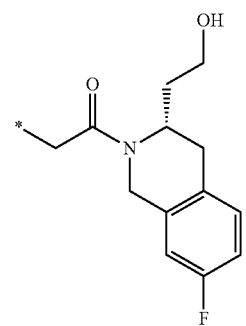
GAL
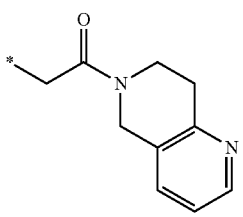
GAM
GAN
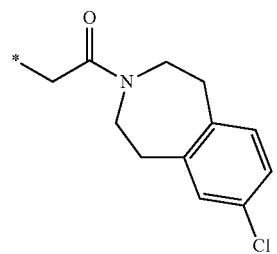
GAO
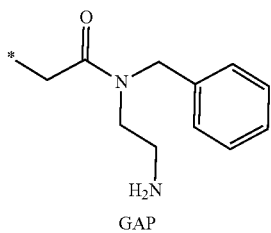 [SMILES: *CC(=O)N(CCN)Cc1ccccc1]
GAP
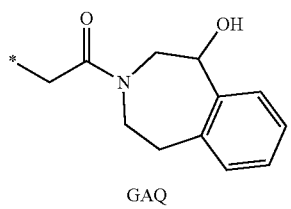 [SMILES: *CC(=O)N1CCc2ccccc2C(O)C1]
GAQ
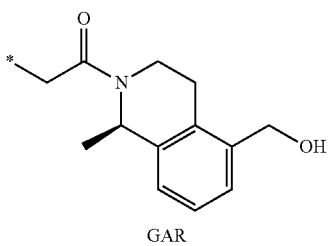 [SMILES: *CC(=O)N1CCc2c(CO)cccc2[C@H]1C]
GAR TABLE 2-continued
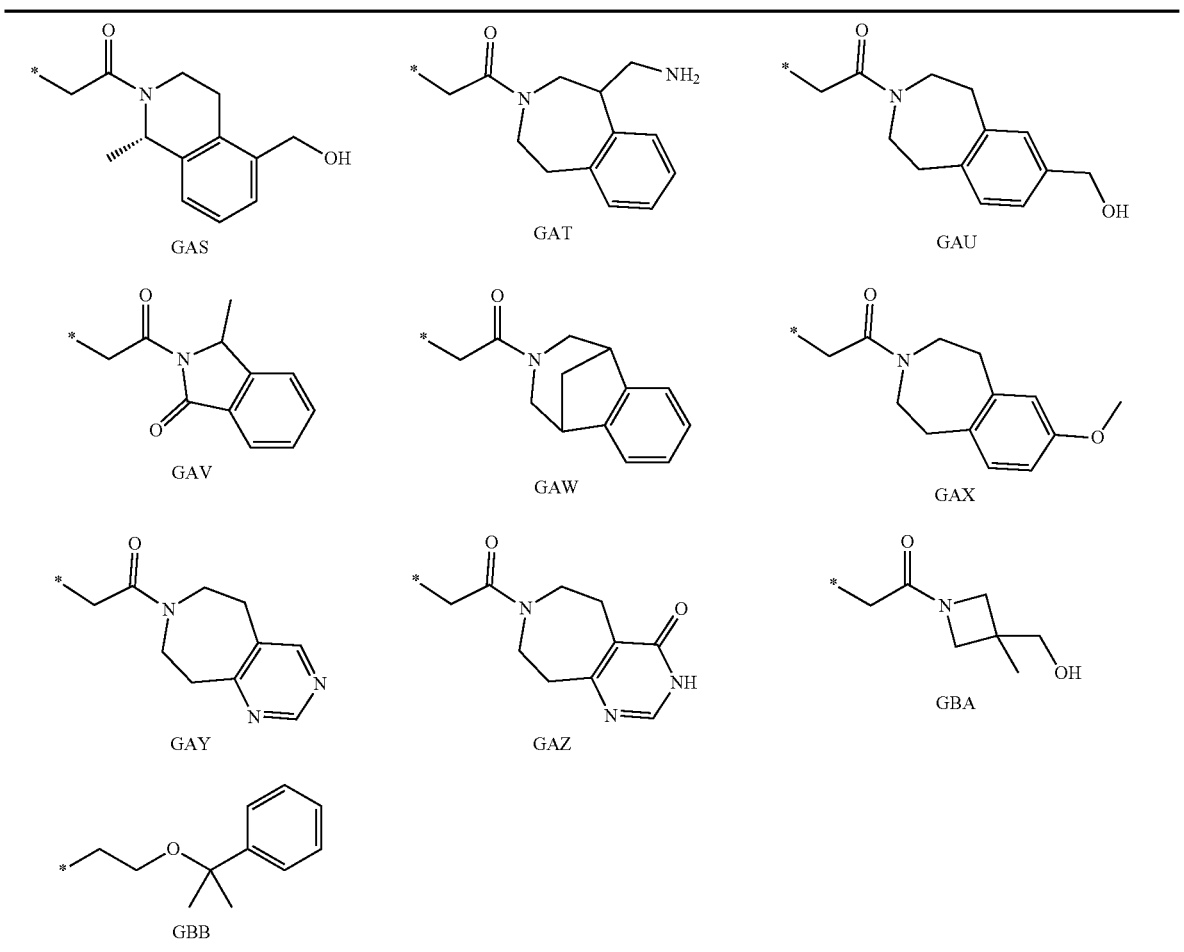
1.170A A compound according to any one of Embodiments 0.1 to 1.100 wherein $R^3$ is selected from groups GEC to GRJ in Table 2A below.
| Group | The group $R^3$ in Example No: |
|---|---|
| GBC | 701 |
| GBD | 702 |
| GBE | 703 |
| GBG | 705 |
| GBH | 706 |
| GBJ | 707 |
| GBI | 708 |
| GBK | 709 |
| GBM | 711 |
| GCQ | 741 |
| GCR | 742 |
| GCS | 743 |
| GCT | 744 |
| GCU | 745 |
| GCV | 746 |
| GCW | 747 |
| GCX | 748 |
| GCY | 749 |
| GCZ | 750 |
| GDA | 751 |
| GDB | 752 |
| GDC | 753 |
| GDD | 754 |
| GDE | 755 |
| GDF | 756 |
| GDG | 757 |
| GDH | 758 |
| GDJ | 759 |
| GDK | 761 |
| GDL | 762 |
| GDM | 763 |
| GDN | 764 |
| GDO | 765 |
| GDP | 766 |
| GDQ | 767 |
| GDR | 768 |
| GDS | 769 |
| GDT | 770 |
| GDU | 771 |
| GDW | 773 |
| GDX | 774 |
| GDY | 775 |
| GDZ | 776 |
| GEA | 777 |
| GEB | 778 |
| GEC | 779 |
| GED | 780 |
| GEE | 781 |
| GEF | 782 |
| GEG | 783 |

| Group | The group R³ in Example No: |
|---|---|
| GEH | 784 |
| GEJ | 785 |
| GEI | 786 |
| GHW | 877 |
| GHX | 878 |
| GHY | 879 |
| GHZ | 880 |
| GIA | 881 |
| GIB | 882 |
| GIC | 883 |
| GID | 884 |
| GIE | 885 |
| GIF | 886 |
| GIG | 887 |
| GIH | 888 |
| GIJ | 889 |
| GII | 890 |
| GIK | 891 |
| GIL | 892 |
| GIM | 893 |
| GIN | 894 |
| GIO | 895 |
| GIP | 896 |
| GIQ | 897 |
| GIR | 898 |
| GIS | 899 |
| GIT | 900 |
| GIU | 901 |
| GIV | 902 |
| GIW | 903 |
| GIX | 904 |
| GIY | 905 |
| GIZ | 906 |
| GJA | 907 |
| GJB | 908 |
| GJC | 909 |
| GJD | 910 |
| GJE | 911 |
| GJF | 912 |
| GJG | 913 |
| GJH | 914 |
| GJJ | 915 |
| GJI | 916 |
| GJK | 917 |
| GJL | 918 |
| GJM | 919 |
| GJN | 920 |
| GMZ | 1010 |
| GNA | 1011 |
| GNB | 1012 |
| GNC | 1013 |
| GND | 1014 |
| GNE | 1015 |
| GNF | 1016 |
| GNG | 1017 |
| GNH | 1018 |
| GNJ | 1019 |
| GNI | 1020 |
| GNK | 1021 |
| GNL | 1022 |
| GNM | 1023 |
| GNN | 1024 |
| GNO | 1025 |
| GNP | 1026 |
| GNQ | 1027 |
| GNR | 1028 |
| GNS | 1029 |
| GNT | 1030 |
| GNU | 1031 |
| GNV | 1032 |
| GNW | 1033 |
| GNX | 1034 |
| GNY | 1035 |
| GNZ | 1036 |
| GOA | 1037 |

| Group | The group R³ in Example No: |
|---|---|
| GOB | 1038 |
| GOC | 1039 |
| GOD | 1040 |
| GOE | 1041 |
| GOF | 1042 |
| GOG | 1043 |
| GOH | 1044 |
| GOJ | 1045 |
| GOI | 1046 |
| GOK | 1047 |
| GBN | 712 |
| GBO | 713 |
| GBP | 714 |
| GBQ | 715 |
| GBR | 716 |
| GBS | 717 |
| GBT | 718 |
| GBU | 719 |
| GBV | 720 |
| GBW | 721 |
| GBX | 722 |
| GBY | 723 |
| GBZ | 724 |
| GEK | 787 |
| GEL | 788 |
| GEM | 789 |
| GEN | 790 |
| GEO | 791 |
| GEP | 792 |
| GEQ | 793 |
| GER | 794 |
| GES | 795 |
| GET | 796 |
| GEU | 797 |
| GEV | 798 |
| GEW | 799 |
| GEX | 800 |
| GEY | 801 |
| GEZ | 802 |
| GFA | 803 |
| GFB | 804 |
| GFC | 805 |
| GFD | 806 |
| GFF | 808 |
| GFG | 809 |
| GFH | 810 |
| GFJ | 811 |
| GFI | 812 |
| GFK | 813 |
| GFL | 814 |
| GFM | 815 |
| GFN | 816 |
| GFO | 817 |
| GFP | 818 |
| GFQ | 819 |
| GFR | 820 |
| GFS | 821 |
| GFT | 822 |
| GFU | 823 |
| GFV | 824 |
| GFW | 825 |
| GFX | 826 |
| GFY | 827 |
| GFZ | 828 |
| GGA | 829 |
| GGB | 830 |
| GGC | 831 |
| GJO | 921 |
| GJP | 922 |
| GJR | 924 |
| GJS | 925 |
| GJT | 926 |
| GJU | 927 |
| GJV | 928 |
| GJW | 929 |

| Group | The group R³ in Example No: |
|---|---|
| GJX | 930 |
| GJY | 931 |
| GJZ | 932 |
| GKA | 933 |
| GKB | 934 |
| GKC | 935 |
| GKD | 936 |
| GKE | 937 |
| GKF | 938 |
| GKG | 939 |
| GKH | 940 |
| GKJ | 941 |
| GKI | 942 |
| GKK | 943 |
| GKL | 944 |
| GKM | 945 |
| GKN | 946 |
| GKO | 947 |
| GKP | 948 |
| GKQ | 949 |
| GKR | 950 |
| GKS | 951 |
| GKT | 952 |
| GKU | 953 |
| GKV | 954 |
| GKW | 955 |
| GKX | 956 |
| GKY | 957 |
| GKZ | 958 |
| GLA | 959 |
| GLB | 960 |
| GLC | 961 |
| GLD | 962 |
| GLE | 963 |
| GLF | 964 |
| GLG | 965 |
| GOL | 1048 |
| GOM | 1049 |
| GON | 1050 |
| GOO | 1051 |
| GOP | 1052 |
| GOQ | 1053 |
| GOR | 1054 |
| GOS | 1055 |
| GOT | 1056 |
| GOU | 1057 |
| GOV | 1058 |
| GOW | 1059 |
| GOX | 1060 |
| GOY | 1061 |
| GOZ | 1062 |
| GPA | 1063 |
| GPB | 1064 |
| GPC | 1065 |
| GPD | 1066 |
| GPE | 1067 |
| GPF | 1068 |
| GPG | 1069 |
| GPH | 1070 |
| GPJ | 1071 |
| GPI | 1072 |
| GPK | 1073 |
| GPL | 1074 |
| GPM | 1075 |
| GPN | 1076 |
| GPO | 1077 |
| GPP | 1078 |
| GPQ | 1079 |
| GPR | 1080 |
| GPS | 1081 |
| GPT | 1082 |
| GPU | 1083 |
| GPV | 1084 |
| GPW | 1085 |
| GCA | 725 |
| GCB | 726 |
| GCC | 727 |
| GOD | 728 |
| GCF | 730 |
| GCG | 731 |
| GCH | 732 |
| GCJ | 733 |
| GC! | 734 |
| GCK | 735 |
| GCM | 737 |
| GCN | 738 |
| GOP | 740 |
| GGD | 832 |
| GGE | 833 |
| GGF | 834 |
| GGG | 835 |
| GGH | 836 |
| GGJ | 837 |
| GGI | 838 |
| GGK | 839 |
| GGL | 840 |
| GGM | 841 |
| GGN | 842 |
| GGO | 843 |
| GGP | 844 |
| GGR | 846 |
| GGS | 847 |
| GGT | 848 |
| GGU | 849 |
| GGV | 850 |
| GGW | 851 |
| GGX | 852 |
| GGY | 853 |
| GGZ | 854 |
| GHA | 855 |
| GHB | 856 |
| GHC | 857 |
| GHD | 858 |
| GHE | 859 |
| GHF | 860 |
| GHG | 861 |
| GHH | 862 |
| GHJ | 863 |
| GHI | 864 |
| GHK | 865 |
| GHL | 866 |
| GHM | 867 |
| GHN | 868 |
| GHO | 869 |
| GHP | 870 |
| GHQ | 871 |
| GHR | 872 |
| GHS | 873 |
| GHT | 874 |
| GHU | 875 |
| GHV | 876 |
| GLH | 966 |
| GLJ | 967 |
| GLI | 968 |
| GLK | 969 |
| GLL | 970 |
| GLM | 971 |
| GLN | 972 |
| GLO | 973 |
| GLP | 974 |
| GLQ | 975 |
| GLR | 976 |
| GLS | 977 |
| GLT | 978 |
| GLU | 979 |
| GLV | 980 |
| GLW | 981 |
| GLX | 982 |
| GLY | 983 |
| GLZ | 984 |

-continued

| Group | The group R³ in Example No: |
|---|---|
| GMA | 985 |
| GMB | 986 |
| GMC | 987 |
| GMD | 988 |
| GME | 989 |
| GMF | 990 |
| GMG | 991 |
| GMH | 992 |
| GMJ | 993 |
| GMI | 994 |
| GMK | 995 |
| GML | 996 |
| GMM | 997 |
| GMN | 998 |
| GMO | 999 |
| GMP | 1000 |
| GMQ | 1001 |
| GMR | 1002 |
| GMS | 1003 |
| GMT | 1004 |
| GMU | 1005 |
| GMV | 1006 |
| GMW | 1007 |
| GMX | 1008 |
| GMY | 1009 |
| GPX | 1086 |
| GPY | 1087 |
| GPZ | 1088 |
| GQA | 1089 |
| GQB | 1090 |
| GQC | 1091 |
| GQD | 1092 |
| GQE | 1093 |
| GQF | 1094 |
| GQG | 1095 |
| GQH | 1096 |
| GQJ | 1097 |
| GQI | 1098 |
| GQK | 1099 |
| GQL | 1100 |
| GQM | 1101 |
| GQN | 1102 |
| GQO | 1103 |
| GQP | 1104 |
| GQQ | 1105 |
| GQR | 1106 |
| GQS | 1107 |
| GQT | 1108 |
| GQU | 1109 |
| GQV | 1110 |
| GQW | 1111 |
| GQX | 1112 |
| GQY | 1113 |
| GQZ | 1114 |
| GRA | 1115 |
| GRB | 1116 |
| GRC | 1117 |
| GRD | 1118 |
| GRE | 1119 |
| GRF | 1120 |
| GRG | 1121 |
| GRH | 1122 |
| GRJ | 1123 |

1.170B A compound according to any one of Embodiments 0.1 to 1.100 or Embodiment 1.169J wherein R³ is selected from groups in GBC, GBD, GMH, GNF and GSA in the table below.

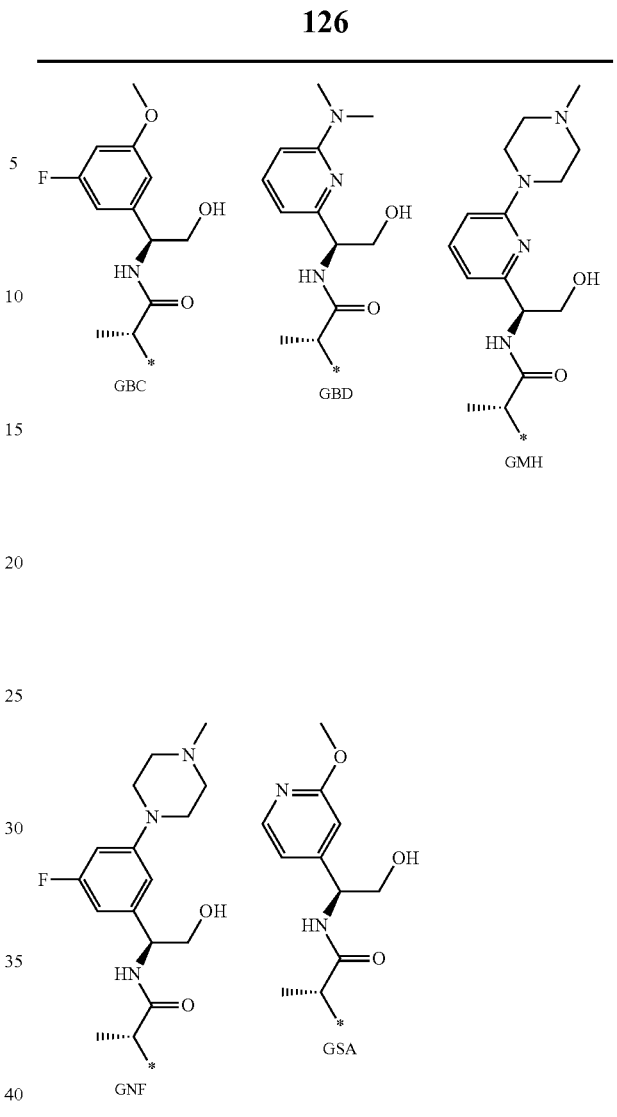

1.171 A compound according to Embodiment 1.170 wherein R³ is selected from groups BA to GP in Table 2.

1.172 A compound according to Embodiment 1.171 wherein R³ is selected from groups CO, DD, DZ, EC, EF, ES, GM, GN, GO and GP in Table 2.

1.172A A compound as defined in any one of Embodiments 0.1 to 1.172, with the proviso that when n is 2 and X is OCH, then Z is C—$R^z$.

1.172B A compound as defined in any one of Embodiments 0.1 to 1.172, with the proviso that when n is 2, then X is N.

1.172C A compound as defined in any one of Embodiments 0.1 to 1.172, with the proviso that when n is 2, Cyc¹ is other than 2-methyl-pyrimidin-4-yl.

1.172D A compound as defined in any one of Embodiments 0.1 to 1.172, with the proviso that when n is 2, Cyc¹ is other than methyl-pyrimidinyl.

1.172E A compound as defined in any one of Embodiments 0.1 to 1.172, with the proviso that when Z is N, then X is N.

1.172F A compound according to Embodiment 1.0 having the formula (10):

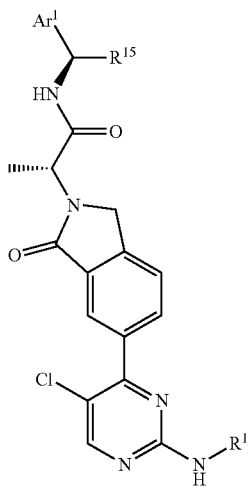

(10)

or a pharmaceutically acceptable salt or tautomer thereof, wherein, $R^1$ is tetrahydropyran; or a 6-membered heterocyclic ring selected from pyridine and pyrimidine optionally substituted with a methyl or methoxy group;

$R^{15}$ is $C_{1-3}$ alkyl or hydroxy-$C_{1-3}$ alkyl; and $Ar^1$ is a benzene or pyridine ring optionally substituted with 1 or 2 substituents selected from fluorine, methoxy, dimethylamino and 4-methylpiperazine.

1.172G A compound having the formula (11):

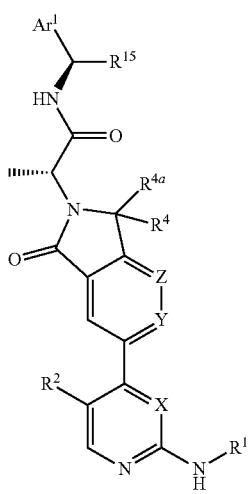

(11)

or a salt or tautomer thereof; wherein:

$R^1$ is tetrahydropyran; or a 6-membered heterocyclic ring selected from pyridine and pyrimidine optionally substituted with a methyl or methoxy group;

$R^{15}$ is $C_{1-3}$ alkyl or hydroxy-$C_{1-3}$ alkyl;

$Ar^1$ is a benzene or pyridine ring optionally substituted with 1 or 2 substituents selected from fluorine, methoxy, dimethylamino and 4-methylpiperazine;

$R^2$, X, Y, Z, $R^4$ and $R^{4a}$ are as defined in any one of Embodiments 0.1, 0.3, 0.4, 1.01, 1.02, 1.06, 1.2 to 1.3, 1.8 to 1.72, 1.80 to 1.88A and 1.90 to 1.100.

1.172H A compound according to Embodiment 1.172F or 1.172G wherein $R^1$ is selected from tetrahydropyran, 2-methyoxypyridin-4-yl and 2-methylpyrimidin-4-yl.

1.172J A compound according to any one of Embodiments 1.172F, 1.172G and 1.172H wherein $R^{15}$ is hydroxymethyl or methyl.

1.173 A compound according to Embodiment 1.1 which is selected from the compounds of any of Examples 1 to 196 herein, or a pharmaceutically acceptable salt thereof.

1.174 A compound according to Embodiment 1.173 which is selected from the compounds of any of Examples 2, 3, 4, 7, 11, 16, 19, 21, 22, 25, 27, 34, 35, 38, 40, 42, 48, 55, 59, 67, 72, 74, 76, 79, 80, 82, 84, 85, 86, 87, 93, 94, 95, 96, 101, 103, 137, 141, 151, 152, 188, 192, 193, 194, 195 and 196 herein, or a pharmaceutically acceptable salt thereof.

1.175 A compound according to Embodiment 1.174 which is selected from the compounds of any of Examples 40, 55, 79 and 82 or a pharmaceutically acceptable salt thereof.

1.175A A compound according to Embodiment 1.0 or Embodiment 1.1 which is selected from the compounds of any of Examples 1 to 699 herein, or a pharmaceutically acceptable salt thereof.

1.175B A compound according to Embodiment 0.1 which is selected from the compounds of Examples 2, 3, 4, 7, 11, 16, 19, 21, 22, 25, 27, 34, 35, 38, 40, 42, 48, 55, 59, 67, 72, 74, 76, 79, 80, 82, 84, 85, 86, 87, 93, 94, 95, 96, 101, 103, 137, 141, 151, 152, 188, 192, 193, 194, 195, 196, 197, 201, 207, 209, 210, 214, 219, 221, 230, 232, 234, 235, 239, 240, 241, 242, 244, 260, 261, 262, 263, 264, 265, 266, 271, 280, 282, 283, 284, 287, 289, 290, 291, 292, 294, 303, 316, 317, 318, 319, 321, 322, 323, 324, 325, 326, 327, 328, 333, 334, 335, 336, 337, 341, 342, 344, 345, 346, 347, 348, 349, 351, 352, 354, 355, 356, 357, 358, 359, 360, 365, 367, 369, 370, 371, 372, 381, 383, 384, 385, 386, 389, 390, 391, 392, 393, 395, 396, 397, 398, 399, 400, 401, 402, 406, 415, 421, 422, 423, 425, 428, 429, 430, 431, 432, 433, 434, 435, 436, 437, 442, 443, 444, 445, 448, 450, 451, 452, 453, 454, 455, 456, 457, 458, 459, 460, 461, 462, 463, 465, 466, 467, 469, 471, 475, 476, 477, 478, 480, 481, 482, 488, 495, 498, 499, 500, 504, 508, 509, 510, 511, 512, 514, 517, 522, 525, 526, 529, 538, 539, 540, 542, 543, 544, 545, 548, 549, 554, 555, 558, 560, 562, 563, 565, 567, 571, 574, 575, 583, 584, 585, 586, 587, 588, 591, 592, 593, 596, 597, 598, 600, 601, 602, 603, 604, 606, 607, 608, 609, 611, 612, 613, 614, 615, 616, 621, 622, 623, 624, 625, 627, 627, 628, 629, 630, 631, 633, 634, 635, 638, 639, 640, 641, 642, 643, 644, 645, 647, 648, 649, 650, 651, 652, 653, 654, 655, 656, 657, 658, 659, 660, 661, 663, 664, 665, 666, 669, 670, 671, 672, 673, 674, 675, 676, 677, 678, 681, 682, 683, 684, 685, 686, 687, 688, 689, 690, 692, 693, 694, 696, 697, 698 and 699 herein, or a pharmaceutically acceptable salt thereof.

1.175C A compound according to Embodiment 1.175B which is selected from the compounds of any of Examples 303, 616, 683 and 675 or a pharmaceutically acceptable salt thereof.

1.175D A compound according to Embodiment 1.175B which is selected from the compounds of any of Examples 685, 697, 698 and 699 or a pharmaceutically acceptable salt thereof.

1.175E A compound according to Embodiment 1.0 which is selected from the compounds of Examples 1 to 1134 herein, or a pharmaceutically acceptable salt thereof.

1.175F A compound according to Embodiment 1.0 which is selected from the compounds of Examples 2, 3, 4, 7, 11, 16, 19, 21, 22, 25, 26, 27, 34, 35, 38, 40, 42, 48, 55, 56, 57, 59, 67, 72, 74, 76, 78, 79, 80, 82, 84, 85, 86, 87, 93, 94, 95, 96, 101, 103, 137, 141, 150, 151, 152, 192, 193, 194, 195, 196, 197, 201, 207, 209, 210, 214, 219, 221, 230, 232, 234, 235, 239, 240, 241, 242, 244, 260, 261, 262, 263, 264, 266, 271, 280, 282, 283, 284, 287, 289, 290, 291, 294, 303, 316, 317, 318, 319, 321, 322, 323, 324, 325, 326, 327, 328, 333, 335, 336, 337, 341, 342, 344, 347, 348, 349, 351, 352, 354, 355, 356, 357, 358, 359, 360, 365, 367, 369, 370, 371, 372, 381, 383, 384, 372, 386, 390, 391, 392, 393, 395, 396, 397, 398, 399, 400, 402, 406, 415, 421, 422, 423, 425, 428, 429, 430, 431, 432, 433, 434, 435, 436, 437, 442, 443, 444, 445, 448, 450, 451, 452, 453, 454, 455, 456, 457, 458, 459, 460, 461, 462, 463, 465, 466, 469, 471, 475, 476, 477, 478, 480, 481, 482, 488, 495, 498, 499, 500, 504, 509, 510, 511, 512, 514, 517, 522, 525, 526, 529, 538, 540, 542, 543, 545, 548, 549, 554, 555, 558, 560, 563, 565, 567, 571, 574, 575, 583, 588, 591, 593, 596, 597, 598, 600, 601, 602, 603, 604, 606, 608, 609, 612, 613, 614, 615, 616, 621, 623, 624, 625, 626, 627, 628, 629, 630, 631, 633, 634, 635, 639, 640, 641, 642, 643, 644, 650, 651, 652, 653, 654, 656, 657, 658, 660, 661, 663, 665, 666, 669, 671, 672, 673, 674, 675, 676, 677, 678, 681, 683, 684, 685, 686, 687, 688, 689, 692, 693, 694, 696, 697, 698, 699, 703, 705, 707, 708, 711, 712, 713, 715, 716, 717, 719, 720, 721, 722, 727, 728, 730, 732, 735, 737, 738, 740, 742, 743, 746, 747, 753, 754, 756, 757, 759, 763, 765, 767, 768, 769, 774, 776, 777, 779, 780, 781, 782, 783, 784, 785, 786, 787, 788, 789, 798, 799, 800, 801, 802, 803, 804, 805, 806, 808, 809, 810, 811, 812, 814, 815, 816, 817, 818, 819, 820, 822, 823, 824, 825, 826, 827, 828, 830, 831, 834, 835, 836, 837, 838, 840, 841, 843, 844, 846, 847, 848, 849, 850, 851, 852, 853, 855, 856, 857, 858, 859, 864, 865, 867, 868, 869, 870, 871, 872, 873, 875, 876, 877, 878, 880, 881, 882, 883, 886, 887, 888, 890, 891, 892, 894, 895, 896, 897, 986, 900, 902, 903, 907, 908, 909, 910, 911, 912, 913, 914, 915, 918, 919, 920, 921, 922, 924, 925, 926, 927, 928, 929, 930, 931, 932, 934, 935, 936, 940, 941, 942, 943, 944, 945, 947, 949, 950, 951, 952, 953, 954, 956, 957, 958, 959, 960, 961, 962, 963, 964, 965, 966, 968, 970, 971, 972, 973, 974, 975, 976, 977, 979, 980, 981, 982, 983, 984, 985, 986, 987, 988, 989, 990, 992, 995, 996, 997, 999, 1000, 1001, 1002, 1003, 1004, 1005, 1007, 1008, 1010, 1011, 1014, 1015, 1016, 1017, 1018, 1019, 1020, 1021, 1022, 1023, 1024, 1025, 1026, 1027, 1029, 1030, 1031, 1033, 1034, 1035, 1036, 1038, 1039, 1040, 1041, 1042, 1043, 1044, 1045, 1046, 1047, 1048, 1049, 1050, 1051, 1052, 1053, 1054, 1056, 1057, 1058, 1060, 1061, 1062, 1063, 1064, 1065, 1066, 1067, 1068, 1069, 1070, 1071, 1072, 1073, 1074, 1075, 1076, 1077, 1078, 1079, 1080, 1081, 1083, 1085, 1086, 1087, 1088, 1089, 1092, 1093, 1094, 1095, 1096, 1097, 1098, 1099, 1100, 1101, 1102, 1103, 598, 1105, 1106, 1107, 1108, 1109, 1110, 1111, 1112, 1113, 1114, 1115, 1116, 1117, 1118, 1119, 1120, 1121, 1122, 1123, 1124, 1125, 1126, 1127, 1128, 1129, 1130, 1131, 1132, 1133 and 1134 or a pharmaceutically acceptable salt thereof.

1.175G A compound according to Embodiment 0.1 which is selected from the compounds of Examples 685, 698, 701, 702, 992 and 1016 or a pharmaceutically acceptable salt thereof.

1.175H A compound according to Embodiment 1.175G which is (2R)-2-(6-{5-chloro-2-[(oxan-4-yl)amino]pyrimidin-4-yl}-1-oxo-2,3-dihydro-1H-isoindol-2-yl)-N-[(1S)-1-(3-fluoro-5-methoxyphenyl)-2-hydroxyethyl]propanamide:

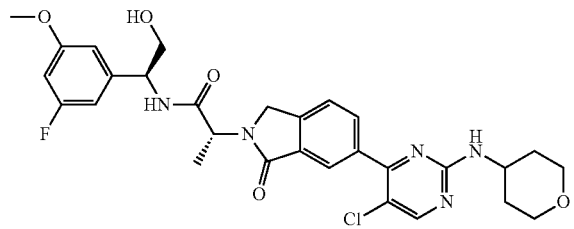 [SMILES: COc1cc(F)cc([C@@H](CO)NC(=O)[C@@H](C)N2Cc3ccc(-c4nc(NC5CCOCC5)ncc4Cl)cc3C2=O)c1]

or a pharmaceutically acceptable salt or tautomer thereof.

1.175J A compound according to Embodiment 1.175H which is (2R)-2-(6-{5-chloro-2-[(oxan-4-yl)amino]pyrimidin-4-yl}-1-oxo-2,3-dihydro-1H-isoindol-2-yl)-N-[(1S)-1-(3-fluoro-5-methoxyphenyl)-2-hydroxyethyl]propanamide.

1.175K A compound according to Embodiment 1.175G which is (2R)-2-(6-{5-Chloro-2-[(oxan-4-yl)amino]pyrimidin-4-yl}-1-oxo-2,3-dihydro-1H-isoindol-2-yl)-N-[(1S)-2-hydroxy-1-(2-methoxypyridin-4-yl)ethyl]propanamide:

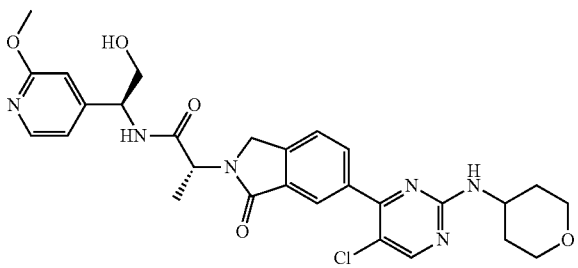 [SMILES: COc1cc([C@@H](CO)NC(=O)[C@@H](C)N2Cc3ccc(-c4nc(NC5CCOCC5)ncc4Cl)cc3C2=O)ccn1]

or a pharmaceutically acceptable salt or tautomer thereof.

1.175L A compound according to Embodiment 1.175K which is (2R)-2-(6-{5-Chloro-2-[(oxan-4-yl)amino]pyrimidin-4-yl}-1-oxo-2,3-dihydro-1H-isoindol-2-yl)-N-[(1S)-2-hydroxy-1-(2-methoxypyridin-4-yl)ethyl]propanamide.

1.175M A compound according to Embodiment 1.175G which is (R)-2-(6-(5-chloro-2-((2-methoxypyridin-4-yl)amino)pyrimidin-4-yl)-1-oxoisoindolin-2-yl)-N—((S)-1-(3-fluoro-5-methoxyphenyl)-2-hydroxyethyl)propanamide:

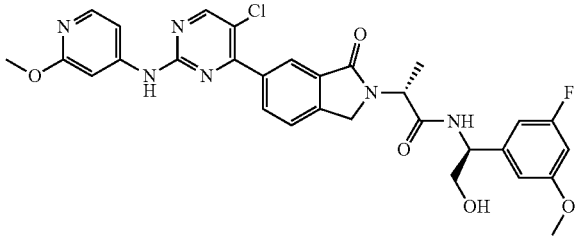 [SMILES: COc1cc(F)cc([C@@H](CO)NC(=O)[C@@H](C)N2Cc3ccc(-c4nc(Nc5ccnc(OC)c5)ncc4Cl)cc3C2=O)c1]

or a pharmaceutically acceptable salt or tautomer thereof.

1.175N A compound according to Embodiment 1.175M which is (R)-2-(6-(5-chloro-2-((2-methoxypyridin-4-yl)amino)pyrimidin-4-yl)-1-oxoisoindolin-2-yl)-N—((S)-1-(3-fluoro-5-methoxyphenyl)-2-hydroxyethyl)propanamide.

1.175P A compound according to Embodiment 1.175G which is (R)-2-(6-(5-chloro-2-((2-methylpyrimidin-4-yl)amino)pyrimidin-4-yl)-1-oxoisoindolin-2-yl)-N—((S)-1-(6-(dimethylamino)pyridin-2-yl)-2-hydroxyethyl)propanamide:

131

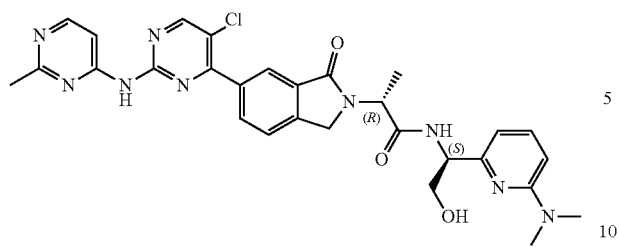

or a pharmaceutically acceptable salt or tautomer thereof.

1.175Q A compound according to Embodiment 1.175P which is (R)-2-(6-(5-chloro-2-((2-methylpyrimidin-4-yl)amino)pyrimidin-4-yl)-1-oxoisoindolin-2-yl)-N—((S)-1-(6-(dimethylamino)pyridin-2-yl)-2-hydroxyethyl)propanamide.

1.175R A compound according to Embodiment 1.175G which is (2R)-2-(6-{5-chloro-2-[(oxan-4-yl)amino]pyrimidin-4-yl}-1-oxo-2,3-dihydro-1H-isoindol-2-yl)-N-[(1S)-2-hydroxy-1-[6-(4-methylpiperazin-1-yl)pyridin-2-yl]ethyl]propanamide:

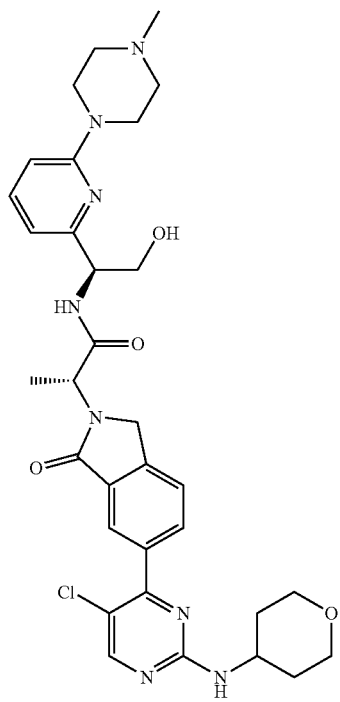 [SMILES: C[C@H](C(=O)N[C@H](CO)c1cccc(N2CCN(C)CC2)n1)N1Cc2ccc(-c3nc(NC4CCOCC4)ncc3Cl)cc2C1=O]

or a pharmaceutically acceptable salt or tautomer thereof.

1.175S A compound according to Embodiment 1.175R which is (2R)-2-(6-{5-chloro-2-[(oxan-4-yl)amino]pyrimidin-4-yl}-1-oxo-2,3-dihydro-1H-isoindol-2-yl)-N-[(1S)-2-hydroxy-1-[6-(4-methylpiperazin-1-yl)pyridin-2-yl]ethyl]propanamide.

1.175T A compound according to Embodiment 1.175G which is 2R)-2-(6-{5-chloro-2-[(oxan-4-yl)amino]pyrimidin-4-yl}-1-oxo-2,3-dihydro-1H-isoindol-2-yl)-N-[(1R)-1-[3-fluoro-5-(4-methylpiperazin-1-yl)phenyl]ethyl]propanamide:

132

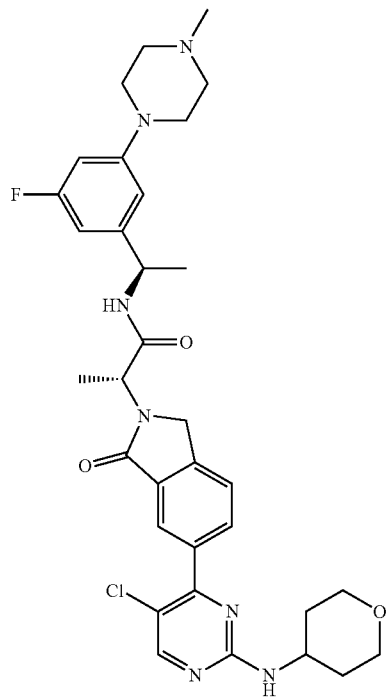 [SMILES: C[C@H](C(=O)N[C@H](C)c1cc(F)cc(N2CCN(C)CC2)c1)N1Cc2ccc(-c3nc(NC4CCOCC4)ncc3Cl)cc2C1=O]

or a pharmaceutically acceptable salt of tautomer thereof.

1.175U A compound according to Embodiment 1.175T which is 2R)-2-(6-{5-chloro-2-[(oxan-4-yl)amino]pyrimidin-4-yl}-1-oxo-2,3-dihydro-1H-isoindol-2-yl)-N-[(1R)-1-[3-fluoro-5-(4-methylpiperazin-1-yl)phenyl]ethyl]propanamide.

1.176 A compound according to any one of Embodiments 0.1 to 1.175U which is in the form of a salt.

1.177 A compound according to Embodiment 1.176 wherein the salt is an acid addition salt.

1.178 A compound according to Embodiment 1.176 or Embodiment 1.177 wherein the salt is a pharmaceutically acceptable salt.

1.179 A compound according to any one of Embodiments 0.1 to 1.175U which is in the form of a free base.

Definitions

Unless the context indicates otherwise, references to formula (1) in all sections of this document (including the uses, methods and other aspects of the invention) include references to formula (0) and to all other sub-formulae (e.g. formulae (2), (3), (3A), (3B), (4), (4A), (4B), (5), (5A), (5B), (6), (6A), (6B), (7), (7A), (7B), (8), (8A), (8B), (9), (9A), (9B), (10) and (11)), sub-groups, preferences, embodiments and examples as defined herein.

By ERK1/2 we mean either or both of the ERK1 and ERK2 isozymes of extracellular signal regulated kinases (ERK).

"Potency" is a measure of drug activity expressed in terms of the amount required to produce an effect of given intensity. A highly potent drug evokes a larger response at low concentrations. Potency is proportional to affinity and efficacy. Affinity is the ability of the drug to bind to an enzyme. Efficacy is the relationship between target occupancy and the ability to initiate a response at the molecular, cellular, tissue or system level.

The term "inhibitor" refers to an enzyme inhibitor that is a type of ligand or drug that blocks or dampens biological responses mediated by ERK1/2. Inhibitors mediate their effects by binding to the active site or to allosteric sites on enzymes, or they may interact at unique binding sites not normally involved in the biological regulation of the enzyme's activity. The inhibition may arise directly or indirectly, and may be mediated by any mechanism and at any physiological level. As a result, inhibition by ligands or drugs may under different circumstances manifest itself in functionally different ways. Inhibitory activity may be reversible or irreversible depending on the longevity of the inhibitor-enzyme complex, which, in turn, depends on the nature of inhibitor-enzyme binding.

The term "treatment" as used herein in the context of treating a condition i.e. state, disorder or disease, pertains generally to treatment and therapy, whether for a human or an animal (e.g. in veterinary applications), in which some desired therapeutic effect is achieved, for example, the inhibition of the progress of the condition, and includes a reduction in the rate of progress, a halt in the rate of progress, amelioration of the condition, diminishment or alleviation of at least one symptom associated or caused by the condition being treated and cure of the condition. For example, treatment can be diminishment of one or several symptoms of a disorder or complete eradication of a disorder.

The term "prophylaxis" (i.e. use of a compound as prophylactic measure) as used herein in the context of treating a condition i.e. state, disorder or disease, pertains generally to the prophylaxis or prevention, whether for a human or an animal (e.g. in veterinary applications), in which some desired preventative effect is achieved, for example, in preventing occurrence of a disease or guarding from a disease. Prophylaxis includes complete and total blocking of all symptoms of a disorder for an indefinite period of time, the mere slowing of the onset of one or several symptoms of the disease, or making the disease less likely to occur and does not include amelioration of the condition, diminishment or alleviation of at least one symptom associated or caused by the condition being treated and cure of the condition.

References to the prophylaxis or treatment of a disease state or condition such as cancer include within their scope alleviating or reducing the incidence e.g. of cancer.

As used herein, the term "mediated", as used e.g. in conjunction with ERK1/2 as described herein (and applied for example to various physiological processes, diseases, states, conditions, therapies, treatments or interventions) is intended to operate limitatively so that the various processes, diseases, states, conditions, treatments and interventions to which the term is applied are those in which the protein plays a biological role. In cases where the term is applied to a disease, state or condition, the biological role played by the protein may be direct or indirect and may be necessary and/or sufficient for the manifestation of the symptoms of the disease, state or condition (or its aetiology or progression). Thus, the protein function (and in particular aberrant levels of function, e.g. over- or under-expression) need not necessarily be the proximal cause of the disease, state or condition: rather, it is contemplated that the mediated diseases, states or conditions include those having multifactorial aetiologies and complex progressions in which the protein in question is only partially involved. In cases where the term is applied to treatment, prophylaxis or intervention, the role played by the protein may be direct or indirect and may be necessary and/or sufficient for the operation of the treatment, prophylaxis or outcome of the intervention. Thus, a disease state or condition mediated by a protein includes the development of resistance to any particular cancer drug or treatment.

The combinations of the invention may produce a therapeutically efficacious effect relative to the therapeutic effect of the individual compounds/agents when administered separately.

The term 'efficacious' includes advantageous effects such as additivity, synergism, reduced side effects, reduced toxicity, increased time to disease progression, increased time of survival, sensitization or resensitization of one agent to another, or improved response rate. Advantageously, an efficacious effect may allow for lower doses of each or either component to be administered to a patient, thereby decreasing the toxicity of chemotherapy, whilst producing and/or maintaining the same therapeutic effect. A "synergistic" effect in the present context refers to a therapeutic effect produced by the combination which is larger than the sum of the therapeutic effects of the agents of the combination when presented individually. An "additive" effect in the present context refers to a therapeutic effect produced by the combination which is larger than the therapeutic effect of any of the agents of the combination when presented individually. The term "response rate" as used herein refers, in the case of a solid tumour, to the extent of reduction in the size of the tumour at a given time point, for example 12 weeks. Thus, for example, a 50% response rate means a reduction in tumour size of 50%. References herein to a "clinical response" refer to response rates of 50% or greater. A "partial response" is defined herein as being a response rate of less than 50% provided that it is greater than 0%.

As used herein, the term "combination", as applied to two or more compounds and/or agents, is intended to define material in which the two or more agents are associated. The terms "combined" and "combining" in this context are to be interpreted accordingly.

The association of the two or more compounds/agents in a combination may be physical or non-physical. Examples of physically associated combined compounds/agents include:

compositions (e.g. unitary formulations) comprising the two or more compounds/agents in admixture (for example within the same unit dose);

compositions comprising material in which the two or more compounds/agents are chemically/physicochemically linked (for example by crosslinking, molecular agglomeration or binding to a common vehicle moiety);

compositions comprising material in which the two or more compounds/agents are chemically/physicochemically co-packaged (for example, disposed on or within lipid vesicles, particles (e.g. micro- or nanoparticles) or emulsion droplets);

pharmaceutical kits, pharmaceutical packs or patient packs in which the two or more compounds/agents are co-packaged or co-presented (e.g. as part of an array of unit doses);

Examples of non-physically associated combined compounds/agents include:

material (e.g. a non-unitary formulation) comprising at least one of the two or more compounds/agents together with instructions for the extemporaneous association of the at least one compound to form a physical association of the two or more compounds/agents;

material (e.g. a non-unitary formulation) comprising at least one of the two or more compounds/agents together with instructions for combination therapy with the two or more compounds/agents;

material comprising at least one of the two or more compounds/agents together with instructions for administration to a patient population in which the other(s) of the two or more compounds/agents have been (or are being) administered;

material comprising at least one of the two or more compounds/agents in an amount or in a form which is specifically adapted for use in combination with the other(s) of the two or more compounds/agents.

As used herein, the term "combination therapy" is intended to define therapies which comprise the use of a combination of two or more compounds/agents (as defined above). Thus, references to "combination therapy", "combinations" and the use of compounds/agents "in combination" in this application may refer to compounds/agents that are administered as part of the same overall treatment regimen. As such, the posology of each of the two or more compounds/agents may differ: each may be administered at the same time or at different times. It will therefore be appreciated that the compounds/agents of the combination may be administered sequentially (e.g. before or after) or simultaneously, either in the same pharmaceutical formulation (i.e. together), or in different pharmaceutical formulations (i.e. separately). Simultaneously in the same formulation is as a unitary formulation whereas simultaneously in different pharmaceutical formulations is non-unitary. The posologies of each of the two or more compounds/agents in a combination therapy may also differ with respect to the route of administration.

As used herein, the term "pharmaceutical kit" defines an array of one or more unit doses of a pharmaceutical composition together with dosing means (e.g. measuring device) and/or delivery means (e.g. inhaler or syringe), optionally all contained within common outer packaging. In pharmaceutical kits comprising a combination of two or more compounds/agents, the individual compounds/agents may unitary or non-unitary formulations. The unit dose(s) may be contained within a blister pack. The pharmaceutical kit may optionally further comprise instructions for use.

As used herein, the term "pharmaceutical pack" defines an array of one or more unit doses of a pharmaceutical composition, optionally contained within common outer packaging. In pharmaceutical packs comprising a combination of two or more compounds/agents, the individual compounds/agents may unitary or non-unitary formulations. The unit dose(s) may be contained within a blister pack. The pharmaceutical pack may optionally further comprise instructions for use.

The term 'optionally substituted' as used herein refers to a group which may be substituted or unsubstituted with a substituent as herein defined.

The prefix "$C_{x-y}$" (where x and y are integers) as used herein refers to the number of carbon atoms in a given group. Thus, a $C_{1-6}$ alkyl group contains from 1 to 6 carbon atoms, a $C_{3-6}$ cycloalkyl group contains from 3 to 6 carbon atoms, a $C_{1-4}$ alkoxy group contains from 1 to 4 carbon atoms, and so on.

The term 'halo' or 'halogen' as used herein refers to fluorine, chlorine, bromine or iodine.

The term 'oxo' as used herein refers to the group =O.

Unless the context indicates otherwise, the term "amino" refers to the group —NH₂.

In the definition of the compounds of the formula (0) above and as used hereinafter, the term "hydrocarbon" (as in "hydrocarbon group") is a generic term encompassing aliphatic, alicyclic and aromatic groups having an all-carbon backbone and consisting of carbon and hydrogen atoms, except where otherwise stated. Each and every hydrogen in the compound (such as in a hydrocarbon group, alkyl group or where referred to as hydrogen) includes all isotopes of hydrogen, in particular $^1H$ and $^2H$ (deuterium).

In certain cases, as defined herein, one or more of the carbon atoms making up the carbon backbone may be replaced by a specified atom or group of atoms. For example, in some embodiments of the invention as defined herein, in an acyclic hydrocarbon group (e.g. a $C_{1-8}$ hydrocarbon or $C_{1-6}$ hydrocarbon group), 1 or 2 but not all of the the carbon atoms of the hydrocarbon group may be replaced by O or N, or by an atom or group O, S, SO, SO₂ or $NR^{11}$. Examples of groups in which 1 or 2 carbon atom of the hydrocarbon group have been replaced by a replacement atom or group as defined above include ethers (e.g. alkoxy groups or alkoxy-alkyl groups) and thioethers (C replaced by O or S), sulphones and sulphoxides (C replaced by SO or SO₂), amines (C replaced by N or $NR^{11}$), esters (one C in C=C moiety replaced by O and another C replaced by O), thioester (one C in C=C moiety replaced by O and another C replaced by S), amides (one C in C=C moiety replaced by O and another C replaced by $NR^{11}$) and nitrile (one C in C≡C moiety replaced by N) groups. However, in one embodiment, no carbon atoms are replaced by O or N, or by an atom or group O, S, SO, SO₂ or $NR^{11}$.

For example, when $R^1$ is an optionally substituted acyclic hydrocarbon group wherein 1 but not all of the carbon atoms of the hydrocarbon group can be replaced by O, examples of such groups $R^1$ include an alkoxyalkyl group such as methoxyethyl or methoxypropyl. In one subset of compounds within each of the embodiments 0.1 to 1.179, no such replacements of carbon atoms with other atoms or groups are present in the acyclic hydrocarbon group $R^1$.

When $R^7$ is selected from an optionally substituted acyclic $C_{1-3}$ hydrocarbon group wherein one but not all of the carbon atoms of the acyclic hydrocarbon group may optionally be replaced by O, examples of such replacments are those that form a $C_{1-4}$ alkoxy group such as methoxy or tert-butyloxy; or an alkoxyalkyl group such as methoxymethyl; or a group CH₂; or a group 0-CH(CH₃)₂). In one subset of compounds within each of the embodiments 0.1 to 1.179, no such replacements of carbon atoms with other atoms or groups are present in the acyclic hydrocarbon group $R^7$.

When $R^9$ is an optionally substituted acyclic hydrocarbon group wherein one or two but not all of the carbon atoms of the acyclic $C_{1-6}$ hydrocarbon group may optionally be replaced by O, examples of such replacements include those which give an O-ether linkage between the acyclic hydrocarbon group and an attached carbocylic group substituent; or give an alkoxy substituent such as methoxy on the acyclic hydrocarbon group. In one subset of compounds within each of the embodiments 0.1 to 1.179, no such replacements of carbon atoms with other atoms or groups are present in the acyclic hydrocarbon group $R^9$.

When $R^{10}$ is an optionally substituted acyclic hydrocarbon group wherein one or two but not all of the carbon atoms of the acyclic $C_{1-3}$ hydrocarbon group may be replaced by O, SO₂ or $NR^{11}$, examples of such replacements are those that give an alkoxy alkyl group such as methoxymethyl or ethoxymethyl; a hydroxyalkoxy group such as hydroxyethoxy; a group C(=O)O—$C_{1-4}$ alkyl; a $C_{1-3}$ alkyl sulphonyl group such as ethylsulphonyl; an alkylamino group such as methylamino, ethylamino, dimethylamino or methyl(ethyl)amino; an alkylaminoalkyl group such as methylaminomethyl or dimethylaminomethyl; an aminoalkoxy group such as aminoethoxy or dimethylaminoethoxy; a hydroxyalkylamino group such as hydroxyethyl(methyl)amino; and an amide group such as C(═O)NH). In one subset of compounds within each of the embodiments 0.1 to 1.179, no such replacements of carbon atoms with other atoms or groups are present in the acyclic hydrocarbon group $R^{10}$.

Examples of hydrocarbon groups include alkyl, cycloalkyl, cycloalkenyl, carbocyclic aryl, alkenyl, alkynyl, cycloalkylalkyl, cycloalkenylalkyl, and carbocyclic aralkyl, aralkenyl and aralkynyl groups. Such groups can be unsubstituted or, where stated, substituted by one or more substituents as defined herein. The examples and preferences expressed below apply to each of the hydrocarbon substituent groups or hydrocarbon-containing substituent groups referred to in the various definitions of substituents for compounds of the formula (0) unless the context indicates otherwise.

Particular examples of non-aromatic hydrocarbon groups are saturated groups such as alkyl, cycloalkyl, alkylcycloalkyl and cycloalkylalkyl groups.

Generally by way of example, the hydrocarbon groups can have up to eight carbon atoms, unless the context requires otherwise. Within the sub-set of hydrocarbon groups having 1 to 8 carbon atoms, particular examples are $C_{1-6}$ hydrocarbon groups, such as $C_{1-4}$ hydrocarbon groups (e.g. $C_{1-3}$ hydrocarbon groups or $C_{1-2}$ hydrocarbon groups), specific examples being any individual value or combination of values selected from $C_1$, $C_2$, $C_3$, $C_4$, $C_5$, $C_6$, $C_7$ and C hydrocarbon groups.

The term "alkyl" covers both straight chain and branched chain alkyl groups. Examples of alkyl groups include methyl, ethyl, propyl, isopropyl, n-butyl, isobutyl, tert-butyl, n-pentyl, 2-pentyl, 3-pentyl, 2-methyl butyl, 3-methyl butyl, and n-hexyl and its isomers. Within the sub-set of alkyl groups having 1 to 8 carbon atoms, particular examples are $C_{1-6}$ alkyl groups, such as $C_{1-4}$ alkyl groups (e.g. $C_{1-3}$ alkyl groups or $C_{1-2}$ alkyl groups).

The term "cycloalkyl" as used herein refers to a saturated monocyclic hydrocarbon ring. Examples of cycloalkyl groups are those derived from cyclopropane, cyclobutane, cyclopentane, cyclohexane, cycloheptane and cyclooctane. Within the sub-set of cycloalkyl groups the cycloalkyl group will have from 3 to 8 carbon atoms, particular examples being $C_{3-6}$ cycloalkyl groups.

The term "alkenyl" as used herein as a group or part of a group refers to a linear or branched hydrocarbon group and containing one or more carbon carbon double bonds. Examples of alkenyl groups include, but are not limited to, ethenyl (vinyl), 1-propenyl, 2-propenyl (allyl), isopropenyl, butenyl, buta-1,4-dienyl, pentenyl, and hexenyl. Within the sub-set of alkenyl groups the alkenyl group will have 2 to 8 carbon atoms, particular examples being $C_{2-6}$ alkenyl groups, such as $C_{2-4}$ alkenyl groups.

The term "cycloalkenyl" as used herein refers to a monocyclic hydrocarbon ring having a carbon carbon double bond.

Examples of cycloalkenyl groups include, but are not limited to, cyclopropenyl, cyclobutenyl, cyclopentenyl, cyclopentadienyl and cyclohexenyl. Within the sub-set of cycloalkenyl groups the cycloalkenyl groups have from 3 to 8 carbon atoms, and particular examples are $C_{3-6}$ cycloalkenyl groups.

The term "alkynyl" as used herein as a group or part of a group refers to a linear or branched hydrocarbon group containing a carbon carbon triple bond. Examples of alkynyl groups include, but are not limited to, ethynyl and 2-propynyl (propargyl) groups. Within the sub-set of alkynyl groups having 2 to 8 carbon atoms, particular examples are $C_{2-6}$ alkynyl groups, such as $C_{2-4}$ alkynyl groups.

The term "alkylene" (e.g. as in $C_{1-4}$ straight chain or branched chain alkylene) as used herein refers to an alkanediyl group, i.e. a divalent saturated acyclic straight chain or branched chain hydrocarbon group. Examples of straight chain alkylene groups include methylene ($CH_2$), ethylene ($CH_2CH_2$) and propylene (($CH_2CH_2CH_2$). Examples of branched chain alkylene groups include $CH(CH_3)$, $CH_2CH(CH_3)CH_2$ and $CH_2(CH_3)CH_2CH_2$.

Where stated, alkylene groups can be substituted with one or more substituents.

Examples of carbocyclic aryl groups include substituted and unsubstituted phenyl groups.

Examples of cycloalkylalkyl, cycloalkenylalkyl, carbocyclic aralkyl, aralkenyl and aralkynyl groups include phenethyl, benzyl, styryl, phenylethynyl, cyclohexylmethyl, cyclopentylmethyl, cyclobutylmethyl, cyclopropylmethyl and cyclopentenylmethyl groups.

When present, and where stated, a hydrocarbon group can be optionally substituted by one or more substituents The term '$C_{1-4}$alkoxy' or '$C_{1-6}$alkoxy' as used herein as a group or part of a group refers to an —O—$C_{1-4}$alkyl group or an —O—$C_{1-6}$alkyl group wherein $C_{1-4}$alkyl and $C_{1-6}$alkyl are as defined herein. Examples of such groups include methoxy, ethoxy, propoxy, butoxy, and the like.

The term 'hydroxy$C_{1-4}$alkyl' or 'hydroxy$C_{1-6}$alkyl' as used herein as a group or part of a group refers to a $C_{1-4}$alkyl or $C_{1-6}$alkyl group as defined herein wherein one or more than one hydrogen atom is replaced with a hydroxyl group. The terms 'hydroxy$C_{1-4}$ alkyl' or 'hydroxy$C_{1-6}$ alkyl' therefore include monohydroxy$C_{1-4}$ alkyl, monohydroxy$C_{1-6}$ alkyl and also polyhydroxy$C_{1-4}$ alkyl and polyhydroxy$C_{1-6}$ alkyl. There may be one, two, three or more hydrogen atoms replaced with a hydroxyl group, so the hydroxy$C_{1-4}$alkyl or hydroxy$C_{1-6}$alkyl may have one, two, three or more hydroxyl groups. Examples of such groups include hydroxymethyl, hydroxyethyl, hydroxypropyl and the like.

The term 'halo$C_{1-4}$alkyl' or 'halo$C_{1-6}$alkyl' as used herein as a group or part of a group refers to a $C_{1-4}$alkyl or $C_{1-6}$alkyl group as defined herein wherein one or more than one hydrogen atom is replaced with a halogen. The term 'halo$C_{1-4}$ alkyl' or 'halo$C_6$alkyl' therefore include monohalo$C_{1-4}$alkyl, monohalo$C_{1-6}$alkyl and also polyhalo$C_{1-4}$alkyl and polyhalo$C_{1-6}$alkyl. There may be one, two, three or more hydrogen atoms replaced with a halogen, so the halo$C_{1-4}$ alkyl or halo$C_6$alkyl may have one, two, three or more halogens. Examples of such groups include fluoroethyl, fluoromethyl, trifluoromethyl or trifluoroethyl and the like.

The term 'halo$C_{1-4}$alkoxy' as used herein as a group or part of a group refers to a —O—$C_{1-4}$alkyl group as defined herein wherein one or more than one hydrogen atom is replaced with a halogen. The terms 'halo$C_{1-4}$alkoxy' therefore include monohalo$C_{1-4}$alkoxy, and also polyhalo$C_{1-4}$ alkoxy. There may be one, two, three or more hydrogen atoms replaced with a halogen, so the halo$C_{1-4}$alkoxy may have one, two, three or more halogens. Examples of such groups include fluoroethyloxy, difluoromethoxy or trifluoromethoxy and the like.

The term phenyl$C_{1-6}$alkyl as used herein refers to a $C_{1-6}$alkyl group as defined herein which is substituted with one phenyl group.

The term cyano$C_{1-6}$alkyl as used herein refers to a $C_{1-6}$alkyl group as defined herein which is substituted with one cyano group.

References to "carbocyclic" and "heterocyclic" groups as used herein shall, unless the context indicates otherwise, include both aromatic and non-aromatic ring systems. Thus, for example, the term "carbocyclic and heterocyclic groups" includes within its scope aromatic, non-aromatic, unsaturated, partially saturated and fully saturated carbocyclic and heterocyclic ring systems.

In general, unless the context indicates otherwise, such groups may be monocyclic or bicyclic (including fused and bridged bicyclic groups) and may contain, for example, 3 to 12 ring members, more usually 5 to 10 ring members. Reference to 4 to 7 ring members include 4, 5, 6 or 7 atoms in the ring and reference to 4 to 6 ring members include 4, 5, or 6 atoms in the ring. Examples of monocyclic groups are groups containing 3, 4, 5, 6, 7 and 8 ring members, more usually 3 to 7, and particularly 5, 6 or 7 ring members, more particularly 5 or 6 ring members. Examples of bicyclic groups are those containing 8, 9, 10, 11 and 12 ring members, and more usually 9 or 10 ring members. The heterocyclic groups can be heteroaryl groups having from 5 to 12 ring members, more usually from 5 to 10 ring members. Where reference is made herein to heterocyclic or carbocyclic groups, the heterocyclic or carbocyclic ring can, unless the context indicates otherwise, be optionally substituted i.e. unsubstituted or substituted, by one or more (e.g. 1, 2, 3, or 4 in particular one or two) substituents as defined herein.

The heterocyclic group can be, for example, a five membered or six membered monocyclic ring or a bicyclic structure formed from fused five and six membered rings, or two fused six membered rings, or two fused five membered rings, or fused six and seven membered rings, or fused five and seven membered rings. Each ring may contain up to five heteroatoms particularly selected from nitrogen, sulfur and oxygen. Typically the heterocyclic ring will contain up to 4 heteroatoms, more particularly up to 3 heteroatoms, more usually up to 2, for example a single heteroatom. In one embodiment, the heterocyclic ring will contain one or two heteroatoms selected from N, O, S and oxidised forms of N or S. In one embodiment, the heterocyclic ring contains at least one ring nitrogen atom. The nitrogen atoms in the heterocyclic rings can be basic, as in the case of an imidazole or pyridine, or essentially non-basic as in the case of an indole or pyrrole nitrogen. In general the number of basic nitrogen atoms present in the heterocyclic group, including any amino group substituents of the ring, will be less than five.

The heterocyclic groups can be attached via a carbon atom or a heteroatom (e.g. nitrogen). Equally the heterocyclic groups can be substituted on a carbon atom or on a heteroatom (e.g. nitrogen).

The term "heteroaryl" is used herein to denote a heterocyclic group having aromatic character. The term "heteroaryl" embraces polycyclic (e.g. bicyclic) ring systems wherein one or more rings are non-aromatic, provided that at least one ring is aromatic. In such polycyclic systems, the group may be attached by the aromatic ring, or by a non-aromatic ring.

Examples of heteroaryl groups are monocyclic and bicyclic groups containing from five to twelve ring members, and more usually from five to ten ring members.

Examples of five membered heteroaryl groups include but are not limited to pyrrole, furan, thiophene (thienyl), imidazole, furazan, oxazole, oxadiazole, oxatriazole, isoxazole, thiazole, thiadiazole, isothiazole, pyrazole, triazole and tetrazole groups.

Examples of six membered heteroaryl groups include but are not limited to pyridine, pyrazine, pyridazine, pyrimidine and triazine.

A bicyclic heteroaryl group may be, for example, a group selected from:
a) a benzene ring fused to a 5-, 6- or 7-membered ring containing 1, 2 or 3 ring heteroatoms;
b) a pyridine ring fused to a 5-, 6- or 7-membered ring containing 0, 1, 2 or 3 ring heteroatoms;
c) a pyrimidine ring fused to a 5-, 6- or 7-membered ring containing 0, 1 or 2 ring heteroatoms;
d) a pyrrole ring fused to a 5-, 6- or 7-membered ring containing 0, 1, 2 or 3 ring heteroatoms;
e) a pyrazole ring fused to a 5- or 6-membered ring containing 0, 1 or 2 ring heteroatoms;
f) an imidazole ring fused to a 5- or 6-membered ring containing 0, 1 or 2 ring heteroatoms;
g) an oxazole ring fused to a 5- or 6-membered ring containing 0, 1 or 2 ring heteroatoms;
h) an isoxazole ring fused to a 5- or 6-membered ring containing 0, 1 or 2 ring heteroatoms
i) a thiazole ring fused to a 5- or 6-membered ring containing 0, 1 or 2 ring heteroatoms;
j) an isothiazole ring fused to a 5- or 6-membered ring containing 0, 1 or 2 ring heteroatoms;
k) a thiophene ring fused to a 5- or 6-membered ring containing 0, 1, 2 or 3 ring heteroatoms;
l) a furan ring fused to a 5- or 6-membered ring containing 0, 1, 2 or 3 ring heteroatoms;
m) a cyclohexyl ring fused to a 5- or 6-membered ring containing 1, 2 or 3 ring heteroatoms; and
n) a cyclopentyl ring fused to a 5- or 6-membered ring containing 1, 2 or 3 ring heteroatoms.

Particular examples of bicyclic heteroaryl groups containing a five membered ring fused to another five membered ring include but are not limited to imidazothiazole (e.g. imidazo[2,1-b]thiazole) and imidazoimidazole (e.g. imidazo[1,2-a]imidazole).

Particular examples of bicyclic heteroaryl groups containing a six membered ring fused to a five membered ring include but are not limited to benzofuran, benzothiophene, benzimidazole, benzoxazole, isobenzoxazole, benzisoxazole, benzthiazole, benzisothiazole, isobenzofuran, indole, isoindole, indolizine, indoline, isoindoline, purine (e.g., adenine, guanine), indazole, pyrazolopyrimidine (e.g. pyrazolo[1,5-a]pyrimidine), triazolopyrimidine, (e.g. [1,2,4]triazolo[1,5-a]pyrimidine), triazolopyrazine, tetrahydrotriazolopyrazine, benzodioxole, imidazopyridine and pyrazolopyridine (e.g. pyrazolo[1,5-a]pyridine) groups.

Particular examples of bicyclic heteroaryl groups containing two fused six membered rings include but are not limited to quinoline, isoquinoline, chroman, thiochroman, isochroman, chromene, isochromene, benzodioxan, quinolizine, benzoxazine, pyridopyridine, quinoxaline, quinazoline, cinnoline, phthalazine, naphthyridine and pteridine groups.

Particular examples of bicyclic heteroaryl groups containing a five membered ring fused to a seven membered ring include pyrrolobenzodiazepines, dihydro-pyrrolobenzodiazepines and tetrahydro-pyrrolobenzodiazepines.

Particular examples of bicyclic heteroaryl groups containing a six membered ring fused to a seven membered ring include dihydrobenzazepines, dihydro- and tetrahydro-benzodiazepines, dihydrobenzo-oxazepines, Examples of polycyclic heteroaryl groups containing an aromatic ring and a non-aromatic ring include, tetrahydroisoquinoline, tetrahydroquinoline, dihydrobenzthiophene, dihydrobenzfuran, 2,3-dihydro-benzo[1,4]dioxine, benzo[1,3]dioxole, 4,5,6,7-tetrahydrobenzofuran, tetrahydrotriazolopyrazine (e.g. 5,6,7,8-tetrahydro-[1,2,4]triazolo[4,3-a]pyrazine), chroman, thiochroman, isochroman, chromene, isochromene, benzodioxan, benzoxazine, benzodiazepine, indoline, isoindoline, 5,6-dihydro-1,7-naphthyridine (e.g. 5,6-dihydro-1,7-naphthyridin-7(8H)-yl), 3,4-dihydropyrrolo[1,2-a]pyrazine (e.g. 3,4-dihydropyrrolo[1,2-a]pyrazin-2(1H)-yl), 4,5-dihydro-1H-benzo[d]azepine (e.g. 4,5-dihydro-1H-benzo[d]azepin-3(2H)-yl), 4,5-dihydro-1H-benzo[c]azepine (e.g. 4,5-dihydro-1H-benzo[c]azepin-2(3H)-yl), 2,3,4,5-tetrahydro-1H-benzo[b]azepine (e.g. 2,3,4,5-tetrahydro-1H-benzo[b]azepin-1-yl), 1,2,4,5-tetrahydro-3H-benzo[d]azepin-3-yl (e.g. 1,2,4,5-tetrahydro-3H-benzo[d]azepin-3-yl), 2,3-dihydrobenzo[f][1,4]oxazepine (e.g. 2,3-dihydrobenzo[f][1,4]oxazepin-4(5H)-yl) and 7,8-dihydropyrido[4,3-d]pyrimidine (e.g. 7,8-dihydropyrido[4,3-d]pyrimidin-6(5H)-yl) groups.

A nitrogen-containing heteroaryl ring must contain at least one ring nitrogen atom. The nitrogen-containing heteroaryl ring can be N-linked or C-linked. Each ring may, in addition, contain up to about four other heteroatoms typically selected from nitrogen, sulfur and oxygen. Typically the heteroaryl ring will contain up to 3 heteroatoms, for example 1, 2 or 3, more usually up to 2 nitrogens, for example a single nitrogen. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five.

Examples of nitrogen-containing heteroaryl groups include, but are not limited to, monocyclic groups such as pyridinyl, pyrrolyl, imidazolyl, oxazolyl, oxadiazolyl, thiadiazolyl, oxatriazolyl, isoxazolyl, thiazolyl, isothiazolyl, furazanyl, pyrazolyl, pyrazinyl, pyrimidinyl, pyridazinyl, triazinyl, triazolyl (e.g., 1,2,3-triazolyl, 1,2,4-triazolyl), tetrazolyl, and bicyclic groups such as quinolinyl, isoquinolinyl, benzimidazolyl, benzoxazolyl, benzisoxazole, benzothiazolyl and benzisothiazole, indolyl, 3H-indolyl, isoindolyl, indolizinyl, isoindolinyl, purinyl (e.g., adenine [6-aminopurine], guanine [2-amino-6-hydroxypurine]), indazolyl, quinolizinyl, benzoxazinyl, benzodiazepinyl, pyridopyridinyl, quinoxalinyl, quinazolinyl, cinnolinyl, phthalazinyl, naphthyridinyl and pteridinyl.

Examples of nitrogen-containing polycyclic heteroaryl groups containing an aromatic ring and a non-aromatic ring include tetrahydroisoquinolinyl, tetrahydroquinolinyl, isoindolinyl and indolinyl.

An oxygen-containing heteroaryl ring must contain at least one ring oxygen atom. The oxygen-containing heteroaryl ring is usually C-linked. Each ring may, in addition, contain up to about four other heteroatoms typically selected from nitrogen, sulfur and oxygen. Typically the heteroaryl ring will contain up to 3 heteroatoms, for example 1, 2 or 3, more usually up to 2 additional nitrogens and a single oxygen.

Examples of oxygen-containing heteroaryl groups include, but are not limited to, monocyclic groups such as furan, oxazole, isoxazole, 1,2,3-oxadiazole, or pyran (e.g. 2H-pyran or 4H-pyran).

Where, in a definition of a cyclic group or ring, it is stated that the cyclic group contains a certain number of heteroatom ring members, e.g. as in the phrase "a 5 or 6 membered ring containing 0, 1 or 2 nitrogen ring members", this is to be taken as meaning that apart from the certain number of heteroatom ring members specified, the remaining ring members are carbon atoms.

The term "non-aromatic group" embraces, unless the context indicates otherwise, unsaturated ring systems without aromatic character, partially saturated and fully saturated heterocyclic ring systems. The terms "unsaturated" and "partially saturated" refer to rings wherein the ring structure(s) contains atoms sharing more than one valence bond i.e. the ring contains at least one multiple bond e.g. a C=C, C≡C or N=C bond. The terms "saturated" or "fully saturated" refers to rings where there are no multiple bonds between ring atoms. Saturated heterocyclic groups include piperidine, morpholine, thiomorpholine. Partially saturated heterocyclic groups include pyrazolines, for example 2-pyrazoline and 3-pyrazoline.

Examples of non-aromatic heterocyclic groups are groups having from 3 to 12 ring members, more usually 5 to 10 ring members. Such groups can be monocyclic or bicyclic, for example, and typically have from 1 to 5 heteroatom ring members (more usually 1, 2, 3 or 4 heteroatom ring members), usually selected from nitrogen, oxygen and sulfur. The heterocyclic groups can contain, for example, cyclic ether moieties (e.g. as in tetrahydrofuran and dioxane), cyclic thioether moieties (e.g. as in tetrahydrothiophene and dithiane), cyclic amine moieties (e.g. as in pyrrolidine), cyclic amide moieties (e.g. as in pyrrolidone, piperidone or caprolactam), cyclic thioamides, cyclic thioesters, cyclic ureas (e.g. as in imidazolidin-2-one) cyclic ester moieties (e.g. as in butyrolactone), cyclic sulfones (e.g. as in sulfolane and sulfolene), cyclic sulfoxides, cyclic sulfonamides (such as an isothiazolidine 1,1-dioxide, [1,2]thiazinane 1,1-dioxide or [1,2]thiazepane 1,1-dioxide) and combinations thereof (e.g. morpholine, thiomorpholine and thiomorpholine-S,S-dioxide).

Particular examples of monocyclic non-aromatic heterocyclic groups include azetidine, pyrrolidine (e.g. 1-pyrrolidinyl, 2-pyrrolidinyl and 3-pyrrolidinyl), piperidine (e.g. 1-piperidinyl, 2-piperidinyl, 3-piperidinyl and 4-piperidinyl), piperidone, azepane, piperazine, diazepane, morpholine, homomorpholine, pyran (2H-pyran or 4H-pyran), imidazoline, imidazolidinone, oxazoline, thiazoline, 6H-1,2,5-thiadiazine, pyrazoline (e.g. 2-pyrazoline and 3-pyrazoline), pyrazolidine, dihydrothiophene, dihydropyran, dihydrofuran, dihydrothiazole, tetrahydrofuran, tetrahydrothiophene, dioxane, oxan (e.g. 4-oxanyl). In addition they include pyrrolidonyl piperazinonyl, and N-alkyl piperazines such as N-methyl piperazinyl. In general, typical non-aromatic heterocyclyl groups include saturated groups such as piperidinyl, pyrrolidinyl, azetidinyl, morpholinyl, piperazinyl and N-alkyl piperazines such as N-methyl piperazinyl.

The terms "oxan" and "oxanyl" as used herein refer to the group:

which may also be referred to as "tetrahydropyran" or tetrahydropyranyl".

The heterocyclic groups can be polycyclic fused ring systems, spiro ring systems or bridged ring systems such as the oxa- and aza analogues of bicycloalkanes, tricycloalkanes (e.g. oxa-adamantane and aza-adamantane). For an explanation of the distinction between fused and bridged ring systems, see *Advanced Organic Chemistry*, by Jerry March, 4th Edition, Wiley Interscience, pages 131-133, 1992.

Particular examples of bicyclic non-aromatic ring systems include aza-bicyclo[2.2.1]heptane (e.g. azabicyclo[2.2.1]heptan-2-yl), aza-bicyclo[2.2.2]octane (e.g. a 1-aza-bicyclo[2.2.2]octan-3-yl group or 2-azabicyclo[2.2.2]octan-2-yl group), aza-bicyclo[3.2.1]octane (e.g. an 8-azabicyclo[3.2.1]octan-8-yl group), hexahydro-1H-isoindolyl (e.g. hexahydro-1H-isoindol-2(3H)-yl), hexahydrocyclopenta[b]pyrrol-1(2H)-yl (e.g. hexahydrocyclopenta[b]pyrrol-1(2H)-yl), octahydroisoquinolinyl (e.g. cis-octahydro-isoquinolin-2(1H)-yl), 4-azaspiro[2.5]octan-4-yl (e.g. 4-azaspiro[2.5]octan-4-yl) and 2-oxaspiro[3.3]heptan-6-yl ring systems.

In a nitrogen-containing non-aromatic heterocyclic ring the ring must contain at least one ring nitrogen atom. The nitrogen-containing heterocyclic ring can be N-linked or C-linked. The heterocylic groups can contain, for example, cyclic amine moieties (e.g. as in pyrrolidinyl), cyclic amides (such as a pyrrolidinonyl, piperidinonyl or caprolactamyl), cyclic sulfonamides (such as an isothiazolidinyl 1,1-dioxide, [1,2]thiazinanyl 1,1-dioxide or [1,2]thiazepanyl 1,1-dioxide) and combinations thereof.

Particular examples of nitrogen-containing non-aromatic heterocyclyl groups include aziridinyl, morpholinyl, thiomorpholinyl, piperidinyl (e.g. piperidin-1-yl, piperidin-2yl, piperidin-3-yl and piperidin-4-yl), pyrrolidinyl; (e.g. pyrrolidin-1-yl, pyrrolidin-2-yl and pyrrolidin-3-yl), pyrrolidonyl, dihydrothiazolyl, imidazolinyl, imidazolidinonyl, oxazolinyl, thiazolinyl, 6H-1,2,5-thiadiazinyl, pyrazolin-2-yl, pyrazolin-3-yl, pyrazolidinyl, piperazinyl, and N-alkyl piperazines such as N-methyl piperazinyl.

In an oxygen-containing non-aromatic heterocyclic ring the ring must contain at least one ring oxygen atom. The oxygen-containing heterocyclic ring is usually C-linked. The heterocylic groups can contain, for example, cyclic ether moieties (e.g. as in oxanyl), cyclic ureas (e.g. as in imidazolidin-2-one), cyclic ester moieties (e.g. as in butyrolactone) and combinations thereof.

Particular examples of oxygen-containing non-aromatic heterocyclyl groups include dioxolanyl, oxanyl, dihydrofuranyl, dioxanyl, or morpholinyl.

The carbocyclic groups can be alicyclic groups (e.g. cycloalkyl or cycloalkenyl groups as defined herein) or aryl groups having from 5 to 12 ring members, more usually from 5 to 10 ring members. The term 'aryl' as used herein refers to carbocyclic aromatic groups having at least one aromatic ring including phenyl, naphthyl, indanyl, indenyl, and tetrahydronaphthyl groups. The term "aryl" embraces polycyclic (e.g. bicyclic) ring systems wherein one or more rings are non-aromatic, provided that at least one ring is aromatic. In such polycyclic systems, the group may be attached by the aromatic ring, or by a non-aromatic ring.

The compound of formula (1) may contain saturated cyclic groups that can be joined to the rest of the molecule by one or more bonds. When the cyclic group is joined to the rest of the molecule by two or more bonds, these bonds (or two of these bonds) can be made to the same atom (usually a carbon atom) of the ring or different atoms of the ring. Where the bonds are made to the same atom of the ring, this results in a cyclic group with a single atom (usually a quaternary carbon) bound to two groups. In other words, when the compound of formula (1) includes a cyclic group that group may either be linked to the rest of the molecule by a bond or the cyclic group and the rest of the molecule can have an atom in common e.g. a spiro compound.

The heterocyclic or carbocyclic groups can each be unsubstituted or substituted by one or more substituent groups where stated. For example, heterocyclic or carbocyclic groups can be unsubstituted or substituted by 1, 2, 3 or 4 substituents. Where the heterocyclic or carbocyclic group is monocyclic or bicyclic, typically it is unsubstituted or has 1, 2 or 3 substituents as defined herein. Where the cyclic group is saturated there may be 2 substituents joined to the same carbon (where the substituents are the same this may be referred to as geminal or 'gem' disubstitution).

A combination of substituents is permissible only if such as combination results in a stable or chemically feasible compound (i.e. one that is not substantially altered when kept at 40° C. or less for at least a week).

The various functional groups and substituents making up the compounds of the invention are typically chosen such that the molecular weight of the compound of the invention does not exceed 1000. More usually, the molecular weight of the compound will be less than 750, for example less than 700, or less than 650, or less than 600, or less than 550. More preferably, the molecular weight is less than 525 and, for example, is 500 or less.

Salts, Solvates, Tautomers, Isomers, N-Oxides, Esters, Prodrugs and Isotopes

A reference to a compound of the formula (0) and sub-groups thereof also includes ionic forms, salts, solvates, isomers (including geometric and stereochemical isomers), tautomers, N-oxides, esters, prodrugs, isotopes and protected forms thereof, for example, as discussed below; particularly the salts or tautomers or isomers or N-oxides or solvates thereof; and more particularly, the salts or tautomers or N-oxides or solvates thereof, even more particularly the salts or tautomers or solvates thereof.

Salts

Many compounds of the formula (0) can exist in the form of salts, for example acid addition salts or, in certain cases salts of organic and inorganic bases such as carboxylate, sulfonate and phosphate salts. All such salts are within the scope of this invention, and references to compounds of the formula (0) include the salt forms of the compounds.

The salts of the present invention can be synthesized from the parent compound that contains a basic or acidic moiety by conventional chemical methods such as methods described in *Pharmaceutical Salts: Properties, Selection, and Use*, P. Heinrich Stahl (Editor), Camille G. Wermuth (Editor), ISBN: 3-90639-026-8, Hardcover, 388 pages, August 2002. Generally, such salts can be prepared by reacting the free acid or base forms of these compounds with the appropriate base or acid in water or in an organic solvent, or in a mixture of the two; generally, nonaqueous media such as ether, ethyl acetate, ethanol, isopropanol, or acetonitrile are used.

Acid addition salts (mono- or di-salts) may be formed with a wide variety of acids, both inorganic and organic. Examples of acid addition salts include mono- or di-salts formed with an acid selected from the group consisting of acetic, 2,2-dichloroacetic, adipic, alginic, ascorbic (e.g. L-ascorbic), L-aspartic, benzenesulfonic, benzoic, 4-acetamidobenzoic, butanoic, (+) camphoric, camphor-sulfonic, (+)-(1S)-camphor-10-sulfonic, capric, caproic, caprylic, cinnamic, citric, cyclamic, dodecylsulfuric, ethane-1,2-disulfonic, ethanesulfonic, 2-hydroxyethanesulfonic, formic, fumaric, galactaric, gentisic, glucoheptonic, D-gluconic, glucuronic (e.g. D-glucuronic), glutamic (e.g. L-glutamic), α-oxoglutaric, glycolic, hippuric, hydrohalic acids (e.g. hydrobromic, hydrochloric, hydriodic), isethionic, lactic (e.g. (+)-L-lactic, (±)-DL-lactic), lactobionic, maleic, malic, (−)-

L-malic, malonic, (±)-DL-mandelic, methanesulfonic, naphthalene-2-sulfonic, naphthalene-1,5-disulfonic, 1-hydroxy-2-naphthoic, nicotinic, nitric, oleic, orotic, oxalic, palmitic, pamoic, phosphoric, propionic, pyruvic, L-pyroglutamic, salicylic, 4-amino-salicylic, sebacic, stearic, succinic, sulfuric, tannic, (+)-L-tartaric, thiocyanic, p-toluenesulfonic, undecylenic and valeric acids, as well as acylated amino acids and cation exchange resins.

One particular group of salts consists of salts formed from acetic, hydrochloric, hydriodic, phosphoric, nitric, sulfuric, citric, lactic, succinic, maleic, malic, isethionic, fumaric, benzenesulfonic, toluenesulfonic, methanesulfonic (mesylate), ethanesulfonic, naphthalenesulfonic, valeric, acetic, propanoic, butanoic, malonic, glucuronic and lactobionic acids. One particular salt is the hydrochloride salt.

If the compound is anionic, or has a functional group which may be anionic (e.g., —COOH may be —COO⁻), then a salt may be formed with an organic or inorganic bases, generating a suitable cation. Examples of suitable inorganic cations include, but are not limited to, alkali metal ions such as $Li^+$, $Na^+$ and $K^+$, alkaline earth metal cations such as $Ca^{2+}$ and $Mg^{2+}$, and other cations such as $Al^{3+}$ or $Zn^+$. Examples of suitable organic cations include, but are not limited to, ammonium ion (i.e., $NH_4^+$) and substituted ammonium ions (e.g., $NH_3R^+$, $NH_2R^{2+}$, $NHR_3^+$, $NR_4^+$). Examples of some suitable substituted ammonium ions are those derived from: methylamine, ethylamine, diethylamine, propylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

Where the compounds of the formula (0) contain an amine function, these may form quaternary ammonium salts, for example by reaction with an alkylating agent according to methods well known to the skilled person. Such quaternary ammonium compounds are within the scope of formula (0).

The compounds of the invention may exist as mono- or di-salts depending upon the pKa of the acid from which the salt is formed.

The salt forms of the compounds of the invention are typically pharmaceutically acceptable salts, and examples of pharmaceutically acceptable salts are discussed in Berge et al., 1977, "Pharmaceutically Acceptable Salts," *J. Pharm. Sci.*, Vol. 66, pp. 1-19. However, salts that are not pharmaceutically acceptable may also be prepared as intermediate forms which may then be converted into pharmaceutically acceptable salts. Such non-pharmaceutically acceptable salts forms, which may be useful, for example, in the purification or separation of the compounds of the invention, also form part of the invention.

In one embodiment of the invention, there is provided a pharmaceutical composition comprising a solution (e.g. an aqueous solution) containing a compound of the formula (0) and sub-groups and examples thereof as described herein in the form of a salt in a concentration of greater than 10 mg/ml, typically greater than 15 mg/ml and particularly greater than 20 mg/ml.

N-Oxides

Compounds of the formula (0) containing an amine function may also form N-oxides. A reference herein to a compound of the formula (0) that contains an amine function also includes the N-oxide.

Where a compound contains several amine functions, one or more than one nitrogen atom may be oxidised to form an N-oxide. Particular examples of N-oxides are the N-oxides of a tertiary amine or a nitrogen atom of a nitrogen-containing heterocycle.

N-Oxides can be formed by treatment of the corresponding amine with an oxidizing agent such as hydrogen peroxide or a per-acid (e.g. a peroxycarboxylic acid), see for example *Advanced Organic Chemistry*, by Jerry March, 4$^{th}$ Edition, Wiley Interscience, pages. More particularly, N-oxides can be made by the procedure of L. W. Deady (*Syn. Comm.* 1977, 7, 509-514) in which the amine compound is reacted with m-chloroperoxybenzoic acid (MCPBA), for example, in an inert solvent such as dichloromethane.

In one embodiment of the invention, the compound is an N-oxide, for example from a nitrogen atom on a heteroaryl group, for example a pyridine N-oxide.

Geometric Isomers and Tautomers Compounds of the formula (0) may exist in a number of different geometric isomeric, and tautomeric forms and references to compounds of the formula (0) include all such forms. For the avoidance of doubt, where a compound can exist in one of several geometric isomeric or tautomeric forms and only one is specifically described or shown, all others are nevertheless embraced by formulae (0), (1) and subformulae thereof.

For example, certain heteroaryl rings can exist in the two tautomeric forms such as A and B shown below. For simplicity, a formula may illustrate one form but the formula is to be taken as embracing both tautomeric forms.

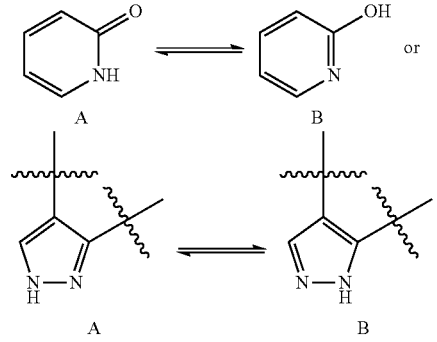

Other examples of tautomeric forms include, for example, keto-, enol-, and enolate-forms, as in, for example, the following tautomeric pairs: keto/enol (illustrated below), imine/enamine, amide/imino alcohol, amidine/enediamines, nitroso/oxime, thioketone/enethiol, and nitro/aci-nitro.

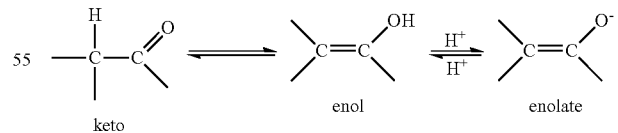

Stereoisomers

Unless otherwise mentioned or indicated, the chemical designation of compounds denotes all possible stereochemically isomeric forms.

Where a structure is not limited to a particular isomeric form, but covers any isomeric form of the compound and mixtures of isomeric forms, the configuration of the stereocentre is not specified and is represented by straight lines.

The convention of using 'hashed' or 'wedged' lines to indicate stereochemistry has been used to designate particular stereochemical forms, for example as illustrated by the two synthetic intermediates below.

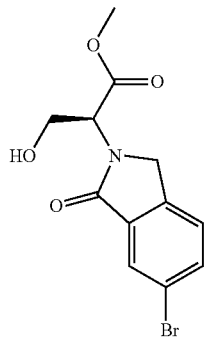 [SMILES: COC(=O)[C@H](CO)N1Cc2ccc(Br)cc2C1=O]

Methyl (S)-2-(6-bromo-1-oxoisoindolin-2-yl)-3-hydroxypropanoate

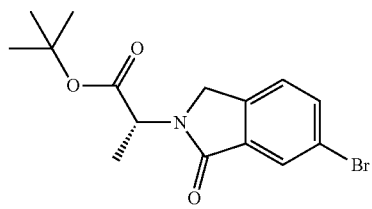 [SMILES: C[C@H](C(=O)OC(C)(C)C)N1Cc2ccc(Br)cc2C1=O]

tert-butyl (R)-2-(6-bromo-1-oxoisoindolin-2-yl)propanoate

Where compounds of the formulae (0), (1) and subformulae thereof contain one or more chiral centres, and can exist in the form of two or more optical isomers, references to compounds of the formulae (0), (1) and subformulae thereof include all optical isomeric forms thereof (e.g. enantiomers, epimers and diastereoisomers), either as individual optical isomers, or mixtures (e.g. racemic and scalemic mixtures) or two or more optical isomers, unless the context requires otherwise.

The optical isomers may be characterised and identified by their optical activity (i.e. as + and -isomers, or d and/ isomers) or they may be characterised in terms of their absolute stereochemistry using the "R and S" nomenclature developed by Cahn, Ingold and Prelog, see *Advanced Organic Chemistry* by Jerry March, 4th Edition, John Wiley & Sons, New York, 1992, pages 109-114, and see also Cahn, Ingold & Prelog, *Angew. Chem. Int. Ed. Engl.*, 1966, 5, 385-415.

Optical isomers can be separated by a number of techniques including chiral chromatography (chromatography on a chiral support) and such techniques are well known to the person skilled in the art.

As an alternative to chiral chromatography, optical isomers can be separated by forming diastereoisomeric salts with chiral acids such as (+)-tartaric acid, (−)-pyroglutamic acid, (−)-di-toluoyl-L-tartaric acid, (+)-mandelic acid, (−)-malic acid, and (−)-camphorsulfonic, separating the diastereoisomers by preferential crystallisation, and then dissociating the salts to give the individual enantiomer of the free base. Likewise, optical isomers of acidic compounds can be separated by forming diastereoisomeric salts with chiral amines such as Brucine, Cinchonidine, quinine etc.

Additionally enantiomeric separation can be achieved by covalently linking a enantiomerically pure chiral auxiliary onto the compound and then performing diastereisomer separation using conventional methods such as chromatography. This is then followed by cleavage of the aforementioned covalent linkage to generate the appropriate enantiomerically pure product. For example, optical isomers of chiral compounds containing a free hydroxyl group can be separated by forming Mosher's acid esters and then separating the resulting diastereoisomers by chromatography, followed by cleavage of the ester to regenerate the free hydroxyl group.

Where compounds of the formulae (0), (1) and subformulae thereof exist as two or more optical isomeric forms, one enantiomer in a pair of enantiomers may exhibit advantages over the other enantiomer, for example, in terms of biological activity. Thus, in certain circumstances, it may be desirable to use as a therapeutic agent only one of a pair of enantiomers, or only one of a plurality of diastereoisomers. Accordingly, the invention provides compositions containing a compound of the formulae (0), (1) and subformulae thereof having one or more chiral centres, wherein at least 55% (e.g. at least 60%, 65%, 70%, 75%, 80%, 85%, 90% or 95%) of the compound of the formulae (0), (1) and subformulae thereof is present as a single optical isomer (e.g. enantiomer or diastereoisomer). In one general embodiment, 99% or more (e.g. substantially all) of the total amount of the compound of the formulae (0), (1) and subformulae thereof may be present as a single optical isomer (e.g. enantiomer or diastereoisomer).

Compounds encompassing double bonds can have an E (entgegen) or Z (zusammen) stereochemistry at said double bond. Substituents on bivalent cyclic or (partially) saturated radicals may have either the cis- or trans-configuration. The terms cis and trans when used herein are in accordance with Chemical Abstracts nomenclature (J. Org. Chem. 1970, 35 (9), 2849-2867), and refer to the position of the substituents on a ring moiety.

Of special interest are those compounds of formulae (0), (1) and subformulae thereof which are stereochemically pure. When a compound of formulae (0), (1) and subformulae thereof is for instance specified as R, this means that the compound is substantially free of the S isomer. If a compound of formulae (0), (1) and subformulae thereof is for instance specified as E, this means that the compound is substantially free of the Z isomer. The terms cis, trans, R, S, E and Z are well known to a person skilled in the art.

Isotopic Variations

The present invention includes all pharmaceutically acceptable isotopically-labeled compounds of the invention, i.e. compounds of formulae (0), (1) and subformulae thereof, wherein one or more atoms are replaced by atoms having the same atomic number, but an atomic mass or mass number different from the atomic mass or mass number usually found in nature.

Examples of isotopes suitable for inclusion in the compounds of the invention comprise isotopes of hydrogen, such as $^2$H (D) and $^3$H (T), carbon, such as $^{11}$C, $^{13}$C and $^{14}$C, chlorine, such as $^{36}$Cl, fluorine, such as $^{18}$F, iodine, such as $^{123}$I, $^{125}$I, and $^{131}$I, nitrogen, such as $^{13}$N and $^{15}$N, oxygen, such as $^{15}$O, $^{17}$O and $^{18}$O, phosphorus, such as $^{32}$P, and sulfur, such as $^{35}$S.

Certain isotopically-labelled compounds of formulae (0), (1) and subformulae thereof, for example, those incorporating a radioactive isotope, are useful in drug and/or substrate tissue distribution studies. The compounds of formulae (0), (1) and subformulae thereof can also have valuable diagnostic properties in that they can be used for detecting or identifying the formation of a complex between a labelled compound and other molecules, peptides, proteins, enzymes or receptors. The detecting or identifying methods can use compounds that are labelled with labelling agents such as radioisotopes, enzymes, fluorescent substances, luminous substances (for example, luminol, luminol derivatives, luciferin, aequorin and luciferase), etc. The radioactive isotopes tritium, i.e. $^3$H (T), and carbon-14, i.e. $^{14}$C, are particularly useful for this purpose in view of their ease of incorporation and ready means of detection.

Substitution with heavier isotopes such as deuterium, i.e. $^2$H (D), may afford certain therapeutic advantages resulting from greater metabolic stability, for example, increased in vivo half-life or reduced dosage requirements, and hence may be preferred in some circumstances. In particular, every reference to hydrogen in the application should be construed as covering $^1$H and $^2$H, whether hydrogen is defined explicitly, or hydrogen is present implicitly to satisfy the relevant atom's (in particular carbon's) valency.

Substitution with positron emitting isotopes, such as $^{11}$C, $^{18}$F, $^{15}$O and $^{13}$N, can be useful in Positron Emission Topography (PET) studies for examining target occupancy.

Isotopically-labeled compounds of formulae (0), (1) and subformulae thereof can generally be prepared by conventional techniques known to those skilled in the art or by processes analogous to those described in the accompanying Examples and Preparations using an appropriate isotopically-labeled reagents in place of the non-labeled reagent previously employed.

Esters

Esters such as carboxylic acid esters, acyloxy esters and phosphate esters of the compounds of formulae (0), (1) and subformulae thereof bearing a carboxylic acid group or a hydroxyl group are also embraced by Formulae (0), (1) and subformulae thereof. Examples of esters are compounds containing the group —C(=O)OR, wherein R is an ester substituent, for example, a $C_{1-7}$ alkyl group, a $C_{3-12}$ heterocyclic group, or a $C_{5-12}$ aryl group, particularly a $C_{1-6}$ alkyl group. Particular examples of ester groups include, but are not limited to, —C(=O)OCH$_3$, —C(=O)OCH$_2$CH$_3$, —C(=O)OC(CH$_3$)$_3$, and —C(=O)OPh. Examples of acyloxy (reverse ester) groups are represented by —OC(=O)R, wherein R is an acyloxy substituent, for example, a $C_{1-6}$ alkyl group, a $C_{3-12}$ heterocyclic group, or a $C_{5-12}$ aryl group, particularly a $C_{1-6}$ alkyl group. Particular examples of acyloxy groups include, but are not limited to, —OC(=O)CH$_3$ (acetoxy), —OC(=O)CH$_2$CH$_3$, —OC(=O)C(CH$_3$)$_3$, —OC(=O)Ph, and —OC(=O)CH$_2$Ph. Examples of phosphate esters are those derived from phosphoric acid.

In one embodiment of the invention, formulae (0), (1) and subformulae thereof includes within its scope esters of compounds of the formulae (0), (1) and subformulae thereof bearing a carboxylic acid group or a hydroxyl group. In another embodiment of the invention, formulae (0), (1) and subformulae thereof does not include within its scope esters of compounds of the formulae (0), (1) and subformulae thereof bearing a carboxylic acid group or a hydroxyl group.

Solvates and Crystalline Forms

Also encompassed by formulae (0), (1) and subformulae thereof are any polymorphic forms of the compounds, and solvates such as hydrates, alcoholates and the like.

The compounds of the invention may form solvates, for example with water (i.e., hydrates) or common organic solvents. As used herein, the term "solvate" means a physical association of the compounds of the present invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. The term "solvate" is intended to encompass both solution-phase and isolatable solvates. Non-limiting examples of suitable solvates include compounds on the invention in combination with water, isopropanol, ethanol, methanol, DMSO, ethyl acetate, acetic acid or ethanolamine and the like. The compounds of the invention may exert their biological effects whilst they are in solution.

Solvates are well known in pharmaceutical chemistry. They can be important to the processes for the preparation of a substance (e.g. in relation to their purification, the storage of the substance (e.g. its stability) and the ease of handling of the substance and are often formed as part of the isolation or purification stages of a chemical synthesis. A person skilled in the art can determine by means of standard and long used techniques whether a hydrate or other solvate has formed by the isolation conditions or purification conditions used to prepare a given compound. Examples of such techniques include thermogravimetric analysis (TGA), differential scanning calorimetry (DSC), X-ray crystallography (e.g. single crystal X-ray crystallography or X-ray powder diffraction) and Solid State NMR (SS-NMR, also known as Magic Angle Spinning NMR or MAS-NMR). Such techniques are as much a part of the standard analytical toolkit of the skilled chemist as NMR, IR, HPLC and MS.

Alternatively the skilled person can deliberately form a solvate using crystallisation conditions that include an amount of the solvent required for the particular solvate. Thereafter the standard methods described above, can be used to establish whether solvates have formed.

Furthermore, the compounds of the present invention may have one or more polymorph or amorphous crystalline forms and as such are intended to be included in the scope of the invention.

Complexes

Formulae (0), (1) and subformulae thereof also includes within its scope complexes (e.g. inclusion complexes or clathrates with compounds such as cyclodextrins, or complexes with metals) of the compounds. Inclusion complexes, clathrates and metal complexes can be formed by means of methods well known the skilled person.

Prodrugs

Also encompassed by formulae (0), (1) and subformulae thereof are any pro-drugs of the compounds of the formulae (0), (1) and subformulae thereof. By "prodrugs" is meant for example any compound that is converted in vivo into a biologically active compound of the formulae (0), (1) and subformulae thereof.

For example, some prodrugs are esters of the active compound (e.g., a physiologically acceptable metabolically labile ester). During metabolism, the ester group (—C(=O) OR) is cleaved to yield the active drug. Such esters may be formed by esterification, for example, of any of the carboxylic acid groups (—C(=O)OH) in the parent compound, with, where appropriate, prior protection of any other reactive groups present in the parent compound, followed by deprotection if required.

Examples of such metabolically labile esters include those of the formula —C(=O)OR wherein R is:

$C_{1-7}$alkyl (e.g., -Me, -Et, -nPr, -iPr, -nBu, -sBu, -iBu, -tBu);

$C_{1-7}$aminoalkyl (e.g., aminoethyl; 2-(N,N-diethylamino) ethyl; 2-(4-morpholino)ethyl); and acyloxy-$C_{1-7}$alkyl (e.g., acyloxymethyl; acyloxyethyl; pivaloyloxymethyl; acetoxymethyl; 1-acetoxyethyl; 1-(1-methoxy-1-methyl)ethyl-carbonxyloxyethyl; 1-(benzoyloxy)ethyl; isopropoxy-carbonyloxymethyl; 1-isopropoxy-carbonyloxyethyl; cyclohexyl-carbonyloxymethyl; 1-cyclohexyl-carbonyloxyethyl; cyclohexyloxy-carbonyloxymethyl; 1-cyclohexyloxy-carbonyloxyethyl; (4-oxanyloxy) carbonyloxymethyl; 1-(4-oxanyloxy)carbonyloxyethyl; (4-oxanyl)carbonyloxymethyl; and 1-(4-oxanyl)carbonyloxyethyl).

Also, some prodrugs are activated enzymatically to yield the active compound, or a compound which, upon further chemical reaction, yields the active compound (for example, as in antigen-directed enzyme pro-drug therapy (ADEPT), gene-directed enzyme pro-drug therapy (GDEPT), and ligand-directed enzyme pro-drug therapy (LIDEPT), etc.). For example, the prodrug may be a sugar derivative or other glycoside conjugate, or may be an amino acid ester derivative. In one embodiment formulae (0), (1) and subformulae thereof does not include pro-drugs of the compounds of the formulae (0), (1) and subformulae thereof within its scope.

Methods for the Preparation of Compounds of Formulae (0), (1) and Subformulae Thereof In this section, as in all other sections of this application unless the context indicates otherwise, references to formula (1) also include formula (0) and all other sub-groups (e.g. formulae (2), (3), (3A), (3B), (4), (4A), (4B), (5), (5A), (5B), (6), (6A), (6B), (7), (7A), (7B), (8), (8A), (8B), (9), (9A), (9B), (10) and (11)), subsets and examples thereof as defined herein.

Compounds of the formulae (0), (1) and subformulae thereof can be prepared in accordance with synthetic methods well known to the skilled person.

According to a further aspect of the invention (Embodiment 2.1) there is provided a process for preparing a compound of formulae (0), (1) and subformulae thereof as defined herein, which process comprises:

(a) (i) reacting a compound of formula (II):

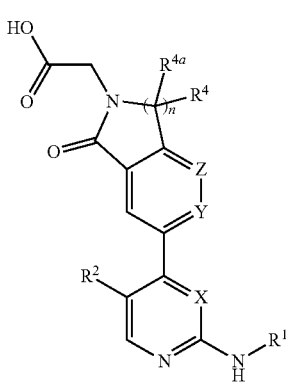

(II)

with a compound of formula $HNR^8R^9$; or (ii) reacting a compound of formula (III):

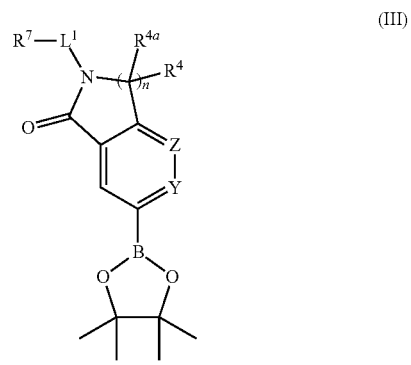

(III)

with a compound of formula (IV):

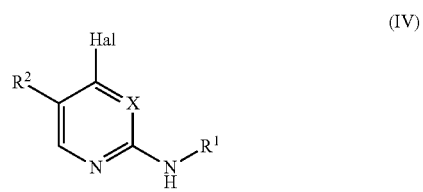

(IV)

in the presence of a palladium catalyst, wherein Hal is a suitable leaving group such as halide; or (iii) reacting a compound of formula (V):

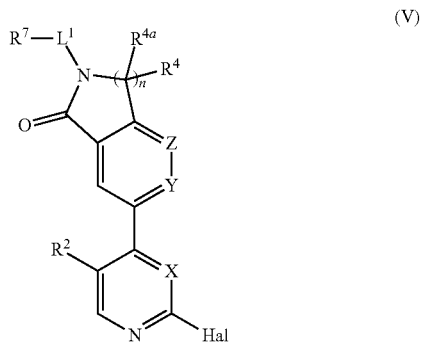

(V)

wherein Hal is a suitable leaving group such as halide, with a compound of formula $R^1NH_2$; or (iv) reacting a compound or formula (VI):

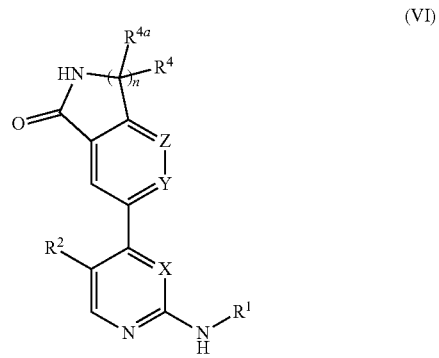

(VI)

with a compound of formula $R^7L^1$-J, wherein J is a suitable leaving group; and/or (b) deprotection of a protected derivative of a compound of formulae (0), (1) and subformulae thereof; and/or (c) interconverting a compound of formulae (0), (1) and subformulae thereof or protected derivative thereof to a further compound of formulae (0), (1) and subformulae thereof or protected derivative thereof; and (d) optionally forming a pharmaceutically acceptable salt of a compound of formulae (0), (1) and subformulae thereof; wherein $R^1$, $R^2$, $R^4$, $R^{4a}$, $R^7$, $L^1$, X, Y and Z are as defined in any one of Embodiments 0.1 to 1.179.

Process (a)(i) typically comprises stirring a compound of formula (II) with a compound of formula $HNR^8R^9$ in the presence of a suitable amide coupling agent such as HATU, TBTU or HBTU or 1-propanephosphonic anhydride and a suitable base such as triethylamine or DIPEA, in a suitable solvent such as dioxane, DMF or DCM or a mixture thereof. Such a process may be carried out at ambient temperature or at elevated temperature e.g. 60° C. An example of such a reaction is shown herein in Example 1.

Process (a)(ii) typically comprises stirring a compound of formula (III) with a compound of formula (IV) in the presence of a suitable catalyst such as tetrakis(triphenylphosphine) palladium and a suitable base such as potassium carbonate in a suitable aqueous solvent mixture such as dioxan/water in an inert atmosphere. Such a process may be carried out at ambient temperature or at elevated temperature e.g. 80 or 100° C. An example of such a reaction is shown herein in Example 124.

Process (a)(iii) typically comprises stirring a compound of formula (V) with a compound of formula $R^1NH_2$ in a suitable solvent such as dioxan, EtOH or a mixture thereof. Such a process may be carried out at ambient temperature or at elevated temperature e.g. 60 or 90° C. An example of such a reaction is shown herein in Example 102.

Process (a)(iii) alternatively comprises stirring the compound of formula (V) with a compound of formula $R^1NH_2$ in the presence of a suitable catalyst such as bis(dibenzylideneacetone) palladium and a suitable ligand such as XPhos and a suitable base such as potassium carbonate in a suitable solvent such as acetonitrile in an inert atmosphere. Such a process may be carried out at ambient temperature or at elevated temperature e.g. 90 or 150° C. An example of such a reaction is shown herein in Example 189.

Process (b) typically comprises any suitable deprotection reaction, the conditions of which will depend on the nature of the protecting group. When the protecting group represents tBoc or 2,4-dimethoxybenzyl, such a deprotection reaction will typically comprise use of a suitable acid in a suitable solvent. For example, the acid may suitably comprise trifluoroacetic acid or hydrogen chloride and the solvent may suitably comprise dichloromethane, ethyl acetate, dioxane, methanol or water, or a mixture thereof. An example of such a reaction is shown herein in Example 113.

It will be appreciated that, when the protecting group represents tBoc, deprotection using a suitable acid as described above may generate a compound of formulae (0), (1) and subformulae thereof as a pharmaceutically acceptable salt, which may be isolated directly. Alternatively, the compound of formulae (0), (1) and subformulae thereof may be isolated as the free base using methods well known in the art and thereafter optionally converted to a pharmaceutically acceptable salt according to process (d).

Process (c) typically comprises interconversion procedures known by those skilled in the art. For example, in compounds of formulae (0), (1) and subformulae thereof, a first substituent may be converted by methods known by those skilled in the art into a second, alternative substituent. A wide range of well-known functional group interconversions are known by a person skilled in the art for converting a precursor compound to a compound of formulae (0), (1) and subformulae thereof as described for example in *Advanced Organic Chemistry* by Jerry March & Michael B Smith, $7^{th}$ edition, John Wiley & Sons, 2013.

Process (d) may be carried out by treatment of a compound of formulae (0), (1) and subformulae thereof in the free base form, dissolved in a suitable solvent, with a stoichiometric amount or an excess of a pharmaceutically acceptable organic or inorganic acid, then isolation of the resulting salt by methods well known in the art, e.g. evaporation of solvent or crystallization.

If appropriate, the reactions previously described in processes (a), (b) and (c) are followed or preceded by one or more reactions known to those skilled in the art and are performed in an appropriate order to achieve the requisite substitutions to afford other compounds of formulae (0), (1) and subformulae thereof. Non-limiting examples of such reactions whose conditions can be found in the literature include:

protection of reactive functions, deprotection of reactive functions, halogenation, dehalogenation, dealkylation, alkylation of amine, aniline, alcohol and phenol, Mitsunobu reaction on hydroxyl groups, cycloaddition reactions on appropriate groups, reduction of nitro, esters, cyano, aldehydes, transition metal-catalyzed coupling reactions, acylation, sulfonylation/introduction of sulfonyl groups, saponification/hydrolysis of esters groups, amidification or transesterification of ester groups, esterification or amidification of carboxylic groups, halogen exchange, nucleophilic substitution with amine, thiol or alcohol, reductive amination, oxime formation on carbonyl and hydroxylamine groups, S-oxidation, N-oxidation, and salification.

Intermediates for Process (a)

Compounds of formula (II) wherein n, $R^1$, $R^2$ and Z are as defined hereinbefore, $R^3$ is —$CH_2CONR^8R^9$, $R^4$ and $R^{4a}$ are H, Y is CH and X is N, may be prepared in accordance with the following Scheme 1:

Step (i) of Scheme 1 typically comprises stirring a compound of formula (VII) with a compound of formula $R^1NH2$ in a suitable solvent such as dioxan, EtOH or a mixture thereof. Such a process may be carried out at ambient temperature or at elevated temperature e.g. 60 or 90° C. An example of such a reaction is shown herein in Preparation 4.

Scheme 1

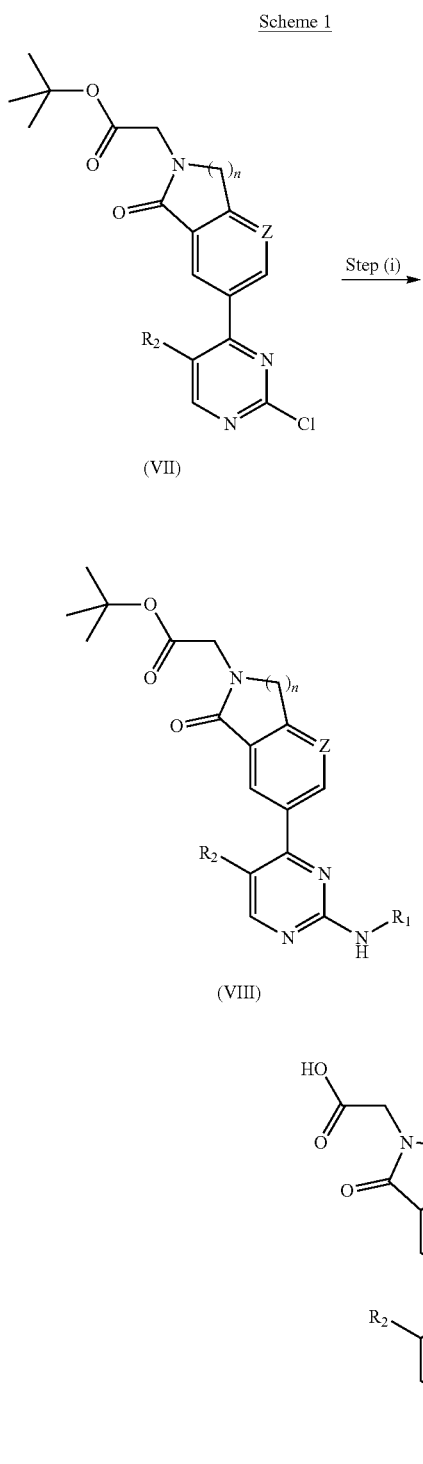

Step (ii) of Scheme 1 typically comprises stirring a compound of formula (VIII) with a suitable acid such as trifluoroacetic acid or hydrogen chloride in a suitable solvent such as dichloromethane, ethyl acetate, dioxane, methanol or water, or a mixture thereof. An example of such a reaction is shown herein in Preparation 5.

Compounds of formula (VII) wherein n, $R^2$, $R^3$, and Z are as defined in formulae (0), (1) and subformulae thereof and $R^4$ and $R^{4a}$ are H, X is N, and Y is CH, may be prepared in accordance with the following Scheme 2:

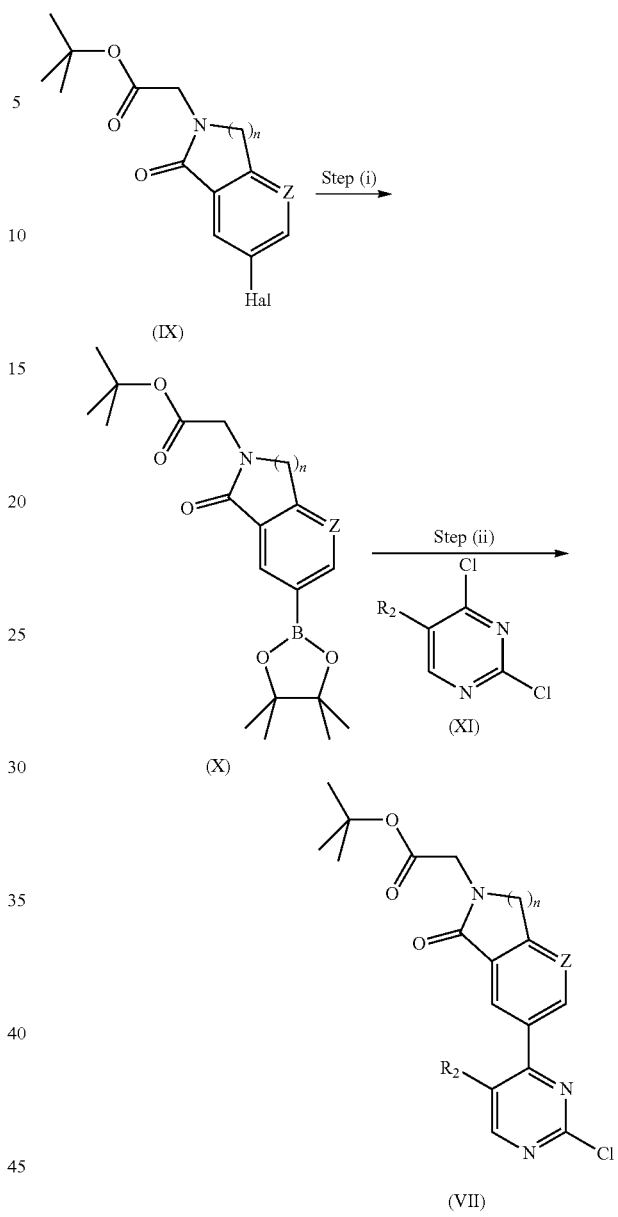

Scheme 2, Hal represents a suitable halogen leaving group, e.g. Cl, Br or I.

Step (i) of Scheme 2 typically comprises stirring a compound of formula (IX) with bis(pinacolato)diboron in the presence of a suitable catalyst such as $PdCl_2(dppf)$ complex and a suitable base such as potassium acetate in a suitable solvent such as dioxan in an inert atmosphere. Such a process may be carried out at ambient temperature or at elevated temperature e.g. 80 to 100° C. An example of such a reaction is shown herein in Preparation 2.

Step (ii) of Scheme 2 typically comprises stirring a compound of formula (X) with a compound of formula (XI) in the presence of a suitable catalyst such as tetrakis(triphenylphosphine) palladium and a suitable base such as potassium carbonate in a suitable aqueous solvent mixture such as dioxan/water in an inert atmosphere. Such a process may be carried out at ambient temperature or at elevated temperature e.g. 80 to 100° C. An example of such a reaction is shown herein in Preparation 3.

Compounds of formula (IX) wherein n=1 or 2, and Y and Z are CH may be prepared in accordance with the following Scheme 3:

Step (i) of Scheme 3 typically comprises stirring a commercially available compound of formula (XII) with a suitable alkylating agent such as tert-butyl 2-bromoacetate in the presence of a suitable base such as sodium hydride in a suitable solvent such as DMF. Such a process may be carried out at ambient temperature or at reduced temperature e.g. 4° C. An example of such a reaction is shown herein in Preparation 1.

Compounds of formula (IX) wherein n=1, Y=CH, and Z is as defined in the general formulae (0), (1) and subformulae thereof above, may be prepared in accordance with the following Scheme 4:

Step (i) of Scheme 4 typically comprises stirring a compound of formula (XIII) with a suitable brominating agent such as N-bromosuccinimide with a suitable radical initiator such as benzoyl peroxide or azaisobutyronitrile in a suitable solvent such as dichloroethane. Such a process may be carried out at ambient temperature or at elevated temperature e.g. 80° C. An example of such a reaction is shown herein in Preparation 6.

Step (ii) of Scheme 4 typically comprises stirring a compound of formula (XIV) with tert-butylglycinate in the presence of a suitable base such as trimethylamine or diisopropylethylamine in a suitable solvent such as toluene or acetonitrile. Such a process may be carried out at ambient temperature or at elevated temperature e.g. 120° C. An example of such a reaction is shown herein in Preparation 7.

Bromination and ring closure to form a lactam (illustrated by formula (IX) above) can also be used to prepare more advanced intermediate compounds, for example intermediates wherein the "Hal" group in formula (IX) is replaced by a 2-halo-pyrimidine group. An example of a sequence of reactions to prepare such intermediates is provided in Preparations 225 to 227, 401 and 402 below.

Alternatively, compounds of formula (II) wherein n, $R^1$, $R^2$, X and Z are as defined hereinabove and Y is CH may be prepared in accordance with the following Scheme 5:

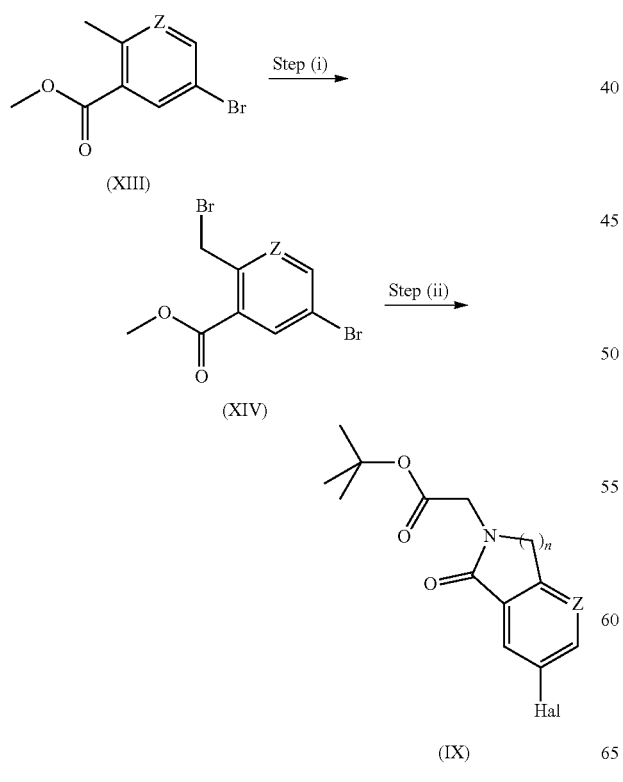

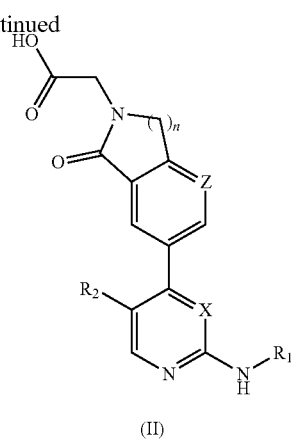

(II)

Step (i) of Scheme 5 typically comprises stirring a compound of formula (X) with a compound of formula (XVI) in the presence of a suitable catalyst such as tetrakis(triphenylphosphine) palladium or XPhos Pd G3 and a suitable base such as potassium carbonate in a suitable aqueous solvent mixture such as dioxan/water in an inert atmosphere. Such a process may be carried out at ambient temperature or at elevated temperature eg. 80 to 100° C. An example procedure for steps (i) and (ii) is shown herein in Preparation 19.

Step (ii) of Scheme 5 typically comprises stirring a compound of formula (XVIII) with a suitable acid such as trifluoroacetic acid or hydrogen chloride in a suitable solvent such as dichloromethane, ethyl acetate, dioxane, methanol or water, or a mixture thereof. An example of such a reaction is shown herein in Preparation 20.

Compounds of formula (IV) wherein X is N may be prepared in accordance with the following Scheme 6:

Scheme 6

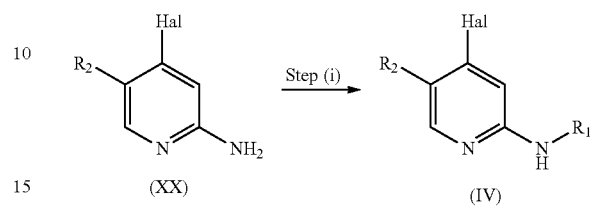

Step (i) of Scheme 6 typically comprises stirring a compound of formula (XIX) with a compound of formula $R^1NH_2$ in a suitable solvent such as dioxan, THF, EtOH or a mixture thereof. Such a process may be carried out at ambient temperature or at elevated temperature e.g. 60 to 90° C. An example of such a reaction is shown herein in Preparation 17.

In a variation of the reaction shown in Scheme 6 above, a compound of formula (XIX) in which "Hal" has been replaced by OH (i.e. the compound is a 4-pyrimidone) and the chlorine atom is replaced by methylsulfanyl can be reacted with an amine $R^1NH_2$ at an elevated temperature (e.g. approximately 130° C.). The hydroxy group on the pyrimidine ring can then be replaced by chlorine by reaction with a chlorinating agent such as POCl. Such a sequence of reactions is illustrated in Preparations 112 and 113 below.

As a further variation of the reaction shown in Scheme 6 above, a palladium catalysed amination reaction can be used (for example under Buchwald Hartwig reaction conditions) to convert the chloro-intermediate (XIX) to the amine (IV).

Compounds of formula (IV) wherein X is CH may be prepared in accordance with the following Scheme 7:

Scheme 7

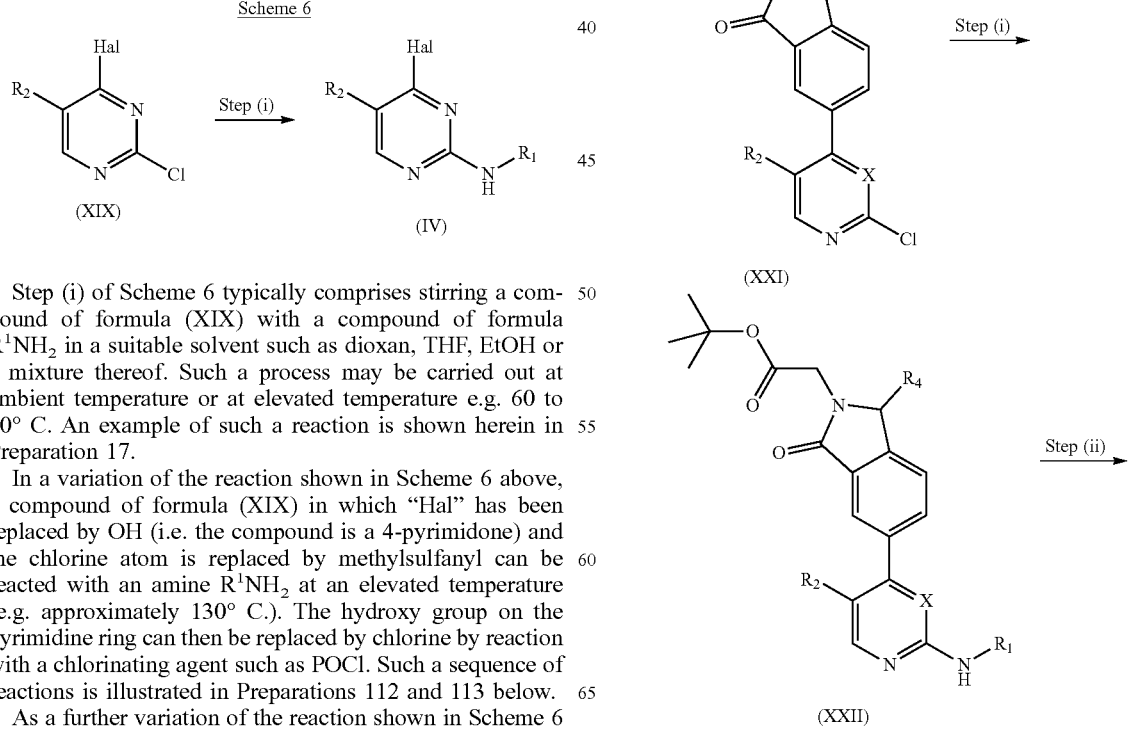

Step (i) of Scheme 7 typically comprises stirring a compound of formula (XX) with a suitable ketone $R^1$=O in the presence of a suitable reducing agent such as sodium triacetoxyborohydride in a suitable solvent such as dichloroethane. Such a process may be carried out at ambient temperature or at reduced or elevated temperature e.g. a temperature in the range from 0° C. to 60° C. An example of such a reaction is shown herein in Preparation 135.

Compounds of formula (II) wherein $R^1$, $R^2$, and X are as defined hereinbefore, Y and Z are CH, n=1, $R^4$ is alkyl and $R^{4a}$ is H, may be prepared in accordance with the following Scheme 8:

Scheme 8

-continued

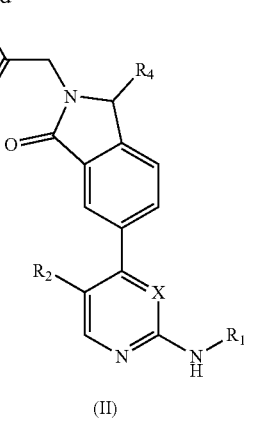

(II)

Step (i) of Scheme 8 typically comprises stirring a compound of formula (XXI) with a compound of formula R¹NH₂ in a suitable solvent such as dioxan, EtOH or a mixture thereof. Such a process may be carried out at ambient temperature or at elevated temperature e.g. 60 or 90° C. An example of such a reaction is shown herein in Preparation 33.

Step (ii) of Scheme 1 typically comprises stirring a compound of formula (XXII) with a suitable acid such as trifluoroacetic acid or hydrogen chloride in a suitable solvent such as dichloromethane, ethyl acetate, dioxane, methanol or water, or a mixture thereof. An example of such a reaction is shown herein in Preparation 5.

Compounds of formula (XXI) wherein $R^2$, X are as defined in formulae (0), (1) and subformulae thereof, Y and Z are CH, n=1, $R^4$ is alkyl and $R^{4a}$ is H, may be prepared in accordance with the following Scheme 9:

Scheme 9

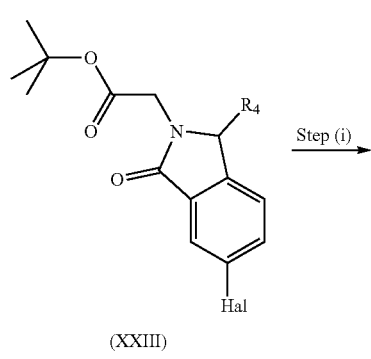

(XXIII)

-continued

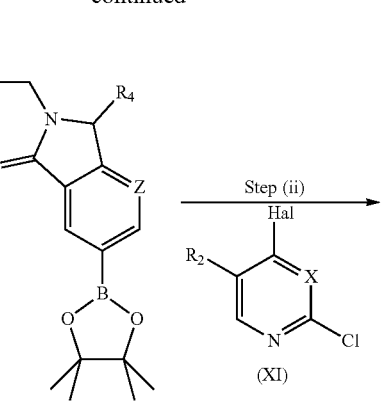

(XXIV)

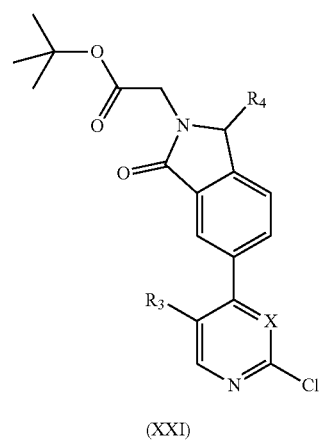

(XXI)

In Scheme 9, Hal represents a suitable halogen leaving group, e.g. Cl, Br or I.

Step (i) of Scheme 9 typically comprises stirring a compound of formula (XXIII) with bis(pinacolato)diboron in the presence of a suitable catalyst such as PdCl₂(dppf) complex and a suitable base such as potassium acetate in a suitable solvent such as dioxan in an inert atmosphere. Such a process may be carried out at ambient temperature or at elevated temperature e.g. 80 or 100° C.

Step (ii) of Scheme 9 typically comprises stirring a compound of formula (XXIV) with a compound of formula (XI) in the presence of a suitable catalyst such as tetrakis (triphenylphosphine) palladium and a suitable base such as potassium carbonate in a suitable aqueous solvent mixture such as dioxan/water in an inert atmosphere. Such a process may be carried out at ambient temperature or at elevated temperature e.g. 80 or 100° C. An example procedure for steps (i) and (ii) is shown herein in Preparation 32.

Compounds of formula (XXIII) wherein n=1, Y and Z are CH, $R^4$ is alkyl and $R^4$ is H, may be prepared in accordance with the following Scheme 10:

Scheme 10

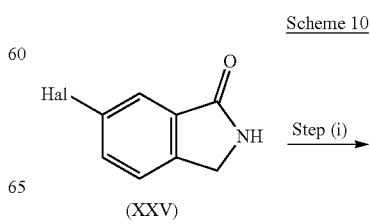

(XXV)

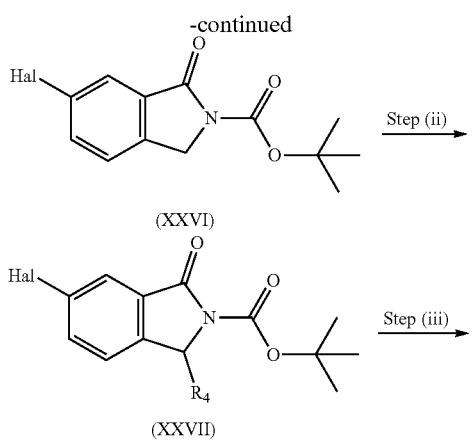

(XXVI)

(XXVII)

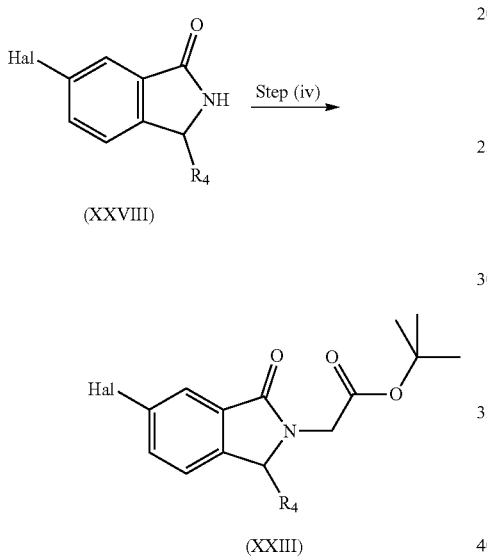

(XXVIII)

(XXIII)

In Scheme 10, Hal represents a suitable halogen leaving group, e.g. Cl, Br or I.

Step (i) of Scheme 10 typically comprises stirring a compound of formula (XXV) with di-tert-butyl dicarbonate in the presence of a suitable base such as trimethylamine and a nucleophilic catalyst such as DMAP in a suitable solvent such as dichloromethane. Such a process may be carried out at ambient temperature or at elevated temperature e.g. 60° C. An example procedure for step (i) is shown herein in Preparation 21.

Step (ii) of Scheme 10 typically comprises stirring a compound of formula (XXVI) with a suitable base such as lithium hexamethyldisilazide for a suitable period such as 1 hour in a suitable solvent such as THF, followed by treatment with a suitable alkylating agent such as an alkyl halide, mesylate or triflate. Such a process may be carried out at ambient temperature or at reduced temperature e.g. −78° C. to 0° C. An example procedure for step (ii) is shown herein in Preparation 29.

Step (iii) of Scheme 10 typically comprises stirring a compound of formula (XXVII) with a suitable acid such as trifluoroacetic acid or hydrochloric acid in a suitable solvent such as dichloromethane or dioxan. Such a process is normally carried out at ambient temperature but may also be carried out at reduced or elevated temperature. An example procedure for step (ii) is shown herein in Preparation 30.

Step (iv) of Scheme 10 typically comprises stirring a compound of formula (XXVIII) with a suitable alkylating agent such as tert-butyl 2-bromoacetate in the presence of a suitable base such as sodium hydride in a suitable solvent such as dimethylformamide or NMP. Such a process is normally carried out at ambient temperature but may also be carried out at reduced or elevated temperature. An example procedure for step (ii) is shown herein in Preparation 1.

Compounds of formula (XXIII) wherein n=1, Y and Z are CH, $R^4$ is alkyl and $R^4$ is H, may also be prepared by a variation of the sequence of reactions in Scheme 4 above but wherein the bromomethyl group in compound (XIV) of Scheme 4 is replaced by a group Alk-CH(Br)—. An example of this variation is illustrated in Preparations 347 and 348 below.

Compounds of formula (III) may be prepared in accordance with the following Scheme 11:

Scheme 11

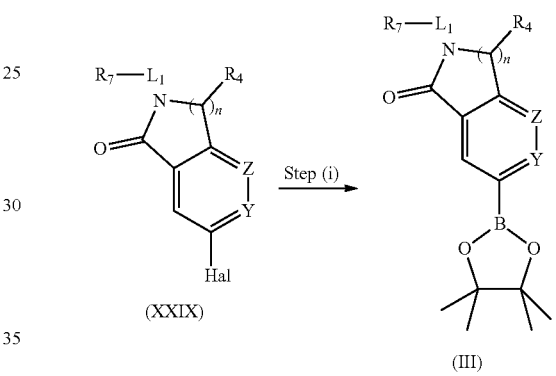

(XXIX)

(III)

Step (i) of Scheme 11 typically comprises stirring a compound of formula (XXIII) with bis(pinacolato)diboron in the presence of a suitable catalyst such as $PdCl_2$(dppf) complex or XPhos Pd G3 and a suitable base such as potassium acetate in a suitable solvent such as dioxan in an inert atmosphere. Such a process may be carried out at ambient temperature or at elevated temperature e.g. 80 or 100° C. An example procedure for step (ii) is shown herein in Preparation 86.

Compounds of formula (XXIX) may be prepared in accordance with the following Scheme 12 or Scheme 13, wherein $R^7L$ is as defined in formulae (0), (1) and subformulae thereof:

Scheme 12

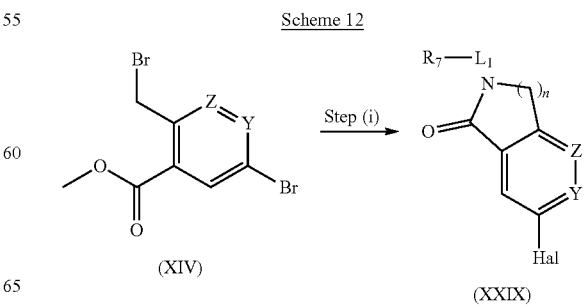

(XIV)

(XXIX)

-continued
Scheme 13

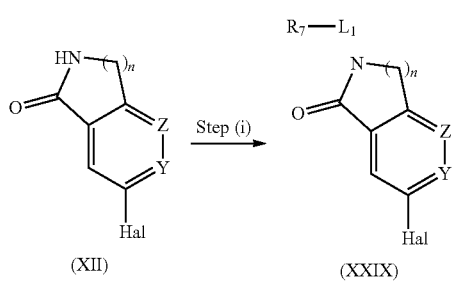

Step (i) of Scheme 12 typically comprises stirring a compound of formula (XIV) with a suitable amine in the presence of a suitable base such as triethylamine in a suitable solvent such as THF, methanol or toluene. Such a process may be carried out at ambient temperature or at elevated temperature e.g. 70° C. or 100° C. An example of such a reaction is shown herein in Preparation 78.

Step (i) of Scheme 13 typically comprises stirring a commercially available compound of formula (XII) with a suitable alkylating agent in the presence of a suitable base such as sodium hydride in a suitable solvent such as DMF. Such a process may be carried out at ambient temperature or at reduced temperature e.g. 4° C. An example of such a reaction is shown herein in Preparation 43.

Compounds of formula (V) may be prepared in accordance with the following Scheme 14:

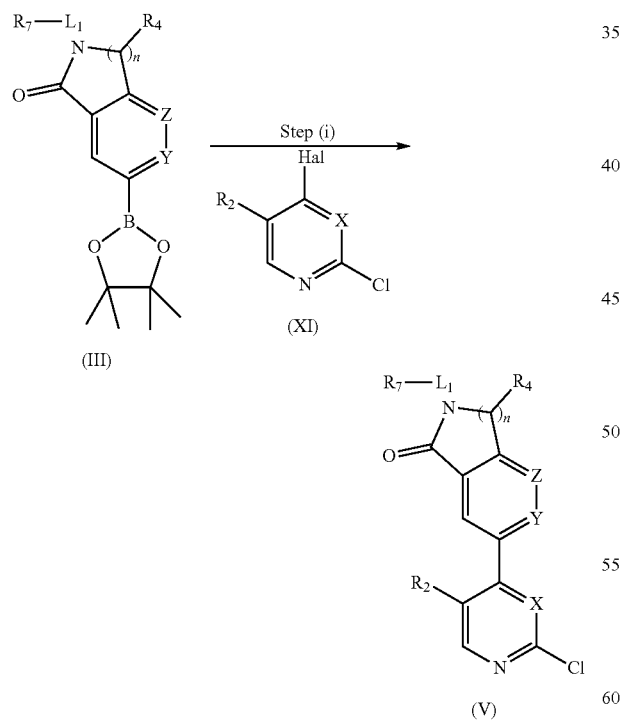

In Scheme 14, Hal represents a suitable halogen leaving group, e.g. Cl, Br or I.

Step (i) of Scheme 14 typically comprises stirring a compound of formula (III) with a compound of formula (XI) in the presence of a suitable catalyst such as tetrakis(triphenylphosphine) palladium and a suitable base such as potassium carbonate in a suitable aqueous solvent mixture such as dioxan/water in an inert atmosphere. Such a process may be carried out at ambient temperature or at elevated temperature e.g. 80 or 100° C. An example procedure for step (ii) is shown herein in Preparation 90.

Intermediates for Process (b)

Compounds of formulae (0), (1) and subformulae thereof wherein n=1, Y and Z are CH, $R^4$ is hydroxyalkyl and $R^4$ is H, may be prepared in accordance with the following Scheme 15:

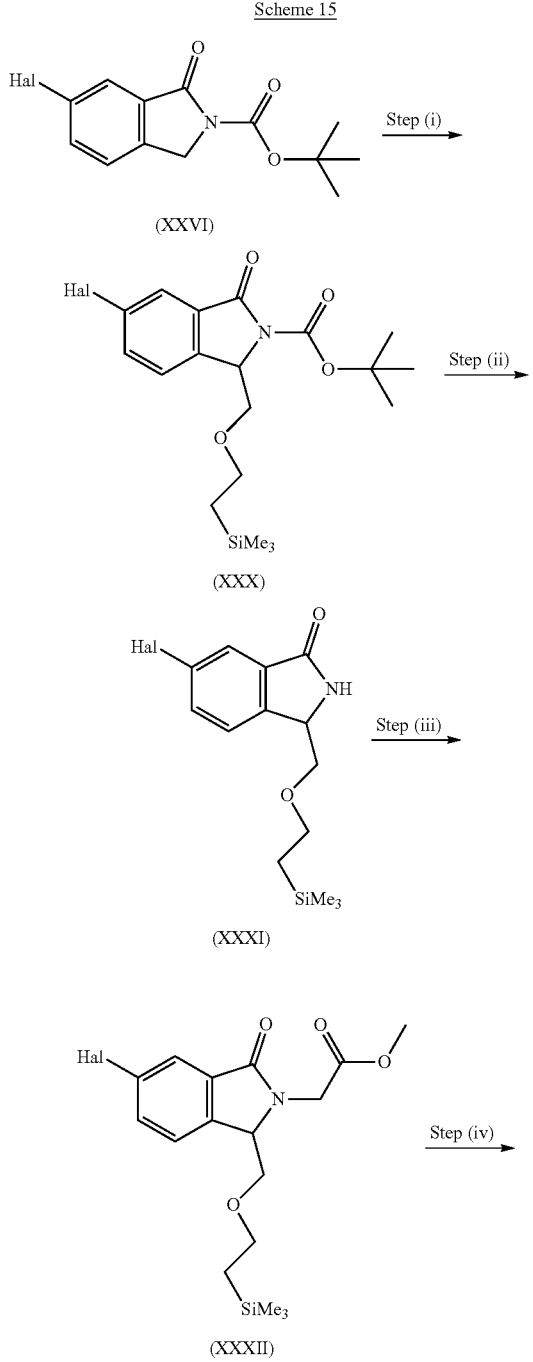

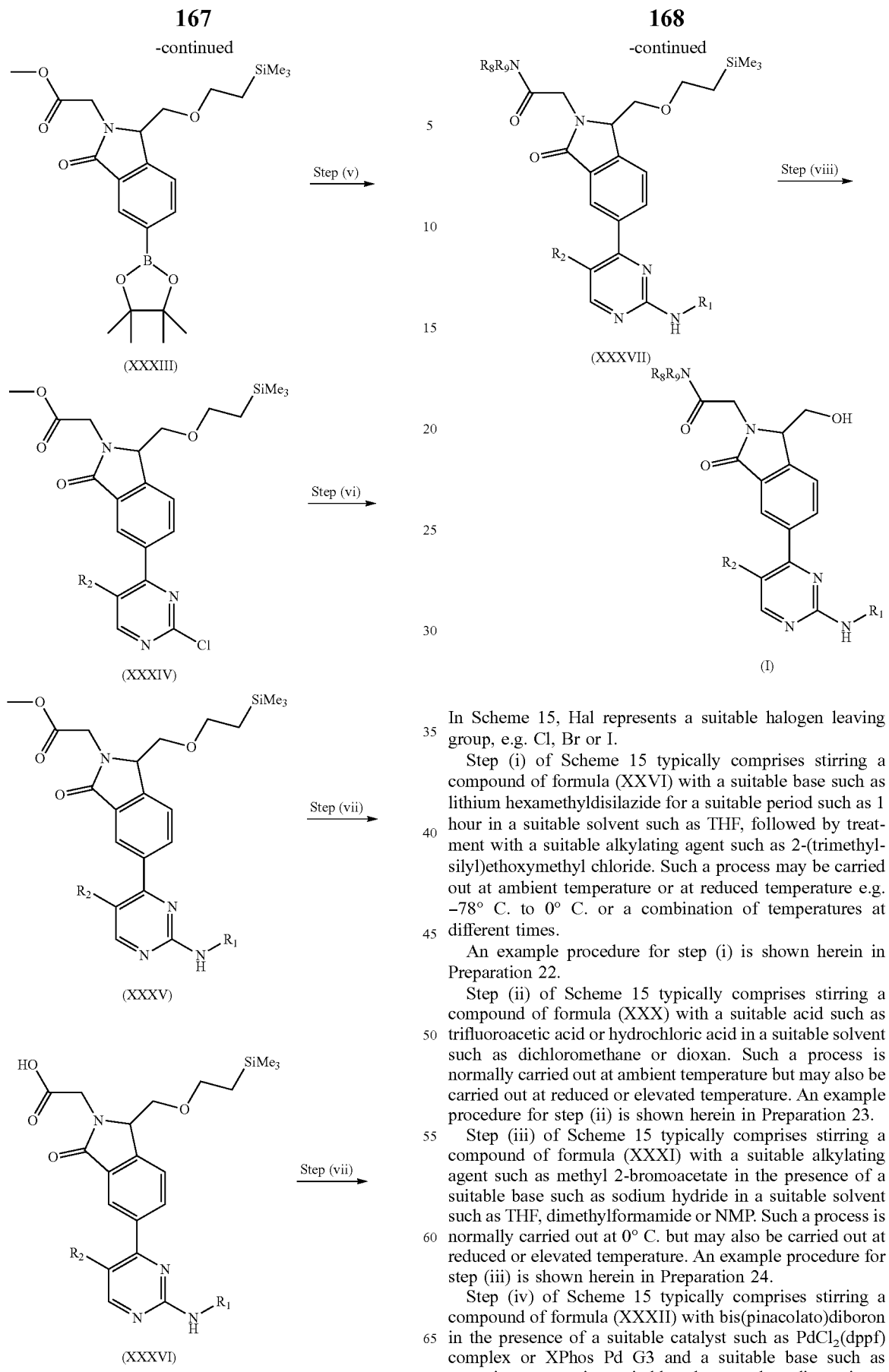

In Scheme 15, Hal represents a suitable halogen leaving group, e.g. Cl, Br or I.

Step (i) of Scheme 15 typically comprises stirring a compound of formula (XXVI) with a suitable base such as lithium hexamethyldisilazide for a suitable period such as 1 hour in a suitable solvent such as THF, followed by treatment with a suitable alkylating agent such as 2-(trimethylsilyl)ethoxymethyl chloride. Such a process may be carried out at ambient temperature or at reduced temperature e.g. −78° C. to 0° C. or a combination of temperatures at different times.

An example procedure for step (i) is shown herein in Preparation 22.

Step (ii) of Scheme 15 typically comprises stirring a compound of formula (XXX) with a suitable acid such as trifluoroacetic acid or hydrochloric acid in a suitable solvent such as dichloromethane or dioxan. Such a process is normally carried out at ambient temperature but may also be carried out at reduced or elevated temperature. An example procedure for step (ii) is shown herein in Preparation 23.

Step (iii) of Scheme 15 typically comprises stirring a compound of formula (XXXI) with a suitable alkylating agent such as methyl 2-bromoacetate in the presence of a suitable base such as sodium hydride in a suitable solvent such as THF, dimethylformamide or NMP. Such a process is normally carried out at 0° C. but may also be carried out at reduced or elevated temperature. An example procedure for step (iii) is shown herein in Preparation 24.

Step (iv) of Scheme 15 typically comprises stirring a compound of formula (XXXII) with bis(pinacolato)diboron in the presence of a suitable catalyst such as PdCl$_2$(dppf) complex or XPhos Pd G3 and a suitable base such as potassium acetate in a suitable solvent such as dioxan in an inert atmosphere. Such a process may be carried out at ambient temperature or at elevated temperature eg. 80 or 100° C. An example procedure for step (ii) is shown herein in Preparation 25.

Step (v) of Scheme 15 typically comprises stirring a compound of formula (XXXIII) with a compound of formula (XI) in the presence of a suitable catalyst such as tetrakis(triphenylphosphine) palladium and a suitable base such as potassium carbonate in a suitable aqueous solvent mixture such as dioxan/water in an inert atmosphere. Such a process may be carried out at ambient temperature or at elevated temperature eg. 80 or 100° C. An example procedure for step (ii) is shown herein in Preparation 26.

Step (vi) of Scheme 15 typically comprises stirring a compound of formula (XXXIV) with a compound of formula $R^1NH_2$ in a suitable solvent such as dioxan, EtOH or a mixture thereof. Such a process may be carried out at ambient temperature or at elevated temperature eg. 60 or 90° C. An example of such a reaction is shown herein in Preparation 27.

Step (vii) of Scheme 15 typically comprises stirring a compound of formula (XXXV) with a suitable base such as lithium hydroxide in a suitable aqueous solvent mixture such as THF-water. Such a process may be carried out at ambient temperature or at elevated temperature e.g. 60 or 90° C. An example of such a reaction is shown herein in Preparation 28.

Step (viii) of Scheme 15 typically comprises stirring a compound of formula (XXXVI) with a compound of formula $HNR^8R^9$ in the presence of a suitable amide coupling agent such as HATU or HBTU or 1-propanephosphonic anhydride and a suitable base such as triethylamine or DIPEA, in a suitable solvent such as dioxane, DMF or DCM or a mixture thereof. Such a process may be carried out at ambient temperature or at elevated temperature e.g. 60° C. An example of such a reaction is shown herein in Example 1.

Step (ix) of Scheme 15 typically comprises stirring a compound of formula (XXX) with a suitable acid such as trifluoroacetic acid in a suitable solvent such as dichloromethane. Such a process is normally carried out at ambient temperature but may also be carried out at reduced or elevated temperature. An example procedure for step (ix) is shown herein in Preparation 28.

Scheme 15 specifically illustrates the preparation of compounds wherein $R^4$ is hydroxymethyl but other hydroxyalkyl compounds can be prepared by using an appropriate alkylating agent in step (i).

Compounds wherein $R^4$ is hydroxyethyl can also be formed by the methods described in Examples 601 to 604 below.

The compounds of formula (XI), (XII), (XIII), (XIV), (XIX) and (XX) are commercially available, known in the literature or can be prepared by methods analogous to those described in the literature or by methods similar to that described in the example experimental procedures below. Other compounds may be prepared by functional group interconversion using methods well known in the art.

It will be appreciated that certain compounds e.g. compounds of formulae (0), (1) and subformulae thereof, can exist in different diastereomeric and/or enantiomeric forms and that processes for their preparation may make use of enantiomerically pure synthetic precursors.

Alternatively racemic precursors may be used and the mixtures of diastereoisomers generated in these process may be separated by methods well known to the person skilled in the art, for example using non-chiral or chiral preparative chromatography or resolution using diastereomeric derivatives: for example crystallisation of a salt formed with an enantiomerically pure acid such as L-tartaric acid; or enantiomer separation of a diastereomeric derivative formed by covalently linking a enantiomerically pure chiral auxiliary onto the compound, followed by separation using conventional methods such as chiral chromatography. The aforementioned covalent linkage is then cleaved to generate the appropriate enantiomerically pure product.

In a further embodiment the invention provides a novel intermediate. In one embodiment the invention provides a novel intermediate selected from the compounds of formulae (II), (III), (IV), (V) and (VI).

Protecting Groups

In many of the reactions described above, it may be necessary to protect one or more groups to prevent reaction from taking place at an undesirable location on the molecule. Examples of protecting groups, and methods of protecting and deprotecting functional groups, can be found in Protective Groups in Organic Synthesis (T. Green and P. Wuts; 3rd Edition; John Wiley and Sons, 1999). In particular the compound may be synthesised in protected forms and the protecting groups removed to generate a compound of formula (1).

A hydroxy group may be protected, for example, as an ether (—OR) or an ester (—OC(=O)R), for example, as: a t-butyl ether; a oxanyl (THP) ether; a benzyl, benzhydryl (diphenylmethyl), or trityl (triphenylmethyl) ether; a trimethylsilyl or t-butyldimethylsilyl ether; or an acetyl ester (—OC(=O)CH_3).

An aldehyde or ketone group may be protected, for example, as an acetal (R—CH(OR)_2) or ketal (R_2C(OR)_2), respectively, in which the carbonyl group (>C=O) is treated with, for example, a primary alcohol. The aldehyde or ketone group is readily regenerated by hydrolysis using a large excess of water in the presence of acid.

An amine group may be protected, for example, as an amide (—NRCO—R) or a carbamate (—NRCO—OR), for example, as: a methyl amide (—NHCO—CH_3); a benzyl carbamate (—NHCO—OCH_2C_6H_5, —NH-Cbz or NH—Z); as a t-butyl carbamate (—NHCO—OC(CH_3)_3, —NH-Boc); a 2-biphenyl-2-propyl carbamate (—NHCO—OC(CH_3)_2 C_6H_4C_6H_5, —NH-Bpoc), as a 9-fluorenylmethyl carbamate (—NH-Fmoc), as a 6-nitroveratryl carbamate (—NH-Nvoc), as a 2-trimethylsilylethyl carbamate (—NH-Teoc), as a 2,2,2-trichloroethyl carbamate (—NH-Troc), as an allyl carbamate (—NH-Alloc), or as a 2(-phenylsulphonyl)ethyl carbamate (—NH-Psec).

For example, in Scheme 1 above, the moiety $R_1NH$—$CHR_2$—$C(=O)NH_2$ contains two amino groups, the first amino group $R_1NH$— can be protected by means of a protecting group as hereinbefore defined, one particular group being the tert-butyloxycarbonyl (Boc) group while the second amide $NH_2$ is introduced. Where no subsequent modification of the amino group is required, the protecting group can be carried through the reaction sequence to give an N-protected form of a compound of the formulae (0), (1) and subformulae thereof which can then be de-protected by standard methods (e.g. treatment with acid in the case of the Boc group) to give the compound of formulae (0), (1) and subformulae thereof.

Other protecting groups for amines, such as cyclic amines and heterocyclic N—H groups, include toluenesulphonyl (tosyl) and methanesulphonyl (mesyl) groups, benzyl groups such as a para-methoxybenzyl (PMB) group and oxanyl (THP) groups.

A carboxylic acid group may be protected as an ester for example, as: an $C_{1-7}$ alkyl ester (e.g., a methyl ester; a t-butyl ester); a $C_{1-7}$ haloalkyl ester (e.g., a $C_{1-7}$ trihaloalkyl ester); a tri$C_{1-7}$ alkylsilyl-$C_{1-7}$alkyl ester; or a $C_{5-20}$ aryl-$C_{1-7}$ alkyl ester (e.g., a benzyl ester; a nitrobenzyl ester; para-methoxybenzyl ester. A thiol group may be protected, for example, as a thioether (—SR), for example, as: a benzyl thioether; an acetamidomethyl ether (—S—CH$_2$NHC(=O)CH$_3$).

Isolation, Purification and Analysis of the Compounds of the Invention

The compounds of the invention can be isolated and purified according to standard techniques well known to the person skilled in the art and examples of such methods include chromatographic techniques such as column chromatography (e.g. flash chromatography) and HPLC.

Preparative LC-MS

One technique of particular usefulness in purifying the compounds is preparative liquid chromatography using mass spectrometry as a means of detecting the purified compounds emerging from the chromatography column.

Preparative LC-MS is a standard and effective method used for the purification of small organic molecules such as the compounds described herein. The methods for the liquid chromatography (LC) and mass spectrometry (MS) can be varied to provide better separation of the crude materials and improved detection of the samples by MS. Optimisation of the preparative gradient LC method will involve varying columns, volatile eluents and modifiers, and gradients. Methods are well known in the art for optimising preparative LC-MS methods and then using them to purify compounds. Such methods are described in Rosentreter U, Huber U.; Optimal fraction collecting in preparative LC-MS; *J Comb Chem.;* 2004; 6(2), 159-64 and Leister W, Strauss K, Wisnoski D, Zhao Z, Lindsley C., Development of a custom high-throughput preparative liquid chromatography/mass spectrometer platform for the preparative purification and analytical analysis of compound libraries; *J Comb Chem.;* 2003; 5(3); 322-9. Examples of such systems for purifying compounds via preparative LC-MS are described in the Examples section of this application.

Achiral Preparative Chromatography

HPLC purification of compounds can be carried out using methods described in Snyder L. R., Dolan J. W., High-Performance Gradient Elution, The Practical Application of the Linear-Solvent-Strength Model, Wiley, Hoboken, 2007, and methods analogous thereto.

Chiral Preparative Chromatography Preparative separations using Chiral Stationary Phases (CSPs) are the natural technique to apply to the resolution of enantiomeric mixtures. Equally, it can be applied to the separation of diastereomers and achiral molecules. Methods are well known in the art for optimising preparative chiral separations on CSPs and then using them to purify compounds. Such methods are described in Beesley T. E., Scott R. P. W.; Chiral Chromatography; Wiley, Chichester, 1998.

Recrystallisation

Methods of recrystallisation of compounds of formulae (0), (1) and subformulae thereof and salt thereof can be carried out by methods well known to the skilled person—see for example (P. Heinrich Stahl (Editor), Camille G. Wermuth (Editor), ISBN: 3-90639-026-8, Handbook of Pharmaceutical Salts: Properties, Selection, and Use, Chapter 8, Publisher Wiley-VCH). Products obtained from an organic reaction are seldom pure when isolated directly from the reaction mixture. If the compound (or a salt thereof) is solid, it may be purified and/or crystallized by recrystallisation from a suitable solvent. A good recrystallisation solvent should dissolve a moderate quantity of the substance to be purified at elevated temperatures but only a small quantity of the substance at lower temperature. It should dissolve impurities readily at low temperatures or not at all. Finally, the solvent should be readily removed from the purified product. This usually means that it has a relatively low boiling point and a person skilled in the art will know recrystallising solvents for a particular substance, or if that information is not available, test several solvents. To get a good yield of purified material, the minimum amount of hot solvent to dissolve all the impure material is used. In practice, 3-5% more solvent than necessary is used so the solution is not saturated. If the impure compound contains an impurity which is insoluble in the solvent it may then be removed by filtration and then allowing the solution to crystallize. In addition, if the impure compound contains traces of coloured material that are not native to the compound, it may be removed by adding a small amount of decolorizing agent e.g. activating charcoal to the hot solution, filtering it and then allowing it to crystallize. Usually crystallization spontaneously occurs upon cooling the solution. If it is not, crystallization may be induced by cooling the solution below room temperature or by adding a single crystal of pure material (a seed crystal). Recrystallisation can also be carried out and/or the yield optimized by the use of an anti-solvent or co-solvent. In this case, the compound is dissolved in a suitable solvent at elevated temperature, filtered and then an additional solvent in which the required compound has low solubility is added to aid crystallization. The crystals are then typically isolated using vacuum filtration, washed and then dried, for example, in an oven or via desiccation.

Miscellaneous Methods of Purification

Other examples of methods for purification include sublimation, which includes an heating step under vacuum for example using a cold finger, and crystallization from melt (Crystallization Technology Handbook 2nd Edition, edited by A. Mersmann, 2001).

Analysis

Compounds of the invention can be analysed and their structures determined by standard methods, for example spectroscopic methods such as liquid chromatography-mass spectrometry (LC-MS) and nuclear magnetic resonance spectroscopy (NMR). LC-MS systems that can be used are set out in the Examples section of this application.

Biological Properties

It is envisaged that the compound of the invention will be useful in medicine or therapy.

The compounds of the invention, subgroups and examples thereof, are inhibitors of ERK1/2, and will be useful in preventing or treating disease states or conditions described herein, for example the diseases and conditions discussed below and the diseases and conditions described in the "Background of the Invention" section above in which ERK1/2 plays a role. In addition the compounds of the invention, and subgroups thereof, will be useful in preventing or treating diseases or conditions mediated by ERK1/2, for example diseases or conditions such as cancers in which ERK1/2 activity is required or upregulated as a result of activating mutations within upstream components (such as RAS, K-RAS, NRAS and RAF) of the MAPK pathway.

References to the preventing or prophylaxis or treatment of a disease state or condition such as cancer include within their scope alleviating or reducing the incidence of the disease or condition. Thus, for example, it is envisaged that the compounds of the invention will be useful in alleviating or reducing the incidence of cancer.

Accordingly, in further embodiments of the invention (Embodiments 3.1 to 3.7), there are provided:

3.1 A compound as defined in any one of Embodiments 0.1 to 1.179 for use in medicine.

3.2 A compound as defined in any one of Embodiments 0.1 to 1.179 for use in preventing or treating a disease or condition mediated by ERK1/2.

3.3 The use of a compound as defined in any one of Embodiments 0.1 to 1.179 for the manufacture of a medicament for preventing or treating a disease or condition mediated by ERK1/2.

3.4 A method of preventing or treating a disease or condition mediated by ERK1/2 in a subject (e.g. a mammalian subject, such as a human, in need thereof), which method comprises administering to the subject a therapeutically effective amount of compound as defined in any one of Embodiments 0.1 to 1.179.

3.5 A compound as defined in any one of Embodiments 0.1 to 1.179 for use in alleviating or reducing the incidence of a disease or condition mediated by ERK1/2.

3.6 The use of a compound as defined in any one of Embodiments 0.1 to 1.179 for the manufacture of a medicament for alleviating or reducing the incidence of a disease or condition mediated by ERK1/2.

3.7 A method of alleviating or reducing the incidence of a disease or condition mediated by ERK1/2 in a subject (e.g. a mammalian subject, such as a human, in need thereof), which method comprises administering to the subject a therapeutically effective amount of compound as defined in any one of Embodiments 0.1 to 1.179.

More particularly, the compounds of the formulae (0), (1) and subformulae thereof and sub-groups thereof are inhibitors of ERK1/2. For example, compounds of the invention have inhibitory potency against ERK1 or ERK2, and in particular against ERK1/2.

Particular compounds of the invention are those having $IC_{50}$ values of less than 0.1 µM.

The ERK inhibitor compounds of formulae (0), (1) and subformulae thereof are capable of binding to ERK1/2 and exhibiting potency for ERK1/2. In one embodiment the inhibitor compounds of formulae (0), (1) and subformulae thereof exhibit selectivity for ERK1/2 over other kinase family members, and may be capable of binding to and/or exhibiting inhibition of ERK1 and/or ERK2 in preference to binding to and/or exhibiting inhibition of other of the kinase family members.

ERK1/2 function in controlling cell signalling, has also been implicated in many diseases, including disorders associated with cell accumulation (e.g. cancer, autoimmune disorders, inflammation and restenosis), disorders where excessive apoptosis results in cell loss (e.g. stroke, heart failure, neurodegeneration such as Alzheimers' disease, Parkinson's disease, Huntington's disease, amyotrophic lateral sclerosis, AIDS, ischemia (stroke, myocardial infarction) and osteoporosis or treating autoimmune diseases such as multiple sclerosis (MS).

The disease or condition mediated by ERK1/2 referred to in any one of Embodiments 3.2 to 3.7 may be any one or more of the above diseases and disorders.

Therefore, it is also envisaged that the compounds of the invention as defined in any one of Embodiments 0.1 to 1.179 may be useful in treating other conditions such as inflammation, hepatitis, ulcerative colitis, gastritis, autoimmunity, inflammation, restenosis, stroke, heart failure, neurodegenerative conditions such as Alzheimers' disease, Parkinson's disease, Huntington's disease, myotonic dystrophy, and amyotrophic lateral sclerosis, AIDS, ischemia such as traumatic brain injury, spinal cord injury, cerebral ischemia, cerebral ischemia/reperfusion (I/R) injury, acute and chronic CNS injury ischemia, stroke or myocardial infarction, degenerative diseases of the musculoskeletal system such as osteoporosis, autoimmune diseases such as multiple sclerosis (MS) and Type I diabetes, and eye diseases such as retinal degeneration which result from loss of control of programmed cell death.

As a consequence of their affinity for ERK1/2, the compounds of the invention will be useful in providing a means of controlling cell signalling. It is therefore anticipated that the compounds may prove useful in treating or preventing proliferative disorders such as cancers.

Accordingly, in further embodiments (Embodiment 3.8 to 3.13), the invention provides:

3.8 A compound as defined in any one of Embodiments 0.1 to 1.179 for use in preventing or treating proliferative disorders such as cancers.

3.9 The use of a compound as defined in any one of Embodiments 0.1 to 1.179 for the manufacture of a medicament for preventing or treating proliferative disorders such as cancers.

3.10 A method of preventing or treating proliferative disorders such as cancers in a subject (e.g. a mammalian subject, such as a human, in need thereof), which method comprises administering to the subject a therapeutically effective amount of compound as defined in any one of Embodiments 0.1 to 1.179.

3.11 A compound as defined in any one of Embodiments 0.1 to 1.179 for use in alleviating or reducing the incidence of proliferative disorders such as cancers.

3.12 The use of a compound as defined in any one of Embodiments 0.1 to 1.179 for the manufacture of a medicament for alleviating or reducing the incidence of proliferative disorders such as cancers.

3.13 A method of alleviating or reducing the incidence of proliferative disorders such as cancers in a subject (e.g. a mammalian subject, such as a human, in need thereof), which method comprises administering to the subject a therapeutically effective amount of compound as defined in any one of Embodiments 0.1 to 1.179.

Examples of cancers (and their benign counterparts) which may be treated (or inhibited) in accordance with Embodiments 3.8 to 3.13 above include, but are not limited to tumours of epithelial origin (adenomas and carcinomas of various types including adenocarcinomas, squamous carcinomas, transitional cell carcinomas and other carcinomas) such as carcinomas of the bladder and urinary tract, breast, gastrointestinal tract (including the esophagus, stomach (gastric), small intestine, colon, rectum and anus), liver (hepatocellular carcinoma), gall bladder and biliary system, exocrine pancreas, kidney, lung (for example adenocarcinomas, small cell lung carcinomas, non-small cell lung carcinomas, bronchioalveolar carcinomas and mesotheliomas), head and neck (for example cancers of the tongue, buccal cavity, larynx, pharynx, nasopharynx, tonsil, salivary glands, nasal cavity and paranasal sinuses), ovary, fallopian tubes, peritoneum, vagina, vulva, penis, cervix, myometrium, endometrium, thyroid (for example thyroid follicular carcinoma), adrenal, prostate, skin and adnexae (for example melanoma, basal cell carcinoma, squamous cell carcinoma, keratoacanthoma, dysplastic naevus); haematological malignancies (i.e. leukemias, lymphomas) and premalignant haematological disorders and disorders of borderline malignancy including haematological malignancies and related conditions of lymphoid lineage (for example acute lymphocytic leukemia [ALL], chronic lymphocytic leukemia [CLL], B-cell lymphomas such as diffuse large B-cell lymphoma [DLBCL], follicular lymphoma, Burkitt's lymphoma, mantle cell lymphoma, T-cell lymphomas and leukaemias, natural killer [NK] cell lymphomas, Hodgkin's lymphomas, hairy cell leukaemia, monoclonal gammopathy of uncertain significance, plasmacytoma, multiple myeloma, and post-transplant lymphoproliferative disorders), and haematological malignancies and related conditions of myeloid lineage (for example acute myelogenous leukemia [AML], chronic myelogenous leukemia [CML], chronic myelomonocytic leukemia [CMML], hypereosinophilic syndrome, myeloproliferative disorders such as polycythaemia vera, essential thrombocythaemia and primary myelofibrosis, myeloproliferative syndrome, myelodysplastic syndrome, and promyelocytic leukemia); tumours of mesenchymal origin, for example sarcomas of soft tissue, bone or cartilage such as osteosarcomas, fibrosarcomas, chondrosarcomas, rhabdomyosarcomas, leiomyosarcomas, liposarcomas, angiosarcomas, Kaposi's sarcoma, Ewing's sarcoma, synovial sarcomas, epithelioid sarcomas, gastrointestinal stromal tumours, benign and malignant histiocytomas, and dermatofibrosarcoma protuberans; neural crest cell-derived tumours including melanocytic tumours (for example malignant melanoma or uveal melanoma), tumours of peripheral and cranial nerves, peripheral neuroblastic tumours (for example neuroblastoma), embryonal tumors of the CNS, paraganglioma; tumours of the central or peripheral nervous system (for example astrocytomas, gliomas and glioblastomas, meningiomas, ependymomas, pineal tumours and schwannomas); endocrine tumours (for example pituitary tumours, adrenal tumours, islet cell tumours, parathyroid tumours, carcinoid tumours and medullary carcinoma of the thyroid); ocular and adnexal tumours (for example retinoblastoma); germ cell and trophoblastic tumours (for example teratomas, seminomas, dysgerminomas, hydatidiform moles and choriocarcinomas); and paediatric and embryonal tumours (for example medulloblastoma, neuroblastoma, Wilms tumour, and primitive neuroectodermal tumours); or syndromes, congenital or otherwise, which leave the patient susceptible to malignancy (for example Xeroderma Pigmentosum). Further examples of cancers (and their benign counterparts) which may be treated (or inhibited) [in accordance with Embodiments 3.8 to 3.13 above] include, but are not limited to tumours of testes and brain (e.g. neuromas).

Thus, in the pharmaceutical compositions, uses or methods of this invention for treating a disease or condition comprising abnormal cell growth (i.e. uncontrolled and/or rapid cell growth), the disease or condition comprising abnormal cell growth in one embodiment is a cancer.

In one embodiment the haematological malignancy is leukaemia. In another embodiment the haematological malignancy is lymphoma. In one embodiment, the compound of the invention is for use in the prophylaxis or treatment of leukemia, such as acute or chronic leukaemia, in particular acute myeloid leukaemia (AML), acute lymphocytic leukaemia (ALL), chronic lymphocytic leukaemia (CLL), or chronic myeloid leukemia (CML). In one embodiment, the compound of the invention is for use in the prophylaxis or treatment of lymphoma, such as acute or chronic lymphoma in particular Burkitt lymphoma, Hodgkin lymphoma, non-Hodgkin lymphoma or diffuse large B-cell lymphoma. In one embodiment, the compound of the invention is for use in the prophylaxis or treatment of acute myeloid leukaemia (AML) or acute lymphocytic leukaemia (ALL). In one embodiment, the cancer is AML. In another embodiment, the cancer is CLL.

Many diseases are characterized by persistent and unregulated angiogenesis. Chronic proliferative diseases are often accompanied by profound angiogenesis, which can contribute to or maintain an inflammatory and/or proliferative state, or which leads to tissue destruction through the invasive proliferation of blood vessels. Tumour growth and metastasis have been found to be angiogenesis-dependent. Compounds of the invention may therefore be useful in preventing and disrupting initiation of tumour angiogenesis. In particular, the compounds of the invention may be useful in the treatment of metastasis and metastatic cancers.

Metastasis or metastatic disease is the spread of a disease from one organ or part to another non-adjacent organ or part. The cancers which can be treated by the compounds of the invention include primary tumours (i.e. cancer cells at the originating site), local invasion (cancer cells which penetrate and infiltrate surrounding normal tissues in the local area), and metastatic (or secondary) tumours i.e. tumours that have formed from malignant cells which have circulated through the bloodstream (haematogenous spread) or via lymphatics or across body cavities (trans-coelomic) to other sites and tissues in the body.

In Embodiments 3.8 to 3.13 above, particular cancers include hepatocellular carcinoma, melanoma, oesophageal, renal, colon, colorectal, lung e.g. mesothelioma or lung adenocarcinoma, breast, bladder, gastrointestinal, ovarian and prostate cancers.

In Embodiments 3.8 to 3.13 above, another subset of cancers consists of renal, melanoma, colon, lung, breast, ovarian and prostate cancers.

Another subset of cancers consists of pancreatic cancers.

Another subset of cancers within Embodiments 3.8 to 3.13 above consists of leukemia, such as acute and chronic leukaemias, acute myeloid leukaemia (AML), and chronic lymphocytic leukaemia (CLL).

A further subset of cancers within Embodiments 3.8 to 3.13 above consists of mesothelioma including malignant peritoneal mesothelioma or malignant pleural mesothelioma.

Certain cancers are resistant to treatment with particular drugs. This can be due to the type of the tumour (most common epithelial malignancies are inherently chemoresistant) or resistance can arise spontaneously as the disease progresses or as a result of treatment. In this regard, references to mesothelioma includes mesothelioma with resistance towards topoisomerase poisons, alkylating agents, antitubulines, antifolates, platinum compounds and radiation therapy, in particular cisplatin-resistant mesothelioma. Similarly references to multiple myeloma includes bortezomib-sensitive multiple myeloma or refractory multiple myeloma and references to chronic myelogenous leukemia includes imitanib-sensitive chronic myelogenous leukemia and refractory chronic myelogenous leukemia. In this regard, references to prostate cancer include prostate cancers with resistance towards anti-androgen therapy, in particular abiraterone or enzalutamide, or castrate-resistant prostate cancer. References to melanoma include melanomas that are resistant to treatment with BRAF and/or MEK inhibitors.

The cancers may be cancers which are sensitive to inhibition of either ERK1 or ERK2 or most particularly ERK1/2.

It is further envisaged that the compounds of the invention, and in particular those compounds having ERK1/2 inhibitory potency will be particularly useful in the treatment or prevention of cancers of a type associated with or characterised by the presence of elevated Ras, BRAF and/or MEK signalling.

Elevated levels of Ras, BRAF or MEK signalling are found in many cancers and are associated with a poor prognosis. In addition, cancers with activating Ras, BRAF or MEK mutations may also be sensitive to an ERK1/2 inhibitor. The elevated levels of Ras, BRAF or MEK signalling and mutations in Ras, BRAF or MEK can be identified by the techniques outlined herein. Whether a particular cancer is one which is sensitive to ERK1/2 inhibition may be determined by a method as set out in the section headed "Methods of Diagnosis".

A further subset of cancers within Embodiments 3.8 to 3.13 above consists of NRas melanoma and NRas AML.

Another subset of cancers within Embodiments 3.8 to 3.13 consists of KRas lung cancer, KRas pancreatic cancer and KRas colorectal cancer (CRC).

Another subset of cancers consists of BRAF colorectal cancer (CRC), BRAF lung cancer and BRAF melanoma.

In further embodiments (Embodiments 3.14 to 3.19), the invention provides:

3.14 A compound as defined in any one of Embodiments 0.1 to 1.179 for use in preventing or treating a disease or condition with mutant Ras, mutant BRAF or mutant MEK.

3.15 The use of a compound as defined in any one of Embodiments 0.1 to 1.179 for the manufacture of a medicament for preventing or treating a disease or condition with mutant Ras, mutant BRAF or mutant MEK.

3.16 A method of preventing or treating a disease or condition with mutant Ras, mutant BRAF or mutant MEK in a subject (e.g. a mammalian subject, such as a human, in need thereof), which method comprises administering to the subject a therapeutically effective amount of compound as defined in any one of Embodiments 0.1 to 1.179.

3.17 A compound as defined in any one of Embodiments 0.1 to 1.179 for use in alleviating or reducing the incidence of a disease or condition with mutant Ras, mutant BRAF or mutant MEK.

3.18 The use of a compound as defined in any one of Embodiments 0.1 to 1.179 for the manufacture of a medicament for alleviating or reducing the incidence of a disease or condition with mutant Ras, mutant BRAF or mutant MEK.

3.19 A method of alleviating or reducing the incidence of a disease or condition with mutant Ras, mutant BRAF or mutant MEK in a subject (e.g. a mammalian subject, such as a human, in need thereof), which method comprises administering to the subject a therapeutically effective amount of compound as defined in any one of Embodiments 0.1 to 1.179.

3.19A A compound as defined in any one of Embodiments 0.1 to 1.179 for use in the treatment of (or reduction in the incidence of) a cancer selected from NRas melanoma and NRas AML.

3.19B A compound as defined in any one of Embodiments 0.1 to 1.179 for use in the treatment of (or reduction in the incidence of) a cancer selected from KRas lung cancer, KRas pancreatic cancer and KRas colorectal cancer (CRC).

3.19C A compound as defined in any one of Embodiments 0.1 to 1.179 for use in the treatment of (or reduction in the incidence of) a cancer selected from BRAF colorectal cancer (CRC), BRAF lung cancer and BRAF melanoma.

3.19D A compound as defined in any one of Embodiments 0.1 to 1.179 for use in the treatment of (or reduction in the incidence of) a cancer which is BRAF melanoma.

3.19E The use of a compound as defined in any one of Embodiments 0.1 to 1.179 for the manufacture of a medicament for preventing or treating a cancer as defined in any one of Embodiments 3.19A to 3.19D.

3.19F A method of treating (or reducing the incidence of) a cancer as defined in any one of Embodiments 3.19A to 3.19D in a subject (e.g. a mammalian subject such as a human), which method comprises administering to the subject a therapeutically effective amount of compound as defined in any one of Embodiments 0.1 to 1.179.

In further Embodiments (Embodiments 3.20 to 3.25), the invention provides:

3.20 A compound as defined in any one of Embodiments 0.1 to 1.179 for use in the treatment of a disease or condition as described herein, in particular cancer.

3.21 The use of a compound as defined in any one of Embodiments 0.1 to 1.179 for the manufacture of a medicament for the treatment of a disease or condition as described herein, in particular cancer.

3.22 A method of preventing or treating a disease or condition as described herein, in particular cancer, in a subject (e.g. a mammalian subject, such as a human, in need thereof), which method comprises administering to the subject a therapeutically effective amount of compound as defined in any one of Embodiments 0.1 to 1.179.

3.33 A compound as defined in any one of Embodiments 0.1 to 1.179 for use in alleviating or reducing the incidence of a disease or condition as described herein, in particular cancer.

3.34 The use of a compound as defined in any one of Embodiments 0.1 to 1.179 for the manufacture of a medicament for alleviating or reducing the incidence of a disease or condition as described herein, in particular cancer.

3.35 A method of alleviating or reducing the incidence of a disease or condition as described herein, in particular cancer, in a subject (e.g. a mammalian subject, such as a human, in need thereof), which method comprises administering to the subject a therapeutically effective amount of compound as defined in any one of Embodiments 0.1 to 1.179.

The compound of formulae (0), (1) and subformulae thereof as defined in any of Embodiments 0.1 to 1.179 may also be useful in the treatment of tumour growth, pathogenesis, resistance to chemo- and radio-therapy by sensitising cells to chemotherapy, and as an anti-metastatic agent.

Therapeutic anticancer interventions of all types necessarily increase the stresses imposed on the target tumour cells. In mitigating the deleterious effects of such stresses, ERK1/2 are directly implicated in resisting the effects of cancer drugs and treatment regimens. Thus, inhibitors of ERK1/2 represent a class of chemotherapeutics with the potential for: (i) sensitizing malignant cells to anticancer drugs and/or treatments; (ii) alleviating or reducing the incidence of resistance to anticancer drugs and/or treatments; (iii) reversing resistance to anticancer drugs and/or treatments; (iv) potentiating the activity of anticancer drugs and/or treatments; (v) delaying or preventing the onset of resistance to anticancer drugs and/or treatments.

As a consequence of their inhibition of ERK1/2, the compounds will be useful in providing a means of controlling cell signalling. Therefore, it is also envisaged that the compounds of the invention may be useful in treating other conditions such as inflammatory disorders such as hepatitis, ulcerative colitis, and gastritis; neurodegenerative conditions such as Alzheimer's disease, Parkinson's disease, Huntington's disease, myotonic dystrophy, and amyotrophic lateral sclerosis; AIDS, ischemia such as restenosis, traumatic brain injury, spinal cord injury, cerebral ischemia, cerebral ischemia/reperfusion (I/R) injury, acute and chronic CNS injury ischemia, stroke or myocardial infarction; degenerative diseases of the musculoskeletal system such as osteoporosis; autoimmune diseases such as multiple sclerosis (MS) and Type I diabetes, and eye diseases such as retinal degeneration.

The affinity of the compounds of the invention as inhibitors of ERK1/2 can be measured using the biological and biophysical assays set forth in the examples herein and the level of inhibition exhibited by a given compound can be defined in terms of the $IC_{50}$ value. Particular compounds of the present invention are compounds having an $IC_{50}$ value of less than 1 µM, more particularly less than 0.1 µM.

In a further embodiment the invention (Embodiment 3.36), the disease or condition as defined in any one of Embodiments 3.2 to 3.35 is one which is mediated by ERK1/2, and the compound of any of Embodiments 0.1 to 1.179 is an inhibitor of ERK1/2 having an $IC_{50}$ of less than 10 µM in at least one assay (e.g. an enzyme activity assay) against ERK1 or ERK2. The disease or condition which is mediated by ERK1/2 can be, for example, a cancer which is characterised by mutation of Ras, BRAF or MEK.

Methods of Diagnosis

Prior to administration of a compound of the formulae (0), (1) and subformulae thereof, a subject (e.g. a patient) may be screened to determine whether a disease or condition from which the patient is or may be suffering is one which would be susceptible to treatment with a compound showing inhibition of ERK1/2. The term 'patient' includes human and veterinary patients.

For example, a biological sample taken from a patient may be analysed to determine whether a condition or disease, such as cancer, that the patient is or may be suffering from is one which is characterised by a genetic abnormality or abnormal protein expression which leads to up-regulation of the levels of ERK1/2 signalling or to sensitisation of a pathway to normal ERK1/2 function or to upregulation of a biochemical pathway downstream of ERK1/2 activation.

Examples of such abnormalities that result in activation or sensitisation of the ERK1/2 pathway, include activating mutations in a Ras isoform such as KRAS or in BRAF, as discussed in the Background section.

Mutations of Ras have been detected in cell lines and primary tumours including but not limited to melanoma, colorectal cancer, non-small cell lung cancer, and cancers of the pancreas, prostate, thyroid, urinary tract and upper respiratory tract (Cancer Res. 2012; 72: 2457-2467).

The term up-regulation includes elevated expression or over-expression, including gene amplification (i.e. multiple gene copies), cytogenetic aberration and increased expression by a transcriptional effect, or increased signalling through activation of ERK1/2. Thus, the patient may be subjected to a diagnostic test to detect a marker characteristic of up-regulation of ERK1/2. The term diagnosis includes screening. By marker we include genetic markers including, for example, the measurement of DNA composition to identify presence of mutations of Ras (e.g. KRAS) or BRAF. The term marker also includes markers which are characteristic of up regulation of ERK1/2, including protein levels, protein state and mRNA levels of the aforementioned proteins. Gene amplification includes greater than 7 copies, as well as gains of between 2 and 7 copies.

Diagnostic assays for detecting KRAS and BRAF mutations are described in de Castro et al. *Br. J. Cancer.* 2012 Jul. 10; 107(2):345-51. doi: 10.1038/bjc.2012.259. Epub 2012 Jun. 19, "A comparison of three methods for detecting KRAS mutations in formalin-fixed colorectal cancer specimens."; and Gonzalez et al., *Br J Dermatol.* 2013, April; 168(4): 700-7. doi: 10.1111/bjd.12248, "BRAF mutation testing algorithm for vemurafenib treatment in melanoma: recommendations from an expert panel" and references cited therein.

A number of diagnostic tests for BRAF mutations have been approved by the FDA and details of the tests can be found on the FDA website. Examples of such diagnostic tests are the cobas 4800 BRAF V600 Mutation Test, a companion assay for Roche's vemurafenib product, and the THxD BRAF test, a companion test for the Tafinlar (dabrafenib) and Mekinist (trametinib) products.

The diagnostic tests and screens are typically conducted on a biological sample (i.e. body tissue or body fluids) selected from tumour biopsy samples, blood samples (isolation and enrichment of shed tumour cells), cerebrospinal fluid, plasma, serum, saliva, stool biopsies, sputum, chromosome analysis, pleural fluid, peritoneal fluid, buccal smears, skin biopsy or urine.

Methods of identification and analysis of cytogenetic aberration, genetic amplification, mutations and up-regulation of proteins are known to a person skilled in the art. Clinical testing for most genetic variants could include, but are not limited to, standard methods such as allele-specific polymerase chain reaction (PCR), reverse-transcriptase polymerase chain reaction (RT-PCR), DNA sequence analysis by conventional Sanger or next-generation sequencing methods, Sanger dideoxy sequencing, pyrosequencing, multiplex ligation-dependent probe amplification (MLPA), or ARMS PCR. Clinical testing for gene copy number and structural gene variations could include, but are not limited to, standard methods such as RNA sequencing (RNAseq), nanostring hybridisation proximity RNA nCounter assays, or in-situ hybridization such as fluorescence in situ hybridization (FISH). Newer, next-generation sequencing (NGS) technologies, such as massively parallel sequencing allow for whole exome sequencing or whole genome sequencing.

In screening by RT-PCR, the level of mRNA in the tumour is assessed by creating a cDNA copy of the mRNA followed by amplification of the cDNA by PCR. Methods of PCR amplification, the selection of primers, and conditions for amplification, are known to a person skilled in the art. Nucleic acid manipulations and PCR are carried out by standard methods, as described for example in Ausubel, F. M. et al., eds. (2004) Current Protocols in Molecular Biology, John Wiley & Sons Inc., or Innis, M. A. et al., eds. (1990) PCR Protocols: a guide to methods and applications, Academic Press, San Diego. Reactions and manipulations involving nucleic acid techniques are also described in Sambrook et al., (2001), $3^{rd}$ Ed, Molecular Cloning: A Laboratory Manual, Cold Spring Harbor Laboratory Press. Alternatively a commercially available kit for RT-PCR (for example Roche Molecular Biochemicals) may be used, or methodology as set forth in U.S. Pat. Nos. 4,666,828; 4,683,202; 4,801,531; 5,192,659, 5,272,057, 5,882,864, and 6,218,529 and incorporated herein by reference. An example of an in-situ hybridisation technique for assessing mRNA expression would be fluorescence in-situ hybridisation (FISH) (see Angerer (1987) Meth. Enzymol., 152: 649).

Generally, in situ hybridization comprises the following major steps: (1) fixation of tissue to be analyzed; (2) prehybridization treatment of the sample to increase accessibility of target nucleic acid, and to reduce nonspecific binding; (3) hybridization of the mixture of nucleic acids to the nucleic acid in the biological structure or tissue; (4) post-hybridization washes to remove nucleic acid fragments not bound in the hybridization, and (5) detection of the hybridized nucleic acid fragments. The probes used in such applications are typically labelled, for example, with radioisotopes or fluorescent reporters. Particular probes are sufficiently long, for example, from about 50, 100, or 200 nucleotides to about 1000 or more nucleotides, to enable specific hybridization with the target nucleic acid(s) under stringent conditions. Standard methods for carrying out FISH are described in Ausubel, F. M. et al., eds. (2004) Current Protocols in Molecular Biology, John Wiley & Sons Inc and Fluorescence In Situ Hybridization: Technical Overview by John M. S. Bartlett in Molecular Diagnosis of Cancer, Methods and Protocols, 2nd ed.; ISBN: 1-59259-760-2; March 2004, pps. 077-088; Series: Methods in Molecular Medicine.

Methods for gene expression profiling are described by (DePrimo et al. (2003), BMC Cancer, 3:3). Briefly, the protocol is as follows: double-stranded cDNA is synthesized from total RNA Using a (dT)24 oligomer for priming first-strand cDNA synthesis e.g. from polyadenylated mRNA, followed by second strand cDNA synthesis with random hexamer primers. The double-stranded cDNA is used as a template for in vitro transcription of cRNA using biotinylated ribonucleotides. cRNA is chemically fragmented according to protocols described by Affymetrix (Santa Clara, Calif., USA), and then hybridized overnight on Human Genome Arrays or to gene-specific oligonucleotide probes on Human Genome Arrays. Alternatively, single nucleotide polymorphism (SNP) arrays, a type of DNA microarray, can be used to detect polymorphisms within a population.

Alternatively, the protein products expressed from the mRNAs may be assayed by immunohistochemistry or immunofluorescence of tumour samples, solid phase immunoassay with microtitre plates, Western blotting, capillary electrophoresis, 2-dimensional SDS-polyacrylamide gel electrophoresis, ELISA, flow cytometry and other methods known in the art for detection of specific proteins. Detection methods would include the use of site specific antibodies. The skilled person will recognize that all such well-known techniques for detection of upregulation of ERK1/2, detection of ERK1/2 variants or mutants, or detection of 11q22 amplification could be applicable in the present case.

Abnormal levels of proteins such as ERK1/2 can be measured using standard protein assays, for example, those assays described herein. Elevated levels or overexpression could also be detected in a tissue sample, for example, a tumour tissue by measuring the protein levels with an assay such as that from Chemicon International. The protein of interest would be immunoprecipitated from the sample lysate and its levels measured. Assay methods also include the use of markers.

ERK overexpression can be measured by tumour biopsy. Methods for assessing gene copy changes include techniques commonly used in cytogenetic laboratories such as MLPA (Multiplex Ligation-dependent Probe Amplification) a multiplex PCR method detecting abnormal copy numbers, or other PCR techniques which can detect gene amplification, gain and deletion.

Ex-functional assays could also be utilised where appropriate, for example measurement of circulating leukemia cells in a cancer patient, to assess the response to challenge with an inhibitor.

Therefore, all of these techniques could also be used to identify tumours particularly suitable for treatment with the compounds of the invention.

Accordingly, in further embodiments (Embodiments 4.1 to 4.9), the invention provides:

4.1 A compound as defined in any one of Embodiments 0.1 to 1.179 for use in the treatment or prophylaxis of (or for use in alleviating or reducing the incidence of) a disease state or condition in a patient who has been screened and has been determined as suffering from, or being at risk of suffering from, a disease or condition which would be susceptible to treatment with a compound showing inhibition of ERK1/2 (i.e. an ERK1/2 inhibitor).

4.2 The use of a compound as defined in any one of Embodiments 0.1 to 1.179 for the manufacture of a medicament for the treatment or prophylaxis of (for use in alleviating or reducing the incidence of) a disease state or condition in a patient who has been screened and has been determined as suffering from, or being at risk of suffering from, a disease or condition which would be susceptible to treatment with a compound showing inhibition of ERK1/2 (i.e. an ERK1/2 inhibitor).

4.3 A method for the treatment or prophylaxis of (for use in alleviating or reducing the incidence of) a disease state or condition in a patient who has been screened and has been determined as suffering from, or being at risk of suffering from, a disease or condition which would be susceptible to treatment with a compound showing inhibition of ERK1/2 (i.e. an ERK1/2 inhibitor), which method comprises administering to the subject a therapeutically effective amount of compound as defined in any one of Embodiments 0.1 to 1.179.

Another aspect of the invention includes a compound of the invention for use in the prophylaxis or treatment of cancer in a patient selected from a sub-population possessing overexpression or an activating mutation in the ERK1/2 signalling pathway (e.g. Ras, BRAF or MEK). Accordingly, in further embodiments, the invention provides:

4.4 A compound as defined in any one of Embodiments 0.1 to 1.179 for use in the treatment or prophylaxis of (or for use in alleviating or reducing the incidence of) cancer in a patient selected from a sub-population possessing overexpression or an activating mutation in the ERK1/2 signalling pathway, for example Ras (e.g. KRAS), BRAF or MEK.

4.5 The use of a compound as defined in any one of Embodiments 0.1 to 1.179 for the manufacture of a medicament for the treatment or prophylaxis of (for use in alleviating or reducing the incidence of) cancer in a patient selected from a sub-population possessing overexpression or an activating mutation in the ERK1/2 signalling pathway Ras (e.g. KRAS), BRAF or MEK.

4.6 A method for the treatment or prophylaxis of (for use in alleviating or reducing the incidence of) cancer in a patient selected from a sub-population possessing overexpression or an activating mutation in the ERK1/2 signalling pathway Ras (e.g. KRAS), BRAF or MEK.

4.7 A method for the diagnosis and treatment of a disease state or condition mediated by ERK1/2, which method comprises (i) screening a patient to determine whether a disease or condition from which the patient is or may be suffering is one which would be susceptible to treatment with a compound having affinity for ERK1/2; and (ii) where it is indicated that the disease or condition from which the patient is thus susceptible, thereafter administering to the patient a compound as defined in any one of Embodiments 0.1 to 1.179.

4.8 A compound as defined in any one of Embodiments 0.1 to 1.179 for use in the method of Embodiment 4.7.

4.9 The use of a compound as defined in any one of Embodiments 0.1 to 1.179 for the manufacture of a medicament for use in the method of Embodiment 4.7.

Pharmaceutical Formulations

While it is possible for the active compound to be administered alone, it is generally presented as a pharmaceutical composition (e.g. formulation).

Thus, in a further embodiment (Embodiment 5.1), the present invention provides a pharmaceutical composition comprising a compound as defined in any one of Embodiments 0.1 to 1.179 and least one pharmaceutically acceptable excipient and optionally other therapeutic or prophylactic agents as described herein.

The invention further provides methods of making a pharmaceutical composition according to Embodiment 5.1 comprising bringing into association (e.g. admixing) at least one said compound, at least one said pharmaceutically acceptable excipient and optionally other therapeutic or prophylactic agents as described herein.

The pharmaceutically acceptable excipient(s) can be selected from, for example, carriers (e.g. a solid, liquid or semi-solid carrier), adjuvants, diluents, fillers or bulking agents, granulating agents, coating agents, release-controlling agents, binding agents, disintegrants, lubricating agents, preservatives, antioxidants, buffering agents, suspending agents, thickening agents, flavouring agents, sweeteners, taste masking agents, stabilisers or any other excipients conventionally used in pharmaceutical compositions. Examples of excipients for various types of pharmaceutical compositions are set out in more detail below.

The term "pharmaceutically acceptable" as used herein refers to compounds, materials, compositions, and/or dosage forms which are, within the scope of sound medical judgment, suitable for use in contact with the tissues of a subject (e.g. a human subject) without excessive toxicity, irritation, allergic response, or other problem or complication, commensurate with a reasonable benefit/risk ratio. Each excipient must also be "acceptable" in the sense of being compatible with the other ingredients of the formulation.

Pharmaceutical compositions containing compounds of the formulae (0), (1) and subformulae thereof can be formulated in accordance with known techniques, see for example, Remington's Pharmaceutical Sciences, Mack Publishing Company, Easton, Pa., USA.

The pharmaceutical compositions can be in any form suitable for oral, parenteral, topical, intranasal, intrabronchial, sublingual, ophthalmic, otic, rectal, intra-vaginal, or transdermal administration. Where the compositions are intended for parenteral administration, they can be formulated for intravenous, intramuscular, intraperitoneal, subcutaneous administration or for direct delivery into a target organ or tissue by injection, infusion or other means of delivery. The delivery can be by bolus injection, short term infusion or longer term infusion and can be via passive delivery or through the utilisation of a suitable infusion pump or syringe driver.

Pharmaceutical formulations adapted for parenteral administration include aqueous and non-aqueous sterile injection solutions which may contain anti-oxidants, buffers, bacteriostats, co-solvents, surface active agents, organic solvent mixtures, cyclodextrin complexation agents, emulsifying agents (for forming and stabilizing emulsion formulations), liposome components for forming liposomes, gellable polymers for forming polymeric gels, lyophilisation protectants and combinations of agents for, interalia, stabilising the active ingredient in a soluble form and rendering the formulation isotonic with the blood of the intended recipient. Pharmaceutical formulations for parenteral administration may also take the form of aqueous and non-aqueous sterile suspensions which may include suspending agents and thickening agents (R. G. Strickly, Solubilizing Excipients in oral and injectable formulations, Pharmaceutical Research, Vol 21(2) 2004, p 201-230).

The formulations may be presented in unit-dose or multi-dose containers, for example sealed ampoules, vials and prefilled syringes, and may be stored in a freeze-dried (lyophilised) condition requiring only the addition of the sterile liquid carrier, for example water for injections, immediately prior to use. In one embodiment, the formulation is provided as an active pharmaceutical ingredient (e.g. in freeze-dried or other finely divided dried form) in a bottle for subsequent reconstitution using an appropriate diluent.

The pharmaceutical formulation can be prepared by lyophilising a compound of formulae (0), (1) and subformulae thereof, or sub-groups thereof. Lyophilisation refers to the procedure of freeze-drying a composition. Freeze-drying and lyophilisation are therefore used herein as synonyms.

Extemporaneous injection solutions and suspensions may be prepared from sterile powders, granules and tablets.

Pharmaceutical compositions of the present invention for parenteral injection can also comprise pharmaceutically acceptable sterile aqueous or non-aqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), carboxymethylcellulose and suitable mixtures thereof, vegetable oils (such as olive oil, sunflower oil, safflower oil, or corn oil), and injectable organic esters such as ethyl oleate. Proper fluidity can be maintained, for example, by the use of coating (or thickening) materials such as lecithin, by the maintenance of the required particle size in the case of dispersions, and by the use of surfactants.

The compositions of the present invention may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol, sorbic acid, and the like. It may also be desirable to include agents to adjust tonicity such as sugars, sodium chloride, and the like. Prolonged absorption of the injectable pharmaceutical form may be brought about by the inclusion of agents which delay absorption such as aluminium monostearate and gelatin.

In one embodiment of the invention (Embodiment 5.2), the pharmaceutical composition is in a form suitable for i.v. administration, for example by injection or infusion. For intravenous administration, the solution can be dosed as is, or can be injected into an infusion bag (containing a pharmaceutically acceptable excipient, such as 0.9% saline or 5% dextrose), before administration.

In another embodiment (Embodiment 5.3), the pharmaceutical composition is in a form suitable for sub-cutaneous (s.c.) administration.

Pharmaceutical dosage forms suitable for oral administration include tablets (coated or uncoated), capsules (hard or soft shell), caplets, pills, lozenges, syrups, solutions, powders, granules, elixirs and suspensions, sublingual tablets, wafers or patches such as buccal patches.

Thus, tablet compositions can contain a unit dosage of active compound together with an inert diluent or carrier such as a sugar or sugar alcohol, eg; lactose, sucrose, sorbitol or mannitol; and/or a non-sugar derived diluent such as sodium carbonate, calcium phosphate, calcium carbonate, or a cellulose or derivative thereof such as microcrystalline cellulose (MCC), methyl cellulose, ethyl cellulose, hydroxypropyl methyl cellulose, and starches such as corn starch. Tablets may also contain such standard ingredients as binding and granulating agents such as polyvinylpyrrolidone, disintegrants (e.g. swellable crosslinked polymers such as crosslinked carboxymethylcellulose), lubricating agents (e.g. stearates), preservatives (e.g. parabens), antioxidants (e.g. BHT), buffering agents (for example phosphate or citrate buffers), and effervescent agents such as citrate/bicarbonate mixtures. Such excipients are well known and do not need to be discussed in detail here.

Tablets may be designed to release the drug either upon contact with stomach fluids (immediate release tablets) or to release in a controlled manner (controlled release tablets) over a prolonged period of time or with a specific region of the GI tract.

Capsule formulations may be of the hard gelatin or soft gelatin variety and can contain the active component in solid, semi-solid, or liquid form. Gelatin capsules can be formed from animal gelatin or synthetic or plant derived equivalents thereof.

The solid dosage forms (e.g. tablets, capsules etc.) can be coated or un-coated. Coatings may act either as a protective film (e.g. a polymer, wax or varnish) or as a mechanism for controlling drug release or may serve aesthetic or identification purposes. The coating (e.g. a Eudragit™ type polymer) can be designed to release the active component at a desired location within the gastro-intestinal tract. Thus, the coating can be selected so as to degrade under certain pH conditions within the gastrointestinal tract, thereby selectively release the compound in the stomach or in the ileum, duodenum, colon or jejenum.

Instead of, or in addition to, a coating, the drug can be presented in a solid matrix comprising a release controlling agent, for example a release delaying agent which may be adapted to release the compound in a controlled manner in the gastrointestinal tract. Alternatively the drug can be presented in a polymer coating e.g. a polymethacrylate polymer coating, which may be adapted to selectively release the compound under conditions of varying acidity or alkalinity in the gastrointestinal tract. Alternatively, the matrix material or release retarding coating can take the form of an erodible polymer (e.g. a maleic anhydride polymer) which is substantially continuously eroded as the dosage form passes through the gastrointestinal tract. In another alternative, the coating can be designed to disintegrate under microbial action in the gut. As a further alternative, the active compound can be formulated in a delivery system that provides osmotic control of the release of the compound. Osmotic release and other delayed release or sustained release formulations (for example formulations based on ion exchange resins) may be prepared in accordance with methods well known to those skilled in the art.

The compound of formulae (0), (1) and subformulae thereof may be formulated with a carrier and administered in the form of nanoparticles. Nanoparticles increase surface area, assisting the absorption of the compound, and offer the possibility of direct penetration into the cell. Nanoparticle drug delivery systems are described in "Nanoparticle Technology for Drug Delivery", edited by Ram B Gupta and Uday B. Kompella, Informa Healthcare, ISBN 9781574448573, published 13 Mar. 2006. Nanoparticles for drug delivery are also described in J. Control. Release, 2003, 91 (1-2), 167-172, and in Sinha et al., Mol. Cancer Ther. August 1, (2006) 5, 1909.

In accordance with Embodiment 5.4 of the invention, the pharmaceutical compositions particularly comprise from approximately 1% (w/w) to approximately 95% active ingredient and from 99% (w/w) to 5% (w/w) of a pharmaceutically acceptable excipient or combination of excipients. Particularly, the compositions comprise from approximately 20% (w/w) to approximately 90%,% (w/w) active ingredient and from 80% (w/w) to 10% of a pharmaceutically excipient or combination of excipients. The pharmaceutical compositions comprise from approximately 1% to approximately 95%, particularly from approximately 20% to approximately 90%, active ingredient. Pharmaceutical compositions according to the invention may be, for example, in unit dose form, such as in the form of ampoules, vials, suppositories, dragees, tablets or capsules, or pre-filled syringes.

The pharmaceutically acceptable excipient(s) can be selected according to the desired physical form of the formulation and can, for example, be selected from diluents (e.g solid diluents such as fillers or bulking agents; and liquid diluents such as solvents and co-solvents), disintegrants, buffering agents, lubricants, flow aids, release controlling (e.g. release retarding or delaying polymers or waxes) agents, binders, granulating agents, pigments, plasticizers, antioxidants, preservatives, flavouring agents, taste masking agents, tonicity adjusting agents and coating agents.

The skilled person will have the expertise to select the appropriate amounts of ingredients for use in the formulations. For example tablets and capsules typically contain 0-20% disintegrants, 0-5% lubricants, 0-5% flow aids and/or 0-99% (w/w) fillers/or bulking agents (depending on drug dose). They may also contain 0-10% (w/w) polymer binders, 0-5% (w/w) antioxidants, 0-5% (w/w) pigments. Slow release tablets would in addition contain 0-99% (w/w) polymers (depending on dose). The film coats of the tablet or capsule typically contain 0-10% (w/w) release-controlling (e.g. delaying) polymers, 0-3% (w/w) pigments, and/or 0-2% (w/w) plasticizers.

Parenteral formulations typically contain 0-20% (w/w) buffers, 0-50% (w/w) cosolvents, and/or 0-99% (w/w) Water for Injection (WFI) (depending on dose and if freeze dried). Formulations for intramuscular depots may also contain 0-99% (w/w) oils.

Pharmaceutical compositions for oral administration can be obtained by combining the active ingredient with solid carriers, if desired granulating a resulting mixture, and processing the mixture, if desired or necessary, after the addition of appropriate excipients, into tablets, dragee cores or capsules. It is also possible for them to be incorporated into a polymer or waxy matrix that allow the active ingredients to diffuse or be released in measured amounts.

The compounds of the invention can also be formulated as solid dispersions. Solid dispersions are homogeneous extremely fine disperse phases of two or more solids. Solid solutions (molecularly disperse systems), one type of solid dispersion, are well known for use in pharmaceutical technology (see (Chiou and Riegelman, J. Pharm. Sci., 60, 1281-1300 (1971)) and are useful in increasing dissolution rates and increasing the bioavailability of poorly water-soluble drugs.

The invention also provides solid dosage forms comprising the solid solution described above. Solid dosage forms include tablets, capsules and chewable tablets, or dispersible or effervescent tablets. Known excipients can be blended with the solid solution to provide the desired dosage form. For example, a capsule can contain the solid solution blended with (a) a disintegrant and a lubricant, or (b) a disintegrant, a lubricant and a surfactant. In addition a capsule can contain a bulking agent, such as lactose or microcrystalline cellulose. A tablet can contain the solid solution blended with at least one disintegrant, a lubricant, a surfactant, a bulking agent and a glidant. A chewable tablet can contain the solid solution blended with a bulking agent, a lubricant, and if desired an additional sweetening agent (such as an artificial sweetener), and suitable flavours. Solid solutions may also be formed by spraying solutions of drug and a suitable polymer onto the surface of inert carriers such as sugar beads ('non-pareils'). These beads can subsequently be filled into capsules or compressed into tablets.

The pharmaceutical formulations may be presented to a patient in "patient packs" containing an entire course of treatment in a single package, usually a blister pack. Patient packs have an advantage over traditional prescriptions, where a pharmacist divides a patient's supply of a pharmaceutical from a bulk supply, in that the patient always has access to the package insert contained in the patient pack, normally missing in patient prescriptions. The inclusion of a package insert has been shown to improve patient compliance with the physician's instructions.

Compositions for topical use and nasal delivery include ointments, creams, sprays, patches, gels, liquid drops and inserts (for example intraocular inserts). Such compositions can be formulated in accordance with known methods.

Examples of formulations for rectal or intra-vaginal administration include pessaries and suppositories which may be, for example, formed from a shaped mouldable or waxy material containing the active compound. Solutions of the active compound may also be used for rectal administration.

Compositions for administration by inhalation may take the form of inhalable powder compositions or liquid or powder sprays, and can be administrated in standard form using powder inhaler devices or aerosol dispensing devices. Such devices are well known. For administration by inhalation, the powdered formulations typically comprise the active compound together with an inert solid powdered diluent such as lactose.

The compounds of the formulae (0), (1) and subformulae thereof will generally be presented in unit dosage form and, as such, will typically contain sufficient compound to provide a desired level of biological activity. For example, a formulation may contain from 1 nanogram to 2 grams of active ingredient, e.g. from 1 nanogram to 2 milligrams of active ingredient. Within this range, particular sub-ranges of compound are 0.1 milligrams to 2 grams of active ingredient (more usually from 10 milligrams to 1 gram, e.g. 50 milligrams to 500 milligrams), or 1 microgram to 20 milligrams (for example 1 microgram to 10 milligrams, e.g. 0.1 milligrams to 2 milligrams of active ingredient).

For oral compositions, a unit dosage form may contain from 1 milligram to 2 grams, more typically 10 milligrams to 1 gram, for example 50 milligrams to 1 gram, e.g. 100 milligrams to 1 gram, of active compound.

The active compound will be administered to a patient in need thereof (for example a human or animal patient) in an amount sufficient to achieve the desired therapeutic effect.

Methods of Treatment

The compounds of the formulae (0), (1) and subformulae thereof and sub-groups as defined herein may be useful in the prophylaxis or treatment of a range of disease states or conditions mediated by ERK1/2. Examples of such disease states and conditions are set out above.

The compounds are generally administered to a subject in need of such administration, for example a human or animal patient, particularly a human.

The compounds will typically be administered in amounts that are therapeutically or prophylactically useful and which generally are non-toxic. However, in certain situations (for example in the case of life threatening diseases), the benefits of administering a compound of the formulae (0), (1) and subformulae thereof may outweigh the disadvantages of any toxic effects or side effects, in which case it may be considered desirable to administer compounds in amounts that are associated with a degree of toxicity.

The compounds may be administered over a prolonged term to maintain beneficial therapeutic effects or may be administered for a short period only. Alternatively they may be administered in a continuous manner or in a manner that provides intermittent dosing (e.g. a pulsatile manner).

A typical daily dose of the compound of formulae (0), (1) and subformulae thereof can be in the range from 100 picograms to 100 milligrams per kilogram of body weight, more typically 5 nanograms to 25 milligrams per kilogram of bodyweight, and more usually 10 nanograms to 15 milligrams per kilogram (e.g. 10 nanograms to 10 milligrams, and more typically 1 microgram per kilogram to 20 milligrams per kilogram, for example 1 microgram to 10 milligrams per kilogram) per kilogram of bodyweight although higher or lower doses may be administered where required. The compound of the formulae (0), (1) and subformulae thereof can be administered on a daily basis or on a repeat basis every 2, or 3, or 4, or 5, or 6, or 7, or 10 or 14, or 21, or 28 days for example.

The compounds of the invention may be administered orally in a range of doses, for example 1 to 1500 mg, 2 to 800 mg, or 5 to 500 mg, e.g. 2 to 200 mg or 10 to 1000 mg, particular examples of doses including 10, 20, 50 and 80 mg. The compound may be administered once or more than once each day to obtain the desired therapeutic effect. The compound can be administered continuously (i.e. taken every day without a break for the duration of the treatment regimen). Alternatively, the compound can be administered intermittently (i.e. taken continuously for a given period such as a week, then discontinued for a period such as a week and then taken continuously for another period such as a week and so on throughout the duration of the treatment regimen). Examples of treatment regimens involving intermittent administration include regimens wherein administration is in cycles of one week on, one week off; or two weeks on, one week off; or three weeks on, one week off; or two weeks on, two weeks off; or four weeks on two weeks off; or one week on three weeks off—for one or more cycles, e.g. 2, 3, 4, 5, 6, 7, 8, 9 or 10 or more cycles. This discontinuous treatment can also be based upon numbers of days rather than a full week. For example, the treatment can comprise daily dosing for 1 to 6 days, no dosing for 1 to 6 days with this pattern repeating during the treatment protocol. The number of days (or weeks) wherein the compounds of the invention are not dosed do not necessarily have to equal the number of days (or weeks) wherein the compounds of the invention are dosed.

In one particular dosing schedule, a patient will be given an infusion of a compound of the formulae (0), (1) and subformulae thereof for periods of one hour daily for up to ten days in particular up to five days for one week, and the treatment repeated at a desired interval such as two to four weeks, in particular every three weeks.

The compounds of the invention can also be administered by bolus or continuous infusion. The compound of the invention can be given daily to once every week, or once every two weeks, or once every three weeks, or once every four weeks during the treatment cycle. If administered daily during a treatment cycle, this daily dosing can be discontinuous over the number of weeks of the treatment cycle: for example, dosed for a week (or a number of days), no dosing for a week (or a number of days), with the pattern repeating during the treatment cycle.

In one dosing schedule, a patient may be given an infusion of a compound of the formulae (0), (1) and subformulae thereof for periods of one hour daily for 5 days and the treatment repeated every three weeks.

In another particular dosing schedule, a patient is given an infusion over 30 minutes to 1 hour followed by maintenance infusions of variable duration, for example 1 to 5 hours, e.g. 3 hours.

In a further particular dosing schedule, a patient is given a continuous infusion for a period of 12 hours to 5 days, an in particular a continuous infusion of 24 hours to 72 hours.

Ultimately, however, the quantity of compound administered and the type of composition used will be commensurate with the nature of the disease or physiological condition being treated and will be at the discretion of the physician.

It has been discovered that ERK1/2 inhibitors can be used as a single agent or in combination with other anticancer agents. For example, it may be beneficial to combine an antagonist that suppresses ERK signalling with another agent which acts via a different point in the signal transduction cascade or a different mechanism to regulate cell growth thus treating two of the characteristic features of cancer development. Combination experiments can be performed, for example, as described in Chou T C, Talalay P. Quantitative analysis of dose-effect relationships: the combined effects of multiple drugs or enzyme inhibitors. Adv Enzyme Regulat 1984; 22: 27-55.

The compounds as defined herein can be administered as the sole therapeutic agent or they can be administered in combination therapy with one or more other compounds (or therapies) for treatment of a particular disease state, for example a neoplastic disease such as a cancer as hereinbefore defined. For the treatment of the above conditions, the compounds of the invention may be advantageously employed in combination with one or more other medicinal agents, more particularly, with other anti-cancer agents or adjuvants (supporting agents in the therapy) in cancer therapy. Examples of other therapeutic agents or treatments that may be administered together (whether concurrently or at different time intervals) with the compounds of the formulae (0), (1) and subformulae thereof include but are not limited to:

Topoisomerase I inhibitors
Antimetabolites
Tubulin targeting agents
DNA binder and topoisomerase II inhibitors
Alkylating Agents
Monoclonal Antibodies
Anti-Hormones
Signal Transduction Inhibitors
Ubiquitin-proteasome pathway Inhibitors
Immunotherapies
Regulators of Cell Death
DNA methyl transferase inhibitors
Cytokines and retinoids
Chromatin targeted therapies
Radiotherapy, and,
Other therapeutic or prophylactic agents.

Particular examples of anti-cancer agents or adjuvants (or salts thereof), include but are not limited to any one or more of the agents selected from groups (i)-(xlviii), and optionally group (xlix) and or (1), below:

(i) Platinum compounds, for example cisplatin (optionally combined with amifostine), carboplatin or oxaliplatin;

(ii) Taxane compounds, for example paclitaxel, paclitaxel protein bound particles (Abraxane™), docetaxel, cabazitaxel or larotaxel;

(iii) Topoisomerase I inhibitors, for example camptothecin compounds, for example camptothecin, irinotecan (CPT11), SN-38, or topotecan;

(iv) Topoisomerase II inhibitors, for example anti-tumour epipodophyllotoxins or podophyllotoxin derivatives for example etoposide, or teniposide;

(v) Vinca alkaloids, for example vinblastine, vincristine, liposomal vincristine (Onco-TCS), vinorelbine, vindesine, vinflunine or vinvesir;

(vi) Nucleoside derivatives, for example 5-fluorouracil (5-FU, optionally in combination with leucovorin), gemcitabine, capecitabine, tegafur, UFT, S1, cladribine, cytarabine (Ara-C, cytosine arabinoside), fludarabine, clofarabine, or nelarabine;

(vii) Antimetabolites, for example clofarabine, aminopterin, or methotrexate, azacitidine, cytarabine, floxuridine, pentostatin, thioguanine, thiopurine, 6-mercaptopurine, or hydroxyurea (hydroxycarbamide) or trifluridine (optionally in combination with tipiracil);

(viii) Alkylating agents, such as nitrogen mustards or nitrosourea, for example cyclophosphamide, chlorambucil, carmustine (BCNU), bendamustine, thiotepa, melphalan, treosulfan, lomustine (CCNU), altretamine, busulfan, dacarbazine, estramustine, fotemustine, ifosfamide (optionally in combination with mesna), pipobroman, procarbazine, streptozocin, temozolomide, uracil, mechlorethamine, methylcyclohexylchloroethylnitrosurea, or nimustine (ACNU);

(ix) Anthracyclines, anthracenediones and related drugs, for example daunorubicin, doxorubicin (optionally in combination with dexrazoxane), liposomal formulations of doxorubicin (eg. Caelyx™, Myocet™, Doxil™), idarubicin, mitoxantrone, epirubicin, amsacrine, or valrubicin;

(x) Epothilones, for example ixabepilone, patupilone, BMS-310705, KOS-862 and ZK-EPO, epothilone A, epothilone B, desoxyepothilone B (also known as epothilone D or KOS-862), aza-epothilone B (also known as BMS-247550), aulimalide, isolaulimalide, or luetherobin;

(xi) DNA methyl transferase inhibitors, for example temozolomide, azacytidine, decitabine or guadecitabine (SGI-110);

(xii) Antifolates, for example methotrexate, pemetrexed disodium, or raltitrexed;

(xiii) Cytotoxic antibiotics, for example antinomycin D, bleomycin, mitomycin C, dactinomycin, carminomycin, daunomycin, levamisole, plicamycin, or mithramycin;

(xiv) Tubulin-binding agents, for example combrestatin, colchicines or nocodazole;

(xv) Signal Transduction inhibitors such as Kinase inhibitors for example receptor tyrosine kinase inhibitors (e.g. EGFR (epithelial growth factor receptor) inhibitors, VEGFR (vascular endothelial growth factor receptor) inhibitors, PDGFR (platelet-derived growth factor receptor) inhibitors, Axl inhibitors, MTKI (multi target kinase inhibitors), Raf inhibitors, ROCK inhibitors, mTOR inhibitors, MEK inhibitors or PI3K Inhibitors) for example imatinib mesylate, erlotinib, gefitinib, dasatinib, lapatinib, dovotinib, axitinib, nilotinib, vandetanib, vatalinib, pazopanib, sorafenib, sunitinib, temsirolimus, everolimus (RAD 001), vemurafenib (PLX4032 or RG7204), dabrafenib, encorafenib, selumetinib (AZD6244), trametinib (GSK121120212), dactolisib (BEZ235), buparlisib (BKM-120; NVP-BKM-120), BYL719, copanlisib (BAY-80-6946), ZSTK-474, CUDC-907, apitolisib (GDC-0980; RG-7422), pictilisib (pictrelisib, GDC-0941, RG-7321), GDC-0032, GDC-0068, GSK-2636771, idelalisib (formerly CAL-101, GS 1101, GS-1101), MLN1117 (INK1117), MLN0128 (INK128), IPI-145 (INK1197), LY-3023414, ipatasertib, afuresertib, MK-2206, MK-8156, LY-3023414, LY294002, SF1126 or PI-103, sonolisib (PX-866), or AT13148.

(xvi) Aurora kinase inhibitors for example AT9283, barasertib (AZD1152), TAK-901, MK0457 (VX680), cenisertib (R-763), danusertib (PHA-739358), alisertib (MLN-8237), or MP-470;

(xvii) CDK inhibitors for example AT7519, roscovitine, seliciclib, alvocidib (flavopiridol), dinaciclib (SCH-727965), 7-hydroxy-staurosporine (UCN-01), JNJ-7706621, BMS-387032 (a.k.a. SNS-032), PHA533533, ZK-304709, or AZD-5438 and including CDK4 inhibitors such as palbociclib (PD332991) and ribociclib (LEE-011);

(xviii) PKA/B inhibitors and PKB (akt) pathway inhibitors for example AT13148, AZ-5363, Semaphore, SF1126 and MTOR inhibitors such as rapamycin analogues, AP23841 and AP23573, calmodulin inhibitors (forkhead translocation inhibitors), API-2/TCN (triciribine), RX-0201, enzastaurin HCl (LY317615), NL-71-101, SR-13668, PX-316, or KRX-0401 (perifosine/NSC 639966);

(xix) Hsp90 inhibitors for example onalespib (AT13387), herbimycin, geldanamycin (GA), 17-allylamino-17-desmethoxygeldanamycin (17-AAG) e.g. NSC-330507, Kos-953 and CNF-1010, 17-dimethylaminoethylamino-17-demethoxygeldanamycin hydrochloride (17-DMAG) e.g. NSC-707545 and Kos-1022, NVP-AUY922 (VER-52296), NVP-BEP800, CNF-2024 (BIIB-021 an oral purine), ganetespib (STA-9090), SNX-5422 (SC-102112), or IPI-504 or TAS-116;

(xx) Monoclonal Antibodies (unconjugated or conjugated to radioisotopes, toxins or other agents), antibody derivatives and related agents, such as anti-CD, anti-VEGFR, anti-HER2 or anti-EGFR antibodies, for example rituximab (CD20), ofatumumab (CD20), ibritumomab tiuxetan (CD20), GA101 (CD20), tositumomab (CD20), epratuzumab (CD22), lintuzumab (CD33), gemtuzumab ozogamicin (CD33), alemtuzumab (CD52), galiximab (CD80), trastuzumab (HER2 antibody), pertuzumab (HER2), trastuzumab-DM1 (HER2), ertumaxomab (HER2 and CD3), cetuximab (EGFR), panitumumab (EGFR), necitumumab (EGFR), nimotuzumab (EGFR), bevacizumab (VEGF), catumaxumab (EpCAM and CD3), abagovomab (CA125), farletuzumab (folate receptor), elotuzumab (CS1), denosumab (RANK ligand), figitumumab (IGF1R), CP751,871 (IGF1R), mapatumumab (TRAIL receptor), metMAB (met), mitumomab (GD3 ganglioside), naptumomab estafenatox (5T4), or siltuximab (L6) or immunomodulating agents such as CTLA-4 blocking antibodies and/or antibodies against PD-1 and PD-L1 and/or PD-L2 for example ipilimumab (CTLA4), MK-3475 (pembrolizumab, formerly lambrolizumab, anti-PD-1), nivolumab (a anti-PD-1), BMS-936559 (anti-PD-L1), MPDL320A, AMP-514 or MED14736 (anti-PD-L1), or tremelimumab (formerly ticilimumab, CP-675, 206, anti-CTLA-4);

(xxi) Estrogen receptor antagonists or selective estrogen receptor modulators (SERMs) or inhibitors of estrogen synthesis, for example tamoxifen, fulvestrant, toremifene, droloxifene, faslodex, or raloxifene;

(xxii) Aromatase inhibitors and related drugs, such as exemestane, anastrozole, letrazole, testolactone aminoglutethimide, mitotane or vorozole;

(xxiii) Antiandrogens (i.e. androgen receptor antagonists) and related agents for example bicalutamide, nilutamide, flutamide, cyproterone, or ketoconazole;

(xxiv) Hormones and analogues thereof such as medroxyprogesterone, diethylstilbestrol (a.k.a. diethylstilboestrol) or octreotide;

(xxv) Steroids for example dromostanolone propionate, megestrol acetate, nandrolone (decanoate, phenpropionate), fluoxymestrone or gossypol, (xxvi) Steroidal cytochrome P450 17alpha-hydroxylase-17, 20-lyase inhibitor (CYP17), e.g. abiraterone;

(xxvii) Gonadotropin releasing hormone agonists or antagonists (GnRAs) for example abarelix, goserelin acetate, histrelin acetate, leuprolide acetate, triptorelin, buserelin, or deslorelin;

(xxviii) Glucocorticoids, for example prednisone, prednisolone, dexamethasone;

(xxix) Differentiating agents, such as retinoids, rexinoids, vitamin D or retinoic acid and retinoic acid metabolism blocking agents (RAMBA) for example accutane, alitretinoin, bexarotene, or tretinoin;

(xxx) Farnesyltransferase inhibitors for example tipifarnib;

(xxxi) Chromatin targeted therapies such as histone deacetylase (HDAC) inhibitors for example sodium butyrate, suberoylanilide hydroxamide acid (SAHA), depsipeptide (FR 901228), dacinostat (NVP-LAQ824), R306465/JNJ-16241199, JNJ-26481585, trichostatin A, vorinostat, chlamydocin, A-173, JNJ-MGCD-0103, PXD-101, or apicidin;

(xxxii) Drugs targeting the ubiquitin-proteasome pathway including proteasome Inhibitors for example bortezomib, carfilzomib, CEP-18770, MLN-9708, or ONX-0912; NEDD8 inhibitors; HDM2 antagonist and deubiquitinases (DUBs);

(xxxiii) Photodynamic drugs for example porfimer sodium or temoporfin;

(xxxiv) Marine organism-derived anticancer agents such as trabectidin;

(xxxv) Radiolabelled drugs for radioimmunotherapy for example with a beta particle-emitting isotope (e.g., Iodine-131, Yittrium-90) or an alpha particle-emitting isotope (e.g., Bismuth-213 or Actinium-225) for example ibritumomab,r Iodine tositumomab or alpha radium;

(xxxvi) Telomerase inhibitors for example telomestatin;

(xxxvii) Matrix metalloproteinase inhibitors for example batimastat, marimastat, prinostat or metastat;

(xxxviii) Recombinant interferons (such as interferon-γ and interferon α) and interleukins (e.g. interleukin 2), for example aldesleukin, denileukin diftitox, interferon alfa 2a, interferon alfa 2b, or peginterferon alfa 2b;

(xxxix) Selective immunoresponse modulators for example thalidomide, or lenalidomide;

(xl) Therapeutic Vaccines such as sipuleucel-T (Provenge) or OncoVex;

(xli) Cytokine-activating agents include Picibanil, Romurtide, Sizofiran, Virulizin, or Thymosin;

(xlii) Arsenic trioxide;

(xliii) Inhibitors of G-protein coupled receptors (GPCR) for example atrasentan;

(xliv) Enzymes such as L-asparaginase, pegaspargase, rasburicase, or pegademase;

(xlv) DNA repair inhibitors such as PARP inhibitors for example, olaparib, velaparib, iniparib, INO-1001, AG-014699, or ONO-2231;

(xlvi) Agonists of Death receptor (e.g. TNF-related apoptosis inducing ligand (TRAIL) receptor), such as mapatumumab (formerly HGS-ETR1), conatumumab (formerly AMG 655), PR095780, lexatumumab, dulanermin, CS-1008, apomab or recombinant TRAIL ligands such as recombinant Human TRAIL/Apo2 Ligand;

(xlvii) Immunotherapies such as immune checkpoint inhibitors; cancer vaccines and CAR-T cell therapy;

(xlviii) Regulators of Cell death (apoptosis) including Bcl-2 (B-cell lymphoma 2) antagonists such as venetoclax (ABT-199 or GDC-0199), ABT-737, ABT-263, TW-37, sabutoclax, obatoclax, and MIM1 and IAP antagonists including LCL-161 (Novartis), Debio-1143 (Debiopharma/Ascenta), AZD5582, Birinapant/TL-32711 (TetraLogic), CUDC-427/GDC-0917/RG-7459 (Genentech), JP1201 (Joyant), T-3256336 (Takeda), GDC-0152 (Genentech), HGS-1029/AEG-40826 (HGS/Aegera) or ASTX-660;

(xlix) Prophylactic agents (adjuncts); i.e. agents that reduce or alleviate some of the side effects associated with chemotherapy agents, for example anti-emetic agents, agents that prevent or decrease the duration of chemotherapy-associated neutropenia and prevent complications that arise from reduced levels of platelets, red blood cells or white blood cells, for example interleukin-11 (e.g. oprelvekin), erythropoietin (EPO) and analogues thereof (e.g. darbepoetin alfa), colony-stimulating factor analogs such as granulocyte macrophage-colony stimulating factor (GM-CSF) (e.g. sargramostim), and granulocyte-colony stimulating factor (G-CSF) and analogues thereof (e.g. filgrastim, pegfilgrastim), agents that inhibit bone resorption such as denosumab or bisphosphonates e.g. zoledronate, zoledronic acid, pamidronate and ibandronate, agents that suppress inflammatory responses such as dexamethasone, prednisone, and prednisolone, agents used to reduce blood levels of growth hormone and IGF-I (and other hormones) in patients with acromegaly or other rare hormone-producing tumours, such as synthetic forms of the hormone somatostatin e.g. octreotide acetate, antidote to drugs that decrease levels of folic acid such as leucovorin, or folinic acid, agents for pain e.g. opiates such as morphine, diamorphine and fentanyl, non-steroidal anti-inflammatory drugs (NSAID) such as COX-2 inhibitors for example celecoxib, etoricoxib and lumiracoxib, agents for mucositis e.g. palifermin, agents for the treatment of side-effects including anorexia, cachexia, oedema or thromoembolic episodes, such as megestrol acetate; and (l) radiotherapy for radical, palliative or prophylactic purposes (or, for adjuvant or neoadjuvant purposes).

Each of the compounds present in the combinations of the invention may be given in individually varying dose schedules and via different routes. As such, the posology of each of the two or more agents may differ: each may be administered at the same time or at different times. A person skilled in the art would know through his or her common general knowledge the dosing regimes and combination therapies to use. For example, the compound of the invention may be used in combination with one or more other agents which are administered according to their existing combination regimen. Examples of standard combination regimens are provided below.

The taxane compound is advantageously administered in a dosage of 50 to 400 mg per square meter ($mg/m^2$) of body surface area, for example 75 to 250 $mg/m^2$, particularly for paclitaxel in a dosage of about 175 to 250 $mg/m^2$ and for docetaxel in about 75 to 150 $mg/m^2$ per course of treatment.

The camptothecin compound is advantageously administered in a dosage of 0.1 to 400 mg per square meter ($mg/m^2$) of body surface area, for example 1 to 300 $mg/m^2$, particularly for irinotecan in a dosage of about 100 to 350 $mg/m^2$ and for topotecan in about 1 to 2 $mg/m^2$ per course of treatment.

The anti-tumour podophyllotoxin derivative is advantageously administered in a dosage of 30 to 300 mg per square meter ($mg/m^2$) of body surface area, for example 50 to 250 $mg/m^2$, particularly for etoposide in a dosage of about 35 to 100 $mg/m^2$ and for teniposide in about 50 to 250 $mg/m^2$ per course of treatment.

The anti-tumour *vinca* alkaloid is advantageously administered in a dosage of 2 to 30 mg per square meter ($mg/m^2$) of body surface area, particularly for vinblastine in a dosage of about 3 to 12 $mg/m^2$, for vincristine in a dosage of about 1 to 2 $mg/m^2$, and for vinorelbine in dosage of about 10 to 30 $mg/m^2$ per course of treatment.

The anti-tumour nucleoside derivative is advantageously administered in a dosage of 200 to 2500 mg per square meter ($mg/m^2$) of body surface area, for example 700 to 1500 $mg/m^2$, particularly for 5-FU in a dosage of 200 to 500 $mg/m^2$, for gemcitabine in a dosage of about 800 to 1200 $mg/m^2$ and for capecitabine in about 1000 to 2500 $mg/m^2$ per course of treatment.

The alkylating agents such as nitrogen mustard or nitrosourea is advantageously administered in a dosage of 100 to 500 mg per square meter ($mg/m^2$) of body surface area, for example 120 to 200 $mg/m^2$, particularly for cyclophosphamide in a dosage of about 100 to 500 $mg/m^2$, for chlorambucil in a dosage of about 0.1 to 0.2 mg/kg, for carmustine in a dosage of about 150 to 200 $mg/m^2$, and for lomustine in a dosage of about 100 to 150 $mg/m^2$ per course of treatment.

The anti-tumour anthracycline derivative is advantageously administered in a dosage of 10 to 75 mg per square meter ($mg/m^2$) of body surface area, for example 15 to 60 $mg/m^2$, particularly for doxorubicin in a dosage of about 40 to 75 $mg/m^2$, for daunorubicin in a dosage of about 25 to 45 $mg/m^2$, and for idarubicin in a dosage of about 10 to 15 $mg/m^2$ per course of treatment.

The antiestrogen agent is advantageously administered in a dosage of about 1 to 100 mg daily depending on the particular agent and the condition being treated. Tamoxifen is advantageously administered orally in a dosage of 5 to 50 mg, particularly 10 to 20 mg twice a day, continuing the therapy for sufficient time to achieve and maintain a therapeutic effect. Toremifene is advantageously administered orally in a dosage of about 60 mg once a day, continuing the therapy for sufficient time to achieve and maintain a therapeutic effect. Anastrozole is advantageously administered orally in a dosage of about 1 mg once a day. Droloxifene is advantageously administered orally in a dosage of about 20-100 mg once a day. Raloxifene is advantageously administered orally in a dosage of about 60 mg once a day. Exemestane is advantageously administered orally in a dosage of about 25 mg once a day.

Antibodies are advantageously administered in a dosage of about 1 to 5 mg per square meter ($mg/m^2$) of body surface area, or as known in the art, if different. Trastuzumab is advantageously administered in a dosage of 1 to 5 mg per square meter (mg/m$^2$) of body surface area, particularly 2 to 4 mg/m$^2$ per course of treatment.

Where the compound of the formulae (0), (1) and sub-formulae thereof is administered in combination therapy with one, two, three, four or more other therapeutic agents (particularly one or two, more particularly one), the compounds can be administered simultaneously or sequentially. In the latter case, the two or more compounds will be administered within a period and in an amount and manner that is sufficient to ensure that an advantageous or synergistic effect is achieved. When administered sequentially, they can be administered at closely spaced intervals (for example over a period of 5-10 minutes) or at longer intervals (for example 1, 2, 3, 4 or more hours apart, or even longer periods apart where required), the precise dosage regimen being commensurate with the properties of the therapeutic agent(s). These dosages may be administered for example once, twice or more per course of treatment, which may be repeated for example every 7, 14, 21 or 28 days.

It will be appreciated that the particular method and order of administration and the respective dosage amounts and regimes for each component of the combination will depend on the particular other medicinal agent and compound of the present invention being administered, their route of administration, the particular tumour being treated and the particular host being treated. The optimum method and order of administration and the dosage amounts and regime can be readily determined by those skilled in the art using conventional methods and in view of the information set out herein.

The weight ratio of the compound according to the present invention and the one or more other anticancer agent(s) when given as a combination may be determined by the person skilled in the art. The ratio and the exact dosage and frequency of administration will depend on the particular compound according to the invention and the other anticancer agent(s) used, the particular condition being treated, the severity of the condition being treated, the age, weight, gender, diet, time of administration and general physical condition of the particular patient, the mode of administration as well as other medication the individual may be taking, as is well known to those skilled in the art. Furthermore, it is evident that the effective daily amount may be lowered or increased depending on the response of the treated subject and/or depending on the evaluation of the physician prescribing the compounds of the instant invention. A particular weight ratio for the present compound of formulae (0), (1) and subformulae thereof and another anticancer agent may range from 1/10 to 10/1, more in particular from 1/5 to 5/1, even more in particular from 1/3 to 3/1.

The compounds of the invention may also be administered in conjunction with non-chemotherapeutic treatments such as radiotherapy, photodynamic therapy, gene therapy; surgery and controlled diets.

The compounds of the present invention also have therapeutic applications in sensitising tumour cells for radiotherapy and chemotherapy. Hence the compounds of the present invention can be used as "radiosensitizer" and/or "chemosensitizer" or can be given in combination with another "radiosensitizer" and/or "chemosensitizer". In one embodiment the compound of the invention is for use as chemosensitiser.

The term "radiosensitizer" is defined as a molecule administered to patients in therapeutically effective amounts to increase the sensitivity of the cells to ionizing radiation and/or to promote the treatment of diseases which are treatable with ionizing radiation.

The term "chemosensitizer" is defined as a molecule administered to patients in therapeutically effective amounts to increase the sensitivity of cells to chemotherapy and/or promote the treatment of diseases which are treatable with chemotherapeutics.

Many cancer treatment protocols currently employ radiosensitizers in conjunction with radiation of x-rays. Examples of x-ray activated radiosensitizers include, but are not limited to, the following: metronidazole, misonidazole, desmethylmisonidazole, pimonidazole, etanidazole, nimorazole, mitomycin C, RSU 1069, SR 4233, E09, RB 6145, nicotinamide, 5-bromodeoxyuridine (BUdR), 5-iododeoxyuridine (IUdR), bromodeoxycytidine, fluorodeoxyuridine (FudR), hydroxyurea, cisplatin, and therapeutically effective analogs and derivatives of the same.

Photodynamic therapy (PDT) of cancers employs visible light as the radiation activator of the sensitizing agent. Examples of photodynamic radiosensitizers include the following, but are not limited to: haematoporphyrin derivatives, Photofrin, benzoporphyrin derivatives, tin etioporphyrin, pheoborbide-a, bacteriochlorophyll-a, naphthalocyanines, phthalocyanines, zinc phthalocyanine, and therapeutically effective analogs and derivatives of the same.

Radiosensitizers may be administered in conjunction with a therapeutically effective amount of one or more other compounds, including but not limited to: compounds which promote the incorporation of radiosensitizers to the target cells; compounds which control the flow of therapeutics, nutrients, and/or oxygen to the target cells; chemotherapeutic agents which act on the tumour with or without additional radiation; or other therapeutically effective compounds for treating cancer or other diseases.

Chemosensitizers may be administered in conjunction with a therapeutically effective amount of one or more other compounds, including but not limited to: compounds which promote the incorporation of chemosensitizers to the target cells; compounds which control the flow of therapeutics, nutrients, and/or oxygen to the target cells; chemotherapeutic agents which act on the tumour or other therapeutically effective compounds for treating cancer or other disease. Calcium antagonists, for example verapamil, are found useful in combination with antineoplastic agents to establish chemosensitivity in tumor cells resistant to accepted chemotherapeutic agents and to potentiate the efficacy of such compounds in drug-sensitive malignancies.

For use in combination therapy with another chemotherapeutic agent, the compound of the formulae (0), (1) and subformulae thereof and one, two, three, four or more other therapeutic agents can be, for example, formulated together in a dosage form containing two, three, four or more therapeutic agents i.e. in a unitary pharmaceutical composition containing all components. In an alternative, the individual therapeutic agents may be formulated separately and presented together in the form of a kit, optionally with instructions for their use.

It will be appreciated from the foregoing that, in a further embodiment (Embodiment 6.1), the invention provides a combination of a compound as defined in any one of Embodiments 0.1 to 1.179 and another therapeutic agent, for example another therapeutic agent as defined above.

In another embodiment (Embodiment 6.2), the invention provides a pharmaceutical composition comprising a compound as defined in any one of Embodiments 0.1 to 1.179 together with a pharmaceutically acceptable carrier and one or more therapeutic agent(s) as defined above.

In further embodiments (Embodiments 6.3 to 6.8), the invention provides:

6.3 A combination as defined in Embodiment 6.1 or a pharmaceutical composition as defined in Embodiment 6.2 for use in the treatment of (for use in alleviating or reducing the incidence of) a disease or condition as described herein, in particular cancer.

6.4 The use of a combination as defined in Embodiment 6.1 for the manufacture of a medicament for the treatment of (for use in alleviating or reducing the incidence of) a disease or condition as described herein, in particular cancer.

6.5 A method of preventing or treating (for use in alleviating or reducing the incidence of) a disease or condition as described herein, in particular cancer, in a subject (e.g. a mammalian subject, such as a human, in need thereof), which method comprises administering to the subject a therapeutically effective amount of a combination as defined in Embodiment 6.1 or a pharmaceutical composition as defined in Embodiment 6.2.

6.6 A combination as defined in Embodiment 6.1 or a pharmaceutical composition as defined in Embodiment 6.2 for use in for inhibiting the growth of tumour cells (e.g. in a patient).

6.7 The use of a combination as defined in Embodiment 6.1 for the manufacture of a medicament for inhibiting growth of tumour cells in a patient.

6.8 A method of inhibiting the growth of tumour cells (e.g. in a patient), which method comprises contacting the tumour cells with a compound as defined in any one of Embodiments 0.1 to 1.179 or a combination as defined in Embodiment 6.1 or a pharmaceutical composition as defined in Embodiment 6.2.

In each of Embodiments 6.3 to 6.8, the compound of Embodiments 0.1 to 1.179 and one or more other therapeutic agents, at least one of which is an anticancer agent, can be administered simultaneously, separately or sequentially in the treatment of patients suffering from cancer.

In a further embodiment (Embodiment 6.9) the invention provides a method for the prophylaxis or treatment of (or alleviating or reducing the incidence of) cancer, which method comprises administering to a patient in combination with radiotherapy or chemotherapy a compound as defined in any one of Embodiments 0.1 to 1.179.

In another embodiment (Embodiment 6.10), the invention provides a compound as defined in any one of Embodiments 0.1 to 1.179 for use the prophylaxis or treatment of (or alleviating or reducing the incidence of) cancer in combination with radiotherapy or chemotherapy.

EXAMPLES

The invention will now be illustrated, but not limited, by reference to the specific embodiments described in the following examples. Compounds are named using an automated naming package such as AutoNom (MDL) or ChemAxon Structure to Name or are as named by the chemical supplier. In the examples, the following abbreviations are used.

By following methods similar and/or analogous to general procedures below, the compounds set out below were prepared.

The following synthetic procedures are provided for illustration of the methods used; for a given preparation or step the precursor used may not necessarily derive from the individual batch synthesised according to the step in the description given.

Where a compound is described as a mixture of two diastereoisomers/epimers, the configuration of the stereocentre is not specified and is represented by straight lines.

As understood by a person skilled in the art, compounds synthesised using the protocols as indicated may exist as a solvate e.g. hydrate, and/or contain residual solvent or minor impurities. Compounds isolated as a salt form, may be integer stoichiometric i.e. mono- or di-salts, or of intermediate stoichiometry.

Some of the compounds below are isolated as the salt, for example depending on the acid used in the purification method. Some compounds are isolated as the free base.

Abbreviations

BINAP, 2,2'-bis(diphenylphosphino)-1,1'-binaphthalene; CDI, 1,1'-carbonyldiimidazole; DCE, 1,2-dichloroethane; DCM, Dichloromethane; DIPEA, diisopropylethylamine; DMSO, dimethylsulfoxide; DMF, N,N-dimethylformamide; DMAP, -(dimethylamino)pyridine; EtOAc, ethyl acetate; h, hour; HATU, N,N,N',N'-tetramethyl-O-(7-azabenzotriazol-1-yl)uronium hexafluorophosphate; HBTU, 3-[Bis(dimethylamino)methyliumyl]-3H-benzotriazol-1-oxide hexafluorophosphate; HCl, Hydrochloric acid; HPLC, High pressure liquid chromatography; LC-MS, Liquid chromatography-mass spectrometry; LiHMDS, lithium bis(trimethylsilyl) amide; mins., Minutes; MeCN, acetonitrile; MS, Mass Spectrometry; NBS, N-bromosuccinimide; NMR, Nuclear Magnetic Resonance Spectroscopy; $PdCl_2(dppf)_2$, (1,1'-Bis (diphenylphosphino)-ferrocene)palladium(II) dichloride; $Pd_2(dba)_3$, tris(dibenzylidine acetone)palladium (0); Petrol, petroleum ether fraction with boiling point range 40-60° C.; PyBOP, benzotriazol-1-yloxy)tris(dimethylamino)phosphonium hexafluorophosphate; RT, room temperature; Sat., Saturated; SCX, solid phase cation exchange resin; SPhos, 2-Dicyclohexylphosphino-2',6'-dimethoxybiphenyl; S-Phos Pd G3, (2-Dicyclohexylphosphino-2',6'-dimethoxybiphenyl) [2-(2'-amino-1,1'-biphenyl)]palladium(II) methanesulfonate; TBDMSCl, tert-butyldimethylsilyl chloride; TBTU, O-(Benzotriazol-1-yl)-N,N,N',N'-tetramethyluronium tetrafluoroborate; TFA, trifluoroacetic acid; THF, Tetrahydrofuran; XPhos, 2-Dicyclohexylphosphino-2',4',6'-triisopropylbiphenyl; XantPhos, 4,5-Bis(diphenylphosphino)-9,9-dimethylxanthene.

Synthetic Methods

All starting materials and solvents were obtained either from commercial sources or prepared according to the literature citation. Unless otherwise stated all reactions were stirred. Organic solutions were routinely dried over anhydrous magnesium sulfate. Hydrogenations were performed on a Parr hydrogenator, a Thales H-cube flow reactor under the conditions stated or under a balloon of hydrogen. Microwave reactions were performed in a CEM Discover and Smithcreator microwave reactor, heating to a constant temperature using variable power microwave irradiation. Normal phase column chromatography was routinely carried out on an automated flash chromatography system such as CombiFlash Companion or CombiFlash RF system using pre-packed silica (230-400 mesh, 40-63 μm) cartridges. SCX was purchased from Supelco and treated with 1M hydrochloric acid prior to use. Unless stated otherwise the reaction mixture to be purified was first diluted with MeOH and made acidic with a few drops of AcOH. This solution was loaded directly onto the SCX and washed with MeOH. The desired material was then eluted by washing with 1% $NH_3$ in MeOH.

Where a compound is described as a mixture of two diastereoisomers/epimers, the configuration of the stereocentre is not specified and is represented by straight lines.

NMR Data $^1H$ NMR spectra were acquired on a Bruker Avance III spectrometer at 400 MHz. Either the central peaks of chloroform-d, dimethylsulfoxide-$d_6$ or an internal standard of tetramethylsilane were used as references. For NMR data, where the number of protons assigned is less than the theoretical number of protons in the molecule, it is assumed that the apparently missing signal(s) is/are obscured by solvent and/or water peaks. In addition, where spectra were obtained in protic NMR solvents, exchange of NH and/or OH protons with solvent occurs and hence such signals are normally not observed.

Analytical and Preparative LC-MS Systems

Analytical LC-MS System and Method Description

In the following examples, compounds were characterised by mass spectroscopy using the systems and operating conditions set out below. Where atoms with different isotopes are present and a single mass quoted, the mass quoted for the compound is the monoisotopic mass (i.e. $^{35}Cl$; $^{79}Br$ etc.).

| Waters Platform LC-MS system: | |
|---|---|
| HPLC System: | Waters 2795 |
| Mass Spec Detector: | Micromass Platform LC |
| PDA Detector: | Waters 2996 PDA |
| Platform MS conditions: | |
| Capillary voltage: | 3.6 kV (3.40 kV on ES negative) |
| Cone voltage: | 30 V |
| Source Temperature: | 120° C. |
| Scan Range: | 125-800 amu |
| Ionisation Mode: | ElectroSpray Positive or ElectroSpray Negative or ElectroSpray Positive & Negative |

| Waters Fractionlynx LC-MS system: | |
|---|---|
| HPLC System: | 2767 autosampler - 2525 binary gradient pump |
| Mass Spec Detector: | Waters ZQ |
| PDA Detector: | Waters 2996 PDA |
| Fractionlynx MS conditions: | |
| Capillary voltage: | 3.5 kV (3.25 kV on ES negative) |
| Cone voltage: | 40 V (25 V on ES negative) |
| Source Temperature: | 120° C. |
| Scan Range: | 125-800 amu |
| Ionisation Mode: | ElectroSpray Positive or ElectroSpray Negative or ElectroSpray Positive & Negative |

| Adilent 1200SL-6140 LC-MS system - RAPID: | |
|---|---|
| HPLC System: | Agilent 1200 series SL |
| Mass Spec Detector: | Agilent 6120 or 6140 single quadrupole |
| Second Detector: | Agilent 1200 MWD SL |
| Agilent MS conditions: | |
| Capillary voltage: | 4000V on ES pos (3500V on ES Neg) |
| Fragmentor/Gain: | 100 |
| Gain: | 1 |

| Adilent 1200SL-6140 LC-MS system - RAPID: | |
|---|---|
| Drying gas flow: | 7.0 L/min |
| Gas Temperature: | 345° C. |
| Nebuliser Pressure: | 35 psig |
| Scan Range: | 125-800 amu |
| Ionisation Mode: | ElectroSpray Positive-Negative switching |
| Columns: | |

A range of commercially available columns—both achiral and chiral—may be used such that, in conjunction with the changes in mobile phase, organic modifier and pH, they enabled the greatest cover in terms of a broad range of selectivity. All columns were used in accordance with the manufacturers recommended operating conditions. For example, columns from Waters (including but not limited to Xselect CSH C18, 2.5 µm, 4.6×30 mm; Xbridge BEH C18, 2.5 µm, 4.6×30).

Preparative LC-MS System and Method Description

Preparative LC-MS is a standard and effective method used for the purification of small organic molecules such as the compounds described herein. The methods for the liquid chromatography (LC) and mass spectrometry (MS) can be varied to provide better separation of the crude materials and improved detection of the samples by MS. Optimisation of the preparative gradient LC method will involve varying columns, volatile eluents and modifiers, and gradients. Methods are well known in the art for optimising preparative LC-MS methods and then using them to purify compounds. Such methods are described in Rosentreter U, Huber U.; Optimal fraction collecting in preparative LC-MS; *J Comb Chem.*; 2004; 6(2), 159-64 and Leister W, Strauss K, Wisnoski D, Zhao Z, Lindsley C., Development of a custom high-throughput preparative liquid chromatography/mass spectrometer platform for the preparative purification and analytical analysis of compound libraries; *J Comb Chem.*; 2003; 5(3); 322-9.

Several systems for purifying compounds via preparative LC-MS are described below although a person skilled in the art will appreciate that alternative systems and methods to those described could be used. From the information provided herein, or employing alternative chromatographic systems, a person skilled in the art could purify the compounds described herein by preparative LC-MS.

| Waters Fractionlynx system: | |
|---|---|
| Hardware: | |
| 2767 Dual Loop Autosampler/Fraction Collector | |
| 2525 preparative pump | |
| CFO (column fluidic organiser) for column selection | |
| RMA (Waters reagent manager) as make up pump | |
| Waters ZQ Mass Spectrometer | |
| Waters 2996 Photo Diode Array detector | |
| Waters ZQ Mass Spectrometer | |
| Waters MS running conditions: | |
| Capillary voltage: | 3.5 kV (3.2 kV on ES Negative) |
| Cone voltage: | 25 V |
| Source Temperature: | 120° C. |
| Scan Range: | 125-800 amu |
| Ionisation Mode: | ElectroSpray Positive or ElectroSpray Negative |

Aqilent 1100 LC-MS preparative system:
Hardware:
Autosampler: 1100 series "prepALS"
Pump: 1100 series "PrepPump" for preparative flow gradient and 1100 series "QuatPump" for pumping modifier in prep flow
UV detector: 1100 series "MWD" Multi Wavelength Detector
MS detector: 1100 series "LC-MSD VL"
Fraction Collector: 2 × "Prep-FC"
Make Up pump: "Waters RMA"
Agilent Active Splitter
Agilent MS running conditions:

| | |
|---|---|
| Capillary voltage: | 4000 V (3500 V on ES Negative) |
| Fragmentor/Gain: | 150/1 |
| Drying gas flow: | 12.0 L/min |
| Gas Temperature: | 350° C. |
| Nebuliser Pressure: | 50 psig |
| Scan Range: | 125-800 amu |
| Ionisation Mode: | ElectroSpray Positive or ElectroSpray Negative |

Columns:

A range of commercially available columns—both achiral and chiral—may be used such that, in conjunction with the changes in mobile phase, organic modifier and pH, they enabled the greatest cover in terms of a broad range of selectivity. All columns were used in accordance with the manufacturers recommended operating conditions. Typically 5 micron particle sized columns were used where available. For example, columns from Waters (including but not limited to XBridge™ Prep OBD™ C18 and Phenyl; Xselect CSH C18, 5 μm, 19×50 mm; Xbridge BEH C18, 5 μm, 19×50 mm; Atlantis® Prep T3 OBD™ and Sunfire™ Prep OBD C18 5 μm 19×100 mm), Phenomenex (including but not limited to Synergy MAX-RP and LUX™ Cellulose-2), Astec (Chirobiotic™ columns including but not limited to V, V2 and T2) and Diacel® (including but not limited to Chiralpak® AD-H) were available for screening.

Eluents:

Mobile phase eluent was chosen in conjunction with column manufacturers recommended stationary phase limitations in order to optimise a columns separation performance. Typical eluents include but are not limited to a gradient of either 0.1% formic acid in MeCN in 0.1% aqueous formic acid or a gradient of MeCN in aqueous 10 mM ammonium bicarbonate.

Methods:

Achiral Preparative Chromatography

The compound examples described have undergone HPLC purification, where indicated, using methods developed following recommendations as described in Snyder L. R., Dolan J. W., High-Performance Gradient Elution The Practical Application of the Linear-Solvent-Strength Model, Wiley, Hoboken, 2007.

Chiral Preparative Chromatography

Preparative separations using Chiral Stationary Phases (CSPs) are the natural technique to apply to the resolution of enantiomeric mixtures. Equally, it can be applied to the separation of diastereomers and achiral molecules. Methods are well known in the art for optimising preparative chiral separations on CSPs and then using them to purify compounds. Such methods are described in Beesley T. E., Scott R. P. W.; Chiral Chromatography; Wiley, Chichester, 1998.

Synthesis of Intermediates

Preparation 1: tert-Butyl 2-(6-bromo-1-oxo-2,3-dihydro-1H-isoindol-2-yl)acetate

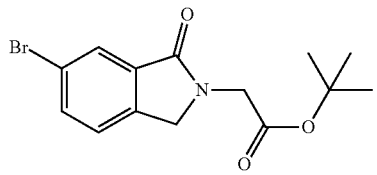 [SMILES: CC(C)(C)OC(=O)CN1Cc2ccc(Br)cc2C1=O]

A suspension of 6-bromo-2,3-dihydro-1H-isoindol-1-one (20 g, 94 mmol) and tert-butyl 2-bromoacetate (16.94 ml, 113 mmol) in DMF (320 mL) was cooled in an ice bath. Sodium hydride (4.53 g, 113 mmol) was added cautiously portionwise and the reaction was allowed to slowly warm to room temperature for 3 h. The reaction was quenched by the addition a saturated solution of $NH_4Cl$ (650 mL) and the crude product was extracted with DCM (2×650 mL). The combined organic extracts were washed with water (4×650 mL) and brine (2×650 mL). The mixture was passed through a phase separator cartridge and the organic phase was concentrated under vacuum to give the crude product (40.1 g) as a dark orange semi-solid. 30 g of the crude product were purified by chromatography ($SiO_2$, 2×220 g column, 0-50% EtOAc in isohexane) to afford the title compound as a yellow solid (19.5 g, 77%). LC-MS: $[M-tBu+H]^+=270/272$.

Preparation 2: tert-Butyl 2-[1-oxo-6-(4,4,5,5-tetramethyl-1,3,2-dioxaborolan-2-yl)-2,3-dihydro-1H-isoindol-2-yl]acetate

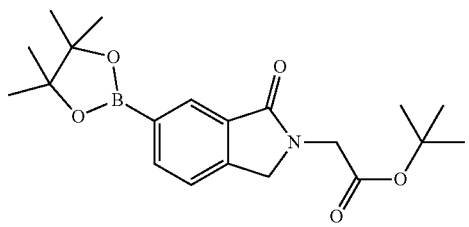 [SMILES: CC(C)(C)OC(=O)CN1Cc2ccc(B3OC(C)(C)C(C)(C)O3)cc2C1=O]

$PdCl_2$(dppf), complex with dichloromethane (1.459 g, 1.751 mmol) was added to a degassed solution (by bubbling nitrogen through the solution) of tert-butyl 2-(6-bromo-1-oxo-2,3-dihydro-1H-isoindol-2-yl)acetate (19.23 g, 58.4 mmol), bis(pinacolato)diboron (17.79 g, 70.0 mmol) and potassium acetate (11.57 g, 117 mmol) in 1-4-dioxane (200 mL). The mixture was degassed with nitrogen for a further 10 minutes then heated at 90° C. under nitrogen overnight. The reaction was cooled to room temperature and partitioned between EtOAc (600 mL) and water (600 mL). The aqueous layer was extracted with EtOAc (600 mL) and the combined organic extracts were washed with brine (1 L), dried ($MgSO_4$), filtered and concentrated under vacuum to give the crude product (27.3 g), which was triturated with isohexane. The resulting precipitate was filtered and dried to afford the title compound as a brown solid (17.1 g, 75%). LC-MS: $[M-tBu+H]^+=318$.

203

Preparation 3: tert-Butyl 2-[6-(2,5-dichloropyrimidin-4-yl)-1-oxo-2,3-dihydro-1H-isoindol-2-yl]acetate

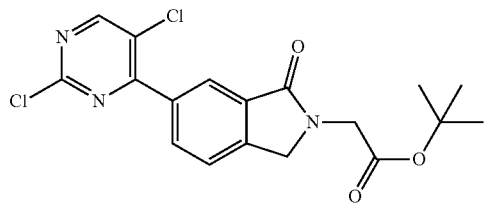 [SMILES: CC(C)(C)OC(=O)CN1Cc2ccc(-c3nc(Cl)ncc3Cl)cc2C1=O]

A mixture of tert-butyl 2-[1-oxo-6-(4,4,5,5-tetramethyl-1,3,2-dioxaborolan-2-yl)-2,3-dihydro-1H-isoindol-2-yl]acetate (17.1 g, 44.0 mmol), 2,4,5-trichloropyrimidine (7.4 mL, 66.2 mmol) and potassium carbonate (12.28 g, 88 mmol) in 1,4-dioxane:water (160 mL, 3:1) was degassed by bubbling nitrogen for 5 minutes. Tetrakis(triphenylphosphine)palladium(0) (2.57 g, 2.199 mmol) was added and degassing with nitrogen continued for 10 minutes. The reaction was then heated at 90° C. under nitrogen overnight. The reaction was cooled to room temperature, diluted with water (500 mL) and the crude product extracted with EtOAc (3×500 mL). The combined organic extracts were washed with brine (1 L), dried (MgSO$_4$), filtered and concentrated under vacuum to give the crude product, which was purified by chromatography (SiO$_2$, 2×220 g columns, 0-100% EtOAc in isohexane) to afford the title compound as a yellow solid (12.04 g, 62%). LC-MS: [M-tBu+H]$^+$=338.

Preparation 4: tert-Butyl 2-(6-{5-chloro-2-[(oxan-4-yl)amino]pyrimidin-4-yl}-1-oxo-2,3-dihydro-1H-isoindol-2-yl)acetate

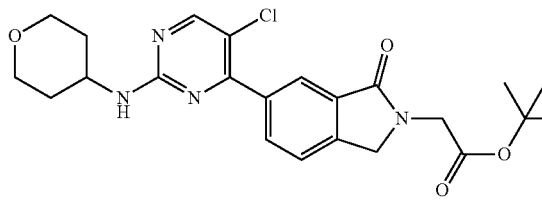

Oxan-4-amine (5 mL, 48.3 mmol) was added to a mixture of tert-butyl 2-[6-(2,5-dichloropyrimidin-4-yl)-1-oxo-2,3-dihydro-1H-isoindol-2-yl]acetate (12 g, 27.1 mmol) and DIPEA (11.95 mL, 67.7 mmol) in 1,4-dioxane (100 mL). The reaction was then heated at 70° C. for 72 h. The reaction was cooled to room temperature and water (450 mL) was added. The crude product was extracted with EtOAc (2×450 mL) and the combined organic extracts were washed with brine (600 mL), dried (MgSO$_4$), filtered and concentrated under vacuum to give the crude product (15.6 g). Purification by chromatography (SiO$_2$, 220 g column, 0-100% EtOAc in isohexane) afforded unreacted starting material (1.8 g, 16%) as a colourless solid and the title compound as a colourless solid (8.86 g, 70.6%). LC-MS: [M-tBu+H]$^+$=403.

Further title compound (1.52 g, 76%) could be obtained using the recovered starting material following the same procedure described above. LC-MS: [M+H]$^+$=459.

204

Preparation 5: Ethyl 5-bromo-2-(bromomethyl)pyridine-3-carboxylate

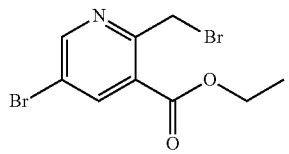

A mixture of ethyl 5-bromo-2-methylpyridine-3-carboxylate (5.0 g, 20.48 mmol) and NBS (5.1 g, 28.7 mmol) in carbon tetrachloride (50 mL, 518 mmol) was heated to 100° C. (external temperature). Benzoyl peroxide (0.143 g, 0.443 mmol) was added and the mixture heated at 90° C. for 7 h. The mixture was allowed to cool to room temperature and was stirred overnight. The reaction mixture was partitioned between DCM (100 mL) and water (100 mL). The layers were separated and the organic extract was washed with water (2×50 mL) and brine (2×50 mL) and then filtered through a phase separator cartridge. The organic fraction was then concentrated under reduced pressure to afford the crude product as a yellow oil (6.7 g), which was dry-loaded on silica. The crude product was purified by chromatography (SiO$_2$, 0-100% (10% EtOAc in iso-hexanes) in iso-hexanes) to afford the title compound as a pale yellow oil (3.8 g, 50%). LC-MS: [M+H]$^+$=322/324/326

Preparation 6: tert-Butyl 2-{3-bromo-5-oxo-5H,6H,7H-pyrrolo[3,4-b]pyridin-6-yl}acetate

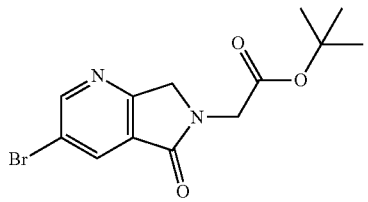 [SMILES: CC(C)(C)OC(=O)CN1Cc2ncc(Br)cc2C1=O]

tert-Butyl 2-aminoacetate hydrochloride (2.578 g, 15.38 mmol) was added to a solution of ethyl 5-bromo-2-(bromomethyl)pyridine-3-carboxylate (3.8 g, 10.24 mmol) and DIPEA (5.4 mL, 30.9 mmol) in acetonitrile (60.0 mL, 1149 mmol) and the resulting solution was heated to 75° C. overnight. After a total of 16.5 h the reaction mixture was allowed to cool to room temperature and was concentrated under reduced pressure. The residue was partitioned between EtOAc (100 mL) and a saturated solution of NH$_4$Cl (50 mL). The layers were separated and the organic fraction was washed with NH$_4$Cl (50 mL), water (50 mL) and brine (2×50 mL), dried (MgSO$_4$), filtered and concentrated under reduced pressure to afford the crude product as an orange solid (3.4 g). The solid was dry-loaded on silica and the product was purified by chromatography (SiO$_2$, 40 g column, 0-100% EtOAc in iso-hexanes) to afford the title compound as a colourless solid (1.28 g, 37.8%). LC-MS: [M+H]$^+$=327/329.

Note: THF could also be used as solvent for the reaction.

Preparation 7: tert-Butyl 2-[3-(2,5-dichloropyrimidin-4-yl)-5-oxo-5H,6H,7H-pyrrolo[3,4-b]pyridin-6-yl]acetate

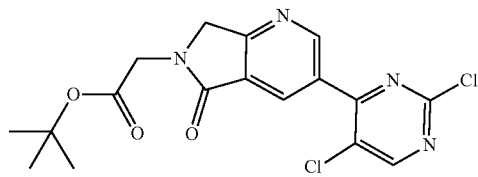 [SMILES: CC(C)(C)OC(=O)CN1Cc2ncc(-c3nc(Cl)ncc3Cl)cc2C1=O]

Potassium acetate (0.764 g, 7.78 mmol) and bis(pinacolato)diboron (1.48 g, 5.83 mmol) were added to a stirred solution of tert-butyl 2-{3-bromo-5-oxo-5H,6H,7H-pyrrolo[3,4-b]pyridin-6-yl}acetate (1.28 g, 3.87 mmol) in 1,4-dioxane (40.0 mL, 468 mmol). The mixture was heated to 40° C. and degassed with nitrogen for 10 minutes. PdCl$_2$(dppf)$_2$ (0.114 g, 0.156 mmol) was added and the mixture was degassed for a further 10 minutes then heated to 90° C. After 3.5 h the mixture was cooled to room temperature and partitioned between DCM (70 mL) and water (70 mL). The layers were separated and the organic fraction was washed with water (50 mL) and brine (3×50 mL) and then filtered through a phase separating cartridge. The organic filtrate was concentrated under reduced pressure to afford the crude product as a black solid. The boronate ester intermediate was used directly in the next step without further purification. LC-MS: [M+H]$^+$=293 (note: the mass for the boronic ester was not observed—it is possible that the product hydrolysed to the boronic acid under the LC-MS conditions). A mixture of crude tert-butyl 2-[5-oxo-3-(4,4,5,5-tetramethyl-1,3,2-dioxaborolan-2-yl)-5H,6H,7H-pyrrolo[3,4-b]pyridin-6-yl]acetate (1.448 g, 3.87 mmol), 2,4,5-trichloropyrimidine (0.670 mL, 5.84 mmol) and potassium carbonate (1.07 g, 7.74 mmol) in 1,4-dioxane (30.0 mL, 351 mmol) and water (10.0 mL, 555 mmol) was degassed with nitrogen at 40° C. After 10 minutes Pd(Ph$_3$P)$_4$ (0.150 g, 0.130 mmol) was added. The mixture was degassed for a further 10 minutes and then heated to 90° C. After 2 h the reaction mixture was cooled to room temperature and then partitioned between EtOAc (75 mL) and water (75 mL). The layers were separated and the crude product was extracted with EtOAc (75 mL). The combined organic extracts were washed with brine (3×50 mL), dried (MgSO$_4$), filtered and concentrated under reduced pressure to afford the crude product as a dark oil (3.17 g). The crude product was dry-loaded on silica and purified by chromatography (SiO$_2$, 40 g column, 0-100% (1% MeOH in DCM) in DCM). The product was further purified by chromatography (SiO$_2$, 24 g column, 0-100% EtOAc in iso-hexanes) to afford the title compound as an orange gum (0.729 g, 44%). LC-MS: [M+H]$^+$=395.

Preparation 8: tert-butyl 2-(3-{5-chloro-2-[(oxan-4-yl)amino]pyrimidin-4-yl}-5-oxo-5H,6H,7H-pyrrolo[3,4-b]pyridin-6-yl)acetate

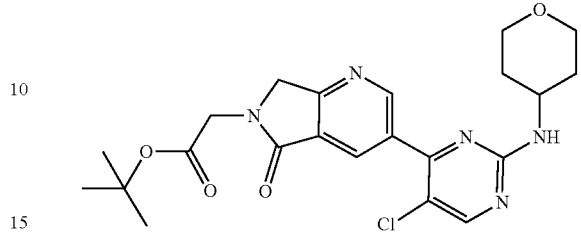

A mixture of tert-butyl 2-[3-(2,5-dichloropyrimidin-4-yl)-5-oxo-5H,6H,7H-pyrrolo[3,4-b]pyridin-6-yl]acetate (0.729 g, 1.697 mmol), oxan-4-amine (0.265 mL, 2.56 mmol) and DIPEA (0.740 mL, 4.24 mmol) in EtOH (10 mL) was refluxed for 3 h. Further oxan-4-amine (0.1 mL, 0.966 mmol) and DIPEA (0.4 mL, 2.292 mmol) were added. After a total of 5 h further oxan-4-amine (0.1 mL, 0.966 mmol) and DIPEA (0.4 mL, 2.292 mmol) were added and the mixture was refluxed overnight. The mixture was cooled to room temperature and was concentrated under reduced pressure. The residue was partitioned between EtOAc (40 mL) and water (40 mL) and the layers were separated. The aqueous layer was extracted with EtOAc (40 mL) and the combined organic extracts were washed with brine (2×30 mL), dried (MgSO$_4$), filtered and concentrated under reduced pressure to afford the title compound as a dark yellow foam (0.758 g, 92%). LC-MS: [M+H]$^+$=460.

Preparation 9: 2-(3-{5-chloro-2-[(oxan-4-yl)amino]pyrimidin-4-yl}-5-oxo-5H,6H,7H-pyrrolo[3,4-b]pyridin-6-yl)acetic acid

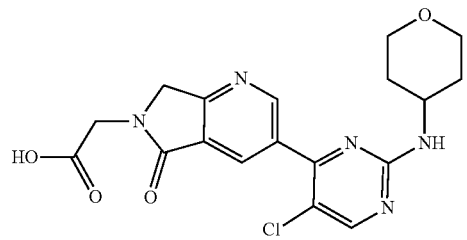 [SMILES: O=C(O)CN1Cc2ncc(-c3nc(NC4CCOCC4)ncc3Cl)cc2C1=O]

TFA (4.0 mL, 51.9 mmol) was added to a stirred solution of tert-butyl 2-(3-{5-chloro-2-[(oxan-4-yl)amino]pyrimidin-4-yl}-5-oxo-5H,6H,7H-pyrrolo[3,4-b]pyridin-6-yl)acetate (0.758 g, 1.566 mmol) in DCM (20 mL, 311 mmol). The reaction mixture was stirred at room temperature overnight and was concentrated under reduced pressure, then azeotroped with toluene (3×30 mL). The residue was triturated with diethyl ether and the resulting solid was filtered, washed with diethyl ether (3×20 mL) and dried in a vacuum oven at 40° C. to afford the title compound as a beige solid (0.607 g, 86%). LC-MS: [M+H]$^+$=404.

Preparation 10: Methyl 5-chloro-3-fluoro-2-methylbenzoate

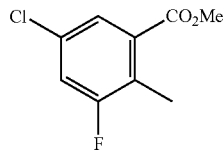

Iodomethane (1.04 mL, 16.6 mmol) was added to a suspension of 5-chloro-3-fluoro-2-methylbenzoic acid (1.57 g, 8.3 mmol) and potassium carbonate (2.30 g, 16.6 mmol) in DMF (30 mL). The reaction was stirred at room temperature for 18 h. A further portion of potassium carbonate (1.15 g, 8.3 mmol) and iodomethane (0.52 mL, 8.3 mmol) were added and the reaction was stirred for a further 3 h. The mixture was diluted with diethyl ether (50 mL) and water (100 mL). The phases were separated and the aqueous phase was extracted with diethyl ether (2×20 mL). The combined organic phases were combined with the crude material prepared from 5-chloro-3-fluoro-2-methylbenzoic acid (0.50 g, 2.7 mmol) from a second experiment according to the procedure described above. The mixture was washed with brine (4×100 mL), dried ($MgSO_4$) and concentrated under vacuum to give the title compound as a pale green oil (2.18 g, 94%). 1H NMR (400 MHz, DMSO-d6) 7.64 (1H, dd), 7.62 (1H, s), 3.85 (3H, s), 2.35 (3H, d).

Preparation 11: methyl 2-(bromomethyl)-5-chloro-3-fluorobenzoate

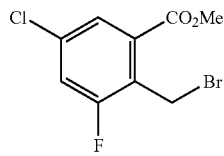 [SMILES: COC(=O)c1cc(Cl)cc(F)c1CBr]

N-Bromosuccinimide (2.30 g, 12.9 mmol) and benzoyl peroxide (75%, 0.174 g, 0.54 mmol) were added to a solution of methyl 5-chloro-3-fluoro-2-methylbenzoate (2.18 g, 10.8 mmol) in chloroform (100 mL). The mixture was heated to 60° C. and stirred for 18 h. The reaction was cooled to RT and hexane (100 mL) was added. The resulting precipitate was removed by filtration and the filtrate was concentrated under vacuum. Purification by chromatography ($SiO_2$, 0-30% DCM in iso-hexane) gave the title compound as a colourless oil (2.34 g, 70% yield, 90% purity). 1H NMR (400 MHz, Chloroform-d) 7.80 (1H, t), 7.31 (1H, dd), 4.97 (2H, d), 3.99 (3H, s).

Preparation 12: tert-butyl 2-(6-chloro-4-fluoro-1-oxo-2,3-dihydro-1H-isoindol-2-yl)acetate

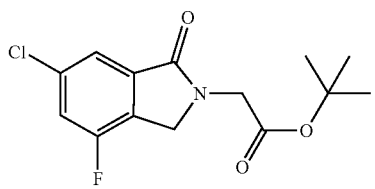 [SMILES: CC(C)(C)OC(=O)CN1Cc2c(F)cc(Cl)cc2C1=O]

Diisopropylethylamine (1.86 mL, 10.7 mmol) and methyl 2-(bromomethyl)-5-chloro-3-fluorobenzoate (1 g, 3.55 mmol) were added to a suspension of tert-butylglycine hydrochloride (0.893 g, 5.33 mmol) in acetonitrile (20 mL). The resulting solution was heated to 75° C. and stirred for 18 h. The reaction mixture was concentrated under vacuum and the residue was dissolved in ethyl acetate (15 mL) and 1 M hydrochloric acid (25 mL). The phases were separated and the aqueous phase was extracted with ethyl acetate (2×20 mL). The combined organic phases were washed with brine (50 mL), dried ($MgSO_4$) and concentrated. Purification by chromatography ($SiO_2$, 0-40% ethyl acetate in iso-hexane) gave the title compound as a colourless solid (823 mg, 77%). LC-MS: $[M+Na]^+$=322.

Preparation 13: tert-butyl 2-[4-fluoro-1-oxo-6-(4,4,5,5-tetramethyl-1,3,2-dioxaborolan-2-yl)-2,3-dihydro-1H-isoindol-2-yl]acetate

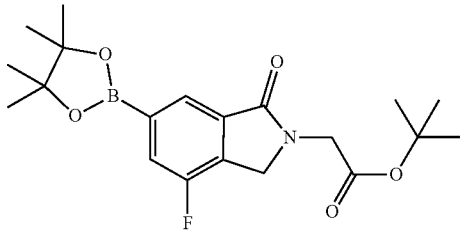 [SMILES: CC(C)(C)OC(=O)CN1Cc2c(F)cc(B3OC(C)(C)C(C)(C)O3)cc2C1=O]

A reaction tube was charged with tert-butyl 2-(6-chloro-4-fluoro-1-oxo-2,3-dihydro-1H-isoindol-2-yl)acetate (335 mg, 1.12 mmol), bis(pinacolato)diboron (341 mg, 1.34 mmol), potassium acetate (329 mg, 3.35 mmol) and XPhos G3 (19 mg, 0.02 mmol). The tube was evacuated and backfilled with nitrogen (3×). 1,4-Dioxane (2.2 mL) was added and the mixture was heated to 110° C. for 1 h. The reaction was diluted with ethyl acetate (10 mL) and passed through a pad of celite, eluting with ethyl acetate (50 mL) and the filtrate was concentrated under vacuum. Purification by chromatography ($SiO_2$, 0-50% ethyl acetate in iso-hexane) gave the title compound (467 mg, quant. yield, 95% purity) as a colourless solid. LC-MS: $[M+Na]^+$=414.

Preparation 14: tert-butyl 2-[6-(2,5-dichloropyrimidin-4-yl)-4-fluoro-1-oxo-2,3-dihydro-1H-isoindol-2-yl]acetate

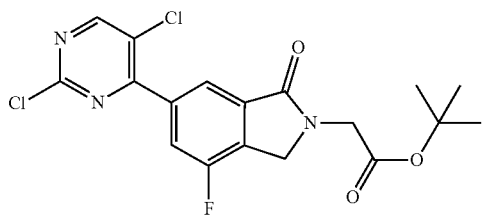 [SMILES: CC(C)(C)OC(=O)CN1Cc2c(F)cc(-c3nc(Cl)ncc3Cl)cc2C1=O]

A mixture of tert-butyl 2-[4-fluoro-1-oxo-6-(4,4,5,5-tetramethyl-1,3,2-dioxaborolan-2-yl)-2,3-dihydro-1H-isoindol-2-yl]acetate (200 mg, 0.51 mmol), 2,4,5-trichloropyrimidine (0.086 mL, 0.77 mmol) in a mixture of 1,4-dioxane (1.2 mL) and 2 M aqueous potassium carbonate solution (0.51 mL, 1.0 mmol) was degassed with nitrogen for 5 minutes.

Tetrakis(triphenylphosphine)palladium(0) (30 mg, 0.03 mmol) was added and degassing continued for 10 minutes. The mixture was heated to 90° C. for 2.5 h. The mixture was diluted with water (20 mL) and extracted with ethyl acetate (3×15 mL). The combined organic phases were washed with brine (30 mL), dried (MgSO$_4$) and concentrated under vacuum. Purification by chromatography (SiO$_2$, 0-40% ethyl acetate in iso-hexane) gave the title compound as a colourless solid (139 mg, 61% yield, 93% purity). LC-MS: [M+Na]$^+$=434.

Preparation 15: tert-butyl 2-(6-{5-chloro-2-[(oxan-4-yl)amino]pyrimidin-4-yl}-4-fluoro-1-oxo-2,3-dihydro-1H-isoindol-2-yl)acetate

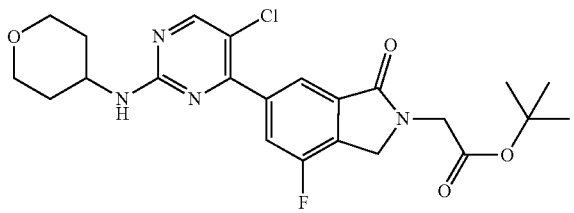 [SMILES: CC(C)(C)OC(=O)CN1Cc2c(F)cc(-c3nc(NC4CCOCC4)ncc3Cl)cc2C1=O]

A solution of tert-butyl 2-[6-(2,5-dichloropyrimidin-4-yl)-4-fluoro-1-oxo-2,3-dihydro-1H-isoindol-2-yl]acetate (139 mg, 0.34 mmol), oxan-4-amine (0.070 mL, 0.67 mmol) and diisopropylethylamine (0.15 mL, 0.85 mmol) in 1,4-dioxane (2 mL) was heated to 85° C. and stirred for 18 h. The reaction was diluted with ethyl acetate (10 mL) and water (10 mL). The phases were separated and the aqueous phase was extracted with ethyl acetate (2×10 mL). The combined organic phases were washed with 1 M hydrochloric acid (30 mL), brine (30 mL), dried (MgSO$_4$) and concentrated under vacuum. Purification by chromatography (SiO$_2$, 0-70% ethyl acetate in iso-hexane) gave the title compound as a colourless solid (102 mg, 62%). LC-MS: [M+H]$^+$=477.

Preparation 16: 2-(6-{5-chloro-2-[(oxan-4-yl)amino]pyrimidin-4-yl}-4-fluoro-1-oxo-2,3-dihydro-1H-isoindol-2-yl)acetic acid

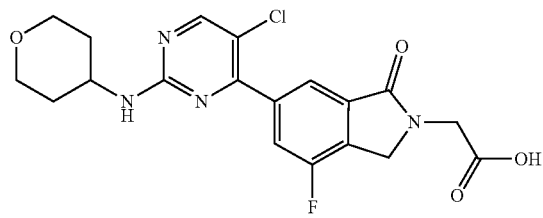 [SMILES: O=C(O)CN1Cc2c(F)cc(-c3nc(NC4CCOCC4)ncc3Cl)cc2C1=O]

Trifluoroacetic acid (0.8 mL, 10.4 mmol) was added to a solution of tert-butyl 2-(6-{5-chloro-2-[(oxan-4-yl)amino]pyrimidin-4-yl}-4-fluoro-1-oxo-2,3-dihydro-1H-isoindol-2-yl)acetate (102 mg, 0.21 mmol) in DCM (2 mL). The reaction mixture was stirred at room temperature for 2.5 h. The reaction mixture was concentrated under vacuum, azeotroped with toluene (3×5 mL) and acetonitrile (10 mL) to give the title compound (93 mg, quant. yield) as a colourless solid. LC-MS: [M+H]$^+$=421.

Preparation 17: 4-chloro-N-(oxan-4-yl)-5-(trifluoromethyl)pyrimidin-2-amine

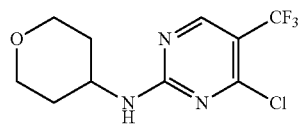 [SMILES: FC(F)(F)c1cnc(NC2CCOCC2)nc1Cl]

A solution of oxan-4-amine (2.1 mL, 20.3 mmol) and diisopropylethylamine (4.25 mL, 23.9 mmol) in THF (130 mL) was added to a stirred solution of 2,4-dichloro-5-(trifluoromethyl)pyrimidine (2.7 mL, 19.7 mmol) in THF (130 mL) at 0° C. The reaction mixture was allowed to warm to room temperature and stirred for 18 h. The reaction mixture was concentrated under vacuum. Purification by chromatography (SiO$_2$, 0-50% ethyl acetate in iso-hexane) gave the title compound (1.66 g, 29%) and its regioisomer 2-chloro-N-(oxan-4-yl)-5-(trifluoromethyl)pyrimidin-4-amine (1.23 g, 22%) as colourless solids. 1H NMR (400 MHz, DMSO-d6) 8.63-8.53 (2H, m), 4.05-3.90 (1H, m), 3.90-3.82 (2H, m), 3.43-3.33 (2H, m), 1.84-1.74 (2H, m), 1.59-1.45 (2H, m). LC-MS: [M+H]$^+$=284.

Preparation 18: tert-butyl 2-(6-{2-[(oxan-4-yl)amino]-5-(trifluoromethyl)pyrimidin-4-yl}-1-oxo-2,3-dihydro-1H-isoindol-2-yl)acetate

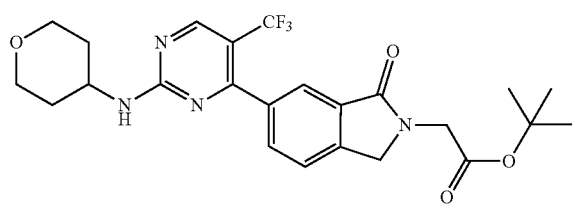 [SMILES: CC(C)(C)OC(=O)CN1Cc2ccc(-c3nc(NC4CCOCC4)ncc3C(F)(F)F)cc2C1=O]

A mixture of tert-butyl 2-[1-oxo-6-(4,4,5,5-tetramethyl-1,3,2-dioxaborolan-2-yl)-2,3-dihydro-1H-isoindol-2-yl]acetate (202 mg, 0.53 mmol), 4-chloro-N-(oxan-4-yl)-5-(trifluoromethyl)pyrimidin-2-amine (224 mg, 0.80 mmol) and potassium carbonate (147 mg, 1.06 mmol) in a mixture of 1,4-dioxane (1.5 mL) and water (0.5 mL) was degassed with nitrogen for 5 minutes. XPhos Pd G3 (14 mg, 0.016 mmol) was added and degassing continued for 10 minutes. The reaction was then heated to 90° C. for 2 h. The reaction was cooled to RT and diluted with water (20 mL). The mixture was extracted with ethyl acetate (3×20 mL). The combined organic phases were washed with brine (50 mL), dried (MgSO$_4$) and concentrated under vacuum. Purification by chromatography (SiO$_2$, 0-100% ethyl acetate in iso-hexane) gave the title compound as a colourless oil (142 mg, 35%). LC-MS: [M+H]$^+$=493.

Preparation 19: 2-(6-{2-[(oxan-4-yl)amino]-5-(trifluoromethyl)pyrimidin-4-yl}-1-oxo-2,3-dihydro-1H-isoindol-2-yl)acetic acid

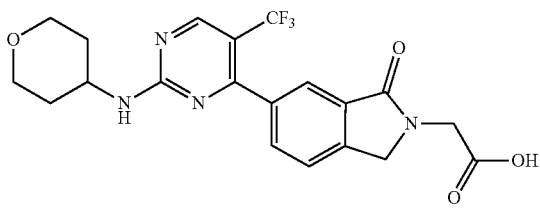 [SMILES: O=C(O)CN1Cc2ccc(-c3nc(NC4CCOCC4)ncc3C(F)(F)F)cc2C1=O]

Trifluoroacetic acid (1 mL, 13.0 mmol) was added to a solution of tert-butyl 2-(6-{2-[(oxan-4-yl)amino]-5-(trifluoromethyl)pyrimidin-4-yl}-1-oxo-2,3-dihydro-1H-isoindol-2-yl)acetate (135 mg, 0.26 mmol) in DCM (4 mL). The reaction mixture was stirred at RT for 18 h. The reaction mixture was concentrated under vacuum, azeotroped with toluene (3×10 mL), triturated with diethyl ether, filtered and dried to give the title compound (76 mg, 53%) as a colourless solid. LC-MS: [M+H]$^+$=437.

Preparation 20: tert-butyl 6-bromo-1-oxo-2,3-dihydro-1H-isoindole-2-carboxylate

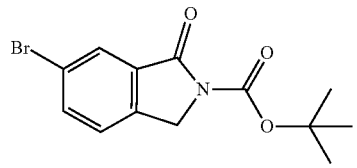 [SMILES: CC(C)(C)OC(=O)N1Cc2ccc(Br)cc2C1=O]

Di-tert-butyl dicarbonate (2.47 g, 11.3 mmol) was added to a suspension of 6-bromo-2,3-dihydro-1H-isoindol-1-one (2.00 g, 9.43 mmol), DMAP (0.058 g, 0.47 mmol) and triethylamine (1.58 mL, 11.3 mmol) in DCM (50 mL) and the mixture was stirred at room temperature for 18 h. The resulting solution was diluted with water (50 mL). The phases were separated and the aqueous phase was extracted with DCM (2×50 mL). The combined organic phases were washed with brine (100 mL), dried (MgSO$_4$) and absorbed on silica. Purification by chromatography (SiO$_2$, 50-100% ethyl acetate in iso-hexane) gave the title compound (2.44 g, 81%) as a colourless solid. LC-MS: [M+Na]$^+$=334.

Preparation 21: tert-butyl 5-bromo-3-oxo-1-{[2-(trimethylsilyl)ethoxy]methyl}-2,3-dihydro-1H-isoindole-2-carboxylate

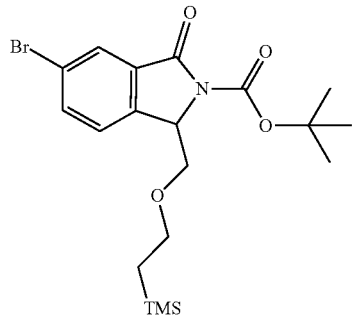 [SMILES: CC(C)(C)OC(=O)N1C(=O)c2cc(Br)ccc2C1COCC[Si](C)(C)C]

LiHMDS (1 M in THF, 7.69 mL, 7.69 mmol) was added to a solution of tert-butyl 6-bromo-1-oxo-2,3-dihydro-1H-isoindole-2-carboxylate (2.00 g, 6.41 mmol) in THF (50 mL) at −78° C. The mixture was stirred for 1 h, then warmed to −50° C. for 10 min and cooled to −78° C. 2-(Trimethylsilyl)ethoxymethyl chloride (2.27 mL, 12.8 mmol) was added dropwise and the mixture was warmed to 0° C. over a period of 2 h. The reaction mixture was quenched with saturated aqueous ammonium chloride solution (5 mL) and extracted with ethyl acetate (3×30 mL). The combined organic phases were washed with brine (30 mL), dried (MgSO$_4$) and concentrated under vacuum. Purification by chromatography (SiO$_2$, 0-15% ethyl acetate in iso-hexane) gave the title compound (950 mg, 33%) as a yellow oil. LC-MS: [M+H]$^+$=464.

Preparation 22: 6-bromo-3-{[2-(trimethylsilyl)ethoxy]methyl}-2,3-dihydro-1H-isoindol-1-one

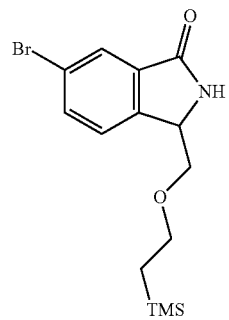 [SMILES: C[Si](C)(C)CCOCC1NC(=O)c2cc(Br)ccc21]

A solution of HCl (4 M in 1,4-dioxane, 8 mL, 32 mmol) was added dropwise to tert-butyl 5-bromo-3-oxo-1-{[2-(trimethylsilyl)ethoxy]methyl}-2,3-dihydro-1H-isoindole-2-carboxylate (950 mg, 2.15 mmol) at 0° C. The solution was stirred at room temperature for 15 minutes then added to saturated aqueous sodium bicarbonate solution (5 mL). The mixture was extracted with ethyl acetate (2×15 mL). The combined organic phases were washed with saturated brine (10 mL), dried (MgSO$_4$) and concentrated under vacuum to afford the title compound (707 mg, 93%) as a yellow oil. LC-MS: [M+H]$^+$=342.

Preparation 23: methyl 2-(5-bromo-3-oxo-1-{[2-(trimethylsilyl)ethoxy]methyl}-2,3-dihydro-1H-isoindol-2-yl)acetate

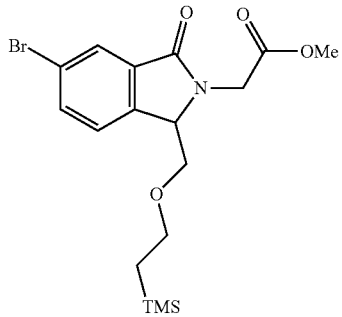 [SMILES: COC(=O)CN1C(=O)c2cc(Br)ccc2C1COCC[Si](C)(C)C]

Sodium hydride (60% dispersion in mineral oil, 99 mg, 2.5 mmol) was added to a solution of 6-bromo-3-{[2-(trimethylsilyl)ethoxy]methyl}-2,3-dihydro-1H-isoindol-1-one (707 mg, 2.07 mmol) in THF (17 mL) at 0° C. The mixture was stirred for 15 minutes before methyl 2-bromoacetate (0.27 mL, 2.48 mmol) was added. The mixture was warmed to room temperature and stirred for 4 h. The reaction was quenched with saturated aqueous ammonium chloride solution (5 mL) and extracted with ethyl acetate (2×40 mL). The combined organic phases were washed with brine (10 mL), dried (MgSO$_4$) and concentrated under vacuum. Purification by chromatography (SiO$_2$, 0-30% ethyl acetate in iso-hexane) gave the title compound (590 mg, 69%) as a yellow oil. LC-MS: [M+Na]$^+$=436.

Preparation 24: methyl 2-[3-oxo-5-(4,4,5,5-tetramethyl-1,3,2-dioxaborolan-2-yl)-1-{[2-(trimethylsilyl)ethoxy]methyl}-2,3-dihydro-1H-isoindol-2-yl]acetate

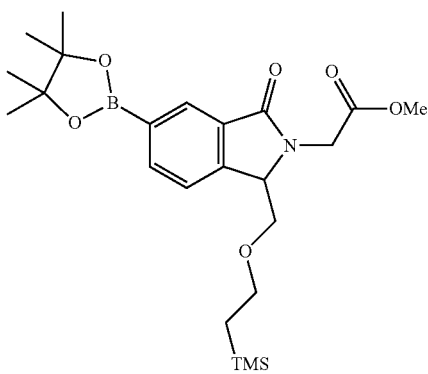 [SMILES: COC(=O)CN1C(=O)c2cc(B3OC(C)(C)C(C)(C)O3)ccc2C1COCC[Si](C)(C)C]

A reaction tube was charged with methyl 2-(5-bromo-3-oxo-1-{[2-(trimethylsilyl)ethoxy]methyl}-2,3-dihydro-1H-isoindol-2-yl)acetate (600 mg, 1.45 mmol), bis(pinacolato)diboron (441 mg, 1.74 mmol), potassium acetate (426 mg, 4.34 mmol) and XPhos Pd G3 (25 mg, 0.029 mmol). The tube was evacuated and backfilled with nitrogen (3×). 1,4-Dioxane (2.9 mL) was added and the mixture was heated to 90° C. for 1 h. The reaction was cooled to room temperature and diluted with ethyl acetate (10 mL), then passed through a pad of celite, eluting with ethyl acetate (30 mL). After concentration of the filtrate, purification by chromatography (SiO$_2$, 0-40% ethyl acetate in iso-hexane) gave the title compound (635 mg, 91%) as a colourless oil. LC-MS: [M+Na]$^+$=484.

Preparation 25: methyl 2-[5-(2,5-dichloropyrimidin-4-yl)-3-oxo-1-{[2-(trimethylsilyl)ethoxy]methyl}-2,3-dihydro-1H-isoindol-2-yl]acetate

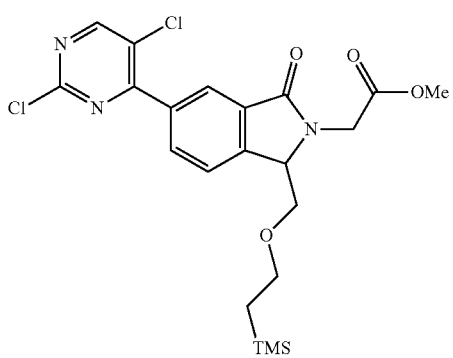 [SMILES: COC(=O)CN1C(=O)c2cc(-c3nc(Cl)ncc3Cl)ccc2C1COCC[Si](C)(C)C]

A mixture of methyl 2-[3-oxo-5-(4,4,5,5-tetramethyl-1,3,2-dioxaborolan-2-yl)-1-{[2-(trimethylsilyl)ethoxy]methyl}-2,3-dihydro-1H-isoindol-2-yl]acetate (640 mg, 1.39 mmol), 2,4,5-trichloropyrimidine (0.233 mL, 2.08 mmol) in a mixture of 1,4-dioxane (3.5 mL) and 2 M aqueous potassium carbonate solution (1.39 mL, 2.77 mmol) was degassed with nitrogen for 5 minutes. Tetrakis(triphenylphosphine)palladium(0) (80 mg, 0.069 mmol) was added and degassing continued for 10 minutes. The mixture was heated to 90° C. for 2.5 h. The mixture was diluted with water (20 mL) and extracted with ethyl acetate (3×15 mL). The combined organic phases were washed with brine (30 mL), dried (MgSO$_4$) and concentrated under vacuum. Purification by chromatography (SiO$_2$, 0-40% ethyl acetate in iso-hexane) gave the title compound (370 mg, 54%) as a yellow oil. LC-MS: [M+Na]$^+$=504.

Preparation 26: methyl 2-(5-{5-chloro-2-[(oxan-4-yl)amino]pyrimidin-4-yl}-3-oxo-1-{[2-(trimethylsilyl)ethoxy]methyl}-2,3-dihydro-1H-isoindol-2-yl)acetate

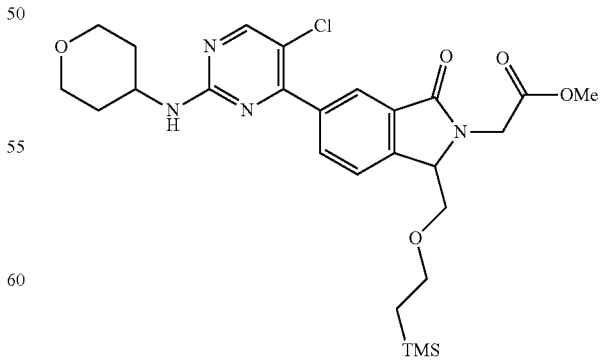

A solution of methyl 2-[5-(2,5-dichloropyrimidin-4-yl)-3-oxo-1-{[2-(trimethylsilyl) ethoxy]methyl}-2,3-dihydro-1H-isoindol-2-yl]acetate (200 mg, 0.415 mmol), oxan-4- amine (0.086 mL, 0.83 mmol) and diisopropylethylamine (0.18 mL, 1.04 mmol) in 1,4-dioxane (3 mL) was heated to 85° C. and stirred for 18 h. The reaction was diluted with ethyl acetate (10 mL) and water (10 mL). The phases were separated and the aqueous phase was extracted with ethyl acetate (2×10 mL). The combined organic phases were washed with 1 M hydrochloric acid (30 mL), brine (30 mL), dried (MgSO$_4$) and concentrated under vacuum. Purification by chromatography (SiO$_2$, 0-70% ethyl acetate in iso-hexane) gave the title compound (150 mg, 66%) as a colourless solid. LC-MS: [M+H]$^+$=547.

Preparation 27: N-tert-butyl-2-(5-{5-chloro-2-[(oxan-4-yl)amino]pyrimidin-4-yl}-3-oxo-1-{[2-(trimethylsilyl)ethoxy]methyl}-2,3-dihydro-1H-isoindol-2-yl)-N-methylacetamide

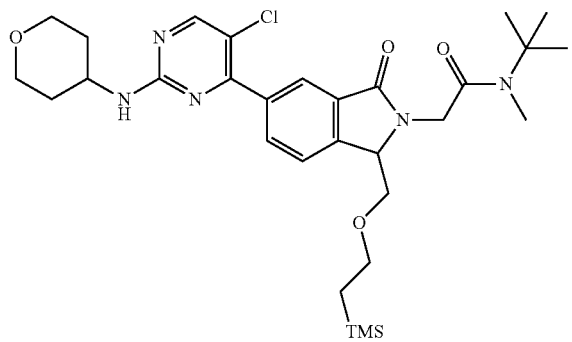 [SMILES: CN(C(=O)CN1C(=O)c2cc(-c3nc(NC4CCOCC4)ncc3Cl)ccc2C1COCC[Si](C)(C)C)C(C)(C)C]

A solution of lithium hydroxide (1 M aqueous, 0.091 mL, 0.091 mmol) was added to a stirred solution of methyl 2-(5-{5-chloro-2-[(oxan-4-yl)amino]pyrimidin-4-yl}-3-oxo-1-{[2-(trimethylsilyl)ethoxy]methyl}-2,3-dihydro-1H-isoindol-2-yl)acetate (50 mg, 0.091 mmol) in THF (1.4 mL) and water (0.4 mL). The resulting mixture was stirred at room temperature for 2 h. The reaction mixture was diluted with ethyl acetate (10 mL) and water (5 mL). The phases were separated and the aqueous phase was acidfied with 1 M hydrochloric acid to pH ~3. The resulting colourless precipitate was collected by filtration, washed with water (5 mL) and dried under vacuum. The residue was suspended in DCM (1.8 mL) and DMF (0.2 mL). HATU (42 mg, 0.11 mmol) and diisopropylethylamine (0.048 mL, 0.27 mmol) were added. The mixture was stirred for 5 minutes, before N-tert-butyl-methylamine (0.012 mL, 0.10 mmol) was added. The mixture was stirred at room temperature for 2 h before being diluted with ethyl acetate (10 mL) and water (15 mL). The phases were separated and the aqueous phase was extracted with ethyl acetate (2×10 mL). The combined organic phases were washed with 1 M hydrochloric acid (50 mL), saturated aqueous sodium bicarbonate (50 mL), brine (3×50 mL), dried (MgSO$_4$) and concentrated under vacuum to give the title compound as an off white solid (50 mg, 82% yield, 90% purity). LC-MS: [M+H]$^+$=602.

Preparation 28: tert-butyl 5-bromo-1-methyl-3-oxo-2,3-dihydro-1H-isoindole-2-carboxylate

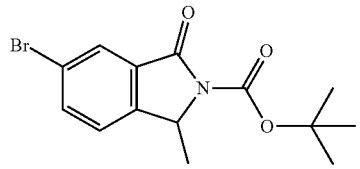 [SMILES: CC1c2ccc(Br)cc2C(=O)N1C(=O)OC(C)(C)C]

LiHMDS (1M in THF, 3.52 mL, 3.52 mmol) was added to a solution of tert-butyl 6-bromo-1-oxo-2,3-dihydro-1H-isoindole-2-carboxylate (Preparation 20) (1.00 g, 3.20 mmol) in THF (15 mL) at −78° C. The mixture was stirred for 1 h before iodomethane (0.22 mL, 3.5 mmol) was added. The mixture was allowed to warm to room temperature and stirred for 45 minutes. Saturated aqueous ammonium chloride solution (20 mL) and ethyl acetate (20 mL) were added to the reaction mixture. The phases were separated and the aqueous phase was extracted with ethyl acetate (20 mL). The combined organic phases were washed with brine (30 mL), dried (MgSO$_4$) and absorbed on silica. Purification by chromatography (SiO$_2$, 0-20% ethyl acetate in iso-hexane) gave the title compound (332 mg, 31%) as a colourless solid. LC-MS: [M-tBu+H]$^+$=270.

Preparation 29: 6-bromo-3-methyl-2,3-dihydro-1H-isoindol-1-one

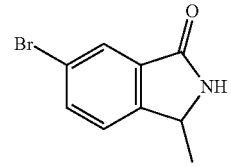

Trifluoroacetic acid (0.50 mL, 6.5 mmol) was added to a mixture of tert-butyl 5-bromo-1-methyl-3-oxo-2,3-dihydro-1H-isoindole-2-carboxylate (330 mg, 0.991 mmol) in DCM (5 mL) and the mixture was stirred for 1 h. The mixture was concentrated under vacuum and azeotroped with toluene (2×5 mL). The residue was dissolved in ethyl acetate (10 mL) and saturated aqueous sodium bicarbonate solution (10 mL) was added. The phases were separated and the aqueous phase was extracted with ethyl acetate (10 mL). The combined organic phases were washed with brine (20 mL), dried (MgSO$_4$) and concentrated under vacuum to give the title compound (174 mg, 75%) as a colourless solid. LC-MS: [M+H]$^+$=226.

Preparation 30: tert-butyl 2-(5-bromo-1-methyl-3-oxo-2,3-dihydro-1H-isoindol-2-yl)acetate

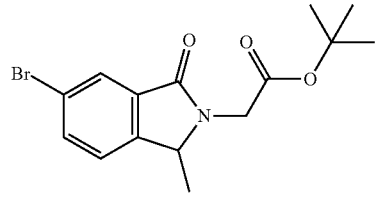 [SMILES: CC1c2ccc(Br)cc2C(=O)N1CC(=O)OC(C)(C)C]

Prepared according to Preparation 1 from 6-bromo-3-methyl-2,3-dihydro-1H-isoindol-1-one (170 mg, 0.752 mmol) and tert-butyl 2-bromoacetate (0.13 mL, 0.90 mmol). The title compound (218 mg, 80%) was obtained as a colourless solid. LC-MS: [M-tBu+H]⁺=284.

Preparation 31: tert-butyl 2-[5-(2,5-dichloropyrimidin-4-yl)-1-methyl-3-oxo-2,3-dihydro-1H-isoindol-2-yl]acetate

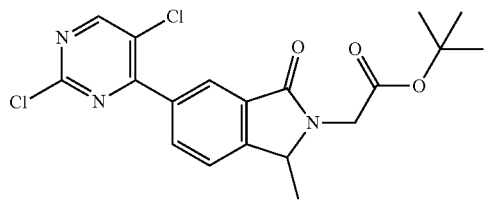 [SMILES: CC1c2ccc(-c3nc(Cl)ncc3Cl)cc2C(=O)N1CC(=O)OC(C)(C)C]

A mixture of tert-butyl 2-(5-bromo-1-methyl-3-oxo-2,3-dihydro-1H-isoindol-2-yl)acetate (215 mg, 0.632 mmol), potassium acetate (186 mg, 1.90 mmol) in 1,4-dioxane (4 mL) was degassed with nitrogen for 10 minutes before bis(pinacolato)diboron (193 mg, 0.758 mmol) and PdCl₂(dppf)₂ (23 mg, 0.032 mmol) were added. The reaction was heated to 100° C. under nitrogen for 4 h. The reaction was diluted with ethyl acetate (20 mL) and water (20 mL). The phases were separated and the aqueous phase was extracted with ethyl acetate (2×20 mL). The combined organic phases were washed with brine (50 mL), dried (MgSO₄) and concentrated. The residue was dissolved in 1,4-dioxane (1 mL) and added to a degassed mixture of 2,4,5-trichloropyrimidine (85 mg, 0.47 mmol) and potassium carbonate (86 mg, 0.62 mmol) in a mixture of 1,4-dioxane (3 mL) and water (1 mL). Tetrakis(triphenylphosphine)palladium(0) (18 mg, 0.016 mmol) was added and the mixture heated to 100° C. under nitrogen for 18 h. The mixture cooled to room temperature and diluted with ethyl acetate (20 mL) and water (20 mL). The phases were separated and the aqueous phase was extracted with ethyl acetate (2×20 mL). The combined organic phases were washed with brine (25 mL), dried (MgSO₄) and absorbed onto silica. Purification by chromatography (SiO₂, 0-40% ethyl acetate in iso-hexane) gave the title compound (34 mg, 26%) as a colourless solid. LC-MS: [M-tBu+H]⁺=352.

Preparation 32: tert-butyl 2-(5-{5-chloro-2-[(oxan-4-yl)amino]pyrimidin-4-yl}-1-methyl-3-oxo-2,3-dihydro-1H-isoindol-2-yl)acetate

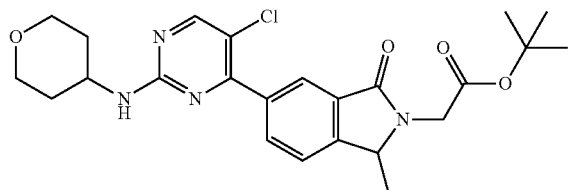 [SMILES: CC1c2ccc(-c3nc(NC4CCOCC4)ncc3Cl)cc2C(=O)N1CC(=O)OC(C)(C)C]

A mixture of tert-butyl 2-[5-(2,5-dichloropyrimidin-4-yl)-1-methyl-3-oxo-2,3-dihydro-1H-isoindol-2-yl]acetate (32 mg, 0.078 mmol), oxan-4-amine (0.012 mL, 0.12 mmol) and diisopropylethylamine (0.041 mL, 0.24 mmol) in ethanol (0.75 mL) was heated to 80° C. for 3 days. The reaction was diluted with ethyl acetate (10 mL) and water (10 mL). The phases were separated and the aqueous phase was extracted with ethyl acetate (2×10 mL). The combined organic phases were dried (MgSO₄) and absorbed onto silica. Purification by chromatography (SiO₂, 0-3% methanol in DCM) gave the title compound (22 mg, 50% yield, 85% purity) as a colourless solid. LC-MS: [M+H]⁺=473.

Preparation 33: Benzyl (1-methylcyclobutyl)carbamate

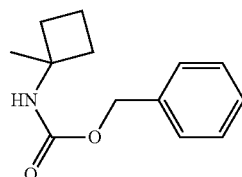

DIPEA (474 µl, 2.71 mmol) was added to a solution of 1-methylcyclobutanamine hydrochloride (150 mg, 1.233 mmol) in THF (20 mL) at 0° C. and the mixture was stirred at 0° C. for 10 minutes. Benzyl chloroformate (194 µl, 1.357 mmol) was added dropwise and the reaction mixture was allowed to warm to room temperature, and stirred for 2 hours. The reaction mixture was concentrated under vacuum and the residue was diluted with EtOAc (50 mL), washed successively with 1M HCl (50 mL), saturated aqueous solution of NaHCO₃ (50 mL), brine (50 mL), and dried via a hydrophobic phase separator. The organic extract was concentrated under vacuum to afford benzyl (1-methylcyclobutyl)carbamate (288 mg, 72% (68% purity)) as a pale yellow oil. 1H NMR (400 MHz, CDCl₃) 7.47-7.30 (m, 5H), 5.07 (s, 2H), 4.88 (br. s, 1H), 2.34-2.30 (m, 2H), 2.00-1.93 (m, 2H), 1.79-1.76 (m, 2H), 1.44 (s, 3H); (32% wt benzyl chloroformate).

Preparation 34: Benzyl methyl(1-methylcyclobutyl)carbamate

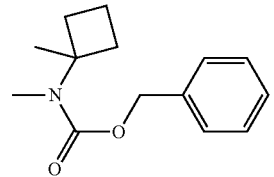 [SMILES: CN(C(=O)OCc1ccccc1)C1(C)CCC1]

Sodium hydride (60% in mineral oil, 79 mg, 1.97 mmol) was added in portions to a solution of benzyl (1-methylcyclobutyl)carbamate (288 mg, 1.313 mmol) in DMF (2 mL) at 0° C. and methyl iodide (99 µl, 1.576 mmol) was added dropwise. The reaction mixture was stirred at room temperature for 2 hours, then diluted with EtOAc (5 mL), washed with water (4×10 mL), brine (10 mL), dried (Na₂SO₄), filtered and concentrated under vacuum. The crude product was purified by chromatography (SiO₂, 4 g column, 0-25% ethyl acetate in iso-hexane) to afford benzyl methyl(1-methylcyclobutyl)carbamate (154 mg, 50%) as a clear colourless oil. 1H NMR (400 MHz, CDCl₃) 7.36-7.30 (m, 5H), 5.09 (s, 2H), 2.73 (s, 3H), 2.25-2.22 (m, 2H), 1.93-1.91 (m, 2H), 1.67-1.64 (m, 2H), 1.34 (s, 3H).

Preparation 35: N,1-Dimethylcyclobutan-1-amine

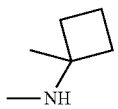

A solution of benzyl methyl(1-methylcyclobutyl)carbamate (154 mg, 0.660 mmol) in EtOAc (6 mL) was hydrogenated in the H-cube (10% Pd—C, Full H$_2$ mode, room temperature, 1 mL/min) for one hour. The reaction mixture was used without further treatment in the next step.

Preparation 36: 2-cyclopropyl-N-methylpropan-2-amine

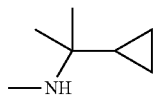

Prepared from 2-cyclopropylpropan-2-amine following an analogous/similar procedure as described for Preparations 33-35.

Preparation 37: tert-butyl (2-(tert-butylamino)ethyl)carbamate

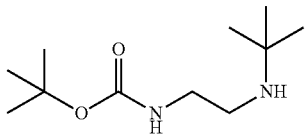

A stirred suspension of 4 Å molecular sieve beads (~2 g) in DMF (6 ml) was treated with cesium hydroxide monohydrate (1148 mg, 6.84 mmol) and stirred for 10 minutes. The suspension was treated with tert-butylamine (718 µl, 6.84 mmol) and stirred for 30 minutes. Tert-butyl (2-bromoethyl)carbamate (1800 mg, 8.03 mmol) was added and the mixture was stirred overnight, then filtered. The filtrate was evaporated and the residue was dissolved in ether (20 ml), washed successively with brine (20 ml), water (20 ml) then dried (Na$_2$SO$_4$) and evaporated to give tert-butyl (2-(tert-butylamino)ethyl)carbamate (680 mg, 1.572 mmol, 23.0%) as a pale yellow oil. LC-MS: [M+H]$^+$=217.

Preparation 38: N-(2-((tert-butyldimethylsilyl)oxy)ethyl)-2-methylpropan-2-amine

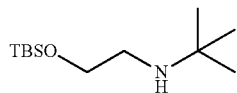

TBDMSCl (577 mg, 3.83 mmol) was added to a stirred solution of 2-(tert-butylamino)ethanol (305 mg, 2.55 mmol) and imidazole (521 mg, 7.65 mmol) in DMF (6 mL) and the reaction mixture was stirred at room temperature overnight. A further quantity of imidazole (521 mg, 7.65 mmol) was added, followed by TBDMS-Cl (577 mg, 3.83 mmol) and stirring continued at room temperature overnight. The reaction mixture was diluted with EtOAc (30 mL), washed with water (3×30 mL) and brine (30 mL) dried (MgSO$_4$), filtered and concentrated under vacuum to give crude N-(2-((tert-butyldimethylsilyl)oxy)ethyl)-2-methylpropan-2-amine as an oil (104 mg, 17%). 1H NMR (400 MHz, DMSO-d6) 3.58 (t, 2H), 2.55 (t, 2H), 1.16 (br. s, 1H), 1.00 (s, 9H), 0.86 (s, 9H), 0.03 (s, 6H).

Preparation 39: methyl(1,1,1-trifluoro-3-phenylpropan-2-yl)carbamate

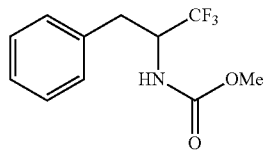 [SMILES: COC(=O)NC(Cc1ccccc1)C(F)(F)F]

Methyl chloroformate (0.343 mL, 4.44 mmol) was added dropwise to a solution of 1,1,1-trifluoro-3-phenylpropan-2-amine (840 mg, 4.44 mmol) and pyridine (1.44 mL, 17.8 mmol) in chloroform (80 mL) at 0° C. The solution was warmed to room temperature and stirred for 18 h. Ice water (30 mL) was added slowly to the mixture and the solution was stirred for 15 minutes. The phases were separated and the aqueous phase was extracted with chloroform (2×30 mL). The combined organic phases were washed with 3 M hydrochloric acid (2×50 mL) and brine (30 mL), dried (Na$_2$SO$_4$) and concentrated under vacuum. Recrystallisation from iso-hexane gave the title compound (906 mg, 3.59 mmol, 81%) as colourless needles. 1H NMR (400 MHz, DMSO-d6) 7.94 (1H, d), 7.34-7.28 (4H, m), 7.27-7.19 (1H, m), 4.47-4.31 (1H, m), 3.46 (3H, s), 3.04 (1H, dd), 2.77 (1H, dd).

Preparation 40: 3-(trifluoromethyl)-3,4-dihydroisoquinolin-1(2H)-one

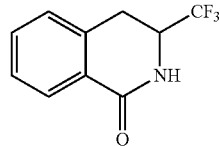 [SMILES: O=C1NC(C(F)(F)F)Cc2ccccc21]

A solution of methyl (1,1,1-trifluoro-3-phenylpropan-2-yl)carbamate (550 mg, 2.23 mmol) in polyphosphoric acid (14.2 g, 145 mmol) was heated to 140° C. for 1 h. The mixture was poured onto ice water (40 mL) and extracted with chloroform (3×25 mL). The combined organic phases were washed with water (20 mL), brine (20 mL), dried (Na$_2$SO$_4$) and concentrated under vacuum. Recrystallisation from iso-hexane gave the title compound (232 mg, 48%) as colourless needles. LC-MS: [M+H]$^+$=216.

Preparation 41: 3-(trifluoromethyl)-1,2,3,4-tetrahydroisoquinoline

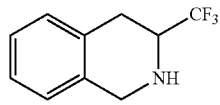

A solution of 3-(trifluoromethyl)-3,4-dihydroisoquinolin-1(2H)-one (200 mg, 0.93 mmol) in THF (15 mL) was added dropwise to a solution of borane THF complex (1 M in THF, 6.5 mL, 6.5 mmol) in THF (15 mL). The reaction was heated to 70° C. for 2 h, then cooled to RT. Methanol (5 mL) was added and the mixture was concentrated under vacuum. The residue was dissolved in methanol (20 mL) and 6 M hydrochloric acid (20 mL) and heated to 65° C. for 2 h, then stirred at room temperature for 18 h. The solution was basified to pH 10 with 10% sodium hydroxide solution. The mixture was extracted with DCM (3×20 mL) and the combined organic phases were washed with brine, dried ($Na_2SO_4$) and concentrated under vacuum. The residue was dissolved in methanol (2 mL) and loaded onto a column of SCX (2 g). The column was washed with methanol and then the product was eluted with 0.7 M ammonia in methanol. The mixture was concentrated under vacuum to give the title compound (125 mg, 67%) as a tan solid. LC-MS: $[M+H]^+$=202.

Preparation 42: 6-bromo-2-[(3-methyloxetan-3-yl)methyl]-2,3-dihydro-1H-isoindol-1-one

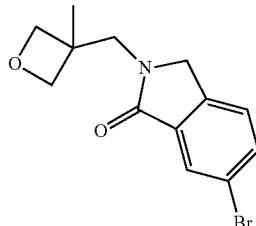

A stirred suspension of 6-bromo-2,3-dihydro-1H-isoindol-1-one (300 mg, 1.42 mmol) in DMF (4 mL) was cooled in an ice-bath and treated with sodium hydride (60% dispersion in mineral oil, 68 mg, 1.70 mmol) and stirred and cooled for 15 min. The mixture was treated with 3-(bromomethyl)-3-methyloxetane (280 mg, 1.70 mmol) and stirred at RT for 18 h. Brine (20 mL) was added and the crude product was extracted with ethyl acetate (2×20 mL). The combined extracts were washed with brine (20 mL), dried ($MgSO_4$) and evaporated. The residue was purified by chromatography ($SiO_2$, 20-100% ethyl acetate in isohexane) to afford the title compound (342 mg, 81%) as a yellow solid. LC-MS: $[M+H]^+$=296/298.

Preparations 43-47

Prepared following an analogous/similar procedure as described for Preparation 42:

| Preparation | Structure | Name | MS: $[M + H]^+$ |
| --- | --- | --- | --- |
| 43 | 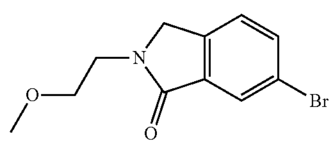 | 6-bromo-2-(2-methoxyethyl)-2,3-dihydro-1H-isoindol-1-one | 270/272 |
| 44 | 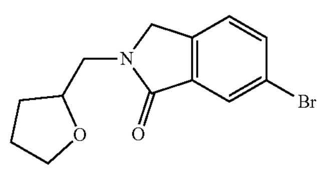 [SMILES: O=C1c2cc(Br)ccc2CN1CC1CCCO1] | 6-bromo-2-[(oxolan-2-yl)methyl]-2,3-dihydro-1H-isoindol-1-one | 296/298 |
| 45 | 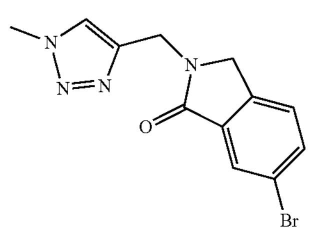 [SMILES: Cn1cc(CN2Cc3ccc(Br)cc3C2=O)nn1] | 6-bromo-2-[(1-methyl-1H-1,2,3-triazol-4-yl)methyl]-2,3-dihydro-1H-isoindol-1-one | 307/309 |

-continued

| Preparation | Structure | Name | MS: [M + H]+ |
|---|---|---|---|
| 46 | ![structure] | 6-bromo-2-[(5-tert-butyl-1,2-oxazol-3-yl)methyl]-2,3-dihydro-1H-isoindol-1-one | 349/351 |
| 47 | ![structure] | tert-butyl 2-[(6-bromo-1-oxo-2,3-dihydro-1H-isoindol-2-yl)methyl]pyrrolidine-1-carboxylate | 295/297 [M-BOC + H]+ |

Preparation 48: 6-bromo-2-[2-(morpholin-4-yl)ethyl]-2,3-dihydro-1H-isoindol-1-one

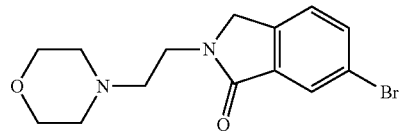 [SMILES: O=C1c2cc(Br)ccc2CN1CCN1CCOCC1]

Sodium hydride (60% dispersion in mineral oil, 34 mg, 1.40 mmol) was added to a suspension of 6-bromo-2,3-dihydro-1H-isoindol-1-one (250 mg, 1.18 mmol) in DMF (5 mL) and the mixture was stirred for 5 min after hydrogen gas evolution ceased. 4-(2-bromoethyl)morpholine (0.18 mL, 1.3 mmol) was added to the resulting brown solution and the mixture was stirred at RT for 18 h. The mixture was diluted with ethyl acetate and transferred into a separating funnel. Water was added and the crude product was extracted with ethyl acetate. The combined organic extracts were washed with brine, dried (MgSO$_4$) and concentrated under vacuum. The residue was triturated with a mixture of diethyl ether and iso-hexane and the resulting precipitate was filtered, washed with iso-hexane and dried under suction to afford the title compound (196 mg, 50%) as a pale yellow solid. LC-MS: [M+H]+=325/327.

Preparation 49: 2-[(3-methyloxetan-3-yl)methyl]-6-(4,4,5,5-tetramethyl-1,3,2-dioxaborolan-2-yl)-2,3-dihydro-1H-isoindol-1-one

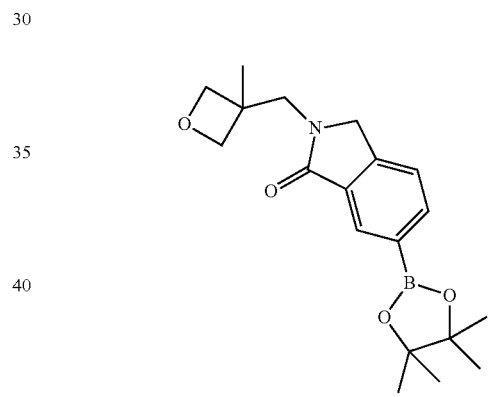

A mixture of 6-bromo-2-[(3-methyloxetan-3-yl)methyl]-2,3-dihydro-1H-isoindol-1-one (338 mg, 1.14 mmol), potassium acetate (336 mg, 3.42 mmol) and bis(pinacolato)diboron (348 mg, 1.37 mmol) in 1,4-dioxane (5 mL) was degassed with nitrogen at 40° C. for 10 min. The mixture was treated with PdCl$_2$(dppf)$_2$ (42 mg, 0.057 mmol), degassed for a further 10 min and stirred at 90° C. for 2 h. The mixture was allowed to cool, diluted with ethyl acetate (20 mL), washed with brine (20 mL), dried (MgSO$_4$) and evaporated. The residue was triturated with a mixture of ether (10 mL) and iso-hexane (10 mL) and the resulting precipitate was collected by filtration, washed with iso-hexane (20 mL) and dried to give the title compound (326 mg, 82%) as a chocolate-brown powder. The product was used without further purification in the next step. LC-MS: [M+H]+=344.

Preparations 50-52

Prepared following an analogous/similar procedure to that described above for Preparation 49:

| Preparation | Structure | Name | MS: [M + H]⁺ |
|---|---|---|---|
| 50 | 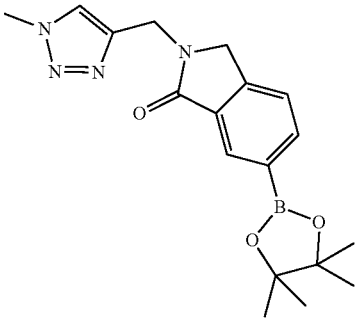 | 2-[(1-methyl-1H-1,2,3-triazol-4-yl)methyl]-6-(4,4,5,5-tetramethyl-1,3,2-dioxaborolan-2-yl)-2,3-dihydro-1H-isoindol-1-one | 355 |
| 51 | 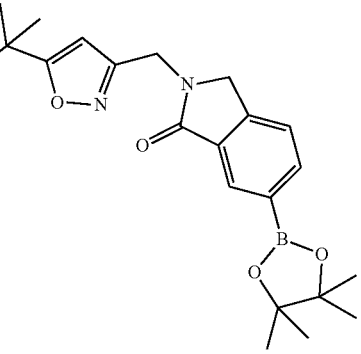 | 2-[(5-tert-butyl-1,2-oxazol-3-yl)methyl]-6-(4,4,5,5-tetramethyl-1,3,2-dioxaborolan-2-yl)-2,3-dihydro-1H-isoindol-1-one | 397 |
| 52 | 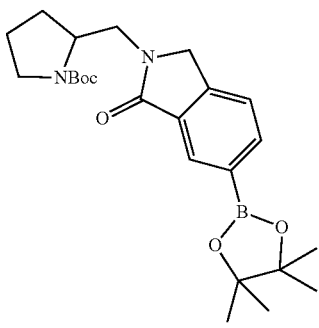 [SMILES: CC(C)(C)OC(=O)N1CCCC1CN1Cc2ccc(B3OC(C)(C)C(C)(C)O3)cc2C1=O] | tert-butyl 2-{[1-oxo-6-(4,4,5,5-tetramethyl-1,3,2-dioxaborolan-2-yl)-2,3-dihydro-1H-isoindol-2-yl]methyl}pyrrolidine-1-carboxylate | 343 [M-Boc + H]⁺ |

Preparation 53: 6-(2,5-dichloropyrimidin-4-yl)-2-[(3-methyloxetan-3-yl)methyl]-2,3-dihydro-1H-isoindol-1-one

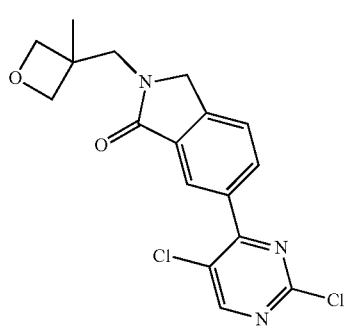 [SMILES: CC1(CN2Cc3ccc(-c4nc(Cl)ncc4Cl)cc3C2=O)COC1]

A mixture of 2-[(3-methyloxetan-3-yl)methyl]-6-(4,4,5,5-tetramethyl-1,3,2-dioxaborolan-2-yl)-2,3-dihydro-1H-isoindol-1-one (326 mg, 0.95 mmol), 2,4,5-trichloropyrimidine (261 mg, 1.43 mmol), 2 M aqueous potassium carbonate solution (0.95 mL, 1.9 mmol) and 1,4-dioxane (10 mL) was stirred and degassed with nitrogen at 40° C. for 10 min, treated with Pd(PPh₃)₄ (55 mg, 0.048 mmol) and degassed for a further 10 min. The mixture was stirred at 90° C. for 5 h, allowed to cool and diluted with water (20 mL). The mixture was extracted with ethyl acetate (3×20 mL) and the combined organic phases were washed with brine (20 mL), dried (Na₂SO₄) and concentrated under vacuum. Purification by chromatography (SiO₂, 10-100% ethyl acetate in iso-hexane) gave the title compound (252 mg, 73%) as an orange solid. LC-MS: [M+H]⁺=364.

Preparations 54-55

Prepared following an analogous/similar procedure to that described for Preparation 53:

| Preparation | Structure | Name | MS: [M + H]⁺ |
|---|---|---|---|
| 54 | 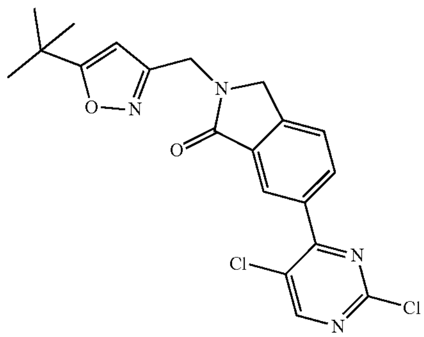 [SMILES: CC(C)(C)c1cc(CN2Cc3ccc(-c4nc(Cl)ncc4Cl)cc3C2=O)no1] | 2-[(5-tert-butyl-1,2-oxazol-3-yl)methyl]-6-(2,5-dichloropyrimidin-4-yl)-2,3-dihydro-1H-isoindol-1-one | 417 |
| 55 | 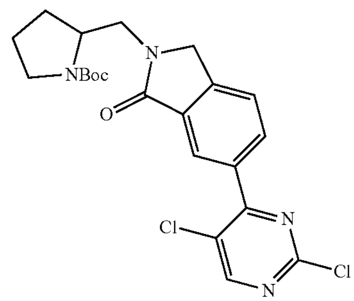 [SMILES: CC(C)(C)OC(=O)N1CCCC1CN1Cc2ccc(-c3nc(Cl)ncc3Cl)cc2C1=O] | tert-butyl 2-{[6-(2,5-dichloropyrimidin-4-yl)-1-oxo-2,3-dihydro-1H-isoindol-2-yl]methyl}pyrrolidine-1-carboxylate | 363 [M-Boc + H]⁺ |

Preparation 56: 6-(2,5-dichloropyrimidin-4-yl)-2-[(1-methyl-1H-1,2,3-triazol-4-yl)methyl]-2,3-dihydro-1H-isoindol-1-one

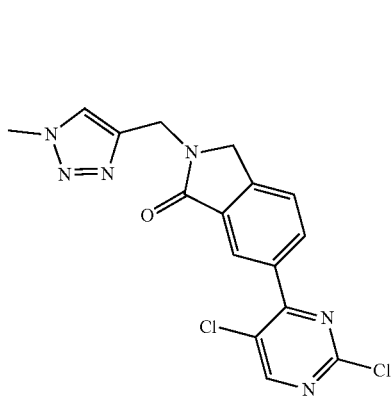 [SMILES: Cn1cc(CN2Cc3ccc(-c4nc(Cl)ncc4Cl)cc3C2=O)nn1]

A mixture of 2,4,5-trichloropyrimidine (179 mg, 0.98 mmol), 2-[(1-methyl-1H-1,2,3-triazol-4-yl)methyl]-6-(4,4,5,5-tetramethyl-1,3,2-dioxaborolan-2-yl)-2,3-dihydro-1H-isoindol-1-one (231 mg, 0.65 mmol) and S-Phos Pd G3 (3 mg, 0.004 mmol) in 1,4-dioxane (8 mL) was treated with 1 M aqueous sodium carbonate (2 mL, 2 mmol) degassed with nitrogen for 10 min and stirred at 50° C. for 1.5 h. The mixture was allowed to cool and partitioned between ethyl acetate (20 mL) and brine (20 mL). The phases were separated and the aqueous phase was extracted with ethyl acetate (15 mL). The combined organic phases were dried (Na₂SO₄) and concentrated. Purification by chromatography (SiO₂, 0-5% methanol in DCM) gave the title compound (223 mg, 82%) as a yellow solid. LC-MS: [M+H]⁺=375.

Preparation 57: 6-(2,5-dichloropyrimidin-4-yl)-2-[2-(morpholin-4-yl)ethyl]-2,3-dihydro-1H-isoindol-1-one

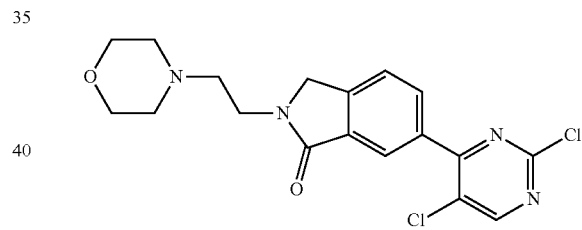

Bis(pinacolato)diboron (178 mg, 0.70 mmol), followed by PdCl₂(dppf)₂ (24 mg, 0.029 mmol) was added to a degassed (nitrogen bubbling) mixture of 6-bromo-2-[2-(morpholin-4-yl)ethyl]-2,3-dihydro-1H-isoindol-1-one (190 mg, 0.58 mmol) and potassium acetate (172 mg, 1.75 mmol) in 1,4-dioxane (4 mL) and the mixture was stirred at 100° C. for 1.5 h. The mixture was allowed to cool to RT and was diluted with ethyl acetate and water. The phases were separated and the aqueous phase was extracted with ethyl acetate. The combined organic phases were washed with brine, dried (MgSO₄) and concentrated under vacuum to afford crude 2-[2-(morpholin-4-yl)ethyl]-6-(4,4,5,5-tetramethyl-1,3,2-dioxaborolan-2-yl)-2,3-dihydro-1H-isoindol-1-one. The product was used without further purification and characterization in the next step. A solution of this material (210 mg, 0.56 mmol) in 1,4-dioxane (2 mL) followed by Pd(PPh₃)₄ (33 mg, 0.028 mmol) were added to a degassed mixture (nitrogen bubbling) of 2,4,5-trichloropyrimidine (155 mg, 0.85 mmol) and potassium carbonate (156 mg, 1.13 mmol) in 1,4-dioxane/H₂O (3:1.8 mL) and the mixture was stirred at 100° C. under nitrogen for 1.5 h. The mixture was allowed to cool to room temperature and was diluted with ethyl acetate, then transferred into a separating funnel.

Water was added and the crude product was extracted with ethyl acetate. The combined organic extracts were washed with brine, dried (MgSO$_4$) and absorbed on silica. The crude product was purified by chromatography (SiO$_2$, 0-10% MeOH in DCM then 10% [1% NH$_3$ in MeOH] in DCM) to afford the title compound (113 mg, 49%) as an orange oil. LC-MS: [M+H]$^+$=393.

Preparations 58-59

Prepared following an analogous/similar procedure to that described for Preparation 57:

| Preparation | Structure | Name | MS: [M + H]$^+$ |
|---|---|---|---|
| 58 | 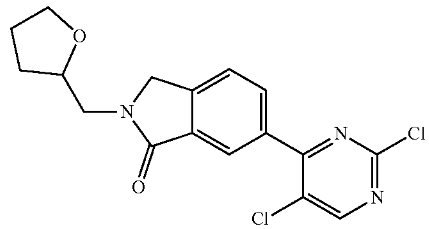 [SMILES: O=C1c2cc(-c3nc(Cl)ncc3Cl)ccc2CN1CC1CCCO1] | 6-(2,5-dichloropyrimidin-4-yl)-2-[(oxolan-2-yl)methyl]-2,3-dihydro-1H-isoindol-1-one | 364 |
| 59 | 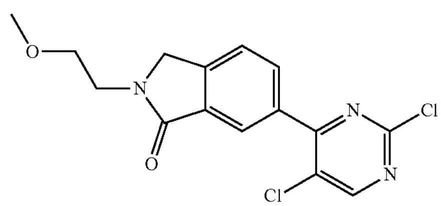 [SMILES: COCCN1Cc2ccc(-c3nc(Cl)ncc3Cl)cc2C1=O] | 6-(2,5-dichloropyrimidin-4-yl)-2-(2-methoxyethyl)-2,3-dihydro-1H-isoindol-1-one | 338 |

Preparations 60-61

Prepared from the corresponding amines (Preparations 37 and 38 respectively) following an analogous/similar procedure to that described for Example 2:

| Preparation | Structure | Name | MS: [M + H]$^+$ |
|---|---|---|---|
| 60 | 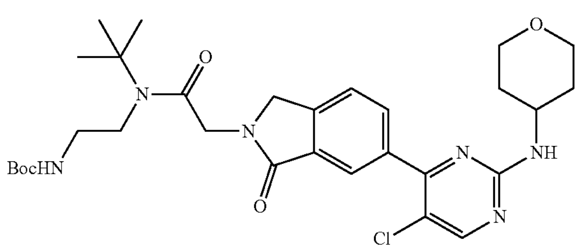 [SMILES: CC(C)(C)OC(=O)NCCN(C(=O)CN1Cc2ccc(-c3nc(NC4CCOCC4)ncc3Cl)cc2C1=O)C(C)(C)C] | tert-butyl N-{2[N-tert-butyl-2-(6-{5-chloro-2-[oxan-4-yl)amino]pyrimidin-4-yl}-1-oxo-2,3-dihydro-1H-isoindol-2-yl)acetamido]ethyl}carbamate | 501 [M-Boc + H]$^{+0}$ |
| 61 | 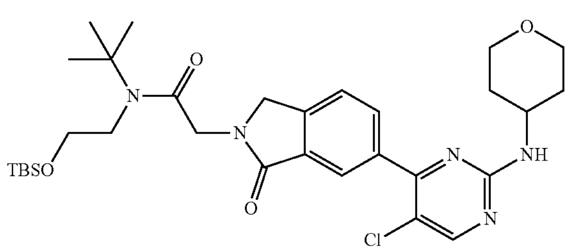 [SMILES: CC(C)(C)N(CCO[Si](C)(C)C(C)(C)C)C(=O)CN1Cc2ccc(-c3nc(NC4CCOCC4)ncc3Cl)cc2C1=O] | N-tert-butyl-N-{2-[(tert-butyldimethylsilyl)oxy]ethyl{-2-(6-{5-chloro-2-[(oxan-4-yl)amino]pyrimidin-4-yl}-1-oxo-2,3-dihydro-1H-isoindol-2-yl)acetamide | 616 |

Preparation 62: N-[(2,4-dimethoxyphenyl)methyl]oxan-4-amine

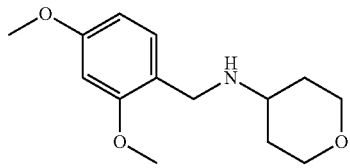 [SMILES: COc1ccc(CNC2CCOCC2)c(OC)c1]

A solution of oxan-4-amine (1.67 g, 16.6 mmol) and 2,4-dimethoxybenzaldehyde (2.50 g, 15.0 mmol) in dichloromethane (25 mL) was stirred for 1 h, treated with sodium triacetoxyborohydride (3.19 g, 15.0 mmol) and stirred at RT for 18 h. The mixture was diluted with dichloromethane (30 mL), washed with saturated aqueous sodium bicarbonate solution (50 mL), followed by brine (50 mL), dried ($Na_2SO_4$) and concentrated under vacuum. Purification by chromatography ($SiO_2$, 0-5% 7M methanolic ammonia solution in dichloromethane) to afford N-(2,4-dimethoxybenzyl)oxan-4-amine (2.68 g, 67%) as a pale yellow oil. LC-MS: $[M+H]^+=252$.

Preparation 63: 6-(4,4,5,5-tetramethyl-1,3,2-dioxaborolan-2-yl)-2,3-dihydro-1H-isoindol-1-one

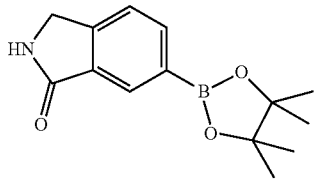 [SMILES: CC1(C)OB(c2ccc3c(c2)C(=O)NC3)OC1(C)C]

A stirred mixture of 6-bromo-2,3-dihydro-1H-isoindol-1-one (780 mg, 3.68 mmol), bis(pinacolato)diboron (1.089 g, 4.28 mmol) and potassium acetate (1.26 g, 12.87 mmol) in anhydrous 1,4-dioxane (12 mL) was degassed with nitrogen for 5 minutes. 1,1'-bis(diphenylphosphino)ferrocene-palladium(II)dichloride dichloromethane complex (150 mg, 0.18 mmol) was then added and the reaction heated under nitrogen at 100° C. for 16 hours. After cooling to room temperature the mixture was diluted with water and extracted with EtOAc (×3). The combined organic layers were washed with brine, dried over $MgSO_4$, filtered and concentrated under vacuum to yield the title compound (1.1 g, 115%) which was used crude without purification. MS: $[M+H]^+=260$.

Preparation 64: 6-(2,5-dichloropyrimidin-4-yl)-2,3-dihydro-1H-isoindol-1-one

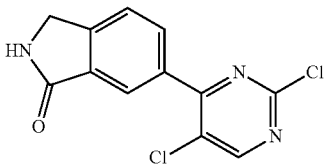 [SMILES: O=C1NCc2ccc(-c3nc(Cl)ncc3Cl)cc21]

A mixture of 2,4,5-trichloropyrimidine (5.25 g, 28.6 mmol), 6-(4,4,5,5-tetramethyl-1,3,2-dioxaborolan-2-yl)-2,3-dihydro-1H-isoindol-1-one (5.25 g, 20.3 mmol) and S-Phos Pd G3 (79 mg, 0.10 mmol) in 1,4-dioxane (250 mL) was treated with 1 M aqueous sodium carbonate (60.8 mL, 60.8 mmol), degassed with nitrogen for 10 min and stirred at 50° C. for 1 h. The mixture was allowed to cool to RT and stirred for 18 h. The mixture was partitioned between ethyl acetate (250 mL) and water (250 mL) and the resulting suspension was filtered. The solid was suspended in ethyl acetate and the mixture was stirred for 3 days. The precipitate was filtered, washed with ethyl acetate and dried to the title compound (7.11 g, 125%) as a brown solid. LC-MS: $[M+H]^+=280$.

Notes: No further product was obtained from the biphasic filtrate. The yield obtained was over 100%, which could be due to the presence of inorganic salts and/or water as 1H NMR analysis of the product did show contamination with organic species.

Preparation 65: 6-(5-chloro-2-{[(2,4-dimethoxyphenyl)methyl](oxan-4-yl)amino}pyrimidin-4-yl)-2,3-dihydro-1H-isoindol-1-one

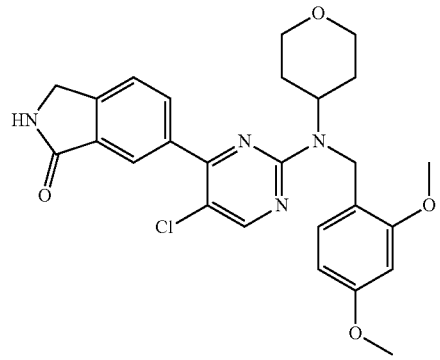 [SMILES: COc1ccc(CN(c2ncc(Cl)c(-c3ccc4c(c3)C(=O)NC4)n2)C2CCOCC2)c(OC)c1]

A stirred suspension of 6-(2,5-dichloropyrimidin-4-yl)-2,3-dihydro-1H-isoindol-1-one (1.00 g, 3.57 mmol), N-[(2,4-dimethoxyphenyl)methyl]oxan-4-amine (0.987 g, 3.93 mmol) and diisopropylethylamine (1.25 mL, 7.16 mmol) in sulfolane (10 mL) was heated to 100° C. for 18 h. The mixture was allowed to cool and was partitioned between water (75 mL) and ethyl acetate (75 mL). The phases were separated and the aqueous phase was extracted with ethyl acetate (2×50 mL). Brine (50 mL) was added to the combined organic phases and the mixture was filtered. The phases from the filtrate were separated and the organic extracts were washed with water (6×50 mL), dried ($Na_2SO_4$) and concentrated. Purification by chromatography ($SiO_2$, 20-100% of ethyl aceate in iso-hexane) gave the title compound (504 mg, 28%) as a yellow foam. LC-MS: $[M+H]^+=495$.

Preparation 66: 6-(5-chloro-2-{[(2,4-dimethoxyphenyl)methyl](oxan-4-yl)amino}pyrimidin-4-yl)-2-[(5-methyl-1,2,4-oxadiazol-3-yl)methyl]-2,3-dihydro-1H-isoindol-1-one

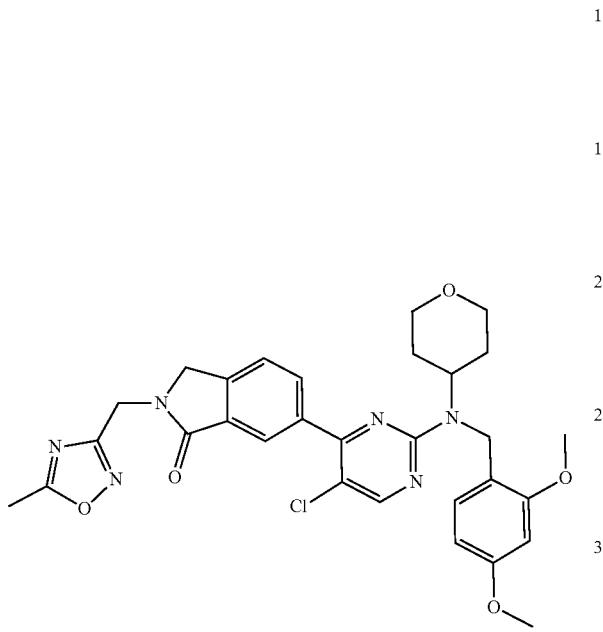

A solution of 6-(5-chloro-2-{[(2,4-dimethoxyphenyl)methyl](oxan-4-yl)amino}pyrimidin-4-yl)-2,3-dihydro-1H-isoindol-1-one (50 mg, 0.10 mmol) in THF (0.5 mL) was cooled to −78° C. and treated with a lithium bis(trimethylsilyl)amide (1 M in THF, 0.15 mL, 0.15 mmol). The solution was stirred for 30 min, then treated with 3-(chloromethyl)-5-methyl-1,2,4-oxadiazole (20 mg, 0.15 mmol), and the mixture allowed to warm to RT and stirred for 18 h. A further portion of lithium bis(trimethylsilyl)amide (1 M in THF, 0.15 mL, 0.15 mmol) was added and the reaction was stirred for 10 min, before 3-(chloromethyl)-5-methyl-1,2,4-oxadiazole (10 mg, 0.075 mmol) was added and the mixture stirred for 4 h. The mixture was treated with tetrabutylammonium iodide (3 mg, 0.008 mmol) and stirred for 3 days. Brine (5 mL) was added and the mixture was extracted with ethyl acetate (3×5 mL). The combined organic phases were washed with brine (5 mL), dried (Na$_2$SO$_4$) and concentrated. Purification by chromatography (SiO$_2$, 10-100% ethyl acetate in iso-hexane) gave the title compound (11 mg, 0.015 mmol, 15%) as a yellow glass. LC-MS: [M+H]$^+$=591.

Preparation 67: 6-(5-chloro-2-{[(2,4-dimethoxyphenyl)methyl](oxan-4-yl)amino}pyrimidin-4-yl)-2-[(3-methyl-1,2-oxazol-5-yl)methyl]-2,3-dihydro-1H-isoindol-1-one

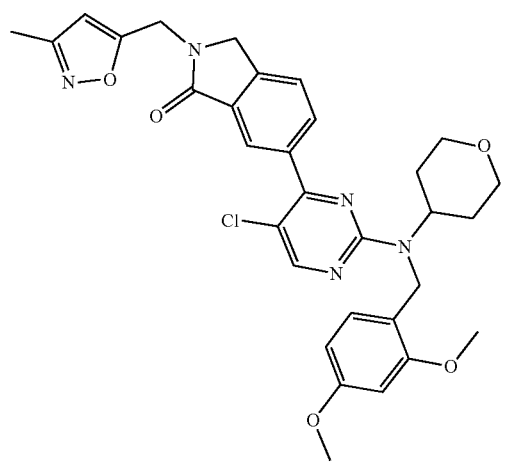 [SMILES: COc1ccc(CN(c2ncc(Cl)c(-c3ccc4c(c3)C(=O)N(Cc3cc(C)no3)C4)n2)C2CCOCC2)c(OC)c1]

A stirred suspension of 6-(5-chloro-2-{[(2,4-dimethoxyphenyl)methyl](oxan-4-yl)amino}pyrimidin-4-yl)-2,3-dihydro-1H-isoindol-1-one (100 mg, 0.20 mmol) in THF (2 mL) was cooled to −78° C. and treated with a lithium bis(trimethylsilyl)amide (1 Min THF, 0.3 mL, 0.3 mmol). The resulting suspension was stirred for 15 min before 5-(bromomethyl)-3-methyl isoxazole (53 mg, 0.30 mmol) was added. The resulting suspension was allowed to reach RT and the resulting orange solution was stirred for 18 h. The mixture was treated at room temperature with more 5-(bromomethyl)-3-methyl isoxazole (53 mg, 0.30 mmol) and stirred for 5 h. Lithium bis(trimethylsilyl)amide (Min THF, 0.15 mL, 0.15 mmol) was added and the mixture was stirred for 15 min before 5-(bromomethyl)-3-methyl isoxazole (53 mg, 0.30 mmol) was added and the mixture stirred for 3 days. Brine (5 mL) was added and the mixture was extracted with ethyl acetate (3×5 mL). The combined organic phases were washed with brine (5 mL), dried (Na$_2$SO$_4$) and concentrated. Purification by chromatography (SiO$_2$, 10-100% ethyl acetate in iso-hexane) gave the title compound (79 mg, 67%) as a yellow foam. LC-MS: [M+H]$^+$= 590.

Preparations 68-69

Prepared following a similar/analogous procedure to that described in Preparation 67:

| Preparation | Structure | Name | MS: [M + H]⁺ |
|---|---|---|---|
| 68 | 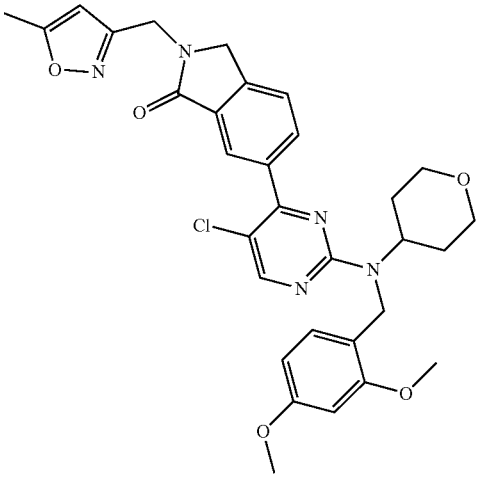 [SMILES: COc1ccc(CN(c2ncc(Cl)c(-c3ccc4c(c3)C(=O)N(Cc3cc(C)on3)C4)n2)C2CCOCC2)c(OC)c1] | 6-(5-chloro-2-{[(2,4-dimethoxyphenyl)methyl](oxan-4-yl)amino}pyrimidin-4-yl)-2-[(5-methyl-1,2-oxazol-3-yl)methyl]-2,3-dihydro-1H-isoindol-1-one | 590 |
| 69 | 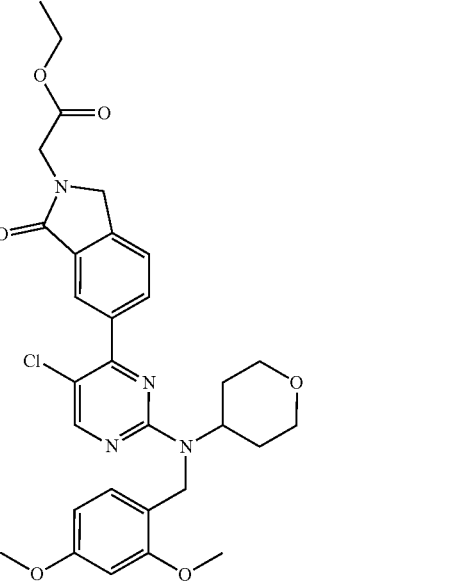 | ethyl 2-[6-(5-chloro-2-{[(2,4-dimethoxyphenyl)methyl](oxan-4-yl)amino}pyrimidin-4-yl)-1-oxo-2,3-dihydro-1H-isoindol-2-yl]acetate | 581 |

Preparation 70: 6-(5-chloro-2-{[(2,4-dimethoxyphenyl)methyl](oxan-4-yl)amino}pyrimidin-4-yl)-2-(2-hydroxyethyl)-2,3-dihydro-1H-isoindol-1-one

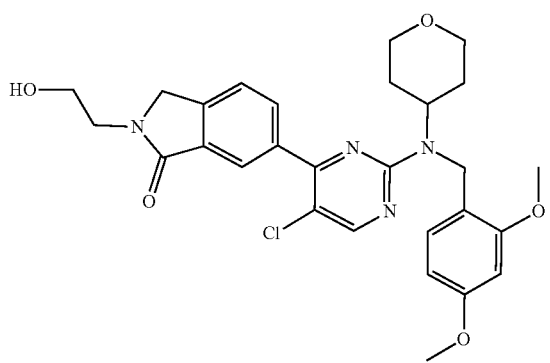 [SMILES: COc1ccc(CN(c2ncc(Cl)c(-c3ccc4c(c3)C(=O)N(CCO)C4)n2)C2CCOCC2)c(OC)c1]

Ethyl 2-[6-(5-chloro-2-{[(2,4-dimethoxyphenyl)methyl](oxan-4-yl)amino}pyrimidin-4-yl)-1-oxo-2,3-dihydro-1H-isoindol-2-yl]acetate (0.285 g, 0.49 mmol) was dissolved in anhydrous MeOH (2.5 mL) and the mixture was cooled to 0° C. Lithium borohydride (2 M in THF, 1.3 mL, 2.6 mmol) was added. The reaction was stirred for 10 min then warmed to RT. The reaction mixture was diluted with methanol (2 mL) and stirred for 2 h. A saturated solution of ammonium chloride (30 mL) was added and the mixture was extracted with ethyl acetate (3×30 mL). The combined organic phases were washed with brine (3×20 mL), dried (MgSO₄) and concentrated to give the title compound (0.228 g, 88%) as an off-white solid. The product was used without further purification in the next step. LC-MS: [M+H]⁺=539.

Preparation 71:2-[6-(5-chloro-2-{[(2,4-dimethoxyphenyl)methyl](oxan-4-yl)amino}pyrimidin-4-yl)-1-oxo-2,3-dihydro-1H-isoindol-2-yl]ethyl methanesulfonate

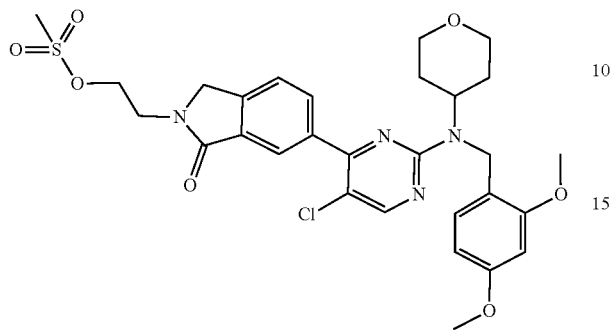

Triethylamine (0.11 mL, 0.79 mmol) followed by methanesulfonyl chloride (0.045 mL, 0.58 mmol) were added to a solution of 6-(5-chloro-2-{[(2,4-dimethoxyphenyl)methyl](oxan-4-yl)amino}pyrimidin-4-yl)-2-(2-hydroxyethyl)-2,3-dihydro-1H-isoindol-1-one (0.228 g, 0.39 mmol) in DCM (4.0 mL) and the mixture was stirred at room temperature for 1.5 h. The reaction mixture was partitioned between DCM (30 mL) and a saturated solution of ammonium chloride (30 mL). The phases were separated and the organic phase was washed with a saturated solution of ammonium chloride (20 mL), water (2×20 mL) and brine (2×20 mL). The organic phase was filtered through a phase separating cartridge and then concentrated to give the title compound (0.220 g, 88%) as a colourless foam. The product was used without further purification in the next step. LC-MS: [M+H]$^+$=617.

Preparation 72:6-(5-chloro-2-{[(2,4-dimethoxyphenyl)methyl](oxan-4-yl)amino}pyrimidin-4-yl)-2-[2-(1,2,3,4-tetrahydroisoquinolin-2-yl)ethyl]-2,3-dihydro-1H-isoindol-1-one

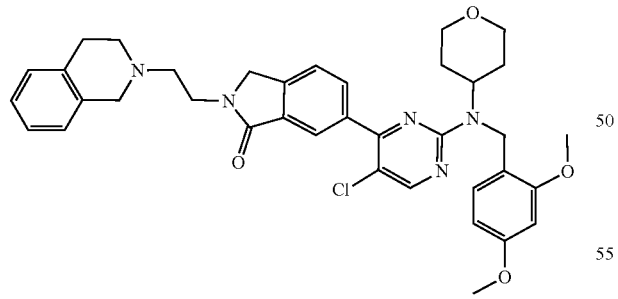

Triethylamine (0.017 mL, 0.12 mmol) and 1,2,3,4-tetrahydroisoquinoline (0.013 mL, 0.10 mmol) were added to a solution of 2-[6-(5-chloro-2-{[(2,4-dimethoxyphenyl)methyl](oxan-4-yl)amino}pyrimidin-4-yl)-1-oxo-2,3-dihydro-1H-isoindol-2-yl]ethyl methanesulfonate (51 mg, 0.080 mmol) in acetonitrile (1.0 mL) in a microwave vial. The reaction mixture was heated in the microwave (CEM, 100° C., max Power=200 W, max pressure=200 psi) for 30 min. The reaction mixture was concentrated under vacuum. Purification by chromatography (SiO$_2$, 0-5% methanol in DCM) gave the title compound (54 mg, 103%) as a yellow gum. LC-MS: [M+H]$^+$=654.

Preparation 73: 6-bromo-2-[2-(tert-butoxy)ethyl]-2,3-dihydro-1H-isoindol-1-one

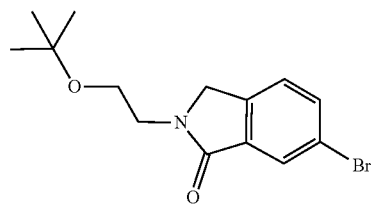 [SMILES: CC(C)(C)OCCN1Cc2ccc(Br)cc2C1=O]

A mixture of methyl 5-bromo-2-(bromomethyl)benzoate (300 mg, 0.97 mmol), 2-(tert-butoxy)ethanamine (171 mg, 1.46 mmol) and DIPEA (0.51 mL, 2.2 mmol) in MeCN (5 mL) was stirred at 75° C. for 3 days. The mixture was allowed to cool to RT and was diluted with ethyl acetate, then transferred into a separating funnel. 1N HCl was added and the crude product was extracted with ethyl acetate. The combined organic extracts were washed with NaHCO$_3$, brine, dried (MgSO$_4$) and concentrated under vacuum to give the title compound (297 mg, 98%) as a thick tan oil. The product was used without further purification in the next step. LC-MS: [M+H]$^+$=312/314.

Preparation 74: methyl (2S)-2-(6-bromo-1-oxo-2,3-dihydro-1H-isoindol-2-yl)-3-hydroxypropanoate

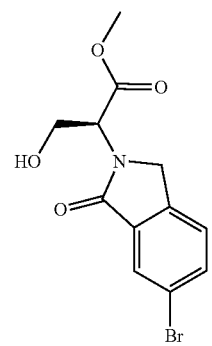 [SMILES: COC(=O)[C@H](CO)N1Cc2ccc(Br)cc2C1=O]

Prepared following an analogous/similar procedure to that described in Preparation 73. LC-MS: [M+H]$^+$=314/316.

Preparation 75: 6-bromo-2-[2-(cyclopentyloxy)ethyl]-2,3-dihydro-1H-isoindol-1-one

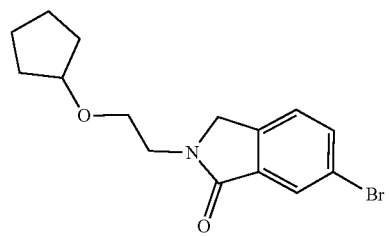 [SMILES: O=C1c2cc(Br)ccc2CN1CCOC1CCCC1]

Prepared following an analogous/similar procedure to that described in Preparation 73. In this case, purification by chromatography (SiO$_2$, 0-100% ethyl acetate in iso-hexane) gave the title compound. LC-MS: [M+H]$^+$=m/z 324/326.

Preparation 76: tert-butyl(2R)-2-(6-bromo-1-oxo-2,3-dihydro-1H-isoindol-2-yl)propanoate

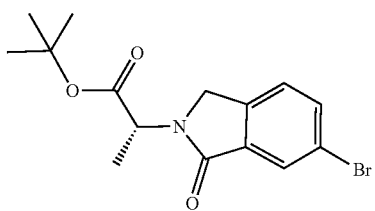 [SMILES: C[C@H](C(=O)OC(C)(C)C)N1Cc2ccc(Br)cc2C1=O]

Prepared following an analogous/similar procedure to that described in Preparation 73. The reaction was carried out in THF at 75° C. in this case. LC-MS: [M+Na]$^+$=362/364.

Preparation 77: tert-butyl 2-(6-bromo-1-oxo-2,3-dihydro-1H-isoindol-2-yl)-2-methylpropanoate

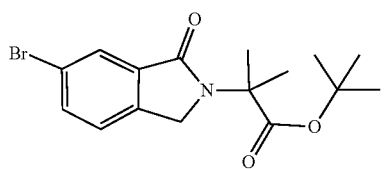 [SMILES: CC(C)(C)OC(=O)C(C)(C)N1Cc2ccc(Br)cc2C1=O]

Prepared following an analogous/similar procedure to that described in Preparation 73. In this case, the reaction was carried out in THF at 75° C. and the product was purified by chromatography (SiO$_2$, 10-50% of ethyl acetate in iso-hexane). LC-MS: [M-$^t$Bu+H]$^+$=298/300.

Preparation 78: 6-bromo-2-(2-hydroxypropyl)-2,3-dihydro-1H-isoindol-1-one

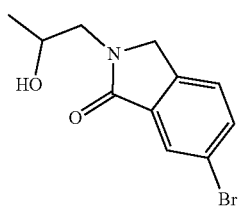

Triethylamine (0.68 mL, 4.90 mmol) and 1-aminopropan-2-ol (0.30 mL, 3.57 mmol) were added to a solution of methyl 5-bromo-2-(bromomethyl)benzoate (1.00 g, 3.25 mmol) in THF (33 mL). The reaction was heated to 70° C. and stirred for 18 h. After cooling to RT, the reaction mixture was concentrated under vacuum and absorbed onto silica. Purification by chromatography (SiO$_2$, 0-2.5% MeOH in ethyl acetate) gave the title compound (704 mg, 79%) as an off-white solid. LC-MS: [M+H]$^+$=270/272.

Preparation 79: 6-bromo-2-[2-(2-oxopyrrolidin-1-yl)ethyl]-2,3-dihydro-1H-isoindol-1-one

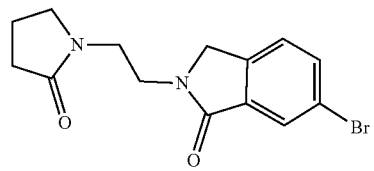 [SMILES: O=C1CCCN1CCN1Cc2ccc(Br)cc2C1=O]

Triethylamine (0.30 mL, 2.2 mmol) followed by 1-(2-aminoethyl)pyrrolidin-2-one oxalate (212 mg, 0.97 mmol) were added to a solution of methyl 5-bromo-2-(bromomethyl)benzoate (272 mg, 0.88 mmol) in MeOH (10 mL). The mixture was stirred at 50° C. for 18 h. The reaction mixture was cooled to RT and concentrated under vacuum. The residue was dissolved in ethyl acetate (10 mL), washed with water (10 mL), dried (MgSO$_4$) and concentrated under vacuum to afford a colourless powder. Trituration with diethyl ether gave the title compound (100 mg, 33%) as a colourless solid. 1H NMR (400 MHz, CDCl$_3$): 7.92 (1H, d), 7.63 (1H, dd), 7.32 (1H, d), 4.45 (2H, s), 3.80 (2H, t), 3.60 (2H, t), 3.52 (2H, t), 2.23 (2H, t), 1.98 (2H, m).

Preparation 80: 6-bromo-2-[2-(oxolan-2-yl)ethyl]-2,3-dihydro-1H-isoindol-1-one

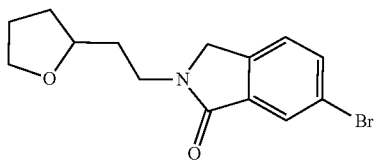 [SMILES: O=C1c2cc(Br)ccc2CN1CCC1CCCO1]

Triethylamine (0.28 mL, 2.0 mmol) followed by 2-(oxolan-2-yl)ethan-1-amine (171 mg, 1.48 mmol) were added to a solution of methyl 5-bromo-2-(bromomethyl)benzoate (500 mg, 1.35 mmol) in THF (15 mL). The mixture was heated to 70° C. for 18 h. The mixture was concentrated under vacuum and the residue was triturated with diethyl ether (20 mL). The resulting precipitate was filtered to afford a pale tan powder. The powder was dissolved in DCM (4 mL), washed with water (10 mL) and the organic phase was separated with a hydrophobic phase separator and concentrated under vacuum to give the title compound (253 mg, 60%) as a pale tan solid. LC-MS: [M+H]$^+$=310/312.

Preparation 81: methyl(2S)-2-(6-bromo-1-oxo-2,3-dihydro-1H-isoindol-2-yl)-3-[(tert-butyldimethylsilyl)oxy]propanoate

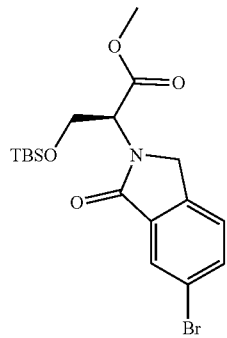 [SMILES: COC(=O)[C@H](CO[Si](C)(C)C(C)(C)C)N1Cc2ccc(Br)cc2C1=O]

TBDMS-Cl (297 mg, 1.97 mmol) was added to a solution of methyl (2S)-2-(6-bromo-1-oxo-2,3-dihydro-1H-isoindol-2-yl)-3-hydroxypropanoate (412 mg, 1.31 mmol) and imidazole (268 mg, 3.93 mmol) in DMF (3 mL) and the mixture was stirred for 18 h. The mixture was diluted with ethyl acetate and transferred into a separating funnel. Water was added and the crude product was extracted with ethyl acetate. The combined organic extracts were washed with brine, dried (MgSO$_4$) and absorbed on silica. Purification by chromatography (SiO$_2$, 0-20% ethyl acetate in iso-hexane) gave the title compound (432 mg, 77%) as a colourless oil. LC-MS: [M+H]$^+$=428/430.

Preparation 82: 2-(2-hydroxypropyl)-6-(4,4,5,5-tetramethyl-1,3,2-dioxaborolan-2-yl)-2,3-dihydro-1H-isoindol-1-one

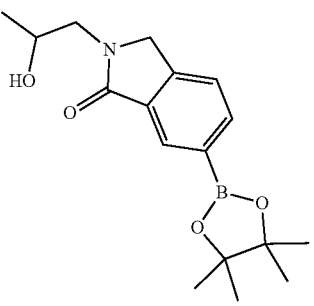 [SMILES: CC(O)CN1Cc2ccc(B3OC(C)(C)C(C)(C)O3)cc2C1=O]

A stirred mixture of 6-bromo-2-(2-hydroxypropyl)-2,3-dihydro-1H-isoindol-1-one (200 mg, 0.740 mmol), potassium acetate (218 mg, 2.22 mmol) and bis(pinacolato)diboron (226 mg, 0.888 mmol) in dioxane (5 mL) was degassed at 40° C. with bubbling nitrogen for 10 min. The mixture was treated with PdCl$_2$(dppf)$_2$ (27 mg, 0.037 mmol), degassed for a further 10 min and stirred at 90° C. for 2 h. The mixture was allowed to cool and was diluted with ethyl acetate (20 mL), washed with brine (20 mL), dried (MgSO$_4$) and concentrated. The residue was triturated with a mixture of ether (10 mL) and isohexane (10 mL) to give a solid. The solid was collected by filtration and washed with isohexane (20 mL) to give the title compound (192 mg, 80%) as a chocolate-brown powder. LC-MS: [M+H]$^+$=318.

Preparation 83: 2-[2-(oxolan-2-yl)ethyl]-6-(4,4,5,5-tetramethyl-1,3,2-dioxaborolan-2-yl)-2,3-dihydro-1H-isoindol-1-one

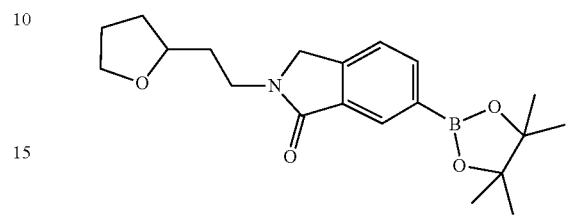

PdCl$_2$(dppf)$_2$ (18 mg, 0.024 mmol) was added to a degassed (nitrogen bubbling) solution of 6-bromo-2-[2-(oxolan-2-yl)ethyl]-2,3-dihydro-1H-isoindol-1-one (250 mg, 0.806 mmol), bis(pinacolato)diboron (246 mg, 0.967 mmol) and potassium acetate (160 mg, 1.61 mmol) in 1,4-dioxane (3 mL). The mixture was degassed for a further 10 min then heated to 90° C. for 3 h. The reaction was cooled to RT and partitioned between ethyl acetate (10 mL) and water (10 mL). The aqueous phase was extracted with ethyl acetate (10 mL). The combined organic phases were washed with brine (10 mL), dried (MgSO$_4$) and concentrated under vacuum. Purification by chromatography (SiO$_2$, 0-100% ethyl acetate in iso-hexane) gave the title compound (173 mg, 51%). LC-MS: [M+H]$^+$=358.

Preparation 84: 2-[2-(tert-butoxy)ethyl]-6-(4,4,5,5-tetramethyl-1,3,2-dioxaborolan-2-yl)-2,3-dihydro-1H-isoindol-1-one

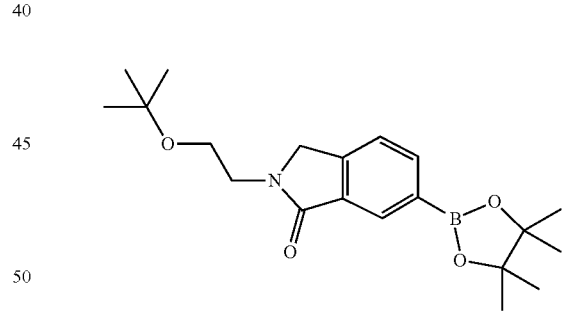

XPhos Pd G3 (16 mg, 0.019 mmol) was added to a degassed (nitrogen bubbling) mixture of 6-bromo-2-[2-(tert-butoxy)ethyl]-2,3-dihydro-1H-isoindol-1-one (304 mg, 0.974 mmol), bis(pinacolato) diboron (297 mg, 1.17 mmol) and potassium acetate (287 mg, 2.92 mmol) in 1,4-dioxane (5 mL) and the mixture was stirred at 90° C. for 1.5 h. The mixture was cooled to RT and diluted with NaHCO$_3$, water and ethyl acetate, then transferred into a separating funnel. The crude product was extracted with ethyl acetate and the combined organic extracts were washed with brine, dried (MgSO$_4$), and concentrated under vacuum. The crude product was used without further purification and characterization in the next step. Quantitative yield was assumed.

Preparation 85: methyl (2S)-3-[(tert-butyldimethyl-silyl)oxy]-2-[1-oxo-6-(4,4,5,5-tetramethyl-1,3,2-di-oxaborolan-2-yl)-2,3-dihydro-1H-isoindol-2-yl]propanoate

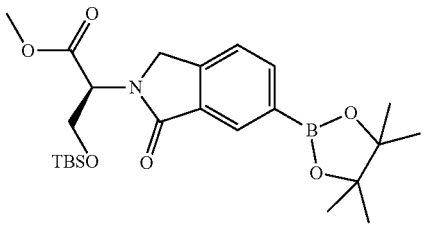

Prepared following the procedure described in Preparation 84.

Preparation 86: tert-butyl 2-methyl-2-[1-oxo-6-(4,4,5,5-tetramethyl-1,3,2-dioxaborolan-2-yl)-2,3-dihydro-1H-isoindol-2-yl]propanoate

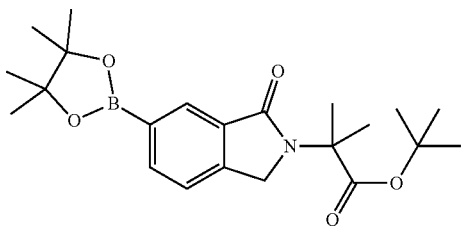 [SMILES: CC(C)(C)OC(=O)C(C)(C)N1Cc2ccc(B3OC(C)(C)C(C)(C)O3)cc2C1=O]

X-Phos Pd G3 (13 mg, 0.015 mmol) was added to a degassed (nitrogen bubbling) solution of tert-butyl 2-(6-bromo-1-oxo-2,3-dihydro-1H-isoindol-2-yl)-2-methylpropanoate (273 mg, 0.771 mmol), bis(pinacolato)diboron (235 mg, 0.925 mmol) and potassium acetate (229 mg, 2.31 mmol) in 1-4-dioxane (5 mL). The mixture was degassed for a further 10 min then heated to 90° C. for 2 h. The reaction was cooled to RT and diluted with ethyl acetate. The mixture was filtered through celite and concentrated under vacuum to give the title compound (401 mg, 93%, 72% purity) as a yellow gum. The product was used without further purification in the next step. 1H NMR (400 MHz, DMSO-d6): 7.91 (1H, m), 7.88 (1H, dd), 7.62 (1H, d), 4.64 (2H, s), 1.54 (6H, s), 1.32 (9H, s), 1.16 (12H, s).

Preparation 87: 2-[2-(2-oxopyrrolidin-1-yl)ethyl]-6-(4,4,5,5-tetramethyl-1,3,2-dioxaborolan-2-yl)-2,3-dihydro-1H-isoindol-1-one

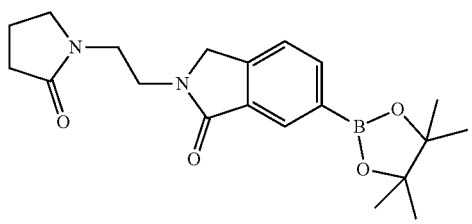 [SMILES: CC1(C)OB(c2ccc3c(c2)C(=O)N(CCN2CCCC2=O)C3)OC1(C)C]

Prepared following the procedure described in Preparation 86. $^1$H NMR (400 MHz, CDCl$_3$): 8.27 (1H, d), 7.94 (1H, dd), 7.44 (1H, d), 4.49 (2H, s), 3.81 (2H, t), 3.60 (2H, t), 3.51 (2H, t), 2.22 (2H, t), 1.96 (2H, tt), 1.35 (12H, s). (The product was contaminated with 40 wt % pinacol and 18 wt % 1,4-dioxane).

Preparation 88: 2-[2-(cyclopentyloxy)ethyl]-6-(4,4,5,5-tetramethyl-1,3,2-dioxaborolan-2-yl)-2,3-dihydro-1H-isoindol-1-one

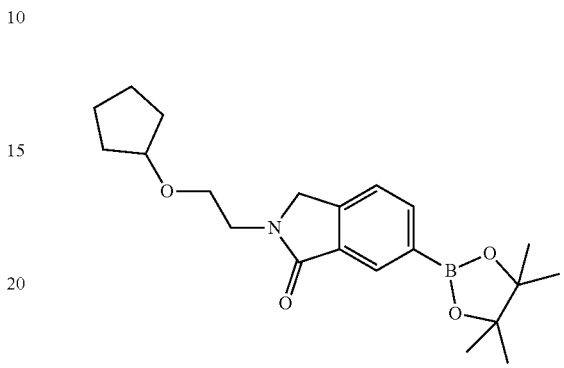

Prepared following the procedure described in Preparation 86. The product was purified by chromatography (SiO$_2$, 0-100% ethyl acetate in iso-hexane). LC-MS: [M+H]$^+$=372.

Preparation 89: tert-butyl(2R)-2-[1-oxo-6-(4,4,5,5-tetramethyl-1,3,2-dioxaborolan-2-yl)-2,3-dihydro-1H-isoindol-2-yl]propanoate

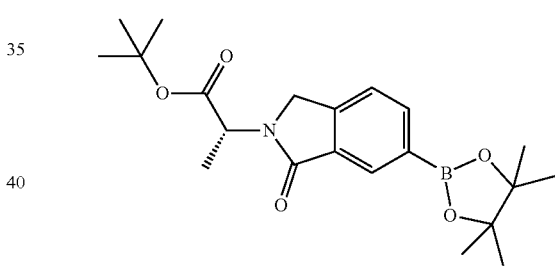

Prepared following the procedure described in Preparation 86. The crude product was purified by chromatography (SiO$_2$, 0-50% ethyl actate in iso-hexane) to give the title compound (1.653 g, 99%) as an off white solid. LC-MS: [M+Na]$^+$=410.

Preparation 90: 2-[2-(cyclopentyloxy)ethyl]-6-(2,5-dichloropyrimidin-4-yl)-2,3-dihydro-1H-isoindol-1-one

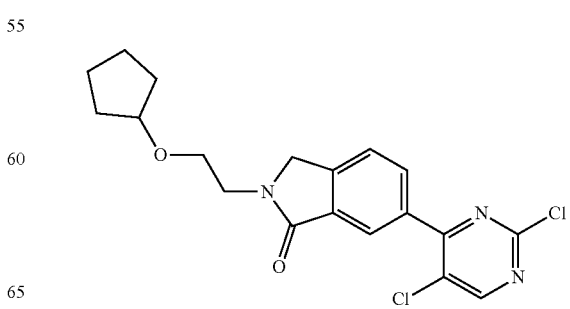

A mixture of 2-[2-(cyclopentyloxy)ethyl]-6-(4,4,5,5-tetramethyl-1,3,2-dioxaborolan-2-yl)-2,3-dihydro-1H-isoindol-1-one (144 mg, 0.349 mmol), 2,4,5-trichloropyrimidine (0.060 mL, 0.52 mmol) and potassium carbonate (103 mg, 0.745 mmol) in 1,4-dioxane (3 mL) and water (1 mL) was heated to 40° C. and degassed (nitrogen bubbling) for 10 min. Pd(PPh$_3$)$_4$ (15 mg, 0.013 mmol) was added and the mixture was degassed for a further 10 min and then heated to 90° C. for 1.75 h. The mixture was allowed to cool to RT and was partitioned between ethyl acetate (30 mL) and water (30 mL). The phases were separated and the aqueous phase was extracted with ethyl acetate (30 mL). The combined organic phases were washed with brine (30 mL), dried (MgSO$_4$) and concentrated onto silica. Purification by chromatography (SiO$_2$, 0-100% ethyl acetate in iso-hexane) gave the title compound (102 mg, 64%) as a yellow gum. LC-MS: [M+H]$^+$=392.

Preparations 91-94

Prepared following an analogous/similar procedure to that described for Preparation 90:

| Preparation | Structure | Name | $^1$H NMR (400 MHz) | MS: [M + H]$^+$ |
|---|---|---|---|---|
| 91 | 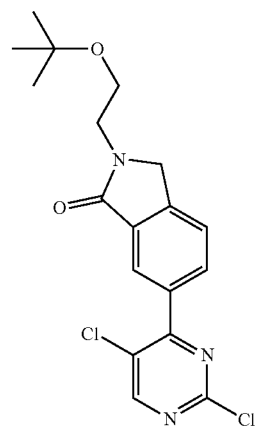 [SMILES: CC(C)(C)OCCN1Cc2ccc(-c3nc(Cl)ncc3Cl)cc2C1=O] | 2-[2-(tert-butoxy)ethyl]-6-(2,5-dichloropyrimidin-4-yl)-2,3-dihydro-1H-isoindol-1-one | — | 380 |
| 92 | 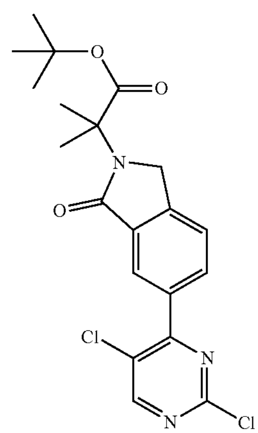 [SMILES: CC(C)(C)OC(=O)C(C)(C)N1Cc2ccc(-c3nc(Cl)ncc3Cl)cc2C1=O] | tert-butyl 2-[6-(2,5-dichloropyrimidin-4-yl)-1-oxo-2,3-dihydro-1H-isoindol-2-yl]-2-methylpropanoate | (DMSO-d6): 9.04 (1H, s), 8.09 (1H, d), 8.05 (1H, dd), 7.81 (1H, d), 4.73 (2H, s), 1.56 (6H, s), 1.36 (9H, s). | — |
| 93 | 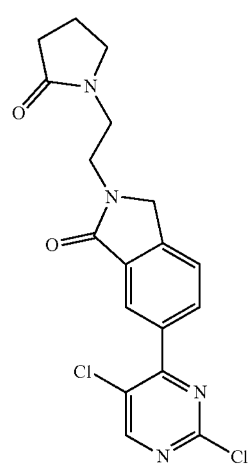 [SMILES: O=C1CCCN1CCN1Cc2ccc(-c3nc(Cl)ncc3Cl)cc2C1=O] | 6-(2,5-dichloropyrimidin-4-yl)-2-[2-(2-oxopyrrolidin-1-yl)ethyl]-2,3-dihydro-1H-isoindol-1-one | — | 391 |

| Preparation | Structure | Name | ¹H NMR (400 MHz) | MS: [M + H]⁺ |
|---|---|---|---|---|
| 94 | 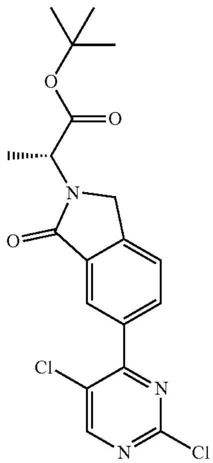 [SMILES: C[C@H](C(=O)OC(C)(C)C)N1Cc2ccc(-c3nc(Cl)ncc3Cl)cc2C1=O] | tert-butyl (2R)-2-[6-(2,5-dichloropyrimidin-4-yl)-1-oxo-2,3-dihydro-1H-isoindol-2-yl]propanoate | — | 430 |

Preparation 95:3-[(tert-butyldimethylsilyl)oxy]-2-[6-(2,5-dichloropyrimidin-4-yl)-1-oxo-2,3-dihydro-1H-isoindol-2-yl]propanoic acid

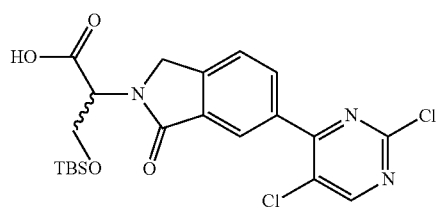 [SMILES: CC(C)(C)[Si](C)(C)OCC(C(=O)O)N1Cc2ccc(-c3nc(Cl)ncc3Cl)cc2C1=O]

Pd(PPh₃)₄ (57 mg, 0.049 mmol) was added to a degassed mixture (nitrogen bubbling) of (S)-methyl (2S)-3-[(tert-butyldimethylsilyl)oxy]-2-[1-oxo-6-(4,4,5,5-tetramethyl-1,3,2-dioxaborolan-2-yl)-2,3-dihydro-1H-isoindol-2-yl]propanoate (470 g, 0.989 mmol), 2,4,5-trichloropyrimidine (272 mg, 1.48 mmol) and potassium carbonate (273 mg, 1.98 mmol) in a mixture of 1,4-dioxane (9 mL) and water (3 mL). The mixture was stirred at 90° C. for 2.5 h. The mixture was cooled to room temperature and was diluted with ethyl acetate, then transferred into a separating funnel. 1 M HCl was added and the crude product was extracted with ethyl acetate. The combined organic phases were washed with brine, dried (MgSO₄) and absorbed on silica. Purification by chromatography (SiO₂, 0-50% ethyl acetate in isohexane, then 0-10% methanol in DCM) to afford (S)-methyl 3-[(tert-butyldimethylsilyl)oxy]-2-[6-(2,5-dichloropyrimidin-4-yl)-1-oxo-2,3-dihydro-1H-isoindol-2-yl]propanoate (68 mg, 10%) as a colourless semi-solid (LC-MS: [M+H]⁺=496), and (S)-3-[(tert-butyldimethylsilyl)oxy]-2-[6-(2,5-dichloropyrimidin-4-yl)-1-oxo-2,3-dihydro-1H-isoindol-2-yl]propanoic acid (87 mg, 14%) as a pale yellow solid. LC-MS: [M-CO₂+H]⁺=437.

Note: The product may have epimerized during the reaction as shown by chiral HPLC analysis of the final product.

Preparation 96:6-(2,5-dichloropyrimidin-4-yl)-2-(2-hydroxypropyl)-2,3-dihydro-1H-isoindol-1-one

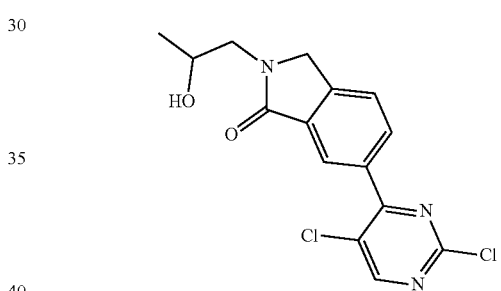

A mixture of 2,4,5-trichloropyrimidine (166 mg, 0.903 mmol), 2-(2-hydroxypropyl)-6-(4,4,5,5-tetramethyl-1,3,2-dioxaborolan-2-yl)-2,3-dihydro-1H-isoindol-1-one (191 mg, 0.602 mmol) and S-Phos Pd G3 (2 mg, 3 µmol) in 1,4-dioxane (8 mL) was treated with 1 M aqueous sodium carbonate (1.8 mL, 1.8 mmol), degassed with bubbling nitrogen for 10 min and stirred at 50° C. for 2 h. The mixture was partitioned between ethyl acetate (20 mL) and brine (20 mL). The phases were separated and the organic phase was dried (Na₂SO₄) and concentrated. Purification by chromatography (SiO₂, 20-100% ethyl acetate in iso-hexane) the title compound (118 mg, 56%) as a yellow solid. LC-MS: [M+H]⁺=338.

Preparation 97:6-(2,5-dichloropyrimidin-4-yl)-2-[2-(oxolan-2-yl)ethyl]-2,3-dihydro-1H-isoindol-1-one

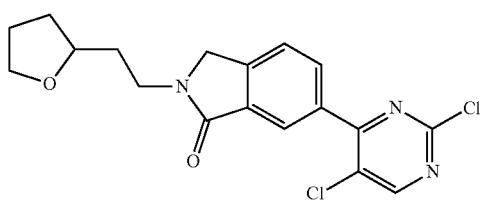 [SMILES: O=C1c2cc(-c3nc(Cl)ncc3Cl)ccc2CN1CCC1CCCO1]

Prepared following an analogous/similar procedure to that described in Preparation 96. LC-MS: [M+H]⁺=378.

Preparation 98: tert-butyl (2R)-2-(6-{5-chloro-2-[(oxan-4-yl)amino]pyrimidin-4-yl}-1-oxo-2,3-dihydro-1H-isoindol-2-yl)propanoate

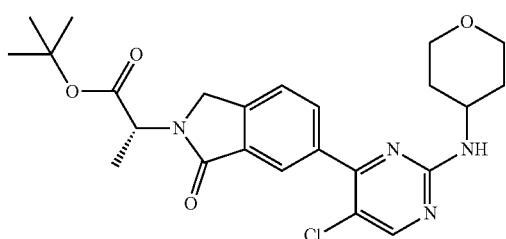

Prepared following a similar procedure to that described in Preparation 8. The reaction was carried out in EtOH at 80° C. for 3 days. LC-MS: [M+H]⁺=473.

Preparation 99: (2R)-2-(6-{5-chloro-2-[(oxan-4-yl)amino]pyrimidin-4-yl}-1-oxo-2,3-dihydro-1H-isoindol-2-yl)propanoic acid

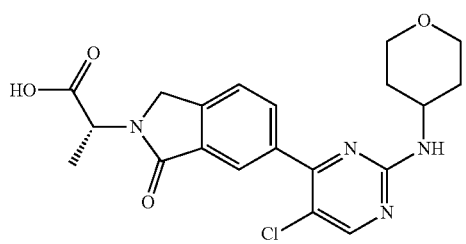 [SMILES: C[C@H](C(=O)O)N1Cc2ccc(-c3nc(NC4CCOCC4)ncc3Cl)cc2C1=O]

Prepared following a similar procedure to that described in Preparation 9. LC-MS: [M+H]⁺=417. Note: The product may have partially epimerized during the reaction as shown by chiral HPLC analysis of the final product.

Preparation 100: tert-butyl 2-(6-{5-chloro-2-[(oxan-4-yl)amino]pyrimidin-4-yl}-1-oxo-2,3-dihydro-1H-isoindol-2-yl)-2-methylpropanoate

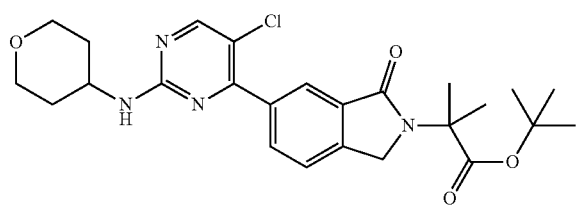 [SMILES: CC(C)(C)OC(=O)C(C)(C)N1Cc2ccc(-c3nc(NC4CCOCC4)ncc3Cl)cc2C1=O]

Prepared following a similar procedure to that described in Preparation 8. The reaction was carried out in 1,4-dioxane at 60° C. overnight. Further oxan-4-amine (2 equ.) and DIPEA (2.5 equ.) were added and the mixture heated at 60° C. overnight. LC-MS: [M+H]⁺=487.

Preparation 101: 2-(6-{5-chloro-2-[(oxan-4-yl)amino]pyrimidin-4-yl}-1-oxo-2,3-dihydro-1H-isoindol-2-yl)-2-methylpropanoic acid

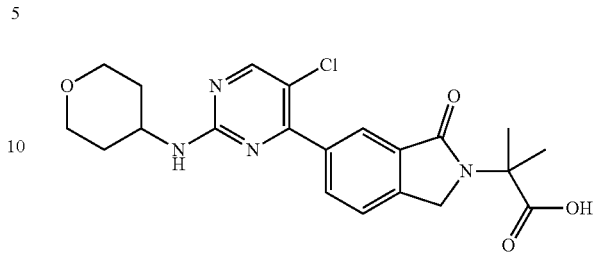

The product was prepared following an analogous/similar procedure as described in Preparation 9. LC-MS: [M+H]⁺= 431.

Preparation 102: tert-butyl (1-(tert-butylamino)-4-(methylthio)-1-oxobutan-2-yl)carbamate

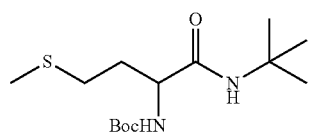 [SMILES: CSCCC(NC(=O)OC(C)(C)C)C(=O)NC(C)(C)C]

Tert-butylamine (1.11 mL, 10.5 mmol) and diisopropylethylamine (7.92 mL, 45.4 mmol) were added to a mixture of rac-(tert-butoxycarbonyl)methionine (2.60 g, 10.4 mmol), EDC (2.10 g, 11.0 mmol) and HOBT (2.08 g, 13.6 mmol) in DCM (100 mL). The reaction was stirred at RT for 24 h. The reaction was diluted with water (100 mL). The phases were separated and the aqueous phase was extracted with DCM (2×50 mL). The combined organic extracts were washed with saturated aqueous sodium bicarbonate solution (200 mL), 1 M hydrochloric acid (200 mL), dried (MgSO₄) and concentrated to give the title compound (2.79 g, 83%) as a colourless solid. 1H NMR (400 MHz, DMSO-d6) 7.31 (1H, s), 6.78 (1H, d), 3.92 (1H, q), 2.45-2.35 (2H, m), 2.03 (3H, s), 1.85-1.67 (2H, m), 1.38 (9H, s), 1.25 (9H, s).

Preparation 103: (3-((tert-butoxycarbonyl)amino)-4-(tert-butylamino)-4-oxobutyl)dimethylsulfonium iodide

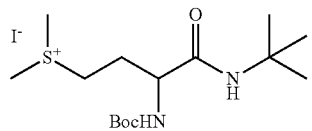 [SMILES: C[S+](C)CCC(NC(=O)OC(C)(C)C)C(=O)NC(C)(C)C ; [I-]]

Iodomethane (1.03 mL, 16.4 mmol) was added to a solution of tert-butyl (1-(tert-butylamino)-4-(methylthio)-1-oxobutan-2-yl)carbamate (1.00 g, 3.28 mmol) in DCM (3 mL). The reaction was stirred at RT in the dark for 4 h, before being diluted with DCM (10 mL). The reaction was stirred at RT for 3 days. The resulting solid was isolated by filtration, washing with diethyl ether (2×20 mL) to give the title compound (1.05 g, 2.24 mmol, 68% yield) as a colourless solid. 1H NMR (400 MHz, DMSO-d6) 7.48 (1H, s), 6.95 (1H, d), 4.04-3.95 (1H, m), 3.24 (2H, t), 2.92-2.85 (6H, m), 2.07-1.87 (2H, m), 1.40 (9H, s), 1.27 (9H, s).

Preparation 104: tert-butyl(1-(tert-butyl)-2-oxopyrrolidin-3-yl)carbamate

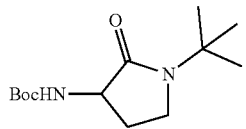 [SMILES: CC(C)(C)OC(=O)NC1CCN(C(C)(C)C)C1=O]

Sodium hydride (60% dispersion in mineral oil, 113 mg, 2.82 mmol) was added to a solution of (3-((tert-butoxycarbonyl)amino)-4-(tert-butylamino)-4-oxobutyl)dimethylsulfonium iodide (1.05 g, 2.35 mmol) in DMF (15 mL) at 0° C. The reaction was stirred at 0° C. for 15 min then warmed to RT and stirred for 1 h. The reaction was quenched with water (2 mL) and then diluted with saturated aqueous ammonium chloride solution (50 mL) and extracted with ethyl acetate (3×20 mL). The combined organic phases were washed with water (50 mL), brine (2×50 mL), dried (MgSO$_4$) and concentrated under vacuum to give the title compound (633 mg, 2.10 mmol, 89% yield, 85% purity) as a yellow oil that solidified on standing. 1H NMR (400 MHz, DMSO-d6) 7.01 (1H, d), 4.05-3.96 (2H, m), 3.40-3.32 (1H, m), 3.24 (1H, td), 2.18-2.08 (1H, m), 1.72-1.59 (1H, m), 1.39 (9H, s), 1.31 (9H, s).

Preparation 105:3-amino-1-(tert-butyl)pyrrolidin-2-one hydrochloride

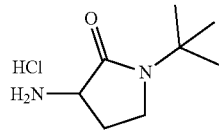

A solution of HCl (4 M in 1,4-dioxane, 2.6 mL, 10.5 mmol) was added to a solution of tert-butyl (1-(tert-butyl)-2-oxopyrrolidin-3-yl)carbamate (633 mg, 2.1 mmol) in 1,4-dioxane (2.5 mL). The reaction was stirred at RT for 18 h. The solvent was removed under vacuum to give the title compound (400 mg, 94%) as an off-white solid. 1H NMR (400 MHz, DMSO-d6) 8.44 (3H, br. s), 3.91-3.82 (1H, m), 3.60-3.41 (2H, m), 3.37 (1H, td), 2.34-2.24 (1H, m), 1.91-1.77 (1H, m), 1.35 (9H, s).

Preparation 106:6-bromo-2-(1-methyl-2-oxopiperidin-3-yl)-2,3-dihydro-1H-isoindol-1-one

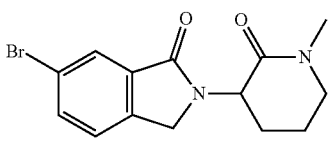 [SMILES: CN1CCCC(N2Cc3ccc(Br)cc3C2=O)C1=O]

A solution of methyl 5-bromo-2-(bromomethyl)benzoate (500 mg, 1.62 mmol), 3-amino-1-methylpiperidin-2-one (208 mg, 1.62 mmol), triethylamine (0.27 mL, 2.0 mmol) in THF (10 mL) was heated to 70° C. for 18 h. The reaction was concentrated under vacuum and diluted with ethyl acetate (10 mL) and water (10 mL). The phases were separated and the aqueous phase was extracted with ethyl acetate (2×10 mL). The combined organic phases were washed with 1 M hydrochloric acid (20 mL), brine (20 mL), dried (MgSO$_4$) and concentrated under vacuum. Purification by chromatography (SiO$_2$, 0-10% methanol in DCM) gave the title compound (208 mg, 39%) as a colourless solid. LC-MS: [M+H]$^+$=323.

Preparation 107:6-bromo-2-(1-tert-butyl-2-oxopyrrolidin-3-yl)-2,3-dihydro-1H-isoindol-1-one

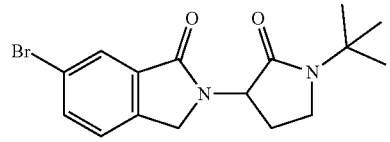 [SMILES: CC(C)(C)N1CCC(N2Cc3ccc(Br)cc3C2=O)C1=O]

Prepared according to Preparation 106 from 3-amino-1-(tert-butyl)pyrrolidin-2-one hydrochloride (473 mg, 2.46 mmol) and triethylamine (0.75 mL, 5.4 mmol). The title compound (533 mg, 60%) was obtained as a tan solid. LC-MS: [M+H]$^+$=351.

Preparation 108:2-(1-tert-butyl-2-oxopyrrolidin-3-yl)-6-(4,4,5,5-tetramethyl-1,3,2-dioxaborolan-2-yl)-2,3-dihydro-1H-isoindol-1-one

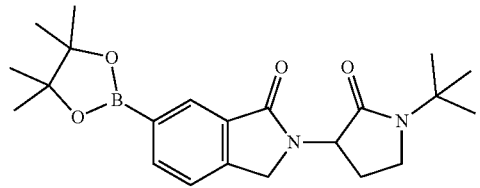 [SMILES: CC(C)(C)N1CCC(N2Cc3ccc(B4OC(C)(C)C(C)(C)O4)cc3C2=O)C1=O]

A mixture of 6-bromo-2-(1-tert-butyl-2-oxopyrrolidin-3-yl)-2,3-dihydro-1H-isoindol-1-one (533 mg, 1.52 mmol), bis(pinacolato)diboron (462 mg, 1.82 mmol) and potassium acetate (298 mg, 3.03 mmol) in 1,4-dioxane (12 mL) was degassed with nitrogen for 10 min before PdCl$_2$(dppf) (33 mg, 0.046 mmol) was added. The degassing was continued for a further 10 min before the reaction was heated to 90° C. for 18 h. The reaction was diluted with ethyl acetate (20 mL) and water (20 mL). The phases were separated and the aqueous phase was extracted with ethyl acetate (2×20 mL). The combined organic phases were washed with brine (50 mL), dried (MgSO$_4$) and concentrated under vacuum. Purification by chromatography (SiO$_2$, 0-100% ethyl acetate in iso-hexane) gave the title compound (308 mg, 50%) as a tan solid. LC-MS: [M+H]$^+$=399.

Preparation 109: 2-(1-methyl-2-oxopiperidin-3-yl)-6-(4,4,5,5-tetramethyl-1,3,2-dioxaborolan-2-yl)-2,3-dihydro-1H-isoindol-1-one

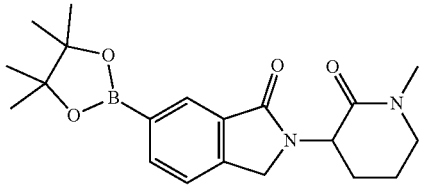

A mixture of 6-bromo-2-(1-methyl-2-oxopiperidin-3-yl)-2,3-dihydro-1H-isoindol-1-one (208 mg, 0.64 mmol), bis(pinacolato)diboron (196 mg, 0.77 mmol) and potassium acetate (126 mg, 1.29 mmol) in 1,4-dioxane (5 mL) was degassed with nitrogen for 10 min before PdCl$_2$(dppf) (14 mg, 0.019 mmol) was added. The degassing was continued for a further 10 min before the reaction was heated to 90° C. for 18 h. The reaction was diluted with ethyl acetate (20 mL) and water (20 mL). The phases were separated and the aqueous phase was extracted with ethyl acetate (2×20 mL). The combined organic phases were washed with brine (50 mL), dried (MgSO$_4$) and concentrated to give the title compound (288 mg, 81%, 67% purity) as a brown oil. LC-MS: [M+H]$^+$=371.

Preparation 110: Methyl Ethanimidothioate Hydroiodide

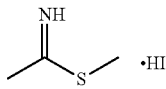

Iodomethane (0.83 mL, 13.3 mmol) was added to a stirred solution of thioacetamide (1.00 g, 13.0 mmol) in acetone (45 mL). The solution was heated to 60° C. for 18 h. Upon cooling to RT, a solid began to precipitate out of solution. The reaction volume was reduced to about a third of its initial volume and the solid collected by filtration, washing with acetone, to give the title compound (790 mg, 27%) as a colourless solid. 1H NMR (400 MHz, DMSO-d6): 11.6 (2H, br. s), 2.67 (3H, s), 2.58 (3H, s).

Preparation 111: 2-(6-{5-chloro-2-[(oxan-4-yl)amino]pyrimidin-4-yl}-1-oxo-2,3-dihydro-1H-isoindol-2-yl)acetohydrazide

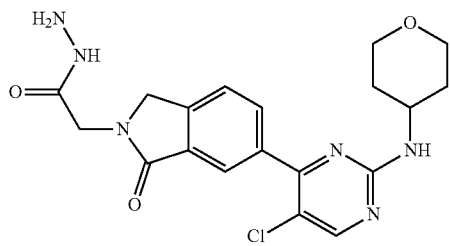 [SMILES: NNC(=O)CN1Cc2ccc(-c3nc(NC4CCOCC4)ncc3Cl)cc2C1=O]

CDI (44 mg, 0.27 mmol) was added to a suspension of 2-(6-{5-chloro-2-[(oxan-4-yl)amino]pyrimidin-4-yl}-1-oxo-2,3-dihydro-1H-isoindol-2-yl)acetic acid (100 mg, 0.246 mmol) in DCM (2 mL). The reaction was stirred at RT for 15 min, before 1 M hydrazine in THF (0.37 mL, 0.37 mmol) was added and the reaction mixture was stirred for 18 h. Saturated aqueous NaHCO$_3$ (15 mL) was added and the crude product was extracted with DCM (2×15 mL). The combined organic phases were passed through a phase separating cartridge then concentrated under vacuum to give the title compound (67 mg, 64%) as a colourless solid. The product was used without further purification in the next step. LC-MS: [M+H]$^+$=417.

Preparation 112: 2-[(1-Methyl-1H-pyrazol-5-yl)amino]pyrimidin-4-ol

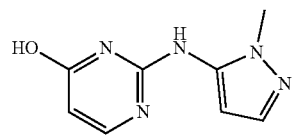

A stirred mixture of 2-(methylsulfanyl)pyrimidin-4-ol (522 mg, 3.67 mmol), 1-methyl-1H-pyrazol-5-ylamine (428 mg, 4.41 mmol) and pivalic acid (3.9 mL) was heated at 130° C. (thermally) under nitrogen for 16 hours. The reaction mixture was allowed to cool slowly and, at approximately 70° C., petrol (~4 mL) was added. The mixture was allowed to cool to room temperature after which the precipitate was filtered and washed with further petrol to yield crude 2-[(1-methyl-1H-pyrazol-5-yl)amino]pyrimidin-4-ol (650 mg, 93%, 70% pure) as a colourless solid which was used as is. MS: [M+H]$^+$=192.

Preparation 113: 4-Chloro-N-(1-methyl-1H-pyrazol-5-yl)pyrimidin-2-amine

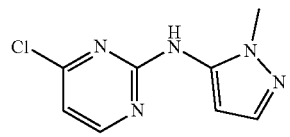

A stirred mixture of 2-[(1-methyl-1H-pyrazol-5-yl)amino]pyrimidin-4-ol (320 mg, 2.25 mmol, 70% pure) and POCl$_3$ (2.5 mL, 27.01 mmol) was heated at 70° C. for 1 hour, under nitrogen. After cooling to room temperature the excess POCl$_3$ was removed by concentration under vacuum. The residue was diluted with equal parts of CH$_2$Cl$_2$ and NaHCO$_3$ (sat. aq.) and stirred until the evolution of gas ceased. The phases were then separated and the aqueous extracted again with CH$_2$Cl$_2$. The combined organic phases were washed with brine, dried over MgSO$_4$, filtered and concentrated under vacuum to yield the title compound used as crude (254 mg, 54%, 70% pure). MS: [M+H]$^+$=210.

Preparation 114: Methyl N-[2-(4-chlorophenyl)ethyl]carbamate

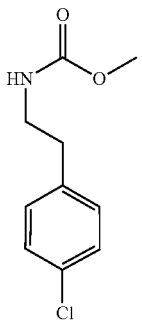

A stirred solution of 2-(4-chlorophenyl)ethan-1-amine (11.30 g, 71.16 mmol) and DIPEA (13.64 mL, 78.27 mmol) in anhydrous THF (158 mL) at 4° C. under nitrogen was treated slowly with methyl chloroformate (6.4 mL, 78.27 mmol). The solution was slowly allowed to warm to room temperature and after a total of 2 hours the reaction was quenched with NH$_4$Cl (aq., sat.). The mixture was extracted with EtOAc (×3) and the combined organic layers were washed with brine, dried over MgSO$_4$, filtered and concentrated under vacuum to yield methyl N-[2-(4-chlorophenyl)ethyl]carbamate (15.4 g, 101%) as a yellow solid which was used as is. MS: [M+H]$^+$=214.

Preparation 115: 7-Chloro-1,2,3,4-tetrahydroisoquinolin-1-one

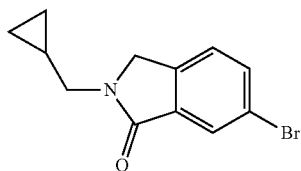 [SMILES: O=C1c2cc(Br)ccc2CN1CC1CC1]

The following reaction was put on in duplicate. Methyl N-[2-(4-chlorophenyl)ethyl]carbamate (7.5 g, 35.10 mmol) in an ice bath, was slowly treated with trifluoromethanesulfonic acid (120 mL) with stirring under nitrogen. After 15 minutes the ice bath was removed, and after a further 30 minutes the reaction was heated to 70° C. (thermally) for 24 hours. After cooling to room temperature, both reactions were combined by pouring onto ice, and once melted, the mixture was further diluted with water. The mixture was extracted with IPA:CHCl$_3$ (1:3, ×3) and the combined organic layers were washed with brine and dried over MgSO$_4$. The filtrate was concentrated under vacuum. The residue was triturated with diethyl ether and the precipitate filtered to yield 7-chloro-1,2,3,4-tetrahydroisoquinolin-1-one (8.5 g, 67%) as a colourless solid. MS: [M+H]$^+$=182. The filtrate was concentrated under vacuum to yield a further 2 g of product crude.

Preparation 116: 7-(4,4,5,5-Tetramethyl-1,3,2-dioxaborolan-2-yl)-1,2,3,4-tetrahydro-isoquinolin-1-one

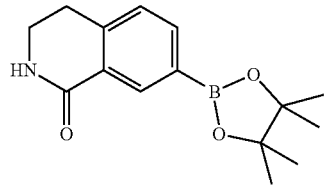 [SMILES: CC1(C)OB(c2ccc3c(c2)C(=O)NCC3)OC1(C)C]

A stirred mixture of 7-chloro-1,2,3,4-tetrahydroisoquinolin-1-one (500 mg, 2.75 mmol) bis(pinacolato)diboron (839 mg, 3.30 mmol), 2-dicyclohexylphosphino-2',4',6'-triisopropylbiphenyl (135 mg, 0.28 mmol) and AcOK (811 mg, 8.26 mmol) in anhydrous 1,4-dioxane (18 mL) was degassed with nitrogen for 10 minutes. Tris(dibenzylidene-acetone)dipalladium (0) (63 mg, 0.07 mmol) was then added and degassing continued for another 10 minutes. The mixture was heated at 80° C. under nitrogen for a total of 18 hours. After cooling to room temperature the mixture was diluted with water and extracted with EtOAc (×3). The combined organic layers were washed with brine, dried over MgSO, filtered and concentrated under vacuum to yield crude 7-(4,4,5,5-tetramethyl-1,3,2-dioxaborolan-2-yl)-1,2,3,4-tetrahydroisoquinolin-1-one (0.8 g, 107%) which was used as is. MS: [M+H]$^+$=274.

Preparation 117: 6-bromo-2-(cyclopropylmethyl)-2,3-dihydro-1H-isoindol-1-one

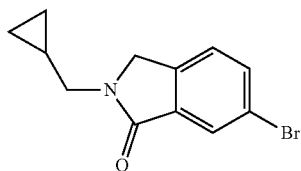 [SMILES: O=C1c2cc(Br)ccc2CN1CC1CC1]

A stirred solution of 6-bromo-2,3-dihydro-1H-isoindol-1-one (350 mg, 1.65 mmol) and cyclopropylmethyl bromide (0.198 μL, 1.98 mmol) in DMF (6 mL) was cooled in an ice bath under nitrogen. Then NaH (99 mg, 2.48 mmol) was added in portions. The reaction was stirred for 1 hour and then quenched with NH$_4$Cl (sat., aq.). The mixture was extracted with IPA:CHCl$_3$ (1:3, ×3). The combined organic layers were washed with brine, dried over MgSO$_4$, filtered and concentrated under vacuum to yield the title compound as a brown oil (~30% pure) which was used crude. MS: [M+H]$^+$=266/268.

Preparation 118: N-benzyl-2-(6-bromo-1-oxo-2,3-dihydro-1H-isoindol-2-yl)-N-methylacetamide

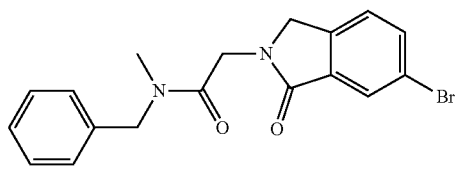 [SMILES: CN(Cc1ccccc1)C(=O)CN1Cc2ccc(Br)cc2C1=O]

Prepared using a similar procedure to Preparation 117 above, using N-benzyl-2-chloro-N-methylacetamide. MS: [M+H]⁺=373/375.

Preparations 119: N-benzyl-N-methyl-2-[1-oxo-6-(4,4,5,5-tetramethyl-1,3,2-dioxaborolan-2-yl)-2,3-dihydro-1H-isoindol-2-yl]acetamide

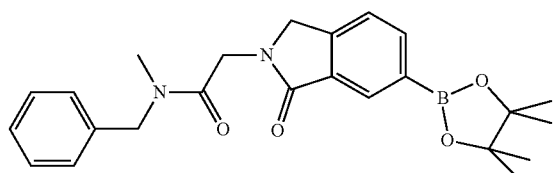

Prepared from N-benzyl-2-(6-bromo-1-oxo-2,3-dihydro-1H-isoindol-2-yl)-N-methylacetamide using a similar procedure to Preparation 116. MS: [M+H]⁺=337.

Preparation 120: 2,5-Dichloropyrimidin-4-ol

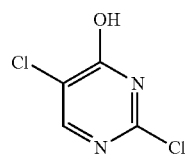

A stirred solution of 2,4,5-trichloropyrimidine (1.1 mL, 9.72 mmol) in 1,4-dioxane (10 mL) was treated with water (2 mL) and then NaOH (11.7 mL, 1M). The reaction was heated at 50° C. in a reacti vial for 24 hours, after which the reaction was allowed to cool and was then diluted with EtOAc. The organic layer (containing starting material) was discarded. The pH of the aqueous was adjusted to ~6 with citric acid (5%, aq.) and the product was re-extracted with IPA:CHCl₃ (1:3×3). These combined organic layers were washed with brine, dried over MgSO₄, filtered and concentrated under vacuum to yield the title compound (410 mg, 26%) which was used crude. MS: [M+H]⁺=165.

Preparation 121: 5-Chloro-2-[(1,5-dimethyl-1H-pyrazol-4-yl)amino]pyrimidin-4-ol

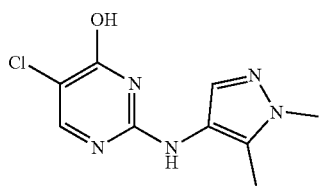 [SMILES: Cc1c(Nc2ncc(Cl)c(O)n2)cnn1C]

A stirred solution of 2,5-dichloropyrimidin-4-ol (410 mg, 2.46 mmol), 1,5-dimethyl-1H-pyrazol-4-amine (602 mg, 5.41 mmol) and p-toluenesulfonic acid monohydrate (702 mg, 3.69 mmol) in 1,4-dioxane (5 mL) was heated in a reacti vial at 105° C. for 24 hours. The reaction was then stirred at room temperature for 2 days, diluted with water, and the product was extracted with CHCl₃:IPA (3:1, ×3). The combined organic layers were washed with brine, dried over MgSO₄, filtered and concentrated under vacuum to yield crude 5-chloro-2-[(1,5-dimethyl-1H-pyrazol-4-yl)amino]pyrimidin-4-ol (280 mg, 48%, 80% pure) as a yellow solid. MS: [M+H]⁺=240.

Preparation 122: 4,5-Dichloro-N-(1,5-dimethyl-1H-pyrazol-4-yl)pyrimidin-2-amine

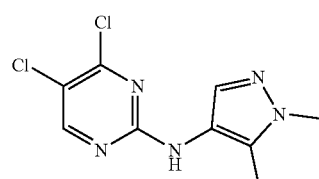

To 5-chloro-2-[(1,5-dimethyl-1H-pyrazol-4-yl)amino]pyrimidin-4-ol (280 mg, 1.17 mmol) was added POCl₃ (0.7 mL, 7.01 mmol) under nitrogen. The mixture was stirred at 90° C. for 1 hour. The reaction mixture was allowed to cool to room temperature and NaHCO₃ (sat. aq.) was carefully added. The mixture was extracted with EtOAc (×3) and the combined organic layers were washed with brine, dried over MgSO₄, filtered and concentrated under vacuum to yield the title compound (210 mg, 70%) as a yellow solid which was used as is. MS: [M+H]⁺=258.

Preparation 123: tert-Butyl 2-(6-{2-chloropyrimidin-4-yl}-1-oxo-2,3-dihydro-1H-isoindol-2-yl)acetate

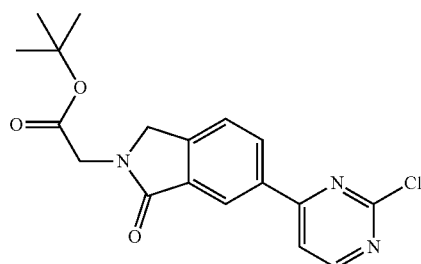

Prepared from 2,4-dichloropyrimidine using a similar procedure to Preparation 3.

Preparation 124: Methyl 3-(6-bromo-1-oxo-2,3-dihydro-1H-isoindol-2-yl)propanoate

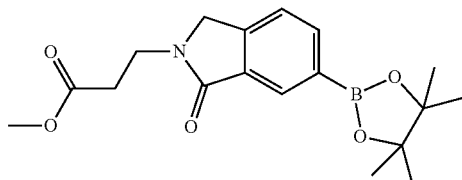

To a stirred solution of 6-bromo-2,3-dihydro-1H-isoindol-1-one (550 mg, 2.59 mmol), 18-crown-6 (69 mg, 0.26 mmol) and methyl 3-bromopropionate (350 µL, 3.11 mmol) in DMF (9 mL) was added Cs₂CO₃ (2.113 g, 6.48 mmol)

under nitrogen. The reaction was heated to 70° C. (thermally) slowly and maintained at this temperature for 18 hours. After cooling and the reaction was quenched with NH₄Cl (sat., aq.). The mixture was extracted with EtOAc (×3) and the combined organic layers were washed with brine, dried over MgSO, filtered and concentrated under vacuum to yield methyl 3-(6-bromo-1-oxo-2,3-dihydro-1H-isoindol-2-yl)propanoate as a yellow oil. LC-MS was consistent with a complex mixture which was taken on as is. To the residue was added bis(pinacolato)diboron (0.746 g, 2.91 mmol), AcOK (0.491 mg, 5.00 mmol) and anhydrous 1,4-dioxane (8 mL). The reaction was degassed with nitrogen for 5 minutes. 1,1'-Bis(diphenylphosphino)ferrocene-palladium (II)dichloride dichloromethane complex (61 mg, 0.08 mmol) was then added and the reaction heated at 90° C. under nitrogen for 16 hours. The reaction was allowed to cool to room temperature and was then diluted with water. The mixture was extracted with EtOAc (×3) and the combined organic layers were washed with brine, dried over MgSO, filtered and concentrated under vacuum to yield the title compound (1.5 g, 168%) which was used without further purification. MS: [M+H]⁺=346.

Preparation 125: Methyl 3-[6-(2,5-dichoropyrimidin-4-yl)-1-oxo-2,3-dihydro-1H-isoindol-2-yl]propanoate

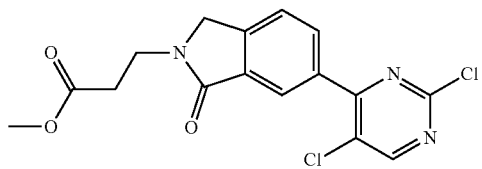 [SMILES: COC(=O)CCN1Cc2ccc(-c3nc(Cl)ncc3Cl)cc2C1=O]

A stirred mixture of methyl 3-[1-oxo-6-(4,4,5,5-tetramethyl-1,3,2-dioxaborolan-2-yl)-2,3-dihydro-1H-isoindol-2-yl]propanoate (1.5 g, 2.17 mmol, ~50% pure), 2,4,5-trichloropyrimidine (370 μL, 3.26 mmol), K₂CO₃ (600 mg, 4.35 mmol) and 1,4-dioxane:water (3:1, 11 mL) was degassed with nitrogen for 5 minutes. Pd(PPh₃)₄ (120 mg, 0.11 mmol) was then added and the reaction heated at 100° C. under nitrogen for a total of 3 hours. The mixture was allowed to cool to room temperature, diluted with water, and extracted with EtOAc (×3). The combined organic layers were washed with brine, dried over MgSO, filtered and concentrated under vacuum and the residue was purified by biotage (0-100 EtOAc/petrol, and then 0-10% MeOH) to yield the title compound (620 mg, 78%) as a red oil. MS: [M−H]⁺=364.

Preparation 126: tert-Butyl 2-(7-{2,5-dichloropyrimidin-4-yl}-1-oxo-1,2,3,4-tetrahydro-isoquinolin-2-yl)acetate

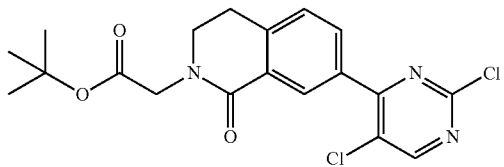 [SMILES: CC(C)(C)OC(=O)CN1CCc2ccc(-c3nc(Cl)ncc3Cl)cc2C1=O]

Prepared from 7-(4,4,5,5-tetramethyl-1,3,2-dioxaborolan-2-yl)-1,2,3,4-tetrahydro-isoquinoin-1-one (Preparation 116) using similar procedures to Preparation 3 and Preparation 1 respectively. LC-MS: [M+H]⁺=408.

Preparation 127: 2-Chloro-1-(1,2,3,4-tetrahydroisoquinolin-2-yl)ethan-1-one

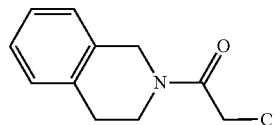

A stirred solution of 1,2,3,4-tetrahydroisoquinoline (2.6 g, 19.48 mmol) and DIPEA (3.7 mmol, 21.25 mmol) in anhydrous CH₂Cl₂ (89 mL) under nitrogen, was cooled in an ice water bath. Chloroacetyl chloride (1.4 mL, 17.71 mmol) was added very slowly, after which the reaction was stirred for 30 minutes, still in the ice water bath. The reaction was quenched with NH₄Cl (sat., aq.) and the product extracted with EtOAc (×3). The combined organic layers were washed with water and brine, dried over MgSO₄, filtered and concentrated under vacuum to yield the title compound (4.6 g, 124%) which was used as is. MS: [M+H]⁺=210.

Preparation 128: 6-(2,5-Dichloropyrimidin-4-yl)-2-[2-oxo-2-(1,2,3,4-tetrahydro isoquinolin-2-yl)ethyl]-2,3-dihydro-1H-isoindol-1-one

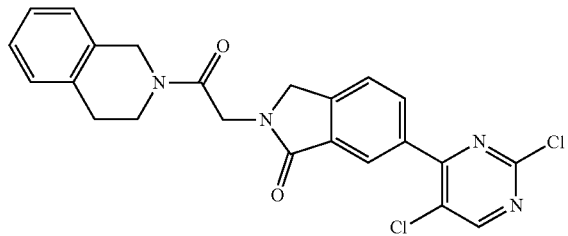 [SMILES: O=C(CN1Cc2ccc(-c3nc(Cl)ncc3Cl)cc2C1=O)N1CCc2ccccc2C1]

A stirred solution of 6-bromo-2,3-dihydro-1H-isoindol-1-one (3.4 g, 14.16 mmol) and 2-chloro-1-(1,2,3,4-tetrahydroisoquinolin-2-yl)ethan-1-one (3.6 g, 17.00 mmol) in DMF (47 mL) was cooled in an ice bath under nitrogen before adding NaH (0.70 g, 17.00 mmol) in portions. The reaction was allowed to warm to room temperature over an hour and was then quenched with NH₄C (sat., aq.). The pH was adjusted to pH 7 with citric acid (5%, aq.) and the product was extracted with IPA:CHCl₃ (1:3, ×3). The combined organic layers were washed brine, dried over MgSO₄, filtered and concentrated under vacuum to yield 6-bromo-2-[2-oxo-2-(1,2,3,4-tetrahydroisoquinolin-2-yl)ethyl]-2,3-dihydro-1H-isoindol-1-one as a brown solid which was used crude. MS: [M+H]⁺=385. To the residue was added bis(pinacolato)diboron (4.236 g, 16.51 mmol), AcOK (2.787 mg, 28.40 mmol) and anhydrous 1,4-dioxane (71 mL). The reaction was degassed with nitrogen for 10 minutes. 1,1'-Bis(diphenylphosphino)ferrocene-palladium(II)dichloride dichloromethane complex (348 mg, 0.43 mmol) was then added and the reaction heated at 90° C. under nitrogen for 1.5 hours. The reaction was allowed to cool to room temperature and was then diluted with water. The product was extracted with EtOAc (×3) and the combined organic layers washed with brine, dried over MgSO$_4$, filtered and concentrated under vacuum to yield crude 2-[2-oxo-2-(1,2,3,4-tetrahydroisoquinolin-2-yl)ethyl]-6-(4,4,5,5-tetramethyl-1,3,2-dioxaborolan-2-yl)-2,3-dihydro-1H-isoindol-1-one (90% pure by LC-MS UV) which was used as is. MS: [M+H]$^+$=433. A stirred mixture of this material, 2,4,5-trichloropyrimidine (2.442 ml mg, 21.30 mmol), K$_2$CO$_3$ (3.925 mg, 28.40 mmol) and 1,4-dioxane/water (3:1, 57 mL) was degassed with nitrogen for 10 minutes. Pd(PPh$_3$)$_4$ (810 mg, 0.70 mmol) was then added and the reaction heated at 90° C. under nitrogen for a total of 16 hours. The reaction was allowed to cool to room temperature and was then diluted with water. The product was extracted with EtOAc (×3) and the combined organic layers were washed with water and brine, dried over MgSO$_4$, filtered and concentrated under vacuum. The residue was purified by biotage (0-100% petrol/EtOAc) to yield the title compound (4.81 g, 75% over 3 steps) as a colourless solid. MS: [M+H]$^+$=453.

Preparations 129-132

Prepared using a similar procedure to Preparation 128 from the corresponding 5-substituted 2,4-dichloropyrimidines:

| Preparation | Structure | Name | MS: [M + H]$^+$ |
|---|---|---|---|
| 129 | 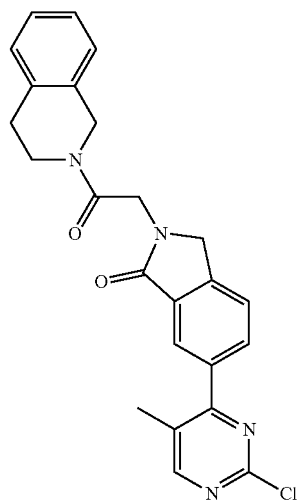 [SMILES: Cc1cnc(Cl)nc1-c1ccc2c(c1)C(=O)N(CC(=O)N1CCc3ccccc3C1)C2] | 6-(2-chloro-5-methylpyrimidin-4-yl)-2-[2-oxo-2-(1,2,3,4-tetrahydroisoquinolin-2-yl)ethyl]-2,3-dihydro-1H-isoindol-1-one | 433 |
| 130 | 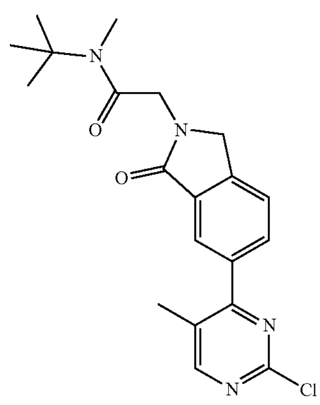 [SMILES: Cc1cnc(Cl)nc1-c1ccc2c(c1)C(=O)N(CC(=O)N(C)C(C)(C)C)C2] | N-tert-butyl-2-[6-(2-chloro-5-methylpyrimidin-4-yl)-1-oxo-2,3-dihydro-1H-isoindol-2-yl]-N-methylacetamide | 387 |

| Preparation | Structure | Name | MS: [M + H]+ |
|---|---|---|---|
| 131 | 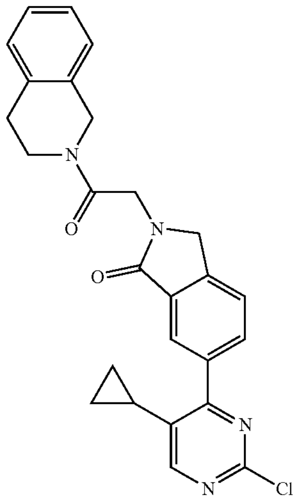 [SMILES: O=C(CN1Cc2ccc(-c3nc(Cl)ncc3C3CC3)cc2C1=O)N1CCc2ccccc2C1] | 6-(2-chloro-5-cyclopropylpyrimidin-4-yl)-2-[2-oxo-2-(1,2,3,4-tetrahydroisoquinolin-2-yl)ethyl]-2,3-dihydro-1H-isoindol-1-one | 459 |
| 132 | 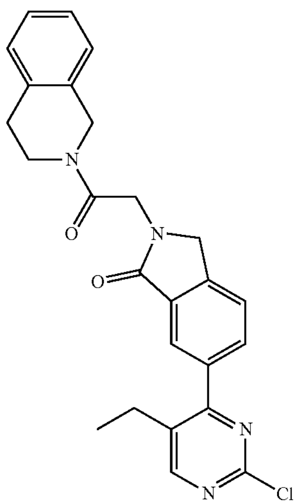 [SMILES: CCc1cnc(Cl)nc1-c1ccc2c(c1)C(=O)N(CC(=O)N1CCc3ccccc3C1)C2] | 6-(2-chloro-5-ethylpyrimidin-4-yl)-2-[2-oxo-2-(1,2,3,4-tetrahydroisoquinolin-2-yl)ethyl]-2,3-dihydro-1H-isoindol-1-one | 447 |

Preparation 133: tert-Butyl N-{8-oxabicyclo[3.2.1]octan-3-yl}carbamate

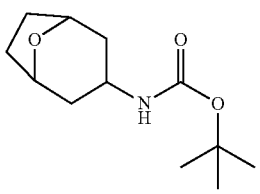 [SMILES: CC(C)(C)OC(=O)NC1CC2CCC(C1)O2]

A stirred mixture of 8-oxabicyclo[3.2.1]octane-3-carboxylic acid (250 mg, 1.60 mmol) in tert-butyl alcohol (2 mL) was treated with DIPEA (341 μL, 1.96) and then diphenylphosphoryl azide (392 μL, 1.77 mmol). The mixture was heated to reflux for 5 hours and then stirred at room temperature for 16 hours. The solvents were evaporated under vacuum. The residue was taken up in EtOAc and the resulting solution washed with water, brine and dried over MgSO₄, filtered and concentrated under vacuum. The residue was purified by biotage (0-100% EtOAc/petrol) to yield the title compound (200 mg, 55%) as a colourless solid. ¹H NMR (400 MHz, Me-d₃-OD): 4.39 (2H, s), 3.89-3.74 (1H, m), 1.99-1.90 (2H, m), 1.90-1.83 (2H, m), 1.83-1.74 (2H, m), 1.59-1.49 (2H, m), 1.45 (9H, s).

Preparation 134: 8-Oxabicyclo[3.2.1]octan-3-amine hydrochloride

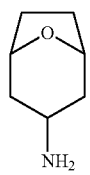

A solution of tert-butyl N-{8-oxabicyclo[3.2.1]octan-3-yl}carbamate (190 mg, 0.84 mmol) in EtOAc saturated with HCl (3 mL) was stirred at room temperature for 1 hour and evaporated under vacuum. The residue was treated with MeOH and concentrated to dryness under vacuum to yield the title compound (122 mg, 114%, contains 20% starting material) as a colourless solid. ¹H NMR (400 MHz, Me-d₃-OD): 4.52-4.46 (2H, m), 3.59-3.51 (1H, m), 2.08-1.98 (2H, m), 1.94-1.88 (2H, m), 1.85-1.79 (2H, m), 1.76-1.67 (2H, m).

Preparation 135: 4-Bromo-5-chloro-N-(oxan-4-yl) pyridin-2-amine

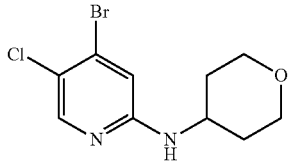 [SMILES: Clc1cnc(NC2CCOCC2)cc1Br]

A stirred mixture of 2-amino-4-bromo-5-chloropyridine (500 mg, 2.34 mmol) and tetrahydro-4H-pyran-4-one (654 µL, 7.01 mmol) in 1,2-dichloroethane (6 mL) was treated with sodium triacetoxyborohydride (1.277 g, 5.84 mmol). After 5 days the mixture was treated with NaOH (1 M, 5 ml). After 30 minutes, the mixture was diluted with water and extracted with CH₂Cl₂ (×3). The combined organic layers were washed with brine, dried over MgSO₄, filtered and concentrated under vacuum. The residue was purified by biotage (0-50% EtOAc) to yield 4-bromo-5-chloro-N-(oxan-4-yl)pyridin-2-amine (530 mg, 78%) as a yellow solid. MS: [M+H]⁺=291/293/295.

Preparation 136: 2-(6-{5-Chloro-2-[(oxan-4-yl)amino]pyridin-4-yl}-1-oxo-2,3-dihydro-1H-isoindol-2-yl)acetic acid

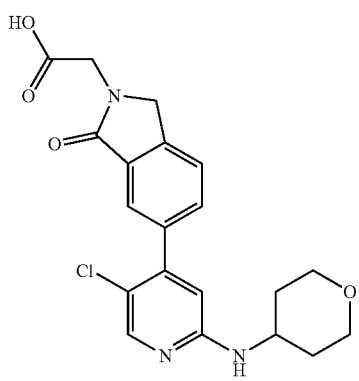 [SMILES: O=C(O)CN1Cc2ccc(-c3cc(NC4CCOCC4)ncc3Cl)cc2C1=O]

A stirred solution of tert-butyl 2-(6-{5-chloro-2-[(oxan-4-yl)amino]pyridin-4-yl}-1-oxo-2,3-dihydro-1H-isoindol-2-yl)acetate (Example 185, 165 mg, 0.36 mmol) in THF/MeOH/water (5:1:1, 4 mL) was treated with NaOH (0.5 mL, 1M). After 18 hours, water was added and the pH adjusted to pH 4-5 with citric acid (5%, aq.). The mixture was extracted with EtOAc (×3). The combined organic layers were washed with brine, dried over MgSO₄, filtered and concentrated under vacuum to yield the title compound (131 mg, 91%) as a colourless solid. MS: [M+H]⁺=402.

Preparation 137: 2-(6-{2-[(oxan-4-yl)amino]pyrimidin-4-yl}-1-oxo-2,3-dihydro-1H-isoindol-2-yl)acetic acid

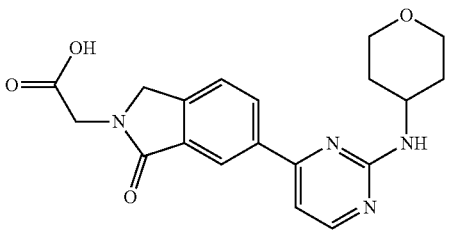 [SMILES: O=C(O)CN1Cc2ccc(-c3ccnc(NC4CCOCC4)n3)cc2C1=O]

Prepared from Example 133 using a similar procedure to Example 1. MS: [M+H]⁺=369.

Preparation 138: 5-chloro-2-[(2-methylpyridin-4-yl)amino]pyrimidin-4-ol

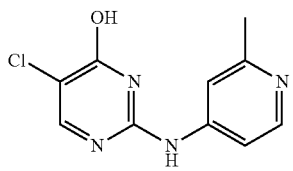 [SMILES: Cc1cc(Nc2ncc(Cl)c(Cl)n2)ccn1]

A solution of 4-amino-2-methylpyridine (594 mg, 5.5 mmol), 2,5-dichloropyrimidin-4-ol (413 mg, 2.5 mmol) and tosic acid (713 mg, 3.8 mmol) in dioxane (5 mL) was heated at 100° C. for 60 h. The solution was poured into water (15 mL), basified to ~pH 8 with saturated aqueous NaHCO₃ and extracted with a 1:3 v/v mixture of IPA and CHCl₃ (3×20 mL). The combined organic phases were dried (MgSO₄) and evaporated under vacuum. The residue was used without further purification. MS: [M+H]⁺=237.

Preparation 139: 4,5-dichloro-N-(2-methylpyridin-4-yl)pyrimidin-2-amine

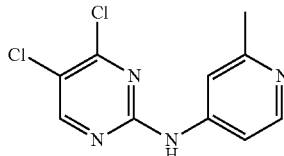

A solution of 5-chloro-2-[(2-methylpyridin-4-yl)amino]pyrimidin-4-ol (2.5 mmol, assumed) in phosphorus oxychloride (1.5 mL, 15 mmol) was heated at 90° C. for 1 h. After cooling, the solution was poured into saturated NaHCO₃ (10 mL) and extracted with EtOAc (3×10 mL). The combined organic phases were dried (MgSO₄) and evaporated under vacuum. The residue was used without further purification. MS: [M+H]⁺=255.

Preparation 140: N-tert-butyl-3-[(tert-butyldimethyl-silyl)oxy]-2-[6-(2,5-dichloropyrimidin-4-yl)-1-oxo-2,3-dihydro-1H-isoindol-2-yl]-N-methylpropanamide

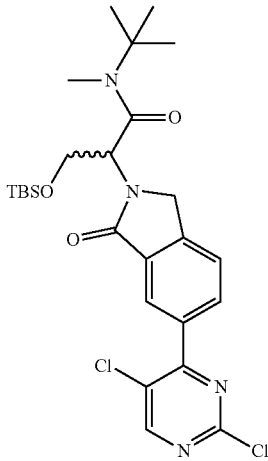 [SMILES: CN(C(=O)C(CO[Si](C)(C)C(C)(C)C)N1Cc2ccc(-c3nc(Cl)ncc3Cl)cc2C1=O)C(C)(C)C]

The product was prepared following an analogous/similar procedure as described in Example 2. In this case, further 0.4 eq. of reagents (N,2-dimethylpropan-2-amine, DIPEA, HATU) were added after 40 minutes and the mixture was stirred for a further 45 minutes. LC-MS: [M+H]⁺=551. Note: The product may have partially epimerized during the reaction as shown by chiral HPLC analysis of the final product.

Preparation 141: 2-chloro-N-phenethylpropanamide

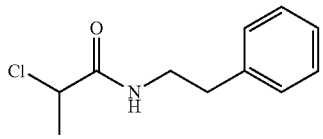

DIPEA (1.9 mL, 10.88 mmol) and then 2-chloropropanoyl chloride (0.950 mL, 9.79 mmol) were added to a stirred solution of 2-phenylethanamine (1.1 mL, 8.73 mmol) in DCM (50 mL, 777 mmol) at room temperature and the resulting pale yellow solution was stirred for 3 h. The reaction mixture was diluted with DCM (50 mL) and washed with saturated aqueous NH₄Cl (50 mL), water (50 mL), saturated aqueous NaHCO₃ (50 mL) and brine (50 mL). The organic fraction was filtered through a phase separating cartridge and then concentrated under reduced pressure and dried in the vacuum oven overnight to give a light brown solid. This material was dry-loaded on silica and purified by chromatography (SiO₂, 40 g column, 0-100% EtOAc in iso-hexanes) to afford the title compound as an off-white solid (1.82 g, 96%). LC-MS: [M+H]⁺=212.

Preparation 142: 1-methyl-2,3,4,5-tetrahydro-1H-3-benzazepin-2-one

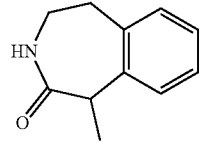

A mixture of 2-chloro-N-phenethylpropanamide (1.82 g, 8.43 mmol) and aluminium chloride (5 g, 37.5 mmol) was heated to 150° C. The resulting dark oil, which started to formed at 90° C. was heated at 150° C. under nitrogen for 4 h. The reaction mixture was allowed to cool to room temperature and was then carefully quenched by the sequential addition of MeOH (10 mL), 10% aq HCl (10 mL) and then EtOAc (20 mL). The mixture was partitioned between water (50 mL) and EtOAc (50 mL) and the layers were separated. The aqueous layer was extracted with EtOAc (2×50 mL) and the combined organic extracts were dried (MgSO₄), filtered and concentrated under reduced pressure to afford the crude product as an orange solid (1.3 g). The crude product was dry-loaded on silica and purified by chromatography (SiO₂, 40 g column, 0-100% (10% MeOH in DCM) in DCM) to afford the title compound as a pale yellow solid (0.639 g, 39%). 1H NMR (400 MHz, DMSO-d6) 7.37 (t (br), 1H), 7.12-7.22 (m, 4H), 4.28 (q, 1H), 3.70-3.78 (m, 1H), 3.14-3.29 (m, 2H), 2.90-3.00 (m, 1H), 1.35 (d, 3H).

Preparation 143: 1-methyl-2,3,4,5-tetrahydro-1H-3-benzazepine

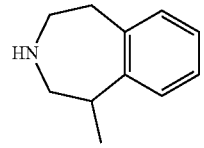

1-methyl-2,3,4,5-tetrahydro-1H-3-benzazepin-2-one (0.102 g, 0.524 mmol) was suspended in THF (5.0 mL, 61.0 mmol) in an oven-dried round bottom flask and the mixture was cooled to 0° C. Boran tetrahydrofuran complex (1 M solution in THF) (1.60 mL, 1.600 mmol) was added and the resulting yellow solution was stirred at 0° C. for 5 minutes, then refluxed under nitrogen for 4 h. Further boran tetrahydrofuran (1 M solution in THF) (1.60 mL, 1.60 mmol) was added and the mixture left to reflux under nitrogen for a further 1 h. The mixture was allowed to cool to room temperature, then cooled with an ice bath. The reaction was quenched by dropwise addition of MeOH (5 mL) and the reaction mixture was concentrated under reduced pressure and coevaporated with MeOH (3×10 mL) to afford the crude product as a pale yellow film. The crude product was dissolved in MeOH (+a few drops of AcOH), absorbed onto SCX, washed with MeOH and then eluted with 1% NH₃ in MeOH. Evaporation of the solvent under reduced pressure afforded the title compound as a yellow oil (0.056 g, 0.278 mmol, 53.0%, 80% purity). 1H NMR (400 MHz, DMSO-d6): 7.09-7.11 (m, 2H), 7.04-7.06 (m, 2H), 3.32 (s (br, overlapped with HDO), 1H), 2.96-3.04 (ddt, 1H), 2.71-2.90 (m, 5H), 2.61 (dd, 1H), 1.24 (d, 3H).

Preparation 144: 2-(2-(2-oxopropyl)phenyl)acetic acid

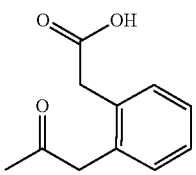

A solution of 2,2'-(1,2-phenylene)diacetic acid (2 g, 10.09 mmol) in THF (140 mL) was cooled to 0° C. 1.6M methyllithium in diethyl ether (14 mL, 22.40 mmol) was added dropwise and the mixture was stirred at 0° C. for 6 h. A further quantity of 1.6M methyllithium in diethyl ether (14 mL, 22.40 mmol) was added and the reaction mixture allowed to warm to room temperature overnight. The mixture was cooled to 0° C., and quenched with 1M HCl (120 mL). The aqueous layer was extracted with EtOAc (2×120 mL) and the combined organic extracts were dried (MgSO$_4$), filtered and concentrated under vacuum to afford the crude product (2.13 g). The crude product was purified by chromatography (SiO$_2$, 120 g column, 0-100% EtOAc (0.5% HCOOH) in isohexane) to afford 2-(2-(2-oxopropyl)phenyl) acetic acid (887 mg, 4.38 mmol, 43.4%) as an orange oil. LC-MS: [M+H]$^+$=193; [M−H]$^−$=191.

Preparation 145: 4-methyl-2,3-dihydro-1H-3-benzazepin-2-one

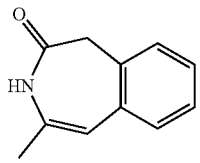

A mixture of 2-(2-(2-oxopropyl)phenyl)acetic acid (400 mg, 1.977 mmol) and ammonium acetate (305 mg, 3.95 mmol) in toluene (11 mL) was heated in a microwave (CEM, 120° C., 150 W) for 3 h. The reaction mixture was concentrated under vacuum and the crude product obtained from a separate experiment carried on the same scale was combined. The crude product was purified by chromatography on silica gel (40 g column, 0-100% EtOAc in isohexane) to afford 4-methyl-1H-benzo[d]azepin-2(3H)-one (370 mg, 2.136 mmol, 49.3%) as a brown solid. LC-MS: [M+H]$^+$=174.

Preparation 146: 4-methyl-2,3,4,5-tetrahydro-1H-3-benzazepin-2-one

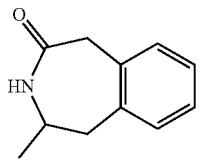

4-methyl-2,3-dihydro-1H-3-benzazepin-2-one (264 mg, 1.448 mmol) was dissolved in MeOH (15 mL) and the reaction mixture was hydrogenated in the H-Cube (10% Pd/C, 30×4 mm, Full hydrogen, 25° C., 1 mL/min) until completion of the reaction as monitored by LC-MS analysis. The reaction mixture was concentrated under vacuum and combined with a crude product obtained from a separate experiment carried out on 100 mg scale. The crude product was purified by chromatography (SiO$_2$, 24 g column, 0-100% EtOAc in isohexane) to afford 4-methyl-4,5-dihydro-1H-benzo[d]azepin-2(3H)-one (186 mg, 1.051 mmol, 51.9%) as a colourless solid. LC-MS: [M+H]$^+$=176.

Preparation 147: 2-methyl-2,3,4,5-tetrahydro-1H-3-benzazepine

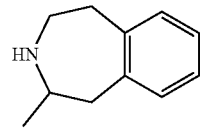

1M borane in THF (2.1 mL, 2.100 mmol) was added to a stirred solution of 4-methyl-2,3,4,5-tetrahydro-1H-3-benzazepin-2-one (183 mg, 1.034 mmol) in THF (40 mL) under nitrogen and the mixture was stirred at room temperature overnight. A further quantity of 1M borane in THF (2.1 mL, 2.100 mmol) was added and stirring continued at room temperature overnight. The reaction mixture was concentrated under vacuum to give a colourless semi-solid (230 mg), which was dissolved in the minimum of MeOH and loaded onto SCX. The column was washed with MeOH (3 column volumes) and the compound was eluted with 1% NH$_3$ in MeOH (3 column volumes). Evaporation of the solvent under vacuum afforded 2-methyl-2,3,4,5-tetrahydro-1H-benzo[d]azepine as an oil (113 mg). 1H NMR (400 MHz, DMSO-d6) 7.04-7.07 (m, 4H), 3.07 (ddd, 1H), 2.87 (ddd, 1H), 2.58-2.80 (m, 4H), 2.47-2.54 (m, 2H (overlapped with DMSO)), 1.06 (d, 3H).

Preparation 148: methyl 2,3,4,5-tetrahydro-1H-3-benzazepine-2-carboxylate

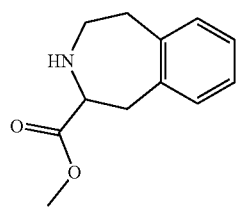

Thionyl chloride (0.160 mL, 2.196 mmol) was added dropwise to a solution of 2,3,4,5-tetrahydro-1H-benzo[d] azepine-2-carboxylic acid hydrochloride (250 mg, 1.098 mmol) in methanol (10 mL) and the mixture was heated at 65° C. for 18 h. The mixture was allowed to cool to room temperature and was concentrated under vacuum. The crude product was loaded onto a column of SCX (3 g) in methanol (2 mL). The column was washed with MeOH and the product was eluted with 0.7 M ammonia in MeOH. The resulting mixture was concentrated under vacuum to afford methyl 2,3,4,5-tetrahydro-1H-benzo[d]azepine-2-carboxylate (218 mg, 1.009 mmol, 92%) as a brown oil. 1H NMR (400 MHz, DMSO-d6): 7.05-7.17 (m, 4H), 3.60 (s, 3H), 3.43 (dd, 1H), 3.18 (s (br), 1H), 3.12 (ddd, 1H), 3.05-3.08 (m, 2H), 2.89 (ddd, 1H), 2.78 (ddd, 1H), 2.61 (ddd, 1H).

Preparation 149: (2,3,4,5-tetrahydro-1H-3-benzazepin-2-yl)methanol

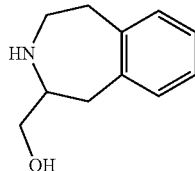

Lithium borohydride (2 M in THF) (1.062 mL, 2.124 mmol) was added to a solution of methyl 2,3,4,5-tetrahydro-1H-3-benzazepine-2-carboxylate (218 mg, 1.062 mmol) in THF (2 mL, 24.41 mmol) and the mixture was stirred at room temperature overnight. The reaction was quenched with 1 M HCl (5 mL) and the crude mixture was loaded onto a column of SCX (5 g). The column was washed with MeOH. The mixture was concentrated under vacuum and the residue was dissolved in 2 M NaOH (5 mL) and extracted with EtOAc (3×5 mL). The combined organic phases were washed with brine (10 mL), dried (MgSO₄) and concentrated under vacuum to give the title compound (100 mg, 0.406 mmol, 38.2%) as a colourless oil. 1H NMR (400 MHz, DMSO-d6): 7.04-7.14 (m, 4H), 4.72 (s (br), 1H), 3.22-3.39 (m, 2H), 3.18 (ddd, 1H), 2.91 (ddd, 1H), 2.61-2.84 (m, 3H), 2.43-2.50 (m, 3H—overlapped with DMSO-d6). LC-MS: [M+H]⁺=178.

Preparation 150: 2-(2-iodophenyl)ethanamine

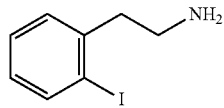

A solution of borane tetrahydrofuran complex (1M in THF) (24.69 ml, 24.69 mmol) was added to a stirred solution of 2-(2-iodophenyl)acetonitrile (1.702 ml, 8.23 mmol) in THF (23.6 ml). The reaction mixture was heated to reflux under nitrogen for 2 h and was allowed to cool to room temperature. The mixture was then cooled to 0° C., and 6M HCl (4 mL) was added. The mixture was then basified with 2 M NaOH and extracted with DCM (3×20 ml). The organic layer was washed with water and brine, dried (MgSO₄), and concentrated under vacuum to afford the title compound (2 g, 7.69 mmol, 93%), which was used in the next step without further purification. LC-MS: [M+H]⁺=248.

Preparation 151: 2,2,2-trifluoro-N-(2-iodophenethyl)acetamide

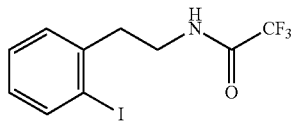 [SMILES: O=C(NCCc1ccccc1I)C(F)(F)F]

Trifluoroacetic anhydride (2.325 ml, 16.46 mmol) in DCM (5 ml) was added dropwise to an ice cold solution of 2-(2-iodophenyl)ethanamine (2.033 g, 8.23 mmol) and triethylamine (3.44 ml, 24.69 mmol) in DCM (10 ml). The reaction mixture was stirred at room temperature overnight. The mixture was then diluted with EtOAc (500 mL), washed sequentially with 10% aqueous HCl (100 mL), water (100 mL), brine (100 mL), dried (MgSO₄) and evaporated under vacuum to give an oil. Purification by chromatography (SiO₂, 40 column, 0-20% EtOAc in isohexane) afforded the title compound (2.5 g, 6.92 mmol, 84%) as a yellow oil. LC-MS: [M+H]⁺=344.

Preparation 152: 2,2,2-trifluoro-N-[2-(2-iodophenyl) ethyl]-N-(prop-2-en-1-yl)acetamide

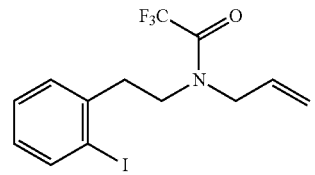 [SMILES: C=CCN(CCc1ccccc1I)C(=O)C(F)(F)F]

2,2,2-trifluoro-N-(2-iodophenethyl)acetamide (2.45 g, 7.14 mmol) was added to a stirred suspension of KOH (1.202 g, 21.42 mmol) and tetrabutylammonium hydrogen sulfate (0.242 g, 0.714 mmol) in toluene (73.8 ml) and the solution was stirred at room temperature for 10 minutes. The resulting mixture was treated with allyl bromide (0.618 ml, 7.14 mmol) followed immediately by Pd(PPh₃)₄ (0.660 g, 0.571 mmol) and the yellow suspension was heated at 60° C. under nitrogen for 20 minutes. The mixture was cooled to 0° C. and treated dropwise with water (5 mL) with stirring. The layers were separated and the aqueous layer was extracted with DCM (50 ml). The combined organic extracts were dried (MgSO₄), filtered and concentrated under vacuum. The residue was purified by chromatography (SiO₂, 80 g column, 0-10% of EtOAc in Hexane) to afford the title compound (1.9 g, 4.71 mmol, 66.0%) as a yellow oil. LC-MS: [M+H]⁺=384.

Preparation 153: 2,2,2-trifluoro-1-(1-methylidene-2, 3,4,5-tetrahydro-1H-3-benzazepin-3-yl)ethan-1-one

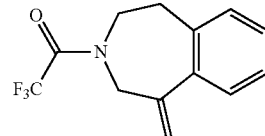

A stirred suspension of 2,2,2-trifluoro-N-[2-(2-iodophenyl)ethyl]-N-(prop-2-en-1-yl)acetamide (1.9 g, 4.96 mmol), palladium (II) acetate (0.111 g, 0.496 mmol), triphenylphosphine (0.260 g, 0.992 mmol), potassium acetate (1.460 g, 14.88 mmol), tetrabutylammonium bromide (1.758 g, 5.45 mmol) in DMF (96 ml, 1240 mmol) was degassed with nitrogen for 10 minutes. The resulting mixture was stirred at 80° C. under nitrogen for 5 h and was allowed to cool to room temperature. The mixture was cooled to 0° C. and diluted with water (75 ml) and Et₂O (75 ml). The layers were separated and the aqueous layer was extracted with Et₂O (50 ml×2). The combined organic extracts were dried (MgSO₄) and evaporated to give a brown oil. The residue was purified by chromatography (SiO₂, 80 g column, 0-10% of EtOAc in Hexane) to afford the title compound (850 mg, 3.30 mmol, 66.5%) as a colourless oil. LC-MS: [M+H]⁺=256.

Preparation 154: 2,2,2-trifluoro-1-[1-(hydroxymethyl)-2,3,4,5-tetrahydro-1H-3-benzazepin-3-yl]ethan-1-one

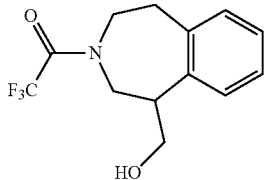 [SMILES: O=C(N1CCc2ccccc2C(CO)C1)C(F)(F)F]

A solution of 2,2,2-trifluoro-1-(1-methylidene-2,3,4,5-tetrahydro-1H-3-benzazepin-3-yl)ethan-1-one (260 mg, 1.019 mmol) in THF (3 mL, 36.6 mmol) was treated with borane tetrahydrofuran complex (1M in THF) (1.121 mL, 1.121 mmol), and stirred at room temperature for 1 h. Water (1.5 mL), saturated aqueous NaHCO₃ (1.5 mL), and 30% H₂O₂ (0.6 mL) were added sequentially and the reaction stirred for 1 h. The reaction mixture was diluted with EtOAc (20 mL) and the layers were separated. The organic extract was then washed with brine (10 mL), dried (MgSO₄) and concentrated to give a brown oil. The residue was purified by chromatography (SiO₂, 12 g column, 0-40% of EtOAc in Hexane) to afford the title compound (70 mg, 0.243 mmol, 23.9%) as a colourless oil. LC-MS: [M+H]⁺=274.

Preparation 155: (2,3,4,5-tetrahydro-1H-3-benzazepin-1-yl)methanol

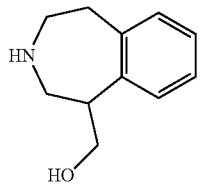 [SMILES: OCC1CNCCc2ccccc21]

A solution of 2,2,2-trifluoro-1-[1-(hydroxymethyl)-2,3,4, 5-tetrahydro-1H-3-benzazepin-3-yl]ethan-1-one (65 mg, 0.238 mmol) in MeOH (1 ml, 24.72 mmol) was treated with 2N NaOH (0.238 ml, 0.476 mmol) and the mixture was stirred at room temperature overnight. Acetic acid (0.041 ml, 0.714 mmol) was added and the mixture was diluted with MeOH (4 ml), then loaded onto a column of SCX (2 g). The column was washed with MeOH and the product was eluted with 0.7 M ammonia in MeOH. Evaporation of the solvent under vacuum afforded the title compound (35 mg, 0.188 mmol, 79%) as a thick colourless oil. LC-MS: [M+H]⁺=178.

Preparation 156: 2-methyl-1-phenoxypropan-2-amine

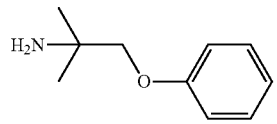

Methyl magnesium bromide (3M in Et₂O) (1314 µl, 3.94 mmol) was added to a solution of 2-phenoxyacetonitrile (138 µl, 1.127 mmol) in THF (5 mL) under nitrogen. The resulting mixture was refluxed under nitrogen for 1 hour and titanium (IV) isopropoxide (330 µl, 1.127 mmol) was added dropwise. After heating overnight under nitrogen at 50° C., brine (10 mL) was added. The mixture was extracted with DCM (2×20 mL), and the combined organic extracts were washed with brine (10 mL), dried (Na₂SO₄) and evaporated under vacuum to give the title compound (136 mg, 69%) as a brown oil. 1H NMR (400 MHz, CDCl₃): 7.26-7.31 (m, 2H), 6.89-6.97 (m, 3H), 3.70 (s, 2H), 1.25 (s, 6H) (2 exchangeable protons were not observed).

Preparation 157: tert-butyl 5-bromo-1-methyl-1,2,3,4-tetrahydroisoquinoline-2-carboxylate

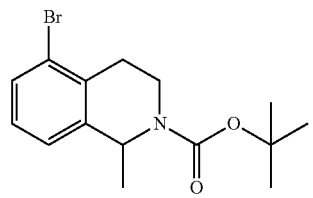 [SMILES: CC1c2cccc(Br)c2CCN1C(=O)OC(C)(C)C]

Di-tert-butyl dicarbonate (1.324 g, 6.07 mmol) was added in THF (5 mL) to a solution of 5-bromo-1-methyl-1,2,3,4-tetrahydroisoquinoline (1.143 g, 5.05 mmol) in THF (15 mL) and the mixture was stirred at room temperature for 3 days. The reaction mixture was absorbed onto silica and the crude product was purified by chromatography (SiO₂, 40 g column, 0-10% EtOAc in isohexane) to afford the title compound (1.549 g, 93%) as a colourless oil, which solidified on standing to a colourless solid. 1H NMR (400 MHz, CDCl₃): 7.42 (dd, 1H), 7.02-7.10 (m, 2H), 5.19 (m (br), 1H), 4.18 (m (br), 1H), 3.15 (m (br), 1H), 2.70-2.94 (m, 2H), 1.49 (s, 9H), 1.44 (d, 3H). LC-MS: [M-tBu+H]⁺=270.

Preparation 158: tert-butyl 5-formyl-1-methyl-1,2,3,4-tetrahydroisoquinoline-2-carboxylate

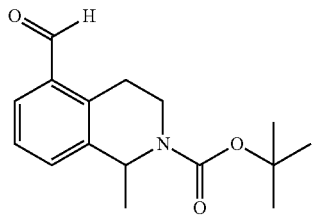 [SMILES: CC1c2cccc(C=O)c2CCN1C(=O)OC(C)(C)C]

Tert-butyl lithium (1.7 M in pentane) (6.03 ml, 10.25 mmol) was added dropwise over 10 minutes to a stirred solution of tert-butyl 5-bromo-1-methyl-1,2,3,4-tetrahydroisoquinoline-2-carboxylate (1.535 g, 4.66 mmol) in THF (26 mL) at −78° C. under nitrogen and the resulting dark orange/red solution was stirred at −78° C. for 30 minutes. Morpholine-4-carbaldehyde (0.700 ml, 6.99 mmol) was added dropwise and the resulting pale-yellow solution allowed to warm slowly to room temperature and stirred for 1.5 h. The reaction was quenched carefully with saturated aqueous NH$_4$Cl (50 mL) and extracted with EtOAc (2×50 mL). The combined organic extracts were washed with brine (1×100 mL), dried (MgSO$_4$), filtered and concentrated under vacuum to afford a pale yellow oil (1.377 g) (1399-40-4a). The crude product was purified by chromatography (SiO$_2$, 24 g column, 0-50% EtOAc in isohexane) to afford the title compound (793 mg, 2.71 mmol, 58.1%) as a pale yellow oil. LC-MS: [M+Na]$^+$=298.

Preparation 159: tert-butyl 5-(hydroxymethyl)-1-methyl-1,2,3,4-tetrahydroisoquinoline-2-carboxylate

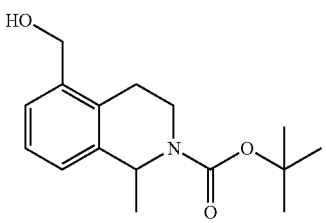 [SMILES: CC1c2cccc(CO)c2CCN1C(=O)OC(C)(C)C]

Sodium borohydride (120 mg, 3.18 mmol) was added to an ice-cooled stirred solution of tert-butyl 5-formyl-1-methyl-1,2,3,4-tetrahydroisoquinoline-2-carboxylate (777 mg, 2.65 mmol) in 1:1 THF/MeOH (19 mL) under nitrogen. The reaction was allowed to warm to room temperature and stirred for 1 h. The reaction was ice-cooled, quenched with saturated aqueous NH$_4$C (75 mL) and extracted with DCM (3×75 mL). The combined organic extracts were washed with brine (1×100 mL), dried (MgSO$_4$), filtered and concentrated under vacuum to afford the title compound (756 mg, 2.59 mmol, 98%) a colourless gum. 1H NMR (400 MHz, CDCl$_3$): 7.18-7.26 (m, 2H), 7.09 (dd, 1H), 5.06-5.32 (m (br), 1H), 4.70 (d, 1H), 4.66 (d, 1H), 3.98-4.31 (m, (br), 1H), 3.07-3.33 (m (br), 1H), 2.77-2.91 (m, 2H), 1.49 (s, 9H), 1.45 (d, 3H). (1 exchangeable proton was not observed).

Preparation 160: (1-methyl-1,2,3,4-tetrahydroisoquinolin-5-yl)methanol

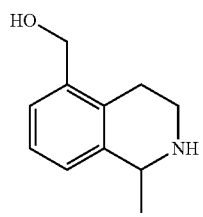

HCl (4M in dioxane) (12.6 mL, 50.4 mmol) was added dropwise at 0° C. to tert-butyl 5-(hydroxymethyl)-1-methyl-1,2,3,4-tetrahydroisoquinoline-2-carboxylate (700 mg, 2.52 mmol) and the resulting solution was stirred at room temperature for 3 h. The mixture was concentrated under vacuum and the residue was loaded onto a column of SCX (10 g) in MeOH (15 ml). The column was washed with MeOH (2×15 ml) and the product was eluted with 0.7 M ammonia in MeOH. Evaporation of the solvents under vacuum afforded the title compound (366 mg, 81%) as a colourless solid. LC-MS: [M+H]$^+$=178.

Preparation 161: 5-{[(tert-butyldimethylsilyl)oxy]methyl}-1-methyl-1,2,3,4-tetrahydro-isoquinoline

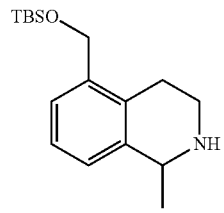 [SMILES: CC1NCCc2c(CO[Si](C)(C)C(C)(C)C)cccc21]

To a stirred solution of (1-methyl-1,2,3,4-tetrahydroisoquinolin-5-yl)methanol (366 mg, 2.065 mmol) in DMF (6.4 mL) under nitrogen at 0° C. was added imidazole (422 mg, 6.19 mmol) and tert-butylchlorodimethylsilane (467 mg, 3.10 mmol). The reaction was allowed to warm slowly to room temperature and stirred for 3 days. The reaction was quenched with water (20 mL) and extracted with EtOAc (20 mL). The organic extracts were combined and washed with brine (3×20 mL) and then dried (MgSO$_4$), filtered and concentrated under vacuum to afford a 3:2 mixture of the title compound and 5-{[(tert-butyldimethylsilyl)oxy]methyl}-1-methyl-1,2,3,4-tetrahydroisoquinoline-2-carbaldehyde as a colourless oil (659 mg). The product was used without further purification in the next step. LC-MS: [M+H]$^+$=292.

Preparation 162: 2-[2-(5-{[(tert-butyldimethylsilyl)oxy]methyl}-1-methyl-1,2,3,4-tetrahydroisoquinolin-2-yl)-2-oxoethyl]-6-{5-chloro-2-[(oxan-4-yl)amino]pyrimidin-4-yl}-2,3-dihydro-1H-isoindol-1-one

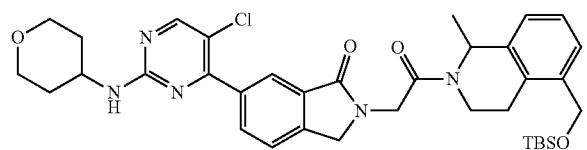 [SMILES: CC1c2cccc(CO[Si](C)(C)C(C)(C)C)c2CCN1C(=O)CN1Cc2ccc(-c3nc(NC4CCOCC4)ncc3Cl)cc2C1=O]

HATU (644 mg, 1.694 mmol) was added to a mixture of 2-(6-{5-chloro-2-[(oxan-4-yl)amino]pyrimidin-4-yl}-1-oxo-2,3-dihydro-1H-isoindol-2-yl)acetic acid (650 mg, 1.614 mmol), 5-{[(tert-butyldimethylsilyl)oxy]methyl}-1-methyl-1,2,3,4-tetrahydro-isoquinoline (659 mg, 1.356 mmol) and triethylamine (337 µl, 2.420 mmol) in DCM (10 ml) and the mixture was stirred for 3 h. The reaction mixture was concentrated under vacuum and then diluted with EtOAc (30 mL) and washed with 1M HCl (30 ml), saturated aqueous NaHCO$_3$ (30 mL), water (30 mL) and brine (30 mL), dried (MgSO$_4$), filtered and concentrated under vacuum to give a yellow oil. The residue was purified by chromatography (SiO$_2$, 12 g column, 0-6% MeOH in DCM) to afford the title compound (390 mg, 0.490 mmol, 30.4%) as a colourless solid. LC-MS: [M+H]$^+$=676.

Preparation 163: tert-Butyl 2-[(6-{5-chloro-2-[(oxan-4-yl)amino]pyrimidin-4-yl}-1-oxo-2,3-dihydro-1H-isoindol-2-yl)methyl]pyrrolidine-1-carboxylate

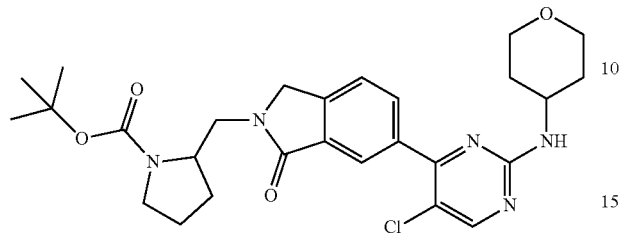

Prepared from tert-butyl 2-{[6-(2,5-dichloropyrimidin-4-yl)-1-oxo-2,3-dihydro-1H-isoindol-2-yl]methyl}pyrrolidine-1-carboxylate (Preparation 55) using a similar procedure to that described for Preparation 4.

Preparation 164: (2S)—N-tert-butyl-3-[(tert-butyldimethylsilyl)oxy]-2-(6-{5-chloro-2-[(oxan-4-yl)amino]pyrimidin-4-yl}-1-oxo-2,3-dihydro-1H-isoindol-2-yl)-N-methylpropanamide

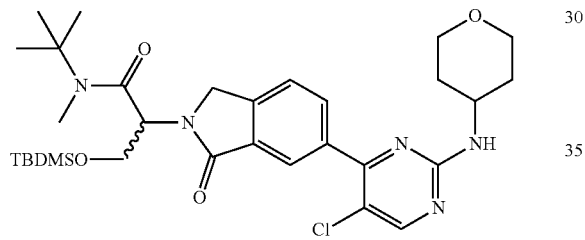

Prepared from N-tert-butyl-3-[(tert-butyldimethylsilyl)oxy]-2-[6-(2,5-dichloropyrimidin-4-yl)-1-oxo-2,3-dihydro-1H-isoindol-2-yl]-N-methylpropanamide (Preparation 140) using a similar procedure to that described for Preparation 4.

Preparation 165: tert-butyl 2-[6-(2-chloropyrimidin-4-yl)-1-oxo-2,3-dihydro-1H-isoindol-2-yl]acetate

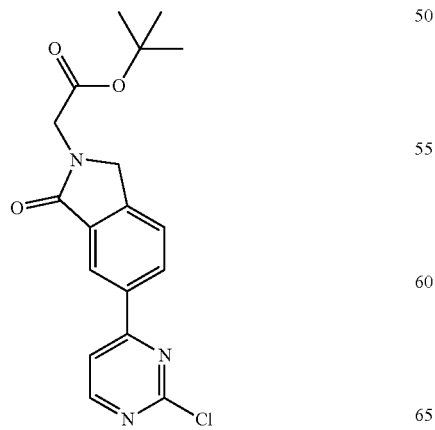

Prepared in an analogous manner to preparation 3 using 2,4-dichloropyrimidine. MS: [M-tBu+H]⁺=304.

Preparation 166: 2-[6-(2-chloropyrimidin-4-yl)-1-oxo-2,3-dihydro-1H-isoindol-2-yl]acetic acid

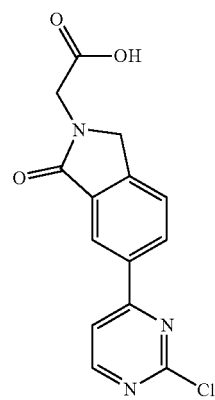 [SMILES: O=C(O)CN1Cc2ccc(-c3ccnc(Cl)n3)cc2C1=O]

Preparation 165 was treated with TFA as described in Preparation 9. MS: [M+H]⁺=304.

Preparation 167: 2-[6-(2-chloropyrimidin-4-yl)-1-oxo-2,3-dihydro-1H-isoindol-2-yl]-N-[(1S)-2-hydroxy-1-(3-methoxyphenyl)ethyl]acetamide

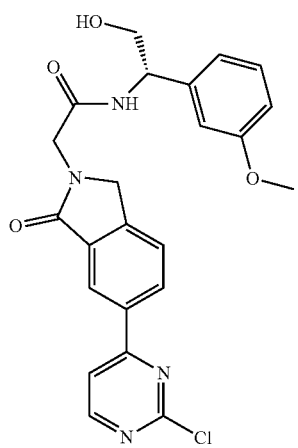 [SMILES: COc1cccc([C@@H](CO)NC(=O)CN2Cc3ccc(-c4ccnc(Cl)n4)cc3C2=O)c1]

Prepared from Preparation 166 using a method analogous to Example 2. MS: [M+H]⁺=453.

Preparation 168: 2-[6-(2,5-dichloropyrimidin-4-yl)-1-oxo-2,3-dihydro-1H-isoindol-2-yl]acetic acid

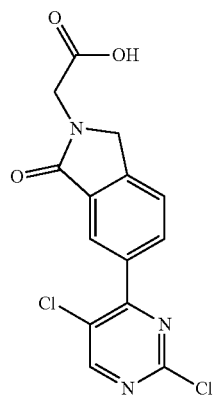 [SMILES: O=C(O)CN1Cc2ccc(-c3nc(Cl)ncc3Cl)cc2C1=O]

Preparation 3 was treated with TFA as described in Preparation 9. MS: [M+H]⁺=338.

Preparations 169-171

The following were prepared from preparation 168 and the corresponding amine using a method analogous to Example 2.

| Preparation | Structure | Name | MS: [M + H]⁺ |
|---|---|---|---|
| 169 | 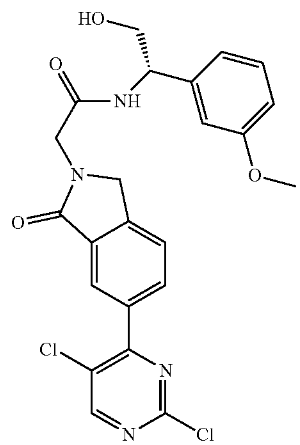 [SMILES: COc1cccc([C@@H](CO)NC(=O)CN2Cc3ccc(-c4nc(Cl)ncc4Cl)cc3C2=O)c1] | 2-[6-(2,5-dichloropyrimidin-4-yl)-1-oxo-2,3-dihydro-1H-isoindol-2-yl]-N-[(1S)-2-hydroxy-1-(3-methoxyphenyl)ethyl]acetamide | 487 |
| 170 | 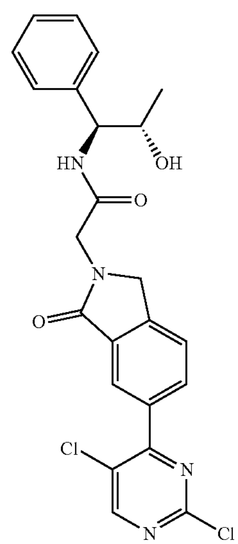 [SMILES: C[C@H](O)[C@@H](NC(=O)CN1Cc2ccc(-c3nc(Cl)ncc3Cl)cc2C1=O)c1ccccc1] | 2-[6-(2,5-dichloropyrimidin-4-yl)-1-oxo-2,3-dihydro-1H-isoindol-2-yl]-N-[(1S,2S)-2-hydroxy-1-phenylpropyl]acetamide | 471 |

| Preparation | Structure | Name | MS: [M + H]+ |
|---|---|---|---|
| 171 | 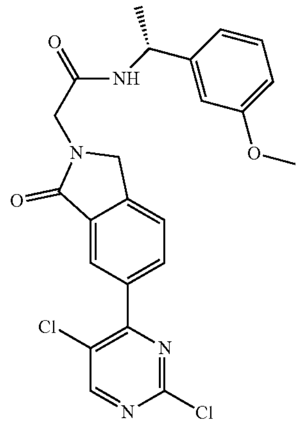 [SMILES: COc1cccc([C@@H](C)NC(=O)CN2Cc3ccc(-c4nc(Cl)ncc4Cl)cc3C2=O)c1] | 2-[6-(2,5-dichloropyrimidin-4-yl)-1-oxo-2,3-dihydro-1H-isoindol-2-yl]-N-[(1R)-1-(3-methoxyphenyl)ethyl]acetamide | 471 |

Preparation 172: tert-butyl 2-[6-(5-amino-2-chloro-pyrimidin-4-yl)-1-oxo-2,3-dihydro-1H-isoindol-2-yl]acetate Preparation 173: tert-butyl 2-[6-(5-bromo-2-chloro-pyrimidin-4-yl)-1-oxo-2,3-dihydro-1H-isoindol-2-yl]acetate

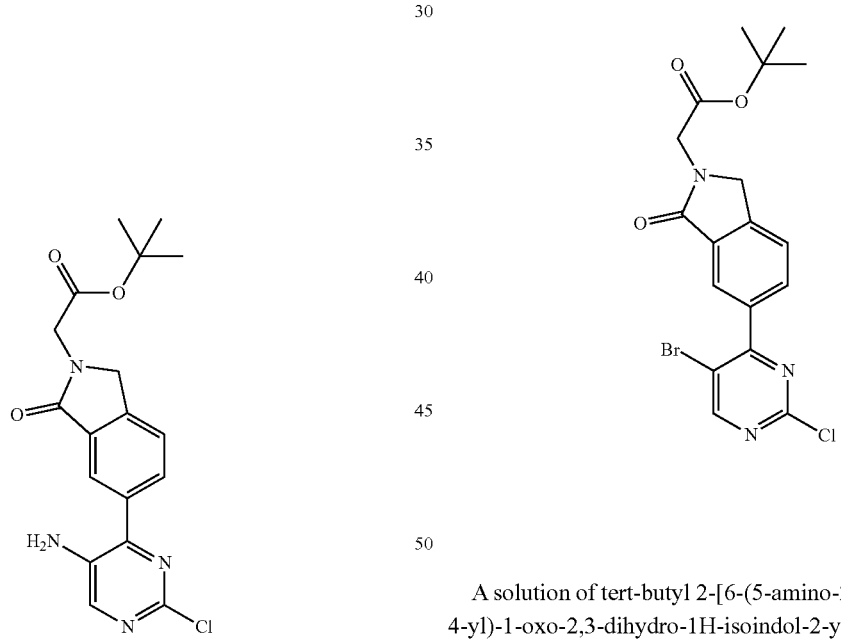

tert-Butyl 2-[1-oxo-6-(4,4,5,5-tetramethyl-1,3,2-dioxaborolan-2-yl)-2,3-dihydro-1H-isoindol-2-yl]acetate (Preparation 2) was coupled with 5-amino-2,4-dichloropyrimidine (1.97 g, 12 mmol) in a manner analogous to preparation 3 to give the title compound (2 g, 5.3 mmol). MS: [M+H]+=375.

A solution of tert-butyl 2-[6-(5-amino-2-chloropyrimidin-4-yl)-1-oxo-2,3-dihydro-1H-isoindol-2-yl]acetate (374 mg, 1 mmol) in MeCN (5 mL) was cooled to 0° C. tert-Butyl nitrite (0.23 mL, 2 mmol) was added, followed by copper (1) bromide (144 mg, 1 mmol). The reaction was stirred overnight whilst warming to room temperature, then water (10 mL) was added. The layers were separated and the aqueous fraction was extracted with DCM (2×10 mL). The combined organic fractions were dried over magnesium sulfate, filtered and concentrated. The residue was purified by chromatography (SiO₂, 25 g column, 20-100% EtOAc in petrol) to give the title compound (175 mg, 40%). MS: [M+H-$^t$Bu]+=384.

283

Preparation 174: tert-butyl 2-(6-{5-bromo-2-[(oxan-4-yl)amino]pyrimidin-4-yl}-1-oxo-2,3-dihydro-1H-isoindol-2-yl)acetate

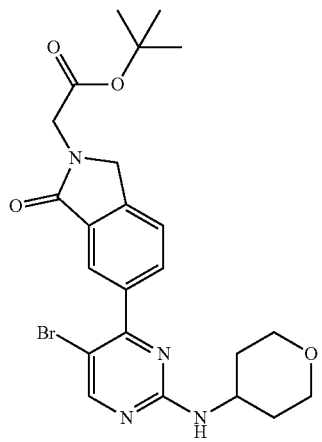 [SMILES: CC(C)(C)OC(=O)CN1Cc2ccc(-c3nc(NC4CCOCC4)ncc3Br)cc2C1=O]

tert-Butyl 2-[6-(5-bromo-2-chloropyrimidin-4-yl)-1-oxo-2,3-dihydro-1H-isoindol-2-yl]acetate (175 mg, 0.4 mmol) was treated with oxan-4-amine in a manner analogous to preparation 4 to give the title compound (100 mg, 50%). MS: [M+H]$^+$=503.

Preparation 175: 2-(6-{5-bromo-2-[(oxan-4-yl)amino]pyrimidin-4-yl}-1-oxo-2,3-dihydro-1H-isoindol-2-yl)acetic acid

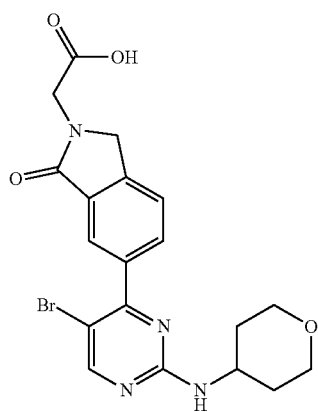 [SMILES: O=C(O)CN1Cc2ccc(-c3nc(NC4CCOCC4)ncc3Br)cc2C1=O]

284 tert-Butyl 2-(6-{5-bromo-2-[(oxan-4-yl)amino]pyrimidin-4-yl}-1-oxo-2,3-dihydro-1H-isoindol-2-yl)acetate (100 mg, 0.2 mmol) was treated with TFA as described in preparation 9 to give the title compound (90 mg, quant.). MS: [M+H]$^+$=447.

Preparation 176: 2-[6-(5-bromo-2-chloropyrimidin-4-yl)-1-oxo-2,3-dihydro-1H-isoindol-2-yl]-N-[(1S)-2-hydroxy-1-(3-methoxyphenyl)ethyl]acetamide

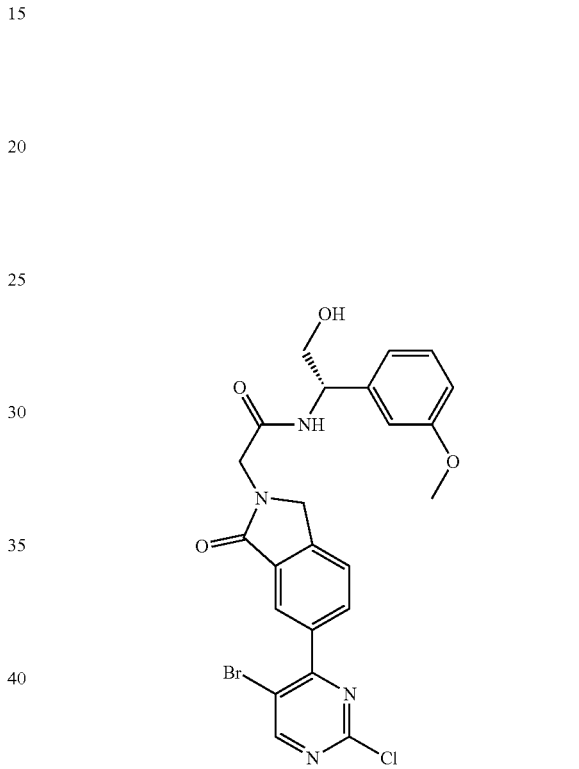

Prepared from (2S)-2-amino-2-(3-methoxyphenyl)ethan-1-ol and 2-[6-(5-bromo-2-chloropyrimidin-4-yl)-1-oxo-2,3-dihydro-1H-isoindol-2-yl]acetic acid in a manner analogous to Example 2. MS: [M+H]$^+$=384.

Preparations 177 and 178

Prepared in similar manner to preparation 176 using the corresponding amine.

| Preparation | Structure | Name | MS: [M + H]+ |
|---|---|---|---|
| 177 | 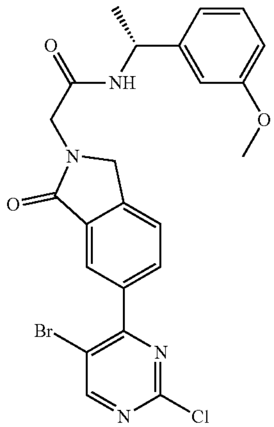 [SMILES: COc1cccc([C@@H](C)NC(=O)CN2Cc3ccc(-c4nc(Cl)ncc4Br)cc3C2=O)c1] | 2-[6-(5-bromo-2-chloropyrimidin-4-yl)-1-oxo-2,3-dihydro-1H-isoindol-2-yl]-N-[(1R)-1-(3-methoxyphenyl)ethyl]acetamide | 515 |
| 178 | 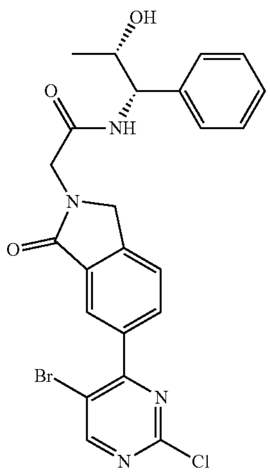 [SMILES: C[C@H](O)[C@@H](NC(=O)CN1Cc2ccc(-c3nc(Cl)ncc3Br)cc2C1=O)c1ccccc1] | 2-[6-(5-bromo-2-chloropyrimidin-4-yl)-1-oxo-2,3-dihydro-1H-isoindol-2-yl]-N-[(1S,2S)-2-hydroxy-1-phenylpropyl]acetamide | 515 |

Preparation 179: methyl 5-(2,5-dichloropyrimidin-4-yl)-2-methylbenzoate

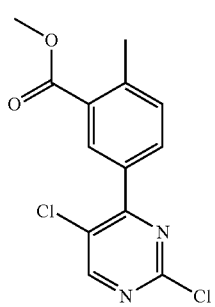 [SMILES: COC(=O)c1cc(-c2nc(Cl)ncc2Cl)ccc1C]

Prepared from methyl 5-bromo-2-methylbenzoate in a manner analogous to preparation 7. MS: [M+H]+=297.

Preparation 180: methyl 2-(bromomethyl)-5-(2,5-dichoropyrimidin-4-yl)benzoate

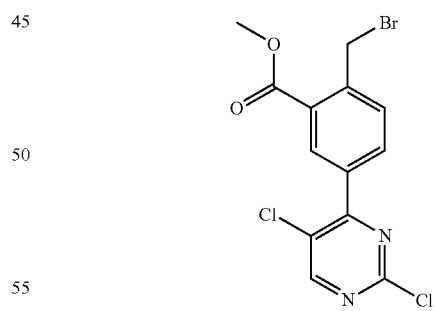

NBS (156 mg, 0.88 mmol) and AIBN (3 mg, 1% by weight of reactant) were added to a solution of methyl 5-(2,5-dichloropyrimidin-4-yl)-2-methylbenzoate (260 mg, 0.88 mmol) in 1,2-dichloroethane (3 mL). The solution was heated to 80° C. for 2 hours. The reaction was quenched by the addition of water (5 mL) and allowed to cool. The layers were separated and the aqueous fraction was further extracted with DCM (2×10 mL). The combined organic fractions were dried over magnesium sulfate, filtered and concentrated. The residue was used without further purification, although contaminated with starting material (10%) and methyl 2-(dibromomethyl)-5-(2,5-dichloropyrimidin-4-yl)benzoate (7%). MS: [M+H]$^+$=375.

Preparation 181: tert-butyl N-[(1R)-2-hydroxy-1-{[(1R)-1-(3-methoxyphenyl)ethyl]carbamoyl}ethyl]carbamate

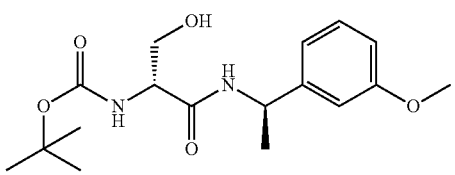 [SMILES: COc1cccc([C@@H](C)NC(=O)[C@@H](CO)NC(=O)OC(C)(C)C)c1]

A solution of N-Boc-D-serine (103 mg, 0.5 mmol), (1R)-1-(3-methoxyphenyl)ethan-1-amine (0.1 mL, 0.5 mmol), HATU (210 mg, 0.55 mmol) and triethylamine (0.3 mL, 1.5 mmol) in DCM (10 mL) was stirred at room temperature overnight. Saturated aqueous sodium hydrogen carbonate (10 mL) was added and the layers were separated. The aqueous fraction was further extracted with DCM (2×10 mL) and the combined organic fractions were dried over magnesium sulfate, filtered and concentrated. The residue was purified by chromatography (SiO$_2$, 25 g column, 0-100% EtOAc in petrol) to give the title compound (164 mg, 97%). MS: [M+H]$^+$=339.

Preparation 182: (2R)-2-amino-3-hydroxy-N-[(1R)-1-(3-methoxyphenyl)ethyl]propanamide

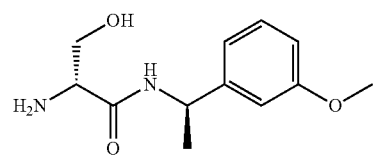 [SMILES: COc1cccc([C@@H](C)NC(=O)[C@H](N)CO)c1]

TFA (0.5 mL) was added to a solution of tert-butyl N-[(1R)-2-hydroxy-1-{[(1R)-1-(3-methoxyphenyl)ethyl]carbamoyl}ethyl]carbamate (164 mg, 0.49 mmol) in DCM (2 mL). The resulting solution was stirred at room temperature for 2 hours, then concentrated in vacuo. Toluene (5 mL) was added to the residue and this was concentrated again. This procedure was repeated. The compound was used without purification. MS: [M+H]$^+$=239.

Preparations 183-206

The following were prepared in an anlogous manner to the sequence in preparations 181 and 182.

| Preparation | Structure | Name | MS: [M + H]$^+$ |
| --- | --- | --- | --- |
| 183 | ![structure] | (2R)-2-amino-3-hydroxy-N-[(1S)-2-hydroxy-1-(3-methoxyphenyl)ethyl]-propanamide | 255 |
| 184 | ![structure] | (2R)-2-amino-N-[(1R)-1-(2-fluoro-5-methoxyphenyl)propyl]-3-hydroxypropanamide | 271 |
| 185 | ![structure] | (2R)-2-amino-N-[(1R)-2,3-dihydro-1H-inden-1-yl]-3-hydroxypropanamide | 221 |
| 186 | ![structure] | (2R)-2-amino-N-[(1R)-1-(2H-1,3-benzodioxol-5-yl)ethyl]-3-hydroxypropanamide | 253 |

-continued

| Preparation | Structure | Name | MS: [M + H]+ |
|---|---|---|---|
| 187 | 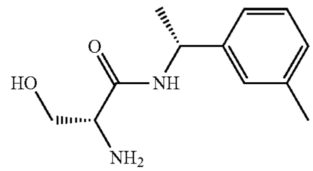 | (2R)-2-amino-3-hydroxy-N-[(1R)-1-(3-methylphenyl)ethyl]-propanamide | 233 |
| 188 | 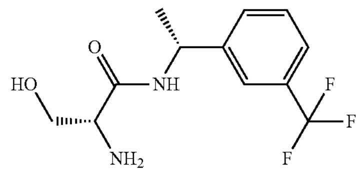 [SMILES: C[C@@H](NC(=O)[C@H](N)CO)c1cccc(C(F)(F)F)c1] | (2R)-2-amino-3-hydroxy-N-[(1R)-1-[3-(trifluoromethyl)phenyl]ethyl]-propanamide | 277 |
| 189 | 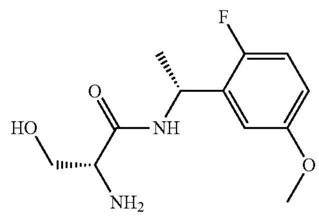 [SMILES: COc1ccc(F)c([C@@H](C)NC(=O)[C@H](N)CO)c1] | (2R)-2-amino-N-[(1R)-1-(2-fluoro-5-methoxyphenyl)ethyl]-3-hydroxypropanamide | 257 |
| 190 | 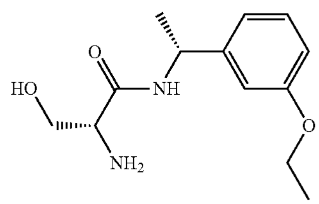 [SMILES: CCOc1cccc([C@@H](C)NC(=O)[C@H](N)CO)c1] | (2R)-2-amino-N-[(1R)-1-(3-methoxyphenyl)ethyl]-3-hydroxypropanamide | 253 |
| 191 | 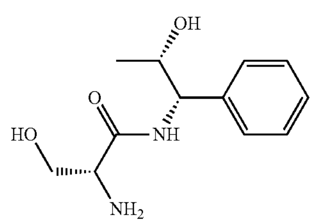 [SMILES: C[C@H](O)[C@@H](NC(=O)[C@H](N)CO)c1ccccc1] | (2R)-2-amino-3-hydroxy-N-[(1S,2S)-2-hydroxy-1-phenylpropyl]propanamide | 239 |
| 192 | 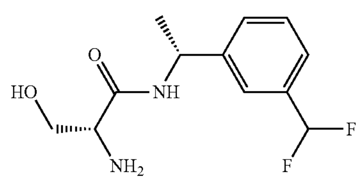 [SMILES: C[C@@H](NC(=O)[C@H](N)CO)c1cccc(C(F)F)c1] | (2R)-2-amino-N-[(1R)-1-[3-(difluoromethyl)phenyl]ethyl]-3-hydroxypropanamide | 259 |
| 193 | 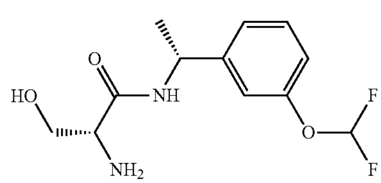 [SMILES: C[C@@H](NC(=O)[C@H](N)CO)c1cccc(OC(F)F)c1] | (2R)-2-amino-N-[(1R)-1-[3-(difluoromethoxy)phenyl]-ethyl]-3-hydroxypropanamide | 275 |
| 194 | 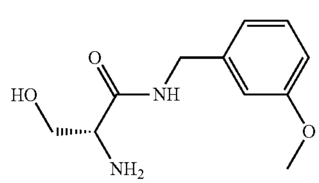 [SMILES: COc1cccc(CNC(=O)[C@H](N)CO)c1] | (2R)-2-amino-3-hydroxy-N-[(3-methoxyphenyl)methyl]-propanamide | 225 |

-continued

| Preparation | Name | MS: [M + H]+ |
|---|---|---|
| 195 | (2R)-2-amino-3-hydroxy-N-[2-(3-methoxyphenyl)propan-2-yl]propanamide | 253 |
| 196 | (2R)-2-amino-N-[(1R)-1-(2-fluoro-5-methylphenyl)ethyl]-3-hydroxypropanamide | 241 |
| 197 | (2R)-2-amino-N-[(1R)-1-(2-fluoro-3-methoxyphenyl)ethyl]-3-hydroxypropanamide | 257 |
| 198 | (2R)-2-amino-N-[(1R)-1-(3-fluoro-5-methylphenyl)ethyl]-3-hydroxypropanamide | 241 |
| 199 | (2R)-2-amino-N-[(1R)-1-(4-fluoro-3-methoxyphenyl)ethyl]-3-hydroxypropanamide | 257 |
| 200 | (2R)-2-amino-N-[(1R)-1-(3-fluoro-5-methoxyphenyl)ethyl]-3-hydroxypropanamide | 257 |
| 201 | (2R)-2-amino-3-hydroxy-N-[(1R)-1-(6-methylpyridin-2-yl)ethyl]propanamide | 224 |
| 202 | (2R)-2-amino-3-hydroxy-N-[(1R)-1-(6-methoxypyridin-2-yl)ethyl]propanamide | 240 |

| Preparation | Structure | Name | MS: [M + H]⁺ |
|---|---|---|---|
| 203 | 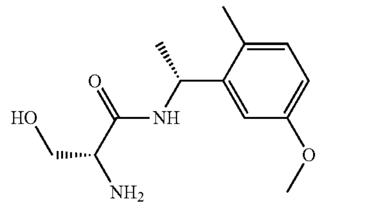 [SMILES: COc1ccc(C)c([C@@H](C)NC(=O)[C@H](N)CO)c1] | (2R)-2-amino-3-hydroxy-N-[(1R)-1-(5-methoxy-2-methylphenyl)ethyl]propanamide | 253 |
| 204 | 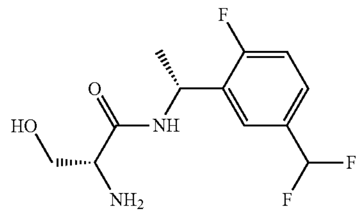 [SMILES: C[C@@H](NC(=O)[C@H](N)CO)c1cc(C(F)F)ccc1F] | (2R)-2-amino-N-[(1R)-1-[5-(difluoromethyl)-2-fluorophenyl]ethyl]-3-hydroxypropanamide | 277 |
| 205 | 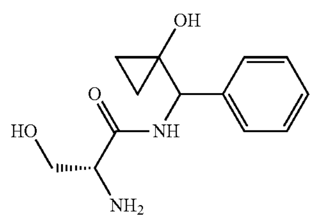 [SMILES: N[C@H](CO)C(=O)NC(c1ccccc1)C1(O)CC1] | (2R)-2-amino-3-hydroxy-N-[(1-hydroxycyclopropyl)(phenyl)methyl]propanamide | 251 |
| 206 | 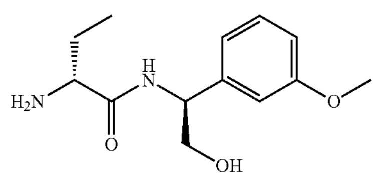 [SMILES: CC[C@@H](N)C(=O)N[C@H](CO)c1cccc(OC)c1] | (2R)-2-amino-N-[(1S)-2-hydroxy-1-(3-methoxyphenyl)ethyl]-butanamide | 253 |

Preparation 207: (2R)-2-[6-(2,5-dichloropyrimidin-4-yl)-1-oxo-2,3-dihydro-1H-isoindol-2-yl]-3-hydroxy-N-[(1R)-1-[3-(trifluoromethyl)phenyl]ethyl]propanamide

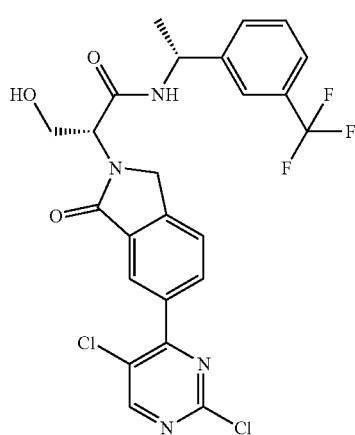 [SMILES: C[C@@H](NC(=O)[C@@H](CO)N1Cc2ccc(-c3nc(Cl)ncc3Cl)cc2C1=O)c1cccc(C(F)(F)F)c1]

A solution of methyl 2-(bromomethyl)-5-(2,5-dichloropyrimidin-4-yl)benzoate (preparation 180, 281 mg, 0.75 mmol), (2R)-2-amino-3-hydroxy-N-[(1R)-1-[3-(trifluoromethyl)phenyl]ethyl]-propanamide (preparation 189,207 mg, 0.75 mmol) and DIPEA (0.26 mL, 1.5 mmol) in MCN (5 mL) was heated to 80° C. overnight. The mixture was concentrated and the residue taken up in water (10 mL) and EtOAc (10 mL). The layers were separated and the aqueous fraction was further extracted with EtOAc (10 mL. The combined organic fractions were dried over magnesium sulfate, filtered and concentrated. The residue was purified by chromatography (SiO₂, 25 g column, 0-100% EtOAc in petrol) to give the title compound (110 mg, 27%). MS: [M+H]⁺=539.

Preparation 208-224

The following were prepared in an anlogous manner to the sequence in preparation 207.

| Preparation | Structure | Name | MS: [M + H]+ |
| --- | --- | --- | --- |
| 208 | 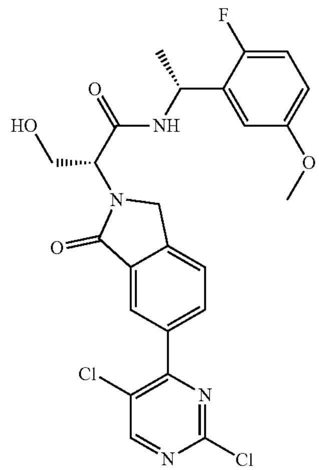 [SMILES: COc1ccc(F)c([C@@H](C)NC(=O)[C@@H](CO)N2Cc3ccc(-c4nc(Cl)ncc4Cl)cc3C2=O)c1] | (2R)-2-[6-(2,5-dichloropyrimidin-4-yl)-1-oxo-2,3-dihydro-1H-isoindol-2-yl]-N-[(1R)-1-(2-fluoro-5-methoxyphenyl)ethyl]-3-hydroxypropanamide | 519 |
| 209 | 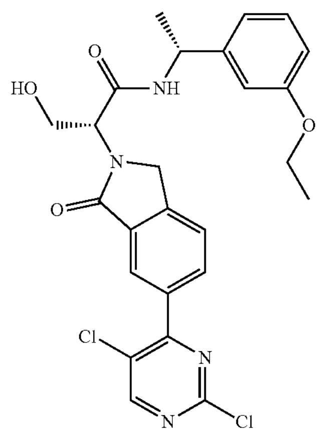 [SMILES: CCOc1cccc([C@@H](C)NC(=O)[C@@H](CO)N2Cc3ccc(-c4nc(Cl)ncc4Cl)cc3C2=O)c1] | (2R)-2-[6-(2,5-dichloropyrimidin-4-yl)-1-oxo-2,3-dihydro-1H-isoindol-2-yl]-N-[(1R)-1-(3-ethoxyphenyl)ethyl]-3-hydroxypropanamide | 515 |
| 210 | 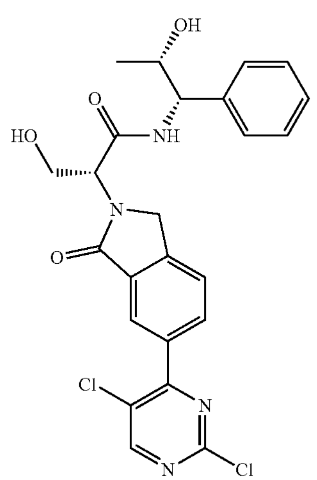 [SMILES: C[C@H](O)[C@@H](NC(=O)[C@@H](CO)N1Cc2ccc(-c3nc(Cl)ncc3Cl)cc2C1=O)c1ccccc1] | (2R)-2-[6-(2,5-dichloropyrimidin-4-yl)-1-oxo-2,3-dihydro-1H-isoindol-2-yl]-3-hydroxy-N-[(1S,2S)-2-hydroxy-1-phenylpropyl]propanamide | 501 |

-continued

| Preparation | Structure | Name | MS: [M + H]+ |
|---|---|---|---|
| 211 | 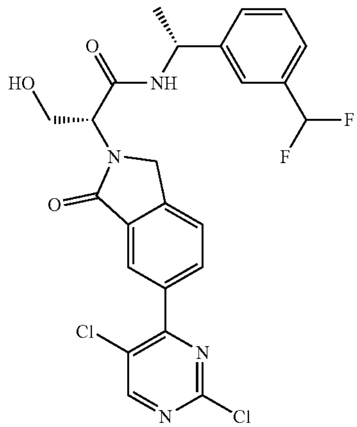 [SMILES: C[C@@H](NC(=O)[C@@H](CO)N1Cc2ccc(-c3nc(Cl)ncc3Cl)cc2C1=O)c1cccc(C(F)F)c1] | (2R)-2-[6-(2,5-dichloropyrimidin-4-yl)-1-oxo-2,3-dihydro-1H-isoindol-2-yl]-N-[(1R)-1-[3-(difluoromethyl)phenyl]ethyl]-3-hydroxypropanamide | 521 |
| 212 | 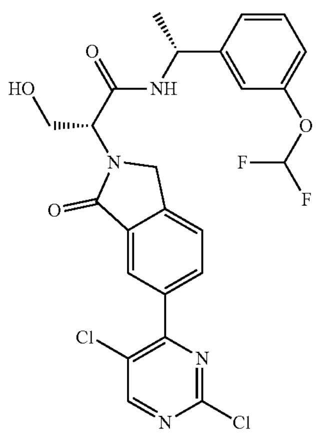 [SMILES: C[C@@H](NC(=O)[C@@H](CO)N1Cc2ccc(-c3nc(Cl)ncc3Cl)cc2C1=O)c1cccc(OC(F)F)c1] | (2R)-2-[6-(2,5-dichloropyrimidin-4-yl)-1-oxo-2,3-dihydro-1H-isoindol-2-yl]-N-[(1R)-1-[3-(difluoromethoxy)phenyl]ethyl]-3-hydroxypropanamide | 537 |
| 213 | 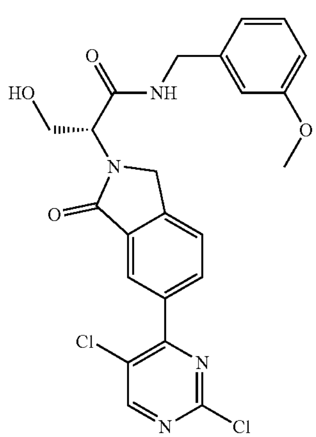 [SMILES: COc1cccc(CNC(=O)[C@@H](CO)N2Cc3ccc(-c4nc(Cl)ncc4Cl)cc3C2=O)c1] | (2R)-2-[6-(2,5-dichloropyrimidin-4-yl)-1-oxo-2,3-dihydro-1H-isoindol-2-yl]-3-hydroxy-N-[(3-methoxyphenyl)methyl]-propanamide | 487 |

| Preparation | Structure | Name | MS: [M + H]+ |
|---|---|---|---|
| 214 | 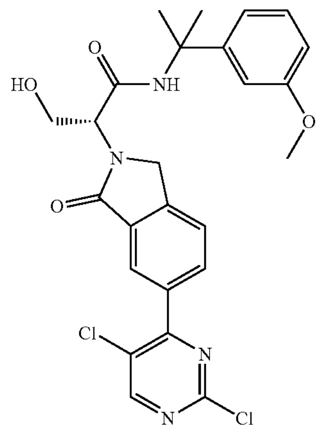 [SMILES: COc1cccc(C(C)(C)NC(=O)[C@@H](CO)N2Cc3ccc(-c4nc(Cl)ncc4Cl)cc3C2=O)c1] | (2R)-2-[6-(2,5-dichloropyrimidin-4-yl)-1-oxo-2,3-dihydro-1H-isoindol-2-yl]-3-hydroxy-N-[2-(3-methoxyphenyl)propan-2-yl]propanamide | 515 |
| 215 | 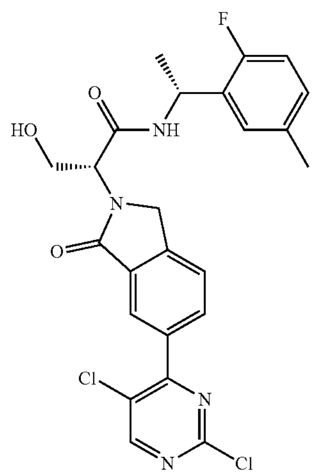 [SMILES: Cc1ccc(F)c([C@@H](C)NC(=O)[C@@H](CO)N2Cc3ccc(-c4nc(Cl)ncc4Cl)cc3C2=O)c1] | (2R)-2-[6-(2,5-dichloropyrimidin-4-yl)-1-oxo-2,3-dihydro-1H-isoindol-2-yl]-N-[(1R)-1-(2-fluoro-5-methylphenyl)ethyl]-3-hydroxypropanamide | 503 |
| 216 | 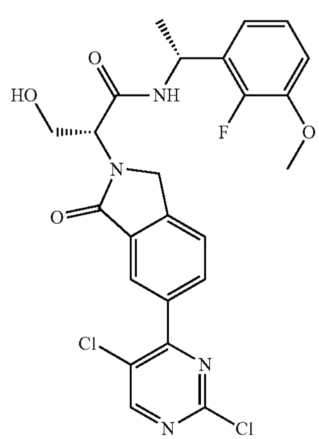 [SMILES: COc1cccc([C@@H](C)NC(=O)[C@@H](CO)N2Cc3ccc(-c4nc(Cl)ncc4Cl)cc3C2=O)c1F] | (2R)-2-[6-(2,5-dichloropyrimidin-4-yl)-1-oxo-2,3-dihydro-1H-isoindol-2-yl]-N-[(1R)-1-(2-fluoro-3-methoxyphenyl)ethyl]-3-hydroxypropanamide | 519 |

| Preparation | Structure | Name | MS: [M + H]+ |
|---|---|---|---|
| 217 | 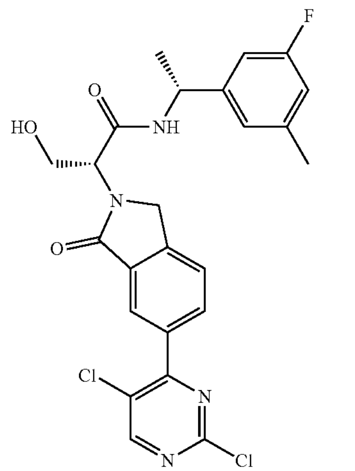 [SMILES: Cc1cc(F)cc([C@@H](C)NC(=O)[C@@H](CO)N2Cc3ccc(-c4nc(Cl)ncc4Cl)cc3C2=O)c1] | (2R)-2-(6-(2,5-dichloropyrimidin-4-yl)-1-oxo-2,3-dihydro-1H-isoindol-2-yl]-N-[(1R)-1-(3-fluoro-5-methylphenyl)ethyl]-3-hydroxypropanamide | 503 |
| 218 | 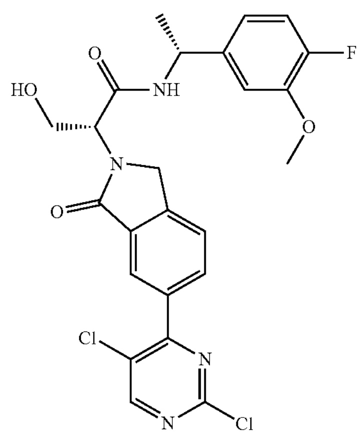 [SMILES: COc1cc([C@@H](C)NC(=O)[C@@H](CO)N2Cc3ccc(-c4nc(Cl)ncc4Cl)cc3C2=O)ccc1F] | (2R)-2-[6-(2,5-dichloropyrimidin-4-yl)-1-oxo-2,3-dihydro-1H-isoindol-2-yl]-N-[(1R)-1-(4-fluoro-3-methoxyphenyl)ethyl]-3-hydroxypropanamide | 519 |
| 219 | 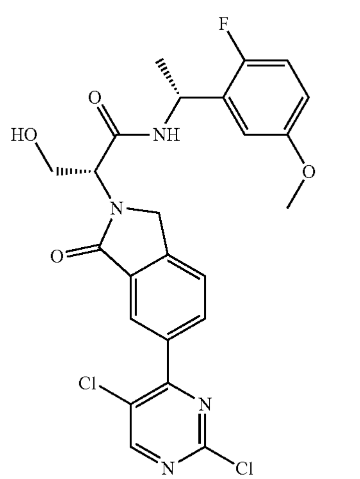 [SMILES: COc1ccc(F)c([C@@H](C)NC(=O)[C@@H](CO)N2Cc3ccc(-c4nc(Cl)ncc4Cl)cc3C2=O)c1] | (2R)-2-[6-(2,5-dichloropyrimidin-4-yl)-1-oxo-2,3-dihydro-1H-isoindol-2-yl]-N-[(1R)-1-(2-fluoro-5-methoxyphenyl)ethyl]-3-hydroxypropanamide | 519 |

-continued

| Preparation | Structure | Name | MS: [M + H]+ |
|---|---|---|---|
| 220 | 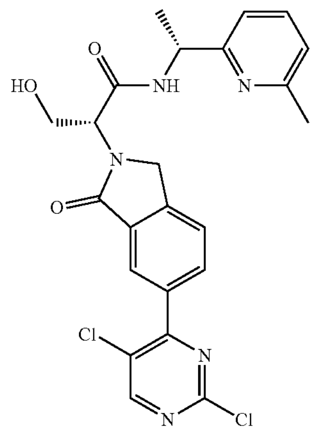 [SMILES: Cc1cccc([C@@H](C)NC(=O)[C@@H](CO)N2Cc3ccc(-c4nc(Cl)ncc4Cl)cc3C2=O)n1] | (2R)-2-[6-(2,5-dichloropyrimidin-4-yl)-1-oxo-2,3-dihydro-1H-isoindol-2-yl]-3-hydroxy-N-[(1R)-1-(6-methylpyridin-2-yl)ethyl]propanamide | 486 |
| 221 | 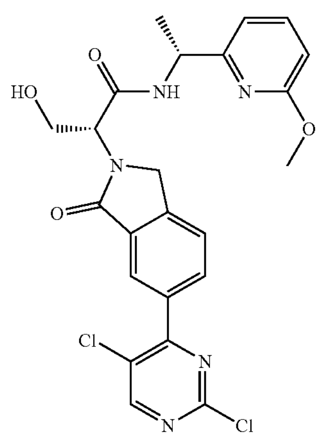 [SMILES: COc1cccc([C@@H](C)NC(=O)[C@@H](CO)N2Cc3ccc(-c4nc(Cl)ncc4Cl)cc3C2=O)n1] | (2R)-2-[6-(2,5-dichloropyrimidin-4-yl)-1-oxo-2,3-dihydro-1H-isoindol-2-yl]-3-hydroxy-N-[(1R)-1-(6-methoxypyridin-2-yl)ethyl]propanamide | 502 |
| 222 | 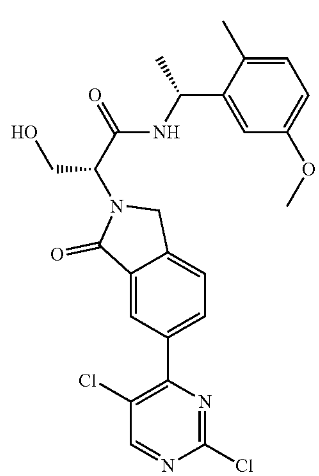 [SMILES: COc1ccc(C)c([C@@H](C)NC(=O)[C@@H](CO)N2Cc3ccc(-c4nc(Cl)ncc4Cl)cc3C2=O)c1] | (2R)-2-[6-(2,5-dichloropyrimidin-4-yl)-1-oxo-2,3-dihydro-1H-isoindol-2-yl]-3-hydroxy-N-[(1R)-1-(5-methoxy-2-methylphenyl)ethyl]-propanamide | 515 |

| Preparation | Structure | Name | MS: [M + H]⁺ |
|---|---|---|---|
| 223 | 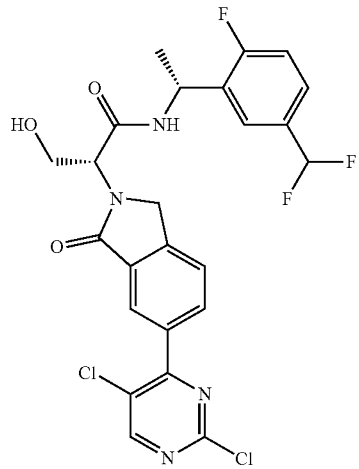 [SMILES: C[C@@H](NC(=O)[C@@H](CO)N1Cc2ccc(-c3nc(Cl)ncc3Cl)cc2C1=O)c1cc(C(F)F)ccc1F] | (2R)-2-[6-(2,5-dichloropyrimidin-4-yl)-1-oxo-2,3-dihydro-1H-isoindol-2-yl]-N-[(1R)-1-[5-(difluoromethyl)-2-fluorophenyl]ethyl]-3-hydroxypropanamide | 539 |
| 224 | 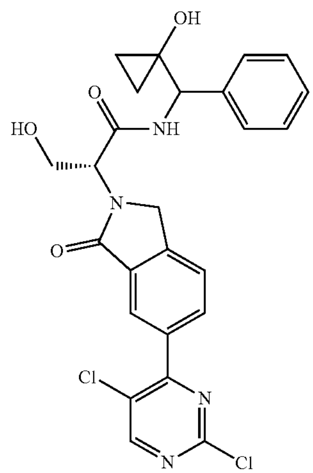 [SMILES: O=C(NC(c1ccccc1)C1(O)CC1)[C@@H](CO)N1Cc2ccc(-c3nc(Cl)ncc3Cl)cc2C1=O] | 2-[6-(2,5-dichloropyrimidin-4-yl)-1-oxo-2,3-dihydro-1H-isoindol-2-yl]-3-hydroxy-N-[(1-hydroxycyclopropyl)(phenyl)methyl]propanamide | 513 |

Preparation 225: methyl 5-(2,5-dichloropyrimidin-4-yl)-3-fluoro-2-methylbenzoate

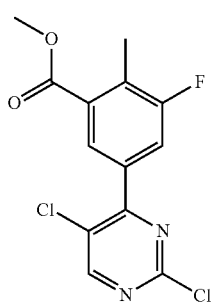 [SMILES: COC(=O)c1cc(-c2nc(Cl)ncc2Cl)cc(F)c1C]

A solution of methyl 5-chloro-3-fluoro-2-methylbenzoate (412 mg, 2.04 mmol), bis(pinacolato)diboron (621 mg, 2.45 mmol), KOAc (599 mg, 6.12 mmol) and XPhos palladacycle G3 (34 mg, 0.041 mmol) in dioxane (4 mL) was heated to 100° C. in a microwave for 1 hour. The resulting mixture was poured into a solution of 2,4,5-trichloropyrimidine (0.3 mL, 2.79 mmol) in dioxane (5 mL) and 1M aqueous sodium carbonate (4 mL, 4 mmol). The reaction was degassed by bubbling through nitrogen, then heated to 90° C. overnight. The reaction was allowed to cool, diluted with water (10 mL) and extracted with EtOAc (3×10 mL). The combined organic fractions were dried, filtered and concentrated. The residue was purified by chromatography (SiO₂, 25 g column, 0-40% EtOAc in petrol) to give the title compound (400 mg, 62%). MS: [M+H]⁺=315.

Preparation 226: methyl 2-(bromomethyl)-3-fluoro-5-(2,5-dichoropyrimidin-4-yl)benzoate

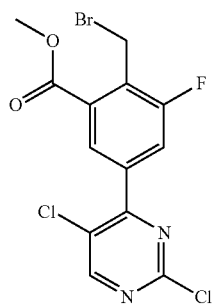 [SMILES: COC(=O)c1cc(-c2nc(Cl)ncc2Cl)cc(F)c1CBr]

Preparation 225 was brominated using a similar procedure to preparation 180. 1H NMR (400 MHz, CDCl3): 8.73 (1H, s), 8.39 (1H, s), 7.88 (1H, dd), 5.06 (2H, d), 4.02 (3H, s).

Preparation 227: (2R)-2-[6-(2,5-dichloropyrimidin-4-yl)-4-fluoro-1-oxo-2,3-dihydro-1H-isoindol-2-yl]-3-hydroxy-N-[(1R)-1-(3-methoxyphenyl)ethyl]propanamide

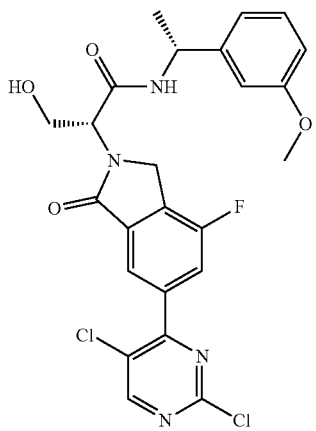 [SMILES: COc1cccc([C@@H](C)NC(=O)[C@@H](CO)N2Cc3c(F)cc(-c4nc(Cl)ncc4Cl)cc3C2=O)c1]

Preparation 226 was treated with preparation 182 as described in preparation 207. MS: [M+H]$^+$=519.

Preparation 228: tert-butyl 2-(7-bromo-1-oxo-1,2,3,4-tetrahydroisoquinolin-2-yl)acetate

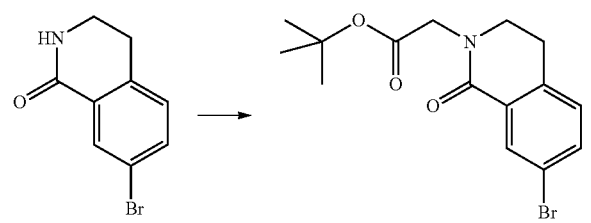 [SMILES: O=C1NCCc2ccc(Br)cc21 ; CC(C)(C)OC(=O)CN1CCc2ccc(Br)cc2C1=O]

To 7-bromo-3,4-dihydro-2H-isoquinolin-1-one (0.500 g, 2.22 mmol) in DMF (7.40 mL), cooled to 0° C. (ice bath) was added sodium hydride (60% in min. oil, 0.098 g, 2.44 mmol) portionwise. The reaction was stirred for 30 min at 0° C. Tert-butyl bromoacetate (0.361 mL, 2.44 mmol) was added and the reaction stirred for 1 h. Water was added and the aqueous extracted with ethyl acetate (3×). The combined organics washed with saturated brine solution (3×), dried over sodium sulfate, filtered and concentrated in vacuo. The crude product was purified by column chromatography on silica gel (gradient elution, 0-50%, ethyl acetate/petrol 40-60° C.), to give the titled compound (694 mg), MS: [M+H]$^+$=284 (-tBu).

Preparation 229: tert-butyl 2-[1-oxo-7-(4,4,5,5-tetramethyl-1,3,2-dioxaborolan-2-yl)-1,2,3,4-tetrahydroisoquinolin-2-yl]acetate

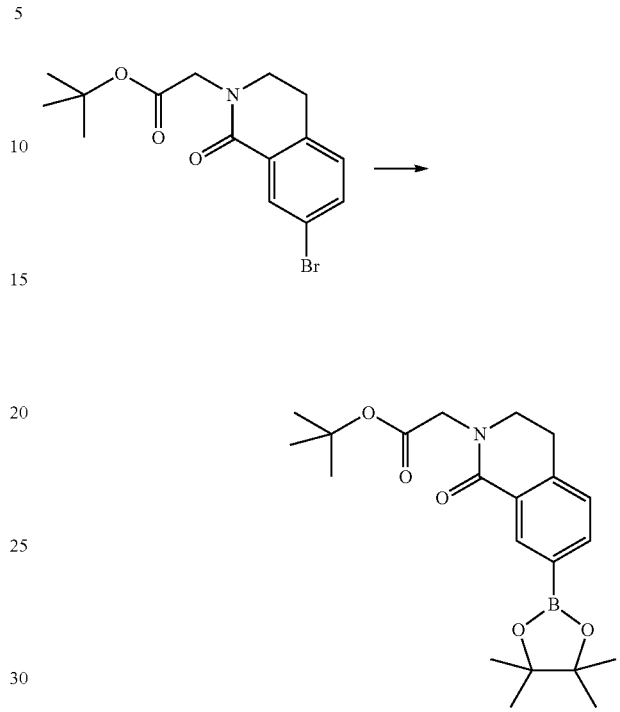

tert-butyl 2-(7-bromo-1-oxo-1,2,3,4-tetrahydroisoquinolin-2-yl)acetate (0.694 g, 2.05 mmol), bispinacolatodiboron (0.676 g, 2.66 mmol) [1,1'-bis(diphenylphosphino)ferrocene]dichloropalladium(II) (0.075 g, 0.10 mmol) and potassium acetate (0.502 g, 5.12 mmol) were dissolved in dioxane (5.12 mL) and degassed under nitrogen (5 mins). The reaction was heated to 90° C. for 18 h. After this time, water and ethyl acetate were added. The mixture was filtered through a phase separator and the organic layer separated. This was dried over sodium sulfate, filtered and concentrated in vacuo, to give the titled compound (777 mg) as a brown solid which was used straight away as a crude mixture.

Preparation 230: tert-butyl 2-[7-(2,5-dichloropyrimidin-4-yl)-1-oxo-1,2,3,4-tetrahydroisoquinolin-2-yl]acetate

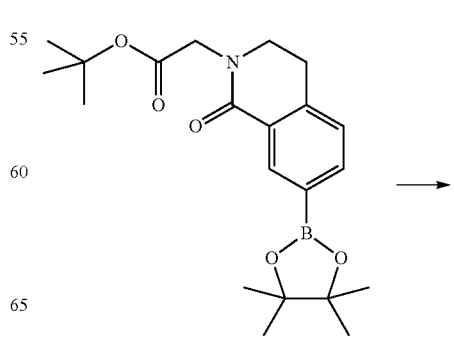

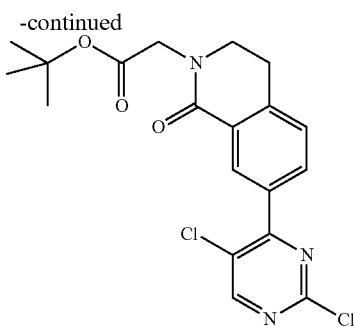

To tert-butyl 2-[1-oxo-7-(4,4,5,5-tetramethyl-1,3,2-dioxaborolan-2-yl)-1,2,3,4-tetrahydroisoquinolin-2-yl]acetate (0.777 g, 2.01 mmol), 2,4,5-trichloropyrimidine (0.555 g, 3.03 mmol) and tetrakis(triphenylphosphine)palladium(0) in dioxane (5.58 mL) and water (2.79 mL) was added potassium carbonate (0.555 g, 4.02 mmol). The reaction was heated to 100° C. for 1 h. The organic layer was separated and washed with saturated brine solution. Passed through a passed separator and concentrated in vacuo. The crude product was purified by column chromatography on silica gel (gradient elution, 0-100%, ethyl acetate/petrol 40-60° C.), to give the titled compound (0.701 g), MS: [M+H]$^+$=352 (-tBu).

Preparation 231: tert-butyl 2-(7-{5-chloro-2-[(oxan-4-yl)amino]pyrimidin-4-yl}-1-oxo-1,2,3,4-tetrahydroisoquinolin-2-yl)acetate

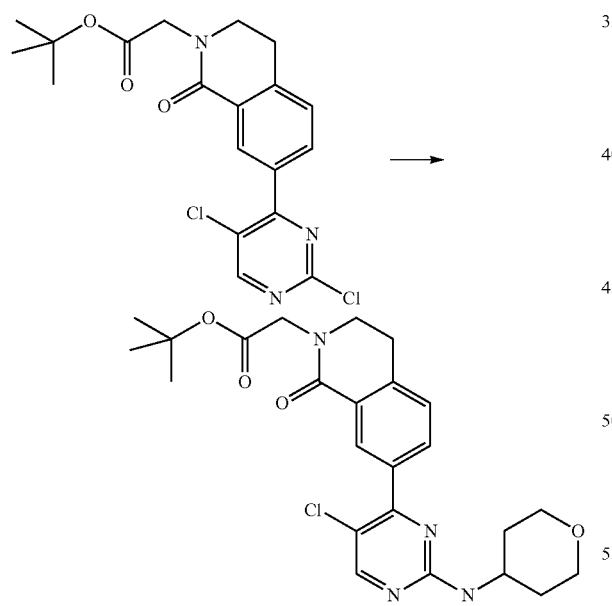

To tert-butyl 2-[7-(2,5-dichloropyrimidin-4-yl)-1-oxo-1,2,3,4-tetrahydroisoquinolin-2-yl]acetate (0.701 g, 1.72 mmol) and 4-aminooxan (0.973 g, 8.61 mmol) in DMF (8.61 mL) was added diisopropylethylamine (0.900 mL, 5.17 mmol). The reaction was heated to 70° C. for 18 h. The reaction was concentrated in vacuo and the residue was purified by reverse phase biotage MeCN/water, 0-40% gradient elution to give the titled compound (0.497 g), MS: [M+H]$^+$=473.

Preparation 232: (2R)-2-[6-(2-chloropyrimidin-4-yl)-1-oxo-2,3-dihydro-1H-isoindol-2-yl]propanoic acid

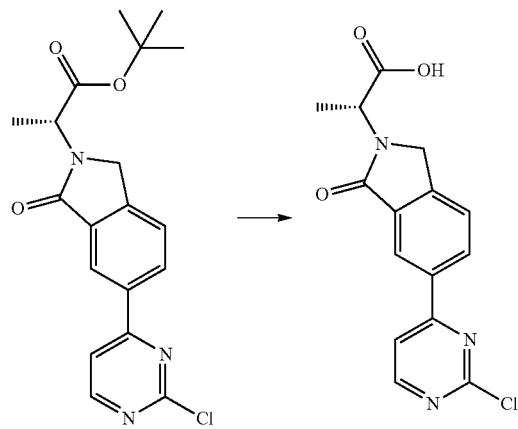 [SMILES: C[C@H](C(=O)OC(C)(C)C)N1Cc2ccc(-c3ccnc(Cl)n3)cc2C1=O ; C[C@H](C(=O)O)N1Cc2ccc(-c3ccnc(Cl)n3)cc2C1=O]

tert-butyl (2R)-2-[6-(2-chloropyrimidin-4-yl)-1-oxo-2,3-dihydro-1H-isoindol-2-yl]propanoate (1.10 g, 2.95 mmol) was dissolved in DCM (19.7 mL) and TFA (9.83 mL), and stirred for 4 h at room temperature. The reaction was concentrated in vacuo and precipitated from diethyl ether. The solid was triturated with diethyl ether and dried in vacuo. To give the titled compound (0.922 g), MS: [M+H]$^+$=318.

Preparation 233: 2-(7-{5-chloro-2-[(oxan-4-yl)amino]pyrimidin-4-yl}-1-oxo-1,2,3,4-tetrahydroisoquinolin-2-yl)acetic acid

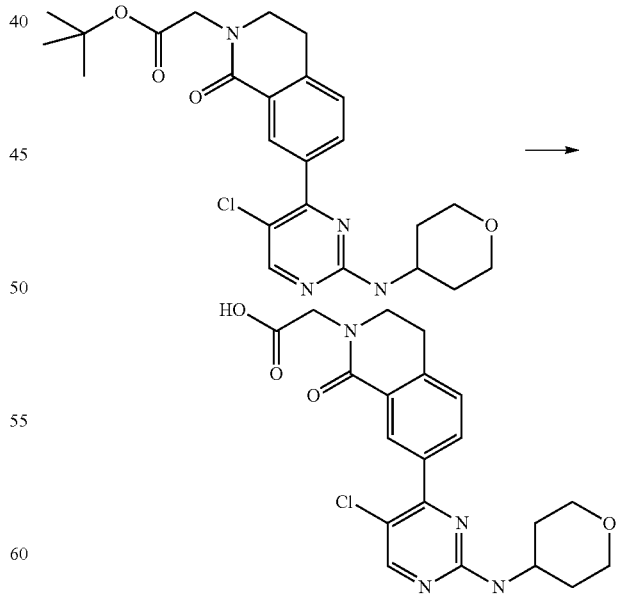

Prepared as above except using tert-butyl 2-(7-{5-chloro-2-[(oxan-4-yl)amino]pyrimidin-4-yl}-1-oxo-1,2,3,4-tetrahydroisoquinolin-2-yl)acetate to give the titled compound (0.305 g) MS: [M+H]$^+$=417.

311

Preparation 234: (2R)-2-[6-(2-chloropyrimidin-4-yl)-1-oxo-2,3-dihydro-1H-isoindol-2-yl]-N-[(1S)-2-hydroxy-1-(3-methylphenyl)ethyl]propanamide

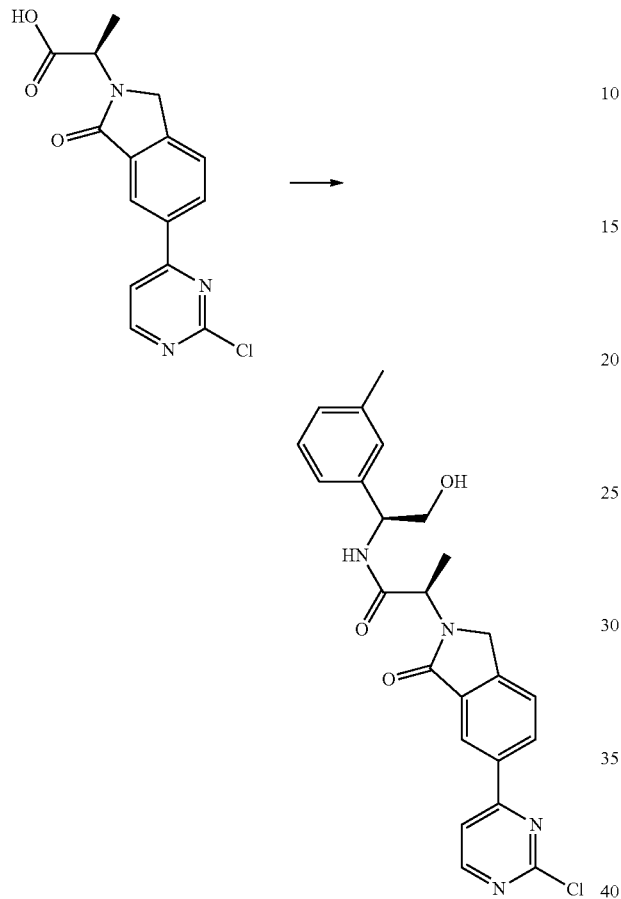

To (2R)-2-[6-(2-chloropyrimidin-4-yl)-1-oxo-2,3-dihydro-1H-isoindol-2-yl]propanoic acid (0.499 g, 1.57 mmol), (2S)-2-amino-2-(3-methylphenyl)ethan-1-ol hydrochloride (0.353 g, 1.89 mmol) and TBTU (0.758 g, 2.36 mmol) in DMF (7.87 mL) was added diisopropylethylamine (1.10 mL, 6.30 mmol). The reaction was stirred at room temperature for 1 h. Water was added and the aqueous was extracted with ethyl acetate (3×). The combined organics were washed concentrated in vacuo. The crude product was purified by column chromatography on silica gel (gradient elution, 0-100%, ethyl acetate/petroleum spirit 40-60° C., to give the titled compound (0.279 g) MS: [M–H]⁻=449.

Preparation 235: (2R)-2-[6-(2-chloropyrimidin-4-yl)-1-oxo-2,3-dihydro-1H-isoindol-2-yl]-N-[(1S)-2-hydroxy-1-(3-methoxyphenyl)ethyl]propanamide Prepared as above except using (2S)-2-amino-2-(3-methoxyphenyl)ethan-1-ol hydrochloride, and the workup was using water was added, the precipitate which formed was collected by vacuum filtration and washed with water and petrol. Dried in a vacuum oven at 40° C. for 2 h, to give the titled compound (0.338 g) MS: [M–H]⁻=465.

312

Preparation 236: 2-[6-(2,5-dichloropyrimidin-4-yl)-1-oxo-2,3-dihydro-1H-isoindol-2-yl]-N-[(1R)-1-(3-methoxyphenyl)ethyl]acetamide

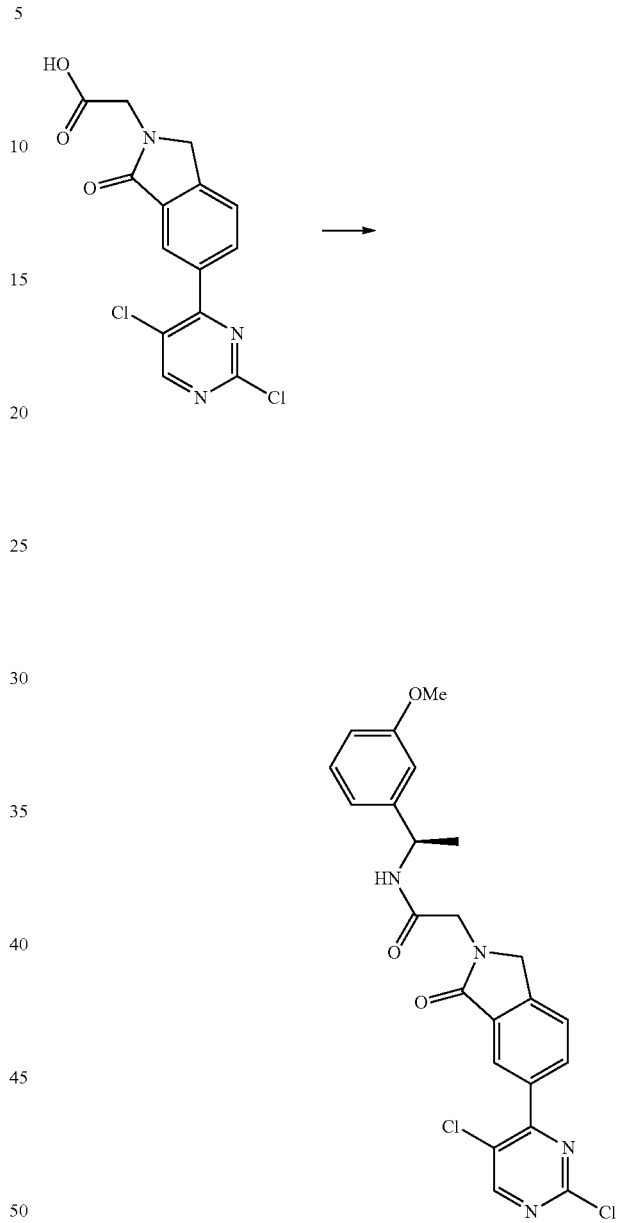

To 2-[6-(2,5-dichloropyrimidin-4-yl)-1-oxo-2,3-dihydro-1H-isoindol-2-yl]acetic acid (1.00 g, 2.97 mmol), (R)-(+)-1-(3-methoxyphenyl)ethylamine) (0.672 g, 4.45 mmol) and HATU (1.693 g, 4.45 mmol) in DMF (14.84 mL) was added diisopropylethylamine (2.07 mL, 11.87 mmol). The reaction was stirred at room temperature for 2 h. Water was added and the aqueous was extracted with ethyl acetate (3×). The combined organics were concentrated in vacuo. The crude product was purified by column chromatography on silica gel (gradient elution, 0-100%, ethyl acetate/petrol 40-60° C.), to give 813 mg, 1H NMR (400 MHz, DMSO-d6): 9.03 (1H, s), 8.57 (1H, d), 8.13 (1H, d), 8.05 (1H, dd), 7.82 (1H, d), 7.28-7.20 (1H, m), 6.94-6.85 (2H, m), 6.85-6.77 (1H, m), 4.99-4.89 (1H, m), 4.63 (2H, s), 4.27 (2H, s), 3.76 (3H, s), 1.38 (3H, d).

Preparation 237: tert-butyl (2R)-2-[6-(5-chloro-2-fluoropyridin-4-yl)-1-oxo-2,3-dihydro-1H-isoindol-2-yl]propanoate

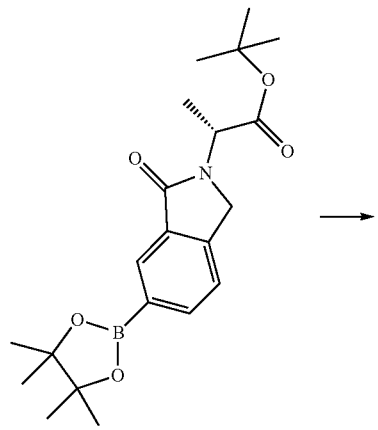

Preparation 238: (2R)-2-[6-(5-chloro-2-fluoropyridin-4-yl)-1-oxo-2,3-dihydro-1H-isoindol-2-yl]propanoic acid

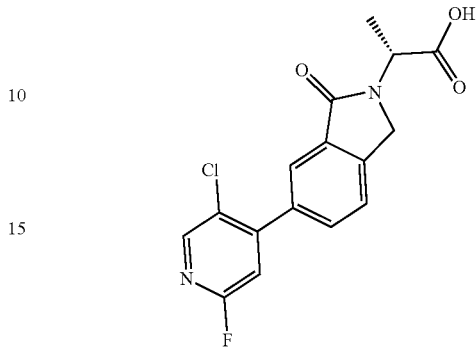

To a solution of tert-butyl (2R)-2-[6-(5-chloro-2-fluoropyridin-4-yl)-1-oxo-2,3-dihydro-1H-isoindol-2-yl]propanoate (403 mg, 1.03 mmol) in DCM (8 mL) was added 4M HCl in dioxane (2.58 mL, 10.3 mmol, 10 eq.) and the reaction stirred at room temperature for 20 h. The reaction mixture was concentrated to dryness to give the title compound (291 mg). LC-MS: [M+H]$^+$=335

Preparation 239: (2R)-2-[6-(5-chloro-2-fluoropyridin-4-yl)-1-oxo-2,3-dihydro-1H-isoindol-2-yl]-N-[(1S)-2-hydroxy-1-(3-methoxyphenyl)ethyl]propanamide

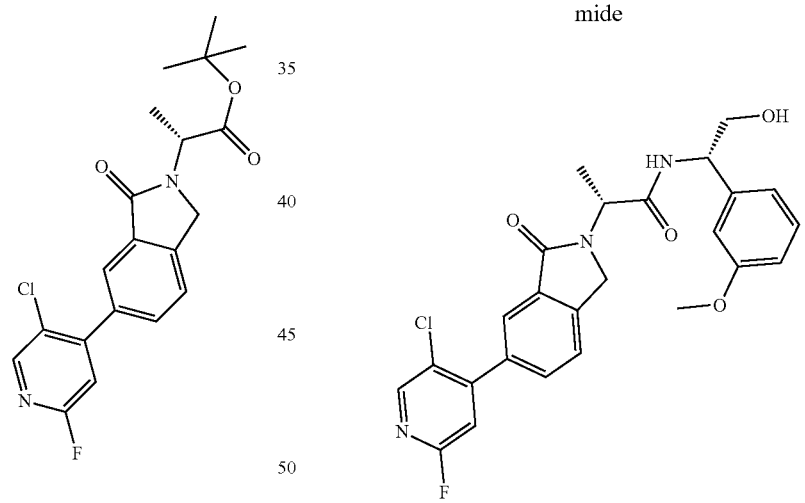

A mixture of tert-butyl (2R)-2-[1-oxo-6-(4,4,5,5-tetramethyl-1,3,2-dioxaborolan-2-yl)-2,3-dihydro-1H-isoindol-2-yl]propanoate (Intermediate 89, 1.13 g, 2.92 mmol), 2-fluoro,4-iodo,5-chloropyridine (1.50 g, 5.84 mmol, 2 eq.), Pd(PPh$_3$)$_4$ (337 mg, 0.1 eq.) aqueous sodium carbonate (2.92 mL, 2M, 5.84 mmol) and dioxane (20 mL) was heated under nitrogen at 90° C. overnight. The mixture was partitioned between EtOAc and water. The aqueous layer was extracted with further EtOAc. The combined organic layer was washed with water (×2) and brine before it was dried (MgSO$_4$), filtered and concentrated to give a brown solid. Purified by silica column, eluting 20-100% EtOAc in petrol to give the title compound (403 mg) as a white solid. LC-MS: [M+H]$^+$=391

To a solution of (2R)-2-[6-(5-chloro-2-fluoropyridin-4-yl)-1-oxo-2,3-dihydro-1H-isoindol-2-yl]propanoic acid (145 mg, 0.43 mmol) in DCM (2 mL) was added triethylamine (242 mL, 1.73 mmol, 4 eq), (2S)-2-amino-2-(3-methoxyphenyl)ethan-1-ol hydrochloride salt (97 mg, 0.48 mmol, 1.1 eq.) and TBTU (153 mg, 0.48 mmol, 1.1 eq.) and the reaction stirred for 66 h. The reaction mixture was partitioned between DCM and water. The aqueous was extracted with further DCM and then the combined organic phase washed with water (×2), sodium bicarbonate (×2) and brine before it was dried (MgSO4), filtered and concentrated. Purified by silica column, eluting 50-100% EtOAc in petrol followed by 0-10% MeOH in EtOAc to give the title compound (108 mg). LC-MS: [M+H]$^+$=484

Preparation 240: 1-(7-nitro-1,2,4,5-tetrahydro-3H-benzo[d]azepin-3-yl)ethan-1-one

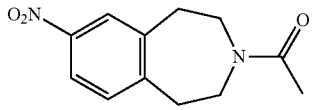

Sulfuric acid (35.0 mL, 35.0 mmol) was added dropwise to a stirred solution of 2,3,4,5-tetrahydro-1H-benzo[d]azepine (3.0 g, 20.4 mmol) in 1,4-dioxane (35 mL) and the solvent was removed in vacuo to afford a sticky paste. A small volume of iso-propanol (ca. 5 mL) was added to induce solidification followed by EtOAc (50 mL) and the resulting mixture was stirred at room temperature for 1 h. The solid was collected by filtration, and the filter cake was washed with EtOAc (25 mL) and iso-hexane (50 mL) to afford 2,3,4,5-tetrahydro-1H-benzo[d]azepine sulfate (4.0 g, 16.1 mmol, 79%) as an off-white solid. The product was used without further purification in the next step. 2,3,4,5-tetrahydro-1H-benzo[d]azepine sulfate (4.0 g, 16.3 mmol) was added at 0° C. in small portions to a stirred mixture of nitric acid (70% w/w, 10.0 mL, 157.0 mmol) and sulfuric acid (95% w/w, 10.0 ml, 178.0 mmol) and the resulting mixture was stirred at 0° C. for 2 h. The cold reaction mixture was poured into ice and allowed to warm to room temperature. The mixture was basified by addition of saturated aqueous NaHCO$_3$ and extracted with EtOAc (3×300 mL). The organic extracts were combined, then dried over Na$_2$SO$_4$, filtered and concentrated in vacuo to afford 7-nitro-2,3,4,5-tetrahydro-1H-benzo[d]azepine as a brown solid (3.5 g, 112%). LC-MS: [M+H]$^+$=504. The product was used without further purification in the next step.

Crude 7-nitro-2,3,4,5-tetrahydro-1H-benzo[d]azepine (3.5 g) was dissolved in DCM (40 mL,) and DIPEA (3.13 mL, 17.94 mmol) was added, followed by drop-wise addition of acetic anhydride (1.69 mL, 17.94 mmol). The mixture was stirred at room temperature for 3 h and was diluted with DCM (50 mL), then washed with saturated aqueous NaHCO$_3$ (50 mL), dried (MgSO$_4$), filtered and concentrated in vacuo to afford a brown solid (5 g). The crude product was purified by chromatography (SiO$_2$, 40 g column, 0-5% MeOH in DCM) to afford the title compound (2.40 g, 7.68 mmol, 47%) as a tan solid. LC-MS: [M+H]+=235.

Preparation 241: 1-(7-amino-1,2,4,5-tetrahydro-3H-benzo[d]azepin-3-yl)ethan-1-one

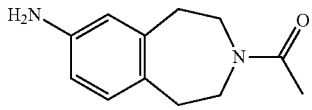 [SMILES: CC(=O)N1CCc2ccc([N+](=O)[O-])cc2CC1]

A mixture of 1-(7-nitro-4,5-dihydro-1H-benzo[d]azepin-3(2H)-yl)ethanone (2.40 g, 7.68 mmol) and Pd—C (150 mg, 0.141 mmol) in EtOH (18 mL) was hydrogenated at 2 Bar for 16 h. The heterogenous mixture was filtered, washed with EtOH (2×40 mL) and then concentrated to give a red solid. The crude product was loaded onto a column of SCX (10 g) in MeOH. The column was washed with MeOH and then the product was eluted with 0.7 M ammonia in MeOH. The resulting mixture was concentrated in vacuo to afford a red solid. The red solid was recrystallised from hot EtOH (~10 mL) and the resulting solid was filtered, washed with EtOH, and dried in vacuo to afford the title compound (650 mg) as a yellow solid. The filter cake was further washed with EtOH (50 mL) and then concentrated to give a second crop of the title compound (440 mg) as a brown solid. The filter cake was further washed with EtOH (50 mL) and then concentrated to give a third crop of the title compound as a brown solid (200 mg). The three fractions were combined to give the title compound (1.29 g, 78%) as a brown solid. LC-MS (poor chromophore): [M+H]+=205.

Preparation 242: 1-(7-chloro-1,2,4,5-tetrahydro-3H-benzo[d]azepin-3-yl)ethan-1-one

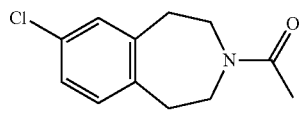

A solution of 1-(7-amino-4,5-dihydro-1H-benzo[d]azepin-3(2H)-yl)ethanone (800 mg, 3.92 mmol) in MeCN (19.6 ml) was added dropwise to a mixture of copper (II) chloride (632 mg, 4.70 mmol) and butyl nitrite (0.687 mL, 5.88 mmol) in MeCN (19.6 mL). The resulting mixture was stirred at room temperature for 16 h. Water (50 mL) was added and the crude product was extracted with EtOAc (3×50 mL). The combined organic extracts were dried (MgSO$_4$), filtered and concentrated in vacuo to give a brown solid. The crude product was purified by chromatography (SiO$_2$, 24 g column, 50-100% EtOAc/isohexane) to afford the title compound (260 mg, 1.10 mmol, 28%) as a colourless oil which solidified on standing to give a tan solid. LC-MS (poor chromophore): [M+H]+=224.

Preparation 243: 7-chloro-2,3,4,5-tetrahydro-1H-benzo[d]azepine

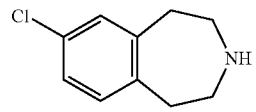 [SMILES: Clc1ccc2c(c1)CCNCC2]

A mixture of 1-(7-chloro-4,5-dihydro-1H-benzo[d]azepin-3(2H)-yl)ethanone (40 mg, 0.18 mmol) and 6 M HCl (2.0 mL, 12.00 mmol) was heated under reflux and stirred for 18 h. The reaction was basifed with 2 M NaOH (aq.) and extracted with EtOAc (3×15 mL). The organic extracts were dried (Na$_2$SO$_4$), filtered and concentrated in vacuo to give the title compound as a yellow oil. The product (80% NMR purity) was used without further purification in the next step. LC-MS (poor chromophore): [M+H]+=182.

Preparation 244: tert-butyl 6-bromo-3,4-dihydroisoquinoline-2(1H)-carboxylate

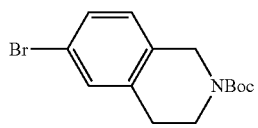

A solution of di-tert-butyldicarbonate (1.11 mL, 4.76 mmol) in DCM (4 mL) was added dropwise to a suspension of 6-bromo-1,2,3,4-tetrahydroisoquinoline (0.990 g, 4.67 mmol) in DCM (6 mL) and the mixture was stirred at room temperature for 3 h. The solvent was removed in vacuo to give tert-butyl 6-bromo-3,4-dihydroisoquinoline-2(1H)-carboxylate (1.564 g, 4.66 mmol, 100%) as an orange oil. The product was used without further purification in the next step. $^1$H NMR (DMSO-d6) δ: 7.39 (1H, d), 7.36 (1H, dd), 7.14 (1H, d), 4.45 (2H, s), 3.53 (2H, dd), 2.77 (2H, dd), 1.43 (9H, s).

Preparation 245: tert-butyl 6-(4-isopropylpiperazin-1-yl)-3,4-dihydroisoquinoline-2(1H)-carboxylate

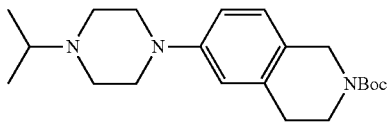 [SMILES: CC(C)N1CCN(c2ccc3c(c2)CCN(C(=O)OC(C)(C)C)C3)CC1]

A microwave tube was charged with RuPhos-Pd G3 (25 mg, 0.030 mmol) and sodium tert-butoxide (92 mg, 0.953 mmol). The tube was evacuated and backfilled with nitrogen (×3). A solution of tert-butyl 6-bromo-3,4-dihydroisoquinoline-2(1H)-carboxylate (200 mg, 0.596 mmol) in THF (1.2 mL) was added, followed by 1-isopropylpiperazine (111 µL, 0.774 mmol) and the mixture was stirred overnight at 65° C. under nitrogen. The reaction was cooled to room temperature, diluted with EtOAc (10 mL) and filtered through celite, eluting with EtOAc (50 mL). The filtrate was concentrated and the crude product was purified by chromatography (SiO$_2$, 12 g column, 0-10% (0.7 M Ammonia/MeOH) in DCM) to afford the title compound (125 mg, 49%) as a yellow oil. $^1$H NMR (DMSO-d6) δ: 6.98 (1H, d), 6.77 (1H, dd), 6.69 (1H, d), 4.38 (2H, s), 3.50 (2H, dd), 3.10-3.03 (4H, m), 2.71 (2H, dd), 2.68-2.62 (1H, m), 2.59-2.52 (4H, m), 1.43 (9H, s), 1.00 (6H, d).

Preparation 246: 6-(4-isopropylpiperazin-1-yl)-1,2,3,4-tetrahydroisoquinoline

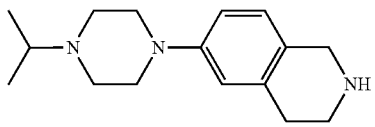

A mixture of tert-butyl 6-(4-isopropylpiperazin-1-yl)-3,4-dihydroisoquinoline-2(1H)-carboxylate (125 mg, 0.29 mmol) and TFA (0.34 mL, 4.38 mmol) in DCM (1 mL,) was stirred overnight at room temperature. The reaction mixture was loaded onto a column of SCX (2 g) in MeOH. The column was washed with MeOH and then the product was eluted with 0.7 M ammonia in MeOH. The resulting mixture was concentrated in vacuo to afford 6-(4-isopropylpiperazin-1-yl)-1,2,3,4-tetrahydroisoquinoline (80 mg, 0.29 mmol, 100%) as a yellow oil. 1H NMR (DMSO-d6) δ: 6.83 (d, 1H), 6.70 (dd, 1H), 6.58 (d, 1H), 4.10 (s, 1H), 3.73 (s, 2H), 3.07-3.00 (m, 4H), 2.90 (dd, 2H), 2.71-2.58 (m, 3H), 2.59-2.51 (m, 4H), 1.00 (d, 6H).

Preparation 247: tert-butyl 6-(pyrimidin-2-yl)-3,4-dihydroisoquinoline-2(1H)-carboxylate

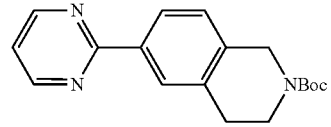 [SMILES: CC(C)(C)OC(=O)N1CCc2cc(-c3ncccn3)ccc2C1]

A microwave tube was charged with tert-butyl 6-(4,4,5,5-tetramethyl-1,3,2-dioxaborolan-2-yl)-3,4-dihydroisoquinoline-2(1H)-carboxylate (0.300 g, 0.835 mmol), 2-chloropyrimidine (0.080 g, 0.696 mmol) and Sphos-Pd G3 (11 mg, 0.014 mmol). The tube was evacuated and back-filled with nitrogen (×3). 1,4-dioxane (7 ml) was added, followed by 2 M lithium hydroxide (aq.) (1.39 ml, 2.78 mmol). The tube was evacuated and back-filled with nitrogen (×2) and stirred overnight at 80° C. The cooled reaction mixture was diluted with EtOAc (15 mL) and water (15 mL). The phases were separated and the aqueous phase was extracted with EtOAc (2×15 mL). The combined organic extracts were washed with brine (50 mL), dried (MgSO$_4$) and concentrated. The crude product was purified by chromatography (SiO$_2$, 12 g column, 0-50% EtOAc in iso-hexane) to afford the title compound (106 mg, 46%) as a colourless oil. $^1$H NMR (DMSO-d6) δ: 8.89 (2H, d), 8.24-8.17 (2H, m), 7.44 (1H, t), 7.33 (1H, d), 4.58 (2H, s), 3.60 (2H, dd), 2.89 (2H, dd), 1.45 (9H, s).

Preparation 248: 6-(pyrimidin-2-yl)-1,2,3,4-tetrahydroisoquinoline

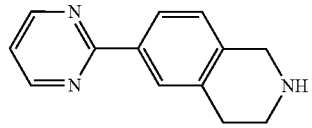 [SMILES: c1cnc(-c2ccc3c(c2)CCNC3)nc1]

Prepared using a similar procedure to preparation 246. The product was obtained in 90% purity and was used without further purification in the next step. $^1$H NMR (DMSO-d6) δ: 8.87 (2H, d), 8.19-8.09 (2H, m), 7.41 (1H, t), 7.16 (1H, d), 4.08 (1H, s), 3.92 (2H, s), 2.99 (2H, dd), 2.79 (2H, dd).

Preparation 249: tert-butyl(2-(4-bromophenyl)propan-2-yl)carbamate

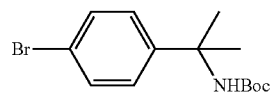

Boc-anhydride (278 µl, 1.197 mmol) and triethylamine (306 µl, 2.195 mmol) were added to a solution of 2-(4-bromophenyl)propan-2-amine.HCl (250 mg, 0.998 mmol) in DCM (10 mL) at 0° C. The reaction mixture was allowed to warm to room temperature and stirred overnight. The reaction mixture was washed with 1 M HCl (aq.) (5 mL), and brine (5 mL), dried (Na$_2$SO$_4$), filtered and concentrated in vacuo to afford the title compound (332 mg, 101%) as a colourless oil which solidified on standing. 1H NMR (Chloroform-d) δ: 7.47-7.38 (m, 2H), 7.31-7.22 (m, 2H), 4.91 (s, 1H), 1.59 (s, 6H), 1.52 (d, 9H).

Preparation 250: tert-butyl (2-(4-cyanophenyl)propan-2-yl)carbamate

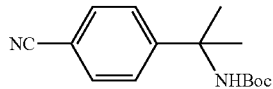

Zinc cyanide (99 mg, 0.845 mmol) and Pd(PPh$_3$)$_4$ (122 mg, 0.106 mmol) were added to a solution of tert-butyl (2-(4-bromophenyl)propan-2-yl)carbamate (332 mg, 1.057 mmol) in DMF (1 mL). The reaction mixture was heated at 100° C. overnight. The mixture was cooled to room temperature, and partitioned between water (2 mL) and Et$_2$O (3 mL). The crude product was extracted with Et$_2$O (2×3 mL) and the combined organic extracts were dried (MgSO$_4$) and concentrated in vacuo to give an oil. Purification by chromatography (SiO$_2$, 0-50% EtOAc in iso-hexane) gave the title compound. LC-MS: [M+Na]+=283

Preparation 251: 4-(2-aminopropan-2-yl)benzonitrile

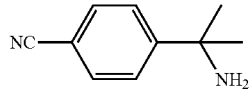

tert-Butyl (2-(4-cyanophenyl)propan-2-yl)carbamate (100 mg, 0.384 mmol) was stirred in formic acid (1 mL) for 3 h at room temperature. The reaction mixture was added dropwise to a stirred solution of sodium carbonate (3.0 g, 28.3 mmol) in water (10 mL). The aqueous phase was extracted with ethyl acetate (3×10 mL) and the combined organic phases were washed with brine (10 mL), dried (Na$_2$SO$_4$) and concentrated to dryness in vacuo to give the title compound (57 mg, 91%) as a colourless oil. The product was used without further purification in the next step. $^1$H NMR (CDCl$_3$) δ: 7.68-7.62 (m, 4H), 1.56-1.50 (m, 6H).

Preparation 252: tert-butyl 6-bromo-1-methyl-3,4-dihydroisoquinoline-2(1H)-carboxylate

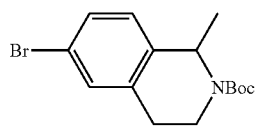

Boc-anhydride (0.360 mL, 1.550 mmol) was added to a solution of 6-bromo-1-methyl-1,2,3,4-tetrahydroisoquinoline (292 mg, 1.291 mmol) in DCM (5 mL) and the mixture was stirred at room temperature overnight. The reaction mixture was concentrated and the crude product was purified by chromatography (12 g column, 0-20% EtOAc in iso-hexane) to afford the title compound (307 mg, 67%) as a colourless oil. LC-MS: [M-tBu]+=270.

Preparation 253: tert-butyl 6-cyano-1-methyl-3,4-dihydroisoquinoline-2(1H)-carboxylate

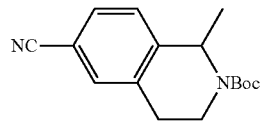

A solution of tert-butyl 6-bromo-1-methyl-3,4-dihydroisoquinoline-2(1H)-carboxylate (85 mg, 0.261 mmol) and zinc cyanide (32 mg, 0.274 mmol) in DMA (2 mL) was degassed with nitrogen for 10 min. and Pd(PPh$_3$)$_4$ (30 mg, 0.026 mmol) was added in 4 portions. The reaction mixture was then heated to 100° C. (block temp) under nitrogen for 2 h and was allowed to cool to room temperature. The mixture was filtered over celite eluting with EtOAc (50 mL). The filtrate was washed with sat. NaHCO$_3$ (aq.) (2×10 mL), water (2×10 mL) and brine (2×10 mL). The organic layer was then dried (Na$_2$SO$_4$), filtered and concentrated. The crude product was purified by chromatography (SiO$_2$, 12 g column, 0-20% EtOAc in iso-hexane) to afford the title compound (56 mg, 78%) as a colourless solid. LC-MS: [M-tBu]+=217.

Preparation 254: 1-methyl-1,2,3,4-tetrahydroisoquinoline-6-carbonitrile

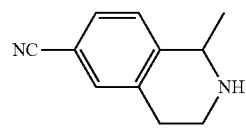

tert-Butyl 6-cyano-1-methyl-3,4-dihydroisoquinoline-2 (1H)-carboxylate (56 mg, 0.206 mmol) was dissolved in DCM (2.6 mL) and TFA (317 μl, 4.11 mmol) was added at 0° C. The reaction was allowed to warm to room temperature and stirred for 1.5 h. The reaction mixture was loaded onto a column of SCX (2 g) in MeOH. The column was washed with MeOH and the product was then eluted with 0.7 M ammonia in MeOH. The resulting mixture was concentrated in vacuo to afford the title compound (32 mg, 86%) as a colourless oil. The product was used without further purification in the next step. LC-MS: [M+H]+=173 (poor chromophore).

Preparation 255: 2,3,4,5-tetrahydro-1H-benzo[d]azepin-1-ol

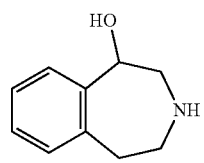 [SMILES: OC1CNCCc2ccccc21]

A solution of 2,2,2-trifluoro-1-(1-methylene-4,5-dihydro-1H-benzo[d]azepin-3(2H)-yl)ethanone (preparation 153) (200 mg, 0.784 mmol) in MeOH (9.5 mL):DCM (10 mL) was cooled to −78° C., then treated with ozone until the solution turned blue (about 15 min.). Nitrogen was bubbled through until disappearance of the blue colour, then NaBH₄ (89 mg, 2.351 mmol) was added and the resulting solution was stirred for 3 h while warming to 20° C. The reaction mixture was concentrated to give 2,2,2-trifluoro-1-(1-hydroxy-4,5-dihydro-1H-benzo[d]azepin-3(2H)-yl)ethanone (100 mg, 49% yield) as a oil, which was used without further characterization and purification in the next step. The crude product was dissolved in MeOH (3.3 mL) was treated with 2 M NaOH (aq.) (0.784 mL, 1.567 mmol), and stirred at rt for 4 h. Acetic acid (0.135 mL, 2.351 mmol) was added and and the mixture was diluted with MeOH (4 mL), then loaded onto a column of SCX (2 g) The column was washed with MeOH and then the product was eluted with 0.7 M ammonia in MeOH. The resulting mixture was concentrated in vacuo to afford 2,3,4,5-tetrahydro-1H-benzo[d]azepin-1-ol (38 mg, 27% yield) as a colourless solid. LC-MS: [M+H]+=164.

Preparation 256: tert-butyl 7-amino-1,2,4,5-tetrahydro-3H-benzo[d]azepine-3-carboxylate

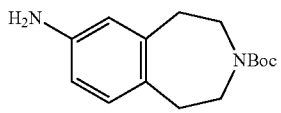 [SMILES: CC(C)(C)OC(=O)N1CCc2ccc(N)cc2CC1]

A mixture of tert-butyl 7-nitro-4,5-dihydro-1H-benzo[d]azepine-3(2H)-carboxylate (1.94 g, 6.64 mmol) and Pd—C (0.127 g, 0.119 mmol) in EtOH (18 mL):THF (4 mL) was hydrogenated at 2 Bar for 16 h. The resulting mixture was filtered through celite, washed with EtOH (2×10 mL) and then concentrated to give the title compound as a yellow oil (1.74 g, 90%). LC-MS [M-tBu+H]+=207

Preparation 257: tert-butyl 7-bromo-1,2,4,5-tetrahydro-3H-benzo[d]azepine-3-carboxylate

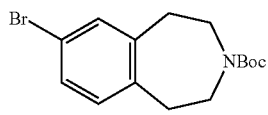

A solution of tert-butyl 7-amino-4,5-dihydro-1H-benzo[d]azepine-3(2H)-carboxylate (1.742 g, 6.64 mmol) in MeCN (33 ml) was added dropwise to a mixture of copper (II) bromide (1.780 g, 7.97 mmol) and butyl nitrite (1.164 ml, 9.96 mmol) in MeCN (33 ml) at 60° C. The reaction mixture was then heated at 80° C. for 2 h then left to stir at room temperature overnight. Water (50 mL) was added and the crude product was extracted with EtOAc (3×50 mL). The combined organic extracts were dried (MgSO₄) and filtered. The filtrate was concentrated in vacuo to dryness to give the crude product as a brown oil, which was purified by chromatography (SiO₂, 24 g column, 0-20% of EtOAc in iso-hexane) to afford the title compound (450 mg, 19%) as a colourless oil. LC-MS [M-tBu+H]+=270 (for ⁷⁹Br).

Preparation 258: tert-butyl 7-cyano-1,2,4,5-tetrahydro-3H-benzo[d]azepine-3-carboxylate

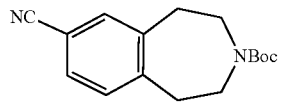 [SMILES: CC(C)(C)OC(=O)N1CCc2ccc(C#N)cc2CC1]

A solution of tert-butyl 7-bromo-4,5-dihydro-1H-benzo[d]azepine-3(2H)-carboxylate (440 mg, 1.349 mmol) and zinc cyanide (166 mg, 1.416 mmol) in DMA (10 mL) was degassed for 10 min. with nitrogen then Pd(PPh₃)₄ (156 mg, 0.135 mmol) was added and the reaction mixture was then heated to 100° C. under nitrogen for 2 h. The reaction mixture was allowed to cool to room temperature and then filtered over celite eluting with EtOAc (50 mL). The filtrate was washed with sat. NaHCO₃ (aq.) (2×10 mL), water (2×10 mL) and brine (2×10 mL). The organic layer was then dried (Na₂SO₄), filtered and concentrated. The crude product was purified by chromatography (SiO₂, 12 g column, 0-20% EtOAc in iso-hexane) to afford the title compound (240 mg, 65%) as a colourless oil which solidified on standing to give a colourless solid. LC-MS: [M-tBu+H]+=217.

Preparation 259: 2,3,4,5-tetrahydro-1H-benzo[d]azepine-7-carbonitrile

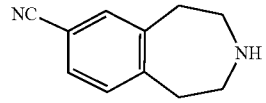 [SMILES: N#Cc1ccc2c(c1)CCNCC2]

tert-Butyl 7-cyano-4,5-dihydro-1H-benzo[d]azepine-3(2H)-carboxylate (50 mg, 0.184 mmol) was dissolved in DCM (2.4 mL) and TFA (283 µl, 3.67 mmol) was added at 0° C. The reaction was allowed to warm to room temperature and stirred for 1.5 h. The crude reaction mixture was loaded onto a column of SCX (2 g) in MeOH. The column was washed with MeOH and the product was eluted with 0.7 M ammonia in MeOH. The resulting solution was concentrated in vacuo to give the title compound (27 mg, 81%) as a colourless oil. LC-MS: [M+H]+=173.

Preparation 260: tert-butyl (2-oxo-1-phenylpropyl)carbamate

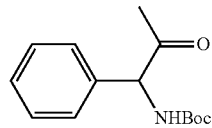 [SMILES: CC(=O)C(NC(=O)OC(C)(C)C)c1ccccc1]

Triethylamine (580 µL, 4.16 mmol) was added to a solution of 1-amino-1-phenylpropan-2-one hydrochloride (350 mg, 1.885 mmol) and Boc-anhydride (462 mg, 2.074 mmol) in THF (14 mL) and the reaction mixture was stirred at room temperature overnight. The reaction mixture was partitioned between sat. NaHCO₃ (aq.) (50 mL) and EtOAc (50 mL). The aqueous layer was extracted with EtOAc (50 mL) and the combined organic extracts were washed with

Preparation 261: tert-butyl (2-hydroxy-1-phenylpropyl)carbamate

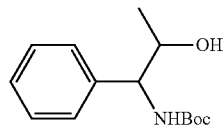

Sodium borohydride (31.9 mg, 0.825 mmol) was added to a solution of tert-butyl (2-oxo-1-phenylpropyl)carbamate (210 mg, 0.825 mmol) in MeOH (3 mL) at 0° C. and the reaction mixture was stirred at room temperature for 1 h. The reaction was quenched with water (20 mL) and extracted with EtOAc (3×20 mL). The combined organic extracts were dried (MgSO$_4$), filtered and concentrated in vacuo to give the crude product as a white solid (200 mg). The crude product was purified by chromatography (SiO$_2$, 40 g column, 0-10% THF in DCM) to afford the title compound (172 mg, 80%) as a white solid. The product was obtained as a 84:16 mixture of cis- and trans-isomers as determined by $^1$H NMR and was used without further purification in the next step. LC-MS: [M-tBu+H]+=196.

Preparation 262: 1-amino-1-phenylpropan-2-ol

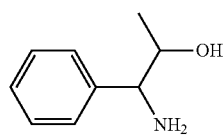

TFA (1.3 mL, 16.70 mmol) was added to a stirred solution of tert-butyl (2-hydroxy-1-phenylpropyl)carbamate (0.170 g, 0.338 mmol) in DCM (5 mL) and the reaction mixture was stirred at room temperature for 2 h. The crude reaction mixture was loaded onto a column packed with SCX. The column was washed with MeOH (3 column volumes), and the product eluted with 1% NH$_3$ in MeOH (3 column volumes). The resulting solution was concentrated in vacuo to give the title compound (104 mg, 95%) as an oil. The product was obtained as a 10:1 mixture of cis- and trans-isomers as determined by $^1$H NMR and was used without further purification in the next step. LC-MS: [M+H]+=152.

Preparation 263: methyl (S)-2-amino-3-(4-fluorophenyl)propanoate hydrochloride

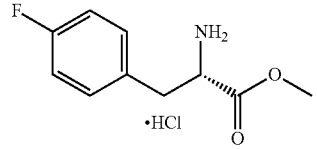

Methanol (10 mL) was stirred and cooled in an ice-bath and treated dropwise with acetyl chloride (1.8 mL, 25.3 mmol). The solution was stirred for 10 min., treated with (S)-2-((tert-butoxycarbonyl)amino)-3-(4-fluorophenyl)propanoic acid (730 mg, 2.58 mmol) and stirred at room temperature overnight. The solution was evaporated to give the title compound (610 mg, 99%) as a yellow solid. LC-MS: [M+H]+=198.

Preparation 264: methyl (S)-2-((ethoxycarbonyl)amino)-3-(4-fluorophenyl)propanoate

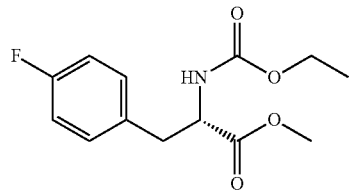 [SMILES: CCOC(=O)N[C@@H](Cc1ccc(F)cc1)C(=O)OC]

A stirred suspension of (S)-methyl 2-amino-3-(4-fluorophenyl)propanoate.HCl (610 mg, 2.61 mmol) in DCM (10 mL) and pyridine (439 µl, 5.43 mmol) was cooled in an ice-bath and treated dropwise with a solution of ethyl chloroformate (266 µl, 2.77 mmol) in DCM (1 mL). The resulting solution was allowed to warm to room temperature and the resulting yellow suspension was stirred for 30 min. The suspension was partitioned between water (20 mL) and ethyl acetate (20 mL) and the layers were separated. The aqueous layer was extracted with ethyl acetate (2×20 mL) and the combined organic extracts were washed with water (20 mL), were dried (MgSO$_4$) and evaporated to give a yellow oil (683 mg) which was purified by chromatography (SiO$_2$, 12 g column, 0-25% EtOAc in iso-hexane) to afford the title compound (648 mg, 91%) as a colourless oil. LC-MS: [M+H]+=270.

Preparation 265: 2-ethyl 3-methyl (S)-7-fluoro-3,4-dihydroisoquinoline-2,3(1H)-dicarboxylate

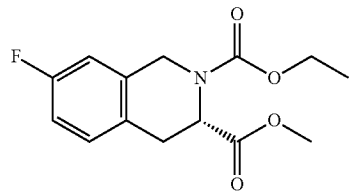 [SMILES: CCOC(=O)N1Cc2cc(F)ccc2C[C@H]1C(=O)OC]

water (50 mL), brine (50 mL), dried (MgSO$_4$) filtered and concentrated in vacuo to give the crude product (470 mg). Purification by chromatography (SiO$_2$, 40 g column, 0-100% EtOAc in iso-hexane) afforded the title compound (183 mg, 38%) as a colourless oil, which solidified on standing. $^1$H NMR (DMSO-d6) δ: 7.60 (1H, d), 7.42-7.23 (5H, m), 5.25 (1H, d), 2.03 (3H, s), 1.38 (9H, s).

A stirred suspension of (S)-methyl 2-((ethoxycarbonyl)amino)-3-(4-fluorophenyl)propanoate (646 mg, 2.399 mmol) and paraformaldehde (76 mg, 2.52 mmol) in acetic acid (3 mL) was treated dropwise with concentrated sulfuric acid (1 mL) and stirred overnight to give a clear solution. The mixture was partitioned between water (20 mL) and ethyl acetate (20 mL). The layers were separated and the aqueous layer was extracted with ethyl acetate (2×20 mL). The combined organic extracts were washed with sat. NaHCO$_3$ (aq.) (2×20 mL) followed by brine (20 mL), were dried (MgSO$_4$) and evaporated. The residue was purified by chromatography (SiO$_2$, 12 g column, 0-25% EtOAc in iso-hexane) to afford the title compound (492 mg, 72%) as colourless oil. LC-MS: [M+H]+=282.

(note: the product was also analysed by $^1$H NMR, which showed a mixture of tetrahydroquinoline conformations)

Preparation 266: (S)-7-fluoro-1,2,3,4-tetrahydroisoquinoline-3-carboxylicacid hydrochloride

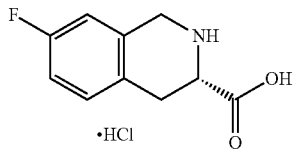 [SMILES: O=C(O)[C@@H]1Cc2ccc(F)cc2CN1 ; Cl]

A mixture of (S)-2-ethyl 3-methyl 7-fluoro-3,4-dihydroisoquinoline-2,3(1H)-dicarboxylate (487 mg, 1.731 mmol) and 5 N hydrochloric acid (8 mL) was stirred and heated under reflux for 24 h and then stirred at room temperature for 2 days to give a white solid suspended in a yellow solution. The mixture was refluxed for a further 6 h to give a clear solution, then a white precipitate. The mixture was allowed to cool and filtered. The solid was washed with water (5 mL) and dried to give the title compound (204 mg, 50%) as a cream solid. Further product (170 mg, 38%) was obtained in 90% purity by concentrating the filtrate under vacuum. Both products were combined and used without further purification in the next step. LC-MS: [M+H]+=196.

Preparation 267: methyl (S)-7-fluoro-1,2,3,4-tetrahydroisoquinoline-3-carboxylate

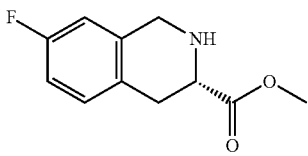

Methanol (10 mL) was stirred and cooled in an ice-bath and treated dropwise with acetyl chloride (1 mL, 14.06 mmol). The mixture was stirred for 10 min., treated with (S)-7-fluoro-1,2,3,4-tetrahydroisoquinoline-3-carboxylic acid.HCl (374 mg, 1.615 mmol) and stirred overnight to give a clear solution. The solution was evaporated and the residue was partitioned between ether (10 mL) and sat. NaHCO$_3$ (aq.) (10 ml). The layers were separated and the aqueous layer was extracted with ether (2×10 mL). The combined organic extracts were washed with brine (10 mL), were dried (Na2SO$_4$) and evaporated to give the title compound (313 mg, 88%) as a brown oil. LC-MS: [M+H]+=210.

Preparation 268: 2-(tert-butyl) 3-methyl (S)-7-fluoro-3,4-dihydroisoquinoline-2,3(1H)-dicarboxylate

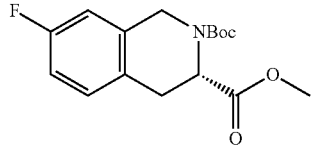 [SMILES: COC(=O)[C@@H]1Cc2ccc(F)cc2CN1C(=O)OC(C)(C)C]

A stirred solution of (S)-methyl 7-fluoro-1,2,3,4-tetrahydroisoquinoline-3-carboxylate (300 mg, 1.434 mmol) and triethylamine (0.440 ml, 3.15 mmol) in THF (5 mL) was treated with Boc-anhydride (0.366 mL, 1.577 mmol) and stirred at room temperature for 3 days. The solution was evaporated and the residue was taken up in ether (20 mL), washed with 1 M aqueous potassium hydrogen sulphate solution (10 mL) followed by saturated aqueous sodium bicarbonate solution (10 mL), brine (10 mL), then dried (MgSO$_4$) and evaporated. The residue was purified by chromatography (SiO$_2$, 12 g column, 0-25% EtOAc in iso-hexane) to afford the title compound (426 mg, 94%) as a colourless oil. LC-MS: [M-CO$_2$tBu+H]+=210.

Preparation 269: tert-butyl (S)-7-fluoro-3-(hydroxymethyl)-3,4-dihydroisoquinoline-2(1H)-carboxylate

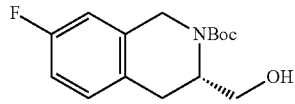 [SMILES: CC(C)(C)OC(=O)N1Cc2cc(F)ccc2C[C@H]1CO]

A stirred solution of (S)-2-tert-butyl 3-methyl 7-fluoro-3,4-dihydroisoquinoline-2,3(1H)-dicarboxylate (148 mg, 0.478 mmol) in THF (3 mL) was treated dropwise with a 2 M solution of lithium borohydride in THF (0.48 mL, 0.960 mmol) and the mixture was stirred at room temperature overnight. The mixture was quenched by the cautious addition of water (10 mL) and extracted with ether (3×10 mL). The combined organic extracts were washed with brine (10 mL), were dried (Na$_2$SO$_4$) and evaporated. The residue was purified by chromatography (SiO$_2$, 4 g column, 0-50% EtOAc in iso-hexane) to afford the title compound (116 mg, 83%) as a colourless oil. LC-MS [M-CO$_2$tBu+H]+=182.

Preparation 270: (S)-(7-fluoro-1,2,3,4-tetrahydroisoquinolin-3-yl)methanol hydrochloride

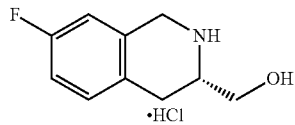 [SMILES: OC[C@@H]1Cc2ccc(F)cc2CN1 ; Cl]

A stirred solution of (S)-tert-butyl 7-fluoro-3-(hydroxymethyl)-3,4-dihydroisoquinoline-2(1H)-carboxylate (108 mg, 0.384 mmol) in ether (2 mL) was treated with a 2 M solution of hydrogen chloride solution in ether (2 mL, 4.00 mmol) and the mixture was stirred for 1 h. Further 2 M solution of hydrogen chloride solution in ether (2 mL, 4.00 mmol) was added and the mixture was stirred at room temperature for 4 h. The resulting white suspension was concentrated under vacuum to afford the title compound (127 mg, 76%) as a white solid. LC-MS: [M+H]+=182.

Preparation 271: 3-(2-aminopropan-2-yl)benzonitrile

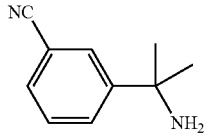

Prepared from 2-(3-bromophenyl)propan-2-amine using a similar procedure to preparations 249, 250 and 251. $^1$H NMR (CDCl$_3$) δ: 7.78 (1H, dd), 7.70 (1H, ddd), 7.43 (1H, ddd), 7.36 (1H, dd), 1.61 (2H, s (br)), 1.42 (6H, s).

Preparation 272: tert-butyl 7-(hydroxymethyl)-1,2,4,5-tetrahydro-3H-benzo[d]azepine-3-carboxylate

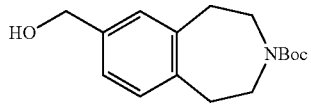 [SMILES: CC(C)(C)OC(=O)N1CCc2ccc(CO)cc2CC1]

A stirred solution of tert-butyl 7-bromo-4,5-dihydro-1H-benzo[d]azepine-3(2H)-carboxylate (350 mg, 1.073 mmol) in THF (10 mL) was treated under nitrogen dropwise over 15 min. at −70 to −65° C. with tert-butyllithium (1.7 M in pentane, 1.39 mL, 2.360 mmol) and stirred at −70° C. for 30 min. to give a dark red solution. The solution was treated dropwise with morpholine-4-carbaldehyde (236 µl, 2.360 mmol) and stirred at room temperature for 1 h. The resulting yellow solution was quenched by the cautious addition of sat. NH$_4$Cl (aq.) (50 mL) and extracted with EtOAc (3×15 mL). The combined organic extracts were washed with brine (50 mL), dried (MgSO$_4$) and evaporated to give tert-butyl 7-formyl-1,2,4,5-tetrahydro-3H-benzo[d]azepine-3-carboxylate as a colourless oil which was used without further purification in the next step. NaBH$_4$ (57 mg, 1.500 mmol) was added to a solution of tert-butyl 7-formyl-4,5-dihydro-1H-benzo[d]azepine-3(2H)-carboxylate (138 mg, 0.500 mmol) in 2M NaOH (500 µl, 1.000 mmol) and MeOH (2 mL) at 0° C. The reaction mixture was allowed to warm to room temperature and stirred overnight. The reaction mixture was concentrated, and then diluted with EtOAc (10 mL) and water (10 mL). The layers were separated and the aqueous layer was further extracted with EtOAc (2×15 mL). The crude product was purified by chromatography (SiO$_2$, 12 g column, 0-50% EtOAc in iso-hexane) to afford the title compound (53 mg, 36%) as a colourless oil. $^1$H NMR (DMSO-d6) δ: 7.07 (3H, q), 5.09 (1H, t), 4.43 (2H, d), 3.47-3.41 (4H, m), 2.85-2.78 (4H, m), 1.42 (9H, s). LC-MS: [M+Na]+=300 (very weak chromophore).

Preparation 273: (2,3,4,5-tetrahydro-1H-benzo[d]azepin-7-yl)methanol

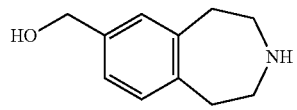 [SMILES: OCc1ccc2c(c1)CCNCC2]

tert-Butyl 7-(hydroxymethyl)-4,5-dihydro-1H-benzo[d]azepine-3(2H)-carboxylate (53 mg, 0.191 mmol) was dissolved in DCM (2.5 mL), cooled in an ice bath, and TFA (294 µl, 3.82 mmol) was added dropwise. The reaction was allowed to warm to room temperature and stirred for 1.5 h. The crude reaction mixture was loaded onto a column of SCX (2 g) in MeOH. The column was washed with MeOH and the product was eluted with 0.7 M ammonia in MeOH. The resulting mixture was concentrated in vacuo to afford the title compound (45 mg, 133%) as a colourless oil. $^1$H NMR (CDCl$_3$) δ: 7.19-7.07 (3H, m), 4.65 (2H, s), 3.05-2.95 (9H, m). (exchangeable proton was not observed) Preparation 274: 7-(((tert-butyldimethylsilyl)oxy)methyl)-2,3,4,5-tetrahydro-1H-benzo[d]azepine

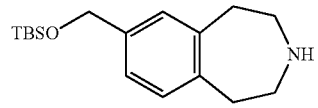 [SMILES: CC(C)(C)[Si](C)(C)OCc1ccc2c(c1)CCNCC2]

Imidazole (52 mg, 0.762 mmol) and tert-butylchlorodimethylsilane (42 mg, 0.279 mmol) were added to a solution of (2,3,4,5-tetrahydro-1H-benzo[d]azepin-7-yl)methanol (45 mg, 0.254 mmol) in DCM (2 mL) at 0° C. The reaction mixture was stirred overnight at room temperature, then diluted with ethyl acetate (5 mL) and water (5 mL). The layers were separated and the organic layer was washed with brine (5 mL), dried (MgSO$_4$), evaporated in vacuo to give the title compound (49 mg, 66%) as a pale yellow oil. $^1$H NMR (CDCl$_3$) δ: 7.12-7.02 (3H, m), 4.69 (2H, s), 3.02-2.90 (9H, m), 0.94 (9H, s), 0.10 (6H, s).

Preparation 275: (E)-N-(2-((tert-butyldimethylsilyl)oxy)ethylidene)-2-methylpropane-2-sulfinamide

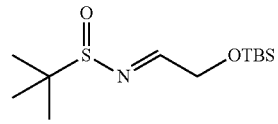 [SMILES: CC(C)(C)S(=O)/N=C/CO[Si](C)(C)C(C)(C)C]

2-methylpropane-2-sulfinamide (200 mg, 1.650 mmol) followed by copper (II) sulfate (527 mg, 3.30 mmol) were added to a solution of 2-((tert-butyldimethylsilyl)oxy)acetaldehyde (0.346 ml, 1.815 mmol) in DCM (5 mL) and the mixture was stirred at room temperature overnight under nitrogen. The reaction mixture was filtered, washing through with DCM. The filtrate was evaporated and the crude product was purified by chromatography (SiO$_2$, 12 g column, 0-40% EtOAC in iso-hexane) to afford the title compound (325 mg, 70%) as a colourless oil which solidified on standing. $^1$H NMR (CDCl$_3$) δ: 8.06 (1H, t), 4.54 (2H, d), 1.21 (9H, s), 0.92 (9H, s), 0.10 (6H, s). LC-MS: [M+H]+=278.

Preparation 276: (S,E)-N-(2-((tert-butyldimethylsilyl)oxy)ethylidene)-2-methylpropane-2-sulfinamide

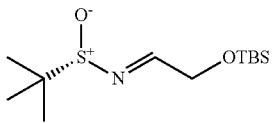

Prepared using a similar procedure to preparation 275. ¹H NMR (CDCl₃) δ: 8.05 (1H, t), 4.54 (2H, d), 1.20 (9H, s), 0.91 (9H, s), 0.09 (6H, s).

Preparation 277: N-(2-((tert-butyldimethylsilyl)oxy)-1-(imidazo[1,2-a]pyridin-8-yl)ethyl)-2-methylpropane-2-sulfinamide

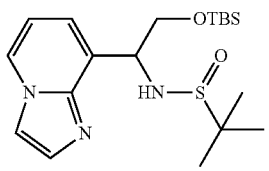

n-BuLi (2.5 M in hexanes, 0.216 mL, 0.541 mmol) was added dropwise to a solution of 8-bromoimidazo[1,2-a]pyridine (97 mg, 0.491 mmol) in dry THF (2 mL) at −78° C. and the mixture was stirred for 1 h before (E)-N-(2-((tert-butyldimethylsilyl)oxy)ethylidene)-2-methylpropane-2-sulfinamide (150 mg, 0.541 mmol) in THF (0.5 mL) was added. The reaction mixture was stirred at −78° C. for 1 h, then warmed to rt and stirred for 1 h. The reaction was quenched with sat. NH₄Cl (aq.) (30 mL) and left to stand overnight. The mixture was extracted with ethyl acetate (3×30 mL) and the combined organic extracts were washed with brine (30 mL), dried (MgSO₄), filtered and concentrated in vacuo to give a yellow oil. The residue was purified by chromatography (SiO₂, 12 g column, 0 to 6% of MeOH in DCM) to afford the title compound (82 mg, 38%) as a colourless solid. LCMS: [M+H]+=396.

Preparation 278: 2-amino-2-(imidazo[1,2-a]pyridin-8-yl)ethan-1-ol (1427-17)

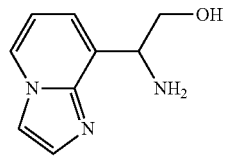 [SMILES: NC(CO)c1cccn2ccnc12]

HCl (4 M solution in dioxane, 0.19 mL, 0.748 mmol) was added to a stirred solution of N-(2-((tert-butyldimethylsilyl)oxy)-1-(imidazo[1,2-a]pyridin-8-yl)ethyl)-2-methylpropane-2-sulfinamide (82 mg, 0.187 mmol) in MeOH (1 mL) at 0° C. and the reaction was stirred at room temperature for 30 min. The reaction mixture was concentrated in vacuo to give the title compound (45 mg, 102%). The product was used without further purification in the next step. LCMS: [M+H]+=178.

Preparation 278: N-(2-((tert-butyldimethylsilyl)oxy)-1-(1,3-dihydroisobenzofuran-4-yl)ethyl)-2-methylpropane-2-sulfinamide

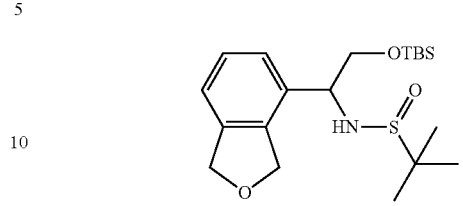

Prepared using a similar procedure to preparation 277. LCMS: [M+H]+=398.

Preparation 280: 2-amino-2-(1,3-dihydroisobenzofuran-4-yl)ethan-1-ol

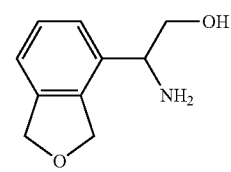 [SMILES: NC(CO)c1cccc2c1COC2]

Prepared using a similar procedure to preparation 278. LCMS: [M+H]+=180.

Preparation 281: tert-butyl (S)-(1-(3-bromophenyl)-2-hydroxyethyl)carbamate

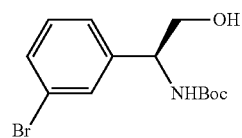

DIPEA (0.207 mL, 1.188 mmol) and Boc-Anhydride (0.138 mL, 0.594 mmol) were added to a suspension of (S)-2-amino-2-(3-bromophenyl)ethanol.HCl (150 mg, 0.594 mmol) in DCM (2 mL) and the reaction was stirred at rt overnight. The solution was washed with water (10 mL) and the aqueous layer was extracted with DCM (30 mL). The combined organic extracts were dried (MgSO₄) and concentrated in vacuo. The crude product was adsorbed onto silica and purified by chromatography (SiO₂, 12 g column, 0-70% EtOAc in iso-hexane) to afford the title compound (164 mg, 86%) as an off white solid. LCMS: [M+Na]+=338.

Preparation 282: tert-butyl (S)-(1-(3-(furan-2-yl)phenyl)-2-hydroxyethyl)carbamate

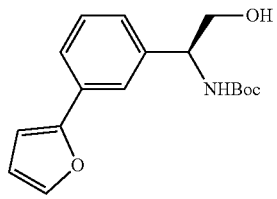 [SMILES: CC(C)(C)OC(=O)N[C@H](CO)c1cccc(-c2ccco2)c1]

A mixture of (S)-tert-butyl (1-(3-bromophenyl)-2-hydroxyethyl)carbamate (50 mg, 0.158 mmol) and furan-2-ylboronic acid (35 mg, 0.316 mmol) in 1,4-dioxane (1 mL) and sodium carbonate (2 M aq.) (0.237 mL, 0.474 mmol) was degassed with nitrogen for 10 min. Pd(PPh$_3$)$_4$ (18.27 mg, 0.016 mmol) was added and the mixture degassed for a further 5 min. The mixture was heated to 90° C. for 6 h, then cooled to room temperature and diluted with water (20 mL) and EtOAc (20 mL). The phases were separated and the aqueous was extracted with EtOAc (2×15 mL). The combined organic extracts were washed with brine (30 mL), dried (MgSO$_4$) and concentrated. The crude product was purified by chromatography (SiO$_2$, 12 g column, 0-40% EtOAc in iso-hexanes) to afford the title compound (38 mg, 78%) as a yellow oil which solidified on standing to give a yellow solid. LCMS: [M+Na]+=326.

Preparation 283: tert-butyl((1S)-2-hydroxy-1-(3-(tetrahydrofuran-2-yl)phenyl)ethyl)carbamate

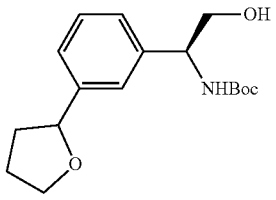 [SMILES: CC(C)(C)OC(=O)N[C@H](CO)c1cccc(C2CCCO2)c1]

A mixture of (S)-tert-butyl (1-(3-(furan-2-yl)phenyl)-2-hydroxyethyl)carbamate (18 mg, 0.059 mmol), and Pd on carbon (3R38H) (1.5 mg, 0.423 μmol) or Pd on alumina (5R325) (1.5 mg, 0.705 μmol) in ethanol (2 ml, 34.3 mmol) was separately hydrogenated at room temperature and 1 bar overnight. The reaction mixtures were then filtered through celite and concentrated to obtain an off white solid. The residues was redissolved in ethanol (2 mL) and Pd on carbon (3R38H) (3 mg, 2.82 μmol) or Pd on alumina (5R325)) (1.5 mg, 0.705 μmol) was added and the mixtures hydrogenated separately at room temperature and 1.5 bar overnight. The suspensions were filtered through celite and the filter cake washed with EtOH (10 mL). The filtrate was concentrated to give the title compound as a colourless oil. palladium on carbon (3R38H) (16 mg, 83%, 95% purity (NMR)); Pd on alumina (5R325): (19 mg, 94%, 90% purity (NMR)). $^1$H NMR (CDCl$_3$) δ: 7.34-7.29 (1H, m), 7.26-7.23 (2H, m), 7.18 (1H, d), 5.22 (1H, s), 4.87 (1H, td), 4.77 (1H, s), 4.14-4.04 (1H, m), 3.99-3.88 (1H, m), 3.83 (2H, d), 2.39-2.26 (1H, m), 2.09-1.93 (2H, m), 1.85-1.71 (1H, m), 1.43 (9H, s). (exchangeable OH was not observed).

Preparation 284: (2S)-2-amino-2-(3-(tetrahydrofuran-2-yl)phenyl)ethan-1-ol

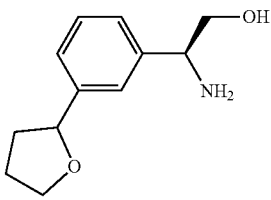 [SMILES: N[C@H](CO)c1cccc(C2CCCO2)c1]

tert-Butyl ((1S)-2-hydroxy-1-(3-(tetrahydrofuran-2-yl)phenyl)ethyl)carbamate (19 mg, 0.062 mmol) was dissolved in DCM (1 mL) and TFA (0.080 mL, 1.041 mmol) was added at room temperature and the mixture was stirred for 3 h. The crude reaction mixture was loaded onto a column of SCX (1.5 g) in MeOH. The column was washed with MeOH and the product was eluted with 0.7 M ammonia in MeOH. The resulting mixture was concentrated in vacuo to afford the title compound (12 mg, 87%) as a colourless oil. LCMS: [M+H]+=208.

Preparation 285 (S)—N—((S,E)-2-(benzyloxy)propylidene)-2-methylpropane-2-sulfinamide

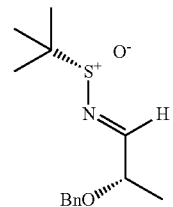

(S)-2-Methylpropane-2-sulfinamide (1.332 g, 10.99 mmol) was added to a solution of (S)-2-(benzyloxy)propanal (1.823 g, 9.99 mmol) and titanium (IV) isopropoxide (7.32 mL, 24.98 mmol) in THF (20 mL) and the mixture was stirred at room temperature overnight. The mixture was poured into brine (50 mL) and filtered through a pad of celite, eluting with EtOAc (200 mL). The filtrate was washed with brine (100 mL), dried (MgSO$_4$) and concentrated. The crude product was purified by chromatography (SiO$_2$, 24 g column, 0-50% EtOAc in iso-hexane) to afford the title compound (1.36 g, 48%) as a colourless oil. $^1$H NMR (CDCl$_3$) δ: 8.07 (1H, d), 7.38-7.32 (4H, m), 7.32-7.28 (1H, m), 4.65 (1H, d), 4.48 (1H, d), 4.39-4.28 (1H, m), 1.41 (3H, d), 1.23 (9H, s) (note: the product was obtained as a 10:1 mixture of stereoisomers).

Preparation 286: (S)—N-((1S,2S)-2-(benzyloxy)-1-(3-methoxyphenyl)propyl)-2-methylpropane-2-sulfinamide

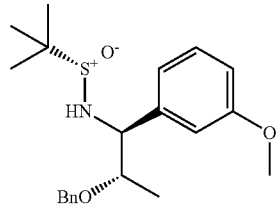

1-Bromo-3-methoxybenzene (1.421 mL, 11.22 mmol) was added to magnesium (0.300 g, 12.34 mmol) in diethyl ether (6 mL) and the mixture was heated to reflux for 1 h. 1,2-dibromoethane (2 drops) was added and the mixture was refluxed for 1 h then cooled to room temperature. Separately, (S,E)-N—((S)-2-(benzyloxy)propylidene)-2-methylpropane-2-sulfinamide (0.5 g, 1.870 mmol) in THF (9.4 mL,) was cooled to −78° C. 3 mL of the Grignard reagent generated above was added dropwise and was stirred for 2 h. A further 1 mL of Grignard solution was added dropwise and the mixture stirred for 1 h. The reaction was quenched by addition of sat. NH4C (aq.) (5 mL) and allowed to warm to room temperature overnight. Brine (15 mL) was added and the mixture was extracted with EtOAc (3×20 mL). The combined organic extracts were washed with brine (50 mL), dried (MgSO4) and concentrated. The crude product was purified by chromatography (SiO2, 24 g column, 0-50% EtOAc in iso-hexane) to afford the title compound (230 mg, 30%) as a colourless oil. $^1$H NMR (CDCl3) δ: 7.43-7.30 (5H, m), 7.28-7.23 (1H, m), 6.95-6.88 (1H, m), 6.88-6.83 (2H, m), 4.72 (1H, d), 4.51 (1H, s (br)), 4.44 (1H, d), 4.28 (1H, dd), 3.81 (3H, s), 3.72-3.61 (1H, m), 1.16 (9H, s), 1.08 (3H, d) (note: A further mixed fraction (200 mg) containing a 1.1:1 mixture of diastereoisomers was also obtained).

Preparation 287: (S)—N-((1S,2S)-2-(benzyloxy)-1-(3-ethylphenyl)propyl)-2-methylpropane-2-sulfinamide

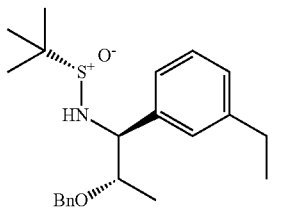

1-Bromo-3-ethylbenzene (2.076 g, 11.22 mmol) was added to magnesium (277 mg, 11.41 mmol) in Et2O (3.7 mL). The mixture was heated to reflux for 1 h, then 1,2-dibromoethane (2 drops) was added and the mixture was refluxed again. After initiation occurred the mixture was heated for 1 h then allowed to cool to room temperature. Separately, (S,E)-N—((S)-2-(benzyloxy)propylidene)-2-methylpropane-2-sulfinamide (556 mg, 1.87 mmol) in toluene (9.4 mL) was cooled to −78° C. 2.5 mL of the Grignard reagent generated above was added dropwise and the mixture was stirred for 2 h. The reaction was quenched by addition of sat. NH4Cl (aq.) (5 mL) and allowed to warm to room temperature. Brine (25 mL) was added and the mixture was extracted with EtOAc (3×20 mL). The combined organic phases were washed with brine (50 mL), dried (MgSO4) and concentrated. The crude product was purified by chromatography (SiO2, 24 g column, 0-50% EtOAc in isohexane) to afford the title compound (482 mg, 64.2%) as a colourless oil. $^1$H NMR (CDCl3) δ: 7.37-7.21 (7H, m), 7.16-7.07 (3H, m), 4.70 (1H, d), 4.50 (1H, s), 4.42 (1H, d), 4.26 (1H, dd), 3.71-3.59 (1H, m), 2.63 (2H, q), 1.22 (2H, t), 1.13 (9H, s), 1.05 (3H, d).

Preparations 288-290

Prepared using an analogous procedure to Preparation 287, from (S)—N—((S,E)-2-(benzyloxy)propylidene)-2-methylpropane-2-sulfinamide (Preparation 285) and the corresponding aryl bromide:

| Preparation | Structure | Name | $^1$H NMR (400 MHz) |
|---|---|---|---|
| 288 | 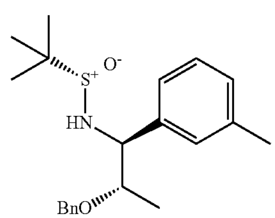 | (S)-N-((1S,2S)-2-(benzyloxy)-1-(m-tolyl)propyl)-2-methylpropane-2-sulfinamide | $^1$H NMR (DMSO-d6) δ: 7.42-7.29 (5H, m), 7.34-7.16 (1H, m), 7.19-7.06 (3H, m), 4.65 (1H, d), 4.63 (1H, s (br)), 4.49 (1H, d), 4.14 (1H, dd), 3.76-3.64 (1H, m), 2.29 (3H, s), 1.04 (9H, s), 0.96 (3H, d) |
| 289 | 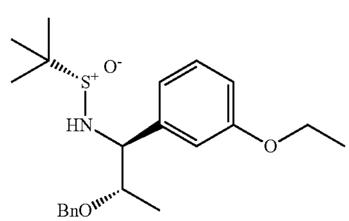 | (S)-N-((1S,2S)-2-(benzyloxy)-1-(3-ethoxyphenyl)propyl)-2-methylpropane-2-sulfinamide | $^1$H NMR (DMSO-d6) δ: 7.43-7.28 (5H, m), 7.33-7.17 (1H, m), 6.92-6.79 (3H, m), 4.67 (1H, d), 4.64 (1H, d), 4.49 (1H, d), 4.16 (1H, dd), 4.06-3.92 (2H, m), 3.77-3.65 (1H, m), 1.32 (3H, t), 1.05 (9H, s), 0.97 (3H, d). |
| 290 | 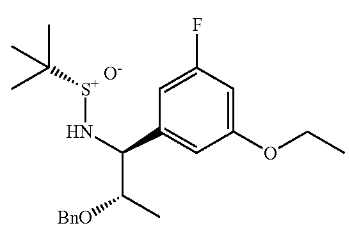 | (S)-N-((1S,2S)-2-(benzyloxy)-1-(3-ethoxy-5-fluorophenyl)propyl)-2-methylpropane-2-sulfinamide | $^1$H NMR (DMSO-d6) δ: 7.43-7.26 (5H, m), 6.79-6.66 (3H,m), 4.78 (1H, d), 4.61 (1H, d), 4.48 (1H, d), 4.21 (1H, dd), 4.08-3.90 (2H, m), 3.79-3.61 (1H, m), 1.30 (3H, t), 1.05 (9H, s), 0.99 (3H, d). |

Preparation 291: (1S,2S)-1-amino-1-(3-methoxyphenyl)propan-2-ol hydrochloride

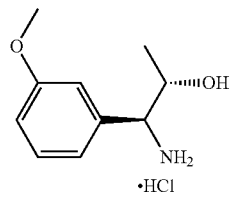

HCl (4 M in 1,4-dioxane) (0.8 mL, 3.20 mmol) was added to a solution of (S)—N-((1S,2S)-2-(benzyloxy)-1-(3-methoxyphenyl)propyl)-2-methylpropane-2-sulfinamide (230 mg, 0.612 mmol) in methanol (6 mL, 148 mmol) and the mixture was stirred at room temperature for 1 h. The solvent was removed in vacuo and the residue was stirred with diethyl ether (5 mL). The resulting white solid was collected by filtration to give (1S,2S)-2-(benzyloxy)-1-(3-methoxyphenyl)propan-1-amine hydrochloride. The crude solid was dissolved in methanol (6 mL, 148 mmol) and Pd/C (10%, Type 39) (50 mg, 0.470 mmol) followed by HCl (4 M in 1,4-dioxane) (0.8 mL, 3.20 mmol) were added. The mixture was stirred under an atmosphere of hydrogen (5 bar) for 2 h., then filtered through celite, eluting with methanol. The filtrate was concentrated and triturated with diethyl ether. The resulting solid was collected by filtration to give the title compound (94 mg, 67% yield) as a tan solid. $^1$H NMR (DMSO-d6) δ: 8.33 (3H, s (br)), 7.34 (1H, dd), 7.16-7.07 (1H, m), 7.05 (1H, d), 6.96 (1H, ddd), 5.64 (1H, s), 3.93-3.88 (2H, m), 3.77 (3H, s), 0.94 (3H, d).

Preparations 292-295

Prepared using an analogous procedure to Preparation 291, from the corresponding protected sulfoximine (preparation 287-290):

| Preparation | Structure | Name | $^1$H NMR (400 MHz) |
|---|---|---|---|
| 292 | 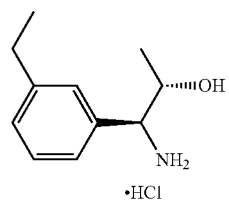 | (1S,2S)-1-amino-1-(3-ethylphenyl)propan-2-ol hydrochloride | $^1$H NMR (DMSO-d6) δ: 8.33 (3H, s (br)), 7.38-7.27 (3H, m), 7.27-7.21 (1H, m), 5.64 (1H, d), 3.91 (2H, d), 2.62 (2H, q), 1.20 (3H, t), 0.92 (3H, d). |
| 293 | 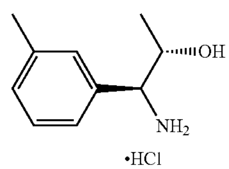 | (1S,2S)-1-amino-1-(m-tolyl)propan-2-ol hydrochloride | $^1$H NMR (DMSO-d6) δ: 8.37 (3H, s (br)), 7.36-7.26 (3H, m), 7.24-7.17 (1H, m), 5.65 (1H, d), 4.00-3.83 (2H, m), 2.32 (3H, s), 0.92 (3H, d). |
| 294 | 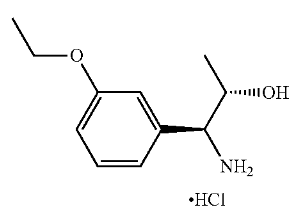 | (1S,2S)-1-amino-1-(3-ethoxyphenyl)-propan-2-ol hydrochloride | $^1$H NMR (DMSO-d6) δ: 8.43 (3H, s (br)), 7.31 (1H, dd), 7.19-7.13 (1H, m), 7.04 (1H, d), 6.93 (1H, dd), 5.66 (1H, d), 4.04 (2H, q), 4.00-3.83 (2H, m), 1.33 (3H, t), 0.92 (3H, d). |
| 295 | 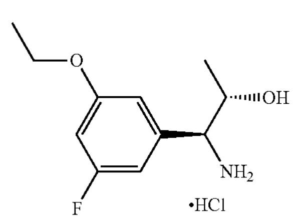 | (1S,2S)-1-amino-1-(3-ethoxy-5-fluorophenyl)-propan-2-ol hydrochloride | $^1$H NMR (DMSO-d6) δ: 8.48 (3H, s (br)), 7.46-7.27 (5H, m), 7.05-6.95 (2H, m), 6.87 (1H, ddd), 4.64 (1H, d), 4.53 (1H, d), 4.25-4.15 (1H, m), 4.05 (2H, q), 3.97-3.84 (1H, m), 1.33 (3H, t), 1.01 (3H, d). |

Preparation 296: (S)—N—((S)-2-((tert-butyldimethylsilyl)oxy)-1-(3-(1,1-difluoroethyl)phenyl)ethyl)-2-methylpropane-2-sulfinamide

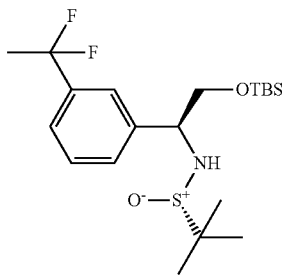 [SMILES: CC(F)(F)c1cccc([C@@H](CO[Si](C)(C)C(C)(C)C)N[S@@+]([O-])C(C)(C)C)c1]

nBuLi (2.5 M in hexanes) (1.600 ml, 4.00 mmol) was added to a solution of 1-bromo-3-(1,1-difluoroethyl)benzene (884 mg, 4.00 mmol) in Et$_2$O (1.6 ml, 15.39 mmol) at −78° C. The reaction was stirred for 1 h, before being added dropwise to a solution of (S,E)-N-(2-((tert-butyldimethylsilyl)oxy)ethylidene)-2-methylpropane-2-sulfinamide (555 mg, 2 mmol) in Et$_2$O (10 ml, 96 mmol) at −78° C. The reaction was stirred for 1 h then quenched with NH$_4$Cl (5 mL) and allow to warm to room temperature. The phases were separated and the aqueous phase was extracted with EtOAc (3×20 mL). The combined organic extracts were washed with brine (20 mL), dried (MgSO$_4$) and concentrated. The crude product was purified by chromatography (SiO$_2$, 40 g column, 0-50% EtOAc in isohexane) to afford the title compound (414 mg, 45.9%) as a colourless oil. 1H NMR (Chloroform-d) δ: 7.49 (s, 1H), 7.47-7.34 (m, 3H), 4.57 (ddd, 1H), 4.29 (d, 1H), 3.80 (dd, 1H), 3.61 (dd, 1H), 1.90 (td, 3H), 1.23 (s, 9H), 0.90 (s, 9H), 0.07 (s, 3H), 0.04 (s, 3H).

(note: the other diastereoisomer S)—N—((R)-2-((tert-butyldimethylsilyl)oxy)-1-(3-(1,1-difluoroethyl)phenyl)ethyl)-2-methylpropane-2-sulfinamide (153 mg, 16.95%) was also isolated as a colourless oil.)

Preparation 297: (S)-2-amino-2-(3-(1,1-difluoroethyl)phenyl)ethan-1-ol hydrochloride

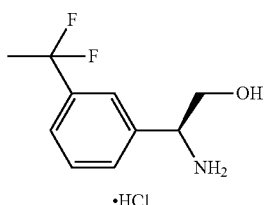

HCl (4 M in 1,4-dioxane) (0.987 ml, 3.95 mmol) was added to a solution of (S)—N—((S)-2-((tert-butyldimethylsilyl)oxy)-1-(3-(1,1-difluoroethyl)phenyl)ethyl)-2-methylpropane-2-sulfinamide (0.414 g, 0.987 mmol) in methanol (4.93 ml, 0.987 mmol) and the mixture was stirred overnight at room temperature. The solvent was removed and the residue was triturated with diethyl ether (5 mL). The resulting solid was isolated by filtration washing with diethyl ether (10 mL) to give the title compound (181 mg, 76%) as a white solid. 1H NMR (DMSO-d6) δ: 8.50 (s, 3H), 7.75 (s, 1H), 7.66-7.51 (m, 3H), 5.58 (t, 1H), 4.38 (dd, 1H), 3.80-3.65 (m, 2H), 1.99 (t, 3H).

Preparation 298: (S)-2-(dibenzylamino)-2-phenylethan-1-ol

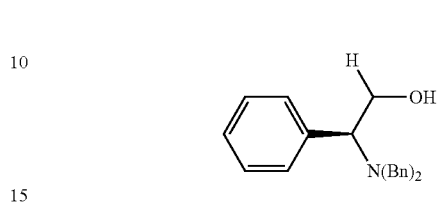

(S)-2-amino-2-phenylethanol (500 mg, 3.64 mmol) in MeCN (25 ml, 479 mmol) was treated with benzyl chloride (1.270 ml, 10.93 mmol) and potassium carbonate (1763 mg, 12.76 mmol) and the suspension stirred and heated at 90° C. for four days. The suspension was cooled, filtered and the solids washed with DCM (50 ml). The filtrate was concentrated to dryness and the residue purified by chromatography (SiO$_2$, 12 g column, 15% EtOAc in isohexane) to afford the title compound (660 mg, 52.5%) as a viscous oil. LCMS: [M+H]+=318.

Preparation 299: (S)-2-(dibenzylamino)-2-phenylacetaldehyde

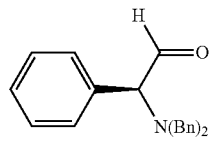

Sulfur trioxide pyridine complex (0.983 g, 6.17 mmol) was added to a solution of (S)-2-(dibenzylamino)-2-phenylethanol (0.49 g, 1.544 mmol) and triethylamine (1.721 mL, 12.35 mmol) in DCM (10 mL, 155 mmol) and DMSO (5 mL, 70.5 mmol) at 0° C. The reaction was warmed to room temperature and stirred for 2 h, then diluted with water (10 mL) and extracted with EtOAc (3×10 mL). The combined organic extracts were washed with brine (3×30 mL), dried (MgSO$_4$) and concentrated to afford the title compound (462 mg, 81%), which was used without further purification in the next step. 1H NMR (CDCl3) δ: 9.73 (d, 1H), 7.48-7.21 (m, 15H), 4.40-4.35 (m, 1H), 3.93-3.84 (m, 2H), 3.52-3.47 (m, 2H).

Preparation 300: (1S,2S)-1-(dibenzylamino)-1-phenylbutan-2-ol

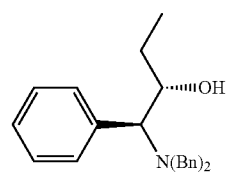

Diethylzinc (1 M in hexanes) (2.930 mL, 2.93 mmol) was added dropwise to a solution of (S)-2-(dibenzylamino)-2- phenylacetadehyde (462 mg, 1.465 mmol) in toluene (5.86 mL, 1.465 mmol) at 0° C. The reaction was stirred for 2 h at 0° C. and allowed to warm to room temperature overnight. The reaction was quenched with NH₄Cl (20 mL) and the phases were separated. The aqueous phase was extracted with diethyl ether (3×20 mL). The combined organic phases were washed with brine (50 mL), dried (MgSO₄) and concentrated. The crude product was purified by chromatography (SiO₂, 24 g column, 0-20% EtOAc in isohexane) to afford the title compound (174 mg, 0.478 mmol, 33% yield) as a colourless oil. 1H NMR (400 MHz, CDCl3) δ 7.51-7.28 (m, 10H), 7.30-7.14 (m, 5H), 4.48 (s, 1H), 4.20-4.07 (m, 1H), 3.96 (d, 2H), 3.49 (d, 1H), 3.02 (d, 2H), 1.30-1.22 (m, 1H), 1.13-0.98 (m, 1H), 0.86 (t, 3H).

Preparation 301:
(1S,2S)-1-amino-1-phenylbutan-2-ol hydrochloride

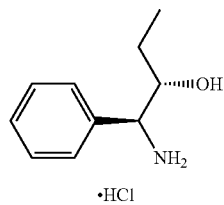

A mixture of (1S,2S)-1-(dibenzylamino)-1-phenylbutan-2-ol (174 mg, 0.504 mmol) and palladium on carbon (Type 39L, 10%) (20 mg, 9.40 μmol) in MeOH (5 mL, 124 mmol) was stirred under hydrogen atmosphere (5 bar) for 3 h. The catalyst was removed by filtration and replaced with fresh catalyst and the reaction was stirred under hydrogen atmosphere (5 bar) for 3 h. A portion of HCl (4 M in 1,4-dioxane) (0.252 mL, 1.007 mmol) was added and the reaction stirred under hydrogen atmosphere (5 bar) for 1 h. The catalyst was removed by filtration and the solvent was removed in vacuo. The residue was dissolved in MeOH (12 mL). The reaction mixture was hydrogenated in the H-Cube (10% Pd/C, 30×4 mm, 20 bar, 60° C., 1 mL/min) on continuous flow for 2 h. HCl (2 M in diethyl ether) (0.504 mL, 1.007 mmol) was added and the solvent was removed in vacuo to give a yellow oil. Repeated evaporation from diethyl ether gave the title compound (70 mg, 0.330 mmol, 66% yield) as a yellow foam. 1H NMR (DMSO-d6) δ: 8.43 (s, 3H), 7.62-7.49 (m, 2H), 7.48-7.34 (m, 3H), 4.02-3.93 (m, 1H), 3.76-3.66 (m, 1H), 1.22-1.06 (m, 2H), 0.80 (t, 3H).

Preparation 302: 2-((2,3,4,5-tetrahydro-1H-benzo[d]azepin-1-yl)methyl)isoindoline-1,3-dione

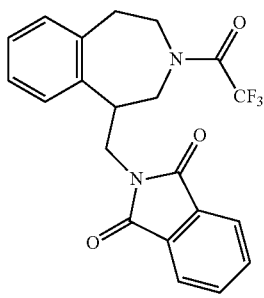 [SMILES: O=C1c2ccccc2C(=O)N1CC1CN(C(=O)C(F)(F)F)CCc2ccccc21]

DIAD (74.0 μl, 0.381 mmol) was added dropwise to a stirred solution of 2,2,2-trifluoro-1-(1-(hydroxymethyl)-4,5-dihydro-1H-benzo[d]azepin-3(2H)-yl)ethanone (preparation 154) (80 mg, 0.293 mmol), phthalimide (56.0 mg, 0.381 mmol) and triphenylphosphine (100 mg, 0.381 mmol) in THF (2.9 mL) and the resulting orange solution was stirred at room temperature for 5 h. The mixture was diluted with EtOAc (10 mL) and water (10 mL). The phases were separated and the aqueous layer was extracted with EtOAc (10 mL). The combined organic extracts were dried (MgSO₄), filtered and reduced in vacuo to give an oil. The crude product was purified by chromatography (SiO₂, 12 g column, 0-100% EtOAc in Isohexane) to afford the title compound (90 mg, 46%) as a white solid. LC-MS: [M+H]+= 403.

Preparation 303: 2-((2,3,4,5-tetrahydro-1H-benzo[d]azepin-1-yl)methyl)isoindoline-1,3-dione

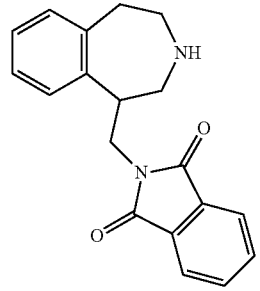 [SMILES: O=C1c2ccccc2C(=O)N1CC1CNCCc2ccccc21]

2-((3-(2,2,2-trifluoroacetyl)-2,3,4,5-tetrahydro-1H-benzo[d]azepin-1-yl)methyl)isoindoline-1,3-dione (90 mg, 0.224 mmol) was dissolved in methanol (941 μl) and was treated with 2M NaOH (224 μl, 0.447 mmol), then stirred at room temperature for 4 h. Acetic acid (38.4 μl, 0.671 mmol) was added and reaction diluted with MeOH (4 ml) and then loaded onto a column packed with SCX (2 g) The column was washed with MeOH and the product was eluted with 0.7 M ammonia in MeOH. The resulting mixture was concentrated in vacuo to afford 2-(((2,3,4,5-tetrahydro-1H-benzo[d]azepin-1-yl)methyl)carbamoyl)benzoic acid (56 mg, 0.173 mmol, 77% yield) as a colourless solid, which was dissolved in 4M HCl in dioxane (1678 μl, 6.71 mmol) and refluxed for 2 h. The reaction mixture was allowed to cool to room temperature and loaded onto a column packed with SCX (2 g). The column was washed with MeOH and the product was eluted with 0.7 M ammonia in MeOH. The resulting mixture was concentrated in vacuo to afford the title compound (30 mg, 42%) as a colourless solid. LC-MS: [M+H]+=307.

Preparation 304: tert-butyl (S)-(2-(2-(6-(5-chloro-2-((oxan-4-yl)amino)pyrimidin-4-yl)-1-oxoisoindolin-2-yl)acetamido)-2-phenylethyl)carbamate

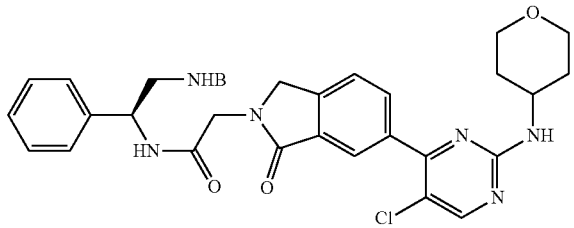

DIPEA (0.036 ml, 0.209 mmol) followed by HATU (0.079 g, 0.209 mmol) were added to a mixture of 2-(6-{5-chloro-2-[(oxan-4-yl)amino]pyrimidin-4-yl}-1-oxo-2,3-dihydro-1H-isoindol-2-yl)acetic acid (0.08 g, 0.199 mmol) and (S)-tert-butyl (2-amino-2-phenylethyl)carbamate (0.049 g, 0.209 mmol) in DMF (1 mL) and the mixture was stirred for 40 minutes. The mixture was diluted with EtOAc and transferred into a separating funnel. 1N HCl was added and the product was extracted with EtOAc. The combined organic extracts were washed with $NaHCO_3$, water, brine, dried ($MgSO_4$) and concentrated under vacuum to afford the title compound (0.112 g, 91%) as a colourless glass. The product was used without further purification and characterization in the next step.

Preparation 305: 2-(2-(7-(((tert-butyldimethylsilyl)oxy)methyl)-1,2,4,5-tetrahydro-3H-benzo[d]azepin-3-yl)-2-oxoethyl)-6-(5-chloro-2-((oxan-4-yl)amino)pyrimidin-4-yl)isoindolin-1-one

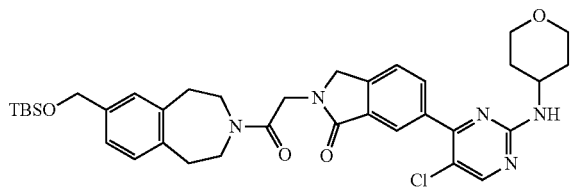 [SMILES: CC(C)(C)[Si](C)(C)OCc1ccc2c(c1)CCN(C(=O)CN1Cc3ccc(-c4nc(NC5CCOCC5)ncc4Cl)cc3C1=O)CC2]

Triethylamine (69.2 µl, 0.496 mmol) was added to a mixture of 2-(6-{5-chloro-2-[(oxan-4-yl)amino]pyrimidin-4-yl}-1-oxo-2,3-dihydro-1H-isoindol-2-yl)acetic acid (50 mg, 0.124 mmol), 7-(((tert-butyldimethylsilyl)oxy)methyl)-2,3,4,5-tetrahydro-1H-benzo[d]azepine (45 mg, 0.154 mmol) and HATU (51.9 mg, 0.137 mmol) in DMF (0.5 mL). The reaction was stirred at room temperature for 1 h and water (15 mL) was added. The resulting precipitate was filtered and washed with water (15 mL). Purification by chromatography ($SiO_2$, 50-100% ethyl acetate in isohexane) gave the title compound (46 mg, 54%) as a colourless foam. LC-MS: [M+H]+=676.

Preparation 306: (R)—N-(1-(3-bromophenyl)ethyl)-2-(6-(5-chloro-2-((oxan-4-yl)amino)pyrimidin-4-yl)-1-oxoisoindolin-2-yl)acetamide

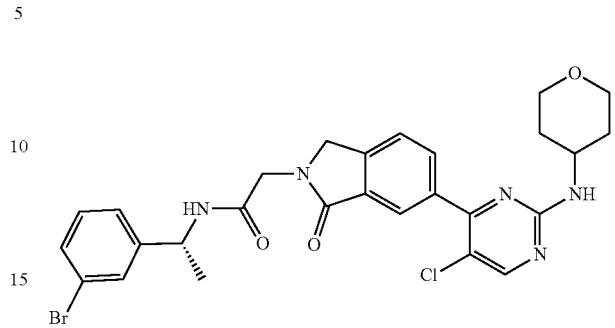

Prepared using a similar procedure to Example 405. LC-MS: [M+H]+=584.

Preparation 307: (R)-2-(6-(5-chloro-2-((oxan-4-yl)amino)pyrimidin-4-yl)-1-oxoisoindolin-2-yl)-N-(1-(3-formylphenyl)ethyl)acetamide

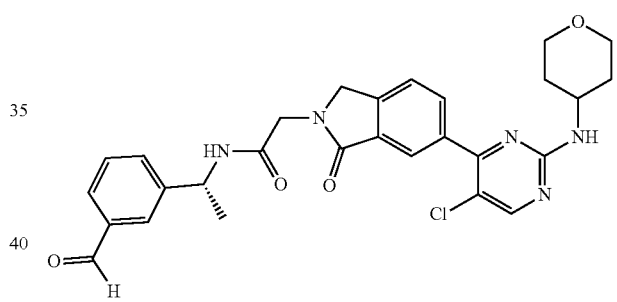

A microwave vial was charged with (R)—N-(1-(3-bromophenyl)ethyl)-2-(6-(5-chloro-2-((oxan-4-yl)amino)pyrimidin-4-yl)-1-oxoisoindolin-2-yl)acetamide (58.5 mg, 0.1 mmol), 3-oxobenzo[d]isothiazole-2(3H)-carbaldehyde 1,1-dioxide (31.7 mg, 0.150 mmol), sodium carbonate (10.60 mg, 0.100 mmol), Pd(OAc)$_2$ (0.674 mg, 3.00 µmol) and 1,4-bis(diphenylphosphino)butane (1.919 mg, 4.50 µmol). The vial was capped and evacuated and back-filled with nitrogen (3×). Triethylsilane (31.9 µl, 0.200 mmol) was added in degassed (nitrogen sparged for 10 minutes) DMF (0.8 mL) and the mixture stirred at room temperature for 10 minutes. The mixture was heated to 80° C. and stirred overnight, then allowed to cool to room temperature. The mixture was diluted with EtOAc (20 mL) and washed with brine (20 mL). The organic extracts were dried ($MgSO_4$), filtered and concentrated in vacuo. The crude product was purified by chromatography ($SiO_2$, 12 g column, 0-100% EtOAc in isohexane) to afford the title compound (10 mg, 18%) as a white solid. LC-MS: [M+H]+=534.

Preparation 308: (R)—N-(1-(3-(allyloxy)phenyl)ethyl)-2-(6-(5-chloro-2-((oxan-4-yl)amino)pyrimidin-4-yl)-1-oxoisoindolin-2-yl)acetamide

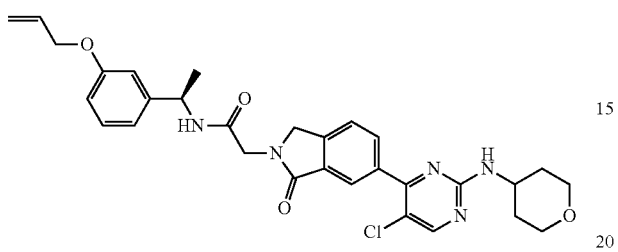

A solution of (R)-2-(6-(5-chloro-2-((oxan-4-yl)amino)pyrimidin-4-yl)-1-oxoisoindolin-2-yl)-N-(1-(3-hydroxyphenyl)ethyl)acetamide (100 mg, 0.192 mmol), potassium carbonate (132 mg, 0.958 mmol) and allyl bromide (49.7 μl, 0.575 mmol) in DMF (1 mL) was stirred at room temperature overnight. Water (2 mL) and EtOAc (2 mL) were added and the layers were separated. The organic layer was washed with brine (2 mL), dried (MgSO₄) and concentrated in vacuo. Purification by chromatography (SiO₂, 0-100% EtOAc in iso-hexane) gave the title compound (51 mg, 45%) as a colourless glass. LCMS: [M+H]+=562.

Preparation 309: (R)-2-(6-(5-chloro-2-((oxan-4-yl)amino)pyrimidin-4-yl)-1-oxoisoindolin-2-yl)-N-(1-(3-(2-(1,3-dioxoisoindolin-2-yl)ethoxy)phenyl)ethyl)acetamide

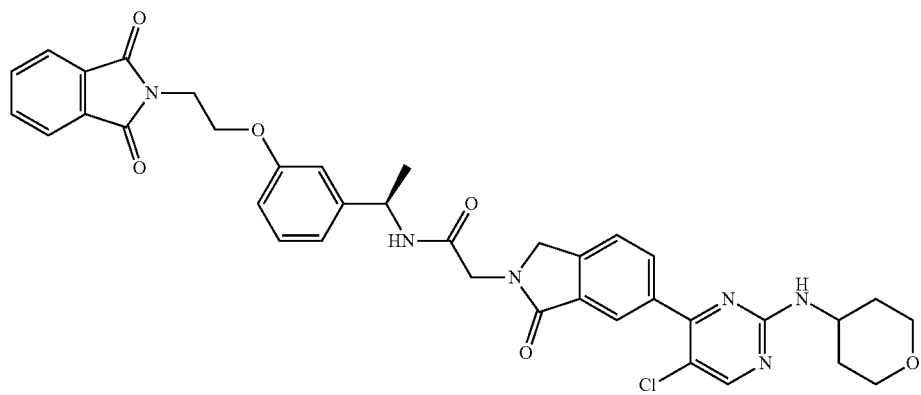 [SMILES: C[C@@H](NC(=O)CN1Cc2ccc(-c3nc(NC4CCOCC4)ncc3Cl)cc2C1=O)c1cccc(OCCN2C(=O)c3ccccc3C2=O)c1]

DIAD (44.7 μl, 0.230 mmol) was added dropwise to a solution of (R)-2-(6-(5-chloro-2-((oxan-4-yl)amino)pyrimidin-4-yl)-1-oxoisoindolin-2-yl)-N-(1-(3-hydroxyphenyl)ethyl)acetamide (100 mg, 0.177 mmol), phthalimide (33.8 mg, 0.230 mmol) and triphenylphosphine (60.2 mg, 0.230 mmol) in THF (2 mL) and the mixture was stirred overnight at room temperature. Water (4 mL) and EtOAc (4 mL) were added and the layers were separated. The organic layer was washed with brine (4 mL), dried (MgSO₄) and concentrated in vacuo. Purification by chromatography (SiO₂, 1-10% (1% NH in MeOH) in DCM) gave the title compound (50 mg, 40%) as a colourless glass. LCMS: [M+H]+=695.

Preparation 310: 2-((3-(2-(6-(5-chloro-2-((oxan-4-yl)amino)pyrimidin-4-yl)-1-oxoisoindolin-2-yl)acetyl)-2,3,4,5-tetrahydro-1H-benzo[d]azepin-1-yl)methyl)isoindoline-1,3-dione

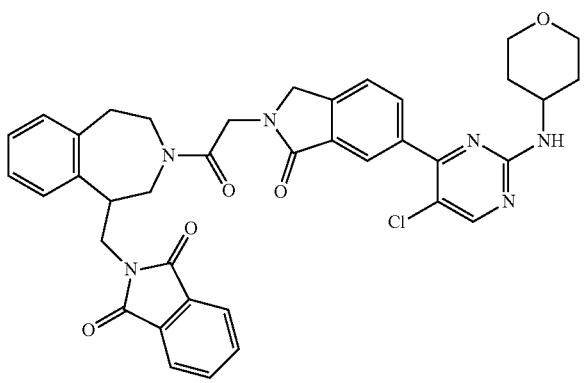 [SMILES: O=C(CN1Cc2ccc(-c3nc(NC4CCOCC4)ncc3Cl)cc2C1=O)N1CCc2ccccc2C(CN2C(=O)c3ccccc3C2=O)C1]

Prepared using a similar procedure to Example 548. LC-MS: [M+H]+=691

Preparation 311: N-(1-(2-bromophenyl)ethyl)-2-(6-(5-chloro-2-((oxan-4-yl)amino)pyrimidin-4-yl)-1-oxoisoindolin-2-yl)acetamide

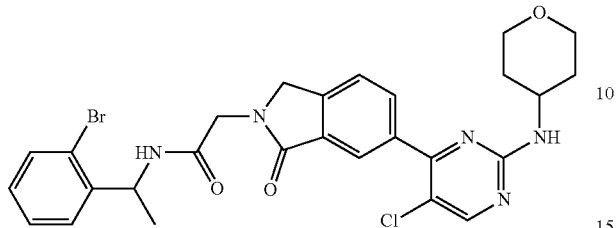

Prepared using a similar procedure to Example 553 (H2O/1M HCl). LC-MS: [M+H]+=584.

Preparation 312: tert-butyl (2-(N-benzyl-2-(6-(5-chloro-2-((oxan-4-yl)amino)pyrimidin-4-yl)-1-oxoisoindolin-2-yl)acetamido)ethyl)carbamate

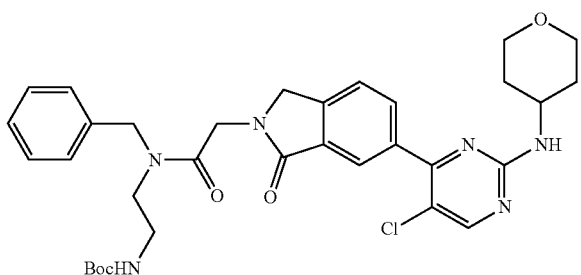 [SMILES: CC(C)(C)OC(=O)NCCN(Cc1ccccc1)C(=O)CN1Cc2ccc(-c3nc(NC4CCOCC4)ncc3Cl)cc2C1=O]

Prepared using a similar procedure to Example 548. LC-MS: [M+Na]+=657.

Preparation 313: (S)—N-(1-(4-bromophenyl)-2-hydroxyethyl)-2-(6-(5-chloro-2-((oxan-4-yl)amino)pyrimidin-4-yl)-1-oxoisoindolin-2-yl)acetamide

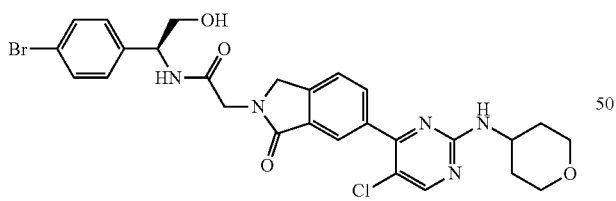

HATU (614 mg, 1.614 mmol) was added to a solution of 2-(6-{5-chloro-2-[(oxan-4-yl)amino]pyrimidin-4-yl}-1-oxo-2,3-dihydro-1H-isoindol-2-yl)acetic acid (500 mg, 1.241 mmol), (S)-2-amino-2-(4-bromophenyl)ethanol hydrochloride (407 mg, 1.614 mmol) and triethylamine (0.865 mL, 6.21 mmol) in DMF (8 mL, 103 mmol) and the mixture was stirred at room temperature for 2 h. The reaction was diluted with water (20 mL) and the resulting white precipitate was filtered and dried on standing. Purification by chromatography (SiO2, 0-10% MeOH in DCM) gave the title compound (560 mg, 68%) as a colourless solid. LCMS: [M+H]+=600.

Preparation 314: Mixture of 6-bromo-2-(2-methoxyethyl)isoindolin-1-one and 6-bromo-2,3-bis(2-methoxyethyl)isoindolin-1-one

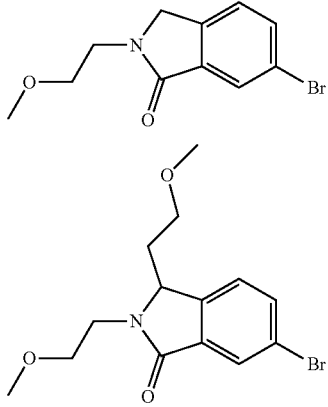

Sodium hydride (60% wt in mineral oil) (0.113 g, 2.83 mmol) was added to a stirred solution of 6-bromoisoindolin-1-one (0.5 g, 2.358 mmol) and 1-bromo-2-methoxyethane (0.277 ml, 2.83 mmol) in DMF (12 mL) under nitrogen at 0° C. The resulting orange solution was allowed to warm slowly to room temperature and stirred for 3 days. The reaction was quenched with water (15 mL) and extracted with EtOAc (3×15 mL). The organic extracts were combined and washed with brine (50 mL), dried (MgSO4), filtered, and concentrated in vacuo to afford a yellow oil. The crude product was purified by chromatography (SiO2, 24 g GRACE column, 0-100% EtOAc in isohexane) to afford a mixture of 6-bromo-2-(2-methoxyethyl)isoindolin-1-one (549 mg, 62.9%) and 6-bromo-2,3-bis(2-methoxyethyl)isoindolin-1-one as a yellow oil (~3:1 ratio by LCMS and NMR analyses). Further purification by chromatography (SiO2, 24 g GRACE column, 0-10% MeOH in DCM) did not improve ratio of products, which was used without further purification in the next step. LCMS: [M+H]+=270 and 328.

Preparation 315: 6-(2,5-dichloropyrimidin-4-yl)-2,3-bis(2-methoxyethyl)isoindolin-1-one

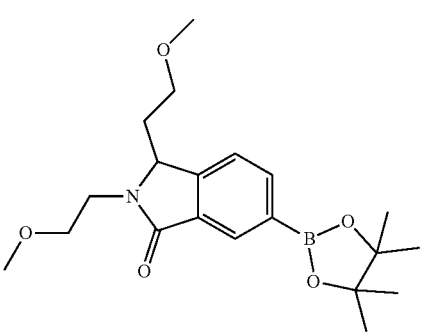

Prepared using a similar procedure to preparation 63. LCMS: [M+H]+=396

Preparation 316: 6-(2,5-dichloropyrimidin-4-yl)-2,3-bis(2-methoxyethyl)isoindolin-1-one

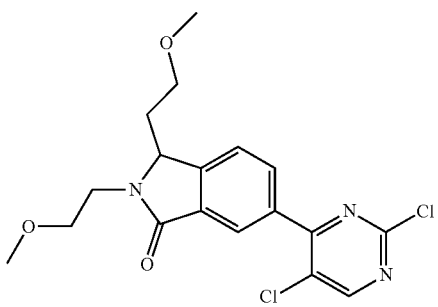 [SMILES: COCCC1c2ccc(-c3nc(Cl)ncc3Cl)cc2C(=O)N1CCOC]

Prepared using a similar procedure to preparation 57 except SPhos-Pd G3 was used instead of Pd(PPh₃)₄ in the second step. In the second step, 1% mol of catalyst was added after 3 h and the mixture was stirred for a further 3 days at 50° C. The product was further purified by chromatography (80 g column, 0-100% EtOAc in iso-hexane) to afford 6-(2,5-dichloropyrimidin-4-yl)-2-(2-methoxyethyl)isoindolin-1-one (225 mg, 0.632 mmol, 32.0% yield) as a pale yellow gum and the title compound (120 mg, 15.4%) as an orange/brown gum. The product was used without further purification in the next step. LMCS: [M+H]⁺=396 Note: the product was obtained in 70% purity and was contaminated with 6-(2,5-dichloropyrimidin-4-yl)-2-(2-methoxyethyl)isoindolin-1-one.

Preparation 317: tert-butyl 5-bromo-1-(2-methoxy-2-oxoethyl)-3-oxoisoindoline-2-carboxylate

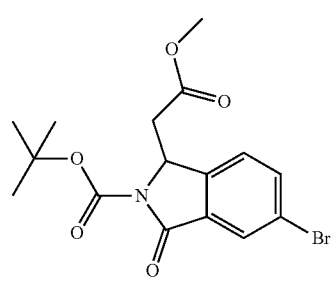 [SMILES: COC(=O)CC1c2ccc(Br)cc2C(=O)N1C(=O)OC(C)(C)C]

Prepared from tert-butyl 6-bromo-1-oxo-2,3-dihydro-1H-isoindole-2-carboxylate (preparation 20) and methyl 2-bromoacetate using a similar procedure to Preparation 28. LCMS: [M-Boc]+=286.

Preparation 318: methyl 2-(5-bromo-3-oxoisoindolin-1-yl)acetate

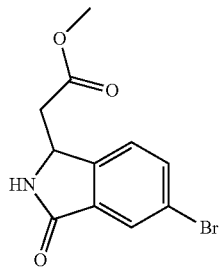 [SMILES: COC(=O)CC1NC(=O)c2cc(Br)ccc21]

HCl (4 M in dioxane) (8.69 ml, 34.7 mmol) was added dropwise at 0° C. to tert-butyl 5-bromo-1-(2-methoxy-2-oxoethyl)-3-oxoisoindoline-2-carboxylate (890 mg, 2.316 mmol) and the resulting solution was stirred at room temperature for 1 h. The reaction was concentrated and azeotroped with MeCN (2×25 ml) to afford the title compound (610 mg, 2.126 mmol, 92% yield) as a yellow solid. LCMS: [M-tBu]+=284.

Preparation 319: tert-butyl 2-(5-bromo-1-(2-methoxy-2-oxoethyl)-3-oxoisoindolin-2-yl)acetate

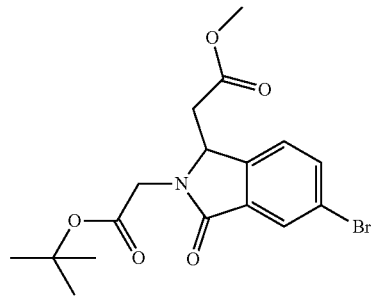 [SMILES: COC(=O)CC1c2ccc(Br)cc2C(=O)N1CC(=O)OC(C)(C)C]

Prepared from methyl 2-(5-bromo-3-oxoisoindolin-1-yl)acetate using a similar procedure to preparation 1 (H2O). LCMS: [M+Na]+=420.

Preparation 320: tert-butyl 2-(1-(2-methoxy-2-oxoethyl)-3-oxo-5-(4,4,5,5-tetramethyl-1,3,2-dioxaborolan-2-yl)isoindolin-2-yl)acetate

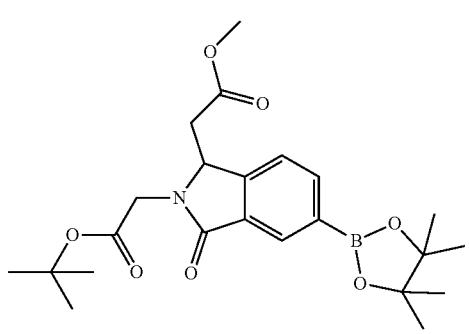 [SMILES: COC(=O)CC1c2ccc(B3OC(C)(C)C(C)(C)O3)cc2C(=O)N1CC(=O)OC(C)(C)C]

Prepared from tert-butyl 2-(5-bromo-1-(2-methoxy-2-oxoethyl)-3-oxoisoindolin-2-yl)acetate using a similar procedure to Preparation 84. LCMS: [M-tBu]+=446.

Preparation 321: tert-butyl 2-(5-(2,5-dichloropyrimidin-4-yl)-1-(2-methoxy-2-oxoethyl)-3-oxoisoindolin-2-yl)acetate

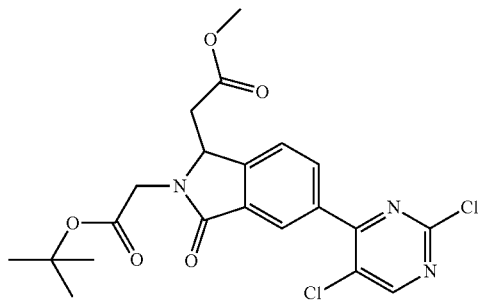 [SMILES: COC(=O)CC1c2ccc(-c3nc(Cl)ncc3Cl)cc2C(=O)N1CC(=O)OC(C)(C)C]

Prepared from tert-butyl 2-(5-(2,5-dichloropyrimidin-4-yl)-1-(2-methoxy-2-oxoethyl)-3-oxoisoindolin-2-yl)acetate using a similar procedure to Preparation 53. LC-MS: [M-tBu]+=410.

Preparation 322: tert-butyl 2-(5-(5-chloro-2-((oxan-4-yl)amino)pyrimidin-4-yl)-1-(2-methoxy-2-oxoethyl)-3-oxoisoindolin-2-yl)acetate

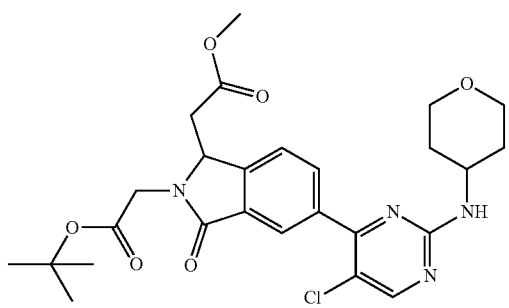 [SMILES: COC(=O)CC1c2ccc(-c3nc(NC4CCOCC4)ncc3Cl)cc2C(=O)N1CC(=O)OC(C)(C)C]

A solution of tert-butyl 2-(5-(2,5-dichloropyrimidin-4-yl)-1-(2-methoxy-2-oxoethyl)-3-oxoisoindolin-2-yl)acetate (630 mg, 1.081 mmol), oxan-4-amine (134 µl, 1.297 mmol) and DIPEA (378 µl, 2.162 mmol) in ethanol (5404 µl, 1.081 mmol) was heated to 85° C. and stirred overnight. The reaction was diluted with EtOAc (10 mL) and water (10 mL). The phases were separated and the aqueous phase was extracted with EtOAc (2×10 mL). The combined organic extracts were washed with brine (30 mL), dried (MgSO₄), filtered, and concentrated to give a yellow oil. The crude product was purified by chromatography (SiO₂, 40 g column, 0-100% EtOAc in isohexanes) to afford the title compound (350 mg, 61.0%) as a colourless solid. LCMS: [M+H]+=531.

Preparation 323: 2-(5-(5-chloro-2-((oxan-4-yl)amino)pyrimidin-4-yl)-1-(2-methoxy-2-oxoethyl)-3-oxoisoindolin-2-yl)acetic acid

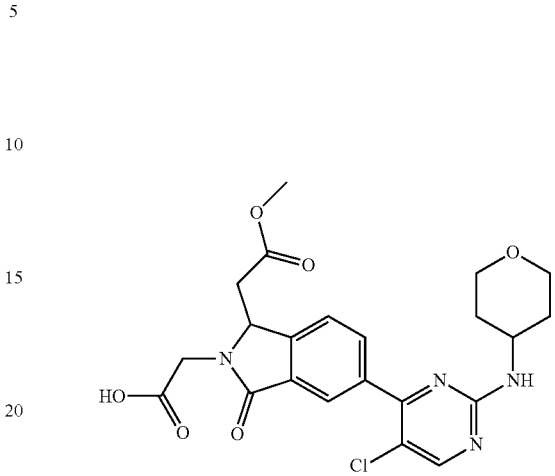

A solution of tert-butyl 2-(5-(5-chloro-2-((oxan-4-yl)amino)pyrimidin-4-yl)-1-(2-methoxy-2-oxoethyl)-3-oxoisoindolin-2-yl)acetate (350 mg, 0.593 mmol) in DCM (6 ml, 93 mmol) and TFA (2.194 ml, 28.5 mmol) was stirred at room temperature for 3 h then concentrated in vacuo. The residue was azeotroped with toluene (3×5 mL) and acetonitrile (5 ml) to afford the title compound (315 mg, 98%) as a white solid. LCMS: [M+H]+=475

Preparation 324: methyl 2-(2-(2-(tert-butyl(methyl)amino)-2-oxoethyl)-5-(5-chloro-2-((oxan-4-yl)amino)pyrimidin-4-yl)-3-oxoisoindolin-1-yl)acetate

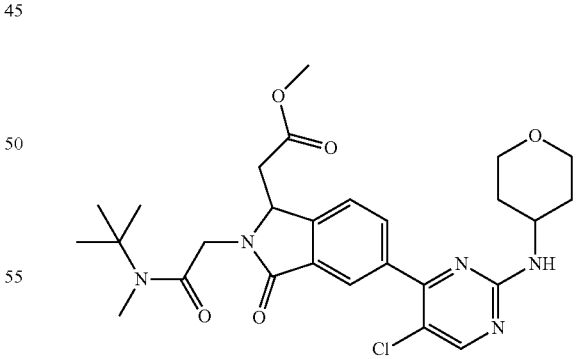

Prepared from 2-(5-(5-chloro-2-((oxan-4-yl)amino)pyrimidin-4-yl)-1-(2-methoxy-2-oxoethyl)-3-oxoisoindolin-2-yl)acetic acid using a similar procedure to Example 407. LCMS: [M+H]+=544.

Preparation 325: methyl 2-(5-(5-chloro-2-((oxan-4-yl)amino)pyrimidin-4-yl)-3-oxo-2-(2-oxo-2-((1-phenylcyclopropyl)amino)ethyl)isoindolin-1-yl)acetate

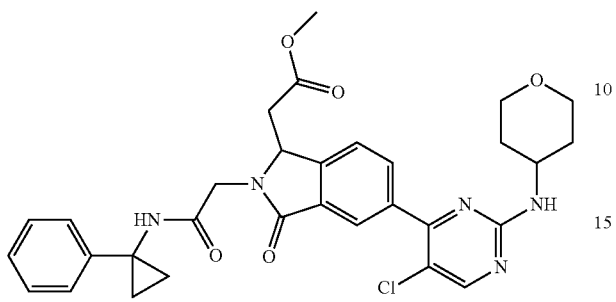

Prepared using a similar procedure to Example 547. LCMS: [M+H]+=590.

Preparation 326: methyl 2-(5-(5-chloro-2-((oxan-4-yl)amino)pyrimidin-4-yl)-3-oxo-2-(2-oxo-2-(1,2,4,5-tetrahydro-3H-benzo[d]azepin-3-yl)ethyl)isoindolin-1-yl)acetate

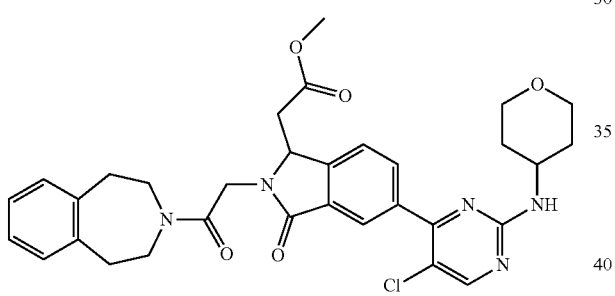

Prepared using a similar procedure to Example 547. LCMS: [M+H]+=604.

Preparation 327: methyl 2-(5-(5-chloro-2-((oxan-4-yl)amino)pyrimidin-4-yl)-2-(2-(methyl(phenethyl)amino)-2-oxoethyl)-3-oxoisoindolin-1-yl)acetate

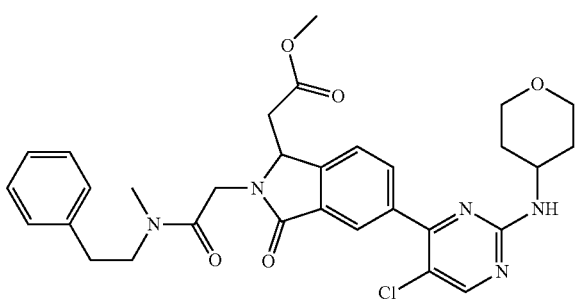 [SMILES: COC(=O)CC1c2ccc(-c3nc(NC4CCOCC4)ncc3Cl)cc2C(=O)N1CC(=O)N(C)CCc1ccccc1]

Prepared using a similar procedure to Example 552. LCMS: [M+H]+=592.

Preparation 328: methyl 2-(5-(5-chloro-2-((oxan-4-yl)amino)pyrimidin-4-yl)-3-oxo-2-(2-oxo-2-((2-phenylpropan-2-yl)amino)ethyl)isoindolin-1-yl)acetate

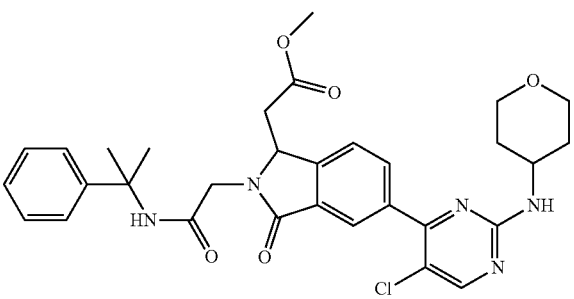 [SMILES: COC(=O)CC1c2ccc(-c3nc(NC4CCOCC4)ncc3Cl)cc2C(=O)N1CC(=O)NC(C)(C)c1ccccc1]

Prepared using a similar procedure to Example 552. LCMS: [M+H]+=592.

Preparation 329: methyl 2-(5-(5-chloro-2-((oxan-4-yl)amino)pyrimidin-4-yl)-2-(2-(((1S,2R)-2-hydroxy-2,3-dihydro-1H-inden-1-yl)amino)-2-oxoethyl)-3-oxoisoindolin-1-yl)acetate

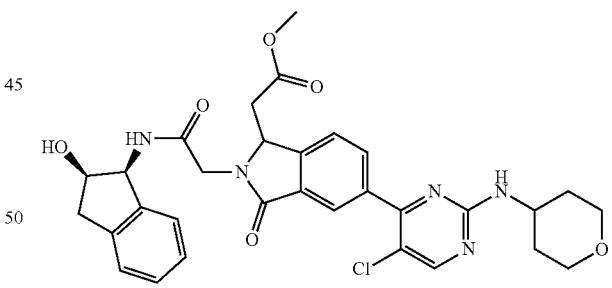

HATU (0.576 g, 1.516 mmol) was added to an ice-cooled solution of 2-(5-(5-chloro-2-((oxan-4-yl)amino)pyrimidin-4-yl)-1-(2-methoxy-2-oxoethyl)-3-oxoisoindolin-2-yl)acetic acid (0.5 g, 1.011 mmol), (1S,2R)-1-amino-2,3-dihydro-1H-inden-2-ol (0.166 g, 1.112 mmol), and triethylamine (0.423 ml, 3.03 mmol) in DMF (10 mL) under nitrogen and the mixture was stirred for 16 h. The reaction mixture was diluted with water (50 mL) and the resulting precipitate filtered, washed with water (3×10 mL) and dried (MgSO4) to give the title compound (472 mg, 74.0%) as a pale pink solid. LCMS: [M+H]+=606.

353

Preparation 330: methyl 2-(2-(2-(((1S,2R)-2-((tert-butyldimethylsilyl)oxy)-2,3-dihydro-1H-inden-1-yl)amino)-2-oxoethyl)-5-(5-chloro-2-((oxan-4-yl)amino)pyrimidin-4-yl)-3-oxoisoindolin-1-yl)acetate

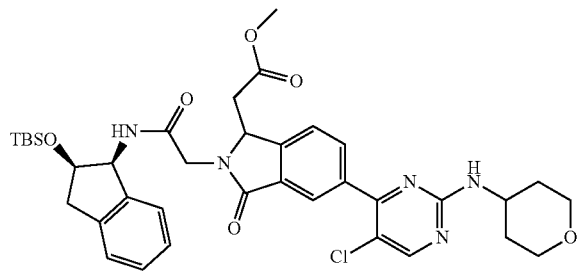 [SMILES: COC(=O)CC1c2ccc(-c3nc(NC4CCOCC4)ncc3Cl)cc2C(=O)N1CC(=O)N[C@H]1c2ccccc2C[C@H]1O[Si](C)(C)C(C)(C)C]

TBSCl (0.222 g, 1.473 mmol) in DCM (3 mL) was added to a stirred solution of methyl 2-(5-(5-chloro-2-((oxan-4-yl)amino)pyrimidin-4-yl)-2-(2-(((1S,2R)-2-hydroxy-2,3-dihydro-1H-inden-1-yl)amino)-2-oxoethyl)-3-oxoisoindolin-1-yl)acetate (0.465 g, 0.737 mmol), DMAP (9.00 mg, 0.074 mmol), and triethylamine (0.205 ml, 1.473 mmol) in DCM (4.4 mL) and the mixture was stirred at room temperature overnight. Further portions of DMAP (9.00 mg, 0.074 mmol), triethylamine (0.205 ml, 1.473 mmol) and TBSCl (0.555 g, 3.68 mmol) in DCM (1 mL) were added and stirring continued overnight. TBSCl (1.110 g, 7.37 mmol) in DCM (1 mL) was added and the reaction stirred overnight. The mixture was diluted with DCM (20 mL) and washed with water (20 mL) and brine (20 mL). The organic extracts were combined, dried (MgSO$_4$), filtered, and concentrated in vacuo. The crude product was purified by chromatography (SiO$_2$, 40 g column, 0-5% MeOH in DCM) to afford the title compound (257 mg, 46.5%) as a pale yellow solid. LCMS: [M+H]+=720.

354

Preparation 331: 2-(2-(2-(tert-butyl(methyl)amino)-2-oxoethyl)-5-(5-chloro-2-((oxan-4-yl)amino)pyrimidin-4-yl)-3-oxoisoindolin-1-yl)acetic acid

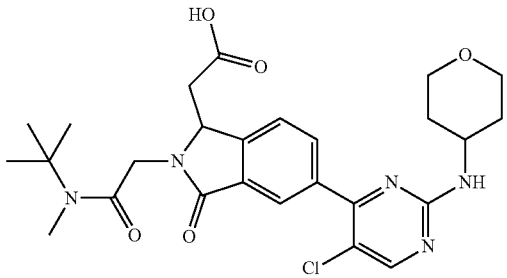 [SMILES: CN(C(=O)CN1C(=O)c2cc(-c3nc(NC4CCOCC4)ncc3Cl)ccc2C1CC(=O)O)C(C)(C)C]

1 M LiOH (0.202 ml, 0.202 mmol) was added to a stirred solution of methyl 2-(2-(2-(tert-butyl(methyl)amino)-2-oxoethyl)-5-(5-chloro-2-((oxan-4-yl)amino)pyrimidin-4-yl)-3-oxoisoindolin-1-yl)acetate (100 mg, 0.184 mmol) in THF (2.4 ml, 29.3 mmol)/water (0.8 ml, 44.4 mmol) and the resulting mixture was stirred at room temperature overnight. The reaction mixture was diluted with EtOAc (10 ml) and water (5 ml) and the aqueous phase was acidified with 1M HCl to pH-3. The aqueous phase was further extracted with EtOAc (2×10 ml). The combined organic extracts were dried (MgSO$_4$), filtered, and concentrated in vacuo to afford the title compound (81 mg, 79%) as colourless solid. LCMS: [M+H]+=530.

Prepared using an analogous procedure to preparation 331 from the appropriate carboxylic ester. The precursor ester used in Preparation 336 can be prepared by methods analogous to those set out in Preparations 321 to 330 above.

| Preparation | Structure | Name | MS: [M + H]+ |
| --- | --- | --- | --- |
| 332 | ![structure] | 2-(5-(5-chloro-2-((oxan-4-yl)amino)pyrimidin-4-yl)-3-oxo-2-(2-oxo-2-((1-phenylcyclopropyl)amino)ethyl)isoindolin-1-yl)acetic acid | 576 |

| Preparation | Structure | Name | MS: [M + H]+ |
|---|---|---|---|
| 333 | 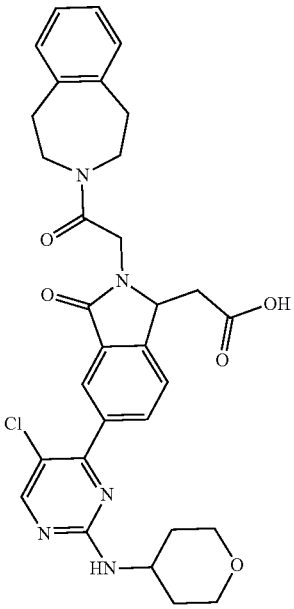 [SMILES: O=C(O)CC1c2ccc(-c3nc(NC4CCOCC4)ncc3Cl)cc2C(=O)N1CC(=O)N1CCc2ccccc2CC1] | 2-(5-(5-chloro-2-((oxan-4-yl)amino)pyrimidin-4-yl)-3-oxo-2-(2-oxo-2-(1,2,4,5-tetrahydro-3H-benzo[d]azepin-3-yl)ethyl)isoindolin-1-yl)acetic acid | 590 |
| 334 | 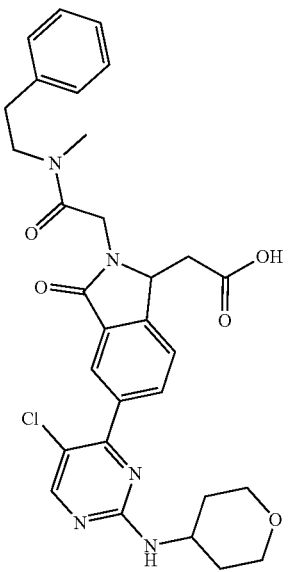 [SMILES: CN(CCc1ccccc1)C(=O)CN1C(=O)c2cc(-c3nc(NC4CCOCC4)ncc3Cl)ccc2C1CC(=O)O] | 2-(5-(5-chloro-2-((oxan-4-yl)amino)pyrimidin-4-yl)-2-(2-(methyl(phenethyl)amino)-2-oxoethyl)-3-oxoisoindolin-1-yl)acetic acid | 578 |

-continued
| Preparation | Structure | Name | MS: [M + H]+ |
|---|---|---|---|
| 335 | 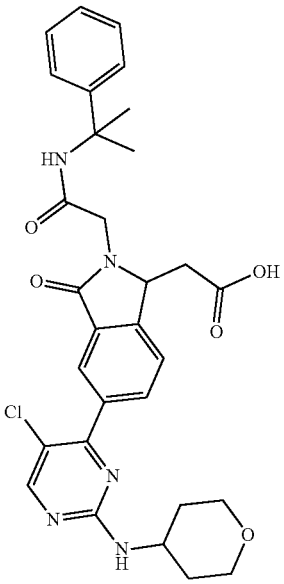 [SMILES: CC(C)(NC(=O)CN1C(=O)c2cc(-c3nc(NC4CCOCC4)ncc3Cl)ccc2C1CC(=O)O)c1ccccc1] | 2-(5-(5-chloro-2-((oxan-4-yl)amino)pyrimidin-4-yl)-3-oxo-2-(2-oxo-2-((2-phenylpropan-2-yl)amino)ethyl)isoindolin-1-yl)acetic acid (1399-87) | 578 |
| 336 | 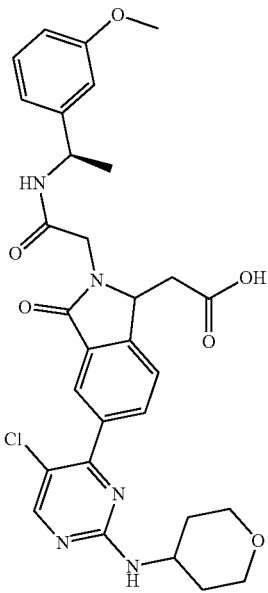 [SMILES: COc1cccc([C@@H](C)NC(=O)CN2C(=O)c3cc(-c4nc(NC5CCOCC5)ncc4Cl)ccc3C2CC(=O)O)c1] | 2-(5-(5-chloro-2-((oxan-4-yl)amino)pyrimidin-4-yl)-2-(2-(((R)-1-(3-methoxyphenyl)ethyl)amino)-2-oxoethyl)-3-oxoisoindolin-1-yl)acetic acid | 594 |

| Preparation | Structure | Name | MS: [M + H]⁺ |
|---|---|---|---|
| 337 | 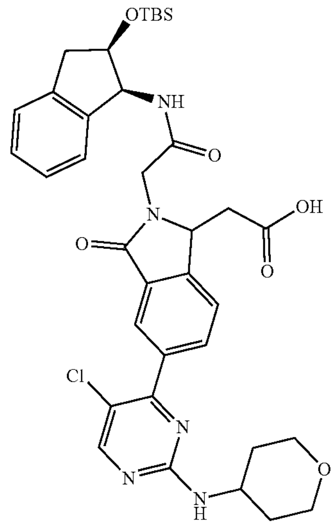 [SMILES: CC(C)(C)[Si](C)(C)O[C@@H]1Cc2ccccc2[C@@H]1NC(=O)CN1C(=O)c2cc(-c3nc(NC4CCOCC4)ncc3Cl)ccc2C1CC(=O)O] | 2-(2-(2-(((1S,2R)-2-((tert-butyldimethylsilyl)oxy)-2,3-dihydro-1H-inden-1-yl)amino)-2-oxoethyl)-5-(5-chloro-2-((oxan-4-yl)amino)pyrimidin-4-yl)-3-oxoisoindolin-1-yl)acetic acid | 706 |

Preparation 338: 2-(5-(5-chloro-2-((oxan-4-yl)amino)pyrimidin-4-yl)-1-(2-hydroxyethyl)-3-oxoisoindolin-2-yl)-N—((R)-1-(3-methoxyphenyl)ethyl)acetamide

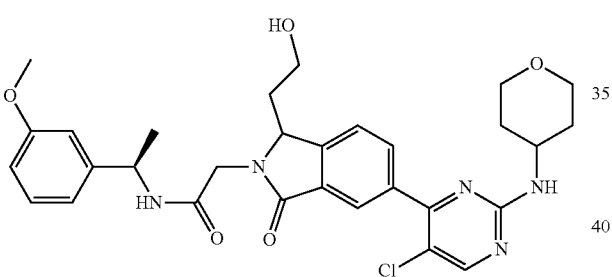

Prepared using a similar procedure to Example 601. LC-MS: [M+H]+=580. This compound also appears in Example 700 below.

Preparation 339: N-((1S,2R)-2-((tert-butyldimethylsilyl)oxy)-2,3-dihydro-1H-inden-1-yl)-2-(5-(5-chloro-2-((oxan-4-yl)amino)pyrimidin-4-yl)-1-(2-hydroxyethyl)-3-oxoisoindolin-2-yl)acetamide

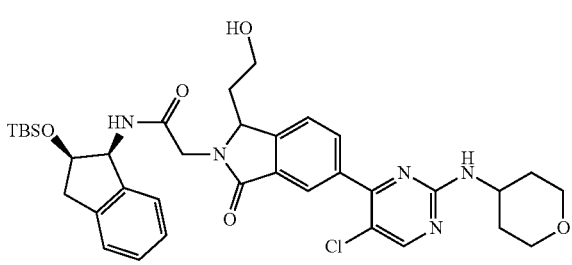 [SMILES: CC(C)(C)[Si](C)(C)O[C@@H]1Cc2ccccc2[C@@H]1NC(=O)CN1C(=O)c2cc(-c3nc(NC4CCOCC4)ncc3Cl)ccc2C1CCO]

Prepared using a similar procedure to Example 601. LC-MS: [M+H]+=692.

Preparation 340: N-(tert-butyl)-2-(5-(5-chloro-2-((oxan-4-yl)amino)pyrimidin-4-yl)-1-(2-(1,3-dioxoisoindolin-2-yl)ethyl)-3-oxoisoindolin-2-yl)-N-methylacetamide

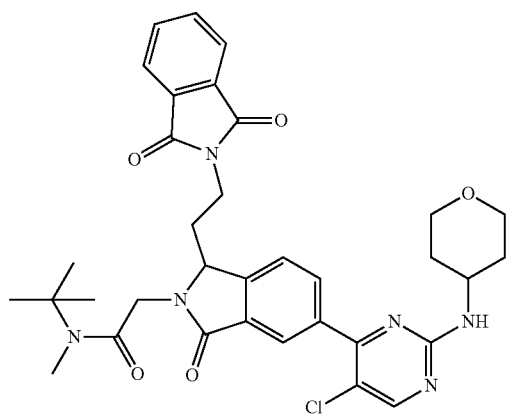 [SMILES: CN(C(=O)CN1C(=O)c2cc(-c3nc(NC4CCOCC4)ncc3Cl)ccc2C1CCN1C(=O)c2ccccc2C1=O)C(C)(C)C]

DIAD (24.49 µl, 0.126 mmol) was added dropwise to a stirred solution of N-(tert-butyl)-2-(5-(5-chloro-2-((oxan-4-yl)amino)pyrimidin-4-yl)-1-(2-hydroxyethyl)-3-oxoisoindolin-2-yl)-N-methylacetamide (example XX) (50 mg, 0.097 mmol), phthalimide (18.53 mg, 0.126 mmol) and triphenylphosphine (33.0 mg, 0.126 mmol) in THF (953 µl). The resulting orange solution was stirred at room temperature for 5 h, then diluted with EtOAc (10 mL). Water (10 mL) was added and the phases were separated. The aqueous layer was extracted with EtOAc (10 mL) and the combined organic extracts were dried (MgSO₄), filtered and reduced in vacuo to give an oil. The crude product was purified by chromatography (12 g column, 0-100% EtOAc in Isohexane) to afford the title compound (48 mg, 76%) as a white solid.

Preparations 341-345
Prepared using an analogous procedure to preparation 340 from the appropriate alcohol.
| Preparation | Structure | Name | MS: [M + H]+ |
|---|---|---|---|
| 341 | 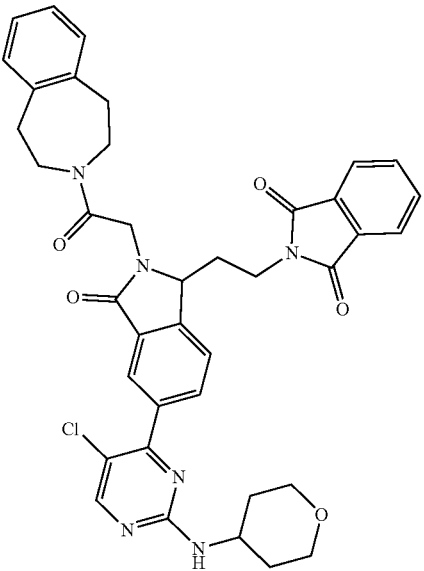 [SMILES: O=C(CN1C(=O)c2cc(-c3nc(NC4CCOCC4)ncc3Cl)ccc2C1CCN1C(=O)c2ccccc2C1=O)N1CCc2ccccc2CC1] | 2-(2-(5-(5-chloro-2-((oxan-4-yl)amino)pyrimidin-4-yl)-3-oxo-2-(2-oxo-2-(1,2,4,5- tetrahydro-3H-benzo[d]azepin-3-yl)ethyl)isoindolin-1-yl)ethyl)isoindoline-1,3-dione | 705 |
| 342 | 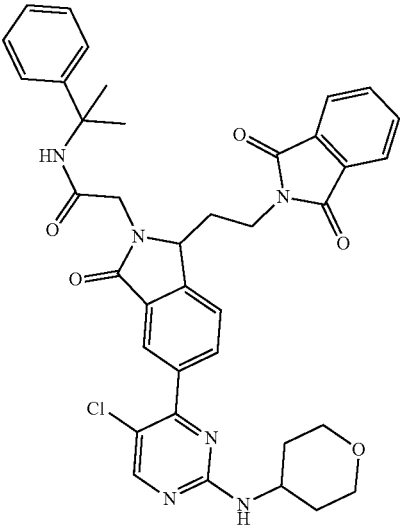 [SMILES: CC(C)(NC(=O)CN1C(=O)c2cc(-c3nc(NC4CCOCC4)ncc3Cl)ccc2C1CCN1C(=O)c2ccccc2C1=O)c1ccccc1] | 2-(5-(5-chloro-2-((oxan-4-yl)amino)pyrimidin-4-yl)-1-(2-(1,3-dioxoisoindolin-2-yl)ethyl)-3-oxoisoindolin-2-yl)-N-(2-phenylpropan-2-yl)acetamide (1427-19) | 693 |

| Preparation | Structure | Name | MS: [M + H]+ |
|---|---|---|---|
| 343 | 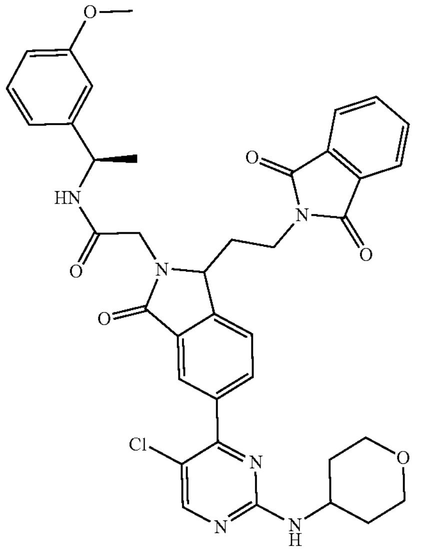 [SMILES: COc1cccc([C@@H](C)NC(=O)CN2C(=O)c3cc(-c4nc(NC5CCOCC5)ncc4Cl)ccc3C2CCN2C(=O)c3ccccc3C2=O)c1] | 2-(5-(5-chloro-2-((oxan-4-yl)amino)pyrimidin-4-yl)-1-(2-(1,3-dioxoisoindolin-2-yl)ethyl)-3-oxoisoindolin-2-yl)-N-((R)-1-(3-methoxyphenyl)ethyl)-acetamide | 709 |
| 344 | 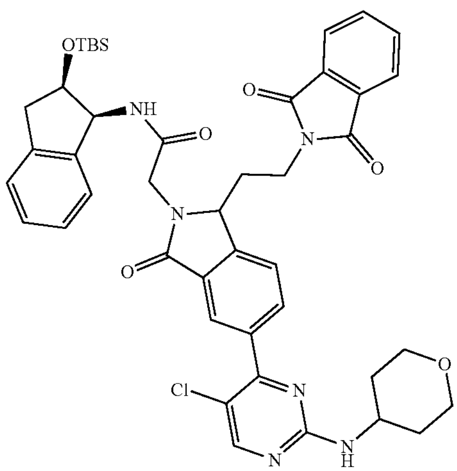 [SMILES: CC(C)(C)[Si](C)(C)O[C@@H]1Cc2ccccc2[C@@H]1NC(=O)CN1C(=O)c2cc(-c3nc(NC4CCOCC4)ncc3Cl)ccc2C1CCN1C(=O)c2ccccc2C1=O] | N-((1S,2R)-2-((tert-butyldimethylsilyl)oxy)-2,3-dihydro-1H-inden-1-yl)-2-(5-(5-chloro-2-((oxan-4-yl)amino)pyrimidin-4-yl)-1-(2-(1,3-dioxoisoindolin-2-yl)ethyl)-3-oxoisoindolin-2-yl)acetamide | 821 |

Preparation 345:2-(5-(5-chloro-2-((oxan-4-yl)amino)pyrimidin-4-yl)-1-(2-(1,3-dioxoisoindolin-2-yl)ethyl)-3-oxoisoindolin-2-yl)-N-((1S,2R)-2-hydroxy-2,3-dihydro-1H-inden-1-yl)acetamide

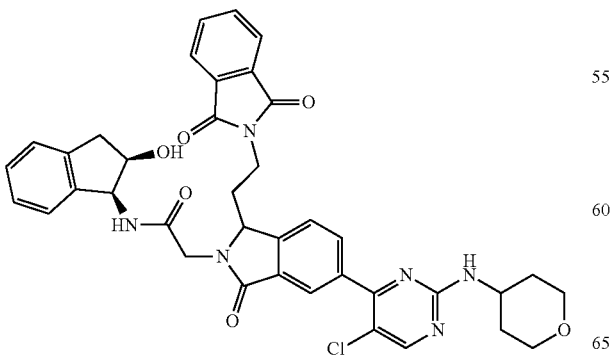

HCl (4.0 M in dioxane) (74.0 μl, 0.296 mmol) was added to a stirred solution of N-((1S,2R)-2-((tert-butyldimethylsilyl)oxy)-2,3-dihydro-1H-inden-1-yl)-2-(5-(5-chloro-2-((oxan-4-yl)amino)pyrimidin-4-yl)-1-(2-(1,3-dioxoisoindolin-2-yl)ethyl)-3-oxoisoindolin-2-yl)acetamide (81 mg, 0.059 mmol) in dioxane (1 mL) and the mixture was stirred at room temperature for 3 h. The mixture was concentrated in vacuo and purified by chromatography (SiO₂, 12 g column, 0-10% MeOH in DCM) to afford the title compound (25 mg, 57.4%) as a white solid. LCMS: [M+H]+ =707.

Preparation 346: methyl 5-bromo-2-ethylbenzoate

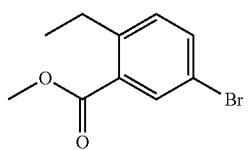

A mixture of methyl 5-bromo-2-iodobenzoate (5.0 g, 14.67 mmol) and PdCl$_2$(dppf)$_2$ (0.107 g, 0.147 mmol) in THF (30 mL) was evacuated and back-filled with nitrogen (×3), then maintained under a nitrogen atmosphere. The mixture was ice-cooled and DIETHYLZINC (1.0 M in hexane) (8.07 ml, 8.07 mmol) added carefully over 15 min. The cooling bath was removed and the mixture was heated to 65° C. and stirred for 3.5 h. After cooling to room temperature, the reaction mixture was poured into ice-cold 1 M HCl (50 mL). The aqueous phase was extracted with EtOAc (3×50 mL) and the combined organic extracts were washed with saturated brine (100 mL), dried (MgSO4), filtered and concentrated in vacuo to afford a dark brown oil (4.1 g). The crude product was dissolved in EtOAc (5 mL) and iso-hexane (100 mL) was added. The mixture was allowed to stand at room temperature for 1 h and the resulting precipitate was filtered through a pad of silica, washing with 5% EtOAc/iso-hexane (200 mL). The filtrate was concentrated in vacuo to give methyl 5-bromo-2-ethylbenzoate (3.89 g, 54.6%) as a pale orange oil (3.89 g). The product was used without further purification in the next step. 1H NMR (Chloroform-d) δ: 7.94 (1H, d), 7.53 (1H, dd), 7.15 (1H, dd), 3.89 (3H, s), 2.93 (2H, q), 1.21 (3H, t). (note: the product was obtained as a ~1:1:0.5 mixture with starting material and des-iodo starting material as shown by NMR).

Preparation 347: methyl 5-bromo-2-(1-bromoethyl)benzoate

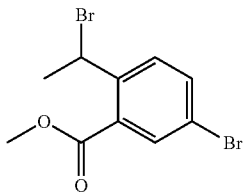

Benzoyl peroxide (75 wt %, remainder water) (0.129 g, 0.400 mmol) and NBS (1.709 g, 9.60 mmol) were added to a stirred solution of methyl 5-bromo-2-ethylbenzoate (3.89 g, 8.00 mmol) in CHCl$_3$ (80 ml, 8.00 mmol) and the mixture was heated to reflux and stirred for 18 h. After cooling to room temperature, further portions of Benzoyl peroxide (75 wt %, remainder water) (0.026 g, 0.080 mmol) and NBS (0.427 g, 2.400 mmol) were added and the mixture heated to reflux and stirred for 2 h. After cooling to room temperature, the mixture was washed with water (100 mL) and the aqueous phase was extracted with DCM (100 mL). The organic extracts were combined and washed with water (100 mL), 10 wt % Na$_2$SO$_3$ (100 mL) and brine (100 mL), then dried (MgSO$_4$), filtered and concentrated in vacuo to afford a yellow oil (4.5 g). The crude product was purified by chromatography (SiO$_2$, 120 g column, 0-50% DCM in isohexane) to afford the title compound (1.442 g, 55.4%) as a white solid. 1H NMR (Chloroform-d) δ: 7.98 (1H, d), 7.69 (1H, d), 7.65 (1H, dd), 6.24 (1H, q), 3.93 (3H, s), 2.01 (3H, d).

Preparation 348: tert-butyl 2-(5-bromo-1-methyl-3-oxoisoindolin-2-yl)acetate

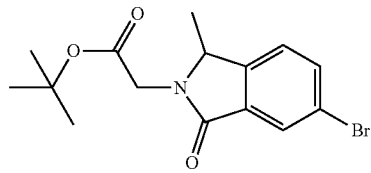 [SMILES: CC1c2ccc(Br)cc2C(=O)N1CC(=O)OC(C)(C)C]

DIPEA (1.627 ml, 9.32 mmol) was added to a stirred suspension of methyl 5-bromo-2-(1-bromoethyl)benzoate (1.0 g, 3.11 mmol) and tert-butyl 2-aminoacetate hydrochloride (0.781 g, 4.66 mmol) in MeCN (31.1 ml, 3.11 mmol) and the mixture was heated to 75° C. and stirred under nitrogen for 16 h. The mixture was cooled to room temperature and the solvent was removed in vacuo. The residue was taken up in EtOAc (100 mL) and washed with 1 M HCl (50 mL). The aqueous phase was extracted with EtOAc (2×50 mL) and the combined organic extracts were washed with brine (100 mL), dried (MgSO$_4$), filtered and concentrated in vacuo to give a pale yellow oil (954 mg). The crude product was purified by chromatography (SiO$_2$, 40 g column, 0-50% EtOAc in isohexane) to afford the title compound (627 mg, 55.2%) as a pale yellow oil. LCMS: [M+Na]+=362.

Preparation 349: (R)-2-(6-(2,5-dichloropyrimidin-4-yl)-1-oxoisoindolin-2-yl)propanoic acid trifluoroacetic acid salt

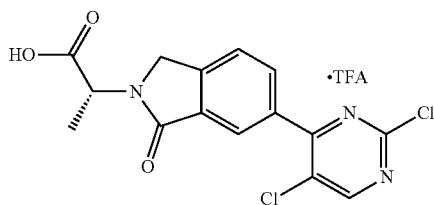 [SMILES: C[C@H](C(=O)O)N1Cc2ccc(-c3nc(Cl)ncc3Cl)cc2C1=O ; "·TFA"]

Prepared from tert-butyl (2R)-2-[6-(2,5-dichloropyrimidin-4-yl)-1-oxo-2,3-dihydro-1H-isoindol-2-yl]propanoate (preparation 94) using a similar procedure to preparations 9 and 19. LCMS: [M+H]+=352.

Preparation 350: tert-butyl 2-(6-(5-chloro-2-(methylamino)pyrimidin-4-yl)-1-oxoisoindolin-2-yl)acetate

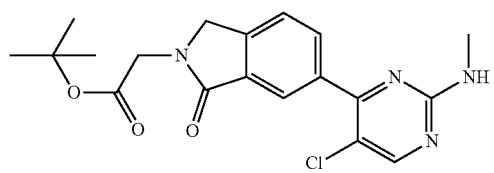 [SMILES: CNc1ncc(Cl)c(-c2ccc3c(c2)C(=O)N(CC(=O)OC(C)(C)C)C3)n1]

DIPEA (486 μl, 2.78 mmol) was added to a stirred solution of tert-butyl 2-(6-(2,5-dichloropyrimidin-4-yl)-1-oxoisoindolin-2-yl)acetate (280 mg, 0.696 mmol) and methylamine hydrochloride (94 mg, 1.392 mmol) in dioxane (1.8 mL) and ethanol (1.8 mL). The mixture was heated in a sealed tube to 80° C. and stirred for 16 h. After cooling, the reaction was diluted with EtOAc (20 mL) and water (20 mL). The phases were separated and the aqueous phase was extracted with EtOAc (2×20 mL). The combined organic extracts were washed with brine (60 mL), dried (MgSO$_4$) and concentrated. The crude product was purified by chromatography (SiO$_2$, 24 g column, 0-100% EtOAc in isohexane) to afford the title compound (230 mg, 0.586 mmol, 84% yield) as a colourless solid. LC-MS: [M+H]+=389.

Preparation 351: 2-(6-(5-chloro-2-(methylamino)pyrimidin-4-yl)-1-oxoisoindolin-2-yl)acetic acid

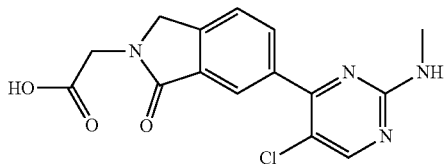 [SMILES: CNc1ncc(Cl)c(-c2ccc3c(c2)C(=O)N(CC(=O)O)C3)n1]

TFA (879 µl, 11.41 mmol) was added to a stirred solution of tert-butyl 2-(6-(5-chloro-2-(methylamino)pyrimidin-4-yl)-1-oxoisoindolin-2-yl)acetate (224 mg, 0.570 mmol) in DCM (6 mL) and the mixture was stirred at room temperature for 2 h. An additional portion of TFA (439 µl, 5.70 mmol) was added and the mixture stirred at room temperature for a further 1.5 h. The solvent was removed in vacuo and the residue was azeotroped with toluene (3×3 mL) and MeCN (3×3 mL) to give the title compound (224 mg, 112%) as a pale yellow solid LC-MS: [M+H]+=333. (note: product could be TFA salt).

Preparation 352: ((R)-2-(6-(2,5-dichloropyrimidin-4-yl)-1-oxoisoindolin-2-yl)-N—((S)-2-hydroxy-1-(3-methoxyphenyl)ethyl)propanamide

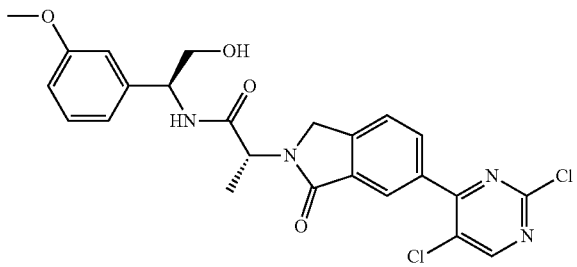 [SMILES: COc1cccc([C@@H](CO)NC(=O)[C@@H](C)N2Cc3ccc(-c4nc(Cl)ncc4Cl)cc3C2=O)c1]

DIPEA (0.982 ml, 5.62 mmol) and HATU (1051 mg, 2.76 mmol) were added to a stirred solution of (R)-2-(6-(2,5-dichloropyrimidin-4-yl)-1-oxoisoindolin-2-yl)propanoic acid (660 mg, 1.874 mmol), and (S)-2-amino-2-(3-methoxyphenyl)ethanol hydrochloride (420 mg, 2.061 mmol) in acetonitrile (5 ml, 1.874 mmol). The resulting solution was stirred at ambient temperature for 1 h, then concentrated under vacuum. The residue was dissolved in a small quantity of DCM and purified by chromatography (SiO$_2$, 12 g column, 100% EtOAc) to afford the title compound (728 mg, 71.3%) as a cream coloured solid. LCMS: [M+H]+=501.

Preparation 353: (S)-2-(6-(2,5-dichloropyrimidin-4-yl)-1-oxoisoindolin-2-yl)-N-(2-hydroxy-1-(m-tolyl)ethyl)acetamide

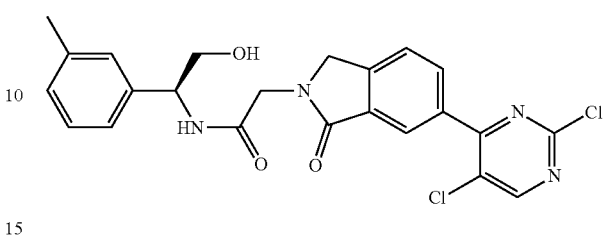

A solution of tert-butyl 2-(6-(2,5-dichloropyrimidin-4-yl)-1-oxoisoindolin-2-yl)acetate (1.5 g, 3.80 mmol) in 1:1 DCM:TFA (15 mL) was stirred under nitrogen for 2 h. The mixture was concentrated under vacuum and the residue was azeotroped with toluene, then Et$_2$O to afford 2-(6-(2,5-dichloropyrimidin-4-yl)-1-oxoisoindolin-2-yl)acetic acid (1.287 g, 3.81 mmol, 100% yield) as a white solid. The product was used without further purification and characterization in the next step. HATU (0.295 g, 0.776 mmol) was added to a mixture of 2-(6-(2,5-dichloropyrimidin-4-yl)-1-oxoisoindolin-2-yl)acetic acid (0.25 g, 0.739 mmol), (S)-2-amino-2-(m-tolyl)ethanol hydrochloride (0.146 g, 0.776 mmol) and DIPEA (0.387 ml, 2.218 mmol) in DMF (2.5 mL) and the mixture was stirred for 45 minutes. The mixture was diluted with EtOAc and transferred into a separating funnel. 1N HCl was added and the product was extracted with EtOAc. The precipitate that formed in the organic extract was filtered and dried under suction to afford the title compound (0.18 g, 51.7%) as a white solid. The filtrate was washed with NaHCO$_3$, water, brine, dried (MgSO$_4$) concentrated under vacuum to afford a second batch of title compound (0.17 g, 048.8%). The products were used without further purification and characterization in the next step.

Preparation 354: ((S)-2-(6-(2,5-dichloropyrimidin-4-yl)-1-oxoisoindolin-2-yl)-N-(1-(2-fluoro-5-methoxyphenyl)-2-hydroxyethyl)acetamide

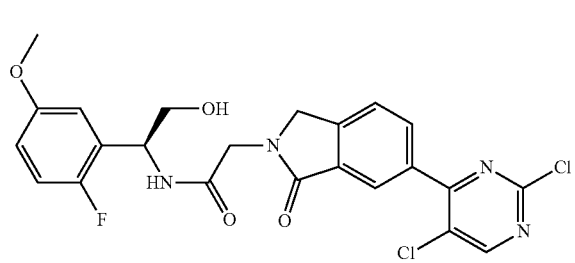 [SMILES: COc1ccc(F)c([C@@H](CO)NC(=O)CN2Cc3ccc(-c4nc(Cl)ncc4Cl)cc3C2=O)c1]

Prepared using a similar procedure to Example 353.

Preparation 355: (R)-2-(6-(2,5-dichloropyrimidin-4-yl)-1-oxoisoindolin-2-yl)-N—((S)-2-hydroxy-1-(m-tolyl)ethyl)propanamide

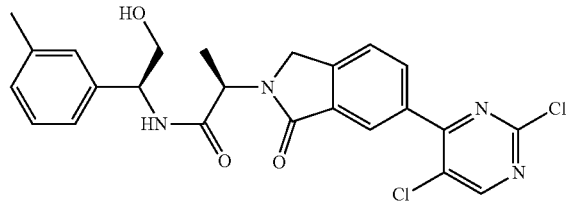 [SMILES: Cc1cccc([C@@H](CO)NC(=O)[C@@H](C)N2Cc3ccc(-c4nc(Cl)ncc4Cl)cc3C2=O)c1]

Prepared using a similar procedure to Example 353.

Preparation 356: Mixture of (R)-2-(6-(2,5-dichloropyrimidin-4-yl)-1-oxoisoindolin-2-yl)-N—((S)-1-(3-fluoro-5-methylphenyl)-2-hydroxyethyl)propanamide and (R)-2-(6-(2-((1H-benzo[d][1,2,3]triazol-1-yl)oxy)-5-chloropyrimidin-4-yl)-1-oxoisoindolin-2-yl)-N—((S)-1-(3-fluoro-5-methylphenyl)-2-hydroxyethyl)propanamide (3:2)

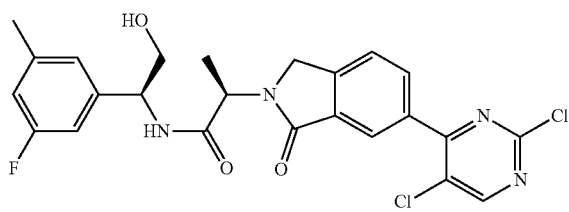

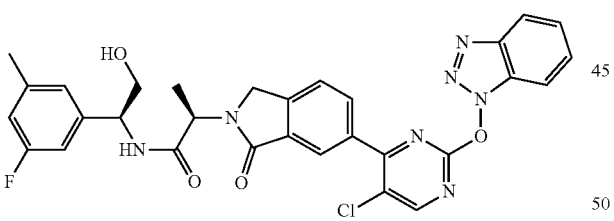

TBTU (0.096 g, 0.298 mmol) was added to a mixture of (R)-2-(6-(2,5-dichloropyrimidin-4-yl)-1-oxoisoindolin-2-yl)propanoic acid (0.1 g, 0.284 mmol), (S)-2-amino-2-(3-fluoro-5-methylphenyl)ethanol hydrochloride (0.061 g, 0.298 mmol) and DIPEA (0.149 ml, 0.852 mmol) in DMF (1 mL) and the mixture was stirred for 2 h. The mixture was diluted with EtOAc and transferred into a separating funnel. 1N HCl was added and the product was extracted with EtOAc. The combined organic extracts were washed with water, NaHCO$_3$, brine, dried (MgSO4) concentrated under vacuum to afford crude. The product was used without further purification and characterization in the next step. (note: the ratio of components was estimated from LCMS analysis of the reaction mixture, which showed formation of a 3:2 mixture).

Preparation 357: (R)-2-(6-(2-((1H-benzo[d][1,2,3]triazol-1-yl)oxy)-5-chloropyrimidin-4-yl)-1-oxoisoindolin-2-yl)-N-(1-(2-fluoro-5-methoxyphenyl)ethyl)acetamide

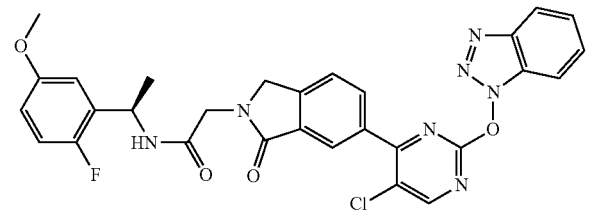 [SMILES: COc1ccc(F)c([C@@H](C)NC(=O)CN2Cc3ccc(-c4nc(On5nnc6ccccc65)ncc4Cl)cc3C2=O)c1]

A mixture of 2-(6-(2,5-dichloropyrimidin-4-yl)-1-oxoisoindolin-2-yl)acetic acid (0.1 g, 0.296 mmol), (R)-1-(2-fluoro-5-methoxyphenyl)ethanamine, HCl (0.067 g, 0.325 mmol), TBTU (0.114 g, 0.355 mmol) and DIPEA (0.207 ml, 1.183 mmol) in DMF (1 mL) was stirred at room temperature for 20 h. The mixture was diluted with EtOAc (20 mL) and the solution was washed sequentially with 1M HCl (15 mL), NaHCO$_3$ (15 mL), water (10 mL) and brine (10 mL). The organic solution was passed through a hydrophobic frit and concentrated in vacuo to afford the title compound (147 mg, 77%) as a pale brown solid. LC-MS: [M+H]+=588. The product was used without further purification in the next step. (note: the product contained ~7% (R)-2-(6-(2,5-dichloropyrimidin-4-yl)-1-oxoisoindolin-2-yl)-N-(1-(2-fluoro-5-methoxyphenyl)ethyl)acetamide(LCMS)).

Preparation 358: (2-(2-nitroethoxy)propan-2-yl)benzene

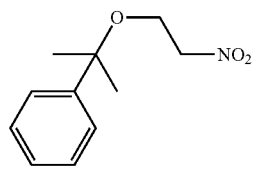

2-nitroethanol (1.0 mL, 13.95 mmol) followed by TFA (0.100 mL, 1.298 mmol) were added to a stirred solution of 2-phenylpropan-2-ol (1.0 g, 7.34 mmol) in DCM (5.0 mL, 78 mmol). The resulting solution was stirred at room temperature overnight, then concentrated under vacuum. The residues was azeoptroped with MeOH (3×20 mL) to afford the crude product as a pale yellow oil (2.16 g), which was purified by chromatography (12 g column, 0-50% EtOAc in isohexane) to afford the title compound (764 mg, 35.8%) as a colourless oil. 1H NMR (400 MHz, CDCl$_3$) δ 7.44-7.32 (m, 4H), 7.30-7.21 (m, 1H), 4.54-4.38 (m, 2H), 3.78-3.55 (m, 2H), 1.56 (s, 6H).

Preparation 359:
2-((2-phenylpropan-2-yl)oxy)ethan-1-amine

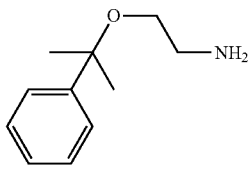

A solution of ammonium chloride (0.214 g, 4.00 mmol) in water (3.5 mL, 194 mmol) was added to a suspension of (2-(2-nitroethoxy)propan-2-yl)benzene (0.764 g, 2.63 mmol) and iron (1.47 g, 26.3 mmol) in ethanol (17.0 mL, 291 mmol) and the resulting mixture was heated to 80° C. for 135 minutes. The mixture was cooled to room temperature and filtered through celite (washing through with EtOH). The filtrate was concentrated under reduced pressure. The residue was partitioned between EtOAc (20 mL) and water (20 mL). The layers were separated and the aqueous layer was extracted with EtOAc (20 mL). The pH of the aqueous layer was adjusted to 8 by the addition of saturated aqueous NaHCO₃ and then extracted with EtOAc (3×30 mL). This combined organic extracts were dried (MgSO₄), filtered and concentrated under reduced pressure to afford the title compound as a pale yellow oil (158 mg, 98%). 1H NMR (400 MHz, Chloroform-d) δ 7.44-7.39 (m, 2H), 7.34 (ddd, J=7.8, 6.8, 1.2 Hz, 2H), 7.26-7.22 (m, 1H), 3.25 (t, J=5.3 Hz, 2H), 3.07 (s (br), 2H), 2.90 (t, J=5.3 Hz, 2H), 1.56 (s, 6H).

Preparation 360: 6-bromo-2-(2-((2-phenylpropan-2-yl)oxy)ethyl)isoindolin-1-one

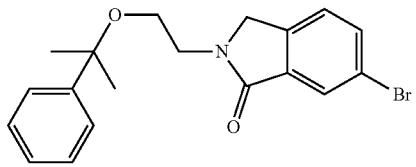 [SMILES: CC(C)(OCCN1Cc2ccc(Br)cc2C1=O)c1ccccc1]

Prepared from methyl 5-bromo-2-(bromomethyl)benzoate and 2-((2-phenylpropan-2-yl)oxy)ethan-1-amine using a similar procedure to preparation 73. In the case, the product was purified by chromatography (SiO₂, 12 g column, 0-50% EtOAc in isohexanes) LC-MS: [M+Na]+=396.

Preparation 361: 2-(2-((2-phenylpropan-2-yl)oxy)ethyl)-6-(4,4,5,5-tetramethyl-1,3,2-dioxaborolan-2-yl)isoindolin-1-one

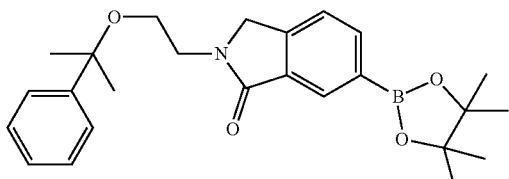

Prepared from 6-bromo-2-(2-((2-phenylpropan-2-yl)oxy)ethyl)isoindolin-1-one using a similar procedure to preparation 84. LC-MS: [M+Na]+=444.

Preparation 362: 6-(2,5-dichloropyrimidin-4-yl)-2-(2-((2-phenylpropan-2-yl)oxy)ethyl)isoindolin-1-one

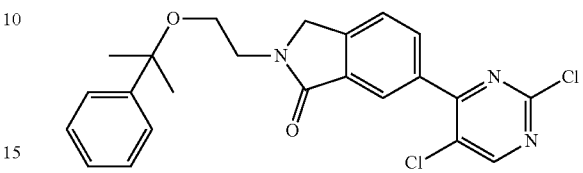

Prepared from 2-(2-((2-phenylpropan-2-yl)oxy)ethyl)-6-(4,4,5,5-tetramethyl-1,3,2-dioxaborolan-2-yl)isoindolin-1-one using a similar procedure to preparation 90. LC-MS: [M+Na]+=464.

Preparation 363: methyl 5-bromo-2-formylnicotinate

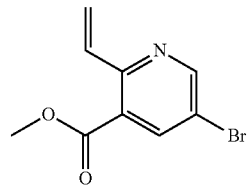

Triethylamine (6.12 ml, 43.9 mmol) was added to a stirred suspension of methyl 5-bromo-2-chloronicotinate (10.0 g, 39.9 mmol) and potassium vinyltrifluoroborate (5.88 g, 43.9 mmol) in ethanol (200 ml, 39.9 mmol). The system was evacuated and back-filled with nitrogen (×3). PdCl₂(dppf)₂ (0.584 g, 0.798 mmol) was added and the system was evacuated and back-filled with nitrogen (×3). The mixture was heated to 80° C. and stirred under nitrogen for 2.5 h. After cooling to room temperature, the mixture was filtered through Celite. The filtrate was concentrated and partitioned between EtOAc (200 mL) and water (200 mL). The organic phase was dried (MgSO₄), filtered and concentrated in vacuo. The crude product was purified by chromatography (220 g column, 0-20% EtOAc in isohexane) to afford the title compound (4.993 g, 20.42 mmol, 51.1% yield) as a pale green solid. LCMS: [M+H]+=242.

Preparation 364: methyl 5-bromo-2-formylnicotinate

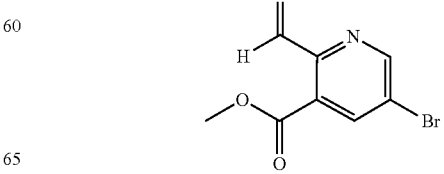

A mixture of ozone/oxygen was bubbled through a stirred solution of methyl 5-bromo-2-vinylnicotinate (1.0 g, 4.13 mmol) in DCM (41.3 ml, 4.13 mmol) cooled to −78° C. After 5 minutes, the solution turned blue. Oxygen was bubbled through the reaction mixture until the solution turned back to yellow, then placed under a nitrogen atmosphere. Dimethyl sulfide (0.917 ml, 12.39 mmol) was added and the mixture was allowed to warm slowly to room temperature overnight. The mixture was diluted with DCM (50 mL) and washed with water (100 mL) and brine (100 mL). The organic extracts were dried (MgSO₄), filtered and concentrated in vacuo to afford methyl 5-bromo-2-formylnicotinate (718 mg, 64.1%) as sticky brown gum. 1H NMR (Chloroform-d) δ: 10.27 (s, 1H), 8.92 (d, 1H), 8.23 (d, 1H), 3.98 (s, 3H).

Preparation 365: tert-butyl (R)-2-(3-bromo-5-oxo-5,7-dihydro-6H-pyrrolo[3,4-b]pyridin-6-yl)propanoate

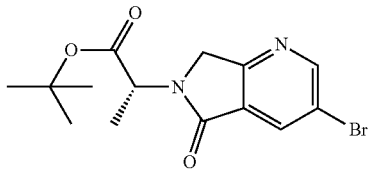 [SMILES: C[C@H](C(=O)OC(C)(C)C)N1Cc2ncc(Br)cc2C1=O]

Procedure A:
Prepared following the procedure described in Preparation 6. LCMS: [M+H]+=341.

Procedure B:
DIPEA (0.382 mL, 2.189 mmol) was added to a stirred solution of (R)-tert-butyl 2-aminopropanoate hydrochloride (0.398 g, 2.189 mmol) in DCM (5 mL). The mixture was stirred at room temperature for 10 minutes before being added to a stirred solution of methyl 5-bromo-2-formylnicotinate (539 mg, 1.988 mmol) in DCM (15 mL). The mixture was stirred at room temperature for 2 h, before sodium triacetoxyborohydride (633 mg, 2.99 mmol) was added and the mixture stirred at room temperature for 24 h. The mixture was diluted with DCM (30 mL) and washed with NaHCO₃ (50 mL). The aqueous phase was extracted with DCM (2×50 mL) and the combined organic extracts were washed with brine (75 mL), dried (MgSO₄), filtered and concentrated in vacuo to afford a brown solid (700 mg). The crude product was adsorbed onto silica and purified by chromatography on (24 g column, 0-100% EtOAc in iso-hexane) to the title compound (277 mg, 0.804 mmol, 40.4% yield) as a pale yellow solid. LCMS: [M+H]+=341.

Preparation 366: tert-butyl (R)-2-(5-oxo-3-(4,4,5,5-tetramethyl-1,3,2-dioxaborolan-2-yl)-5,7-dihydro-6H-pyrrolo[3,4-b]pyridin-6-yl)propanoate

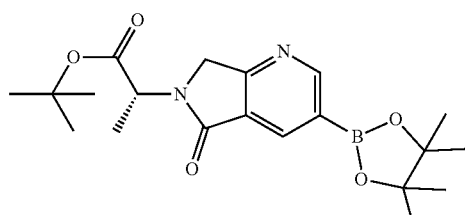

Prepared following the procedure described in Preparation 86. The crude product was purified by chromatography (SiO₂, 0-50% ethyl actate in iso-hexane) to give the title compound (1.653 g, 99%) as an off white solid. LC-MS: [M-C₃H₁₀]+=307.

Preparation 367: tert-butyl (R)-2-(3-(2,5-dichloropyrimidin-4-yl)-5-oxo-5,7-dihydro-6H-pyrrolo[3,4-b]pyridin-6-yl)propanoate

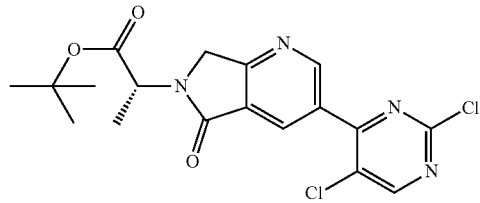 [SMILES: C[C@H](C(=O)OC(C)(C)C)N1Cc2ncc(-c3nc(Cl)ncc3Cl)cc2C1=O]

Prepared using a similar procedure to Preparation 53. LCMS: [M+H]+=409.

Preparation 368: 2-(3-(2,5-dichloropyrimidin-4-yl)-5-oxo-5,7-dihydro-6H-pyrrolo[3,4-b]pyridin-6-yl)acetic acid

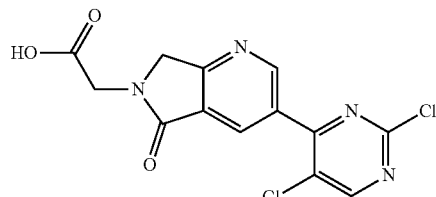

TFA (4.0 mL, 51.9 mmol) was added to a solution of crude tert-butyl 2-(3-(2,5-dichloropyrimidin-4-yl)-5-oxo-5H-pyrrolo[3,4-b]pyridin-6(7H)-yl)acetate (0.989 g, 2.002 mmol) in DCM (20.0 mL, 311 mmol). The resulting solution was stirred at room temperature overnight, then concentrated under vacuum. The residue was azeotroped with toluene (3×30 mL) and then dried in a vacuum oven overnight. LCMS: [M+H]+=339.

Preparation 369: (R)-2-(3-(2,5-dichloropyrimidin-4-yl)-5-oxo-5,7-dihydro-6H-pyrrolo[3,4-b]pyridin-6-yl)propanoic acid

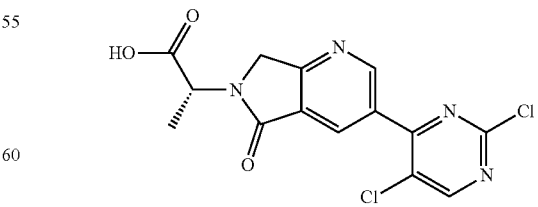

A solution of (R)-tert-butyl 2-(3-(2,5-dichloropyrimidin-4-yl)-5-oxo-5H-pyrrolo[3,4-b]pyridin-6(7H)-yl)propanoate (Preparation 367, 0.38 g, 0.928 mmol) in 1:1 DCM:TFA (5 mL) was stirred for 3 h. The mixture was concentrated under vacuum and the residue was azeoptroped with toluene. The residue was triturated with Et₂O and the resulting suspension was concentrated under vacuum to afford the title compound (0.418 g, 0.929 mmol, 100% yield) as a yellow solid. The products were used without further purification and characterization in the next step. Quantitative yield was assumed.

Preparation 370: (R)-2-(3-(2,5-dichloropyrimidin-4-yl)-5-oxo-5,7-dihydro-6H-pyrrolo[3,4-b]pyridin-6-yl)-N—((S)-2-hydroxy-1-(3-methoxyphenyl)ethyl)propanamide

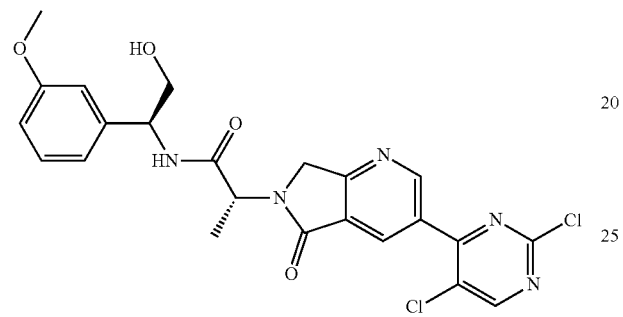

A solution of (R)-tert-butyl 2-(3-(2,5-dichloropyrimidin-4-yl)-5-oxo-5H-pyrrolo[3,4-b]pyridin-6(7H)-yl)propanoate (0.35 g, 0.855 mmol) in 1:1 DCM:TFA (5 mL) was stirred for 2.5 h. The mixture was concentrated under vacuum and the residue was azeoptroped with toluene. The residue was triturated with a ~5:1 Isohexane:Et₂O mixture and the resulting precipitate was filtered, washed with Isohexane and dried under suction to afford (R)-2-(3-(2,5-dichloropyrimidin-4-yl)-5-oxo-5H-pyrrolo[3,4-b]pyridin-6(7H)-yl)propanoic acid (0.206 g, 53.5%) as a white solid. The filtrate was concentrated under vacuum and the residue was suspended in Et₂O. The suspension was concentrated to dryness under vacuum to afford (R)-2-(3-(2,5-dichloropyrimidin-4-yl)-5-oxo-5H-pyrrolo[3,4-b]pyridin-6(7H)-yl)propanoic acid (0.044 g, 0.125 mmol, 14.57% yield) as a white solid. The products were used without further purification and characterization in the next step. HATU (0.133 g, 0.350 mmol) was added to a mixture of (R)-2-(3-(2,5-dichloropyrimidin-4-yl)-5-oxo-5H-pyrrolo[3,4-b]pyridin-6(7H)-yl)propanoic acid (0.15 g, 0.333 mmol), (S)-2-amino-2-(3-methoxyphenyl)ethanol hydrochloride (0.071 g, 0.350 mmol) and DIPEA (0.180 ml, 1.033 mmol) in DMF (1.5 mL) and the mixture was stirred for 45 minutes. The mixture was diluted with EtOAc and transferred into a separating funnel. Saturated aqueous NH4Cl was added and the product was extracted with EtOAc. The combined organic extracts were washed with NaHCO₃, water, brine, dried (MgSO4) concentrated under vacuum to afford crude (R)-2-(3-(2,5-dichloropyrimidin-4-yl)-5-oxo-5H-pyrrolo[3,4-b] pyridin-6(7H)-yl)-N—((S)-2-hydroxy-1-(3-methoxyphenyl)ethyl)propanamide (0.160 g, 96%). The product was used without further purification and characterization in the next step.

Preparation 371: (R)-2-(3-(2,5-dichloropyrimidin-4-yl)-5-oxo-5,7-dihydro-6H-pyrrolo[3,4-b]pyridin-6-yl)-N—((S)-2-hydroxy-1-(m-tolyl)ethyl)propanamide

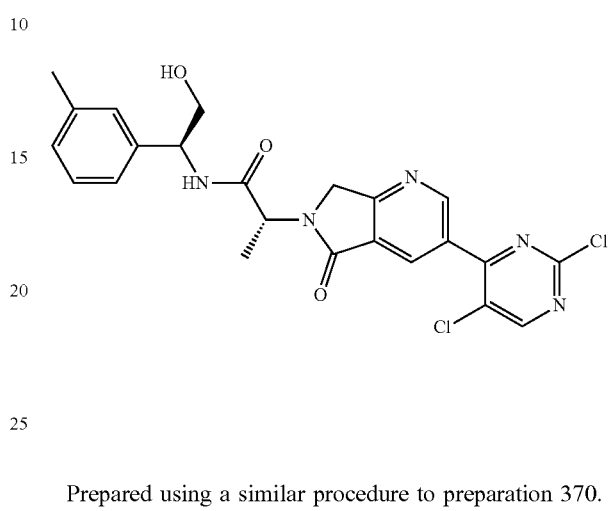

Prepared using a similar procedure to preparation 370.

Preparation 372: (S)-2-(3-(2,5-dichloropyrimidin-4-yl)-5-oxo-5,7-dihydro-6H-pyrrolo[3,4-b]pyridin-6-yl)-N-(2-hydroxy-1-(m-tolyl)ethyl)acetamide

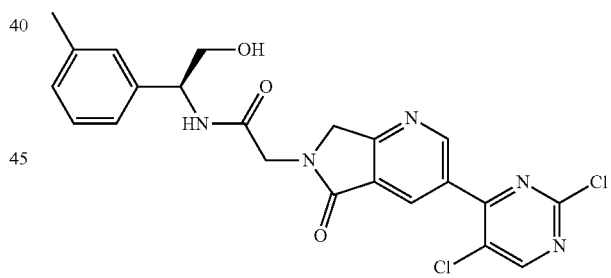

HATU (83 mg, 0.219 mmol) was added to an ice-cooled solution of 2-(3-(2,5-dichloropyrimidin-4-yl)-5-oxo-5H-pyrrolo[3,4-b]pyridin-6(7H)-yl)acetic acid (62 mg, 0.146 mmol), (S)-2-amino-2-(m-tolyl)ethanol hydrochloride (30.2 mg, 0.161 mmol) and triethylamine (61.2 µl, 0.439 mmol) in DMF (1.4 mL) under nitrogen. The mixture was stirred at room temperature for 2 h, then diluted with EtOAc (30 mL). The organic phase was washed with water (30 mL), brine (3×30 mL), dried (MgSO₄), filtered and concentrated in vacuo to give a yellow/brown solid (80 mg, 94%). The crude product was used without further purification in the next step. LCMS: [M+H]+=472.

Preparation 373: Mixture of (R)-2-(3-(2,5-dichloro-pyrimidin-4-yl)-5-oxo-5,7-dihydro-6H-pyrrolo[3,4-b]pyridin-6-yl)-N-(1-(m-tolyl)ethyl)acetamide and (R)-2-(3-(2-((1H-benzo[d][1,2,3]triazol-1-yl)oxy)-5-chloropyrimidin-4-yl)-5-oxo-5H-pyrrolo[3,4-b]pyridin-6(7H)-yl)-N-(1-(m-tolyl)ethyl)acetamide

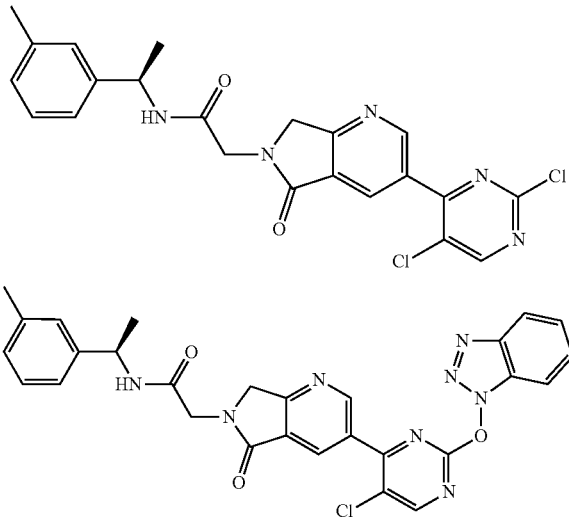

TBTU (54.6 mg, 0.233 mmol) was added to a stirred solution of 2-(3-(2,5-dichloropyrimidin-4-yl)-5-oxo-5H-pyrrolo[3,4-b]pyridin-6(7H)-yl)acetic acid, TFA (120 mg, 0.212 mmol), (R)-1-(m-tolyl)ethanamine hydrochloride (54.6 mg, 0.318 mmol) and DIPEA (148 μl, 0.847 mmol) in dioxane (2 ml). The resulting mixture was stirred at room temperature for 4 h, then partitioned between DCM (50 ml) and 1N HCl (50 ml). The organic phase was collected, washed with NaHCO₃ (50 ml), dried (MgSO₄) and concentrated to give the title mixture (~1:1) as a gum. The product was used without further purification in the next step. LCMS: [M+H]+=456 and 555.

Preparation 374: Mixture of (R)-2-(3-(2,5-dichloro-pyrimidin-4-yl)-5-oxo-5H-pyrrolo[3,4-b]pyridin-6(7H)-yl)-N—((S)-2-hydroxy-1-(m-tolyl)ethyl)propanamide with (R)-2-(3-(2-((1H-benzo[d][1,2,3]triazol-1-yl)oxy)-5-chloropyrimidin-4-yl)-5-oxo-5H-pyrrolo[3,4-b]pyridin-6(7H)-yl)-N—((S)-2-hydroxy-1-(m-tolyl)ethyl)propanamide (3:2)

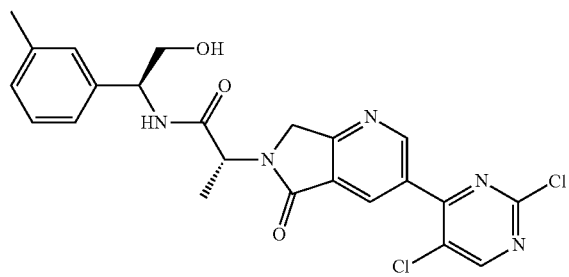

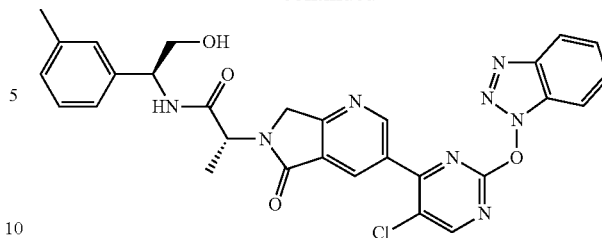

TBTU (0.096 g, 0.299 mmol) was added to a mixture of ((R)-2-(3-(2,5-dichloropyrimidin-4-yl)-5-oxo-5H-pyrrolo[3,4-b]pyridin-6(7H)-yl)propanoic acid (0.128 g, 0.284 mmol), (S)-2-amino-2-(m-tolyl)ethanol hydrochloride (0.056 g, 0.299 mmol) and DIPEA (0.154 ml, 0.881 mmol) in DMF (1 mL) and the mixture was stirred for 3.5 h. The mixture was diluted with EtOAc and transferred into a separating funnel. NH4Cl was added and the product was extracted with EtOAc. The combined organic extracts were washed with NaHCO₃, water, brine, dried (MgSO4) concentrated under vacuum to afford crude (R)-2-(3-(2,5-di-chloropyrimidin-4-yl)-5-oxo-5H-pyrrolo[3,4-b]pyridin-6(7H)-yl)-N—((S)-2-hydroxy-1-(m-tolyl)ethyl)propanamide compound with (R)-2-(3-(2-((1H-benzo[d][1,2,3]triazol-1-yl)oxy)-5-chloropyrimidin-4-yl)-5-oxo-5H-pyrrolo[3,4-b]pyridin-6(7H)-yl)-N—((S)-2-hydroxy-1-(m-tolyl)ethyl)propanamide (3:2) (0.149 g, 0.284 mmol, 100% yield) as an orange solid. The product was used without further purification and characterization in the next step. Quantitative yield was assumed.

Preparation 375: Mixture of (R)-2-(3-(2,5-dichloro-pyrimidin-4-yl)-5-oxo-5H-pyrrolo[3,4-b]pyridin-6(7H)-yl)-N—((S)-2-hydroxy-1-(3-methoxyphenyl)ethyl)propanamide with (R)-2-(3-(2-((1H-benzo[d][1,2,3]triazol-1-yl)oxy)-5-chloropyrimidin-4-yl)-5-oxo-5H-pyrrolo[3,4-b]pyridin-6(7H)-yl)-N—((S)-2-hydroxy-1-(3-methoxyphenyl)ethyl)propanamide (1:1)

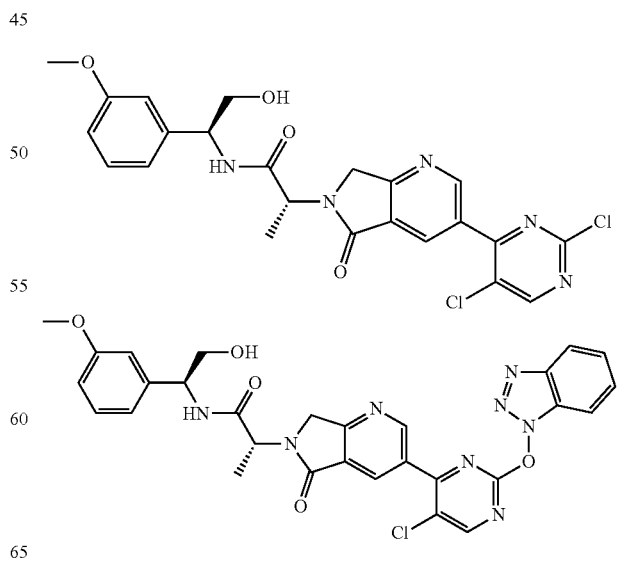

Prepared using a similar procedure to preparation 374.

Preparation 376: methyl 2-(bromomethyl)-5-chloro-3-fluorobenzoate

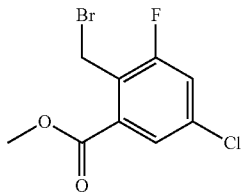

NBS (5.30 g, 29.8 mmol) and benzoyl peroxide (0.401 g, 1.241 mmol) were added to a solution of methyl 5-chloro-3-fluoro-2-methylbenzoate (5.03 g, 24.83 mmol) in chloroform (200 mL, 2480 mmol) and the mixture was heated to reflux and stirred overnight. The reaction was cooled to room temperature and hexane (300 mL) was added. The resulting precipitate was removed by filtration and the filtrate was concentrated in vacuo. The crude product was purified by chromatography (SiO$_2$, 120 g column, 0-30% DCM in isohexane) to afford the title compound (5.908 g, %) as a colourless oil. The product was used without further purification in the next step. 1H NMR (CDCl$_3$) δ: 7.78 (dd, 1H), 7.29 (dd, 1H), 4.94 (d, 2H), 3.96 (s, 3H).

Preparation 377: tert-butyl (R)-2-(6-chloro-4-fluoro-1-oxoisoindolin-2-yl)propanoate

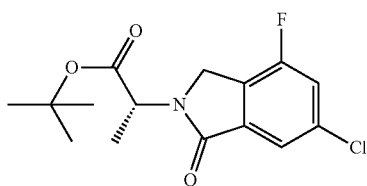 [SMILES: C[C@H](C(=O)OC(C)(C)C)N1Cc2c(F)cc(Cl)cc2C1=O]

A mixture of methyl 2-(bromomethyl)-5-chloro-3-fluorobenzoate (1.54 g, 5.20 mmol), (R)-tert-butyl 2-aminopropanoate hydrochloride (1.43 g, 7.87 mmol) and DIPEA (3.0 mL, 17.18 mmol) in MeCN (30.0 mL, 574 mmol) was heated to 75° C. overnight, then allowed to cool to room temperature and stirred for 2 days. The reaction mixture was concentrated under reduced pressure and the residue was partitioned between EtOAc (30 mL) and 1 M HCl (30 mL). The layers were separated and the aqueous fraction was extracted with EtOAc (30 mL). The combined organic extracts were washed with brine (3×50 mL), dried (MgSO$_4$), filtered and concentrated under reduced pressure to afford the crude product as a pale beige solid (1.52 g). The product was used without further purification in the next step. LCMS: [M-tBu+H]+=258.

Preparation 378: tert-butyl (R)-2-(4-fluoro-1-oxo-6-(4,4,5,5-tetramethyl-1,3,2-dioxaborolan-2-yl)isoindolin-2-yl)propanoate

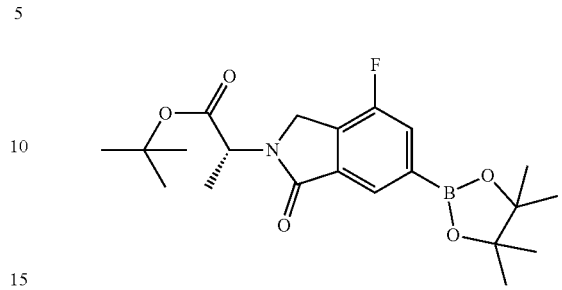

A mixture of (R)-tert-butyl 2-(6-chloro-4-fluoro-1-oxoisoindolin-2-yl)propanoate (1.52 g, 4.84 mmol), bis(pinacolato)diboron (1.47 g, 5.79 mmol) and potassium acetate (1.44 g, 14.67 mmol) in 1,4-dioxane (10.0 mL, 117 mmol) was degassed (bubbling nitrogen) for 10 minutes at 40° C. XPhos Pd G3 (0.054 g, 0.064 mmol) was added and the mixture was degassed for a further 10 minutes and then heated to 100° C. for 65 minutes. The reaction mixture was cooled to room temperature and filtered through celite, washing with EtOAc (3×50 mL). The filtrate was concentrated under reduced pressure to afford the crude product as a grey gum (4.4 g). Purification by chromatography (SiO$_2$, 24 g column, 0-50% EtOAc in iso-hexane) afforded the title compound (1.98 g, 91%) as an off-white solid. LCMS: [M-tBu+H]+=350.

Preparation 379: tert-butyl (R)-2-(6-(2,5-dichloropyrimidin-4-yl)-4-fluoro-1-oxoisoindolin-2-yl)propanoate

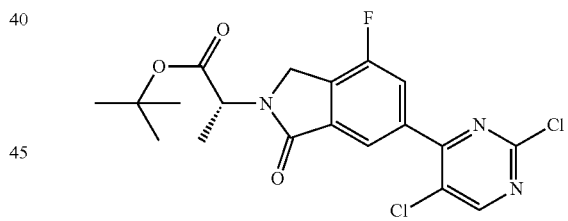

A mixture of (R)-tert-butyl 2-(4-fluoro-1-oxo-6-(4,4,5,5-tetramethyl-1,3,2-dioxaborolan-2-yl)isoindolin-2-yl)propanoate (1.98 g, 4.40 mmol), 2,4,5-trichloropyrimidine (0.800 mL, 6.98 mmol) and potassium carbonate (1.23 g, 8.90 mmol) in 1,4-dioxane (12.0 mL, 140 mmol) and water (4.0 mL, 222 mmol) was degassed (bubbling nitrogen) at 40° C. for 10 minutes. Pd(Ph$_3$P)$_4$ (0.250 g, 0.216 mmol) was added and the mixture degassed for a further 10 minutes then heated to 90° C. for 3.5 h. The mixture was cooled to room temperature and then partitioned between EtOAc (30 mL) and water (30 mL). The layers were separated and the aqueous fraction was extracted with EtOAc (30 mL). The combined organic extracts were washed with brine (3×30 mL), dried (MgSO$_4$), filtered and concentrated under reduced pressure to afford the crude product as an orange oil. Purification by chromatography (SiO$_2$, 24 g column, 0-50% EtOAc in iso-hexane) afforded the title compound (1.15 g, 60.1%) as an off-white solid. LCMS: [M-tBu+H]+=370.

Preparation 380: tert-butyl (R)-2-(6-(5-chloro-2-((oxan-4-yl)amino)pyrimidin-4-yl)-4-fluoro-1-oxoisoindolin-2-yl)propanoate

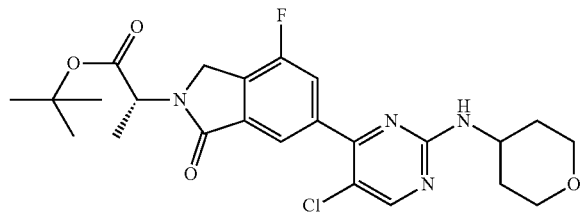 [SMILES: C[C@H](C(=O)OC(C)(C)C)N1Cc2c(F)cc(-c3nc(NC4CCOCC4)ncc3Cl)cc2C1=O]

DIPEA (0.370 mL, 2.118 mmol) and oxan-4-amine (0.120 mL, 1.159 mmol) were added to a mixture of (R)-tert-butyl 2-(6-(2,5-dichloropyrimidin-4-yl)-4-fluoro-1-oxoisoindolin-2-yl)propanoate (0.298 g, 0.685 mmol) in 1,4-dioxane (5.0 mL, 58.5 mmol) and the mixture was stirred at 90° C. for 21 h. Further oxan-4-amine (0.120 mL, 1.159 mmol) and DIPEA (0.370 mL, 2.118 mmol) was added and the mixture was stirred at 90° C. for a further 5 h, then cooled to room temperature and partitioned between EtOAc (50 mL) and water (50 mL). The layers were separated and the aqueous was extracted with EtOAc (50 mL). The combined organic extracts was washed with brine (3×30 mL), dried (MgSO$_4$), filtered and concentrated under reduced pressure to afford the crude product which was dried in a vacuum oven over for 3 days to afford the title compound (0.303 g, 89%) as a yellow gum. The product was used without further purification in the next step. LCMS: [M+H]+=491.

Preparation 381: (R)-2-(6-(5-chloro-2-((oxan-4-yl)amino)pyrimidin-4-yl)-4-fluoro-1-oxoisoindolin-2-yl)propanoic acid

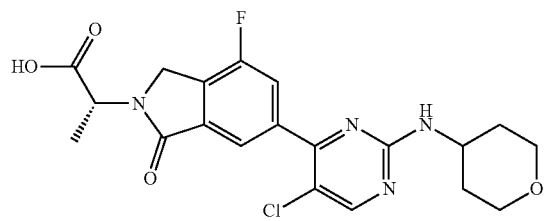 [SMILES: C[C@H](C(=O)O)N1Cc2c(F)cc(-c3nc(NC4CCOCC4)ncc3Cl)cc2C1=O]

TFA (1.0 mL, 12.98 mmol) was added to a stirred solution of (R)-tert-butyl 2-(6-(5-chloro-2-((oxan-4-yl)amino)pyrimidin-4-yl)-4-fluoro-1-oxoisoindolin-2-yl)propanoate (0.303 g, 0.611 mmol) in DCM (5.0 mL, 78 mmol) and the mixture was stirred for 22.5 h, then concentrated under vacuum. The residue was azeotroped with toluene (3×30 mL) to afford the crude product which was dried in a vacuum oven overnight to give a yellow gum (347 mg). The crude was triturated with ether (10 mL) and the resulting suspension was decantated to give a solid, which was dried in a vacuum oven overnight. The ether filtrate was combined with the solid and concentrated under reduced pressure, then azeotroped with MeCN (3×10 mL) and dried a the vacuum oven to afford the title compound (279 g, 95%) as a yellow solid. LCMS: [M+H]+=435.

Preparation 382: 2-(6-(2,5-dichloropyrimidin-4-yl)-4-fluoro-1-oxoisoindolin-2-yl)acetic acid

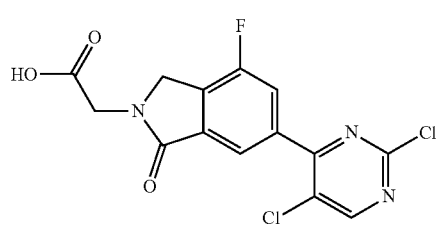 [SMILES: O=C(O)CN1Cc2c(F)cc(-c3nc(Cl)ncc3Cl)cc2C1=O]

A stirred solution of tert-butyl 2-(6-(2,5-dichloropyrimidin-4-yl)-4-fluoro-1-oxoisoindolin-2-yl)acetate (390 mg, 0.918 mmol) in dichloromethane (2 ml) was treated with TFA (2 ml) and stirred at room temperature for 2 h. The mixture was evaporated and the residue was taken up in toluene (3×10 ml) and evaporated to give 2-(6-(2,5-dichloropyrimidin-4-yl)-4-fluoro-1-oxoisoindolin-2-yl)acetic acid (356 mg, 0.910 mmol, 99% yield) as a cream foam. LCMS: [M+H]+=356.

Preparation 383: (R)-2-(6-(2,5-dichloropyrimidin-4-yl)-4-fluoro-1-oxoisoindolin-2-yl)-N-(1-(3-methoxyphenyl)ethyl)acetamide

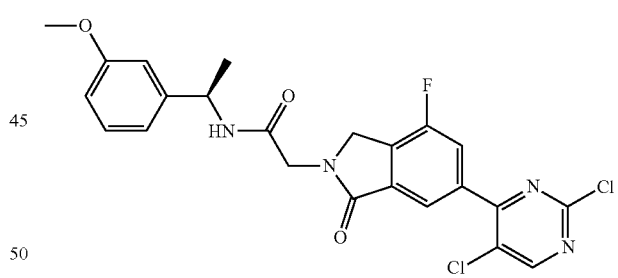

A stirred solution of 2-(6-(2,5-dichloropyrimidin-4-yl)-4-fluoro-1-oxoisoindolin-2-yl)acetic acid (100 mg, 0.281 mmol), (R)-1-(3-methoxyphenyl)ethanamine (48 mg, 0.317 mmol) and triethylamine (0.117 ml, 0.842 mmol) in DMF (1 ml) was cooled in an ice-bath, treated with T3P (50% solution in ethyl acetate, 0.25 ml, 0.424 mmol) and stirred at room temperature for 3 h. The solution was diluted with water (5 ml) and extracted with ethyl acetate (3×5 ml). The combined organic extracts were washed with 1M KHSO$_4$ (5 ml) followed by NaHCO$_3$ (5 ml), brine (2×5 ml), then dried (Na$_2$SO$_4$) and evaporated to give the title compound (131 mg, 89%) as a cream solid. LCMS: [M+H]+=489.

Preparation 384: (S)-2-(6-(2-((3H-[1,2,3]triazolo[4,5-b]pyridin-3-yl)oxy)-5-chloropyrimidin-4-yl)-4-fluoro-1-oxoisoindolin-2-yl)-N-(2-hydroxy-1-(3-methoxyphenyl)ethyl)acetamide

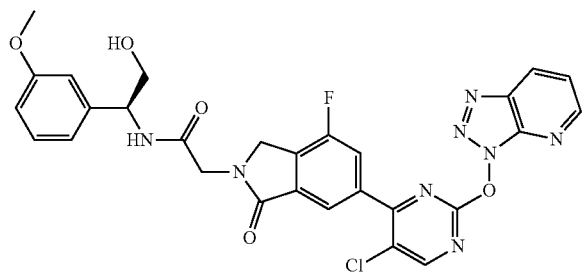 [SMILES: COc1cccc([C@@H](CO)NC(=O)CN2Cc3c(F)cc(-c4nc(On5nnc6cccnc65)ncc4Cl)cc3C2=O)c1]

A stirred solution of 2-(6-(2,5-dichloropyrimidin-4-yl)-4-fluoro-1-oxoisoindolin-2-yl)acetic acid (100 mg, 0.281 mmol), (S)-2-amino-2-(3-methoxyphenyl)ethanol, HCl (69 mg, 0.339 mmol) and DIPEA (0.196 ml, 1.123 mmol) in DMF (2 ml) was treated with HATU (117 mg, 0.309 mmol) and stirred at room temperature overnight. The mixture was diluted with ethyl acetate (10 ml), washed successively with 1M KHSO₄ (10 ml), NaHCO₃ (10 ml), brine (2×10 ml), then dried (MgSO₄) and evaporated. The residue was suspended in a mixture of ethyl acetate and dichloromethane (~5 ml), absorbed onto silica and purified by chromatography (SiO₂, 12 g column, 50-100% EtOAc in isohexane) to afford the title compound (62 mg, 35.4%). LCMS: [M+H]+=605.

Preparation 385: (tert-butyl (R)-2-(6-(5-chloro-2-(((S)-1-hydroxypropan-2-yl)amino)pyrimidin-4-yl)-4-fluoro-1-oxoisoindolin-2-yl)propanoate

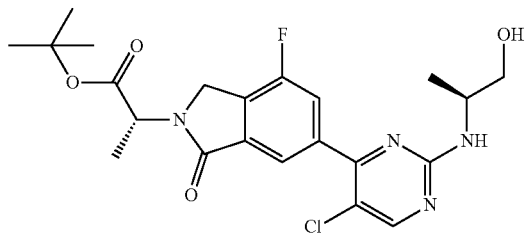 [SMILES: C[C@H](C(=O)OC(C)(C)C)N1Cc2c(F)cc(-c3nc(N[C@@H](C)CO)ncc3Cl)cc2C1=O]

A stirred solution of (R)-tert-butyl 2-(6-(2,5-dichloropyrimidin-4-yl)-4-fluoro-1-oxoisoindolin-2-yl)propanoate (100 mg, 0.235 mmol), (S)-2-aminopropan-1-ol (27 mg, 0.359 mmol) and Hunig's base (102 µl, 0.586 mmol) in dioxane (2 ml) was stirred at 70° C. (bath) overnight. LC/MS showed the mixture to contain mostly the required product and 14% starting material. The solution was allowed to cool, was diluted with ethyl acetate (10 ml), was washed with 1M aqueous potassium hydrogen sulphate solution (5 ml) followed by saturated aqueous sodium bicarbonate solution (5 ml) and then brine (5 ml), was dried (MgSO4) and evaporated. The residue was purified on 12 g graceresolv silica cartridge, using a gradient of 50 to 100% of ethyl acetate in isohexane as eluent to give (R)-tert-butyl 2-(6-(5-chloro-2-(((S)-1-hydroxypropan-2-yl)amino)pyrimidin-4-yl)-4-fluoro-1-oxoisoindolin-2-yl)propanoate (67 mg, 0.138 mmol, 59.0% yield). LCMS: [M+H]+=465.

Preparation 386: (R)-2-(6-(5-chloro-2-(((S)-1-hydroxypropan-2-yl)amino)pyrimidin-4-yl)-4-fluoro-1-oxoisoindolin-2-yl)propanoic acid trifluoroacetate

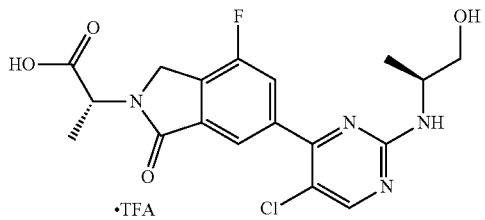 [SMILES: C[C@H](C(=O)O)N1Cc2c(F)cc(-c3nc(N[C@@H](C)CO)ncc3Cl)cc2C1=O ; "·TFA"]

A stirred solution of (R)-tert-butyl 2-(6-(5-chloro-2-(((S)-1-hydroxypropan-2-yl)amino)pyrimidin-4-yl)-4-fluoro-1-oxoisoindolin-2-yl)propanoate (65 mg, 0.140 mmol) in dichloromethane (4 ml) was treated with TFA (4 ml) and stirred at room temp. for 2 h. The residue was taken up in toluene (3×5 ml) and evaporated to give (R)-2-(6-(5-chloro-2-(((S)-1-hydroxypropan-2-yl)amino)pyrimidin-4-yl)-4-fluoro-1-oxoisoindolin-2-yl)propanoic acid (91 mg, 0.140 mmol, 100% yield) as a yellow glass. LCMS: [M+H]+=409.

Preparation 387: methyl 3-((tert-butyldimethylsilyl)oxy)-2-(6-(2,5-dichloropyrimidin-4-yl)-1-oxoisoindolin-2-yl)propanoate

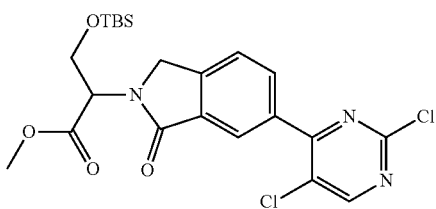 [SMILES: COC(=O)C(CO[Si](C)(C)C(C)(C)C)N1Cc2ccc(-c3nc(Cl)ncc3Cl)cc2C1=O]

The title compound could be obtained by following Preparation 95.

Alternatively, the following procedure could be used: A stirred mixture of methyl 3-((tert-butyldimethylsilyl)oxy)-2-(1-oxo-6-(4,4,5,5-tetramethyl-1,3,2-dioxaborolan-2-yl)isoindolin-2-yl)propanoate (1.448 g, 3.05 mmol), 2,4,5-trichloropyrimidine (0.511 mL, 4.57 mmol) in dioxane (8 ml) and sodium carbonate (2M aqueous solution) (3.1 mL, 6.20 mmol) was degassed with nitrogen for 10 minutes, treated with Pd(PPh₃)₄ (0.176 g, 0.152 mmol) and stirred at 80° C. under nitrogen for 3.5 h. The mixture was allowed to cool, diluted with brine (25 ml) and extracted with ethyl acetate (3×25 ml). The combined extracts were washed with brine (25 ml), (Na₂SO₄) and evaporated. The residue was purified by chromatography (SiO₂, 40 g column, 0-50% EtOAc in isohexane) to give the title compound (862 mg, 51.3%) as a cream foam. LC-MS: [M+H]+=496.

Preparation 388: Methyl 3-((tert-butyldimethylsilyl)oxy)-2-(6-(5-chloro-2-((oxan-4-yl)amino)pyrimidin-4-yl)-1-oxoisoindolin-2-yl)propanoate

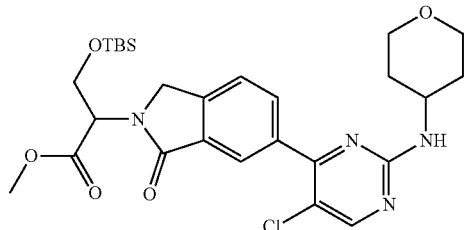 [SMILES: COC(=O)C(CO[Si](C)(C)C(C)(C)C)N1Cc2ccc(-c3nc(NC4CCOCC4)ncc3Cl)cc2C1=O]

Prepared using a similar procedure to Example 102. LC-MS: [M+H]+=561.

Preparation 389:3-((tert-butyldimethylsilyl)oxy)-2-(6-(5-chloro-2-((oxan-4-yl)amino)pyrimidin-4-yl)-1-oxoisoindolin-2-yl)propanoic acid

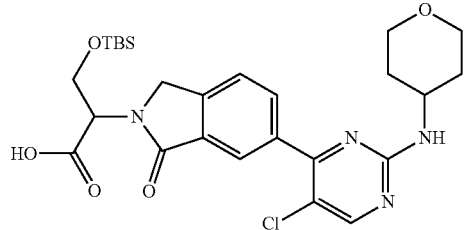 [SMILES: CC(C)(C)[Si](C)(C)OCC(C(=O)O)N1Cc2ccc(-c3nc(NC4CCOCC4)ncc3Cl)cc2C1=O]

1M LiOH (249 µl, 0.249 mmol) was added to a solution of methyl 3-((tert-butyldimethylsilyl)oxy)-2-(6-(5-chloro-2-((oxan-4-yl)amino)pyrimidin-4-yl)-1-oxoisoindolin-2-yl)propanoate (70 mg, 0.125 mmol) in 3:1 THF (1.8 mL):water (0.6 mL) and the reaction mixture was stirred for 4 h at room temperature. EtOAc (5 mL) was added, and the layers separated. The aqueous layer was acidified with 1M HCl (0.5 mL) and extracted with EtOAc. The combined organic extracts were dried (Na$_2$SO$_4$) and concentrated in vacuo to give the crude title compound (52 mg, 50.3%) as a yellow gum LC-MS: [M+H]+=547.

Preparation 390: (tert-butyl((R)-4-hydroxy-1-(((R)-1-(3-methoxyphenyl)ethyl)amino)-1-oxobutan-2-yl)carbamate

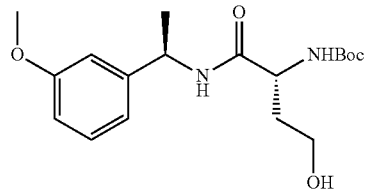 [SMILES: COc1cccc([C@@H](C)NC(=O)[C@@H](CCO)NC(=O)OC(C)(C)C)c1]

Triethylamine (0.260 mL, 1.865 mmol), (R)-1-(3-methoxyphenyl)ethanamine (0.150 mL, 1.015 mmol) followed by PyBOP (0.520 g, 0.999 mmol) were added to a stirred solution of (R)-2-((tert-butoxycarbonyl)amino)-4-hydroxybutanoic acid (0.200 g, 0.912 mmol) in DMF (2.0 mL, 25.8 mmol) and the mixture was stirred overnight, then partitioned between DCM (20 mL) and water (20 mL). The layers were separated and the aqueous fraction was extracted with DCM (20 mL). The combined organic extracts were washed with brine (3×20 mL), filtered through a phase separating cartridge and concentrated under reduced pressure. The residue was dried a vacuum oven overnight. The crude product was purified by chromatography (SiO$_2$, 12 g column, 0-100% EtOAc in iso-hexane) to afford the title compound (0.116 g, 0.296 mmol, 32.5% yield) as a pale yellow gum. 1H NMR (DMSO-d6, 400 MHz) δ 8.15 (1H, d), 7.21 (1H, t), 6.85 (2H, d), 6.83-6.73 (2H, m), 4.87 (1H, t), 4.50 (1H, t), 4.06-3.99 (1H, m), 3.74 (3H, s), 3.45-3.35 (2H, m), 1.80-1.53 (2H, m), 1.39-1.33 (12H, m).

Preparation 391: (R)-2-amino-4-hydroxy-N—((R)-1-(3-methoxyphenyl)ethyl)butanamide trifluoroacetate

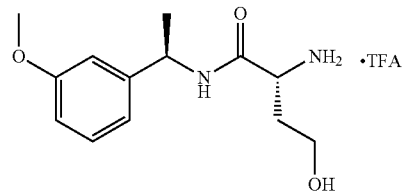 [SMILES: COc1cccc([C@@H](C)NC(=O)[C@H](N)CCO)c1 ; "·TFA"]

TFA (0.200 mL, 2.60 mmol) was added was added to a suspension of tert-butyl ((R)-4-hydroxy-1-(((R)-1-(3-methoxyphenyl)ethyl)amino)-1-oxobutan-2-yl)carbamate (0.110 g, 0.281 mmol) in DCM (1.0 mL, 15.54 mmol) and the resulting mixture was stirred a room temperature for 4.5 h The reaction mixture was concentrated under reduced pressure and azeotroped with toluene (3×20 mL), then dried in a vacuum oven for 5 days to afford the title compound (0.083 g, 94%) as a white solid. The product was used without further purification in the next step. 1H NMR (DMSO-d6) δ: 8.95 (s (br), 1H), 8.08 (s (br), 3H), 7.25 (dd, 1H), 6.92-6.85 (m, 2H), 6.85-6.75 (m, 1H), 4.98-4.86 (m, 1H), 3.96-3.76 (m, 2H), 3.75 (s, 3H), 1.96-1.65 (m, 2H), 1.37 (d, 3H) (note: CH proton was not observed and was overlapped with DMSO or water peak).

Preparation 392: tert-butyl ((2R,3S)-3-hydroxy-1-(((R)-1-(3-methoxyphenyl)ethyl)amino)-1-oxobutan-2-yl)carbamate

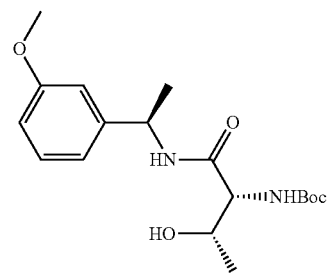 [SMILES: COc1cccc([C@@H](C)NC(=O)[C@H](NC(=O)OC(C)(C)C)[C@H](C)O)c1]

A solution of (2R,3S)-2-((tert-butoxycarbonyl)amino)-3-hydroxybutanoic acid (500 mg, 2.281 mmol) and (R)-1-(3-methoxyphenyl)ethanamine (371 µl, 2.509 mmol) in DMF (3 mL) was stirred at room temperature, triethylamine (636

μl, 4.56 mmol) and PyBop (1306 mg, 2.509 mmol) were added, and the resulting mixture was stirred overnight at room temperature. The reaction was partitioned with DCM (10 mL) and water (10 mL). The organic layer was extracted with DCM (2×10 mL). The combined organic layers were washed with brine (2×10 mL), filtered via a hydrophobic phase separator and concentrated in vacuo. Purification by chromatography (SiO$_2$, 0-10% MeOH in DCM) gave the title compound (504 mg, 87%) as a colourless gum. 1H NMR (DMSO-d6) δ: 8.15 (d, 1H), 7.20 (dd, 1H), 6.91-6.84 (m, 2H), 6.78 (dd, 1H), 6.32 (d, 1H), 4.97-4.85 (m, 1H), 4.74 (d, 1H), 3.92-3.87 (m, 2H), 3.73 (s, 3H), 1.40 (s, 9H), 1.35 (d, 3H), 1.01 (d, 3H).

Preparation 393: (2R,3S)-2-amino-3-hydroxy-N—((R)-1-(3-methoxyphenyl)ethyl)butanamide hydrochloride

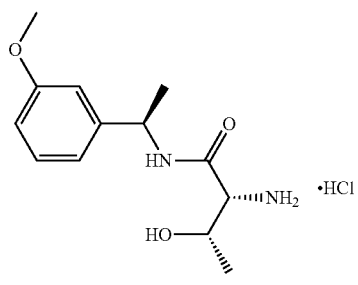 [SMILES: COc1cccc([C@@H](C)NC(=O)[C@H](N)[C@H](C)O)c1 ; Cl]

HCl (1 ml, 4.00 mmol) was added to a solution of tert-butyl ((2R,3S)-3-hydroxy-1-(((R)-1-(3-methoxyphenyl)ethyl)amino)-1-oxobutan-2-yl)carbamate (504 mg, 1.187 mmol) in DCM (5 mL), and the resulting mixture stirred at room temperature for 3 h. The reaction was concentrated under reduced pressure and azeotroped with toluene (10 mL) to afford the title compound (394 mg, 99%). The product was used without further purification in the next step. 1H NMR (DMSO-d6) δ: 9.06 (d, J=8.1 Hz, 1H), 8.17 (s, 3H), 7.24 (dd, 1H), 6.98-6.84 (m, 2H), 6.81 (ddd, 1H), 5.57 (d, 1H), 5.02-4.86 (m, 1H), 3.94-3.78 (m, 1H), 3.74 (s, 3H), 3.63-3.55 (m, 1H), 1.39 (d, 3H), 1.05 (d, 3H).

Preparation 394: tert-butyl (S)-2-(6-bromo-1-oxoisoindolin-2-yl)propanoate

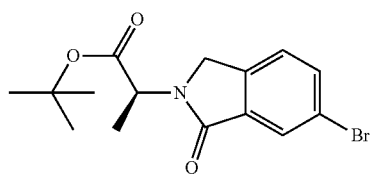 [SMILES: C[C@@H](C(=O)OC(C)(C)C)N1Cc2ccc(Br)cc2C1=O]

Prepared using a similar procedure to preparation 73. LCMS: [M-tBu]+=284.

Preparation 395: tert-butyl (R)-2-(6-bromo-1-oxoisoindolin-2-yl)butanoate

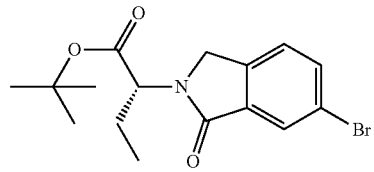 [SMILES: CC[C@H](C(=O)OC(C)(C)C)N1Cc2ccc(Br)cc2C1=O]

Prepared using a similar procedure to preparation 73. LCMS: [M-tBu]+=298.

Preparation 396: tert-butyl (S)-2-(1-oxo-6-(4,4,5,5-tetramethyl-1,3,2-dioxaborolan-2-yl)isoindolin-2-yl)propanoate Prepared using a similar procedure to preparation 89. LCMS: [M-tBu]+=332.

Preparation 397: tert-butyl (R)-2-(1-oxo-6-(4,4,5,5-tetramethyl-1,3,2-dioxaborolan-2-yl)isoindolin-2-yl)butanoate Prepared using a similar procedure to preparation 88. 1H NMR (Chloroform-d) δ: 8.37-8.31 (m, 1H), 7.97 (dd, 1H), 7.46 (dd, 1H), 4.91 (dd, 1H), 4.69 (d, 1H), 4.34 (d, 1H), 2.18-2.02 (m, 1H), 1.89-1.72 (m, 1H), 1.43 (s, 9H), 1.35 (s, 12H), 0.94 (t, 3H).

Preparation 398: tert-butyl (S)-2-(6-(2,5-dichloropyrimidin-4-yl)-1-oxoisoindolin-2-yl)propanoate

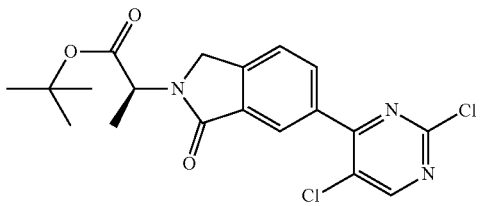 [SMILES: C[C@@H](C(=O)OC(C)(C)C)N1Cc2ccc(-c3nc(Cl)ncc3Cl)cc2C1=O]

Prepared using a similar procedure to preparation 90. LCMS: [M-tBu]+=352.

Preparation 399: tert-butyl (R)-2-(6-(2,5-dichloropyrimidin-4-yl)-1-oxoisoindolin-2-yl)butanoate

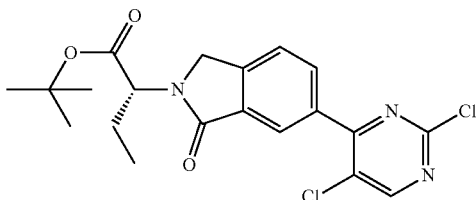

A stirred solution of (R)-tert-butyl 2-(1-oxo-6-(4,4,5,5-tetramethyl-1,3,2-dioxaborolan-2-yl)isoindolin-2-yl)butanoate (576 mg, 1.435 mmol), 2,4,5-trichloropyrimidine (241 µl, 2.153 mmol), and sodium carbonate (2.0 M aq.) (1.43 mL, 2.87 mmol) in dioxane (13 mL) and H$_2$O (3 mL) was degassed with nitrogen for 10 minutes. Pd(PPh$_3$)$_4$ (83 mg, 0.072 mmol) was added and the system degassed with nitrogen for a further 5 minutes. The reaction was heated to 90° C. and stirred overnight. After cooling to room temperature, the reaction was partitioned between water (30 ml) and ethyl acetate (40 ml). The phases were separated and the aqueous was extracted with EtOAc (2×20 mL). The combined organic extracts were washed with brine (40 mL), dried (MgSO$_4$) and concentrated to give the crude product. Purification by chromatography (SiO$_2$, 0-100% EtOAc in isohexane) afforded the title compound (331 mg, 54.6%) as a colourless gum. LCMS: [M-tBu]+=366.

Preparation 400: methyl 2-methyl-5-(4,4,5,5-tetramethyl-1,3,2-dioxaborolan-2-yl)benzoate

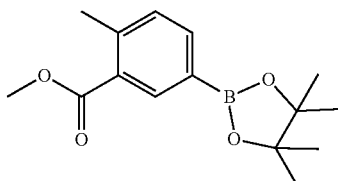

A mixture of methyl 5-bromo-2-methylbenzoate (5.0 g, 21.83 mmol), bis(pinacolato)diboron (6.7 g, 26.4 mmol) and potassium acetate (4.3 g, 43.8 mmol) in 1,4-dioxane (50.0 mL, 585 mmol) was degassed (bubbling nitrogen) at 40° C. for 10 minutes. PdCl$_2$(dppf)$_2$ (0.800 g, 1.093 mmol) was added and the mixture was degassed for a further 10 minutes and then heated to 90° C. After 3.5 h the reaction mixture was cooled to room temperature, filtered through celite, washing with EtOAc. The filtrate was concentrated under reduced pressure to afford a dark solid. The crude product was purified by chromatography (SiO$_2$, 120 g column, 0-100% (20% EtOAc in iso-hexanes) in iso-hexanes) to afford two fractions (2.44 g, 39.7%) and (0.821 g, 12.26%) of the title compound. Both fractions were combined in the next step.). LCMS: [M+H]+=277.

Preparation 401: methyl 5-(2,5-dichloropyrimidin-4-yl)-2-methylbenzoate

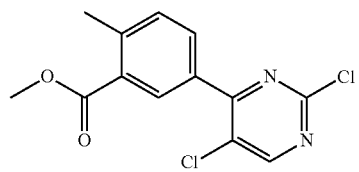 [SMILES: COC(=O)c1cc(-c2nc(Cl)ncc2Cl)ccc1C]

A mixture of methyl 2-methyl-5-(4,4,5,5-tetramethyl-1,3,2-dioxaborolan-2-yl)benzoate (3.26 g, 10.63 mmol), 2,4,5-trichloropyrimidine (1.6 mL, 13.96 mmol) and potassium carbonate (2.94 g, 21.27 mmol) in 1,4-dioxane (30.0 mL, 351 mmol) and water (10.0 mL, 555 mmol) was degassed (bubbling nitrogen) at 40° C. for 10 minutes. Pd(Ph$_3$P)$_4$ (0.266 g, 0.230 mmol) was added and the mixture degassed for a further 10 minutes and then heated to 90° C. After 5 h the reaction mixture was allowed to cool to room temperature and was partitioned between EtOAc (100 mL) and water (100 mL). The layers were separated and the aqueous fraction was extracted with EtOAc (100 mL). The combined organic extracts were washed with brine (3×100 mL), dried (MgSO$_4$), filtered and concentrated under reduced pressure to afford the crude product as a pale yellow solid (4.27 g). The crude product was purified by chromatography (SiO$_2$, 12 g column, 10-100% DCM in iso-hexane) to afford the title compound (2.27 g, 70.5%). LCMS: [M+H]+=297.

Preparation 402: methyl 2-(bromomethyl)-5-(2,5-dichloropyrimidin-4-yl)benzoate

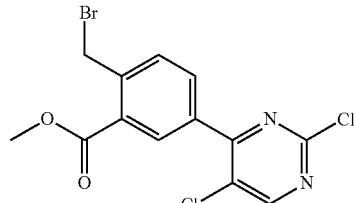

NBS (0.493 g, 2.77 mmol) followed by benzoyl peroxide (0.038 g, 0.118 mmol) were added to a stirred solution of methyl 5-(2,5-dichloropyrimidin-4-yl)-2-methylbenzoate (0.698 g, 2.302 mmol) in chloroform (15.0 mL, 186 mmol) and the resulting mixture was heated to reflux overnight. After 24 h the reaction mixture was allowed to cool to room temperature and iso-hexane (20 mL) was added. The mixture was filtered and the filtrate was concentrated under reduced pressure to afford the crude product which was dried in a vacuum oven for 3 days to give the title compound (0.924 g, 85%) as a yellow solid. The product was used without further purification in the next step. 1H NMR (DMSO-d6) δ: 9.05 (s, 1H), 8.32 (d, 1H), 8.07 (dd, 1H), 7.82 (d, 1H), 5.10 (s, 2H), 3.92 (s, 3H).

Preparation 403: (R)-2-(6-(2,5-dichoropyrimidin-4-yl)-1-oxoisoindolin-2-yl)-4-hydroxy-N—((R)-1-(3-methoxyphenyl)ethyl)butanamide (1432-65)

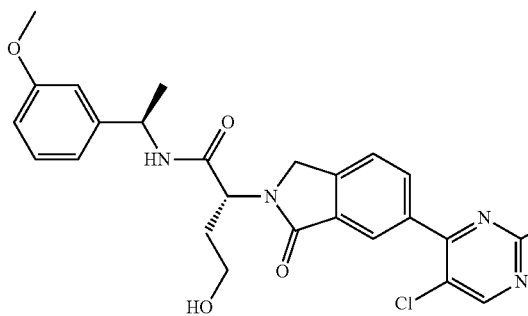

A mixture of crude methyl 2-(bromomethyl)-5-(2,5-dichloropyrimidin-4-yl)benzoate (0.075 g, 0.160 mmol), crude (R)-2-amino-4-hydroxy-N—((R)-1-(3-methoxyphenyl)ethyl)butanamide (0.080 g, 0.254 mmol) and DIPEA (0.110 mL, 0.630 mmol) in MeCN (5.0 mL, 96 mmol) was heated to 80° C. overnight. After 17 h the reaction mixture was allowed to cool to room temperature and concentrated under reduced pressure. The residue was partitioned between EtOAc (30 mL) and NH₄Cl (30 mL). The layers were separated and the organic fraction was washed with NH₄Cl (20 mL), water (20 mL), NaHCO₃ (2×20 mL) and brine (3×20 mL), then dried (MgSO₄), filtered and concentrated under reduced pressure to afford the crude product as a pale yellow gum (74 mg). The crude product was purified by chromatography (SiO₂, 4 g column, 0-100% EtOAc in iso-hexanes) to afford the title compound (0.023 g, 27.1%) as a glassy white solid. LCMS: [M+H]+=515.

Preparation 404: (2R,3S)-2-(6-(2,5-dichloropyrimidin-4-yl)-1-oxoisoindolin-2-yl)-3-hydroxy-N—((R)-1-(3-methoxyphenyl)ethyl)butanamide

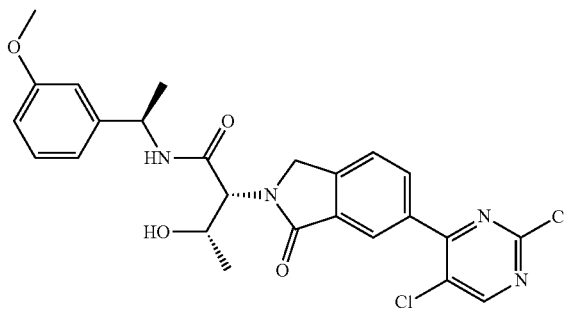 [SMILES: COc1cccc([C@@H](C)NC(=O)[C@@H]([C@H](C)O)N2Cc3ccc(-c4nc(Cl)ncc4Cl)cc3C2=O)c1]

DIPEA (0.553 mL, 3.17 mmol) was added to a mixture of crude methyl 2-(bromomethyl)-5-(2,5-dichloropyrimidin-4-yl)benzoate (298 mg, 0.791 mmol) and (2R,3S)-2-amino-3-hydroxy-N—((R)-1-(3-methoxyphenyl)ethyl)butanamide (374 mg, 1.187 mmol) in MeCN (8 mL, 153 mmol). The resulting mixture was heated to 80° C. (external temperature) for 6 hours, then overnight at room temperature. The reaction mixture was concentrated in vacuo. Purification by chromatography (SiO2, 0-100% EtOAc in iso-hexanes) gave the title compound (2R,3S)-2-(6-(2,5-dichloropyrimidin-4-yl)-1-oxoisoindolin-2-yl)-3-hydroxy-N—((R)-1-(3-methoxyphenyl)ethyl)butanamide (326 mg, 0.576 mmol, 72.7% yield). LCMS: [M+H]+=515.

Preparation 405: (R)-2-(6-(2,5-dichloropyrimidin-4-yl)-1-oxoisoindolin-2-yl)-N—((S)-2-hydroxy-1-(m-tolyl)ethyl)propanamide

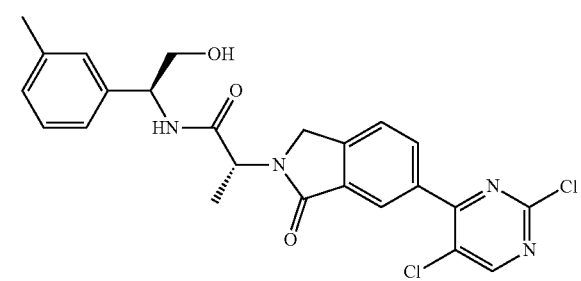 [SMILES: Cc1cccc([C@@H](CO)NC(=O)[C@@H](C)N2Cc3ccc(-c4nc(Cl)ncc4Cl)cc3C2=O)c1]

HATU (404 mg, 1.063 mmol) was added to a stirred mixture of (R)-2-(6-(2,5-dichloropyrimidin-4-yl)-1-oxoisoindolin-2-yl)propanoic acid (260 mg, 0.709 mmol), (S)-2-amino-2-(m-tolyl)ethanol hydrochloride (146 mg, 0.780 mmol) and DIPEA (309 μl, 1.772 mmol) in acetontrile (2 ml) and the mixture was stirred for 0.5 h. The mixture was diluted with DCM (100 ml) and the solution washed with 1M HCl (2×50 ml). The organic phase was collected, dried (MgSO₄), filtered and concentrated to afford the title compound (400 mg, 93%) as a foam. The product was used without further purification in the next step. LCMS: [M+H]+=485.

Preparation 406: tert-butyl (S)-2-(6-(5-chloro-2-((oxan-4-yl)amino)pyrimidin-4-yl)-1-oxoisoindolin-2-yl)propanoate

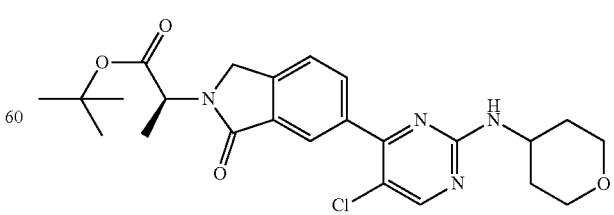

Prepared using a similar procedure to preparation 111. LCMS: [M+H]+=473.

Preparation 407 tert-butyl (R)-2-(6-(5-chloro-2-((oxan-4-yl)amino)pyrimidin-4-yl)-1-oxoisoindolin-2-yl)butanoate

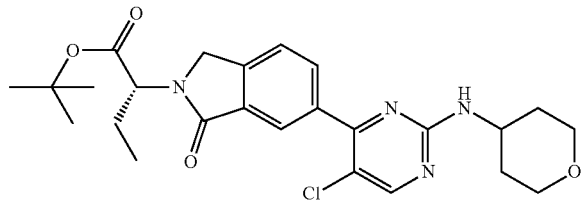 [SMILES: CC[C@H](C(=O)OC(C)(C)C)N1Cc2ccc(-c3nc(NC4CCOCC4)ncc3Cl)cc2C1=O]

Prepared using a similar procedure to preparation 2. LCMS: [M+H]+=487.

Preparation 408: (R)-2-(6-(2,5-dichloropyrimidin-4-yl)-1-oxoisoindolin-2-yl)propanoic acid

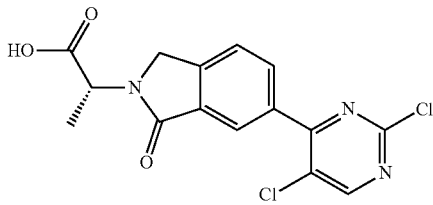 [SMILES: C[C@H](C(=O)O)N1Cc2ccc(-c3nc(Cl)ncc3Cl)cc2C1=O]

TFA (1 mL, 12.98 mmol) was added to a stirred solution of (R)-tert-butyl 2-(6-(2,5-dichloropyrimidin-4-yl)-1-oxoisoindolin-2-yl)propanoate (304 mg, 0.745 mmol) in DCM (4 mL) and reaction mixture stirred at 40° C. for 1 h. The solution was concentrated in vacuo and the residue azeotroped with toluene (3×10 mL), triturated with diethyl ether (10 ml), filtered and dried to afford the title compound (260 mg, 0.709 mmol, 95% yield) as a white solid. The product was used without further purification in the next step. LCMS: [M+H]+=352.

Preparation 409: (S)-2-(6-(5-chloro-2-((oxan-4-yl)amino)pyrimidin-4-yl)-1-oxoisoindolin-2-yl)propanoic acid

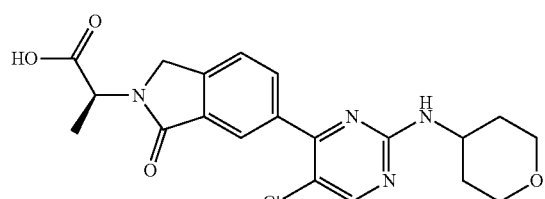

Prepared using a similar procedure to preparation 408. LCMS: [M+H]+=417.

Preparation 410 (R)-2-(6-(5-chloro-2-((oxan-4-yl)amino)pyrimidin-4-yl)-1-oxoisoindolin-2-yl)butanoic acid

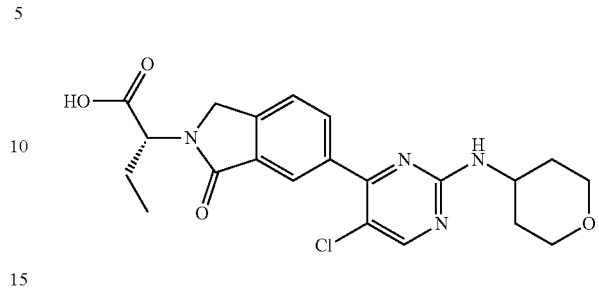

Prepared using a similar procedure to preparation 408. LCMS: [M+H]+=431.

Preparation 411: 3-((tert-butyldimethylsilyl)oxy)-2-(6-(5-chloro-2-((oxan-4-yl)amino)pyrimidin-4-yl)-1-oxoisoindolin-2-yl)propanoic acid and mixture of 2-(6-(5-chloro-2-((oxan-4-yl)amino)pyrimidin-4-yl)-1-oxoisoindolin-2-yl)-3-hydroxypropanoic acid and 2-(6-(5-chloro-2-((oxan-4-yl)amino)pyrimidin-4-yl)-1-oxoisoindolin-2-yl)-3-methoxypropanoic acid

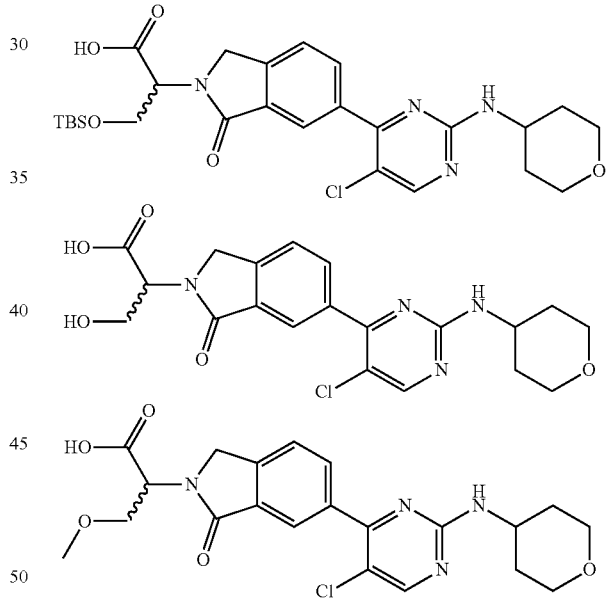

A stirred solution of methyl 3-((tert-butyldimethylsilyl)oxy)-2-(6-(5-chloro-2-((oxan-4-yl)amino)pyrimidin-4-yl)-1-oxoisoindolin-2-yl)propanoate (0.580 g, 1.034 mmol) in THF (3 ml) was treated with a solution of lithium hydroxide (0.05 g, 2.088 mmol) in water (1 ml) followed by methanol (1 ml) to give an homogenous solution which was stirred at room temperature overnight. The mixture was was diluted with brine (10 min) and extracted with ether (10 ml). The combined organic extracts were dried and concentrated under vacuum to afford 3-((tert-butyldimethylsilyl)oxy)-2-(6-(5-chloro-2-((oxan-4-yl)amino)pyrimidin-4-yl)-1-oxoisoindolin-2-yl)propanoic acid (116 mg, 14.36%, LCMS: [M+H]+=547) as an orange solid. The aqueous layer was acidified with 1M KHSO₄ and extracted with ethyl acetate (3×10 ml). The combined organic extracts were washed with brine (10 ml), dried (Na$_2$SO$_4$) and evaporated. The residue was dissolved in TFA (4 ml), stirred for 2 minutes and evaporated. The residue was suspended in toluene (3×10 ml) and evaporated, then dissolved in THF (3 ml), treated with a solution of lithium hydroxide (0.1 g, 4.18 mmol) in water (1 ml) followed by methanol (1 ml) to give an homogenous solution which was stirred overnight. The mixture was diluted with brine (10 min), washed with ether (10 ml), acidified with 1M KHSO$_4$ and extracted with ethyl acetate (3×10 ml). The combined organic extracts were washed with brine (10 ml), dried (Na2SO4) and evaporated to give a mixture of 2-(6-(5-chloro-2-((oxan-4-yl)amino)pyrimidin-4-yl)-1-oxoisoindolin-2-yl)-3-hydroxypropanoic acid and 2-(6-(5-chloro-2-((oxan-4-yl)amino)pyrimidin-4-yl)-1-oxoisoindolin-2-yl)-3-methoxypropanoic acid as an orange foam (555 mg, LCMS: [M+H]+=433 and 447).

Preparation 412: Mixture of 3-((tert-butyldimethylsilyl)oxy)-2-(6-(5-chloro-2-((oxan-4-yl)amino)pyrimidin-4-yl)-1-oxoisoindolin-2-yl)propanoic acid and 2-(6-(5-chloro-2-((oxan-4-yl)amino)pyrimidin-4-yl)-1-oxoisoindolin-2-yl)-3-methoxypropanoic acid

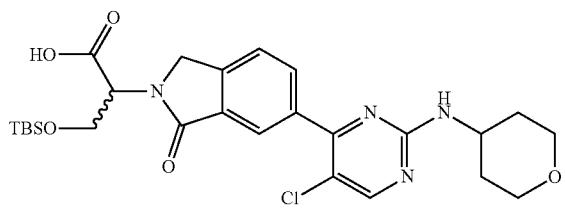

A stirred solution of a mixture of 2-(6-(5-chloro-2-((oxan-4-yl)amino)pyrimidin-4-yl)-1-oxoisoindolin-2-yl)-3-hydroxypropanoic acid and 2-(6-(5-chloro-2-((oxan-4-yl)amino)pyrimidin-4-yl)-1-oxoisoindolin-2-yl)-3-methoxypropanoic acid 548 mg) and imidazole (259 mg, 3.80 mmol) in DMF (2 ml) was treated with TBDMS-Cl (286 mg, 1.898 mmol) and stirred overnight. The solution was quenched with brine (20 ml), acidified with 1M KHSO$_4$ and extracted with ethyl acetate (20 ml and 2×10 ml). The combined extracts were washed with brine (2×20 ml), dried (MgSO$_4$) and evaporated to give the title mixture as a yellow oil (629 mg).). LCMS: [M+H]+=447 and 547.

Preparation 413:3-((tert-butyldimethylsilyl)oxy)-2-(6-(5-chloro-2-((oxan-4-yl)amino)pyrimidin-4-yl)-1-oxoisoindolin-2-yl)-N—((R)-1-(3-methoxyphenyl)ethyl)propanamide (1419-38)

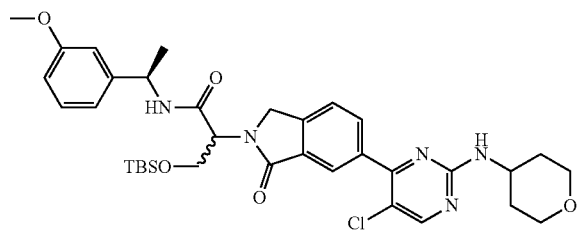 [SMILES: COc1cccc([C@@H](C)NC(=O)C(CO[Si](C)(C)C(C)(C)C)N2Cc3ccc(-c4nc(NC5CCOCC5)ncc4Cl)cc3C2=O)c1]

A stirred solution of 3-((tert-butyldimethylsilyl)oxy)-2-(6-(5-chloro-2-((oxan-4-yl)amino)pyrimidin-4-yl)-1-oxoisoindolin-2-yl)propanoic acid (629 mg, 1.150 mmol) (mixture with 2-(6-(5-chloro-2-((oxan-4-yl)amino)pyrimidin-4-yl)-1-oxoisoindolin-2-yl)-3-methoxypropanoic acid (629 mg)), (R)-1-(3-methoxyphenyl)ethanamine (209 mg, 1.382 mmol) and DIPEA (0.8 ml, 4.58 mmol) in DMF (4 ml) was treated with HATU (481 mg, 1.265 mmol) and stirred for 3 h. The mixture was diluted with ethyl acetate (40 ml), was washed successively with 1N KHSO$_4$ (20 ml), NaHCO$_3$ (20 ml), brine (2×10 ml), then dried (MgSO$_4$) and evaporated. The residue was purified by chromatography (SiO$_2$, 25 g column, 10-100% EtOAc in isohexane) to afford the title compound (261 mg, 31.7%) as a cream foam. LCMS: [M+H]+=680.

Note: 2-(6-(5-chloro-2-((oxan-4-yl)amino)pyrimidin-4-yl)-1-oxoisoindolin-2-yl)-3-methoxy-N—((R)-1-(3-methoxyphenyl)ethyl)propanamide, which was further purified by reversed phase preparative HPLC on a Waters Xbridge BEH C18 OBD, 130 Å, 5 μm, 19 mm×50 mm column, using a gradient of 20 to 50% of acetonitrile in 10 mM aqueous ammonium bicarbonate solution at 28 ml/min as eluent was also isolated from this reaction.

Preparation 414: 3-((tert-butyldimethylsilyl)oxy)-2-(6-(5-chloro-2-((oxan-4-yl)amino)pyrimidin-4-yl)-1-oxoisoindolin-2-yl)-N—((R)-1-(m-tolyl)ethyl)propanamide

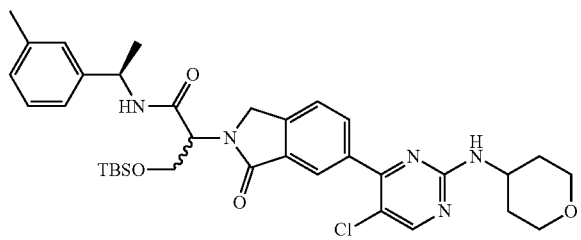 [SMILES: Cc1cccc([C@@H](C)NC(=O)C(CO[Si](C)(C)C(C)(C)C)N2Cc3ccc(-c4nc(NC5CCOCC5)ncc4Cl)cc3C2=O)c1]

Triethylamine (39.7 μl, 0.285 mmol) was added to a mixture of 3-((tert-butyldimethylsilyl)oxy)-2-(6-(5-chloro-2-((oxan-4-yl)amino)pyrimidin-4-yl)-1-oxoisoindolin-2-yl) propanoic acid (52 mg, 0.095 mmol), (R)-1-phenylethanamine (13.82 mg, 0.114 mmol) and HATU (39.8 mg, 0.105 mmol) in DMF (0.5 mL) and the mixture was stirred for 1 h. Water (5 mL) was added, and the resulting precipitate filtered, washed with water (5 mL). Purification by chromatography (SiO$_2$, 20-100% ethyl acetate in iso- Preparation 415: tert-butyl (R)-2-(3-(5-chloro-2-((oxan-4-yl)amino)pyrimidin-4-yl)-5-oxo-5,7-dihydro-6H-pyrrolo[3,4-b]pyridin-6-yl)propanoate

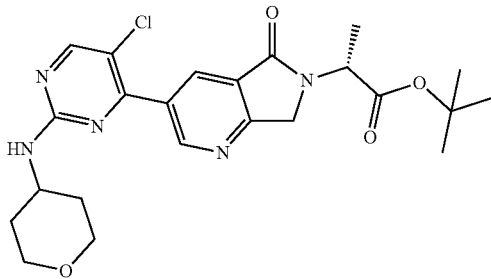 [SMILES: C[C@H](C(=O)OC(C)(C)C)N1Cc2ncc(-c3nc(NC4CCOCC4)ncc3Cl)cc2C1=O]

Oxan-4-amine (0.540 ml, 5.22 mmol) and DIPEA (1.140 ml, 6.53 mmol) were added to a solution of (R)-tert-butyl 2-(3-(2,5-dichloropyrimidin-4-yl)-5-oxo-5H-pyrrolo[3,4-b]pyridin-6(7H)-yl)propanoate (Preparation 367, 1.526 g, 2.61 mmol) in 1,4-dioxane (13.05 ml, 2.61 mmol) and the mixture stirred at 90° C. for 24 h, then cooled to room temperature. The mixture was concentrated in vacuo and the residue was dissolved in EtOAc (100 mL). The organic solution was washed sequentially with NH₄Cl (50 mL), NaHCO₃ (50 mL) and brine, then dried (MgSO₄), filtered and absorbed on silica. The crude product was purified by chromatography (SiO₂, 40 g column, 0-100% EtOAc in isohexane) to afford the title compound (910 mg, 66.2%) as an orange oil. LCMS: [M+H]+=474.

Preparation 416: (R)-2-(3-(5-chloro-2-((oxan-4-yl)amino)pyrimidin-4-yl)-5-oxo-5,7-dihydro-6H-pyrrolo[3,4-b]pyridin-6-yl)propanoic acid

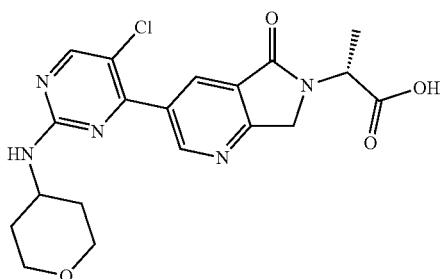 [SMILES: C[C@H](C(=O)O)N1Cc2ncc(-c3nc(NC4CCOCC4)ncc3Cl)cc2C1=O]

A stirred solution of (R)-tert-butyl 2-(3-(5-chloro-2-((oxan-4-yl)amino)pyrimidin-4-yl)-5-oxo-5H-pyrrolo[3,4-b]pyridin-6(7H)-yl)propanoate (Preparation 415, 910 mg, 1.920 mmol) in dichloromethane (9 mL) was treated with TFA (8 mL) and the mixture was stirred at room temperature for 2 h. The solution was concentrated in vacuo and residual TFA removed by co-evaporation with toluene (3×20 mL). The residue was triturated with diethyl ether (20 mL) and the solid collected by filtration, washed with diethyl ether (10 mL) and dried under suction to afford the title compound (588 mg, 68.9%) as a yellow solid. The filtrate was concentrated in vacuo and then evaporated from diethyl ether (3 mL) to afford a second batch of the title compound (209 mg, 24.75%) as a yellow solid. LCMS: [M+H]+=418.

Preparation 417: (R)-2-(6-(5-chloro-2-((2-methyl-2H-1,2,3-triazol-4-yl)amino)pyrimidin-4-yl)-1-oxoisoindolin-2-yl)propanoic acid

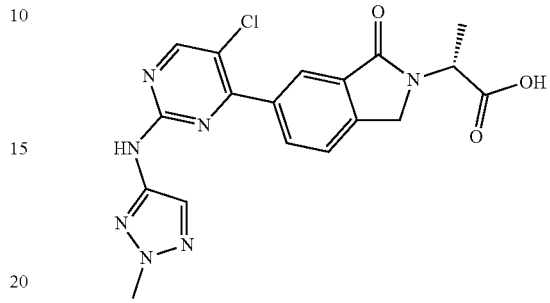

A solution of (R)-2-(6-(2,5-dichloropyrimidin-4-yl)-1-oxoisoindolin-2-yl)propanoic acid (Preparation 349) (2 g, 4.77 mmol) and 2-methyl-2H-1,2,3-triazol-4-amine hydrobromide (0.939 g, 5.25 mmol) in dry DMF (25 ml) was treated with cesium carbonate (3.26 g, 10.02 mmol) and the suspension sonicated for 15 minutes to form a finely divided suspension. The suspension was degassed for 3 minutes by passing a stream of nitrogen through the mixture. t-BuBrettPhos Allyl (Pd-175) (0.186 g, 0.239 mmol) was added and the suspension stirred at 70° C. for 1 h. Diethyl ether (70 ml) was added to the cooled reaction mixture and the resulting solid was collected by filtration. The filtrate was discarded and the solid dissolved in water (100 ml). The solution was treated with 1M HCl until pH 1 and the mixture was extracted with 2-methyl THF ((2×150 ml). The organic extract was dried (MgSO₄), filtered and absorbed on silica. The crude product was purified by chromatography (SiO₂, 40 g column, 40-80% 2-methyl THF in isohexane) to afford the title compound (1.6 g, 72.1%) as a yellow solid. LCMS: [M+H]+=414.

Preparation 418: (1R)-1-[6-(4-Methylpiperazin-1-yl)pyridin-2-yl]ethan-1-amine

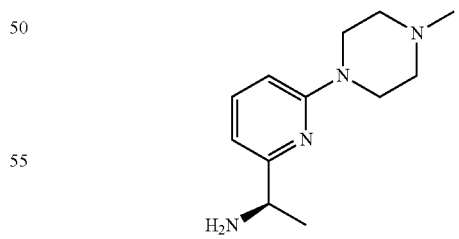

A solution of (1R)-1-(6-fluoropyridin-2-yl)ethan-1-amine hydrochloride (1.0 g, 5.6 mmol) in N-methyl-piperazine (6.0 mL, 54 mmol) was heated at 100° C. for 16 h. The reaction mixture was cooled, 1M Na₂CO₃ (30 mL) was added and the product was extracted with CHCl₃/2-propanol (9:1, 2×30 mL). The combined organic phases were dried, filtered and concentrated to dryness to afford the title compound as a brown oil (1.23 g, 99%). MS: [M+H]+=221. 1H NMR (400

MHz, DMSO-d6): 7.46 (1H, dd), 6.71-6.56 (2H, m), 3.79 (1H, q), 3.46 (4H, t), 2.39 (4H, t), 2.21 (3H, s), 1.79 (2H, s), 1.24 (3H, d).

Preparation 419: 6-(2,5-Dichloropyrimidin-4-yl)-2-{2-[(1-hydroxy-2-phenylpropan-2-yl)amino]ethyl}-2,3-dihydro-1H-isoindol-1-one A. 2-[(2-Aminoethyl)amino]-2-phenylpropan-1-ol

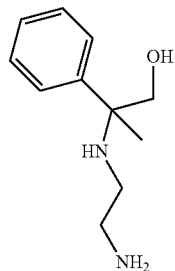

To 2-amino-2-phenylpropan-1-ol (100 mg, 0.66 mmol) in CHCl₃ (2.2 mL) was added tert-butyl n-(2-oxoethyl)carbamate (134 mg, 0.76 mmol) and then sodium triacetoxyborohydride (217 mg, 0.99 mmol), at room temperature under nitrogen. The mixture was stirred for 16 hours. The reaction was quenched with NaHCO₃ (sat., aq.) and the product extracted with CHCl₃ (×3). The combined organic layers were washed with water, brine and dried over MgSO₄. The product was filtered and evaporated to dryness. The product was purified by biotage (0-100% EtOAc in petrol). To the residue was added HCl in EtOAc (sat.). The mixture rewash stirred for 2 hours and evaporated to dryness, and again from MeOH to yield a light brown foam (81 mg, 42%). ¹H NMR (Me-d3-OD): 7.66 (2H, d), 7.59-7.44 (3H, m), 4.17 (1H, d), 3.88 (1H, d), 3.31 (2H, d), 3.20-3.02 (2H, m), 1.84 (3H, s). LC-MS: [M+H]⁺=195.

B. 6-(2,5-Dichloropyrimidin-4-yl)-2-{2-[(1-hydroxy-2-phenylpropan-2-yl)amino]ethyl}-2,3-dihydro-1H-isoindol-1-one

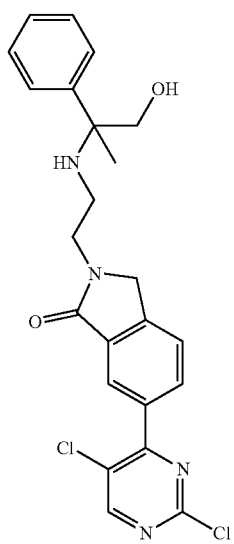 [SMILES: CC(CO)(NCCN1Cc2ccc(-c3nc(Cl)ncc3Cl)cc2C1=O)c1ccccc1]

Methyl 2-(bromomethyl)-5-(2,5-dichloropyrimidin-4-yl) benzoate (Preparation 180) (52 mg, 0.14 mmol) and 2-[(2-aminoethyl)amino]-2-phenylpropan-1-ol (38 mg, 0.17 mmol) and DIPEA (53 µL, 0.31 mmol) in THF (0.5 mL) was stirred at room temperature for 24 hours. The sample was concentrated and purified by preparative HPLC to yield the product as a colourless oil (10 mg, 16%). ¹H NMR (Me-d3-OD): 8.86 (1H, s), 8.33 (1H, d), 8.16 (1H, dd), 7.76 (1H, d), 7.41-7.37 (2H, m), 7.23-7.17 (3H, m), 4.63 (1H, d), 4.58-4.50 (1H, m), 3.83-3.72 (2H, m), 3.68-3.59 (2H, m), 2.89-2.79 (1H, m), 2.72-2.62 (1H, m), 1.52 (3H, s). LC-MS: [M+H]⁺=457.

Preparation 420: (R)-2-(6-bromo-1-oxoisoindolin-2-yl)propanoic acid

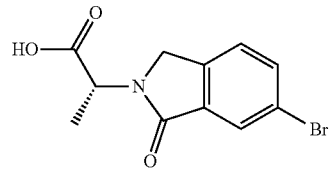 [SMILES: C[C@H](C(=O)O)N1Cc2ccc(Br)cc2C1=O]

A stirred solution of (R)-tert-butyl 2-(6-bromo-1-oxoisoindolin-2-yl)propanoate (61.7 mmol) in DCM (100 mL) was treated with TFA (75 mL, 973 mmol) and stirred at room temperature for 2 h. The mixture was concentrated and the residue was evaporated with toluene (3×100 mL), then triturated with diethyl ether, filtered and dried in vacuo at 50° C. overnight to afford the title compound (16.22 g, 92%) as an off-white solid. LCMS: [M+H]⁺=284.

Preparation 421: (R)-2-(6-bromo-1-oxoisoindolin-2-yl)-N—((S)-1-(3-fluoro-5-methoxyphenyl)-2-hydroxyethyl)propanamide

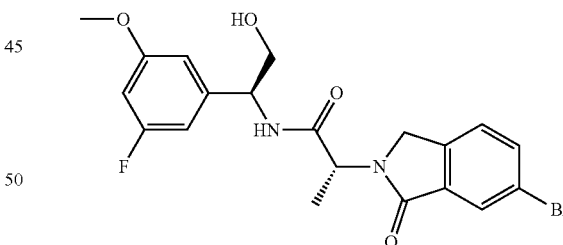

A stirred solution of (S)-2-amino-2-(3-fluoro-5-methoxyphenyl)ethanol hydrochloride (1.716 g, 7.74 mmol), (R)-2-(6-bromo-1-oxoisoindolin-2-yl)propanoic acid (2 g, 7.04 mmol) and triethylamine (3.92 ml, 28.2 mmol) in DMF (10 ml) was treated with TBTU (2.373 g, 7.39 mmol) and stirred at room temperature for 1.5 h. Saturated aqueous NH₄Cl (100 mL) was added and the resulting precipitate was filtered, washed with water, then dried in a vacuum oven at 40° C. overnight to give a light brown solid (2.94 g). The crude product was purified by chromatography (SiO₂, 0-10% (1% NH3 MeOH) in DCM) to afford the tile compound (2.6 g, 80%) as a cream coloured foam. LCMS: [M+H]⁺=451.

Preparation 422: (R)—N—((S)-1-(3-fluoro-5-methoxyphenyl)-2-hydroxyethyl)-2-(1-oxo-6-(4,4,5,5-tetramethyl-1,3,2-dioxaborolan-2-yl)isoindolin-2-yl)propanamide

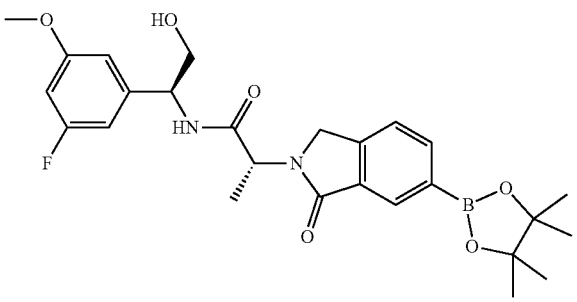

A mixture of (R)-2-(6-bromo-1-oxoisoindolin-2-yl)-N—((S)-1-(3-fluoro-5-methoxyphenyl)-2-hydroxyethyl)propanamide (2.6 g, 5.76 mmol), bis(pinacolato)diboron (2.195 g, 8.64 mmol), potassium acetate (1.696 g, 17.28 mmol) and XPhos G3 (0.244 g, 0.288 mmol) was evacuated and back-filled with nitrogen (×3). 1,4-dioxane (11.52 ml, 5.76 mmol) was added and the system evacuated and back-filled with nitrogen (×3). The mixture was heated to 90° C. and stirred for 1.5 h. The reaction mixture was allowed to cool, diluted with EtOAc (50 mL), then filtered through a bed of celite, washing with EtOAc (100 mL). The mixture was concentrated to give the crude product as a dark brown gum. The crude product was purified by chromatography (SiO$_2$, 0-10% MeOH in DCM) to afford the title compound (1.52 g, 47.5%) as a white solid. LCMS: [M+H]$^+$=499.

Preparation 423: (R)-2-(6-bromo-1-oxoisoindolin-2-yl)-N—((S)-1-(6-(dimethylamino)pyridin-2-yl)-2-hydroxyethyl)propanamide

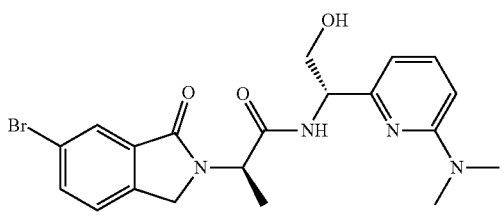 [SMILES: C[C@H](C(=O)N[C@H](CO)c1cccc(N(C)C)n1)N1Cc2ccc(Br)cc2C1=O]

TBTU (0.831 g, 2.59 mmol) was added to a mixture of (S)-2-amino-2-(6-(dimethylamino)pyridin-2-yl)ethanol (0.491 g, 2.71 mmol), (R)-2-(6-bromo-1-oxoisoindolin-2-yl)propanoic acid (0.7 g, 2.464 mmol) and triethylamine (1.374 ml, 9.86 mmol) in DMF (12.32 ml, 2.464 mmol) and the mixture was stirred overnight at room temperature. Water (100 mL) was added and the resulting precipitate was filtered, washed with water, dried under reduced pressure, then in a vacuum oven overnight. The crude product was triturated with Et$_2$O, filtered and dried to afford the title compound (844 mg, 75%) as a pale brown solid. LCMS: [M+H]$^+$=447.

Preparation 424: (R)—N—((S)-1-(6-(dimethylamino)pyridin-2-yl)-2-hydroxyethyl)-2-(1-oxo-6-(4,4,5,5-tetramethyl-1,3,2-dioxaborolan-2-yl)isoindolin-2-yl)propanamide

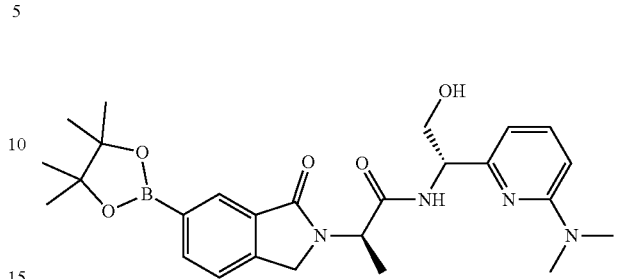

A mixture of (R)-2-(6-bromo-1-oxoisoindolin-2-yl)-N—((S)-1-(6-(dimethylamino)pyridin-2-yl)-2-hydroxyethyl) propanamide (0.800 g, 1.788 mmol bis(pinacolato)diboron (0.681 g, 2.68 mmol), potassium acetate (0.527 g, 5.37 mmol) and XPhos Pd G3 (0.076 g, 0.089 mmol) was evacuated and back-filled with nitrogen (×3). 1,4-dioxane (3.58 ml, 1.788 mmol) was added and the system evacuated and back-filled with nitrogen (×3). The mixture was heated to 90° C. and stirred for 1.5 h, then left to stand at room temperature overnight. The reaction mixture was diluted with EtOAc (50 mL), filtered through celite washing with EtOAc (100 mL). The filtrate was concentrated to give a dark brown gum. The crude product was triturated with diisopropyl ether (50 mL), sonicated and left to stir to give a light brown solid which was collected by filtration and dried in a vacuum oven at 40° C. to give the title compound (763 mg, 82%). LCMS: [M+H]$^+$=495.

Preparation 425: 5-chloro-2-((2-methoxypyridin-4-yl)amino)pyrimidin-4-ol

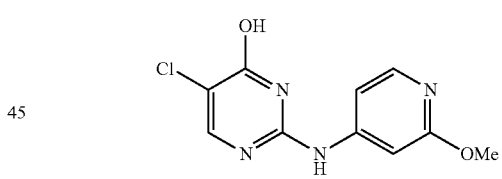

Cs$_2$CO$_3$ (1.775 g, 5.45 mmol) was added to a solution of 2,5-dichloropyrimidin-4-ol (0.428 g, 2.59 mmol) and 2-methoxypyridin-4-amine (0.354 g, 2.85 mmol) in DMF (8 mL, 103 mmol). The mixture was degassed (3× with nitrogen) then [Pd(allyl)tBuBrettPhos)]OTf (Pd-175) (0.071 g, 0.091 mmol) was added. The reaction was further degassed then placed under nitrogen and heated to 90° C. for 3 h. The mixture was allowed to cool to room temperature and Et$_2$O (30 mL) was added. The resulting yellow-brown solid was collected by filtration and washed with Et$_2$O (15 mL). The filtrate was concentrated in vacuo then combined with the solid and suspended in DCM (20 mL). 4M HCl in dioxane (4.5 mL) was added whilst stirring then the mixture stirred before collecting the pale brown solid by filtration in vacuo. The solid was washed with DCM (15 mL) then air dried to afford the crude title compound (2.48 g). The product, which contained a mixture of cesium salts, was used without further purification in the next step. LCMS: [M+H]$^+$=253.

Preparation 426: 4,5-dichloro-N-(2-methoxypyridin-4-yl)pyrimidin-2-amine

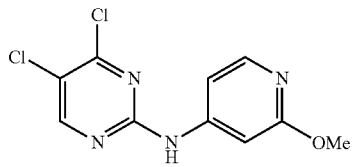 [SMILES: COc1cc(Nc2ncc(Cl)c(Cl)n2)ccn1]

POCl₃ (0.966 ml, 10.36 mmol) was added to a stirred suspension of 5-chloro-2-((2-methoxypyridin-4-yl)amino)pyrimidin-4-ol (654 mg, 2.59 mmol) in toluene (10 ml, 94 mmol) and the mixture was heated to 90° C. for 2.5 h. An additional 0.75 mL of POCl₃ was added then stirring continued at 90° C. for 4 h. The mixture was allowed to cool to ambient temperature then an additional 0.5 mL of POCl₃ was added and heating at 90° C. continued for 3 h. A further portion POCl₃ (0.5 mL) was added and heating at 90° C. was continued for 3 hour. The mixture was concentrated in vacuo and the residue was azeotroped with toluene (3×5 mL) then suspended in water (45 mL) and basified to pH=14 with 2M NaOH (aq). The yellow solid was collected by filtration then washed with water (20 mL), air dried overnight then in a dessicator to afford the title compound (277 mg, 33%). The product was used without further purification in the next step. LCMS: [M+H]⁺=271.

Preparation 427: 5-chloro-2-((2-methylpyrimidin-4-yl)amino)pyrimidin-4-ol

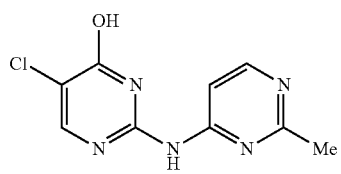 [SMILES: Cc1nccc(Nc2ncc(Cl)c(O)n2)n1]

Cs₂CO₃ (27.0 g, 83 mmol) was added to a solution of 2,5-dichloropyrimidin-4-ol (6.5 g, 39.4 mmol) and 2-methylpyrimidin-4-amine (4.51 g, 41.4 mmol) in DMF (100 mL, 1291 mmol). The mixture was degassed (3× with nitrogen) then [Pd(allyl)tBuBrettPhos)]OTf (Pd-175) (0.646 g, 0.827 mmol) was added. The reaction was further degassed then placed under nitrogen and heated to 95° C. for 3 h, then at room temperature overnight. Et₂O (300 mL) was added and the resulting pale yellow solid collected by filtration and washed with Et₂O (150 mL). The solid was suspended in DCM (100 mL) and 4M HCl in dioxane (60 mL) was added in portions (pH=1). The pale yellow solid was collected by filtration and washed with DCM (50 mL) then dried in vacuo to afford the title compound (38.66 g). The product, which contained a mixture of cesium salts, was used without further purification in the next step. LCMS: [M+H]⁺=238.

Preparation 428: 4,5-dichloro-N-(2-methylpyrimidin-4-yl)pyrimidin-2-amine

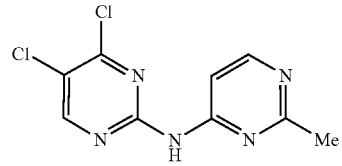 [SMILES: Cc1nccc(Nc2ncc(Cl)c(Cl)n2)n1]

POCl₃ (14.69 mL, 158 mmol) was added to a stirred suspension of 5-chloro-2-((2-methylpyrimidin-4-yl)amino)pyrimidin-4-ol (9.36 g, 39.4 mmol) in toluene (150 mL, 1408 mmol). The reaction was heated to 90° C. for 130 minutes then the solvents were removed in vacuo. The residue was azeotroped with toluene (3×75 mL) then suspended in water (300 mL). The stirred suspension was basified to pH=14 with 2M NaOH (aq, 100 mL) then diluted with water (100 mL). The resulting pale yellow solid was collected by filtration in vacuo then washed with water (100 mL then 50 mL). The solid was transferred to a flask using MeCN (100 mL) and toluene (75 mL) then concentrated in vacuo. The yellow solid was then azeotroped with toluene (2×75 mL) to afford the title compound (7.7 g, 73%). LCMS: [M+H]⁺=256.

Preparation 429: (R)-2-(6-(5-chloro-2-((2-methoxypyridin-4-yl)amino)pyrimidin-4-yl)-1-oxoisoindolin-2-yl)propanoic acid

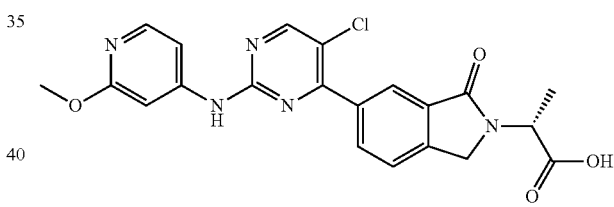

A 250 mL round bottom flask was charged with (R)-2-(6-(2,5-dichloropyrimidin-4-yl)-1-oxoisoindolin-2-yl)propanoic acid (4.85 g, 13.50 mmol), 2-methoxypyridin-4-amine (2.51 g, 20.25 mmol), cesium carbonate (9.24 g, 28.4 mmol), and Xantphos (0.391 g, 0.675 mmol). The system was evacuated and back-filled with nitrogen (×3) and DMF (90 ml, 13.50 mmol) was added. The mixture was once again evacuated and back-filled with nitrogen (×3) then heated to 75° C. and stirred for 15 minutes, before addition of palladium(II) acetate (0.152 g, 0.675 mmol) in a single portion. The mixture was stirred at 75° C. for 110 minutes, then cooled with an ice bath and poured onto Et₂O (400 mL). The resulting precipitate was collected by filtration and washed with further portions of Et₂O (2×100 mL) then dried to give the crude material as a light brown solid. The crude product was dissolved in DCM containing 5% AcOH in MeOH, absorbed on silica and purified by chromatography (SiO₂, 3-10% (5% (AcOH in 10% MeOH/DCM) in DCM) to afford the product as a cream solid. The solid was triturated with Et₂O, filtered and washed with further portions of Et₂O (3×50 mL). The solid was then collected and azeotroped with toluene (3×40 mL). Further trituration with Et₂O afforded the title compound (4.744 g, 79%) as a white solid. LCMS: [M+H]⁺=440.

EXAMPLES

Compounds of Formula (1)

Example 1: 2-(6-{5-chloro-2-[(oxan-4-yl)amino]pyrimidin-4-yl}-1-oxo-2,3-dihydro-1H-isoindol-2-yl)acetic acid

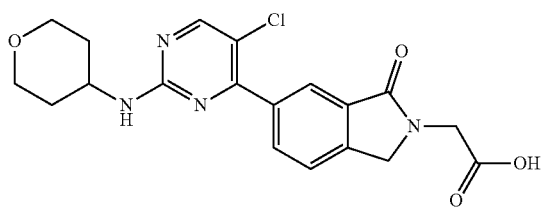 [SMILES: O=C(O)CN1Cc2ccc(-c3nc(NC4CCOCC4)ncc3Cl)cc2C1=O]

Method A:

TFA (75 mL, 954 mmol) was added to a stirred solution of tert-Butyl 2-(6-{5-chloro-2-[(oxan-4-yl)amino]pyrimidin-4-yl}-1-oxo-2,3-dihydro-1H-isoindol-2-yl) acetate (Preparation 4) (8.9 g, 19.39 mmol) in DCM (150 mL) and the reaction was stirred at room temperature overnight. The mixture was concentrated under vacuum and the residue was azeotroped with toluene (3×150 mL) then triturated with diethyl ether. The resulting precipitate was filtered and dried to afford the title compound (7.49 g, 18.41 mmol, 95%) as a colourless solid. 1H NMR (400 MHz, Me-$d_3$-OD): 8.35 (1H, s), 8.23 (1H, d), 8.06 (1H, dd), 7.71 (1H, dd), 4.70 (2H, s), 4.32 (2H, s), 4.11-4.02 (1H, m), 4.02-3.95 (2H, m), 3.55 (2H, td), 2.05-1.98 (2H, m), 1.70-1.57 (2H, m). LC-MS: [M+H]$^+$=403.

Method B:

tert-Butyl 2-(6-{5-chloro-2-[(oxan-4-yl)amino]pyrimidin-4-yl}-1-oxo-2,3-dihydro-1H-isoindol-2-yl)acetate (Preparation 4) (1.2 g) was taken up in EtOAc saturated in HCl (5 mL) sealed with a stopper and stirred for 2 hours at room temperature. Ethyl ester was present by trans-esterification, as well as desired product. The reaction was evaporated under vacuum and taken up in THF/MeOH/water (5:1:1, 2 mL) and NaOH (1 M, 0.5 ml) was added. The mixture was stirred at room temperature for 24 hours, diluted with water, and the pH adjusted to ~pH 4-5 with citric acid (5%, aq.). The mixture was extracted with CHCl$_3$:

IPA (3:1, ×3) and the combined organic layers washed with brine, dried over MgSO, filtered and concentrated under vacuum to yield the product which was used crude for further reactions. Purification of a portion (~60 mg) by preparative HPLC gave the title compound (16 mg, 25%) as a colourless solid. 1H NMR (400 MHz, Me-$d_3$-OD): 8.35 (1H, s), 8.23 (1H, d), 8.06 (1H, dd), 7.71 (1H, dd), 4.70 (2H, s), 4.32 (2H, s), 4.11-4.02 (1H, m), 4.02-3.95 (2H, m), 3.55 (2H, dt), 2.05-1.98 (2H, m), 1.70-1.57 (2H, m).

Example 2: N-tert-butyl-2-(6-{5-chloro-2-[(oxan-4-yl)amino]pyrimidin-4-yl}-1-oxo-2,3-dihydro-1H-isoindol-2-yl)-N-methylacetamide

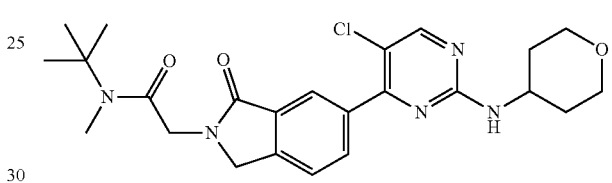

Triethylamine (0.071 mL, 0.51 mmol) was added to a solution of 2-(6-{5-chloro-2-[(oxan-4-yl)amino]pyrimidin-4-yl}-1-oxo-2,3-dihydro-1H-isoindol-2-yl)acetic acid (Example 1, 70 mg, 0.17 mmol), N-tert-butyl-methylamine (0.021 mL, 0.17 mmol) and HATU (71 mg, 0.19 mmol) in DCM (2.7 mL) and DMF (0.3 mL). The mixture was stirred at RT for 18 h. The reaction was diluted with water (10 mL) and extracted with ethyl acetate (3×10 mL). The combined organic phases were washed with brine (3×20 mL), dried (MgSO$_4$) and concentrated. Purification by chromatography (SiO$_2$, 0-5% methanol in EtOAc) gave the title compound (46 mg, 56%) as a colourless solid. 1H NMR (400 MHz, DMSO-d6) 8.45 (1H, s), 8.03-8.02 (1H, m), 7.97 (1H, dd), 7.74 (1H, d), 7.62 (1H, br. s), 4.53 (2H, s), 4.39 (2H, s), 3.96-3.85 (3H, m), 3.40-3.34 (2H, m), 2.92 (3H, s), 1.84 (2H, br. d), 1.57-1.47 (2H, m), 1.35 (9H, s). LC-MS: [M+H]$^+$=472.

Examples 3-88

Prepared using an analogous procedure to Example 2, from 2-(6-{5-chloro-2-[(oxan-4-yl)amino]pyrimidin-4-yl}-1-oxo-2,3-dihydro-1H-isoindol-2-yl)acetic acid (Example 1) and the corresponding amine:

| Example | Structure | Name | ¹H NMR (400 MHz) | MS: [M + H]⁺ |
|---|---|---|---|---|
| 3 | 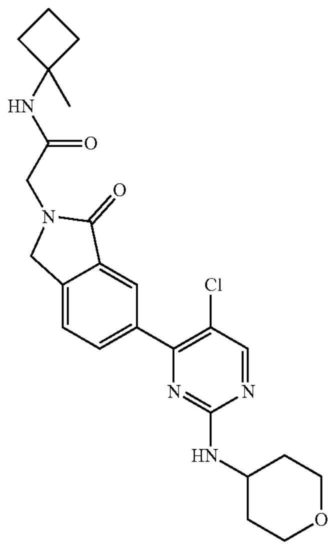 [SMILES: CC1(NC(=O)CN2Cc3ccc(-c4nc(NC5CCOCC5)ncc4Cl)cc3C2=O)CCC1] | 2-(6-{5-chloro-2-[(oxan-4-yl)amino]pyrimidin-4-yl}-1-oxo-2,3-dihydro-1H-isoindol-2-yl)-N-(1-methylcyclobutyl)-acetamide | (DMSO-d6) 8.45 (1H, s), 8.19 (1H, s), 8.03-8.02 (1H, m), 7.98 (1H, dd), 7.75 (1H, d), 7.63 (1H, br. s), 4.59 (2H, s), 4.14 (2H, s), 3.98-3.84 (3H, m), 3.41-3.35 (2H, m), 2.31-2.23 (2H, m), 1.92-1.72 (6H, m), 1.58-1.48 (2H, m), 1.38 (3H, s). | 470 |
| 4 | 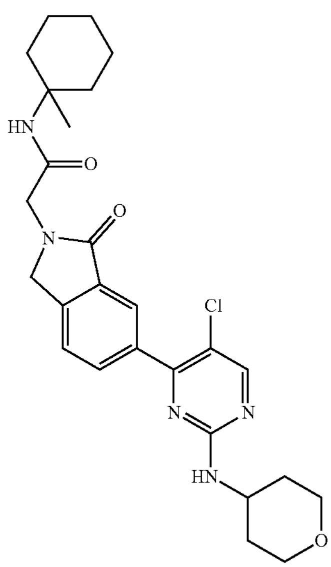 [SMILES: CC1(NC(=O)CN2Cc3ccc(-c4nc(NC5CCOCC5)ncc4Cl)cc3C2=O)CCCCC1] | 2-(6-{5-chloro-2-[(oxan-4-yl)amino]pyrimidin-4-yl}-1-oxo-2,3-dihydro-1H-isoindol-2-yl)-N-(1-methylcyclohexyl)-acetamide | (DMSO-d6) 8.45 (1H, s), 8.02-8.01 (1H, m), 7.97 (1H, dd), 7.74 (1H, d), 7.62 (1H, br. s), 7.50 (1H, s), 4.58 (2H, s), 4.18 (2H, s), 3.97-3.85 (3H, m), 3.41-3.34 (2H, m), 2.03-2.00 (2H, m), 1.86-1.83 (2H, m), 1.57-1.37 (7H, m), 1.31-1.20 (6H, m). | 498 |

| Example | Structure | Name | $^1$H NMR (400 MHz) | MS: [M + H]$^+$ |
|---|---|---|---|---|
| 5 | 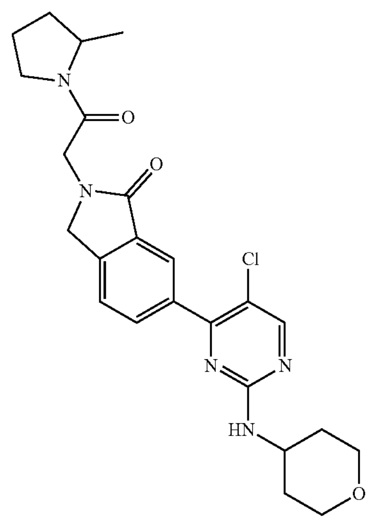 [SMILES: CC1CCCN1C(=O)CN1Cc2ccc(-c3nc(NC4CCOCC4)ncc3Cl)cc2C1=O] | 6-{5-chloro-2-[(oxan-4-yl)amino]pyrimidin-4-yl}-2-[2-(2-methylpyrrolidin-1-yl)-2-oxoethyl]-2,3-dihydro-1H-isoindol-1-one | (DMSO-d6, VT T = 373 K) 8.40 (1H, s), 8.10-8.07 (1H, m), 8.01 (1H, dd), 7.74-7.70 (1H, m), 7.13 (1H, d), 4.63 (2H, s), 4.37 (2H, s), 4.12 (1H, s), 4.05-3.94 (1H, m), 3.89 (2H, dt), 3.58-3.37 (4H, m), 1.99 (2H, s), 1.91 (3H, d), 1.68-1.50 (3H, m), 1.21 (3H, s). | 470 |
| 6 | 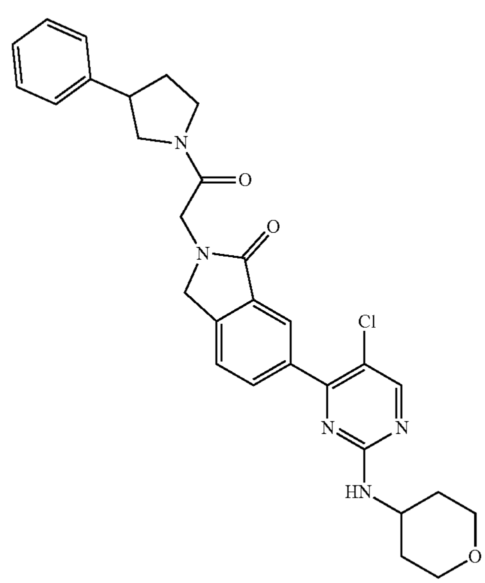 [SMILES: O=C(CN1Cc2ccc(-c3nc(NC4CCOCC4)ncc3Cl)cc2C1=O)N1CCC(c2ccccc2)C1] | 6-{5-chloro-2-[(oxan-4-yl)amino]pyrimidin-4-yl}-2-[2-oxo-2-(3-phenylpyrrolidin-1-yl)ethyl]-2,3-dihydro-1H-isoindol-1-one | (DMSO-d6) 8.46 (1H, s), 8.04 (1H, s), 7.99 (1H, dd), 7.76 (1H, d), 7.62 (1H, br. s), 7.37-7.32 (4H, m), 7.29-7.25 (1H, m), 4.61 (2H, d), 4.46 (2H, dd), 3.77-4.04 (4H, m), 3.64 (1H, m), 3.49 (1H, m), 3.38 (3H, m), 3.24 (1H, m), 2.21-2.40 (1H, m), 1.92-2.13 (1H, m), 1.84-1.87 (2H, m), 1.53 (2H, ddd). | 532 |

-continued

| Example | Structure | Name | ¹H NMR (400 MHz) | MS: [M + H]⁺ |
|---|---|---|---|---|
| 7 | 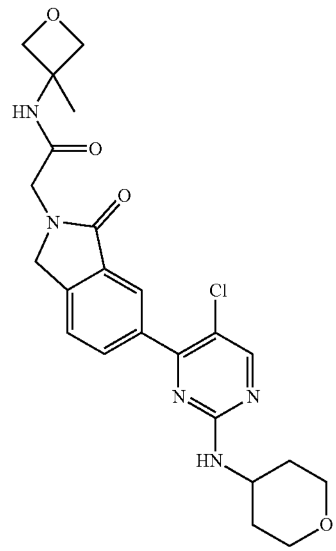 [SMILES: CC1(NC(=O)CN2Cc3ccc(-c4nc(NC5CCOCC5)ncc4Cl)cc3C2=O)COC1] | 2-(6-{5-chloro-2-[(oxan-4-yl)amino]pyrimidin-4-yl}-1-oxo-2,3-dihydro-1H-isoindol-2-yl)-N-(3-methyloxetan-3-yl)acetamide | (DMSO-d6) 8.60 (s, 1H), 8.44 (1H, s), 8.03 (1H, d), 7.98 (1H, dd), 7.75 (1H, d), 7.60 (1H, br. s), 4.61-4.59 (4H, m), 4.29 (2H, d), 4.19 (2H, s), 3.94-3.85 (3H, m), 3.40-3.37 (2H, m), 1.85 (2H, d), 1.57-1.47 (5H, m). | 472 |
| 8 | 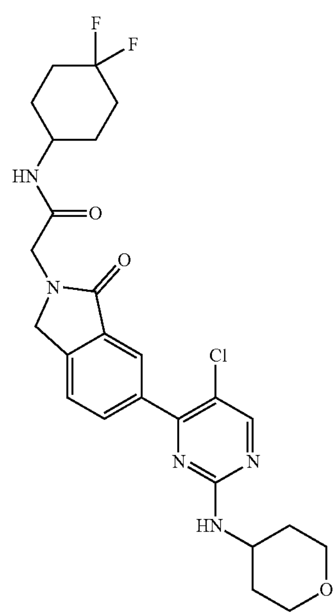 [SMILES: O=C(CN1Cc2ccc(-c3nc(NC4CCOCC4)ncc3Cl)cc2C1=O)NC1CCC(F)(F)CC1] | 2-(6-{5-chloro-2-[(oxan-4-yl)amino]pyrimidin-4-yl}-1-oxo-2,3-dihydro-1H-isoindol-2-yl)-N-(4,4-difluorocyclohexyl)-acetamide | (DMSO-d6) 8.44 (1H, s), 8 12 (1H, d), 8.02 (1H, s), 7.98 (1H, dd), 7.74 (1H, d), 7.60 (1H, br. s), 4.58 (2H, s), 4.19 (2H, s), 3.92-3.80 (4H, m), 3.17 (1H, d), 1.99-1.79 (9H, m), 1.57-1.47 (4H, m). | 520 |

| Example | Structure | Name | ¹H NMR (400 MHz) | MS: [M + H]⁺ |
|---|---|---|---|---|
| 9 | 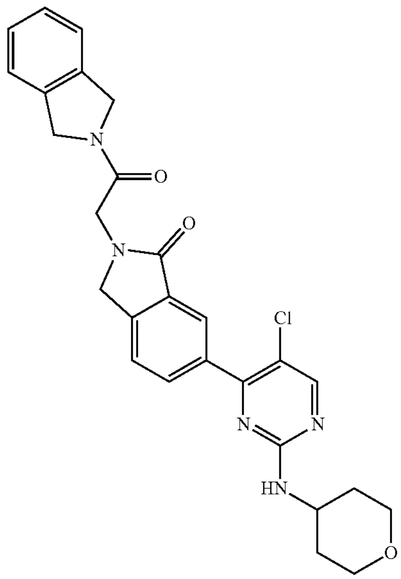 [SMILES: O=C(CN1Cc2ccc(-c3nc(NC4CCOCC4)ncc3Cl)cc2C1=O)N1Cc2ccccc2C1] | 6-{5-chloro-2-[(oxan-4-yl)amino]pyrimidin-4-yl}-2-[2-(2,3-dihydro-1H-isoindol-2-yl)-2-oxoethyl]-2,3-dihydro-1H-isoindol-1-one | (DMSO-d6) 8.45 (1H, s), 8.06-8.04 (1H, br. m), 7.99 (1H, dd), 7.77 (1H, d), 7.62 (1H, br. s), 7.40-7.37 (2H, m), 7.35-7.32 (2H, m), 4.97 (2H, s), 4.70 (2H, s), 4.62 (2H, s), 4.54 (2H, s), 3.97-3.90 (1H, m), 3.90-3.83 (2H, m), 3.38 (2H, t), 1.89-1.81 (2H, m), 1.58-1.48 (2H, m). | 504 |
| 10 | 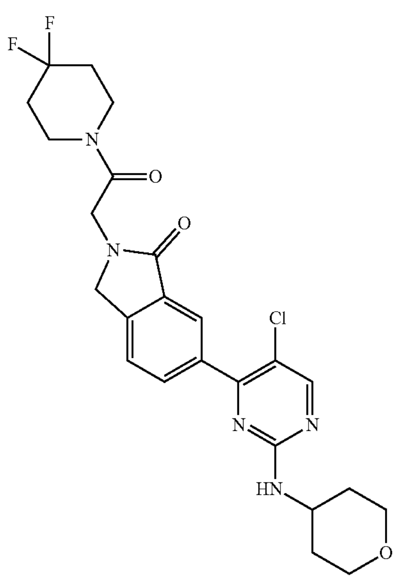 [SMILES: O=C(CN1Cc2ccc(-c3nc(NC4CCOCC4)ncc3Cl)cc2C1=O)N1CCC(F)(F)CC1] | 6-{5-chloro-2-[(oxan-4-yl)amino]pyrimidin-4-yl}-2-[2-(4,4-difluoropiperidin-1-yl)-2-oxoethyl]-2,3-dihydro-1H-isoindol-1-one | (DMSO-d6) 8.45 (1H, s), 8.04 (1H, d), 7.99 (1H, dd), 7.76 (1H, d), 7.61 (1H, br. s), 4.57 (2H, s), 4.55 (2H, s), 3.95-3.86 (3H, m), 3.63-3.58 (4H, m), 3.38-3.35 (2H, m), 2.16-1.84 (6H, m), 1.58-1.48 (2H, m). | 506 |

-continued

| Example | Structure | Name | ¹H NMR (400 MHz) | MS: [M + H]⁺ |
|---|---|---|---|---|
| 11 | 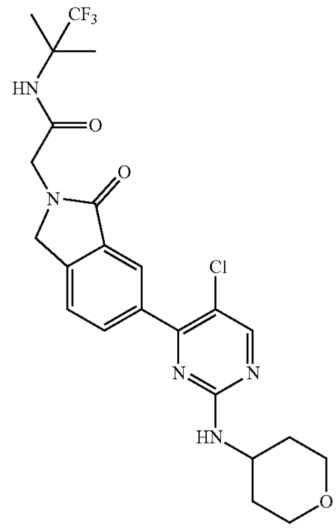 [SMILES: CC(C)(NC(=O)CN1Cc2ccc(-c3nc(NC4CCOCC4)ncc3Cl)cc2C1=O)C(F)(F)F] | 2-(6-{5-chloro-2-[(oxan-4-yl)amino]pyrimidin-4-yl}-1-oxo-2,3-dihydro-1H-isoindol-2-yl)-N-(1,1,1-trifluoro-2-methylpropan-2-yl)acetamide | (DMSO-d6) 8.44 (1H, s), 8.24 (1H, s), 8.02 (1H, t), 7.98 (1H, dd), 7.74 (1H, d), 7.61 (1H, s), 4.58 (2H, s), 4.24 (2H, s), 3.98-3.81 (3H, m), 3.42-3.33 (2H, m), 1.84 (2H, d), 1.57-1.47 (8H, m). | 512 |
| 12 | 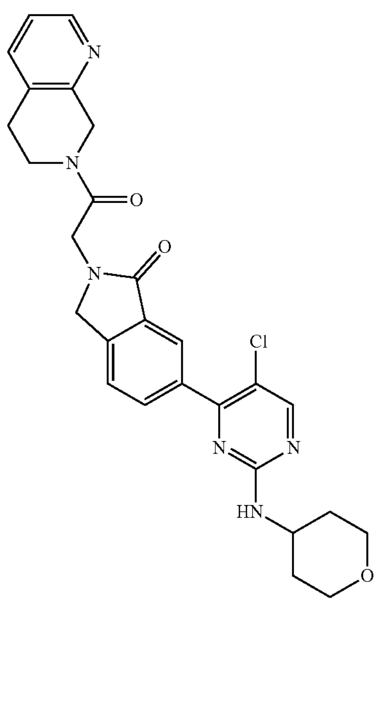 [SMILES: O=C(CN1Cc2ccc(-c3nc(NC4CCOCC4)ncc3Cl)cc2C1=O)N1CCc2cccnc2C1] | 6-{5-chloro-2-[(oxan-4-yl)amino]pyrimidin-4-yl}-2-[2-oxo-2-(5,6,7,8-tetrahydro-1,7-naphthyridin-7-yl)ethyl]-2,3-dihydro-1H-isoindol-1-one | (DMSO-d6) 8.48-8.37 (2H, m), 8.06-8.02 (1H, m), 7.99 (1H, dd), 7.76 (1H, d), 7.64 (2H, d), 7.30-7.20 (1H, m), 4.79 (1H, s), 4.68-4.55 (5H, m), 3.98-3.79 (4H, m), 3.76 (1H, t), 3.39 (2H, d), 2.97 (1H, t), 2.83 (1H, t), 1.85 (2H, d), 1.53 (2H, qd). | 519 |

| Example | Structure | Name | ¹H NMR (400 MHz) | MS: [M + H]⁺ |
|---|---|---|---|---|
| 13 | 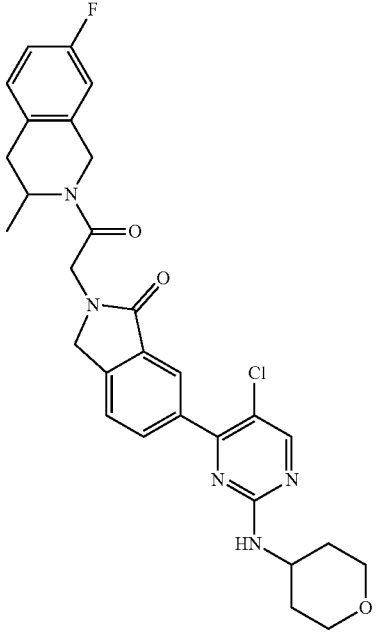 [SMILES: CC1Cc2ccc(F)cc2CN1C(=O)CN1Cc2ccc(-c3nc(NC4CCOCC4)ncc3Cl)cc2C1=O] | 6-{5-chloro-2-[(oxan-4-yl)amino]pyrimidin-4-yl}-2-[2-(7-fluoro-3-methyl-1,2,3,4-tetrahydroisoquinolin-2-yl)-2-oxoethyl]-2,3-dihydro-1H-isoindol-1-one | (DMSO-d6, 353 K) 8.41 (1H, s), 8.09-8.06 (1H, m), 8.00 (1H, dd), 7.73 (1H, dd), 7.28-7.20 (2H, m), 7.08 (1H, dd), 7.02 (1H, td), 4.91 (1H, d), 4.75-4.27 (6H, m), 3.96 (1H, ddt), 3.88 (2H, dt), 3.41 (2H, td), 2.69 (1H, d), 1.89 (2H, dd), 1.66-1.51 (2H, m), 1.10 (3H, d). | 550 |
| 14 | 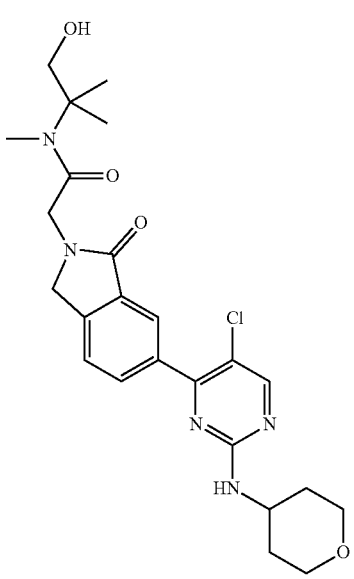 [SMILES: CN(C(=O)CN1Cc2ccc(-c3nc(NC4CCOCC4)ncc3Cl)cc2C1=O)C(C)(C)CO] | 2-(6-{5-chloro-2-[(oxan-4-yl)amino]pyrimidin-4-yl}-1-oxo-2,3-dihydro-1H-isoindol-2-yl)-N-(1-hydroxy-2-methylpropan-2-yl)-N-methylacetamide | (DMSO-d6) 8.45 (1H, s), 8.02 (1H, d), 7.97 (1H, dd), 7.74 (1H, d), 7.62 (1H, br. s), 4.77 (1H, t), 4.54 (2H, s), 4.40 (2H, s), 3.94-3.86 (3H, m), 3.56 (2H, d), 3.40-3.35 (2H, m), 2.96 (3H, s), 1.86-1.83 (2H, m), 1.57-1.47 (2H, m), 1.29 (6H, s). | 488 |

-continued

| Example | Structure | Name | ¹H NMR (400 MHz) | MS: [M + H]⁺ |
|---|---|---|---|---|
| 15 | 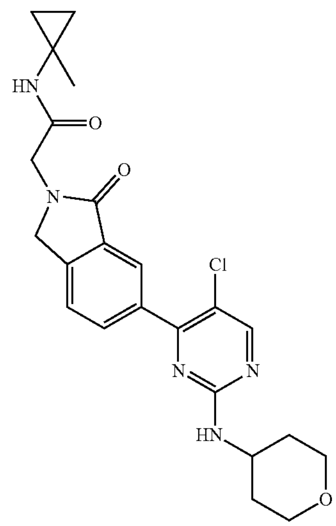 [SMILES: CC1(NC(=O)CN2Cc3ccc(-c4nc(NC5CCOCC5)ncc4Cl)cc3C2=O)CC1] | 2-(6-{5-chloro-2-[(oxan-4-yl)amino]pyrimidin-4-yl}-1-oxo-2,3-dihydro-1H-isoindol-2-yl)-N-(1-methylcyclopropyl)acetamide | (DMSO-d6) 8.45 (1H, s), 8.36 (1H, s), 8.02-8.01 (1H, br. m), 7.97 (1H, dd), 7.74 (1H, d), 7.62 (1H, br. s), 4.56 (2H, s), 4.09 (2H, s), 3.98-3.82 (3H, m), 3.37-3.40 (2H, m), 1.88-1.80 (2H, m), 1.57-1.47 (2H, m), 1.27 (3H, s), 0.64-0.61 (2H, m), 0.54-0.51 (2H, m). | 456 |
| 16 | 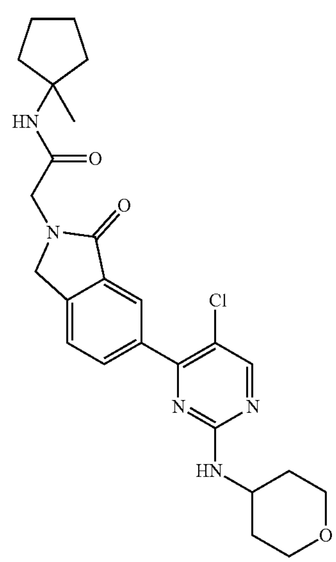 [SMILES: CC1(NC(=O)CN2Cc3ccc(-c4nc(NC5CCOCC5)ncc4Cl)cc3C2=O)CCCC1] | 2-(6-{5-chloro-2-[(oxan-4-yl)amino]pyrimidin-4-yl}-1-oxo-2,3-dihydro-1H-isoindol-2-yl)-N-(1-methylcyclopentyl)-acetamide | (DMSO-d6) 8.45 (1H, s), 8.02-8.01 (1H, m), 7.97 (1H, dd), 7.85 (1H, s), 7.74 (1H, d), 7.63 (1H, br. s), 4.58 (2H, s), 4.14 (2H, s), 3.97-3.85 (3H, m), 3.37 (2H, t), 2.00-1.92 (2H, m), 1.87-1.81 (2H, br. m), 1.70-1.46 (8H, m), 1.32 (3H, s). | 484 |

| Example | Structure | Name | ¹H NMR (400 MHz) | MS: [M + H]⁺ |
|---|---|---|---|---|
| 17 | 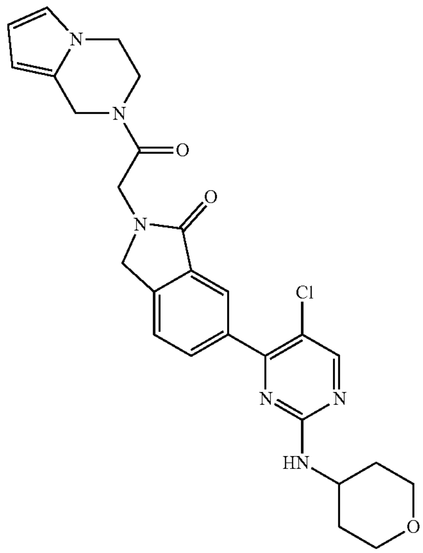 [SMILES: O=C(CN1Cc2ccc(-c3nc(NC4CCOCC4)ncc3Cl)cc2C1=O)N1CCn2cccc2C1] | 6-{5-chloro-2-[(oxan-4-yl)amino]pyrimidin-4-yl}-2-(2-oxo-2-{1H,2H,3H,4H-pyrrolo[1,2-a]pyrazin-2-yl}ethyl)-2,3-dihydro-1H-isoindol-1-one | (DMSO-d6) 8.46 (1H, s), 8.04 (1H, s), 7.99 (1H, dd), 7.76 (1H, d), 7.63 (1H, br. s), 6.72 (1H. m), 6.03 (1H, dt), 5.87 (1H, m), 4.80 (1H, s), 4.58-4.62 (5H, m), 4.10 (1H, m), 3.82-3.99 (6H, m), 3.34-3.41 (2H, m), 1.85 (2H, m), 1.53 (2H, ddd). | 507 |
| 18 | 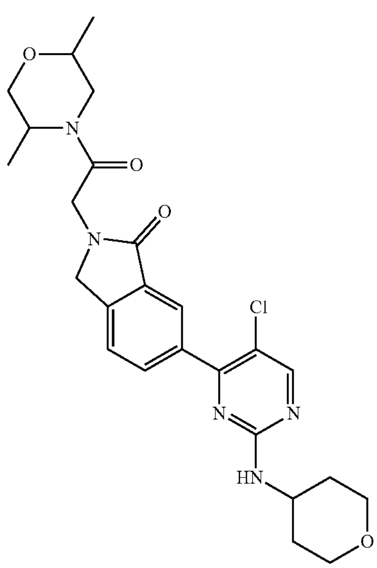 [SMILES: CC1CN(C(=O)CN2Cc3ccc(-c4nc(NC5CCOCC5)ncc4Cl)cc3C2=O)C(C)CO1] | 6-{5-chloro-2-[(oxan-4-yl)amino]pyrimidin-4-yl}-2-[2-(2,5-dimethylmorpholin-4-yl)-2-oxoethyl]-2,3-dihydro-1H-isoindol-1-one | (DMSO-d6, 373 K) 8.41 (1H, s), 8.08 (1H, d), 8.01 (1H, dd), 7.74 (1H, d), 7.27 (1H, d), 4.60 (2H, d), 4.49 (1H, d), 4.43 (1H, d), 4.18 (0.68H, m), 3.86-3.99 (5H, m), 3.61-3.69 (2H, m), 3.35-3.48 (4H, m), 1.89 (2H, m), 1.59 (2H, m), 1.15-1.28 (8H, m) (additional hydrogen count due to presence of rotamers and stereoisomers). | 500 |

| Example | Structure | Name | ¹H NMR (400 MHz) | MS: [M + H]⁺ |
|---|---|---|---|---|
| 19 | 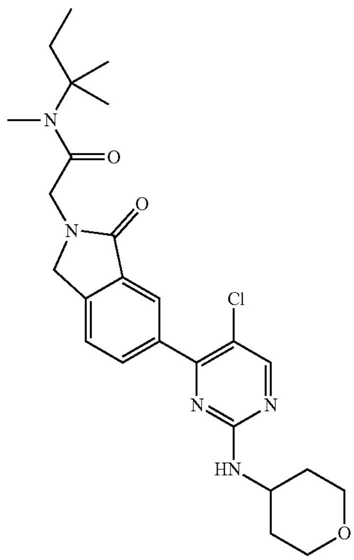 [SMILES: CCC(C)(C)N(C)C(=O)CN1Cc2ccc(-c3nc(NC4CCOCC4)ncc3Cl)cc2C1=O] | 2-(6-{5-chloro-2-[(oxan-4-yl)amino]pyrimidin-4-yl}-1-oxo-2,3-dihydro-1H-isoindol-2-yl)-N-methyl-N-(2-methylbutan-2-yl)acetamide | (DMSO-d6) 8.46 (1H, s), 8.03 (1H, s), 7.97 (1H, dd), 7.75 (1H, d), 7.63 (1H, br. s), 4.54 (2H, s), 4.43 (2H,s), 3.93 (1H, m), 3.87 (2H, m), 3.37-3.41 (2H, m), 2.93 (3H, s), 1.80-1.86 (4H, m), 1.53 (2H, ddd), 1.31 (6H, s), 0.76 (3H, t). | 486 |
| 20 | 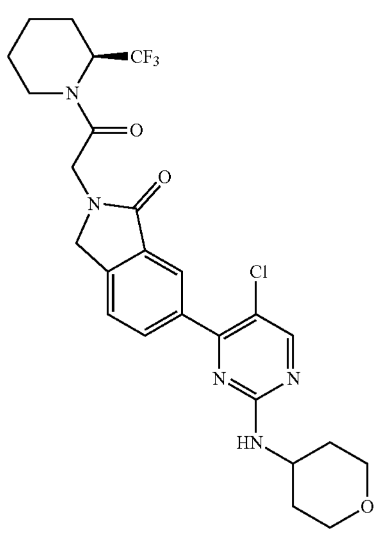 [SMILES: O=C1c2cc(-c3nc(NC4CCOCC4)ncc3Cl)ccc2CN1CC(=O)N1CCCC[C@H]1C(F)(F)F] | 6-{5-chloro-2-[(oxan-4-yl)amino]pyrimidin-4-yl}-2-{2-oxo-2-[(2S)-2-(trifluoromethyl)piperidin-1-yl]ethyl}-2,3-dihydro-1H-isoindol-1-one | (DMSO-d6) 8.45 (1H, s), 8.03 (1H, d), 7.98 (1H, dd), 7.75 (1H d), 7.62 (1H, s), 5.20-5.08 (0.75H, m, major rotamer), 4.98-4.84 (0.25H, m, minor rotamer). 4.77-4.32 (4H, m), 3.98-3.82 (4H, m), 3.42-3.34 (2H, m), 3.16 (0.75H, t, major rotamer), 2.66 (0.25H, t, minor rotamer), 2.04-1.43 (10H, m). | 538 |

-continued

| Example | Structure | Name | ¹H NMR (400 MHz) | MS: [M + H]⁺ |
|---|---|---|---|---|
| 21 | 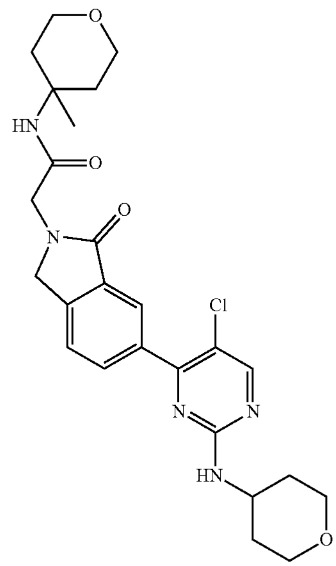 [SMILES: CC1(NC(=O)CN2Cc3ccc(-c4nc(NC5CCOCC5)ncc4Cl)cc3C2=O)CCOCC1] | 2-(6-{5-chloro-2-[(oxan-4-yl)amino]pyrimidin-4-yl}-1-oxo-2,3-dihydro-1H-isoindol-2-yl)-N-(4-methyloxan-4-yl)acetamide | (DMSO-d6) 8.45 (1H, s), 8.03 (1H, br. s), 7.98 (1H, dd), 7.75 (2H, m), 7.63 (1H, br. s), 4.60 (2H, s), 4.22 (2H, s), 3.83-3.98 (3H, m), 3.51-3.62 (4H, m), 3.35-3.41 (2H, m), 2.01-2.04 (2H, m), 1.81-1.88 (2H, m), 1.45-1.58 (4H, m), 1.31 (3H, s). | 500 |
| 22 | 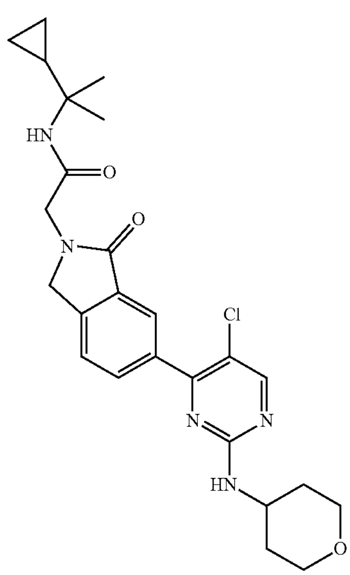 [SMILES: CC(C)(NC(=O)CN1Cc2ccc(-c3nc(NC4CCOCC4)ncc3Cl)cc2C1=O)C1CC1] | 2-(6-{5-chloro-2-[(oxan-4-yl)amino]pyrimidin-4-yl}-1-oxo-2,3-dihydro-1H-isoindol-2-yl)-N-(2-cyclopropylpropan-2-yl)acetamide | (DMSO-d6) 8.45 (1H, s), 8.03 (1H, dd), 7.98 (1H, dd), 7.74 (1H, dd), 7.67 (1H, s), 7.61 (1H, br. s), 4.59 (2H, s), 4.17 (2H, s), 3.99-3.79 (3H, m), 3.44-3.34 (2H, m), 1.85 (2H, d), 1.64-1.45 (2H, m), 1.30-1.22 (1H, m), 1.18 (6H, s), 0.33 (4H, ddt). | 484 |

-continued
| Example | Structure | Name | ¹H NMR (400 MHz) | MS: [M + H]⁺ |
|---|---|---|---|---|
| 23 | 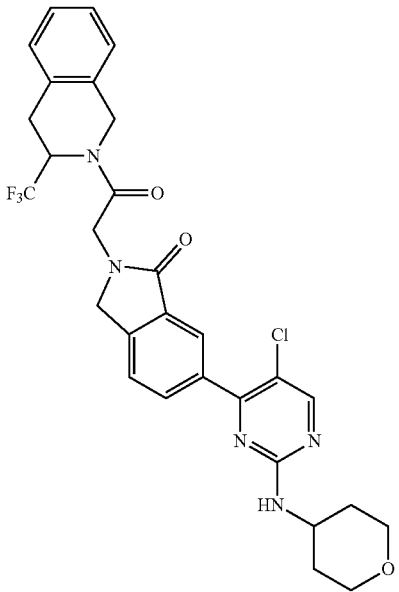 [SMILES: O=C1c2cc(-c3nc(NC4CCOCC4)ncc3Cl)ccc2CN1CC(=O)N1Cc2ccccc2CC1C(F)(F)F] | 6-{5-chloro-2-[(oxan-4-yl)amino]pyrimidin-4-yl}-2-{2-oxo-2-[3-(trifluoromethyl)-1,2,3,4-tetrahydro isoquinolin-2-yl]ethyl}-2,3-dihydro-1H-isoindol-1-one | (DMSO-d6) 8.46 (1H, s), 8.05 (1H, s), 8.00 (1H, dd), 7.77 (1H, d), 7.63 (1H, s), 7.34-7.19 (4H, m), 5.51-5.41 (0.6H, m), 5.49-5.32 (0.4H, m), 5.11-4.99 (1H, m), 4.84-4.52 (4.6H, m), 4.20 (0.4H, d), 4.00-3.81 (3H, m), 3.48-3.35 (2H, m), 3.30-3.05 (2H, m), 1.85 (2H, d), 1.53 (2H, qd). | 586 |
| 24 | 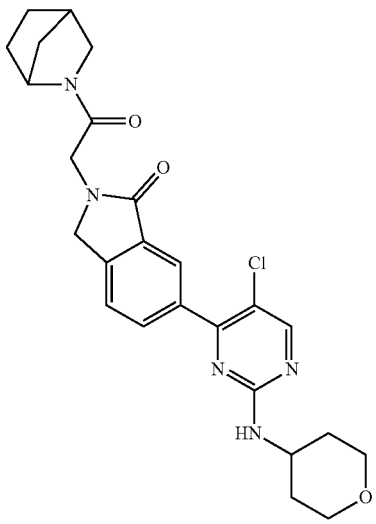 [SMILES: O=C1c2cc(-c3nc(NC4CCOCC4)ncc3Cl)ccc2CN1CC(=O)N1CC2CCC1C2] | 2-(2-{2-azabicyclo[2.2.1]heptan-2-yl}-2-oxoethyl)-6-{5-chloro-2-[(oxan-4-yl)amino] pyrimidin-4-yl}-2,3-dihydro-1H-isoindol-1-one | (DMSO-d6) 8.45 (1H, s), 8.02 (1H, s), 7.98 (1H, dd), 7.74 (1H, d), 7.61 (1H, br. s), 4.59-4.19 (5H, m), 3.97-3.83 (3H, m), 3.48-3.43 (0.5H, br. m), 3.40-3.35 (2H, m), 3.23-3.17 (1H, m), 3.01-2.98 (0.5H, m), 2.63-2.54 (1H, m), 1.86-1.83 (2H, m), 1.73-1.34 (8H, m). | 482 |

| Example | Structure | Name | ¹H NMR (400 MHz) | MS: [M + H]⁺ |
|---|---|---|---|---|
| 25 | 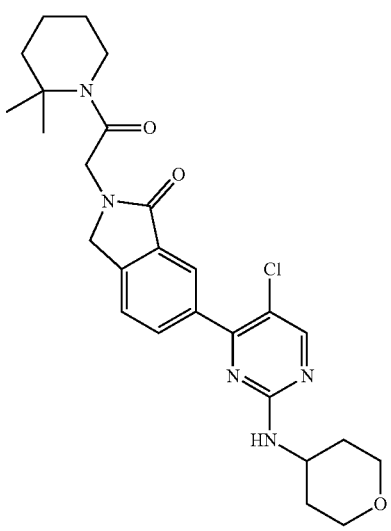 [SMILES: CC1(C)CCCCN1C(=O)CN1Cc2ccc(-c3nc(NC4CCOCC4)ncc3Cl)cc2C1=O] | 6-{5-chloro-2-[(oxan-4-yl)amino]pyrimidin-4-yl}-2-[2-(2,2-dimethylpiperidin-1-yl)-2-oxoethyl]-2,3-dihydro-1H-isoindol-1-one | (DMSO-d6) 8.46 (1H, s), 8.03 (1H, s), 7.98 (1H, dd), 7.75 (1H, d), 7.63 (1H, br. s), 4.53 (2H, s), 4.39 (2H, s), 3.90-3.97 (1H, m), 3.87 (2H, m), 3.34-3.41 (4H, m), 1.85 (2H, m), 1.48-1.67 (8H, m), 1.39 (6H, s). | 498 |
| 26 | 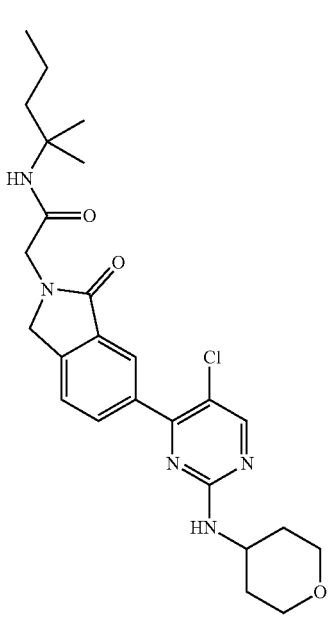 [SMILES: CCCC(C)(C)NC(=O)CN1Cc2ccc(-c3nc(NC4CCOCC4)ncc3Cl)cc2C1=O] | 2-(6-{5-chloro-2-[(oxan-4-yl)amino]pyrimidin-4-yl}-1-oxo-2,3-dihydro-1H-isoindol-2-yl)-N-(2-methylpentan-2-yl)acetamide | (DMSO-d6) 8.44 (1H, s), 8.01 (1H, d), 7.97 (1H, dd), 7.74 (1H, d), 7.63 (1H, s), 7.63 (1H, br. s), 4.58 (2H, s), 4.14 (2H, s), 3.89-3.97 (1H, m), 3.86 (2H, m), 3.35-3.40 (2H, m), 1.81-1.87 (2H, m), 1.47-1.61 (4H, m), 1.19-1.29 (2H, m), 1.22 (6H, s), 0.86 (3H, t). | 486 |

| Example | Structure | Name | ¹H NMR (400 MHz) | MS: [M + H]⁺ |
|---|---|---|---|---|
| 27 | 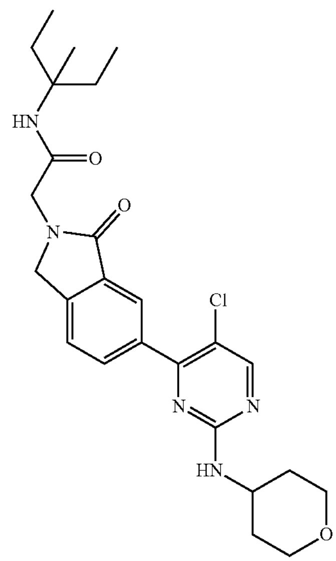 [SMILES: CCC(C)(CC)NC(=O)CN1Cc2ccc(-c3nc(NC4CCOCC4)ncc3Cl)cc2C1=O] | 2-(6-{5-chloro-2-[(oxan-4-yl)amino]pyrimidin-4-yl}-1-oxo-2,3-dihydro-1H-isoindol-2-yl)-N-(3-methylpentan-3-yl)acetamide | (DMSO-d6) 8.44 (1H, s), 0.01 (1H, d), 7.96 (1H, dd), 7.74 (1H, d), 7.61 (1H, br. s), 7.44 (1H, s), 4.58 (2H, s), 4.17 (2H, s), 3.89-3.97 (1H, m), 3.86 (2H, m), 3.34-3.40 (2H, m), 1.80-1.87 (2H, m), 1.75 (1H, qt), 1.72 (1H, qt), 1.46-1.57 (4H, m), 1.13 (3H, s), 0.78 (6H, t). | 486 |
| 28 | 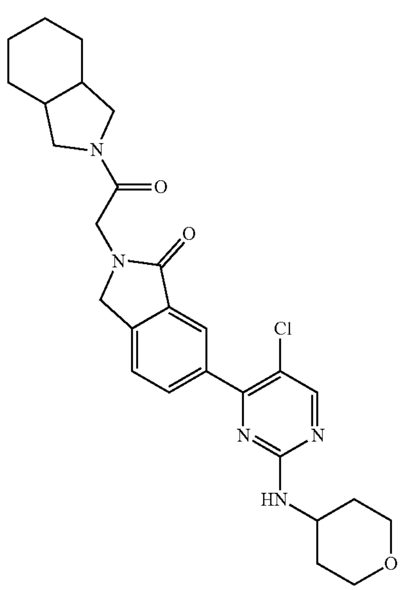 [SMILES: O=C(CN1Cc2ccc(-c3nc(NC4CCOCC4)ncc3Cl)cc2C1=O)N1CC2CCCCC2C1] | 6-{5-chloro-2-[(oxan-4-yl)amino]pyrimidin-4-yl}-2-[2-(octahydro-1H-isoindol-2-yl)-2-oxoethyl]-2,3-dihydro-1H-isoindol-1-one | (DMSO-d6) 8.45 (1H, br. s), 8.03 (1H, br. s), 7.99 (1H, dd), 7.75 (1H, d), 7.63 (1H, br. s), 4.58 (2H, s), 4.42 (1H, d), 4.35 (1H, d), 3.93 (1H, m), 3.87 (2H, m), 3.54 (1H, dd), 3.31-3.42 (4H, m), 3.22 (1H, dd), 2.30 (1H, m), 2.15 (1H, m), 1.85 (2H, m), 1.28-1.63 (10H, m). | 510 |

| Example | Structure | Name | ¹H NMR (400 MHz) | MS: [M + H]⁺ |
|---|---|---|---|---|
| 29 | 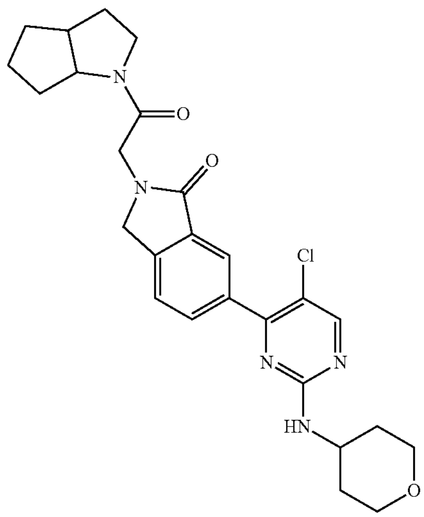 [SMILES: O=C1c2cc(-c3nc(NC4CCOCC4)ncc3Cl)ccc2CN1CC(=O)N1CCC2CCCC21] | 6-{5-chloro-2-[(oxan-4-yl)amino]pyrimidin-4-yl}-2-(2-{octahydro cyclopenta[b]pyrrol-1-yl}-2-oxoethyl)-2,3-dihydro-1H-isoindol-1-one | (DMSO-d6) 8.46 (1H, br. s), 8.03 (1H, br. s), 7.98 (1H, dd), 7.75 (1H, d), 7.63 (1H, br. s), 4.59 (2H, m), 4.32-4.52 (4H, m), 4.16 (0.75H, ddd), 3.93 (1H, m), 3.87 (2H, m), 3.62 (1.25H, m), 3.49 (0.75H, m), 3.31-3.40 (2H, m), 3.25 (0.75H, m), 2.80 (0.5H, m), 2.62 (0.75H, m), 2.12 (0.5H, m), 2.10 (0.75H, m), 1.36-1.90 (12H, m). (partial integrals due to the presence of rotamers). | 496 |
| 30 | 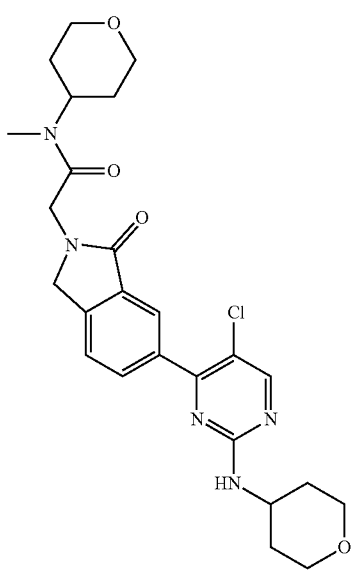 [SMILES: CN(C(=O)CN1Cc2ccc(-c3nc(NC4CCOCC4)ncc3Cl)cc2C1=O)C1CCOCC1] | 2-(6-{5-chloro-2-[(oxan-4-yl)amino]pyrimidin-4-yl}-1-oxo-2,3-dihydro-1H-isoindol-2-yl)-N-methyl-N-(oxan-4-yl)acetamide | (DMSO-d6, VT T = 350 K) 8.42 (1H, s), 8.07 (1H, d), 8.01 (1H, dd), 7.74 (1H, d), 7.28 (1H, br. d), 4.59 (2H, s), 4.49 (2H, br. s), 3.86-4.00 (5H, m), 3.38-3.44 (5H, m), 3.05 (3H, br. s), 1.89 (2H, m), 1.80 (2H, m), 1.50-1.64 (4H, m). | 500 |

| Example | Structure | Name | ¹H NMR (400 MHz) | MS: [M + H]⁺ |
|---|---|---|---|---|
| 31 | 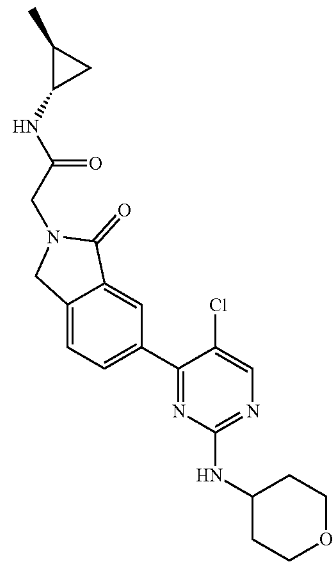 [SMILES: C[C@H]1C[C@@H]1NC(=O)CN1Cc2ccc(-c3nc(NC4CCOCC4)ncc3Cl)cc2C1=O] | 2-(6-{5-chloro-2-[(oxan-4-yl)amino]pyrimidin-4-yl}-1-oxo-2,3-dihydro-1H-isoindol-2-yl)-N-[(1R,2R)-2-methylcyclopropyl]-acetamide | (DMSO-d6, VT T = 350 K) 8.45 (1H, s), 8.18 (1H, d), 8.02 (1H, d), 7.98 (1H, dd), 7.74 (1H, d), 7.63 (1H, br. s), 4.58 (2H, s), 4.13 (2H, s), 3.93 (1H, m), 3.87 (2H, m), 3.39 (2H, m), 2.35 (1H, m), 1.85 (2H, m), 1.53 (2H, m), 1.00 (3H, d), 0.77-0.84 (1H, m), 0.58-0.63 (1H, m), 0.40-0.44 (1H, m). | 456 |
| 32 | 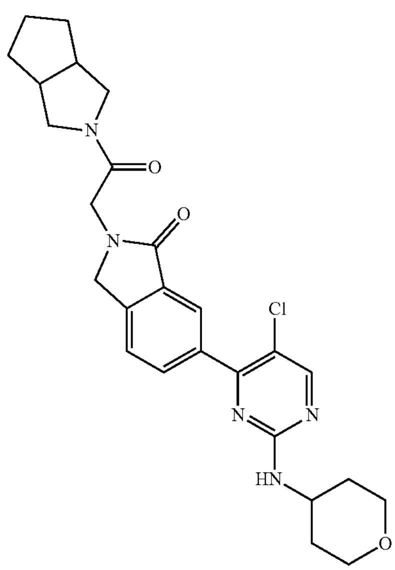 [SMILES: O=C(CN1Cc2ccc(-c3nc(NC4CCOCC4)ncc3Cl)cc2C1=O)N1CC2CCCC2C1] | 6-{5-chloro-2-[(oxan-4-yl)amino]pyrimidin-4-yl}-2-(2-{octahydrocyclopenta[c]pyrrol-2-yl}-2-oxoethyl)-2,3-dihydro-1H-isoindol-1-one | (DMSO-d6) 8.44 (1H, s), 8.02 (1H, d), 7.97 (1H, dd), 7.74 (1H, d), 7.62 (1H, br. s), 4.57 (2H, s), 4.36 (2H, s), 3.93-3.85 (3H, m), 3.72 (1H, dd), 3.55 (1H, dd), 3.41-3.34 (2H, m), 3.29 (1H, dd), 3.12 (1H, dd), 2.76-2.69 (1H, m), 2.63-2.56 (1H, m), 1.86-1.69 (5H, m), 1.60-1.37 (5H, m). | 496 |

| Example | Structure | Name | ¹H NMR (400 MHz) | MS: [M + H]⁺ |
|---|---|---|---|---|
| 33 | 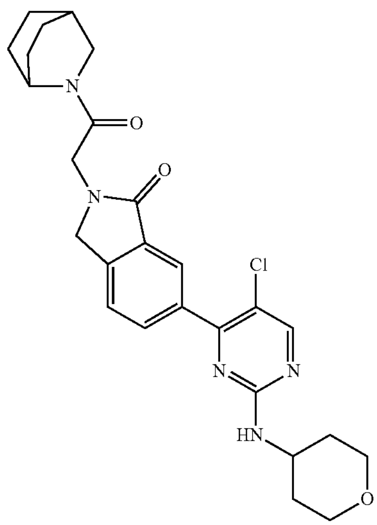 [SMILES: O=C1c2cc(-c3nc(NC4CCOCC4)ncc3Cl)ccc2CN1CC(=O)N1CC2CCC1CC2] | 2-(2-{2-azabicyclo[2.2.2]octan-2-yl}-2-oxoethyl)-6-{5-chloro-2-[(oxan-4-yl)amino]pyrimidin-4-yl}-2,3-dihydro-1H-isoindol-1-one | (DMSO-d6) 8.45 (1H, s), 8.03-8.02 (1H, m), 7.98 (1H, dd), 7.74 (1H, d), 7.62 (1H, br. s), 4.58 (2H, d), 4.39 (2H, d), 3.94-3.85 (3H, m), 3.55 (1H, d), 3.41-3.35 (2H, m), 3.27 (1H, d), 1.94-1.83 (4H, m), 1.72-1.47 (10H, m). | 496 |
| 34 | 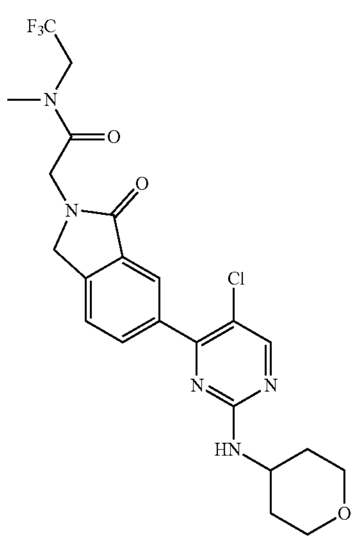 [SMILES: CN(CC(F)(F)F)C(=O)CN1Cc2ccc(-c3nc(NC4CCOCC4)ncc3Cl)cc2C1=O] | 2-(6-{5-chloro-2-[(oxan-4-yl)amino]pyrimidin-4-yl}-1-oxo-2,3-dihydro-1H-isoindol-2-yl)-N-methyl-N-(2,2,2-trifluoroethyl)-acetamide | (DMSO-d6) 8.45 (1H, s), 8.04-8.03 (1H, m), 7.99 (1H, dd), 7.75 (1H, dd), 7.61 (1H, br. s), 4.59 (2H, s), 4.55 (2H, s), 4.43 (0.6H, q), 4.19 (1.4H, q), 3.96-3.85 (3H, m), 3.41-3.31 (2H, m), 3.19 (2H, s), 2.95 (1H, s), 1.86-1.83 (2H, m), 1.57-1.48 (2H, m). | 499 |

| Example | Structure | Name | ¹H NMR (400 MHz) | MS: [M + H]⁺ |
|---|---|---|---|---|
| 35 | 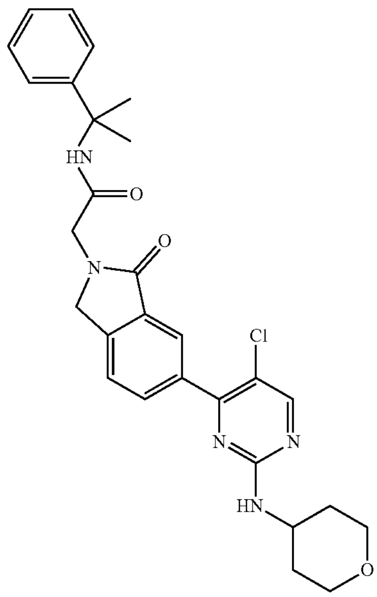 [SMILES: CC(C)(NC(=O)CN1Cc2ccc(-c3nc(NC4CCOCC4)ncc3Cl)cc2C1=O)c1ccccc1] | 2-(6-{5-chloro-2-[(oxan-4-yl)amino]pyrimidin-4-yl}-1-oxo-2,3-dihydro-1H-isoindol-2-yl)-N-(2-phenylpropan-2-yl)acetamide | (DMSO-d6) 8.45 (1H, s), 8.39 (1H, s), 8.01 (1H, dd), 7.96 (1H, dd), 7.72 (1H, d), 7.62 (1H, br. s), 7.38-7.33 (2H, m), 7.29 (2H, dd), 7.22-7.08 (1H, m), 4.56 (2H, s), 4.26 (2H, s), 3.91-3.83 (3H, m), 3.44-3.34 (2H, m), 1.84 (2H. d), 1.58 (6H, s), 1.56-1.45 (2H, m). | 520 |
| 36 | 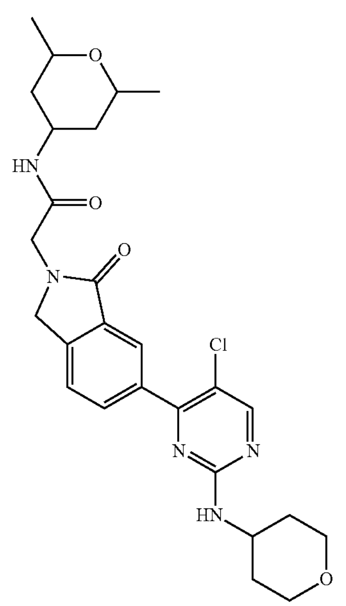 [SMILES: CC1CC(NC(=O)CN2Cc3ccc(-c4nc(NC5CCOCC5)ncc4Cl)cc3C2=O)CC(C)O1] | 2-(6-{5-chloro-2-[(oxan-4-yl)amino]pyrimidin-4-yl}-1-oxo-2,3-dihydro-1H-isoindol-2-yl)-N-(2,6-dimethyloxan-4-yl)acetamide | (DMSO-d6) 8.45 (1H, s), 8.26 (0.5H, d), 8.06 (0.5H, d), 8.02 (1H, br. s), 7.99-7.95 (1H, m), 7.74 (1H, d), 7.62 (1H, br. s), 4.59 (2H, d), 4.20 (2H, d), 4.05-4.01 (0.5H, m), 3.94-3.90 (0.5H, m), 3.88-3.81 (3H, m), 3.78-3.71 (1H, m), 3.46-3.37 (3H, m), 1.84 (2H, d), 1.74 (1H, dd), 1.60-1.47 (3H, m), 1.34-1.26 (1H, m), 1.08 (3H, d), 1.04 (3H, d), 1.01-0.95 (1H, m). | 514 |

| Example | Structure | Name | ¹H NMR (400 MHz) | MS: [M + H]⁺ |
|---|---|---|---|---|
| 37 | 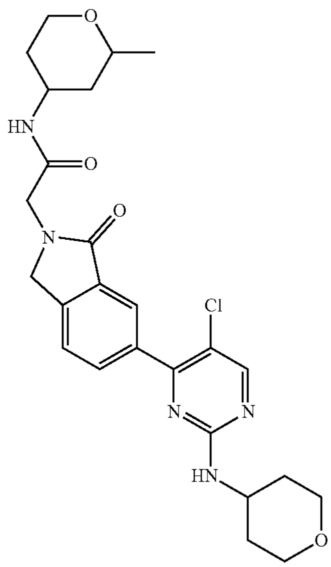 [SMILES: CC1CC(NC(=O)CN2Cc3ccc(-c4nc(NC5CCOCC5)ncc4Cl)cc3C2=O)CCO1] | 2-(6-{5-chloro-2-[(oxan-4-yl)amino]pyrimidin-4-yl}-1-oxo-2,3-dihydro-1H-isoindol-2-yl)-N-(2-methyloxan-4-yl)acetamide | (DMSO-d6) 8.44 (1H, s), 8.27 (0.8H, d), 8.10 (0.2H, d), 8.02 (1H, s), 7.97 (1H, d), 7.74 (1H, d), 7.61 (1H, br. s), 4.60 (1.6H, s), 4.58 (0.4H, s), 4.26 (1.6H, s), 4.17 (0.4H, s), 4.03-4.02 (1H, m), 3.94-3.85 (3H, m), 3.74-3.64 (3H, m), 3.40-3.37 (2H, m), 1.86-1.82 (2H, m), 1.69-1.47 (5H, m), 1.44-1.36 (1H, m), 1.06 (3H, d). | 500 |
| 38 | 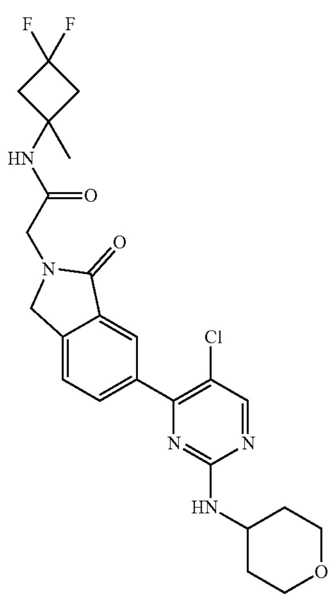 [SMILES: CC1(NC(=O)CN2Cc3ccc(-c4nc(NC5CCOCC5)ncc4Cl)cc3C2=O)CC(F)(F)C1] | 2-(6-{5-chloro-2-[(oxan-4-yl)amino)pyrimidin-4-yl}-1-oxo-2,3-dihydro-1H-isoindol-2-yl)-N-(3,3-difluoro-1-methyl cyclobutyl)acetamide | (DMSO-d6) 8.49 (2H, d), 8.03 (1H, d) 7.98 (1H, dd), 7.74 (1H, d), 7.62 (1H, br. s), 4.59 (2H, s), 4.18 (2H, s), 3.98-3.83 (3H, m), 3.37 (2H, t), 2.95-2.84 (2H, m), 2.69-2.54 (2H, m), 1.88-1.80 (2H, m), 1.60-1.46 (2H, m), 1.43 (3H, s). | 506 |

| Example | Structure | Name | ¹H NMR (400 MHz) | MS: [M + H]⁺ |
|---|---|---|---|---|
| 39 | 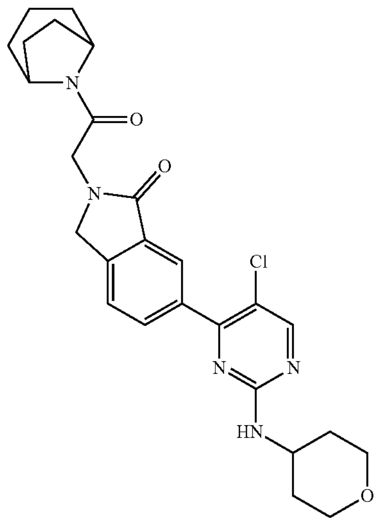 [SMILES: O=C1c2cc(-c3nc(NC4CCOCC4)ncc3Cl)ccc2CN1CC(=O)N1C2CCCC1CC2] | 2-(2-{8-azabicyclo [3.2.1]octan-8-yl}-2-oxoethyl)-6-{5-chloro-2-[(oxan-4-yl)amino] pyrimidin-4-yl}-2,3-dihydro-1H-isoindol-1-one | (DMSO-d6) 8.45 (1H, s), 8.03 (1H, d), 7.99 (1H, dd), 7.75 (1H, d) ,7.61 (1H, br. s), 4.61 (2H, s), 4.32-4.47 (4H, m), 3.85-3.97 (3H, m), 3.36-3.41 (2H, m), 1.97-2.04 (1H, m), 1.42-1.86 (13H, m). | 496 |
| 40 | 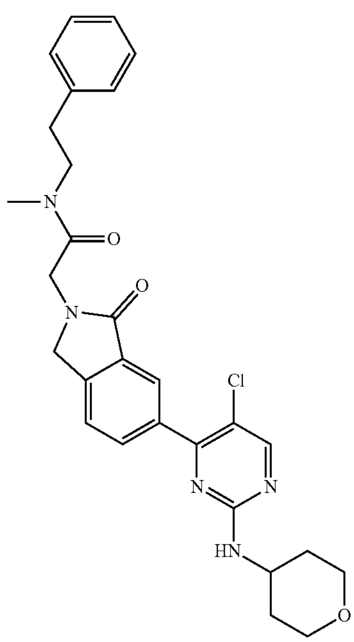 [SMILES: CN(CCc1ccccc1)C(=O)CN1Cc2ccc(-c3nc(NC4CCOCC4)ncc3Cl)cc2C1=O] | 2-(6-{5-chloro-2-[(oxan-4-yl)amino] pyrimidin-4-yl}-1-oxo-2,3-dihydro-1H-isoindol-2-yl)-N-methyl-N-(2-phenyl ethyl)acetamide | (DMSO-d6) 8.45 (1H, s), 8.03 (1H, d), 7.98 (1H, m), 7.74 (1H, m), 7.61 (1H, br. s), 7.19-7.37 (5H, m), 4.51 (1H, s), 4.43 (1H, s), 4.37 (1H, s), 4.20 (1H, s), 3.85-3.98 (3H, m), 3.60 (1H, br. t), 3.51 (1H, br. t), 3.35-3.40 (2H, m), 3.01 (1.5H, s), 2.91 (1H, br. t), 2.88 (1.5H, s), 2.77 (1H, br. t), 1.85 (2H, m), 1.53 (2H, m). | 520 |

| Example | Structure | Name | ¹H NMR (400 MHz) | MS: [M + H]⁺ |
|---|---|---|---|---|
| 41 | 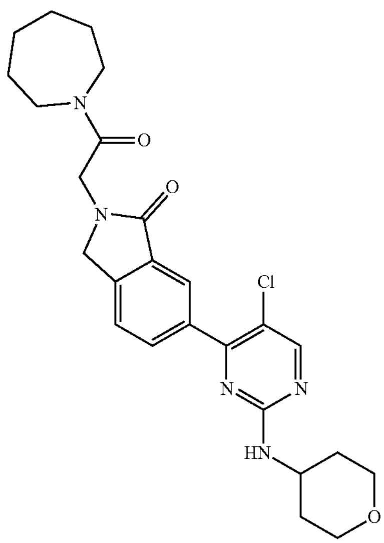 [SMILES: O=C(CN1Cc2ccc(-c3nc(NC4CCOCC4)ncc3Cl)cc2C1=O)N1CCCCCC1] | 2-[2-(azepan-1-yl)-2-oxoethyl]-6-{5-chloro-2-[(oxan-4-yl)amino]pyrimidin-4-yl}-2,3-dihydro-1H-isoindol-1-one | (DMSO-d6) 8.46 (1H, s), 8.03 (1H, d), 7.98 (1H, dd), 7.75 (1H, d), 7.63 (1H, br. s), 4.59 (2H, s), 4.47 (2H, s), 3.99-3.86 (3H, m), 3.52 (2H, t), 3.46-3.34 (4H, m), 1.85 (2H, br. d), 1.78-1.73 (2H, m), 1.66-1.45 (8H, m). | 484 |
| 42 | 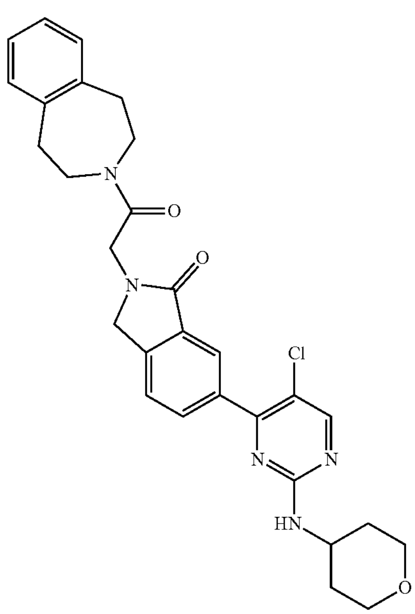 [SMILES: O=C(CN1Cc2ccc(-c3nc(NC4CCOCC4)ncc3Cl)cc2C1=O)N1CCc2ccccc2CC1] | 6-{5-chloro-2-[(oxan-4-yl)amino]pyrimidin-4-yl}-2-[2-oxo-2-(2,3,4,5-tetrahydro-1H-3-benzazepin-3-yl)ethyl]-2,3-dihydro-1H-isoindol-1-one | (DMSO-d6) 8.45 (1H, s), 8.03 (1H, d), 7.98 (1H, dd), 7.74 (1H, d), 7.62 (1H, br. s), 7.23-7.08 (4H, m), 4.56 (4H, d), 3.98-3.82 (3H, m), 3.70-3.54 (4H, m), 3.37 (2H, t), 3.00-2.95 (2H, m), 2.88-2.83 (2H, m), 1.88-1.81 (2H, m), 1.57-1.47 (2H, m). | 532 |

-continued

| Example | Structure | Name | ¹H NMR (400 MHz) | MS: [M + H]⁺ |
|---|---|---|---|---|
| 43 | 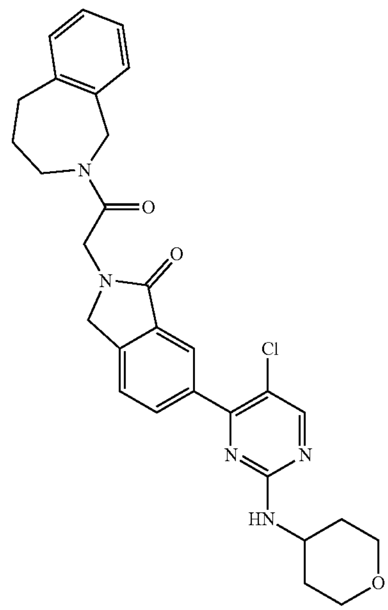 [SMILES: O=C(CN1Cc2ccc(-c3nc(NC4CCOCC4)ncc3Cl)cc2C1=O)N1CCCc2ccccc2C1] | 6-{5-chloro-2-[(oxan-4-yl)amino]pyrimidin-4-yl}-2-[2-oxo-2-(2,3,4,5-tetrahydro-1H-2-benzazepin-2-yl)ethyl]-2,3-dihydro-1H-isoindol-1-one | (DMSO-d6) 8.44 (1H, s), 8.06-7.88 (2H, m), 7.70 (1H, d), 7.61 (1H, br. s), 7.45-7.41 (0.5H, m), 7.26-7.06 (3.5H, m), 4.69 (1H, s), 4.50-4.44 (5H, m), 3.97-3.74 (5H, m), 3.36 (2H, t), 3.02-2.96 (2H, br. m), 1.89-1.75 (3H, m), 1.72-1.62 (1H, m), 1.56-1.47 (2H, m). | 532 |
| 44 | 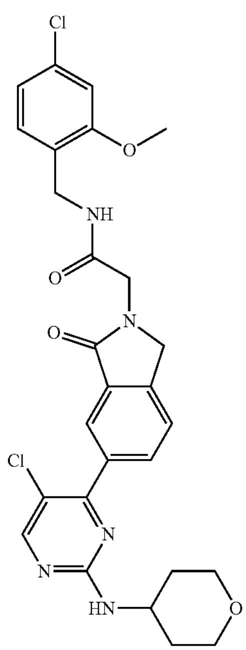 [SMILES: COc1cc(Cl)ccc1CNC(=O)CN1Cc2ccc(-c3nc(NC4CCOCC4)ncc3Cl)cc2C1=O] | 2-(6-{5-chloro-2-[(oxan-4-yl)amino]pyrimidin-4-yl}-1-oxo-2,3-dihydro-1H-isoindol-2-yl)-N-[(4-chloro-2-methoxyphenyl)methyl]acetamide | (DMSO-d6) 8.49 (t, 1H), 8.44 (s, 1H), 8.03 (d, 1H), 7.98 (dd, 1H), 7.75 (d, 1H), 7.61 (br. s, 1H), 7.19 (d, 1H), 7.06 (d, 1H), 7.98 (dd, 1H), 4.61 (s, 2H), 4.27 (s, 2H), 4.22 (d, 2H), 3.90-3.84 (m, 3H), 3.83 (s, 3H), 3.40-3.34 (m, 2H), 1.86-1.82 (m, 2H), 1.57-1.47 (m, 2H). | 556 |

| Example | Structure | Name | $^1$H NMR (400 MHz) | MS: [M + H]$^+$ |
|---|---|---|---|---|
| 45 | 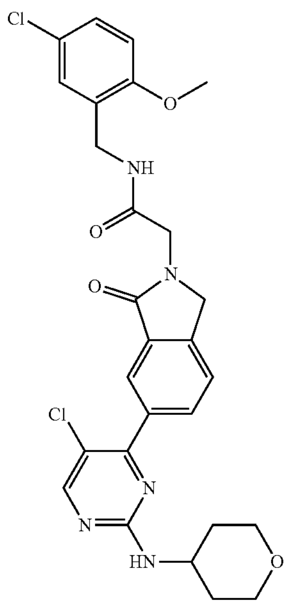 [SMILES: COc1ccc(Cl)cc1CNC(=O)CN1Cc2ccc(-c3nc(NC4CCOCC4)ncc3Cl)cc2C1=O] | 2-(6-{5-chloro-2-[(oxan-4-yl)amino]pyrimidin-4-yl}-1-oxo-2,3-dihydro-1H-isoindol-2-yl)-N-[(5-chloro-2-methoxyphenyl)methyl]acetamide | (DMSO-d6) 8.52 (t, 1H), 8.44 (s, 1H), 8.04 (d, 1H), 7.98 (dd, 1H), 7.75 (d, 1H), 7.61 (br. s, 1H), 7.28 (dd, 1H), 7.20 (d, 1H), 7.01 (d, 1H), 4.62 (s, 2H), 4.29 (s, 2H), 4.24 (d, 2H), 3.93-3.85 (m, 3H), 3.80 (s, 3H), 3.40-3.35 (m, 2H), 1.86-1.83 (m, 2H), 1.57-1.47 (m, 2H). | 556 |
| 46 | 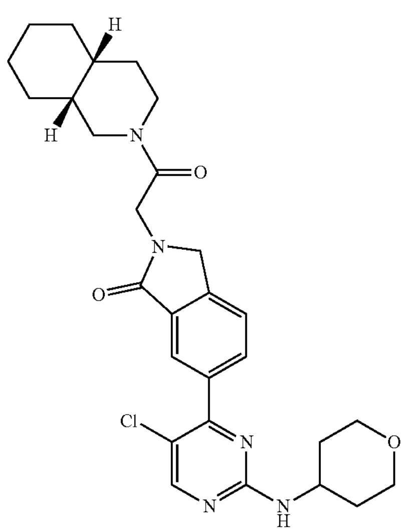 [SMILES: O=C(CN1Cc2ccc(-c3nc(NC4CCOCC4)ncc3Cl)cc2C1=O)N1CC[C@H]2CCCC[C@H]2C1] | 2-{2-[(4aR,8aR)-decahydroisoquinolin-2-yl]-2-oxoethyl}-6-{5-chloro-2-[(oxan-4-yl)amino]pyrimidin-4-yl}-2,3-dihydro-1H-isoindol-1-one | (DMSO-d6, VT T = 350K) 8.41 (s, 1H), 8.07 (m, 1H), 8.00 (dd, 1H), 7.73 (dd, 1H). 7.28 (d, 1H), 4.59 (s, 2H), 4.44 (br. s, 2H). 3.92-4.02 (m, 1H), 3.85-3.92 (m, 2H), 3.64-3.83 (m, 1H), 3.38-3.45 (m, 2H), 3.00-3.31 (m, 1H), 1.85-1.93 (m, 3H), 1.26-1.80 (m, 15H). | 524 |

-continued

| Example | Structure | Name | ¹H NMR (400 MHz) | MS: [M + H]⁺ |
|---|---|---|---|---|
| 47 | 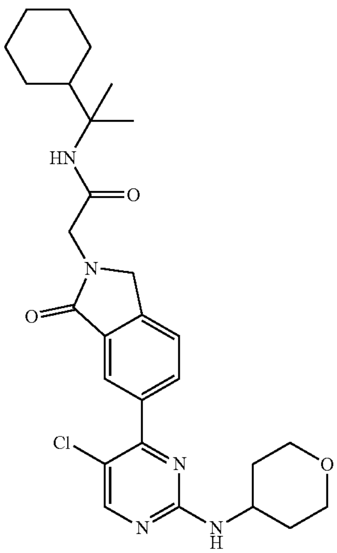 [SMILES: CC(C)(NC(=O)CN1Cc2ccc(-c3nc(NC4CCOCC4)ncc3Cl)cc2C1=O)C1CCCCC1] | 2-(6-{5-chloro-2-[(oxan-4-yl)amino]pyrimidin-4-yl}-1-oxo-2,3-dihydro-1H-isoindol-2-yl)-N-(2-cyclohexylpropan-2-yl)acetamide | (DMSO-d6) 8.45 (s, 1H), 8.02 (dd, 1H), 7.75 (d, 1H), 7.62 (s (br), 1H), 7.55 (s, 1H), 4.58 (s, 2H), 4.16 (s, 2H), 3.90-3.98 (m, 1H), 3.83-3.91 (m, 2H), 3.34-3.42 (m, 2H), 1.81-1.91 (m, 3H), 1.59-1.78 (m, 6H), 1.48-1.58 (m, 2H), 1.20 (s, 6H), 1.05-1.20 (m, 2H), 0.91-0.99 (m, 2H). | 526 |
| 48 | 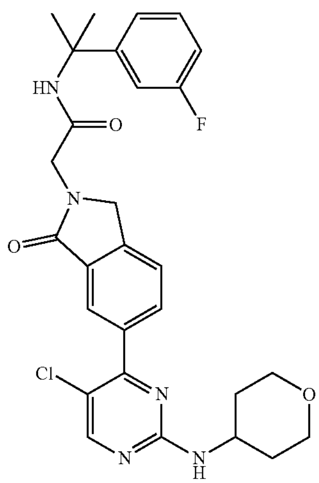 [SMILES: CC(C)(NC(=O)CN1Cc2ccc(-c3nc(NC4CCOCC4)ncc3Cl)cc2C1=O)c1cccc(F)c1] | 2-(6-{5-chloro-2-[(oxan-4-yl)amino]pyrimidin-4-yl}-1-oxo-2,3-dihydro-1H-isoindol-2-yl)-N-[2-(3-fluorophenyl)propan-2-yl]acetamide | (DMSO-d6) 8.45 (s, 2H), 8.01 (d, 1H), 7.96 (dd, 1H), 7.72 (d, 1H), 7.61 (s, 1H), 7.33 (ddd, 1H), 7.19 (m, 1H), 7.13 (m, 1H), 7.00 (m, 1H), 4.56 (s, 2H), 4.27 (s, 2H), 3.82-3.97 (m, 3H), 3.35-3.42 (m, 2H), 1.83-1.88 (m, 2H), 1.57 (s, 6H), 1.47-1.57 (m, 2H). | 538 |
| 49 | 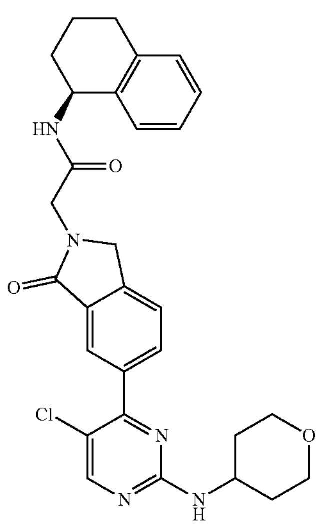 [SMILES: O=C(CN1Cc2ccc(-c3nc(NC4CCOCC4)ncc3Cl)cc2C1=O)N[C@H]1CCCc2ccccc21] | 2-(6-{5-chloro-2-[(oxan-4-yl)amino]pyrimidin-4-yl}-1-oxo-2,3-dihydro-1H-isoindol-2-yl)-N-[(1S)-1,2,3,4-tetrahydronaphthalan-1-yl]acetamide | (DMSO-d6) 8.54 (d, 1H), 8.45 (s, 1H), 8.04 (d, 1H), 7.98 (dd, 1H), 7.76 (d, 1H), 7.62 (br. s, 1H), 7.14-7.22 (m, 3H), 7.08-7.13 (m, 1H), 4.99-5.05 (m, 1H), 4.64 (s, 2H), 4.27 (s, 2H), 3.83-3.98 (m, 3H), 3.35-3.41 (m, 2H), 2.67-2.81 (m, 2H), 1.81-1.94 (m, 4H), 1.67-1.78 (m, 2H), 1.47-1.58 (m, 2H). | 532 |

| Example | Structure | Name | ¹H NMR (400 MHz) | MS: [M + H]⁺ |
|---|---|---|---|---|
| 50 | 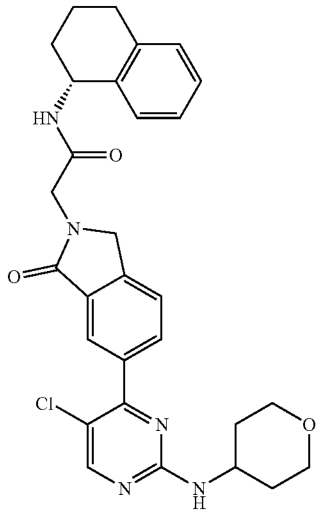 [SMILES: O=C(CN1Cc2ccc(-c3nc(NC4CCOCC4)ncc3Cl)cc2C1=O)N[C@@H]1CCCc2ccccc21] | 2-(6-{5-chloro-2-[(oxan-4-yl)amino]pyrimidin-4-yl}-1-oxo-2,3-dihydro-1H-isoindol-2-yl)-N-[(1R)-1,2,3,4-tetrahydronaphthalen-1-yl]acetamide | (DMSO-d6) 8.54 (d, 1H), 8.45 (s, 1H), 8.04 (d, 1H), 7.98 (dd, 1H), 7.76 (d, 1H), 7.62 (br. s, 1H), 7.14-7.22 (m, 3H), 7.08-7.13 (m, 1H), 4.99-5.05 (m, 1H), 4.64 (s, 2H), 4.27 (s, 2H), 3.83-3.98 (m, 3H), 3.35-3.41 (m, 2H), 2.67-2.81 (m, 2H), 1.81-1.94 (m, 4H), 1.67-1.78 (m, 2H), 1.47-1.58 (m, 2H). | 532 |
| 51 | 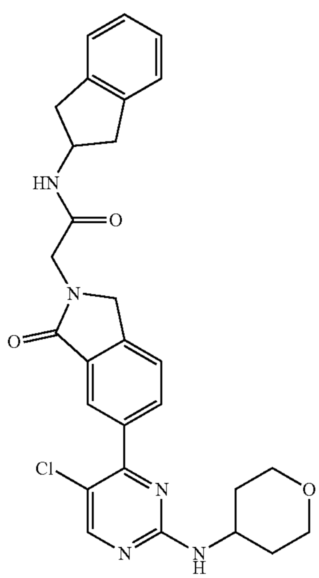 [SMILES: O=C(CN1Cc2ccc(-c3nc(NC4CCOCC4)ncc3Cl)cc2C1=O)NC1Cc2ccccc2C1] | 2-(6-{5-chloro-2-[(oxan-4-yl)amino]pyrimidin-4-yl}-1-oxo-2,3-dihydro-1H-isoindol-2-yl)-N-(2,3-dihydro-1H-inden-2-yl)acetamide | (DMSO-d6) 8.47 (s, 1H), 8.45 (s, 1H), 8.02 (d, 1H), 7.98 (dd, 1H), 7.74 (d, 1H), 7.61 (br. s, 1H), 7.23-7.22 (m, 2H), 7.16-7.14 (m, 2H), 4.60 (s. 2H), 4.52-4.47 (m, 1H), 4.19 (s, 2H), 3.95-3.85 (m, 3H), 3.40-3.37 (m, 2H), 3.18 (dd, 2H), 2.80 (dd, 2H), 1.86-1.83 (m, 2H), 1.57-1.47 (m, 2H). | 518 |

-continued

| Example | Structure | Name | ¹H NMR (400 MHz) | MS: [M + H]⁺ |
|---|---|---|---|---|
| 52 | 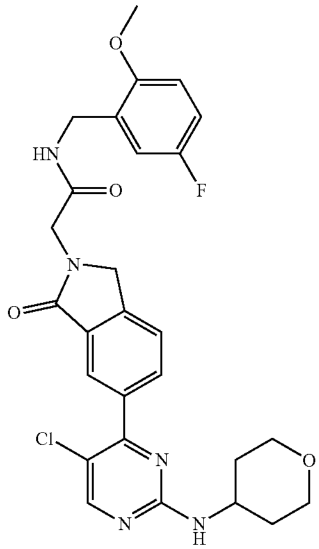 | 2-(6-{5-chloro-2-[(oxan-4-yl)amino]pyrimidin-4-yl}-1-oxo-2,3-dihydro-1H-isoindol-2-yl)-N-[(5-fluoro-2-methoxyphenyl)methyl]acetamide | (DMSO-d6) 8.53 (t, 1H), 8.44 (s, 1H), 8.03 (d, 1H), 7.98 (dd, 1H), 7.75 (d, 1H), 7.61 (br. s, 1H), 7.08-6.96 (m, 3H), 4.62 (s, 2H), 4.30 (s, 2H), 4.25 (d, 2H), 3.95-3.85 (m, 3H), 3.79 (s, 3H), 3.39-3.34 (m, 2H), 1.86-1.83 (m, 2H), 1.57-1.47 (m, 2H). | 540 |
| 53 | 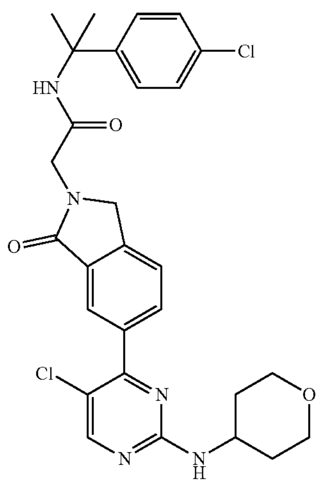 | 2-(6-{5-chloro-2-[(oxan-4-yl)amino]pyrimidin-4-yl}-1-oxo-2,3-dihydro-1H-isoindol-2-yl)-N-[2-(4-chlorophenyl)propan-2-yl]acetamide | (DMSO-d6) 8.45 (s, 1H), 8.44 (s, 1H), 8.01 (d, 1H), 7.96 (dd, 1H), 7.72 (d, 1H), 7.61 (br. s, 1H), 7.38-7.32 (m, 4H), 4.55 (s, 2H), 4.25 (s, 2H), 3.93-3.85 (m, 3H), 3.40-3.35 (m, 2H), 1 86-1.83 (m, 2H), 1.56-1.51 (m, 8H). | 554 |
| 54 | 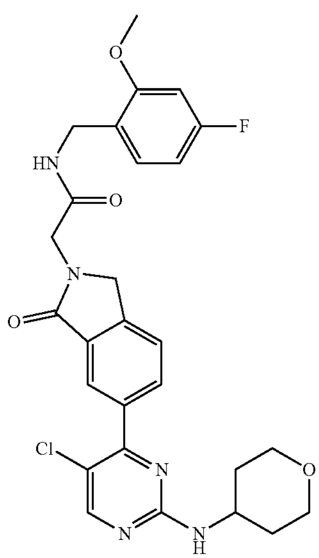 | 2-(6-{5-chloro-2-[(oxan-4-yl)amino]pyrimidin-4-yl}-1-oxo-2,3-dihydro-1H-isoindol-2-yl)-N-[(4-fluoro-2-methoxyphenyl)methyl]acetamide | (DMSO-d6) 8.48-8.45 (m, 2H), 8.04 (d, 1H), 7.98 (dd, 1H), 7.75 (d, 1H), 7.61 (br. s, 1H), 7.21 (dd, 1H), 6.90 (dd, 1H), 6.75 (td, 1H), 4.62 (s, 2H), 4.27 (s, 2H), 4.22 (d, 2H), 3.95-3.86 (m, 3H), 3.82 (s, 3H), 3.40-3.37 (m, 2H), 1.86-1.84 (m, 2H), 1.58-1.48 (m, 2H). | 540 |

| Example | Structure | Name | ¹H NMR (400 MHz) | MS: [M + H]⁺ |
|---|---|---|---|---|
| 55 | 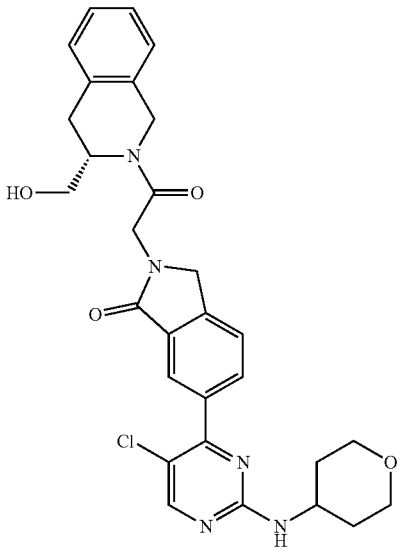 [SMILES: O=C1c2cc(-c3nc(NC4CCOCC4)ncc3Cl)ccc2CN1CC(=O)N1Cc2ccccc2C[C@H]1CO] | 6-{5-chloro-2-[(oxan-4-yl)amino]pyrimidin-4-yl)-2-{2-[(3S)-3-(hydroxy methyl)-1,2,3,4-tetrahydro isoquinolin-2-yl]-2-oxoethyl}-2,3-dihydro-1H-isoindol-1-one | (DMSO-d6, VT T = 353K) 8.41 (s, 1H), 8.07 (d, 1H), 8.00 (dd, 1H), 7.72 (d, 1H), 7.26 (d, 1H), 7.19 (s, 4H), 5.00-4.75 (br. s, 3H), 4.62-4.60 (m, 4H), 4.52-4.17 (br. s, 2H), 4.00-3.86 (m, 3H), 3.44-3.38 (m, 4H), 2.95-2.85 (br. s, 1H), 1.92-1.87 (m, 2H), 1.63-1.53 (m, 2H). | 548 |
| 56 | 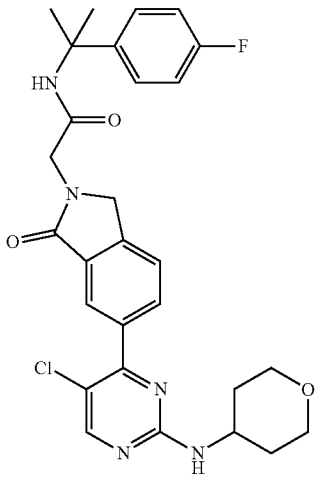 [SMILES: CC(C)(NC(=O)CN1Cc2ccc(-c3nc(NC4CCOCC4)ncc3Cl)cc2C1=O)c1ccc(F)cc1] | 2-(6-{5-chloro-2-[(oxan-4-yl)amino]pyrimidin-4-yl}-1-oxo-2,3-dihydro-1H-isoindol-2-yl)-N-[2-(4-fluorophenyl)propan-2-yl]acetamide | DMSO-d6) 8.44 (s, 1H), 8.40 (s, 1H), 8.00 (d, 1H), 7.95 (dd, 1H), 7.71 (d, 1H), 7.60 (br. s, 1H), 7.39-7.35 (m, 2H), 7.11-7.07 (m, 2H), 4.54 (s, 2H), 4.24 (s, 2H), 3.93-3.84 (m, 3H), 3.41-3.36 (m, 2H), 1.85-1.82 (m, 2H), 1.57 (s, 6H), 1.56-1.47 (m, 2H). | 538 |
| 57 | 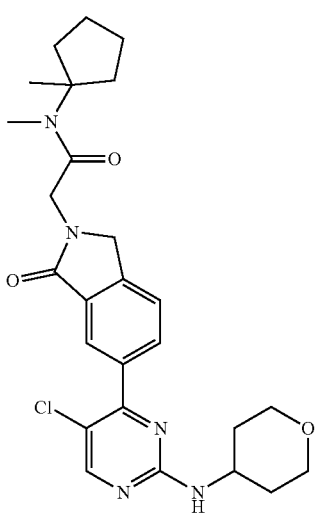 [SMILES: CN(C(=O)CN1Cc2ccc(-c3nc(NC4CCOCC4)ncc3Cl)cc2C1=O)C1(C)CCCC1] | 2-(6-{5-chloro-2-[(oxan-4-yl)amino]pyrimidin-4-yl}-1-oxo-2,3-dihydro-1H-isoindol-2-yl)-N-methyl-N-(1-methylcyclopentyl)acetamide | DMSO-d6) 8.45 (s, 1H), 8.02 (d, 1H), 7.97 (dd, 1H), 7.74 (d, 1H), 7.61 (br. s, 1H), 4.53 (s, 2H), 4.39 (s, 2H), 3.95-3.85 (m, 3H), 3.40-3.34 (m, 2H), 2.96 (s, 3H), 1.96-1.93 (m, 2H), 1.86-1.78 (m, 4H), 1.62-1.50 (m, 6H), 1.19 (s, 3H). | 498 |

-continued

| Example | Structure | Name | ¹H NMR (400 MHz) | MS: [M + H]⁺ |
|---|---|---|---|---|
| 58 | 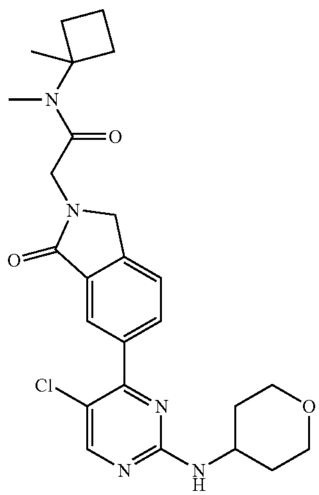 [SMILES: CN(C(=O)CN1Cc2ccc(-c3nc(NC4CCOCC4)ncc3Cl)cc2C1=O)C1(C)CCC1] | 2-(6-{5-chloro-2-[(oxan-4-yl)amino]pyrimidin-4-yl}-1-oxo-2,3-dihydro-1H-isoindol-2-yl)-N-methyl-N-(1-methylcyclobutyl)acetamide | (DMSO-d6, VT T = 353K) 8.40 (s, 1H), 8.05 (d, 1H), 7.99 (dd, 1H), 7.72 (d, 1H), 7.25 (d, 1H), 4.58 (s, 2H), 4.33 (s, 2H), 3.99 3.86 (m, 3H), 3.44-3.38 (m, 2H), 2.80 (s, 3H), 2.27 (br. s, 2H), 1.98-1.87 (m, 4H), 1.75-1.62 (m, 2H), 1.59-1.53 (m, 2H), 1.38 (br. s, 3H). | 484 |
| 59 | 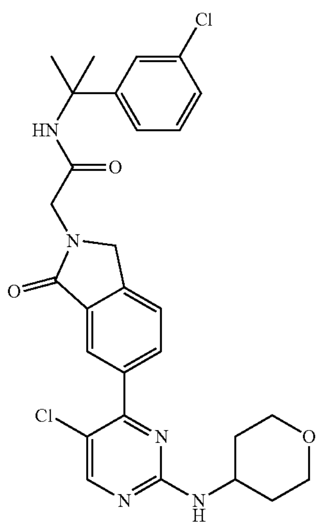 [SMILES: CC(C)(NC(=O)CN1Cc2ccc(-c3nc(NC4CCOCC4)ncc3Cl)cc2C1=O)c1cccc(Cl)c1] | 2-(6-{5-chloro-2-[(oxan-4-yl)amino]pyrimidin-4-yl}-1-oxo-2,3-dihydro-1H-isoindol-2-yl)-N-[2-(3-chlorophenyl)propan-2-yl]acetamide | (DMSO-d6) 8.48 (s, 1H), 8.44 (s, 1H), 8.02 (dd, 1H), 7.72 (d, 1H), 7.62 (s (br), 1H), 7.36 (m, 1H), 7.30-7.33 (m, 2H), 7.23-7.27 (m, 1H), 4.55 (s, 2H), 4.26 (s, 2H), 3.82-3.97 (m, 3H), 3.35-3.41 (m, 2H), 1.81-1.89 (m, 2H), 1.57 (s, 6H), 1.47-1.57 (m, 2H). | 554 |
| 60 | 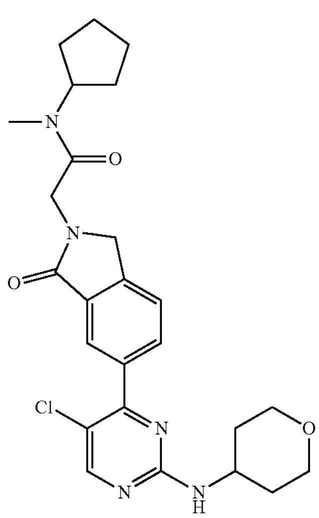 [SMILES: CN(C(=O)CN1Cc2ccc(-c3nc(NC4CCOCC4)ncc3Cl)cc2C1=O)C1CCCC1] | 2-(6-{5-chloro-2-[(oxan-4-yl)amino]pyrimidin-4-yl}-1-oxo-2,3-dihydro-1H-isoindol-2-yl)-N-cyclopentyl-N-methylacetamide | (DMSO-d6, VT T = 350K) 8.41 (s, 1H), 8.07 (d, 1H), 8.00 (dd, 1H), 7.72 (d, 1H), 7.21 (d, 1H), 4.59 (s, 2H), 4.39-4.60 (m, 1H), 4.47 (s, 2H), 3.93-4.02 (m, 1H), 3.86-3.91 (m, 2H), 3.42 (ddd, 2H), 2.85 (s (br), 3H), 1.86-1.93 (m, 2H), 1.66-1.85 (m, 4H), 1.53-1.65 (m, 6H). | 484 |

-continued

| Example | Structure | Name | ¹H NMR (400 MHz) | MS: [M + H]⁺ |
|---|---|---|---|---|
| 61 | 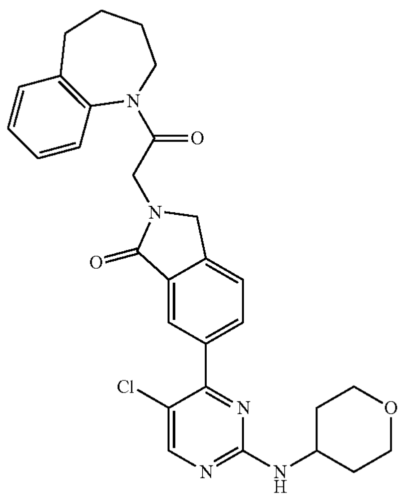 [SMILES: O=C1c2cc(-c3nc(NC4CCOCC4)ncc3Cl)ccc2CN1CC(=O)N1CCCCc2ccccc21] | 6-{5-chloro-2-[(oxan-4-yl)amino]pyrimidin-4-yl}-2-[2-oxo-2-(2,3,4,5-tetrahydro-1H-1-benzazepin-1-yl)ethyl]-2,3-dihydro-1H-isoindol-1-one | (DMSO-d6) 8.44 (s, 1H), 7.99-7.95 (m, 2H), 7.74 (d, 1H), 7.61 (br. s, 1H), 7.46-7.40 (m, 2H), 7.35-7.32 (m, 2H), 4.66-4.47 (m, 3H), 4.32 (d, 1H), 3.95-3.84 (m, 3H), 3.76 (d, 1H), 3.40-3.34 (m, 2H), 2.84-2.79 (m, 2H), 2.64-2.57 (m, 1H), 1.99-1.94 (m, 1H), 1.85-1.71 (m, 4H), 1.57-1.47 (m, 2H), 1.34-1.31 (m, 1H). | 532 |
| 62 | 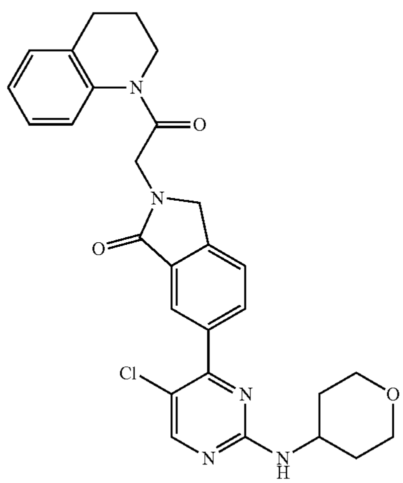 [SMILES: O=C1c2cc(-c3nc(NC4CCOCC4)ncc3Cl)ccc2CN1CC(=O)N1CCCc2ccccc21] | 6-{5-chloro-2-[(oxan-4-yl)amino]pyrimidin-4-yl}-2-[2-oxo-2-(1,2,3,4-tetrahydroquinolin-1-yl)ethyl]-2,3-dihydro-1H-isoindol-1-one | (DMSO-d6) 8.45 (s, 1H), 8.03 (d, 1H), 7.98 (dd, 1H), 7.75 (d, 1H), 7.62 (br. s, 2H), 7.23-7.12 (m, 3H), 4.61 (s, 4H), 3.93-3.85 (m, 3H), 3.75 (dd, 2H), 3.37 (dd, 2H), 2.75 (dd, 2H), 1.96-1.91 (m, 2H), 1.86-1.83 (m, 2H), 1.57-1.47 (m, 2H). | 518 |
| 63 | 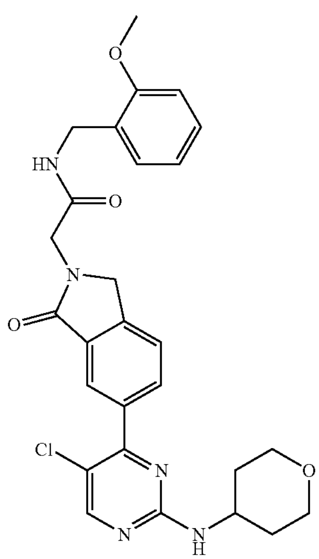 [SMILES: COc1ccccc1CNC(=O)CN1Cc2ccc(-c3nc(NC4CCOCC4)ncc3Cl)cc2C1=O] | 2-(6-{5-chloro-2-[(oxan-4-yl)amino)pyrimidin-4-yl}-1-oxo-2,3-dihydro-1H-isoindol-2-yl)-N-[(2-methoxyphenyl)methyl]-acetamide | (DMSO-d6) 8.47-8.44 (m, 2H), 8.04-8.02 (m, 1H), 7.98 (dd, 1H), 7.75 (d, 1H), 7.61 (brs, 1H), 7.27-7.18 (m, 2H), 6.99-6.90 (m, 2H), 4.62 (s, 2H), 4.27-4.26 (m, 4H), 3.96-3.83 (m, 3H), 3.80 (s, 3H), 3.37 (t, 2H), 1.86-1.83 (m, 2H), 1.57-1.57 (m, 2H). | 522 |

-continued

| Example | Structure | Name | ¹H NMR (400 MHz) | MS: [M + H]⁺ |
|---|---|---|---|---|
| 64 | 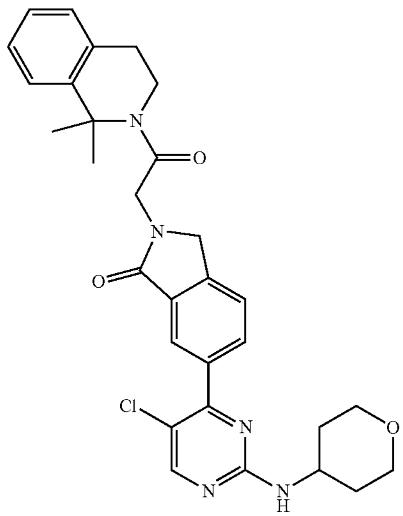 [SMILES: CC1(C)c2ccccc2CCN1C(=O)CN1Cc2ccc(-c3nc(NC4CCOCC4)ncc3Cl)cc2C1=O] | 6-{5-chloro-2-[(oxan-4-yl)amino]pyrimidin-4-yl}-2-[2-(1,1-dimethyl-1,2,3,4-tetrahydroisoquinolin-2-yl)-2-oxoethyl]-2,3-dihydro-1H-isoindol-1-one | (DMSO-d6) 8.45 (s, 1H), 8.05-8 04 (m, 1H), 7.99 (dd, 1H), 7.75 (d, 1H), 7.62 (br s, 1H), 7.40 (d, 1H), 7.27-7.21 (m, 1H), 7.17-7.12 (m, 2H), 4.57-4.56 (m, 4H), 3.98-3.83 (m, 3H), 3.60-3.58 (m, 2H), 3.37 (t, 2H), 2.86-2.83 (m, 2H), 1.86-1.83 (br m, 2H), 1.74 (s, 6H), 1.57-1.48 (m, 2H). | 546 |
| 65 | 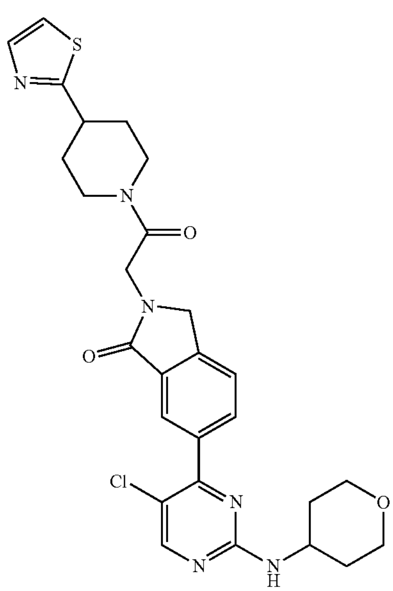 [SMILES: O=C(CN1Cc2ccc(-c3nc(NC4CCOCC4)ncc3Cl)cc2C1=O)N1CCC(c2nccs2)CC1] | 6-{5-chloro-2-[(oxan-4-yl)amino]pyrimidin-4-yl}-2-{2-oxo-2-[4-(1,3-thiazol-2-yl)piperidin-1-yl]ethyl}-2,3-dihydro-1H-isoindol-1-one | (DMSO-d6) 8.45 (s, 1H), 8.03-8.02 (m, 1H), 7.98 (dd, 1H), 7.76-7.73 (m, 2H), 7.68 (m, 1H), 7.63 (d, 1H), 4.57-4.47 (m, 4H), 4.38 (d, 1H), 4.01 (d, 1H), 3.96-3.82 (m, 3H), 3.42-3.22 (m, 4H), 2.86-2.79 (m, 1H), 2.14-2.06 (m, 2H), 1.86-1.70 (m, 3H), 1.60-1.47 (m, 3H). | 553 |

-continued

| Example | Structure | Name | ¹H NMR (400 MHz) | MS: [M + H]⁺ |
|---|---|---|---|---|
| 66 | 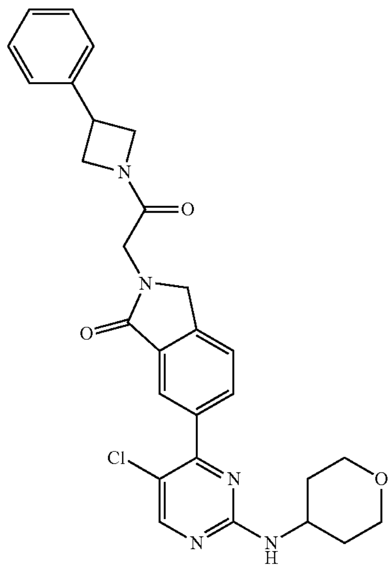 [SMILES: O=C(CN1Cc2ccc(-c3nc(NC4CCOCC4)ncc3Cl)cc2C1=O)N1CC(c2ccccc2)C1] | 6-{5-chloro-2-[(oxan-4-yl)amino]pyrimidin-4-yl}-2-[2-oxo-2-(3-phenylazetidin-1-yl)ethyl]-2,3-dihydro-1H-isoindol-1-one | (DMSO-d6) 8.45 (br. s, 1H), 8.04 (d, 1H), 7.99 (dd, 1H), 7.76 (d, 1H), 7.63 (s (br), 1H), 7.37-7.43 (m, 4H), 7.27-7.31 (m, 1H), 4.63-4.67 (m, 1H), 4.60 (s, 2H), 4.26-4.36 (m, 4H), 3.84-3.98 (m, 5H), 3.36-3.42 (m, 2H), 1.85 (m, 2H), 1.53 (m, 2H). | 518 |
| 67 | 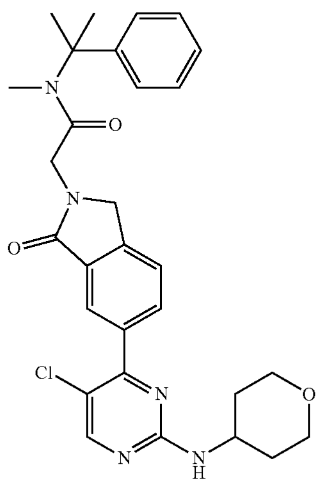 [SMILES: CN(C(=O)CN1Cc2ccc(-c3nc(NC4CCOCC4)ncc3Cl)cc2C1=O)C(C)(C)c1ccccc1] | 2-(6-{5-chloro-2-[(oxan-4-yl)amino]pyrimidin-4-yl}-1-oxo-2,3-dihydro-1H-isoindol-2-yl)-N-methyl-N-(2-phenylpropan-2-yl)acetamide | (DMSO-d6) 8.43 (s, 1H), 7.98 (d, 1H), 7.93 (dd, 1H), 7.69 (d, 1H), 7.60 (br. s, 1H), 7.27-7.25 (m, 4H), 7.15-7.12 (m, 1H), 4.40 (s, 4H), 3.92-3.84 (m, 3H), 3.40-3.36 (m, 2H), 3.12 (s, 3H), 1.85-1.81 (m, 2H), 1.60 (s, 6H), 1.56-1.46 (m, 2H). | 534 |
| 68 | 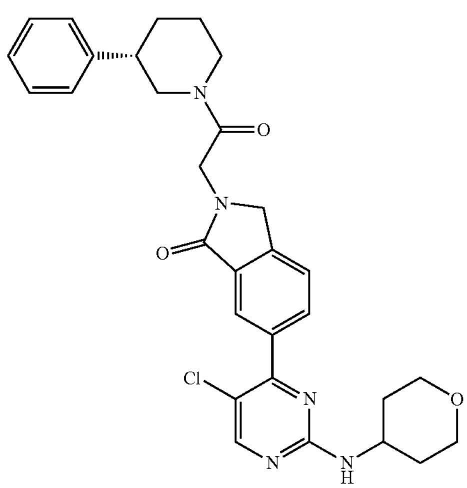 [SMILES: O=C(CN1Cc2ccc(-c3nc(NC4CCOCC4)ncc3Cl)cc2C1=O)N1CCC[C@@H](c2ccccc2)C1] | 6-{5-chloro-2-[(oxan-4-yl)amino]pyrimidin-4-yl}-2-{2-oxo-2-[(3S)-3-phenylpiperidin-1-yl]ethyl}-2,3-dihydro-1H-isoindol-1-one | (DMSO-d6) 8.45 (s, 1H), 8.03-8.02 (m, 1H), 7.98 (dd, 1H), 7.75 (d, 1H), 7.61 (br. s, 1H), 7.34-7.20 (m, 5H), 4.60-4.35 (m, 5H), 3.99-3.85 (m, 4H), 3.41-3.34 (m, 2H), 3.27-3.10 (m, 1H), 2.74-2.60 (m, 2H), 1.95-1.73 (m, 5H), 1.57-1.47 (m, 3H). | 546 |

-continued

| Example | Structure | Name | ¹H NMR (400 MHz) | MS: [M + H]⁺ |
|---|---|---|---|---|
| 69 | 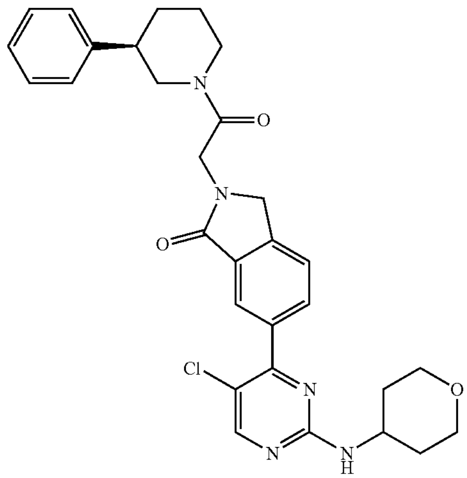 [SMILES: O=C(CN1Cc2ccc(-c3nc(NC4CCOCC4)ncc3Cl)cc2C1=O)N1CCC[C@H](c2ccccc2)C1] | 6-{5-chloro-2-[(oxan-4-yl)amino]pyrimidin-4-yl}-2-{2-oxo-2-[(3R)-3-phenylpiperidin-1-yl]ethyl}-2,3-dihydro-1H-isoindol-1-one | (DMSO-d6) 8.45 (s, 1H), 8.03-8.02 (m, 1H), 7.98 (dd, 1H), 7.75 (d, 1H), 7.61 (br. s, 1H), 7.34-7.21 (m, 5H), 4.60-4.35 (m, 5H), 3.99-3.85 (m, 4H), 3.41-3.34 (m, 2H), 3.27-3.10 (m, 1H), 2.74-2.60 (m, 2H), 1.95-1.73 (m, 5H), 1.57-1.47 (m, 3H). | 546 |
| 70 | 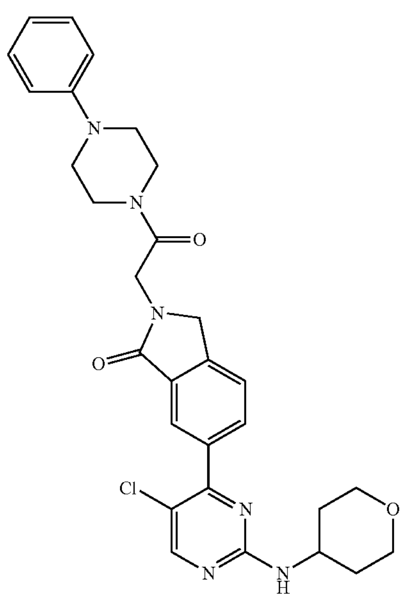 [SMILES: O=C(CN1Cc2ccc(-c3nc(NC4CCOCC4)ncc3Cl)cc2C1=O)N1CCN(c2ccccc2)CC1] | 6-{5-chloro-2-[(oxan-4-yl)amino]pyrimidin-4-yl}-2-[2-oxo-2-(4-phenylpiperazin-1-yl)ethyl]-2,3-dihydro-1H-isoindol-1-one | (DMSO-d6) 8.45 (1H, s), 8.03 (1H, d), 7.99 (1H, dd), 7.75 (1H d), 7.59 (1H, br. s), 7.24 (2H, dd), 6.98 (2H, d), 6.82 (1H, dd), 4.58 (2H, s), 4.54 (2H, s), 3.95-3.91 (1H, m), 3.88-3.85 (2H, m), 3.69-3.67 (2H, m), 3.63-3.61 (2H, m), 3.40-3.35 (2H, m), 3.23-3.21 (2H, m), 3.15-3.13 (2H, m), 1.87-1.83 (2H, m), 1.58-1.49 (2H, m). | 547 |

| Example | Structure | Name | ¹H NMR (400 MHz) | MS: [M + H]⁺ |
|---|---|---|---|---|
| 71 | 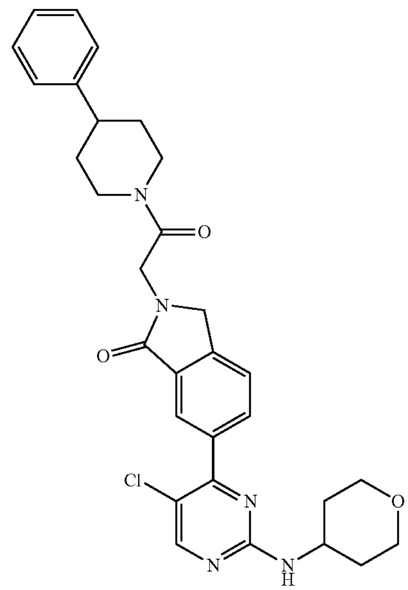 [SMILES: O=C(CN1Cc2ccc(-c3nc(NC4CCOCC4)ncc3Cl)cc2C1=O)N1CCC(c2ccccc2)CC1] | 6-{5-chloro-2-[(oxan-4-yl)amino]pyrimidin-4-yl}-2-[2-oxo-2-(4-phenylpiperidin-1-yl)ethyl]-2,3-dihydro-1H-isoindol-1-one | (DMSO-d6) 8.45 (1H, s), 8.04 (1H, d), 7.99 (1H, dd), 7.75 (1H, d), 7.61 (1H, br. s), 7.33-7.18 (5H, m), 4.59 (2H, s), 4.53-4.47 (3H, m), 4.05 (1H, d), 3.95-3.85 (3H, m), 3.41-3.35 (2H, m), 3.19 (1H, t), 2.83-2.66 (2H, m), 1.86-1.79 (4H, m), 1.68-1.64 (1H, m), 1.58-1.48 (3H, m). | 546 |
| 72 | 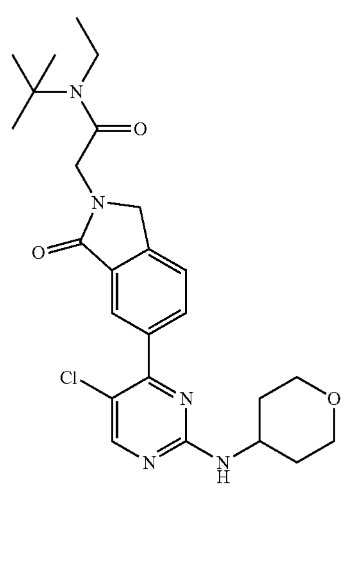 [SMILES: CCN(C(=O)CN1Cc2ccc(-c3nc(NC4CCOCC4)ncc3Cl)cc2C1=O)C(C)(C)C] | N-tert-butyl-2-(6-{5-chloro-2-[(oxan-4-yl)amino]pyrimidin-4-yl}-1-oxo-2,3-dihydro-1H-isoindol-2-yl)-N-ethylacetamide | (DMSO-d6) 8.45 (1H, s), 8.03 (1H, d), 7.98 (1H, dd), 7.75 (1H, d), 7.62 (1H, br. s), 4.58 (2H, s), 4.44 (2H, s), 3.96-3.86 (3H, m), 3.46-3.35 (4H, m), 1.87-1.84 (2H, m), 1.58-1.54 (2H. m), 1.39 (9H, s), 1.23 (3H, t). | 486 |

-continued

| Example | Structure | Name | ¹H NMR (400 MHz) | MS: [M + H]⁺ |
|---|---|---|---|---|
| 73 | 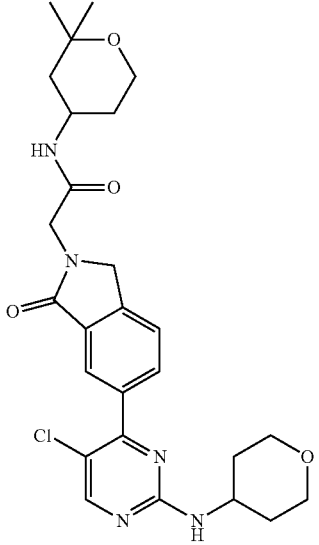 [SMILES: CC1(C)CC(NC(=O)CN2Cc3ccc(-c4nc(NC5CCOCC5)ncc4Cl)cc3C2=O)CCO1] | 2-(6-{5-chloro-2-[(oxan-4-yl)amino]pyrimidin-4-yl}-1-oxo-2,3-dihydro-1H-isoindol-2-yl)-N-(2,2-dimethyloxan-4-yl)acetamide | (DMSO-d6) 8.45 (1H, s), 8.05-8.03 (2H, m), 7.98 (1H, dd), 7.75 (1H, d), 7.61 (1H, br. s), 4.59 (2H, s), 4.17 (2H, s), 3.98-3.86 (4H, m), 3.66-3.54 (2H, m), 3.41-3.35 (2H, m), 1.87-1.84 (2H, m), 1.71-1.66 (2H, m), 1.58-1.48 (2H, m), 1.36-1.20 (2H, m), 1.16 (3H, s), 1.14 (3H, s). | 514 |
| 74 | 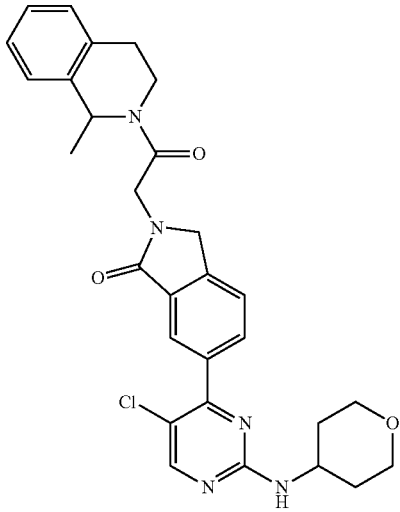 [SMILES: CC1c2ccccc2CCN1C(=O)CN1Cc2ccc(-c3nc(NC4CCOCC4)ncc3Cl)cc2C1=O] | 6-{5-chloro-2-[(oxan-4-yl)amino]pyrimidin-4-yl}-2-[2-(1-methyl-1,2,3,4-tetrahydroisoquinolin-2-yl)-2-oxoethyl]-2,3-dihydro-1H-isoindol-1-one | (DMSO-d6) 8.45 (1H, s), 8.04-8.02 (1H, m), 7.98 (1H, dd), 7.75 (1H, d), 7.61 (1H, br. s), 7.27-7.14 (4H, m), 5.43 (0.75H, q), 5.24 (0.25H, q), 4.72-4.47 (4H, m), 4.42-4.37 (0.5H, m), 3.97-3.83 (4H, m), 3.59-3.52 (0.5H, m), 3.37 (2H, t), 3.14-2.75 (2H, m), 1.86-1.83 (2H, br. m), 1.57-1.47 (3H, m), 1.38 (2H, d). (A mixture of rotamers was observed). | 532 |
| 75 | 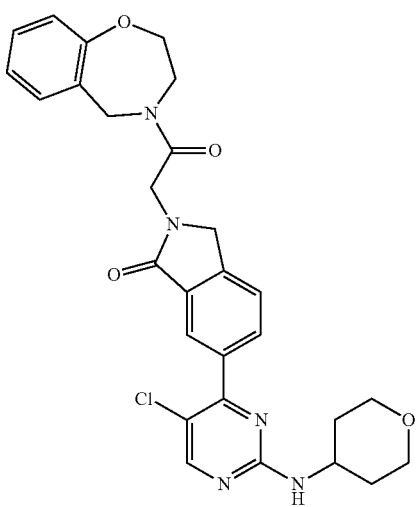 [SMILES: O=C(CN1Cc2ccc(-c3nc(NC4CCOCC4)ncc3Cl)cc2C1=O)N1CCOc2ccccc2C1] | 6-{5-chloro-2-[(oxan-4-yl)amino]pyrimidin-4-yl}-2-[2-oxo-2-(2,3,4,5-tetrahydro-1,4-benzoxazepin-4-yl)ethyl]-2,3-dihydro-1H-isoindol-1-one | (DMSO-d6) 8.44 (1H, s), 8.02-7.93 (2H, m), 7.71 (1H, dd), 7.61 (1H, br. s), 7.47-7.45 (0.5H, m), 7.29-7.17 (1.5H, m), 7.11-6.97 (2H, m), 4.73 (1H, s), 4.60 (1H, s), 4.53-4.50 (4H, m), 4.21-4.19 (1H, m), 4.11-4.09 (1H, m), 3.97-3.80 (5H, m). 3.36 (2H, t), 1.89-1.79 (2H, m), 1.57-1.47 (2H, m). | 534 |

-continued

| Example | Structure | Name | $^1$H NMR (400 MHz) | MS: [M + H]$^+$ |
|---|---|---|---|---|
| 76 | 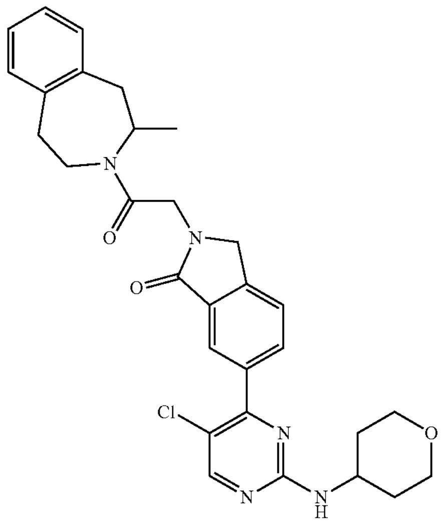 [SMILES: CC1Cc2ccccc2CCN1C(=O)CN1Cc2ccc(-c3nc(NC4CCOCC4)ncc3Cl)cc2C1=O] | 6-{5-chloro-2-[(oxan-4-yl)amino]pyrimidin-4-yl}-2-[2-(2-methyl-2,3,4,5-tetrahydro-1H-3-benzazepin-3-yl)-2-oxoethyl]-2,3-dihydro-1H-isoindol-1-one | (DMSO-d6) 8.44 (s, 1H), 8.01-7.96 (m, 2H), 7.70 (t, 1H), 7.61 (br s, 1H), 7.15-6.99 (m, 4H), 4 81-4.71 (m, 0.5H), 4.57-4.25 (m, 5H), 3.97-3.85 (m, 3.5H), 3.45-3.34 (m, 2.5H), 3.06-2.82 (m, 4.5H), 1.88-1.81 (m, 2H), 2.57-1.47 (m, 2H), 1.10 (d, 1.3H), 0.98 (d, 1.7H). (A mixture of rotamers was observed). | 546 |
| 77 | 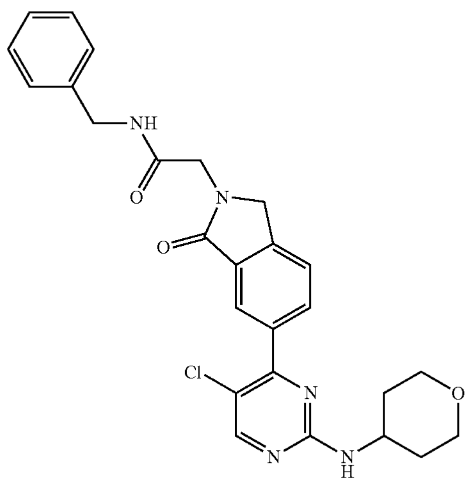 [SMILES: O=C(CN1Cc2ccc(-c3nc(NC4CCOCC4)ncc3Cl)cc2C1=O)NCc1ccccc1] | N-benzyl-2-(6-{5-chloro-2-[(oxan-4-yl)amino]pyrimidin-4-yl}-1-oxo-2,3-dihydro-1H-isoindol-2-yl)acetamide | (DMSO-d6) 8.63 (t, 1H), 8.44 (s, 1H), 8.04 (s, 1H), 7.98 (dd, 1H), 7.75 (d, 1H), 7.60 (brs, 1H), 7.35-7.22 (m, 5H), 4.61 (s, 2H), 4.31 (d, 2H), 4.26 (s, 2H), 3.98-3.85 (m, 3H). 3.37 (t, 2H), 1.86-1.83 (m, 2H), 1.57-1.47 (m, 2H). | 492 |
| 78 | 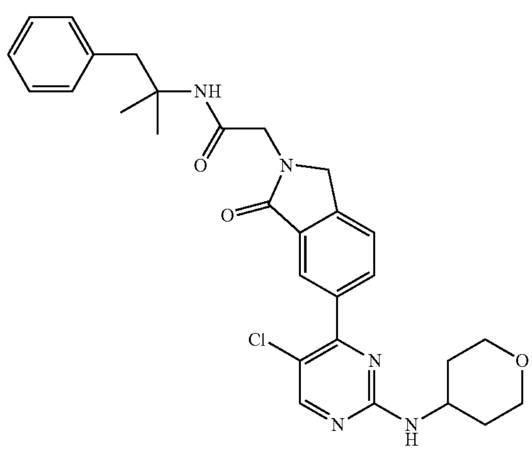 [SMILES: CC(C)(Cc1ccccc1)NC(=O)CN1Cc2ccc(-c3nc(NC4CCOCC4)ncc3Cl)cc2C1=O] | 2-(6-{5-chloro-2-[(oxan-4-yl)amino]pyrimidin-4-yl}-1-oxo-2,3-dihydro-1H-isoindol-2-yl)-N-(2-methyl-1-phenyl propan-2-yl)acetamide | (DMSO-d6) 8.45 (s, 1H), 8.05-8.04 (m, 1H), 7.99 (dd, 1H), 7.76 (d, 1H), 7.61 (br s, 1H), 7.58 (s, 1H), 7.31-7.27 (m, 2H), 7.24-7.20 (m, 1H) 7.14-7.12 (m, 2H), 4.63 (s, 2H), 4.13 (s, 2H), 3.97-3.85 (m, 3H), 3.41-3.35 (m, 2H), 2.97 (s, 2H), 1.87-1.84 (m, 2H), 1.58-1.48 (m, 2H), 1.23 (s, 6H). | 534 |

-continued

| Example | Structure | Name | ¹H NMR (400 MHz) | MS: [M + H]⁺ |
|---|---|---|---|---|
| 79 | 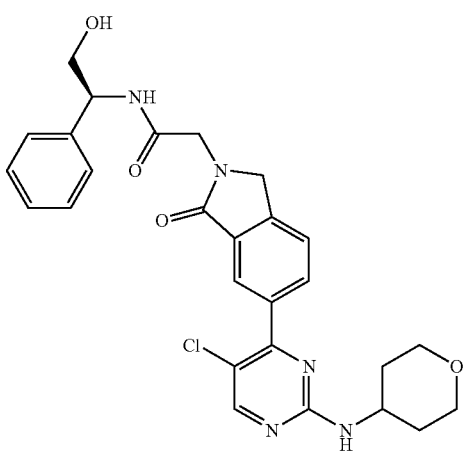 [SMILES: O=C(CN1Cc2ccc(-c3nc(NC4CCOCC4)ncc3Cl)cc2C1=O)N[C@H](CO)c1ccccc1] | 2-(6-{5-chloro-2-[(oxan-4-yl)amino]pyrimidin-4-yl}-1-oxo-2,3-dihydro-1H-isoindol-2-yl)-N-[(1S)-2-hydroxy-1-phenyl ethyl]acetamide | (DMSO-d6) 8.56 (d, 1H), 8.44 (s, 1H), 8.03-8.02 (m, 1H), 7.97 (dd, 1H), 7.73 (d, 1H), 7.60 (br s, 1H), 7.35-7.30 (m, 4H), 7.27-7.22 (m, 1H), 4.93-4.85 (m, 2H), 4.59 (s, 2H), 4.29 (dd, 2H) 3.97-3.85 (m, 3H), 3.59-3.56 (m, 2H), 3.39-3.34 (m, 2H), 1.85-1.82 (m, 2H), 1.57-1.47 (m, 2H). | 522 |
| 80 | 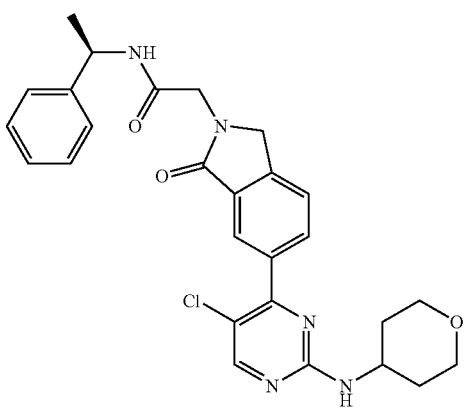 [SMILES: C[C@@H](NC(=O)CN1Cc2ccc(-c3nc(NC4CCOCC4)ncc3Cl)cc2C1=O)c1ccccc1] | 2-(6-{5-chloro-2-[(oxan-4-yl)amino]pyrimidin-4-yl}-1-oxo-2,3-dihydro-1H-isoindol-2-yl)-N-[(1R)-1-phenylethyl]acetamide | (DMSO-d6) 8.60 (d, 1H), 8.45 (s, 1H), 8.03 (d, 1H), 7.98 (dd, 1H), 7.74 (d, 1H), 7.61 (s (br), 1H), 7.31-7.37 (m, 4H), 7.24 (m, 1H), 4 97 (dq, 1H), 4.59 (s, 2H), 4.28 (d, 1H), 4.23 (d, 1H), 3.82-3.98 (m, 3H), 3.33-3.42 (m, 2H), 1.80-1.89 (m, 2H), 1.46-1.59 (m, 2H), 1.39 (d, 3H). | 506 |
| 81 | 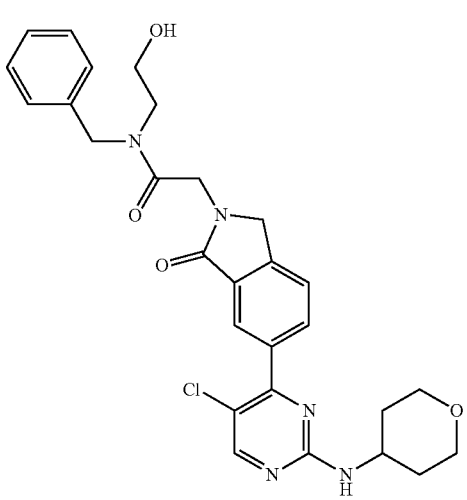 [SMILES: O=C(CN1Cc2ccc(-c3nc(NC4CCOCC4)ncc3Cl)cc2C1=O)N(CCO)Cc1ccccc1] | N-benzyl-2-(6-{5-chloro-2-[(oxan-4-yl)amino]pyrimidin-4-yl}-1-oxo-2,3-dihydro-1H-isoindol-2-yl)-N-(2-hydroxyethyl)acetamide | (DMSO-d6) 8.45 (s, 1H), 8.03-7.96 (m, 2H), 7.76-7.73 (m, 1H), 7.62 (brs, 1H), 7.44-7.24 (m, 5H), 5.03 (t, 0.8H), 4.74-4.48 (m, 6.2H), 3.97-3.85 (m, 3H), 3.62-3.47 (m, 2H), 3.42-3.30 (m, 4H), 1.86-1.83 (m, 2H), 1.52 (qd, 2H). | 536 |

-continued

| Example | Structure | Name | ¹H NMR (400 MHz) | MS: [M + H]⁺ |
|---|---|---|---|---|
| 82 | 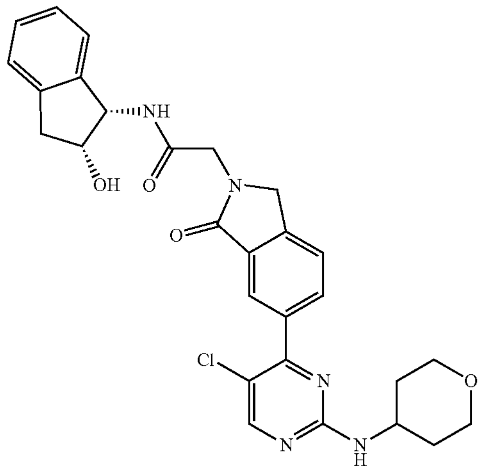 [SMILES: O=C(CN1Cc2ccc(-c3nc(NC4CCOCC4)ncc3Cl)cc2C1=O)N[C@H]1c2ccccc2C[C@H]1O] | 2-(6-{5-chloro-2-[(oxan-4-yl)amino]pyrimidin-4-yl)-1-oxo-2,3-dihydro-1H-isoindol-2-yl)-N-[(1S,2R)-2-hydroxy-2,3-dihydro-1H-inden-1-yl]acetamide | (DMSO-d6) 8.45 (s, 1H), 8.25 (d, 1H), 8.05-8.04 (m, 1H), 7.98 (dd, 1H), 7.76 (d, 1H), 7.62 (br s, 1H), 7.25-7.18 (m, 4H), 5.22 (dd, 1H), 5.09 (d, 1H), 4.66 (s, 2H), 4.46-4.38 (m, 1H), 4.38 (s, 2H), 3.97-3.85 (m, 3H), 3.43-3.34 (m, 2H), 3.06 (dd, 1H), 2.81 (dd, 1H), 1.86-1.83 (m, 2H), 1.59-1.45 (m, 2H). | 534 |
| 83 | 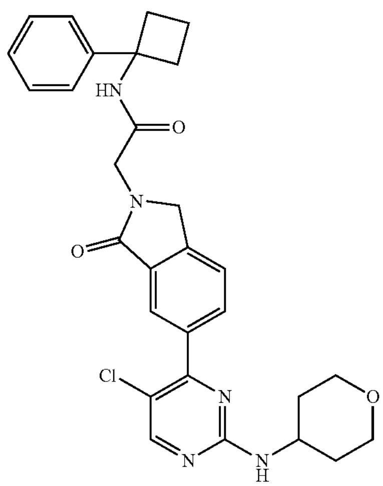 [SMILES: O=C(CN1Cc2ccc(-c3nc(NC4CCOCC4)ncc3Cl)cc2C1=O)NC1(c2ccccc2)CCC1] | 2-(6-{5-chloro-2-[(oxan-4-yl)amino]pyrimidin-4-yl}-1-oxo-2,3-dihydro-1H-isoindol-2-yl)-N-(1-phenylcyclobutyl)acetamide | (DMSO-d6) 8.79 (1H, s), 8.45 (1H, s), 8.02 (1H, dd), 7.97 (1H, dd), 7.73 (1H, d), 7.62 (1H, s), 7.46-7.37 (2H, m), 7.32 (2H, dd), 7.26-7.13 (1H, m), 4.56 (2H, s), 4.22 (2H, s), 3.90 (3H, dd), 3.39 (2H, d), 2.48-2.40 (4H, m), 2.09- 1.94 (1H, m), 1.90- 1.76 (3H, m), 1.53 (2H, m). | 532 |
| 84 | 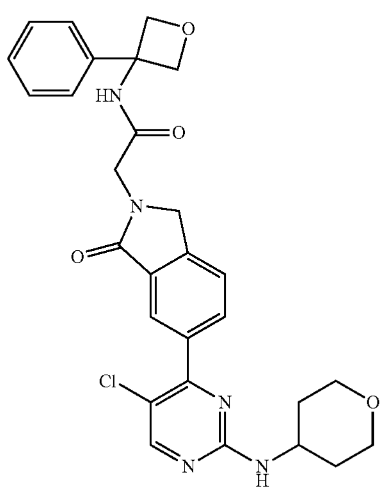 [SMILES: O=C(CN1Cc2ccc(-c3nc(NC4CCOCC4)ncc3Cl)cc2C1=O)NC1(c2ccccc2)COC1] | 2-(6-{5-chloro-2-[(oxan-4-yl)amino]pyrimidin-4-yl}-1-oxo-2,3-dihydro-1H-isoindol-2-yl)-N-(3-phenyloxetan-3-yl)acetamide | (DMSO-d6) 9.21 (s, 1H), 8.44 (s, 1H), 8.05-8.04 (m, 1H), 7.98 (dd, 1H), 7.75 (d, 1H), 7.61 (br s, 1H), 7.56-7.51 (m, 2H), 7.42-7.38 (m, 2H), 7.32-7.28 (m, 1H), 4.90 (d, 2H), 4.69 (d, 2H), 4.62 (s, 2H), 4.33 (s, 2H), 3.96-3.84 (m, 3H), 3.39-3.34 (m, 2H), 1.86-1.82 (m, 2H), 1.57-1.47 (m, 2H). | 534 |

| Example | Structure | Name | ¹H NMR (400 MHz) | MS: [M + H]⁺ |
|---|---|---|---|---|
| 85 | 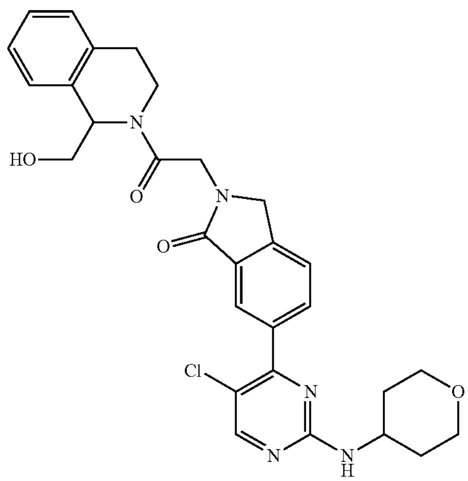 [SMILES: O=C1c2cc(-c3nc(NC4CCOCC4)ncc3Cl)ccc2CN1CC(=O)N1CCc2ccccc2C1CO] | 6-{5-chloro-2-[(oxan-4-yl)amino]pyrimidin-4-yl}-2-{2-[1-(hydroxy methyl)-1,2,3,4-tetrahydro isoquinolin-2-yl]-2-oxoethyl}-2,3-dihydro-1H-isoindol-1-one | (DMSO-d6) 8.44 (s, 1H), 8.04-8.03 (m, 1H), 7.99-7.96 (m, 1H), 7.76-7.72 (m, 1H), 7.62 (s (br), 1H), 7.29-7.15 (m, 4H), 5.44 (t, 0.6H), 5.35 (t, 0.4 H), 5.14-5.11 (m, 0.6H), 4.90-4.87 (m, 0.4H), 4.75-4.44 (m, 4.5H), 3.97-3.61 (m, 6H), 3.40-3.34 (m, 2H), 3.17-2.84 (m, 1.5H), 2.79-2.76 (m, 1H), 1.86-1.83 (m (br), 2H), 1.57-1.47 (m, 2H) (a mixture of rotamers was observed). | 548 |
| 86 | 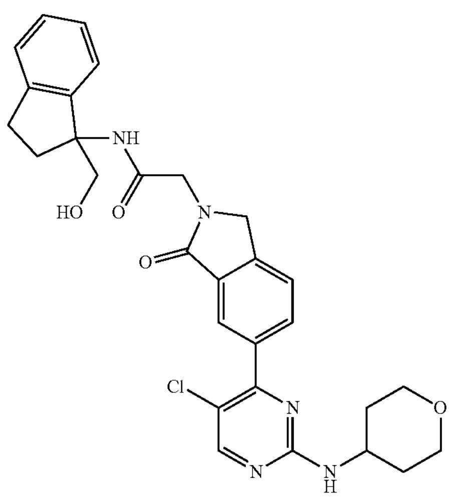 [SMILES: O=C(CN1Cc2ccc(-c3nc(NC4CCOCC4)ncc3Cl)cc2C1=O)NC1(CO)CCc2ccccc21] | 2-(6-{5-chloro-2-[(oxan-4-yl)amino]pyrimidin-4-yl}-1-oxo-2,3-dihydro-1H-isoindol-2-yl)-N-[1-(hydroxymethyl)-2,3-dihydro-1H-inden-1-yl]acetamide | (DMSO-d6) 8.44 (s, 1H), 8.08 (s, 1H), 8.01-8.00 (m, 1H), 7.96 (dd, 1H), 7.72 (d, 1H), 7.61 (s (br), 1H), 7.33-7.30 (m, 1H), 7.20-7.12 (m, 3H), 5.01 (t (br), 1H), 4.60-4.50 (m, 2H), 4.27-4.19 (m, 2H), 3.97-3.84 (m, 3H), 3.68-3.64 (m, 1H), 3.57-3.53 (m, 1H), 3.41-3.33 (m, 2H), 2.95-2.88 (m, 1H), 2.84-2.76 (m, 1H), 2.39-2.24 (m, 2H), 1.85-1.82 (m, 2H), 1.57-1.47 (m, 2H). | 548 |
| 87 | 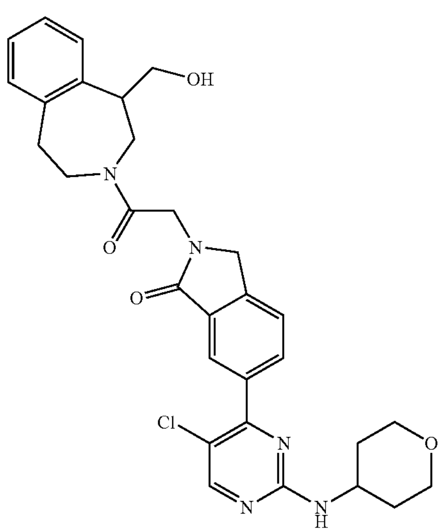 [SMILES: O=C(CN1Cc2ccc(-c3nc(NC4CCOCC4)ncc3Cl)cc2C1=O)N1CCc2ccccc2C(CO)C1] | 6-{5-chloro-2-[(oxan-4-yl)amino]pyrimidin-4-yl}-2-{2-[1-(hydroxyl methyl)-2,3,4,5-tetrahydro-1H-3-benzazepin-3-yl]-2-oxoethyl}-2,3-dihydro-1H-isoindol-1-one | (DMSO-d6) 8.45 (1H, s), 8.02 (1H, s), 7.98 (1H, ddd), 7.73 (1H, dd), 7.63 (1H, s), 7.22-7.02 (4H, m), 5.11 (0.6H, dd), 4.77 (0.6H, d), 4.62-4.34 (3.8H, m), 4.00-3.34 (11H, m), 3.25-3.10 (1H, m), 3.02 (1H, t), 2.92-2.74 (1H, m), 1.85 (2H, d), 1.53 (2H, qd) (a 3:2 mixture of rotamers was observed). | 562 |

Example 88: 6-{5-chloro-2-[(oxan-4-yl)amino]pyrimidin-4-yl}-2-(2-oxo-2-{5H,6H,7H,8H-pyrido[4,3-d]pyrimidin-6-yl}ethyl)-2,3-dihydro-1H-isoindol-1-one

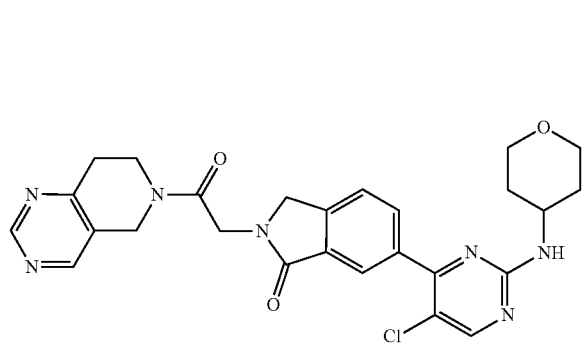 [SMILES: O=C(CN1Cc2ccc(-c3nc(NC4CCOCC4)ncc3Cl)cc2C1=O)N1CCc2ncncc2C1]

HATU (0.079 g, 0.21 mmol) was added to a mixture of 2-(6-{5-chloro-2-[(oxan-4-yl)amino]pyrimidin-4-yl}-1-oxo-2,3-dihydro-1H-isoindol-2-yl)acetic acid (Example 1) (0.08 g, 0.20 mmol), 5,6,7,8-tetrahydropyrido[4,3-d]pyrimidine (0.028 g, 0.21 mmol) and DIPEA (0.036 mL, 0.21 mmol) in DMF (1 mL) and the mixture was stirred for 1 h. 5,6,7,8-tetrahydropyrido[4,3-d]pyrimidine (8.05 mg, 0.060 mmol) followed by HATU (0.023 g, 0.060 mmol) were added and the mixture was stirred for a further 2.75 h. Further portions of 5,6,7,8-tetrahydropyrido[4,3-d]pyrimidine (0.081 g, 0.60 mmol), HATU (0.079 g, 0.21 mmol) and DIPEA (0.139 ml, 0.79 mmol) were added and the mixture was stirred for a further 1.5 h, then diluted with EtOAc and transferred into a separating funnel. 1N HCl was added and the crude product was extracted with EtOAc. The combined organic extracts were washed with saturated aqueous NaHCO$_3$, brine, then dried (MgSO$_4$). The acidic aqueous layer was basified to pH 8-9 by the addition of 2N NaOH and the crude product was extracted with EtOAc. The combined organic extracts were washed with brine, dried (MgSO$_4$) and absorbed on silica. The crude product was purified by chromatography (SiO$_2$, 0-10% MeOH in DCM) to afford a colourless solid. The product was dissolved in MeOH and loaded on a column packed with SCX. The column was washed with MeOH and the compound eluted with 1% NH$_3$ in MeOH to afford a colourless solid. The solid was dissolved in DCM (and few drops MeOH) and the solution was filtered through cotton wool. The filtrate was concentrated under vacuum to afford the title compound (0.022 g, 20%) as a colourless solid. 1H NMR (400 MHz, DMSO-d6, VT T=350K) 8.96 (s, 1H), 8.64 (s, 1H), 8.42 (s, 1H), 8.08 (dd, 1H), 8.01 (dd, 1H), 7.74 (dd, 1H), 7.28 (d (br), 1H), 4.78 (s (br), 2H), 4.61 (m, 4H), 3.92-4.03 (m, 1H), 3.86-3.92 (m, 4H), 3.38-3.86 (m, 2H), 3.00 (s, 2H), 1.85-1.93 (m, 2H), 1.53-1.64 (m, 2H). LC-MS: [M+H]$^+$=520.

Example 89: 2-(6-{5-chloro-2-[(oxan-4-yl)amino]pyrimidin-4-yl}-1-oxo-2,3-dihydro-1H-isoindol-2-yl)-N-(1,2,3,4-tetrahydronaphthalen-2-yl)acetamide

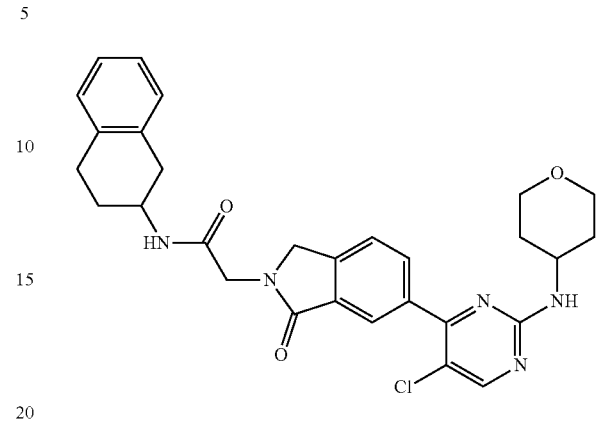

HATU (0.079 g, 0.21 mmol) was added to a mixture of 2-(6-{5-chloro-2-[(oxan-4-yl)amino]pyrimidin-4-yl}-1-oxo-2,3-dihydro-1H-isoindol-2-yl)acetic acid (Example 1) (0.08 g, 0.20 mmol), 1,2,3,4-tetrahydronaphthalen-2-amine (0.031 g, 0.21 mmol) and DIPEA (0.036 mL, 0.21 mmol) in DMF (1 mL) and the mixture was stirred for 30 minutes. The resulting thick suspension was diluted with 1N HCl and the precipitate was filtered, washed successively with water, NaHCO$_3$, water and dried under suction. The resulting solid was dried in a vacuum oven at 40° C. overnight to afford the title compound (0.096 g, 90%) as a colourless solid. 1H NMR (400 MHz, DMSO-d6) 8.45 (s, 1H), 8.25 (d, 1H), 8.04 (d, 1H), 7.99 (dd, 1H), 7.76 (d, 1H), 7.62 (s (br), 1H), 7.05-7.12 (m, 4H), 4.62 (s, 2H), 4.23 (s, 2H), 3.84-4.05 (m, 4H), 3.34-3.42 (m, 2H), 2.98 (dd, 1H), 2.78-2.90 (m, 2H), 2.67 (dd, 1H), 1.92-2.00 (m, 1H), 1.80-1.90 (m, 2H), 1.64-1.75 (m, 1H), 1.47-1.59 (m, 2H). LC-MS: [M+H]$^+$=532.

Example 90: 2-(6-{5-chloro-2-[(oxan-4-yl)amino]pyrimidin-4-yl}-1-oxo-2,3-dihydro-1H-isoindol-2-yl)-N-(2,3-dihydro-1H-inden-1-yl)acetamide

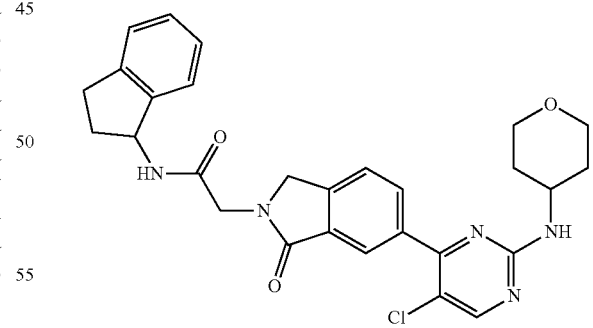

Prepared according to Example 2 using diisopropylethylamine as base and DMF as solvent. In this case, the product obtained after purification by chromatography was dissolved in EtOAc and further washed successively with 1N HCl, water, saturated aqueous NaHCO$_3$, brine, then dried (MgSO$_4$), filtered and concentrated under vacuum. 1H NMR (400 MHz, DMSO-d6) 8.54 (d, 1H), 8.45 (s, 1H), 8.04 (d, 1H), 7.98 (dd, 1H), 7.76 (d, 1H), 7.62 (s (br), 1H), 7.18-7.27 (m, 4H), 5.34 (dd, 1H), 4.64 (s, 2H), 4.27 (s, 2H), 3.83-3.98 (m, 3H), 3.36-3.42 (m, 2H), 2.94 (ddd, 1H), 2.77-2.85 (m, 1H), 2.36-2.44 (m, 1H), 1.79-1.89 (m, 3H), 1.48-1.58 (m, 2H). LC-MS: [M+H]⁺=518.

Example 91: 6-{5-chloro-2-[(oxan-4-yl)amino]pyrimidin-4-yl}-2-{2-oxo-2-[8-(trifluoro methyl)-1,2,3,4-tetrahydroisoquinolin-2-yl]ethyl}-2,3-dihydro-1H-isoindol-1-one

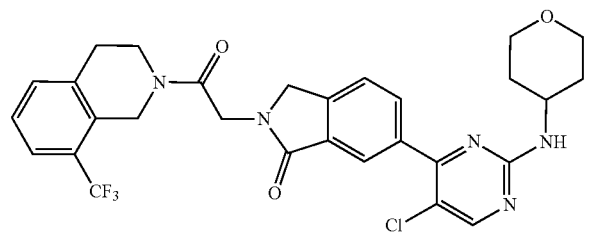 [SMILES: O=C(CN1Cc2ccc(-c3nc(NC4CCOCC4)ncc3Cl)cc2C1=O)N1CCc2cccc(C(F)(F)F)c2C1]

Prepared according to Example 2 using diisopropylethylamine as base and DMF as solvent. In this case, the product obtained after purification by chromatography was dissolved in EtOAc and further washed successively with 1N HCl, water, saturated aqueous NaHCO₃, brine, then dried (MgSO₄), filtered and concentrated under vacuum. 1H NMR (400 MHz, DMSO-d6, VT T=350K) 8.41 (s, 1H), 8.07 (d, 1H), 8.01 (dd, 1H), 7.73 (dd, 1H), 7.61 (d, 1H), 7.54 (d, 1H), 7.44 (m, 1H), 7.28 (d, 1H), 4.86 (s, 2H), 4.61 (s, 2H), 4.58 (s, 2H), 3.92-4.02 (m, 1H), 3.88 (m, 2H), 3.82 (m, 2H), 3.43 (dd, 1H), 3.40 (dd, 1H), 1.85-1.92 (m, 2H), 1.53-1.64 (m, 2H) (2 protons overlapped with water peak). LC-MS: [M+H]⁺=586.

Example 92: N-[2-(tert-butylamino)ethyl]-2-(6-{5-chloro-2-[(oxan-4-yl)amino]pyrimidin-4-yl}-1-oxo-2,3-dihydro-1H-isoindol-2-yl)acetamide

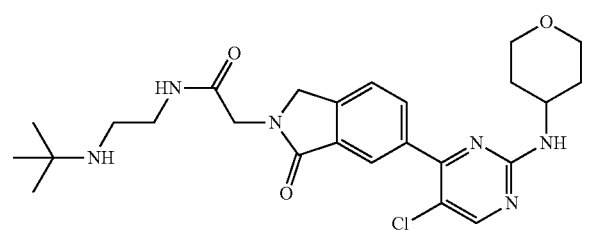 [SMILES: CC(C)(C)NCCNC(=O)CN1Cc2ccc(-c3nc(NC4CCOCC4)ncc3Cl)cc2C1=O]

A mixture of tert-butyl N-{2-[N-tert-butyl-2-(6-{5-chloro-2-[(oxan-4-yl)amino]pyrimidin-4-yl}-1-oxo-2,3-dihydro-1H-isoindol-2-yl)acetamido]ethyl}carbamate (Preparation 60, 63 mg, 0.105 mmol) in formic acid (1 mL) was stirred for 3 h. The solution was added dropwise to a stirred aqueous solution of sodium carbonate (3 g, 28.3 mmol) in water (20 mL) and extracted with ethyl acetate (20 mL then 2×10 mL). The combined organic extracts were washed with brine (20 ml), dried (Na₂SO₄), filtered and evaporated. The residue was purified by chromatography (SiO₂, 4 g column, 0-5% of 7M methanolic ammonia solution in dichloromethane) to give the title compound (30 mg, 56%) as a colourless foam and not the expected N-tert-butyl-2-(6-{5-chloro-2-[(oxan-4-yl)amino]pyrimidin-4-yl}-1-oxo-2,3-dihydro-1H-isoindol-2-yl)-N-(2-aminoethyl)acetamide. 1H NMR (400 MHz, DMSO-d6) 8.44 (s, 1H), 8.05 (t, 1H), 8.05-8.00 (m, 1H), 7.98 (dd, 1H), 7.74 (d, 1H), 7.60 (s, 1H), 4.59 (s, 2H), 4.18 (s, 2H), 3.97-3.81 (m, 3H), 3.41-3.32 (m, 2H), 3.11 (m, 2H), 2.55-2.51 (m, 2H), 1.84 (d, 2H), 1.62-1.32 (m, 3H), 1.00 (s, 9H). LC-MS: [M+H]⁺=501.

Example 93: N-tert-butyl-2-(6-{5-chloro-2-[(oxan-4-yl)amino]pyrimidin-4-yl}-1-oxo-2,3-dihydro-1H-isoindol-2-yl)-N-(2-hydroxyethyl)acetamide

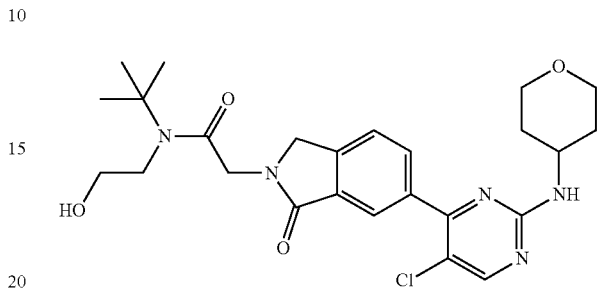

1M TBAF in THF (70.1 µl, 0.070 mmol) was added to a solution of N-tert-butyl-N-{2-[(tert-butyldimethylsilyl)oxy]ethyl}-2-(6-{5-chloro-2-[(oxan-4-yl)amino]pyrimidin-4-yl}-1-oxo-2,3-dihydro-1H-isoindol-2-yl)acetamide (Preparation 61, 36 mg, 0.058 mmol) in anhydrous THF (1 mL) at 0° C. The reaction mixture was allowed to warm to RT and stirred for 1 h. The reaction mixture was partitioned between EtOAc (15 mL) and water (15 mL) and the organic layer was washed with brine (15 mL), dried (MgSO₄), filtered and concentrated under vacuum to give the crude product (46 mg). The crude product was purified by chromatography (SiO₂, 0-10% MeOH in EtOAc) to give a colourless glass, which was triturated with diethyl ether and dried to afford the title compound (13 mg, 44%) as a colourless solid. 1H NMR (400 MHz, DMSO-d6) 8.45 (s, 1H), 8.02-8.01 (br m, 1H), 7.97 (dd, 1H), 7.74 (d, 1H), 7.62 (br s, 1H), 5.00 (t, 1H), 4.53 (d, 4H), 3.99-3.84 (m, 3H), 3.61-3.56 (m, 2H), 3.47-3.34 (m, 4H), 1.86-1.83 (br m, 2H), 1.57-1.47 (m, 2H), 1.37 (s, 9H). LC-MS: [M+H]⁺=502.

Example 94: 2-(6-{5-chloro-2-[(oxan-4-yl)amino]pyrimidin-4-yl}-1-oxo-2,3-dihydro-1H-isoindol-2-yl)-N-(2-cyclopropylpropan-2-yl)-N-methylacetamide

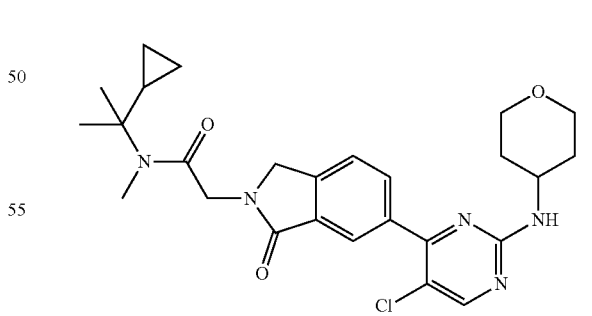

Prepared according to Example 2. Following purification by chromatography (SiO₂), the product was further purified by preparative HPLC (Varian, Basic (0.1% Ammonium Bicarbonate), Basic, Waters X-Bridge Prep-C18, 5 µm, 19×50 mm column, 20-50% MeCN in Water). 1H NMR (400 MHz, CDCl3) 8.30 (s, 1H), 8.28 (d, 1H), 7.96 (dd, 1H), 7.53 (d, 1H), 5.16 (d, 1H), 4.62 (s, 2H), 4.42 (s, 2H), 4.06-3.96 (m, 3H), 3.56-3.51 (m, 2H), 3.09 (s, 3H), 2.07-2.02 (m, 2H), 1.60-1.50 (m, 2H), 1.31 (s, 6H), 1.27-1.23 (m, 1H), 0.53-0.48 (m, 2H), 0.41-0.37 (m, 2H). LC-MS: [M+H]$^+$=498.

Example 95: N-tert-butyl-2-(3-{5-chloro-2-[(oxan-4-yl)amino]pyrimidin-4-yl}-5-oxo-5H,6H,7H-pyrrolo[3,4-b]pyridin-6-yl)-N-methylacetamide

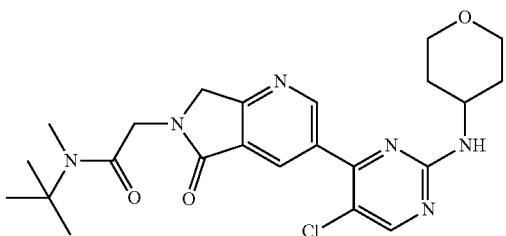 [SMILES: CN(C(=O)CN1Cc2ncc(-c3nc(NC4CCOCC4)ncc3Cl)cc2C1=O)C(C)(C)C]

N,2-dimethylpropan-2-amine (0.015 mL, 0.13 mmol), DIPEA (0.035 mL, 0.2 mmol) followed by HATU (52 mg, 0.14 mmol) were added to a stirred solution of 2-(3-{5-chloro-2-[(oxan-4-yl)amino]pyrimidin-4-yl}-5-oxo-5H,6H,7H-pyrrolo[3,4-b]pyridin-6-yl)acetic acid (Preparation 9) (41 mg, 0.088 mmol) in DMF (2 mL) and the resulting solution was stirred at room temperature for 1.5 h. The reaction mixture was partitioned between ethyl acetate (30 mL) and a saturated solution of NH$_4$Cl (20 mL). The layers were separated and the organic phase was washed with NH$_4$Cl (20 mL), water (2×20 mL), saturated NaHCO$_3$ (2×20 mL) and brine (2×20 mL). The organic phase was dried (MgSO$_4$) and concentrated under vacuum. Purification by chromatography (SiO$_2$, 0-10% methanol in DCM) gave the title compound (17 mg, 39%) as a colourless solid. 1H NMR (400 MHz, DMSO-d6) 9.10 (1H, s), 8.50 (1H, s), 8.42 (1H, d), 7.72 (1H, s), 4.58 (2H, s), 4.44 (2H, s), 4.02-3.82 (3H, m), 3.38 (2H, t), 2.93 (3H, s), 1.86 (2H, br. d), 1.53 (2H, m), 1.36 (9H, s). LC-MS: [M+H]$^+$=473.

Example 96: N-tert-butyl-2-(6-{5-chloro-2-[(oxan-4-yl)amino]pyrimidin-4-yl}-4-fluoro-1-oxo-2,3-dihydro-1H-isoindol-2-yl)-N-methylacetamide

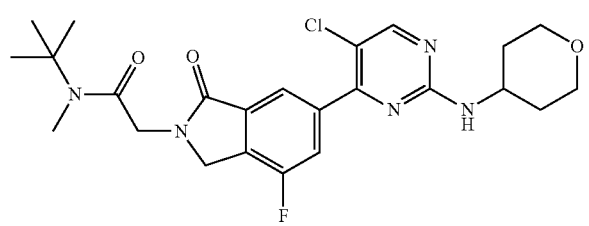 [SMILES: CN(C(=O)CN1Cc2c(F)cc(-c3nc(NC4CCOCC4)ncc3Cl)cc2C1=O)C(C)(C)C]

Diisopropylethylamine (0.11 mL, 0.64 mmol was added to a suspension of 2-(6-{5-chloro-2-[(oxan-4-yl)amino]pyrimidin-4-yl}-4-fluoro-1-oxo-2,3-dihydro-1H-isoindol-2-yl)acetic acid (Preparation 16) (90 mg, 0.21 mmol) and HATU (98 mg, 0.26 mmol) in a mixture of DCM (1.8 mL) and DMF (0.2 mL). The reaction was stirred for 5 min before N-tert-butyl-methylamine (0.028 mL, 0.24 mmol) was added. The mixture was stirred at RT for 18 h. The mixture was diluted with ethyl acetate (10 mL) and water (15 mL). The phases were separated and the aqueous phase was extracted with ethyl acetate (2×10 mL). The combined organic phases were washed with hydrochloric acid (1 M, 50 mL), saturated aqueous sodium bicarbonate (50 mL), brine (3×50 mL), dried (MgSO$_4$) and concentrated under vacuum. Purification by chromatography (SiO$_2$, 0-5% methanol in DCM) gave the title compound (72 mg, 67%) as a colourless solid. 1H NMR (400 MHz, DMSO-d6) 8.47 (1H, s), 7.91 (1H, d), 7.82 (1H, dd), 7.67 (1H, s), 4.60 (2H, s), 4.40 (2H, s), 3.98-3.89 (1H, m), 3.86 (2H, d), 3.43-3.34 (2H, m), 2.92 (3H, s), 1.84 (2H, d), 1.60-1.46 (2H, m), 1.35 (9H, s). LC-MS: [M+H]$^+$=490.

Example 97: N-tert-butyl-N-methyl-2-(6-{2-[(oxan-4-yl)amino]-5-(trifluoromethyl)pyrimidin-4-yl}-1-oxo-2,3-dihydro-1H-isoindol-2-yl)acetamide

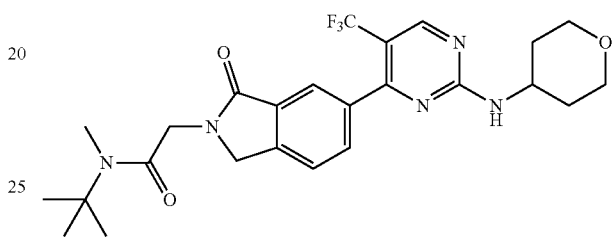

A stirred solution of 2-(6-{2-[(oxan-4-yl)amino]-5-(trifluoromethyl)pyrimidin-4-yl}-1-oxo-2,3-dihydro-1H-isoindol-2-yl)acetic acid (Preparation 19) (73 mg, 0.17 mmol) in DCM (2.7 mL) and DMF (0.3 mL), was treated with triethylamine (70 μL, 0.50 mmol), N-tert-butyl-methylamine (21 μL, 0.17 mmol) and HATU (70 mg, 0.18 mmol). After 2 h the mixture was diluted with ethyl acetate (30 mL) and washed with 1 M hydrochloric acid (30 mL), saturated aqueous sodium bicarbonate (30 mL), water (30 mL), brine (30 mL), dried (MgSO$_4$) and concentrated under vacuum. Purification by chromatography (SiO$_2$, 0-10% methanol in ethyl acetate) gave a glass, which was triturated with diethyl ether, and dried to give the title compound (46 mg, 54%) as a colourless solid. 1H NMR (400 MHz, DMSO-d6) 8.72-8.67 (1H, m), 8.23 (1H, dd), 7.76-7.72 (3H, m), 4.53 (2H, s), 4.39 (2H, s), 4.11-3.81 (3H, m), 3.43-3.31 (2H, m), 2.92 (3H, s), 1.89-1.80 (2H, br. m), 1.62-1.49 (2H, m), 1.35 (9H, s). LC-MS: [M+H]$^+$=506.

Example 98: N-tert-butyl-2-(5-{5-chloro-2-[(oxan-4-yl)amino]pyrimidin-4-yl}-1-(hydroxymethyl)-3-oxo-2,3-dihydro-1H-isoindol-2-yl)-N-methylacetamide

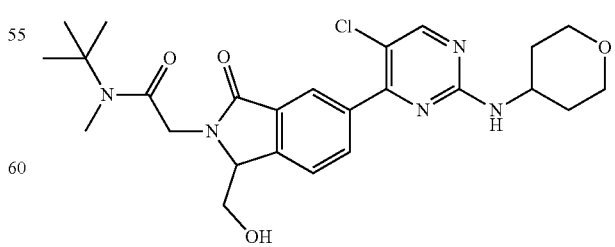

Trifluoroacetic acid (0.12 mL, 1.5 mmol) was added to a solution of N-tert-butyl-2-(5-{5-chloro-2-[(oxan-4-yl)amino]pyrimidin-4-yl}-3-oxo-1-{[2-(trimethylsilyl)ethoxy]

methyl}-2,3-dihydro-1H-isoindol-2-yl)-N-methylacetamide (Preparation 27, 50 mg, 0.075 mmol, 90% purity) in DCM (0.9 mL) at 0° C. The reaction was allowed to warm to RT and stirred for 1.5 h. The mixture was added to ice cold saturated aqueous sodium bicarbonate solution (20 mL) and extracted with DCM (2×15 mL). The combined organic phases were combined and dried (MgSO$_4$) and concentrated under vacuum. Preparative HPLC (acidic method, 20-50% MeCN) gave the title compound (13 mg, 34%) as a colourless solid. 1H NMR (400 MHz, DMSO-d6) 8.45 (1H, s), 8.03-7.95 (2H, m), 7.80 (1H, d), 7.60 (1H, d), 5.00 (1H, t), 4.69 (1H, t), 4.57 (1H, d), 4.28 (1H, d), 4.00-3.81 (5H, m), 3.43-3.34 (2H, m), 2.95 (3H, s), 1.85 (2H, d), 1.60-1.47 (2H, m), 1.36 (9H, s). LC-MS: [M+H]$^+$=502.

Example 99: 2-(5-{5-chloro-2-[(oxan-4-yl)amino]pyrimidin-4-yl}-1-(hydroxymethyl)-3-oxo-2,3-dihydro-1H-isoindol-2-yl)-N-methylacetamide

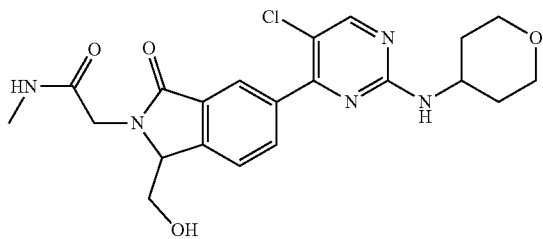 [SMILES: CNC(=O)CN1C(=O)c2cc(-c3nc(NC4CCOCC4)ncc3Cl)ccc2C1CO]

The title compound was obtained as a side-product of Example 98 (6 mg, 18%) as a colourless solid. 1H NMR (400 MHz, DMSO-d6) 8.45 (1H, s), 8.14 (1H, d), 8.02-7.96 (2H, m), 7.79 (1H, d), 7.60 (1H, d), 5.14 (1H, dd), 4.75 (1H, t), 4.34 (1H, d), 4.07 (1H, d), 3.91 (5H, m), 3.38 (2H, t), 2.63 (3H, d), 1.85 (2H, d), 1.53 (2H, m). LC-MS: [M+H]$^+$=446.

Example 100: 2-(5-{5-chloro-2-[(oxan-4-yl)amino]pyrimidin-4-yl}-1-(hydroxymethyl)-3-oxo-2,3-dihydro-1H-isoindol-2-yl)-N-cyclopentylacetamide

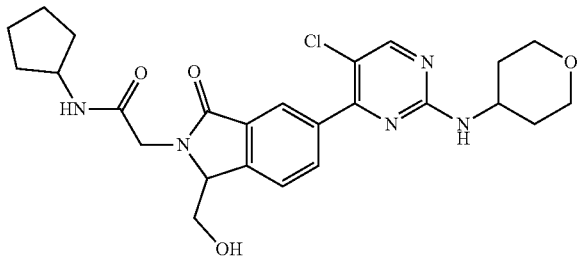 [SMILES: O=C(CN1C(=O)c2cc(-c3nc(NC4CCOCC4)ncc3Cl)ccc2C1CO)NC1CCCC1]

A solution of lithium hydroxide (1 M aqueous, 0.24 mL, 0.24 mmol) was added to a stirred solution of methyl 2-(5-{5-chloro-2-[(oxan-4-yl)amino]pyrimidin-4-yl}-3-oxo-1-{[2-(trimethylsilyl)ethoxy]methyl}-2,3-dihydro-1H-isoindol-2-yl)acetate (Preparation 26, 130 mg, 0.24 mmol) in THF (3.5 mL) and water (1 mL). The resulting mixture was stirred at RT for 2 h. The reaction mixture was diluted with ethyl acetate (10 mL) and water (5 mL). The phases were separated and the aqueous phase was acidfied with 1 M hydrochloric acid to pH ~3. The resultant colourless precipitate was collected by filtration, washing with water (5 mL) and dried under vacuum. The residue was suspended in DCM (4 mL). HATU (108 mg, 0.285 mmol) and diisopropylethylamine (0.048 mL, 0.27 mmol) were added. The mixture was stirred for 5 min, before cyclopentylamine (0.026 mL, 0.26 mmol) was added. The mixture was stirred at RT for 2 h before being diluted with ethyl acetate (10 mL) and water (10 mL). The phases were separated and the aqueous phase was extracted with ethyl acetate (2×10 mL). The combined organic phases were washed with 1 M hydrochloric acid (20 mL), saturated aqueous sodium bicarbonate (20 mL), brine (3×10 mL), dried (MgSO$_4$) and concentrated under vacuum. The residue was dissolved in DCM (3 mL) and trifluoroacetic acid (0.37 mL, 4.8 mmol) was added. The mixture was stirred at RT for 18 h. The solvent was removed under vacuum and the residue was dissolved in methanol (0.9 mL). Potassium carbonate (99 mg, 0.71 mmol) was added and the mixture was stirred at RT for 3 h. The reaction mixture was concentrated under vacuum and redissolved in water (10 mL) and 10% methanol in DCM (10 mL). The phases were separated and the aqueous phase was extracted with 10% methanol in DCM (2×10 mL). The combined organic phases were dried (MgSO$_4$) and concentrated under vacuum. The resulting solid was recrystallised from hot ethanol (~5 mL). The resultant solid was filtered, rinsing with ethanol (2 mL) to give the title compound (60 mg, 50%) as a colourless solid. 1H NMR (DMSO-d6, 400 MHz) 8.45 (1H, s), 8.20 (1H, d), 8.05-7.91 (2H, m), 7.79 (1H, d), 7.59 (1H, d), 4.75 (1H, t), 4.32 (1H, d), 4.08 (1H, d), 3.98-3.82 (5H, m), 3.55-3.30 (3H, m), 1.91-1.75 (5H, m), 1.72-1.60 (2H, m), 1.60-1.34 (6H, m). LC-MS: [M+H]$^+$=500.

Example 101: N-tert-butyl-2-(5-{5-chloro-2-[(oxan-4-yl)amino]pyrimidin-4-yl}-1-methyl-3-oxo-2,3-dihydro-1H-isoindol-2-yl)-N-methylacetamide

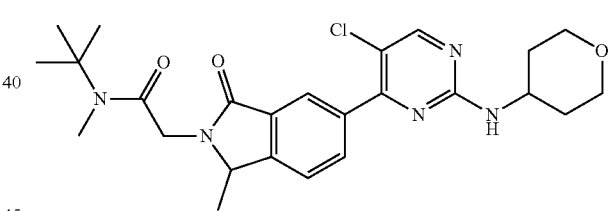

Trifluoroacetic acid (0.05 mL, 0.6 mmol) was added to a solution of tert-butyl 2-(5-{5-chloro-2-[(oxan-4-yl)amino]pyrimidin-4-yl}-1-methyl-3-oxo-2,3-dihydro-1H-isoindol-2-yl)acetate (Preparation 32, 20 mg, 0.042 mmol) in DCM (0.5 mL). The mixture was stirred at RT for 5 h. The solvent was removed under vacuum and the residue was azeotroped with toluene (3×5 mL), then diethyl ether (5 mL). The residue was dissolved in a DMF (0.5 mL). N-tert-butyl-methylamine (0.005 mL, 0.04 mmol) was added, followed by diisopropylethylamine (0.015 mL, 0.084 mmol) and HATU (16 mg, 0.042 mmol) and the mixture was stirred at RT for 45 min. The reaction was diluted with ethyl acetate (5 mL) and 1 M hydrochloric acid (5 mL). The phases were separated and the aqueous phase was extracted with ethyl acetate (2×5 mL). The combined organic phases were washed with saturated aqueous sodium bicarbonate solution (5 mL), brine (5 mL), dried (MgSO$_4$) and absorbed onto silica. Purification by chromatography (SiO$_2$, 0-3% methanol in DCM) gave the title compound (15 mg, 75%) as a colourless solid. 1H NMR (400 MHz, DMSO-d6) 8.45 (1H, s), 8.01 (1H, br. s), 7.99 (1H, dd), 7.77 (1H, d), 7.60 (1H, br.

d), 4.70 (1H, qt), 4.57 (1H, d), 4.11 (1H, d), 3.93 (1H, m), 3.86 (2H, m) 3.37 (2H, m), 2.94 (3H, s), 1.84 (2H, m), 1.52 (2H, m), 1.44 (3H, d), 1.34 (9H, s). LC-MS: [M+H]⁺=486.

Example 102: 6-{5-chloro-2-[(oxan-4-yl)amino]pyrimidin-4-yl}-2-[(3-methyloxetan-3-yl)methyl]-2,3-dihydro-1H-isoindol-1-one

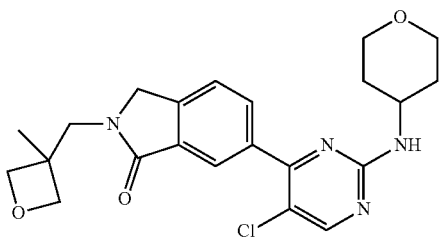 [SMILES: CC1(CN2Cc3ccc(-c4nc(NC5CCOCC5)ncc4Cl)cc3C2=O)COC1]

A stirred solution of 6-(2,5-dichloropyrimidin-4-yl)-2-[(3-methyloxetan-3-yl)methyl]-2,3-dihydro-1H-isoindol-1-one (Preparation 53, 249 mg, 0.684 mmol) and diisopropylethylamine (0.36 mL, 2.1 mmol) in 1,4-dioxane (10 mL) was treated with oxan-4-amine (0.21 mL, 2.1 mmol) and stirred at 80° C. for 18 h. The mixture was allowed to cool, was diluted with brine (20 mL) and extracted with ethyl acetate (2×20 mL). The combined organic phases were washed with brine (20 mL), dried (Na₂SO₄) and concentrated under vacuum. Purification by chromatography (SiO₂, 50-100% ethyl acetate in iso-hexane) gave the title compound (106 mg, 36%) as a cream powder. 1H NMR (400 MHz, DMSO-d6): 8.44 (1H, s), 8.02 (1H, dd), 7.97 (1H, dd), 7.72 (1H, d), 7.60 (1H, s), 4.60-4.52 (4H, m), 4.30 (2H, d), 3.99-3.81 (3H, m), 3.79 (2H, s), 3.43-3.33 (2H, m), 1.84 (2H, d), 1.59-1.45 (2H, m), 1.24 (3H, s). LC-MS: [M+H]⁺=429.

Examples 103-107

Prepared following similar/analogous methods to Example 102.

| Example | Structure | Name | ¹H NMR (400 MHz) | MS: [M + H]⁺ |
|---|---|---|---|---|
| 103 | 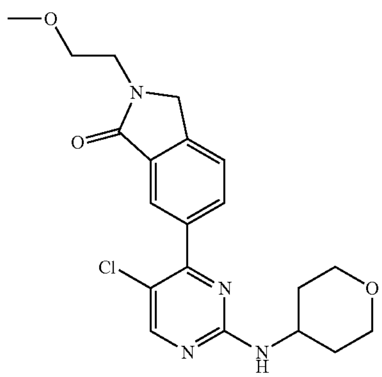 [SMILES: COCCN1Cc2ccc(-c3nc(NC4CCOCC4)ncc3Cl)cc2C1=O] | 6-{5-chloro-2-[(oxan-4-yl)amino]pyrimidin-4-yl}-2-(2-methoxyethyl)-2,3-dihydro-1H-isoindol-1-one | (CDCl₃): 8.30 (2H, m), 7.97 (1H, dd), 7.54 (1H, d), 5.15 (1H, br. d), 4.60 (2H, s), 4.05 (1H, m), 3.99 (2H, dt), 3.83 (2H, t), 3.66 (2H, t), 3.55 (2H, dt), 3.37 (3H, s), 2.05 (2H, m), 1.56 (2H, m). | 403 |
| 104 | 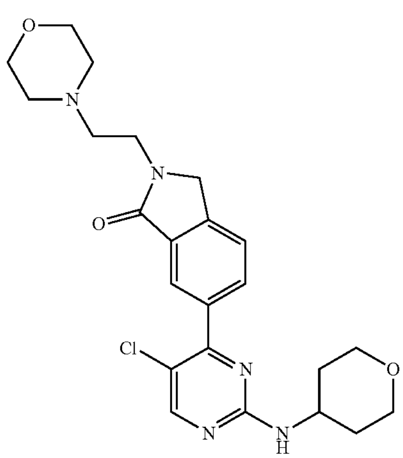 [SMILES: O=C1c2cc(-c3nc(NC4CCOCC4)ncc3Cl)ccc2CN1CCN1CCOCC1] | 6-{5-chloro-2-[(oxan-4-yl)amino]pyrimidin-4-yl}-2-[2-(morpholin-4-yl)ethyl]-2,3-dihydro-1H-isoindol-1-one | (DMSO-d6) 8.45 (1H, br. s), 8.01 (1H, s), 7.97 (1H, dd), 7.74 (1H, d), 7.61 (1H, br. s), 4.64 (2H, s), 3.86-3.96 (3H, m), 3.68 (2H, m), 3.56 (4H, m), 3.39 (2H, m), 2.57 (2H, m), 2.44 (4H, m), 1.85 (2H, m), 1.53 (2H, ddd). | 458 |

-continued

| Example | Structure | Name | ¹H NMR (400 MHz) | MS: [M + H]⁺ |
|---|---|---|---|---|
| 105 | 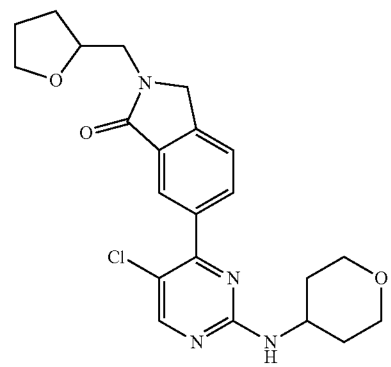 [SMILES: O=C1c2cc(-c3nc(NC4CCOCC4)ncc3Cl)ccc2CN1CC1CCCO1] | 6-{5-chloro-2-[(oxan-4-yl)amino]pyrimidin-4-yl}-2-[(oxolan-2-yl)methyl]-2,3-dihydro-1H-isoindol-1-one | (DMSO-d6): 8.45 (1H, br. s), 8.02 (1H, d), 7.96 (1H, dd), 7.74 (1H, d), 7.61 (1H, br. s), 4.68 (1H, d), 4.61 (1H, d), 4.08 (1H, m), 3.84-3.96 (3H, m), 3.80 (1H, dd), 3.66 (2H, m), 3.55 (1H, dd), 3.39 (2H, m), 1.93-2.01 (1H, m), 1.84 (4H, m), 1.48-1.62 (3H, m). | 429 |
| 106 | 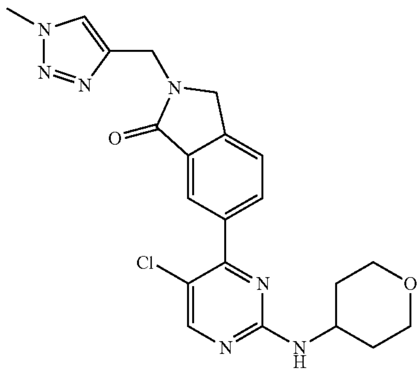 [SMILES: Cn1cc(CN2Cc3ccc(-c4nc(NC5CCOCC5)ncc4Cl)cc3C2=O)nn1] | 6-{5-chloro-2-[(oxan-4-yl)amino]pyrimidin-4-yl}-2-[(1-methyl-1H-1,2,3-triazol-4-yl)methyl]-2,3-dihydro-1H-isoindol-1-one | DMSO-d6): 8.44 (1H, s), 8.04 (1H, s), 8.02 (1H, dd), 7.96 (1H, dd), 7.72 (1H, d), 7.60 (1H, s), 4.80 (2H, s), 4.55 (2H, s), 4.01 (3H, s), 3.97-3.80 (3H, m), 3.41-3.33 (2H, m), 1.84 (2H, d), 1.59-1.46 (2H, m). | 440 |
| 107 | 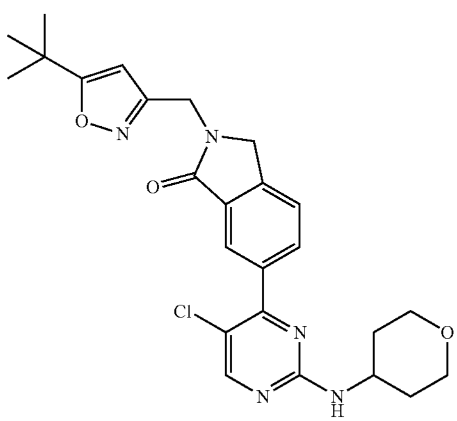 [SMILES: CC(C)(C)c1cc(CN2Cc3ccc(-c4nc(NC5CCOCC5)ncc4Cl)cc3C2=O)no1] | 2-[(5-tert-butyl-1,2-oxazol-3-yl)methyl]-6-{5-chloro-2-[(oxan-4-yl)amino]pyrimidin-4-yl}-2,3-dihydro-1H-isoindol-1-one | DMSO-d6): 8.44 (1H, s), 8.04 (1H, dd), 7.98 (1H, dd), 7.74 (1H, d), 7.60 (1H, d), 6.22 (1H, s), 4.79 (2H, s), 4.59 (2H, s), 3.97-3.83 (3H, m), 3.41-3.33 (2H, m), 1.84 (2H, d), 1.52 (2H, qd), 1.27 (9H, s). | 482 |

Example 108: 6-{5-chloro-2-[(oxan-4-yl)amino]pyrimidin-4-yl}-2-[2-(oxolan-2-yl)ethyl]-2,3-dihydro-1H-isoindol-1-one

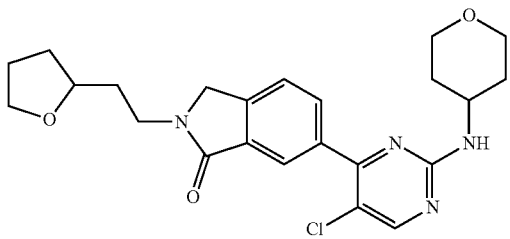 [SMILES: O=C1c2cc(-c3nc(NC4CCOCC4)ncc3Cl)ccc2CN1CCC1CCCO1]

Prepared according to the procedure for Example 102. The reaction was carried out in 1,4-dioxane, 60° C. for 18 h in this case. 1H NMR (400 MHz, CDCl$_3$) 8.32 (1H, s), 8.27 (1H, d), 7.96 (1H, dd), 7.54 (1H, dd), 5.15 (1H, d), 4.49 (2H, s), 4.07-3.96 (3H, m), 3.90-3.85 (2H, m), 3.77-3.70 (3H, m), 3.54 (2H, td), 2.07-2.02 (3H, m), 1.95-1.87 (4H, m), 1.61-1.49 (3H, m). LC-MS: [M+H]$^+$=443.

Example 109: 6-{5-chloro-2-[(oxan-4-yl)amino]pyrimidin-4-yl}-2-(2-hydroxypropyl)-2,3-dihydro-1H-isoindol-1-one

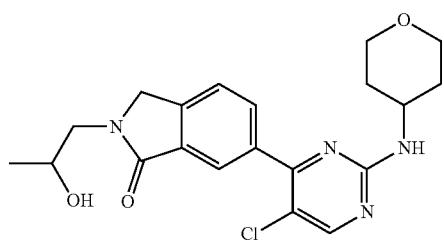 [SMILES: CC(O)CN1Cc2ccc(-c3nc(NC4CCOCC4)ncc3Cl)cc2C1=O]

Prepared according to the procedure for Example 102. The reaction was carried out in 1,4-dioxane, 80° C. for 18 h. 1H NMR (400 MHz, DMSO-d6): 8.44 (1H, s), 8.00 (1H, dd), 7.95 (1H, dd), 7.73 (1H, d), 7.60 (1H, s), 4.88 (1H, d), 4.65 (2H, d), 4.00-3.77 (4H, m), 3.55-3.33 (4H, m), 1.84 (2H, d), 1.52 (2H, qd), 1.08 (3H, d). LC-MS: [M+H]$^+$=403.

Example 110: 2-[2-(tert-butoxy)ethyl]-6-{5-chloro-2-[(oxan-4-yl)amino]pyrimidin-4-yl}-2,3-dihydro-1H-isoindol-1-one

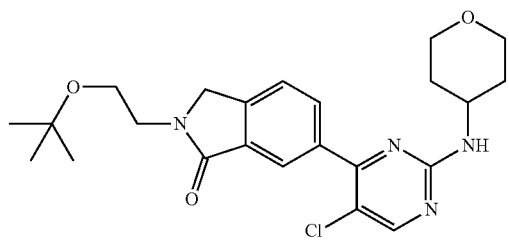 [SMILES: CC(C)(C)OCCN1Cc2ccc(-c3nc(NC4CCOCC4)ncc3Cl)cc2C1=O]

Prepared according to the procedure for Example 102. The reaction was carried out in 1:1 EtOH:dioxane at 80° C. for 18 h. 1H NMR (400 MHz, DMSO-d6): 8.45 (1H, s), 8.02 (1H, d), 7.96 (1H, dd), 7.74 (1H, d), 7.61 (1H, br. s), 4.64 (2H, s), 3.83-3.97 (3H, m), 3.65 (2H, t), 3.56 (2H, t), 3.35-3.40 (2H, m), 1.81-1.89 (2H, m), 1.47-1.58 (2H, m), 1.13 (9H, s). LC-MS: [M+H]$^+$=445.

Example 111: 6-{5-chloro-2-[(oxan-4-yl)amino]pyrimidin-4-yl}-2-[2-(2-oxopyrrolidin-1-yl)ethyl]-2,3-dihydro-1H-isoindol-1-one

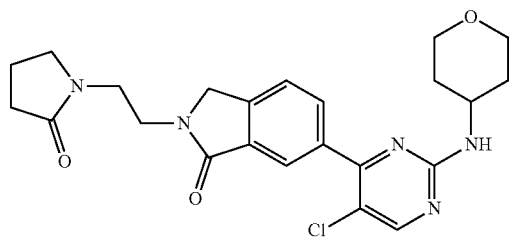 [SMILES: O=C1CCCN1CCN1Cc2ccc(-c3nc(NC4CCOCC4)ncc3Cl)cc2C1=O]

Prepared according to the procedure for Example 102. The reaction was carried out in 1,4-dioxane at 60° C. for 2 days. 1H NMR (400 MHz, CDCl3): 8.31 (1H, s), 8.24 (1H, d), 7.96 (1H, dd), 7.54 (1H, d), 5.16 (1H, d), 4.56 (2H, s), 4.07-3.96 (3H, m), 3.85-3.82 (2H, m), 3.64-3.61 (2H, m), 3.57-3.51 (4H, m), 2.25-2.21 (2H, m), 2.07-1.96 (4H, m), 1.61-1.54 (2H, m). LC-MS: [M+H]$^+$=456.

Example 112: 6-{5-chloro-2-[(oxan-4-yl)amino]pyrimidin-4-yl}-2-[2-(cyclopentyloxy)ethyl]-2,3-dihydro-1H-isoindol-1-one

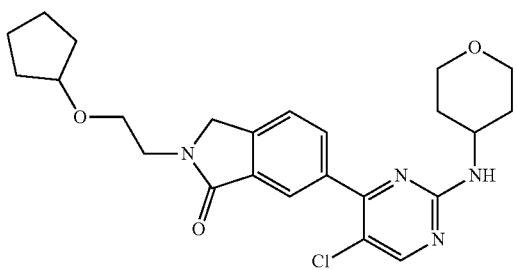 [SMILES: O=C1c2cc(-c3nc(NC4CCOCC4)ncc3Cl)ccc2CN1CCOC1CCCC1]

Prepared according to the procedure for Example 102. The reaction was carried out in 1:1 EtOH:dioxane at 80° C. for 18 h. Further oxan-4-amine (1.5 equ.) and DIPEA (2.55 equ.) were added after 18 h and the mixture was stirred for a further 24 h. 1H NMR (400 MHz, DMSO-d6): 8.45 (1H, s), 8.01 (1H, dd), 7.96 (1H, dd), 7.75 (1H, d), 7.67-7.52 (1H, m), 4.61 (2H, s), 3.98-3.81 (4H, m), 3.68 (2H, t), 3.58 (2H, t), 3.42-3.34 (2H, m), 1.85 (2H, br. d), 1.71-1.39 (10H, m). LC-MS: [M+H]$^+$=457.

Example 113: 6-{5-chloro-2-[(oxan-4-yl)amino]pyrimidin-4-yl}-2-[(pyrrolidin-2-yl)methyl]-2,3-dihydro-1H-isoindol-1-one

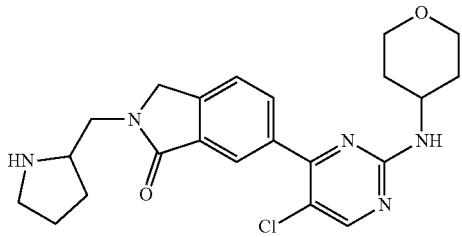 [SMILES: O=C1c2cc(-c3nc(NC4CCOCC4)ncc3Cl)ccc2CN1CC1CCCN1]

A stirred solution of tert-butyl 2-[(6-{5-chloro-2-[(oxan-4-yl)amino]pyrimidin-4-yl}-1-oxo-2,3-dihydro-1H-isoindol-2-yl)methyl]pyrrolidine-1-carboxylate (Preparation 163, 35 mg, 0.066 mmol) in dichloromethane (1 mL) was treated with TFA (1 mL) and stirred for 30 min. The solution was concentrated and the residue was partitioned between ethyl acetate (5 mL) and saturated aqueous sodium bicarbonate solution (5 mL). The phases were separated and the aqueous phase was extracted with ethyl acetate (2×5 mL). The combined organic phases were washed with brine (5 mL), dried (Na$_2$SO$_4$) and concentrated. Purification by chromatography (SiO$_2$, 0-10% 7M methanolic ammonia solution in dichloromethane) gave the title compound (21 mg, 73%) as a colourless foam. 1H NMR (400 MHz, DMSO-d6): 8.44 (1H, s), 8.00 (1H, d), 7.95 (1H, dd), 7.72 (1H, d), 7.60 (1H, s), 4.77-4.52 (2H, m), 3.97-3.81 (3H, m), 3.56 (1H, dd), 3.45-3.35 (4H, m), 2.87-2.69 (2H, m), 1.90-1.31 (9H, m). LC-MS: [M+H]$^+$=428.

Example 114: 6-{5-chloro-2-[(oxan-4-yl)amino]pyrimidin-4-yl}-2-[(5-methyl-1,2,4-oxadiazol-3-yl)methyl]-2,3-dihydro-1H-isoindol-1-one

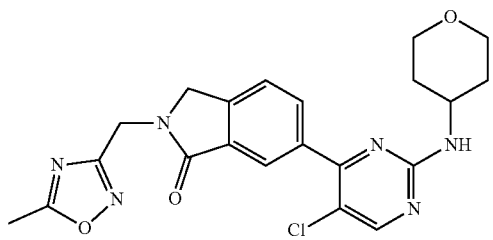 [SMILES: Cc1nc(CN2Cc3ccc(-c4nc(NC5CCOCC5)ncc4Cl)cc3C2=O)no1]

A stirred solution of 6-(5-chloro-2-{[(2,4-dimethoxyphenyl)methyl](oxan-4-yl)amino}pyrimidin-4-yl)-2-[(5-methyl-1,2,4-oxadiazol-3-yl)methyl]-2,3-dihydro-1H-isoindol-1-one (11 mg, 0.019 mmol) in dichloromethane (1 mL) was treated with TFA (1 mL) and stirred for 30 min. The mixture was concentrated under vacuum and dissolved in ethyl acetate (5 mL), washed with saturated aqueous sodium bicarbonate solution (5 mL), brine (5 mL) and was filtered through a phase-separating cartridge, then concentrated. Purification by chromatography (SiO$_2$, 0-5% methanol in dichloromethane) gave the title compound (5.7 mg, 68%) as a yellow powder. 1H NMR (400 MHz, DMSO-d6): 8.45 (1H, s), 8.04 (1H, d), 7.99 (1H, dd), 7.76 (1H, d), 7.63 (1H, s), 4.89 (2H, s), 4.63 (2H, s), 3.98-3.82 (3H, m), 3.43-3.28 (2H, m), 2.57 (3H, s), 1.88-1.80 (2H, m), 1.59-1.45 (2H, m). LC-MS: [M+H]$^+$=441.

Examples 115-117

Prepared following a similar/analogous procedure to that described above for Example 114.

Example 115: 6-{5-chloro-2-[(oxan-4-yl)amino]pyrimidin-4-yl}-2-[(3-methyl-1,2-oxazol-5-yl)methyl]-2,3-dihydro-1H-isoindol-1-one

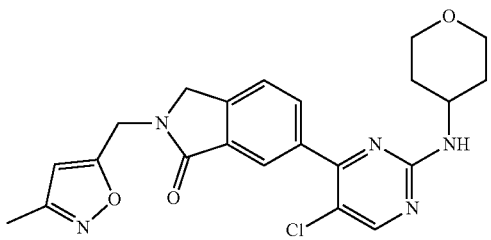 [SMILES: Cc1cc(CN2Cc3ccc(-c4nc(NC5CCOCC5)ncc4Cl)cc3C2=O)on1]

In this case, the product was purified by reverse phase preparative HPLC on a Waters XSelect CSH C18 OBD, 130 Å, 5 µm, 19 mm×50 mm column, using a gradient of 25 to 45% of acetonitrile in water with 0.1% fomic acid in both at 28 ml/min as eluent, followed by evaporation of the clean fractions and azeoptroping successively with MeCN and diethyl ether. 1H NMR (400 MHz, DMSO-d6): 8.44 (1H, s), 8.05 (1H, d), 7.99 (1H, dd), 7.74 (1H, d), 7.61 (1H, s), 6.35 (1H, s), 4.89 (2H, s), 4.59 (2H, s), 3.96-3.80 (3H, m), 3.43-3.28 (2H, m), 2.20 (3H, s), 1.89-1.79 (2H, m), 1.60-1.44 (2H, m). LC-MS: [M+H]$^+$=440.

Example 116: 6-{5-chloro-2-[(oxan-4-yl)amino]pyrimidin-4-yl}-2-[(5-methyl-1,2-oxazol-3-yl)methyl]-2,3-dihydro-1H-isoindol-1-one

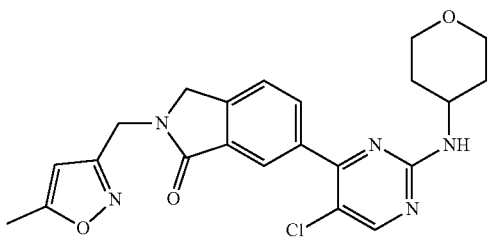 [SMILES: Cc1cc(CN2Cc3ccc(-c4nc(NC5CCOCC5)ncc4Cl)cc3C2=O)no1]

1H NMR (400 MHz, DMSO-d6): 8.44 (1H, s), 8.04 (1H, d), 7.98 (1H, dd), 7.73 (1H, d), 7.62 (1H, s), 6.21 (1H, d), 4.78 (2H, s), 4.56 (2H, s), 3.98-3.82 (3H, m), 3.41-3.34 (2H, m), 2.37 (3H, d), 1.84 (2H, d), 1.60-1.43 (2H, m). LC-MS: [M+H]$^+$=440.

Example 117: 6-{5-chloro-2-[(oxan-4-yl)amino]pyrimidin-4-yl}-2-[2-(1,2,3,4-tetrahydroisoquinolin-2-yl)ethyl]-2,3-dihydro-1H-isoindol-1-one

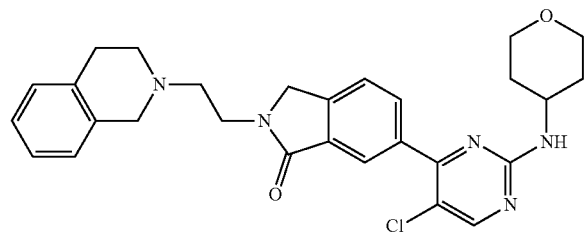 [SMILES: O=C1c2cc(-c3nc(NC4CCOCC4)ncc3Cl)ccc2CN1CCN1CCc2ccccc2C1]

1H NMR (400 MHz, DMSO-d6): 8.44 (1H, s), 8.00 (1H, dd), 7.94 (1H, dd), 7.72 (1H, d), 7.60 (1H, s), 7.13-7.00 (4H, m), 4.65 (2H, s), 3.98-3.82 (3H, m), 3.78 (2H, t), 3.66 (2H, s), 3.41-3.34 (2H, m), 2.83-2.71 (6H, m), 1.88-1.78 (2H, m), 1.59-1.43 (2H, m). LC-MS: [M+H]⁺=504.

Example 118: N-tert-butyl-2-(6-{5-chloro-2-[(oxan-4-yl)amino]pyrimidin-4-yl}-1-oxo-2,3-dihydro-1H-isoindol-2-yl)-N,2-dimethylpropanamide

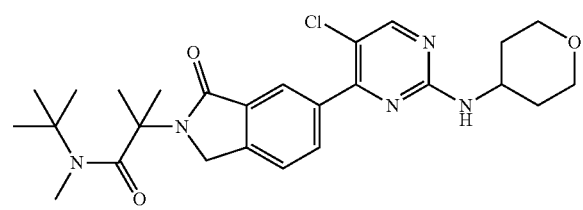 [SMILES: CN(C(=O)C(C)(C)N1Cc2ccc(-c3nc(NC4CCOCC4)ncc3Cl)cc2C1=O)C(C)(C)C]

The product was prepared following an analogous/similar procedure as described in Example 2. In this case, after 1 h, further N,2-dimethylpropan-2-amine (1.2 equ.) was added and the reaction was left stirring overnight. Additional N,2-dimethylpropan-2-amine (1.2 equ.), and HATU (1.1 equ.) were added and the mixture stirred for 4 hours. A final 1.2 equivalents of N,2-dimethylpropan-2-amine (1.2 equ.) were added and the reaction was stirred overnight. 1H NMR (400 MHz, DMSO-d6): 8.44 (s, 1H), 7.98 (s, 1H), 7.97 (d, 1H), 7.74 (d, 1H), 7.59 (d, 1H), 4.71 (s, 2H), 3.91-3.85 (m, 3H), 3.40-3.37 (m, 2H), 2.66 (s, 3H), 1.85-1.82 (m, 2H), 1.53-1.47 (m, 8H), 1.34 (s, 9H). LC-MS: [M+H]⁺=500.

Example 119: (2R)—N-tert-butyl-2-(6-{5-chloro-2-[(oxan-4-yl)amino]pyrimidin-4-yl}-1-oxo-2,3-dihydro-1H-isoindol-2-yl)-N-methylpropanamide

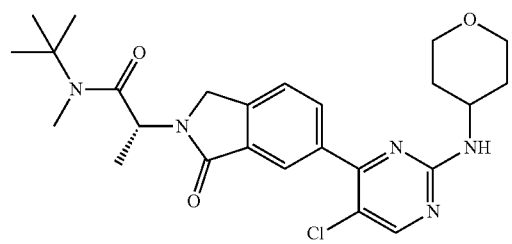 [SMILES: C[C@H](C(=O)N(C)C(C)(C)C)N1Cc2ccc(-c3nc(NC4CCOCC4)ncc3Cl)cc2C1=O]

The product was prepared following an analogous/similar procedure as described in Example 2. 1H NMR (400 MHz, DMSO-d6): 8.44 (1H, s), 8.04-8.00 (1H, m), 7.97 (1H, dd), 7.76 (1H, d), 7.61 (1H, br. s), 5.26 (1H, q), 4.60 (1H, d), 4.52 (1H, d), 3.98-3.79 (3H, m), 3.43-3.30 (2H, m), 2.91 (3H, s), 1.89-1.78 (2H, m), 1.60-1.45 (2H, m), 1.36-1.32 (12H, m). LC-MS: [M+H]⁺=486. Note: The product may have partially epimerized during the reaction as shown by chiral HPLC analysis of the final product.

Example 120: N-tert-butyl-2-(6-{5-chloro-2-[(oxan-4-yl)amino]pyrimidin-4-yl}-1-oxo-2,3-dihydro-1H-isoindol-2-yl)-3-hydroxy-N-methylpropanamide

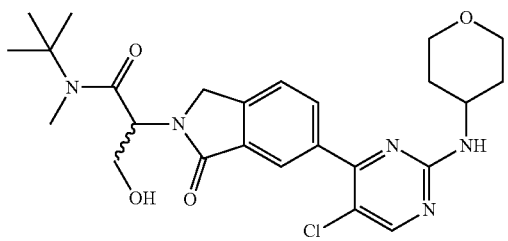 [SMILES: CN(C(=O)C(CO)N1Cc2ccc(-c3nc(NC4CCOCC4)ncc3Cl)cc2C1=O)C(C)(C)C]

TBAF (1M in THF, 0.055 mL, 0.055 mmol) was added to a solution of (2S)—N-tert-butyl-3-[(tert-butyldimethylsilyl)oxy]-2-(6-{5-chloro-2-[(oxan-4-yl)amino]pyrimidin-4-yl}-1-oxo-2,3-dihydro-1H-isoindol-2-yl)-N-methylpropanamide (Preparation 164, 28 mg, 0.045 mmol) in THF (0.5 mL) and the mixture was stirred for 1 h. The reaction was quenched by the addition of saturated aqueous NaHCO₃ and water and the mixture was diluted with ethyl acetate, then transferred into a separating funnel. The crude product was extracted with ethyl acetate and the combined organic extracts were washed with brine, dried (MgSO₄), filtered and absorbed on silica. Purification by chromatography (SiO₂, 0-10% MeOH in DCM) gave the title compound (13 mg, 55%) as a colourless solid. 1H NMR (400 MHz, DMSO-d6): 8.46 (1H, s), 8.03 (1H, d), 7.98 (1H, dd), 7.78 (1H, d), 7.63 (1H, br. s), 5.24 (1H, dd), 7.93 (1H, t), 4.61 (2H, s), 3.71-3.97 (5H, m), 3.36-3.41 (2H, m), 2.97 (3H, s), 1.85 (2H, m), 1.53 (2H, m), 1.35 (9H, s). LC-MS: [M+H]⁺= 502.

Example 121: 6-{5-chloro-2-[(oxan-4-yl)amino]pyrimidin-4-yl}-2-(1-methyl-2-oxopiperidin-3-yl)-2,3-dihydro-1H-isoindol-1-one

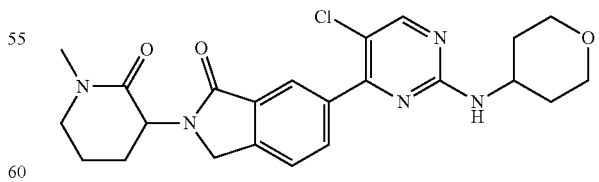

A mixture of 2,4,5-trichloropyrimidine (0.13 mL, 1.17 mmol), 2-(1-methyl-2-oxopiperidin-3-yl)-6-(4,4,5,5-tetramethyl-1,3,2-dioxaborolan-2-yl)-2,3-dihydro-1H-isoindol-1-one (Preparation 109) (288 mg, 0.78 mmol) and potassium carbonate (215 mg, 1.56 mmol) in 1,4-dioxane (2 mL) and water (0.6 mL) was degassed with nitrogen for 10 mins.

Tetrakis(triphenylphosphine)palladium(0) (45 mg, 0.039 mmol) was added and the reaction was heated to 100° C. for 1 h. The mixture cooled to RT and diluted with ethyl acetate (20 mL) and water (20 mL). The phases were separated and the aqueous phase was extracted with ethyl acetate (2×20 mL). The combined organic phases were washed with brine (25 mL), dried (MgSO$_4$) and concentrated under vacuum. The residue was dissolved in 1,4-dioxane (5 mL) and oxan-4-amine (0.14 mL, 1.4 mmol) and diisopropylethylamine (0.30 mL, 1.70 mmol) were added. The mixture was heated to 90° C. for 18 h. The reaction was diluted with water (10 mL) and ethyl acetate (10 mL). The aqueous phase was extracted with ethyl acetate (2×10 mL). The combined organic phases were washed with 1 M hydrochloric acid (25 mL). The acidic aqueous phase was basified with 2 M sodium hydroxide solution to pH 8 and extracted with ethyl acetate (3×20 mL). The combined organic phases were washed with brine (25 mL), dried (MgSO$_4$) and concentrated under vacuum. Purification by chromatography (SiO$_2$, 0-10% methanol in DCM) gave the title compound (80 mg, 25%) as a pale yellow foam. 1H NMR (400 MHz, DMSO-d6) 8.45 (1H, s), 8.02 (1H, dd), 7.97 (1H, dd), 7.72 (1H, d), 7.63 (1H, s), 4.75 (1H, dd), 4.54 (1H, d), 4.32 (1H, d), 3.98-3.78 (3H, m), 3.41-3.33 (4H, m), 2.85 (3H, s), 2.18-2.04 (1H, m), 2.04-1.93 (3H, m), 1.84 (2H, d), 1.52 (2H, qd). LC-MS: [M+H]$^+$=456.

Example 122:2-(1-tert-butyl-2-oxopyrrolidin-3-yl)-6-{5-chloro-2-[(oxan-4-yl)amino]pyrimidin-4-yl}-2,3-dihydro-1H-isoindol-1-one

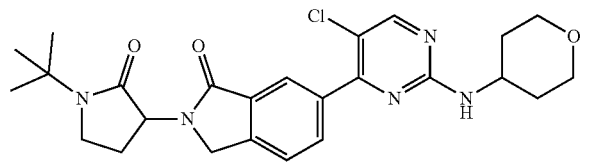 [SMILES: CC(C)(C)N1CCC(N2Cc3ccc(-c4nc(NC5CCOCC5)ncc4Cl)cc3C2=O)C1=O]

Prepared according to Example 121 from 2-(1-tert-butyl-2-oxopyrrolidin-3-yl)-6-(4,4,5,5-tetramethyl-1,3,2-dioxaborolan-2-yl)-2,3-dihydro-1H-isoindol-1-one (Preparation 108) (150 mg, 0.38 mmol). The title compound (96 mg, 50%) was obtained as a pale yellow foam. 1H NMR (400 MHz, DMSO-d6) 8.45 (1H, s), 8.03 (1H, dd), 7.98 (1H, dd), 7.75 (1H, d), 7.64 (1H, s), 4.94 (1H, dd), 4.62 (1H, d), 4.31 (1H, d), 3.99-3.81 (3H, m), 3.59-3.51 (1H, m), 3.49-3.34 (3H, m), 2.30-2.20 (1H, m), 2.15-2.00 (1H, m), 1.84 (2H, d), 1.54 (2H, dt), 1.37 (9H, s). LC-MS: [M+H]$^+$=484.

Example 123:6-{5-chloro-2-[(oxan-4-yl)amino]pyrimidin-4-yl}-2-[(5-methyl-4H-1,2,4-triazol-3-yl)methyl]-2,3-dihydro-1H-isoindol-1-one

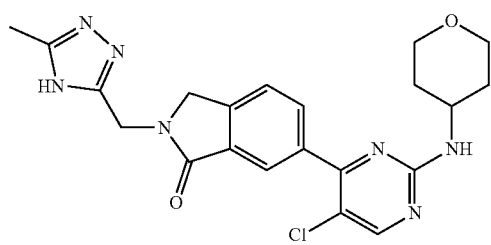 [SMILES: Cc1nnc(CN2Cc3ccc(-c4nc(NC5CCOCC5)ncc4Cl)cc3C2=O)[nH]1]

Triethylamine (0.065 mL, 0.47 mmol), ammonium acetate (120 mg, 1.55 mmol) and silica gel (120 mg) were added to a solution of 2-(6-{5-chloro-2-[(oxan-4-yl)amino]pyrimidin-4-yl}-1-oxo-2,3-dihydro-1H-isoindol-2-yl)acetohydrazide (Preparation 111) (66 mg, 0.16 mmol) and methyl ethanimidothioate hydroiodide (36 mg, 0.16 mmol) in DMF (2 mL). The reaction was heated at 120° C. for 2.5 h. The reaction was cooled to RT, diluted with ethyl acetate (20 mL) and filtered through celite. The filtrate was washed with water (20 mL) and brine (2×20 mL) then dried (MgSO$_4$) and concentrated under vacuum. Purification by chromatography (SiO$_2$, 0-10% methanol in ethyl acetate) to give a colourless glass, which was triturated with diethyl ether and dried to give the title compound (36 mg, 52%) as a colourless solid. 1H NMR (400 MHz, DMSO-d6) 13.50 (1H, s), 8.44 (1H, s), 8.03 (1H, d), 7.97 (1H, dd), 7.73 (1H, d), 7.61 (1H, br. s), 4.74 (2H, s), 4.59 (2H, s), 3.97-3.85 (3H, m), 3.37 (2H, t), 2.29 (3H, s), 1.84 (2H, br. d), 1.57-1.47 (2H, m). LC-MS: [M+H]$^+$=440.

Example 124:6-{2-[(1-methyl-1H-pyrazol-5-yl)amino]pyrimidin-4-yl}-2,3-dihydro-1H-isoindol-1-one

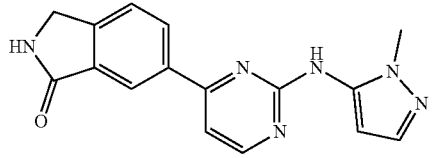 [SMILES: Cn1nccc1Nc1nccc(-c2ccc3c(c2)C(=O)NC3)n1]

A stirred mixture of 4-chloro-N-(1-methyl-1H-pyrazol-5-yl)pyrimidin-2-amine (Preparation 113) (250 mg, 1.19 mmol, 70% pure), 6-(4,4,5,5-tetramethyl-1,3,2-dioxaboroan-2-yl)-2,3-dihydro-1H-isoindol-1-one (Preparation 63) (773 mg, 2.39 mmol), K$_2$CO$_3$ (330 mg, 2.39 mmol) and 1,4-dioxane:water (3:1, 4 mL) was degassed with nitrogen for 5 minutes. Pd(PPh$_3$)$_4$ (68 mg, 0.06 mmol) was then added and the reaction heated under nitrogen at 90° C. for a total of 24 hours. After cooling to room temperature the mixture was diluted with water and extracted with EtOAc (×3). The combined organic layers were washed with brine, dried over MgSO, filtered and concentrated under vacuum. The residue was purified by preparative HPLC to yield 6-{2-[(1-methyl-1H-pyrazol-5-yl)amino]pyrimidin-4-yl}-2,3-dihydro-1H-isoindol-1-one (46 mg, 12%). $^1$H NMR (400 MHz, Me-d$_3$-OD): 8.54 (1H, d), 8.51 (1H, d), 8.40 (1H, dd), 7.73 (1H, dd), 7.48-7.45 (2H, m), 6.39 (1H, d), 4.56 (2H, s), 3.80 (3H, s). MS: [M+H]$^+$=307. Examples 125-135 Prepared from the corresponding boronate ester and substituted 4-chloropyrimidine using an analogous procedure to Example 124:

| Example | Structure | Name | ¹H NMR (400 MHz) | MS: [M + H]⁺ |
|---|---|---|---|---|
| 125 | 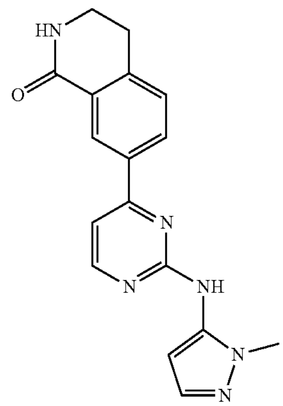 [SMILES: Cn1nccc1Nc1nccc(-c2ccc3c(c2)C(=O)NCC3)n1] | 7-{2-[(1-methyl-1H-pyrazol-5-yl)amino]pyrimidin-4-yl}-1,2,3,4-tetrahydroisoquinolin-1-one | (Me-d$_3$-OD): 8.71 (1H, d), 8.48 (1H, d), 8.26 (1H, dd), 7.48-7.45 (2H, m), 7.42 (1H, d), 6.38 (1H, d), 3.79 (3H, s), 3.56 (2H, t), 3.09 (2H, t). | 321 |
| 126 | 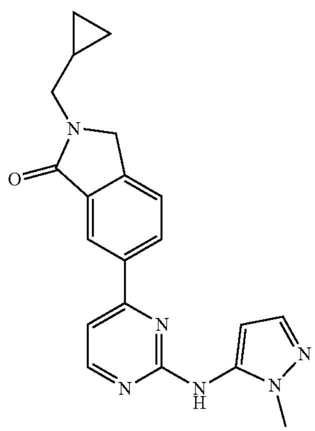 [SMILES: Cn1nccc1Nc1nccc(-c2ccc3c(c2)C(=O)N(CC2CC2)C3)n1] | 2-(cyclopropyl methyl)-6-{2-[(1-methyl-1H-pyrazol-5-yl)amino]pyrimidin-4-yl}-2,3-dihydro-1H-isoindol-1-one | (Me-d$_3$-OD): 8.52-8.50 (2H, m), 8.38 (1H, dd), 7.73 (1H, dd), 7.48 (1H, d), 7.46 (1H, d), 6.39(1H, d), 4.72 (2H, s), 3.80 (3H, s), 3.54 (2H, d), 1.20-1.11 (1H, m), 0.68-0.60 (2H, m), 0.44-0.37 (2H, m). | 361 |
| 127 | 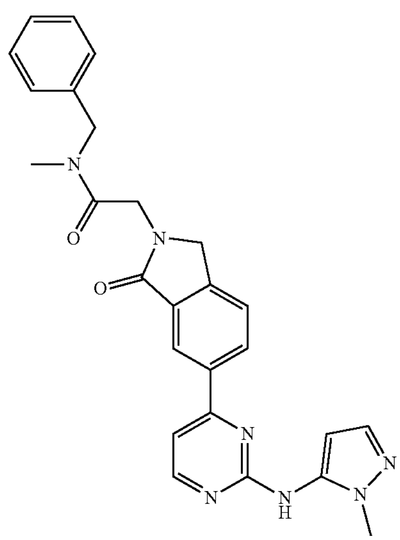 [SMILES: CN(Cc1ccccc1)C(=O)CN1Cc2ccc(-c3ccnc(Nc4ccnn4C)n3)cc2C1=O] | N-benzyl-N-methyl-2-(6-{2-[(1-methyl-1H-pyrazol-5-yl)amino]pyrimidin-4-yl}-1-oxo-2,3-dihydro-1H-isoindol-2-yl)acetamide | (Me-d$_3$-OD): 8.55 (0.6H, d), 8.51 (1.4H, dd), 8.42-8.37 (1H, m), 7.73 (1H, t), 7.52-7.26 (8H, m), 6.39 (1H, d), 4.73 (0.7H, s), 4.70 (1.3H, s), 4.67-4.63 (4H, m), 3.80 (3H, s), 3.09 (2H, s), 2.98 (1H, s). | 468 |

-continued

| Example | Name | ¹H NMR (400 MHz) | MS: [M + H]⁺ |
|---------|------|------------------|--------------|
| 128 | 6-{5-chloro-2-[(oxan-4-yl)amino]pyrimidin-4-yl}-2,3-dihydro-1H-isoindol-1-one | (Me-d₃-OD): 8.36 (1H, s), 8.24 (1H, s), 8.08 (1H, dd), 7.72 (1H, d), 4.57 (2H, s), 4.12-4.02 (1H, m), 4.02-3.93 (2H, m), 3.59-3.51 (2H, m), 2.02 (2H, dd), 1.69-1.57 (2H, m). | 345 |
| 129 | N-methyl-2-(6-{2-[(1-methyl-1H-pyrazol-5-yl)amino]pyrimidin-4-yl}-1-oxo-2,3-dihydro-1H-isoindol-2-yl)-N-(2-phenylethyl) acetamide | (Me-d3-OD): 8.55-8.48 (2H, m), 8.42-8.35 (1H, m), 7.70 (1H, dd), 7.49-7.43 (2H, m), 7.41-7.36 (1H, m), 7.34-7.19 (4H, m), 6.39 (1H, dd), 4.58 (1H, s), 4.52 (1H, s), 4.35 (1H, s), 4.14 (1H, s), 3.80 (1.7H, s), 3.79 (1.3H, s), 3.71 (1H, t), 3.64 (1H, t), 3.07-2.99 (4H, m), 2.89 (1H, t). | 482 |
| 130 | 6-{5-chloro-2-[(1,5-dimethyl-1H-pyrazol-4-yl)amino]pyrimidin-4-yl}-2,3-dihydro-1H-isoindol-1-one | (DMSO-d₆): 9.05 (1H, s), 8.68 (1H, s), 8.49 (1H, s), 8.03 (1H, s), 7.99 (1H, d), 7.73 (1H, d), 7.50 (1H, s), 4.47 (2H, s), 3.71 (3H, s), 2.18 (3H, s). | 355 |

| Example | Structure | Name | $^1$H NMR (400 MHz) | MS: [M + H]$^+$ |
|---|---|---|---|---|
| 131 | 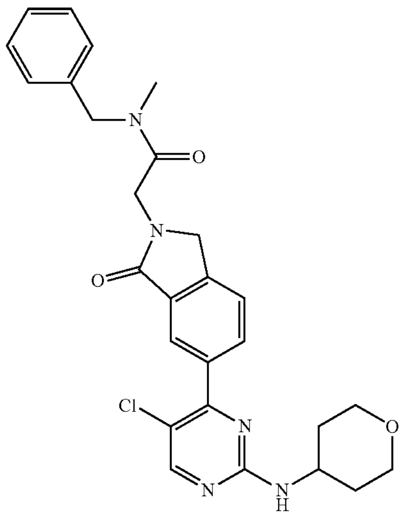 [SMILES: CN(Cc1ccccc1)C(=O)CN1Cc2ccc(-c3nc(NC4CCOCC4)ncc3Cl)cc2C1=O] | N-benzyl-2-(6-{5-chloro-2-[(oxan-4-yl)amino]pyrimidin-4-yl}-1-oxo-2,3-dihydro-1H-isoindol-2-yl)-N-methylacetamide | (Me-d$_3$-OD): 8.35 (1H, s), 8.24 (1H, d), 8.13-8.03 (1H, m), 7.76-7.60 (1H, m), 7.44-7.27 (5H, m), 4.72 (2H, d), 4.68-4.63 (4H, m), 4.12-4.02 (1H, m), 3.98 (2H, dt), 3.54 (2H, dt), 3.09 (2H, s), 2.98 (1H, s), 2.01 (2H, d), 1.70-1.56 (2H, m). | 504 |
| 132 | 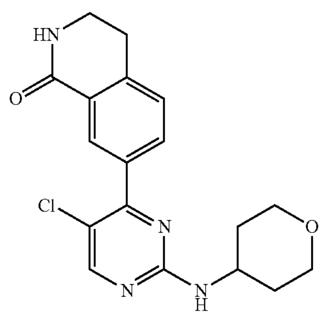 [SMILES: O=C1NCCc2ccc(-c3nc(NC4CCOCC4)ncc3Cl)cc21] | 7-{5-chloro-2-[(oxan-4-yl)amino]pyrimidin-4-yl}-1,2,3,4-tetrahydroisoquinolin-1-one | (DMSO-d$_6$): 8.42 (1H, s), 8.26 (1H, d), 8.01 (1H, s), 7.86 (1H, dd), 7.59-7.51 (1H, m), 7.45 (1H, d), 3.99-3.83 (3H, m), 3.45-3.37 (4H, m), 2.99 (2H, t), 1.89-1.80 (2H, m), 1.60-1.47 (2H, m). | 359 |
| 133 | 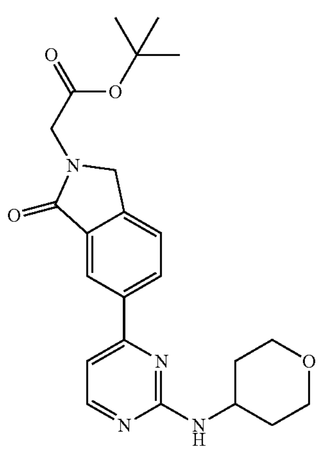 [SMILES: CC(C)(C)OC(=O)CN1Cc2ccc(-c3ccnc(NC4CCOCC4)n3)cc2C1=O] | tert-butyl 2-(6-{2-[(oxan-4-yl)amino] pyrimidin-4-yl}-1-oxo-2,3-dihydro-1H-isoindol-2-yl)acetate | (CDCl$_3$): 8.48 (1H, s), 8.37 (1H, d), 8.29 (1H, dd), 7.57 (1H, d), 7.06 (1H, d), 4.60 (2H, s), 4.34 (2H, s), 4.24-4.12 (1H, m), 4.07-3.98 (2H, m), 3.66-3.55 (2H, m), 2.11 (2H, d), 1.69-1.55 (2H, m), 1.50 (9H, s). | 425 |

| Example | Structure | Name | ¹H NMR (400 MHz) | MS: [M + H]⁺ |
|---|---|---|---|---|
| 134 | 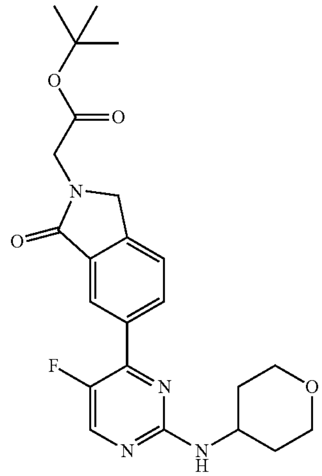 [SMILES: CC(C)(C)OC(=O)CN1Cc2ccc(-c3nc(NC4CCOCC4)ncc3F)cc2C1=O] | tert-butyl 2-(6-{5-fluoro-2-[(oxan-4-yl)amino]pyrimidin-4-yl}-1-oxo-2,3-dihydro-1H-isoindol-2-yl)acetate | (Me-d3-OD): 8.49 (1H, s), 8.35 (1H, d), 8.31 (1H, d), 7.73 (1H, d), 4.71-4.62 (2H, m), 4.36 (2H, s), 4.16-4.04 (1H, m), 4.04-3.95 (2H, m), 3.59 (2H, t), 2.04 (2H, d), 1.71-1.57 (2H, m), 1.51 (9H, s). | 443 |
| 135 | 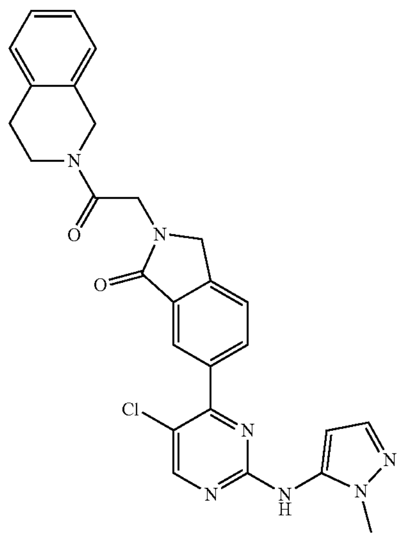 [SMILES: Cn1nccc1Nc1ncc(Cl)c(-c2ccc3c(c2)C(=O)N(CC(=O)N2CCc4ccccc4C2)C3)n1] | 6-{5-chloro-2-[(1-methyl-1H-pyrazol-5-yl)amino]pyrimidin-4-yl}-2-[2-oxo-2-(1,2,3,4-tetrahydro isoquinolin-2-yl)ethyl]-2,3-dihydro-1H-isoindol-1-one | (Me-d3-OD): 8.52 (1H, d), 8.28 (1H, s), 8.13-8.06 (1H, m), 7.42 (1H, d), 7.25-7.13 (5H, m), 6.38-6.33 (1H, m), 4.75-4.64 (6H, m), 3.83 (2H, q), 3.80-3.73 (3H, m), 3.02 (1H, t), 2.90 (1H, t). | 514 |

Example 136: 6-{5-methyl-2-[(oxan-4-yl)amino]pyrimidin-4-yl}-2,3-dihydro-1H-isoindol-1-one formate salt

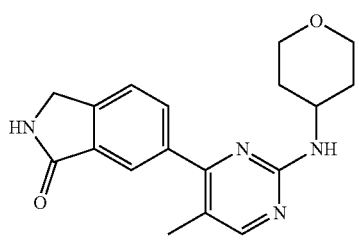 [SMILES: Cc1cnc(NC2CCOCC2)nc1-c1ccc2c(c1)C(=O)NC2]

A stirred mixture of 2,4-dichloro-5-methylpyrimidine (157 mg, 0.96 mmol), 6-(4,4,5,5-tetramethyl-1,3,2-dioxaborolan-2-yl)-2,3-dihydro-1H-isoindol-1-one (Preparation 63) (250 mg, 0.96 mmol), K₂CO₃ (266 mg, 1.93 mmol) and 1,4-dioxane:water (3:1, 3 mL) was degassed with nitrogen for 5 minutes. Pd(PPh₃)₄ (55 mg, 0.05 mmol) was then added and the mixture heated at 80° C. under nitrogen for a total of 16 hours. The reaction was allowed to cool to room temperature and then diluted with water. The mixture was extracted with EtOAc (×3) and the combined organic layers were filtered and evaporated under vacuum to yield 6-(2-chloro-5-methylpyrimidin-4-yl)-2,3-dihydro-1H-isoindol-1-one as a colourless solid. MS: [M+H]⁺=260/262. A solution of this material (50 mg, 0.19 mmol) and DIPEA (117 μL, 0.67 mmol) in anhydrous 1,4-dioxane (1.9 mL) was treated with 4-aminooxan (41 μL, 0.39 mmol) and sealed in a reacti vial. The reaction was stirred at 90° C. for 16 hours and then allowed to cool. The mixture was diluted with water and extracted with EtOAc (×3). The combined organic layers were washed with brine, dried over MgSO, filtered and concentrated under vacuum. The residue was purified by preparative HPLC to yield the title compound (7 mg, 11%) as a colourless solid. ¹H NMR (400 MHz, Me-d₃-OD): 8.23 (1H, s), 8.15 (1H, s), 8.02 (1H, d), 7.88 (1H, dd), 7.72 (1H, dd), 4.56 (2H, s), 4.12-4.02 (1H, m), 4.00 (1H, t), 3.97 (1H, t), 3.55 (2H, dt), 2.21 (3H, s), 2.06-1.98 (2H, m), 1.69-1.55 (2H, m). MS: [M+H]⁺=325.

Example 137: tert-Butyl 2-(6-{5-chloro-2-[(oxan-4-yl)amino]pyrimidin-4-yl}-1-oxo-2,3-dihydro-1H-isoindol-2-yl)acetate

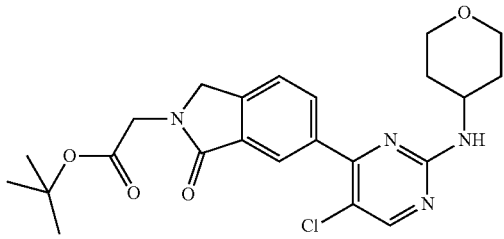 [SMILES: CC(C)(C)OC(=O)CN1Cc2ccc(-c3nc(NC4CCOCC4)ncc3Cl)cc2C1=O]

A stirred solution of tert-butyl 2-[6-(2,5-dichloropyrimidin-4-yl)-1-oxo-2,3-dihydro-1H-isoindol-2-yl]acetate (Preparation 3) (1.87 g, 6.58 mmol, ~60% pure) and DIPEA (2.865 mL, 16.44 mmol) in anhydrous 1,4-dioxane (21.9 mL) was treated with 4-aminooxan (0.998 mL, 9.86 mmol) under nitrogen. The reaction was heated to 90° C. for 16 hours. The reaction was allowed to cool, diluted with water, and extracted with EtOAc (×3). The combined organic layers were washed with brine, dried over MgSO$_4$, filtered and concentrated under vacuum. A ~100 mg portion of the residue was purified by preparative HPLC to yield the title compound as a colourless solid (63 mg). $^1$H NMR (400 MHz, Me-d$_3$-OD): 8.36 (1H, s), 8.24 (1H, d), 8.09 (1H, dd), 7.73 (1H, dd), 4.68 (2H, s), 4.37 (2H, s), 4.12-4.02 (1H, m), 4.02-3.94 (2H, m), 3.60-3.51 (2H, m), 2.05-1.97 (2H, m), 1.69-1.58 (2H, m), 1.51 (9H, s). MS: [M+H]$^+$=459.

Example 138: 3-(6-{5-Chloro-2-[(oxan-4-yl)amino]pyrimidin-4-yl}-1-oxo-2,3-dihydro-1H-isoindol-2-yl)propanoic acid

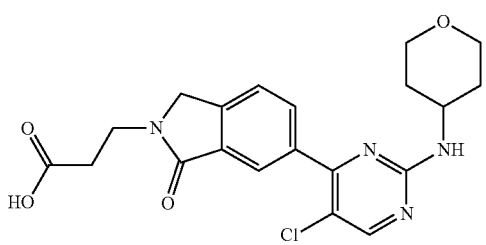 [SMILES: O=C(O)CCN1Cc2ccc(-c3nc(NC4CCOCC4)ncc3Cl)cc2C1=O]

A stirred solution of methyl 3-[6-(2,5-dichloropyrimidin-4-yl)-1-oxo-2,3-dihydro-1H-isoindol-2-yl]propanoate (Preparation 125, 550 mg, 1.50 mmol) and DIPEA (785 μL, 4.51 mol) in anhydrous 1,4-dioxane (7.5 mL) was treated with 4-aminooxan (277 μL, 1.95 mmol). The reaction was heated to 90° C. under nitrogen for 16 hours. The reaction was allowed to cool and then NaOH (3 ml, 1M) was added. The mixture was stirred at room temperature for 24 hours. The pH was adjusted to ~pH 5 with citric acid (5%, aq.) before the product was extracted with CHCl$_3$:IPA (3:1, ×2). The combined organic layers were washed with brine, dried over MgSO and concentrated under vacuum, and the residue purified by preparative HPLC to give the title compound (104 mg, 17%) as a colourless solid. $^1$H NMR (400 MHz, Me-d$_3$-OD): 8.35 (1H, s), 8.20 (1H, d), 8.05 (1H, dd), 7.70 (1H, dd), 4.68 (2H, s), 4.11-4.02 (1H, m), 4.02-3.92 (4H, m), 3.59-3.51 (2H, m), 2.71 (2H, t), 2.06-1.97 (2H, m), 1.69-1.57 (2H, m). MS: [M+H]$^+$=417.

Example 139: 6-{5-Chloro-2-[(oxan-4-yl)amino]pyrimidin-4-yl}-2-[3-oxo-3-(pyrrolidin-1-yl)propyl]-2,3-dihydro-1H-isoindol-1-one

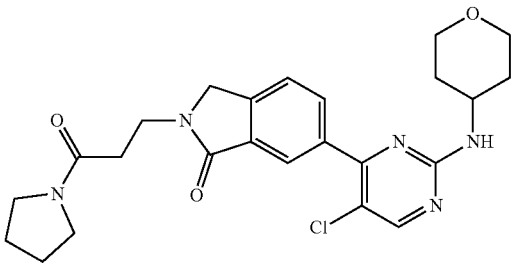 [SMILES: O=C(CCN1Cc2ccc(-c3nc(NC4CCOCC4)ncc3Cl)cc2C1=O)N1CCCC1]

A stirred solution of 3-(6-{5-chloro-2-[(oxan-4-yl)amino]pyrimidin-4-yl}-1-oxo-2,3-dihydro-1H-isoindol-2-yl)propanoic acid (Example 138) (99 mg, 0.24 mmol) in anhydrous 1,4-dioxane: DMF (3:1, 3 mL) under nitrogen was treated with DIPEA (62 μL, 0.36 mmol), HBTU (138 mg, 0.36 mmol) and then pyrrolidine (25 μL, 0.36 mmol). The reaction was stirred for 16 hours at room temperature and quenched by adding NaHCO$_3$ (aq., sat.). The product was extracted with EtOAc (×3) and the combined organic layers washed with brine, dried over MgSO$_4$, filtered and concentrated under vacuum. The residue was purified by preparative HPLC to give the title compound (69 mg, 61%) as a colourless solid. $^1$H NMR (400 MHz, Me-d$_3$-OD): 8.35 (1H, s), 8.20 (1H, d), 8.05 (1H, dd), 7.70 (1H, dd), 4.69 (2H, s), 4.10-4.03 (1H, m), 4.02-3.94 (4H, m), 3.58-3.51 (4H, m), 3.43 (2H, t), 2.81 (2H, t), 2.05-1.94 (4H, m), 1.93-1.85 (2H, m), 1.70-1.57 (2H, m). MS: [M+H]$^+$=470.

Example 140: tert-Butyl 2-(7-{5-chloro-2-[(oxan-4-yl)amino]pyrimidin-4-yl}-1-oxo-1,2,3,4-tetrahydroisoquinolin-2-yl)acetate

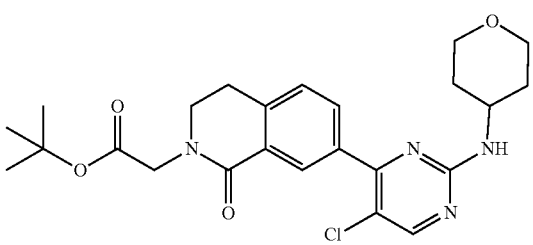 [SMILES: CC(C)(C)OC(=O)CN1CCc2ccc(-c3nc(NC4CCOCC4)ncc3Cl)cc2C1=O]

Prepared using a similar procedure to Example 137. A small portion of the crude (~40 mg) was purified by preparative HPLC to yield the title compound (7 mg) as a yellow solid. $^1$H NMR (400 MHz, Me-d$_3$-OD): 8.43 (1H, d), 8.33 (1H, s), 7.97 (1H, dd), 7.45 (1H, d), 4.28 (2H, s), 4.09-4.04 (1H, m), 3.99 (2H, dd), 3.75 (2H, t), 3.59-3.51 (2H, m), 3.17 (2H, t), 2.01 (2H, s), 1.69-1.56 (2H, m), 1.51 (9H, s). MS: [M+H]$^+$=473.

Example 141: N-tert-Butyl-2-(6-{5-chloro-2-[(oxan-4-yl)amino]pyrimidin-4-yl}-1-oxo-2,3-dihydro-1H-isoindol-2-yl)acetamide

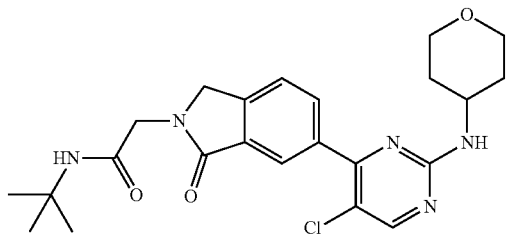 [SMILES: CC(C)(C)NC(=O)CN1Cc2ccc(-c3nc(NC4CCOCC4)ncc3Cl)cc2C1=O]

A stirred solution of 2-(6-{5-chloro-2-[(oxan-4-yl)amino]pyrimidin-4-yl}-1-oxo-2,3-dihydro-1H-isoindol-2-yl)acetic acid (Example 1, 60 mg, 0.10 mmol, 70% pure) in anhydrous 1,4-dioxane/DMF (3:1, 1.5 mL) under nitrogen was treated with DIPEA (36 μL, 0.21 mmol), HBTU (81 mg, 0.21 mmol) and then tert-butylamine (17 μL, 0.16 mmol). The reaction was stirred for 4 days at room temperature and quenched by adding water. The product was extracted with EtOAc (×3) and the combined organic layers washed with brine, dried over MgSO$_4$, filtered and concentrated under vacuum. Purification by preparative HPLC gave the title compound (32 mg, 70%) as a colourless solid. $^1$H NMR (400 MHz, Me-d$_3$-OD): 8.36 (1H, s), 8.24 (1H, d), 8.08 (1H, dd), 7.71 (1H, dd), 4.66 (2H, s), 4.28 (2H, s), 4.11-4.02 (1H, m), 4.02-3.95 (2H, m), 3.59-3.51 (2H, m), 2.05-1.97 (2H, m), 1.69-1.58 (2H, m), 1.38 (9H, s). MS: [M+H]$^+$=458.

Examples 142-158

Prepared using a similar procedure to Example 141.

| Example | Structure | Name | $^1$H NMR (400 MHz) | MS: [M + H]$^+$ |
|---------|-----------|------|---------------------|------------------|
| 142 | 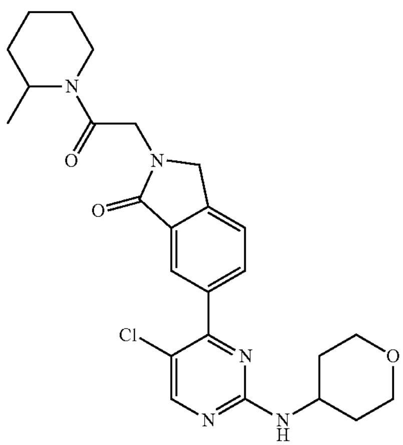 [SMILES: CC1CCCCN1C(=O)CN1Cc2ccc(-c3nc(NC4CCOCC4)ncc3Cl)cc2C1=O] | 6-{5-chloro-2-[(oxan-4-yl)amino]pyrimidin-4-yl}-2-[2-(2-methylpiperidin-1-yl)-2-oxoethyl]-2,3-dihydro-1H-isoindol-1-one | (Me-d$_3$-OD): 8.36 (1H, s), 8.24 (1H, d), 8.08 (1H, dd), 7.72 (1H, dd), 4.62 (4H, s), 4.44-4.26 (1H, m), 4.11-4.03 (1H, m), 4.03-3.94 (2H, m), 3.86-3.70 (1H, m), 3.55 (2H, dt), 2.05-1.98 (2H, m), 1.86-1.57 (7H, m), 1.40 (2H, d), 1.24 (2H, d). | 484 |
| 143 | 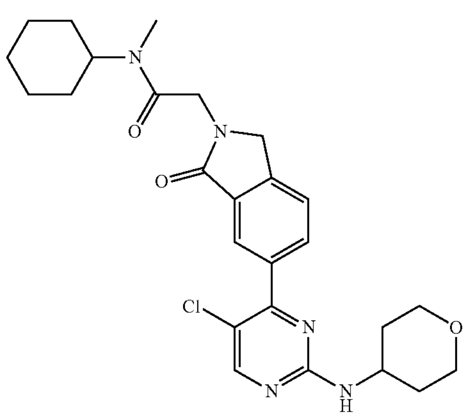 [SMILES: CN(C(=O)CN1Cc2ccc(-c3nc(NC4CCOCC4)ncc3Cl)cc2C1=O)C1CCCCC1] | 2-(6-{5-chloro-2-[(oxan-4-yl)amino]pyrimidin-4-yl}-1-oxo-2,3-dihydro-1H-isoindol-2-yl)-N-cyclohexyl-N-methylacetamide | (Me-d$_3$-OD): 8.36 (1H, s), 8.24 (1H, s), 8.08 (1H, dd), 7.72 (1H, dd), 4.67 (2H, s), 4.62 (1H, s), 4.56 (1H, s), 4.39-4.28 (0.5H, m), 4.11-4.02 (1H, m), 4.02-3.95 (2H, m), 3.81-3.70 (0.5H, m), 3.59-3.51 (2H, m), 3.01 (2H, s), 2.88 (1H, s), 2.05-1.98 (2H, m), 1.94-1.77 (3H, m), 1.76-1.33 (8H, m), 1.27-1.15 (1H, m). | 498 |

-continued

| Example | Structure | Name | ¹H NMR (400 MHz) | MS: [M + H]⁺ |
|---|---|---|---|---|
| 144 | 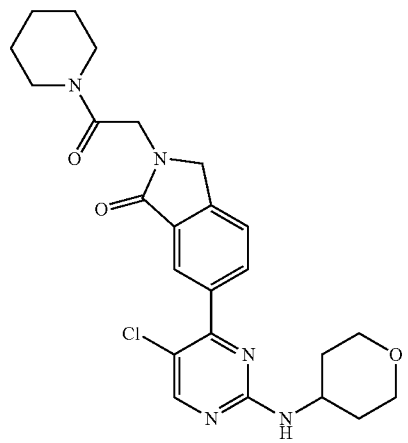 [SMILES: O=C(CN1Cc2ccc(-c3nc(NC4CCOCC4)ncc3Cl)cc2C1=O)N1CCCCC1] | 6-{5-chloro-2-[(oxan-4-yl)amino] pyrimidin-4-yl}-2-[2-oxo-2-(piperidin-1-yl)ethyl]-2,3-dihydro-1H-isoindol-1-one | (DMSO-d₆): 8.45 (1H, s), 8.03 (1H, s), 7.99 (1H, dd), 7.75 (1H, d), 7.62-7.55 (1H, m), 4.57 (2H, s), 4.46 (2H, s), 3.99-3.90 (1H, m), 3.87 (2H, d), 3.50-3.42 (4H, m), 3.38 (2H, t), 1.89-1.82 (2H, m), 1.65-1.51 (6H, m), 1.51-1.43 (2H, m). | 470 |
| 145 | 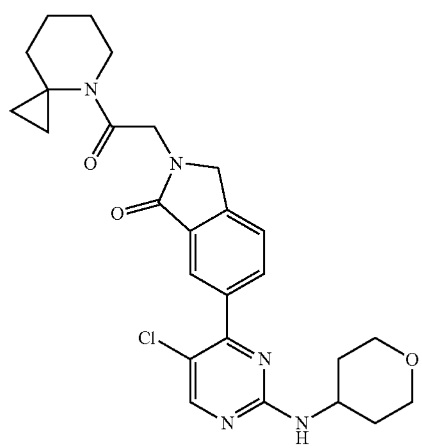 [SMILES: O=C1c2cc(-c3nc(NC4CCOCC4)ncc3Cl)ccc2CN1CC(=O)N1CCCCC12CC2] | 2-(2-{4-azaspiro[2.5] octan-4-yl}-2-oxoethyl)-6-{5-chloro-2-[(oxan-4-yl)amino] pyrimidin-4-yl}-2,3-dihydro-1H-isoindol-1-one | (Me-d₃-OD): 8.36 (1H, s), 8.24 (1H, s), 8.08 (1H, dd), 7.72 (1H, d), 4.76-4.62 (4H, m), 4.12-3.95 (4H, m), 3.68-3.59 (1H, m), 3.59-3.51 (2H, m), 2.02 (2H, d), 1.95-1.49 (8H, m), 1.27-0.70 (4H, m). | 496 |
| 146 | 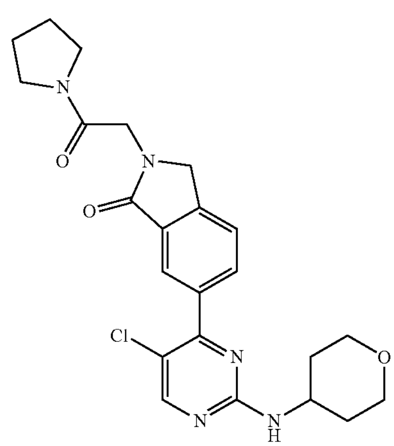 [SMILES: O=C(CN1Cc2ccc(-c3nc(NC4CCOCC4)ncc3Cl)cc2C1=O)N1CCCC1] | 6-{5-chloro-2-[(oxan-4-yl)amino] pyrimidin-4-yl}-2-[2-oxo-2-(pyrrolidin-1-yl)ethyl]-2,3-dihydro-1H-isoindol-1-one | (Me-d₃-OD): 8.36 (1H, s), 8.24 (1H, d), 8.08 (1H, dd), 7.72 (1H, dd), 4.70 (2H, s), 4.51 (2H, s), 4.12-4.02 (1H, m), 4.02-3.96 (2H, m), 3.62 (2H, t), 3.55 (2H, dt), 3.49 (2H, t), 2.11-1.98 (4H, m), 1.98-1.90 (2H, m), 1.69-1.57 (2H, m). | 456 |

-continued

| Example | Structure | Name | ¹H NMR (400 MHz) | MS: [M + H]⁺ |
|---|---|---|---|---|
| 147 | 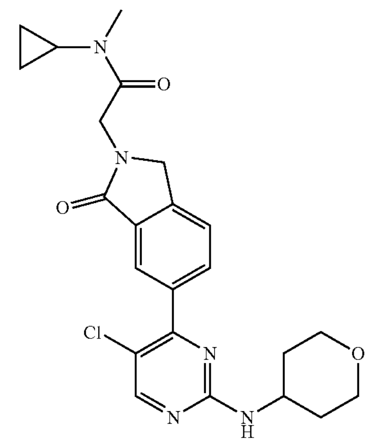 [SMILES: CN(C(=O)CN1Cc2ccc(-c3nc(NC4CCOCC4)ncc3Cl)cc2C1=O)C1CC1] | 2-(6-{5-chloro-2-[(oxan-4-yl)amino]pyrimidin-4-yl}-1-oxo-2,3-dihydro-1H-isoindol-2-yl)-N-cyclopropyl-N-methylacetamide | (DMSO-d$_6$): 8.45 (1H, s), 8.03 (1H, d), 7.99 (1H, dd), 7.75 (1H, d), 7.59 (1H, br s), 4.62-4.58 (4H, m), 3.99-3.91 (1H, m), 3.91-3.84 (2H, m), 3.43-3.38 (2H, m), 2.90-2.81 (4H, m), 1.90-1.81 (2H, m), 1.60-1.47 (2H, m), 0.95-0.83 (4H, m). | 456 |
| 148 | 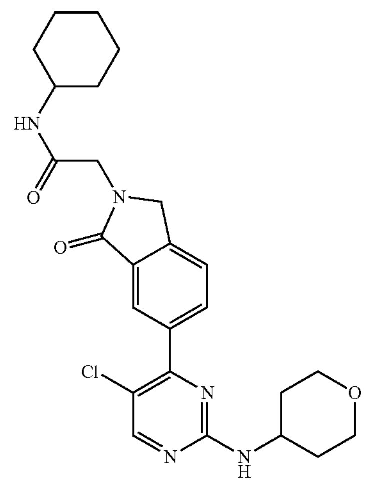 [SMILES: O=C(CN1Cc2ccc(-c3nc(NC4CCOCC4)ncc3Cl)cc2C1=O)NC1CCCCC1] | 2-(6-{5-chloro-2-[(oxan-4-yl)amino]pyrimidin-4-yl}-1-oxo-2,3-dihydro-1H-isoindol-2-yl)-N-cyclohexyl acetamide | (DMSO-d$_6$): 8.45 (1H, s), 8.04-8.02 (1H, m), 8.01-7.96 (2H, m), 7.74 (1H, d), 7.63-7.54 (1H, m), 4.59 (2H, s), 4.17 (2H, s), 3.98-3.90 (1H, m), 3.90-3.83 (2H, m), 3.61-3.52 (1H, m), 1.85 (2H, d), 1.79-1.65 (4H, m), 1.61-1.47 (3H, m), 1.31-1.10 (5H, m). | 484 |
| 149 | 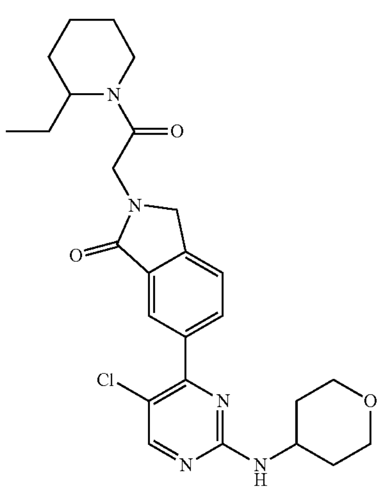 [SMILES: CCC1CCCCN1C(=O)CN1Cc2ccc(-c3nc(NC4CCOCC4)ncc3Cl)cc2C1=O] | 6-{5-chloro-2-[(oxan-4-yl)amino]pyrimidin-4-yl}-2-[2-(2-ethylpiperidin-1-yl)-2-oxoethyl]-2,3-dihydro-1H-isoindol-1-one | (DMSO-d$_6$): 8.45 (1H, s), 8.03 (1H, s), 7.98 (1H, dd), 7.75 (1H, d), 7.59 (1H, br s), 4.64-4.38 (4.5H, m), 4.27 (0.5H, d), 3.99-3.83 (3.5H, m), 3.72 (0.5H, d), 3.43-3.35 2.5H, m), 3.14-3.02 (0.5H, m), 1.90-1.22 (12H, m), 0.97-0.85 (1.5H, m), 0.78 (1.5H, t). | 498 |

| Example | Name | ¹H NMR (400 MHz) | MS: [M + H]⁺ |
|---|---|---|---|
| 150 | 6-{5-chloro-2-[(oxan-4-yl)amino]pyrimidin-4-yl}-2-[2-oxo-2-(1,2,3,4-tetrahydroisoquinolin-2-yl)ethyl]-2,3-dihydro-1H-isoindol-1-one | (Me-d₃-OD): 8.36 (1H, s), 8.25 (1H, s), 8.11-8.06 (1H, m), 7.74-7.69 (1H, m), 7.25-7.19 (4H, m), 4.73 (1.5H, s), 4.72-4.66 (4.5H, m), 4.11-4.03 (1H, m), 4.03-3.95 (2H, m), 3.89-3.81 (2H, m), 3.55 (2H, dt), 3.03 (1H, t), 2.92 (1H, t), 2.05-1.98 (2H, m), 1.70-1.58 (2H, m). | 518 |
| 151 | 2-(6-{5-chloro-2-[(oxan-4-yl)amino]pyrimidin-4-yl}-1-oxo-2,3-dihydro-1H-isoindol-2-yl)-N-(2-methylbutan-2-yl)acetamide | (Me-d₃-OD): 8.36 (1H, s), 8.24 (1H, d), 8.08 (1H, dd), 7.71 (1H, d), 4.67 (2H, s), 4.30 (2H, s), 4.11-4.02 (1H, m), 4.02-3.95 (2H, m), 3.55 (2H, dt), 2.05-1.98 (2H, m), 1.77 (2H, q), 1.70-1.57 (2H, m), 1.33 (6H, s), 0.91 (3H, t). | 472 |
| 152 | 6-{5-chloro-2-[(oxan-4-yl)amino]pyrimidin-4-yl}-2-[2-(3-methyl-1,2,3,4-tetrahydroisoquinolin-2-yl)-2-oxoethyl]-2,3-dihydro-1H-isoindol-1-one | (Me-d₃-OD): 8.36 (1H, s), 8.25 (1H, d), 8.09 (1H, d), 7.72 (1H, dd), 7.30-7.16 (4H, m), 5.04 (0.5H, d), 4.97-4.90 (0.5H, m), 4.76-4.59 (5H, m), 4.63-4.58 (0.5H, m), 4.35 (0.5H, d), 4.12-4.02 (1H, m), 4.02-3.94 (2H, m), 3.59-3.51 (2H, m), 3.30-3.23 (0.5H, m), 3.17-3.07 (0.5H, m), 2.83-2.68 (1H, m), 2.02 (2H, d), 1.69-1.58 (2H, m), 1.27 (1.5H, d), 1.12 (1.5H, d). | 532 |

Formate salt

| Example | Structure | Name | ¹H NMR (400 MHz) | MS: [M + H]⁺ |
|---|---|---|---|---|
| 153 | 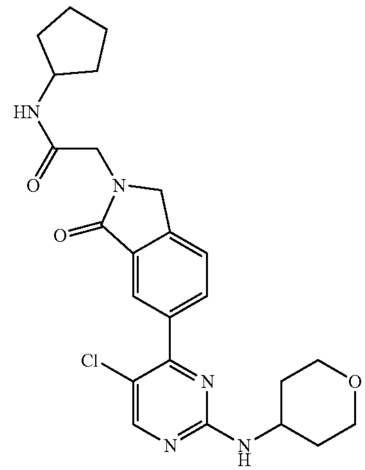 [SMILES: O=C(CN1Cc2ccc(-c3nc(NC4CCOCC4)ncc3Cl)cc2C1=O)NC1CCCC1] | 2-(6-{5-chloro-2-[(oxan-4-yl)amino]pyrimidin-4-yl}-1-oxo-2,3-dihydro-1H-isoindol-2-yl)-N-cyclopentyl acetamide | (Me-d$_3$-OD): 8.36 (1H, s), 8.24 (1H, d), 8.08 (1H, dd), 7.72 (1H, dd), 4.68 (2H, s), 4.32 (2H, s), 4.21-4.13 (1H, m), 4.10-4.02 (1H, m), 4.02-3.95 (2H, m), 3.55 (2H, dt), 2.05-1.92 (4H, m), 1.80-1.69 (2H, m), 1.69-1.57 (4H, m), 1.57-1.48 (2H, m). | 470 |
| 154 | 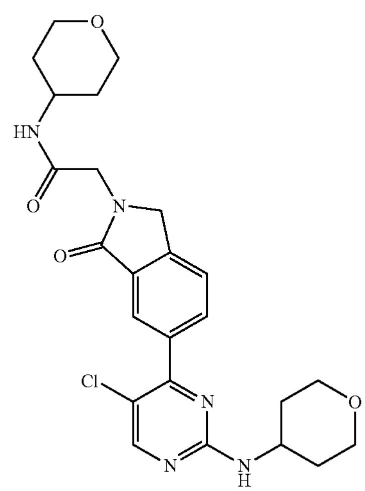 [SMILES: O=C(CN1Cc2ccc(-c3nc(NC4CCOCC4)ncc3Cl)cc2C1=O)NC1CCOCC1] | 2-(6-{5-chloro-2-[(oxan-4-yl)amino]pyrimidin-4-yl}-1-oxo-2,3-dihydro-1H-isoindol-2-yl)-N-(oxan-4-yl) acetamide | (Me-d$_3$-OD): 8.36 (1H, s), 0.24 (1H, s), 8.08 (1H, dd), 7.72 (1H, dd), 4.68 (2H, s), 4.35 (2H, s), 4.10-4.02 (1H, m), 4.02-3.91 (5H, m), 3.59-3.45 (4H, m), 2.05-1.98 (2H, m), 1.91-1.83 (2H, m), 1.69-1.53 (4H, m). | 486 |
| 155 | 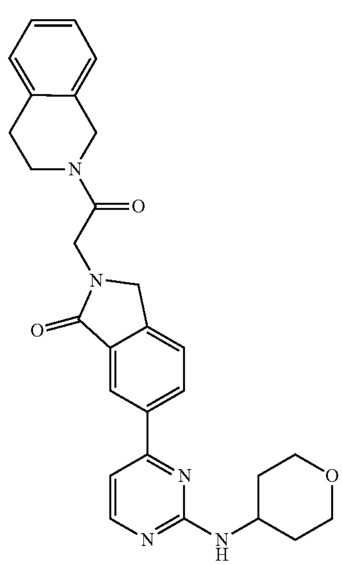 [SMILES: O=C(CN1Cc2ccc(-c3ccnc(NC4CCOCC4)n3)cc2C1=O)N1CCc2ccccc2C1] | 6-{2-[(oxan-4-yl)amino]pyrimidin-4-yl}-2-[2-oxo-2-(1,2,3,4-tetrahydro isoquinolin-2-yl)ethyl]-2,3-dihydro-1H-isoindol-1-one | (CDCl3): 8.49 (1H, s), 8.38 (1H, d), 8.29 (1H, d), 7.56 (1H, t), 7.26-7.20 (2H, m), 7.20-7.12 (2H, m), 7.06 (1H, d), 5.19 (1H, d), 4.76 (2H, s), 4.66 (2H, d), 4.59 (2H, d), 4.26-4.14 (1H, m), 4.08-3.99 (2H, m), 3.90-3.80 (2H, m), 3.67-3.56 (2H, m), 2.99-2.87 (2H, m), 2.12 (2H, d), 1.79 (2H, s), 1.71-1.56 (2H, m). | 484 |

-continued

| Example | Structure | Name | ¹H NMR (400 MHz) | MS: [M + H]⁺ |
|---|---|---|---|---|
| 156 | 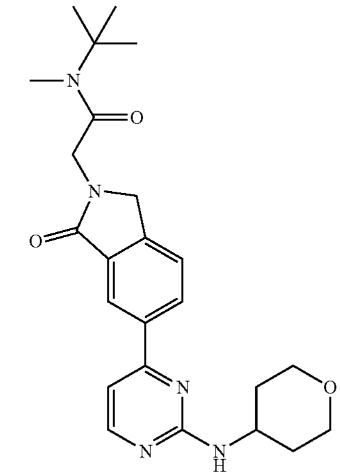 [SMILES: CN(C(=O)CN1Cc2ccc(-c3ccnc(NC4CCOCC4)n3)cc2C1=O)C(C)(C)C] | N-tert-butyl-N-methyl-2-(6-{2-[(oxan-4-yl)amino]pyrimidin-4-yl}-1-oxo-2,3-dihydro-1H-isoindol-2-yl)acetamide | (CDCl3): 8.48 (1H, s), 8.38 (1H, d), 8.29 (1H, dd), 7.57 (1H, d), 7.07 (1H, d), 5.13 (1H, d), 4.65 (2H, s), 4.44 (2H, s), 4.28-4.13 (1H, m), 4.11-3.98 (2H, m), 3.69-3.56 (2H, m), 3.01 (3H, s), 2.22-2.04 (2H, m), 1.66-1.60 (2H, m), 1.45 (9H, s). | 438 |
| 157 | 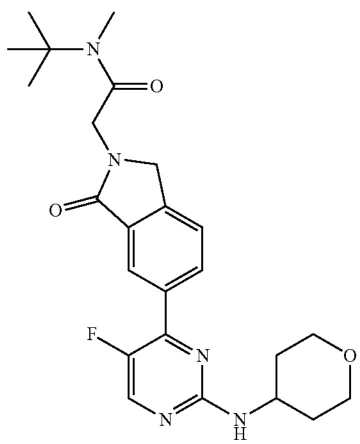 [SMILES: CN(C(=O)CN1Cc2ccc(-c3nc(NC4CCOCC4)ncc3F)cc2C1=O)C(C)(C)C] | N-tert-butyl-2-(6-{5-fluoro-2-[(oxan-4-yl)amino]pyrimidin-4-yl}-1-oxo-2,3-dihydro-1H-isoindol-2-yl)-N-methyl acetamide | (Me-d3-OD): 8.51 (1H, s), 8.36 (1H, d), 8.31 (1H, d), 7.73 (1H, d), 4.65 (2H, s), 4.52 (2H, s), 4.17-4.05 (1H, m), 4.05-3.93 (2H, m), 3.66-3.54 (2H, m), 3.06 (3H, s), 2.05 (2H, d), 1.74-1.54 (2H, m), 1.46 (9H, s). | 456 |
| 158 | 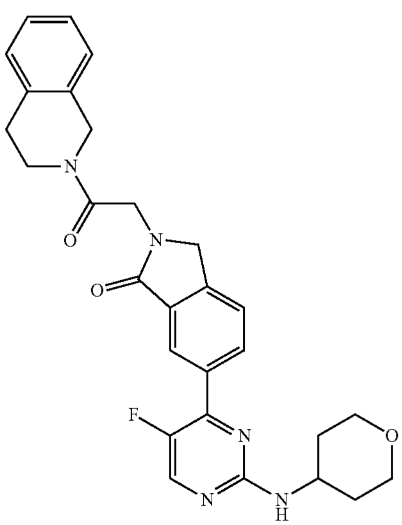 | 6-{5-fluoro-2-[(oxan-4-yl)amino]pyrimidin-4-yl}-2-[2-oxo-2-(1,2,3,4-tetrahydroisoquinolin-2-yl)ethyl]-2,3-dihydro-1H-isoindol-1-one | (CDCl3): 8.58 (1H, s), 8.30-8.25 (2H, m), 7.63-7.54 (1H, m), 7.25-7.15 (4H, m), 4.76 (2H, s), 4.67 (2H, d), 4.59 (2H, d), 4.12-3.99 (3H, m), 3.89-3.81 (2H, m), 3.64-3.56 (2H, m), 2.98-2.89 (2H, m), 2.10 (2H, d), 1.66-1.60 (2H, m). | 502 |

Examples 159-179

These were synthesised by the following procedure.
General S$_N$AR displacement.

A mixture of 6-(2,5-dichloropyrimidin-4-yl)-2-[2-oxo-2-(1,2,3,4-tetrahydroisoquinolin-2-yl)ethyl]-2,3-dihydro-1H-isoindol-1-one (Preparation 128, 130 mg, 0.29 mmol), amine (0.57 mmol) and DIPEA (0.100 μL, 0.57 mmol) in anhydrous 1,4-dioxane (2.0 mL) was stirred in a reacti vial at 90° C. for 16 hours. The mixture was allowed to cool to room temperature and was then diluted with water. The product was extracted with EtOAc (×3) and the combined organic layers were washed with water and brine, dried over MgSO$_4$, filtered and concentrated under vacuum. The residue was purified by preparative HPLC to yield the product.

| Example | Structure | Name | $^1$H NMR (400 MHz) | MS: [M + H]$^+$ |
|---|---|---|---|---|
| 159 | 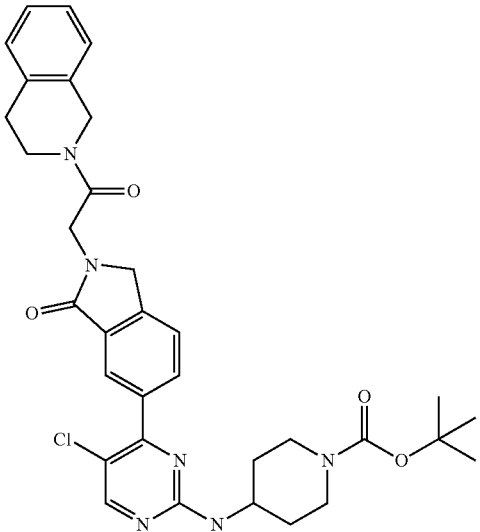 | tert-butyl 4-[(5-chloro-4-{3-oxo-2-[2-oxo-2-(1,2,3,4-tetrahydro isoquinolin-2-yl)ethyl]-2,3-dihydro-1H-isoindol-5-yl}pyrimidin-2-yl)amino]piperidine-1-carboxylate | (Me-d$_3$-OD): 8.36 (1H, s), 8.25 (1H, s), 8.08 (1H, d), 7.74-7.69 (1H, m), 7.24-7.17 (4H, m), 4.75-4.62 (6H, m), 4.09-3.99 (3H, m), 3.89-3.79 (2H, m), 3.06-2.89 (4H, m), 2.05 (1H, d), 2.01 (1H, s), 1.50-1.46 (11H, m). | 615 |
| 160 | 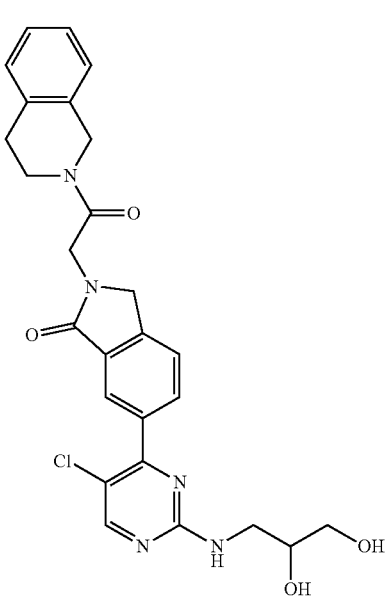 [SMILES: O=C(CN1Cc2ccc(-c3nc(NCC(O)CO)ncc3Cl)cc2C1=O)N1CCc2ccccc2C1] | 6-{5-chloro-2-[(2,3-dihydroxypropyl)amino]pyrimidin-4-yl}-2-[2-oxo-2-(1,2,3,4-tetrahydroisoquinolin-2-yl)ethyl]-2,3-dihydro-1H-isoindol-1-one | (Me-d$_3$-OD): 8.38 (1H, s), 8.26 (1H, s), 8.13-8.07 (1H, m), 7.75-7.69 (1H, m)t 7.24-7.19 (4H, m), 4.76-4.65 (6H, m), 3.89-3.81 (3H, m), 3.66-3.54 (3H, m), 3.47 (1H, dd), 3.03 (1H, t), 2.92 (1H, t). | 508 |

| Example | Structure | Name | ¹H NMR (400 MHz) | MS: [M + H]⁺ |
|---|---|---|---|---|
| 161 | 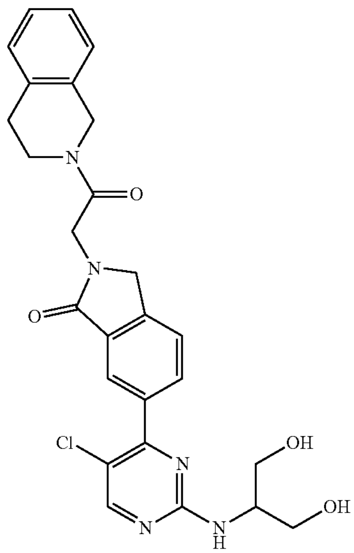 [SMILES: O=C(CN1Cc2ccc(-c3nc(NC(CO)CO)ncc3Cl)cc2C1=O)N1CCc2ccccc2C1] | 6-{5-chloro-2-[(1,3-dihydroxypropan-2-yl)amino]pyrimidin-4-yl}-2-[2-oxo-2-(1,2,3,4-tetrahydroisoquinolin-2-yl)ethyl]-2,3-dihydro-1H-isoindol-1-one | (Me-d₃-OD): 8.38 (1H, s), 8.27 (1H, s), 8.13-8.08 (1H, m), 7.75-7.69 (1H, m), 7.24-7.19 (4H, m), 4.74-4.66 (6H, m), 4.21-4.14 (1H, m), 3.85 (2H, q), 3.78-3.74 (4H, m), 3.03 (1H, t), 2.92 (1H, t). | 508 |
| 162 | 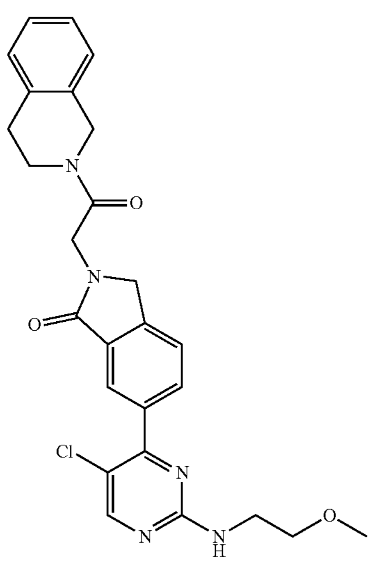 [SMILES: COCCNc1ncc(Cl)c(-c2ccc3c(c2)C(=O)N(CC(=O)N2CCc4ccccc4C2)C3)n1] | 6-{5-chloro-2-[(2-methoxyethyl)amino]pyrimidin-4-yl}-2-[2-oxo-2-(1,2,3,4-tetrahydroisoquinolin-2-yl)ethyl]-2,3-dihydro-1H-isoindol-1-one | (Me-d₃-OD): 8.36 (1H, s), 8.26 (1H, s), 8.12-8.07 (1H, m), 7.72 (1H, dd), 7.24-7.19 (4H, m), 4.75-4.66 (6H, m), 3.88-3.82 (2H, m), 3.63-3.58 (4H, m), 3.40 (3H, s), 3.03 (1H, t), 2.92 (1H, t). | 492 |

-continued

| Example | Structure | Name | ¹H NMR (400 MHz) | MS: [M + H]⁺ |
|---|---|---|---|---|
| 163 | 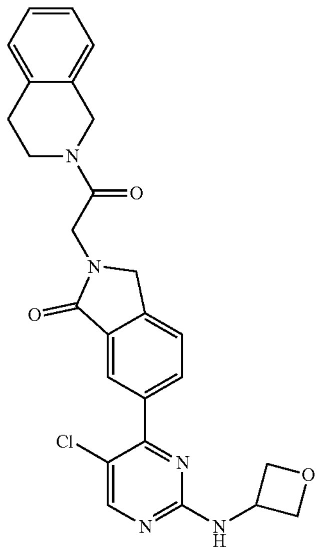 [SMILES: O=C(CN1Cc2ccc(-c3nc(NC4COC4)ncc3Cl)cc2C1=O)N1CCc2ccccc2C1] | 6-{5-chloro-2-[(oxetan-3-yl)amino]pyrimidin-4-yl}-2-[2-oxo-2-(1,2,3,4-tetrahydroisoquinolin-2-yl)ethyl]-2,3-dihydro-1H-isoindol-1-one | (Me-d₃-OD): 8.39 (1H, s), 8.26 (1H, s), 8.12-8.07 (1H, m), 7.72 (1H, dd), 7.21 (4H, d), 5.13-5.06 (1H, m), 4.96 (2H, t), 4.77-4.63 (8H, m), 3.88-3.81 (2H, m), 3.04 (1H, t), 2.92 (1H, t). | 490 |
| 164 | 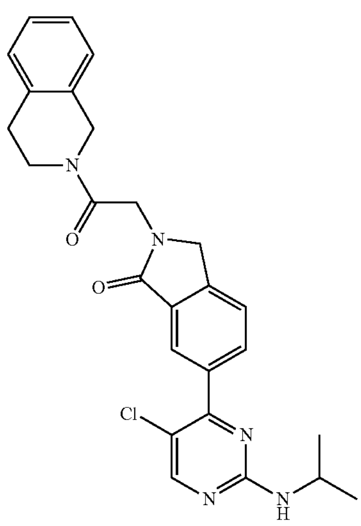 [SMILES: CC(C)Nc1ncc(Cl)c(-c2ccc3c(c2)C(=O)N(CC(=O)N2CCc4ccccc4C2)C3)n1] | 6-{5-chloro-2-[(propan-2-yl)amino]pyrimidin-4-yl}-2-[2-oxo-2-(1,2,3,4-tetrahydroisoquinolin-2-yl)ethyl]-2,3-dihydro-1H-isoindol-1-one | (Me-d₃-OD): 8.34 (1H, s), 8.26 (1H, S), 8.09 (1H, d), 7.71 (1H dd), 7.25-7.15 (4H, m), 4.75-4.63 (6H, m), 4.21-4.11 (1H, m), 3.89-3.80 (2H, m), 3.03 (1H, t), 2.92 (1H, t), 1.26 (6H, d). | 476 |

| Example | Structure | Name | ¹H NMR (400 MHz) | MS: [M + H]⁺ |
|---|---|---|---|---|
| 165 | 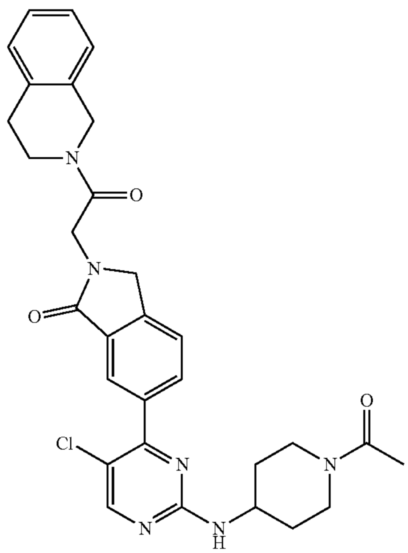 [SMILES: CC(=O)N1CCC(Nc2ncc(Cl)c(-c3ccc4c(c3)C(=O)N(CC(=O)N3CCc5ccccc5C3)C4)n2)CC1] | 6-{2-[(1-acetylpiperidin-4-yl)amino]-5-chloropyrimidin-4-yl}-2-[2-oxo-2-(1,2,3,4-tetrahydroisoquinolin-2-yl)ethyl]-2,3-dihydro-1H-isoindol-1-one | (Me-d₃-OD): 8.37 (1H, s), 8.25 (1H, s), 8.12-8.07 (1H, m), 7.72 (1H, dd), 7.24-7.17 (4H, m), 4.75-4.66 (6H, m), 4.48-4.40 (1H, m), 4.15-4.07 (1H, m), 3.94 (1H, d), 3.88-3.81 (2H, m), 3.30-3.26 (1H, m), 3.03 (1H, t), 2.97-2.86 (2H, m), 2.18-2.06 (5H, m), 1.53 (2H, d). | 559 |
| 166 | 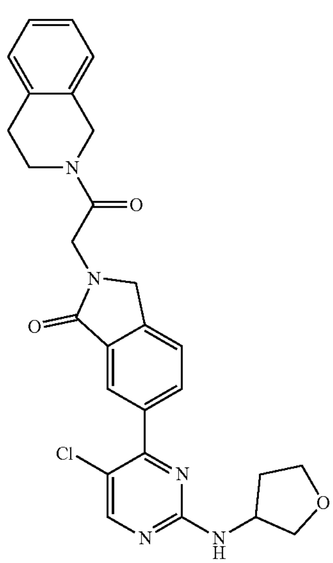 [SMILES: O=C(CN1Cc2ccc(-c3nc(NC4CCOC4)ncc3Cl)cc2C1=O)N1CCc2ccccc2C1] | 6-{5-chloro-2-[(oxolan-3-yl)amino]pyrimidin-4-yl}-2-[2-oxo-2-(1,2,3,4-tetrahydroisoquinolin-2-yl)ethyl]-2,3-dihydro-1H-isoindol-1-one | (Me-d₃-OD): 8.38 (1H, s), 8.27 (1H, s), 8.13-8.08 (1H, m), 7.75-7.69 (1H, m), 7.24-7.18 (4H, m), 4 74-4.66 (6H, m), 4.59-4.52 (1H, m), 4.04-3.96 (2H, m), 3.89-3.82 (3H, m), 3.74 (1H, dd), 3.03 (1H, t), 2.92 (1H, t), 2.37-2.27 (1H, m), 2.04-1.95 (1H, m). | 504 |

-continued

| Example | Structure | Name | $^1$H NMR (400 MHz) | MS: [M + H]$^+$ |
|---|---|---|---|---|
| 167 | 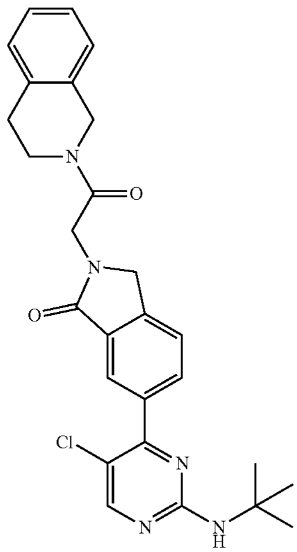 [SMILES: CC(C)(C)Nc1ncc(Cl)c(-c2ccc3c(c2)C(=O)N(CC(=O)N2CCc4ccccc4C2)C3)n1] | 6-[2-(tert-butylamino)-5-chloropyrimidin-4-yl]-2-[2-oxo-2-(1,2,3,4-tetrahydroisoquinolin-2-yl)ethyl]-2,3-dihydro-1H-isoindol-1-one | (Me-d$_3$-OD): 8.34 (1H, s), 8.30-8.23 (1H, m), 8.12-8.05 (1H, m), 7.75-7.68 (1H, m), 7.25-7.16 (4H, m), 4.77-4.63 (6H, m), 3.88-3.80 (2H, m), 3.03 (1H, t), 2.92 (1H, t), 1.48 (9H, s). | 490 |
| 168 | 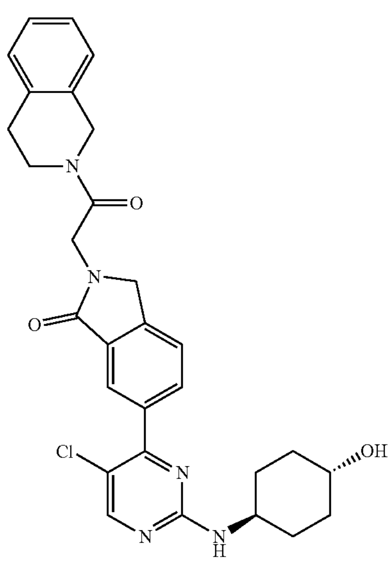 [SMILES: O=C(CN1Cc2ccc(-c3nc(N[C@H]4CC[C@H](O)CC4)ncc3Cl)cc2C1=O)N1CCc2ccccc2C1] | 6-(5-chloro-2-{[trans-4-hydroxycyclohexyl]amino}pyrimidin-4-yl)-2-[2-oxo-2-(1,2,3,4-tetrahydroisoquinolin-2-yl)ethyl]-2,3-dihydro-1H-isoindol-1-one | (DMSO-d$_6$): 8.43 (1H, s), 8.04 (1H, s), 7.99 (1H, d), 7.75 (1H, d), 7.43 (1H, s), 7.21 (4H, d), 4.76 (1H, s), 4.63 (1H, s), 4.59 (4H, s), 4.50 (1H, s), 3.77 (1H, t), 3.73-3.61 (2H, m), 3 44-3.35 (1H, m), 2.94 (1H, t), 2.82 (1H, t), 1.88 (4H, dd), 1.37-1.18 (4H, m). | 532 |

| Example | Structure | Name | ¹H NMR (400 MHz) | MS: [M + H]⁺ |
|---|---|---|---|---|
| 169 | 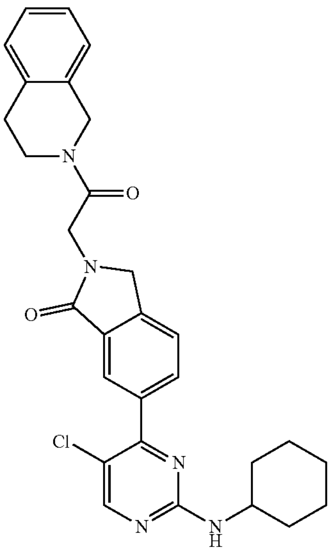 [SMILES: O=C(CN1Cc2ccc(-c3nc(NC4CCCCC4)ncc3Cl)cc2C1=O)N1CCc2ccccc2C1] | 6-[5-chloro-2-(cyclohexylamino)pyrimidin-4-yl]-2-[2-oxo-2-(1,2,3,4-tetrahydroisoquinolin-2-yl)ethyl]-2,3-dihydro-1H-isoindol-1-one | (Me-d₃-OD): 8.33 (1H, s), 8.24 (1H, s), 8.10-8.05 (1H, m), 7.74-7.68 (1H, m), 7.24-7.17 (4H, m), 4.75-4.62 (6H, m), 3.88-3.79 (3H, m), 3.03 (1H, t), 2.92 (1H, t), 2.07-2.00 (2H, m), 1.85-1.76 (2H, m), 1.73-1.62 (1H, m), 1.46-1.28 (5H, m). | 516 |
| 170 | 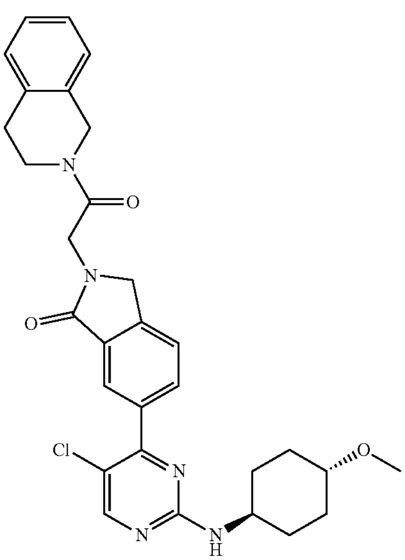 [SMILES: CO[C@H]1CC[C@H](Nc2ncc(Cl)c(-c3ccc4c(c3)C(=O)N(CC(=O)N3CCc5ccccc5C3)C4)n2)CC1] | 6-(5-chloro-2-{[trans-4-methoxycyclohexyl]amino}pyrimidin-4-yl)-2-[2-oxo-2-(1,2,3,4-tetrahydroisoquinolin-2-yl)ethyl]-2,3-dihydro-1H-isoindol-1-one | (DMSO-d₆): 8.43 (1H, s), 8.04 (1H, s), 7.99 (1H, dd), 7.75 (1H, d), 7.53-7.42 (1H, m), 7.21 (4H, d), 4.76 (1H, s), 4.63 (1H, s), 4.59 (4H, s), 3.77 (1H, t), 3.74-3.64 (2H, m), 3.24 (3H, s), 3.17-3.05 (1H, m), 2.94 (1H, t), 2.82 (1H, t), 2.06-1.91 (4H, m), 1.39-1.28 (2H, m), 1.26-1.15 (2H, m). | 546 |

| Example | Structure | Name | ¹H NMR (400 MHz) | MS: [M + H]⁺ |
|---|---|---|---|---|
| 171 | 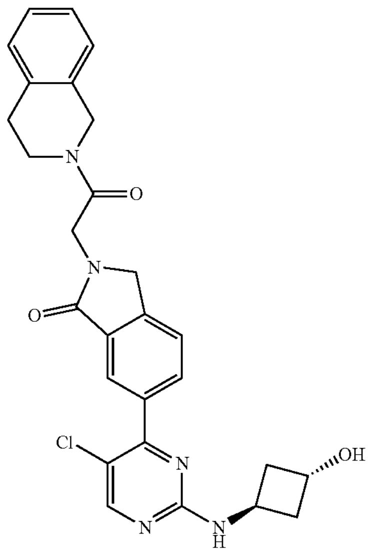 [SMILES: O=C(CN1Cc2ccc(-c3nc(N[C@H]4C[C@H](O)C4)ncc3Cl)cc2C1=O)N1CCc2ccccc2C1] | 6-(5-chloro-2-{[trans-3-hydroxycyclobutyl]amino}pyrimidin-4-yl)-2-[2-oxo-2-(1,2,3,4-tetrahydroisoquinolin-2-yl)ethyl]-2,3-dihydro-1H-isoindol-1-one | (DMSO-d₆): 8.44 (1H, s), 8.05 (1H, s), 8.03-7.97 (1H, m), 7.89-7.84 (1H, m), 7.75 (1H, d), 7.25-7.18 (5H, m), 4.97 (1H, d) 4.64-4.57 (6H, m), 4.37-4.28 (2H, m), 3.77 (1H, t), 3.70 (1H, t), 2.94 (1H, t), 2.82 (1H, t), 2.28-2.21 (2H, m), 2.19-2.12 (2H, m). | 504 |
| 172 | 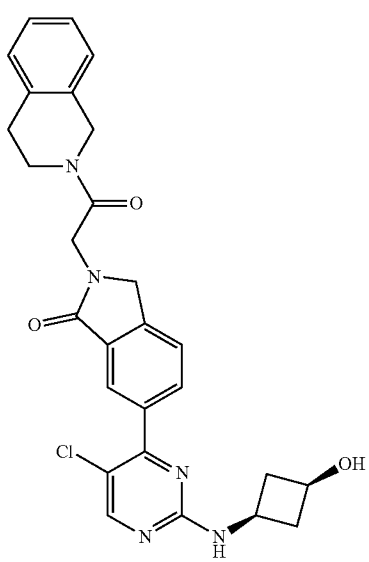 [SMILES: O=C(CN1Cc2ccc(-c3nc(N[C@H]4C[C@@H](O)C4)ncc3Cl)cc2C1=O)N1CCc2ccccc2C1] | 6-(5-chloro-2-{[cis-3-hydroxycyclobutyl]amino}pyrimidin-4-yl)-2-[2-oxo-2-(1,2,3,4-tetrahydroisoquinolin-2-yl)ethyl]-2,3-dihydro-1H-isoindol-1-one | (DMSO-d₆): 8.42 (1H, s), 8.04 (1H, s), 8.02-7.96 (1H, m), 7.84-7.77 (1H, m), 7.75 (1H, d), 7.21 (4H, d), 4.77 (1H, s), 4.60 (6H, d), 3.88-3.75 (3H, m), 3.70 (1H, t), 2.94 (1H, t), 2.85-2.78 (1H, m), 2.63-2.54 (1H, m), 1.89-1.79 (2H, m). | [M − H] ion 502 |

| Example | Structure | Name | ¹H NMR (400 MHz) | MS: [M + H]⁺ |
|---|---|---|---|---|
| 173 | 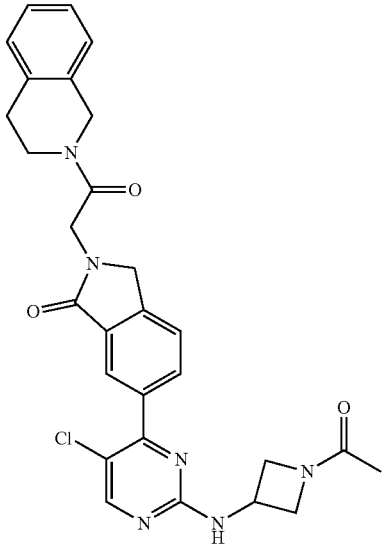 [SMILES: CC(=O)N1CC(Nc2ncc(Cl)c(-c3ccc4c(c3)C(=O)N(CC(=O)N3CCc5ccccc5C3)C4)n2)C1] | 6-{2-[(1-acetylazetidin-3-yl)amino]-5-chloropyrimidin-4-yl}-2-[2-oxo-2-(1,2,3,4-tetrahydroisoquinolin-2-yl)ethyl]-2,3-dihydro-1H-isoindol-1-one | (DMSO-$d_6$): 8.51 (1H, s), 8.23 (1H, br s), 8.07 (1H, s), 8.01 (1H, dd), 7.76 (1H, d), 7.25-7.19 (4H, m), 4.77 (0.8H, s), 4.63 (1.2H, s), 4.62-4.54 (5H, m), 4.40 (1H, t), 4.12 (1H, t), 4.03 (1H, dd), 3.87-3.80 (1H, m), 3.77 (1H, t), 3.70 (1H, t), 2.94 (1H, t), 2.82 (1H, t), 1.76 (3H, s). | 531 |
| 174 | 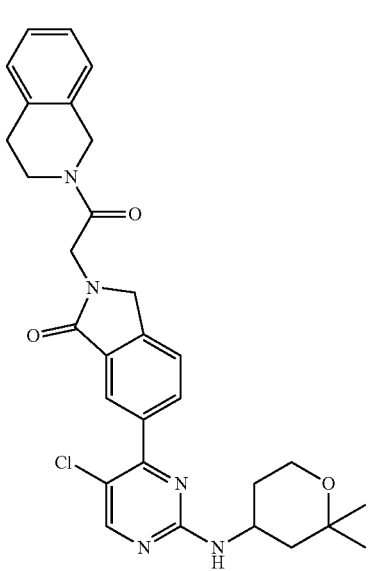 [SMILES: CC1(C)CC(Nc2ncc(Cl)c(-c3ccc4c(c3)C(=O)N(CC(=O)N3CCc5ccccc5C3)C4)n2)CCO1] | 6-{5-chloro-2-[(2,2-dimethyloxan-4-yl)amino]pyrimidin-4-yl}-2-[2-oxo-2-(1,2,3,4-tetrahydroisoquinolin-2-yl)ethyl]-2,3-dihydro-1H-isoindol-1-one | (Me-$d_3$-OD): 8.36 (1H, s), 8.26 (1H, s), 8.13-8.07 (1H, m), 7.75-7.68 (1H, m), 7.24-7.17 (4H, m), 4.75-4.66 (6H, m), 4.30-4.20 (1H, m), 3.88-3.77 (4H, m), 3.03 (1H, t), 2.92 (1H, t), 2.04-1.95 (2H, m), 1.56-1.46 (1H, m), 1.46-1.33 (1H, m), 1.32 (3H, s), 1.26 (3H, s). | 546 |

| Example | Structure | Name | ¹H NMR (400 MHz) | MS: [M + H]⁺ |
|---|---|---|---|---|
| 175 | 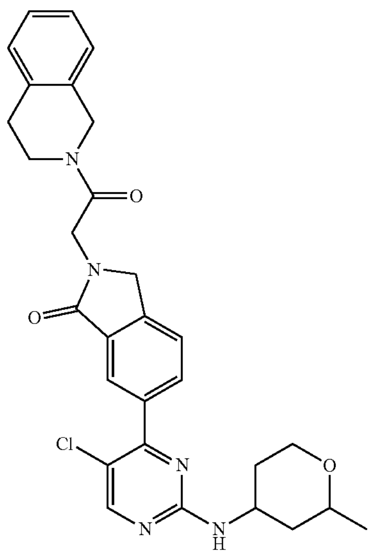 [SMILES: CC1CC(Nc2ncc(Cl)c(-c3ccc4c(c3)C(=O)N(CC(=O)N3CCc5ccccc5C3)C4)n2)CCO1] | 6-{5-chloro-2-[(2-methyloxan-4-yl)amino]pyrimidin-4-yl}-2-[2-oxo-2-(1,2,3,4-tetrahydroisoquinolin-2-yl)ethyl]-2,3-dihydro-1H-isoindol-1-one | (Me-d₃-OD): 8.38 (0.7H, s), 8.35 (0.3H, s), 8.26 (0.7H, s), 8.24 (0.3H, s), 8.12-8.06 (1H, m), 7.71 (1H, dd), 7.24-7.16 (4H, m), 4.76-4.62 (6H, m), 4.32-4.25 (0.7H, m), 4.11-3.97 (0.7H, m), 3.94-3.78 (4.3H, m), 3.61-3.49 (0.7H, m), 3.03 (1H, t), 2.91 (1H, t), 2.10-1.98 (0.8H m), 1.96-1.79 (2.2H, m), 1.67-1.58 (0.7H, m), 1.52 (0.3H, dd), 1.21 (0.9H, d), 1.18 (2.1H, d). | 532 |
| 176 | 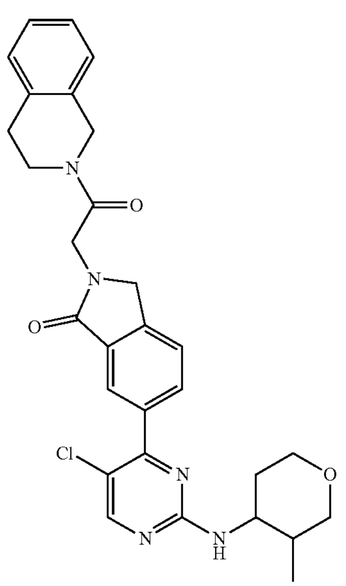 [SMILES: CC1COCCC1Nc1ncc(Cl)c(-c2ccc3c(c2)C(=O)N(CC(=O)N2CCc4ccccc4C2)C3)n1] | 6-{5-chloro-2-[(3-methyloxan-4-yl)amino]pyrimidin-4-yl}-2-[2-oxo-2-(1,2,3,4-tetrahydroisoquinolin-2-yl)ethyl]-2,3-dihydro-1H-isoindol-1-one | (Me-d₃-OD): 8.37 (1H, s), 8.34 (1H, s), 8.25 (1H, s), 8.12-8.05 (1H, m), 7.72 (1H, dd), 7.25-7.16 (4H, m), 4.76-4.63 (6H, m), 4.32-4.24 (0.5H, m), 4.03-3.75 (4.5H, m), 3.73-3.57 (1.5H, m), 3.57-3.48 (0.5H, m), 3.03 (1H, t), 2.92 (1H, t), 2.26-2.17 (0.5H, m), 2.04-1.98 (0.5H, m), 1.96-1.85 (0.5H, m), 1.85-1.70 (1H, m), 1.66-1.55 (0.5H, m), 1.02 (1.5H, d), 0.92 (1.5H, d). | 532 |

-continued

| Example | Structure | Name | ¹H NMR (400 MHz) | MS: [M + H]⁺ |
|---|---|---|---|---|
| 177 | 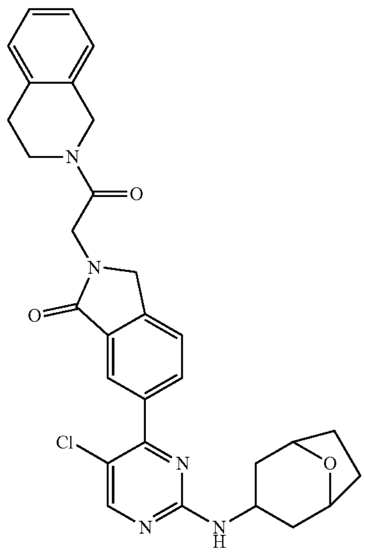 [SMILES: O=C(CN1Cc2ccc(-c3nc(NC4CC5CCC(C4)O5)ncc3Cl)cc2C1=O)N1CCc2ccccc2C1] | 6-[5-chloro-2-({8-oxabicyclo[3.2.1]octan-3-yl}amino)pyrimidin-4-yl]-2-[2-oxo-2-(1,2,3,4-tetrahydroisoquinolin-2-yl)ethyl]-2,3-dihydro-1H-isoindol-1-one | (Me-d₃-OD): 8.35 (1H, br s), 8.28-8.24 (1H, m), 8.12-8.07 (1H, m), 7.75-7.69 (1H, m), 7.21 (4H, d), 4.74-4.67 (6H, m), 4.45 (2H, s), 4.41-4.32 (1H, m), 3.88-3.82 (2H, m), 3.03 (1H, t), 2.92 (1H, t), 2.03-1.90 (6H, m), 1.73-1.63 (2H, m). | [M − H] 542 |
| 178 | 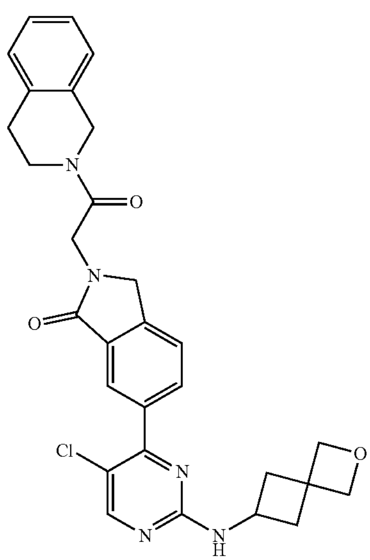 [SMILES: O=C(CN1Cc2ccc(-c3nc(NC4CC5(COC5)C4)ncc3Cl)cc2C1=O)N1CCc2ccccc2C1] | 6-[5-chloro-2-({2-oxaspiro[3.3]heptan-6-yl}amino)pyrimidin-4-yl]-2-[2-oxo-2-(1,2,3,4-tetrahydroisoquinolin-2-yl)ethyl]-2,3-dihydro-1H-isoindol-1-one | (Me-d₃-OD): 8.34 (1H, s), 8.24 (1H, s), 8.11-8.06 (1H, m), 7.74-7.68 (1H, m), 7.24-7.17 (4H, m), 4.78 (2H, s), 4.73 (1H, s), 4.72-4.61 (7H, m), 4.30-4.20 (1H, m), 3.85 (2H, q), 3.03 (1H, t), 2.92 (1H, t), 2.78-2.70 (2H, m), 2.28-2.20 (2H, m). | 530 |

Examples 179-182

Prepared using a similar procedure to Examples 159-179 from the corresponding 2-chloropyrimidines (Preparations 129-132) and amines.

| Example | Structure | Name | ¹H NMR (400 MHz) | MS: [M + H]⁺ |
|---|---|---|---|---|
| 179 | 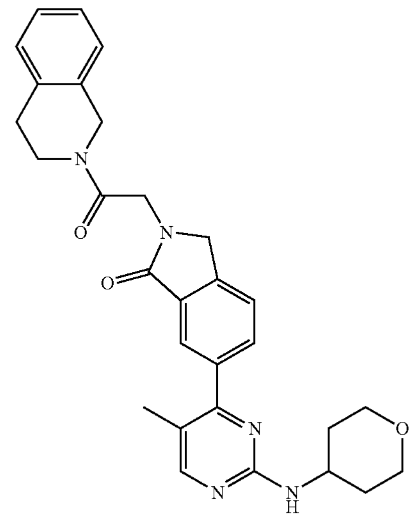 [SMILES: Cc1cnc(NC2CCOCC2)nc1-c1ccc2c(c1)C(=O)N(CC(=O)N1CCc3ccccc3C1)C2] | 6-{5-methyl-2-[(oxan-4-yl)amino]pyrimidin-4-yl}-2-[2-oxo-2-(1,2,3,4-tetrahydroisoquinolin-2-yl)ethyl]-2,3-dihydro-1H-isoindol-1-one | (CDCl3): 8.22 (1H, s), 8.08 (1H, s), 7.85-7.72 (1H, m), 7.56 (1H, t), 7.25-7.15 (4H, m), 4.76 (2H, s), 4.66 (2H, d), 4.59 (2H, d), 4.21-4.06 (1H, m), 4.04-3.97 (2H, m), 3.89-3.82 (2H, m), 3.62-3.53 (2H, m), 2.98-2.90 (2H, m), 2.22 (3H, s), 2.12-2.05 (2H, m), 1.64-1.59 (2H, m). | 498 |
| 180 | 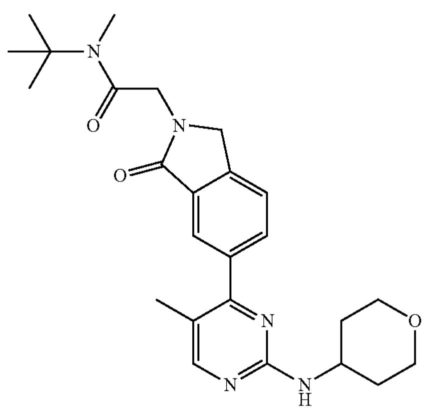 [SMILES: Cc1cnc(NC2CCOCC2)nc1-c1ccc2c(c1)C(=O)N(CC(=O)N(C)C(C)(C)C)C2] | N-tert-butyl-N-methyl-2-(6-{5-methyl-2-[(oxan-4-yl)amino] pyrimidin-4-yl}-1-oxo-2,3-dihydro-1H-isoindol-2-yl) acetamide | (CDCl3): 8.16 (1H, s), 8.05 (1H, s), 7.75 (1H, dd), 7.57 (1H, d), 4.64 (2H, s), 4.44 (2H, s), 4.09 (1H, d), 4.04-3.76 (2H, m), 3.62-3.37 (2H, m), 3.05-2.90 (3H, m), 2.20 (3H, s), 2.13-2.01 (2H, m), 1.71-1.56 (2H, m), 1.44 (9H, s). | 452 |
| 181 | 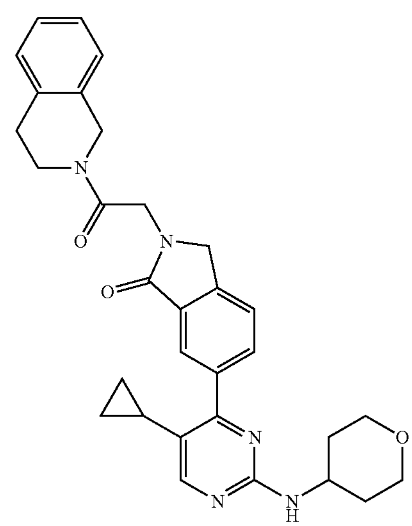 [SMILES: O=C(CN1Cc2ccc(-c3nc(NC4CCOCC4)ncc3C3CC3)cc2C1=O)N1CCc2ccccc2C1] | 6-{5-cyclopropyl-2-[(oxan-4-yl)amino] pyrimidin-4-yl}-2-[2-oxo-2-(1,2,3,4-tetrahydroisoquinolin-2-yl)ethyl]-2,3-dihydro-1H-isoindol-1-one | (CDCl3): 8.27 (1H, s), 8.11 (1H, s), 7.70-7.65 (1H, m), 7.59-7.54 (1H, m), 7.25-7.13 (4H, m), 4.76 (2H, s), 4.72-4.63 (2H, m), 4.60 (2H, d), 4.16-4.06 (1H, m), 4.05-3.96 (2H, m), 3.90-3.75 (2H, m), 3.62-3.52 (2H, m), 3.00-2.89 (2H, m), 2.11-2.03 (2H, m), 1.90-1.79 (1H, m), 1.68-1.55 (2H, m), 0.93-0.81 (2H, m), 0.56-0.49 (2H, m). | 360 |

| Example | Structure | Name | $^1$H NMR (400 MHz) | MS: [M + H]$^+$ |
|---|---|---|---|---|
| 182 | 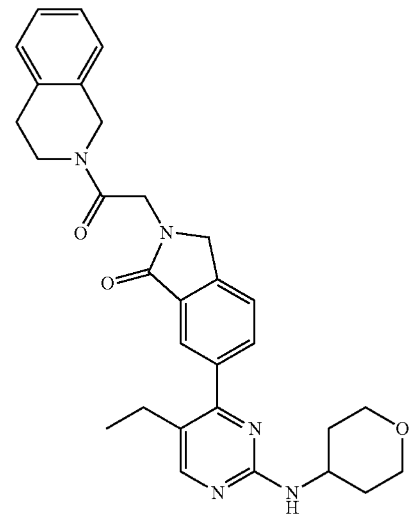 [SMILES: CCc1cnc(NC2CCOCC2)nc1-c1ccc2c(c1)C(=O)N(CC(=O)N1CCc3ccccc3C1)C2] | 6-{5-ethyl-2-[(oxan-4-yl)amino]pyrimidin-4-yl}-2-[2-oxo-2-(1,2,3,4-tetrahydroisoquinolin-2-yl)ethyl]-2,3-dihydro-1H-isoindol-1-one | (CDCl3): 8.27 (1H, s), 8.02 (1H, s), 7.73-7.68 (1H, m), 7.58-7.53 (1H, m), 7.26-7.14 (4H, m), 4.76 (2H, s), 4.66 (2H, d), 4.59 (2H, d), 4.22-4.04 (1H, m), 4.04-3.97 (2H, m), 3.89-3.81 (2H, m), 3.61-3.52 (2H, m), 2.98-2.89 (2H, m), 2.57 (2H, q), 2.12-2.04 (2H, m), 1.61-1.52 (2H, m), 1.09 (3H, t). | 512 |

Example 183: 6-{5-chloro-2-[(piperidin-4-yl)amino]pyrimidin-4-yl}-2-[2-oxo-2-(1,2,3,4-tetrahydroisoquinolin-2-yl)ethyl]-2,3-dihydro-1H-isoindol-1-one Hydrochloride Prepared according to the above general procedure with the following additional deprotection step. A mixture of tert-butyl 4-[(5-chloro-4-{3-oxo-2-[2-oxo-2-(1,2,3,4-tetrahydroisoquinolin-2-yl)ethyl]-2,3-dihydro-1H-isoindol-5-yl}pyrimidin-2-yl)amino]piperidine-1-carboxylate (~80 mg, 0.13 mmol), EtOAc saturated with HCl (2 mL) and MeOH (2 mL) was stirred at room temperature for 2 hours, and was then concentrated to dryness under vacuum. EtOAc was then added and the new precipitate was isolated by filtration and then re-dissolved in MeOH. The solution was re-evaporated under vacuum to yield the title compound as the HCl salt (74 mg, 102%) as a very pale yellow solid. MS: [M+H]$^+$=517.

Example 184: 6-{5-Chloro-2-[(1,5-dimethyl-1H-pyrazol-4-yl)amino]pyrimidin-4-yl}-2-[2-oxo-2-(1,2,3,4-tetrahydroisoquinolin-2-yl)ethyl]-2,3-dihydro-1H-isoindol-1-one

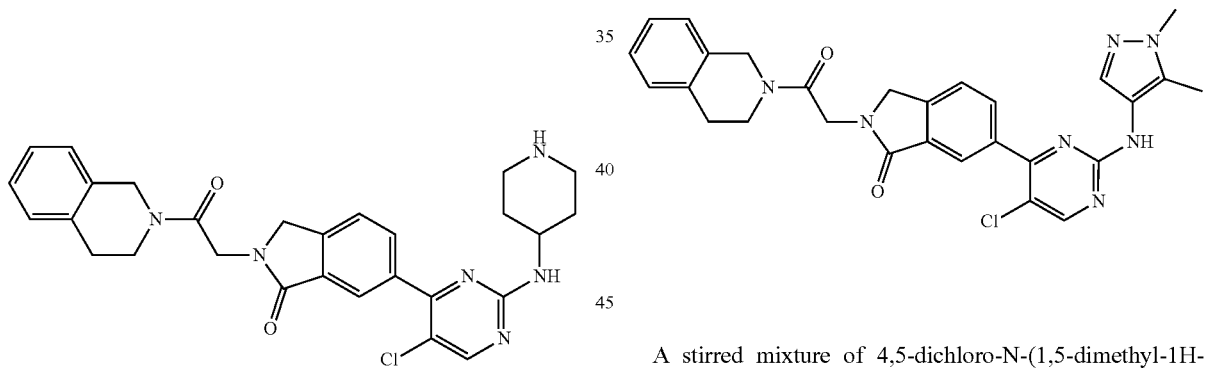

A stirred mixture of 4,5-dichloro-N-(1,5-dimethyl-1H-pyrazol-4-yl)pyrimidin-2-amine (Preparation 122, 233 mg, 0.27 mmol, 70% pure), 2-[2-oxo-2-(1,2,3,4-tetrahydroisoquinolin-2-yl)ethyl]-6-(4,4,5,5-tetramethyl-1,3,2-dioxaborolan-2-yl)-2,3-dihydro-1H-isoindol-1-one (Preparation 128, 112 mg, 0.18 mmol) and K$_2$CO$_3$ (50 mg, 0.36 mmol) in 1,4-dioxane:water (3:1, 2 mL) was degassed with nitrogen for 10 minutes. Pd(PPh$_3$)$_4$ (10 mg, 0.0.01 mmol) was then added and the mixture heated at 90° C. under nitrogen for a total of 16 hours. The reaction was allowed to cool to room temperature and was then diluted with water. The product was extracted with EtOAc (×3) and the combined organic layers were washed with brine, dried over MgSO$_4$, filtered and concentrated under vacuum. The residue was purified by preparative HPLC to yield the title compound (45 mg, 47%) as a pale yellow solid. $^1$H NMR (400 MHz, Me-d$_3$-OD): 8.40 (1H, s), 8.26 (1H, s), 8.09 (1H, d), 7.74-7.66 (1H, m), 7.58 (1H, s), 7.25-7.19 (4H, m), 4.77-4.63 (6H, m), 3.84 (2H, q), 3.79 (3H, s), 3.03 (1H, t), 2.92 (1H, t), 2.25 (3H, s). MS: [M+H]$^+$=528.

Example 185: tert-Butyl 2-(6-{5-chloro-2-[(oxan-4-yl)amino]pyridin-4-yl}-1-oxo-2,3-dihydro-1H-isoindol-2-yl)acetate

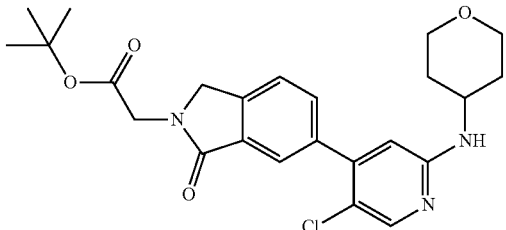

A stirred mixture of 4-bromo-5-chloro-N-(oxan-4-yl)pyridin-2-amine (Preparation 135, 310 mg, 1.06 mmol), tert-butyl 2-[1-oxo-6-(4,4,5,5-tetramethyl-1,3,2-dioxaborolan-2-yl)-2,3-dihydro-1H-isoindol-2-yl]acetate (Preparation 2, 397 mg, 1.06 mmol) and K$_2$CO$_3$ (294 mg, 2.13 mmol) in 1,4-dioxane/water (3:1, 4 mL) was degassed with nitrogen for 10 minutes. Pd(PPh$_3$)$_4$ (61 mg, 0.05 mmol) was then added and the mixture heated at 90° C. under nitrogen for a total of 16 hours. After cooling to room temperature the mixture was diluted with water and extracted with EtOAc (×3). The combined organic layers were washed with brine, dried over MgSO$_4$, filtered and concentrated under vacuum. Approximately 40 mg of the residue was purified by preparative HPLC to yield the title compound (10 mg) as a colourless solid. $^1$H NMR (400 MHz, Me-d$_3$-OD): 8.05 (1H, s), 7.86 (1H, s), 7.73 (1H, dd), 7.71 (1H, dd), 6.57 (1H, s), 4.66 (2H, s), 4.37 (2H, s), 4.02-3.93 (3H, m), 3.61-3.53 (2H, m), 2.05-1.97 (2H, m), 1.62-1.53 (2H, m), 1.51 (9H, s). MS: [M+H]$^+$=458.

Example 186: 6-{5-chloro-2-[(oxan-4-yl)amino]pyridin-4-yl}-2-[2-(3-methyl-1,2,3,4-tetrahydroisoquinolin-2-yl)-2-oxoethyl]-2,3-dihydro-1H-isoindol-1-one

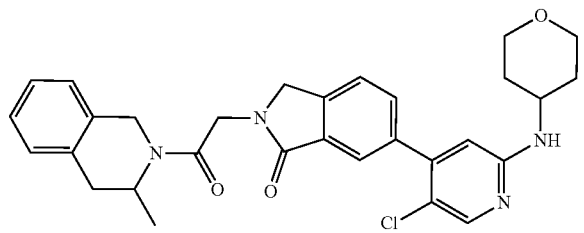 [SMILES: CC1Cc2ccccc2CN1C(=O)CN1Cc2ccc(-c3cc(NC4CCOCC4)ncc3Cl)cc2C1=O]

A stirred solution of 2-(6-{5-chloro-2-[(oxan-4-yl)amino]pyridin-4-yl}-1-oxo-2,3-dihydro-1H-isoindol-2-yl)acetic acid (Preparation 136, 130 mg, 0.32 mmol) in anhydrous 1,4-dioxane (3.2 mL) under nitrogen was treated with DIPEA (113 μL, 0.65 mmol), HBTU (250 mg, 0.65 mmol) and then 3-methyl-1,2,3,4-tetrahydro-isoquinoline (71 mg, 0.49 mmol). After 16 hours the mixture was diluted with water and extracted with EtOAc (×3). The combined organic layers were washed with brine, dried over MgSO$_4$, filtered and concentrated under vacuum. The residue was purified by preparative HPLC to give the title compound (57 mg, 34%) as a colourless solid. $^1$H NMR (400 MHz, Me-d$_3$-OD): 8.05 (1H, s), 7.87 (1H, s), 7.74-7.67 (2H, m), 7.23 (4H, d), 6.57 (1H, s), 5.04 (1H, d), 4.73-4.64 (5H, m), 4.64-4.60 (1H, m), 4.38-4.31 (1H, m), 3.99 (3H, d), 3.60-3.54 (4H, m), 3.17-3.08 (1H, m), 2.82-2.69 (1H, m), 2.01 (2H, d), 1.62-1.50 (2H, m), 1.27 (2H, d), 1.12 (2H, d). MS: [M+H]$^+$=531.

Example 187: 6-[5-chloro-2-(phenylamino)pyrimidin-4-yl]-2-[2-oxo-2-(1,2,3,4-tetrahydroisoquinolin-2-yl)ethyl]-2,3-dihydro-1H-isoindol-1-one

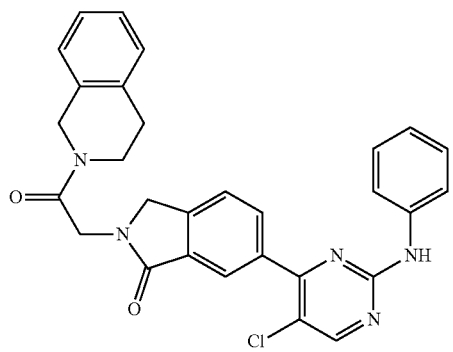 [SMILES: O=C(CN1Cc2ccc(-c3nc(Nc4ccccc4)ncc3Cl)cc2C1=O)N1CCc2ccccc2C1]

Potassium carbonate (69 mg, 0.5 mmol) was added to a solution of aniline (0.035 mL, 0.38 mmol) and 6-(2,5-dichloropyrimidin-4-yl)-2-[2-oxo-2-(1,2,3,4-tetrahydroisoquinolin-2-yl)ethyl]-2,3-dihydro-1H-isoindol-1-one (Preparation 128, 113 mg, 0.25 mmol) in MeCN (2 mL). Nitrogen was bubbled through the mixture for 5 mins, before XPhos (9 mg, 0.013 mmol) and bis (dibenzylideneacetone)palladium (7 mg, 0.013 mmol) were added. The resulting mixture was heated under microwave irradiation to 150° C. for 30 mins. The mixture was partitioned between water (10 mL) and EtOAc (3×10 mL). The combined organic phases were dried (MgSO$_4$) and evaporated under vacuum and the residue purified by preparative HPLC (acidic method) to give the title compound (9 mg, 7%). 1H NMR (400 MHz, Me-d3-OD): 8.51 (1H, s), 8.33 (1H, s), 8.16 (1H, dd), 7.71 (1H, s), 7.45 (1H, dd), 7.37-7.25 (3H, m), 7.24-7.19 (4H, m), 7.01 (1H, t), 5.50 (2H, s), 4.69 (4H, d), 3.84 (2H, q), 3.03 (1H, t), 2.91 (1H, t). MS: [M+H]$^+$=510.

Example 188: 6-{5-chloro-2-[(2-methylpyridin-4-yl)amino]pyrimidin-4-yl}-2-[2-oxo-2-(1,2,3,4-tetrahydroisoquinolin-2-yl)ethyl]-2,3-dihydro-1H-isoindol-1-one

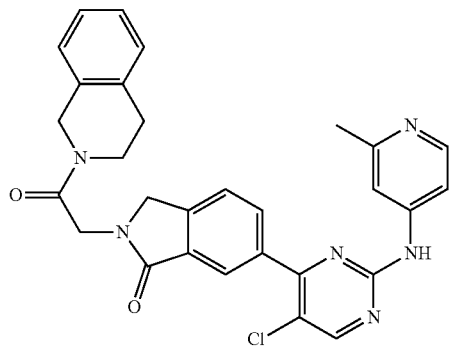 [SMILES: Cc1cc(Nc2ncc(Cl)c(-c3ccc4c(c3)C(=O)N(CC(=O)N3CCc5ccccc5C3)C4)n2)ccn1]

549

Prepared from 4,5-dichloro-N-(2-methylpyridin-4-yl)pyrimidin-2-amine (Preparation 139) and 2-[2-oxo-2-(1,2,3,4-tetrahydroisoquinolin-2-yl)ethyl]-6-(4,4,5,5-tetramethyl-1,3,2-dioxaborolan-2-yl)-2,3-dihydro-1H-isoindol-1-one (Preparation 128) using a similar procedure to that described in Example 124. 1H NMR (400 MHz, Me-d3-OD): 8.75 (1H, s), 8.36 (1H, s), 8.32 (1H, s), 8.29 (1H, d), 8.22 (1H, d), 7.99-7.88 (2H, m), 7.78 (1H, dd), 7.27-7.14 (4H, m), 4.77-4.63 (6H, m), 3.89-3.80 (2H, m), 3.04 (1H, t), 2.92 (1H, t), 2.69-2.54 (3H, m). MS: [M+H]$^+$=525.

Example 189: 6-{2-[(oxan-4-yl)amino]-5-(ethenyl)pyrimidin-4-yl}-2-[2-oxo-2-(1,2,3,4-tetrahydroisoquinolin-2-yl)ethyl]-2,3-dihydro-1H-isoindol-1-one

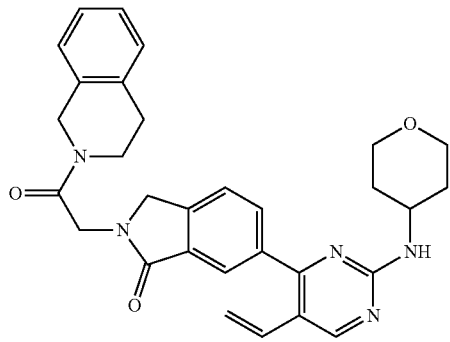 [SMILES: C=Cc1cnc(NC2CCOCC2)nc1-c1ccc2c(c1)C(=O)N(CC(=O)N1CCc3ccccc3C1)C2]

A solution of 6-{5-chloro-2-[(oxan-4-yl)amino]pyrimidin-4-yl}-2-[2-oxo-2-(1,2,3,4-tetrahydro-isoquinolin-2-yl)ethyl]-2,3-dihydro-1H-isoindol-1-one (Example 150, 52 mg, 0.1 mmol), potassium vinyltrifluoroborate (16 mg, 0.12 mmol) and cesium fluoride (30 mg, 0.2 mmol) in DME (1 mL) and water (1 mL) was degassed by bubbling nitrogen through it for 5 mins. [1,1'-bis(diphenylphosphino)ferrocene]dichloropalladium (II) (8 mg, 0.01 mmol) was added and the resulting mixture was heated by microwave irradiation at 140° C. for 20 mins. The mixture was partitioned between water (10 mL) and EtOAc (3×10 mL). The combined organic phases were dried (MgSO$_4$), evaporated under vacuum and purified using preparative hplc (basic method). The resulting solid was triturated with MeOH and Et$_2$O to give the title compound (2 mg, 4%). 1H NMR (400 MHz, CDCl3): 8.55 (1H, s), 8.13 (1H, s), 7.86-7.78 (1H, m), 7.55 (1H, t), 7.25-7.15 (4H, m), 6.58 (1H, dd), 5.61 (1H, d), 5.17 (1H, d), 4.76 (2H, s), 4.66 (2H, d), 4.58 (2H, d), 4.22-4.09 (1H, m), 4.01 (2H, d), 3.89-3.80 (2H, m), 3.64-3.44 (2H, m), 3.01-2.87 (2H, m), 2.09 (2H, d), 1.67-1.52 (2H, m). MS: [M+H]$^+$=510.

550

Example 190: 6-{2-[(oxan-4-yl)amino]-5-(prop-1-en-2-yl)pyrimidin-4-yl}-2-[2-oxo-2-(1,2,3,4-tetrahydroisoquinolin-2-yl)ethyl]-2,3-dihydro-1H-isoindol-1-one

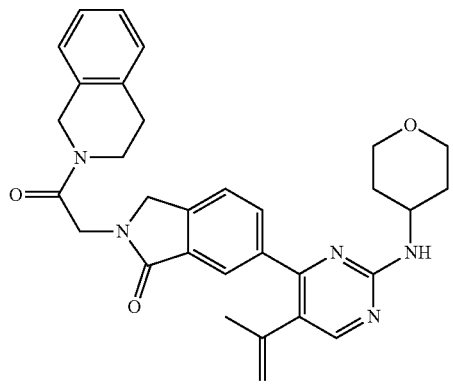 [SMILES: C=C(C)c1cnc(NC2CCOCC2)nc1-c1ccc2c(c1)C(=O)N(CC(=O)N1CCc3ccccc3C1)C2]

Prepared in a manner analogous to Example 190 using potassium isopropenyl trifluoroborate. 1H NMR (400 MHz, CDCl3): 8.37-8.04 (2H, m), 7.52 (2H, s), 7.34-6.99 (4H, m), 6.22-5.90 (1H, m), 5.12 (1H, d), 4.95-4.49 (6H, m), 4.15 (1H, s), 4.01 (2H, s), 3.84 (2H, s), 3.58 (2H, s), 2.94 (2H, d), 2.07 (2H, s), 1.86-1.48 (5H, m). MS: [M+H]$^+$=524.

Example 191: 6-{2-[(oxan-4-yl)amino]-5-(propan-2-yl)pyrimidin-4-yl}-2-[2-oxo-2-(1,2,3,4-tetrahydroisoquinolin-2-yl)ethyl]-2,3-dihydro-1H-isoindol-1-one

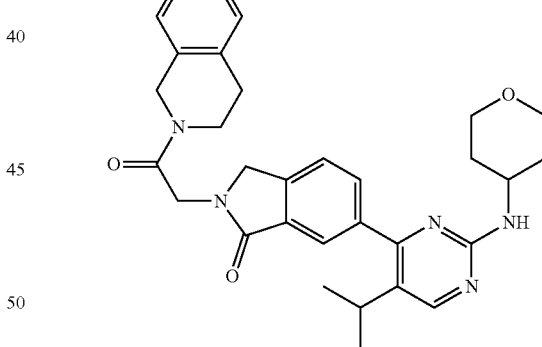

A solution of 6-{2-[(oxan-4-yl)amino]-5-(prop-1-en-2-yl)pyrimidin-4-yl}-2-[2-oxo-2-(1,2,3,4-tetrahydroisoquinolin-2-yl)ethyl]-2,3-dihydro-1H-isoindol-1-one (Example 190, 30 mg, 0.057 mmol) in MeOH (3 mL) was treated with palladium on carbon (10 wt. %) (5 mg, 0.005 mmol) and shaken under an atmosphere of hydrogen for 96 h. The reaction mixture was filtered through celite, washing with MeOH and concentrated. The residue was redissolved in MeOH and poured onto an SCX ion exchange cartridge. The cartridge was washed with MeOH and the product was eluted with a 2M solution of ammonia in MeOH. The solvent was removed under vacuum to give the title compound (1.5 mg, 5%). 1H NMR (400 MHz, CDCl3): 8.37 (1H, s), 7.98-7.93 (1H, m), 7.70-7.61 (1H, m), 7.55 (1H, t), 7.25-7.14 (4H, m), 4.76 (2H, s), 4.66 (2H, d), 4.58 (2H, d), 4.20-4.04 (1H, m), 4.04-3.94 (2H, m), 3.91-3.77 (2H, m), 3.63-3.50 (2H, m), 3.10-2.87 (3H, m), 2.14-2.02 (2H, m), 1.65-1.49 (2H, m), 1.32-1.16 (6H, m). MS: [M+H]⁺=526.

Example 192: 6-{5-chloro-2-[(oxan-4-yl)amino]pyrimidin-4-yl}-2-{2-[5-(hydroxymethyl)-1-methyl-1,2,3,4-tetrahydroisoquinolin-2-yl]-2-oxoethyl}-2,3-dihydro-1H-isoindol-1-one

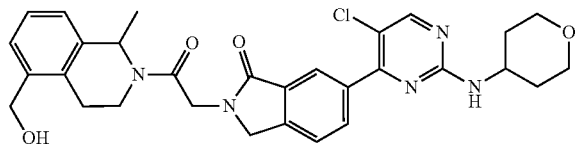 [SMILES: CC1c2cccc(CO)c2CCN1C(=O)CN1Cc2ccc(-c3nc(NC4CCOCC4)ncc3Cl)cc2C1=O]

TBAF (1M in THF) (0.588 ml, 0.588 mmol) was added to a solution of 2-[2-(5-{[(tert-butyldimethylsilyl)oxy]methyl}-1-methyl-1,2,3,4-tetrahydroisoquinolin-2-yl)-2-oxoethyl]-6-{5-chloro-2-[(oxan-4-yl)amino]pyrimidin-4-yl}-2,3-dihydro-1H-isoindol-1-one (390 mg, 0.490 mmol) in THF (5 ml, 61.0 mmol) and the mixture was stirred for 1 h. The reaction was quenched by the addition of saturated aqueous NaHCO₃ and water (15 ml) and the mixture was diluted with EtOAc (30 ml). The layers were separated and the aqueous phase was further extracted with EtOAc (2×20 ml). The combined organic extracts were washed with brine (15 ml), dried (MgSO₄) and concentrated under vacuum. The residue was purified by chromatography (SiO₂, 12 g column, 0-8% of MeOH in DCM) to afford the title compound (170 mg, 0.299 mmol, 61.1%) as a colourless solid. 1H NMR (400 MHz, 297K, DMSO-d6) δ 8.45 (s (br), 1H), 8.04 (m, 1H), 7.99 (dd, 1H), 7.75 (d, 1H), 7.63 (s (br), 1H), 7.12-7.31 (m, 3H), 5.44 (q, 0.7H), 5.23 (q, 0.3H), 5.07-5.13 (m, 1H), 4.41-4.71 (m, 6H), 3.82-4.06 (m, 4H), 3.47-3.57 (m, 0.7H), 3.33-3.42 (m, 2H), 3.03-3.13 (m, 0.3H), 2.73-2.96 (m, 1.4H), 2.60-2.71 (m, 0.6H), 1.80-1.90 (m, 2H), 1.47-1.61 (m, 2.9H), 1.40 (d, 2.1H). LC-MS: [M+H]⁺=562.

Example 193: 6-{5-chloro-2-[(oxan-4-yl)amino]pyrimidin-4-yl}-2-[2-(1-methyl-2,3,4,5-tetrahydro-1H-3-benzazepin-3-yl)-2-oxoethyl]-2,3-dihydro-1H-isoindol-1-one

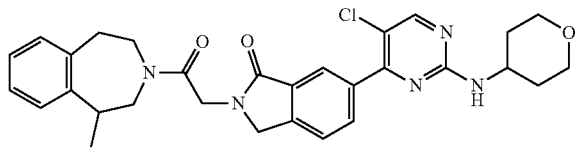 [SMILES: CC1CN(C(=O)CN2Cc3ccc(-c4nc(NC5CCOCC5)ncc4Cl)cc3C2=O)CCc2ccccc21]

Prepared according to Example 2 using diisopropylethylamine as base and DMF as solvent. The product was further purified by preparative HPLC (Basic Method) (0.007 g, 11.6% yield) in this case. 1H NMR (400 MHz, 297K, DMSO-d6) δ 8.45 (1H, s), 8.03 (1H, d), 7.98 (1H, dd), 7.73 (1H, d), 7.62 (1H, br. s), 7.22-7.06 (4H, m), 4.64-4.52 (1H, m), 4.51-4.37 (3H, m), 3.99-3.74 (5H, m), 3.66 (1H, t), 3.53-3.37 (3.5H, m), 3.21-3.10 (1.5H, m), 3.08-2.79 (1H, m), 1.85 (d, 2H), 1.53 (2H, qd), 1.32 (1.3H, d), 1.20 (1.7H, d). 1H NMR (400 MHz, DMSO-d6, T=373K) δ 8.40 (1H, s), 8.08 (1H, d), 8.00 (1H, dd), 7.71-7.66 (1H, m), 7.21-7.04 (5H, m), 4.55-4.37 (4H, m), 4.04-3.93 (1H, m), 3.89 (2H, dt), 3.85-3.79 (1H, m), 3.68 (2H, br. s), 3.59-3.37 (4H, m), 3.29-3.20 (1H, m), 3.14-3.07 (1H, m), 1.92-1.87 (2H, m), 1.65-1.55 (2H, m), 1.30 (3H, br. d). LC-MS: [M+H]⁺=546.

Example 194: 2-(6-{5-chloro-2-[(oxan-4-yl)amino]pyrimidin-4-yl}-1-oxo-2,3-dihydro-1H-isoindol-2-yl)-N-(1-phenylcyclopropyl)acetamide

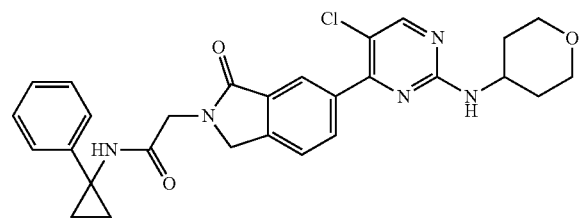 [SMILES: O=C(CN1Cc2ccc(-c3nc(NC4CCOCC4)ncc3Cl)cc2C1=O)NC1(c2ccccc2)CC1]

1-phenylcyclopropanamine (30.6 mg, 0.218 mmol) in DMF (1.0 mL) was added to an ice-cooled stirred solution of 2-(6-{5-chloro-2-[(oxan-4-yl)amino]pyrimidin-4-yl}-1-oxo-2,3-dihydro-1H-isoindol-2-yl)acetic acid (Example 1) (80 mg, 0.199 mmol), 1-propanephosphonic anhydride (T3P, 50% wt in EtOAc) (176 μl, 0.298 mmol) and triethylamine (83 μl, 0.596 mmol) in DMF (3.0 mL) under nitrogen. The reaction was allowed to warm to room temperature and stirred for 20 h. The reaction mixture was diluted with 1 M HCl (aq.) (10 mL) and extracted with EtOAc (20 mL). The combined organic extracts were washed with saturated NaHCO₃ solution (1×20 mL), brine (2×20 mL), dried (MgSO₄), filtered and concentrated under vacuum to afford the title compound (78 mg, 0.148 mmol, 74.3%) as a pale yellow solid. 1H NMR (DMSO-d6, 400 MHz) δ 8.87 (1H, s), 8.44 (1H, s), 8.03 (1H, dd), 7.97 (1H, dd), 7.80-7.70 (1H, m), 7.67-7.56 (1H, br m), 7.33-7.23 (2H, m), 7.21-7.10 (3H, m), 4.60 (2H, s), 4.24 (2H, s), 3.98-3.79 (3H, m), 3.43-3.33 (2H, m), 1.91-1.79 (2H, m), 1.52 (2H, qd), 1.17 (4H, s). LC-MS: [M+H]⁺=518.

Example 195: 6-{5-chloro-2-[(oxan-4-yl)amino]pyrimidin-4-yl}-2-{2-[2-(hydroxymethyl)-2,3,4,5-tetrahydro-1H-3-benzazepin-3-yl]-2-oxoethyl}-2,3-dihydro-1H-isoindol-1-one

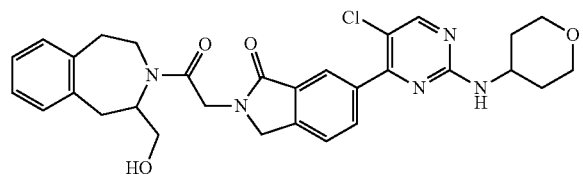 [SMILES: O=C1c2cc(-c3nc(NC4CCOCC4)ncc3Cl)ccc2CN1CC(=O)N1CCc2ccccc2CC1CO]

Prepared according to Example 2. Following purification by chromatography (SiO₂), the product was further purified by preparative HPLC (Gilson, Acidic (0.1% Formic acid), Acidic, Waters X-Select Prep-C18, 5 μm, 19×50 mm column, 20-50% MeCN in Water) to afford the title compound as a colourless solid (7 mg, 9%). 1H NMR (DMSO-d6, 400 MHz) δ 8.45 (1H, s), 8.01 (1H, dt), 7.97 (1H, ddd), 7.70 (1H, dd), 7.63 (1H, br. s), 7.16-7.04 (3.4H, m), 7.02-6.95 (0.6H, m), 4.99 (0.6H, t), 4.73 (0.4H, t), 4.66-4.30 (4.6H, m), 4.25-4.11 (1.4H, m), 3.98-3.82 (4H, m), 3.56-3.36 (3H, m), 3.08-2.83 (5H, m), 1.85 (2H, d), 1.53 (2H, qd) (mixture of rotamers was observed). LC-MS: [M+H]⁺=562.

Example 196:2-(6-{5-chloro-2-[(oxan-4-yl)amino]pyrimidin-4-yl}-1-oxo-2,3-dihydro-1H-isoindol-2-yl)-N-(2-methyl-1-phenoxypropan-2-yl)acetamide

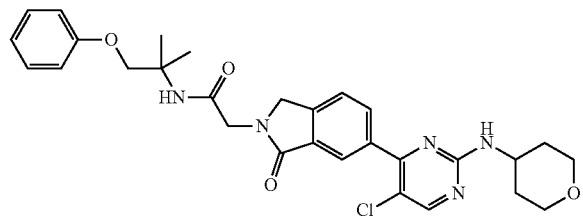 [SMILES: CC(C)(COc1ccccc1)NC(=O)CN1Cc2ccc(-c3nc(NC4CCOCC4)ncc3Cl)cc2C1=O]

A stirred mixture of 2-(6-{5-chloro-2-[(oxan-4-yl)amino]pyrimidin-4-yl}-1-oxo-2,3-dihydro-1H-isoindol-2-yl)acetic acid (Example 1) (70 mg, 0.170 mmol), 2-methyl-1-phenoxypropan-2-amine (29.6 mg, 0.170 mmol) and triethylamine (71.2 µL, 0.511 mmol) in DMF (1 mL) was cooled in an ice bath. 1-Propanephosphonic anhydride (T3P, 50% wt in EtOAc) (150 µL, 0.252 mmol) was added, the ice bath was removed and the reaction mixture allowed to warm to room temperature for 2 h. Water (5 mL) was added, and the resulting colourless precipitate was filtered and purified by preparative HPLC (basic method) to give the title compound (25 mg, 0.045 mmol, 26.2% yield) as a colourless powder. 1H NMR (CDCl₃, 400 MHz) δ 8.35-8.29 (2H, m), 8.01 (1H, dd), 7.51 (1H, dd), 7.20-7.14 (2H, m), 6.88 (1H, tt), 6.75-6.70 (2H, m), 6.23 (1H, s), 5.18 (1H, d), 4.50 (2H, s), 4.19 (2H, s), 4.13-3.95 (5H, m), 3.54 (2H, td), 2.09-2.01 (2H, m), 1.57 (2H, dtd), 1.45 (6H, s). LC-MS: [M+H]⁺=550.

Examples 197 to 295 were synthesised as follows.

To the HATU or TBTU (1.5 eq.) and 2-(6-{5-chloro-2-[(oxan-4-yl)amino]pyrimidin-4-yl}-1-oxo-2,3-dihydro-1H-isoindol-2-yl)acetic acid (Example 1) (1.0 eq.) was added DCM (0.05-0.10 M), then DIPEA (1.2 to 3.5 eq.) under nitrogen. After 10 minutes the amine coupling partner was added. The mixture was stirred for 2-16 hours at room temperature. The reaction was quenched by diluting with citric acid (5%, aq.) and extracting with EtOAc (×3). The combined organic layers were washed with brine and dried over MgSO₄. The products were filtered and evaporated to dryness. The product was purified by silica chromatography or reverse-phase preparative HPLC.

| Example | Structure | Name | ¹H NMR (400 MHz) | MS: [M + H]⁺ |
|---|---|---|---|---|
| 197 | 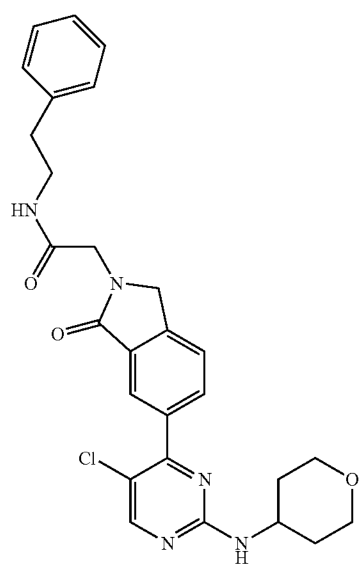 [SMILES: O=C(CN1Cc2ccc(-c3nc(NC4CCOCC4)ncc3Cl)cc2C1=O)NCCc1ccccc1] | 2-(6-{5-chloro-2-[(oxan-4-yl)amino]pyrimidin-4-yl}-1-oxo-2,3-dihydro-1H-isoindol-2-yl)-N-(2-phenylethyl)acetamide | (Me-d3-OD): 8.38-8.35 (1H, m), 8.25-8.23 (1H, m), 8.08 (1H, dd), 7.70 (1H, dd), 7.30-7.17 (5H, m), 4.57 (2H, s), 4.30 (2H, s), 4.10-4.02 (1H, m), 4.02-3.95 (2H, m), 3.59-3.51 (2H, m), 3.51-3.47 (2H, m), 2.84 (2H, t), 2.06-1.98 (2H, m), 1.69-1.59 (2H, m). | 506 |

-continued

| Example | Structure | Name | ¹H NMR (400 MHz) | MS: [M + H]⁺ |
|---|---|---|---|---|
| 198 | 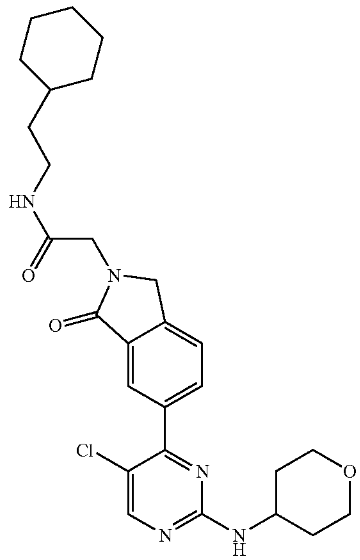 [SMILES: O=C(CN1Cc2ccc(-c3nc(NC4CCOCC4)ncc3Cl)cc2C1=O)NCCC1CCCCC1] | 2-(6-{5-chloro-2-[(oxan-4-yl)amino]pyrimidin-4-yl}-1-oxo-2,3-dihydro-1H-isoindol-2-yl)-N-(2-cyclohexylethyl)acetamide | (Me-d3-OD): 8.36 (1H, s), 8.24 (1H, d), 8.08 (1H, dd), 7.72 (1H, d), 4 67 (2H, s), 4 33 (2H, s), 4.11-4.02 (1H, m), 4.02-3.95 (2H, m), 3.55 (2H, td), 3.27 (2H, t), 2.05-1.98 (2H, m), 1.82-1.56 (7H, m), 1.44 (2H, q), 1.40-1.13 (4H, m), 1.02-0.89 (2H, m). | 512 |
| 199 | 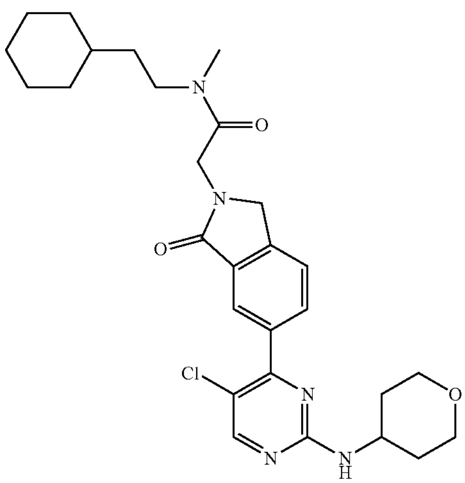 [SMILES: CN(CCC1CCCCC1)C(=O)CN1Cc2ccc(-c3nc(NC4CCOCC4)ncc3Cl)cc2C1=O] | 2-(6-{5-chloro-2-[(oxan-4-yl)amino]pyrimidin-4-yl}-1-oxo-2,3-dihydro-1H-isoindol-2-yl)-N-(2-cyclohexylethyl)-N-methylacetamide | (Me-d3-OD): 8.36 (1H, s), 8.24 (1H, d), 8.08 (1H, dd), 7.72 (1H, d), 4.67 (2H, d), 4.57 (2H, d), 4.12-4.02 (1H, m), 4.02-3.94 (2H, m), 3.55 (2H, dt), 3.50-3.41 (2H, m), 3.13 (2H, s), 2.97 (1H, s), 2.05-1.98 (2H, m), 1.88-1.53 (8H, m), 1.48 (1H, q), 1.41-1.17 (4H, m), 1.12-0.91 (2H, m). | 526 |
| 200 | 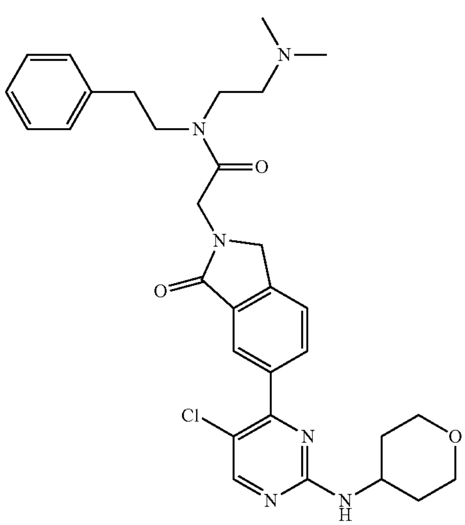 [SMILES: CN(C)CCN(CCc1ccccc1)C(=O)CN1Cc2ccc(-c3nc(NC4CCOCC4)ncc3Cl)cc2C1=O] | 2-(6-{5-chloro-2-[(oxan-4-yl)amino]pyrimidin-4-yl}-1-oxo-2,3-dihydro-1H-isoindol-2-yl)-N-[2-(dimethylamino)ethyl]-N-(2-phenylethyl)acetamide | (Me-d3-OD): 8.36 (1H, d), 8.23 (1H, d), 8.12-8.04 (1H, m), 7.70 (1H, dd), 7.42-7.17 (5H, m), 4.65 (1H, s), 4.60 (1H, s), 4.43 (1H, s), 4.25 (1H, s), 4.12-4.03 (1H, m), 4.03-3.93 (2H, m), 3.70 (1H, t), 3.65-3.49 (4H, m), 3.46-3.39 (1H, m), 3.03 (1H, t), 2.91 (1H, t), 2.55 (2H, q), 2.33 (3H, s), 2.30 (3H, s), 2.06-1.97 (2H, m), 1.70-1.58 (2H, m). | 577 |

-continued

| Example | Structure | Name | ¹H NMR (400 MHz) | MS: [M + H]⁺ |
|---|---|---|---|---|
| 201 | 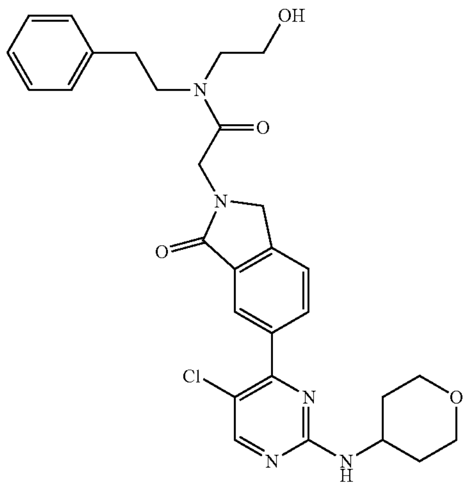 [SMILES: O=C(CN1Cc2ccc(-c3nc(NC4CCOCC4)ncc3Cl)cc2C1=O)N(CCO)CCc1ccccc1] | 2-(6-{5-chloro-2-[(oxan-4-yl)amino]pyrimidin-4-yl}-1-oxo-2,3-dihydro-1H-isoindol-2-yl)-N-(2-hydroxyethyl)-N-(2-phenylethyl)acetamide | (Me-d3-OD): 8.36 (1H, d), 8.23 (1H, dd), 8.11-8.04 (1H, m), 7.70 (1H, dd), 7.41-7.16 (5H, m), 4.67 (1H, s), 4.62 (1H, s), 4.42 (1H, s), 4.24 (1H, s), 4.11-4.03 (1H, m), 3.99 (2H, d), 3.81-3.70 (3H, m), 3.67-3.61 (1H, m), 3.59-3.45 (4H, m), 3.03 (1H, t), 2.91 (1H, t), 2.05-1.98 (2H, m), 1.70-1.57 (2H, m). | 550 |
| 202 | 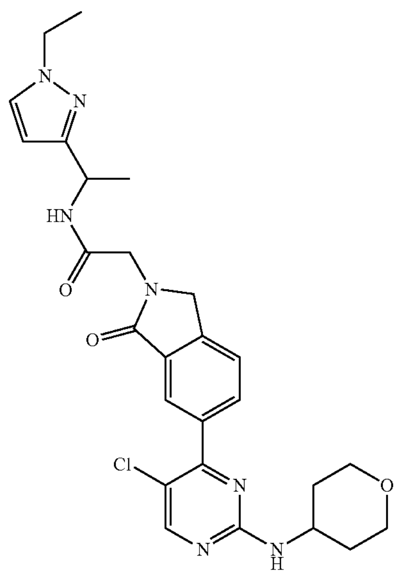 [SMILES: CCn1ccc(C(C)NC(=O)CN2Cc3ccc(-c4nc(NC5CCOCC5)ncc4Cl)cc3C2=O)n1] | 2-(6-{5-chloro-2-[(oxan-4-yl)amino]pyrimidin-4-yl}-1-oxo-2,3-dihydro-1H-isoindol-2-yl)-N-[1-(1-ethyl-1H-pyrazol-3-yl)ethyl]acetamide | (Me-d3-OD): 8.36 (1H, s), 8.24 (1H, d), 8.08 (1H, dd), 7.71 (1H, d), 7.54 (1H, d), 6.24 (1H, d), 5.15 (1H, q), 4.69 (2H, s), 4.39 (2H, s), 4.14 (2H, q), 4.11-4.02 (1H, m), 4.02-3.94 (2H, m), 3.55 (2H, dt), 2.06-1.98 (2H, m), 1.70-1.56 (2H, m), 1.51 (3H, d), 1.43 (3H, t). | 524 |
| 203 | 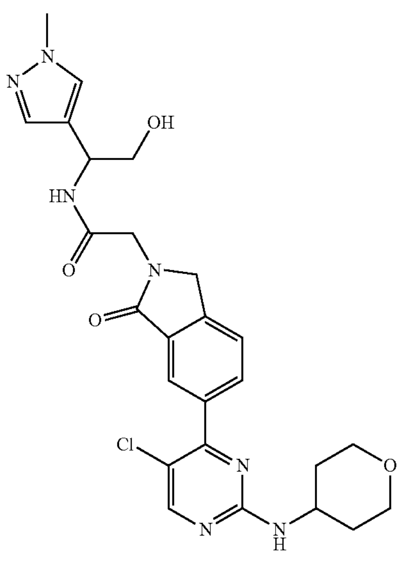 [SMILES: Cn1cc(C(CO)NC(=O)CN2Cc3ccc(-c4nc(NC5CCOCC5)ncc4Cl)cc3C2=O)cn1] | 2-(6-{5-chloro-2-[(oxan-4-yl)amino]pyrimidin-4-yl}-1-oxo-2,3-dihydro-1H-isoindol-2-yl)-N-[2-hydroxy-1-(1-methyl-1H-pyrazol-4-yl)ethyl]acetamide | (Me-d3-OD): 8.35 (1H, s), 8.24 (1H, d), 8.08 (1H, dd), 7.71 (1H, d), 7.59 (1H, s), 7.48 (1H, s), 5.06 (1H, t), 4.69 (2H, s), 4.40 (2H, s), 4.11-4.02 (1H, m), 4.02-3.92 (2H, m), 3.87 (3H, s), 3.78 (2H, dq), 3.54 (2H, dt), 2.06-1.96 (2H, m), 1.69-1.57 (2H, m). | 526 |

| Example | Structure | Name | $^1$H NMR (400 MHz) | MS: [M + H]$^+$ |
|---|---|---|---|---|
| 204 | 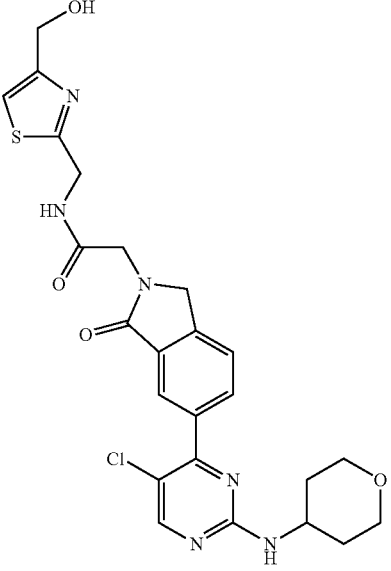 [SMILES: O=C(CN1Cc2ccc(-c3nc(NC4CCOCC4)ncc3Cl)cc2C1=O)NCc1nc(CO)cs1] | 2-(6-{5-chloro-2-[(oxan-4-yl)amino]pyrimidin-4-yl}-1-oxo-2,3-dihydro-1H-isoindol-2-yl)-N-{[4-(hydroxymethyl)-1,3-thiazol-2-yl]methyl}acetamide | (Me-d3-OD): 8.36 (1H, s), 8.25 (1H, d), 8.08 (1H, dd), 7.72 (1H, d), 7.34 (1H, t), 4.71 (4H, s), 4.67 (2H, d), 4.44 (2H, s), 4.11-4.02 (1H, m), 4.02-3.93 (2H, m), 3.54 (2H, dt), 2.04-1.96 (2H, m), 1.69-1.57 (2H, m). | 529 |
| 205 | 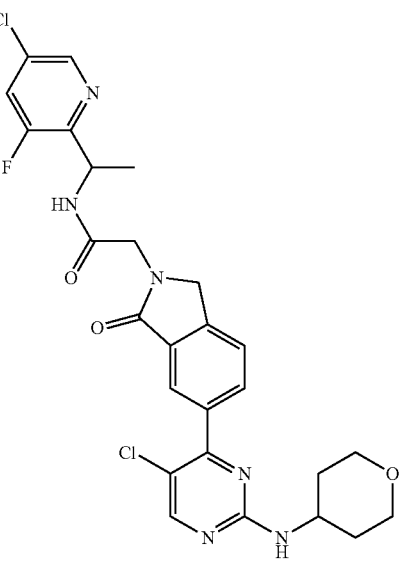 | 2-(6-{5-chloro-2-[(oxan-4-yl)amino]pyrimidin-4-yl}-1-oxo-2,3-dihydro-1H-isoindol-2-yl)-N-[1-(5-chloro-3-fluoropyridin-2-yl)ethyl]acetamide | (Me-d3-OD): 8.40 (1H, d), 8.35 (1H, s), 8.23 (1H, d), 8.07 (1H, dd), 7.75 (1H, dd), 7.70 (1H, dd), 5.40 (1H, dq), 4.65 (2H, s), 4.42 (1H, d), 4.39 (1H, d), 4.11-4.02 (1H, m), 4.01-3.95 (2H, m), 3.54 (2H, dt), 2.04-1.98 (2H, m), 1.69-1.57 (2H, m), 1.50 (3H, d). | 559 |

| Example | Structure | Name | ¹H NMR (400 MHz) | MS: [M + H]⁺ |
|---|---|---|---|---|
| 206 | 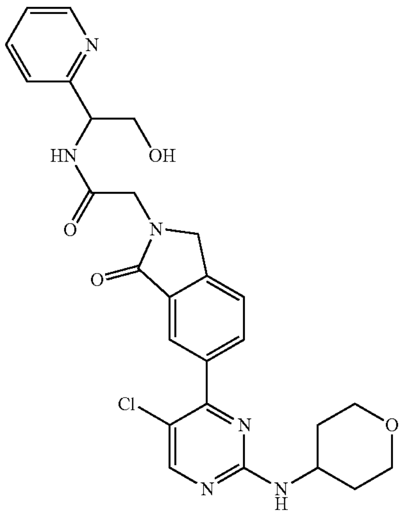 [SMILES: O=C(CN1Cc2ccc(-c3nc(NC4CCOCC4)ncc3Cl)cc2C1=O)NC(CO)c1ccccn1] | 2-(6-{5-chloro-2-[(oxan-4-yl)amino]pyrimidin-4-yl}-1-oxo-2,3-dihydro-1H-isoindol-2-yl)-N-[2-hydroxy-1-(pyridin-2-yl)ethyl]acetamide | (Me-d3-OD): 8.53 (1H, dq), 8.35 (1H, s), 8.24 (1H, d), 8.08 (1H, dd), 7.82 (1H, dt), 7.71 (1H, dd), 7.49 (1H, d), 7.32 (1H, ddd), 5.14 (1H, t), 4.69 (2H, s), 4.48 (2H, s), 4.11-4.02 (1H, m), 4.02-3.95 (2H, m), 3.95-3.84 (2H, m), 3.54 (2H, dt), 2.04-1.98 (2H, m), 1.71-1.56 (2H, m). | 523 |
| 207 | 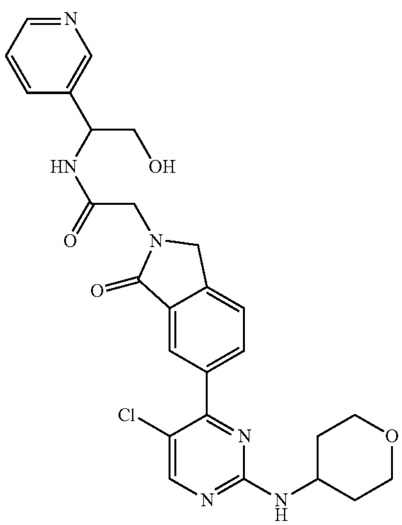 [SMILES: O=C(CN1Cc2ccc(-c3nc(NC4CCOCC4)ncc3Cl)cc2C1=O)NC(CO)c1cccnc1] | 2-(6-{5-chloro-2-[(oxan-4-yl)amino]pyrimidin-4-yl}-1-oxo-2,3-dihydro-1H-isoindol-2-yl)-N-[2-hydroxy-1-(pyridin-3-yl)ethyl]acetamide | (Me-d3-OD): 8.59 (1H, d), 8.47 (1H, dd), 8.35 (1H, s), 8.24 (1H, d), 8.08 (1H, dd), 7.91-7.86 (1H, m), 7.71 (1H, dd), 7.45 (1H, ddd), 5.09 (1H, t), 4.68 (2H, s), 4.47 (1H, d), 4.43 (1H, d), 4.11-4.02 (1H, m), 4.02-3.95 (2H, m), 3.85 (2H, dd), 3.55 (2H, dt), 2.04-1.98 (2H, m), 1.70-1.58 (2H, m). | 523 |
| 208 | 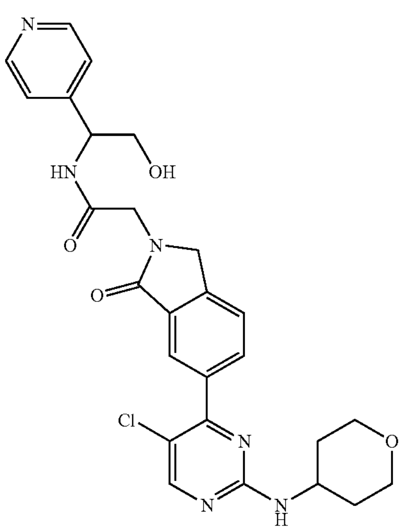 [SMILES: O=C(CN1Cc2ccc(-c3nc(NC4CCOCC4)ncc3Cl)cc2C1=O)NC(CO)c1ccncc1] | 2-(6-{5-chloro-2-((oxan-4-yl)amino]pyrimidin-4-yl}-1-oxo-2,3-dihydro-1H-isoindol-2-yl)-N-[2-hydroxy-1-(pyridin-4-yl)ethyl]acetamide | (Me-d3-OD): 8.53-8.49 (2H, m), 8.36 (1H, s), 8.24 (1H, d), 8.08 (1H, dd), 7.71 (1H, d), 7.47 (2H, d), 5.06 (1H, t), 4.69 (2H, s), 4.48 (2H, d), 4.10-4.02 (1H, m), 4.02-3.94 (2H, m), 3.86 (1H, dd), 3.82 (1H, dd), 3.54 (2H, dt), 2.04-1.98 (2H, m), 1.69-1.58 (2H, m). | 523 |

-continued

| Example | Structure | Name | ¹H NMR (400 MHz) | MS: [M + H]⁺ |
|---|---|---|---|---|
| 209 | 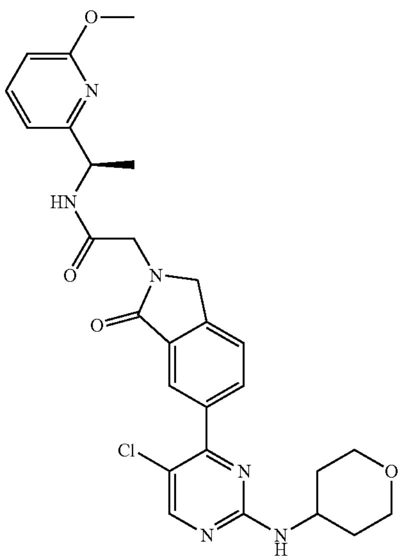 [SMILES: COc1cccc([C@@H](C)NC(=O)CN2Cc3ccc(-c4nc(NC5CCOCC5)ncc4Cl)cc3C2=O)n1] | 2-(6-{5-chloro-2-((oxan-4-yl)amino]pyrimidin-4-yl}-1-oxo-2,3-dihydro-1H-isoindol-2-yl)-N-[(1R)-1-(6-methoxypyridin-2-yl)ethyl]acetamide | (Me-d3-OD): 8.35 (1H, s), 8.23 (1H, d), 8.07 (1H, dd), 7.70 (1H, d), 7.61 (1H, dd), 6.93 (1H, d), 6.64 (1H, d), 5.05 (1H, q), 4.68 (2H, s), 4.43 (2H, s), 4.11-4.02 (1H, m), 4.02-3.95 (2H, m), 3.84 (3H, s), 3.54 (2H, dt), 2.04-1.98 (2H, m), 1.69-1.57 (2H, m), 1.51 (3H, d). | 537 |
| 210 | 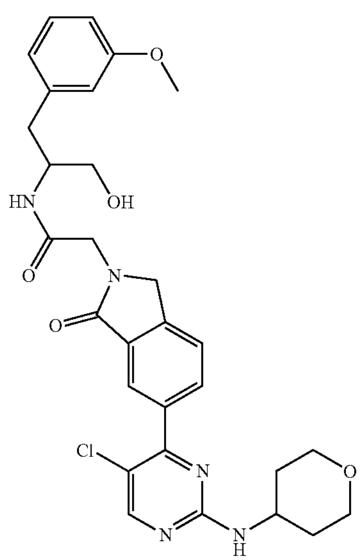 [SMILES: COc1cccc(CC(CO)NC(=O)CN2Cc3ccc(-c4nc(NC5CCOCC5)ncc4Cl)cc3C2=O)c1] | 2-(6-{5-chloro-2-[(oxan-4-yl)amino]pyrimidin-4-yl}-1-oxo-2,3-dihydro-1H-isoindol-2-yl)-N-[1-hydroxy-3-(3-methoxyphenyl)propan-2-yl]acetamide | (Me-d3-OD): 8.36 (1H, s), 8.23(1H, d), 8.08 (1H, dd), 7.67 (1H, dd), 7.19-7.13 (1H, m), 6.84-6.80 (2H, m), 6.78-6.73 (1H, m), 4.43 (2H, s), 4.28 (2H, s), 4.26-4.17 (1H, m), 4.11-4.02 (1H, m), 4.02-3.94 (2H, m), 3.77 (3H, s), 3.64-3.51 (4H, m), 2.94 (1H, dd), 2.73 (1H, dd), 2.05-1.98 (2H, m), 1.70-1.57 (2H, m). | 566 |

| Example | Structure | Name | ¹H NMR (400 MHz) | MS: [M + H]⁺ |
|---|---|---|---|---|
| 211 | 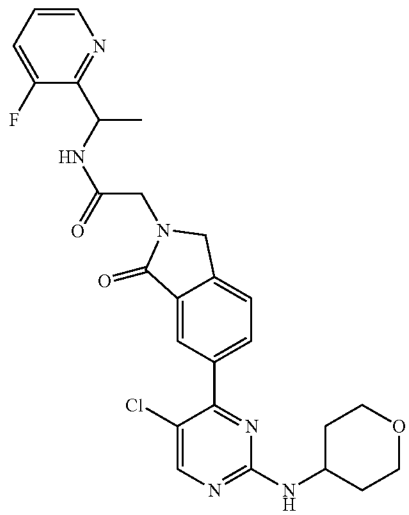 [SMILES: CC(NC(=O)CN1Cc2ccc(-c3nc(NC4CCOCC4)ncc3Cl)cc2C1=O)c1ncccc1F] | 2-(6-{5-chloro-2-[(oxan-4-yl)amino]pyrimidin-4-yl}-1-oxo-2,3-dihydro-1H-isoindol-2-yl)-N-[1-(3-fluoropyridin-2-yl)ethyl]acetamide | (Me-d3-OD): 8.37 (1H, dt), 8.35 (1H, s), 8.23 (1H, d), 8.07(1H, dd), 7.70 (1H, dd), 7.58 (1H, ddd), 7.37 (1H, quintet), 5.48-5.41 (1H, m), 4.66 (2H, s), 4.44 (1H, d), 4.41 (1H, d), 4.11-4.02 (1H, m), 4.02-3.95 (2H, m), 3.54 (2H, td), 2.04-1.98 (2H, m), 1.70-1.56 (2H, m), 1.51 (3H, d). | 525 |
| 212 | 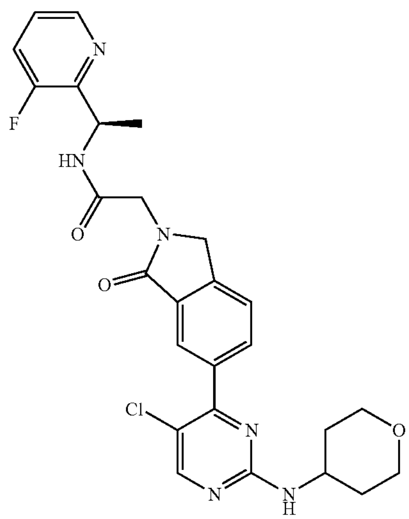 [SMILES: C[C@@H](NC(=O)CN1Cc2ccc(-c3nc(NC4CCOCC4)ncc3Cl)cc2C1=O)c1ncccc1F] | 2-(6-{5-chloro-2-[(oxan-4-yl)amino]pyrimidin-4-yl}-1-oxo-2,3-dihydro-1H-isoindol-2-yl)-N-[(1R)-1-(3-fluoropyridin-2-yl)ethyl]acetamide | (Me-d3-OD): 8.37 (1H, dt), 8.35 (1H, s), 8.23 (1H, s), 8.07 (1H, dd), 7.70 (1H, d), 7.58 (1H, ddd), 7.41-7.34 (1H, m), 5.44 (1H, q), 4.66 (2H, s), 4.44 (1H, d), 4.41 (1H, d), 4 11-4.02 (1H, m), 4.02-3.94 (2H, m), 3.54 (2H, td), 2.05-1.98 (2H, m), 1.70-1.57 (2H, m), 1.51 (3H, d). | 525 |
| 213 | 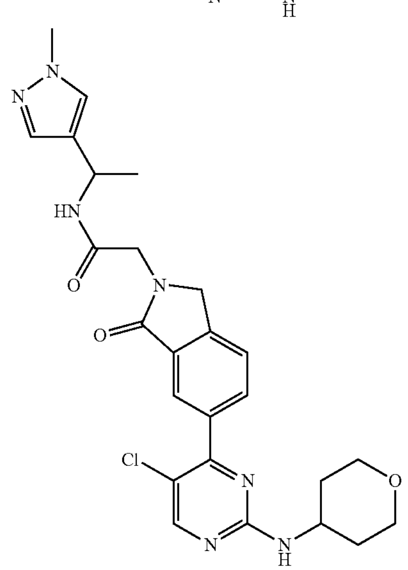 | 2-(6-{5-chloro-2-[(oxan-4-yl)amino]pyrimidin-4-yl}-1-oxo-2,3-dihydro-1H-isoindol-2-yl)-N-[1-(1-methyl-1H-pyrazol-4-yl)ethyl]acetamide | (Me-d3-OD): 8.36 (1H, s), 8.24 (1H, d), 8.08 (1H, dd), 7.71 (1H, dd), 7.56 (1H, s), 7.45 (1H, s), 5.08 (1H, q), 4.68 (2H, s), 4.35 (2H, s), 4.12-4.02 (1H, m), 4.02-3.93 (2H, m), 3.86 (3H, s), 3.55 (2H, td), 2.05-1.97 (2H, m), 1.70-1.57 (2H, m), 1.50 (3H, d). | 510 |

-continued

| Example | Name | ¹H NMR (400 MHz) | MS: [M + H]⁺ |
|---|---|---|---|
| 214 | 2-(6-{5-chloro-2-[(oxan-4-yl)amino]pyrimidin-4-yl}-1-oxo-2,3-dihydro-1H-isoindol-2-yl)-N-[2-hydroxy-1-(1-methyl-1H-pyrazol-3-yl)ethyl]acetamide | (Me-d3-OD): 8.36 (1H, s), 8.24 (1H, s), 8.10-8.06 (1H, m), 7.72 (1H, d), 7.51 (1H, d), 6.28 (1H, d), 5.17-5.13 (1H, m), 4.70 (2H, s), 4.44 (2H, s), 4.10-4.02 (1H, m), 3.99 (2H, d), 3.91-3.84 (4H, m), 3.83-3.78 (1H, m), 3.58-3.51 (2H, m), 2.06-1.98 (2H, m), 1.69-1.58 (2H, m). | 526 |
| 215 | 2-(6-{5-chloro-2-[(oxan-4-yl)amino]pyrimidin-4-yl}-1-oxo-2,3-dihydro-1H-isoindol-2-yl)-N-[1-(1,3-dimethyl-1H-pyrazol-4-yl)ethyl]acetamide | (Me-d3-OD): 8.36 (1H, s), 8.24(1H, d), 8.08 (1H, dd), 7.71 (1H, d), 7.48 (1H, s), 5.09-4.99 (1H, m), 4.68 (2H, s), 4.33 (2H, s), 4.13-4.02 (1H, m), 4.02-3.94 (2H, m), 3.79 (3H, s), 3.55 (2H, td), 2.21 (3H, s), 2.06-1.97 (2H, m), 1.70-1.57 (2H, m), 1.48 (3H, d). | 524 |

-continued

| Example | Structure | Name | ¹H NMR (400 MHz) | MS: [M + H]⁺ |
|---|---|---|---|---|
| 216 | 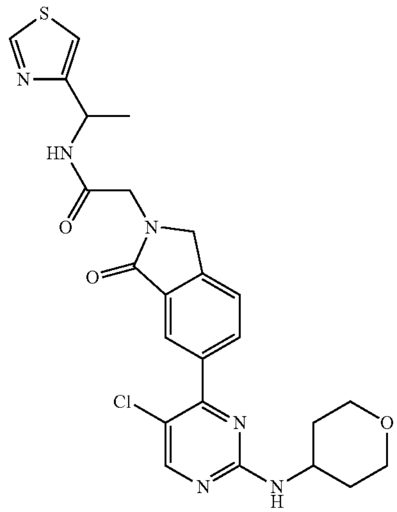 [SMILES: CC(NC(=O)CN1Cc2ccc(-c3nc(NC4CCOCC4)ncc3Cl)cc2C1=O)c1cscn1] | 2-(6-{5-chloro-2-[(oxan-4-yl)amino]pyrimidin-4-yl}-1-oxo-2,3-dihydro-1H-isoindol-2-yl)-N-[1-(1,3-thiazol-4-yl)ethyl]acetamide | (Me-d3-OD): 8.97 (1H, d), 8.35 (1H, s), 8.24 (1H, d), 8.08 (1H, dd), 7.71 (1H, dd), 7.47 (1H, dd), 5.29 (1H, q), 4.69 (2H, s), 4.41 (2H, s), 4.11-4.02 (1H, m), 4.02-3.95 (2H, m), 3.54 (2H, td), 2.06-1.97 (2H, m), 1.70-1.60 (2H, m), 1.58 (3H, d). | 513 |
| 217 | 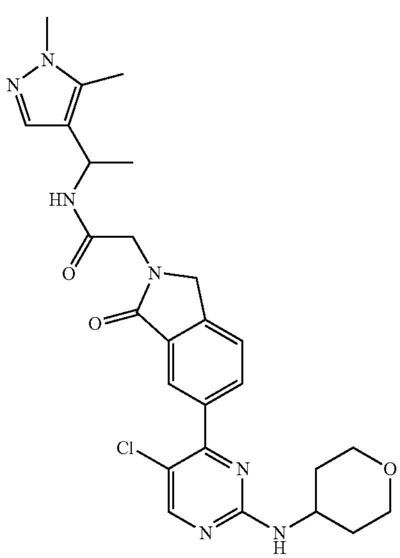 [SMILES: Cc1c(C(C)NC(=O)CN2Cc3ccc(-c4nc(NC5CCOCC5)ncc4Cl)cc3C2=O)cnn1C] | 2-(6-{5-chloro-2-[(oxan-4-yl)amino]pyrimidin-4-yl}-1-oxo-2,3-dihydro-1H-isoindol-2-yl)-N-[1-(1,5-dimethyl-1H-pyrazol-4-yl)ethyl]acetamide | (DMSO-d6): 8.45 (1H, s), 8.30 (1H, d), 8.04-8.02 (1H, m), 7.98 (1H, dd), 7.74 (1H, d) 7.58 (1H, br s), 7.31 (1H, s), 4.92-4.83 (1H, m), 4.58 (2H, s), 4.17 (2H, s), 3.98-3.90 (1H, m), 3.90-3.83 (2H, m), 3.68 (3H, s), 3.38 (2H, t), 2.18 (3H, s), 1.89-1.81 (2H, m), 1.60-1.47 (2H, m), 1.36 (3H, d). | 524 |

| Example | Structure | Name | ¹H NMR (400 MHz) | MS: [M + H]⁺ |
|---|---|---|---|---|
| 218 | 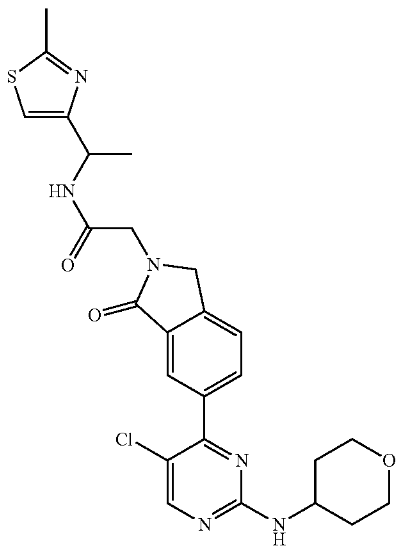 [SMILES: Cc1nc(C(C)NC(=O)CN2Cc3ccc(-c4nc(NC5CCOCC5)ncc4Cl)cc3C2=O)cs1] | 2-(6-{5-chloro-2-[(oxan-4-yl)amino]pyrimidin-4-yl}-1-oxo-2,3-dihydro-1H-isoindol-2-yl)-N-[1-(2-methyl-1,3-thiazol-4-yl)ethyl]acetamide | (Me-d3-OD): 8.36 (1H, s), 8.24 (1H, d), 8.08 (1H, dd), 7.71 (1H, dd), 7.21 (1H, d), 5.17 (1H, q), 4.69 (2H, s), 4.40 (2H, s), 4.12-4.02 (1H, m), 4.02-3.95 (2H, m), 3.61-3.48 (2H, m), 2.69 (3H, s), 2.05-1.97 (2H, m), 1.69-1.58 (2H, m), 1.54 (3H, d). | 527 |
| 219 | 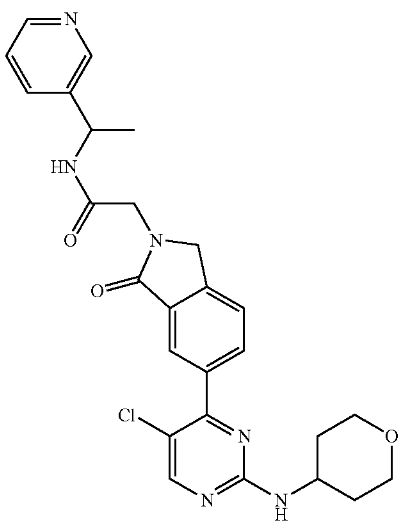 [SMILES: CC(NC(=O)CN1Cc2ccc(-c3nc(NC4CCOCC4)ncc3Cl)cc2C1=O)c1cccnc1] | 2-(6-{5-chloro-2-[(oxan-4-yl)amino]pyrimidin-4-yl}-1-oxo-2,3-dihydro-1H-isoindol-2-yl)-N-[1-(pyridin-3-yl)ethyl]acetamide | (Me-d3-OD): 8.57 (1H, d), 8.44 (1H, dd), 8.35 (1H, s), 8.23 (1H, d), 8.07 (1H, dd), 7.89-7.84 (1H, m), 7.70 (1H, dd), 7.44 (1H, ddd), 5.13 (1H, q), 4.67 (2H, s), 4.42 (1H, d), 4.38 (1H, d), 4 10-4.02 (1H, m), 4.01-3.94 (2H, m), 3.54 (2H, td), 2.04-1.97 (2H, m), 1.68-1.58 (2H, m), 1.55 (3H, d). | 507 |
| 220 | 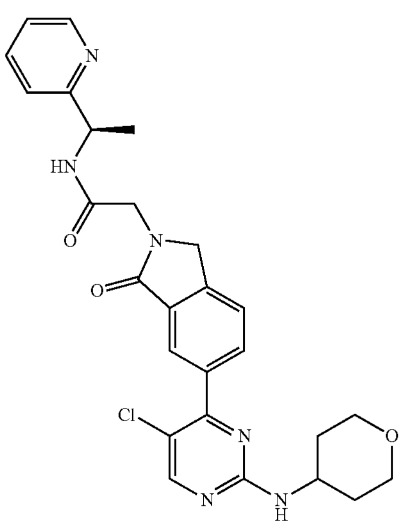 [SMILES: C[C@@H](NC(=O)CN1Cc2ccc(-c3nc(NC4CCOCC4)ncc3Cl)cc2C1=O)c1ccccn1] | 2-(6-{5-chloro-2-[(oxan-4-yl)amino]pyrimidin-4-yl}-1-oxo-2,3-dihydro-1H-isoindol-2-yl)-N-[(1R)-1-(pyridin-2-yl)ethyl]acetamide | (Me-d3-OD): 8.50 (1H, ddd), 8.36 (1H, s), 8.24 (1H, d), 8.07 (1H, dd), 7.82 (1H, dt), 7.71 (1H, dd), 7.46 (1H, d), 7.30 (1H, ddd), 5.12 (1H, q), 4.68 (2H, s), 4.44 (2H, s), 4.11-4.02 (1H, m), 4.02-3.94 (2H, m), 3.54 (2H, td), 2.04-1.98 (2H, m), 1.69-1.57 (2H, m), 1.53 (3H, d). | 507 |

| Example | Structure | Name | ¹H NMR (400 MHz) | MS: [M + H]⁺ |
|---|---|---|---|---|
| 221 | 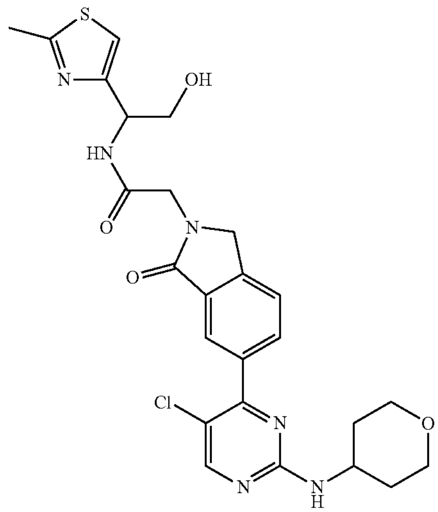 [SMILES: Cc1nc(C(CO)NC(=O)CN2Cc3ccc(-c4nc(NC5CCOCC5)ncc4Cl)cc3C2=O)cs1] | 2-(6-{5-chloro-2-[(oxan-4-yl)amino]pyrimidin-4-yl}-1-oxo-2,3-dihydro-1H-isoindol-2-yl)-N-[2-hydroxy-1-(2-methyl-1,3-thiazol-4-yl)ethyl]acetamide | (Me-d3-OD): 8.35 (1H, s), 8.24 (1H, d), 8.08 (1H, dd), 7.71 (1H, dd), 7.28 (1H, d), 5.18 (1H, t), 4.70 (2H, s), 4.45 (2H, s), 4.11-4.02 (1H, m), 4.02-3.96 (2H, m), 3.93 (1H, dd), 3.86 (1H, dd), 3.54 (2H, td), 2.69 (3H, s), 2.04-1.97 (2H, m), 1.70-1.56 (2H, m). | 543 |
| 222 | 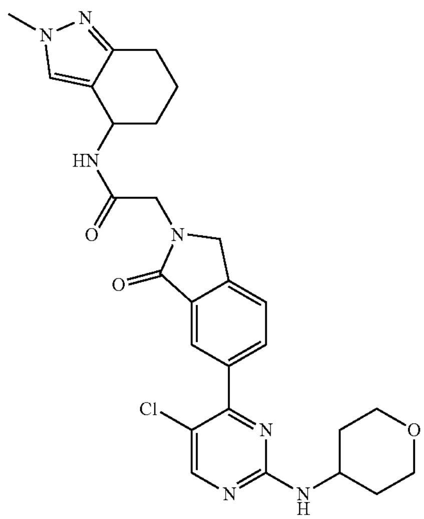 [SMILES: Cn1cc2c(n1)CCCC2NC(=O)CN1Cc2ccc(-c3nc(NC4CCOCC4)ncc3Cl)cc2C1=O] | 2-(6-{5-chloro-2-[(oxan-4-yl)amino]pyrimidin-4-yl}-1-oxo-2,3-dihydro-1H-isoindol-2-yl)-N-(2-methyl-4,5,6,7-tetrahydro-2H-indazol-4-yl)acetamide | (Me-d3-OD): 8.36 (1H, s), 8.24 (1H, d), 8.08 (1H, dd), 7.72 (1H, d), 7.47 (1H, s), 5.01 (1H, dd), 4.70 (2H, s), 4.37 (1H, d), 4.33 (1H, d), 4.12-4.02 (1H, m), 4.02-3.95 (2H, m), 3.82 (3H, s), 3.55 (2H, td), 2.67-2.59 (2H, m), 2.05-1.97 (4H, m), 1.89-1.70 (2H, m), 1.70-1.56 (2H, m). | 536 |
| 223 | 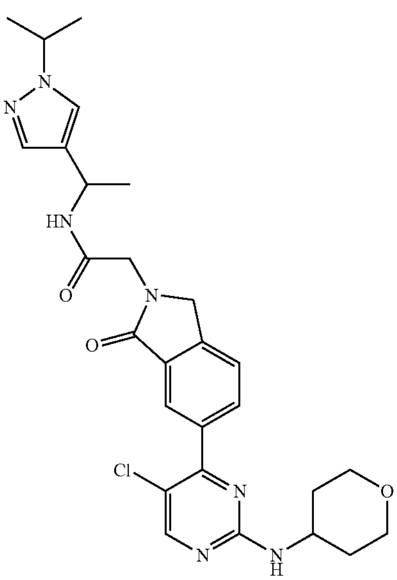 [SMILES: CC(NC(=O)CN1Cc2ccc(-c3nc(NC4CCOCC4)ncc3Cl)cc2C1=O)c1cnn(C(C)C)c1] | 2-(6-{5-chloro-2-[(oxan-4-yl)amino]pyrimidin-4-yl}-1-oxo-2,3-dihydro-1H-isoindol-2-yl)-N-{1-[1-(propan-2-yl)-1H-pyrazol-4-yl]ethyl}acetamide | (Me-d3-OD): 8.36 (1H, s), 8.24 (1H, d), 8.08 (1H, dd), 7.71 (1H, dd), 7.64 (1H, s), 7.47 (1H, s), 5.09 (1H, q), 4.68 (2H, s), 4.56-4.43 (1H, m), 4.35 (2H, s), 4.11-4.02 (1H, m), 4.02-3.95 (2H, m), 3.54 (2H, td), 2.04-1.98 (2H, m), 1.69-1.58 (2H, m), 1.50 (3H, d), 1.48 (6H, d). | 538 |

-continued

| Example | Structure | Name | ¹H NMR (400 MHz) | MS: [M + H]⁺ |
|---|---|---|---|---|
| 224 | 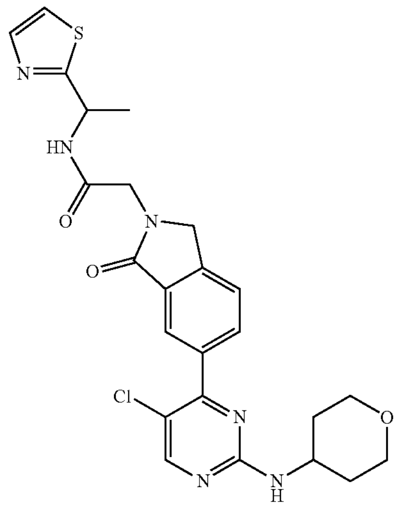 [SMILES: CC(NC(=O)CN1Cc2ccc(-c3nc(NC4CCOCC4)ncc3Cl)cc2C1=O)c1nccs1] | 2-(6-{5-chloro-2-[(oxan-4-yl)amino]pyrimidin-4-yl}-1-oxo-2,3-dihydro-1H-isoindol-2-yl)-N-[1-(1,3-thiazol-2-yl)ethyl]acetamide | (Me-d3-OD): 8.36 (1H, s), 8.24 (1H, d), 8.08 (1H, dd), 7.74 (1H, d), 7.72 (1H, d), 7.52 (1H, d), 5.40 (1H, q), 4.70 (2H, s), 4.45 (1H, d), 4.43 (1H, d), 4.11-4.02 (1H, m), 4.02-3.95 (2H, m), 3.55 (2H, td), 2.05-1.98 (2H, m), 1.69-1.58 (5H, m). | 513 |
| 225 | 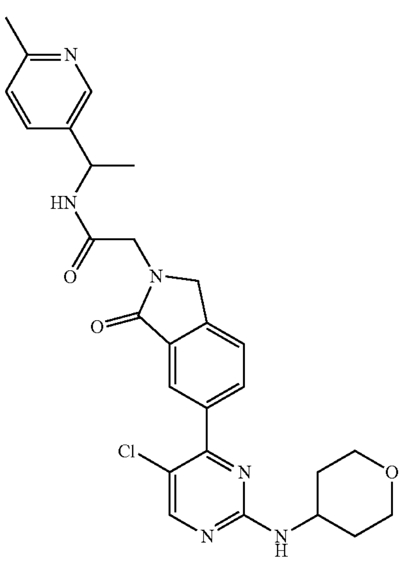 [SMILES: Cc1ccc(C(C)NC(=O)CN2Cc3ccc(-c4nc(NC5CCOCC5)ncc4Cl)cc3C2=O)cn1] | 2-(6-{5-chloro-2-[(oxan-4-yl)amino]pyrimidin-4-yl}-1-oxo-2,3-dihydro-1H-isoindol-2-yl)-N-[1-(6-methylpyridin-3-yl)ethyl]acetamide | (Me-d3-OD): 8.41 (1H, d), 8.35 (1H, s), 8.23 (1H, d), 8.07 (1H, dd), 7.74 (1H, dd), 7.70 (1H, d), 7.29 (1H, d), 5.09 (1H, q), 4.66 (2H, s), 4.41 (1H, d), 4.36 (1H, d), 4.11-4.03 (1H, m), 4.02-3.95 (2H, m), 3.54 (2H, td), 2.52 (3H, s), 2.04-1.97 (2H, m), 1.69-1.58 (2H, m), 1.53 (3H, d). | 521 |

-continued

| Example | Name | ¹H NMR (400 MHz) | MS: [M + H]⁺ |
|---------|------|------------------|--------------|
| 226 | 2-(6-{5-chloro-2-[(oxan-4-yl)amino]pyrimidin-4-yl}-1-oxo-2,3-dihydro-1H-isoindol-2-yl)-N-[1-(3,5-dimethylphenyl)propan-2-yl]acetamide | (Me-d3-OD): 8.36 (1H, s), 8.23 (1H, d), 8.08 (1H, dd), 7.68 (1H, dd), 6.83 (3H, br s), 4.45 (2H, s), 4.25 (2H, s), 4.23-4.14 (1H, m), 4.12-4.02 (1H, m), 4.02-3.95 (2H, m), 3.55 (2H, td), 2.73 (1H, dd), 2.70 (1H, dd), 2.26 (6H, s), 2.04-1.97 (2H, m), 1.70-1.57 (2H, m), 1.18 (3H, d). | 548 |
| 227 | 2-(6-{5-chloro-2-[(oxan-4-yl)amino]pyrimidin-4-yl}-1-oxo-2,3-dihydro-1H-isoindol-2-yl)-N-[1-(4,5-dimethyl-1,3-thiazol-2-yl)ethyl]acetamide | (Me-d3-OD): 8.35 (1H, s), 8.24 (1H, d), 8.08 (1H, dd), 7.72 (1H, dd), 5.25 (1H, q), 4.69 (2H, s), 4.43 (1H, d), 4.41 (1H, d), 4 11-4.02 (1H, m), 4.02-3.95 (2H, m), 3.54 (2H, td), 2.34 (3H, s), 2.29 (2H, s), 2.28 (1H, s), 2.05-1.98 (2H, m), 1.70-1.61 (2H, m), 1.59 (3H, d). | 541 |

| Example | Structure | Name | $^1$H NMR (400 MHz) | MS: [M + H]$^+$ |
|---|---|---|---|---|
| 228 | 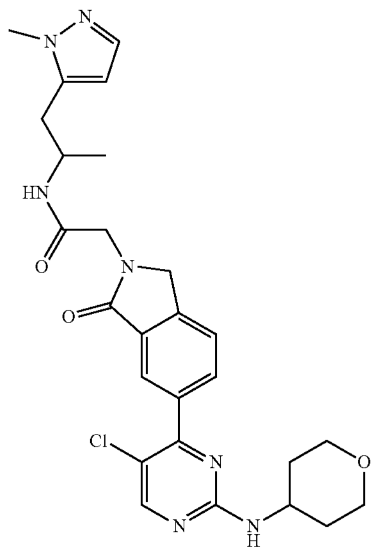 [SMILES: CC(Cc1ccnn1C)NC(=O)CN1Cc2ccc(-c3nc(NC4CCOCC4)ncc3Cl)cc2C1=O] | 2-(6-{5-chloro-2-[(oxan-4-yl)amino]pyrimidin-4-yl}-1-oxo-2,3-dihydro-1H-isoindol-2-yl)-N-[1-(1-methyl-1H-pyrazol-5-yl)propan-2-yl]acetamide | (DMSO-d6): 8.45 (1H, s), 8.11 (1H, d), 8.05-8.03 (1H, m), 7.99 (1H, dd), 7.74 (1H, d), 7.58 (1H, br d), 7.29 (1H, d), 6.05 (1H, d), 4.53 (2H, s), 4.17 (1H, d), 4.15 (1H, d), 4.09-3.99 (1H, m), 3.99-3.91 (1H, m), 3.91-3.83 (2H, m), 3.75 (3H, s), 3.38 (2H, t), 2.81 (1H, dd), 2.73 (1H, dd), 1.90-1.81 (2H, m), 1.60-1.47 (2H, m), 1.12 (3H, d). | 524 |
| 229 | 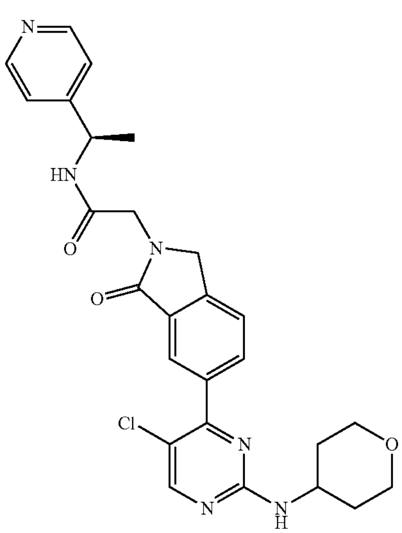 [SMILES: C[C@@H](NC(=O)CN1Cc2ccc(-c3nc(NC4CCOCC4)ncc3Cl)cc2C1=O)c1ccncc1] | 2-(6-{5-chloro-2-[(oxan-4-yl)amino]pyrimidin-4-yl}-1-oxo-2,3-dihydro-1H-isoindol-2-yl)-N-[(1R)-1-(pyridin-4-yl)ethyl]acetamide | (DMSO-d6): 8.68 (1H, d), 8.53-8.50 (2H, m), 8.44 (1H, s), 8.05-8.02 (1H, m), 7.98 (1H, dd), 7.74 (1H, d), 7.58 (1H, br d), 7.35-7.32 (2H, m), 4.98-4.90 (1H, m), 4.60 (2H, s), 4.29 (2H, s), 3.98-3.90 (1H, m), 3.90-3.82 (2H, m), 3.38 (2H, t), 1.90-1.80 (2H, m), 1.60-1.47 (2H, m), 1.39 (3H, d). | 507 |

-continued

| Example | Structure | Name | ¹H NMR (400 MHz) | MS: [M + H]⁺ |
|---|---|---|---|---|
| 230 | 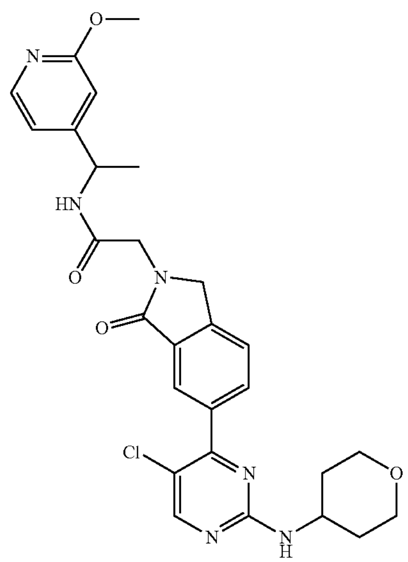 [SMILES: COc1cc(C(C)NC(=O)CN2Cc3ccc(-c4nc(NC5CCOCC5)ncc4Cl)cc3C2=O)ccn1] | 2-(6-{5-chloro-2-[(oxan-4-yl)amino]pyrimidin-4-yl}-1-oxo-2,3-dihydro-1H-isoindol-2-yl)-N-[1-(2-methoxypyridin-4-yl)ethyl]acetamide | (DMSO-d6): 8.63 (1H, d), 8.44 (1H, s), 8.10 (1H, dd), 8.04-8.02 (1H, m), 7.98 (1H, dd), 7.74 (1H, d), 7.58 (1H, br d), 6.94 (1H, dd), 6.75-6.73 (1H, m), 4.94-4.85 (1H, m), 4.59 (2H, s), 4.28 (2H, s), 3.98-3.91 (1H, m), 3.91-3.85 (2H, m), 3.84 (3H, s), 3.38 (2H, t), 1.90-1.79 (2H, m), 1.60-1.47 (2H, m), 1.37 (3H, d). | 537 |
| 231 | 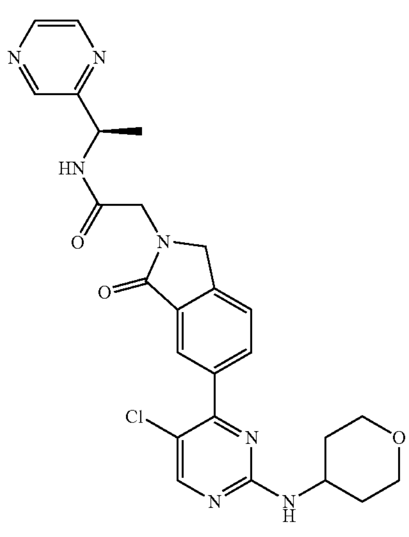 [SMILES: C[C@@H](NC(=O)CN1Cc2ccc(-c3nc(NC4CCOCC4)ncc3Cl)cc2C1=O)c1cnccn1] | 2-(6-{5-chloro-2-[(oxan-4-yl)amino]pyrimidin-4-yl}-1-oxo-2,3-dihydro-1H-isoindol-2-yl)-N-[(1R)-1-(pyrazin-2-yl)ethyl]acetamide | (DMSO-d6): 8.74 (1H, d), 8.67 (1H, d), 8.61 (1H, dd), 8.55 (1H, d), 8.44 (1H, s), 8.04-8.02 (1H, m), 7.98 (1H, dd), 7.74 (1H, d), 7.58 (1H, br d), 5.11-5.02 (1H, m), 4.60 (2H, s), 4.29 (2H, s), 3.98-3.90 (1H, m), 3.90-3.82 (2H, m), 3.38 (2H, t), 1.89-1.81 (2H, m), 1.60-1.48 (2H, m), 1.45 (3H, d). | 508 |

| Example | Structure | Name | ¹H NMR (400 MHz) | MS: [M + H]⁺ |
|---|---|---|---|---|
| 232 | 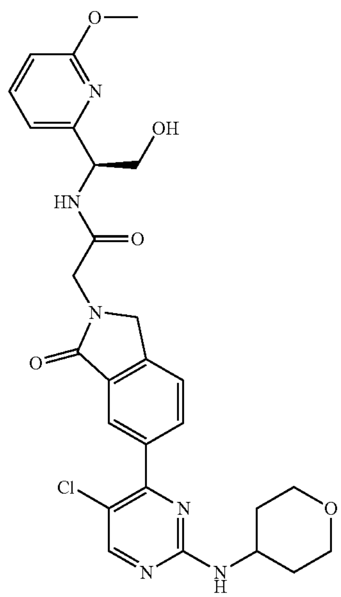 [SMILES: COc1cccc([C@@H](CO)NC(=O)CN2Cc3ccc(-c4nc(NC5CCOCC5)ncc4Cl)cc3C2=O)n1] | 2-(6-{5-chloro-2-[(oxan-4-yl)amino]pyrimidin-4-yl}-1-oxo-2,3-dihydro-1H-isoindol-2-yl)-N-[(1S)-2-hydroxy-1-(6-methoxypyridin-2-yl)ethyl]acetamide | (DMSO-d6): 8.45 (1H, s), 8.42 (1H, d), 8.05-8.03 (1H, m), 7.98 (1H, dd), 7.75 (1H, d), 7.66 (1H, dd), 7.58 (1H, br d), 6.96 (1H, d), 6.68 (1H, d), 4.90-4.83 (2H, m), 4.62 (2H, s), 4.34 (2H, s), 3.98-3.85 (3H, m), 3.84 (3H, s), 3.81-3.74 (1H, m), 3.74-3.64 (1H, m), 3.38 (2H, t), 1.89-1.81 (2H, m), 1.60-1.47 (2H, m). | 553 |
| 233 | 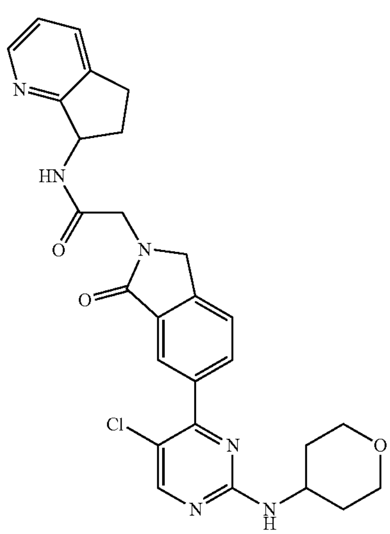 [SMILES: O=C(CN1Cc2ccc(-c3nc(NC4CCOCC4)ncc3Cl)cc2C1=O)NC1CCc2cccnc21] | 2-(6-{5-chloro-2-[(oxan-4-yl)amino]pyrimidin-4-yl}-1-oxo-2,3-dihydro-1H-isoindol-2-yl)-N-{5H,6H,7H-cyclopenta[b]pyridin-7-yl}acetamide | (DMSO-d6): 8.52 (1H, d), 8.45 (1H, s), 8.42-8.39 (1H, m), 8.05-8.03 (1H, m), 7.99 (1H, dd), 7.76 (1H, d), 7.69-7.65 (1H, m), 7.62-7.55 (1H, m), 7.22 (1H, ddd), 5.28 (1H, q), 4.65 (2H, s), 4.27 (2H, d), 3.99-3.90 (1H, m), 3.90-3.83 (2H, m), 3.43-3.33 (2H, m), 2.99-2.90 (1H, m), 2.89-2.79 (1H, m), 1.91-1.78 (4H, m), 1.59-1.48 (2H, m). | 519 |

-continued

| Example | Structure | Name | $^1$H NMR (400 MHz) | MS: [M + H]$^+$ |
|---|---|---|---|---|
| 234 | 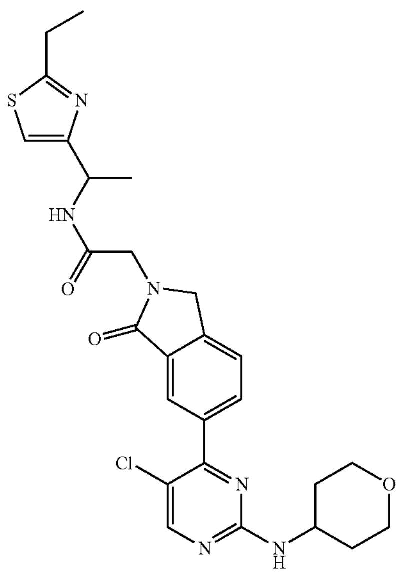 [SMILES: CCc1nc(C(C)NC(=O)CN2Cc3ccc(-c4nc(NC5CCOCC5)ncc4Cl)cc3C2=O)cs1] | 2-(6-{5-chloro-2-[(oxan-4-yl)amino]pyrimidin-4-yl}-1-oxo-2,3-dihydro-1H-isoindol-2-yl)-N-[1-(2-ethyl-1,3-thiazol-4-yl)ethyl]acetamide | (DMSO-d6): 8.55 (1H, d), 8.45 (1H, s), 8.05-8.02 (1H, m), 7.98 (1H, dd), 7.74 (1H, d), 7.58 (1H, br d), 7.25 (1H, d), 5.10-5.00 (1H, m), 4.61 (2H, s), 4.27 (1H, d), 4.25 (1H, d), 3.99-3.90 (1H, m), 3.90-3.82 (2H, m), 3.38 (2H, t), 2.97 (2H, q), 1.89-1.81 (2H, m), 1.61-1.47 (2H, m), 1.42 (3H, d), 1.30 (3H, t). | 541 |
| 235 | 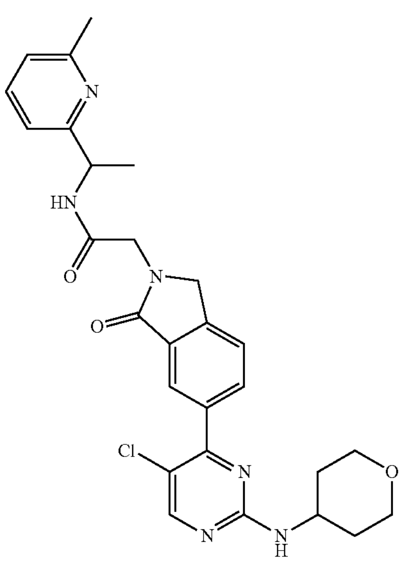 [SMILES: Cc1cccc(C(C)NC(=O)CN2Cc3ccc(-c4nc(NC5CCOCC5)ncc4Cl)cc3C2=O)n1] | 2-(6-{5-chloro-2-[(oxan-4-yl)amino]pyrimidin-4-yl}-1-oxo-2,3-dihydro-1H-isoindol-2-yl)-N-[1-(6-methylpyridin-2-yl)ethyl]acetamide | (DMSO-d6): 8.57 (1H, d), 8.44 (1H, s), 8.04-8.02 (1H, m), 7.98 (1H, dd), 7.74 (1H, d), 7.65 (1H, t), 7.58 (1H, br d), 7.16 (1H, d), 7.12 (1H, d), 4.99-4.90 (1H, m), 4.62 (1H, d), 4.60 (1H, d), 4.28 (2H, s), 3.99-3.90 (1H, m), 3.90-3.82 (2H, m), 3.38 (2H, t), 2.45 (3H, s), 1.89-1.81 (2H, m), 1.60-1.47 (2H, m), 1.40 (3H, d). | 521 |

| Example | Structure | Name | ¹H NMR (400 MHz) | MS: [M + H]⁺ |
|---|---|---|---|---|
| 236 | 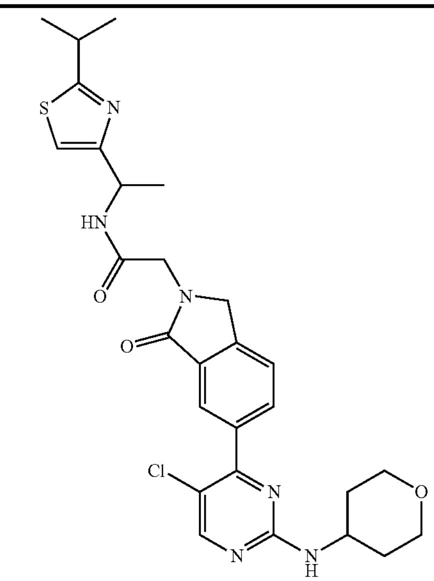 | 2-(6-{5-chloro-2-[(oxan-4-yl)amino]pyrimidin-4-yl}-1-oxo2,3-dihydro-1H-isoindol-2-yl)-N-{1-[2-(propan-2-yl)-1,3-thiazol-4-yl]ethyl}acetamide | (DMSO-d6): 8.54 (1H, d), 8.45 (1H, s), 8.05-8.03 (1H, m), 7.98 (1H, dd), 7.74 (1H, d), 7.58 (1H, br d), 7.26 (1H, d), 5.10-5.00 (1H, m), 4.62 (2H, s), 4.28 (1H, d), 4.25 (1H, d), 3.99-3.90 (1H, m), 3.90-3.82 (2H, m), 3.38 (2H, t), 3.29-3.21 (1H, m), 1.89-1.81 (2H, m), 1.60-1.47 (2H, m), 1.42 (3H, d), 1.33 (6H, d). | 555 |
| 237 | 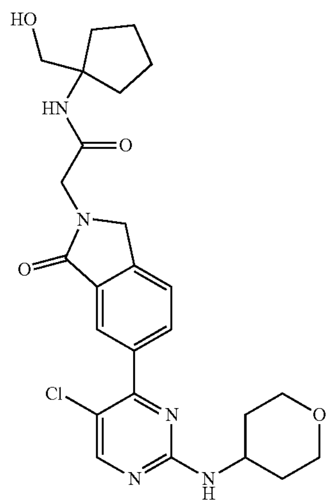 [SMILES: O=C(CN1Cc2ccc(-c3nc(NC4CCOCC4)ncc3Cl)cc2C1=O)NC1(CO)CCCC1] | 2-(6-{5-chloro-2-[(oxan-4-yl)amino]pyrimidin-4-yl}-1-oxo-2,3-dihydro-1H-isoindol-2-yl)-N-[1-(hydroxymethyl)cyclopentyl]acetamide | (Me-d3-OD): 8.36 (1H, s), 8.24 (1H, d), 8.08 (1H, dd), 7.71 (1H, d), 4.68 (2H, s), 4.34 (2H, s), 4.10-4.02 (1H, m), 4.02-3.92 (2H, m), 3.55 (2H, td), 2.03-1.90 (4H, m), 1.84-1.73 (5H, m), 1.72-1.57 (5H, m). | 500 |
| 238 | 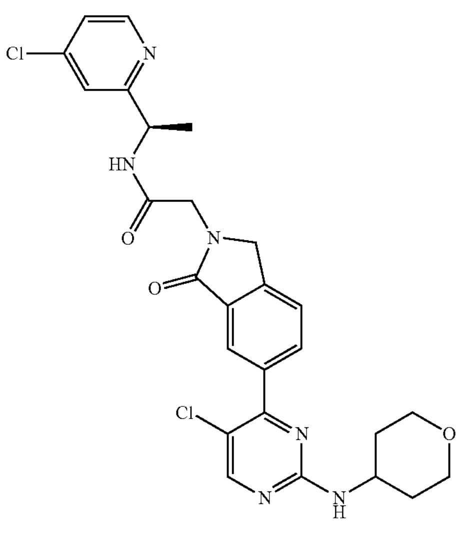 [SMILES: C[C@@H](NC(=O)CN1Cc2ccc(-c3nc(NC4CCOCC4)ncc3Cl)cc2C1=O)c1cc(Cl)ccn1] | 2-(6-{5-chloro-2-[(oxan-4-yl)amino]pyrimidin-4-yl}-1-oxo-2,3-dihydro-1H-isoindol-2-yl)-N-[(1R)-1-(4-chloropyridin-2-yl)ethyl]acetamide | (DMSO-d6): 8.66 (1H, d), 8.51 (1H, dd) 8.44 (1H, s), 8.04-8.02 (1H, m), 7.98 (1H, dd), 7.74 (1H, d), 7.58 (1H, br d), 7.50 (1H, d), 7.42 (1H, dd), 5.04-4.95 (1H, m), 4.60 (2H, s), 4.30 (2H, s), 3.99-3.91 (1H, m), 3.91-3.82 (2H, m), 3.38 (2H, t), 1.89-1.81 (2H, m), 1.60-1.46 (2H, m), 1.42 (3H, d). | 541 |

| Example | Structure | Name | $^1$H NMR (400 MHz) | MS: [M + H]$^+$ |
|---|---|---|---|---|
| 239 | 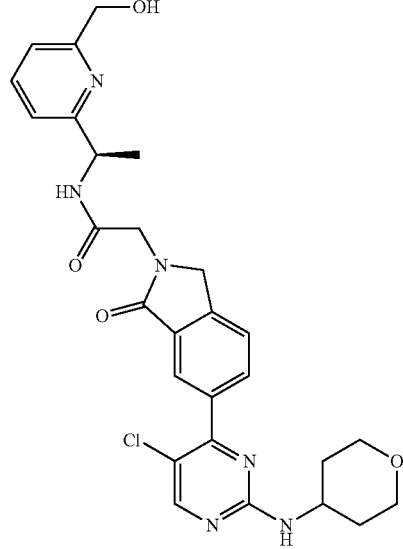 [SMILES: C[C@@H](NC(=O)CN1Cc2ccc(-c3nc(NC4CCOCC4)ncc3Cl)cc2C1=O)c1cccc(CO)n1] | 2-(6-{5-chloro-2-[(oxan-4-yl)amino]pyrimidin-4-yl}-1-oxo-2,3-dihydro-1H-isoindol-2-yl)-N-[(1R)-1-[6-(hydroxymethyl)pyridin-2-yl]ethyl]acetamide | (DMSO-d6): 8.59 (1H, d), 8.44 (1H, s), 8.05-8.02 (1H, m), 7.98 (1H, dd), 7.80-7.72 (2H, m), 7.58 (1H, br d), 7.34 (1H, d), 7.23 (1H, d), 5.35 (1H, t), 5.02-4.92 (1H, m), 4.61 (2H, d), 4.55 (2H, d), 4 29 (2H, s), 3.99-3.90 (1H, m), 3.90-3.82 (2H, m), 3.38 (2H, t), 1.89-1.81 (2H, m), 1.59-1.48 (2H, m), 1.40 (3H, d). | 537 |
| 240 | 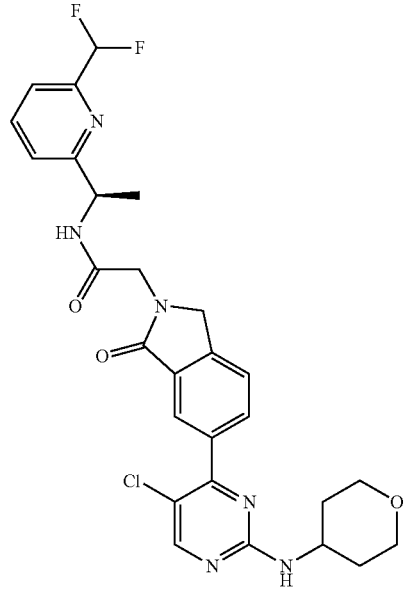 [SMILES: C[C@@H](NC(=O)CN1Cc2ccc(-c3nc(NC4CCOCC4)ncc3Cl)cc2C1=O)c1cccc(C(F)F)n1] | 2-(6-{5-chloro-2-[(oxan-4-yl)amino]pyrimidin-4-yl}-1-oxo-2,3-dihydro-1H-isoindol-2-yl)-N-[(1R)-1-[6-(difluoromethyl)pyridin-2-yl]ethyl]acetamide | (DMSO-d6): 8.70 (1H, d), 8.44 (1H, s), 8.04-8.02 (1H, m), 8.02-7.96 (2H, m), 7.74 (1H, d), 7.57 (3H, dd), 6.92 (1H, t), 5.08-4.98 (1H, m), 4.62 (1H, d), 4.59 (1H, d), 4.30 (2H, s), 3.99-3.90 (1H, m), 3.90-3.81 (2H, m), 3.38 (2H, t), 1.89-1.81 (2H, m), 1.59-1.48 (2H, m), 1.44 (3H, d). | 557 |

-continued

| Example | Structure | Name | ¹H NMR (400 MHz) | MS: [M + H]⁺ |
|---------|-----------|------|------------------|--------------|
| 241 | 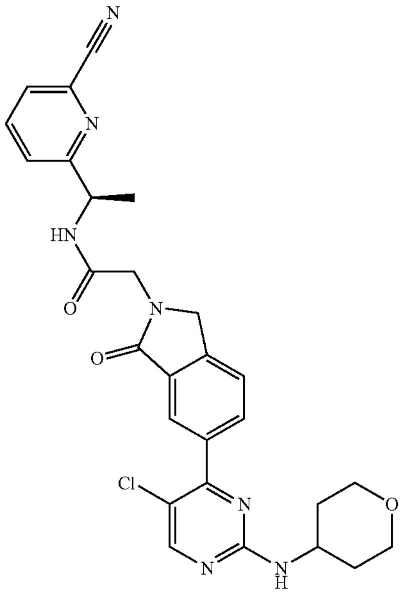 [SMILES: C[C@@H](NC(=O)CN1Cc2ccc(-c3nc(NC4CCOCC4)ncc3Cl)cc2C1=O)c1cccc(C#N)n1] | 2-(6-{5-chloro-2-[(oxan-4-yl)amino]pyrimidin-4-yl}-1-oxo-2,3-dihydro-1H-isoindol-2-yl)-N-[(1R)-1-(6-cyanopyridin-2-yl)ethyl]acetamide | (DMSO-d6): 8.75 (1H, d), 8.44 (1H, s), 8.08-8.02 (2H, m), 7.98 (1H, dd), 7.93 (1H, dd), 7.76-7.71 (2H, m), 7.58 (1H, br d), 5.07-4.99 (1H, m), 4.61 (1H, d), 4.59 (1H, d), 4.29 (2H, s), 3.98-3.90 (1H, m), 3.90-3.82 (2H, m), 3.38 (2H, t), 1.89-1.81 (2H, m), 1.59-1.48 (2H, m), 1.43 (3H, d). | 532 |
| 242 | 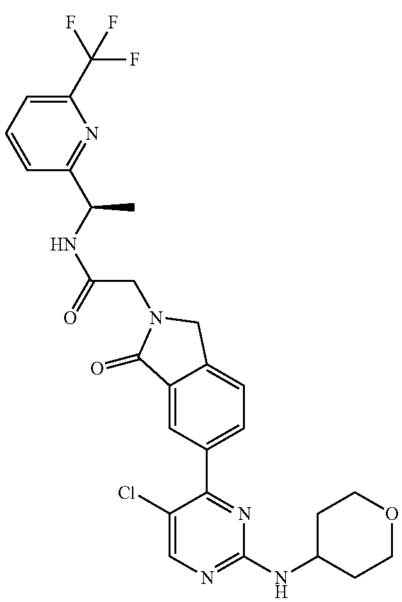 [SMILES: C[C@@H](NC(=O)CN1Cc2ccc(-c3nc(NC4CCOCC4)ncc3Cl)cc2C1=O)c1cccc(C(F)(F)F)n1] | 2-(6-{5-chloro-2-[(oxan-4-yl)amino]pyrimidin-4-yl}-1-oxo-2,3-dihydro-1H-isoindol-2-yl)-N-[(1R)-1-[6-(trifluoromethyl)pyridin-2-yl]ethyl]acetamide | (DMSO-d6): 8.75 (1H, d), 8.44 (1H, s), 8.08 (1H, t), 8.04-8.02 (1H, m), 7.98 (1H, dd), 7.78 (1H, d), 7.72 (2H, t), 7.58 (1H, br d), 5.09-5.00 (1H, m), 4.61 (1H, d), 4.58 (1H, d), 4.30 (2H, s), 3.98-3.90 (1H, m), 3.90-3.82 (2H, m), 3.38 (2H, t), 1.90-1.80 (2H, m), 1.59-1.48 (2H, m), 1.45 (3H, d). | 575 |

-continued

| Example | Structure | Name | ¹H NMR (400 MHz) | MS: [M + H]⁺ |
|---|---|---|---|---|
| 243 | 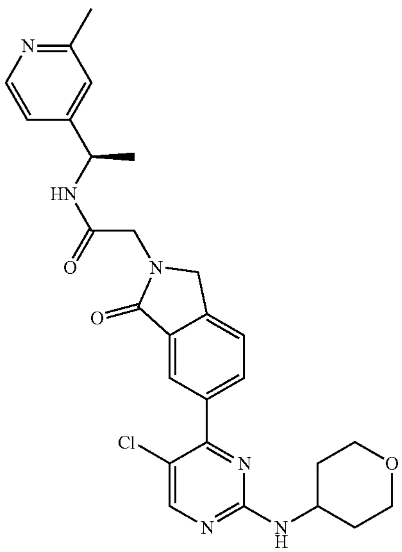 [SMILES: Cc1cc([C@@H](C)NC(=O)CN2Cc3ccc(-c4nc(NC5CCOCC5)ncc4Cl)cc3C2=O)ccn1] | 2-(6-{5-chloro-2-[(oxan-4-yl)amino]pyrimidin-4-yl}-1-oxo-2,3-dihydro-1H-isoindol-2-yl)-N-[(1R)-1-(2-methylpyridin-4-yl)ethyl]acetamide | (DMSO-d6): 8.64 (1H, d), 8.44 (1H, s), 8.38 (1H, d), 8.05-8.02 (1H, m), 7.98 (1H, dd), 7.74 (1H, d), 7.58 (1H, br d), 7.19 (1H, s), 7.15-7.11 (1H, m), 4.95-4.85 (1H, m), 4.60 (2H, s), 4.28 (2H, s), 3.98-3.90 (1H, m), 3.90-3.82 (2H, m), 3 38 (2H, t), 1.89-1.81 (2H, m), 1.59-1.47 (2H, m), 1.38 (3H, d). | 521 |
| 244 | 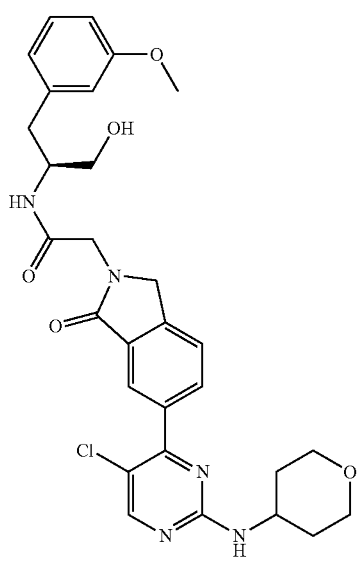 [SMILES: COc1cccc(C[C@@H](CO)NC(=O)CN2Cc3ccc(-c4nc(NC5CCOCC5)ncc4Cl)cc3C2=O)c1] | 2-(6-{5-chloro-2-[(oxan-4-yl)amino]pyrimidin-4-yl}-1-oxo-2(3-dihydro-1H-isoindol-2-yl)-N-[(2S)-1-hydroxy-3-(3-methoxyphenyl)propan-2-yl]acetamide | (Me-d3-OD): 8.36 (1H, s), 8.24-8.22 (1H, m), 8.08 (1H, dd), 7.68 (1H, dd), 7.19-7.14 (1H, m), 6.84-6.80 (2H, m), 6.78-6.73 (1H, m), 4.43 (2H, s), 4.28 (2H, s), 4.25-4.18 (1H, m), 4.11-4.02 (1H, m), 4.02-3.95 (2H, m), 3.77 (3H, s), 3.61-3.50 (4H, m), 2.98-2.90 (1H, m), 2.79-2.68 (1H, m), 2.05-1.98 (2H, m), 1.69-1.58 (2H, m). | 566 |

| Example | Structure | Name | $^1$H NMR (400 MHz) | MS: [M + H]$^+$ |
|---|---|---|---|---|
| 245 | 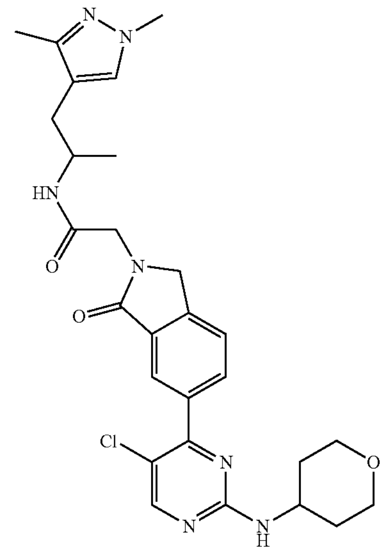 [SMILES: Cc1nn(C)cc1CC(C)NC(=O)CN1Cc2ccc(-c3nc(NC4CCOCC4)ncc3Cl)cc2C1=O] | 2-(6-{5-chloro-2-[(oxan-4-yl)amino]pyrimidin-4-yl}-1-oxo-2,3-dihydro-1H-isoindol-2-yl)-N-[1-(1,3-dimethyl-1H-pyrazol-4-yl)propan-2-yl]acetamide | (DMSO-d6): 8.45 (1H, s), 8.05-8.03 (1H, m), 8.01-7.96 (2H, m), 7.75 (1H, d), 7.59 (1H, br d), 7.14 (1H, s), 4.55 (2H, s), 4.17 (1H, d), 4.15 (1H, d), 3.99-3.90 (1H, m), 3.90-3.78 (3H, m), 3.68 (3H, s), 3.38 (2H, t), 2.49-2.37 (2H, m), 2.16 (3H, s), 1.85 (2H, d), 1.61-1.47 (2H, m), 1.03 (3H, d). | 538 |
| 246 | 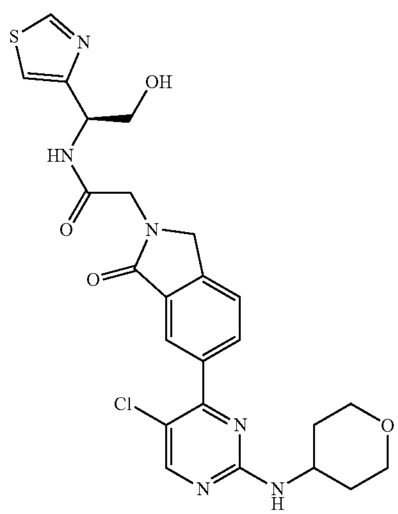 [SMILES: O=C(CN1Cc2ccc(-c3nc(NC4CCOCC4)ncc3Cl)cc2C1=O)N[C@H](CO)c1cscn1] | 2-(6-{5-chloro-2-[(oxan-4-yl)amino]pyrimidin-4-yl}-1-oxo-2(3-dihydro-1H-isoindol-2-yl)-N-[(1S)-2-hydroxy-1-(1,3-thiazol-4-yl)ethyl]acetamide | (DMSO-d6): 9.07 (1H, d), 8.53 (1H, d), 8.45 (1H, s), 8.05-8.03 (1H, m), 7.98 (1H, dd), 7.75 (1H, d), 7.58 (1H, br d), 7.50 (1H, dd), 5.15-5.08 (1H, m), 4.89 (1H, t), 4.61 (2H, s), 4.32 (1H, d), 4.30 (1H, d), 3.99-3.90 (1H, m), 3.90-3.83 (2H, m), 3.81-3.74 (1H, m), 3.72-3.65 (1H, m), 3.38 (2H, t), 1.90-1.81 (2H, m), 1.60-1.47 (2H, m). | 529 |
| 247 | 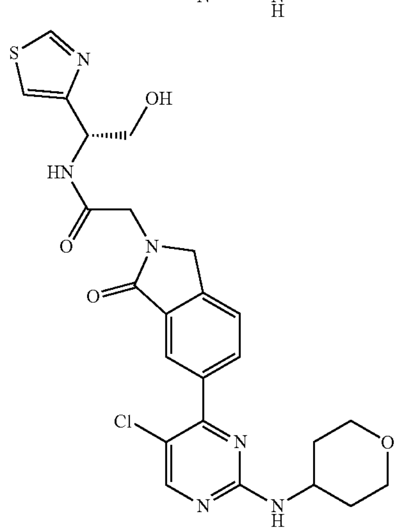 | 2-(6-{5-chloro-2-[(oxan-4-yl)amino]pyrimidin-4-yl}-1-oxo-2,3-dihydro-1H-isoindol-2-yl)-N-[(1R)-2-hydroxy-1-(1,3-thiazol-2-yl)ethyl]acetamide | (DMSO-d6): 8.86 (1H, d), 8.45 (1H, s), 8.05-8.03 (1H, m), 7.99 (1H, dd), 7.77-7.73 (2H, m), 7.64 (1H, d), 7.58 (1H, br d), 5.23-5.17 (1H, m), 5.11 (1H, t), 4.62 (2H, s), 4.35 (1H, d), 4.32 (1H, d), 3.98-3.90 (1H, m), 3.90-3.80 (3H, m), 3.80-3.72 (1H, m), 3 38 (2H, t), 1.90-1.80 (2H, m), 1.60-1.47 (2H, m). | 529 |

| Example | Structure | Name | ¹H NMR (400 MHz) | MS: [M + H]⁺ |
|---|---|---|---|---|
| 248 | 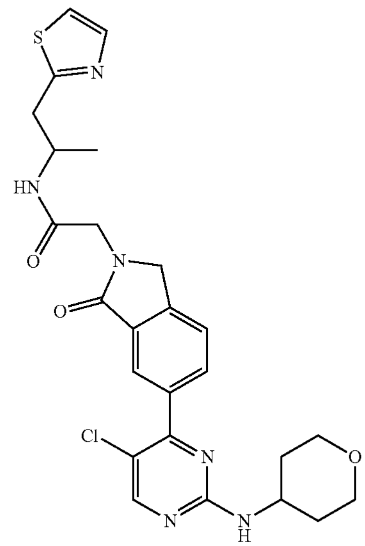 [SMILES: CC(Cc1nccs1)NC(=O)CN1Cc2ccc(-c3nc(NC4CCOCC4)ncc3Cl)cc2C1=O] | 2-(6-{5-chloro-2-[(oxan-4-yl)amino]pyrimidin-4-yl}-1-oxo-2,3-dihydro-1H-isoindol-2-yl)-N-[1-(1,3-thiazol-2-yl)propan-2-yl]acetamide | (DMSO-d6): 8.45 (1H, s), 8.18 (1H, d), 8.05-8.03 (1H, m), 7.99 (1H, dd), 7.75 (1H, d), 7.70 (1H, d), 7.63-7.54 (2H, m), 4.55 (1H, d), 4.53 (1H, d), 4.23-4.10 (3H, m), 3.99-3.90 (1H, m), 3.90-3.82 (2H, m), 3.42-3.35 (2H, m), 3.16 (1H, dd), 3.13 (1H, dd), 1.90-1.81 (2H, m), 1.61-1.47 (2H, m), 1.13 (3H, d). | 527 |
| 249 | 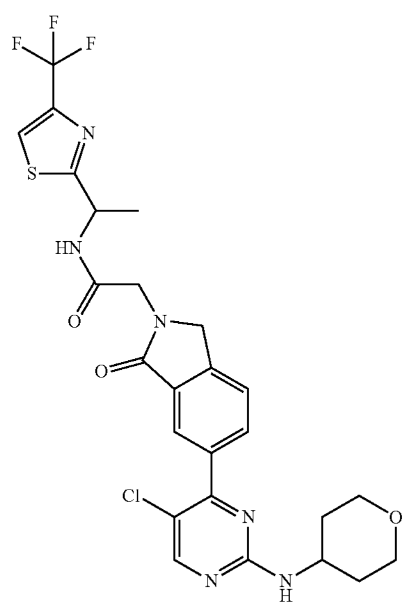 [SMILES: CC(NC(=O)CN1Cc2ccc(-c3nc(NC4CCOCC4)ncc3Cl)cc2C1=O)c1nc(C(F)(F)F)cs1] | 2-(6-{5-chloro-2-[(oxan-4-yl)amino]pyrimidin-4-yl}-1-oxo-2,3-dihydro-1H-isoindol-2-yl)-N-{1-[4-(trifluoromethyl)-1,3-thiazol-2-yl]ethyl}acetamide | (DMSO-d6): 9.04 (1H, d), 8.45 (1H, s), 8.43-8.41 (1H, m), 8.05-8.03 (1H, m), 7.99 (1H, dd), 7.75 (1H, d), 7.58 (1H, br d), 5.30-5.22 (1H, m), 4.63 (1H, d), 4.61 (1H, d), 4.31 (2H, s), 3.98-3.90 (1H, m), 3.90-3.83 (2H, m), 3.38 (2H, dd), 1.90-1.81 (2H, m), 1.59-1.48 (5H, m). | 581 |

-continued

| Example | Structure | Name | $^1$H NMR (400 MHz) | MS: [M + H]$^+$ |
|---|---|---|---|---|
| 250 | 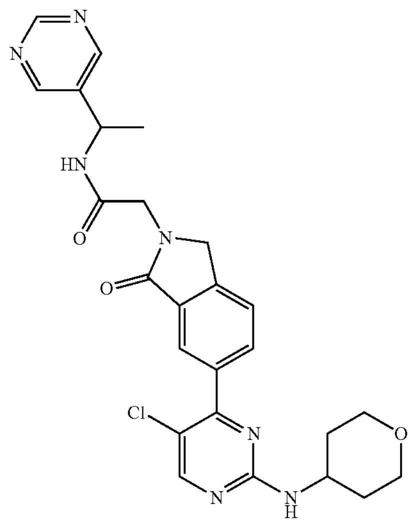 [SMILES: CC(NC(=O)CN1Cc2ccc(-c3nc(NC4CCOCC4)ncc3Cl)cc2C1=O)c1cncnc1] | 2-(6-{5-chloro-2-[(oxan-4-yl)amino]pyrimidin-4-yl}-1-oxo-2,3-dihydro-1H-isoindol-2-yl)-N-[1-(pyrimidin-5-yl)ethyl]acetamide | (DMSO-d6): 9.09 (1H, s), 8.78 (2H, s), 8.70 (1H, d), 8.44 (1H, s), 8.05-8.02 (1H, m), 7.98 (1H, dd), 7.74 (1H, d), 7.58 (1H, br d), 5.06-4.98 (1H, m), 4.59 (2H, s), 4.28 (2H, s), 3.98-3.90 (1H, m), 3.90-3.83 (2H, m), 3.38 (2H, t), 1.90-1.80 (2H, m), 1.59-1.48 (2H, m), 1.46 (3H, d). | 508 |
| 251 | 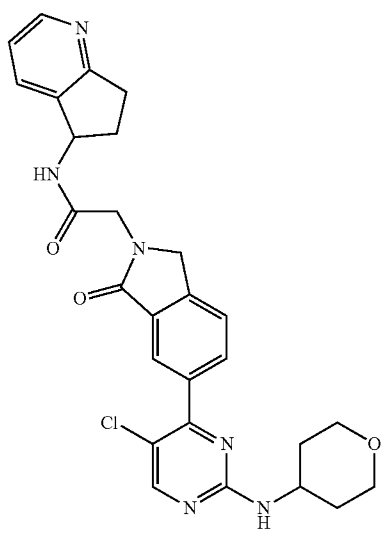 [SMILES: O=C(CN1Cc2ccc(-c3nc(NC4CCOCC4)ncc3Cl)cc2C1=O)NC1CCc2ncccc21] | 2-(6-{5-chloro-2-[(oxan-4-yl)amino]pyrimidin-4-yl}-1-oxo-2,3-dihydro-1H-isoindol-2-yl)-N-{5H,6H,7H-cyclopenta[b]pyridin-5-yl}acetamide | (DMSO-d6): 8.58 (1H, d), 8.45 (1H, s), 8.40-8.37 (1H, m), 8.05-8.03 (1H, m), 7.99 (1H, dd), 7.76 (1H, d), 7.62-7.55 (2H, m), 7.20 (1H, dd), 5.36 (1H, q), 4.64 (2H, s), 4.27 (2H, s), 3.99-3.90 (1H, m), 3.90-3.82 (2H, m), 3.38 (2H, t), 3.02-2.85 (2H, m), 2.48-2.41 (2H, m), 1.88-1.82 (2H, m), 1.61-1.47 (2H, m). | 519 |
| 252 | 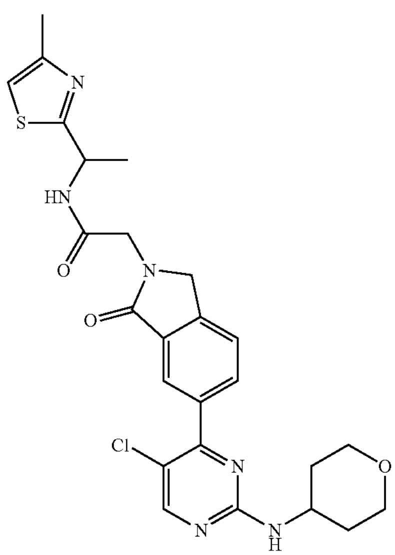 [SMILES: Cc1csc(C(C)NC(=O)CN2Cc3ccc(-c4nc(NC5CCOCC5)ncc4Cl)cc3C2=O)n1] | 2-(6-{5-chloro-2-[(oxan-4-yl)amino]pyrimidin-4-yl}-1-oxo-2,3-dihydro-1H-isoindol-2-yl)-N-[1-(4-methyl-1,3-thiazol-2-yl)ethyl]acetamide | (DMSO-d6): 8.89 (1H, d), 8.45 (1H, s), 8.05-8.03 (1H, m), 7.99 (1H, dd), 7.75 (1H, d), 7.58 (1H, br d), 7.16-7.14 (1H, m), 5.24-5.15 (1H, m), 4.63 (1H, d), 4.61 (1H, d), 4.28 (2H, s), 3.98-3.90 (1H, m), 3.87 (2H, d), 3.38 (2H, t), 2.34 (3H, d), 1.89-1.82 (2H, m), 1.59-1.48 (5H, m) | 527 |

| Example | Structure | Name | ¹H NMR (400 MHz) | MS: [M + H]⁺ |
|---|---|---|---|---|
| 253 | 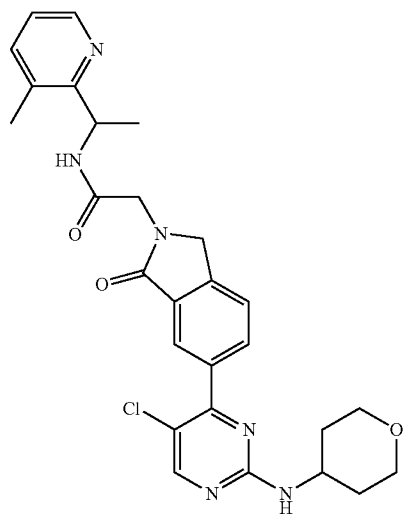 [SMILES: Cc1cccnc1C(C)NC(=O)CN1Cc2ccc(-c3nc(NC4CCOCC4)ncc3Cl)cc2C1=O] | 2-(6-{5-chloro-2-[(oxan-4-yl)amino]pyrimidin-4-yl}-1-oxo-2,3-dihydro-1H-isoindol-2-yl)-N-[1-(3-methylpyridin-2-yl)ethyl]acetamide | (DMSO-d6): 8.55 (1H, d), 8.44 (1H, s), 8.40 (1H, d), 8.02 (1H, s), 7.99-7.96 (1H, m), 7.73 (1H, d), 7.61-7.54 (2H, m), 7.21 (1H, dd), 5.28-5.20 (1H, m), 4.58 (2H, s), 4.24 (2H, d), 3.97-3.90 (1H, m), 3.90-3.83 (2H, m), 3.38 (2H, t), 2.34 (3H, s), 1.90-1.81 (2H, m), 1.59-1.47 (2H, m), 1.37 (3H, d). | 521 |
| 254 | 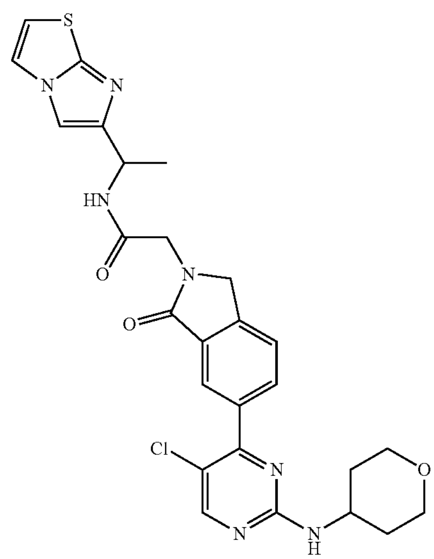 [SMILES: CC(NC(=O)CN1Cc2ccc(-c3nc(NC4CCOCC4)ncc3Cl)cc2C1=O)c1cn2ccsc2n1] | 2-(6-{5-chloro-2-[(oxan-4-yl)amino]pyrimidin-4-yl}-1-oxo-2,3-dihydro-1H-isoindol-2-yl)-N-(1-{imidazo[2,1-b][1,3]thiazol-6-yl}ethyl)acetamide | (DMSO-d6): 8.47 (1H, d), 8.44 (1H, s), 8.04-8.03 (1H, m), 7.98 (1H, dd), 7.87 (1H, d) 7.75 (1H, d), 7.61-7.56 (2H, m), 7.21 (1H, d), 5.05-4.96 (1H, m), 4.61 (2H, s), 4.24 (2H, s), 3.98-3.90 (1H, m), 3.90-3.82 (2H, m), 3.38 (2H, t), 1.85 (2H, d), 1.59-1.48 (2H, m), 1.43 (3H, d). | 552 |
| 255 | Trans racemic | 2-(6-{5-chloro-2-[(oxan-4-yl)amino]pyrimidin-4-yl}-1-oxo-2,3-dihydro-1H-isoindol-2-yl)-N-(2-hydroxycyclohexyl)acetamide | (DMSO-d6): 8.45 (1H, s), 8.04 (1H, s), 7.98 (1H, dd), 7.89 (1H, d), 7.75 (1H, d), 7.62-7.55 (1H, m), 4.60 (2H, s), 4.55 (1H, d), 4.23 (1H, d), 4.18 (1H, d), 3.98-3.90 (1H, m), 3.90-3.83 (2H, m), 3.49-3.34 (3H, m), 3.28-3.24 (1H, m), 1.89-1.82 (3H, m), 1.82-1.76 (1H, m), 1.66-1.49 (4H, m), 1.27 (1H, t), 1.21-1.15 (3H, m). | 500 |

-continued

| Example | Structure | Name | ¹H NMR (400 MHz) | MS: [M + H]⁺ |
|---|---|---|---|---|
| 256 | 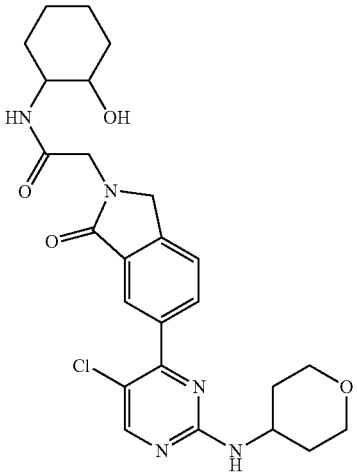 Cis racemic | 2-(6-{5-chloro-2-[(oxan-4-yl)amino]pyrimidin-4-yl}-1-oxo-2,3-dihydro-1H-isoindol-2-yl)-N-(2-hydroxycyclohexyl)acetamide | (DMSO-d6): 8.45 (1H, s), 8.04-8.02 (1H, m), 7.98 (1H, dd), 7.76 (2H, dd), 7.58 (1H, br d), 4.61-4.58 (3H, m), 4.25 (1H, d), 4.23 (1H, d), 3.98-3.90 (1H, m), 3.90-3.83 (2H, m), 3.77-3.72 (1H, m), 3.72-3.64 (1H, m), 3.38 (2H, td), 1.89-1.82 (2H, m), 1.73-1.64 (1H, m), 1.64-1.48 (5H, m), 1.48-1.36 (2H, m), 1.28 (2H, d). | 500 |
| 257 | 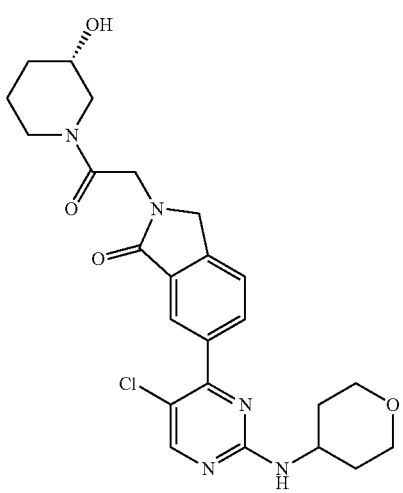 [SMILES: O=C(CN1Cc2ccc(-c3nc(NC4CCOCC4)ncc3Cl)cc2C1=O)N1CCC[C@H](O)C1] | 6-{5-chloro-2-[(oxan-4-yl)amino]pyrimidin-4-yl}-2-{2-[(3S)-3-hydroxypiperidin-1-yl]-2-oxoethyl}-2,3-dihydro-1H-isoindol-1-one | (DMSO-d6): 8.45 (1H, s), 8.03 (1H, s), 7.99 (1H, dd), 7.74 (1H, d), 7.58 (1H, br s), 4.90 (1H, dd), 4.56 (2H, s), 4.49-4.45 (2H, m), 4.04 (0.5H, d), 4.00-3.91 (1H, m), 3.87 (2H, d), 3.70-3.61 (1H, m), 3.60-3.53 (0.5H, m), 3.52-3.30 (4H, m), 3.22 (0.5H, dd), 3.15-3.06 (0.5H, m), 1.90-1.65 (4H, m), 1.61-1.28 (4H, m). | 486 |
| 258 | 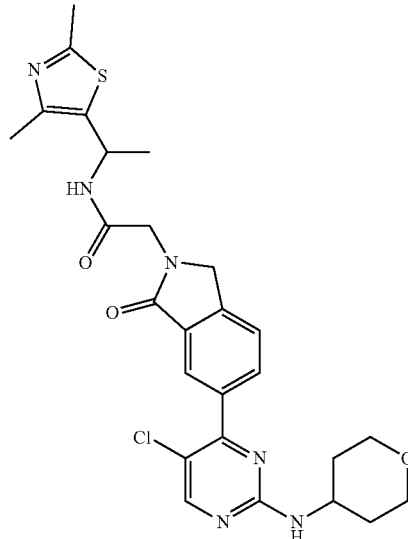 | 2-(6-{5-chloro-2-[(oxan-4-yl)amino]pyrimidin-4-yl}-1-oxo-2,3-dihydro-1H-isoindol-2-yl)-N-[1-(2,4-dimethyl-1,3-thiazol-5-yl)ethyl]acetamide | (DMSO-d6): 8.62 (1H, d), 8.44 (1H, s), 8.03 (1H, s), 7.98 (1H, dd), 7.74 (1H, d), 7.58 (1H, br d), 5.20-5.12 (1H, m), 4.57 (2H, s), 4.20 (1H, d), 4.18 (1H, d), 3.98-3.90 (1H, m), 3.90-3.82 (2H, m), 3.38 (2H, t), 2.55 (3H, s), 2.26 (3H, s), 1.89-1.81 (2H, m), 1.59-1.48 (2H, m), 1.41 (3H, d). | 541 |

-continued

| Example | Structure | Name | ¹H NMR (400 MHz) | MS: [M + H]⁺ |
|---|---|---|---|---|
| 259 | 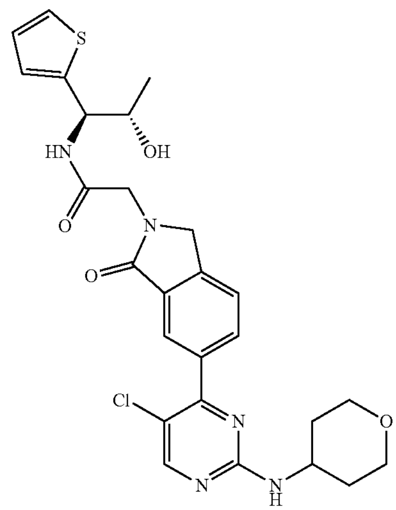 [SMILES: C[C@H](O)[C@@H](NC(=O)CN1Cc2ccc(-c3nc(NC4CCOCC4)ncc3Cl)cc2C1=O)c1cccs1] | 2-(6-{5-chloro-2-[(oxan-4-yl)amino]pyrimidin-4-yl}-1-oxo-2,3-dihydro-1H-isoindol-2-yl)-N-[(1R,2S)-2-hydroxy-1-(thiophen-2-yl)propyl]acetamide | (Me-d3-OD): 8.35 (1H, s), 8.24 (1H, d), 8.08 (1H, dd), 7.70 (1H, dd), 7.32 (1H, dd), 7.11-7.08 (1H, m), 7.00 (1H, dd), 5.20 (1H, d), 4.67 (2H, s), 4.44 (1H, d), 4.40 (1H, d), 4.18-3.93 (5H, m), 3.55 (2H, td), 2.01 (2H, d), 1.69-1.57 (2H, m), 1.19 (3H, d). | 542 |
| 260 | 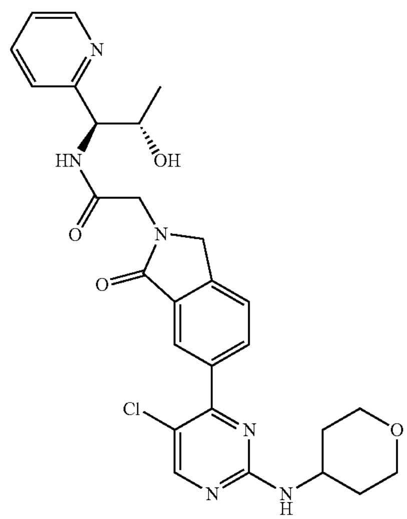 [SMILES: C[C@H](O)[C@@H](NC(=O)CN1Cc2ccc(-c3nc(NC4CCOCC4)ncc3Cl)cc2C1=O)c1ccccn1] | 2-(6-{5-chloro-2-[(oxan-4-yl)amino]pyrimidin-4-yl}-1-oxo-2,3-dihydro-1H-isoindol-2-yl)-N-[(1S,2S)-2-hydroxy-1-(pyridin-2-yl)propyl]acetamide | (DMSO-d6): 8.54-8.51 (1H, m), 8.46-8.42 (2H, m), 8.03 (1H, s), 7.98 (1H, dd), 7.79-7.72 (2H, m), 7.63-7.54 (1H, m), 7.39 (1H, d), 7.27 (1H, ddd), 4.84 (1H, dd), 4.81 (1H, d), 4.60 (2H, s), 4.39 (1H, d), 4.37 (1H, d), 4.16-4.08 (1H, m), 3.98-3.90 (1H, m), 3.90-3.84 (2H, m), 3.38 (2H, t), 1.89-1.82 (2H, m), 1.60-1.47 (2H, m), 1.05 (3H, d). | 537 |
| 261 | 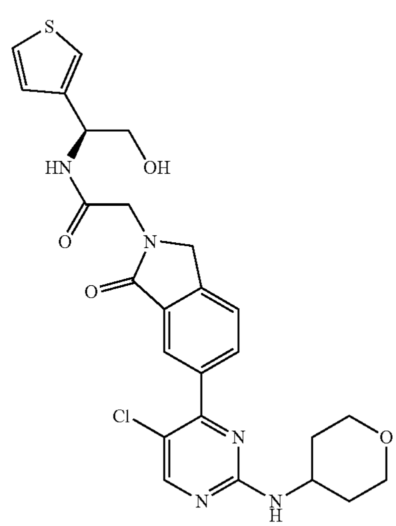 [SMILES: O=C(CN1Cc2ccc(-c3nc(NC4CCOCC4)ncc3Cl)cc2C1=O)N[C@H](CO)c1ccsc1] | 2-(6-{5-chloro-2-[(oxan-4-yl)amino]pyrimidin-4-yl}-1-oxo-2,3-dihydro-1H-isoindol-2-yl)-N-[(1S)-2-hydroxy-1-(thiophen-3-yl)ethyl]acetamide | (Me-d3-OD): 8.35 (1H, s), 8.24 (1H, d), 8.07 (1H, dd), 7.71 (1H, dd), 7.40 (1H, dd), 7.35-7.32 (1H, m), 7.13 (1H, dd), 5.18 (1H, dd), 4.69 (2H, s), 4.44 (1H, d), 4.43 (1H, d), 4.11-4.02 (1H, m), 4.02-3.93 (2H, m), 3.86 (1H, dd), 3.79 (1H, dd), 3.54 (2H, td), 2.05-1.98 (2H, m), 1.69-1.57 (2H, m) | 528 |

-continued

| Example | Structure | Name | ¹H NMR (400 MHz) | MS: [M + H]⁺ |
|---|---|---|---|---|
| 262 | 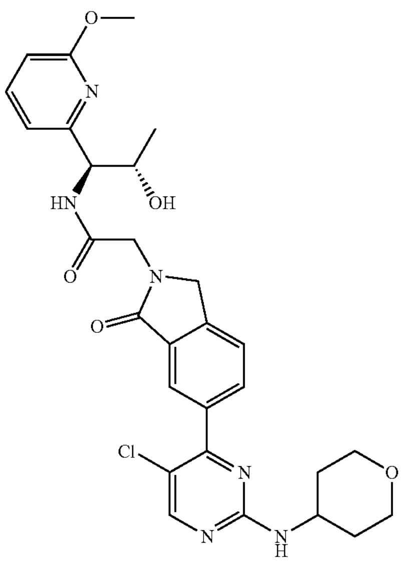 [SMILES: COc1cccc([C@H](NC(=O)CN2Cc3ccc(-c4nc(NC5CCOCC5)ncc4Cl)cc3C2=O)[C@H](C)O)n1] | 2-(6-{5-chloro-2-[(oxan-4-yl)amino]pyrimidin-4-yl}-1-oxo-2,3-dihydro-1H-isoindol-2-yl)-N-[(1S,2S)-2-hydroxy-1-(6-methoxypyridin-2-yl)propyl]acetamide | (DMSO-d6): 8.45 (1H, s), 8.30 (1H, d), 8.05-8.03 (1H, m), 7.98 (1H, dd), 7.75 (1H, d), 7.66 (1H, dd), 7.58 (1H, br d), 6.97 (1H, d), 6.67 (1H, d), 4.77-4.73 (2H, m), 4.61 (2H, s), 4.40 (1H, d), 4.38 (1H, d), 4.22-4.14 (1H, m), 3.98-3.91 (1H, m), 3.91-3.84 (2H, m), 3.83 (3H, s), 3.38 (2H, t), 1.89-1.81 (2H, m), 1.60-1.47 (2H, m), 1.08 (3H, d). | 567 |
| 263 | 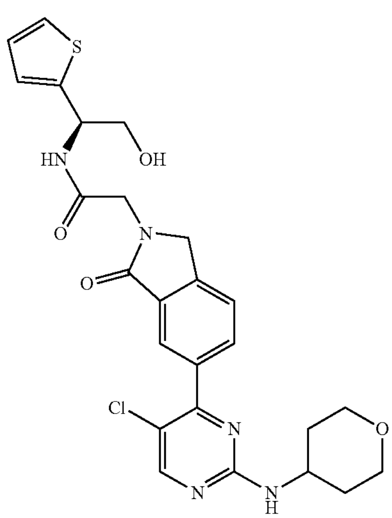 [SMILES: O=C(CN1Cc2ccc(-c3nc(NC4CCOCC4)ncc3Cl)cc2C1=O)N[C@H](CO)c1cccs1] | 2-(6-{5-chloro-2-[(oxan-4-yl)amino]pyrimidin-4-yl}-1-oxo-2,3-dihydro-1H-isoindol-2-yl)-N-[(1R)-2-hydroxy-1-(thiophen-2-yl)ethyl]acetamide | (Me-d3-OD): 8.35 (1H, s), 8.24 (1H, d), 8.07 (1H, dd), 7.71 (1H, d), 7.32 (1H, dd), 7.08 (1H, dt), 6.99 (1H, dd), 5.36-5.31 (1H, m), 4.68 (2H, s), 4.44 (1H, d), 4.41 (1H, d), 4.09-4.02 (1H, m), 4.02-3.93 (2H, m), 3.89 (1H, dd), 3.84 (1H, dd), 3.54 (2H, td), 2.04-1.98 (3H, m), 1.69-1.57 (2H, m). | 528 |

-continued

| Example | Structure | Name | ¹H NMR (400 MHz) | MS: [M + H]⁺ |
|---|---|---|---|---|
| 264 | 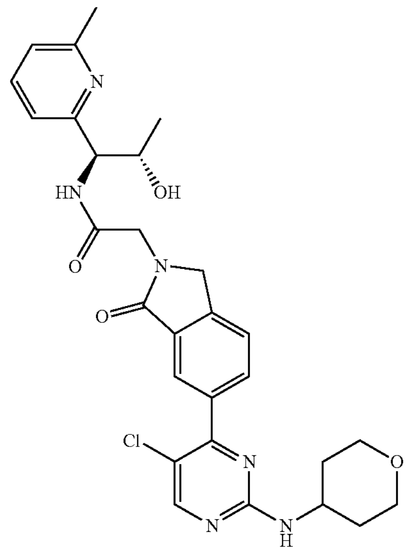 [SMILES: Cc1cccc([C@H](NC(=O)CN2Cc3ccc(-c4nc(NC5CCOCC5)ncc4Cl)cc3C2=O)[C@H](C)O)n1] | 2-(6-{5-chloro-2-[(oxan-4-yl)amino]pyrimidin-4-yl}-1-oxo-2,3-dihydro-1H-isoindol-2-yl)-N-[(1S,2S)-2-hydroxy-1-(6-methylpyridin-2-yl)propyl]acetamide | (DMSO-d6): 8.44 (1H, s), 8.36 (1H, d), 8.04-8.03 (1H, m), 7.98 (1H, dd), 7.74 (1H, d), 7.64 (1H, t), 7.58 (1H, br d), 7.18 (1H, d), 7.12 (1H, d), 4.81-4.75 (2H, m), 4.61 (2H, s), 4.38 (2H, s), 4.16-4.08 (1H, m), 3.98-3.90 (1H, m), 3.90-3.82 (2H, m), 3.38 (2H, t), 2.44 (3H, s), 1.89-1.81 (2H, m), 1.60-1.47 (2H, m), 1.05 (3H, d). | 551 |
| 265 | 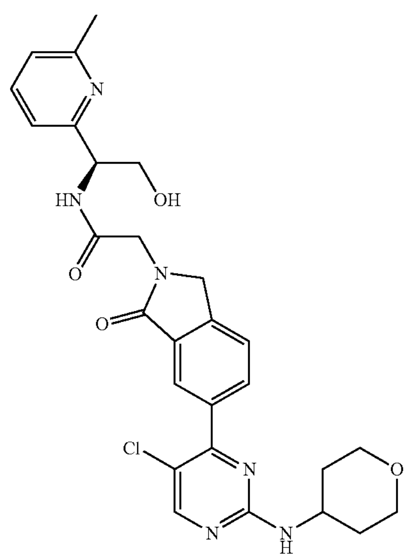 [SMILES: Cc1cccc([C@@H](CO)NC(=O)CN2Cc3ccc(-c4nc(NC5CCOCC5)ncc4Cl)cc3C2=O)n1] | 2-(6-{5-chloro-2-[(oxan-4-yl)amino]pyrimidin-4-yl}-1-oxo-2,3-dihydro-1H-isoindol-2-yl)-N-[(1S)-2-hydroxy-1-(6-methylpyridin-2-yl)ethyl]acetamide | (DMSO-d6): 8.48 (1H, d), 8.44 (1H, s), 8.05-8.03 (1H, m), 7.98 (1H, dd), 7.74 (1H, d), 7.64 (1H, t), 7.58 (1H, br d), 7.16 (1H, d), 7.12 (1H, d), 4.94-4.88 (1H, m), 4.86 (1H, t), 4.61 (2H, s), 4.33 (2H, s), 3.98-3.90 (1H, m), 3.90-3.82 (2H, m), 3.78-3.70 (1H, m), 3.70-3.63 (1H, m), 3.38 (2H, t), 1.89-1.81 (2H, m), 1.60-1.47 (2H, m). | 537 |

-continued

| Example | Structure | Name | ¹H NMR (400 MHz) | MS: [M + H]⁺ |
|---|---|---|---|---|
| 266 | 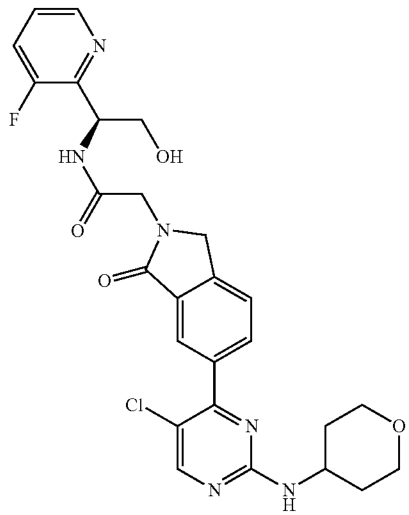 [SMILES: O=C(CN1Cc2ccc(-c3nc(NC4CCOCC4)ncc3Cl)cc2C1=O)N[C@H](CO)c1ncccc1F] | 2-(6-{5-chloro-2-[(oxan-4-yl)amino]pyrimidin-4-yl}-1-oxo-2,3-dihydro-1H-isoindol-2-yl)-N-[(1S)-1-(3-fluoropyridin-2-yl)-2-hydroxyethyl]acetamide | (DMSO-d6): 8.56 (1H, d), 8.46-8.43 (2H, m), 8.03-8.01 (1H, m), 7.98 (1H, dd), 7.73 (1H, d), 7.68 (1H, ddd), 7.58 (1H, br d), 7.44-7.39 (1H, m), 5.32 (1H, q), 4.95 (1H, br s), 4.58 (2H, s), 4.30 (1H, d), 4.26 (1H, d), 3.99-3.90 (1H, m), 3.90-3.82 (2H, m), 3.69 (2H, d), 3.42-3.37 (2H, m), 1.85 (2H, d), 1.60-1.47 (2H, m). | 541 |
| 267 | 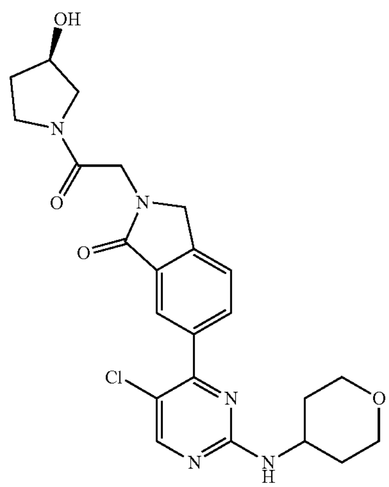 [SMILES: O=C(CN1Cc2ccc(-c3nc(NC4CCOCC4)ncc3Cl)cc2C1=O)N1CC[C@@H](O)C1] | 6-{5-chloro-2-[(oxan-4-yl)amino]pyrimidin-4-yl}-2-{2-[(3R)-3-hydroxypyrrolidin-1-yl]-2-oxoethyl}-2,3-dihydro-1H-isoindol-1-one | (DMSO-d6): 8.45 (1H, s), 8.05-8.03 (1H, m), 7.99 (1H, dd), 7.75 (1H, d), 7.59 (1H, br d), 5.07 (0.5H, d), 4.96 (0.5H, d), 4.59 (2H, s), 4.48-4.32 (2.5H, m), 4.31-4.26 (0.5H, m), 4.00-3.91 (1H, m), 3.91-3.81 (2H, m), 3.67-3.53 (1.5H, m), 3.50-3.31 (4.5H, m), 2.06-1.70 (4H, m), 1.60-1.48 (2H, m). | 472 |
| 268 | Trans racemic | 2-(6-{5-chloro-2-[(oxan-4-yl)amino]pyrimidin-4-yl}-1-oxo-2,3-dihydro-1H-isoindol-2-yl)-N-(2-hydroxycyclopentyl)acetamide | (Me-d3-OD): 8.36 (1H, s), 8.24 (1H, d), 8.08 (1H, dd), 7.72 (1H, dd), 4.69 (2H, s), 4.36 (2H, s), 4.11-3.94 (5H, m), 3.55 (2H, dt), 2.18-2.08 (1H, m), 2.05-1.92 (3H, m), 1.86-1.70 (2H, m), 1.70-1.47 (4H, m). | 486 |

| Example | Structure | Name | ¹H NMR (400 MHz) | MS: [M + H]⁺ |
|---|---|---|---|---|
| 269 | 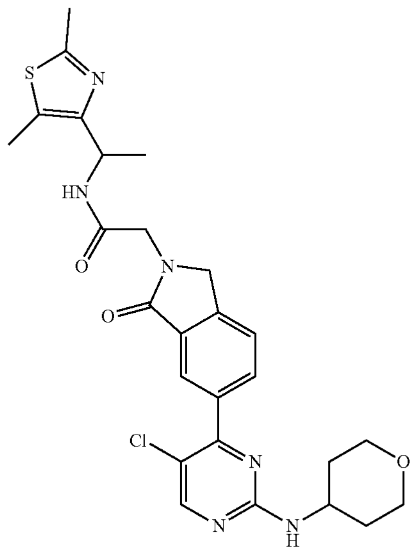 [SMILES: Cc1nc(C(C)NC(=O)CN2Cc3ccc(-c4nc(NC5CCOCC5)ncc4Cl)cc3C2=O)c(C)s1] | 2-(6-{5-chloro-2-[(oxan-4-yl)amino]pyrimidin-4-yl}-1-oxo-2,3-dihydro-1H-isoindol-2-yl)-N-[1-(2,5-dimethyl-1,3-thiazol-4-yl)ethyl]acetamide | (DMSO-d6): 8.53 (1H, d), 8.44 (1H, s), 8.03-8.01 (1H, m), 7.97 (1H, dd), 7.73 (1H, d), 7.58 (1H, br d), 5.09-4.99 (1H, m), 4.58 (2H, s), 4.20 (2H, s), 3.99-3.90 (1H, m), 3.90-3.82 (2H, m), 3.38 (2H, t), 2.57 (3H, s), 2.34 (3H, s), 1.89-1.81 (2H, m), 1.60-1.46 (2H, m), 1.39 (3H, d). | 541 |
| 270 | 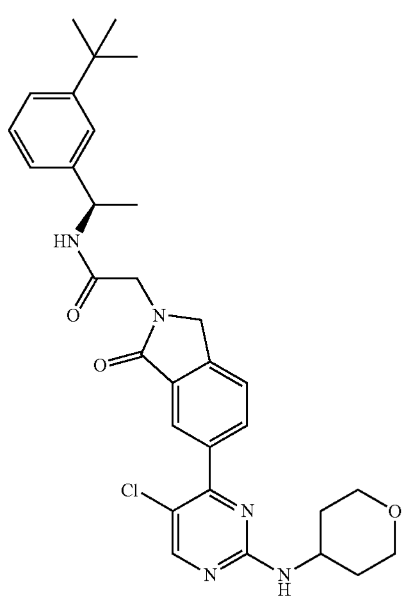 [SMILES: C[C@@H](NC(=O)CN1Cc2ccc(-c3nc(NC4CCOCC4)ncc3Cl)cc2C1=O)c1cccc(C(C)(C)C)c1] | N-[(1R)-1-(3-tert-butylphenyl)ethyl]-2-(6-{5-chloro-2-[(oxan-4-yl)amino]pyrimidin-4-yl}-1-oxo-2,3-dihydro-1H-isoindol-2-yl)acetamide | (Me-d3-OD): 8.35 (1H, s), 8.23 (1H, d), 8.07 (1H, dd), 7.70 (1H, dd), 7.41-7.39 (1H, m), 7.30 (1H, dt), 7.29-7.24 (1H, m), 7.19-7.15 (1H, m), 5.07 (1H, q), 4.66 (2H, s), 4.40 (1H, d), 4.38 (1H, d), 4.11-4.02 (1H, m), 4.02-3.95 (2H, m), 3.54 (2H, td), 2.06-1.97 (2H, m), 1.69-1.58 (2H, m), 1.50 (3H, d), 1.33 (9H, s). | 562 |

-continued

| Example | Structure | Name | $^1$H NMR (400 MHz) | MS: [M + H]$^+$ |
|---|---|---|---|---|
| 271 | 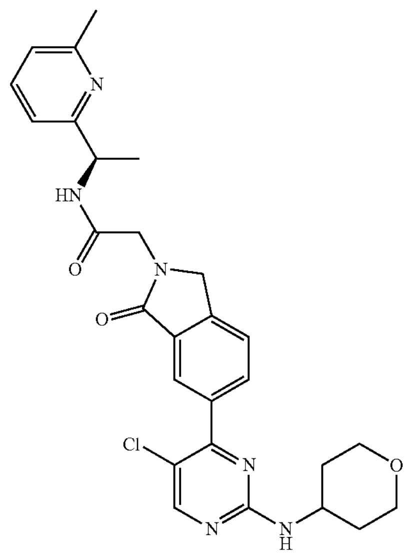 [SMILES: Cc1cccc([C@@H](C)NC(=O)CN2Cc3ccc(-c4nc(NC5CCOCC5)ncc4Cl)cc3C2=O)n1] | 2-(6-{5-chloro-2-[(oxan-4-yl)amino]pyrimidin-4-yl}-1-oxo-2,3-dihydro-1H-isoindol-2-yl)-N-[(1R)-1-(6-methylpyridin-2-yl)ethyl]acetamide | (DMSO-d6): 8.57 (1H, d), 8.44 (1H, s), 8.04-8.02 (1H, m), 7.98 (1H, dd), 7.74 (1H, d), 7.65 (1H, t), 7.58 (1H, br d), 7.16 (1H, d), 7.12 (1H, d), 4.99-4.89 (1H, m), 4.62 (1H, d), 4.60 (1H, d), 4.28 (2H, s), 3.99-3.90 (1H, m), 3.90-3.82 (2H, m), 3.38 (2H, t), 2.45 (3H, s), 1.89-1.81 (2H, m), 1.59-1.48 (2H, m), 1.40 (3H, d). | 521 |
| 272 | 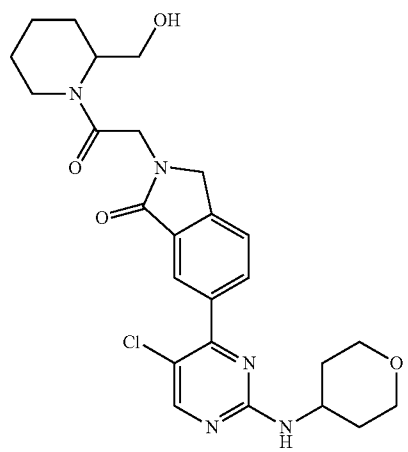 [SMILES: O=C1c2cc(-c3nc(NC4CCOCC4)ncc3Cl)ccc2CN1CC(=O)N1CCCCC1CO] | 6-{5-chloro-2-[(oxan-4-yl)amino]pyrimidin-4-yl}-2-{2-[2-(hydroxymethyl)piperidin-1-yl]-2-oxoethyl}-2,3-dihydro-1H-isoindol-1-one | (DMSO-d6): 8.45 (1H, s), 8.03 (1H, s), 7.98 (1H, dd), 7.74 (1H, d), 7.58 (1H, br d), 5.01-4.93 (1H, m), 4.71-4.23 (5H, m), 4.07-3.98 (1H, m), 3.98-3.91 (1H, m), 3.87 (2H, d), 3.75 (1H, d), 3.59-3.43 (1H, m), 3.38 (2H, t), 3.10 (0.5H, s), 2.71-2.60 (0.5H, m), 1.92-1.21 (10H, m). | 500 |
| 273 | 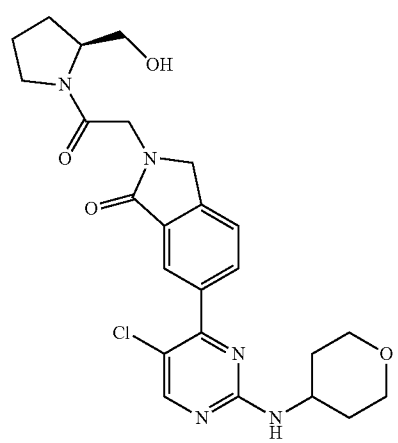 [SMILES: O=C1c2cc(-c3nc(NC4CCOCC4)ncc3Cl)ccc2CN1CC(=O)N1CCC[C@H]1CO] | 6-{5-chloro-2-[(oxan-4-yl)amino]pyrimidin-4-yl}-2-{2-[(2S)-2-(hydroxymethyl)pyrrolidin-1-yl]-2-oxoethyl}-2,3-dihydro-1H-isoindol-1-one | (DMSO-d6): 8.45 (1H, s), 8.04 (1H, s), 8.01-7.96 (1H, m), 7.75 (1H, dd), 7.59 (1H, br d), 5.06 (0.3H, t), 4.72 (0.7H, t), 4.59 (2H, s), 4.53 (0.7H, s), 4.38 (1.3H, s), 4.13-4.09 (0.3H, m), 4.00-3.90 (1.7H, m), 3.90-3.82 (2H, m), 3.56-3.31 (6H, m), 2.01-1.74 (6H, m), 1.61-1.47 (2H, m). | 486 |

| Example | Structure | Name | ¹H NMR (400 MHz) | MS: [M + H]⁺ |
|---------|-----------|------|------------------|--------------|
| 274 | 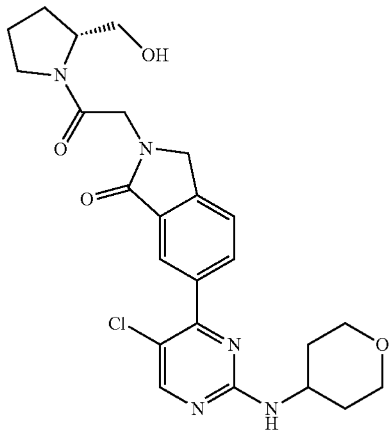 [SMILES: O=C1c2cc(-c3nc(NC4CCOCC4)ncc3Cl)ccc2CN1CC(=O)N1CCC[C@@H]1CO] | 6-{5-chloro-2-[(oxan-4-yl)amino]pyrimidin-4-yl}-2-{2-[(2R)-2-(hydroxymethyl)pyrrolidin-1-yl]-2-oxoethyl}-2,3-dihydro-1H-isoindol-1-one | (DMSO-d6): 8.45 (1H, s), 8.05-8.02 (1H, m), 8.01-7.96 (1H, m), 7.75 (1H, dd), 7.58 (1H, br d), 5.06 (0.3H, t), 4.72 (0.7H, t), 4.59 (2H, s), 4.54 (0.7H, s), 4.38 (1.3H, s), 4.14-4.05 (0.3H, m), 4.00-3.90 (1.7H, m), 3.90-3.81 (2H, m), 3.56-3.32 (6H, m), 2.03-1.78 (6H, m), 1.60-1.48 (2H, m). | 486 |
| 275 | 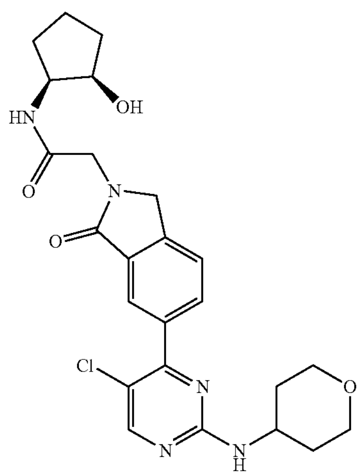 [SMILES: O=C(CN1Cc2ccc(-c3nc(NC4CCOCC4)ncc3Cl)cc2C1=O)N[C@H]1CCC[C@H]1O] | 2-(6-{5-chloro-2-[(oxan-4-yl)amino]pyrimidin-4-yl}-1-oxo-2,3-dihydro-1H-isoindol-2-yl)-N-[(1S,2R)-2-hydroxycyclopentyl]acetamide | (DMSO-d6): 8.45 (1H, s), 8.04-8.03 (1H, m), 7.98 (1H, dd), 7.80 (1H, d), 7.74 (1H, d), 7.58 (1H, br m), 4.67 (1H, d), 4.60 (2H, s), 4.26 (1H, d), 4.23 (1H, d), 3.98-3.91 (2H, m), 3.91-3.83 (3H, m), 3.38 (2H, t), 1.89-1.66 (5H, m), 1.61-1.42 (5H, m). | 486 |
| 276 | 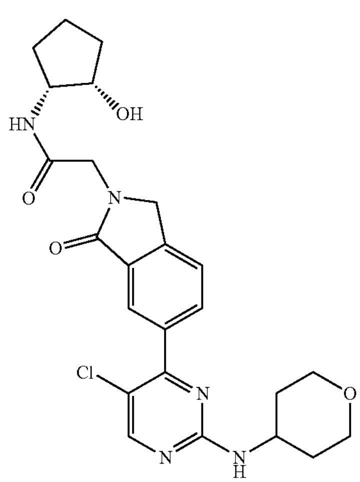 [SMILES: O=C(CN1Cc2ccc(-c3nc(NC4CCOCC4)ncc3Cl)cc2C1=O)N[C@@H]1CCC[C@@H]1O] | 2-(6-{5-chloro-2-[(oxan-4-yl)amino]pyrimidin-4-yl}-1-oxo-2,3-dihydro-1H-isoindol-2-yl)-N-[(1R,2S)-2-hydroxycyclopentyl]acetamide | (DMSO-d6): 8.45 (1H, s), 8.03 (1H, s), 7.98 (1H, dd), 7.80 (1H, d), 7.74 (1H, d), 7.58 (1H, br d), 4.67 (1H, d), 4.60 (2H, s), 4.26 (1H, d), 4.23 (1H, d), 3.98-3.92 (2H, m), 3.91-3.83 (3H, m), 3.38 (2H, t), 1.85 (2H, d), 1.81-1.65 (3H, m), 1.62-1.41 (5H, m). | 486 |

-continued

| Example | Structure | Name | ¹H NMR (400 MHz) | MS: [M + H]⁺ |
|---|---|---|---|---|
| 277 | 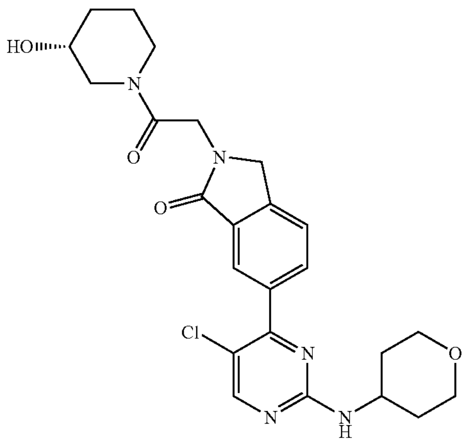 [SMILES: O=C(CN1Cc2ccc(-c3nc(NC4CCOCC4)ncc3Cl)cc2C1=O)N1CCC[C@@H](O)C1] | 6-{5-chloro-2-[(oxan-4-yl)amino]pyrimidin-4-yl}-2-{2-[(3R)-3-hydroxypiperidin-1-yl]-2-oxoethyl}-2,3-dihydro-1H-isoindol-1-one | (DMSO-d6): 8.45 (1H, s), 8.04-8.02 (1H, m), 7.99 (1H, dd), 7.74 (1H, d), 7.58 (1H, br d), 4.89 (1H, br s), 4.56 (2H, s), 4.49-4.44 (2H, m), 4.07-4.01 (0.5H, m), 3.98-3.91 (1H, m), 3.90-3.83 (2H, m), 3.65 (1H, t), 3.56 (0.5H, dd), 3.42-3.34 (4H, m), 3.25-3.19 (0.5H, m), 3.15-3.07 (0.5H, m), 1.90-1.66 (4H, m), 1.61-1.28 (4H, m). | 486 |
| 278 | 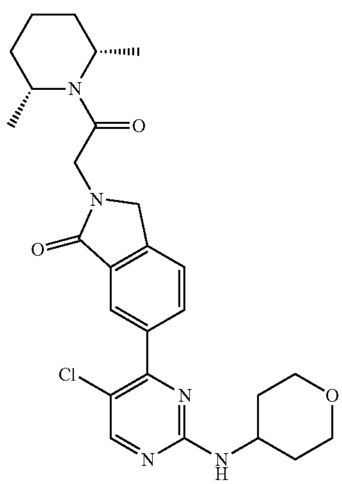 [SMILES: C[C@@H]1CCC[C@H](C)N1C(=O)CN1Cc2ccc(-c3nc(NC4CCOCC4)ncc3Cl)cc2C1=O] | 6-{5-chloro-2-[(oxan-4-yl)amino]pyrimidin-4-yl}-2-{2-[(2R,6S)-2,6-dimethylpiperidin-1-yl]-2-oxoethyl}-2,3-dihydro-1H-isoindol-1-one | (DMSO-d6): 8.45 (1H, s), 8.03 (1H, s), 7.99 (1H, dd), 7.75 (1H, d), 7.59 (1H, br d), 4.69-4.44 (4H, m), 4.44-4.10 (2H, m), 4.00-3.90 (1H, m), 3.90-3.81 (2H, m), 3.38 (2H, t), 1.92-1.72 (3H, m), 1.72-1.37 (7H, m), 1.37-1.02 (6H, m). | 498 |
| 279 | 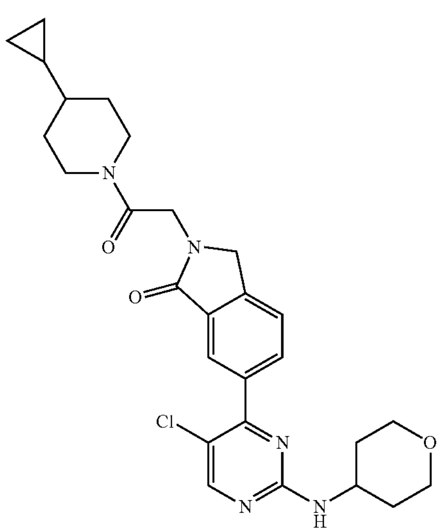 [SMILES: O=C(CN1Cc2ccc(-c3nc(NC4CCOCC4)ncc3Cl)cc2C1=O)N1CCC(C2CC2)CC1] | 6-{5-chloro-2-[(oxan-4-yl)amino]pyrimidin-4-yl}-2-[2-(4-cyclopropylpiperidin-1-yl)-2-oxoethyl]-2,3-dihydro-1H-isoindol-1-one | (DMSO-d6): 8.45 (1H, s), 8.04-8.02 (1H, m), 7.99 (1H, dd), 7.75 (1H, d), 7.58 (1H, br d), 4.57 (2H, s), 4.49 (1H, d), 4.45 (1H, d), 4.31 (1H, d), 3.99-3.82 (4H, m), 3.42-3.35 (2H, m), 3.01 (1H, t), 2.62-2.53 (1H, m), 1.89-1.82 (2H, m), 1.80-1.68 (2H, m), 1.59-1.48 (2H, m), 1.37-1.23 (1H, m), 1.23-1.08 (1H, m), 0.86-0.75 (1H, m), 0.64-0.54 (1H, m), 0.41-0.35 (2H, m), 0.14-0.09 (2H, m). | 510 |

-continued

| Example | Structure | Name | ¹H NMR (400 MHz) | MS: [M + H]⁺ |
|---|---|---|---|---|
| 280 | 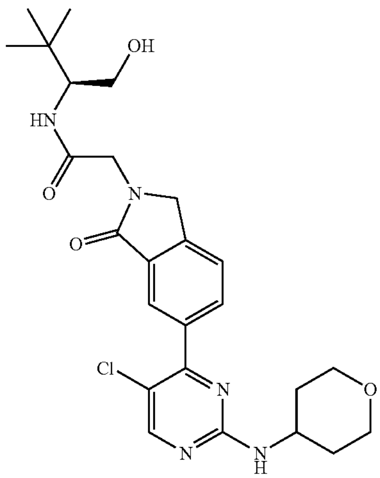 [SMILES: CC(C)(C)[C@@H](CO)NC(=O)CN1Cc2ccc(-c3nc(NC4CCOCC4)ncc3Cl)cc2C1=O] | 2-(6-{5-chloro-2-[(oxan-4-yl)amino]pyrimidin-4-yl}-1-oxo-2,3-dihydro-1H-isoindol-2-yl)-N-[(2S)-1-hydroxy-3,3-dimethylbutan-2-yl]acetamide | (DMSO-d6): 8.45 (1H, s), 8.04 (1H, s), 7.98 (1H, dd), 7.77-7.71 (2H, m), 7.59 (1H, br d), 4.60 (2H, s), 4.43 (1H, t), 4.29 (1H, d), 4.26 (1H, d), 3.99-3.90 (1H, m), 3.90-3.82 (2H, m), 3.69-3.55 (2H, m), 3.42-3.36 (2H, m), 1.90-1.81 (2H, m), 1.59-1.48 (2H, m), 0.88 (9H, s). | 502 |
| 281 | 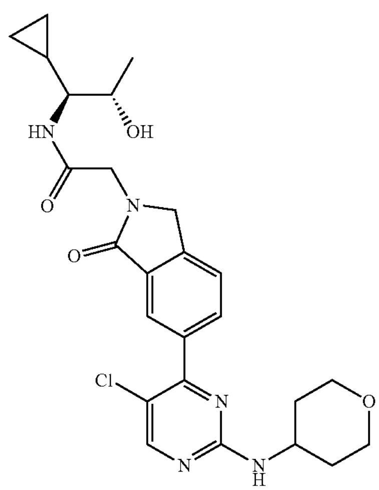 [SMILES: C[C@H](O)[C@@H](NC(=O)CN1Cc2ccc(-c3nc(NC4CCOCC4)ncc3Cl)cc2C1=O)C1CC1] | 2-(6-{5-chloro-2-[(oxan-4-yl)amino]pyrimidin-4-yl}-1-oxo-2,3-dihydro-1H-isoindol-2-yl)-N-[(1S,2S)-1-cyclopropyl-2-hydroxypropyl]acetamide | (DMSO-d6): 8.45 (1H, s), 8.05-8.03 (1H, m), 7.98 (1H, dd), 7.83 (1H, d), 7.75 (1H, d), 7.58 (1H, br d), 4.63 (1H, d), 4.59 (2H, s), 4.27 (1H, d), 4.24 (1H, d), 3.99-3.90 (1H, m), 3.90-3.82 (2H, m), 3.79-3.71 (1H, m), 3.38 (2H, t), 3.09 (1H, td), 1.85 (2H, d), 1.60-1.47 (2H, m), 1.06 (3H, d), 1.04-0.94 (1H, m), 0.48-0.40 (1H, m), 0.40-0.32 (1H, m), 0.25-0.20 (2H, m). | 500 |
| 282 | 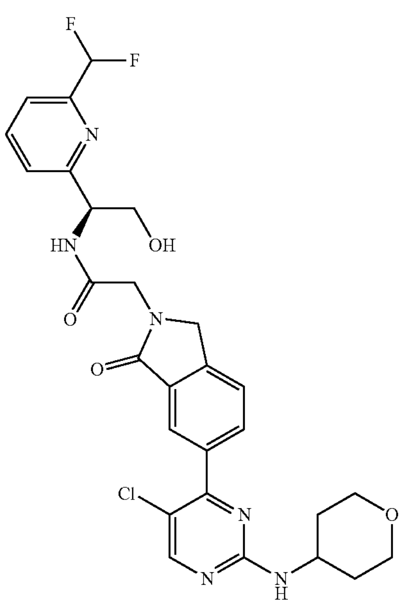 [SMILES: O=C(CN1Cc2ccc(-c3nc(NC4CCOCC4)ncc3Cl)cc2C1=O)N[C@H](CO)c1cccc(C(F)F)n1] | 2-(6-{5-chloro-2-[(oxan-4-yl)amino]pyrimidin-4-yl}-1-oxo-2,3-dihydro-1H-isoindol-2-yl)-N-[(1S)-1-[6-(difluoromethyl)pyridin-2-yl]-2-hydroxyethyl]acetamide | (DMSO-d6): 8.63 (1H, d), 8.44 (1H, s), 8.03 (1H, s), 8.01-7.96 (2H, m), 7.74 (1H, d), 7.61-7.54 (3H, m), 6.92 (1H, t), 5.02-4.97 (1H, m), 4.95 (1H, t), 4.61 (2H, d), 4.35 (2H, s), 3.98-3.90 (1H, m), 3.90-3.82 (2H, m), 3.82-3.68 (2H, m), 3.38 (2H, t), 1.90-1.81 (2H, m), 1.60-1.47 (2H, m). | 573 |

-continued

| Example | Structure | Name | ¹H NMR (400 MHz) | MS: [M + H]⁺ |
|---|---|---|---|---|
| 283 | 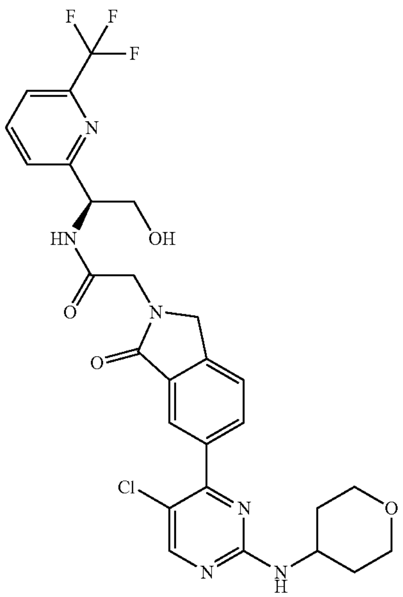 [SMILES: O=C(CN1Cc2ccc(-c3nc(NC4CCOCC4)ncc3Cl)cc2C1=O)N[C@H](CO)c1cccc(C(F)(F)F)n1] | 2-(6-{5-chloro-2-[(oxan-4-yl)amino]pyrimidin-4-yl}-1-oxo-2,3-dihydro-1H-isoindol-2-yl)-N-[(1S)-2-hydroxy-1-[6-(trifluoromethyl)pyridin-2-yl]ethyl]acetamide | (DMSO-d6): 8.67 (1H, d), 8.44 (1H, s), 8.08 (1H, t), 8.04-8.02 (1H, m), 7.98 (1H, dd), 7.79 (1H, d), 7.73 (1H, d), 7.70 (1H, d), 7.58 (1H, br d), 5.03-4.95 (2H, m), 4.61 (1H, d), 4.59 (1H, d), 4.35 (2H, s), 3.93 (1H, d), 3.90-3.82 (2H, m), 3.82-3.70 (2H, m), 3.43-3.34 (2H, m), 1.89-1.81 (2H, m), 1.59-1.48 (2H, m). | 591 |
| 284 | 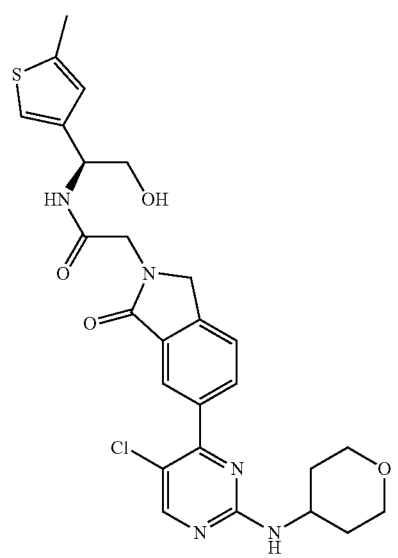 [SMILES: Cc1cc([C@@H](CO)NC(=O)CN2Cc3ccc(-c4nc(NC5CCOCC5)ncc4Cl)cc3C2=O)cs1] | 2-(6-{5-chloro-2-[(oxan-4-yl)amino]pyrimidin-4-yl}-1-oxo-2,3-dihydro-1H-isoindol-2-yl)-N-[(1S)-2-hydroxy-1-(5-methylthiophen-3-yl)ethyl]acetamide | (Me-d3-OD): 8.36 (1H, s), 8.26-8.23 (1H, m), 8.08 (1H, dd), 7.71 (1H, dd), 7.05-7.03 (1H, m), 6.81-6.78 (1H, m), 5.07 (1H, dd), 4.69 (2H, s), 4.43 (2H, s), 4.11-4.02 (1H, m), 4.02-3.93 (2H, m), 3.83 (1H, dd), 3.75 (1H, dd), 3.55 (2H, td), 2.46 (3H, d), 2.05-1.97 (2H, m), 1.69-1.57 (2H, m). | 542 |

| Example | Structure | Name | $^1$H NMR (400 MHz) | MS: [M + H]$^+$ |
|---|---|---|---|---|
| 285 | 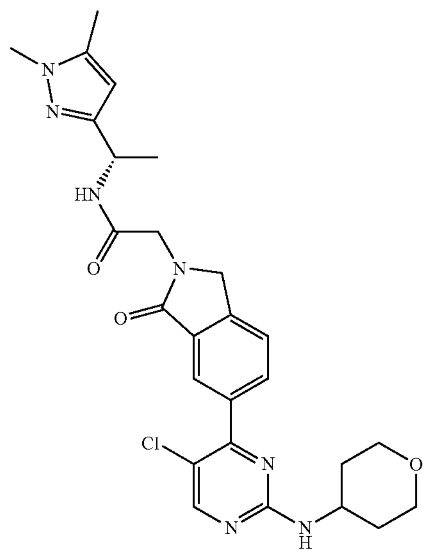 [SMILES: Cc1cc([C@H](C)NC(=O)CN2Cc3ccc(-c4nc(NC5CCOCC5)ncc4Cl)cc3C2=O)nn1C] | 2-(6-{5-chloro-2-[(oxan-4-yl)amino]pyrimidin-4-yl}-1-oxo-2,3-dihydro-1H-isoindol-2-yl)-N-[(1S)-1-(1,5-dimethyl-1H-pyrazol-3-yl)ethyl]acetamide | (DMSO-d6): 8.45 (1H, s), 8.36 (1H, d), 8.04-8.02 (1H, m), 7.98 (1H, dd), 7.75 (1H, d), 7.58 (1H, br d), 5.93 (1H, s), 4.95-4.87 (1H, m), 4.61 (2H, s), 4.21 (2H, s), 3.98-3.91 (1H, m), 3.87 (2H, d), 3.66 (3H, s), 3.38 (2H, t), 2.21 (3H, s), 1.85 (2H, d), 1.60-1.47 (2H, m), 1.34 (3H, d). | 524 |
| 286 | 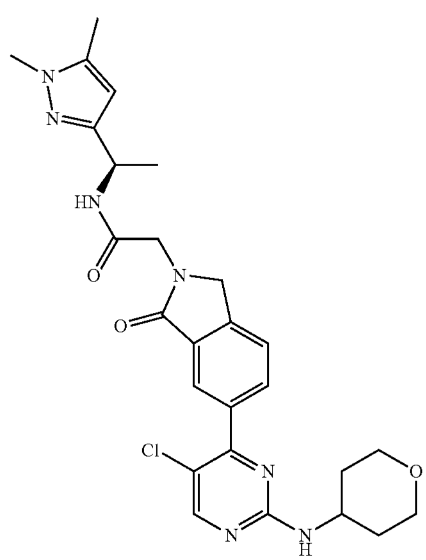 [SMILES: Cc1cc([C@@H](C)NC(=O)CN2Cc3ccc(-c4nc(NC5CCOCC5)ncc4Cl)cc3C2=O)nn1C] | 2-(6-{5-chloro-2-[(oxan-4-yl)amino]pyrimidin-4-yl}-1-oxo-2,3-dihydro-1H-isoindol-2-yl)-N-[(1R)-1-(1,5-dimethyl-1H-pyrazol-3-yl)ethyl]acetamide | (DMSO-d6): 8.45 (1H, s), 8.36 (1H, d), 8.04-8.02 (1H, m), 7.98 (1H, dd), 7.75 (1H, d), 7.58 (1H, br d), 5.93 (1H, s), 4.96-4.87 (1H, m), 4.61 (2H, s), 4.21 (2H, s), 3.98-3.90 (1H, m), 3.90-3.83 (2H, m), 3.66 (3H, s), 3.38 (2H, t), 2.21 (3H, s), 1.90-1.81 (2H, m), 1.60-1.47 (2H, m), 1.34 (3H, d). | 524 |

-continued

| Example | Structure | Name | ¹H NMR (400 MHz) | MS: [M + H]⁺ |
|---|---|---|---|---|
| 287 | 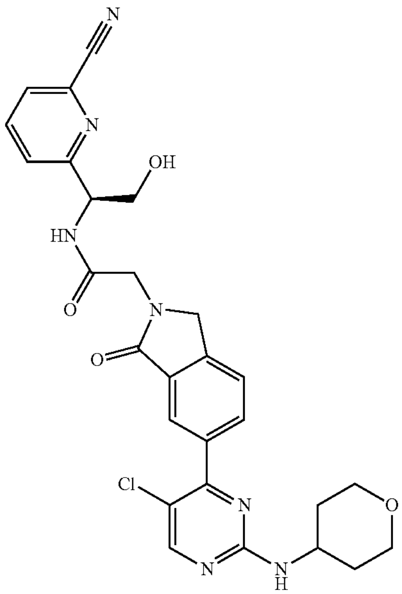 [SMILES: N#Cc1cccc([C@@H](CO)NC(=O)CN2Cc3ccc(-c4nc(NC5CCOCC5)ncc4Cl)cc3C2=O)n1] | 2-(6-{5-chloro-2-[(oxan-4-yl)amino]pyrimidin-4-yl}-1-oxo-2,3-dihydro-1H-isoindol-2-yl)-N-[(1S)-1-(6-cyanopyridin-2-yl)-2-hydroxyethyl]acetamide | (DMSO-d6): 8.69 (1H, d), 8.44 (1H, s), 8.07-8.01 (2H, m), 7.98 (1H, dd), 7.94 (1H, dd), 7.76-7.69 (2H, m), 7.58 (1H, br d), 5.02-4.95 (2H, m), 4.61 (1H, d), 4.59 (1H, d), 4.34 (2H, s), 3.98-3.90 (1H, m), 3.90-3.82 (2H, m), 3.77-3.71 (2H, m), 3.38 (2H, t), 1.89-1.81 (2H, m), 1.60-1.47 (2H, m). | 548 |
| 288 | 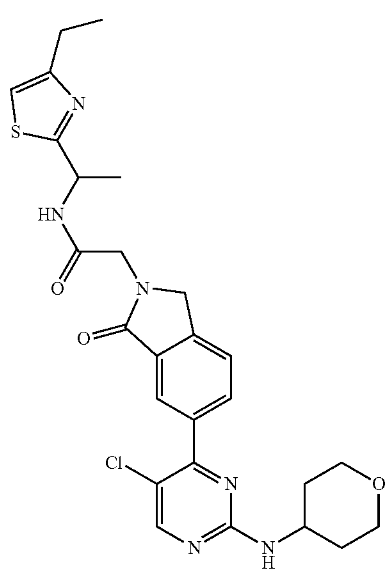 [SMILES: CCc1csc(C(C)NC(=O)CN2Cc3ccc(-c4nc(NC5CCOCC5)ncc4Cl)cc3C2=O)n1] | 2-(6-{5-chloro-2-[(oxan-4-yl)amino]pyrimidin-4-yl}-1-oxo-2,3-dihydro-1H-isoindol-2-yl)- N-[1-(4-ethyl-1,3-thiazol-2-yl)ethyl]acetamide | (DMSO-d6): 8.89 (1H, d), 8.45 (1H, s), 8.05-8.03 (1H, m), 7.98 (1H, dd), 7.75 (1H, d), 7.62-7.55 (1H, m), 7.15 (1H, s), 5.24-5.16 (1H, m), 4.63 (1H, d), 4.61 (1H, d), 4.28 (2H, s), 3.99-3.90 (1H, m), 3.90-3.83 (2H, m), 3.38 (2H, t), 2.73-2.68 (2H, m), 1.89-1.81 (2H, m), 1.59-1.47 (5H, m), 1.21 (3H, t). | 541 |

| Example | Structure | Name | ¹H NMR (400 MHz) | MS: [M + H]⁺ |
|---|---|---|---|---|
| 289 | 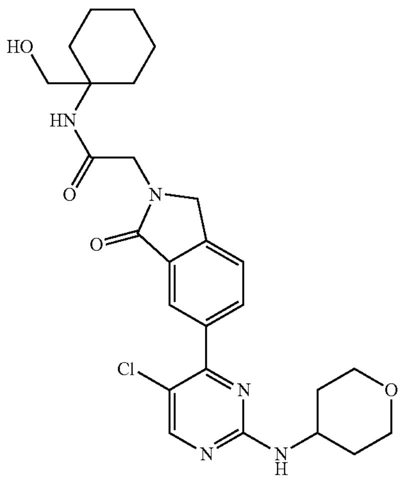 [SMILES: O=C(CN1Cc2ccc(-c3nc(NC4CCOCC4)ncc3Cl)cc2C1=O)NC1(CO)CCCCC1] | 2-(6-{5-chloro-2-[(oxan-4-yl)amino]pyrimidin-4-yl}-1-oxo-2,3-dihydro-1H-isoindol-2-yl)-N-[1-(hydroxymethyl)cyclohexyl]acetamide | (DMSO-d6): 8.45 (1H, s), 8.04-8.02 (1H, m), 7.98 (1H, dd), 7.74 (1H, d), 7.63-7.53 (1H, m), 7.35 (1H, s), 4.62 (1H, t), 4.59 (2H, s), 4.23 (2H, s), 3.99-3.90 (1H, m), 3.90-3.82 (2H, m), 3.45 (2H, d), 3.38 (2H, t), 2.05-1.98 (2H, m), 1.85 (2H, d), 1.60-1.40 (7H, m), 1.35-1.14 (3H, m). | 514 |
| 290 | 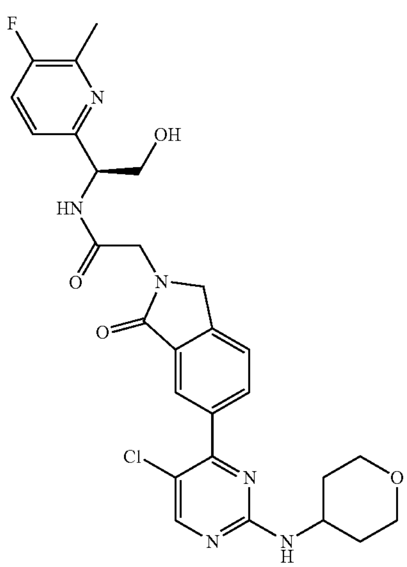 [SMILES: Cc1nc([C@@H](CO)NC(=O)CN2Cc3ccc(-c4nc(NC5CCOCC5)ncc4Cl)cc3C2=O)ccc1F] | 2-(6-{5-chloro-2-[(oxan-4-yl)amino]pyrimidin-4-yl}-1-oxo-2,3-dihydro-1H-isoindol-2-yl)-N-[(1S)-1-(5-fluoro-6-methylpyridin-2-yl)-2-hydroxyethyl]acetamide | (DMSO-d6): 8.51 (1H, d), 8.45 (1H, s), 8.04-8.02 (1H, m), 7.98 (1H, dd), 7.74 (1H, d), 7.62-7.55 (2H, m), 7.26 (1H, dd), 4.91 (1H, q), 4.86 (1H, t), 4.61 (2H, s), 4.32 (2H, s), 3.99-3.90 (1H, m), 3.90-3.82 (2H, m), 3.76-3.62 (2H, m), 3.38 (2H, t), 2.43 (3H, d), 1.85 (2H, d), 1.60-1.47 (2H, m). | 555 |

-continued

| Example | Structure | Name | ¹H NMR (400 MHz) | MS: [M + H]⁺ |
|---|---|---|---|---|
| 291 | 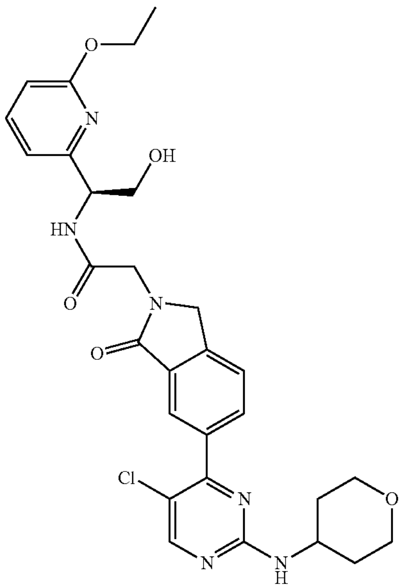 [SMILES: CCOc1cccc([C@@H](CO)NC(=O)CN2Cc3ccc(-c4nc(NC5CCOCC5)ncc4Cl)cc3C2=O)n1] | 2-(6-{5-chloro-2-[(oxan-4-yl)amino]pyrimidin-4-yl}-1-oxo-2,3-dihydro-1H-isoindol-2-yl)-N-[(1S)-1-(6-ethoxypyridin-2-yl)-2-hydroxyethyl]acetamide | (Me-d3-OD): 8.36 (1H, s), 8.25 (1H, s), 8.09 (1H, dd), 7.72 (1H, d), 7.65-7.60 (1H, m), 6.96 (1H, dd), 6.65 (1H, d), 5.05 (1H, t), 4.71 (2H, s), 4.47 (2H, s), 4.34-4.20 (2H, m), 4.11-4.02 (1H, m), 4.02-3.96 (2H, m), 3.93 (1H, dd), 3.87 (1H, dd), 3.55 (2H, td), 2.05-1.98 (2H, m), 1.70-1.57 (2H, m), 1.31 (3H, t). | 567 |
| 292 | 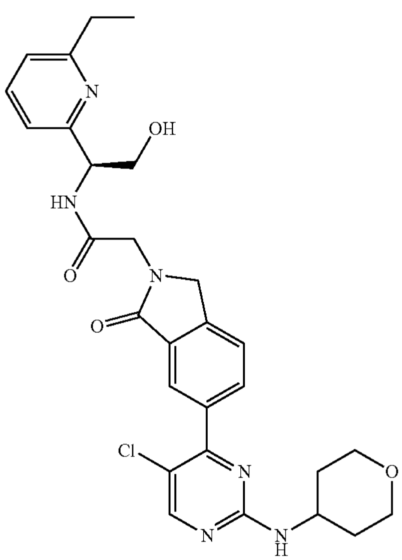 [SMILES: CCc1cccc([C@@H](CO)NC(=O)CN2Cc3ccc(-c4nc(NC5CCOCC5)ncc4Cl)cc3C2=O)n1] | 2-(6-{5-chloro-2-[(oxan-4-yl)amino]pyrimidin-4-yl}-1-oxo-2,3-dihydro-1H-isoindol-2-yl)-N-[(1S)-1-(6-ethylpyridin-2-yl)-2-hydroxyethyl]acetamide TFA | (Me-d3-OD): 8.47-8.39 (1H, m), 8.36 (1H, s), 8.24-8.21 (1H, m), 8.08 (1H, dd), 7.90-7.85 (1H, m), 7.83-7.78 (1H, m), 7.71 (1H, d), 5.19 (1H, t), 4.70 (1H, d), 4.67 (1H, d), 4.50 (1H, d), 4.45 (1H, d), 4.10-4.02 (1H, m), 4.01-3.93 (4H, m), 3.54 (2H, td), 3.12-3.05 (2H, m), 2.04-1.96 (2H, m), 1.70-1.56 (2H, m), 1.41 (3H, t). | 551 |

-continued

| Example | Structure | Name | ¹H NMR (400 MHz) | MS: [M + H]⁺ |
|---|---|---|---|---|
| 293 | 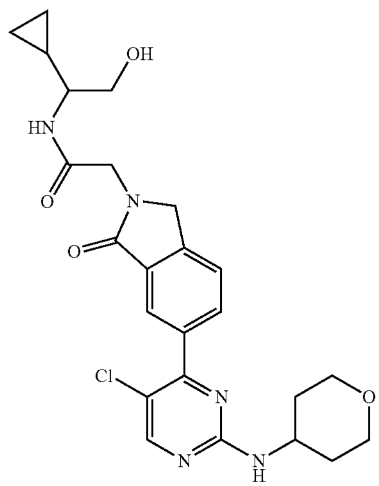 [SMILES: O=C(CN1Cc2ccc(-c3nc(NC4CCOCC4)ncc3Cl)cc2C1=O)NC(CO)C1CC1] | 2-(6-{5-chloro-2-[(oxan-4-yl)amino]pyrimidin-4-yl}-1-oxo-2,3-dihydro-1H-isoindol-2-yl)-N-(1-cyclopropyl-2-hydroxyethyl)acetamide | (DMSO-d6): 8.45 (1H, s), 8.05-8.03 (1H, m), 7.98 (1H, dd), 7.94 (1H, d), 7.75 (1H, d), 7.58 (1H, br d), 4.65 (1H, t), 4.59 (2H, s), 4.23 (1H, d), 4.21 (1H, d), 3.98-3.90 (1H, m), 3.90-3.84 (2H, m), 3.52-3.42 (2H, m), 3.38 (2H, t), 1.89-1.81 (2H, m), 1.59-1.48 (2H, m), 0.96-0.86 (1H, m), 0.47-0.39 (1H, m), 0.39-0.31 (1H, m), 0.29-0.16 (2H, m). | 486 |
| 294 | 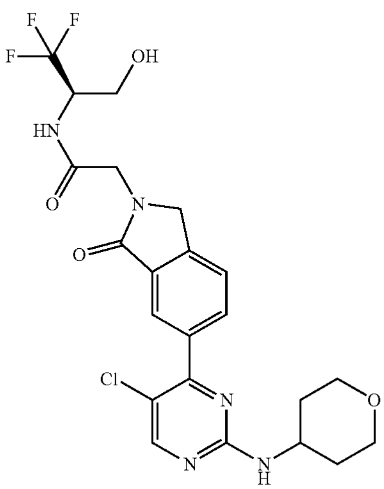 [SMILES: O=C(CN1Cc2ccc(-c3nc(NC4CCOCC4)ncc3Cl)cc2C1=O)N[C@H](CO)C(F)(F)F] | 2-(6-{5-chloro-2-[(oxan-4-yl)amino]pyrimidin-4-yl}-1-oxo-2,3-dihydro-1H-isoindol-2-yl)-N-[(2R)-1,1,1-trifluoro-3-hydroxypropan-2-yl]acetamide | (DMSO-d6): 8.71 (1H, d), 8.45 (1H, s), 8.05-8.04 (1H, m), 7.99 (1H, dd), 7.76 (1H, d), 7.59 (1H, br d), 5.20 (1H, t), 4.60 (2H, s), 4.59-4.51 (1H, m), 4.37 (1H, d), 4.31 (1H, d), 3.99-3.90 (1H, m), 3.90-3.82 (2H, m), 3.74-3.66 (1H, m), 3.66-3.58 (1H, m), 3.38 (2H, td), 1.90-1.81 (2H, m), 1.61-1.47 (2H, m). | 514 |
| 295 | 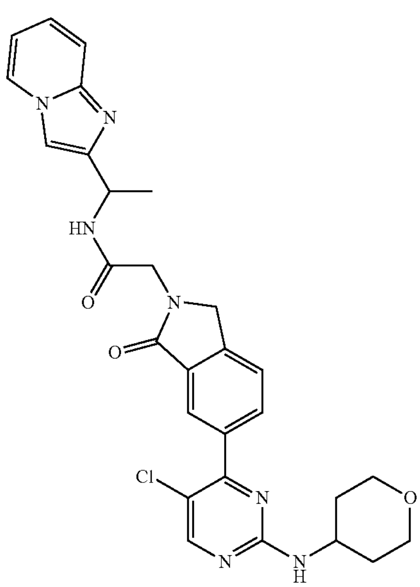 [SMILES: CC(NC(=O)CN1Cc2ccc(-c3nc(NC4CCOCC4)ncc3Cl)cc2C1=O)c1cn2ccccc2n1] | 2-(6-{5-chloro-2-[(oxan-4-yl)amino]pyrimidin-4-yl}-1-oxo-2,3-dihydro-1H-isoindol-2-yl)-N-(1-{imidazo[1,2-a]pyridin-2-yl}ethyl)acetamide | (DMSO-d6): 8.56 (1H, d), 8.53-8.49 (1H, m), 8.45 (1H, s), 8.05-8.03 (1H, m), 7.98 (1H, dd), 7.79 (1H, s), 7.75 (1H, d), 7.58 (1H, br d), 7.50 (1H, dd), 7.24-7.19 (1H, m), 6.86 (1H, td), 5.17-5.09 (1H, m), 4.63 (2H, s), 4.27 (2H, s), 3.98-3.90 (1H, m), 3.90-3.83 (2H, m), 3.38 (2H, t), 1.89-1.81 (2H, m), 1.59-1.51 (2H, m), 1.49 (3H, d). | 546 |

Examples 296 and 297 tert-Butyl 3-{1-[2-(6-{5-chloro-2-[(oxan-4-yl)amino]pyrimidin-4-yl}-1-oxo-2,3-dihydro-1H-isoindol-2-yl)acetamido]ethyl}piperidine-1-carboxylate

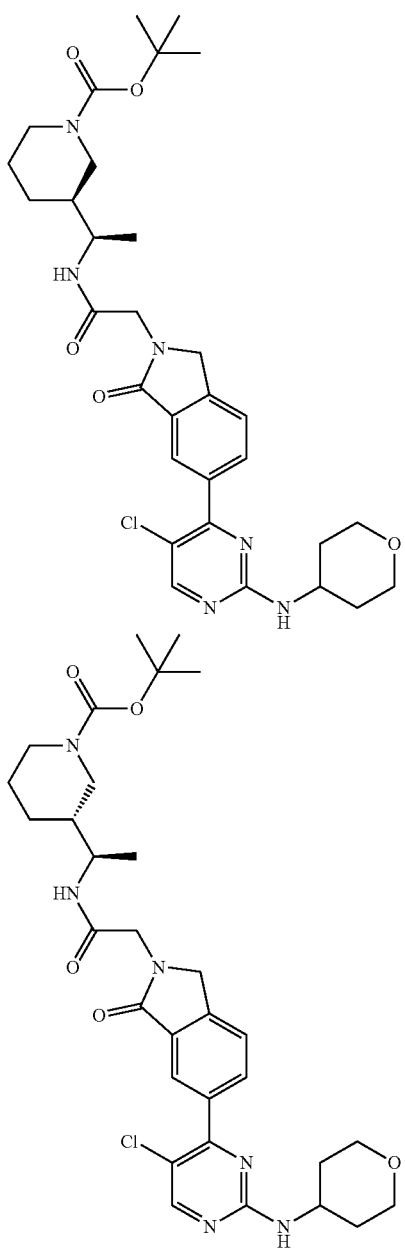

To HATU (1.2 eq.) and 2-(6-{5-chloro-2-[(oxan-4-yl)amino]pyrimidin-4-yl}-1-oxo-2,3-dihydro-1H-isoindol-2-yl)acetic acid (Example 1)(1.0 eq.) was added DCM (0.1 M), DIPEA (1.2 eq.) and then 3-(1-amino-ethyl)-piperidine-1-carboxylic acid tert-butyl ester (1.5 eq.) was added under nitrogen. The mixture was stirred for 4 hours at room temperature. The reaction was quenched by diluting with water and extracting with EtOAc (×3). The combined organic layers were washed with brine and dried over MgSO$_4$. The products were filtered and evaporated to dryness. The diastereomers (Examples 296 and 297) were separated by preparative HPLC.

First diastereomer (Example 296): 1H NMR (400 MHz, Me-d3-OD): 8.35 (1H, s), 8.24 (1H, d), 8.08 (1H, dd), 7.72 (1H, dd), 4.68 (2H, s), 4.35 (2H, s), 4.12-4.02 (1H, m), 4.02-3.95 (3H, m), 3.92-3.77 (2H, m), 3.54 (2H, dt), 2.92-2.82 (1H, m), 2.82-2.58 (1H, m), 2.01 (2H, d), 1.94-1.85 (1H, m), 1.76-1.69 (1H, m), 1.69-1.58 (2H, m), 1.57-1.49 (1H, m), 1.47 (9H, s), 1.44-1.37 (1H, m), 1.31 (1H, d), 1.21 (3H, d). LC-MS: [M+H]$^+$=613.

Second diastereomer (Example 297): 1H NMR (400 MHz, Me-d3-OD): 8.36 (1H, s), 8.25 (1H, d), 8.08 (1H, dd), 7.72 (1H, d), 4.70 (2H, s), 4.37 (2H, s), 4.11-4.03 (2H, m), 4.02-3.93 (3H, m), 3.86-3.77 (1H, m), 3.55 (2H, dt), 2.83-2.71 (1H, m), 2.56 (1H, s), 2.01 (2H, d), 1.96-1.86 (1H, m), 1.76-1.69 (1H, m), 1.69-1.58 (2H, m), 1.48 (10H, s), 1.33-1.21 (2H, m), 1.19 (3H, d). LC-MS: [M+H]$^+$=613.

Examples 298 and 299: 2-(6-{5-chloro-2-[(oxan-4-yl)amino]pyrimidin-4-yl}-1-oxo-2,3-dihydro-1H-isoindol-2-yl)-N-[1-(piperidin-3-yl)ethyl]acetamide HCl

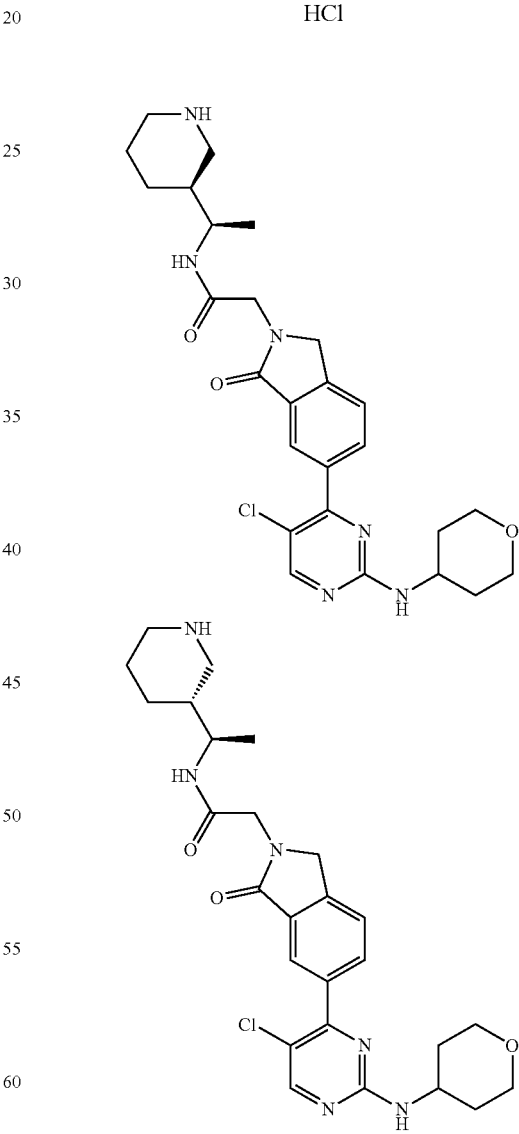

To each diastereomer of tert-butyl 3-{1-[2-(6-{5-chloro-2-[(oxan-4-yl)amino]pyrimidin-4-yl}-1-oxo-2,3-dihydro-1H-isoindol-2-yl)acetamido]ethyl}piperidine-1-carboxylate (Example 296 or 297), was added HCl saturated in EtOAc and the reactions were stirred for 2 hours. The mixture was evaporated in vacuo, and again after addition of MeOH (×2) to yield the Example 298 or 299 as a colourless solid (HCl salt).

First diastereomer (Example 298): 1H NMR (400 MHz, Me-d3-OD): 8.44 (1H, s), 8.26 (1H, d), 8.20 (0.5H, d), 8.12 (1H, dd), 7.76 (1H, dd), 4.74 (1H, d), 4.70 (1H, d), 4.42 (1H, d), 4.30 (1H, d), 4.15-4.04 (1H, m), 4.04-3.96 (3H, m), 3.55 (2H, td), 3.40-3.34 (2H, m), 2.92 (1H, td), 2.78 (1H, t), 2.05-1.88 (5H, m), 1.78-1.61 (3H, m), 1.44-1.33 (1H, m), 1.23 (3H, d).

Second diastereomer (Example 299): 1H NMR (400 MHz, Me-d3-OD): 8.36 (1H, s), 8.22 (1H, s), 8.21 (0.5, m), 8.08 (1H, dd), 7.73 (1H, d), 4.74 (1H, d), 4.69 (1H, d), 4.40 (1H, d), 4.29 (1H, d), 4.11-4.02 (1H, m), 4.02-3.94 (2H, m), 3.93-3.83 (1H, m), 3.54 (2H, td), 3.41 (1H, d), 2.99-2.86 (1H, m), 2.76 (1H, t), 2.04-1.93 (4H, m), 1.88-1.58 (4H, m), 1.44-1.33 (1H, m), 1.24 (3H, d).

Examples 300 and 301: N-[1-(1-acetylpiperidin-3-yl)ethyl]-2-(6-{5-chloro-2-[(oxan-4-yl)amino]pyrimidin-4-yl}-1-oxo-2,3-dihydro-1H-isoindol-2-yl)acetamide

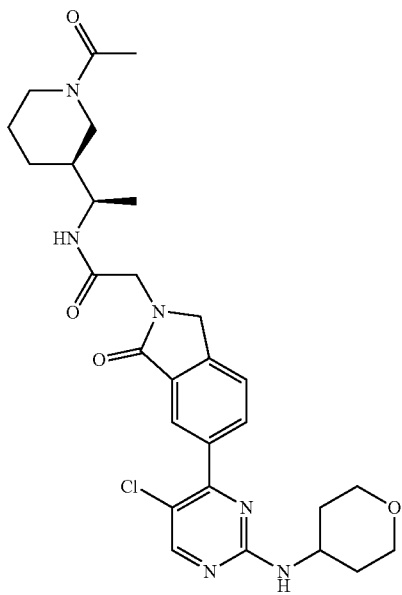

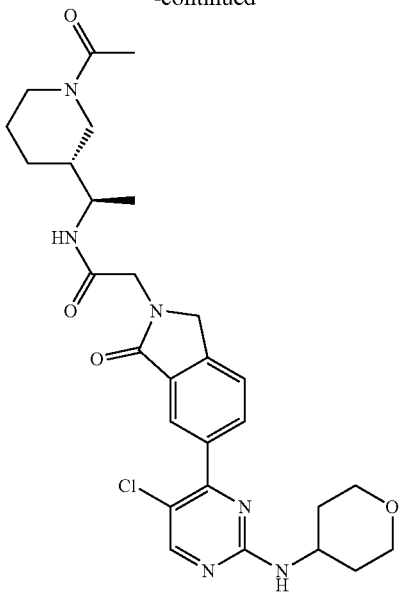

To HATU (1.2 eq.) and 2-(6-{5-chloro-2-[(oxan-4-yl)amino]pyrimidin-4-yl}-1-oxo-2,3-dihydro-1H-isoindol-2-yl)-N-[1-(piperidin-3-yl)ethyl]acetamide HCl (Example 298 or 299) (1.0 eq.) was added DCM (0.1 M), DIPEA (1.2 eq.) and then acetic acid (1.2 eq.) was added under nitrogen. The mixture was stirred for 4 hours at room temperature. The reaction was quenched by diluting with citric acid (5%, aq.) and extracting with EtOAc (×3). The combined organic layers were washed with brine and dried over MgSO₄. The products were filtered and evaporated to dryness to yield the diastereomer Examples 300 or 301.

First diastereomer (Example 300): 1H NMR (400 MHz, (Me-d3-OD): 8.36 (1H, s), 8.24 (1H, d), 8.11-8.05 (1H, m), 7.72 (1H, d), 4.69 (2H, d), 4.49-4.32 (3H, m), 4.10-4.02 (1H, m), 4.02-3.84 (3H, m), 3.83-3.68 (1H, m), 3.58-3.47 (2H, m), 3.18-3.10 (0.5H, m), 2.91 (0.5H, dd), 2.73-2.54 (1H, m), 2.05-1.93 (3H, m), 1.86-1.75 (1H, m), 1.69-1.58 (2H, m), 1.55-1.32 (6H, m), 1.23 (1.5H, d), 1.21 (1.5H, d). LC-MS: [M+H]⁺=555.

Second diastereomer (Example 301): 1H NMR (400 MHz, (Me-d3-OD): 8.36 (1H, s), 8.25-8.22 (1H, m), 8.08 (1H, dt), 7.76-7.71 (1H, m), 4.73-4.69 (2H, m), 4.52-4.32 (3H, m), 4.10-4.02 (1H, m), 4.02-3.96 (2H, m), 3.93-3.75 (2H, m), 3.55 (2H, td), 3.14-3.05 (0.5H, m), 2.89 (0.5H, dd), 2.73-2.63 (0.5H, m), 2.49 (0.5H, dd), 2.02 (2H, d), 1.97-1.92 (1H, m), 1.86-1.73 (1H, m), 1.69-1.55 (3H, m), 1.52-1.34 (5H, m), 1.21 (2H, d), 1.19 (1H, d). LC-MS: [M+H]⁺=555.

Example 302: 6-{5-Chloro-2-[(oxan-4-yl)amino]pyrimidin-4-yl}-2-{2-[(1-hydroxy-2-phenylpropan-2-yl)amino]ethyl}-2,3-dihydro-1H-isoindol-1-one

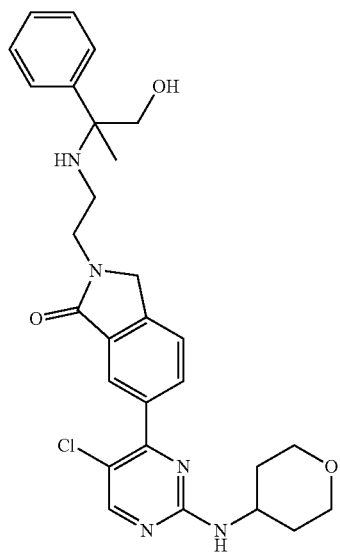 [SMILES: CC(CO)(NCCN1Cc2ccc(-c3nc(NC4CCOCC4)ncc3Cl)cc2C1=O)c1ccccc1]

To 6-(2,5-dichloropyrimidin-4-yl)-2-{2-[(1-hydroxy-2-phenylpropan-2-yl)amino]ethyl}-2,3-dihydro-1H-isoindol-1-one (Preparation 419) (10 mg, 0.02 mmol) in EtOH was added 4-aminooxan (7 μL, 0.07 mmol) and DIPEA (11 μL, 0.07 mmol). The mixture was stirred in reacti vial at 90° C. for 24 hours. The mixture was evaporated in vacuo and purified directly by preparative HPLC to yield the product as a colourless solid (2 mg, 18%). 1H NMR (400 MHz, Me-d3-OD): 8.37 (1H, s), 8.23 (1H, d), 8.07 (1H, dd), 7.69 (1H, d), 7.40-7.33 (2H, m), 7.19-7.14 (3H, m), 4.65-4.47 (2H, m), 4.12-4.03 (1H, m), 4.03-3.95 (2H, m), 3.80-3.65 (2H, m), 3.63-3.51 (4H, m), 2.83-2.75 (1H, m), 2.66-2.57 (1H, m), 2.05-1.98 (2H, m), 1.70-1.58 (2H, m), 1.49 (3H, s). LC-MS: [M+H]$^+$=522.

Example 303: 2-(6-{5-Chloro-2-[(oxan-4-yl)amino]pyrimidin-4-yl}-1-oxo-2,3-dihydro-1H-isoindol-2-yl)-N-[(1S)-1-[6-(dimethylamino)pyridin-2-yl]-2-hydroxyethyl]acetamide

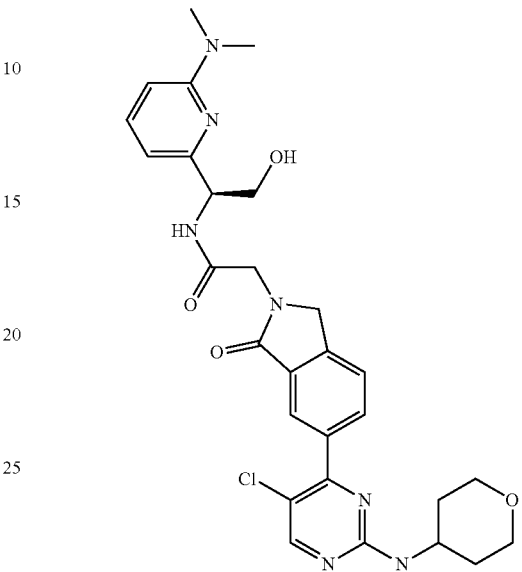

(2S)-2-Amino-2-(6-bromopyridin-2-yl)ethanol HCl (100 mg, 0.40 mmol) was taken up in dimethylamine (3.0 mL, 2M in THF). The mixture was heated by microwave at 60° C. for 1 hr, followed by 120° C. for a total of 18 hr. The reaction was quenched by diluting with K$_2$CO$_3$ (sat., aq.) and extracting with EtOAc (×3). The combined organic layers were washed with brine and dried over MgSO$_4$. The product was filtered and evaporated in vacuo and used in the next reaction as is. LC-MS: [M+H]$^+$=182. To the TBTU (99 mg, 0.30 mmol) and 2-(6-{5-chloro-2-[(oxan-4-yl)amino]pyrimidin-4-yl}-1-oxo-2,3-dihydro-1H-isoindol-2-yl)acetic acid (Example 1) (80 mg, 0.20 mmol) was added DCM (4.0 mL), then DIPEA (52 μL, 0.30 mmol) under nitrogen. After 10 minutes the amine was added. The mixture was stirred for 4 hours at room temperature. The reaction was quenched by diluting with citric acid (5%, aq.) and extracting with EtOAc (×3). The combined organic layers were washed with brine and dried over MgSO$_4$. The product was filtered and evaporated in vacuo. The product was purified by preparative HPLC, and dried by genevac, to yield 2-(6-{5-chloro-2-[(oxan-4-yl)amino]pyrimidin-4-yl}-1-oxo-2,3-dihydro-1H-isoindol-2-yl)-N-[(1S)-1-[6-(dimethylamino)pyridin-2-yl]-2-hydroxyethyl]acetamide (Example 303) as a colourless solid (53 mg, 47%). 1H NMR (400 MHz, DMSO-d6): 8.45 (1H, s), 8.28 (1H, d), 8.05-8.03 (1H, m), 7.98 (1H, dd), 7.75 (1H, d), 7.63-7.53 (1H, m), 7.45 (1H, dd), 6.55 (1H, d), 6.50 (1H, d), 4.82-4.76 (2H, m), 4.62 (2H, s), 4.34 (1H, d), 4.31 (1H, d), 3.99-3.90 (1H, m), 3.90-3.82 (2H, m), 3.77-3.70 (1H, m), 3.68-3.61 (1H, m), 3.38 (2H, t), 2.98 (6H, s), 1.89-1.81 (2H, m), 1.60-1.48 (2H, m). LC-MS: [M+H]$^+$=566.

Example 304: Methyl 2-(6-{5-chloro-2-[(oxan-4-yl)amino]pyrimidin-4-yl}-1-oxo-2,3-dihydro-1H-isoindol-2-yl)acetate

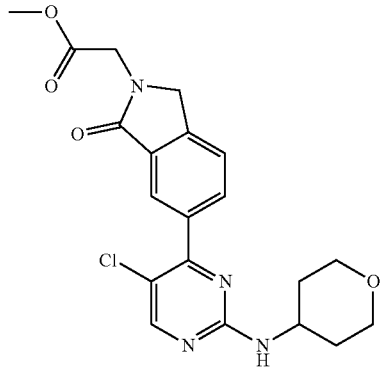 [SMILES: COC(=O)CN1Cc2ccc(-c3nc(NC4CCOCC4)ncc3Cl)cc2C1=O]

The title compound was prepared using a similar procedure to Preparation 4.

1H NMR (400 Mz, Me-d3-OD): 8.36 (1H, s), 8.24 (1H, s), 8.10 (1H, dd), 7.73 (1H, dd), 4.69 (2H, s), 4.49 (2H, s), 4.11-4.02 (1H, m), 4.02-3.95 (2H, m), 3.80 (3H, s), 3.59-3.51 (2H, m), 2.06-1.98 (2H, m), 1.70-1.58 (2H, m). LC-MS: [M+H]⁺=417.

Examples 305-316

Prepared using an analogous procedure to Example 2, from 2-(6-{5-chloro-2-[(oxan-4-yl)amino]pyrimidin-4-yl}-1-oxo-2,3-dihydro-1H-isoindol-2-yl)acetic acid (Example 1) and the corresponding amine:

| Example | Structure | Name | $^1$H NMR (400 MHz) | MS: [M + H]$^+$ |
|---|---|---|---|---|
| 305 | 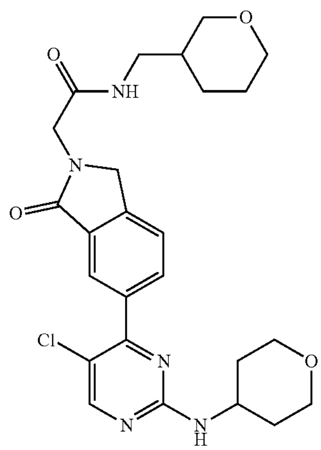 [SMILES: O=C(CN1Cc2ccc(-c3nc(NC4CCOCC4)ncc3Cl)cc2C1=O)NCC1CCCOC1] | 2-(6-{5-chloro-2-[(oxan-4-yl)amino]pyrimidin-4-yl}-1-oxo-2,3-dihydro-1H-isoindol-2-yl)-N-[(oxan-3-yl)methyl]acetamide | 1H NMR (400 MHz, CDCl3): 8.34 (1H, s), 8.30 (1H, s), 8.02 (1H, dd), 7.57 (1H, d), 6.64 (1H, s), 5.31 (1H, d), 4.63 (2H, s), 4.28 (2H, s), 4.14-4.04 (1H, m), 4.04-3.89 (2H, m), 3.89-3.71 (2H, m), 3.63-3.46 (2H, m), 3.45-3.30 (1H, m), 3.25-3.07 (3H, m), 2.12-1.97 (2H, m), 1.83-1.76 (2H, m), 1.70-1.36 (4H, m), 1.34-1.17 (1H, m). | 500 |
| 306 | 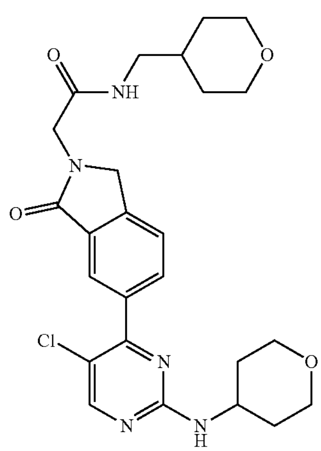 | 2-(6-{5-chloro-2-[(oxan-4-yl)amino]pyrimidin-4-yl}-1-oxo-2,3-dihydro-1H-isoindol-2-yl)-N-[(oxan-4-yl)methyl]acetamide | 1H NMR (400 MHz, CDCl3): 8.35 (1H, s), 8.33 (1H, s), 8.04 (1H, dd), 7.60 (1H, d), 6.49 (1H, s), 5.18 (1H, d), 4.64 (2H, s), 4.28 (2H, s), 4.17-4.06 (1H, m), 4.06-3.92 (4H, m), 3.61-3.48 (3H, m), 3.42-3.30 (2H, m), 3.23-3.11 (2H, m), 2.12-2.04 (2H, m), 1.83-1.70 (1H, m), 1.59-1.54 (2H, m), 1.38-1.20 (3H, m). | 500 |

-continued

| Example | Structure | Name | ¹H NMR (400 MHz) | MS: [M + H]⁺ |
|---------|-----------|------|------------------|--------------|
| 307 | 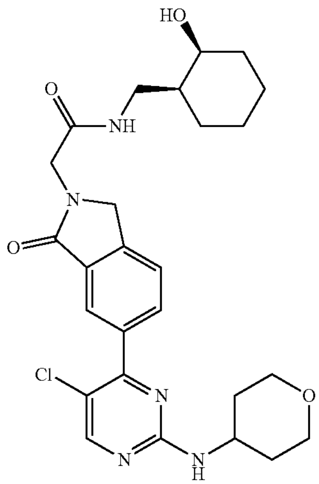 [SMILES: O=C(CN1Cc2ccc(-c3nc(NC4CCOCC4)ncc3Cl)cc2C1=O)NC[C@@H]1CCCC[C@@H]1O] | 2-(6-{5-chloro-2-[(oxan-4-yl)amino]pyrimidin-4-yl}-1-oxo-2,3-dihydro-1H-isoindol-2-yl)-N-{[(1S,2S)-2-hydroxycyclohexyl]methyl}acetamide | 1H NMR (400 MHz, CDCl3): 8.39-8.32 (1H, m), 8.30 (1H, s), 8.03 (1H, d), 7.58 (1H, d), 6.82 (1H, s), 5.33-5.17 (1H, m), 4.72-4.52 (2H, m), 4.39-4.18 (2H, m), 4.18-3.88 (3H, m), 3.88-3.71 (1H, m), 3.64-3.47 (3H, m), 3.04-2.88 (1H, m), 2.07 (2H, d), 1.88-1.67 (5H, m), 1.65-1.53 (4H, m), 1.48-1.38 (3H, m). | 514 |
| 308 | 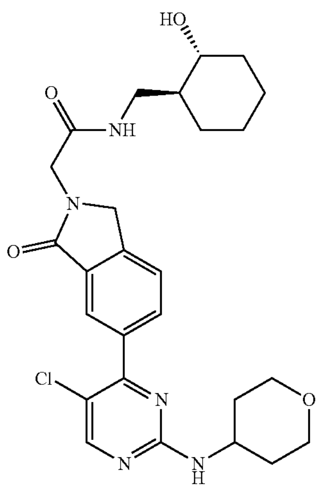 [SMILES: O=C(CN1Cc2ccc(-c3nc(NC4CCOCC4)ncc3Cl)cc2C1=O)NC[C@@H]1CCCC[C@H]1O] | 2-(6-{5-chloro-2-[(oxan-4-yl)amino]pyrimidin-4-yl}-1-oxo-2,3-dihydro-1H-isoindol-2-yl)-N-{[(1S,2R)-2-hydroxycyclohexyl]methyl}acetamide | 1H NMR (400 MHz, CDCl3): 8.34 (1H, s), 8.31 (1H, s), 8.03 (1H, dd), 7.59 (1H, d), 7.06 (1H, s), 5.26 (1H, d), 4.64 (2H, s), 4.30 (2H, d), 4.14-3.95 (3H, m), 3.87-3.75 (1H, m), 3.61-3.46 (2H, m), 3.24-3.15 (1H, m), 2.97-2.86 (1H, m), 2.06 (2H, d), 1.91 (1H, d), 1.73-1.52 (6H, m), 1.46-1.33 (1H, m), 1.33-1.11 (3H, m), 1.11-0.96 (1H, m). | 514 |
| 309 | 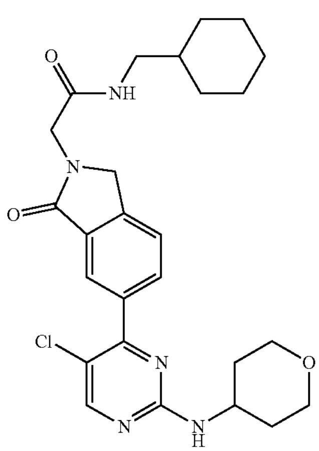 [SMILES: O=C(CN1Cc2ccc(-c3nc(NC4CCOCC4)ncc3Cl)cc2C1=O)NCC1CCCCC1] | 2-(6-{5-chloro-2-[(oxan-4-yl)amino]pyrimidin-4-yl}-1-oxo-2,3-dihydro-1H-isoindol-2-yl)-N-(cyclohexylmethyl)acetamide | 1H NMR (400 MHz, CDCl3): 8.35 (1H, s), 8.33 (1H, s), 8.04 (1H, dd), 7.60 (1H, d), 6.32 (1H, s), 5.18 (1H, d), 4.63 (2H, s), 4.28 (2H, d), 4.17-3.96 (3H, m), 3.62-3.49 (2H, m), 3.12 (2H, t), 2.07 (2H, d), 1.70 (5H, d), 1.53-1.38 (2H, m), 1.33-1.13 (4H, m), 0.98-0.86 (2H, m). | 498 |

| Example | Structure | Name | ¹H NMR (400 MHz) | MS: [M + H]⁺ |
|---|---|---|---|---|
| 310 | 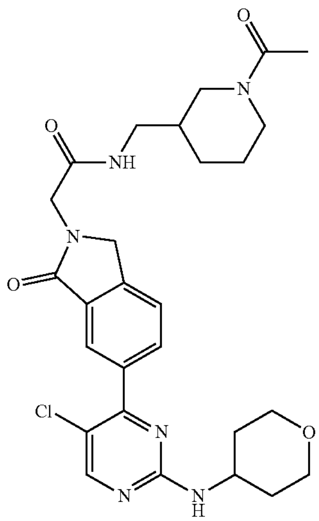 [SMILES: CC(=O)N1CCCC(CNC(=O)CN2Cc3ccc(-c4nc(NC5CCOCC5)ncc4Cl)cc3C2=O)C1] | N-[(1-acetylpiperidin-3-yl)methyl]-2-(6-{5-chloro-2-[(oxan-4-yl)amino]pyrimidin-4-yl}-1-oxo-2,3-dihydro-1H-isoindol-2-yl)acetamide | 1H NMR (400 MHz, CDCl3): 8.32 (1H, d), 8.26 (1H, d), 8.04-7.94 (1H, m), 7.56 (1H, d), 7.09 (1H, s), 4.64 (2H, s), 4.30 (2H, d), 4.10-4.02 (2H, m), 3.99 (2H, d), 3.58-3.50 (3H, m), 3.40-3.24 (1H, m), 3.24-3.08 (1H, m), 3.08-2.94 (1H, m), 2.86-2.70 (1H, m), 2.41-2.22 (2H, m), 2.06-2.04 (2H, m), 2.00 (3H, s), 1.82 (1H, d), 1.77-1.64 (2H, m), 1.64-1.50 (2H, m). | 541 |
| 311 | 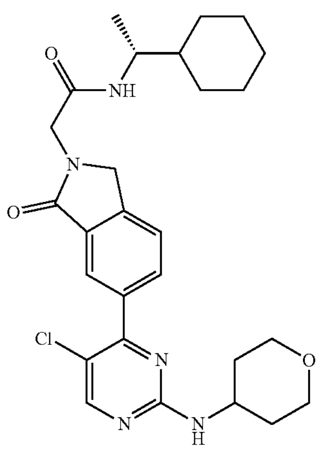 [SMILES: C[C@@H](NC(=O)CN1Cc2ccc(-c3nc(NC4CCOCC4)ncc3Cl)cc2C1=O)C1CCCCC1] | 2-(6-{5-chloro-2-[(oxan-4-yl)amino]pyrimidin-4-yl}-1-oxo-2,3-dihydro-1H-isoindol-2-yl)-N-[(1R)-1-cyclohexylethyl]acetamide | 1H NMR (400 MHz, CDCl3): 8.35 (1H, s), 8.34 (1H, s), 8.04 (1H, dd), 7.60 (1H, d), 6.07 (1H, d), 5.16 (1H, d), 4.64 (2H, s), 4.34-4.18 (2H, m), 4.17-4.05 (1H, m), 4.05-3.94 (2H, m), 3.92-3.80 (1H, m), 3.62-3.53 (2H, m), 3.51 (3H, d), 2.08 (2H, d), 1.77-1.67 (3H, m), 1.67-1.59 (3H, m), 1.38-1.26 (1H, m), 1.10 (3H, d), 1.00-0.90 (3H, m). | 512 |
| 312 | 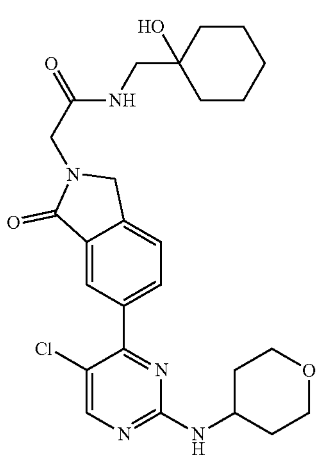 [SMILES: O=C(CN1Cc2ccc(-c3nc(NC4CCOCC4)ncc3Cl)cc2C1=O)NCC1(O)CCCCC1] | 2-(6-{5-chloro-2-[(oxan-4-yl)amino]pyrimidin-4-yl}-1-oxo-2,3-dihydro-1H-isoindol-2-yl)-N-[(1-hydroxycyclohexyl)methyl]acetamide | 1H NMR (400 MHz, CDCl3): 8.35 (1H, s), 8.34 (1H, s), 8.04 (1H, dd), 7.60 (1H, d), 6.61-6.46 (1H, m), 5.15 (1H, d), 4.65 (2H, s), 4.33 (2H, s), 4.20-4.05 (1H, m), 4.05-3.93 (2H, m), 3.66-3.45 (2H, m), 3.32 (2H, d), 2.08 (2H, d), 1.66-1.60 (2H, m), 1.47-1.38 (3H, m), 1.38-1.20 (4H, m), 0.94-0.79 (3H, m). | 514 |

| Example | Structure | Name | ¹H NMR (400 MHz) | MS: [M + H]⁺ |
|---|---|---|---|---|
| 313 | 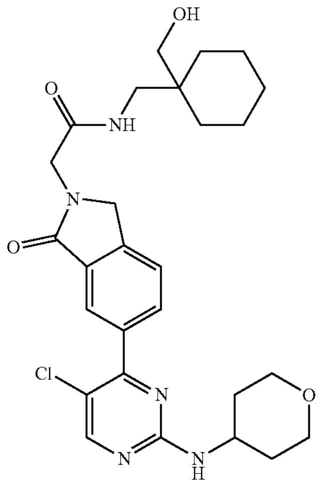 [SMILES: O=C(CN1Cc2ccc(-c3nc(NC4CCOCC4)ncc3Cl)cc2C1=O)NCC1(CO)CCCCC1] | 2-(6-{5-chloro-2-[(oxan-4-yl)amino]pyrimidin-4-yl}-1-oxo-2,3-dihydro-1H-isoindol-2-yl)-N-{[1-(hydroxymethyl)cyclo-hexyl]methyl}acetamide | 1H NMR (400 MHz, CDCl3): 8.36 (1H, s), 8.33 (1H, s), 8.05 (1H, dd), 7.61 (1H, d), 6.79 (1H, d), 5.17 (1H, d), 4.64 (2H, s), 4.31 (2H, s), 4.17-4.05 (1H, m), 4.05-3.91 (2H, m), 3.66-3.46 (2H, m), 3.31 (2H, d), 3.25 (3H, t), 2.07 (2H, d), 1.45 (6H, s), 1.39-1.32 (2H, m), 1.32-1.22 (3H, m). | 528 |
| 314 | 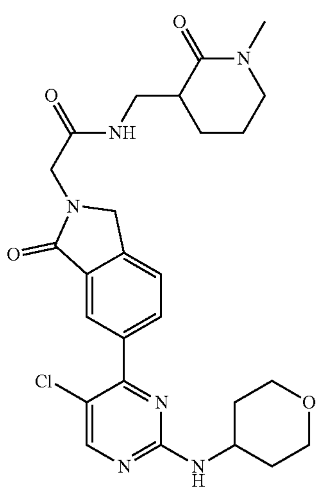 [SMILES: CN1CCCC(CNC(=O)CN2Cc3ccc(-c4nc(NC5CCOCC5)ncc4Cl)cc3C2=O)C1=O] | 2-(6-{5-chloro-2-[(oxan-4-yl)amino]pyrimidin-4-yl}-1-oxo-2,3-dihydro-1H-isoindol-2-yl)-N-[(1-methyl-2-oxopiperidin-3-yl)methyl]acetamide | 1H NMR (400 MHz, CDCl3): 8.35 (1H, s), 8.34 (1H, s), 8.04 (1H, dd), 7.60 (1H, d), 6.06 (1H, d), 5.16 (1H, d), 4.64 (2H, s), 4.37-4.19 (2H, m), 4.16-4.05 (1H, m), 4.05-3.96 (2H, m), 3.92-3.80 (1H, m), 3.62-3.53 (2H, m), 3.51 (3H, d), 2.08 (2H, d), 1.75-1.60 (6H, m), 1.38-1.11 (4H, m), 0.99-0.91 (3H, m). | 528 |

| Example | Structure | Name | ¹H NMR (400 MHz) | MS: [M + H]⁺ |
|---|---|---|---|---|
| 315 | 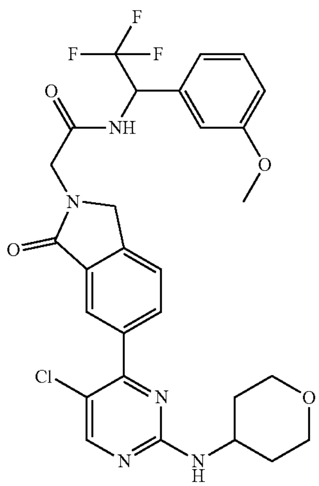 [SMILES: COc1cccc(C(NC(=O)CN2Cc3ccc(-c4nc(NC5CCOCC5)ncc4Cl)cc3C2=O)C(F)(F)F)c1] | 2-(6-{5-chloro-2-[(oxan-4-yl)amino]pyrimidin-4-yl}-1-oxo-2,3-dihydro-1H-isoindol-2-yl)-N-[2,2,2-trifluoro-1-(3-methoxyphenyl)ethyl]acetamide | 1H NMR (400 MHz, Me-d3-OD): 8.33 (1H, s), 8.22 (1H, s), 8.05 (1H, dd), 7.67 (1H, d), 7.34 (1H, t), 7.09 (2H, d), 7.04-6.94 (1H, m), 5.73 (1H, q), 4.65 (2H, s), 4.57-4.42 (2H, m), 4.08-3.90 (3H, m), 3.83 (3H, s), 3.60-3.46 (2H, m), 2.02-1.96 (2H, m), 1.70-1.54 (2H, m). | 591 |
| 316 | 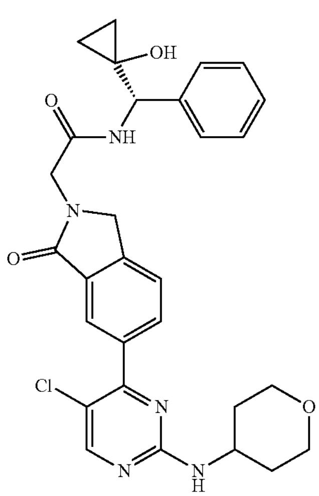 [SMILES: O=C(CN1Cc2ccc(-c3nc(NC4CCOCC4)ncc3Cl)cc2C1=O)N[C@@H](c1ccccc1)C1(O)CC1] | 2-(6-{5-chloro-2-[(oxan-4-yl)amino]pyrimidin-4-yl}-1-oxo-2,3-dihydro-1H-isoindol-2-yl)-N-[(S)-(1-hydroxycyclopropyl)(phenyl)methyl]acetamide | 1H NMR (400 MHz, Me-d3-OD): 8.30 (1H, s), 8.21 (1H, s), 8.01 (1H, d), 7.62 (1H, d), 7.44 (2H, d), 7.39-7.29 (2H, m), 7.25 (1H, t), 4.80 (1H, s), 4.61 (2H, s), 4.54-4.36 (2H, m), 4.06-3.88 (3H, m), 3.50 (2H, t), 1.97 (2H, d), 1.80-1.51 (2H, m), 0.85-0.64 (4H, m). | 549 |

Example 317: N-[(1S)-2-hydroxy-1-(3-methoxyphenyl)ethyl]-2-(6-{2-[(oxan-4-yl)amino]pyrimidin-4-yl}-1-oxo-2,3-dihydro-1H-isoindol-2-yl)acetamide

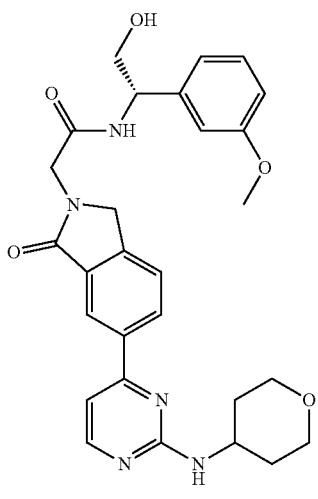 [SMILES: COc1cccc([C@@H](CO)NC(=O)CN2Cc3ccc(-c4ccnc(NC5CCOCC5)n4)cc3C2=O)c1]

Prepared using a method analogous to Preparation 4 from 2-[6-(2-chloropyrimidin-4-yl)-1-oxo-2,3-dihydro-1H-isoindol-2-yl]-N-[(1S)-2-hydroxy-1-(3-methoxyphenyl)ethyl]acetamide (Preparation 167) with EtOH as solvent. 1H NMR (400 MHz, CDCl3): 8.47 (1H, s), 8.39 (1H, d), 8.29 (1H, dd), 7.57 (1H, d), 7.25 (1H, t), 7.12 (1H, d), 7.05 (1H, d), 6.89 (1H, d), 6.85 (1H, d), 6.82 (1H, dd), 5.20 (1H, d), 5.08 (1H, q), 4.77-4.53 (2H, m), 4.44-4.28 (2H, m), 4.27-4.11 (1H, m), 4.09-3.98 (2H, m), 3.94-3.82 (2H, m), 3.78 (3H, s), 3.68-3.54 (2H, m), 2.12 (2H, d), 1.70-1.64 (2H, m). MS: [M+H]$^+$=518.

Examples 318-325

Prepared using a method analogous to Preparation 4 from 2-[6-(2,5-dichloropyrimidin-4-yl)-1-oxo-2,3-dihydro-1H-isoindol-2-yl]-N-[(1S)-2-hydroxy-1-(3-methoxyphenyl)ethyl]acetamide (Preparation 169) with EtOH as solvent.

| Example | Structure | Name | $^1$H NMR (400 MHz) | MS: [M + H]$^+$ |
|---|---|---|---|---|
| 318 | 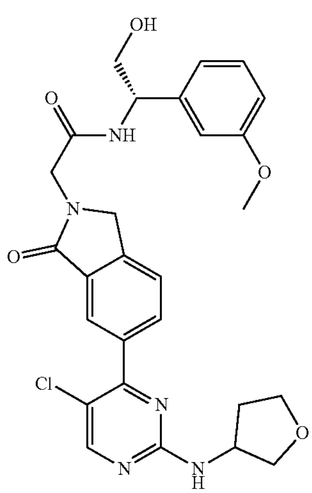 [SMILES: COc1cccc([C@@H](CO)NC(=O)CN2Cc3ccc(-c4nc(NC5CCOC5)ncc4Cl)cc3C2=O)c1] | 2-(6-{5-chloro-2-[(oxolan-3-yl)amino]pyrimidin-4-yl}-1-oxo-2,3-dihydro-1H-isoindol-2-yl)-N-[(1S)-2-hydroxy-1-(3-methoxyphenyl)ethyl]-acetamide | 1H NMR (400 MHz, CDCl3): 8.36 (1H, s), 8.33 (1H, s), 8.04 (1H, d), 7.57 (1H, d), 7.25 (1H, t), 7.20 (1H, d), 6.89 (1H, d), 6.85 (1H, s), 6.81 (1H, dd), 5.49 (1H, d), 5.07 (1H, q), 4.76-4.57 (3H, m), 4.43-4.24 (2H, m), 4.05-3.97 (2H, m), 3.92-3.85 (3H, m), 3.83-3.73 (5H, m), 2.44-2.29 (1H, m), 1.98-1.87 (1H, m). | 538 |

-continued

| Example | Structure | Name | ¹H NMR (400 MHz) | MS: [M + H]⁺ |
|---|---|---|---|---|
| 319 | 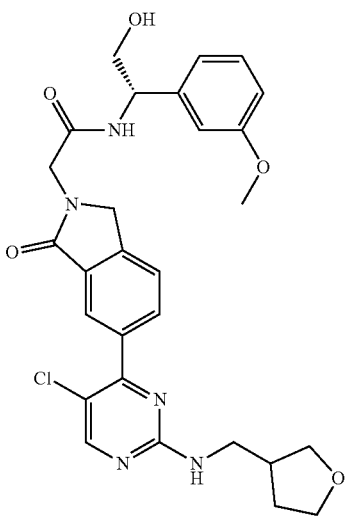 [SMILES: COc1cccc([C@@H](CO)NC(=O)CN2Cc3ccc(-c4nc(NCC5CCOC5)ncc4Cl)cc3C2=O)c1] | 2-[6-(5-chloro-2-{[(oxolan-3-yl)methyl]amino}-pyrimidin-4-yl)-1-oxo-2,3-dihydro-1H-isoindol-2-yl]-N-[(1S)-2-hydroxy-1-(3-methoxyphenyl)ethyl]-acetamide | 1H NMR (400 MHz, CDCl3): 8.38-8.33 (1H, m), 8.32 (1H, s), 8.04 (1H, d), 7.57 (1H, d), 7.24 (1H, t), 7.18 (1H, d), 6.89 (1H, d), 6.85 (1H, d), 6.81 (1H, dd), 5.42 (1H, s), 5.08 (1H, q), 4.75-4.49 (2H, m), 4.49-4.23 (2H, m), 3.98-3.80 (5H, m), 3.80-3.71 (4H, m), 3.71-3.60 (1H, m), 3.53-3.46 (3H, m), 2.16-2.05 (1H, m), 1.76-1.67 (1H, m). | 552 |
| 320 | 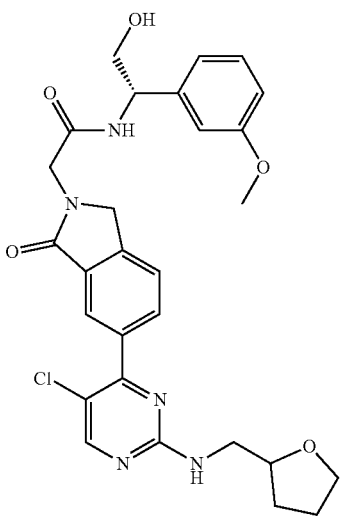 [SMILES: COc1cccc([C@@H](CO)NC(=O)CN2Cc3ccc(-c4nc(NCC5CCCO5)ncc4Cl)cc3C2=O)c1] | 2-[6-(5-chloro-2-{[(oxolan-2-yl)methyl]amino}-pyrimidin-4-yl)-1-oxo-2,3-dihydro-1H-isoindol-2-yl]-N-[(1S)-2-hydroxy-1-(3-methoxyphenyl)ethyl]-acetamide | 1H NMR (400 MHz, CDCl3): 8.34 (1H, s), 8.32 (1H, s), 8.04 (1H, d), 7.55 (1H, d), 7.27-7.15 (2H, m), 6.89 (1H, d), 6.85 (1H, d), 6.81 (1H, dd), 5.61 (1H, d), 5.08 (1H, q), 4.76-4.55 (2H, m), 4.45-4.28 (2H, m), 4.22-4.04 (1H, m), 3.98-3.82 (3H, m), 3.80 (1H, d), 3.77 (3H, s), 3.74-3.65 (1H, m), 3.55-3.43 (2H, m), 1.97 (3H, s), 1.73-1.66 (1H, m). | 552 |
| 321 | 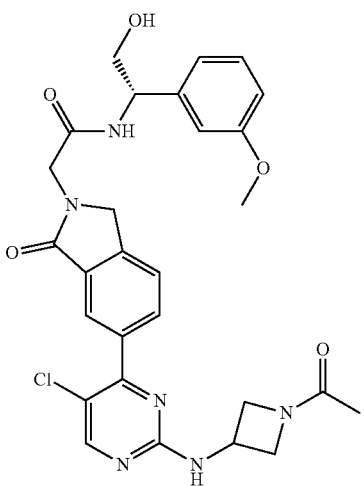 [SMILES: COc1cccc([C@@H](CO)NC(=O)CN2Cc3ccc(-c4nc(NC5CN(C(C)=O)C5)ncc4Cl)cc3C2=O)c1] | 2-(6-{2-[(1-acetylazetidin-3-yl)amino]-5-chloropyrimidin-4-yl}-1-oxo-2,3-dihydro-1H-isoindol-2-yl)-N-[(1S)-2-hydroxy-1-(3-methoxyphenyl)ethyl]-acetamide | 1H NMR (400 MHz, CDCl3): 8.39 (1H, s), 8.34 (1H, s), 8.06 (1H, d), 7.59 (1H, d), 7.25 (1H, d), 6.89 (1H, d), 6.86 (1H, s), 6.82 (1H, dd), 5.15-4.97 (1H, m), 4.81-4.55 (3H, m), 4.53-4.23 (4H, m), 4.10-3.96 (1H, m), 3.88 (3H, s), 3.81-3.71 (3H, m), 2.86-2.57 (1H, m), 1.89 (3H, s). | 565 |

| Example | Structure | Name | ¹H NMR (400 MHz) | MS: [M + H]⁺ |
|---|---|---|---|---|
| 322 | 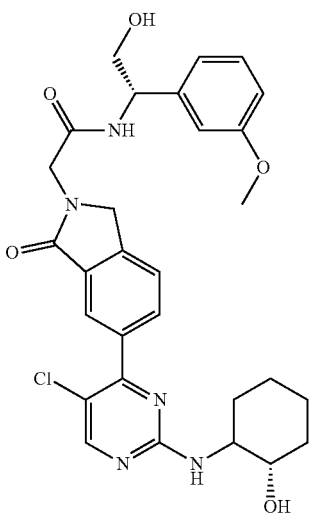 [SMILES: COc1cccc([C@@H](CO)NC(=O)CN2Cc3ccc(-c4nc(NC5CCCC[C@@H]5O)ncc4Cl)cc3C2=O)c1] | 2-[6-(5-chloro-2-{[(1S,2S)-2-hydroxycyclohexyl]amino}pyrimidin-4-yl)-1-oxo-2,3-dihydro-1H-isoindol-2-yl]-N-[(1S)-2-hydroxy-1-(3-methoxyphenyl)ethyl]-acetamide | 1H NMR (400 MHz, CDCl3): 8.29 (1H, d), 8.20 (1H, s), 7.97 (1H, d), 7.62-7.41 (2H, m), 7.21 (1H, t), 6.96-6.83 (2H, m), 6.78 (1H, dd), 5.13-5.00 (1H, m), 4.86 (1H, s), 4.77-4.50 (2H, m), 4.50-4.22 (2H, m), 4.22-3.99(1H, m), 3.95 (1H, d), 3.91-3.77 (3H, m), 3.75 (3H, s), 3.73-3.59 (2H, m), 3.28-2.95 (2H, m), 2.13-2.02 (2H, m), 1.75-1.58 (2H, m). | 566 |
| 323 | 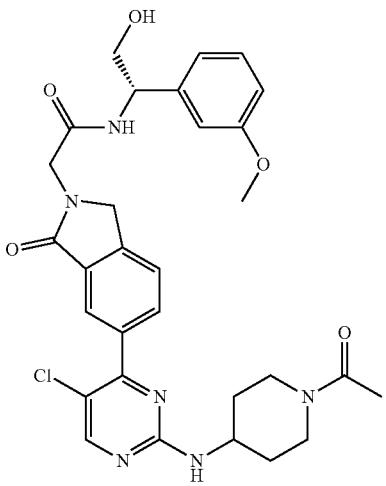 [SMILES: COc1cccc([C@@H](CO)NC(=O)CN2Cc3ccc(-c4nc(NC5CCN(C(C)=O)CC5)ncc4Cl)cc3C2=O)c1] | 2-(6-{2-[(1-acetylpiperidin-4-yl)amino]-5-chloropyrimidin-4-yl}-1-oxo-2,3-dihydro-1H-isoindol-2-yl)-N-[(1S)-2-hydroxy-1-(3-methoxyphenyl)ethyl]-acetamide | 1H NMR (400 MHz, CDCl3): 8.35 (1H, s), 8.31 (1H, s), 8.02 (1H, dd), 7.57 (1H, d), 7.25 (1H, t), 6.89 (1H, d), 6.85 (1H, s), 6.81 (1H, dd), 5.08 (1H, q), 4.75-4.56 (2H, m), 4.54-4.27 (3H, m), 3.95-3.81 (3H, m), 3.77 (3H, s), 3.34-3.10 (1H, m), 3.10-2.68 (3H, m), 2.21-2.01 (5H, m), 1.55-1.22 (2H, m). | 593 |
| 324 | 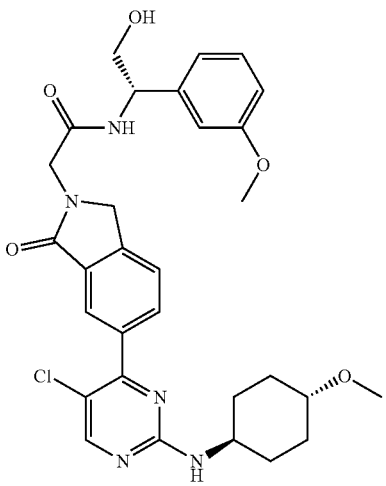 [SMILES: COc1cccc([C@@H](CO)NC(=O)CN2Cc3ccc(-c4nc(N[C@H]5CC[C@H](OC)CC5)ncc4Cl)cc3C2=O)c1] | 2-[6-(5-chloro-2-{[trans-4-methoxycyclohexyl]amino}pyrimidin-4-yl)-1-oxo-2,3-dihydro-1H-isoindol-2-yl]-N-[(1S)-2-hydroxy-1-(3-methoxyphenyl)ethyl]-acetamide | 1H NMR (400 MHz, CDCl3): 8.31 (1H, s), 8.24 (1H, s), 7.97 (1H, d), 7.61 (1H, s), 7.50 (1H, d), 7.20 (1H, t), 6.95-6.83 (2H, m), 6.76 (1H, dd), 5.28 (1H, s), 5.07 (1H, s), 4.74-4.50 (2H, m), 4.50-4.20 (2H, m), 3.99-3.76 (3H, m), 3.73 (3H, s), 3.36 (3H, s), .28-3.09 (1H, m), 2.13 (5H, dd), 1.47-1.26 (4H, m). | 580 |

| Example | Structure | Name | ¹H NMR (400 MHz) | MS: [M + H]⁺ |
|---|---|---|---|---|
| 325 | 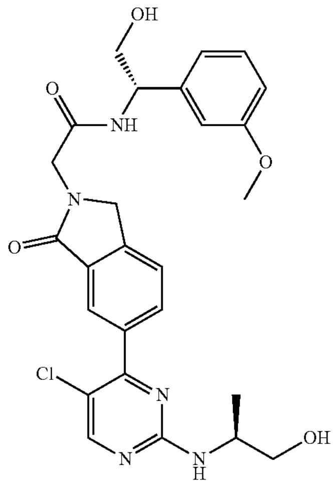 [SMILES: COc1cccc([C@@H](CO)NC(=O)CN2Cc3ccc(-c4nc(N[C@@H](C)CO)ncc4Cl)cc3C2=O)c1] | 2-[6-(5-chloro-2-{[(2S)-1-hydroxypropan-2-yl]amino}pyrimidin-4-yl)-1-oxo-2,3-dihydro-1H-isoindol-2-yl]-N-[(1S)-2-hydroxy-1-(3-methoxyphenyl)ethyl]-acetamide | 1H NMR (400 MHz, CDCl3): 8.29 (1H, s), 8.23 (1H, s), 7.99 (1H, dd), 7.62 (1H, d), 7.50 (1H, d), 7.21 (1H, t), 6.92-6.82 (2H, m), 6.78 (1H, dd), 5.59 (1H, s), 5.11-5.02 (1H, m), 4.75-4.49 (2H, m), 4.48-4.22 (2H, m), 4.23-4.10 (1H, m), 3.92-3.79 (2H, m), 3.77-3.61 (7H, m), 1.27 (3H, d). | 526 |

Examples 326-328

Prepared using a method analogous to Preparation 4 from 2-[6-(2,5-dichloropyrimidin-4-yl)-1-oxo-2,3-dihydro-1H-isoindol-2-yl]-N-[(1S,2S)-2-hydroxy-1-phenylpropyl]acetamide (Preparation 170) with EtOH as solvent.

| Example | Structure | Name | ¹H NMR (400 MHz) | MS: [M + H]⁺ |
|---|---|---|---|---|
| 326 | 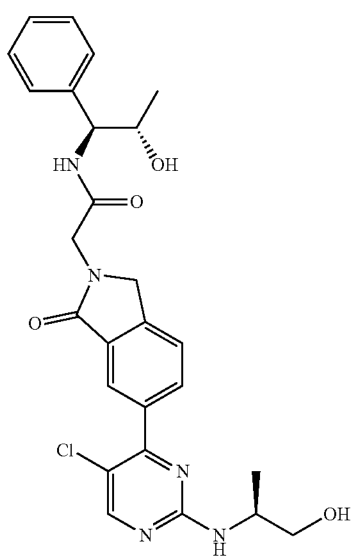 [SMILES: C[C@H](O)[C@@H](NC(=O)CN1Cc2ccc(-c3nc(N[C@@H](C)CO)ncc3Cl)cc2C1=O)c1ccccc1] | 2-[6-(5-chloro-2-{[(2S)-1-hydroxypropan-2-yl]amino}pyrimidin-4-yl)-1-oxo-2,3-dihydro-1H-isoindol-2-yl]-N-[(1S,2S)-2-hydroxy-1-phenylpropyl]-acetamide | 1H NMR (400 MHz, CDCl3): 8.30 (1H, s), 8.27 (1H, s), 8.01 (1H, dd), 7.60-7.40 (2H, m), 7.30-7.28 (4H, m), 7.27-7.18 (1H, m), 5.55 (1H, d), 4.88 (1H, dd), 4.77-4.49 (2H, m), 4.49-4.24 (2H, m), 4.24-4.12 (1H, m), 4.12-4.01 (1H, m), 3.80-3.61 (2H, m), 3.31-3.18 (1H, m), 1.28 (3H, d), 1.18 (3H, d). | 510 |

-continued

| Example | Structure | Name | ¹H NMR (400 MHz) | MS: [M + H]⁺ |
|---|---|---|---|---|
| 327 | 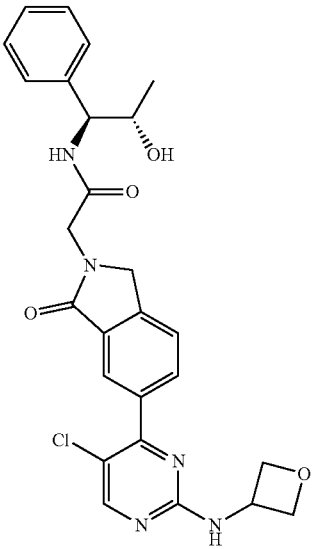 [SMILES: C[C@H](O)[C@@H](NC(=O)CN1Cc2ccc(-c3nc(NC4COC4)ncc3Cl)cc2C1=O)c1ccccc1] | 2-(6-{5-chloro-2-[(oxetan-3-yl)amino]pyrimidin-4-yl}-1-oxo-2,3-dihydro-1H-isoindol-2-yl)-N-[(1S,2S)-2-hydroxy-1-phenylpropyl]-acetamide | 1H NMR (400 MHz, Me-d3-OD): 8.38 (1H, s), 8.24 (1H, s), 8.07 (1H, d), 7.69 (1H, d), 7.43-7.31 (4H, m), 7.31-7.21 (1H, m), 5.13-5.03 (1H, m), 4.95 (2H, t), 4.73-4.57 (4H, m), 4.57-4.29 (2H, m), 4.09-3.99 (1H, m), 3.39-3.34 (1H, m), 1.46-1.19 (1H, m), 1.13 (3H, d). | 508 |
| 328 | 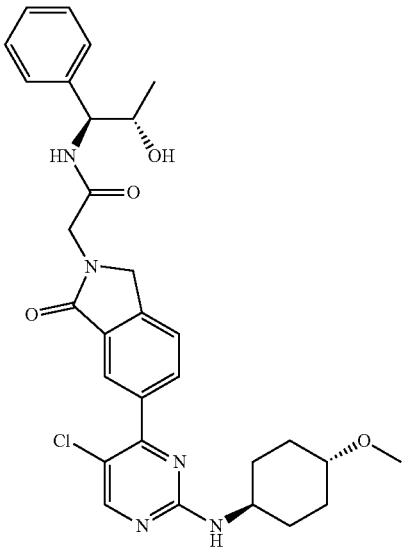 [SMILES: CO[C@H]1CC[C@H](Nc2ncc(Cl)c(-c3ccc4c(c3)C(=O)N(CC(=O)N[C@@H](c3ccccc3)[C@H](C)O)C4)n2)CC1] | 2-[6-(5-chloro-2-{[trans-4-methoxycyclohexyl]-amino}pyrimidin-4-yl)-1-oxo-2,3-dihydro-1H-isoindol-2-yl]-N-[(1S,2S)-2-hydroxy-1-phenylpropyl] acetamide | 1H NMR (400 MHz, Me-d3-OD): 8.34 (1H, s), 8.23 (1H, s), 8.10-8.03 (1H, m), 7.70 (1H, d), 7.43-7.30 (4H, m), 4.66 (2H, s), 4.52-4.36 (2H, m), 4.09-4.00 (1H, m), 3.81 (1H, d), 3.37 (3H, s), 3.32-3.19 (3H, m), 2.18-2.03 (4H, m), 1.46-1.27 (4H, m), 1.12 (3H, d). | 564 |

Example 329: 2-[6-(5-chloro-2-{[trans-4-hydroxy-cyclohexyl]amino}pyrimidin-4-yl)-1-oxo-2,3-dihydro-1H-isoindol-2-yl]-N-[(1R)-1-(3-methoxyphenyl)ethyl]acetamide

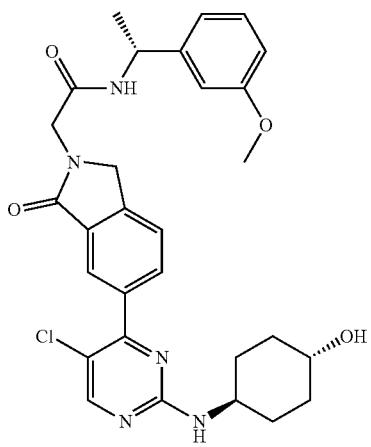 [SMILES: COc1cccc([C@@H](C)NC(=O)CN2Cc3ccc(-c4nc(N[C@H]5CC[C@H](O)CC5)ncc4Cl)cc3C2=O)c1]

Prepared using a method analogous to Preparation 4 from 2-[6-(2,5-dichloropyrimidin-4-yl)-1-oxo-2,3-dihydro-1H-isoindol-2-yl]-N-[(1R)-1-(3-methoxyphenyl)ethyl]acetamide (Preparation 171) with EtOH as solvent. 1H NMR (400 MHz, CDCl3): 8.33 (1H, s), 8.29 (1H, s), 8.02 (1H, d), 7.55 (1H, d), 7.20 (1H, t), 7.03-6.85 (2H, m), 6.82 (1H, s), 6.76 (1H, dd), 5.39 (1H, d), 5.14-5.02 (1H, m), 4.72-4.52 (2H, m), 4.30 (2H, s), 3.94 (2H, d), 3.75 (3H, s), 1.85-1.72 (8H, m), 1.47 (3H, d). MS: [M+H]+=564.

Examples 330 and 331: 6-{5-chloro-2-[(oxan-4-yl)amino]pyridin-4-yl}-2-{2-[(3S)-methyl-1,2,3,4-tetrahydroisoquinolin-2-yl]-2-oxoethyl}-2,3-dihydro-1H-isoindol-1-one and 6-{5-chloro-2-[(oxan-4-yl)amino]pyridin-4-yl}-2-{2-[(3R)-methyl-1,2,3,4-tetrahydroisoquinolin-2-yl]-2-oxoethyl}-2,3-dihydro-1H-isoindol-1-one

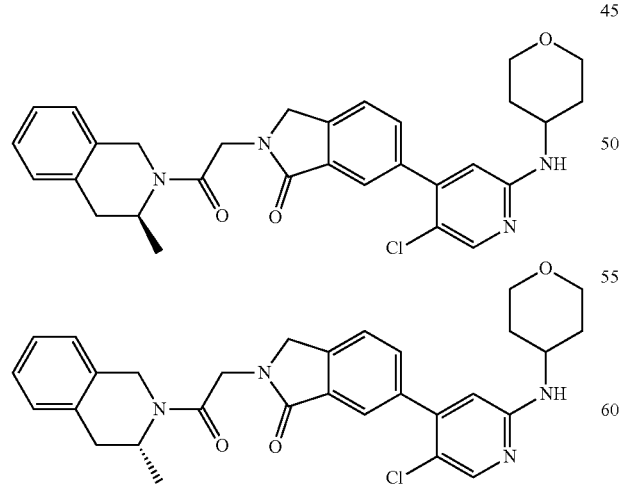

Example 186 (106 mg, 0.20 mmol) was separated using chiral, preparative HPLC to give the two enantiomers as colourless solids.

Example 330 (3 mg) 1H NMR (400 MHz, Me-d3-OD): 8.76 (1H, s), 8.64-8.57 (1H, m), 8.28 (1H, s), 7.68 (1H, d), 7.27-7.20 (4H, m), 5.15-4.98 (1H, m), 4.74-4.64 (6H, m), 4.41-4.28 (1H, m), 4.14-3.92 (2H, m), 3.73-3.63 (2H, m), 3.20-3.05 (1H, m), 2.84-2.69 (1H, m), 2.05 (3H, d), 1.87-1.71 (2H, m), 1.12 (3H, d). MS: [M+H]+=531.

Example 331 (3 mg) 1H NMR (400 MHz, Me-d3-OD): 8.76 (1H, s), 8.67-8.52 (1H, m), 8.32-8.27 (1H, m), 7.69 (1H, d), 7.27-7.20 (4H, m), 5.10-4.97 (1H, m), 4.73-4.66 (6H, m), 4.41-4.27 (1H, m), 4.05 (2H, d), 3.68 (2H, dd), 3.19-3.04 (1H, m), 2.81-2.70 (1H, m), 2.09-1.99 (3H, m), 1.84-1.73 (2H, m), 1.12 (3H, d). MS: [M+H]+=531.

Example 332: 6-(5-chloro-2-{[2-(propan-2-yl)oxan-4-yl]amino}pyrimidin-4-yl)-2-[2-oxo-2-(1,2,3,4-tetrahydroisoquinolin-2-yl)ethyl]-2,3-dihydro-1H-isoindol-1-one

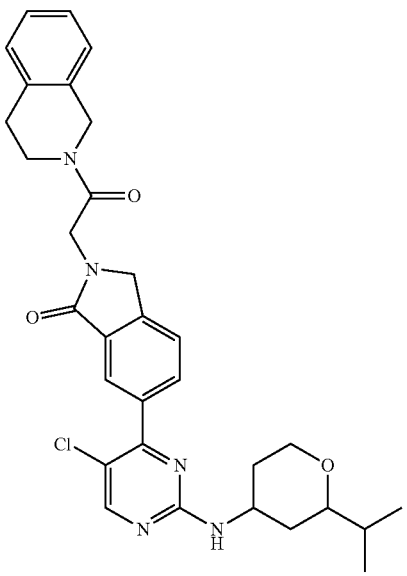 [SMILES: CC(C)C1CC(Nc2ncc(Cl)c(-c3ccc4c(c3)C(=O)N(CC(=O)N3CCc5ccccc5C3)C4)n2)CCO1]

Prepared in an analogous manner to Examples 159-179 using racemic 2-iso-propyloxan-4-amine as a 1:1 mixture of diastereomers. 1H NMR (400 MHz, Me-d3-OD): 8.41-8.30 (1H, m), 8.30-8.15 (1H, m), 8.09 (1H, t), 7.75-7.64 (1H, m), 7.29-7.11 (4H, m), 5.50 (2H, s), 4.71 (2H, d), 4.68 (2H, s), 4.36-4.26 (1H, m), 3.94-3.72 (4H, m), 3.47-3.38 (1H, m), 3.08-2.97 (1H, m), 2.97-2.85 (1H, m), 2.04 (2H, s), 1.96-1.61 (4H, m), 1.07-0.83 (6H, m). MS: [M+H]+=560.

Example 333: 2-(6-{5-bromo-2-[(oxan-4-yl)amino] pyrimidin-4-yl}-1-oxo-2,3-dihydro-1H-isoindol-2-yl)-N-[(1S)-2-hydroxy-1-(3-methoxyphenyl)ethyl] acetamide

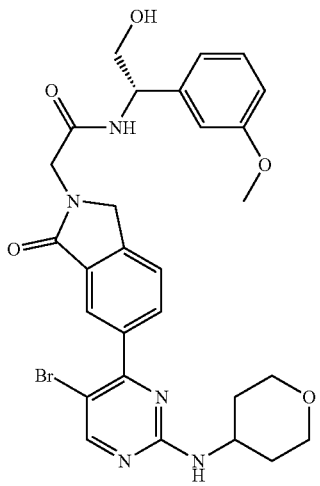 [SMILES: COc1cccc([C@@H](CO)NC(=O)CN2Cc3ccc(-c4nc(NC5CCOCC5)ncc4Br)cc3C2=O)c1]

Prepared from 2-(6-{5-bromo-2-[(oxan-4-yl)amino]pyrimidin-4-yl}-1-oxo-2,3-dihydro-1H-isoindol-2-yl)acetic acid (Preparation 175) and the corresponding amine in a manner analogous to Preparation 2. 1H NMR (400 MHz, CDCl3): 8.44 (1H, s), 8.20 (1H, s), 7.93 (1H, d), 7.58-7.40 (2H, m), 7.21 (1H, t), 6.95-6.83 (2H, m), 6.83-6.72 (1H, m), 5.35 (1H, d), 5.08 (1H, q), 4.77-4.52 (2H, m), 4.52-4.20 (2H, m), 4.20-3.93 (3H, m), 3.93-3.79 (2H, m), 3.74 (3H, s), 3.54 (2H, t), 2.05 (2H, d), 1.67-1.48 (2H, m). MS: [M+H]$^+$=596.

Example 334: 2-(6-{5-bromo-2-[(propan-2-yl) amino]pyrimidin-4-yl}-1-oxo-2,3-dihydro-1H-isoindol-2-yl)-N-[(1S)-2-hydroxy-1-(3-methoxyphenyl) ethyl]acetamide

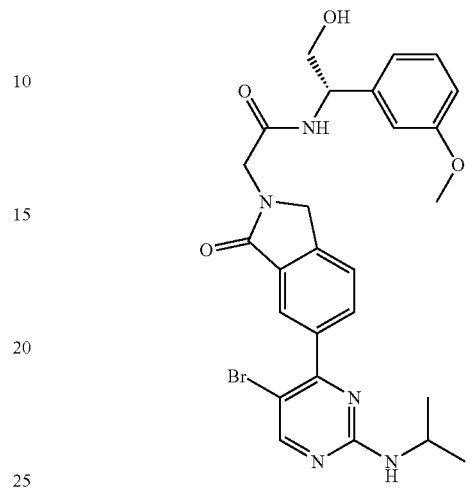

Prepared from 2-[6-(5-bromo-2-chloropyrimidin-4-yl)-1-oxo-2,3-dihydro-1H-isoindol-2-yl]-N-[(1S)-2-hydroxy-1-(3-methoxyphenyl)ethyl]acetamide (Preparation 176) and iso-propylamine in a manner analogous to Preparation 4. 1H NMR (400 MHz, CDCl3): 8.45 (1H, s), 8.29 (1H, s), 8.04-7.92 (1H, m), 7.58 (1H, d), 7.26-7.24 (1H, m), 7.07-6.94 (1H, m), 6.88 (1H, d), 6.86-6.77 (2H, m), 5.13-5.01 (2H, m), 4.73-4.55 (2H, m), 4.35 (2H, d), 4.23-4.12 (1H, m), 3.94-3.84 (2H, m), 3.78 (3H, s), 1.28 (6H, d). MS: [M+H]$^+$=554.

Examples 335 and 336

Prepared in a similar manner to Example 334 from Preparations 177 and 178.

| Example | Structure | Name | $^1$H NMR (400 MHz) | MS: [M + H]$^+$ |
|---|---|---|---|---|
| 335 | 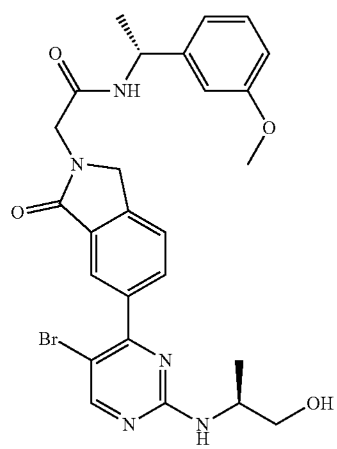 [SMILES: COc1cccc([C@@H](C)NC(=O)CN2Cc3ccc(-c4nc(N[C@@H](C)CO)ncc4Br)cc3C2=O)c1] | 2-[6-(5-bromo-2-{[(2S)-1-hydroxypropan-2-yl]amino}pyrimidin-4-yl)-1-oxo-2,3-dihydro-1H-isoindol-2-yl]-N-[(1R)-1-(3-methoxyphenyl)ethyl]-acetamide | 1H NMR (400 MHz, CDCl3): 8.41 (1H, s), 8.21 (1H, s), 7.95 (1H, dd), 7.53 (1H, d), 7.20 (1H, t), 6.91 (1H, d), 6.87 (1H, d), 6.83 (1H, s), 6.76 (1H, dd), 5.51 (1H, d), 5.14-5.03 (1H, m), 4.68-4.51 (2H, m), 4.29 (2H, s), 4.24-4.10 (1H, m), 3.81-3.62 (5H, m), 1.47 (3H, d), 1.29 (3H, d). | 554 |

| Example | Structure | Name | ¹H NMR (400 MHz) | MS: [M + H]⁺ |
|---|---|---|---|---|
| 336 | 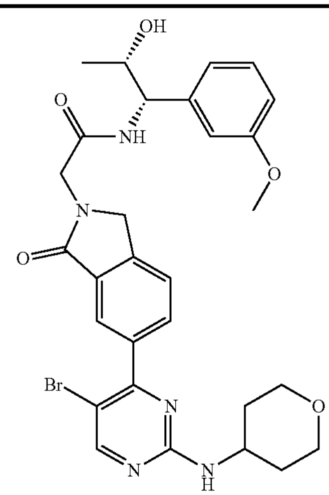 | 2-(6-{5-bromo-2-[(oxan-4-yl)amino]pyrimidin-4-yl}-1-oxo-2,3-dihydro-1H-isoindol-2-yl)-N-[(1S,2S)-2-hydroxy-1-phenylpropyl]-acetamide | 1H NMR (400 MHz, CDCl3): 8.43 (1H, s), 8.21 (1H, s), 7.93 (1H, dd), 7.51 (2H, dd), 7.29 (3H, s), 7.27-7.19 (1H, m), 5.41-5.29 (1H, m), 4.91-4.81 (1H, m), 4.71-4.54 (2H, m), 4.45-4.26 (2H, m), 4.10-4.02 (2H, m), 3.53 (2H, t), 3.42-3.35 (1H, m), 1.76 (2H, dd), 1.63-1.52 (2H, m), 1.42-1.34 (1H, m), 1.18 (4H, d). | 580 |

Example 337: (2R)-2-(6-{5-chloro-2-[(propan-2-yl)amino]pyrimidin-4-yl}-1-oxo-2,3-dihydro-1H-isoindol-2-yl)-3-hydroxy-N-[(1R)-1-(3-methoxyphenyl)ethyl]propanamide

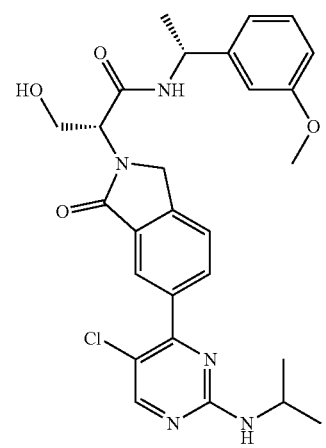 [SMILES: COc1cccc([C@@H](C)NC(=O)[C@@H](CO)N2Cc3ccc(-c4nc(NC(C)C)ncc4Cl)cc3C2=O)c1]

A stirred solution of methyl 2-(bromomethyl)-5-(2,5-dichloropyrimidin-4-yl)benzoate (Preparation 180, 100 mg, 0.27 mmol), (2R)-2-amino-3-hydroxy-N-[(1R)-1-(3-methoxyphenyl)ethyl]propanamide (Preparation 182, 95 mg, 0.4 mmol) and DIPEA (0.09 mL, 0.5 mmol) in MeCN (3 mL) was heated to 90° C. for 3 hours. iso-Propylamine (0.1 mL, 1.17 mmol) was added and heating continued overnight. The reaction was concentrated and partitioned between water (10 mL) and EtOAc (10 mL). The aqueous fraction was further extracted with EtOAc (2×10 mL) and the combined organic fractions were dried over magnesium sulfate, filtered and concentrated. The residue was purified by reverse phase column chromatography (20-60% MeCN in water) to give the title compound (52 mg, 37%). 1H NMR (400 MHz, CDCl3): 8.38-8.25 (2H, m), 8.05 (1H, d), 7.61-7.52 (1H, m), 7.26 (1H, d), 7.20 (1H, d), 6.91 (1H, d), 6.87 (1H, d), 6.81 (1H, dd), 5.12 (1H, d), 5.09-5.00 (1H, m), 4.92 (1H, t), 4.85-4.72 (2H, m), 4.27-4.12 (2H, m), 4.06 (1H, d), 3.80 (4H, d), 1.44 (3H, d), 1.28 (6H, d). MS: [M+H]⁺= 524

Examples 338-343

The following compounds were made from methyl 2-(bromomethyl)-5-(2,5-dichloropyrimidin-4-yl)benzoate (Preparation 180) in a similar way to example 337 using the appropriate amine (Preparations 183-187) and oxan-4-amine.

| Example | Structure | Name | ¹H NMR (400 MHz) | MS: [M + H]⁺ |
|---|---|---|---|---|
| 338 | 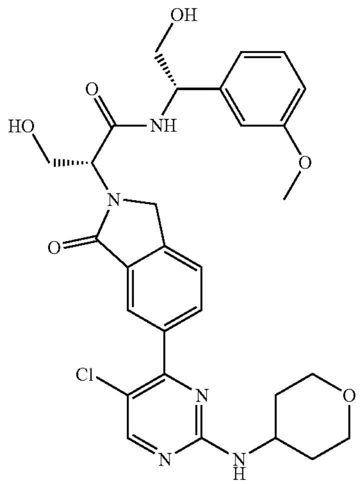 [SMILES: COc1cccc([C@@H](CO)NC(=O)[C@@H](CO)N2Cc3ccc(-c4nc(NC5CCOCC5)ncc4Cl)cc3C2=O)c1] | (2R)-2-(6-{5-chloro-2-[(oxan-4-yl)amino]pyrimidin-4-yl}-1-oxo-2,3-dihydro-1H-isoindol-2-yl)-3-hydroxy-N-[(1S)-2-hydroxy-1-(3-methoxyphenyl)ethyl]-propanamide | 1H NMR (400 MHz, Me-d3-OD): 8.35 (1H, s), 8.31-8.21 (1H, m), 8.12-8.02 (1H, m), 7.75-7.66 (1H, m), 7.26 (1H, t), 7.00-6.88 (2H, m), 6.88-6.81 (1H, m), 5.11 (1H, dd), 5.00 (1H, dd), 4.89 (1H, d), 4.78-4.72 (1H, m), 4.18-4.02 (3H, m), 3.98 (2H, d), 3.89-3.79 (3H, m), 3.79-3.70 (2H, m), 3.54 (2H, dd), 2.02 (2H, d), 1.71-1.55 (2H, m). | 582 |
| 339 | 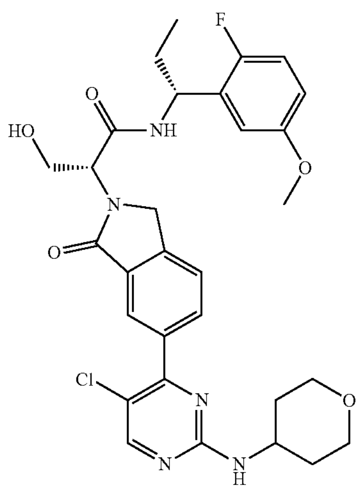 [SMILES: CC[C@@H](NC(=O)[C@@H](CO)N1Cc2ccc(-c3nc(NC4CCOCC4)ncc3Cl)cc2C1=O)c1cc(OC)ccc1F] | (2R)-2-(6-{5-chloro-2-[(oxan-4-yl)amino]pyrimidin-4-yl}-1-oxo-2,3-dihydro-1H-isoindol-2-yl)-N-[(1R)-1-(2-fluoro-5-methoxyphenyl)-propyl]-3-hydroxypropanamide | 1H NMR (400 MHz, Me-d3-OD): 8.49-828 (1H, m), 8.28-8.14 (1H, m), 8.07 (1H, d), 7.71 (1H, d), 7.00 (1H, t), 6.96-6.88 (1H, m), 6.86-6.76 (1H, m), 5.09 (1H, t), 5.06-5.01 (1H, m), 4.18-3.90 (7H, m), 3.79 (3H, s), 3.54 (2H, t), 3.43 (1H, t), 2.09-1.94 (2H, m), 1.86-1.79 (2H, m), 1.75-1.54 (2H, m), 1.53-1.39 (1H, m), 1.01-0.81 (3H, m). | 598 |
| 340 | 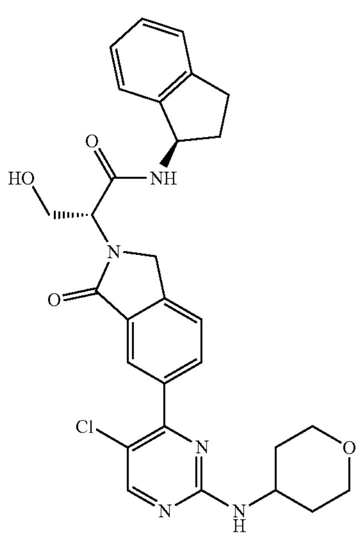 [SMILES: O=C(N[C@@H]1CCc2ccccc21)[C@@H](CO)N1Cc2ccc(-c3nc(NC4CCOCC4)ncc3Cl)cc2C1=O] | (2R)-2-(6-{5-chloro-2-[(oxan-4-yl)amino]pyrimidin-4-yl}-1-oxo-2,3-dihydro-1H-isoindol-2-yl)-N-[(1R)-2,3-dihydro-1H-inden-1-yl]-3-hydroxypropanamide | 1H NMR (400 MHz, CDCl3): 8.35-8.29 (1H, m), 8.15 (1H, s), 8.02-7.94 (1H, m), 7.59-7.51 (1H, m), 7.28-7.22 (1H, m), 7.22-7.14 (3H, m), 5.50-5.30 (2H, m), 5.07-4.99 (1H, m), 4.77 (2H, s), 4.30-4.16 (1H, m), 4.16-4.04 (2H, m), 4.00 (2H, d), 3.54 (2H, t), 3.07-2.89 (1H, m), 2.89-2.75 (1H, m), 2.63-2.46 (1H, m), 2.09-2.01 (2H, m), 1.83-1.72 (1H, m), 1.69-1.50 (2H, m). | 548 |

| Example | Structure | Name | ¹H NMR (400 MHz) | MS: [M + H]⁺ |
|---|---|---|---|---|
| 341 | 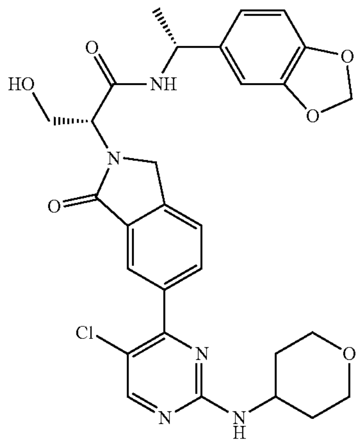 [SMILES: C[C@@H](NC(=O)[C@@H](CO)N1Cc2ccc(-c3nc(NC4CCOCC4)ncc3Cl)cc2C1=O)c1ccc2c(c1)OCO2] | (2R)-N-[(1R)-1-(2H-1,3-benzodioxol-5-yl)ethyl]-2-(6-{5-chloro-2-[(oxan-4-yl)amino]pyrimidin-4-yl}-1-oxo-2,3-dihydro-1H-isoindol-2-yl)-3-hydroxypropanamide | 1H NMR (400 MHz, CDCl3): 8.35 (1H, s), 8.32 (1H, s), 8.06 (1H, d), 7.65 (1H, d), 6.95 (1H, d), 6.79 (3H, d), 5.96 (2H, s), 5.07-4.93 (1H, m), 4.89 (1H, d), 4.88-4.66 (2H, m), 4.27 (1H, dd), 4.21-4.10 (1H, m), 4.10-3.94 (3H, m), 3.62-3.48 (2H, m), 1.69 (2H, d), 1.42 (3H, d) 0.96-0.79 (2H, m). | 580 |
| 342 | 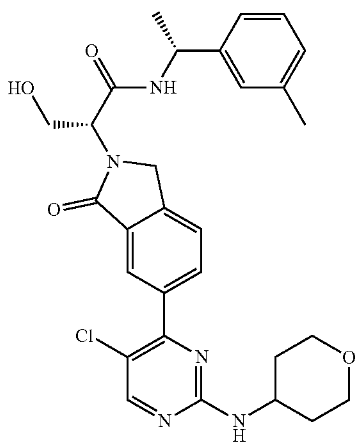 [SMILES: Cc1cccc([C@@H](C)NC(=O)[C@@H](CO)N2Cc3ccc(-c4nc(NC5CCOCC5)ncc4Cl)cc3C2=O)c1] | (2R)-2-(6-{5-chloro-2-[(oxan-4-yl)amino]pyrimidin-4-yl}-1-oxo-2,3-dihydro-1H-isoindol-2-yl)-3-hydroxy-N-[(1R)-1-(3-methylphenyl)ethyl]-propanamide | 1H NMR (400 MHz, CDCl3): 8.38-8.33 (1H, m), 8.30 (1H, s), 8.03 (1H, dd), 7.59 (1H, d), 7.27-7.20 (1H, m), 7.17-7.06 (4H, m), 5.24 (1H, d), 5.10-4.99 (1H, m), 4.99-4.89 (1H, m), 4.87-4.66 (2H, m), 4.23 (1H, dd), 4.14-3.95 (4H, m), 3.62-3.51 (2H, m), 2.35 (3H, s), 2.13-2.04 (2H, m), 1.63-1.54 (2H, m), 1.44 (3H, d). | 550 |
| 343 | 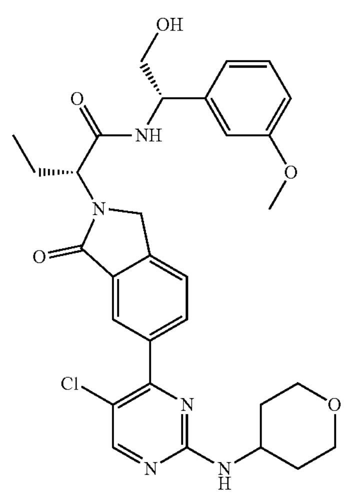 [SMILES: CC[C@H](C(=O)N[C@H](CO)c1cccc(OC)c1)N1Cc2ccc(-c3nc(NC4CCOCC4)ncc3Cl)cc2C1=O] | (2R)-2-(6-{5-chloro-2-[(oxan-4-yl)amino]pyrimidin-4-yl}-1-oxo-2,3-dihydro-1H-isoindol-2-yl)-N-[(1S)-2-hydroxy-1-(3-methoxyphenyl)ethyl]-butanamide | 1H NMR (400 MHz, Me-d3-OD): 8.35 (1H, s), 8.22 (1H, s), 8.08 (1H, dd), 7.72 (1H, d), 7.31-7.21 (1H, m), 6.98-6.88 (2H, m), 6.84 (1H, dd), 5.14-5.10 (1H, m), 4.97 (1H, t), 4.86 (1H, d), 4.70 (1H, d), 4.12-4.01 (1H, m), 4.01-3.90 (2H, m), 3.82 (3H, s), 3.79-3.66 (2H, m), 3.60-3.52 (2H, m), 2.01 (2H, d), 1.70-1.52 (4H, m), 1.14 (3H, t). | 566 |

Examples 344-367

The following were prepared in an analogous manner to Preparation 4 using the appropriate dichloropyrimidine (Preparations 207-224, 227) and the corresponding amine with EtOH as solvent.

| Example | Structure | Name | ¹H NMR (400 MHz) | MS: [M + H]⁺ |
|---|---|---|---|---|
| 344 | 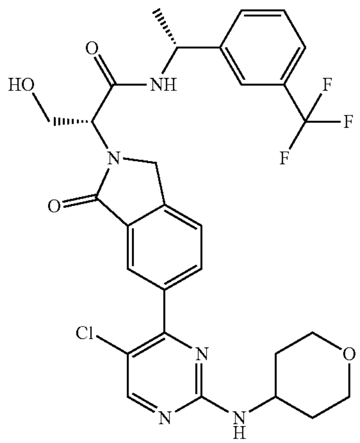 [SMILES: C[C@@H](NC(=O)[C@@H](CO)N1Cc2ccc(-c3nc(NC4CCOCC4)ncc3Cl)cc2C1=O)c1cccc(C(F)(F)F)c1] | (2R)-2-(6-{5-chloro-2-[(oxan-4-yl)amino]pyrimidin-4-yl}-1-oxo-2,3-dihydro-1H-isoindol-2-yl)-3-hydroxy-N-[(1R)-1-[3-(trifluoromethyl)phenyl]ethyl]propanamide | 1H NMR (400 MHz, CDCl3): 8.31 (1H, s), 8.18 (1H, s), 7.96 (1H, d), 7.89 (1H, d), 7.59 (1H, s), 7.56-7.46 (3H, m), 7.42 (1H, t), 5.46 (1H, d), 5.17-5.03 (2H, m), 4.87-4.64 (2H, m), 4.64-4.64 (1H, m), 4.09-3.94 (5H, m), 3.53 (2H, t), 2.04 (2H, d), 1.57 (2H, dd), 1.48 (3H, d). | 604 |
| 345 | 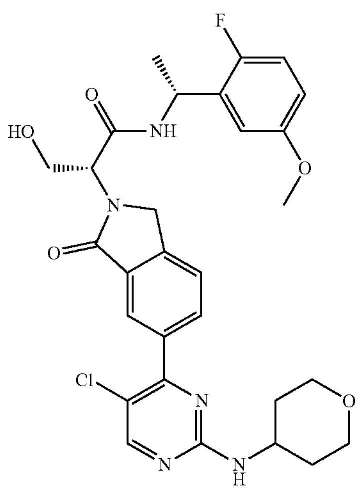 [SMILES: COc1ccc(F)c([C@@H](C)NC(=O)[C@@H](CO)N2Cc3ccc(-c4nc(NC5CCOCC5)ncc4Cl)cc3C2=O)c1] | (2R)-2-(6-{5-chloro-2-[(oxan-4-yl)amino]pyrimidin-4-yl}-1-oxo-2,3-dihydro-1H-isoindol-2-yl)-N-[(1R)-1-(2-fluoro-5-methoxyphenyl)ethyl]-3-hydroxypropanamide | 1H NMR (400 MHz, CDCl3): 8.36 (1H, s), 8.33 (1H, s), 8.04 (1H, dd), 7.59 (1H, d), 7.21 (1H, d), 6.98 (1H, t), 6.82 (1H, dd), 6.79-6.72 (1H, m), 5.26-5.16 (2H, m), 4.90 (1H, t), 4.87-4.67 (2H, m), 4.26 (1H, dd), 4.12-3.95 (5H, m), 3.79 (3H, s), 3.62-3.51 (2H, m), 2.08 (2H, d), 1.65-1.58 (2H, m), 1.46 (3H, d). | 584 |
| 346 | 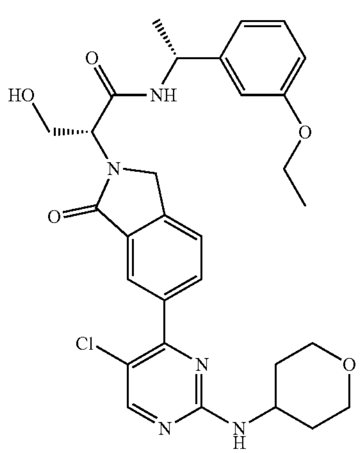 [SMILES: CCOc1cccc([C@@H](C)NC(=O)[C@@H](CO)N2Cc3ccc(-c4nc(NC5CCOCC5)ncc4Cl)cc3C2=O)c1] | (2R)-2-(6-{5-chloro-2-[(oxan-4-yl)amino]pyrimidin-4-yl}-1-oxo-2,3-dihydro-1H-isoindol-2-yl)-N-[(1R)-1-(3-ethoxyphenyl)ethyl]-3-hydroxypropanamide | 1H NMR (400 MHz, CDCl3): 8.34 (1H, s), 8.27 (1H, s), 8.01 (1H, dd), 7.56 (1H, d), 7.29 (1H, d), 7.23 (1H, t), 6.89 (1H, d), 6.86 (1H, d), 6.78 (1H, dd), 5.37-5.22 (1H, m), 5.09-5.00 (1H, m), 5.00-4.92 (1H, m), 4.83-4.70 (2H, m), 4.19 (1H, dd), 4.16-3.97 (7H, m), 3.56 (2H, t), 2.09-2.04 (2H, m), 1.66-1.52 (2H, m), 1.44 (3H, d), 1.40 (3H, t). | 580 |

-continued

| Example | Structure | Name | ¹H NMR (400 MHz) | MS: [M + H]⁺ |
|---|---|---|---|---|
| 347 | 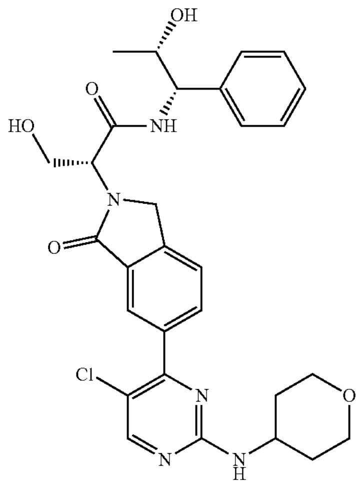 [SMILES: C[C@H](O)[C@@H](NC(=O)[C@@H](CO)N1Cc2ccc(-c3nc(NC4CCOCC4)ncc3Cl)cc2C1=O)c1ccccc1] | (2R)-2-(6-{5-chloro-2-[(oxan-4-yl)amino]pyrimidin-4-yl}-1-oxo-2,3-dihydro-1H-isoindol-2-yl)-3-hydroxy-N-[(1S,2S)-2-hydroxy-1-phenylpropyl]-propanamide | 1H NMR (400 MHz, CDCl3): 8.32 (1H, s), 8.22 (1H, s), 8.03 (1H, d), 7.97 (1H, dd), 7.50 (1H, d), 7.36-7.30 (3H, m), 7.27-7.20 (1H, m), 5.45 (1H, s), 5.21-5.11 (1H, m), 4.92-4.66 (3H, m), 4.17-3.92 (7H, m), 3.54 (2H, t), 2.04 (2H, d), 1.66-1.47 (2H, m), 1.45-1.22 (1H, m), 1.10 (3H, d). | 566 |
| 348 | 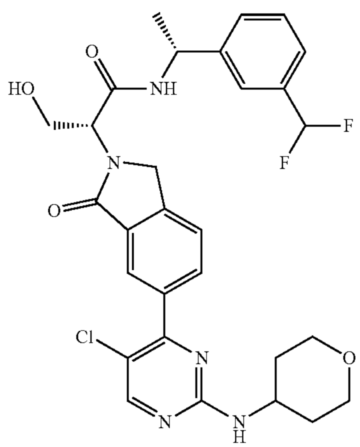 [SMILES: C[C@@H](NC(=O)[C@@H](CO)N1Cc2ccc(-c3nc(NC4CCOCC4)ncc3Cl)cc2C1=O)c1cccc(C(F)F)c1] | (2R)-2-(6-{5-chloro-2-[(oxan-4-yl)amino]pyrimidin-4-yl}-1-oxo-2,3-dihydro-1H-isoindol-2-yl)-N-[(1R)-1-[3-(difluoromethyl)-phenyl]ethyl]-3-hydroxypropanamide | 1H NMR (400 MHz, CDCl3): 8.34 (1H, s), 8.25 (1H, s), 8.00 (1H, dd), 7.55 (2H, d), 7.49-7.38 (4H, m), 6.63 (1H, t), 5.32 (1H, d), 5.15-5.04 (1H, m), 5.00 (1H, t), 4.76 (2H, s), 4.17 (1H, dd), 4.13-3.94 (5H, m), 3.60-3.50 (2H, m), 2.06 (2H, d), 1.66-1.51 (2H, m), 1.48 (3H, d). | 586 |
| 349 | 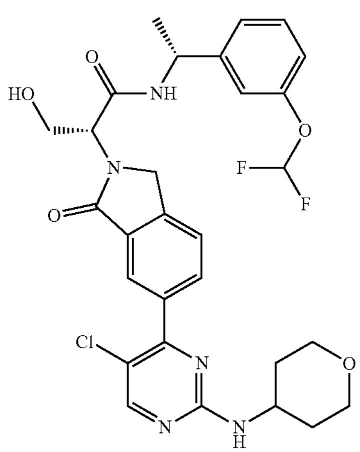 [SMILES: C[C@@H](NC(=O)[C@@H](CO)N1Cc2ccc(-c3nc(NC4CCOCC4)ncc3Cl)cc2C1=O)c1cccc(OC(F)F)c1] | (2R)-2-(6-{5-chloro-2-[(oxan-4-yl)amino]pyrimidin-4-yl}-1-oxo-2,3-dihydro-1H-isoindol-2-yl)-N-[(1R)-1-[3-(difluoromethoxy)-phenyl]ethyl]-3-hydroxypropanamide | 1H NMR (400 MHz, CDCl3): 8.35 (1H, s), 8.28 (1H, s), 8.02 (1H, dd), 7.57 (1H, d), 7.38 (1H, d), 7.33 (1H, t), 7.18 (1H, d), 7.09 (1H, s), 7.02 (1H, d), 6.53 (1H, t), 5.26 (1H, d), 5.11-5.01 (1H, m), 4.95 (1H, t), 4.84-4.69 (2H, m), 4.22 (1H, dd), 4.11-3.98 (4H, m), 3.61-3.51 (2H, m), 2.14-2.03 (2H, m), 1.63-1.57 (2H, m), 1.46 (3H, d). | 602 |

| Example | Structure | Name | ¹H NMR (400 MHz) | MS: [M + H]⁺ |
|---|---|---|---|---|
| 350 | 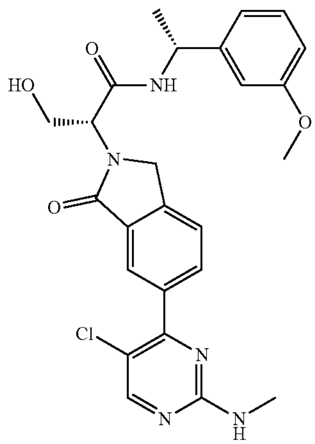 | (2R)-2-{6-[5-chloro-2-(methylamino)-pyrimidin-4-yl]-1-oxo-2,3-dihydro-1H-isoindol-2-yl}-3-hydroxy-N-[(1R)-1-(3-methoxyphenyl)ethyl]-propanamide | 1H NMR (400 MHz, CDCl3): 8.35 (1H, s), 8.29 (1H, s), 8.04 (1H, d), 7.55 (1H, d), 7.32 (1H, d), 7.26 (1H, t), 6.92 (1H, d), 6.88 (1H, d), 6.80 (1H, dd), 5.31 (1H, s), 5.10-4.99 (1H, m), 4.96 (1H, t), 4.83-4.69 (2H, m), 4.21 (1H, dd), 4.05 (1H, dd), 3.80 (3H, s), 3.05 (3H, d), 1.45 (3H, d). | 496 |
| 351 | 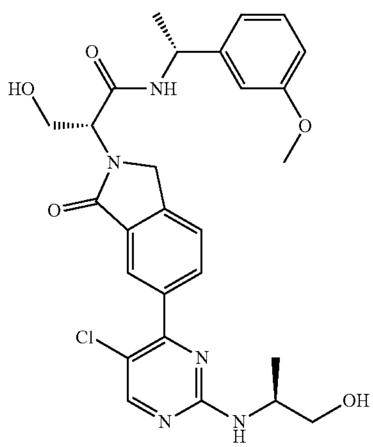 [SMILES: COc1cccc([C@@H](C)NC(=O)[C@@H](CO)N2Cc3ccc(-c4nc(N[C@@H](C)CO)ncc4Cl)cc3C2=O)c1] | (2R)-2-[6-(5-chloro-2-{[(2S)-1-hydroxypropan-2-yl]amino}pyrimidin-4-yl)-1-oxo-2,3-dihydro-1H-isoindol-2-yl]-3-hydroxy-N-[(1R)-1-(3-methoxyphenyl)ethyl]-propanamide | 1H NMR (400 MHz, CDCl3): 8.31 (1H, s), 8.28-8.20 (1H, m), 8.00 (1H, dd), 7.50 (1H, d), 7.27-7.19 (1H, m), 7.08 (1H, t), 6.76 (1H, d), 6.73-6.64 (2H, m), 5.46 (1H, d), 5.11-5.01 (1H, m), 5.01-4.92 (1H, m), 4.79-4.68 (1H, m), 4.51 (1H, d), 4.28-4.14 (2H, m), 4.06 (1H, dd), 3.82-3.75 (1H, m), 3.68 (1H, dd), 3.62 (3H, s), 1.48 (3H, d), 1.30 (4H, d). | 540 |
| 352 | 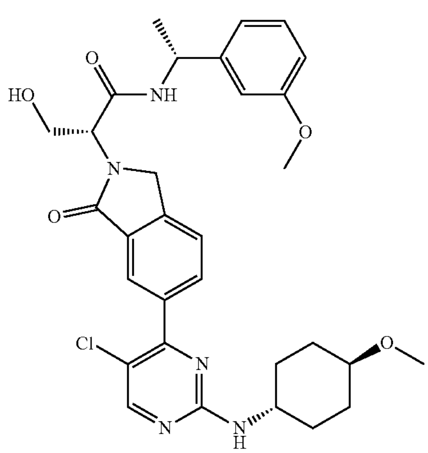 [SMILES: COc1cccc([C@@H](C)NC(=O)[C@@H](CO)N2Cc3ccc(-c4nc(N[C@H]5CC[C@H](OC)CC5)ncc4Cl)cc3C2=O)c1] | (2R)-2-[6-(5-chloro-2-{[trans-4-methoxycyclohexyl]-amino}pyrimidin-4-yl)-1-oxo-2,3-dihydro-1H-isoindol-2-yl]-3-hydroxy-N-[(1R)-1-(3-methoxyphenyl)ethyl]-propanamide | 1H NMR (400 MHz, CDCl3): 8.33 (1H, s), 8.27 (1H, d), 8.01 (1H, t), 7.52 (1H, d), 7.18 (1H, d), 7.13-7.03 (1H, m), 6.74 (1H, d), 6.72-6.66 (2H, m), 5.17 (1H, d), 5.10-5.00 (1H, m), 4.97 (1H, t), 4.78-4.71 (1H, m), 4.51 (1H, d), 4.24 (1H, dd), 4.06 (1H, dd), 3.91-3.82 (1H, m), 3.38 (3H, s), 3.36 (2H s), 3.26-3.17 (1H, m), 3.17-3.08 (1H, m), 2.76-2.66 (1H, m), 2.19 (2H, d), 2.14-2.03 (4H, m), 1.89 (2H, d), 1.49 (3H, d). | 594 |

-continued

| Example | Structure | Name | ¹H NMR (400 MHz) | MS: [M + H]⁺ |
|---|---|---|---|---|
| 353 | 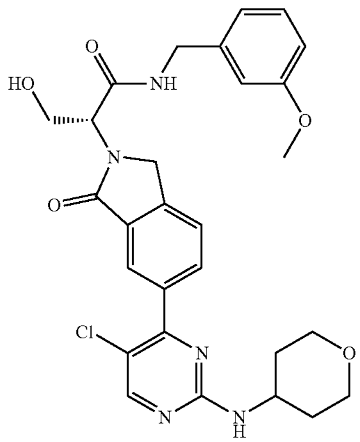 [SMILES: COc1cccc(CNC(=O)[C@@H](CO)N2Cc3ccc(-c4nc(NC5CCOCC5)ncc4Cl)cc3C2=O)c1] | (2R)-2-(6-{5-chloro-2-[(oxan-4-yl)amino]pyrimidin-4-yl}-1-oxo-2,3-dihydro-1H-isoindol-2-yl)-3-hydroxy-N-[(3-methoxyphenyl)methyl]propanamide | 1H NMR (400 MHz, DMSO-d6): 8.43 (1H, s), 8.05 (1H, s), 7.98 (1H, dd), 7.76 (1H, d), 7.24-7.17 (1H, m), 6.84-6.80 (2H, m), 6.78 (1H, dd), 4.90 (1H, dd), 4.77 (1H, d), 4.70 (1H, d), 4.27 (2H, s), 3.98-3.91 (3H, m), 3.87 (2H, d), 3.72 (3H, s), 3.43-3.32 (3H, m), 1.85 (2H, d), 1.61-1.47 (2H, m). | 552 |
| 354 | 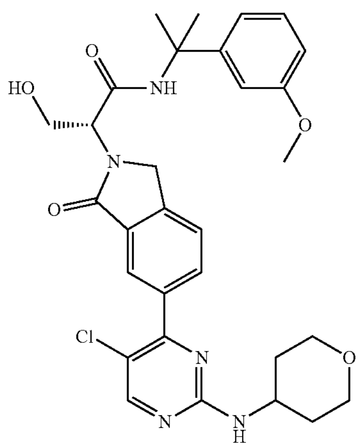 [SMILES: COc1cccc(C(C)(C)NC(=O)[C@@H](CO)N2Cc3ccc(-c4nc(NC5CCOCC5)ncc4Cl)cc3C2=O)c1] | (2R)-2-(6-{5-chloro-2-[(oxan-4-yl)amino]pyrimidin-4-yl}-1-oxo-2,3-dihydro-1H-isoindol-2-yl)-3-hydroxy-N-[2-(3-methoxyphenyl)-propan-2-yl]propanamide | 1H NMR (400 MHz, CDCl3): 8.35 (2H, d), 8.05 (1H, d), 7.59 (1H, d), 7.17 (1H, s), 7.13 (1H, d), 6.86 (1H, d), 6.82 (1H, s), 6.73 (1H, dd), 5.24 (1H, d), 4.97-4.87 (1H, m), 4.78 (1H, d), 4.63 (1H, d), 4.21 (1H, dd), 4.03 (3H, d), 3.90-3.74 (1H, m), 3.69 (3H, s), 3.57 (2H, t), 2.13-1.96 (2H, m), 1.70 (6H, s), 1.62-1.54 (2H, m). | 580 |
| 355 | 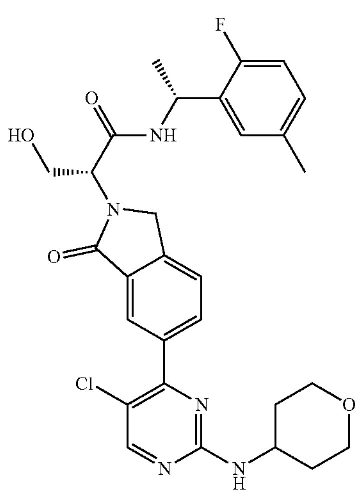 [SMILES: Cc1ccc(F)c([C@@H](C)NC(=O)[C@@H](CO)N2Cc3ccc(-c4nc(NC5CCOCC5)ncc4Cl)cc3C2=O)c1] | (2R)-2-(6-{5-chloro-2-[(oxan-4-yl)amino]pyrimidin-4-yl}-1-oxo-2,3-dihydro-1H-isoindol-2-yl)-N-[(1R)-1-(2-fluoro-5-methylphenyl)ethyl]-3-hydroxypropanamide | 1H NMR (400 MHz, CDCl3): 8.35 (1H, s), 8.33 (1H, s), 8.04 (1H, dd), 7.60 (1H, d), 7.20 (1H, d), 7.08 (1H, d), 7.06-7.00 (1H, m), 6.93 (1H, dd), 5.29-5.14 (2H, m), 4.91(1H, t), 4.86-4.67 (2H, m), 4.24 (1H, dd), 4.14-3.98 (4H, m), 3.63-3.51 (2H, m), 2.31 (3H, s), 2.07 (2H, d), 1.61-1.54 (2H, m), 1.45 (3H, d). | 568 |

-continued

| Example | Structure | Name | ¹H NMR (400 MHz) | MS: [M + H]⁺ |
|---|---|---|---|---|
| 356 | 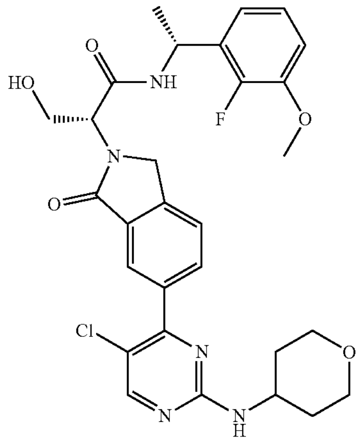 [SMILES: COc1cccc([C@@H](C)NC(=O)[C@@H](CO)N2Cc3ccc(-c4nc(NC5CCOCC5)ncc4Cl)cc3C2=O)c1F] | (2R)-2-(6-{5-chloro-2-[(oxan-4-yl)amino]pyrimidin-4-yl}-1-oxo-2,3-dihydro-1H-isoindol-2-yl)-N-[(1R)-1-(2-fluoro-3-methoxyphenyl)ethyl]-3-hydroxypropanamide | 1H NMR (400 MHz, CDCl3): 8.34 (1H, s), 8.30 (1H, s), 8.02 (1H, dd), 7.58 (1H, d), 7.34 (1H, d), 7.11-6.99 (1H, m), 6.93-6.81 (2H, m), 5.33-5.20 (2H, m), 4.96 (1H, t), 4.84-4.70 (2H, m), 4.20 (1H, dd), 4.15-3.94 (4H, m), 3.88 (3H, s), 3.64-3.48 (2H, m), 2.07 (2H, d), 1.67-1.50 (2H, m), 1.46 (3H, d). | 584 |
| 357 | 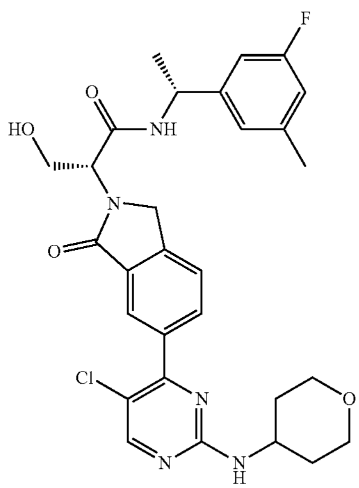 [SMILES: Cc1cc(F)cc([C@@H](C)NC(=O)[C@@H](CO)N2Cc3ccc(-c4nc(NC5CCOCC5)ncc4Cl)cc3C2=O)c1] | (2R)-2-(6-{5-chloro-2-[(oxan-4-yl)amino]pyrimidin-4-yl}-1-oxo-2,3-dihydro-1H-isoindol-2-yl)-N-[(1R)-1-(3-fluoro-5-methylphenyl)ethyl]-3-hydroxypropanamide | 1H NMR (400 MHz, CDCl3): 8.36 (1H, s), 8.33 (1H, s), 8.05 (1H, dd), 7.61 (1H, d), 7.14 (1H, d), 6.90 (1H, s), 6.81 (2H, t), 5.20 (1H, d), 5.08-4.95 (1H, m), 4.90 (1H, t), 4.88-4.61 (2H, m), 4.35-4.21 (1H, m), 4.11-3.98 (4H, m), 3.69 (1H, s), 3.63-3.50 (2H, m), 2.35 (3H, s), 2.11-2.06 (2H, m), 1.60-1.53 (2H, m), 1.42 (3H, d). | 568 |
| 358 | 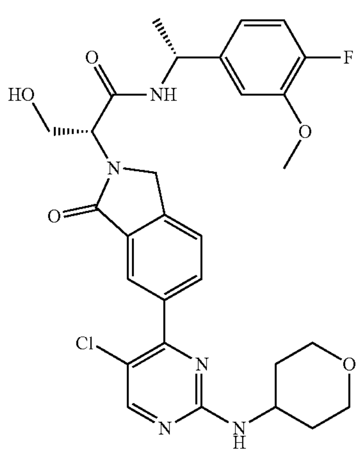 [SMILES: COc1cc([C@@H](C)NC(=O)[C@@H](CO)N2Cc3ccc(-c4nc(NC5CCOCC5)ncc4Cl)cc3C2=O)ccc1F] | (2R)-2-(6-{5-chloro-2-[(oxan-4-yl)amino]pyrimidin-4-yl}-1-oxo-2,3-dihydro-1H-isoindol-2-yl)-N-[(1R)-1-(4-fluoro-3-methoxyphenyl)ethyl]-3-hydroxypropanamide | 1H NMR (400 MHz, CDCl3): 8.35 (1H, s), 8.31 (1H, s), 8.04 (1H, dd), 7.60 (1H, d), 7.24 (1H, d), 7.04 (1H, dd), 6.93 (1H, dd), 6.88-6.79 (1H, m), 5.23 (1H, d), 5.09-4.97 (1H, m), 4.89 (1H, t), 4.86-4.77 (2H, m), 4.28-4.19 (1H, m), 4.11-3.98 (5H, m), 3.90 (3H, s), 3.62-3.49 (2H, m), 2.07 (2H, d), 1.62-1.54 (2H, m), 1.44 (3H, d). | 584 |

-continued

| Example | Structure | Name | ¹H NMR (400 MHz) | MS: [M + H]⁺ |
|---------|-----------|------|------------------|--------------|
| 359 | | (2R)-2-(6-{5-chloro-2-[(oxan-4-yl)amino]pyrimidin-4-yl}-1-oxo-2,3-dihydro-1H-isoindol-2-yl)-N-[(1R)-1-(3-fluoro-5-methoxyphenyl)ethyl]-hydroxypropanamide | 1H NMR (400 MHz, CDCl3): 8.36 (1H, s), 8.32 (1H, s), 8.04 (1H, dd), 7.60 (1H, d), 7.16 (1H, d), 6.71-6.58 (2H, m), 6.57-6.44 (1H, m), 5.20 (1H, d), 5.06-4.95 (1H, m), 4.90 (1H, t), 4.87-4.65 (2H, m), 4.35-4.21 (1H, m), 4.11-3.97 (4H, m), 3.80 (3H, s), 3.74-3.64 (1H, m), 3.62-3.49 (2H, m), 2.11-2.06 (2H, m), 1.43(3H, d). | 584 |
| 360 | | (2R)-2-(6-{5-chloro-2-[(oxan-4-yl)amino]pyrimidin-4-yl}-1-oxo-2,3-dihydro-1H-isoindol-2-yl)-3-hydroxy-N-[(1R)-1-(6-methylpyridin-2-yl)ethyl]propanamide | 1H NMR (400 MHz, Me-d3-OD): 8.35 (1H, s), 8.26 (1H, s), 8.08 (1H, dd), 7.72 (1H, d), 7.67 (1H, t), 7.22 (1H, d), 7.14 (1H, d), 5.11-4.99 (2H, m), 4.87 (1H, d), 4.80-4.75 (1H, m), 4.18-4.02 (3H, m), 3.98 (2H, d), 3.59-3.48 (2H, m), 2.47 (3H, s), 2.01 (2H, d), 1.70-1.55 (2H, m), 1.48 (3H, d). | 551 |
| 361 | | (2R)-2-(6-{5-chloro-2-[(oxan-4-yl)amino]pyrimidin-4-yl}-1-oxo-2,3-dihydro-1H-isoindol-2-yl)-3-hydroxy-N-[(1R)-1-(6-methoxypyridin-2-yl)ethyl]propanamide | 1H NMR (400 MHz, CDCl3): 8.36 (1H, s), 8.32 (1H, s), 7.69 (1H, d), 7.61 (1H, d), 7.54 (1H, dd), 6.79 (1H, d), 6.61 (1H, d), 5.23 (1H, d), 5.12-5.00 (2H, m), 4.88-4.66 (2H, m), 4.31 (1H, dd), 4.15-4.06 (2H, m), 4.05-3.97 (2H, m), 3.73 (3H, s), 3.61-3.52 (2H, m), 2.08 (2H, d), 1.62-1.55 (2H, m), 1.43 (3H, d). | 567 |

| Example | Structure | Name | $^1$H NMR (400 MHz) | MS: [M + H]$^+$ |
|---|---|---|---|---|
| 362 | 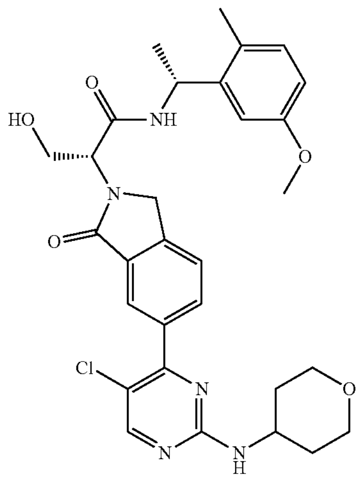 [SMILES: COc1ccc(C)c([C@@H](C)NC(=O)[C@@H](CO)N2Cc3ccc(-c4nc(NC5CCOCC5)ncc4Cl)cc3C2=O)c1] | (2R)-2-(6-{5-chloro-2-[(oxan-4-yl)amino]pyrimidin-4-yl}-1-oxo-2,3-dihydro-1H-isoindol-2-yl)-3-hydroxy-N-[(1R)-1-(5-methoxy-2-methylphenyl)ethyl]-propanamide | 1H NMR (400 MHz, Me-d3-OD): 8.33 (1H, s), 8.23 (1H, d), 8.10-7.99 (1H, m), 7.66 (1H, dd), 7.03 (1H, dd), 6.90 (1H, dd), 6.76-6.59 (1H, m), 5.23-5.11 (1H, m), 5.11-5.01 (1H, m), 4.87 (1H, d), 4.81 (5H, s), 4.76-4.63 (1H, m), 4.15-3.84 (5H, m), 3.53 (2H, t), 2.29 (3H, d), 2.00 (2H, d), 1.71-1.54 (2H, m), 1.41 (3H, dd). | 580 |
| 363 | 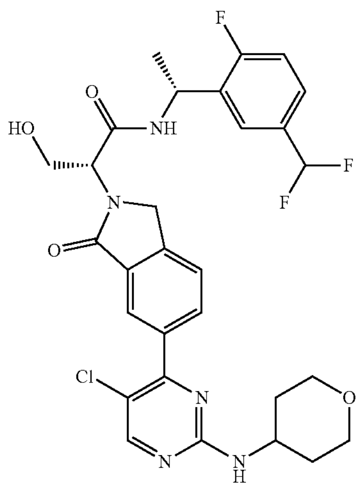 [SMILES: C[C@@H](NC(=O)[C@@H](CO)N1Cc2ccc(-c3nc(NC4CCOCC4)ncc3Cl)cc2C1=O)c1cc(C(F)F)ccc1F] | (2R)-2-(6-{5-chloro-2-[(oxan-4-yl)amino]pyrimidin-4-yl}-1-oxo-2,3-dihydro-1H-isoindol-2-yl)-N-[(1R)-1-[5-(difluoromethyl)-2-fluorophenyl]ethyl]-3-hydroxypropanamide | 1H NMR (400 MHz, Me-d3-OD): 8.34 (1H, d), 8.24 (1H, d), 8.12-8.00 (1H, m), 7.68 (1H, dd), 7.60-7.42 (1H, m), 7.42-7.26 (1H, m), 7.26-7.18 (1H, m), 6.74 (1H, dt), 5.35-5.23 (1H, m), 5.14-5.01 (1H, m), 4.87 (1H, d), 4.77-4.69 (1H, m), 4.23-4.01 (3H, m), 3.97 (2H, d), 3.64-3.48 (2H, m), 2.01 (2H, d), 1.70-1.55 (2H, m), 1.51 (3H, dd). | 604 |
| 364 | 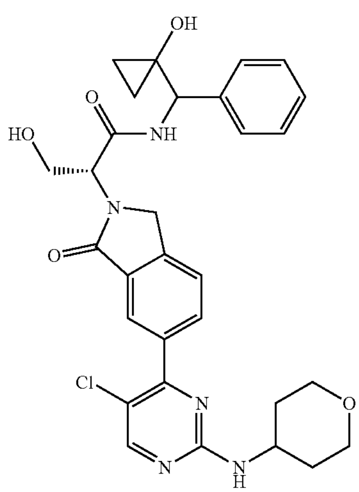 [SMILES: O=C(NC(c1ccccc1)C1(O)CC1)[C@@H](CO)N1Cc2ccc(-c3nc(NC4CCOCC4)ncc3Cl)cc2C1=O] | 2-(6-{5-chloro-2-[(oxan-4-yl)amino]pyrimidin-4-yl}-1-oxo-2,3-dihydro-1H-isoindol-2-yl)-3-hydroxy-N-[(1-hydroxycyclopropyl)(phenyl)methyl]-propanamide | 1H NMR (400 MHz, Me-d3-OD): 8.36 (1H, s), 8.26 (1H, s), 8.19-8.03 (1H, m), 7.71 (1H, dd), 7.45 (1H, d), 7.36 (2H, t), 7.32-7.16 (2H, m), 5.20-5.06 (1H, m), 4.88 (1H, d), 4.79 (1H, s), 4.16-4.03 (4H, m), 3.99 (2H, d), 3.80-3.68 (1H, m), 3.56 (2H, d), 2.01 (2H, s), 1.67-1.60 (2H, m), 0.89 (4H, s). | 578 |

-continued

| Example | Structure | Name | ¹H NMR (400 MHz) | MS: [M + H]⁺ |
|---|---|---|---|---|
| 365 | 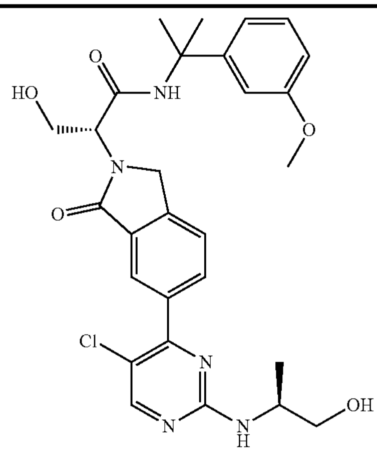 | (2R)-2-[6-(5-chloro-2-{[(2S)-1-hydroxypropan-2-yl]amino}pyrimidin-4-yl)-1-oxo-2,3-dihydro-1H-isoindol-2-yl]-3-hydroxy-N-[2-(3-methoxyphenyl)-propan-2-yl]propanamide | 1H NMR (400 MHz, Me-d3-OD): 8.32 (1H, s), 8.26 (1H, s), 8.04 (1H, d), 7.63 (1H, d), 7.14 (1H, t), 6.93 (1H, d), 6.89 (1H, t), 6.70 (1H, dd), 5.06 (1H, dd), 4.78-4.58 (2H, m), 4.23-4.11 (1H, m), 4.11-3.90 (2H, m), 3.68 (3H, s), 3.67-3.52 (2H, m), 1.68 (3H, s), 1.61 (3H, s), 1.26 (3H, d). | 554 |
| 367 | 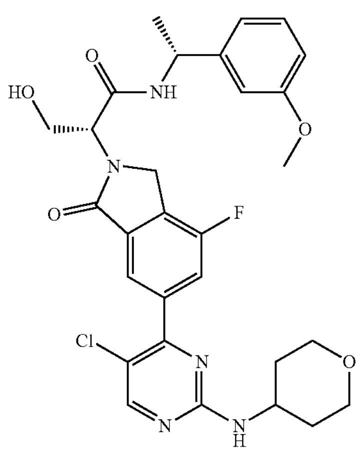 [SMILES: COc1cccc([C@@H](C)NC(=O)[C@@H](CO)N2Cc3c(F)cc(-c4nc(NC5CCOCC5)ncc4Cl)cc3C2=O)c1] | (2R)-2-(6-{5-chloro-2-[(oxan-4-yl)amino]pyrimidin-4-yl}-4-fluoro-1-oxo-2,3-dihydro-1H-isoindol-2-yl)-3-hydroxy-N-[(1R)-1-(3-methoxyphenyl)ethyl]-propanamide | 1H NMR (400 MHz, CDCl3): 8.37 (1H, s), 8.17 (1H, d), 7.77 (1H, dd), 6.91 (2H, d), 6.88-6.79 (2H, m), 5.19 (1H, d), 5.11-5.00 (1H, m), 4.90-4.73 (3H, m), 4.33-4.22 (1H, m), 4.11-3.98 (4H, m), 3.83 (3H, s), 3.60-3.54 (2H, m), 2.07 (2H, d), 1.65-1.58 (2H, m), 1.46 (3H, d). | 584 |

Examples 368-400

The compounds in the table below were prepared using procedures analogous to that described in Preparation 231, starting from the appropriate halo substituted pyrimidine.

| Example | Structure | Name | LCMS [M + H]+ | NMR |
|---|---|---|---|---|
| 368 | 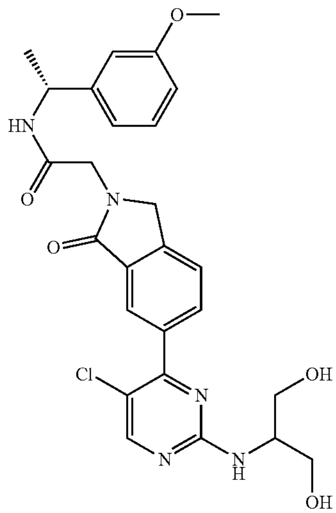 [SMILES: COc1cccc([C@@H](C)NC(=O)CN2Cc3ccc(-c4nc(NC(CO)CO)ncc4Cl)cc3C2=O)c1] | 2-(6-{5-chloro-2-[(1,3-dihydroxypropan-2-yl)amino]pyrimidin-4-yl}-1-oxo-2,3-dihydro-1H-isoindol-2-yl)-N-[(1R)-1-(3-methoxyphenyl)-ethyl]acetamide | 526 | 1H NMR (400 MHz, Me-d3-OD): 8.37 (1H, s), 8.26 (1H, s), 8.09 (1H, d), 7.70 (1H, d), 7.25 (1H, t), 7.01-6.88 (2H, m), 6.88-6.78 (1H, m), 5.11-4.96 (1H, m), 4.66 (2H, s), 4.49-4.32 (2H, m), 4.24-4.12 (1H, m), 3.86-3.79 (3H, m), 3.79-3.71 (4H, m), 1.50 (3H, d). |
| 369 | 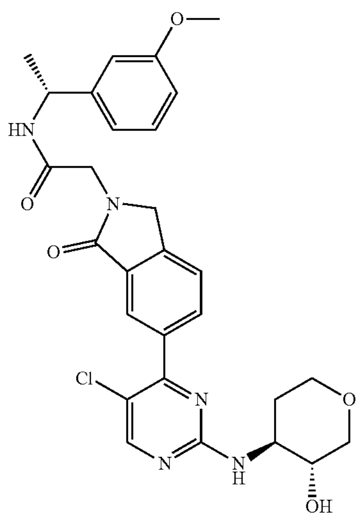 [SMILES: COc1cccc([C@@H](C)NC(=O)CN2Cc3ccc(-c4nc(N[C@H]5CCOC[C@@H]5O)ncc4Cl)cc3C2=O)c1] | 2-[6-(5-chloro-2-{[(3R,4S)-3-hydroxyoxan-4-yl]amino}pyrimidin-4-yl)-1-oxo-2,3-dihydro-1H-isoindol-2-yl]-N-[(1R)-1-(3-methoxyphenyl)-ethyl]acetamide | 552 | 1H NMR (400 MHz, Me-d3-OD): 8.36 (1H, s), 8.24 (1H, s), 8.08 (1H, dd), 7.70 (1H, d), 7.25 (1H, t), 6.94 (2H, d), 6.82 (1H, dd), 5.14-4.97 (1H, m), 4.66 (2H, s), 4.57-4.31 (2H, m), 4.02-3.87 (3H, m), 3.81 (3H, s), 3.73-3.56 (1H, m), 3.56-3.42 (1H, m), 3.29-3.03 (1H, m), 2.25-2.09 (1H, m), 1.78-1.56 (1H, m), 1.48 (3H, d). |
| 370 | 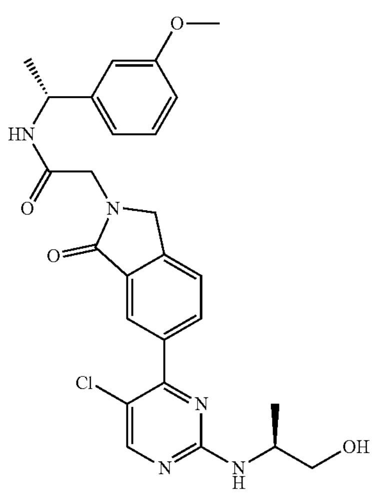 [SMILES: COc1cccc([C@@H](C)NC(=O)CN2Cc3ccc(-c4nc(N[C@@H](C)CO)ncc4Cl)cc3C2=O)c1] | 2-[6-(5-chloro-2-{[(2S)-1-hydroxypropan-2-yl]amino}pyrimidin-4-yl)-1-oxo-2,3-dihydro-1H-isoindol-2-yl]-N-[(1R)-1-(3-methoxyphenyl)-ethyl]acetamide | 510 | 1H NMR (400 MHz, DMSO-d6): 8.55 (1H, d), 8.42 (1H, s), 8.06-7.95 (2H, m), 7.74 (1H, d), 7.24 (2H, t), 6.93-6.86 (2H, m), 6.84-6.77 (1H, m), 4.98-4.89 (1H, m), 4.69-4.54 (3H, m), 4.25 (2H, s), 4.03-3.93 (1H, m), 3.76 (3H, s), 3.53-3.44 (1H, m), 3.39-3.31 (1H, m), 1.37 (3H, d), 1.14 (3H, d). |

| Example | Structure | Name | LCMS [M + H]+ | NMR |
|---|---|---|---|---|
| 371 | 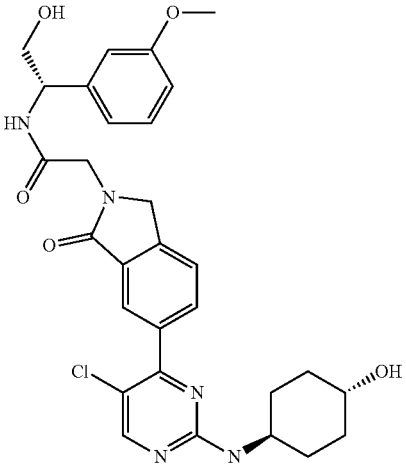 | 2-[6-(5-chloro-2-{[trans-4-hydroxycyclohexyl]amino}pyrimidin-4-yl)-1-oxo-2,3-dihydro-1H-isoindol-2-yl]-N-[(1S)-2-hydroxy-1-(3-methoxyphenyl)-ethyl]acetamide | 564 | 1H NMR (400 MHz, DMSO-d6): 8.50 (1H, d), 8.42 (1H, s), 8.06-7.93 (2H, m), 7.74 (1H, d), 7.42 (1H, s), 7.24 (1H, t), 6.90 (2H, d), 6.85-6.78 (1H, m), 4.92-4.82 (2H, m), 4.60 (2H, s), 4.50 (1H, s), 4.36-4.23 (2H, m), 3.75 (3H, s), 3.71-3.52 (3H, m), 3.45-3.34 (1H, m), 1.97-1.66 (4H, m), 1.38-1.11 (4H, m). |
| 372 | 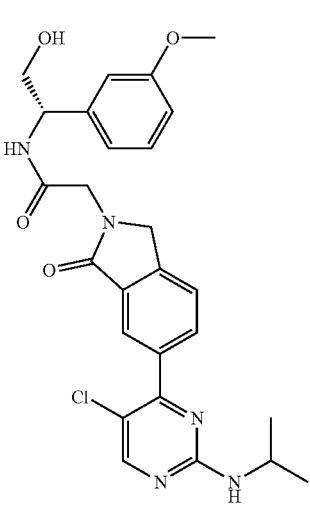 [SMILES: COc1cccc([C@@H](CO)NC(=O)CN2Cc3ccc(-c4nc(NC(C)C)ncc4Cl)cc3C2=O)c1] | 2-(6-{5-chloro-2-[(propan-2-yl)amino]pyrimidin-4-yl}-1-oxo-2,3-dihydro-1H-isoindol-2-yl)-N-[(1S)-2-hydroxy-1-(3-methoxyphenyl)-ethyl]acetamide | 508 | 1H NMR (400 MHz, DMSO-d6): 8.51 (1H, d), 8.42 (1H, s), 8.07-7.94 (2H, m), 7.74 (1H, d), 7.42 (1H, d), 7.23 (1H, t), 6.90 (2H, d), 6.85-6.78 (1H, m), 4.92-4.82 (2H, m), 4.60 (2H, s), 4.40-4.23 (2H, m), 4.10-3.98 (1H, m), 3.75 (3H, s), 3.63-3.51 (2H, m), 1.18 (6H, d). |
| 373 | 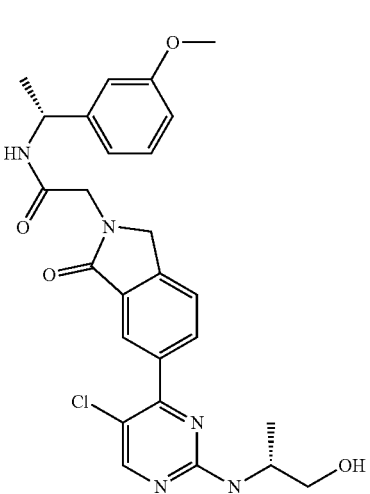 | 2-[6-(5-chloro-2-{[(2R)-1-hydroxypropan-2-yl]amino}pyrimidin-4-yl)-1-oxo-2,3-dihydro-1H-isoindol-2-yl]-N-[(1R)-1-(3-methoxyphenyl)-ethyl]acetamide | 510 | 1H NMR (400 MHz, DMSO-d6): 8.55 (1H, d), 8.43 (1H, s), 8.06-7.95 (2H, m), 7.74 (1H, d), 7.24 (2H, t), 6.90 (2H, d), 6.84-6.77 (1H, m), 4.98-4.89 (1H, m), 4.65 (1H, t), 4.60 (2H, s), 4.25 (2H, s), 4.03-3.93 (1H, m), 3.76 (3H, s), 3.53-3.45 (1H, m), 3.39-3.33 (1H, m), 1.37 (3H, d), 1.14 (3H, d). |

| Example | Structure | Name | LCMS [M + H]⁺ | NMR |
|---|---|---|---|---|
| 374 | 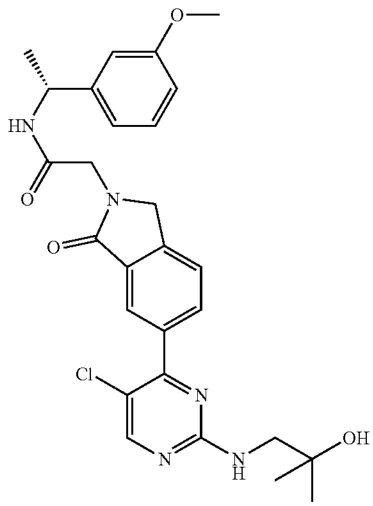 [SMILES: COc1cccc([C@@H](C)NC(=O)CN2Cc3ccc(-c4nc(NCC(C)(C)O)ncc4Cl)cc3C2=O)c1] | 2-(6-{5-chloro-2-[(2-hydroxy-2-methylpropyl)amino]-pyrimidin-4-yl}-1-oxo-2,3-dihydro-1H-isoindol-2-yl)-N-[(1R)-1-(3-methoxyphenyl)-ethyl]acetamide | 524 | 1H NMR (400 MHz, DMSO-d6): 8.55 (1H, d), 8.43 (1H, s), 8.04 (1H, s), 7.99 (1H, dd), 7.75 (1H, d), 7.28-7.16 (2H, m), 6.94-6.86 (2H, m), 6.84-6.77 (1H, m), 4.99-4.89 (1H, m), 4.60 (2H, s), 4.50 (1H, s), 4.25 (2H, s), 3.76 (3H, s), 3.33 (2H, d), 1.38 (3H, d), 1.13 (6H, s). |
| 375 | 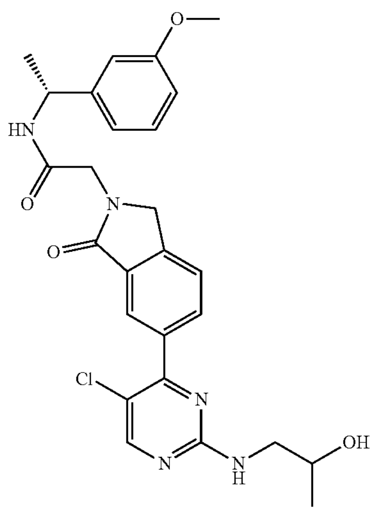 [SMILES: COc1cccc([C@@H](C)NC(=O)CN2Cc3ccc(-c4nc(NCC(C)O)ncc4Cl)cc3C2=O)c1] | 2-(6-{5-chloro-2-[(2-hydroxypropyl)-amino]pyrimidin-4-yl}-1-oxo-2,3-dihydro-1H-isoindol-2-yl)-N-[(1R)-1-(3-methoxyphenyl)-ethyl]acetamide | 510 | 1H NMR (400 MHz, DMSO-d6): 8.55 (1H, d), 8.43 (1H, s), 8.04 (1H, s), 7.99 (1H, d), 7.74 (1H, d), 7.40 (1H, s), 7.24 (1H, t), 6.90 (2H, d), 6.84-6.77 (1H, m), 4.99-4.89 (1H, m), 4.67 (1H, d), 4.60 (2H, s), 4.25 (2H, s), 3.87-3.79 (1H, m), 3.76 (3H, s), 3.28-3.21 (2H, m), 1.38 (3H, d), 1.08 (3H, d). |
| 376 | 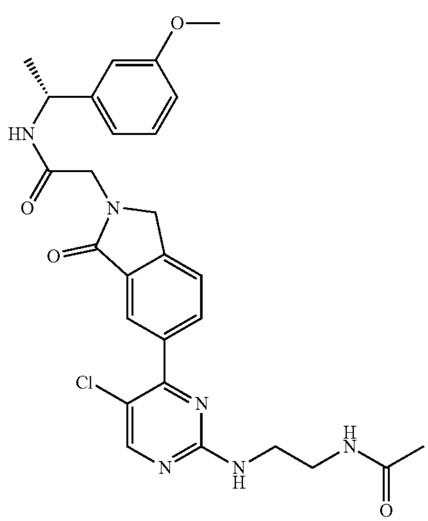 [SMILES: COc1cccc([C@@H](C)NC(=O)CN2Cc3ccc(-c4nc(NCCNC(C)=O)ncc4Cl)cc3C2=O)c1] | 2-(6-{5-chloro-2-[(2-acetamidoethyl)-amino]pyrimidin-4-yl}-1-oxo-2,3-dihydro-1H-isoindol-2-yl)-N-[(1R)-1-(3-methoxyphenyl)-ethyl]acetamide | 537 | 1H NMR (400 MHz, DMSO-d6): 8.56 (1H, d), 8.45 (1H, s), 8.02 (2H, d), 7.91 (1H, d), 7.75 (1H, d), 7.54 (1H, s), 7.24 (1H, t), 6.90 (2H, d), 6.84-6.77 (1H, m), 4.98-4.89 (1H, m), 4.60 (2H, s), 4.26 (2H, s), 3.76 (3H, s), 3.42-3.32 (2H, m), 3.28-3.20 (2H, m), 1.79 (3H, s), 1.38 (3H, d). |

-continued

| Example | Structure | Name | LCMS [M + H]⁺ | NMR |
|---|---|---|---|---|
| 377 | 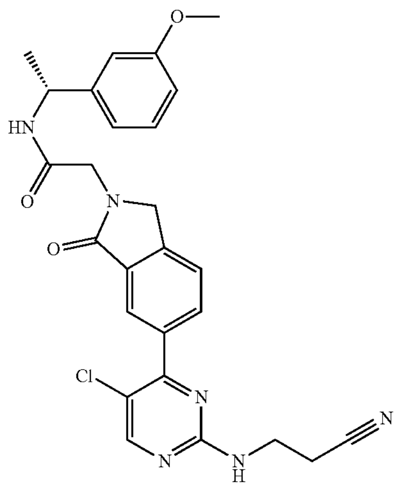 [SMILES: COc1cccc([C@@H](C)NC(=O)CN2Cc3ccc(-c4nc(NCCC#N)ncc4Cl)cc3C2=O)c1] | 2-(6-{5-chloro-2-[(2-cyanoethyl)amino]-pyrimidin-4-yl}-1-oxo-2,3-dihydro-1H-isoindol-2-yl)-N-[(1R)-1-(3-methoxyphenyl)-ethyl]acetamide | 505 | 1H NMR (400 MHz, DMSO-d6): 8.55 (1H, d), 8.50 (1H, s), 8.09-7.94 (2H, m), 7.88 (1H, s), 7.75 (1H, d), 7.28-7.21 (1H, m), 6.93-6.86 (2H, m), 6.84-6.77 (1H, m), 4.99-4.89 (1H, m), 4.60 (2H, s), 4.25 (2H, s), 3.76 (3H, s), 3.56 (2H, q), 2.80 (2H, t), 1.38 (3H, d). |
| 378 | 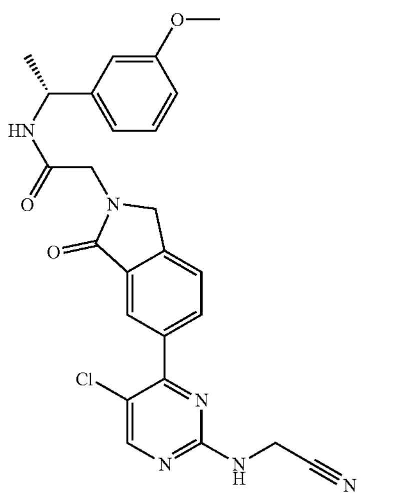 [SMILES: COc1cccc([C@@H](C)NC(=O)CN2Cc3ccc(-c4nc(NCC#N)ncc4Cl)cc3C2=O)c1] | 2-(6-{5-chloro-2-[(cyanomethyl)-amino]pyrimidin-4-yl}-1-oxo-2,3-dihydro-1H-isoindol-2-yl)-N-[(1R)-1-(3-methoxyphenyl)-ethyl]acetamide | 489 | 1H NMR (400 MHz, DMSO-d6): 8.62 (1H, s), 8.56 (1H, d), 8.21-7.94 (3H, m), 7.80-7.72 (1H, m), 7.28-7.21 (1H, m), 6.93-6.85 (2H, m), 6.84-6.77 (1H, m), 4.98-4.90 (1H, m), 4.61 (2H, s), 4.35 (2H, d), 4.26 (2H, s), 3.79-3.72 (3H, m), 1.38 (3H, d). |
| 379 | 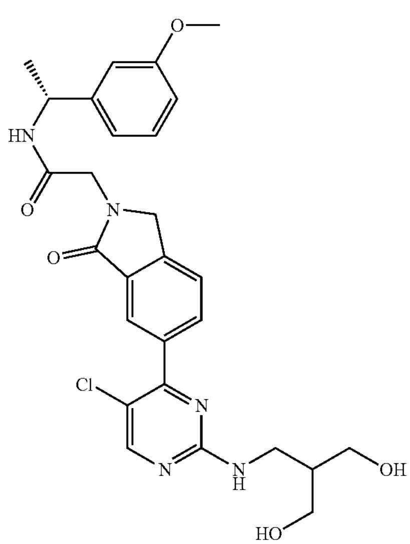 [SMILES: COc1cccc([C@@H](C)NC(=O)CN2Cc3ccc(-c4nc(NCC(CO)CO)ncc4Cl)cc3C2=O)c1] | 2-[6-(5-chloro-2-{[3-hydroxy-2-(hydroxymethyl)-propyl]amino}-pyrimidin-4-yl)-1-oxo-2,3-dihydro-1H-isoindol-2-yl]-N-[(1R)-1-(3-methoxyphenyl)-ethyl]acetamide | 526 | 1H NMR (400 MHz, DMSO-d6): 8.55 (1H, d), 8.44 (1H, s), 8.08-7.93 (2H, m), 7.74 (1H, d), 7.36-7.20 (2H, m), 6.94-6.85 (2H, m), 6.85-6.77 (1H, m), 4.99-4.89 (1H, m), 4.73 (1H, d), 4.60 (2H, s), 4.52 (1H, t), 4.26 (2H, s), 4.13-4.00 (3H, m), 3.76 (3H, s), 3.72-3.63 (1H, m), 3.49-3.33 (3H, m), 3.26 (1H, dd), 1.38 (3H, d). |

| Example | Structure | Name | LCMS [M + H]+ | NMR |
|---|---|---|---|---|
| 380 | | 2-(6-{5-chloro-2-[(2-hydroxyethyl)-amino]-pyrimidin-4-yl}-1-oxo-2,3-dihydro-1H-isoindol-2-yl)-N-[(1R)-1-(3-methoxyphenyl)-ethyl]acetamide | 496 | 1H NMR (400 MHz, DMSO-d6): 8.55 (1H, d), 8.43 (1H, s), 8.04 (1H, s), 7.99 (1H, d), 7.74 (1H, d), 7.43 (1H, s), 7.28-7.21 (1H, m), 6.90 (2H, d), 6.84-6.77 (1H, m), 4.99-4.89 (1H, m), 4.69-4.55 (3H, m), 4.25 (2H, s), 3.76 (3H, s), 3.54 (2H, q), 3.38 (2H, q), 1.38 3H, d). |
| 381 | | 2-[6-(5-chloro-2-{[trans-3-hydroxycyclobutyl]-amino}pyrimidin-4-yl)-1-oxo-2,3-dihydro-1H-isoindol-2-yl]-N-[(1R)-1-(3-methoxyphenyl)-ethyl]acetamide | 522 | 1H NMR (400 MHz, DMSO-d6): 8.56 (1H, d), 8.43 (1H, s), 8.04 (1H, s), 7.98 (1H, d), 7.86 (1H, s), 7.74 (1H, d), 724 (1H, t), 6.90 (2H, d), 6.85-6.76 (1H, m), 5.00-4.88 (2H, m), 4.60 (2H, s), 4.39-4.19 (4H, m), 3.76 (3H, s), 2.36-2.07 (4H, m), 1.38 (3H, d). |
| 382 | | 2-[6-(5-chloro-2-{[1-(hydroxymethyl)-cyclopropyl]-amino}-pyrimidin-4-yl)-1-oxo-2,3-dihydro-1H-isoindol-2-yl]-N-[(1R)-1-(3-methoxyphenyl)-ethyl]acetamide | 522 | 1H NMR (400 MHz, DMSO-d6): 8.56 (1H, d), 8.43 (1H, s), 8.04 (1H, s), 7.99 (1H, dd), 7.74 (1H, d), 7.39 (1H, s), 7.28-7.20 (1H, m), 6.94-6.86 (2H, m), 6.84-6.77 (1H, m), 5.35 (1H, s), 4.99-4.89 (1H, m), 4.60 (2H, s), 4.25 (2H, s), 3.76 3H, s), 3.50 (2H, d), 1.38 (3H, d), 0.55 (4H, s), |

| Example | Structure | Name | LCMS [M + H]+ | NMR |
|---|---|---|---|---|
| 383 | 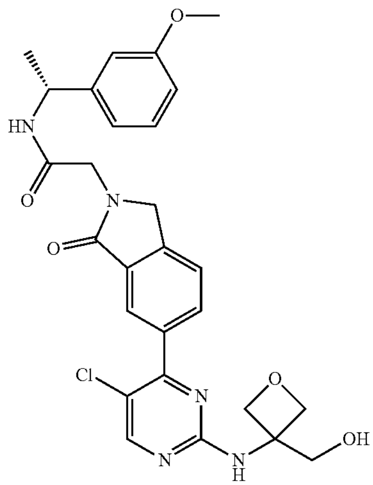 [SMILES: COc1cccc([C@@H](C)NC(=O)CN2Cc3ccc(-c4nc(NC5(CO)COC5)ncc4Cl)cc3C2=O)c1] | 2-[6-(5-chloro-2-{[3-(hydroxymethyl)-oxetan-3-yl]amino}pyrimidin-4-yl)-1-oxo-2,3-dihydro-1H-isoindol-2-yl]-N-[(1R)-1-(3-methoxyphenyl)-ethyl]acetamide | 538 | 1H NMR (400 MHz, DMSO-d6): 8.55 (1H, d), 8.44 (1H, s), 8.04 (2H, d), 7.96 (1H, d), 7.74 (1H, d), 7.28-7.20 (1H, m), 6.93-6.85 (2H, m), 6.84-6.76 (1H, m), 5.06 (1H, t), 4.99-4.89 (1H, m), 4.66-4.57 (4H, m), 4.53 (2H, d), 4.25 (2H, s), 3.79-3.73 (5H, m), 1.38 (3H, d). |
| 384 | 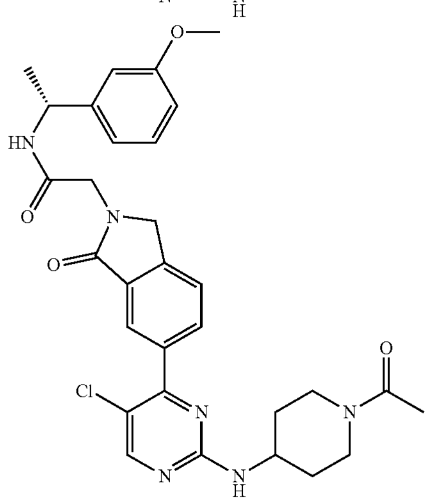 | 2-(6-{2-[(1-acetylpiperidin-4-yl)amino]-5-chloropyrimidin-4-yl}-1-oxo-2,3-dihydro-1H-isoindol-2-yl)-N-[(1R)-1-(3-methoxyphenyl)-ethyl]acetamide | 577 | 1H NMR (400 MHz, DMSO-d6): 8.56 (1H, d), 8.45 (1H, s), 8.05-7.94 (2H, m), 7.74 (1H, d), 7.60 (1H, s), 7.28-7.21 (1H, m), 6.93-6.86 (2H, m), 6.84-6.77 (1H, m), 4.98-4.89 (1H, m), 4.60 (2H, s), 4.25 (3H, s), 4.02-3.91 (1H, m), 3.85-3.70 (4H, m), 3.20-3.09 (1H, m), 2.80-2.66 (1H, m), 2.00 (3H, s), 1.98-1.78(2H, m), 1.52-1.26 (5H, m). |
| 385 | 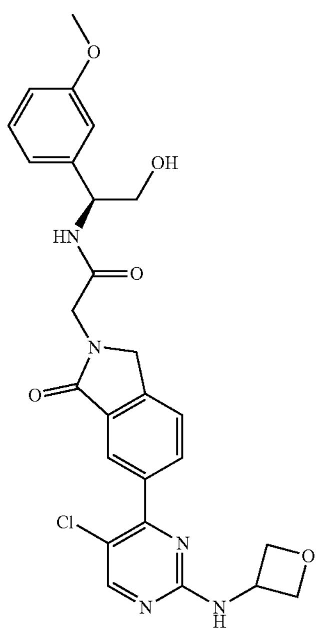 [SMILES: COc1cccc([C@@H](CO)NC(=O)CN2Cc3ccc(-c4nc(NC5COC5)ncc4Cl)cc3C2=O)c1] | 2-(6-{5-chloro-2-[(oxetan-3-yl)amino]pyrimidin-4-yl}-1-oxo-2,3-dihydro-1H-isoindol-2-yl)-N-[(1S)-2-hydroxy-1-(3-methoxyphenyl)-ethyl]acetamide | 524 | 1H NMR (400 MHz, DMSO-d6): 8.53-8.46 (2H, m), 8.31 (1H, s), 8.05 (1H, s), 7.99 (1H, dd), 7.75 (1H, d), 7.24 (1H, t), 6.90 (2H, d), 6.85-6.78 (1H, m), 4.97-4.82 (3H, m), 4.77 (2H, t), 4.60 (2H, s), 4.55 (2H, t), 4.38-4.22 (2H, m), 3.76 (3H, s), 3.63-3.53 (2H, m). |

| Example | Structure | Name | LCMS [M + H]+ | NMR |
|---|---|---|---|---|
| 386 | 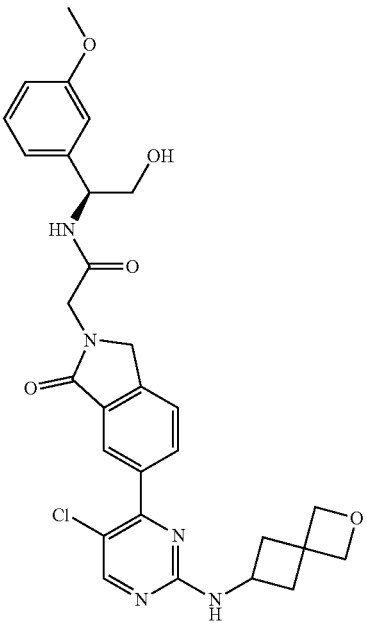 [SMILES: COc1cccc([C@@H](CO)NC(=O)CN2Cc3ccc(-c4nc(NC5CC6(COC6)C5)ncc4Cl)cc3C2=O)c1] | 2-{6-[5-chloro-2-({2-oxaspiro[3.3]heptan-6-yl}amino)pyrimidin-4-yl]-1-oxo-2,3-dihydro-1H-isoindol-2-yl}-N-[(1S)-2-hydroxy-1-(3-methoxyphenyl)-ethyl]acetamide | 564 | 1H NMR (400 MHz, DMSO-d6): 8.50 (1H, d), 8.43 (1H, s), 8.03 (1H, s), 7.97 (1H, d), 7.82 (1H, s), 7.74 (1H, d), 7.24 (1H, t), 6.90 (2H, d), 6.85-6.78 (1H, m), 4.91-4.80 (2H, m), 4.60 (4H, d), 4.50 (2H, s), 4.37-4.23 2H, m), 4.20-4.07 (1H, m), 3.75 (3H, s), 3.67-3.51 (2H, m), 2.64-2.55 (2H, m), 2.18 (2H, d). |
| 387 | 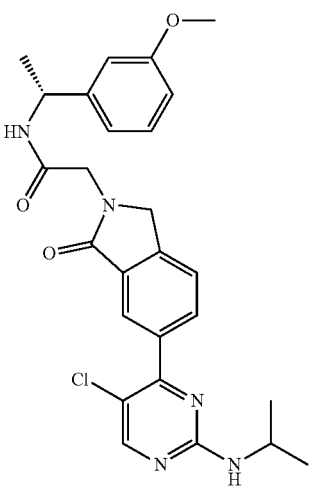 [SMILES: COc1cccc([C@@H](C)NC(=O)CN2Cc3ccc(-c4nc(NC(C)C)ncc4Cl)cc3C2=O)c1] | 2-(6-{5-chloro-2-[(propan-2-yl)amino]pyrimidin-4-yl}-1-oxo-2,3-dihydro-1H-isoindol-2-yl)-N-[(1R)-1-(3-methoxyphenyl)-ethyl]acetamide | 492 | 1H NMR (400 MHz, DMSO-d6): 8.55 (1H, d), 8.42 (1H, s), 8.04 (1H, s), 7.99 (1H, d), 7.74 (1H, d), 7.42 (1H, d), 7.24 (1H, t), 6.93-6.86 (2H, m), 6.84-6.77 (1H, m), 4.99-4.89 (1H, m), 4.60 (2H, s), 4.25 (2H, s), 4.10-3.98 (1H, m), 3.76 (3H, s), 1.38 (3H, d), 1.18 (6H, d). |

-continued

| Example | Structure | Name | LCMS [M + H]+ | NMR |
|---|---|---|---|---|
| 388 | 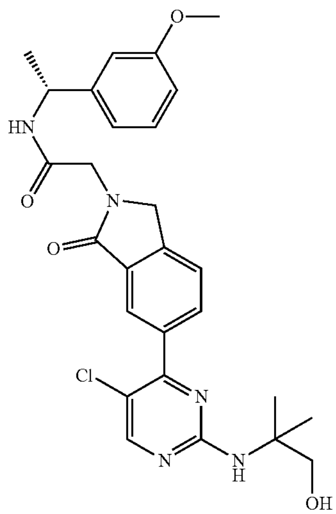 [SMILES: COc1cccc([C@@H](C)NC(=O)CN2Cc3ccc(-c4nc(NC(C)(C)CO)ncc4Cl)cc3C2=O)c1] | 2-(6-{5-chloro-2-[(1-hydroxy-2-methylpropan-2-yl)amino]pyrimidin-4-yl}-1-oxo-2,3-dihydro-1H-isoindol-2-yl)-N-[(1R)-1-(3-methoxyphenyl)-ethyl]acetamide | 524 | 1H NMR (400 MHz, DMSO-d6): 8.55 (1H, d), 8.43 (1H, s), 8.05 (1H, s), 7.99 (1H, dd), 7.75 (1H, d), 7.28-7.21 (1H, m), 6.94-6.86 (2H, m), 6.86-6.76 (2H, m), 4.99-4.89 (1H, m), 4.82 (1H, t), 4.60 (2H, s), 4.25 (2H, s), 3.76 (3H, s), 3.53 (2H, d), 1.38 (3H, d), 1.33 (6H, s). |
| 389 | 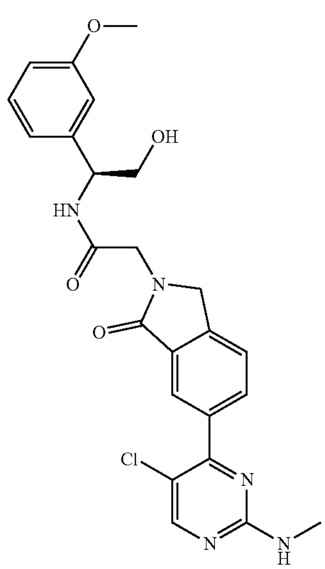 [SMILES: CNc1ncc(Cl)c(-c2ccc3c(c2)C(=O)N(CC(=O)N[C@H](CO)c2cccc(OC)c2)C3)n1] | 2-{6-[5-chloro-2-(methylamino)-pyrimidin-4-yl]-1-oxo-2,3-dihydro-1H-isoindol-2-yl}-N-[(1S)-2-hydroxy-1-(3-methoxyphenyl)-ethyl]acetamide | 482 | 1H NMR (400 MHz, DMSO-d6): 8.50 (1H, d), 8.44 (1H, s), 8.02 (2H, d), 7.74 (1H, d), 7.47 (1H, s), 7.24 (1H, t), 6.90 (2H, d), 6.85-6.78 (1H, m), 4.91-4.82 (2H, m), 4.60 (2H, s), 4.37-4.22 (2H, m), 3.75 (3H, s), 3.63-3.53 (2H, m), 2.84 (3H, d). |

-continued

| Example | Structure | Name | LCMS [M + H]+ | NMR |
|---|---|---|---|---|
| 390 | 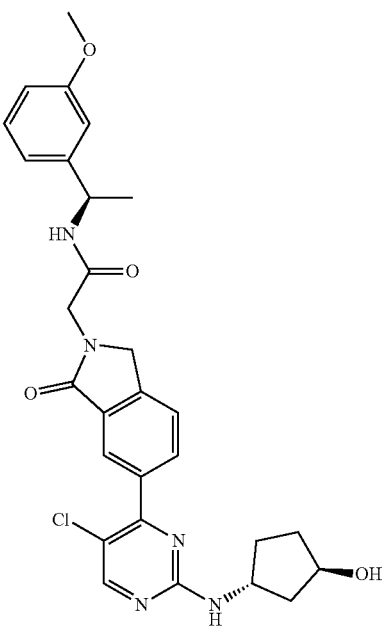 [SMILES: COc1cccc([C@@H](C)NC(=O)CN2Cc3ccc(-c4nc(N[C@@H]5CC[C@@H](O)C5)ncc4Cl)cc3C2=O)c1] | 2-[6-(5-chloro-2-{[(1R,3R)-3-hydroxycyclopentyl]amino}pyrimidin-4-yl)-1-oxo-2,3-dihydro-1H-isoindol-2-yl]-N-[(1R)-1-(3-methoxyphenyl)-ethyl]acetamide | 536 | 1H NMR (400 MHz, DMSO-d6): 8.55 (1H, d), 8.42 (1H, s), 8.07-7.94 (2H, m), 7.74 (1H, d), 7.56 (1H, d), 7.28-7.21 (1H, m), 6.93-6.87 (2H, m), 6.84-6.77 (1H, m), 4.99-4.89 (1H, m), 4.60 (2H, s), 4.46 (1H, d), 4.37 (1H, dd), 4.26 (2H, s), 4.24-4.16 (1H, m), 3.76 (3H, s), 2.15-2.02 (1H, m), 1.98-1.83 (2H, m), 1.75-1.62 (1H, m), 1.54-1.41 (2H, m), 1.38 (3H, d). |
| 391 | 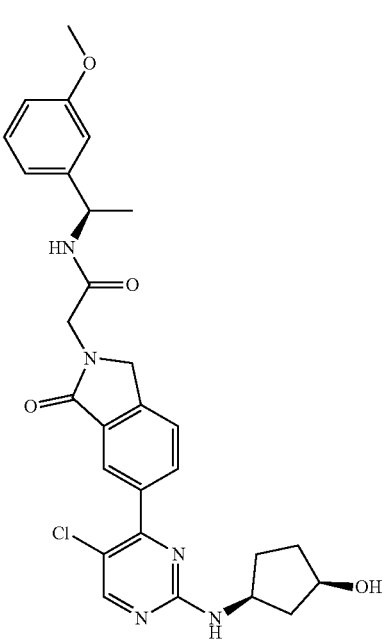 [SMILES: COc1cccc([C@@H](C)NC(=O)CN2Cc3ccc(-c4nc(N[C@H]5CC[C@@H](O)C5)ncc4Cl)cc3C2=O)c1] | 2-[6-(5-chloro-2-{[(1S,3R)-3-hydroxycyclopentyl]amino}pyrimidin-4-yl)-1-oxo-2,3-dihydro-1H-isoindol-2-yl]-N-[(1R)-1-(3-methoxyphenyl)-ethyl]acetamide | 536 | 1H NMR (400 MHz, DMSO-d6): 8.55 (1H, d), 8.42 (1H, s), 8.06-7.94 (2H, m), 7.74 (1H, d), 7.46 (1H, d), 7.28-7.21 (1H, m), 6.93-6.87 (2H, m), 6.84-6.77 (1H, m), 4.99-4.89 (1H, m), 4.60 (2H, d), 4.25 (2H, s), 4.20-4.08 (2H, m), 3.76 (3H, s), 2.25-2.14 (1H, m), 1.98-1.85 (1H, m), 1.79-1.55 (3H, m), 1.55-1.43 (1H, m), 1.38 (3H, d). |

-continued

| Example | Structure | Name | LCMS [M + H]+ | NMR |
|---|---|---|---|---|
| 392 | | 2-[6-(5-chloro-2-{[(3R)-oxan-3-yl]amino}pyrimidin-4-yl)-1-oxo-2,3-dihydro-1H-isoindol-2-yl]-N-](1S)-2-hydroxy-1-(3-methoxyphenyl)-ethyl]acetamide | 552 | 1H NMR (400 Mhz, DMSO-d6): 8.50 (1H, d), 8.45 (1H. s), 8.06 7.94 (2H, m), 7.74 (1H, d), 7.48 (1H, s), 7.24 (1H, t), 6.93-6.86 (2H, m), 6.85-6.78 (1H, m), 4.92-4.82 (2H, m), 4.60 (2H, s), 4.39-4.21 (2H, m,), 3.87 (2H, d), 3.79 3.69 (4H, m), 3.63-3.52 (2H, m), 3.12 (1H, t), 1.97 (1H, s), 1.70 (1H, s), 1.56 (2H, t). |
| 393 | | 2-[6-(5-chloro-2-{[(2S)-1-methoxypropan-2-yl]amino}pyrimidin-4-yl)-1-oxo-2,3-dihydro-1H-isoindol-2-yl]-N-](1S)-2-hydroxy-1-(3-methoxyphenyl)-ethyl]acetamide | 540 | 1H NMR (400 MHz, DMSO-d6): 8.50 (1H, d), 8.43 (1H, s), 8.07-7.96 (2H, m), 7.74 (1H, d), 7.39 (1H, d), 7.24 (1H, t), 6.90 (2H, d), 6.85-6.78 (1H, m), 4.91-4.82 (2H, m), 4.60 (2H, s), 4.36-4.30 (1H, m), 4.30-4.23 (1H, m), 4.21-4.11 (1H, m), 3.75 (3H, s), 3.63-3.52 (2H, m), 3.43 (1H, dd), 3.26 (3H, s), 1.15 (3H, d). |

| Example | Structure | Name | LCMS [M + H]+ | NMR |
|---|---|---|---|---|
| 394 | 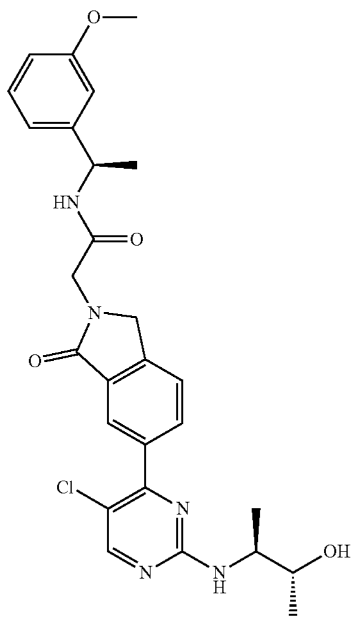 [SMILES: COc1cccc([C@@H](C)NC(=O)CN2Cc3ccc(-c4nc(N[C@@H](C)[C@@H](C)O)ncc4Cl)cc3C2=O)c1] | 2-[6-(5-chloro-2-{[(2S,3R)-3-hydroxybutan-2-yl]amino}pyrimidin-4-yl)-1-oxo-2,3-dihydro-1H-isoindol-2-yl]-N-[(1R)-1-(3-methoxyphenyl)ethyl]acetamide | 524 | 1H NMR (400 MHz, DMSO-d6): 8.55 (1H, d), 8.42 (1H, s), 8.06-7.95 (2H, m), 7.74 (1H, d), 7.28-7.13 (2H, m), 6.93-6.86 (2H, m), 6.84-6.77 (1H, m), 4.99-4.89 (1H, m), 4.60 (2H, s), 4.25 (2H, s), 3.90-3.80 (1H, m), 3.76 (3H, s), 3.73-3.63 (1H, m), 1.38 (3H, d), 1.10 (6H, dd). |
| 395 | 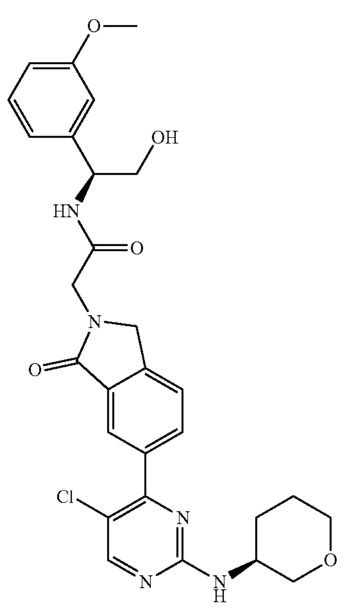 [SMILES: COc1cccc([C@@H](CO)NC(=O)CN2Cc3ccc(-c4nc(N[C@H]5CCCOC5)ncc4Cl)cc3C2=O)c1] | 2-[6-(5-chloro-2-{[(3S)-oxan-3-yl]amino}pyrimidin-4-yl)-1-oxo-2,3-dihydro-1H-isoindol-2-yl]-N-[(1S)-2-hydroxy-1-(3-methoxyphenyl)etyl]acetamide | 552 | 1H NMR (400 MHz, DMSO-d6): 8.50 (1H, d), 8.45 (1H, s), 8.04 (1H, s), 7.99 (1H, d), 7.74 (1H, d), 7.48 (1H, d), 7.24 (1H, t), 6.90 (2H, d), 6.85-6.78 (1H, m), 4.91-4.82 (2H, m), 4.60 (2H, s), 4.36-4.23 (2H, m), 3.93-3.80 (2H, m), 3.79-3.70 (4H, m), 3.63-3.53 (2H, m), 3.12 (1H, t), 1.97 (1H, s), 1.70 (1H, s), 1.57 (2H, t). |

| Example | Structure | Name | LCMS [M + H]+ | NMR |
|---|---|---|---|---|
| 396 | | 2-[6-(5-chloro-2-{[(2S)-1-hydroxybutan-2-yl]amino}pyrimidin-4-yl)-1-oxo-2,3-dihydro-1H-isoindol-2-yl]-N-[(1R)-1-(3-methoxyphenyl)-ethyl]acetamide | 524 | 1H NMR (400 MHz, DMSO-d6): 8.55 (1H, d), 8.41 (1H, s), 8.07-7.96 (2H, m), 7.74 (1H, d), 7.28-7.13 (2H, m), 6.90 (2H, d), 6.84-6.77 (1H, m), 4.99-4.89 (1H, m), 4.60 (2H, s), 4.25 (2H, s), 3.91-3.80 (1H, m), 3.76 (3H, s), 3.53-3.44 (1H, m), 3.44-3.34 (1H, m), 1.77-1.61 (1H, m), 1.54-1.40 (1H, m), 1.38 (3H, d), 0.94-0.87 (3H, m). |
| 397 | | 2-[6-(5-chloro-2-{[1-(hydroxymethyl)-cyclobutyl]amino}pyrimidin-4-yl)-1-oxo-2,3-dihydro-1H-isoindol-2-yl]-N-[(1R)-1-(3-methoxyphenyl)-ethyl]acetamide | 536 | 1H NMR (400 MHz, DMSO-d6): 8.55 (1H, d), 8.46-8.40 (1H, m), 8.05 (1H, s), 8.04-7.96 (1H, m), 7.74 (1H, d), 7.45 (1H, s), 7.28-7.21 (1H, m), 6.93-6.87 (2H, m), 6.84-6.77 (1H, m), 4.98-4.90 (1H, m), 4.72 (1H, t), 4.60 (2H, s), 4.25 (2H, s), 3.76 (3H, s), 3.66 (2H, d), 2.31-2.19 (2H, m), 2.19-2.07 (2H, m), 1.89-1.68 (2H, m), 1.38 (3H, d). |

| Example | Structure | Name | LCMS [M + H]+ | NMR |
|---|---|---|---|---|
| 398 | 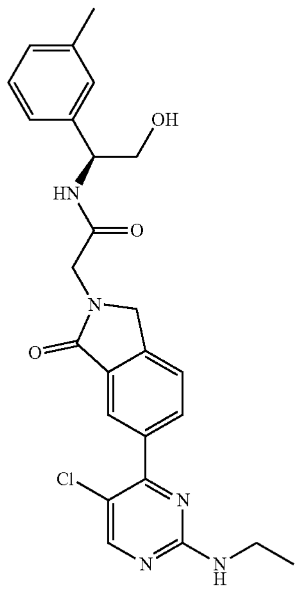 [SMILES: CCNc1ncc(Cl)c(-c2ccc3c(c2)C(=O)N(CC(=O)N[C@H](CO)c2cccc(C)c2)C3)n1] | 2-{6-[5-chloro-2-(ethylamino)pyrimidin-4-yl]-1-oxo-2,3-dihydro-1H-isoindol-2-yl}-N-[(1S)-2-hydroxy-1-(3-methylphenyl)-ethyl]acetamide | 480 | 1H NMR (400 MHz, DMSO-d6): 8.49 (1H, d), 8.43 (1H, s), 8.04 (1H, s), 8.01-7.92 (1H, m), 7.74 (1H, d), 7.54 (1H, s), 7.21 (1H, t), 7.16-7.09 (2H, m), 7.06 (1H, d), 4.90-4.80 (2H, m), 4.59 (2H, s), 4.38-4.22 (2H, m), 3.57 (2H, t), 3.37-3.32 (1H, m), 2.30 (3H, s), 1.15 (3H, t). |
| 399 | 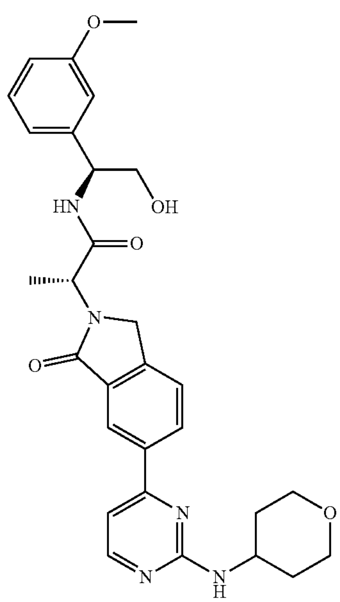 [SMILES: COc1cccc([C@@H](CO)NC(=O)[C@@H](C)N2Cc3ccc(-c4ccnc(NC5CCOCC5)n4)cc3C2=O)c1] | (2R)-N-[(1S)-2-hydroxy-1-(3-methoxyphenyl)-ethyl]-2-(6-{2-[(oxan-4-yl)amino]pyrimidin-4-yl}-1-oxo-2,3-dihydro-1H-isoindol-2-yl)propanamide | 532 | 1H NMR (400 MHz, DMSO-d6): 8.52 (1H, d), 8.47-8.30 (3H, m), 7.74 (1H, d), 7.30-7.18 (3H, m), 6.89 (2H, d), 6.84-6.77 (1H, m), 5.02 (1H, q), 4.88-4.71 (3H, m), 4.60 (1H, d), 4.10-3.97 (1H, m), 3.90 (2H, d), 3.75 (3H, s), 3.61-3.50 (2H, m), 3.43 (2H, t), 1.89 2H, d), 1.63-1.49 (2H, m), 1.45 (3H, d). |

-continued

| Example Structure | Name | LCMS [M + H]+ | NMR |
|---|---|---|---|
| 400 | (2R)-N-[(1S)-2-hydroxy-1-(3-methylphenyl)-ethyl]-2-(6-{2-[(oxan-4-yl)amino]pyrimidin-4-yl}-1-oxo-2,3-dihydro-1H-isoindol-2-yl)propanamide | 516 | 1H NMR (400 MHz, DMSO-d6): 8.50 (1H, d), 8.47-8.30 (3H, m), 7.74 (1H, d), 7.29-7.17 (3H, m), 7.14-7.02 (3H, m), 5.01 (1H, q), 4.86-4.71 (3H, m), 4.59 (1H, d), 4.10-3.98 (1H, m), 3.90 (2H, d), 3.59-3.50 (2H, m), 3.43 (2H, t), 2.29 (3H, s), 1.90 (2H, d), 1.63-1.49 (2H, m), 1.43(3H, d). |

Example 401: 2-(6-{5-chloro-2-[(1,5-dimethyl-1H-pyrazol-4-yl)amino]pyrimidin-4-yl}-1-oxo-2,3-dihydro-1H-isoindol-2-yl)-N-[(1S)-2-hydroxy-1-(3-methoxyphenyl)ethyl]acetamide

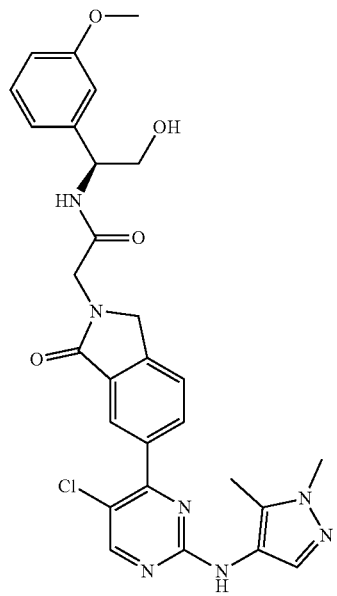 [SMILES: COc1cccc([C@@H](CO)NC(=O)CN2Cc3ccc(-c4nc(Nc5cnn(C)c5C)ncc4Cl)cc3C2=O)c1]

A stirred solution of 2-[6-(2,5-dichloropyrimidin-4-yl)-1-oxo-2,3-dihydro-1H-isoindol-2-yl]-N-[(1S)-2-hydroxy-1-(3-methoxyphenyl)ethyl]acetamide (Preparation 169, 0.05 g, 0.10 mmol) and 1,5-dimethyl-1H-pyrazol-4-amine (0.011 g, 0.10 mmol) and 4M HCL in dioxane (3 µL, 0.01 mmol) in N-methyl pyrrolidinone (0.23 mL) was heated at 100° C. for 18 h. The reaction mixture was directly purified by reverse phase biotage (gradient elution, 0-40%, MeCN/water), to give the title compound. 1H NMR (400 MHz, DMSO-d6): 9.08-9.03 (1H, m), 8.50 (2H, d), 8.08-7.97 (2H, m), 7.75 (1H, d), 7.49 (1H, s), 7.24 (1H, t), 6.93-6.87 (2H, m), 6.84-6.79 (1H, m), 4.91-4.83 (2H, m), 4.60 (2H, s), 4.36-4.24 (2H, m), 3.75 (3H, s), 3.70 (3H, s), 3.62-3.54 (2H, m), 2.18 (3H, s). MS: [M+H]+=562.

Example 402: 2-(7-{5-chloro-2-[(oxan-4-yl)amino]pyrimidin-4-yl}-1-oxo-1,2,3,4-tetrahydroisoquinolin-2-yl)-N-[(1S)-2-hydroxy-1-(3-methoxyphenyl)ethyl]acetamide To 2-(7-{5-chloro-2-[(oxan-4-yl)amino]pyrimidin-4-yl}-1-oxo-1,2,3,4-tetrahydroisoquinolin-2-yl)acetic acid (Preparation 233, 0.200 g, 0.48 mmol), (2S)-2-amino-2-(3-methylphenyl)ethan-1-ol hydrochloride (0.088 g, 0.53 mmol) and HATU (0.274 g, 0.53 mmol) in DCM (7.87 mL) was added diisopropylethylamine (1.10 mL, 6.30 mmol). The reaction was stirred at room temperature for 1 h. Water was added and the aqueous was extracted with ethyl acetate (3×). The combined organics were concentrated in vacuo. The crude product was purified by by reverse phase biotage (gradient elution, 0-40%, MeCN/water), to give the title compound. 1H NMR (400 MHz, DMSO-d6): 8.42 (1H, s), 8.37 (1H, d), 8.27 (1H, d), 7.87 (1H, dd), 7.57 (1H, s), 7.44 (1H, d), 7.23 (1H, t), 6.93-6.86 (2H, m), 6.84-6.77 (1H, m), 4.89-4.80 (2H, m), 4.31-4.18 (2H, m), 3.98-3.81 (3H, m), 3.76 (3H, s), 3.68-3.55 (4H, m), 3.38 (2H, t), 3.12-3.00 (2H, m), 1.84 (2H, d), 1.59-1.45 (2H, m). MS: [M+H]$^+$=566.

and then the combined organics washed with water (×2) and brine, dried (MgSO4), filtered and concentrated. Purified by silica column, 10 g SNAP—0-10% MeOH in EtOAc. The product was further purified by reverse phase C18 cartridge (30 g SNAP), eluting 45-70% MeCN in water to give the title compound (20 mg) as a white solid. LC-MS: [M+H]$^+$=565. $^1$H NMR (400 MHz, DMSO-d$_6$): 8.51 (1H, d), 8.09 (1H, s), 7.75-7.63 (3H, m), 7.27-7.20 (1H, m), 6.91-6.84 (2H, m), 6.84-6.75 (2H, m), 6.57-6.52 (1H, m), 5.01 (1H, q), 4.88-4.79 (2H, m), 4.75 (1H, d), 4.59 (1H, d), 3.98-3.83 (3H, m), 3.75 (3H, s), 3.60-3.51 (2H, m), 3.42 (2H, dd), 1.89 (2H, d), 1.48-1.41 (5H, m).

Example 404:6-{5-chloro-2-[(oxan-4-yl)amino]pyrimidin-4-yl}-2-(2-oxo-2-{6-[4-(propan-2-yl)piperazin-1-yl]-1,2,3,4-tetrahydroisoquinolin-2-yl}ethyl)-2,3-dihydro-1H-isoindol-1-one

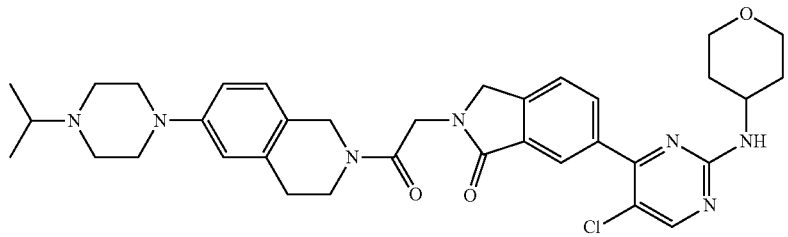

Example 403: (2R)-2-(6-{5-chloro-2-[(oxan-4-yl)amino]pyridin-4-yl}-1-oxo-2,3-dihydro-1H-isoindol-2-yl)-N-[(1S)-2-hydroxy-1-(3-methoxyphenyl)ethyl]propanamide

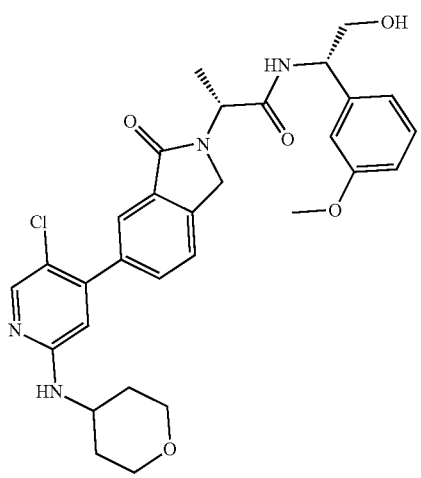 [SMILES: COc1cccc([C@@H](CO)NC(=O)[C@@H](C)N2Cc3ccc(-c4cc(NC5CCOCC5)ncc4Cl)cc3C2=O)c1]

A solution of (2R)-2-[6-(5-chloro-2-fluoropyridin-4-yl)-1-oxo-2,3-dihydro-1H-isoindol-2-yl]-N-[(1S)-2-hydroxy-1-(3-methoxyphenyl)ethyl]propanamide (Preparation 239, 54 mg, 0.11 mmol) in NMP (0.1 mL), N,N-diisopropylethylamine (58 µL, 0.33 mmol, 3 eq.) and 4-aminooxan (58 µL, 0.56 mmol, 5 eq.) was heated in the microwave at 140° C. for 2 hours. Partial reaction—heated for a further 2 hrs at 140° C. The mixture was partitioned between EtOAc and water. The aqueous layer was extracted with further EtOAc Prepared using a similar procedure to Example 2. The product was further purified by SCX (3 g) in MeOH. The column was washed with MeOH and the product was eluted with 0.7 M ammonia in MeOH. The resulting mixture was concentrated in vacuo to afford the title compound (69 mg, 0.105 mmol, 44% yield) as a white solid. 1H NMR (DMSO-d6, 400 MHz) δ 8.45 (1H, s), 8.06-8.02 (1H, m), 7.99 (1H, dd), 7.75 (1H, d), 7.62 (1H, s (br)), 7.09-7.01 (1H, m), 6.85-6.73 (2H, m), 4.67-4.49 (6H, m), 3.99-3.83 (3H, m), 3.72 (1H, t), 3.65 (1H, t), 3.42-3.35 (2H, m), 3.09 (4H, br. s), 2.87 (1H, t), 2.75 (1H, t), 2.58 (4H, br. s), 1.90-1.82 (2H, m), 1.61-1.47 (2H, m), 1.02 (6H, d) (one proton obscured by solvent peak). LC-MS: [M+H]+=644.

Example 405: 6-{5-chloro-2-[(oxan-4-yl)amino]pyrimidin-4-yl}-2-{2-oxo-2-[6-(pyrimidin-2-yl)-1,2,3,4-tetrahydroisoquinolin-2-yl]ethyl}-2,3-dihydro-1H-isoindol-1-one

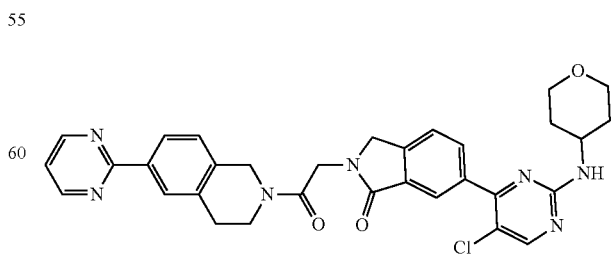

Prepared using a similar procedure to Example 2. The product was further purified by SCX (3 g) in MeOH. The column was washed with MeOH and the product was eluted with 0.7 M ammonia in MeOH. The resulting mixture was concentrated in vacuo to afford the title compound (63 mg, 46%) as a white solid. $^1$H NMR (DMSO-d$_6$, 400 MHz) δ 8.91 (2H, d), 8.46 (1H, s), 8.30-8.21 (2H, m), 8.06-8.03 (1H, m), 7.99 (1H, dd), 7.76 (1H, d), 7.62 (1H, br. s), 7.48-7.43 (1H, m), 7.38 (1H, dd), 4.86 (1H, s), 4.71 (1H, s), 4.65-4.59 (4H, m), 3.99-3.80 (4H, m), 3.75 (1H, t), 3.43-3.35 (2H, m), 3.06 (1H, t), 2.93 (1H, t), 1.90-1.82 (2H, m), 1.60-1.47 (2H, m). LC-MS: [M+H]+=596.

Example 406: 2-(6-{5-chloro-2-[(oxan-4-yl)amino]pyrimidin-4-yl}-1-oxo-2,3-dihydro-1H-isoindol-2-yl)-N-[1-(4-chlorophenyl)-2-hydroxyethyl]acetamide

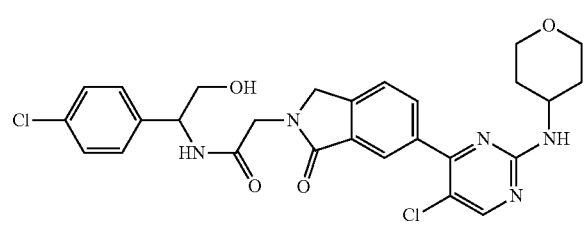 [SMILES: O=C(CN1Cc2ccc(-c3nc(NC4CCOCC4)ncc3Cl)cc2C1=O)NC(CO)c1ccc(Cl)cc1]

Prepared using a similar procedure to Example 2. 1H NMR (DMSO-d6) δ: 8.61 (d, 1H), 8.45 (s, 1H), 8.03 (d, 1H), 7.97 (dd, 1H), 7.74 (d, 1H), 7.62 (s (br)), 1H), 7.45-7.29 (m, 4H), 4.97 (t, 1H), 4.87 (dt, 1H), 4.58 (s, 2H), 4.32 (d, 1H), 4.26 (d, 1H), 3.99-3.79 (m, 3H), 3.57 (dd, 2H), 3.45-3.35 (m, 2H), 1.93-1.77 (m, 2H), 1.60-1.43 (m, 2H). LC-MS: [M+H]+=556.

Example 407: 6-{5-chloro-2-[(oxan-4-yl)amino]pyrimidin-4-yl}-2-[2-(4-methyl-4-phenylpiperidin-1-yl)-2-oxoethyl]-2,3-dihydro-1H-isoindol-1-one Triethylamine (83 μl, 0.596 mmol) was added to a mixture of 2-(6-{5-chloro-2-[(oxan-4-yl)amino]pyrimidin-4-yl}-1-oxo-2,3-dihydro-1H-isoindol-2-yl)acetic acid (Example 1, 80 mg, 0.199 mmol), 4-methyl-4-phenylpiperidine (34.8 mg, 0.199 mmol) and HATU (83 mg, 0.218 mmol) in DCM:DMF (3 mL (10:1)). The reaction was stirred at room temperature for 1 h. The mixture was diluted with DCM (5 mL), then washed with 1M HCl (5 mL), saturated aqueous NaHCO$_3$ (5 mL), brine (5 mL), dried (MgSO$_4$), then concentrated in vacuo. The crude product was purified by chromatography (SiO$_2$, 4 g column, 50-100% EtOAc in isohexane) to give a colourless glass. Trituration with diethyl ether and drying to afford the title compound (75 mg, 66%) as a colourless powder. 1H NMR (400 MHz, DMSO-d6) δ 8.44 (s, 1H), 8.02 (d, 1H), 7.97 (dd, 1H), 7.73 (d, 1H), 7.61 (bs, 1H), 7.42-7.39 (m, 2H), 7.37-7.33 (m, 2H), 7.23-7.19 (m, 1H), 4.55 (s, 2H), 4.48 (d, 2H), 3.93-3.85 (m, 3H), 3.60-3.51 (m, 2H), 3.45-3.34 (m, 4H), 2.12-2.08 (m, 1H), 2.00-1.96 (m, 1H), 1.86-1.83 (m, 2H), 1.79-1.74 (m, 1H), 1.69-1.65 (m, 1H), 1.57-1.47 (m, 2H), 1.25 (s, 3H). LC-MS: [M+H]+=560.

Examples 408-436

Prepared using an analogous procedure to Example 407, from 2-(6-{5-chloro-2-[(oxan-4-yl)amino]pyrimidin-4-yl}-1-oxo-2,3-dihydro-1H-isoindol-2-yl)acetic acid (Example 1) and the corresponding amine:

| Example | Structure | Name | ¹H NMR (400 MHz) | MS: [M + H]⁺ |
|---|---|---|---|---|
| 408 | 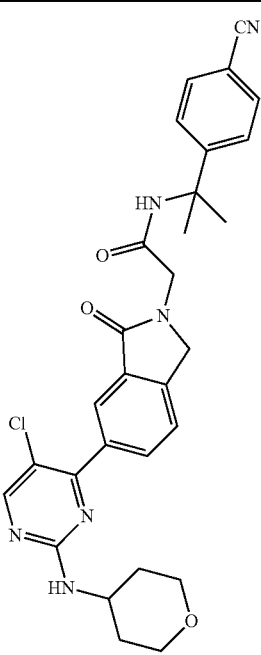 | 2-(6-{5-chloro-2-[(oxan-4-yl)amino]pyrimidin-4-yl}-1-oxo-2,3-dihydro-1H-isoindol-2-yl)-N-(4-cyanophenyl)-propan-2-yl]acetamide | 1H NMR (400 MHz, DMSO-d6) δ 8.55 (s, 1H), 8.43 (s, 1H), 8.01 (d, 1H), 7.95 (dd, 1H), 7.75 (d, 2H), 7.71 (d, 1H), 7.59 (s (br), 1H), 7.54 (d, 2H), 4.54 (s, 2H), 4.26 (s, 2H), 3.93-3.84 (m, 3H), 3.40-3.34 (m, 2H), 1.86-1.82 (m, 2H), 1.57 (s, 6H), 1.54-1.47 (m, 2H) | 545 |
| 409 | 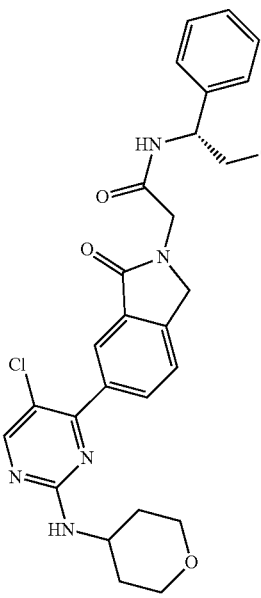 | 2-(6-{5-chloro-2-[(oxan-4-yl)amino]pyrimidin-4-yl}-1-oxo-2,3-dihydro-1H-isoindol-2-yl)-N-[(1R)-2-hydroxy-1-phenylethyl]acetamide | 1H NMR (400 MHz, DMSO-d6) : 8.56 (d, 1H), 8.44 (s, 1H), 8.03-8.02 (br m, 1H), 7.97 (dd, 1H), 7.73 (d, 1H), 7.60 (s (br), 1H), 7.35-7.30 (m, 4H), 7.27-7.22 (m, 1H), 4.97-4.85 (m, 2H), 4.59 (s, 2H), 4.29 (dd, 2H), 3.97-3.85 (m, 3H), 3.59-3.56 (m, 2H), 3.40-3.34 (m, 2H), 1.87-1.83 (br m, 2H), 1.57-1.47 (m, 2H) | 522 |

| Example | Structure | Name | ¹H NMR (400 MHz) | MS: [M + H]⁺ |
|---------|-----------|------|------------------|--------------|
| 410 | 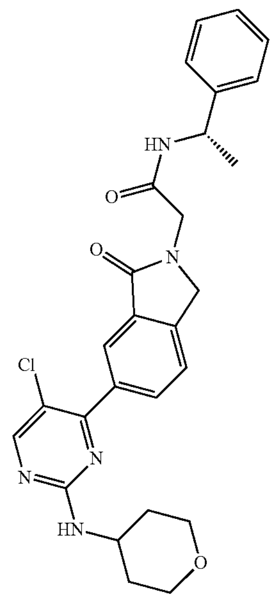 [SMILES: C[C@H](NC(=O)CN1Cc2ccc(-c3nc(NC4CCOCC4)ncc3Cl)cc2C1=O)c1ccccc1] | 2-(6-{5-chloro-2-[(oxan-4-yl)amino]pyrimidin-4-yl}-1-oxo-2,3-dihydro-1H-isoindol-2-yl)-N-[(1S)-1-phenylethyl]acetamide | 1H NMR (400 MHz, DMSO-d6) δ: 8.60 (d, 1H), 8.45 (s, 1H), 8.03 (d, 1H), 7.98 (dd, 1H), 7.74 (d, 1H), 7.61 (s (br)), 1H), 7.31-7.37 (m, 4H), 7.24 (m, 1H), 4.97 (dq, 1H), 4.59 (s, 2H), 4.28 (d, 1H), 4.23 (d, 1H), 3.82-3.98 (m, 3H), 3.33-3.43 (m, 2H), 1.80-1.89 (m, 2H), 1.46-1.59 (m, 2H), 1.39 (d, 3H) | 506 |
| 411 | 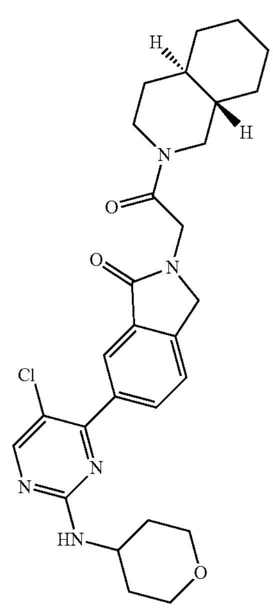 [SMILES: O=C(CN1Cc2ccc(-c3nc(NC4CCOCC4)ncc3Cl)cc2C1=O)N1CC[C@H]2CCCC[C@@H]2C1] | (trans) 2-{2-[(4aS, 8aR)-decahydroisoquinolin-2-yl]-2-oxoethyl}-6-{5-chloro-2-[(oxan-4-yl)amino]pyrimidin-4-yl}-2,3-dihydro-1H-isoindol-1-one | 1H NMR (400 MHz, DMSO-d6) δ: 8.45 (s, 1H), 8.02-8.01 (m, 1H), 7.98 (dd, 1H), 7.74 (d, 1H), 7.62 (s (br), 1H), 4.55-4.38 (m, 5H), 4.25-4.22, 3.78-3.74, 3.07-3.01, 2.71-2.65 and 2.57-2.51 (m, 2H), 3.97-3.74 (m, 4H), 3.40-3.34 (m, 2H), 1.86-1.83 (br m, 2H), 1.70-1.47 (m, 8H), 1.31-0.88 (m, 6H) | 524 |

-continued

| Example | Structure | Name | ¹H NMR (400 MHz) | MS: [M + H]⁺ |
|---|---|---|---|---|
| 412 | 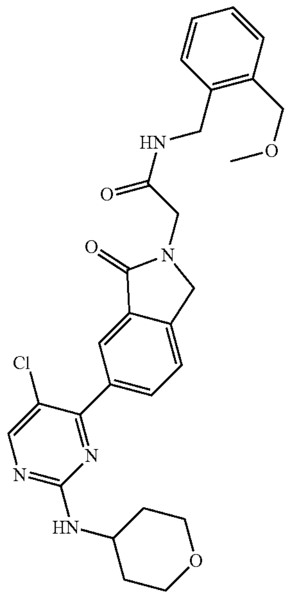 [SMILES: COCc1ccccc1CNC(=O)CN1Cc2ccc(-c3nc(NC4CCOCC4)ncc3Cl)cc2C1=O] | 2-(6-{5-chloro-2-[(oxan-4-yl)amino]pyrimidin-4-yl}-1-oxo-2,3-dihydro-1H-isoindol-2-yl)-N-{[2-(methoxymethyl)phenyl]methyl}acetamide | 1H NMR (400 MHz, DMSO d6) δ: 8.51 (t, 1H), 8.44 (s, 1H), 8.03-8.02 (m, 1H), 7.98 (dd, 1H), 7.75 (d, 1H), 7.62 (s (br), 1H), 7.34-7.23 (m, 4H), 4.62 (s, 2H), 4.46 (s, 2H), 4.35 (d, 2H), 4.27 (s, 2H), 3.97-3.85 (m, 3H), 3.37 (t, 2H), 3.29 (s, 3H), 1.86-1.83 (br m, 2H), 1.52 (qd, 2H) | 536 |
| 413 | 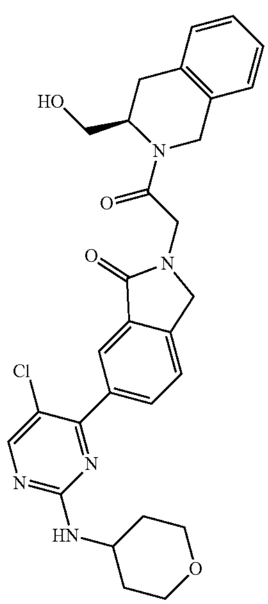 [SMILES: O=C1c2cc(-c3nc(NC4CCOCC4)ncc3Cl)ccc2CN1CC(=O)N1Cc2ccccc2C[C@@H]1CO] | 6-{5-chloro-2-[(oxan-4-yl)amino]pyrimidin-4-yl}-2-{2-[(3R)-3-(hydroxymethyl)-1,2,3,4-tetrahydroisoquinolin-2-yl]-2-oxoethyl}-2,3-dihydro-1H-isoindol-1-one | 1H NMR (400 MHz, DMSO-d6 @ 373 K) δ: 8.40 (s, 1H), 8.09-8.08 (m, 1H), 8.01 (dd, 1H), 7.71 (d, 1H), 7.24-7.10 (m, 5H), 5.11-4.15 (br m, 9H), 4.03-3.86 (m, 3H), 3.47-3.31 (m, 4H), 3.07 (s (br), 1H), 1.92-1.89 (br m, 2H), 1.65-1.55 (m, 2H). | 548 |

-continued

| Example | Structure | Name | $^1$H NMR (400 MHz) | MS: [M + H]$^+$ |
|---|---|---|---|---|
| 414 | 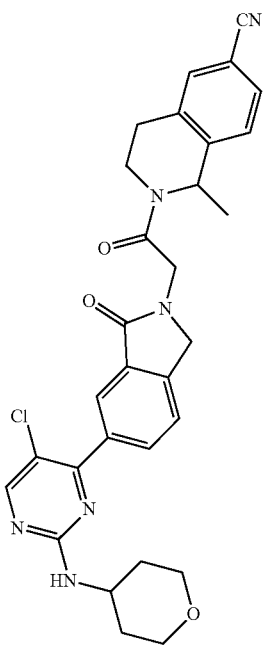 [SMILES: CC1c2ccc(C#N)cc2CCN1C(=O)CN1Cc2ccc(-c3nc(NC4CCOCC4)ncc3Cl)cc2C1=O] | 2-[2-(6-{5-chloro-2-(oxan-4-yl)amino]pyrimidin-4-yl}-1-oxo-2,3-dihydro-1H-isoindol-2-yl)acetyl]-1-methyl-1,2,3,4-tetrahydroisoquinoline-6-carbonitrile | 1H NMR (DMSO-d6, 400 MHz) δ 8.45 (1H, s), 8.07-8.01 (1H, m), 7.99 (1H, dd), 7.80-7.55 (4H, m), 7.50 (1H, t), 5.52 (0.6H, q), 5.37 (0.4H, q), 4.76-4.39 (4H, m), 4.06-3.81 (4H, m), 3.55 (1H, ddd), 3.44-3.34 (1H, m), 3.14-2.76 (3H, m), 1.85 (2H, d), 1.61-1.46 (3H, m), 1.40 (2H, d). (3:2 mixture of rotamers). | 557 |
| 415 | 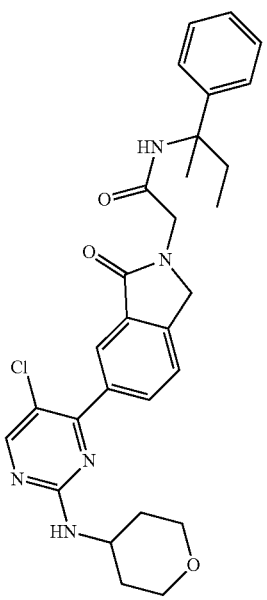 [SMILES: CCC(C)(NC(=O)CN1Cc2ccc(-c3nc(NC4CCOCC4)ncc3Cl)cc2C1=O)c1ccccc1] | 2-(6-{5-chloro-2-[(oxan-4-yl)amino]pyrimidin-4-yl}-1-oxo-2,3-dihydro-1H-isoindol-2-yl)-N-(2-phenylbutan-2-yl)acetamide | 1H NMR (400 MHz, DMSO-d6) δ: 8.44(s, 1H), 8.19 (s, 1H), 8.01-8.00 (m, 1H), 7.95 (dd, 1H), 7.72 (d, 1H), 7.61 (s (br), 1H), 7.32-7.26 (m, 4H), 7.19-7.14 (m, 1H), 4.60-4.50 (m, 2H), 4.33-4.25 (m, 2H), 3.95-3.84 (m, 3H), 3.39-3.34 (m, 2H), 2.05-1.96 (m, 1H), 1.85-1.71 (m, 3H), 1.56-1.47 (m, 5H), 0.76 (t, 3H). | 534 |

| Example | Structure | Name | ¹H NMR (400 MHz) | MS: [M + H]⁺ |
|---|---|---|---|---|
| 416 | 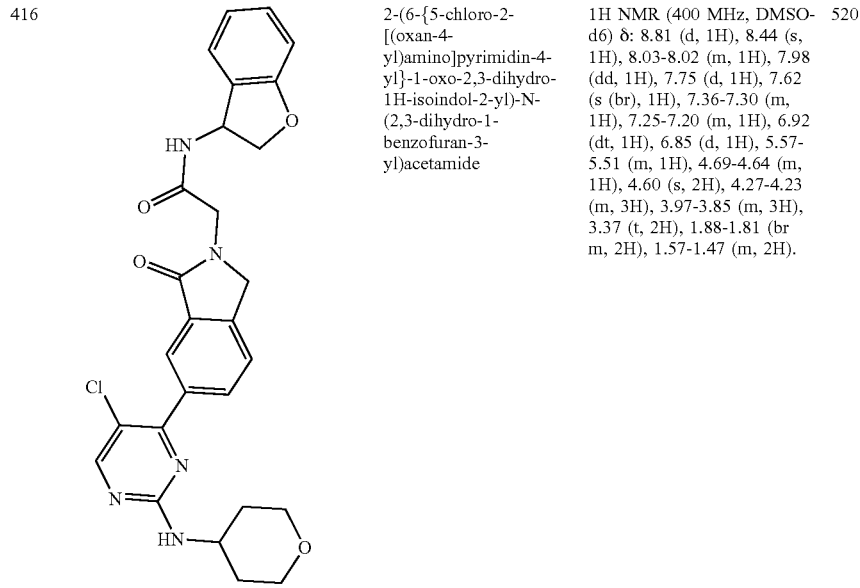 | 2-(6-{5-chloro-2-[(oxan-4-yl)amino]pyrimidin-4-yl}-1-oxo-2,3-dihydro-1H-isoindol-2-yl)-N-(2,3-dihydro-1-benzofuran-3-yl)acetamide | 1H NMR (400 MHz, DMSO-d6) δ: 8.81 (d, 1H), 8.44 (s, 1H), 8.03-8.02 (m, 1H), 7.98 (dd, 1H), 7.75 (d, 1H), 7.62 (s (br), 1H), 7.36-7.30 (m, 1H), 7.25-7.20 (m, 1H), 6.92 (dt, 1H), 6.85 (d, 1H), 5.57-5.51 (m, 1H), 4.69-4.64 (m, 1H), 4.60 (s, 2H), 4.27-4.23 (m, 3H), 3.97-3.85 (m, 3H), 3.37 (t, 2H), 1.88-1.81 (br m, 2H), 1.57-1.47 (m, 2H). | 520 |
| 417 | 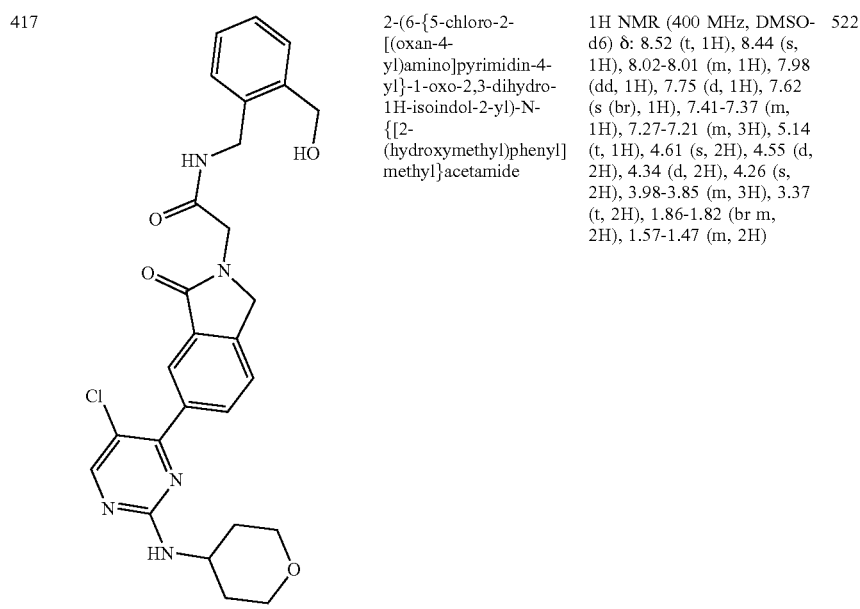 | 2-(6-{5-chloro-2-[(oxan-4-yl)amino]pyrimidin-4-yl}-1-oxo-2,3-dihydro-1H-isoindol-2-yl)-N-{[2-(hydroxymethyl)phenyl]methyl}acetamide | 1H NMR (400 MHz, DMSO-d6) δ: 8.52 (t, 1H), 8.44 (s, 1H), 8.02-8.01 (m, 1H), 7.98 (dd, 1H), 7.75 (d, 1H), 7.62 (s (br), 1H), 7.41-7.37 (m, 1H), 7.27-7.21 (m, 3H), 5.14 (t, 1H), 4.61 (s, 2H), 4.55 (d, 2H), 4.34 (d, 2H), 4.26 (s, 2H), 3.98-3.85 (m, 3H), 3.37 (t, 2H), 1.86-1.82 (br m, 2H), 1.57-1.47 (m, 2H) | 522 |

-continued

| Example | Structure | Name | ¹H NMR (400 MHz) | MS: [M + H]⁺ |
|---|---|---|---|---|
| 418 | 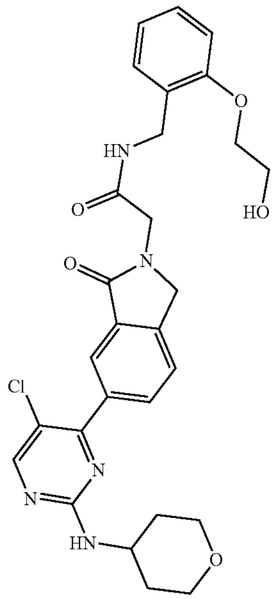 [SMILES: O=C(CN1Cc2ccc(-c3nc(NC4CCOCC4)ncc3Cl)cc2C1=O)NCc1ccccc1OCCO] | 2-(6-{5-chloro-2-[(oxan-4-yl)amino]pyrimidin-4-yl}-1-oxo-2,3-dihydro-1H-isoindol-2-yl)-N-{[2-(2-hydroxyethoxy)phenyl]methyl}acetamide | 1H NMR (DMSO-d6, 400 MHz) δ 8.44 (2H, d), 8.03 (1H, dd), 7.98 (1H, dd), 7.80-7.70 (1H, m), 7.62 (1H, s), 7.31-7.14 (2H, m), 6.97 (1H, dd), 6.91 (1H, app td), 4.88 (1H, t), 4.62 (2H, s), 4.31 (2H, d), 4.27 (2H, s), 4.01 (2H, dd), 3.98-3.80 (3H, m), 3.77-3.69 (2H, m), 3.42-3.35 (2H, m), 1.89-1.78(2H, m), 1.59-1.46 (2H, m). | 552 |
| 419 | 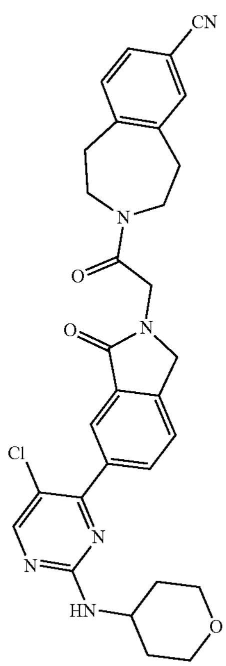 [SMILES: N#Cc1ccc2c(c1)CCN(C(=O)CN1Cc3ccc(-c4nc(NC5CCOCC5)ncc4Cl)cc3C1=O)CC2] | 3-[2-(6-{5-chloro-2-[(oxan-4-yl)amino]pyrimidin-4-yl}-1-oxo-2,3-dihydro-1H-isoindol-2-yl)acetyl]-2,3,4,5-tetrahydro-1H-3-benzazepine-7-carbonitrile | 1H NMR (DMSO-d6, 400 MHz) δ 8.45 (1H, s), 8.06-8.02 (1H, m), 7.99 (1H, dd), 7.80-7.55 (4H, m), 7.41 (1H, dd), 4.56 (4H, d), 3.87 (3H, s), 3.73-3.56 (4H, m), 3.38 (2H, t), 3.14-3.00 (2H, m), 3.01-2.86 (2H, m), 1.85 (2H, d), 1.53 (2H, qd). | 557 |

-continued

| Example | Structure | Name | ¹H NMR (400 MHz) | MS: [M + H]⁺ |
|---|---|---|---|---|
| 420 | 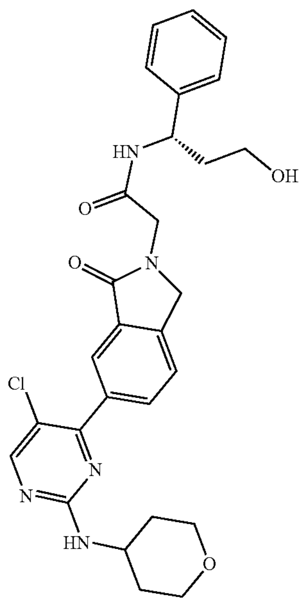 [SMILES: O=C(CN1Cc2ccc(-c3nc(NC4CCOCC4)ncc3Cl)cc2C1=O)N[C@@H](CCO)c1ccccc1] | 2-(6-{5-chloro-2-[(oxan-4-yl)amino]pyrimidin-4-yl}-1-oxo-2,3-dihydro-1H-isoindol-2-yl)-N-[(1S)-3-hydroxy-1-phenylpropyl]acetamide | 1H NMR (DMSO-d6) δ 8.57 (d, 1H), 8.45 (s, 1H), 8.03 (d, 1H), 7.98 (dd, 1H), 7.74 (d, 1H), 7.61 (s (br), 1H), 7.37-7.27 (m, 4H), 7.23 (m, 1H), 4.96 (dd, 1H), 4.58 (s, 2H), 4.52 (t, 1H), 4.28 (d, 1H), 4.21 (d, 1H), 3.82-3.98 (m, 3H), 3.46-3.35 (m, 4H), 1.76-1.95 (m, 4H), 1.53 (qd, 2H). | 536 |
| 421 | 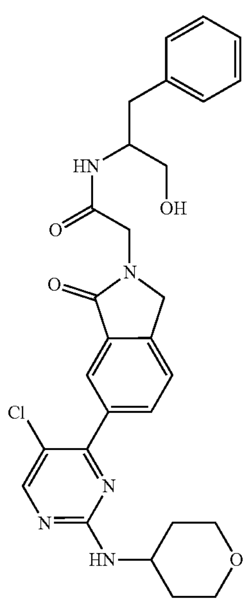 [SMILES: O=C(CN1Cc2ccc(-c3nc(NC4CCOCC4)ncc3Cl)cc2C1=O)NC(CO)Cc1ccccc1] | 2-(6-{5-chloro-2-[(oxan-4-yl)amino]pyrimidin-4-yl}-1-oxo-2,3-dihydro-1H-isoindol-2-yl)-N-(1-hydroxy-3-phenylpropan-2-yl)acetamide | 1H NMR (400 MHz, DMSO-d6) δ 8.45 (s, 1H), 8.05-8.00 (m, 2H), 7.98 (dd, 1H), 7.72 (d, 1H), 7.62 (s (br), 1H), 7.33-7.16 (m, 5H), 4.84 (t, 1H), 4.44 (d, 1H), 4.37 (d, 1H), 4.17 (d, 1H), 4.10 (d, 1H), 3.83-4.01 (m, 4H), 3.43-3.35 (m, 4H), 2.86 (dd, 1H), 2.65 (dd, 1H), 1.85 (m, 2H), 1.53 (qd, 2H). | 536 |

-continued

| Example | Structure | Name | ¹H NMR (400 MHz) | MS: [M + H]⁺ |
|---|---|---|---|---|
| 422 | 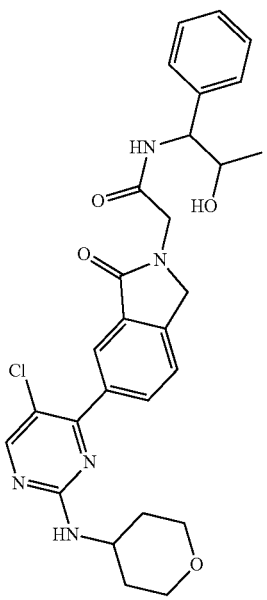 [SMILES: CC(O)C(NC(=O)CN1Cc2ccc(-c3nc(NC4CCOCC4)ncc3Cl)cc2C1=O)c1ccccc1] | 2-(6-{5-chloro-2-[(oxan-4-yl)amino]pyrimidin-4-yl}-1-oxo-2,3-dihydro-1H-isoindol-2-yl)-N-(2-hydroxy-1-phenylpropyl)-acetamide | 1H NMR (DMSO-d6) δ: 8.51 (dd, 1H), 8.50 (dd, 0.22H), 8.44 (s (br), 1.22H), 8.01 (d, 1.22H), 7.96 (dd, 1.22H), 7.73 (d, 1.22H), 7.62 (s, 1.22H), 7.36-7.26 (m, 4.88H), 7.26-7.19 (m, 1.22H), 4.82 (d, 0.22H), 4.74 (d, 2H), 4.70-4.73 (m, 1.22H), 4.57 (s (br), 2.44H), 4.37 (d, 0.22H), 4.32 (d, 1H), 4.28 (d, 0.22H), 4.25 (d, 1H), 3.98-3.79 (m, 4.88H), 3.42-3.33 (m, 2.44H), 1.88-1.79 (m, 2.44H), 1.58-1.46 (m, 2.44H), 1.02 (d, 3H), 0.99 (d, 0.66H). (82:18 mixture of cis- and trans-isomers). | 536 |
| 423 | 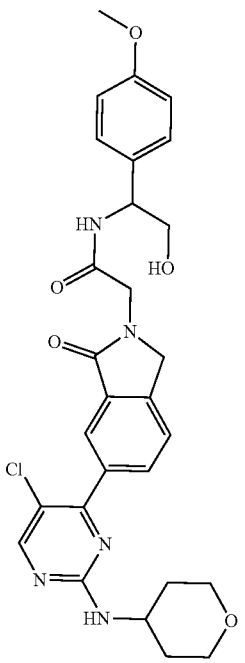 [SMILES: COc1ccc(C(CO)NC(=O)CN2Cc3ccc(-c4nc(NC5CCOCC5)ncc4Cl)cc3C2=O)cc1] | 2-(6-{5-chloro-2-[(oxan-4-yl)amino]pyrimidin-4-yl}-1-oxo-2,3-dihydro-1H-isoindol-2-yl)-N-[2-hydroxy-1-(4-methoxyphenyl)ethyl]acetamide | 1H NMR (DMSO-d6) δ: 8.49 (d, 1H), 8.45 (s, 1H), 8.03 (s, 1H), 7.98 (dd, 1H), 7.74 (d, 1H), 7.62(s (br), 1H), 7.24 (d, 2H), 6.89 (d, 2H), 4.88 (t, 1H), 4.83 (dt, 1H), 4.24 (d, 1H), 3.98-3.81 (m, 3H), 3.74 (s, 3H), 3.54 (dd, 2H), 3.45-3.35 (m, 2H), 1.92-1.77 (m, 2H), 1.61-1.45 (m, 2H). | 552 |

-continued

| Example | Structure | Name | ¹H NMR (400 MHz) | MS: [M + H]⁺ |
|---|---|---|---|---|
| 424 | 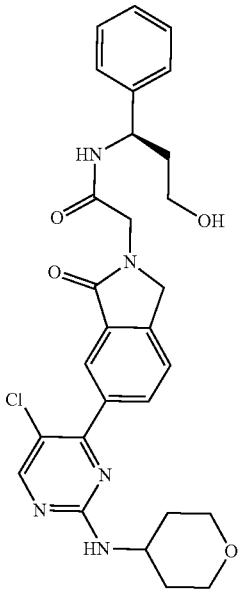 [SMILES: O=C(CN1Cc2ccc(-c3nc(NC4CCOCC4)ncc3Cl)cc2C1=O)N[C@H](CCO)c1ccccc1] | 2-(6-{5-chloro-2-[(oxan-4-yl)amino]pyrimidin-4-yl}-1-oxo-2,3-dihydro-1H-isoindol-2-yl)-N-[(1R)-3-hydroxy-1-phenylpropyl]acetamide | 1H NMR (DMSO-d6) δ: 8.57 (d, 1H), 8.45 (s, 1H), 8.02 (d, 1H), 7.98 (dd, 1H), 7.74 (d, 1H), 7.62 (s (br), 1H), 7.37-7.28 (m, 4H), 7.28-7.20 (m, 1H), 4.96 (td, 1H), 4.58 (s, 2H), 4.53 (s (br), 1H), 4.28 (d, 1H), 4.21 (d, 1H), 3.99-3.79 (m, 3H), 3.47-3.36 (m, 4H), 1.96-1.74 (m, 4H), 1.60-1.44 (m, 2H) | 536 |
| 425 | 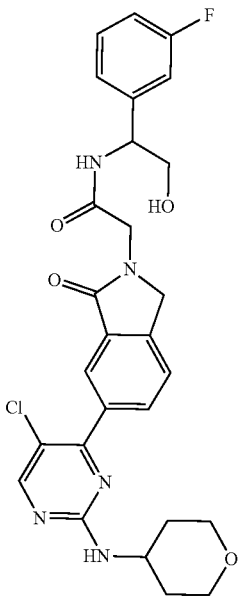 [SMILES: O=C(CN1Cc2ccc(-c3nc(NC4CCOCC4)ncc3Cl)cc2C1=O)NC(CO)c1cccc(F)c1] | 2-(6-{5-chloro-2-[(oxan-4-yl)amino]pyrimidin-4-yl}-1-oxo-2,3-dihydro-1H-isoindol-2-yl)-N-[1-(3-fluorophenyl)-2-hydroxyethyl]acetamide | 1H NMR (DMSO-d6) δ: 8.59 (d, 1H), 8.45 (s, 1H), 8.03 (d, 1H), 7.98 (dd, 1H), 7.74 (d, 1H), 7.63 (s (br), 1H), 7.42-7.32 (m, 1H), 7.21-7.13 (m, 2H), 7.13-7.03 (m, 1H), 4.99 (t, 1H), 4.91 (td, 1H), 4.59 (s, 2H), 4.34 (d, 1H), 4.28 (d, 1H), 4.00-3.80 (m, 3H), 3.64-3.53 (m, 2H), 3.44-3.35 (m, 2H), 1.91-1.79 (m, 2H), 1.60-1.44 (m, 2H) | 540 |

| Example | Structure | Name | ¹H NMR (400 MHz) | MS: [M + H]⁺ |
|---|---|---|---|---|
| 426 | 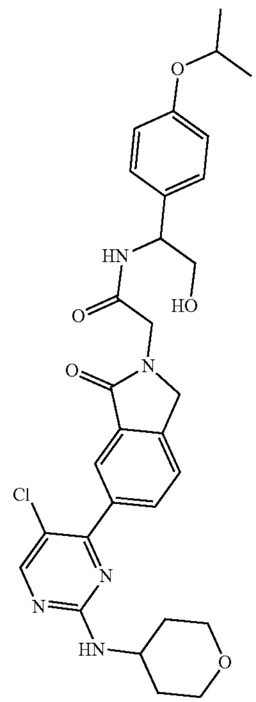 [SMILES: CC(C)Oc1ccc(C(CO)NC(=O)CN2Cc3ccc(-c4nc(NC5CCOCC5)ncc4Cl)cc3C2=O)cc1] | 2-(6-{5-chloro-2-[(oxan-4-yl)amino]pyrimidin-4-yl}-1-oxo-2,3-dihydro-1H-isoindol-2-yl)-N-{2-hydroxy-1-[4-(propan-2-yloxy)phenyl]ethyl}acetamide | 1H NMR (DMSO-d6) δ: 8.48 (d, 1H), 8.45 (s, 1H), 8.03 (d, 1H), 7.98 (dd, 1H), 7.74 (d, 1H), 7.61 (s (br), 1H), 7.21 (d, 2H), 6.86 (d, 2H), 4.86 (t, 1H), 4.82 (dt, 1H), 4.62-4.52 (m, 3H), 4.31 (d, 1H), 4.24 (d, 1H), 4.00-3.81 (m, 3H), 3.55 (dd, 2H), 3.44-3.34 (m, 2H), 1.91-1.78 (m, 2H), 1.60-1.46 (m, 2H), 1.25 (d, 6H) | 580 |
| 427 | 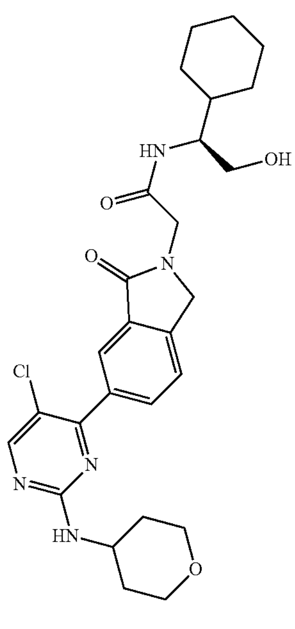 [SMILES: O=C(CN1Cc2ccc(-c3nc(NC4CCOCC4)ncc3Cl)cc2C1=O)N[C@H](CO)C1CCCCC1] | 2-(6-{5-chloro-2-[(oxan-4-yl)amino]pynmidin-4-yl}-1-oxo-2,3-dihydro-1H-isoindol-2-yl)-N-[(1S)-1-cyclohexyl-2-hydroxyethyl]-acetamide | 1H NMR (400 MHz, DMSO-d6) δ 8.44 (s, 1H), 8.02 (dd, 1H), 7.97 (dd, 1H), 7.81 (d, 1H), 7.74 (d, 1H), 7.62 (s (br), 1H), 4.59 (s, 3H), 4.27-4.18 (m, 2H), 3.98-3.81 (m, 3H), 3.63-3.56 (m, 1H), 3.42-3.35 (m, 4H), 1.86-1.83 (br m, 2H), 1.75-1.42 (m, 7H), 1.26-0.84 (m, 6H) | 528 |

| Example | Structure | Name | ¹H NMR (400 MHz) | MS: [M + H]⁺ |
|---|---|---|---|---|
| 428 | 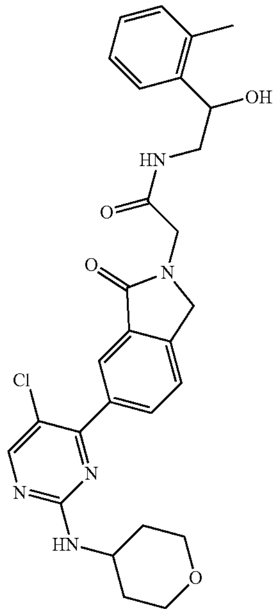 [SMILES: Cc1ccccc1C(O)CNC(=O)CN1Cc2ccc(-c3nc(NC4CCOCC4)ncc3Cl)cc2C1=O] | 2-(6-{5-chloro-2-[(oxan-4-yl)amino]pyrimidin-4-yl}-1-oxo-2,3-dihydro-1H-isoindol-2-yl)-N-[2-hydroxy-2-(2-methylphenyl)ethyl]-acetamide | 1H NMR (DMSO-d6) δ: 8.46 (s, 1H), 8.35 (dd, 1H), 8.03 (d, 1H), 7.99 (dd, 1H), 7.75 (d, 1H), 7.63 (s (br), 1H), 7.45 (d, 1H), 7.23-7.08 (m, 3H), 5.38 (d, 1H), 4.86 (dt, 1H), 4.56 (s, 2H), 4.26 (d, 1H), 4.19 (d, 1H), 4.01-3.82 (m, 3H), 3.43-3.29 (m, 3H), 3.04-2.93 (m, 1H), 2.31 (s, 3H), 1.90-1.79 (m, 2H), 1.61-1.45 (m, 2H). | 536 |
| 429 | 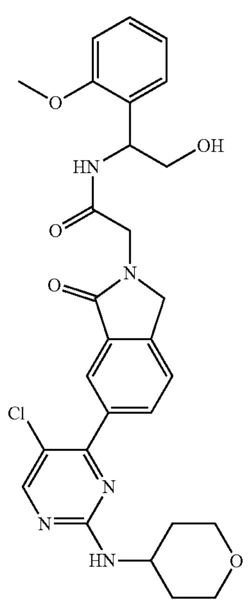 [SMILES: COc1ccccc1C(CO)NC(=O)CN1Cc2ccc(-c3nc(NC4CCOCC4)ncc3Cl)cc2C1=O] | 2-(6-{5-chloro-2-[(oxan-4-yl)amino]pyrimidin-4-yl}-1-oxo-2,3-dihydro-1H-isoindol-2-yl)-N-[2-hydroxy-1-(2-methoxyphenyl)ethyl]acetamide | 1H NMR (DMSO-d6, 400 MHz) δ 8.50-8.43 (2H, m), 8.06- 8.01 (1H, m), 7.97 (1H, dd), 7.74 (1H, d), 7.62 (1H, br. s), 7.29 (1H, dd), 7.26-7.21 (1H, m), 6.97 (1H, dd), 6.95-6.90 (1H, m), 5.29-5.22 (1H, m), 4.88 (1H, t), 4.59 (2H, s), 4.34 (1H, d), 4.27 (1H, d), 3.98-3.83 (3H, m), 3.79 (3H, s), 3.59-3.52 (1H, m), 3.47-3.36 (3H, m), 1.89-1.81 (2H, m), 1.59-1.47 (2H, m). | 552 |

| Example | Structure | Name | ¹H NMR (400 MHz) | MS: [M + H]⁺ |
|---|---|---|---|---|
| 430 | 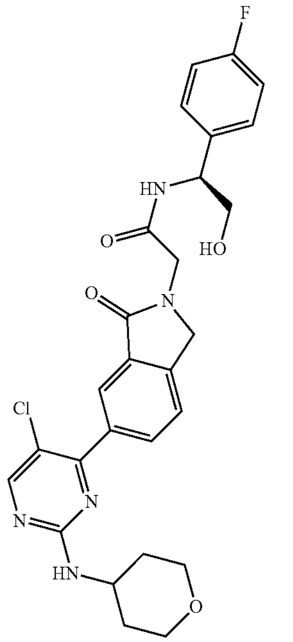 [SMILES: O=C(CN1Cc2ccc(-c3nc(NC4CCOCC4)ncc3Cl)cc2C1=O)N[C@H](CO)c1ccc(F)cc1] | 2-(6-{5-chloro-2-[(oxan-4-yl)amino]pyrimidin-4-yl}-1-oxo-2,3-dihydro-1H-isoindol-2-yl)-N-[(1S)-1-(4-fluorophenyl)-2-hydroxyethyl]-acetamide | 1H NMR (DMSO-d6) δ: 8.57 (d, 1H), 8.45 (s, 1H), 8.03 (dd, 1H), 7.98 (dd, 1H), 7.74 (d, 1H), 7.62 (s (br), 1H), 7.40-7.33 (m, 2H), 7.20-7.11 (m, 2H), 4.95 (t, 1H), 4.88 (m, 1H), 4.59 (s, 2H), 4.32 (d, 1H), 4.26 (d, 1H), 3.97-3.82 (m, 3H), 3.57 (dd, 2H), 3.44-3.33 (m, 2H), 1.90-1.80 (m, 2H), 1.58-1.48 (m, 2H). | 540 |
| 431 | 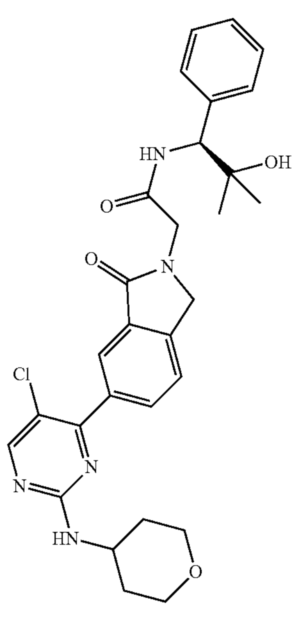 [SMILES: CC(C)(O)[C@@H](NC(=O)CN1Cc2ccc(-c3nc(NC4CCOCC4)ncc3Cl)cc2C1=O)c1ccccc1] | 2-(6-{5-chloro-2-[(oxan-4-yl)amino]pyrimidin-4-yl}-1-oxo-2,3-dihydro-1H-isoindol-2-yl)-N-[(1S)-2-hydroxy-2-methyl-1-phenylpropyl]-acetamide | 1H NMR (DMSO-d6) δ: 8.48 (d, 1H), 8.45 (s, 1H), 8.01 (d, 1H), 7.97 (dd, 1H), 7.73 (d, 1H), 7.62 (s (br), 1H), 7.41-7.33 (m, 2H), 7.32-7.26 (m, 2H), 7.26-7.21 (m, 1H), 4.75 (d, 1H), 4.59 (s, 1H), 4.56 (s, 2H), 4.38 (d, 1H), 4.28 (d, 1H), 3.97-3.81 (m, 3H), 3.43-3.36 (m, 2H), 1.89-1.79 (m, 2H), 1.58-1.46 (m, 2H), 1.14 (s, 3H), 1.01 (s, 3H). | 550 |

| Example | Structure | Name | ¹H NMR (400 MHz) | MS: [M + H]⁺ |
|---|---|---|---|---|
| 432 | 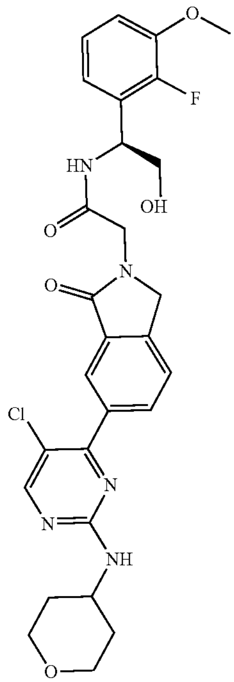 [SMILES: COc1cccc([C@@H](CO)NC(=O)CN2Cc3ccc(-c4nc(NC5CCOCC5)ncc4Cl)cc3C2=O)c1F] | 2-(6-{5-chloro-2-[(oxan-4-yl)amino]pyrimidin-4-yl}-1-oxo-2,3-dihydro-1H-isoindol-2-yl)-N-[(1S)-1-(2-fluoro-3-methoxyphenyl)-2-hydroxyethyl]-acetamide | 1H NMR (DMSO-d6) δ: 8.63 (d, 1H), 8.45 (s (br), 1H), 8.02 (d, 1H), 7.98 (dd 1H), 7.74 (d, 1H), 7.62 (s (br), 1H), 7.16-7.02 (m, 2H), 6.99-6.93 (m, 1H), 5.21-5.12 (m, 1H), 5.04 (t, 1H), 4.58 (s, 2H), 4.32 (d, 1H), 4.26 (d, 1H), 3.98-3.83 (m, 3H), 3.82 (s, 3H), 3.59-3.51 (m, 2H), 3.41-3.34 (m, 2H), 1.90-1.78 (m, 2H), 1.62-1.45 (m, 2H). | 570 |
| 434 | 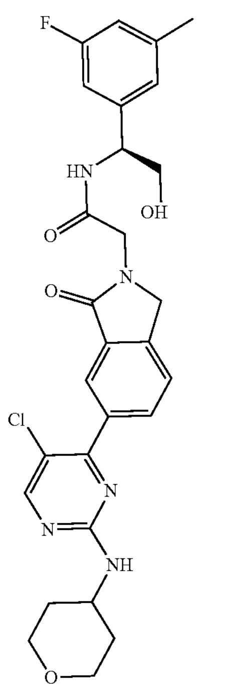 [SMILES: Cc1cc(F)cc([C@@H](CO)NC(=O)CN2Cc3ccc(-c4nc(NC5CCOCC5)ncc4Cl)cc3C2=O)c1] | 2-(6-{5-chloro-2-[(oxan-4-yl)amino]pyrimidin-4-yl}-1-oxo-2,3-dihydro-1H-isoindol-2-yl)-N-[(1S)-1-(3-fluoro-5-methylphenyl)-2-hydroxyethyl]acetamide | 1H NMR (DMSO-d6) δ: 8.55 (d, 1H), 8.45 (s, 1H), 8.03 (d, 1H), 7.98 (dd, 1H), 7.74 (d, 1H), 7.62 (s (br), 1H), 7.01-6.97 (m, 1H), 6.97-6.87 (m, 2H), 4.96 (t, 1H), 4.85 (td, 1H), 4.59 (s, 2H), 4.33 (d, 1H), 4.28 (d, 1H), 3.99-3.81 (m, 3H), 3.62-3.52 (m, 2H), 3.43-3.35 (m, 2H), 2.31 (s, 3H), 1.90-1.78 (m, 2H), 1.60-1.44 (m, 2H). | 554 |

-continued

| Example | Structure | Name | ¹H NMR (400 MHz) | MS: [M + H]⁺ |
|---|---|---|---|---|
| 435 | 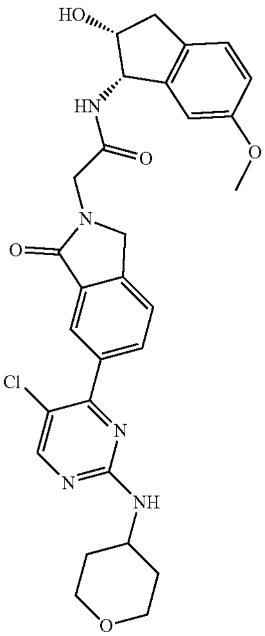 [SMILES: COc1ccc2c(c1)[C@H](NC(=O)CN1Cc3ccc(-c4nc(NC5CCOCC5)ncc4Cl)cc3C1=O)[C@H](O)C2] | 2-(6-{5-chloro-2-[(oxan-4-yl)amino]pyrimidin-4-yl}-1-oxo-2,3-dihydro-1H-isoindol-2-yl)-N-[(1S,2R)-2-hydroxy-6-methoxy-2,3-dihydro-1H-inden-1-yl]acetamide | 1H NMR (DMSO-d6) δ: 8.46 (s, 1H), 8.23 (d, 1H), 8.05 (d, 1H), 7.99 (dd, 1H), 7.77 (d, 1H), 7.63 (s (br), 1H), 7.14 (d, 1H), 6.82-6.73 (m, 2H), 5.19 (dd, 1H), 5.05 (d, 1H), 4.67 (s, 2H), 4.46-4.36 (m, 3H), 4.00-3.82 (m, 3H), 3.74 (s, 3H), 3.44-3.36 (m, 2H), 2.98 (dd, 1H), 2.74 (d, 1H), 1.90-1.77 (m, 2H), 1.60-1.45 (m, 2H). | 564 |
| 436 | 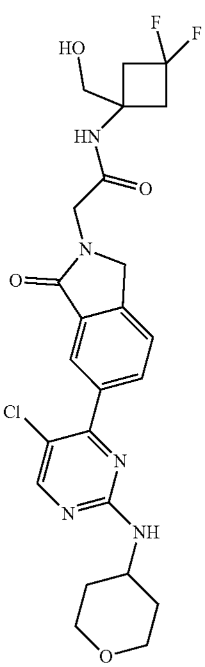 [SMILES: O=C(CN1Cc2ccc(-c3nc(NC4CCOCC4)ncc3Cl)cc2C1=O)NC1(CO)CC(F)(F)C1] | 2-(6-{5-chloro-2-[(oxan-4-yl)amino]pyrimidin-4-yl}-1-oxo-2,3-dihydro-1H-isoindol-2-yl)-N-[3,3-difluoro-1-(hydroxymethyl)cyclobutyl]acetamide | 1H NMR (DMSO-d6) δ: 8.52 (s, 1H), 8.45 (s, 1H), 8.03 (d, 1H), 7.98 (dd, 1H), 7.75 (d, 1H), 7.63 (s (br), 1H), 5.17 (t, 1H), 4.59 (s, 2H), 4.21 (s, 2H), 3.99-3.81 (m, 3H), 3.51 (d, 2H), 3.43-3.35 (m, 2H), 2.84-2.63 (m, 4H), 1.89-1.80 (m, 2H), 1.61-1.47(m, 2H). | 522 |

Examples 437-443

Prepared using an analogous procedure to Example 407, from 2-(6-{5-chloro-2-[(oxan-4-yl)amino]pyrimidin-4-yl}-1-oxo-2,3-dihydro-1H-isoindol-2-yl)acetic acid (Example 1) and the corresponding amine. In these cases, the products were further purified by preparative HPLC (acidic or basic methods as specified):

| Example | Structure/prep. Conditions | Name | ¹H NMR (400 MHz) | MS: [M + H]⁺ |
|---|---|---|---|---|
| 437 | 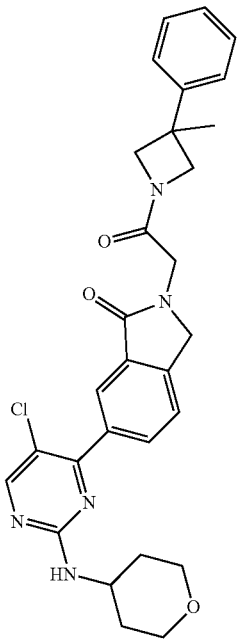<br>(basic method) | 6-{5-chloro-2-[(oxan-4-yl)amino]pyrimidin-4-yl}-2-[2-(3-methyl-3-phenylazetidin-1-yl)-2-oxoethyl]-2,3-dihydro-1H-isoindol-1-one | 1H NMR (400 MHz, CDCl3) δ 8.30 (d, 2H), 7.98 (d, 1H), 7.56 (d, 1H), 7.38- 7.34 (m, 2H), 7.27-7.25 (m, 1H), 7.21-7.19 (m, 1H), 5.21 (d, 1H), 4.72-4.60 (m, 2H), 4.52 (d, 1H), 4.36-4.22 (m, 4H), 4.08-3.96 (m, 4H), 3.57-3.50 (m, 2H), 2.06-2.02 (m, 2H), 1.83 (bs, 1H), 1.66 (s, 3H), 1.61-1.51 (m, 2H) | 532 |
| 438 | 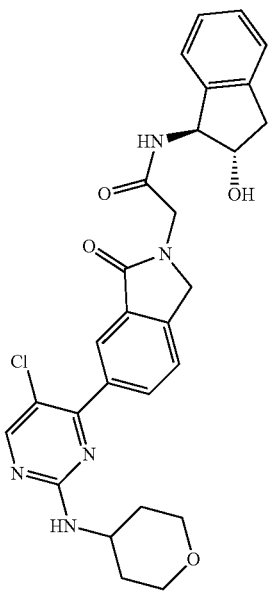<br>(acidic method) | 2-(6-{5-chloro-2-[(oxan-4-yl)amino]pyrimidin-4-yl}-1-oxo-2,3-dihydro-1H-isoindol-2-yl)-N-[(1S,2S)-2-hydroxy-2,3-dihydro-1H-inden-1-yl]acetamide | 1H NMR (DMSO-d6, 400 MHz) δ 8.50 (1H, d), 8.45 (1H, s), 8.06-8.01 (1H, m), 7.98 (1H, dd), 7.76 (1H, d), 7.61 (1H, s), 7.23-7.16 (3H, m), 7.16-7.08 (1H, m), 5.33 (1H, d), 5.07 (1H t), 4.65 (2H, d), 4.37-4.19 (3H, m), 3.99-3.80 (3H, m), 3.42-3.33 (2H, m), 3.11 (1H, dd), 2.77-2.63 (1H, m), 1.84 (2H, d), 1.52 (2H, qd). | 534 |

-continued

| Example | Structure/prep. Conditions | Name | ¹H NMR (400 MHz) | MS: [M + H]⁺ |
|---|---|---|---|---|
| 439 | 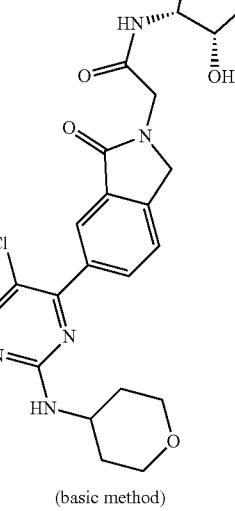<br>(basic method) | 2-(6-{5-chloro-2-[(oxan-4-yl)amino]pyrimidin-4-yl}-1-oxo-2,3-dihydro-1H-isoindol-2-yl)-N-[(1R,2S)-2-hydroxy-2,3-dihydro-1H-inden-1-yl]acetamide | 1H NMR (DMSO, 400 MHz) δ 8.45 (1H, s), 8.25 (1H, d), 8.04 (1H, d), 7.98 (1H, dd), 7.76 (1H, d), 7.62 (1H, bs), 7.26-7.17 (4H, m), 5.22 (1H, dd), 5.09 (1H, d), 4.66 (2H, s), 4.44 (1H, dd), 4.38 (2H, s), 3.95-3.85 (3H, m), 3.42-3.34 (2H, m), 3.06 (1H, dd), 2.81 (1H, dd), 1.85 (2H, d), 1.53 (2H, qd). | 534 |
| 440 | 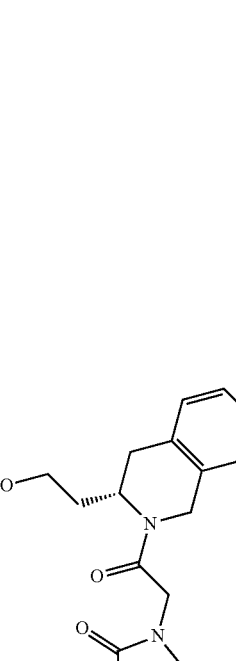<br>(acidic method) | 6-{5-chloro-2-[(oxan-4-yl)amino]pyrimidin-4-yl}-2-{2-[(3S)-3-(2-hydroxyethyl)-1,2,3,4-tetrahydroisoquinolin-2-yl]-2-oxoethyl}-2,3-dihydro-1H-isoindol-1-one | 1H NMR (DMSO-d6, 400 MHz) δ 8.45 (1H, s), 8.03 (1H, t), 7.98 (1H, dd), 7.77-7.72 (1H, m), 7.62 (1H, s), 7.25-7.16 (4H, m), 5.06 (0.7H, d, major rotamer), 4.90-4.81 (0.7H, m, major rotamer), 4.74-4.72 (0.5H, m, minor rotamer), 4.68-4.44 (5H, m), 4.37-4.33 (0.5H, m, minor rotamer), 4.09 (0.7H, d, major rotamer), 3.99-3.80 (3H, m), 3.55-3.47 (0.7H, m, major rotamer), 3.44-3.34 (3H, m), 3.19 (0.7H, dd, major rotamer), 2.94 (0.5H, dd, minor rotamer), 2.81-2.64 (1.3H, m), 1.84 (2H, d), 1.70-1.36 (4H, m). | 562 |

| Example | Structure/prep. Conditions | Name | ¹H NMR (400 MHz) | MS: [M + H]⁺ |
|---|---|---|---|---|
| 441 | (acidic method) | 6-{5-chloro-2-[(oxan-4-yl)amino]pyrimidin-4-yl}-2-{2-[(3S)-7-fluoro-3-(hydroxymethyl)-1,2,3,4-tetrahydroisoquinolin-2-yl]-2-oxoethyl}-2,3-dihydro-1H-isoindol-1-one | 1H NMR (DMSO-d6, 400 MHz) δ 8.45 (1H, s), 8.04-8.03 (1H, m), 7.98 (1H, dd), 7.75 (1H, d), 7.62 (1H, s), 7.23 (1H, ddd), 7.11 (1H, ddd), 7.03 (1H, qd), 5.11 (1H, t), 4.99 (1H, d), 4.88-4.32 (5H, m), 4.39-4.32 (1H, m), 4.16 (1H, d), 3.97-3.83 (3H, m), 3.41-3.34 (2H, m), 3.20-3.01 (1H, m), 2.93-2.78 (1H, m), 1.84 (2H, d), 1.60-1.44 (2H, m). | 566 |
| 442 | (acidic method) | N-(2-benzyl-1-hydroxypropan-2-yl)-2-(6-{5-chloro-2-[(oxan-4-yl)amino]pyrimidin-4-yl}-1-oxo-2,3-dihydro-1H-isoindol-2-yl)acetamide | 1H NMR (DMSO-d6, 400 MHz, 90° C.) 6 8.41 (1H, s), 8.09 (1H, d), 8.01 (1H, dd), 7.73 (1H, dd), 7.29-7.14 (6H, m), 7.09 (1H, s), 4.61-4.57 (3H, m), 4.17 (2H, s), 4.03-3.86 (3H, m), 357-3.34 (4H, m), 3.11 (1H, d), 2.89 (1H, d), 1.96- 1.82 (2H, m), 1.69-1.50 (2H, m), 1.18 (3H, s). | 550 |

| Example | Structure/prep. Conditions | Name | ¹H NMR (400 MHz) | MS: [M + H]⁺ |
|---|---|---|---|---|
| 443 | | 2-(6-{5-chloro-2-[(oxan-4-yl)amino]pyrimidin-4-yl}-1-oxo-2,3-dihydro-1H-isoindol-2-yl)-N-[(1S)-2-hydroxy-1-(3-methylphenyl)ethyl]acetamide | 1H NMR (DMSO-d6, 400 MHz) δ 8.45 (1H, d), 8.44 (1H, s), 8.02 (1H, d), 7.97 (1H, dd), 7.73 (1H, d), 7.62 (1H, s), 7.20 (1H, t), 7.15-7.07 (2H, m), 7.05 (1H, d), 4.93 (1H, s), 4.83 (1H, q), 4.58 (2H, s), 4.35-4.22 (2H, m), 3.97-3.81 (3H, m), 3.56 (2H, d), 2.29 (3H, s), 1.89-1.79 (2H, m), 1.59-1.46 (2H, m). (2 protons signals overlapped with water peak). | 536 |

Examples 444, 445 and 456: 2-(6-{5-chloro-2-[(oxan-4-yl}amino]pyrimidin-4-yl}-1-oxo-2,3-dihydro-1H-isoindol-2-yl)-N-[2-hydroxy-1-(3-methoxyphenyl)ethyl]acetamide, 2-(6-{5-chloro-2-[(oxan-4-yl)amino]pyrimidin-4-yl}-1-oxo-2,3-dihydro-1H-isoindol-2-yl)-N-[(1R)-2-hydroxy-1-(3-methoxyphenyl)ethyl]acetamide and 2-(6-{5-chloro-2-[(oxan-4-yl)amino]pyrimidin-4-yl}-1-oxo-2,3-dihydro-1H-isoindol-2-yl)-N-[(1S)-2-hydroxy-1-(3-methoxyphenyl)ethyl]acetamide

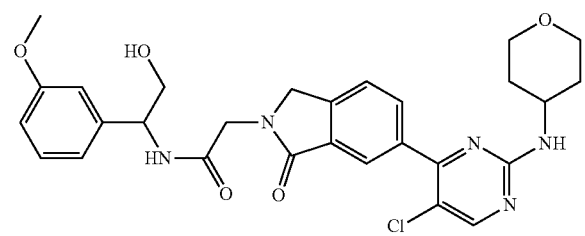

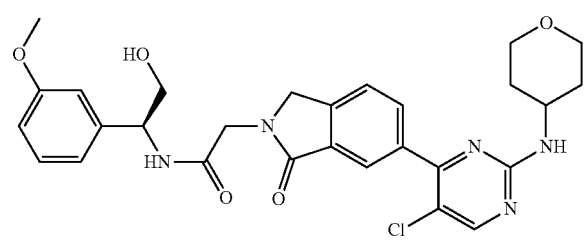

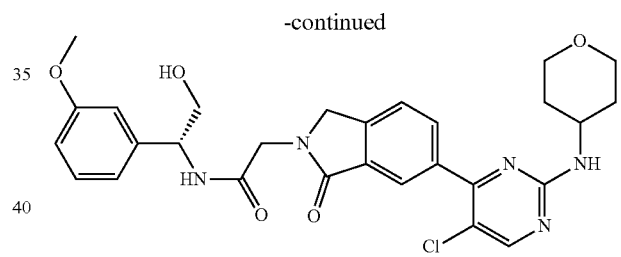

2-(6-{5-chloro-2-[(oxan-4-yl)amino]pyrimidin-4-yl}-1-oxo-2,3-dihydro-1H-isoindol-2-yl)-N-[2-hydroxy-1-(3-methoxyphenyl)ethyl]acetamide was prepared using a similar procedure to Example 407. 1H NMR (DMSO-d6) δ: 8.54 (d, 1H), 8.45 (s, 1H), 8.03 (d, 1H), 7.98 (dd, 1H), 7.74 (d, 1H), 7.63 (s (br), 1H), 7.28-7.18 (m, 1H), 6.95-6.85 (m, 2H), 6.84-6.78 (m, 1H), 4.92 (t, 1H), 4.86 (m, 1H), 4.60 (s, 2H), 4.33 (d, 1H), 4.27 (d, 1H), 3.99-3.81 (m, 3H), 3.75 (s, 3H), 3.64-3.51 (m, 2H), 3.43-3.33 (m, 2H), 1.85 (m, 2H), 1.60-1.43 (m, 2H). LC-MS: [M+H]+=552. The enantiomers were separated by preparative HPLC on a Lux C4 (21.2 mm×250 mm, m) column, using a 0.1% NH₃ in MeOH at 21 ml/min as eluent to give 2-(6-{5-chloro-2-[(oxan-4-yl)amino]pyrimidin-4-yl}-1-oxo-2,3-dihydro-1H-isoindol-2-yl)-N-[(1R)-2-hydroxy-1-(3-methoxyphenyl)ethyl]acetamide and and 2-(6-{5-chloro-2-[(oxan-4-yl)amino]pyrimidin-4-yl}-1-oxo-2,3-dihydro-1H-isoindol-2-yl)-N-[(1S)-2-hydroxy-1-(3-methoxyphenyl)ethyl]acetamide as white solids.

Example 447: 2-(6-{5-chloro-2-[(oxan-4-yl)amino]pyrimidin-4-yl}-1-oxo-2,3-dihydro-1H-isoindol-2-yl)-N-[(1S)-1-(3-chlorophenyl)-2-hydroxyethyl]acetamide

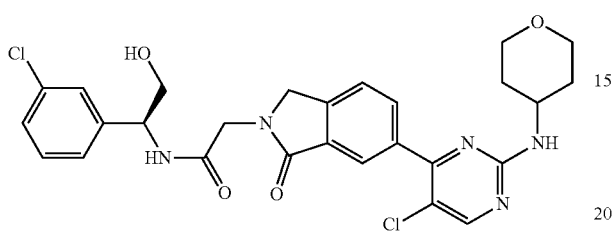

The title compound can be prepared using a similar procedure to Example 407 or methods analogous thereto.

Example 448: 2-(6-{5-chloro-2-[(oxan-4-yl)amino]pyrimidin-4-yl}-1-oxo-2,3-dihydro-1H-isoindol-2-yl)-N-[(1S)-1-(4-cyclopropylphenyl)-2-hydroxyethyl]acetamide

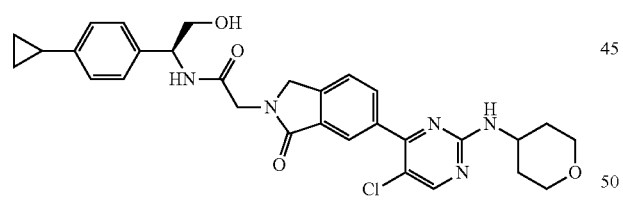

Prepared using a similar procedure to Example 407. In this case, the product was further purified by preparative HPLC (Varian, Acidic (0.1% Formic acid), Acidic, Waters X-Select Prep-C18, 5 μm, 19×50 mm column, 20-50% MeCN in Water) followed by washing with HCl, NaHCO₃ and brine. 1H NMR (DMSO-d6, 400 MHz) δ 8.51 (1H, d), 8.44 (1H, s), 8.02 (1H, d), 7.97 (1H, dd), 7.73 (1H, d), 7.61 (1H, s), 7.21-7.15 (2H, m), 7.06-6.98 (2H, m), 4.86-4.78 (1H, m), 4.58 (2H, s), 4.33-4.20 (2H, m), 3.98-3.81 (3H, m), 3.54 (2H, d), 3.42-3.36 (2H, m), 1.93-1.78 (3H, m), 1.60-1.45 (2H, m), 0.94-0.88 (2H, m), 0.66-0.60 (2H, m). (note: OH not observed). LCMS: [M+H]+=562.

Example 449: 6-{5-chloro-2-[(oxan-4-yl)amino]pyrimidin-4-yl}-2-[2-oxo-2-(5,6,7,8-tetrahydro-1,6-naphthyridin-6-yl)ethyl]-2,3-dihydro-1H-isoindol-1-one

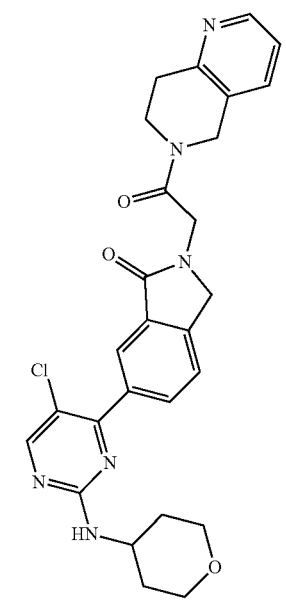 [SMILES: O=C(CN1Cc2ccc(-c3nc(NC4CCOCC4)ncc3Cl)cc2C1=O)N1CCc2ncccc2C1]

Prepared using an analogous procedure to Example 95, from 2-(6-{5-chloro-2-[(oxan-4-yl)amino]pyrimidin-4-yl}-1-oxo-2,3-dihydro-1H-isoindol-2-yl)acetic acid (Example 1) and the corresponding amine. 1H NMR (400 MHz, DMSO-d6, VT T=350K) δ: 8.38-8.43 (m, 2H), 8.08 (d, 1H), 8.01 (dd, 1H), 7.73 (dd, 1H), 7.57-7.67 (m (br), 2H), 7.28 (d (br), 1H), 7.23 (dd, 1H), 4.74 (s (br), 1H), 4.61 (s, 2H), 4.60 (s, 2H), 3.82-4.03 (m, 5H), 3.41 (ddd, 2H), 3.01 (m (br), 2H), 1.85-1.94 (m, 2H), 1.53-1.65 (m, 2H). MS: [M+H]+= 519.

Example 450: 2-(6-{5-chloro-2-[(oxan-4-yl)amino]pyrimidin-4-yl}-1-oxo-2,3-dihydro-1H-isoindol-2-yl)-N-[(1S)-1-(2-fluoro-5-methylphenyl)-2-hydroxyethyl]acetamide

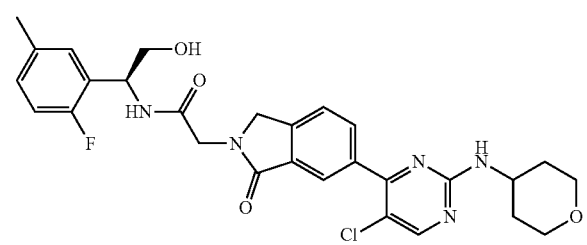 [SMILES: Cc1ccc(F)c([C@@H](CO)NC(=O)CN2Cc3ccc(-c4nc(NC5CCOCC5)ncc4Cl)cc3C2=O)c1]

Prepared using a similar procedure to Example 95. In this case and following purification, the product was dissolved in EtOAc (20 mL) and washed with 1 M HCl (10 mL). The layers were separated and the organic extract was washed with water (2×10 mL), NaHCO$_3$ (10 mL) and brine (3×10 mL), dried (MgSO$_4$), filtered, concentrated under reduced pressure. 1H NMR (DMSO-d6, 400 MHz) δ 8.60 (1H, d), 8.45 (1H, s), 8.03 (1H, dd), 7.98 (1H, dd), 7.74 (1H, d), 7.63 (1H, br. s), 7.24-7.18 (1H, m), 7.13-6.99 (2H, m), 5.14 (1H, q), 5.04 (1H, t), 4.59 (2H, s), 4.30 (2H, d), 3.97-3.84 (3H, m), 3.61-3.51 (2H, m), 3.40-3.33 (2H, m), 2.29 (3H, s), 1.85 (2H, br. d), 1.53 (2H, qd). LCMS: [M+H]+=554.

Example 451: 2-(6-{5-chloro-2-[(oxan-4-yl)amino]pyrimidin-4-yl}-1-oxo-2,3-dihydro-1H-isoindol-2-yl)-N-[(1S,2S)-2-hydroxy-1-phenylpropyl]acetamide

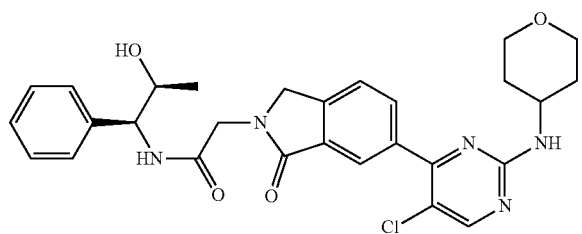 [SMILES: C[C@H](O)[C@@H](NC(=O)CN1Cc2ccc(-c3nc(NC4CCOCC4)ncc3Cl)cc2C1=O)c1ccccc1]

HATU (104 mg, 0.273 mmol) was added to a mixture of 2-(6-{5-chloro-2-[(oxan-4-yl)amino]pyrimidin-4-yl}-1-oxo-2,3-dihydro-1H-isoindol-2-yl)acetic acid (100 mg, 0.248 mmol), (1S,2S)-1-amino-1-phenylpropan-2-ol hydrochloride (51.2 mg, 0.273 mmol), and triethylamine (0.138 mL, 0.993 mmol) in DMF (1.5 mL, 19.37 mmol). The reaction was stirred for 2 h at room temperature. The reaction was diluted with water (20 mL), then extracted with EtOAc (3×10 mL). The combined organic extracts were washed with 1 M HCl (2×20 mL), brine (3×20 mL), dried (MgSO$_4$) and concentrated. The crude product was purified by chromatography (SiO$_2$, 12 g column, 0-10% MeOH in DCM) to afford title compound 2-(6-(5-chloro-2-((oxan-4-yl)amino)pyrimidin-4-yl)-1-oxoisoindolin-2-yl)-N-((1S,2S)-2-hydroxy-1-phenylpropyl)acetamide (73 mg, 54.3%) as a white solid. 1H NMR (DMSO-d6, 400 MHz) δ 8.50 (1H, d), 8.45 (1H, s), 8.04-8.01 (1H, m), 7.97 (1H, dd), 7.73 (1H, d), 7.62 (1H, br. s), 7.38-7.28 (4H, m), 7.26-7.20 (1H, m), 4.82 (1H, d), 4.72 (1H, dd), 4.58 (2H, s), 4.37 (1H, d), 4.29 (1H, d), 4.00-3.82 (4H, m), 3.41-3.35 (2H, m), 1.90-1.81 (2H, m), 1.59-1.46 (2H, m), 1.00 (3H, d). LC-MS: [M+H]+=536.

Examples 452-462

Prepared using an analogous procedure to Example 451, from 2-(6-{5-chloro-2-[(oxan-4-yl)amino]pyrimidin-4-yl}-1-oxo-2,3-dihydro-1H-isoindol-2-yl)acetic acid (Example 1) and the corresponding amine.

| Example | Structure | Name | $^1$H NMR (400 MHz) | MS: [M + H]$^+$ |
|---|---|---|---|---|
| 452 | 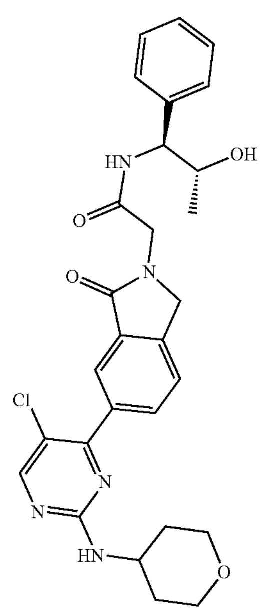 [SMILES: C[C@@H](O)[C@@H](NC(=O)CN1Cc2ccc(-c3nc(NC4CCOCC4)ncc3Cl)cc2C1=O)c1ccccc1] | 2-(6-{5-chloro-2-[(oxan-4-yl)amino]pyrimidin-4-yl}-1-oxo-2,3-dihydro-1H-isoindol-2-yl)-N-[(1S,2R)-2-hydroxy-1-phenylpropyl]acetamide | 1H NMR (DMSO-d6, 400 MHz) δ 8.51 (1H, d), 8.45 (1H, s), 8.03-8.01 (1H, m), 7.97 (1H, dd), 7.74 (1H, d), 7.62 (1H, br. s), 7.35-7.28 (4H, m), 7.26-7.20 (1H, m), 4.76-4.70 (2H, m), 4.57 (2H, s), 4.32 (1H, d), 4.26 (1H, d), 4.01-3.82 (4H, m), 3.42-3.35 (2H, m), 1.89-1.81 (2H, m), 1.60-1.46 (2H, m), 1.03 (3H, d). | 536 |

| Example | Structure | Name | ¹H NMR (400 MHz) | MS: [M + H]⁺ |
|---|---|---|---|---|
| 453 | 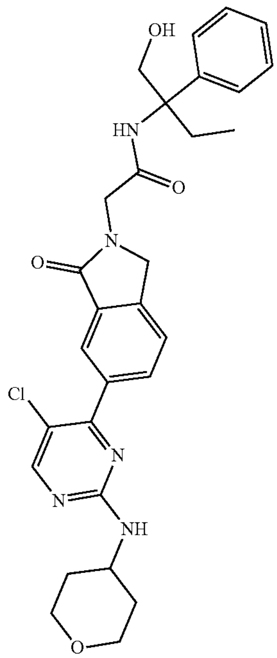 [SMILES: CCC(CO)(NC(=O)CN1Cc2ccc(-c3nc(NC4CCOCC4)ncc3Cl)cc2C1=O)c1ccccc1] | 2-(6-{5-chloro-2-[(oxan-4-yl)amino]pyrimidin-4-yl}-1-oxo-2,3-dihydro-1H-isoindol-2-yl)-N-(1-hydroxy-2-phenylbutan-2-yl)acetamide | 1H NMR (DMSO-d6, 400 MHz) δ 8.45 (1H, s), 8.04-7.94 (3H, m), 7.73 (1H, d), 7.63 (1H, br. s), 7.32-7.25 (4H, m), 7.21-7.14 (1H, m), 4.85 (1H, t), 4.60 (1H, d), 4.54 (1H, d), 4.34 (2H, s), 3.99-3.82 (4H, m), 3.74 (1H, dd), 3.42-3.36 (2H, m), 2.04-1.91 (2H, m), 1.89-1.82 (2H, m), 1.59-1.45 (2H, m), 0.73 (3H, t) | 550 |
| 454 | 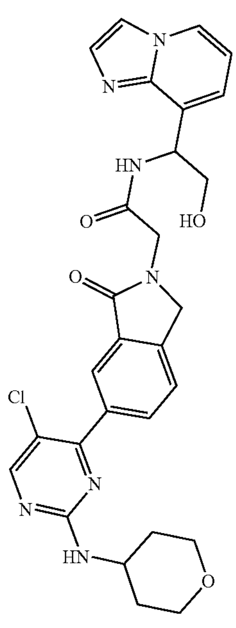 [SMILES: O=C(CN1Cc2ccc(-c3nc(NC4CCOCC4)ncc3Cl)cc2C1=O)NC(CO)c1cccn2ccnc12] | 2-(6-{5-chloro-2-[(oxan-4-yl)amino]pyrimidin-4-yl}-1-oxo-2,3-dihydro-1H-isoindol-2-yl)-N-(2-hydroxy-1-{imidazo[1,2-a]pyridin-8-yl}ethyl)acetamide | 1H NMR (DMSO-d6, 400 MHz) δ 8.87 (1H, d), 8.45 (1H, s), 8.05 (1H, s), 8.03 (1H, d,), 7.98 (1H, dd), 7.79(1H, d), 7.74 (1H, d), 7.63 (1H, s (br)), 7.63 (d, 1H), 7.43 (1H, dd), 7.05 (1H, d), 5.36 (1H, q), 5.20 (1H, t), 4.59 (2H, s), 4.38 (1H, d), 4.30 (1H, d), 3.85 (5H, td), 3.42-3.37 (2H, m), 1.84 (2H, d), 1.53 (2H, qd). | 562 |

| Example | Structure | Name | ¹H NMR (400 MHz) | MS: [M + H]⁺ |
|---------|-----------|------|------------------|--------------|
| 455 | 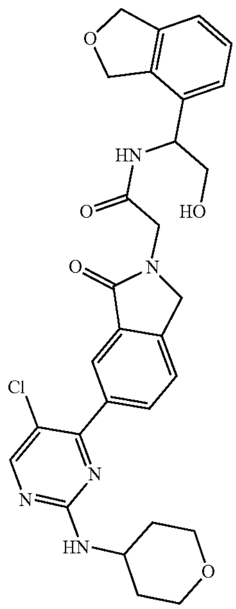 [SMILES: O=C(CN1Cc2ccc(-c3nc(NC4CCOCC4)ncc3Cl)cc2C1=O)NC(CO)c1cccc2c1COC2] | 2-(6-{5-chloro-2-[(oxan-4-yl)amino]pyrimidin-4-yl}-1-oxo-2,3-dihydro-1H-isoindol-2-yl)-N-[1-(1,3-dihydro-2-benzofuran-4-yl)-2-hydroxyethyl]-acetamide | 1H NMR (DMSO-d6, 400 MHz) δ 8.60 (1H, d), 8.45 (1H, s), 8.02 (1H, dd), 7.97 (1H, dd), 7.73 (1H, d), 7.61 (1H, s), 7.32-7.22 (2H, m), 7.19 (1H, d), 5.08 (2H, d), 4.94-501 (3H, m), 4.75 (1H, q), 4.58 (2H, s), 4.36-4.19 (2H, m), 3.90 (3H, dd), 3.67-3.49 (2H, m), 3.39 (1H, d), 1.85 (2H, d), 1.53 (2H, qd) | 564 |
| 456 | 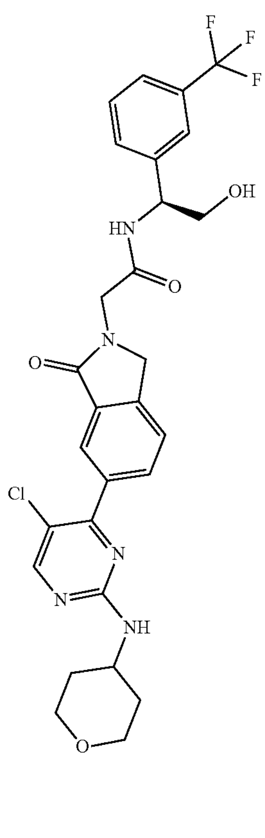 [SMILES: O=C(CN1Cc2ccc(-c3nc(NC4CCOCC4)ncc3Cl)cc2C1=O)N[C@H](CO)c1cccc(C(F)(F)F)c1] | 2-(6-{5-chloro-2-[(oxan-4-yl)amino]pyrimidin-4-yl}-1-oxo-2,3-dihydro-1H-isoindol-2-yl)-N-[(1S)-2-hydroxy-1-[3-(trifluoromethyl)phenyl]ethyl]acetamide | 1H NMR (DMSO-d6, 400 MHz) δ 8.70 (1H, d), 8.45 (1H, s), 8.03 (1H, dd), 7.98 (1H, dd), 7.80-7.68 (2H, m), 7.68-7.54 (4H, m), 5.03 (1H, t), 5.01-4.94 (1H, m), 4.59 (2H, s), 4.44-4.23 (2H, m), 3.89 (3H, dd), 3.62 (2H, t), 3.33-3.43 (2H, m), 1.85 (2H, d), 1.52 (2H, qd). | 590 |

| Example | Structure | Name | ¹H NMR (400 MHz) | MS: [M + H]⁺ |
|---|---|---|---|---|
| 457 | 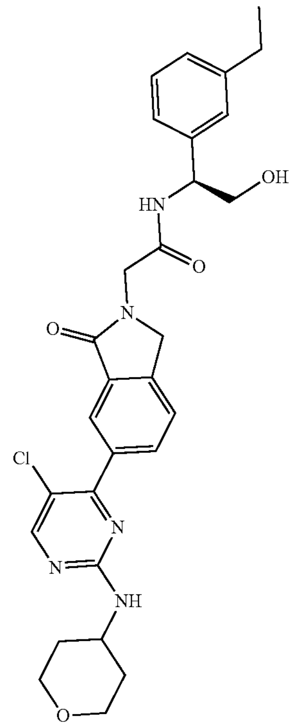 [SMILES: CCc1cccc([C@@H](CO)NC(=O)CN2Cc3ccc(-c4nc(NC5CCOCC5)ncc4Cl)cc3C2=O)c1] | 2-(6-{5-chloro-2-[(oxan-4-yl)amino]pyrimidin-4-yl}-1-oxo-2,3-dihydro-1H-isoindol-2-yl)-N-[(1S)-1-(3-ethylphenyl)-2-hydroxyethyl]-acetamide | 1H NMR (DMSO-d6, 400 MHz) δ 8.54 (1H, d), 8.45 (1H, s), 8.03 (1H, dd), 7.98 (1H, dd), 7.74 (1H, d), 7.62 (1H, s), 7.24 (1H, t), 7.19-7.06 (3H, m), 4.92 (1H, t), 4.86 (1H, q), 4.59 (2H, s), 4.29 (2H, d), 3.89 (3H, dd), 3.61-3.53 (2H, m), 3.33-3.43 (2H, m), 2.59 (2H, q), 1.85 (2H, d), 1.53 (2H, qd), 1.18 (3H, t). | 550 |
| 458 | 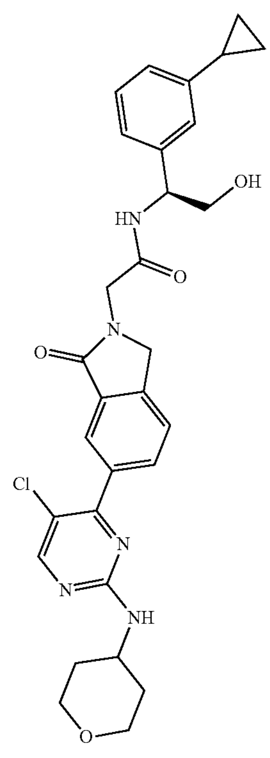 [SMILES: O=C(CN1Cc2ccc(-c3nc(NC4CCOCC4)ncc3Cl)cc2C1=O)N[C@H](CO)c1cccc(C2CC2)c1] | 2-(6-{5-chloro-2-[(oxan-4-yl)amino]pyrimidin-4-yl}-1-oxo-2,3-dihydro-1H-isoindol-2-yl)-N-[(1S)-1-(3-cyclopropylphenyl)-2-hydroxyethyl]acetamide | 1H NMR (DMSO-d6, 400 MHz) δ 8.52 (1H, d), 8.45 (1H, s), 8.03 (1H, dd), 7.98 (1H, dd), 7.74 (1H, d), 7.62 (1H, s), 7.19 (1H, t), 7.11-7.01 (2H, m), 6.93 (1H, dt), 4.91 (1H, t), 4.83 (1H, q), 4.59 (2H, s), 4.29 (2H, dd), 3.90 (3H, dd), 3.55 (2H, t), 3.33-3.43 (2H, m), 1.94-1.79 (3H, m), 1.53 (2H, qd), 0.99-0.88 (2H, m), 0.73-0.58 (2H, m) | 562 |

-continued

| Example | Structure | Name | ¹H NMR (400 MHz) | MS: [M + H]⁺ |
|---|---|---|---|---|
| 459 | 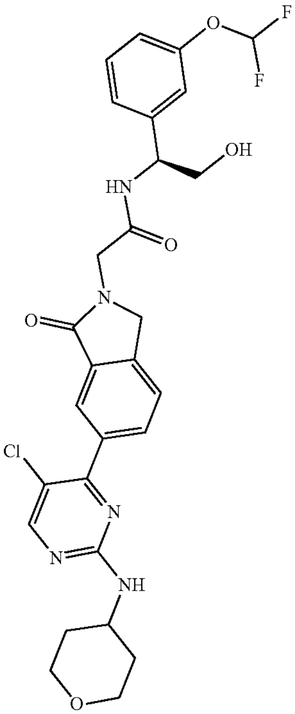 [SMILES: O=C(CN1Cc2ccc(-c3nc(NC4CCOCC4)ncc3Cl)cc2C1=O)N[C@H](CO)c1cccc(OC(F)F)c1] | 2-(6-{5-chloro-2-[(oxan-4-yl)amino]pyrimidin-4-yl}-1-oxo-2,3-dihydro-1H-isoindol-2-yl)-N-[(1S)-1-[3-(difluoromethoxy)phenyl]-2-hydroxyethyl]acetamide | 1H NMR (DMSO-d6, 400 MHz) δ 8.61 (1H, d, J = 8.2 Hz), 8.44 (1H, s), 8.02 (1H, dd), 7.97 (1H, dd), 7.73 (1H, d), 7.62 (1H, s), 7.43-7.35 (1H, m), 7.25-7.18 (2H, m), 7.14 (1H, t), 7.08-7.02 (1H, m), 4.99 (1H,), 4.89 (1H, q), 4.58 (2H, s), 4.38-4.22 (2H, m), 3.89 (3H, dd), 3.58 (2H, t), 3.42-3.34 (2H, m), 1.84 (2H, d), 1.52 (2H, dddd). | 588 |
| 460 | 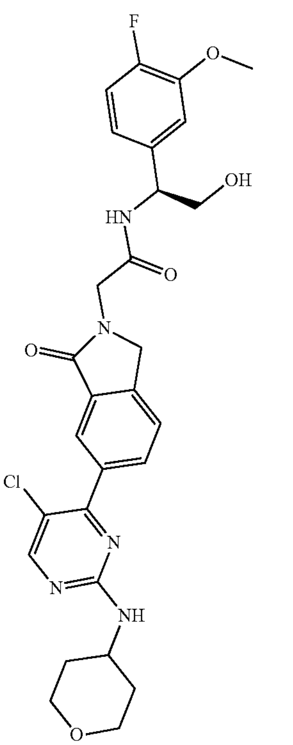 [SMILES: COc1cc([C@@H](CO)NC(=O)CN2Cc3ccc(-c4nc(NC5CCOCC5)ncc4Cl)cc3C2=O)ccc1F] | 2-(6-{5-chloro-2-[(oxan-4-yl)amino]pyrimidin-4-yl}-1-oxo-2,3-dihydro-1H-isoindol-2-yl)-N-[(1S)-1-(4-fluoro-3-methoxyphenyl)-2-hydroxyethyl]-acetamide | 1H NMR (DMSO-d6, 400 MHz) δ 8.54 (1H, d), 8.44 (1H, s), 8.02 (1H, d), 7.97 (1H, dd), 7.74 (1H, d), 7.62 (1H, s), 7.20-7.09 (2H, m), 6.87 (1H, ddd), 4.92 (1H, t), 4.86 (1H, q), 4.59 (2H, s), 4.29 (2H, s), 3.99-3.78 (6H, m), 3.62-3.52 (2H, m), 3.43-3.32 (2H, m), 1.90-1.78 (2H, m), 1.52 (2H, dddd). | 570 |

| Example | Structure | Name | ¹H NMR (400 MHz) | MS: [M + H]⁺ |
|---|---|---|---|---|
| 461 | 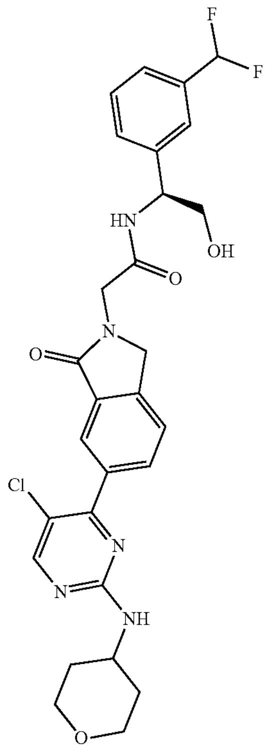 [SMILES: O=C(CN1Cc2ccc(-c3nc(NC4CCOCC4)ncc3Cl)cc2C1=O)N[C@H](CO)c1cccc(C(F)F)c1] | 2-(6-{5-chloro-2-[(oxan-4-yl)amino]pyrimidin-4-yl}-1-oxo-2,3-dihydro-1H-isoindol-2-yl)-N-[(1S)-1-[3-(difluoromethyl)phenyl]-2-hydroxyethyl]-acetamide | 1H NMR (DMSO-d6, 400 MHz) δ 8.66 (1H, d), 8.44 (1H, s), 8.02 (1H, dd), 7.97 (1H, dd), 7.73 (1H, d), 7.62 (1H, s), 7.56-7.42 (4H, m), 7.03 (1H, t), 5.03-4.96 (1H, m), 4.96-4.89 (1H,m), 4.58 (2H, s), 4.33 (1H, d), 4.27 (1H, d), 4.00-3.78 (3H, m), 3.60 (2H, dd), 3.45-3.34 (2H, m), 1.88-1.78 (2H, m), 1.61-1.43 (2H, m). | 572 |
| 462 | 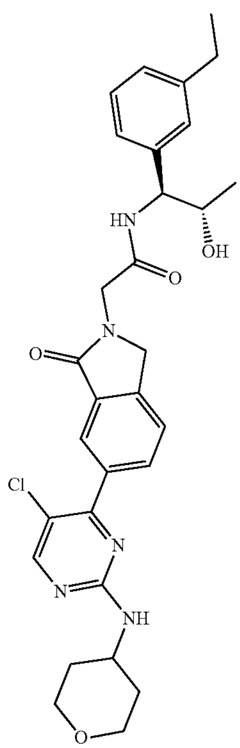 [SMILES: CCc1cccc([C@H](NC(=O)CN2Cc3ccc(-c4nc(NC5CCOCC5)ncc4Cl)cc3C2=O)[C@H](C)O)c1] | 2-(6-{5-chloro-2-[(oxan-4-yl)amino]pyrimidin-4-yl}-1-oxo-2,3-dihydro-1H-isoindol-2-yl)-N-[(1S,2S)-1-(3-ethylphenyl)-2-hydroxypropyl]-acetamide | 1H NMR (DMSO-d6, 400 MHz) δ 8.50-8.44 (2H, m), 8.06-8.00 (1H, m), 7.97 (1H, dd), 7.73 (1H, d), 7.63 (1H, br. s), 7.25- 7.20 (1H, m), 7.18-7.12 (2H, m), 7.09-7.04 (1H, m), 4.80 (1H, d), 4.70 (1H, dd), 4.58 (2H, s), 4.36 (1H, d), 4.30 (1H, d), 4.00-3.81 (4H, m), 3.42-3.36 (2H, m), 2.59 (2H, q), 1.91-1.81 (2H, m), 1.58- 1.46(2H, m), 1.18 (3H, t), 1.00 (3H, d). | 564 |

Example 463, 464 and 465: 2-(6-{5-chloro-2-[(oxan-4-yl)amino]pyrimidin-4-yl}-1-oxo-2,3-dihydro-1H-isoindol-2-yl)-N-[1-(hydroxymethyl)-6-methoxy-2,3-dihydro-1H-inden-1-yl]acetamide, 2-(6-{5-chloro-2-[(oxan-4-yl)amino]pyrimidin-4-yl}-1-oxo-2,3-dihydro-1H-isoindol-2-yl)-N-[(1R)-1-(hydroxymethyl)-6-methoxy-2,3-dihydro-1H-inden-1-yl]acetamide and 2-(6-{5-chloro-2-[(oxan-4-yl)amino]pyrimidin-4-yl}-1-oxo-2,3-dihydro-1H-isoindol-2-yl)-N-[(1S)-1-(hydroxymethyl)-6-methoxy-2,3-dihydro-1H-inden-1-yl]acetamide

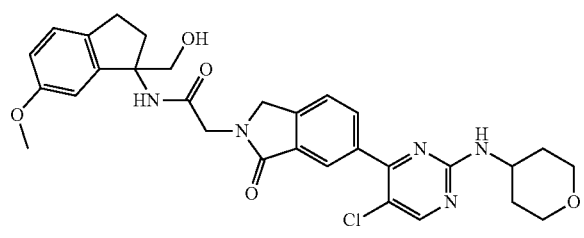

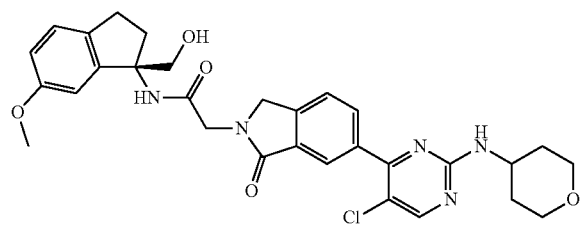

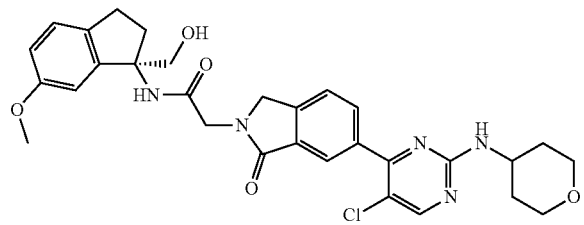

Prepared using a similar procedure to Example 451. 1H NMR (DMSO-d6, 400 MHz) δ 8.45 (1H, s), 8.06 (1H, s), 8.02 (1H, dd), 7.97 (1H, dd), 7.73 (1H, d), 7.62 (1H, s), 7.09 (1H, d), 6.88 (1H, d), 6.77 (1H, dd), 5.02 (1H, t), 4.57 (2H, s), 4.33-4.15 (2H, m), 3.90 (3H, dd), 3.72 (3H, s), 3.64 (1H, dd), 3.56 (1H, dd), 3.33-3.42 (2H, m), 2.83 (1H, ddd), 2.73 (1H, dt), 2.43-2.23 (2H, m), 1.85 (2H, d), 1.53 (2H, qd). LCMS: [M+H]+=578. The enantiomers were separated by chiral preparative HPLC (Gilson, IA column, isocratic 20% EtOH with 80% 4:1 (i-Hexane+0.2% diethylamine):DCM).

Example 466: 2-(6-{5-chloro-2-[(oxan-4-yl)amino]pyrimidin-4-yl}-1-oxo-2,3-dihydro-1H-isoindol-2-yl)-N-(1,3-dihydroxy-2-phenylpropan-2-yl)acetamide

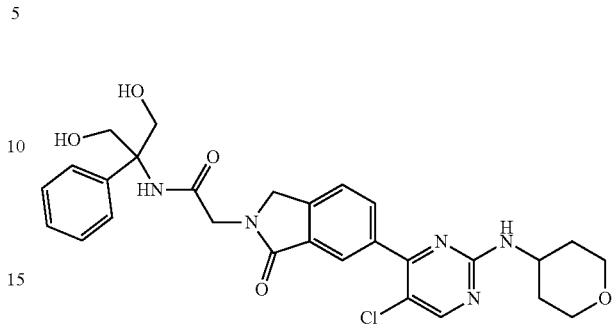

Prepared using a similar procedure to Example 451. In this case, the product was further purified by preparative HPLC (Waters, Basic (0.1% Ammonium Bicarbonate), Basic, Waters X-Bridge Prep-C18, 5 μm, 19×50 mm column, 20-40% MeCN in Water). 1H NMR (DMSO-d6, 400 MHz) δ 8.45 (1H, s), 8.06-8.01 (2H, m), 7.97 (1H, dd), 7.74 (1H, d), 7.62 (1H, br. s), 7.37-7.32 (2H, m), 7.31-7.25 (2H, m), 7.22-7.15 (1H, m), 4.88 (2H, t), 4.59 (2H, s), 4.36 (2H, s), 3.99-3.80 (7H, m), 3.42-3.35 (2H, m), 1.90-1.80 (2H, m), 1.59-1.46 (2H, m). LCMS: [M+H]+=552.

Example 467: 2-(6-{5-chloro-2-[(oxan-4-yl)amino]pyrimidin-4-yl}-1-oxo-2,3-dihydro-1H-isoindol-2-yl)-N-[(1S)-2-hydroxy-1-[3-(oxolan-2-yl)phenyl]ethyl]acetamide

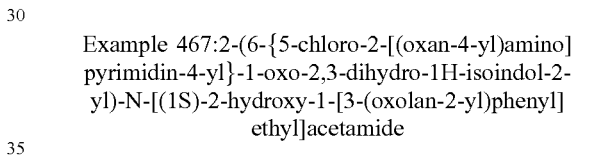

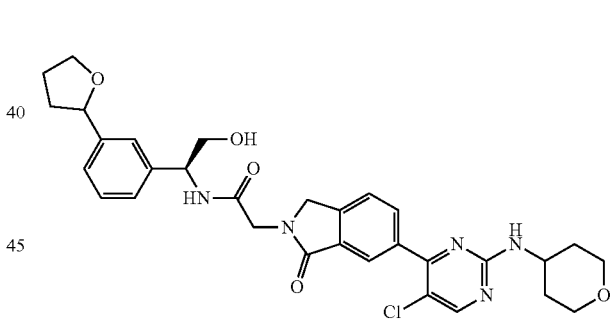

Prepared using a similar procedure to Example 451. After purification, the product was dissolved in EtOAc and further washed with 1N HCl. The aqueous layer was extracted with EtOAc and the combined organic extracts were washed with NaHCO3, brine, dried (MgSO4) and concentrated under vacuum, to afford the title compound (0.007 g, 0.011 mmol) as a white solid after trituration and evaporation from Et2O. 1H NMR (DMSO-d6) δ: 8.58 (d, 1H), 8.45 (s, 1H), 8.03 (d, 1H), 7.98 (dd, 1H), 7.74 (d, 1H), 7.63 (s (br), 1H), 7.32-7.24 (m, 2H), 7.24-7.15 (m, 2H), 4.93 (t, 1H), 4.87 (td, 1H), 4.81-4.74 (m, 1H), 4.59 (s, 2H), 4.32 (d, 1H), 4.26 (d, 1H), 4.04-3.76 (m, 5H), 3.62-3.53 (m, 2H), 3.42-3.35 (m, 2H), 2.34-2.23 (m, 1H), 1.98-1.89 (m, 2H), 1.88-1.80 (m, 2H), 1.70-1.59 (m, 1H), 1.58-1.46 (m, 2H). LCMS: [M+H]+=592.

Example 468: 6-{5-chloro-2-[(oxan-4-yl)amino] pyrimidin-4-yl}-2-[2-(2,3-dihydro-1H-indol-1-yl)-2-oxoethyl]-2,3-dihydro-1H-isoindol-1-one

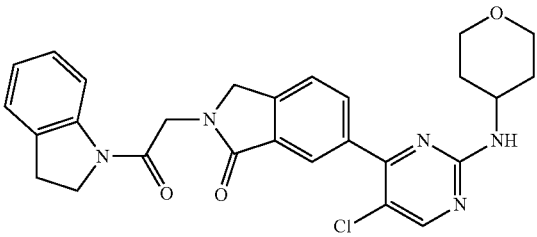 [SMILES: O=C1c2cc(-c3nc(NC4CCOCC4)ncc3Cl)ccc2CN1CC(=O)N1CCc2ccccc21]

DIPEA (0.090 mL, 0.515 mmol), indoline (0.040 mL, 0.356 mmol) and then HATU (0.142 g, 0.373 mmol) were added to a stirred solution of 2-(6-{5-chloro-2-[(oxan-4-yl)amino]pyrimidin-4-yl}-1-oxo-2,3-dihydro-1H-isoindol-2-yl)acetic acid (Example 1, 0.100 g, 0.246 mmol) in DMF (2.0 mL, 25.8 mmol) at room temperature. After 2.5 h the reaction mixture was partitioned between EtOAc (30 mL) and NH₄Cl (30 mL). The layers were separated and the aqueous was extracted with EtOAc (30 mL). The combined organic fraction was washed with water (20 mL), NaHCO₃ (20 mL) and brine (2×20 mL) and then concentrated under vacuum. The aqueous layer contained a white solid which was isolated by filtration and then washed with water (10 mL) and then ether (2×10 mL). This solid was triturated with ether (3 mL), sonicated and then the solution was decanted (repeated ×3). The solid was then suspended in MeOH:water (5 mL, 1:1), sonicated and then heated to give a white solution. The solution was allowed to cool overnight and the resulting solid was isolated by decanting the solvent. The solid was dried in a desiccator at 50° C. for 5 h to afford the title compound (0.049 g, 37.2%). 1H NMR (400 MHz, DMSO-d6) δ 8.46 (1H, s), 8.07 (1H, d), 8.01 (2H, dd), 7.79 (1H, d), 7.63 (1H, s), 7.29 (1H, d), 7.16 (1H, t), 7.03 (1H, t), 4.62 (4H, d), 4.23 (2H, t), 3.98-3.85 (3H, m), 3.39 (2H, t), 3.23 (2H, t), 1.86 (2H, d), 1.54 (2H, qd). LC-MS: [M+H]+=504.

Example 469:2-[2-(7-chloro-2,3,4,5-tetrahydro-1H-3-benzazepin-3-yl)-2-oxoethyl]-6-{5-chloro-2-[(oxan-4-yl)amino]pyrimidin-4-yl}-2,3-dihydro-1H-isoindol-1-one

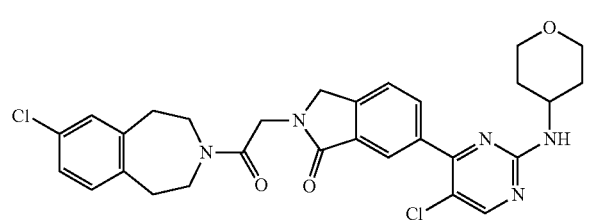 [SMILES: O=C(CN1Cc2ccc(-c3nc(NC4CCOCC4)ncc3Cl)cc2C1=O)N1CCc2ccc(Cl)cc2CC1]

Triethylamine (67.5 µl, 0.484 mmol) was added to a stirred solution of 2-(6-{5-chloro-2-[(oxan-4-yl)amino]pyrimidin-4-yl}-1-oxo-2,3-dihydro-1H-isoindol-2-yl)acetic acid (Example 1, 65 mg, 0.161 mmol), 7-chloro-2,3,4,5-tetrahydro-1H-benzo[d]azepine (29.3 mg, 0.161 mmol) and HATU (67.5 mg, 0.177 mmol) in DCM (3 mL) and the mixture was stirred at room temperature overnight. The reaction mixture was diluted with EtOAc (30 mL) and washed with 1M HCl (30 ml), sat. aq. NaHCO₃ (30 mL), water (30 mL) and brine (30 mL), dried (MgSO₄), filtered and concentrated in vacuo to give the crude product. The crude product was purified by chromatography (SiO₂, 40 g column, 0-10% MeOH in EtOAc) to afford the title compound (50 mg, 0.087 mmol, 54.2%) as a white solid. 1H NMR (DMSO-d6, 400 MHz) δ 8.45 (1H, s), 8.04 (1H, d), 7.99 (1H, dd), 7.75 (1H, d), 7.62 (1H, s), 7.29 (1H, dd), 7.25-7.14 (2H, m), 4.56 (4H, t), 4.00-3.82 (3H, m), 3.72-3.55 (4H, m), 3.45-3.34 (2H, m), 2.99 (2H, t), 2.87 (2H, q), 1.85 (2H, d), 1.53 (2H, qd). LC-MS: [M+H]+=566.

Example 470:2-(6-{5-chloro-2-[(oxan-4-yl)amino]pyrimidin-4-yl}-1-oxo-2,3-dihydro-1H-isoindol-2-yl)-N-[(1R)-2,3-dihydro-1H-inden-1-yl]acetamide

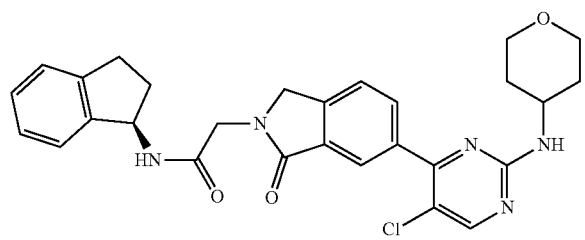 [SMILES: O=C(CN1Cc2ccc(-c3nc(NC4CCOCC4)ncc3Cl)cc2C1=O)N[C@@H]1CCc2ccccc21]

DIPEA (0.073 ml, 0.417 mmol) followed by HATU (0.079 g, 0.209 mmol) were added to a mixture of 2-(6-{5-chloro-2-[(oxan-4-yl)amino]pyrimidin-4-yl}-1-oxo-2,3-dihydro-1H-isoindol-2-yl)acetic acid (Example 1, 0.08 g, 0.199 mmol) and (R)-2,3-dihydro-1H-inden-1-amine hydrochloride (0.035 g, 0.209 mmol) in DMF (1 mL) and the mixture was stirred for 30 minutes. 1N HCl was added and the mixture was diluted with water. The resulting precipitate was filtered, washed with water, NaHCO₃, water and dried under suction. The solid was then dissolved in DCM and brine was added. The layers were separated through a phase separating cartridge and the organic layer was dried (MgSO₄) and concentrated under vacuum to afford the title compound (0.065 g, 62.6%) as a white solid after trituration and evaporation from Et₂O.1H NMR (DMSO-d6) δ: 8.55 (d, 1H), 8.45 (s (br), 1H), 8.04 (d, 1H), 7.99 (dd, 1H), 7.76 (d, 1H), 7.62 (s (br), 1H), 7.23 (m, 4H), 5.34 (dd, 1H), 4.64 (s, 2H), 4.27 (s, 2H), 4.05-3.79 (m, 3H), 3.39 (d, 2H), 2.94 (ddd, 1H), 2.81 (m, 1H), 2.40 (dtd, 1H), 1.83 (m, 3H), 1.53 (qd, 2H). LC-MS: [M+H]+=518.

Example 471: 2-(6-{5-chloro-2-[(oxan-4-yl)amino]pyrimidin-4-yl}-1-oxo-2,3-dihydro-1H-isoindol-2-yl)-N-[(1R,2R)-2-hydroxy-2,3-dihydro-1H-inden-1-yl]acetamide

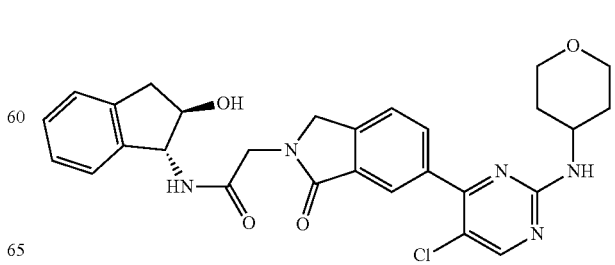

HATU (83 mg, 0.218 mmol) followed by triethylamine (83 µl, 0.596 mmol) were added to a solution of 2-(6-{5-chloro-2-[(oxan-4-yl)amino]pyrimidin-4-yl}-1-oxo-2,3-dihydro-1H-isoindol-2-yl)acetic acid (Example 1, 80 mg, 0.199 mmol) and (1R,2R)-1-amino-2,3-dihydro-1H-inden-2-ol (29.6 mg, 0.199 mmol) in DMF (3 mL). HCl (1M, 2 mL) followed by water (10 mL) were added. The resulting white precipitate was filtered, washed with NaHCO$_3$ (10 mL), dried in vacuo at 40° C. The residue was triturated with a mixture of MeOH in Et$_2$O to give the title compound (63 mg, 58.2%) as a pale tan powder. 1H NMR (CDCl3, 400 MHz) δ 8.33 (1H, s), 8.28 (1H, d), 8.02 (1H, dd), 7.59 (1H, d), 7.25-7.15 (3H, m), 7.08 (1H, d), 5.18 (1H, d), 5.11 (1H, t), 4.67 (2H, s), 4.46-4.36 (4H, m), 4.11-3.94 (3H, m), 3.58-3.50 (2H, m), 3.28 (1H, dd), 2.92 (1H, dd), 2.05 (2H, d), 1.56 (2H, qd) (one exchangeable proton was not observed). LC-MS: [M+H]+=534.

Example 472: N-(2-aminoethyl)-N-benzyl-2-(6-{5-chloro-2-[(oxan-4-yl)amino]pyrimidin-4-yl}-1-oxo-2,3-dihydro-1H-isoindol-2-yl)acetamide

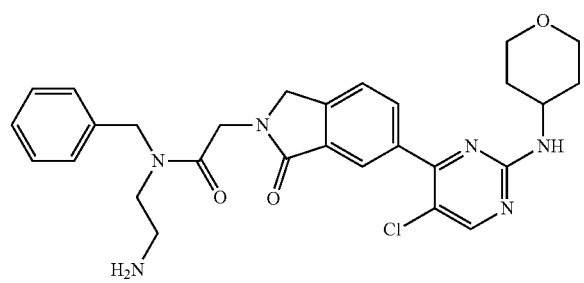 [SMILES: NCCN(Cc1ccccc1)C(=O)CN1Cc2ccc(-c3nc(NC4CCOCC4)ncc3Cl)cc2C1=O]

TFA (455 µl, 5.90 mmol) was added to a stirred solution of tert-butyl (2-(N-benzyl-2-(6-(5-chloro-2-((oxan-4-yl)amino)pyrimidin-4-yl)-1-oxoisoindolin-2-yl)acetamido)ethyl)carbamate (Preparation 312, 75 mg, 0.118 mmol) in DCM (1.2 mL, 0.1 M) under nitrogen. The reaction was stirred at room temperature for 30 minutes. The mixture was concentrated in vacuo and the residue was azeotroped with toluene (4×3 mL) and MeCN (2×3 mL) to give the crude product as a pale yellow solid (60 mg). The crude product was loaded onto a column of SCX (600 mg) in MeOH. The column was washed with MeOH and then the product was eluted with 0.7 M ammonia in MeOH. The resulting mixture was concentrated in vacuo to afford the title compound (51 mg, 77%) as a white solid. 1H NMR (DMSO-d6, 400 MHz @ 60° C.) δ 8.42 (1H, s), 8.05 (1H, s), 8.03-7.95 (1H, m), 7.73 (1H, t), 7.42-7.24 (6H, m), 4.79-4.44 (6H, m), 4.03-3.80 (3H, m), 3.49-3.27 (4H, m), 2.81-2.66 (2H, m), 1.93-1.83 (2H, m), 1.64-1.49 (2H, m) (NH2 missing—probably overlapped with water peak). LC-MS: [M+H]+=535.

Example 473: 2-(6-{5-chloro-2-[(oxan-4-yl)amino]pyrimidin-4-yl}-1-oxo-2,3-dihydro-1H-isoindol-2-yl)-N-[2-(2-methoxyphenyl)propan-2-yl]acetamide

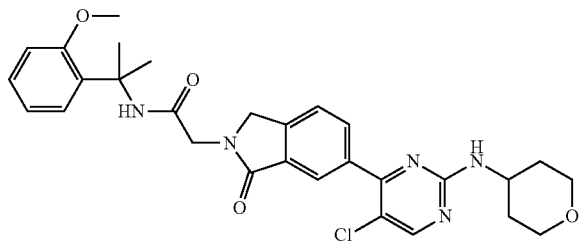 [SMILES: COc1ccccc1C(C)(C)NC(=O)CN1Cc2ccc(-c3nc(NC4CCOCC4)ncc3Cl)cc2C1=O]

HATU (83 mg, 0.218 mmol) followed by triethylamine (83 µl, 0.596 mmol) were added to a solution of 2-(6-{5-chloro-2-[(oxan-4-yl)amino]pyrimidin-4-yl}-1-oxo-2,3-dihydro-1H-isoindol-2-yl)acetic acid (Example 1, 80 mg, 0.199 mmol) and 2-(2-methoxyphenyl)propan-2-amine (32.8 mg, 0.199 mmol) in DMF (1 mL). The reaction mixture was stirred for 1 h at room temperature. Water (10 mL) was added and the resulting white precipitate was filtered. The solid was triturated (MeOH/Et$_2$O) to give the title compound (76 mg, 66.8%) as a colourless powder. 1H NMR (DMSO, 400 MHz) δ 8.44 (1H, s), 8.16 (1H, s), 8.01 (1H, dd), 7.95 (1H, dd), 7.72 (1H, d), 7.62 (1H, bs), 7.24-7.15 (2H, m), 6.97 (1H, dd), 6.85 (1H, td), 4.54 (2H, s), 4.22 (2H, s), 3.99-3.82 (3H, m), 3.80 (3H, s), 3.41-3.35 (2H, m), 1.84 (2H, d), 1.64 (6H, s), 1.52 (2H, qd). LC-MS: [M+H]+=550.

Example 474: 2-(6-{5-chloro-2-[(oxan-4-yl)amino]pyrimidin-4-yl}-1-oxo-2,3-dihydro-1H-isoindol-2-yl)-N-{[3-(hydroxymethyl)phenyl]methyl}acetamide

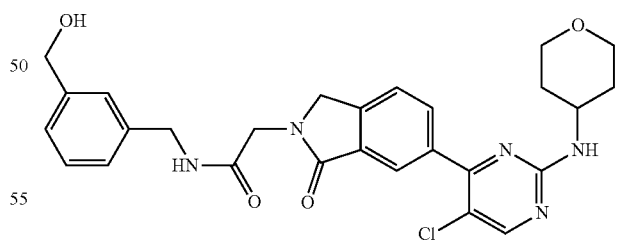

Prepared using a similar procedure to Example 94. 1H NMR (CDCl3, 400 MHz) δ 8.33 (1H, s), 8.22 (1H, s), 7.99 (1H, dd), 7.59-7.54 (1H, m), 7.25-7.12 (4H, m), 6.85 (1H, bs), 5.30 (1H, bs), 4.63 (2H, s), 4.58 (2H, s), 4.42 (2H, d), 4.30 (2H, s), 4.11-3.93 (3H, m), 3.53 (2H, td), 2.09-1.99 (2H, m), 1.62-1.49 (2H, m). (1 exchangeable proton not observed). LC-MS: [M+H]+=522.

Example 475: 2-(6-{5-chloro-2-[(oxan-4-yl)amino]pyrimidin-4-yl}-1-oxo-2,3-dihydro-1H-isoindol-2-yl)-N-[2-hydroxy-1-(2-methylphenyl)ethyl]acetamide

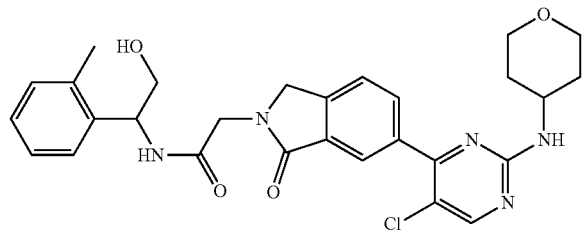 [SMILES: Cc1ccccc1C(CO)NC(=O)CN1Cc2ccc(-c3nc(NC4CCOCC4)ncc3Cl)cc2C1=O]

HATU (83 mg, 0.218 mmol) followed by triethylamine (83 μl, 0.596 mmol) were added to a solution of 2-(6-{5-chloro-2-[(oxan-4-yl)amino]pyrimidin-4-yl}-1-oxo-2,3-dihydro-1H-isoindol-2-yl)acetic acid (Example 1, 80 mg, 0.199 mmol) and 2-amino-2-(o-tolyl)ethanol (30.0 mg, 0.199 mmol) in DMF (1 mL). The reaction mixture was stirred for 1 h at room temperature. Water (10 mL) was added and the resulting white precipitate was filtered. The crude product was purified by chromatography (SiO$_2$, 0-5% MeOH in EtOAc) to give the title (12 mg, 11.05%) as a colourless powder. 1H NMR (CDCl$_3$, 400 MHz) δ 8.33 (1H, s), 8.31-8.28 (1H, m), 8.00 (1H, dd), 7.58-7.53 (1H, m), 7.24-7.10 (4H, m), 7.06 (1H, d), 5.35-5.27 (2H, m), 4.62 (2H, dd), 4.32 (2H, dd), 4.11-3.95 (3H, m), 3.87-3.76 (2H, m), 3.58-3.48 (2H, m), 2.39 (3H, s), 2.05 (2H, d), 1.62-1.50 (2H, m). (1 exchangeable proton in water peak). LC-MS: [M+H]+=536.

Example 476, 477 and 478: 2-(6-{5-chloro-2-[(oxan-4-yl)amino]pyrimidin-4-yl}-1-oxo-2,3-dihydro-1H-isoindol-2-yl)-N-(1-hydroxy-2-phenylpropan-2-yl)acetamide, 2-(6-{5-chloro-2-[(oxan-4-yl)amino]pyrimidin-4-yl}-1-oxo-2,3-dihydro-1H-isoindol-2-yl)-N-[(2R)-1-hydroxy-2-phenylpropan-2-yl]acetamide, 2-(6-{5-chloro-2-[(oxan-4-yl)amino]pyrimidin-4-yl}-1-oxo-2,3-dihydro-1H-isoindol-2-yl)-N-[(2S)-1-hydroxy-2-phenylpropan-2-yl]acetamide

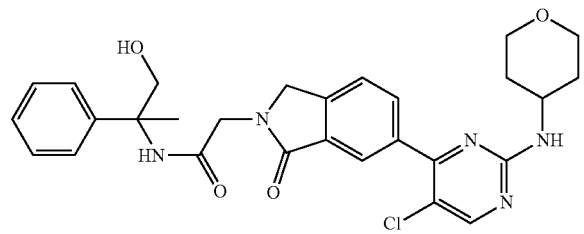 [SMILES: CC(CO)(NC(=O)CN1Cc2ccc(-c3nc(NC4CCOCC4)ncc3Cl)cc2C1=O)c1ccccc1]

HATU (83 mg, 0.218 mmol) followed by triethylamine (83 μl, 0.596 mmol) were added to a solution of 2-(6-{5-chloro-2-[(oxan-4-yl)amino]pyrimidin-4-yl}-1-oxo-2,3-dihydro-1H-isoindol-2-yl)acetic acid (80 mg, 0.199 mmol) and 2-amino-2-phenylpropan-1-ol (30.0 mg, 0.199 mmol) in DMF (1 mL). The reaction mixture was stirred for 1 h at room temperature. Water (10 mL) was added and the resulting white precipitate was filtered, purified by chromatography (SiO$_2$, 0-5% MeOH in ethyl acetate), followed by preparative HPLC (acidic) to give the title compound (22 mg, 20.46%) as a colourless powder. 1H NMR (DMSO, 400 MHz) δ 8.44 (1H, s), 8.16 (1H, s), 8.01 (1H, d), 7.96 (1H, dd), 7.72 (1H, d), 7.61 (1H, bs), 7.35-7.25 (4H, m), 7.21-7.15 (1H, m), 5.07 (1H, s), 4.56 (2H, s), 4.30 (2H, s), 3.99-3.81 (3H, m), 3.67 (1H, d), 3.54-3.46 (1H, m), 3.42-3.35 (2H, m), 1.84 (2H, dd), 1.60 (3H, s), 1.58-1.46 (2H, m). LC-MS: [M+H]+=536. The enantiomers were separated by chiral preperative HPLC (Daicel IA 2 cm×25 cm 5 μm, 60% (iso-hexanes+0.2% TFA):40% EtOH, 60 min run time) to give 2 fractions:

Fration 1 was further purified by flash chromatography (SiO2, 0-5% MeOH in DCM) to afford 2-(6-{5-chloro-2-[(oxan-4-yl)amino]pyrimidin-4-yl}-1-oxo-2,3-dihydro-1H-isoindol-2-yl)-N-[(2R)-1-hydroxy-2-phenylpropan-2-yl]acetamide. 1H NMR (DMSO-d6, 400 MHz) δ 8.45 (1H, s), 8.14 (1H, s), 8.02 (1H, dd), 7.96 (1H, dd), 7.73 (1H, d), 7.62 (1H, br. s), 7.36-7.25 (4H, m), 7.22-7.14 (1H, m), 5.03 (1H, t), 4.57 (2H, s), 4.31 (2H, s), 3.99-3.85 (3H, m), 3.67 (1H, dd), 3.50 (1H, dd), 3.41-3.34 (2H, m), 1.84 (2H, br. d), 1.60 (3H, s), 1.58-1.48 (2H, m) ppm. LC-MS: [M+H]+=536.

Fration 1 was further purified by flash chromatography (SiO2, 20% (1% NH$_3$ in MeOH) in DCM) and then further flash chromatography (SiO2, 0-10% MeOH in DCM) to afford clean peak 2 (19 mg).

Peak 2: 2-(6-{5-chloro-2-[(oxan-4-yl)amino]pyrimidin-4-yl}-1-oxo-2,3-dihydro-1H-isoindol-2-yl)-N-[(2S)-1-hydroxy-2-phenylpropan-2-yl]acetamide. 1H NMR (DMSO-d6, 400 MHz) δ 8.45 (1H, s), 8.14 (1H, s), 8.02 (1H, dd), 7.96 (1H, dd), 7.73 (1H, d), 7.62 (1H, br. s), 7.36-7.25 (4H, m), 7.22-7.14 (1H, m), 5.03 (1H, t), 4.57 (2H, s), 4.31 (2H, s), 3.99-3.85 (3H, m), 3.67 (1H, dd), 3.50 (1H, dd), 3.41-3.34 (2H, m), 1.84 (2H, br. d), 1.60 (3H, s), 1.58-1.48 (2H, m) ppm. LC-MS: [M+H]+=536.

Example 479: 2-(6-{5-chloro-2-[(oxan-4-yl)amino]pyrimidin-4-yl}-1-oxo-2,3-dihydro-1H-isoindol-2-yl)-N-[2-(3-cyanophenyl)propan-2-yl]acetamide

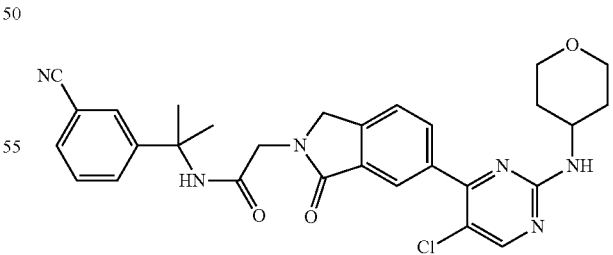

Prepared using a similar procedure to Example 476. 1H NMR (CDCl$_3$, 400 MHz) δ 8.37-8.30 (2H, m), 8.03 (1H, dd), 7.62-7.54 (3H, m), 7.49 (1H, dt), 7.39-7.33 (1H, m), 6.88 (1H, bs), 5.20 (1H, d), 4.61 (2H, s), 4.23 (2H, s), 4.12-3.94 (3H, m), 3.54 (2H, td), 2.12-2.00 (2H, m), 1.65 (6H, s), 1.59-1.52 (2H, m). LC-MS: [M+H]+=545.

Example 480: 6-{5-chloro-2-[(oxan-4-yl)amino]
pyrimidin-4-yl}-2-[2-(1-hydroxy-2,3,4,5-tetrahydro-
1H-3-benzazepin-3-yl)-2-oxoethyl]-2,3-dihydro-1H-
isoindol-1-one

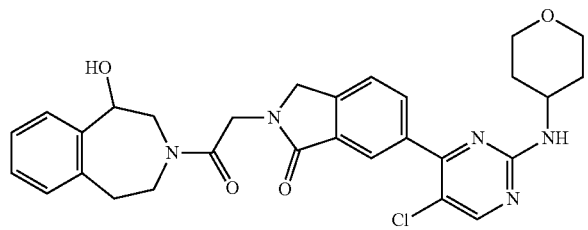 [SMILES: O=C(CN1Cc2ccc(-c3nc(NC4CCOCC4)ncc3Cl)cc2C1=O)N1CCc2ccccc2C(O)C1]

Triethylamine (67.5 µl, 0.484 mmol) was added to a stirred solution of 2-(6-{5-chloro-2-[(oxan-4-yl)amino]pyrimidin-4-yl}-1-oxo-2,3-dihydro-1H-isoindol-2-yl)acetic acid (Example 1, 65 mg, 0.161 mmol), 2,3,4,5-tetrahydro-1H-benzo[d]azepin-1-ol (26.3 mg, 0.161 mmol) and HATU (67.5 mg, 0.177 mmol) in DCM (3 mL). The mixture was stirred at room temperature overnight. The reaction mixture was diluted with EtOAc (30 mL) and washed with 1M HCl (30 ml), sat. aq. NaHCO₃ (30 mL), water (30 mL) and brine (30 mL) and dried (MgSO₄). The precipitate that formed in the aqueous layer was collected by filtration, washed with water (5 ml×2), and then dissolved in 20% MeOH:DCM (50 ml). The resulting solution was dried (MgSO₄) and concentrated in vacuo to afford the title compound (38 mg, 42.5%) as a colourless solid. 1H NMR (DMSO-d6, 400 MHz) δ 8.46 (1H, s), 8.06-8.01 (1H, m), 7.99 (1H, dd), 7.75 (1H, d), 7.63 (1H, s), 7.48-7.33 (1H, m), 7.27-7.10 (3H, m), 5.78-5.71 (1H, m), 4.78 (1H, d), 4.68 (1H, s), 4.63 (1H, d), 4.59-4.46 (3H, m), 3.99-3.75 (5H, m), 3.61 (1H, d), 3.40 (2H, d), 3.11 (1H, dd), 2.73 (1H, dd), 1.85 (2H, d), 1.53 (2H, qd). LC-MS: [M+H]+=548. (note: NMR showed several different rotamers).

Example 481: N-[(1S)-2-amino-1-phenylethyl]-2-(6-
{5-chloro-2-[(oxan-4-yl)amino]pyrimidin-4-yl}-1-
oxo-2,3-dihydro-1H-isoindol-2-yl)acetamide

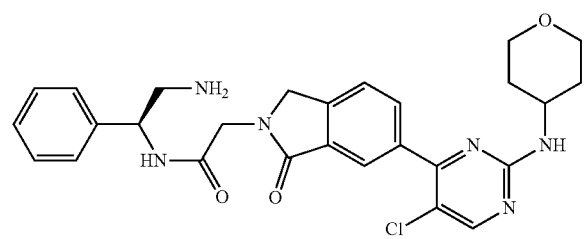 [SMILES: NC[C@@H](NC(=O)CN1Cc2ccc(-c3nc(NC4CCOCC4)ncc3Cl)cc2C1=O)c1ccccc1]

TFA (0.3 ml, 0.177 mmol) was added to a mixture of (S)-tert-butyl (2-(2-(6-(5-chloro-2-((oxan-4-yl)amino)pyrimidin-4-yl)-1-oxoisoindolin-2-yl)acetamido)-2-phenylethyl)carbamate (Preparation 304, 0.11 g, 0.177 mmol) in DCM (1 mL) and the mixture was stirred for 1 h. The mixture was concentrated under vacuum and NaHCO₃ and DCM were added. The layers were separated through a phase separating cartridge and the organic layer was concentrated under vacuum. The residue was dissolved in MeOH and loaded on a column packed with SCX. The column was washed with MeOH and the product was eluted with 1% NH₃ in MeOH. The mixture was concentrated under vacuum and the residue was dissolved in DCM and filtered through cotton wool. The mixture was concentrated under vacuum and the residue was triturated with Et₂O, then concentrated under vacuum to afford the title compound (0.072 g, 76%) as a white solid. 1H NMR (DMSO-d6, VT T=350K) δ: 8.41 (s, 1H), 8.32 (s (br, 1H), 8.07 (d, 1H), 8.00 (dd, 1H), 7.72 (dd, 1H), 7.34 (d, 4H), 7.31-7.20 (m, 2H), 4.88 (m, 1H), 4.61 (s, 2H), 4.35 (d, 2H), 4.28 (d, 1H), 4.02-3.83 (m, 3H), 3.41 (td, 3H), 2.95-2.87 (m, 2H), 1.89 (m, 2H), 1.58 (m, 2H). LC-MS: [M+H]+=521.

Example 482 and 483: 6-{5-chloro-2-[(oxan-4-yl)
amino]pyrimidin-4-yl}-2-{2-[(1R)-5-(hydroxymethyl)-1-methyl-1,2,3,4-tetrahydroisoquinolin-2-yl]-
2-oxoethyl}-2,3-dihydro-1H-isoindol-1-one and
6-{5-chloro-2-[(oxan-4-yl)amino]pyrimidin-4-yl}-2-
{2-[(1S)-5-(hydroxymethyl)-1-methyl-1,2,3,4-tetrahydroisoquinolin-2-yl]-2-oxoethyl}-2,3-dihydro-1H-
isoindol-1-one

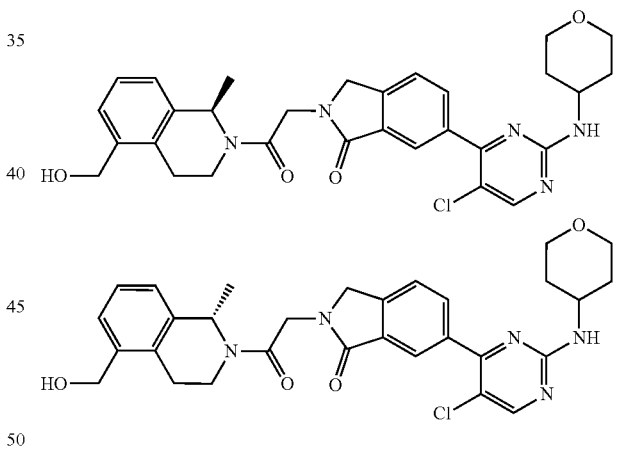

The enantiomers of 6-{5-chloro-2-[(oxan-4-yl)amino]pyrimidin-4-yl}-2-{2-[5-(hydroxymethyl)-1-methyl-1,2,3,4-tetrahydroisoquinolin-2-yl]-2-oxoethyl}-2,3-dihydro-1H-isoindol-1-one (Example 192, 170 mg) were separated by preparative chiral HPLC (Gilson, Chiralpak IA, 2 cm×25 cm, 40% EtOH in 3:1 Hexane(+0.2% TFA):DCM) to afford 6-(5-chloro-2-((oxan-4-yl)amino)pyrimidin-4-yl)-2-(2-(5-(hydroxymethyl)-1-methyl-3,4-dihydroisoquinolin-2(1H)-yl)-2-oxoethyl)isoindolin-1-one (isomer 1, 20 mg, 7.3%) (rt 24 mins) and 6-(5-chloro-2-((oxan-4-yl)amino)pyrimidin-4-yl)-2-(2-(5-(hydroxymethyl)-1-methyl-3,4-dihydroisoquinolin-2(1H)-yl)-2-oxoethyl)isoindolin-1-one (isomer 2, 20 mg, 7.3%) as colourless solids. Upon contraction of the solution, the products were obtained as a mixture with c.a.

10% of their trifluoroacetates ((2-(2-(6-(5-chloro-2-((oxan-4-yl)amino)pyrimidin-4-yl)-1-oxoisoindolin-2-yl)acetyl)-1-methyl-1,2,3,4-tetrahydroisoquinolin-5-yl)methyl 2,2,2-trifluoroacetate). The colourless solids of each enantiomers were dissolved in methanol (1.5 ml, 37.1 mmol), K₂CO₃ (16.94 mg, 0.123 mmol) was added and the mixture was stirred at room temperature for 2 h. The reaction mixture was concentrated and then diluted with DCM (30 ml) and then washed with water (10 mL). The organic was dried (MgSO₄), filtered and concentrated in vacuo to afford both title compounds (17 mg, 6.1%) as colourless solids. LC-MS: [M+H]+=562.

Example 484: 2-{2-[1-(aminomethyl)-2,3,4,5-tetrahydro-1H-3-benzazepin-3-yl]-2-oxoethyl}-6-{5-chloro-2-[(oxan-4-yl)amino]pyrimidin-4-yl}-2,3-dihydro-1H-isoindol-1-one

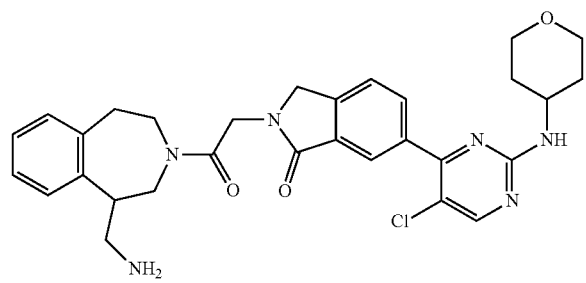 [SMILES: NCC1CN(C(=O)CN2Cc3ccc(-c4nc(NC5CCOCC5)ncc4Cl)cc3C2=O)CCc2ccccc21]

A stirred solution of 2-((3-(2-(6-(5-chloro-2-((oxan-4-yl)amino)pyrimidin-4-yl)-1-oxoisoindolin-2-yl)acetyl)-2,3,4,5-tetrahydro-1H-benzo[d]azepin-1-yl)methyl)isoindoline-1,3-dione (Preparation 310, 20 mg, 0.029 mmol) in ethanol (1 ml) was treated with hydrazine hydrate (5.68 µl, 0.116 mmol) and the resulting white suspension was heated under reflux for 3 h. The reaction mixture was concentrated under vacuum and the residue was purified by chromatography (SiO₂, 12 g column, 0 to 10% of MeOH in DCM) to the title compound (8 mg, 0.014 mmol, 48.8% yield) as a colourless solid. 1H NMR (CD3OD, 400 MHz) δ 8.39-8.33 (1H, m), 8.26-8.19 (1H, m), 8.14-8.04 (1H, m), 7.73-7.66 (1H, m), 7.29-7.04 (4H, m), 4.72-4.45 (4H, m), 4.25-4.16 (1H, m), 4.10-3.85 (4H, m), 3.55 (2H, td), 3.23-3.12 (1H, m), 3.11-2.77 (3H, m), 2.07-1.97 (2H, m), 1.73-1.55 (2H, m) (exchangeable NH and NH2 were not observed, 4 protons signals overlapped with MeOD and/or water peaks). LC-MS: [M+H]+=561.

Example 485: 6-{5-chloro-2-[(oxan-4-yl)amino]pyrimidin-4-yl}-2-{2-[7-(hydroxymethyl)-2,3,4,5-tetrahydro-1H-3-benzazepin-3-yl]-2-oxoethyl}-2,3-dihydro-1H-isoindol-1-one

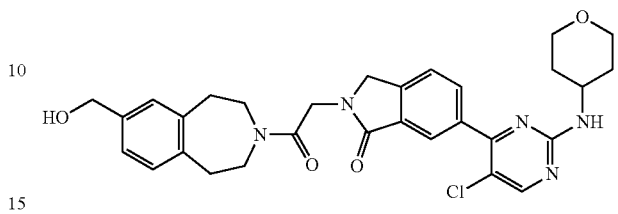

1M TBAF in THF (81 µl, 0.081 mmol) was added to a stirred solution of 2-(2-(7-(((tert-butyldimethylsilyl)oxy)methyl)-4,5-dihydro-1H-benzo[d]azepin-3(2H)-yl)-2-oxoethyl)-6-(5-chloro-2-((oxan-4-yl)amino)pyrimidin-4-yl)isoindolin-1-one (Preparation 305, 46 mg, 0.067 mmol) in THF (1 mL) and the mixture was stirred at room temperature overnight. The reaction mixture was partitioned between EtOAc (30 mL) and water (15 mL). The organic layer was washed with brine (15 mL), dried (MgSO₄), filtered and concentrated in vacuo to give the crude product (70 mg). Purification by chromatography (SiO₂, 24 g column, 0-10% MeOH in EtOAc) afforded a glass, which was triturated with diethyl ether and dried to afford the title compound (10 mg, 25.9%) as a white solid. 1H NMR (400 MHz, DMSO-d6) δ 8.45 (s, 1H), 8.03-8.02 (m, 1H), 7.98 (dd, 1H), 7.74 (d, 1H), 7.62 (s (br), 1H), 7.15-7.03 (m, 3H), 5.11 (t, 1H), 4.55 (s, 4H), 4.44 (d, 2H), 3.97-3.85 (m, 3H), 3.67-3.55 (m, 4H), 3.37 (t, 2H), 2.97-2.93 (m, 2H), 2.87-2.81 (m, 2H), 1.86-1.83 (br m, 2H), 1.52 (qd, 2H). LC-MS: [M+H]+=562.

Example 486: 6-{5-chloro-2-[(oxan-4-yl)amino]pyrimidin-4-yl}-2-[2-(1-methyl-3-oxo-2,3-dihydro-1H-isoindol-2-yl)-2-oxoethyl]-2,3-dihydro-1H-isoindol-1-one

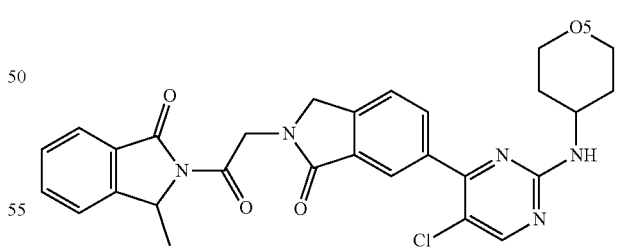

A microwave vial was charged with N-(1-(2-bromophenyl)ethyl)-2-(6-(5-chloro-2-((oxan-4-yl)amino)pyrimidin-4-yl)-1-oxoisoindolin-2-yl)acetamide (Preparation 311, 102 mg, 0.167 mmol), 3-oxobenzo[d]isothiazole-2(3H)-carbaldehyde 1,1-dioxide (52.9 mg, 0.251 mmol), sodium carbonate (17.70 mg, 0.167 mmol), Pd(OAc)₂ (1.125 mg, 5.01 µmol) and 1,4-bis(diphenylphosphino)butane (3.20 mg, 7.52 µmol). The vial was capped and evacuated and back-filled with nitrogen (3×). Triethylsilane (34.7 μl, 0.217 mmol) was added in degassed (nitrogen sparged for 10 minutes) DMF (0.8 mL) and the mixture stirred at room temperature for 10 minutes. The mixture was heated to 80° C. and stirred under nitrogen overnight. The reaction mixture was diluted with EtOAc (10 mL) and washed with brine (10 mL). The aqueous phase was extracted with EtOAc (1×10 mL) and the combined organic extracts dried (MgSO₄), filtered and concentrated in vacuo to afford a yellow gum (120 mg). The crude product was purified by chromatography (SiO₂, 12 g column, 0-100% EtOAc in isohexane) to afford the title compound (16 mg, 17.83%) as a colourless glass. 1H NMR (DMSO-d6) δ: 8.45 (s, 1H), 8.06 (d, 1H), 8.01 (dd, 1H), 7.89 (d, 1H), 7.83-7.75 (m, 2H), 7.72 (dd, 1H), 7.60 (dd, 1H), 7.60 (s (br), 1H), 5.24 (q, 1H), 5.06 (d, 1H), 5.01 (d, 1H), 4.65 (s, 2H), 4.00-3.81 (m, 3H), 3.43-3.33 (m, 2H), 1.91-1.80 (m, 2H), 1.57 (d, 3H), 1.55-1.47 (m, 2H). LC-MS: [M+H]+=532.

Example 487:2-(6-{5-chloro-2-[(oxan-4-yl)amino] pyrimidin-4-yl}-1-oxo-2,3-dihydro-1H-isoindol-2-yl)-N-[1-(2-fluorophenyl)ethyl]acetamide

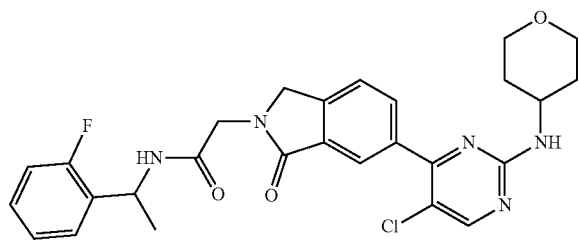 [SMILES: CC(NC(=O)CN1Cc2ccc(-c3nc(NC4CCOCC4)ncc3Cl)cc2C1=O)c1ccccc1F]

A solution of 1-(2-fluorophenyl)ethanamine (5.5 mg, 0.040 mmol), 2-(6-{5-chloro-2-[(oxan-4-yl)amino]pyrimidin-4-yl}-1-oxo-2,3-dihydro-1H-isoindol-2-yl)acetic acid (Example 1, 15 mg, 0.037 mmol) and Hunig's base (0.020 ml, 0.112 mmol) in DMF (0.2 ml) was treated with a solution of HATU (14.5 mg, 0.038 mmol) in DMF (0.2 ml) and shaken until homogeneous. The mixture was allowed to stand for 1 h, then diluted with methanol (40 μL), filtered and purified by reversed phase preparative HPLC on a Waters XSelect CSH C18 OBD, 130 Å, 5 μm, 19 mm×50 mm column, using a gradient of 5 to 95% of acetonitrile in water with 0.1% fomic acid in both at 28 ml/min as eluent. The eluent was evaporated to give a colourless glass (17.3 mg). The product was further purified by reverse phase preparative HPLC on a Waters XBridge BEH C18 OBD, 130 Å, 5 μm, 19 mm×50 mm column, using a gradient of 5 to 95% of acetonitrile in 10 mM aqueous ammonium bicarbonate solution at 28 ml/min as eluent. The clean fractions were combined and evaporated to afford the title compound (11.3 mg, 55.0%) as a white solid. 1H NMR (DMSO, 400 MHz) δ 8.70 (1H, d), 8.44 (1H, s), 8.02 (1H, dd), 7.97 (1H, dd), 7.73 (1H, d), 7.63 (1H, s), 7.47-7.38 (1H, m), 7.34-7.25 (1H, m), 7.24-7.08 (2H, m), 5.17 (1H, p), 4.58 (2H, s), 4.26 (2H, s), 3.98-3.81 (3H, m), 3.47-3.35 (2H, m), 1.84 (2H, d), 1.62-1.44 (2H, m), 1.38 (3H, d). LC-MS: [M+H]+=524.

Example 488:2-(6-{5-chloro-2-[(oxan-4-yl)amino] pyrimidin-4-yl}-1-oxo-2,3-dihydro-1H-isoindol-2-yl)-N-[(1R)-1-[3-(hydroxymethyl)phenyl]ethyl]acetamide

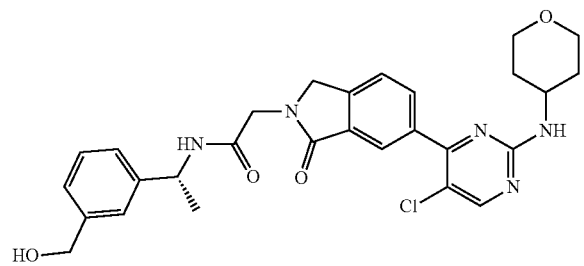 [SMILES: C[C@@H](NC(=O)CN1Cc2ccc(-c3nc(NC4CCOCC4)ncc3Cl)cc2C1=O)c1cccc(CO)c1]

Sodium borohydride (0.808 mg, 0.021 mmol) was added to an ice-cooled stirred solution of (R)-2-(6-(5-chloro-2-((oxan-4-yl)amino)pyrimidin-4-yl)-1-oxoisoindolin-2-yl)-N-(1-(3-formylphenyl)ethyl)acetamide (Preparation 307, 10 mg, 0.018 mmol) in 1:1 THF/MeOH (1 mL) under nitrogen. The mixture was allowed to warm to room temperature and stirred overnight. A further portion of sodium borohydride (0.808 mg, 0.021 mmol) was added and stirring continued at room temperature for 1 h. The reaction was quenched with NH₄Cl (aq.) (10 mL) and extracted with DCM (3×10 mL). The organic extracts were combined and washed with brine (1×30 mL) and then dried (MgSO₄), filtered and concentrated in vacuo. The crude product was purified by chromatography (SiO₂, 4 g column, 0-5% MeOH in DCM) to afford the title compound (7 mg, 71.9%) as a white solid. 1H NMR (DMSO-d6, 400 MHz) δ 8.61 (1H, d), 8.44 (1H, s), 8.02 (1H, dd), 7.97 (1H, dd), 7.73 (1H, d), 7.62 (1H, s), 7.32-7.24 (2H, m), 7.21-7.15 (2H, m), 5.19 (1H, t), 4.94 (1H, dq), 4.58 (21H, s), 4.49 (2H, d), 4.24 (2H, d), 3.98-3.81 (3H, m), 3.42-3.35 (2H, in), 1.84 (2H, d), 1.58-1.46 (2H, m), 1.37 (3H, d). LC-MS: [M+H]+=536.

Example 489-537

Solutions of generic amine (0.039 mol), 2-(6-{5-chloro-2-[(oxan-4-yl)amino]pyrimidin-4-yl}-1-oxo-2,3-dihydro-1H-isoindol-2-yl)acetic acid (Example 1.15 mg, 0.037 mmol) and DIPEA (0.026 ml, 0.149 mmol) in DMF (0.2 ml) were treated with solutions of HATU (15.5 mg, 0.041 mmol) in DMF (0.2 ml) and shaken until homogenous. The mixtures were allowed to stand overnight and purified by reversed phase preparative HPLC on a Waters XBridge BEH C18 OBD, 130 Å, 5 μm, 19 mm×50 mm column, using a gradient of either 20 to 50% (conditions A), 35 to 65% (conditions B) or 50 to 80% (conditions C) of acetonitrile in 10 mM aqueous ammonium bicarbonate solution at 28 ml/min as eluent. The clean fractions were evaporated in the genevac. Solid residues were submitted directly, otherwise residues were treated as specified in the table below.

| Example | Structure | Prep. | Name | ¹H NMR (400 MHz) | MS: [M + H]⁺ |
|---|---|---|---|---|---|
| 489 | 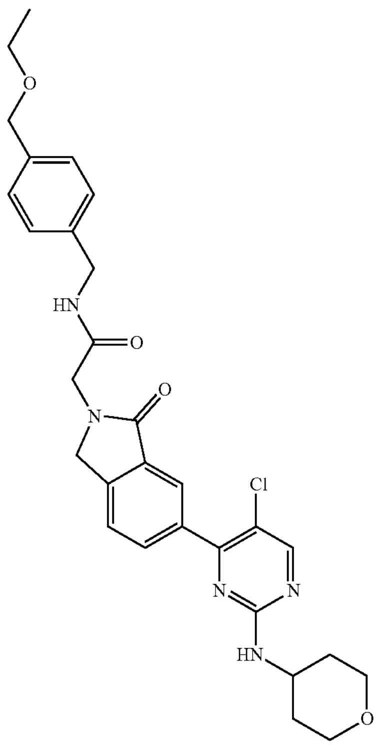 [SMILES: CCOCc1ccc(CNC(=O)CN2Cc3ccc(-c4nc(NC5CCOCC5)ncc4Cl)cc3C2=O)cc1] | B | 2-(6-{5-chloro-2-[(oxan-4-yl)amino]pyrimidin-4-yl}-1-oxo-2,3-dihydro-1H-isoindol-2-yl)-N-{[4-(ethoxymethyl)phenyl]methyl}acetamide | 1H NMR (DMSO-d6) δ: 8.64 (t, 1H), 8.44 (s, 1H), 8.03 (d, 1H), 7.98 (dd, 1H), 7.75 (d, 1H), 7.61 (s (br), 1H), 7.27 (d, 2H), 7.24 (d, 2H), 4.61 (s, 2H), 4.42 (s, 2H), 4.29 (d, 2H), 4.26 (s, 2H), 3.98-3.81 (m, 3H), 3.45 (q, 2H), 3.41-3.34 (m, 2H), 1.89-1.78 (m, 2H), 1.58-1.44 (m, 2H), 1.13 (t, 3H). | 550 |
| 490 | 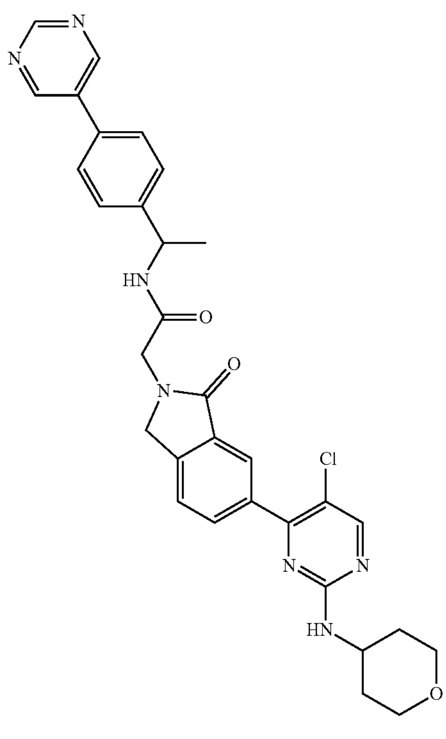 [SMILES: CC(NC(=O)CN1Cc2ccc(-c3nc(NC4CCOCC4)ncc3Cl)cc2C1=O)c1ccc(-c2cncnc2)cc1] | B | 2-(6-{5-chloro-2-[(oxan-4-yl)amino]pyrimidin-4-yl}-1-oxo-2,3-dihydro-1H-isoindol-2-yl)-N-{1-[4-(pyrimidin-5-yl)phenyl]ethyl}acetamide | 1H NMR (DMSO-d6) δ: 9.18 (s, 1H), 9.13 (s, 2H), 8.69 (d, 1H), 8.44 (s, 1H), 8.02 (d, 1H), 7.97 (dd, 1H), 7.82-7.76 (m, 2H), 7.74 (d, 1H), 7.61 (s (br), 1H), 7.53-7.44 (m, 2H), 5.01 (qd, 1H), 4.60 (s, 2H), 4.27 (s, 2H), 4.01-3.77 (m, 3H), 3.44-3.35 (m, 2H), 1.84 (d, 2H), 1.57-1.45 (m, 2H), 1.42 (d, 3H) | 584 |

-continued

| Example | Structure | Prep. | Name | ¹H NMR (400 MHz) | MS: [M + H]⁺ |
|---|---|---|---|---|---|
| 491 | 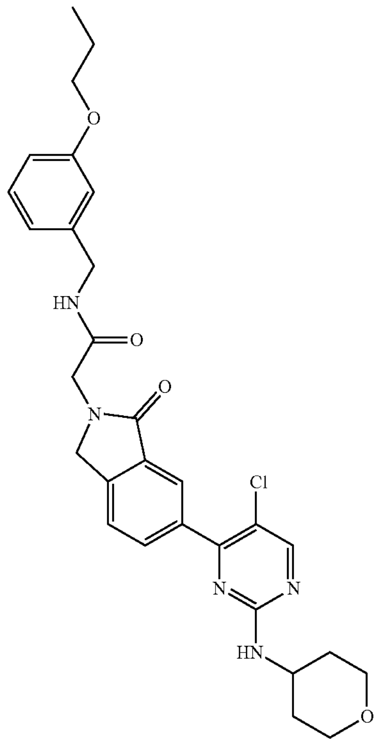 [SMILES: CCCOc1cccc(CNC(=O)CN2Cc3ccc(-c4nc(NC5CCOCC5)ncc4Cl)cc3C2=O)c1] | B | 2-(6-{5-chloro-2-[(oxan-4-yl)amino]pyrimidin-4-yl}-1-oxo-2,3-dihydro-1H-isoindol-2-yl)-N-[(3-propoxyphenyl)methyl]acetamide | 1H NMR (DMSO-d6) δ: 8.61 (t, 1H), 8.45 (s, 1H), 8.03 (d, 1H), 7.98 (dd, 1H), 7.75 (d, 1H), 7.62 (s (br), 1H), 7.22 (dd, 1H), 6.86-6.76 (m, 3H), 4.61 (s, 2H), 4.27 (d, 2H), 4.26 (s, 2H), 3.91 (t, 2H), 3.93-3.80 (m, 3H), 3.38 (d, 2H), 1.90-1.77 (m, 2H), 1.78-1.64 (m, 2H), 1.60-1.45 (m, 2H), 0.97 (t, 3H) | 550 |
| 492 | 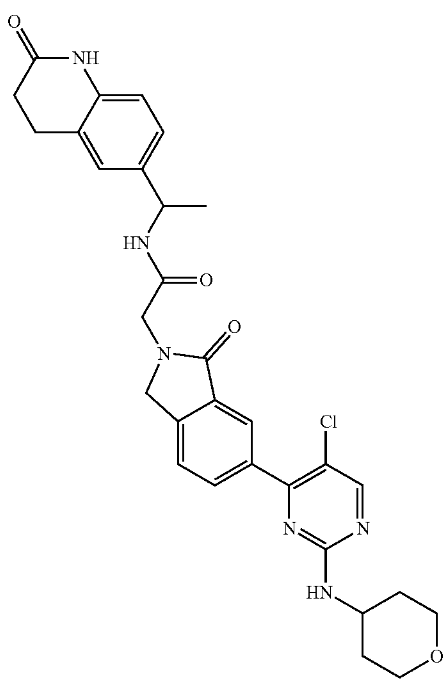 [SMILES: CC(NC(=O)CN1Cc2ccc(-c3nc(NC4CCOCC4)ncc3Cl)cc2C1=O)c1ccc2c(c1)CCC(=O)N2] | A | 2-(6-{5-chloro-2-[(oxan-4-yl)amino]pyrimidin-4-yl}-1-oxo-2,3-dihydro-1H-isoindol-2-yl)-N-[1-(2-oxo-1,2,3,4-tetrahydroquinolin-6-yl)ethyl]acetamide | 1H NMR (DMSO-d6) δ: 10.03 (s, 1H), 8.52 (d, 1H), 8.44 (s, 1H), 8.02 (d, 1H), 7.97 (dd, 1H), 7.74 (d, 1H), 7.61 (s, 1H), 7.12 (d, 1H), 7.08 (dd, 1H), 6.79 (d, 1H), 4.93-4.82 (m, (s, 2H), 3.99-3.81 (m, 3H), 3.45-3.35 (m, 2H), 2.89-2.80 (m, 2H), 2.43 (dd, 2H), 1.91-1.78 (m, 2H), 1.60-1.45 (m, 2H), 1.35 (d, 3H) | 575 |

-continued

| Example | Prep. | Name | 1H NMR (400 MHz) | MS: [M + H]+ |
|---|---|---|---|---|
| 493 | B | 2-(6-{5-chloro-2-[(oxan-4-yl)amino]pyrimidin-4-yl}-1-oxo-2,3-dihydro-1H-isoindol-2-yl)-N-[1-(2,6-difluorophenyl)ethyl] acetamide | 1H NMR (DMSO-d6) δ: 8.73 (d, 1H), 8.44 (s, 1H), 8.00 (d, 1H), 7.96 (dd, 1H), 7.71 (d, 1H), 7.62 (s (br), 1H), 7.38-7.28 (m, 1H), 7.10-7.00 (m, 2H), 5.23 (qd, 1H), 4.55 (s, 2H), 4.25 (d, 1H), 4.19 (d, 1H), 4.00-3.76 (m, 3H), 3.46-3.34 (m, 2H), 1.90-1.77 (m, 2H), 1.57-1.48 (m, 2H), 1.47 (d, 3H) | 542 |
| 494 | B | 2-(6-{5-chloro-2-[(oxan-4-yl)amino]pyrimidin-4-yl}-1-oxo-2,3-dihydro-1H-isoindol-2-yl)-N-{1-[5-fluoro-2-(1H-pyrazol-1-yl)phenyl]ethyl} acetamide | 1H NMR (DMSO-d6) δ: 8.68 (d, 1H), 8.44 (s, 1H), 8.00 (dd, 1H), 7.99 (dd, 1H), 7.96 (dd, 1H), 7.72 (d, 1H), 7.70 (dd, 1H), 7.61 (s (br), 1H), 7.40 (dd, 1H), 7.36 (dd, 1H) 7.27-7.19 (m, 1H), 6.48 (dd, 1H), 4.88 (qd, 1H), 4.56 (d, 1H), 4.51 (d, 1H), 4.23 (d, 1H), 4.19 (d, 1H), 4.00-3.77 (m, 3H), 3.48-3.34 (m, 2H), 1.95-1.75 (m, 2H), 1.63-1.40 (m, 2H), 1.25 (d, 3H) | 590 |

| Example | Structure | Prep. | Name | ¹H NMR (400 MHz) | MS: [M + H]⁺ |
|---|---|---|---|---|---|
| 495 | 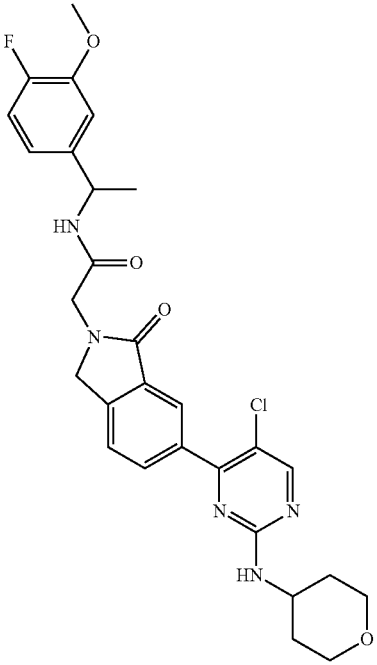 [SMILES: COc1cc(C(C)NC(=O)CN2Cc3ccc(-c4nc(NC5CCOCC5)ncc4Cl)cc3C2=O)ccc1F] | B | 2-(6-{5-chloro-2-[(oxan-4-yl)amino]pyrimidin-4-yl}-1-oxo-2,3-dihydro-1H-isoindol-2-yl)-N-[1-(4-fluoro-3-methoxyphenyl)ethyl]acetamide | 1H NMR (DMSO-d6) δ: 8.59 (d, 1H), 8.44 (s, 1H), 8.02 (d, 1H), 7.97 (dd, 1H), 7.74 (d, 1H), 7.61 (s (br), 1H), 7.13 (dd, 1H), 7.12 (dd, 1H), 6.88 (ddd, 1H), 4.94 (qd, 1H), 4.59 (s, 2H), 4.25 (s, 2H), 3.96-3.85 (m, 3H), 3.84 (s, 3H), 3.44-3.35 (m, 2H), 1.91-1.76 (m, 2H), 1.59-1.44 (m, 2H), 1.37 (d, 3H) | 554 |
| 496 | 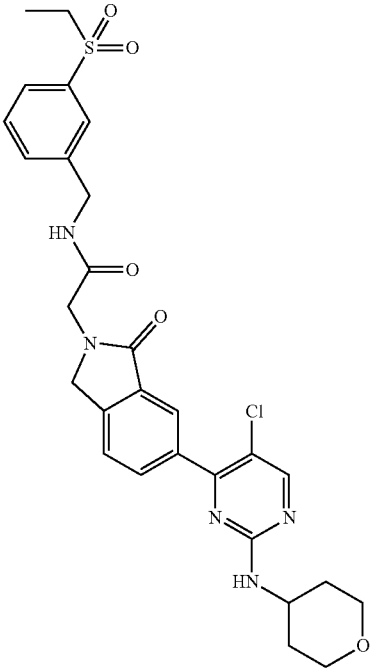 [SMILES: CCS(=O)(=O)c1cccc(CNC(=O)CN2Cc3ccc(-c4nc(NC5CCOCC5)ncc4Cl)cc3C2=O)c1] | A | 2-(6-{5-chloro-2-[(oxan-4-yl)amino]pyrimidin-4-yl}-1-oxo-2,3-dihydro-1H-isoindol-2-yl)-N-{[3-(ethanesulfonyl)phenyl]methyl}acetamide | 1H NMR (DMSO-d6) δ: 8.77 (t, 1H), 8.45 (s, 1H), 8.03 (d, 1H), 7.98 (dd, 1H), 7.82-7.70 (m, 3H), 7.68-7.55 (m, 3H), 4.61 (s, 2H), 4.42 (d, 2H), 4.28 (s, 2H), 3.86 (d, 3H), 3.44-3.35 (m, 2H), 3.29 (q, 2H), 1.92-1.77 (m, 2H), 1.61-1.46 (m, 2H), 1.10 (t, 3H) | 584 |

-continued

| Example | Structure | Prep. | Name | ¹H NMR (400 MHz) | MS: [M + H]⁺ |
|---|---|---|---|---|---|
| 497 | 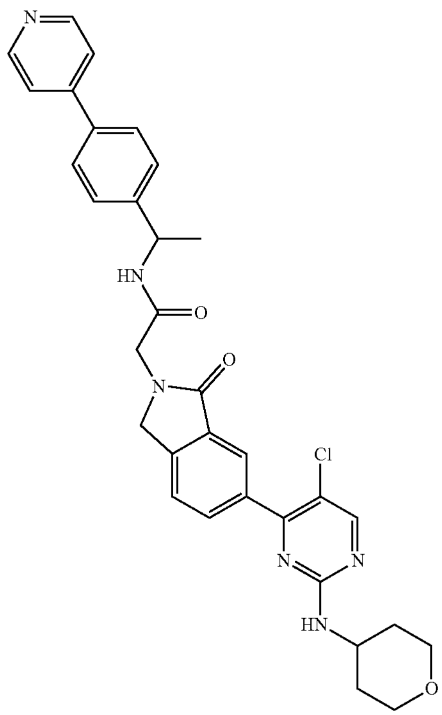 [SMILES: CC(NC(=O)CN1Cc2ccc(-c3nc(NC4CCOCC4)ncc3Cl)cc2C1=O)c1ccc(-c2ccncc2)cc1] | B | 2-(6-{5-chloro-2-[(oxan-4-yl)amino]pyrimidin-4-yl}-1-oxo-2,3-dihydro-1H-isoindol-2-yl)-N-{1-[4-(pyridin-4-yl)phenyl]ethyl}acetamide | 1H NMR (DMSO-d6) δ: 8.68 (d, 1H), 8.65-8.59 (m, 2H), 8.44 (s, 1H), 8.02 (d, 1H), 7.97 (dd, 1H), 7.77 (d, 2H), 7.74 (d, 1H), 7.71-7.67 (m, 2H), 7.62 (s, 1H), 7.51-7.44 (m, 2H), 5.01 (qd, 1H), 4.60 (s, 2H), 4.27 (s, 2H), 4.01-3.79 (m, 3H), 3.42-3.34 (m, 2H), 1.92-1.76 (m, 2H), 1.58-1.45 (m, 2H), 1.42 (d, 3H) | 583 |
| 498 | 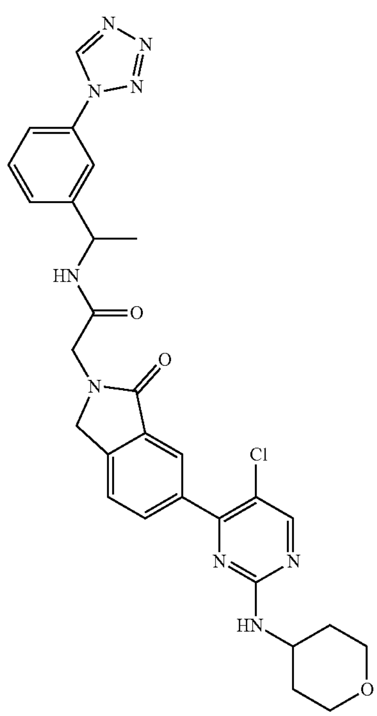 [SMILES: CC(NC(=O)CN1Cc2ccc(-c3nc(NC4CCOCC4)ncc3Cl)cc2C1=O)c1cccc(-n2cnnn2)c1] | B | 2-(6-{5-chloro-2-[(oxan-4-yl)amino]pyrimidin-4-yl}-1-oxo-2,3-dihydro-1H-isoindol-2-yl)-N-{1-[3-(1H-1,2,3,4-tetrazol-1-yl)phenyl]ethyl}acetamide | 1H NMR (DMSO-d6) δ: 10.12 (s, 1H), 8.74 (d, 1H), 8.44 (s, 1H), 8.02 (d, 1H), 7.97 (dd, 1H), 7.90-7.84 (m, 1H), 7.78 (ddd, 1H), 7.73 (d, 1H), 7.62 (dd, 2H), 7.57-7.50 (m, 1H), 5.06 (qd, 1H), 4.60 (s, 2H), 4.28 (s, 2H), 4.00-3.79 (m, 3H), 3.37 (d, 2H), 1.90-1.77 (m, 2H), 1.58-1.47 (m, 2H), 1.45 (d, 3H) | 574 |

-continued

| Example | Structure | Prep. | Name | ¹H NMR (400 MHz) | MS: [M + H]⁺ |
|---|---|---|---|---|---|
| 499 | 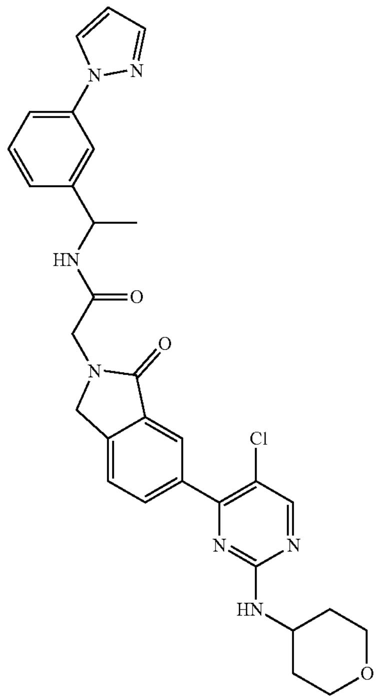 [SMILES: CC(NC(=O)CN1Cc2ccc(-c3nc(NC4CCOCC4)ncc3Cl)cc2C1=O)c1cccc(-n2cccn2)c1] | B | 2-(6-{5-chloro-2-[(oxan-4-yl)amino]pyrimidin-4-yl}-1-oxo-2,3-dihydro-1H-isoindol-2-yl)-N-{1-[3-(1H-pyrazol-1-yl)phenyl]ethyl}acetamide | 1H NMR (DMSO-d6) δ: 8.70 (d, 1H), 8.51 (dd, 1H), 8.44 (s, 1H), 8.02 (d, 1H), 7.97 (dd, 1H), 7.84-7.78 (m, 1H), 7.75 (dd, 1H), 7.73 (d, 1H), 7.70 (ddd, 1H), 7.62 (s (br), 1H), 7.45 (dd, 1H), 7.31-7.23 (m, 1H), 6.55 (dd, 1H), 5.02 (qd, 1H), 4.60 (s, 2H), 4.27 (s, 2H), 3.98-3.78 (m, 3H), 3.42-3.34 (m, 2H), 1.91-1.78 (m, 2H), 1.59-1.46 (m, 2H), 1.43 (d, 3H) | 572 |
| 500 | 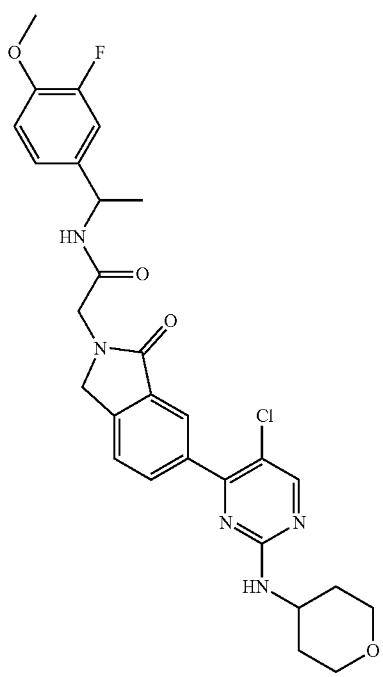 [SMILES: COc1ccc(C(C)NC(=O)CN2Cc3ccc(-c4nc(NC5CCOCC5)ncc4Cl)cc3C2=O)cc1F] | B | 2-(6-{5-chloro-2-[(oxan-4-yl)amino]pyrimidin-4-yl}-1-oxo-2,3-dihydro-1H-isoindol-2-yl)-N-[1-(3-fluoro-4-methoxyphenyl)ethyl]acetamide | 1H NMR (DMSO-d6) δ: 8.55 (d, 1H), 8.44 (s, 1H), 8.02 (d, 1H), 7.97 (dd, 1H), 7.74 (d, 1H), 7.61 (s (br), 1H), 7.19-7.04 (m, 3H), 4.90 (qd, 1H), 4.58 (s, 2H), 4.24 (s, 2H), 3.98-3.83 (m, 3H), 3.81 (s, 3H), 3.43-3.33 (m, 2H), 1.92-1.77 (m, 2H), 1.61-1.44 (m, 2H), 1.35 (d, 3H) | 554 |

-continued

| Example | Structure | Prep. | Name | ¹H NMR (400 MHz) | MS: [M + H]⁺ |
|---|---|---|---|---|---|
| 501 | 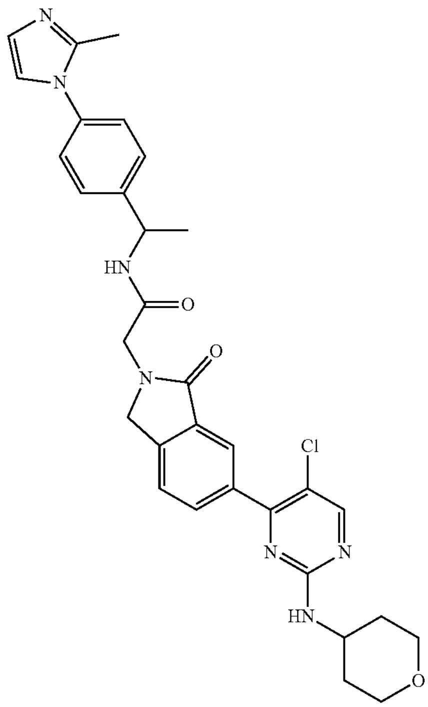 [SMILES: Cc1nccn1-c1ccc(C(C)NC(=O)CN2Cc3ccc(-c4nc(NC5CCOCC5)ncc4Cl)cc3C2=O)cc1] | B | 2-(6-{5-chloro-2-[(oxan-4-yl)amino]pyrimidin-4-yl}-1-oxo-2,3-dihydro-1H-isoindol-2-yl)-N-{1-[4-(2-methyl-1H-imidazol-1-yl)phenyl]ethyl}acetamide | 1H NMR (DMSO-d6) δ: 8.69 (d, 1H), 8.44 (s, 1H), 8.02 (d, 1H), 7.97 (dd, 1H), 7.74 (d, 1H), 7.61 (s (br), 1H), 7.48 (d, 2H), 7.41 (d, 2H), 7.26 (d, 1H), 6.90 (d, 1H), 5.03 (qd, 1H), 4.60 (s, 2H), 4.27 (s, 2H), 3.97-3.78 (m, 3H), 3.42-3.36 (m, 2H), 2.28 (s, 3H), 1.90-1.77 (m, 2H), 1.59-1.46 (m, 2H), 1.42 (d, 3H) | 586 |
| 502 | 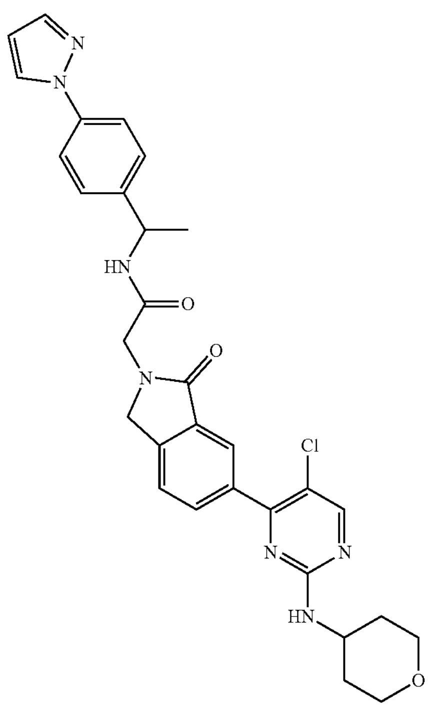 [SMILES: CC(NC(=O)CN1Cc2ccc(-c3nc(NC4CCOCC4)ncc3Cl)cc2C1=O)c1ccc(-n2cccn2)cc1] | B | 2-(6-{5-chloro-2-[(oxan-4-yl)amino]pyrimidin-4-yl}-1-oxo-2,3-dihydro-1H-isoindol-2-yl)-N-{1-[4-(1H-pyrazol-1-yl)phenyl]ethyl}acetamide | 1H NMR (DMSO-d6) δ: 8.65 (d, 1H), 8.47 (dd, 1H), 8.44 (s, 1H), 8.02 (d, 1H), 7.97 (dd, 1H), 7.79 (d, 2H), 7.75-7.70 (m, 2H), 7.61 (s (br), 1H), 7.44 (d, 2H), 6.53 (dd, 1H), 5.00 (qd, 1H), 4.59 (s, 2H), 4.29 (d, 1H), 4.24 (d, 1H), 3.98-3.78 (m, 3H), 3.43-3.35 (m, 2H), 1.90-1.75 (m, 2H), 1.59-1.44 (m, 2H), 1.41 (d, 3H) | 572 |

| Example | Structure | Prep. | Name | ¹H NMR (400 MHz) | MS: [M + H]⁺ |
|---|---|---|---|---|---|
| 503 | 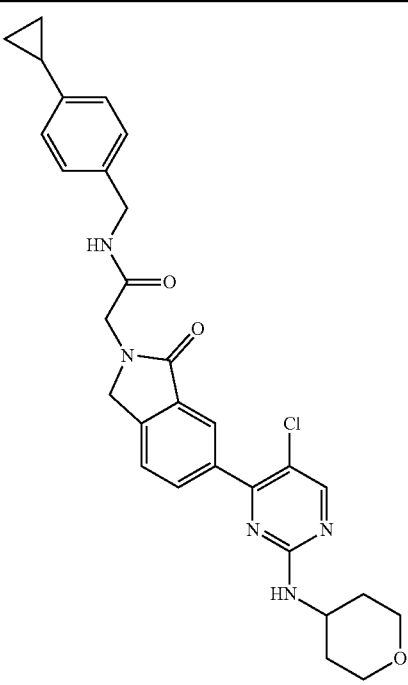 | B | 2-(6-{5-chloro-2-[(oxan-4-yl)amino]pyrimidin-4-yl}-1-oxo-2,3-dihydro-1H-isoindol-2-yl)-N-[(4-cyclopropylphenyl)methyl]acetamide | 1H NMR (DMSO-d6) δ: 8.58 (t, 1H), 8.45 (s, 1H), 8.02 (d, 1H), 7.98 (dd, 1H), 7.75 (d, 1H), 7.62 (s (br), 1H), 7.14 (d, 2H), 7.04-6.98 (m, 2H), 4.60 (s, 2H), 4.29-4.16 (m, 4H), 3.98-3.81 (m, 3H), 3.44-3.35 (m, 2H), 1.94-1.77 (m, 3H), 1.61-1.44 (m, 2H), 0.95-0.85 (m, 2H), 0.68-0.57 (m, 2H) | 532 |
| 504 | 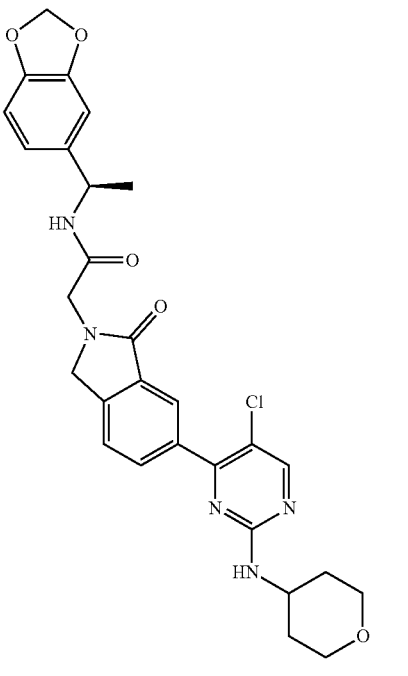 [SMILES: C[C@@H](NC(=O)CN1Cc2ccc(-c3nc(NC4CCOCC4)ncc3Cl)cc2C1=O)c1ccc2c(c1)OCO2] | B | N-[(1R)-1-(2H-1,3-benzodioxol-5-yl)ethyl]-2-(6-{5-chloro-2-[(oxan-4-yl)amino]pyrimidin-4-yl}-1-oxo-2,3-dihydro-1H-isoindol-2-yl)acetamide | 1H NMR (DMSO-d6) δ: 8.52 (d, 1H), 8.44 (s, 1H), 8.02 (d, 1H), 7.97 (dd, 1H), 7.74 (d, 1H), 7.62 (s (br), 1H), 6.91 (d, 1H), 6.85 (d, 1H), 6.78 (dd, 1H), 5.98 (s, 2H), 4.88 (qd, 1H), 4.58 (s, 2H), 4.25 (d, 1H), 4.20 (d, 1H) 3.99-3.79 (m, 3H), 3.45-3.35 (m, 2H), 1.91-1.77 (m, 2H), 1.59-1.44 (m, 2H), 1.34 (d, 3H) | 550 |

-continued

| Example | Structure | Prep. | Name | ¹H NMR (400 MHz) | MS: [M + H]⁺ |
|---|---|---|---|---|---|
| 505 | 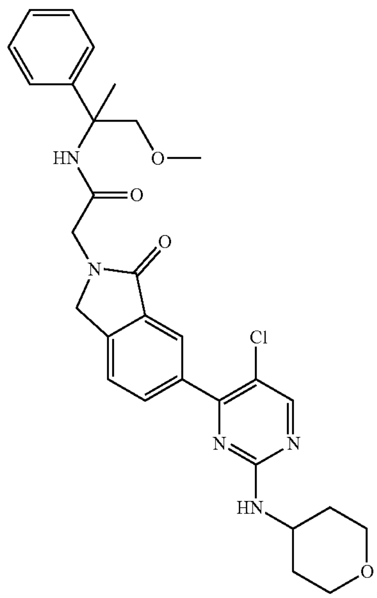 [SMILES: COCC(C)(NC(=O)CN1Cc2ccc(-c3nc(NC4CCOCC4)ncc3Cl)cc2C1=O)c1ccccc1] | B | 2-(6-{5-chloro-2-[(oxan-4-yl)amino]pyrimidin-4-yl}-1-oxo-2,3-dihydro-1H-isoindol-2-yl)-N-(1-methoxy-2-phenylpropan-2-yl)acetamide | 1H NMR (DMSO-d6) δ: 8.43 (s, 1H), 8.27 (s, 1H), 8.01 (d, 1H), 7.95 (dd, 1H), 7.72 (d, 1H), 7.61 (s (br), 1H), 7.37-7.24 (m, 4H), 7.24-7.15 (m, 1H), 4.57 (d, 1H), 4.52 (d, 1H), 4.29 (s, 2H), 3.95-3.82 (m, 3H), 3.60 (d, 1H), 3.51 (d, 1H), 3.42-3.36 (m, 2H), 3.26 (s, 3H), 1.88-1.79 (m, 2H), 1.62 (s, 3H), 1.59-1.44 (m, 2H) | 550 |
| 506 | 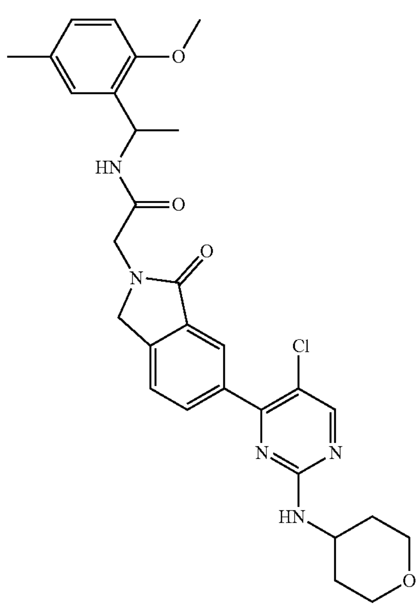 [SMILES: COc1ccc(C)cc1C(C)NC(=O)CN1Cc2ccc(-c3nc(NC4CCOCC4)ncc3Cl)cc2C1=O] | B | 2-(6-{5-chloro-2-[(oxan-4-yl)amino]pyrimidin-4-yl}-1-oxo-2,3-dihydro-1H-isoindol-2-yl)-N-[1-(2-methoxy-5-methylphenyl)ethyl]acetamide | 1H NMR (DMSO-d6) δ: 8.48 (d, 1H), 8.44 (s, 1H), 8.02 (d, 1H), 7.97 (dd, 1H), 7.73 (d, 1H), 7.61 (s (br), 1H), 7.10 (d, 1H), 7.00 (dd, 1H), 6.84 (d, 1H), 5.19 (qd, 1H), 4.59 (s, 2H), 4.25 (s, 2H), 3.98-3.79 (m, 3H), 314 (s, 3H), 3.44-3.35 (m, 2H), 2.24 (s, 3H), 1.92-1.77 (m, 2H), 1.61-1.44 (m, 2H), 1.28 (d, | 550 |

-continued

| Example | Structure | Prep. | Name | ¹H NMR (400 MHz) | MS: [M + H]⁺ |
|---|---|---|---|---|---|
| 507 | 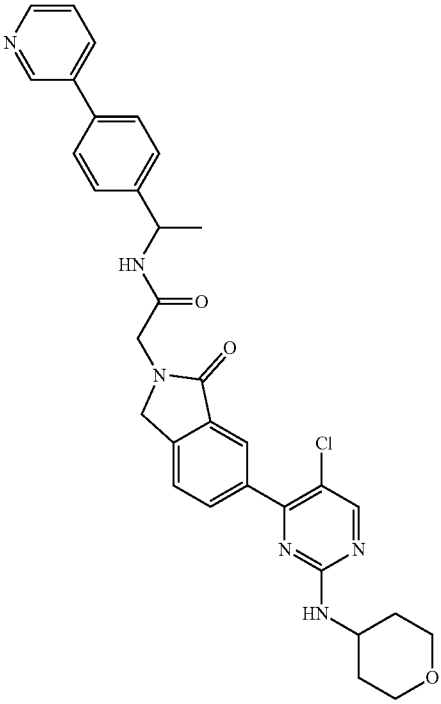 [SMILES: CC(NC(=O)CN1Cc2ccc(-c3nc(NC4CCOCC4)ncc3Cl)cc2C1=O)c1ccc(-c2cccnc2)cc1] | B | 2-(6-{5-chloro-2-[(oxan-4-yl)amino]pyrimidin-4-yl}-1-oxo-2,3-dihydro-1H-isoindol-2-yl)-N-{1-[4-(pyridin-3-yl)phenyl]ethyl}acetamide | 1H NMR (DMSO-d6) δ: 8.89 (dd, 1H), 8.69 (d, 1H), 8.57 (dd, 1H), 8.45 (s, 1H), 8.07 (ddd, 1H), 8.03 (d, 1H), 7.98 (dd, 1H), 7.74 (d, 1H), 7.70 (d, 2H), 7.62 (s (br), 1H), 7.52-7.43 (m, 3H), 5.02 (qd, 1H), 4.61 (s, 2H), 4.28 (s, 2H), 3.98-3.81 (m, 3H), 3.42-3.37 (m, 2H), 1.90-1.79 (m, 2H), 1.60-1.47 (m, 2H), 1.43 (d, 3H) | 583 |
| 508 | 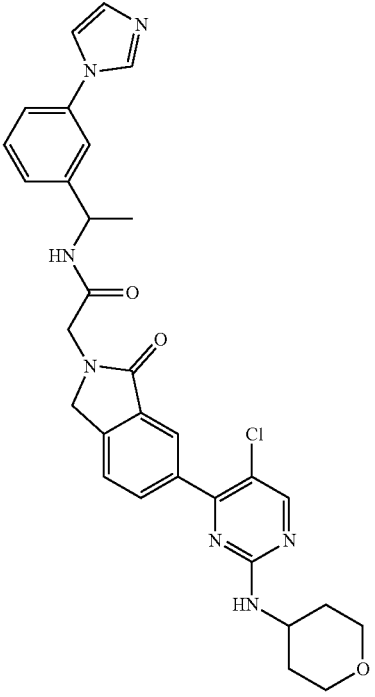 [SMILES: CC(NC(=O)CN1Cc2ccc(-c3nc(NC4CCOCC4)ncc3Cl)cc2C1=O)c1cccc(-n2ccnc2)c1] | B | 2-(6-{5-chloro-2-[(oxan-4-yl)amino]pyrimidin-4-yl}-1-oxo-2,3-dihydro-1H-isoindol-2-yl)-N-{1-[3-(1H-imidazol-1-yl)phenyl]ethyl}acetamide | 1H NMR (DMSO) δ: 8.67 (d, 1H), 8.45 (s, 1H), 8.27 (dd, 1H), 8.03 (d, 1H), 7.98 (dd, 1H), 7.77 (dd, 1H), 7.74 (d, 1H), 7.62 (s (br), 1H), 7.61-(m, 1H), 7.55-7.44 (m, 2H), 7.33 (d, 1H), 7.12 (dd, 1H), 5.03 (qd, 1H), 4.61 (s, 2H), 4.31 (d, 1H), 4.26 (d, 1H), 4.01-3.81 (m, 3H), 3.33-3.45 (m, 2H), 1.91-1.78 (m, 2H), 1.60-1.47 (m, 2H), 1.43 (d, 3H) | 572 |

-continued

| Example | Structure | Prep. | Name | ¹H NMR (400 MHz) | MS: [M + H]⁺ |
|---|---|---|---|---|---|
| 509 | 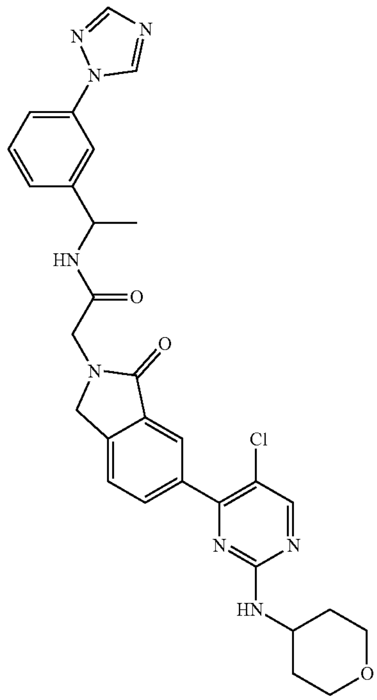 | B | 2-(6-{5-chloro-2-[(oxan-4-yl)amino]pyrimidin-4-yl}-1-oxo-2,3-dihydro-1H-isoindol-2-yl)-N-{1-[3-(1H-1,2,4-triazol-1-yl)phenyl]ethyl} acetamide | 1H NMR (DMSO-d6) δ: 9.32 (s, 1H), 8.73 (d, 1H), 8.45 (s, 1H), 8.26 (s, 1H), 8.03 (d, 1H), 7.97 (dd, 1H), 7.83 (td, 1H), 7.74 (d, 2H), 7.62 (s (br), 1H), 7.53 (dd, 1H), 7.43-7.36 (m, 1H), 5.05 (qd, 1H), 4.61 (s, 2H), 4.28 (s, 2H), 3.96-3.82 (m, 3H), 3.38 (d, 2H) 1.88-1.80(m, 2H), 1.60-1.45(m, 2H), 1.44 (d, 3H) | 573 |
| 510 | 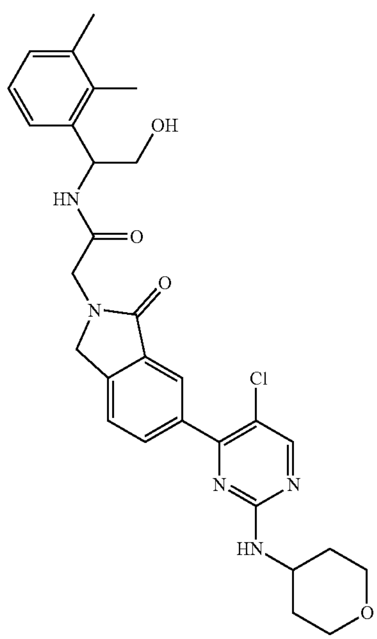 [SMILES: Cc1cccc(C(CO)NC(=O)CN2Cc3ccc(-c4nc(NC5CCOCC5)ncc4Cl)cc3C2=O)c1C] | B | 2-(6-{5-chloro-2-[(oxan-4-yl)amino]pyrimidin-4-yl}-1-oxo-2,3-dihydro-1H-isoindol-2-yl)-N-[1-(2,3-dimethylphenyl)-2-hydroxyethyl] acetamide | 1H NMR (DMSO-d6) δ: 8.59 (d, 1H), 8.45 (s, 1H), 8.02 (d, 1H), 7.97 (dd, 1H), 7.73 (d, 1H), 7.62 (s (br), 1H), 7.24-7.15 (m, 1H), 7.11-6.99 (m, 2H), 5.23-5.10 (m, 1H), 4.94 (t, 1H), 4.58 (s, 2H), 4.31 (d, 1H), 4.23 (d, 1H), 3.98-3.80 (m, 3H), 3.56-3.44 (m, 2H), 3.42-3.36 (m, 2H), 2.24 (s, 3H), 2.22 (s, 3H), 1.91-1.77 (m, 2H), 1.60-1.43 (m, 2H) | 550 |

-continued

| Example | Structure | Prep. | Name | ¹H NMR (400 MHz) | MS: [M + H]⁺ |
|---|---|---|---|---|---|
| 511 | 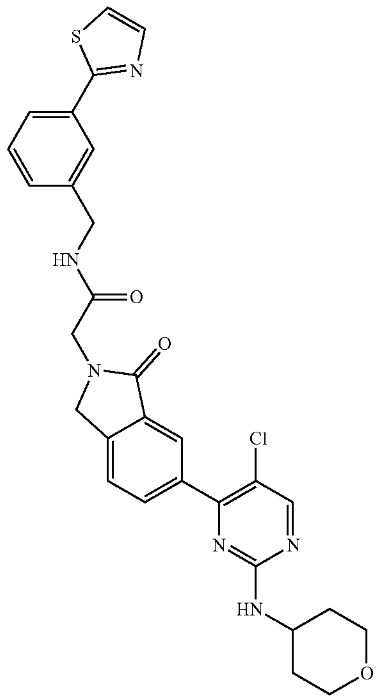 [SMILES: O=C(CN1Cc2ccc(-c3nc(NC4CCOCC4)ncc3Cl)cc2C1=O)NCc1cccc(-c2nccs2)c1] | B | 2-(6-{5-chloro-2-[(oxan-4-yl)amino]pyrimidin-4-yl}-1-oxo-2,3-dihydro-1H-isoindol-2-yl)-N-{[3-(1,3-thiazol-2-yl)phenyl]methyl}acetamide | 1H NMR (DMSO-d6) δ: 8.75 (t, 1H), 8.44 (s, 1H), 8.03 (d, 1H), 7.98 (dd, 1H), 7.94 (d, 1H), 7.89-7.86 (m, 1H), 7.86-7.81 (m, 1H), 7.80 (d, 1H), 7.75 (d, 1H), 7.62 (s (br), 1H), 7.47 (dd, 1H), 7.42-7.36 (m, 1H), 4.63 (s, 2H), 4.39 (d, 2H), 4.28 (s, 2H), 3.98-3.78 (m, 3H), 3.43-3.34 (m, 2H), 1.90-1.77 (m, 2H), 1.60-1.44 (m, 2H) | 575 |
| 512 | 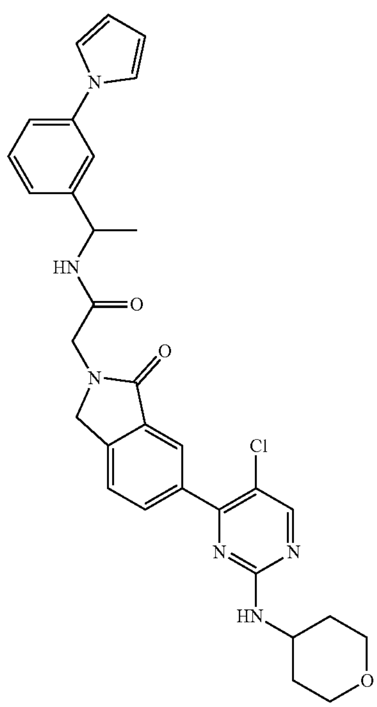 [SMILES: CC(NC(=O)CN1Cc2ccc(-c3nc(NC4CCOCC4)ncc3Cl)cc2C1=O)c1cccc(-n2cccc2)c1] | B | 2-(6-{5-chloro-2-[(oxan-4-yl)amino]pyrimidin-4-yl}-1-oxo-2,3-dihydro-1H-isoindol-2-yl)-N-{1-[3-(1H-pyrrol-1-yl)phenyl]ethyl}acetamide | 1H NMR (DMSO-d6) δ: 8.65 (d, 1H), 8.44 (s, 1H), 8.03 (d, 1H), 7.97 (dd, 1H), 7.73 (d, 1H), 7.61 (s (br), 1H), 7.53-7.49 (m, 1H), 7.45-7.38 (m, 2H), 7.38-7.36 (m, 2H), 7.24-7.17 (m, 1H), 6.27 (dd, 2H), 5.02 (qd, 1H), 4.60 (s, 2H), 4.27 (s, 2H), 3.99-3.74 (m, 3H), 3.43-3.35 (m, 2H), 1.94-1.73 (m, 2H), 1.60-1.44 (m, 2H), 1.42 (d, 3H) | 571 |

| Example | Structure | Prep. | Name | ¹H NMR (400 MHz) | MS: [M + H]⁺ |
|---|---|---|---|---|---|
| 513 | 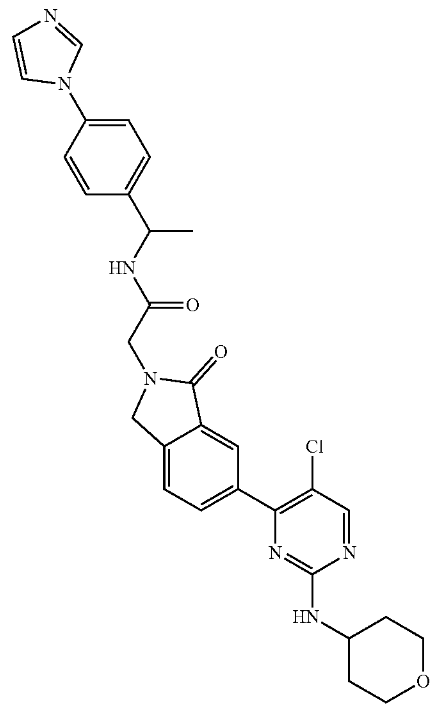 [SMILES: CC(NC(=O)CN1Cc2ccc(-c3nc(NC4CCOCC4)ncc3Cl)cc2C1=O)c1ccc(-n2ccnc2)cc1] | B | 2-(6-{5-chloro-2-[(oxan-4-yl)amino]pyrimidin-4-yl}-1-oxo-2,3-dihydro-1H-isoindol-2-yl)-N-{1-[4-(1H-imidazol-1-yl)phenyl]ethyl}acetamide | 1H NMR (DMSO-d6) δ: 8.66 (d, 1H), 8.44 (s, 1H), 8.22 (dd, 1H), 8.02 (d, 1H), 7.97 (dd, 1H), 7.74 (d, 1H), 7.72 (dd, 1H), 7.67-7.57 (m, 3H), 7.46 (d, 2H), 7.10 (dd, 1H), 5.00 (qd, 1H), 4.59 (s, 2H), 4.26 (s, 2H), 4.00-3.79 (m, 3H), 3.42-3.35 (m, 2H), 1.90-1.78 (m, 2H), 1.60-1.45 (m, 2H), 1.41 (d, 3H). | 572 |
| 514 | 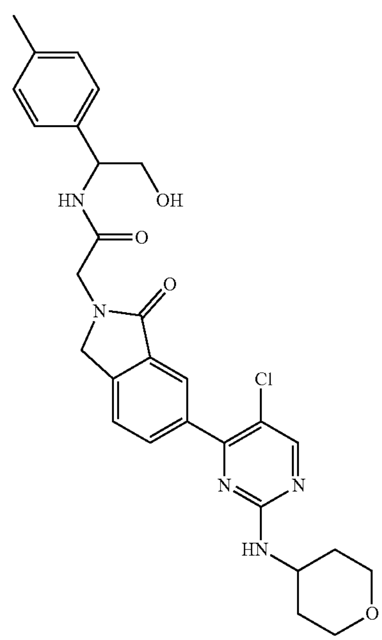 [SMILES: Cc1ccc(C(CO)NC(=O)CN2Cc3ccc(-c4nc(NC5CCOCC5)ncc4Cl)cc3C2=O)cc1] | A | 2-(6-{5-chloro-2-[(oxan-4-yl)amino]pyrimidin-4-yl}-1-oxo-2,3-dihydro-1H-isoindol-2-yl)-N-[2-hydroxy-1-(4-methylphenyl)ethyl]acetamide | 1H NMR (DMSO, 400 MHz) δ 8.51 (1H, d), 8.44(1H, s), 8.02 (1H, d), 7.97 (1H, dd), 7.73 (1H, d), 7.61 (1H, s), 7.20 (2H, d), 7.12 (2H, d), 4.89 (1H, t), 4.83 (1H, q), 4.58 (2H, s), 4.29 (2H, dd), 3.99-3.80 (3H, m), 3.54 (2H, t), 3.38 (2H, d), 2.27 (3H, s), 1.84 (2H, d), 1.59-1.43 (2H, m) | 536 |

| Example | Structure | Prep. | Name | ¹H NMR (400 MHz) | MS: [M + H]⁺ |
|---|---|---|---|---|---|
| 515 | 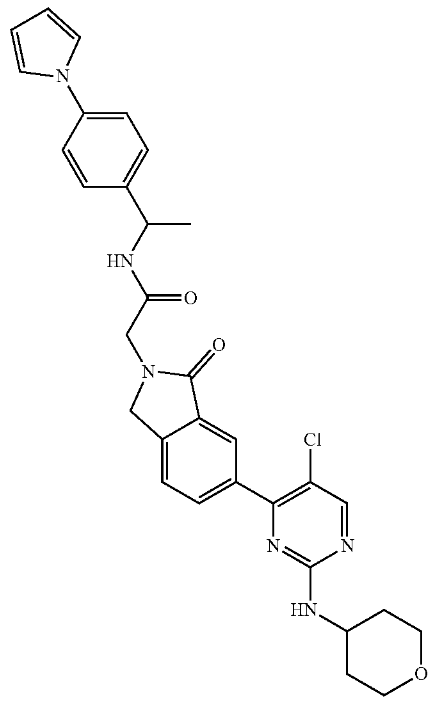 [SMILES: CC(NC(=O)CN1Cc2ccc(-c3nc(NC4CCOCC4)ncc3Cl)cc2C1=O)c1ccc(-n2cccc2)cc1] | B | 2-(6-{5-chloro-2-[(oxan-4-yl)amino]pyrimidin-4-yl}-1-oxo-2,3-dihydro-1H-isoindol-2-yl)-N-{1-[4-(1H-pyrrol-1-yl)phenyl]ethyl}acetamide | 1H NMR (DMSO, 400 MHz) δ 8.63 (1H, d), 8.44 (1H, s), 8.02 (1H, dd), 7.97 (1H, dd), 7.74 (1H, d), 7.61 (1H, s), 7.55-7.49 (2H, m), 7.42-7.36 (2H, m), 7.33 (2H, t), 6.25 (2H, t), 4.98 (1H, p), 4.59 (2H, s), 4.26 (2H, dd), 3.99-3.79 (3H, m), 3.42-3.35 (2H, m), 1.84 (2H, d), 1.59-1.45(2H, m), 1.40 (3H, d) | 571 |
| 516 | 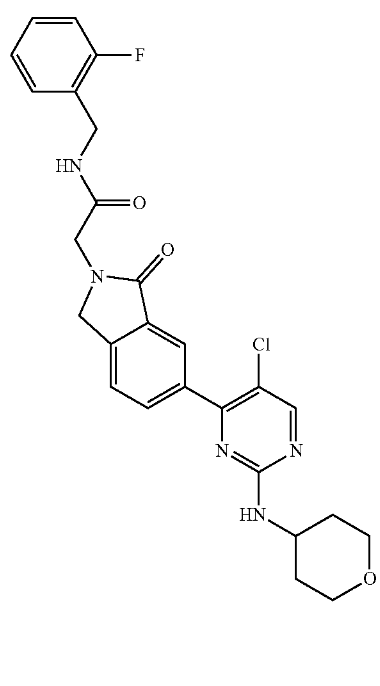 [SMILES: O=C(CN1Cc2ccc(-c3nc(NC4CCOCC4)ncc3Cl)cc2C1=O)NCc1ccccc1F] | B | 2-(6-{5-chloro-2-[(oxan-4-yl)amino]pyrimidin-4-yl}-1-oxo-2,3-dihydro-1H-isoindol-2-yl)-N-[(2-fluorophenyl)methyl]acetamide | 1H NMR (DMSO, 400 MHz) δ 8.65 (1H, t), 8.44 (1H, s), 8.04-8.01 (1H, m), 7.98 (1H, dd), 7.75 (1H, d), 7.62 (1H, s), 7.39-7.28 (2H, m), 7.22-7.13 (2H, m), 4.61 (2H, s), 4.34 (2H, d), 4.27 (2H, s), 3.99-3.79 (3H, m), 3.43-3.36 (2H, m), 1.84 (2H, d), 1.60-1.45 (2H, m) | 510 |

-continued

| Example | Structure | Prep. | Name | ¹H NMR (400 MHz) | MS: [M + H]⁺ |
|---|---|---|---|---|---|
| 517 | 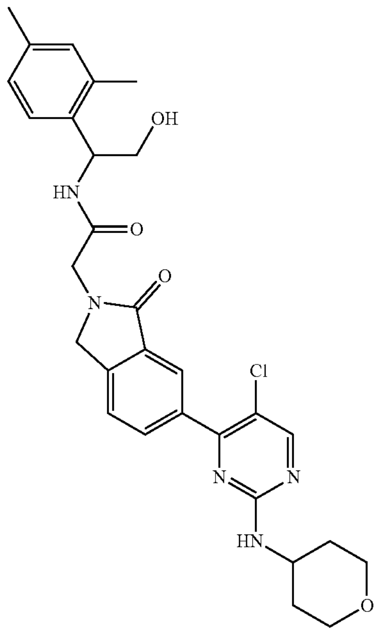 [SMILES: Cc1ccc(C(CO)NC(=O)CN2Cc3ccc(-c4nc(NC5CCOCC5)ncc4Cl)cc3C2=O)c(C)c1] | B | 2-(6-{5-chloro-2-[(oxan-4-yl)amino]pyrimidin-4-yl}-1-oxo-2,3-dihydro-1H-isoindol-2-yl)-N-[1-(2,4-dimethylphenyl)-2-hydroxyethyl]acetamide | 1H NMR (DMSO, 400 MHz) δ 8.55 (1H, d), 8.44 (1H, s), 8.04-7.99 (1H, m), 7.96 (1H, dd), 7.73 (1H, d), 7.62 (1H, s), 7.19 (1H, d), 6.97 (1H, d), 6.94 (1H, s), 5.03 (1H, q), 4.92 (1H, t), 4.56 (2H, s), 4.26 (2H, q), 3.97-3.78 (3H, m), 3.48 (2H, t), 3.42-3.34 (2H, m), 2.28 (3H, s), 2.22 (3H, s), 1.84 (2H, d), 1.59-1.43 (2H, m) | 550 |
| 518 | 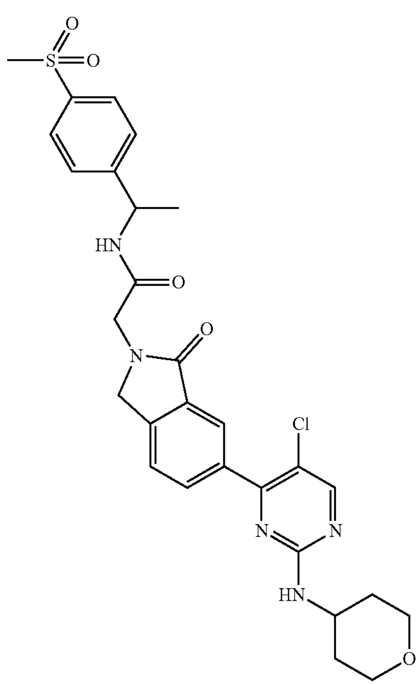 [SMILES: CC(NC(=O)CN1Cc2ccc(-c3nc(NC4CCOCC4)ncc3Cl)cc2C1=O)c1ccc(S(C)(=O)=O)cc1] | A | 2-(6-{5-chloro-2-[(oxan-4-yl)amino]pyrimidin-4-yl}-1-oxo-2,3-dihydro-1H-isoindol-2-yl)-N-[1-(4-methanesulfonylphenyl)ethyl]acetamide | 1H NMR (DMSO, 400 MHz) δ 8.75 (1H, d), 8.44 (1H, s), 8.04-8.00 (1H, m), 7.97 (1H, dd), 7.92-7.86 (2H, m), 7.73 (1H, d), 7.66-7.55 (3H, m), 5.02 (1H, p), 4.58 (2H, s), 4.27 (2H, s), 3.99-3.78 (3H, m), 3.44-3.35 (2H, m), 3.20 (3H, s), 1.84 (2H, d), 1.60-1.44 (2H, m), 1.40 (3H, d) | 584 |

| Example | Structure | Prep. | Name | ¹H NMR (400 MHz) | MS: [M + H]⁺ |
|---|---|---|---|---|---|
| 519 | 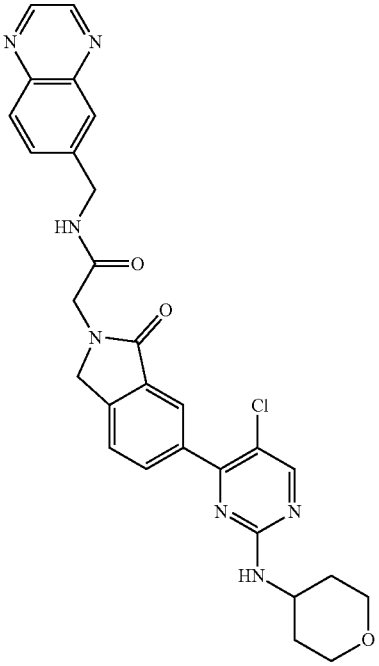 [SMILES: O=C(CN1Cc2ccc(-c3nc(NC4CCOCC4)ncc3Cl)cc2C1=O)NCc1ccc2nccnc2c1] | A | 2-(6-{5-chloro-2-[(oxan-4-yl)amino]pyrimidin-4-yl}-1-oxo-2,3-dihydro-1H-isoindol-2-yl)-N-[(quinoxalin-6-yl)methyl]acetamide | 1H NMR (DMSO, 400 MHz) δ 8.96-8.89 (2H, m), 8.86 (1H, t), 8.44 (1H, s), 8.10-8.02 (2H, m), 8.00-7.94 (2H, m), 7.82-7.72 (2H, m), 7.62 (1H, s), 4.64 (2H, s), 4.58 (2H, d), 4.33 (2H, s), 3.99-3.80 (3H, m), 3.41-3.35 (2H, m), 1.84 (2H, d), 1.59-1.43 (2H, m) | 544 |
| 520 | 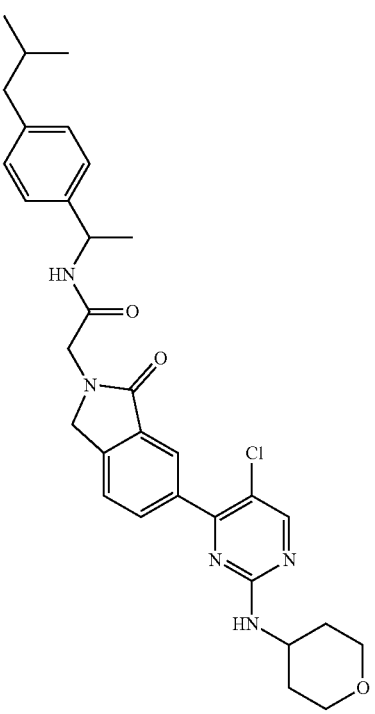 [SMILES: CC(C)Cc1ccc(C(C)NC(=O)CN2Cc3ccc(-c4nc(NC5CCOCC5)ncc4Cl)cc3C2=O)cc1] | C | 2-(6-{5-chloro-2-[(oxan-4-yl)amino]pyrimidin-4-yl}-1-oxo-2,3-dihydro-1H-isoindol-2-yl)-N-{1-[4-(2-methylpropyl)phenyl]ethyl}acetamide | 1H NMR (DMSO, 400 MHz) δ 8.56 (1H, d), 8.44 (1H, s), 8.02 (1H, dd), 7.97 (1H, dd), 7.73 (1H, d), 7.62 (1H, s), 7.23 (2H, d), 7.11 (2H, d), 4.94 (1H, p), 4.49 (2H, s), 4.29-4.17 (2H, m), 3.99-3.79 (3H, m), 3.43-3.35 (2H, m), 2.41 (2H, d), 1.91-1.72 (3H, m), 1.59-1.43 (2H, m), 1.37 (3H, d), 0.85 (6H, dd) | 562 |

| Example | Structure | Prep. | Name | ¹H NMR (400 MHz) | MS: [M + H]⁺ |
|---|---|---|---|---|---|
| 521 | 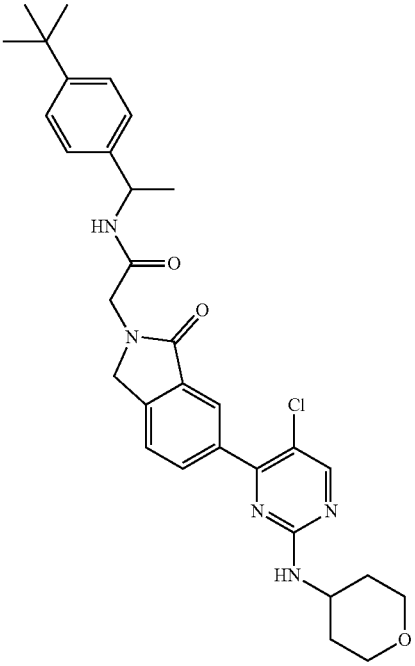 [SMILES: CC(NC(=O)CN1Cc2ccc(-c3nc(NC4CCOCC4)ncc3Cl)cc2C1=O)c1ccc(C(C)(C)C)cc1] | B | N-[1-(4-tert-butylphenyl)ethyl]-2-(6-{5-chloro-2-[(oxan-4-yl)amino]pyrimidin-4-yl}-1-oxo-2,3-dihydro-1H-isoindol-2-yl)acetamide | 1H NMR (DMSO, 400 MHz) δ 8.56 (1H, d), 8.44 (1H, s), 8.01 (1H, d), 7.97 (1H, dd), 7.73 (1H, d), 7.62 (1H, s), 7.34 (2H, d), 7.24 (2H, d), 4.92 (1H, p), 4.59 (2H, s), 4.23 (2H, s), 3.98-3.80 (3H, m), 3.42-3.35 (2H, m), 1.84 (2H, d), 1.59-1.44 (2H, m), 1.36 (3H, d), 1.26 (9H, s) | 562 |
| 522 | 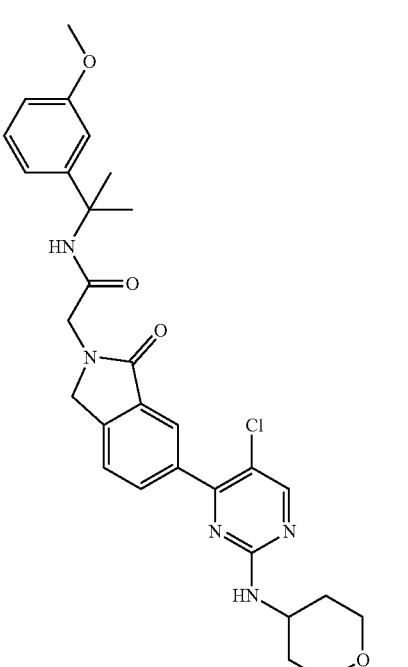 | B | 2-(6-{5-chloro-2-[(oxan-4-yl)amino]pyrimidin-4-yl}-1-oxo-2,3-dihydro-1H-isoindol-2-yl)-N-[2-(3-methoxyphenyl)propan-2-yl]acetamide | 1H NMR (DMSO, 400 MHz) δ 8.44 (1H, s), 8.38 (1H, s), 8.00 (1H, dd), 7.95 (1H, dd), 7.72 (1H, d), 7.62 (1H, s), 7.20 (1H, t), 6.92 (1H, ddd), 6.87 (1H, t), 6.74 (1H, ddd), 4.56 (2H, s), 4.25 (2H, s), 3.98-3.80 (3H, m), 3.73 (3H, s), 3.42-3.34 (2H, m), 1.84 (2H, d), 1.58-1.45 (8H, m) | 550 |

-continued

| Example | Structure | Prep. | Name | ¹H NMR (400 MHz) | MS: [M + H]⁺ |
|---|---|---|---|---|---|
| 523 | 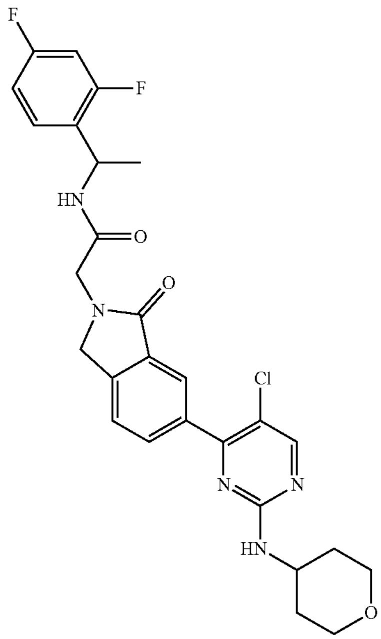 [SMILES: CC(NC(=O)CN1Cc2ccc(-c3nc(NC4CCOCC4)ncc3Cl)cc2C1=O)c1ccc(F)cc1F] | B | 2-(6-{5-chloro-2-[(oxan-4-yl)amino]pyrimidin-4-yl}-1-oxo-2,3-dihydro-1H-isoindol-2-yl)-N-[1-(2,4-difluorophenyl)ethyl]acetamide | 1H NMR (DMSO, 400 MHz) δ 8.70 (1H, d), 8.44 (1H, s), 8.04-7.99 (1H, m), 7.97 (1H, dd), 7.73 (1H, d), 7.62 (1H, s), 7.49-7.40 (1H, m), 7.24-7.16 (1H, m), 7.14-7.05 (1H, m), 5.13 (1H, p), 4.57 (2H, s), 4.25 (2H, s), 3.99-3.80 (3H, m), 3.44-3.35 (2H, m), 1.84 (2H, d), 1.63-1.44 (2H, m), 1.37(3H, d) | 542 |
| 524 | 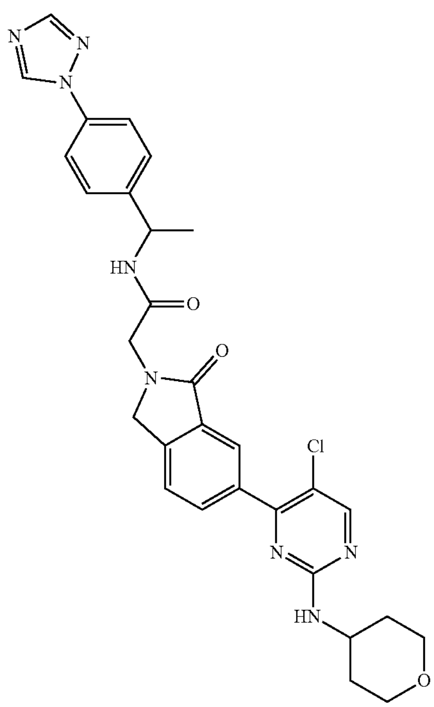 [SMILES: CC(NC(=O)CN1Cc2ccc(-c3nc(NC4CCOCC4)ncc3Cl)cc2C1=O)c1ccc(-n2cncn2)cc1] | A | 2-(6-{5-chloro-2-[(oxan-4-yl)amino]pyrimidin-4-yl}-1-oxo-2,3-dihydro-1H-isoindol-2-yl)-N-{1-[4-(1H-1,2,4-triazol-1-yl)phenyl]ethyl}acetamide | 1H NMR (DMSO, 400 MHz) δ 9.26 (1H, s), 8.68 (1H, d), 8.44 (1H, s), 8.22 (1H, s), 8.05-8.00 (1H, m), 7.97 (1H, dd), 7.85-7.78 (2H, m), 7.74 (1H, d), 7.62 (1H, s), 7.54-7.48 (2H, m), 5.01 (1H, p), 4.59 (2H, s), 4.27 (2H, s), 3.99-3.80 (3H, m), 3.43-3.34 (2H, m), 1.84 (2H, d), 1.58-1.44 (2H, m), 1.41 (3H, d) | 573 |

| Example | Structure | Prep. | Name | ¹H NMR (400 MHz) | MS: [M + H]⁺ |
|---|---|---|---|---|---|
| 525 | 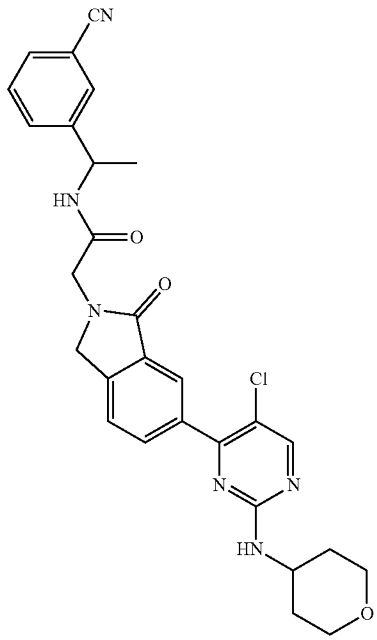 [SMILES: CC(NC(=O)CN1Cc2ccc(-c3nc(NC4CCOCC4)ncc3Cl)cc2C1=O)c1cccc(C#N)c1] | B | 2-(6-{5-chloro-2-[(oxan-4-yl)amino]pyrimidin-4-yl}-1-oxo-2,3-dihydro-1H-isoindol-2-yl)-N-[1-(3-cyanophenyl)ethyl]acetamide | 1H NMR (DMSO, 400 MHz) δ 8.68 (1H, d), 8.44 (1H, s), 8.04-8.00 (1H, m), 7.97 (1H, dd), 7.79 (1H, d), 7.76-7.65 (3H, m), 7.62 (1H, s), 7.55 (1H, t), 4.99 (1H, p), 4.58 (2H, s), 4.27 (2H, s), 4.00-3.79 (3H, m), 3.43-3.34 (2H, m), 1.84 (2H, d), 1.59-1.43 (2H, m), 1.39 (3H, d) | 531 |
| 526 | 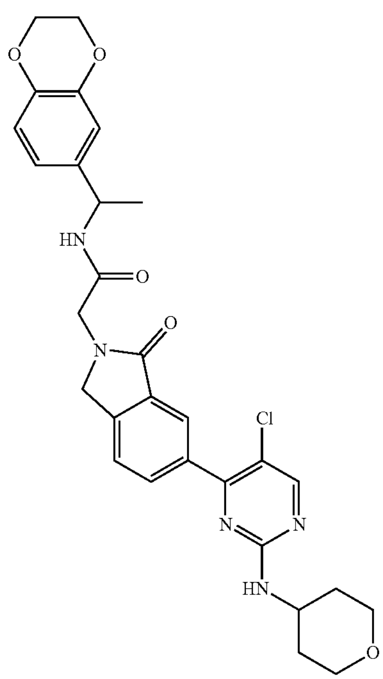 [SMILES: CC(NC(=O)CN1Cc2ccc(-c3nc(NC4CCOCC4)ncc3Cl)cc2C1=O)c1ccc2c(c1)OCCO2] | B | 2-(6-{5-chloro-2-[(oxan-4-yl)amino]pyrimidin-4-yl}-1-oxo-2,3-dihydro-1H-isoindol-2-yl)-N-[1-(2,3-dihydro-1,4-benzodioxin-6-yl)ethyl]acetamide | 1H NMR (DMSO-d6, 400 MHz) δ 8.56-8.40 (2H, m), 8.02 (1H, d), 7.97 (1H, dd), 7.73 (1H, d), 7.61 (1H, s), 6.86-6.73 (3H, m), 4.84 (1H, p), 4.58 (2H, s), 4.29-4.14 (6H, m), 4.00-3.79 (3H, m), 3.43-3.33 (2H, m), 1.84 (2H, d), 1.61-1.44 (2H, m), 1.32 (3H, d) | 564 |

| Example | Structure | Prep. | Name | ¹H NMR (400 MHz) | MS: [M + H]⁺ |
|---|---|---|---|---|---|
| 528 | 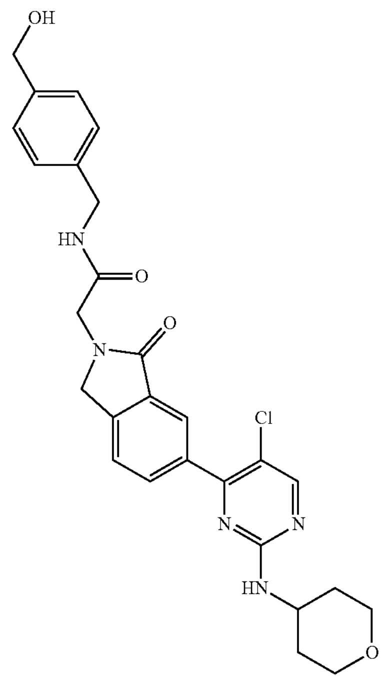 [SMILES: O=C(CN1Cc2ccc(-c3nc(NC4CCOCC4)ncc3Cl)cc2C1=O)NCc1ccc(CO)cc1] | A | 2-(6-{5-chloro-2-[(oxan-4-yl)amino]pyrimidin-4-yl}-1-oxo-2,3-dihydro-1H-isoindol-2-yl)-N-{[4-(hydroxymethyl)phenyl]methyl}acetamide | 1H NMR (DMSO, 400 MHz) δ 8.62 (1H, t), 8.44 (1H, s), 8.04-8.00 (1H, m), 7.97 (1H, dd), 7.75 (1H, d), 7.62 (1H, s), 7.29-7.18 (4H, m), 5.15 (1H, t), 4.61 (2H, s), 4.46 (2H, d), 4.33-4.22 (4H, m), 3.89 (3H, dd), 3.40-3.36 (2H, m), 1.84 (2H, d), 1.60-1.42 (2H, m) | 522 |
| 529 | 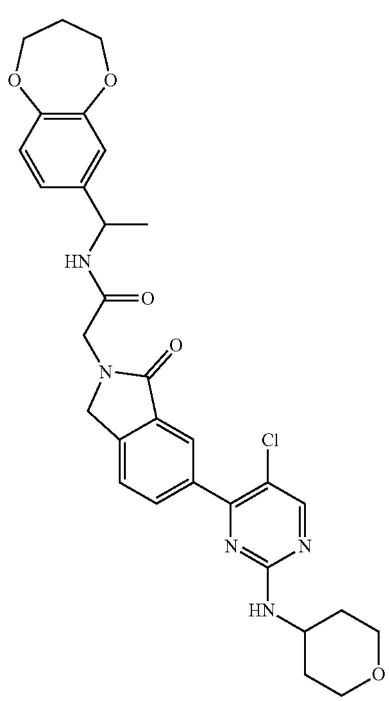 [SMILES: CC(NC(=O)CN1Cc2ccc(-c3nc(NC4CCOCC4)ncc3Cl)cc2C1=O)c1ccc2c(c1)OCCCO2] | B | 2-(6-{5-chloro-2-[(oxan-4-yl)amino]pyrimidin-4-yl}-1-oxo-2,3-dihydro-1H-isoindol-2-yl)-N-[1-(3,4-dihydro-2H-1,5-benzodioxepin-7-yl)ethyl]acetamide | 1H NMR (DMSO-d6, 400 MHz) δ 8.53 (1H, d), 8.44 (1H, s), 8.02 (1H, dd), 7.97 (1H, dd), 7.74 (1H, d), 7.62 (1H, s), 6.97-6.84 (3H, m), 4.87 (1H, p), 4.58 (2H, s), 4.23 (2H, s), 4.16-4.03 (4H, m), 4.00-3.80 (3H, m), 3.38 (2H, d), 2.16-2.04 (2H, m), 1.84 (2H, d), 1.52 (2H, qd), 1.33 (3H, d) | 578 |

-continued

| Example | Structure | Prep. | Name | ¹H NMR (400 MHz) | MS: [M + H]⁺ |
|---|---|---|---|---|---|
| 530 | 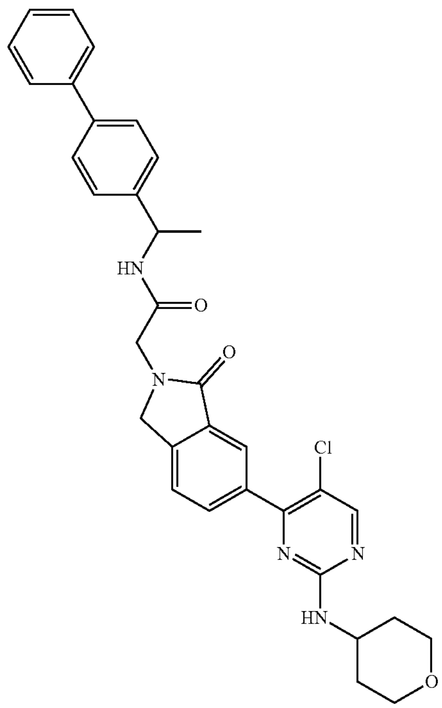 [SMILES: CC(NC(=O)CN1Cc2ccc(-c3nc(NC4CCOCC4)ncc3Cl)cc2C1=O)c1ccc(-c2ccccc2)cc1] | B | N-(1-{[1,1'-biphenyl]-4-yl}ethyl)-2-(6-chloro-2-[(oxan-4-yl)amino]pyrimidin-4-yl}-1-oxo-2,3-dihydro-1H-isoindol-2-yl)acetamide | 1H NMR (DMSO-d6, 400 MHz) δ 8.66 (1H, d), 8.44 (1H, s), 8.02 (1H, dd), 7.97 (1H, dd), 7.74 (1H, d), 7.69-7.56 (5H, m), 7.52-7.39 (4H, m), 7.39-7.31 (1H, m), 5.00 (1H, p), 4.60 (2H, s), 4.27 (2H, d), 4.00-3.78 (3H, m), 3.43-3.34(2H, m), 1.84 (2H, d), 1.52 (2H, qd), 1.42 (3H, d) | 582 |
| 531 | 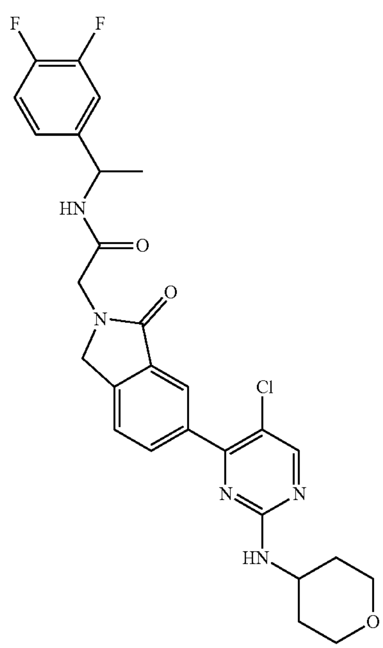 [SMILES: CC(NC(=O)CN1Cc2ccc(-c3nc(NC4CCOCC4)ncc3Cl)cc2C1=O)c1ccc(F)c(F)c1] | B | 2-(6-{5-chloro-2-[(oxan-4-yl)amino]pyrimidin-4-yl}-1-oxo-2,3-dihydro-1H-isoindol-2-yl)-N-[1-(3,4-difluorophenyl)ethyl]acetamide | 1H NMR (DMSO-d6, 400 MHz) δ 8.62 (1H, d), 8.44 (1H, s), 8.02 (1H, dd), 7.97 (1H, dd), 7.74 (1H, d), 7.62 (1H, s), 7.44-7.34 (2H, m), 7.15-7.21 (1H, m), 4.95 (1H, p), 4.58 (2H, s), 4.25 (2H, s), 4.02-3.79 (3H, m), 3.44-3.33 (2H, 1.84 (2H, d), 1.52 (2H, qd), 1.36 (3H, d) | 542 |

-continued

| Example | Structure | Prep. | Name | ¹H NMR (400 MHz) | MS: [M + H]⁺ |
|---|---|---|---|---|---|
| 532 | 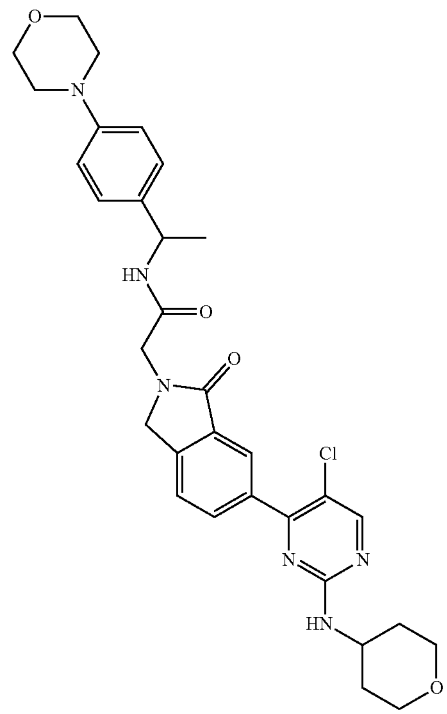 [SMILES: CC(NC(=O)CN1Cc2ccc(-c3nc(NC4CCOCC4)ncc3Cl)cc2C1=O)c1ccc(N2CCOCC2)cc1] | A | 2-(6-{5-chloro-2-[(oxan-4-yl)amino]pyrimidin-4-yl}-1-oxo-2,3-dihydro-1H-isoindol-2-yl)-N-{1-[4-(morpholin-4-yl)phenyl]ethyl}acetamide | 1H NMR (DMSO-d6, 400 MHz) δ 8.49 (1H, d), 8.44 (1H, s), 8.02 (1H, dd), 7.97 (1H, dd), 7.79-7.69 (1H, m), 7.62 (1H, s), 7.25-7.13 (2H, m), 6.96-6.85 (2H, m), 4.88 (1H, p), 4.58 (2H, s), 4.22 (2H, d), 4.00-3.80 (3H, m), 3.80-3.67 (4H, m), 3.48-3.34 (2H, m), 3.14-2.98 (4H, m), 1.84 (2H, d), 1.59-1.45 (2H, m), 1.34 (3H, d) | 591 |
| 533 | 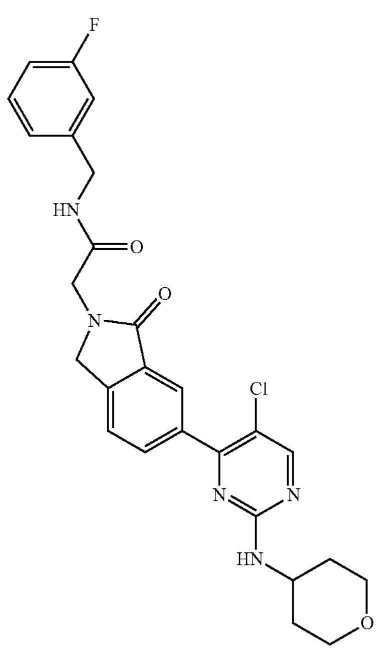 [SMILES: O=C(CN1Cc2ccc(-c3nc(NC4CCOCC4)ncc3Cl)cc2C1=O)NCc1cccc(F)c1] | B | 2-(6-{5-chloro-2-[(oxan-4-yl)amino]pyrimidin-4-yl}-1-oxo-2,3-dihydro-1H-isoindol-2-yl)-N-[(3-fluorophenyl)methyl]acetamide | 1H NMR (DMSO, 400 MHz) δ 8.68 (1H, t), 8.44 (1H, s), 8.06-8.01 (1H, m), 7.98 (1H, dd), 7.75 (1H, d), 7.62 (1H, s), 7.41-7.33 (1H, m), 7.14-7.03 (3H, m), 4.61 (2H, s), 4.32 (2H, d), 4.28 (2H, s), 3.98-3.78 (3H, m), 3.43-3.35 (2H, m), 1.84 (2H, d), 1.58-1.45 (2H, m) | 510 |

| Example | Structure | Prep. | Name | ¹H NMR (400 MHz) | MS: [M + H]⁺ |
|---|---|---|---|---|---|
| 534 | 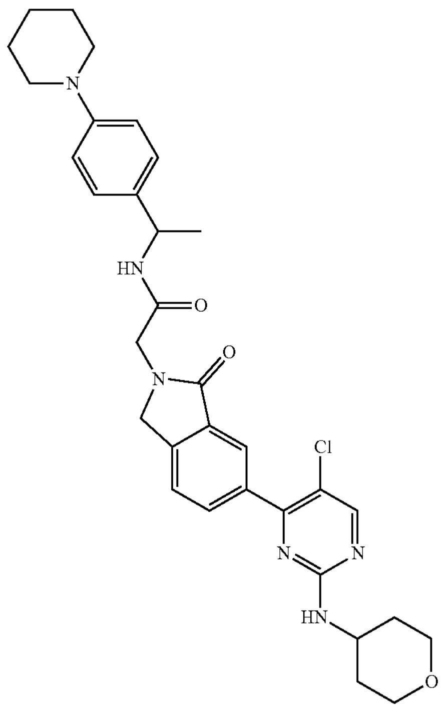 [SMILES: CC(NC(=O)CN1Cc2ccc(-c3nc(NC4CCOCC4)ncc3Cl)cc2C1=O)c1ccc(N2CCCCC2)cc1] | B | 2-(6-{5-chloro-2-[(oxan-4-yl)amino]pyrimidin-4-yl}-1-oxo-2,3-dihydro-1H-isoindol-2-yl)-N-{1-[4-(piperidin-1-yl)phenyl]ethyl}acetamide | 1H NMR (DMSO, 400 MHz) δ 8.50-8.42 (2H, m), 8.03-8.00 (1H, m), 7.97 (1H, dd), 7.73 (1H, d), 7.62 (1H, s), 7.15 (2H, d), 6.87 (2H, d), 4.87 (1H, p), 4.58 (2H, s), 4.29-4.15 (2H, m), 3.99-3.79 (3H, m), 3.43-3.34 (4H, m), 3.14-3.01 (3H, m), 1.84 (2H, d), 1.65-1.43 (7H, m), 1.34 (3H, d) | 589 |
| 535 | 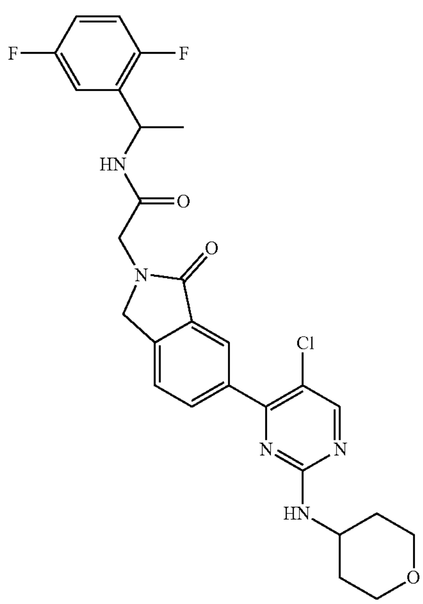 [SMILES: CC(NC(=O)CN1Cc2ccc(-c3nc(NC4CCOCC4)ncc3Cl)cc2C1=O)c1cc(F)ccc1F] | B | 2-(6-{5-chloro-2-[(oxan-4-yl)amino]pyrimidin-4-yl}-1-oxo-2,3-dihydro-1H-isoindol-2-yl)-N-[1-(2,5-difluorophenyl)ethyl]acetamide | 1H NMR (DMSO, 400 MHz) δ 8.69 (1H, d), 8.44 (1H, s), 8.05-8.00 (1H, m), 7.97 (1H, dd), 7.73 (1H, d), 7.61 (1H, s), 7.28-7.18 (2H, m), 7.18-7.07 (1H, m), 5.14 (1H, p), 4.58 (2H, s), 4.27 (2H, s), 4.00-3.77 (3H, m), 3.43-3.35 (2H, m), 1.84 (2H, d), 1.62-1.42 (2H, m), 1.37 (3H, d) | 542 |

| Example | Structure | Prep. | Name | ¹H NMR (400 MHz) | MS: [M + H]⁺ |
|---|---|---|---|---|---|
| 536 | 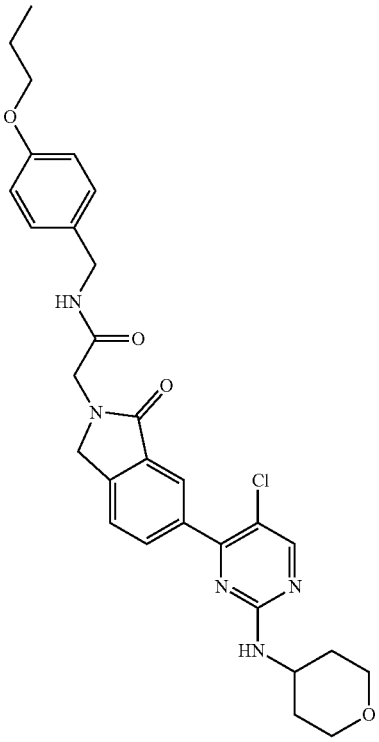 [SMILES: CCCOc1ccc(CNC(=O)CN2Cc3ccc(-c4nc(NC5CCOCC5)ncc4Cl)cc3C2=O)cc1] | B | 2-(6-{5-chloro-2-[(oxan-4-yl)amino]pyrimidin-4-yl}-1-oxo-2,3-dihydro-1H-isoindol-2-yl)-N-[(4-propoxyphenyl)methyl]acetamide | 1H NMR (DMSO, 400 MHz) δ 8.57 (1H, t), 8.44 (1H, s), 8.05-8.00 (1H, m), 7.98 (1H, dd), 7.75 (1H, d), 7.62 (1H, s), 7.20-7.14 (2H, m), 6.90-6.83 (2H, m), 4.60 (2H, s), 4.27-4.18 (4H, m), 3.99-3.80 (5H, m), 3.38 (2H, d), 1.84 (2H, d), 1.77-1.63 (2H, m), 1.60-1.45 (2H, m), 0.96 (3H, t) | 550 |
| 537 | 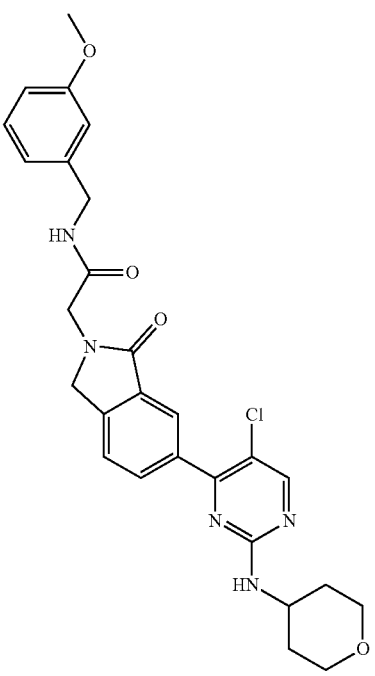 [SMILES: COc1cccc(CNC(=O)CN2Cc3ccc(-c4nc(NC5CCOCC5)ncc4Cl)cc3C2=O)c1] | B | 2-(6-{5-chloro-2-[(oxan-4-yl)amino]pyrimidin-4-yl}-1-oxo-2,3-dihydro-1H-isoindol-2-yl)-N-[(3-methoxyphenyl)methyl]acetamide | 1H NMR (DMSO, 400 MHz) δ 8.63 (1H, t), 8.45 (1H, s), 8.05-8.00 (1H, m), 7.98 (1H, dd), 7.75 (1H, d), 7.62 (1H, s), 7.24 (1H, t), 6.87-6.77 (3H, m), 4.61 (2H, s), 4.32-4.22 (4H, m), 3.97-3.81 (3H, m), 3.74 (3H, s), 3.44-3.34 (2H, m), 1.84 (2H, d), 1.52 (2H, qd) | 522 |

Example 538: 2-(6-{5-chloro-2-[(oxan-4-yl)amino]pyrimidin-4-yl}-1-oxo-2,3-dihydro-1H-isoindol-2-yl)-N-{2-[3-(hydroxymethyl)phenyl]propan-2-yl}acetamide

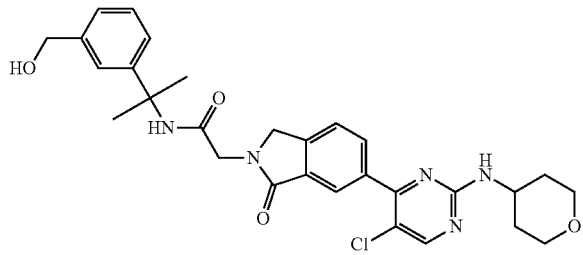 [SMILES: CC(C)(NC(=O)CN1Cc2ccc(-c3nc(NC4CCOCC4)ncc3Cl)cc2C1=O)c1cccc(CO)c1]

Triethylamine (208 μl, 1.489 mmol) was added to a mixture of 2-(6-{5-chloro-2-[(oxan-4-yl)amino]pyrimidin-4-yl}-1-oxo-2,3-dihydro-1H-isoindol-2-yl)acetic acid (Example 1, 150 mg, 0.372 mmol), (3-(2-aminopropan-2-yl)phenyl)methanol, HCl (83 mg, 0.410 mmol) and HATU (156 mg, 0.410 mmol) in DMF (5 mL) and the mixture was stirred for 1 h. Water (15 mL) was added, and the resulting precipitate filtered, washed with water (15 mL). Purification by preparative HPLC (acidic) gave the title compound (60 mg, 29.0%) as a colourless powder. 1H NMR (DMSO, 400 MHz) δ 8.44 (1H, s), 8.40 (1H, s), 8.00 (1H, d), 7.95 (1H, dd), 7.71 (1H, d), 7.62 (1H, s), 7.31 (1H, d), 7.26-7.18 (2H, m), 7.12 (1H, dt), 5.16 (1H, s), 4.55 (2H, s), 4.48 (2H, s), 4.25 (2H, s), 3.97-3.80 (3H, m), 3.39-3.35 (2H, m), 1.87-1.79 (2H, m), 1.57 (6H, s), 1.56-1.45 (21H, m). LC-MS: [M+H]+=550.

Example 539: 2-(6-{5-chloro-2-[(oxan-4-yl)amino]pyrimidin-4-yl}-1-oxo-2,3-dihydro-1H-isoindol-2-yl)-N-[(1R)-1-[3-(2-hydroxyethoxy)phenyl]ethyl]acetamide

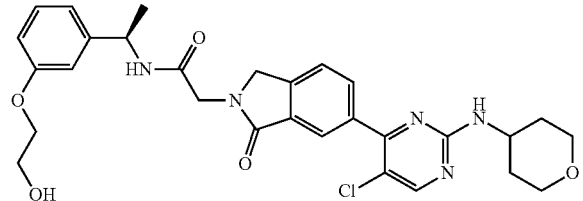 [SMILES: C[C@@H](NC(=O)CN1Cc2ccc(-c3nc(NC4CCOCC4)ncc3Cl)cc2C1=O)c1cccc(OCCO)c1]

Triethylamine (277 μl, 1.986 mmol) was added to a mixture of 2-(6-{5-chloro-2-[(oxan-4-yl)amino]pyrimidin-4-yl}-1-oxo-2,3-dihydro-1H-isoindol-2-yl)acetic acid (Example 1, 200 mg, 0.496 mmol), (R)-2-(3-(1-aminoethyl)phenoxy)ethanol, HCl (99 mg, 0.455 mmol) and HATU (208 mg, 0.546 mmol) in DMF (2 mL) and the mixture was stirred for 1 h. Water (15 mL) was added, and the resulting precipitate filtered, washed with water (15 mL). Purification by chromatography (SiO$_2$, 0-5% MeOH in iso-hexane) gave the title compound (98 mg, 33.5%) as a colourless powder. 1H NMR (DMSO, 400 MHz) δ 8.58 (1H, d), 8.44 (1H, s), 8.02 (1H, s), 7.97 (1H, dd), 7.73 (1H, d), 7.62 (1H, bs), 7.22 (1H, t), 6.91-6.86 (2H, m), 6.80 (1H, ddd), 4.97-4.89 (1H, m), 4.86 (1H, m), 4.59 (2H, t), 4.25 (2H, s), 3.97 (2H, t), 3.94-3.81 (3H, m), 3.71 (2H, q), 3.38 (2H, m), 1.84 (2H, m), 1.52 (2H, m), 1.36 (3H, d). LC-MS: [M+H]+=566.

Example 540: 2-(6-{5-chloro-2-[(oxan-4-yl)amino]pyrimidin-4-yl}-1-oxo-2,3-dihydro-1H-isoindol-2-yl)-N-[(1R)-1-(3-hydroxyphenyl)ethyl]acetamide

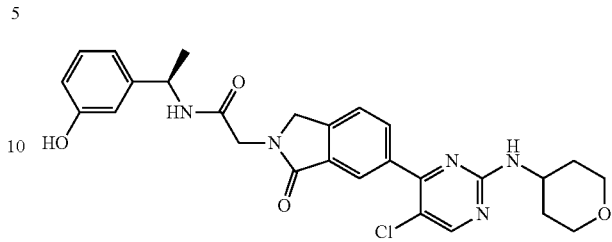

Triethylamine (277 μl, 1.986 mmol) was added to a mixture of 2-(6-{5-chloro-2-[(oxan-4-yl)amino]pyrimidin-4-yl}-1-oxo-2,3-dihydro-1H-isoindol-2-yl)acetic acid (Example 1, 200 mg, 0.496 mmol), (R)-3-(1-aminoethyl)phenol (79 mg, 0.546 mmol) and HATU (208 mg, 0.546 mmol) in DMF (2 mL) and the mixture was stirred for 1 h. Water (15 mL) was added, and the resulting precipitate filtered, washed with water (15 mL), dried, to give the title compound (211 mg, 80%) as a colourless powder. 1H NMR (DMSO, 400 MHz) δ 9.37 (1H, s), 8.57 (1H, d), 8.44 (1H, s), 8.02 (1H, s), 7.97 (1H, dd), 7.73 (1H, d), 7.62 (1H, bs), 7.10 (1H, dd), 6.76-6.70 (2H, m), 6.62 (1H, ddd), 4.90-4.81 (1H, m), 4.58 (2H, s), 4.23 (2H, d), 3.99-3.78 (3H, m), 3.42-3.35 (2H, m), 1.84 (2H, m), 1.52 (2H, m), 1.34 (3H, d). LC-MS: [M+H]+=522.

Example 541: 2-(6-{5-chloro-2-[(oxan-4-yl)amino]pyrimidin-4-yl}-1-oxo-2,3-dihydro-1H-isoindol-2-yl)-N-[(1R)-1-{3-[(dimethylamino)methyl]phenyl}ethyl]acetamide

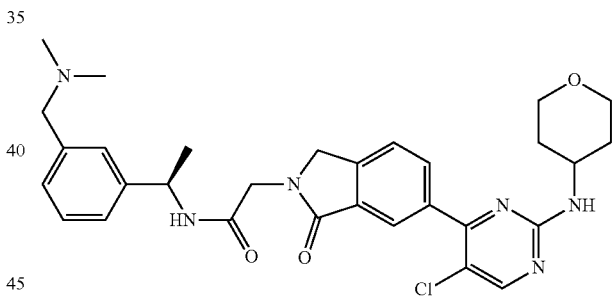

A microwave tube was charged with (R)—N-(1-(3-bromophenyl)ethyl)-2-(6-(5-chloro-2-((oxan-4-yl)amino)pyrimidin-4-yl)-1-oxoisoindolin-2-yl)acetamide (Preparation 306, 50 mg, 0.081 mmol), potassium ((dimethylamino)methyl)trifluoroborate (20.10 mg, 0.122 mmol), Pd(OAc)$_2$ (0.912 mg, 4.06 μmol), XPhos and Cs$_2$CO$_3$ (79 mg, 0.244 mmol). The tube was evacuated and backfilled with nitrogen (3×). 1,4-dioxane (0.8 mL, 9.35 mmol) and water (0.2 mL, 11.10 mmol) were added and the reaction was heated to 100° C. for 1.5 h. The mixture was diluted with water (10 mL) and extracted with EtOAc (3×10 mL). The combined organic extracts were washed with NaHCO$_3$ (10 mL), brine (10 mL), dried (MgSO4) and concentrated. The crude product was purified by chromatography (SiO$_2$, 12 g column, 0-10% (0.7 M Ammonia/MeOH) in DCM) to afford the title compound (16 mg, 33.2%) as a pale yellow solid. 1H NMR (DMSO-d6, 400 MHz) δ 8.62 (1H, d), 8.45 (1H, s), 8.03 (1H, d), 7.98 (1H, dd), 7.74 (1H, d), 7.63 (1H, br. s), 7.31-7.24 (2H, m), 7.24-7.19 (1H, m), 7.17-7.13 (1H, m), 5.02-4.91 (1H, m), 4.64-4.53 (2H, m), 4.25 (2H, s), 4.04-3.81 (3H, m), 3.41-3.36 (3H, m), 2.14 (6H, s), 1.89-1.80 (2H, m), 1.58-1.47 (3H, m), 1.38 (3H, d). LCMS: [M+H]+=563.

Example 542: 2-(6-{5-chloro-2-[(oxan-4-yl)amino]pyrimidin-4-yl}-1-oxo-2,3-dihydro-1H-isoindol-2-yl)-N-[(1R)-1-[3-(2,3-dihydroxypropoxy)phenyl]ethyl]acetamide

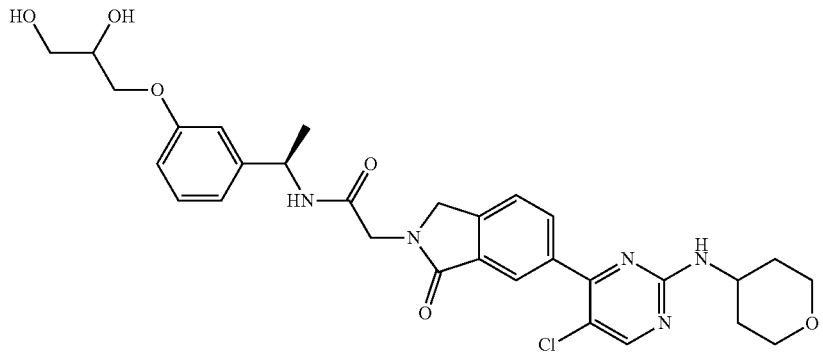 [SMILES: C[C@@H](NC(=O)CN1Cc2ccc(-c3nc(NC4CCOCC4)ncc3Cl)cc2C1=O)c1cccc(OCC(O)CO)c1]

A solution of potassium osmate dihydrate (0.656 mg, 1.779 μmol) in water (50 μL) was added to a solution of (R)—N-(1-(3-(allyloxy)phenyl)ethyl)-2-(6-(5-chloro-2-((oxan-4-yl)amino)pyrimidin-4-yl)-1-oxoisoindolin-2-yl)acetamide (Preparation 308, 50 mg, 0.089 mmol) and NMO (15.63 mg, 0.133 mmol) in tBuOH/H$_2$O (2:1, 1 mL). The reaction mixture was stirred at room temperature for 2 days. An aqueous solution of sodium sulfite (3 mL) was added, and the aqueous layer was extracted with EtOAc (2×3 mL). The combined organic layers were dried (MgSO$_4$) and concentrated in vacuo. Purification by chromatography (SiO$_2$, 0-10% MeOH in DCM) gave the title compound (31 mg, 0.051 mmol, 57.9% yield) as a colourless powder. 1H NMR (DMSO-d6, 400 MHz) δ 8.59 (1H, d), 8.44 (1H, s), 8.02 (1H, dd), 7.97 (1H, dd), 7.73 (1H, d), 7.62 (1H, s), 7.22 (1H, t), 6.92-6.86 (2H, m), 6.79 (1H, dd), 4.98-4.87 (2H, m), 4.68 (1H, td), 4.59 (2H, s), 4.25 (2H, m), 3.99 (1H, ddd), 3.94-3.82 (2H, m), 3.79 (1H, m), 3.45 (2H, t), 3.40-3.36 (2H, m), 2.54 (2H, s), 1.88-1.80 (2H, m), 1.52 (2H, m), 1.36 (3H, d). LCMS: [M+H]+=596.

Example 543: N-[(1R)-1-[3-(2-aminoethoxy)phenyl]ethyl]-2-(6-{5-chloro-2-[(oxan-4-yl)amino]pyrimidin-4-yl}-1-oxo-2,3-dihydro-1H-isoindol-2-yl)acetamide

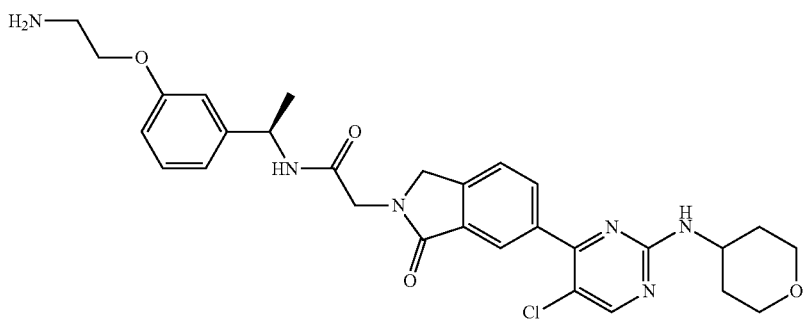 [SMILES: C[C@@H](NC(=O)CN1Cc2ccc(-c3nc(NC4CCOCC4)ncc3Cl)cc2C1=O)c1cccc(OCCN)c1]

Hydrazine hydrate (60% in water, 106 μl, 1.295 mmol) was added to a stirred solution of (R)-2-(6-(5-chloro-2-((oxan-4-yl)amino)pyrimidin-4-yl)-1-oxoisoindolin-2-yl)-N-(1-(3-(2-(1,3-dioxoisoindolin-2-yl)ethoxy)phenyl)ethyl)acetamide (Preparation 309, 90 mg, 0.129 mmol) in THF (2.5 mL) under nitrogen and the mixture was heated to 65° C. and stirred for 2 h. The mixture was cooled to room temperature. The resulting suspension was filtered via a hydrophobic phase separator, washed with EtOAc (1 mL) and the filtrate was concentrated in vacuo. Trituration with Et$_2$O (3 mL) gave the title compound (31 mg, 41.1%) as a pale tan powder. 1H NMR (DMSO-d6, 400 MHz) δ 8.58 (1H, d), 8.44 (1H, s), 8.02 (1H, d), 7.97 (1H, dd), 7.73 (1H, d), 7.62 (1H, s), 7.22 (1H, dd), 6.92-6.84 (2H, m), 6.79 (1H, d), 4.92 (1H, dq), 4.59 (2H, s), 4.25 (2H, s), 3.98-3.82 (4H, m), 3.43-3.35 (3H, m), 2.87 (2H, t), 1.89-1.78 (2H, m), 1.60-1.44 (2H, m), 1.36 (3H, d). (2 protons signals overlapped with water peak) LCMS: [M+H]+=565.

Example 544: (2R)-2-(6-{5-chloro-2-[(oxan-4-yl)amino]pyrimidin-4-yl}-1-oxo-2,3-dihydro-1H-isoindol-2-yl)-N-[(1S)-1-[3-(difluoromethoxy)phenyl]-2-hydroxyethyl]propanamide

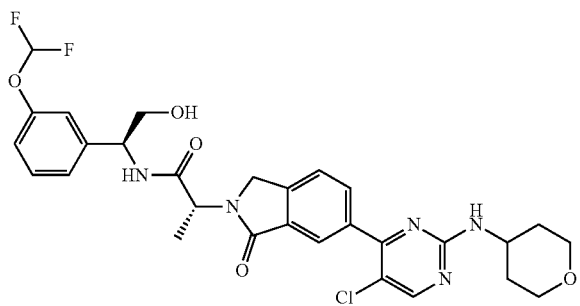 [SMILES: C[C@H](C(=O)N[C@H](CO)c1cccc(OC(F)F)c1)N1Cc2ccc(-c3nc(NC4CCOCC4)ncc3Cl)cc2C1=O]

DIPEA (111 μl, 0.637 mmol) and HATU (121 mg, 0.318 mmol) were added to a stirred solution of (2R)-2-(6-{5-chloro-2-[(oxan-4-yl)amino]pyrimidin-4-yl}-1-oxo-2,3-dihydro-1H-isoindol-2-yl)propanoic acid (Preparation 99), 90 mg, 0.216 mmol), and (S)-2-amino-2-(3-(difluoromethoxy)phenyl)ethanol hydrochloride (51.7 mg, 0.216 mmol) in acetonitrile (8.86 mg, 0.216 mmol) and the mixture was stirred for 1 h. The solution was concentrated and the residue dissolved in a small quantity of DCM, then purified by chromatography (SiO₂, 12 g column, 100% EtOAc). Pure fractions were collected and concentrated to afford a colourless solid (75 mg). The solid was dissolved in methanol (2 ml) and the solution loaded on column packed with SCX. The column was washed with methanol and the product eluted with 1% ammonia in methanol. Concentration of the resulting solution afforded a glass which upon stirring overnight in ether (4 ml) afforded the title compound (50 mg, 38.5%), which was collected by filtration. 1H NMR (DMSO-d6, 400 MHz) δ 8.63 (1H, d), 8.45 (1H, s), 8.04 (1H, s), 7.98 (1H, d), 7.75 (1H, d), 7.63 (1H, s), 7.46-6.96 (5H, m), 5.06-4.9 (2H, m), 4.85 (1H, q), 4.76 (1H, d), 4.61 (1H, d), 3.99-3.8 (3H, d), 3.62-3.50 (2H, m), 3.44-3.28 (2H, m), 1.85 (2H, m), 1.6-1.46 (2H, m), 1.45 (3H, d). LCMS: [M+H]+=602.

Example 545:2-(6-{5-chloro-2-[(oxan-4-yl)amino]pyrimidin-4-yl}-1-oxo-2,3-dihydro-1H-isoindol-2-yl)-N-[(1S,2S)-2-hydroxy-1-(3-methoxyphenyl)propyl]acetamide

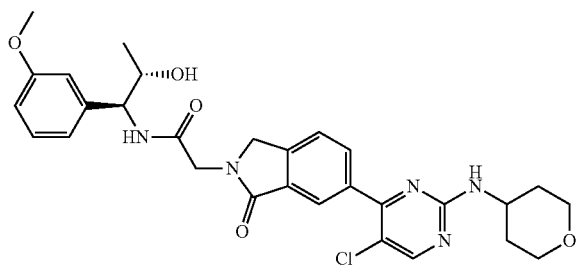 [SMILES: COc1cccc([C@H](NC(=O)CN2Cc3ccc(-c4nc(NC5CCOCC5)ncc4Cl)cc3C2=O)[C@H](C)O)c1]

Triethylamine (0.111 mL, 0.794 mmol) was added to a suspension of 2-(6-{5-chloro-2-[(oxan-4-yl)amino]pyrimidin-4-yl}-1-oxo-2,3-dihydro-1H-isoindol-2-yl)acetic acid (Preparation 1, 80 mg, 0.199 mmol) and (1S,2S)-1-amino-1-(3-methoxyphenyl)propan-2-ol hydrochloride (47.6 mg, 0.218 mmol) in DCM (1 mL, 15.54 mmol). After 15 minutes, HATU (83 mg, 0.218 mmol) was added and the mixture was stirred for 2 h at room temperature. The reaction was diluted with EtOAc (10 mL) and water (10 mL). The phases were separated and the aqueous phase was extracted with EtOAc (2×10 mL). The combined organic extracts were washed with 1 M HCl (20 mL), brine (2×20 mL), dried (MgSO₄) and concentrated. The crude product was purified by chromatography (SiO₂, 12 g column, 0-10% MeOH/DCM). The product was dissolved in MeOH and loaded onto a column packed with SCX (2 g). The column was washed with MeOH and then the product was eluted with 0.7 M ammonia in MeOH. The resulting mixture was concentrated in vacuo to afford a colourless glass (50 mg). The product was further purified by chromatography (SiO₂, 12 g column, 0-10% MeOH/DCM) to afford the title compound (50 mg, 43.6%) as a white solid. 1H NMR (DMSO-d6, 400 MHz) δ 8.52-8.41 (2H, m), 8.03-8.01 (1H, m), 7.97 (1H, dd), 7.74 (1H, d), 7.63 (1H, br. s), 7.25-7.19 (1H, m), 6.94-6.88 (2H, m), 6.83-6.78 (1H, m), 4.81 (1H, d), 4.70 (1H, dd), 4.58 (2H, s), 4.36 (1H, d), 4.29 (1H, d), 3.98-3.82 (4H, m), 3.75 (3H, s), 3.40-3.36 (2H, m), 1.90-1.79 (2H, m), 1.58-1.46 (2H, m), 1.00 (3H, d). LCMS: [M+H]+=566.

Example 546:2-(6-{5-chloro-2-[(oxan-4-yl)amino]pyrimidin-4-yl}-1-oxo-2,3-dihydro-1H-isoindol-2-yl)-N-[(1S)-1-{4-[(dimethylamino)methyl]phenyl}-2-hydroxyethyl]acetamide hydrochloride

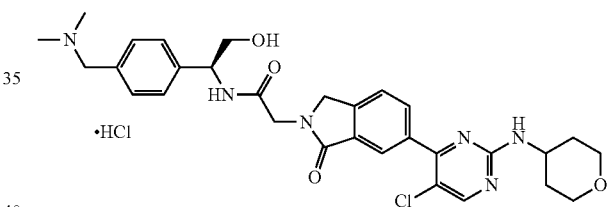

A mixture of (S)—N-(1-(4-bromophenyl)-2-hydroxyethyl)-2-(6-(5-chloro-2-((oxan-4-yl)amino)pyrimidin-4-yl)-1-oxoisoindolin-2-yl)acetamide (Preparation 313, 130 mg, 0.216 mmol), potassium ((dimethylamino)methyl)trifluoroborate (54 mg, 0.327 mmol), XPhos Pd G3 (11 mg, 0.023 mmol), cesium carbonate (211 mg, 0.649 mmol) and palladium (II) acetate (3 mg, 0.013 mmol) was sealed in a microwave vial, evacuated and purged with nitrogen (3×), treated with 1,4-dioxane (0.8 mL) and water (0.2 mL) and stirred at 100° C. (bath) for 4 h. The mixture was allowed to cool, diluted with water (5 ml) and extracted with ethyl acetate (3×5 ml). The combined extracts were washed with brine (5 ml), dried (Na₂SO₄) and evaporated to give a gum (55 mg). The aqueous layers were combined and extracted with 2-methyl-THF (3×10 ml) and the combined extracts were dried (Na₂SO₄), combined with the ethyl acetate extract and evaporated to give a white solid (115 mg). The solid was purified by reversed phase preparative HPLC on a Waters XBridge BEH C18 OBD, 130A, 5 μm, 19 mm×50 mm column, using a gradient of 15 to 35% acetonitrile in 10 mM aqueous ammonium bicarbonate solution at 28 ml/min as eluent. The clean fractions were pooled and concentrated to remove most of the acetonitrile. The residue was freeze-dried, then taken up in a mixture of methanol (1 ml) and acetic acid (0.1 ml) and loaded on a column packed with SCX. The solution was allowed to soak-in for 1 h and then washed with methanol (6 ml). The resin was eluted with 3M methanolic ammonia solution (6 ml) and the eluents were evaporated to give a glass. The glass was triturated with ether (3 ml) to give a solid, which was collected by filtration, washed with ether (1 ml) and dried to a cream powder (27 mg). The product was further purified by reversed phase preparative HPLC on a Waters XSelect CSH C18 OBD, 130A, 5 μm, 19 mm×50 mm column, using a gradient of 5 to 20% of acetonitrile in water with 0.1% formic acid in both at 28 ml/min as eluent. The clean fractions were pooled and evaporated. The residue was taken up in methanol (5 ml), treated with a drop of concentrated hydrochloric acid and evaporated (3×) and the residue was taken up in water (5 ml) and freeze-dried to give the title compound (19 mg, 13.84%) as a yellow solid. 1H NMR (DMSO-d6, 400 MHz) δ 10.70 (1H, s), 8.71 (1H, d), 8.44 (1H, s), 8.04-8.00 (1H, m), 7.97 (1H, dd), 7.74 (1H, d), 7.64 (1H, s), 7.52 (2H, d), 7.41 (2H, d), 4.97-4.85 (1H, m), 4.59 (2H, s), 4.37-4.26 (2H, m), 4.23 (2H, d), 3.97-3.86 (3H, m), 3.59 (2H, d), 3.36 (2H, t), 2.67 (6H, d), 1.89-1.77 (2H, m), 1.59-1.43 (2H, m). LCMS: [M+H]+=579.

Example 547:2-(6-{5-chloro-2-[(oxan-4-yl)amino]pyrimidin-4-yl}-1-oxo-2,3-dihydro-1H-isoindol-2-yl)-N-[(1R)-1-(2-methoxyphenyl)ethyl]acetamide

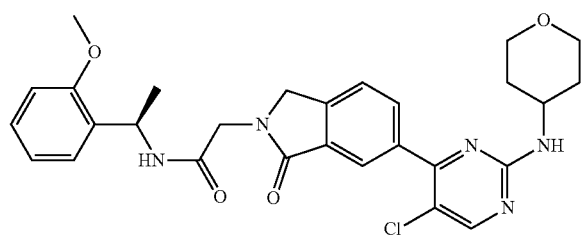 [SMILES: COc1ccccc1[C@@H](C)NC(=O)CN1Cc2ccc(-c3nc(NC4CCOCC4)ncc3Cl)cc2C1=O]

T3P (50 wt % in EtOAc) (0.177 mL, 0.298 mmol) was added to a solution of 2-(6-{5-chloro-2-[(oxan-4-yl)amino]pyrimidin-4-yl}-1-oxo-2,3-dihydro-1H-isoindol-2-yl)acetic acid (Example 1, 80 mg, 0.199 mmol), (R)-1-(2-methoxyphenyl)ethanamine (33.0 mg, 0.218 mmol) and triethylamine (0.083 mL, 0.596 mmol) in DMF (2 mL, 25.8 mmol). The reaction was stirred at room temperature for 2 h. The reaction was diluted with 1 M HCl (3 mL) and water (10 mL). The resulting precipitate was isolated by filtration and washed with water (10 mL). The solid was dissolved in DCM (3 mL) and washed with brine (5 mL) and passed through a phase separating cartridge, then concentrated in vacuo to give the title compound product as a white solid. 1H NMR (DMSO-d6, 400 MHz) δ 8.52 (1H, d), 8.45 (1H, s), 8.03 (1H, dd), 7.97 (1H, dd), 7.74 (1H, d), 7.61 (1H, br. s), 7.30 (1H, dd), 7.22 (1H, ddd), 7.00-6.91 (2H, m), 5.24 (1H, dq), 4.59 (2H, s), 4.26 (2H, s), 3.99-3.83 (3H, m), 3.80 (3H, s), 3.44-3.35 (2H, m), 1.85 (2H, br. d), 1.53 (2H, qd), 1.30 (3H, d). LC-MS: [M+H]+=536.

Example 548:2-(6-{5-chloro-2-[(oxan-4-yl)amino]pyrimidin-4-yl}-1-oxo-2,3-dihydro-1H-isoindol-2-yl)-N-[(1R)-1-phenylpropyl]acetamide

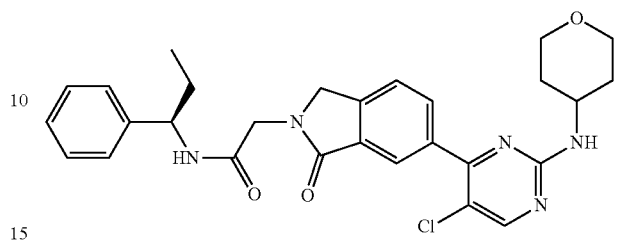

Prepared using a similar procedure to Example 547. 1H NMR (DMSO-d6, 400 MHz) δ 8.54 (1H, d), 8.45 (1H, s), 8.05-8.01 (1H, m), 7.98 (1H, dd), 7.74 (1H, d), 7.61 (1H, br. s), 7.37-7.29 (4H, m), 7.27-7.20 (1H, m), 4.73 (1H, q?), 4.59 (2H, s), 4.30 (1H, d), 4.24 (1H, d), 3.99-3.81 (3H, m), 3.42-3.34 (2H, m), 1.89-1.81 (2H, m), 1.72 (2H, qd), 1.53 (2H, qd), 0.86 (3H, t). LC-MS: [M+H]+=520.

Example 549:2-(6-{5-chloro-2-[(oxan-4-yl)amino]pyrimidin-4-yl}-1-oxo-2,3-dihydro-1H-isoindol-2-yl)-N-[(1R)-1-(2-methylphenyl)ethyl]acetamide

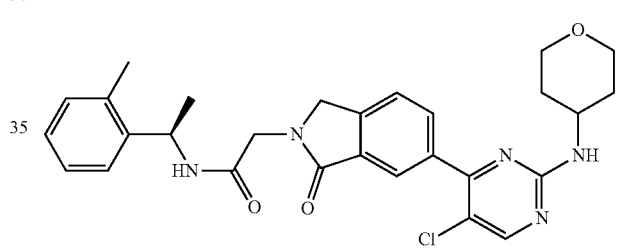

Prepared using a similar procedure to Example 547. 1H NMR (DMSO-d6, 400 MHz) δ 8.61 (1H, d), 8.44 (1H, s), 8.01 (1H, dd), 7.96 (1H, dd), 7.81-7.67 (1H, m), 7.61 (1H, s), 7.35 (1H, d), 7.23-7.16 (1H, m), 7.14-7.11 (2H, m), 5.10 (1H, dq), 4.59 (1H, d), 4.54 (1H, d), 4.24 (1H, d), 4.19 (1H, d), 4.00-3.79 (3H, m), 3.44-3.35 (2H, m), 2.30 (3H, s), 1.94-1.75 (2H, m), 1.59-1.45 (2H, m), 1.34 (3H, d). LC-MS: [M+H]+=520

Example 550:2-(6-{5-chloro-2-[(oxan-4-yl)amino]pyrimidin-4-yl}-1-oxo-2,3-dihydro-1H-isoindol-2-yl)-N-(5-fluoro-2,3-dihydro-1H-inden-1-yl)acetamide

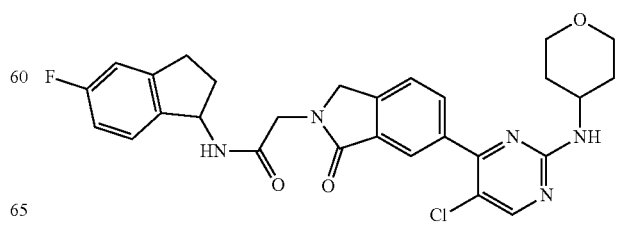

5-fluoro-2,3-dihydro-1H-inden-1-amine hydrochloride (43.1 mg, 0.218 mmol) was added to an ice-cooled stirred solution of 2-(6-{5-chloro-2-[(oxan-4-yl)amino]pyrimidin-4-yl}-1-oxo-2,3-dihydro-1H-isoindol-2-yl)acetic acid (Example 1, 80 mg, 0.199 mmol), T3P (50% wt in EtOAc) (176 µl, 0.298 mmol) and triethylamine (111 µl, 0.794 mmol) in DMF (3.0 mL) under nitrogen. The reaction was allowed to warm to room temperature and stirred for 20 h. The reaction mixture was diluted with 1 M HCl (10 mL) and the resulting precipitate filtered and washed with water (10 mL), NaHCO$_3$ (10 mL) and water (10 mL). The collected solid was re-dissolved in DCM (20 mL) and washed with brine (20 mL). The organic extracts were combined and then dried (MgSO$_4$), filtered and concentrated in vacuo to afford the title compound (77 mg, 71.6%) as an off white solid. 1H NMR (DMSO-d6, 400 MHz) δ 8.53 (1H, d), 8.44 (1H, s), 8.03 (1H, dd), 7.98 (1H, dd), 7.83-7.70 (1H, m), 7.61 (1H, s), 7.23 (1H, ddd), 7.08 (1H, dd), 7.05-6.97 (1H, m), 5.28 (1H, dd), 4.63 (2H, s), 4.26 (2H, s), 4.01-3.78 (3H, m), 3.43-3.32 (2H, m), 2.94 (1H, ddd), 2.81 (1H, dt), 2.41 (1H, dtd), 1.95-1.77 (3H, m), 1.62-1.45 (2H, m). LC-MS: [M+H]+=536.

Example 551: N-(5-chloro-2,3-dihydro-1H-inden-1-yl)-2-(6-{5-chloro-2-[(oxan-4-yl)amino]pyrimidin-4-yl}-1-oxo-2,3-dihydro-1H-isoindol-2-yl)acetamide Prepared using a similar procedure to Example 547. 1H NMR (DMSO-d6, 400 MHz) δ 8.55 (1H, d), 8.44 (1H, s), 8.03 (1H, dd), 7.98 (1H, dd), 7.75 (1H, dd), 7.61 (1H, s), 7.32 (1H, d), 7.28-7.20 (2H, m), 5.29 (1H, q), 4.63 (2H, s), 4.26 (2H, s), 3.89 (3H, dd), 3.44-3.32 (2H, m), 2.93 (1H, ddd), 2.81 (1H, dt), 2.40 (1H, dtd), 1.86 (3H, m), 1.52 (2H, m). LC-MS: [M+H]+=552.

Example 552:2-(6-{5-chloro-2-[(oxan-4-yl)amino]pyrimidin-4-yl}-1-oxo-2,3-dihydro-1H-isoindol-2-yl)-N-[(1S)-2,3-dihydro-1H-inden-1-yl]acetamide 2,4,6-tripropyl-13,5,2,4,6-trioxatriphosphinane 2,4,6-trioxide (50% wt in EtOAc) (150 µL, 0.252 mmol) was added to a stirred mixture of 2-(6-{5-chloro-2-[(oxan-4-yl)amino]pyrimidin-4-yl}-1-oxo-2,3-dihydro-1H-isoindol-2-yl)acetic acid (Example, 70 mg, 0.170 mmol), (S)-2,3-dihydro-1H-inden-1-amine (24.95 mg, 0.187 mmol) and triethylamine (71.2 µL, 0.511 mmol) in DMF (1 mL) and the reaction mixture was stirred at room temperature for 3 h. Water (10 mL) was added, and the resulting precipitate was filtered, dried to give the title compound (S)-2-(6-(5-chloro-2-((oxan-4-yl)amino)pyrimidin-4-yl)-1-oxoisoindolin-2-yl)-N-(2,3-dihydro-1H-inden-1-yl)acetamide (75 mg, 0.140 mmol, 82% yield) as a colourless powder. 1H NMR (DMSO, 400 MHz) 8.54 (1H, d), 8.44 (1H, s), 8.03 (1H, d), 7.98 (1H, dd), 7.75 (1H, d), 7.62 (1H, bs), 7.28-7.16 (4H, m), 5.33 (1H, q), 4.63 (2H, s), 4.26 (2H, s), 3.97-3.81 (3H, m), 2.93 (1H, ddd), 2.81 (1H, dt), 2.44-2.33 (1H, m), 1.84 (3H, qd), 1.60-1.41 (3H, m), 1.15-1.08 (1H, m), 0.93-0.91 (0.5H, m). LC-MS: [M+H]+=518.

Example 553-562

Prepared using an analogous procedure to Example 552, from 2-(6-{5-chloro-2-[(oxan-4-yl)amino]pyrimidin-4-yl}-1-oxo-2,3-dihydro-1H-isoindol-2-yl)acetic acid (Example 1) and the corresponding amine.

| Example | Structure | Name | ¹H NMR (400 MHz) | MS: [M + H]⁺ |
|---|---|---|---|---|
| 553 | 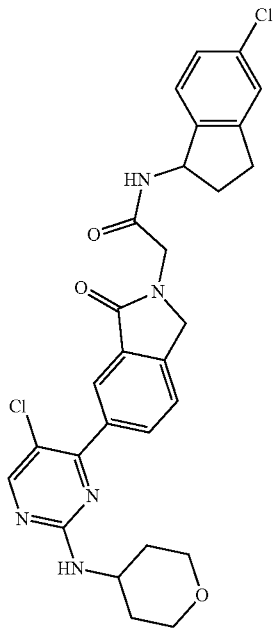 [SMILES: O=C(CN1Cc2ccc(-c3nc(NC4CCOCC4)ncc3Cl)cc2C1=O)NC1CCc2cc(Cl)ccc21] | 2-(6-{5-chloro-2-[(oxan-4-yl)amino]pyrimidin-4-yl}-1-oxo-2,3-dihydro-1H-isoindol-2-yl)-N-(5-cyano-2,3-dihydro-1H-inden-1-yl)acetamide | 1H NMR (DMSO, 400 MHz) δ 8.63 (1H, d), 8.45 (1H, s), 8.06-8.01 (1H, m), 7.98 (1H, dd), 7.78-7.64 (3H, m), 7.61 (1H, bs), 7.39 (1H, d), 5.38 (1H, q), 4.63 (2H, s), 4.28 (2H, s), 3.98-3.81 (3H, m), 3.39-3.35 (2H, m), 2.98 (1H, ddd), 2.86 (1H, dt), 2.47-2.38 (1H, m), 1.92-1.79 (3H, m), 1.52 (2H, qd). | 543 |
| 554 | 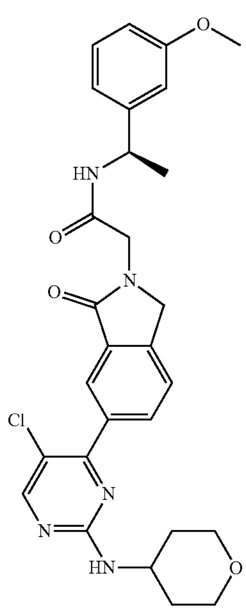 [SMILES: COc1cccc([C@@H](C)NC(=O)CN2Cc3ccc(-c4nc(NC5CCOCC5)ncc4Cl)cc3C2=O)c1] | 2-(6-{5-chloro-2-[(oxan-4-yl)amino]pyrimidin-4-yl}-1-oxo-2,3-dihydro-1H-isoindol-2-yl)-N-[(1R)-1-(3-methoxyphenyl)-ethyl]acetamide | 1H NMR (DMSO-d6) δ: 8.59 (d, 1H), 8.45 (s, 1H), 8.03 (dd, 1H), 7.98 (dd, 1H), 7.74 (d, 1H), 7.62 (s, 1H), 7.25 (t, 1H), 6.93-6.86 (m, 2H), 6.81 (m, 1H), 4.94 (dq, 1H), 4.60 (s, 2H), 4.26 (s, 2H), 3.87 (m, 3H), 3.76 (s, 3H), 3.34-344 (m, 2H), 1.85 (m, 2H), 1.53 (m, 2H), 1.37 (d, 3H). | 536 |

-continued

| Example | Structure | Name | ¹H NMR (400 MHz) | MS: [M + H]⁺ |
|---|---|---|---|---|
| 555 | 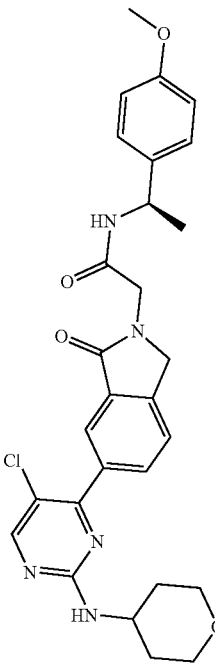 | 2-(6-{5-chloro-2-[(oxan-4-yl)amino]pyrimidin-4-yl}-1-oxo-2,3-dihydro-1H-isoindol-2-yl)-N-[(1R)-1-(4-methoxyphenyl)-ethyl]acetamide | 1H NMR (DMSO-d6) δ: 8.53 (d, 1H), 8.45 (s, 1H), 8.03 (dd, 1H), 7.98 (dd, 1H), 7.74 (d, 1H), 7.62 (s, 1H), 7.25 (d, 2H), 6.90 (d, 2H), 4.92 (dq, 1H), 4.59 (s, 2H), 4.26 (d, 1H), 4.21 (d, 1H), 3.82-3.98 (m, 3H), 3.74 (s, 3H), 3.34-3.42 (m, 2H), 1.85 (m, 2H), 1.53 (m, 2H), 1.36 (d, 3H). | 536 |
| 556 | 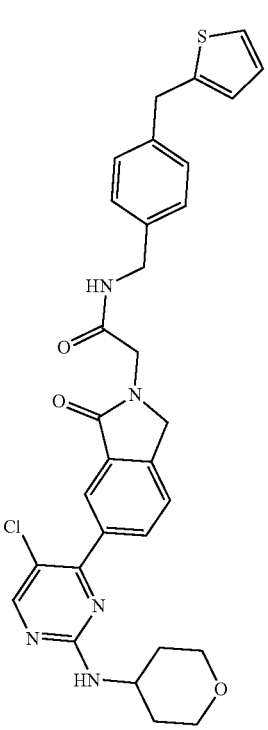 [SMILES: O=C(CN1Cc2ccc(-c3nc(NC4CCOCC4)ncc3Cl)cc2C1=O)NCc1ccc(Cc2cccs2)cc1] | 2-(6-{5-chloro-2-[(oxan-4-yl)amino]pyrimidin-4-yl}-1-oxo-2,3-dihydro-1H-isoindol-2-yl)-N-({4-[(thiophen-2-yl)methyl]phenyl}-methyl)acetamide | 1H NMR (DMSO-d6) δ: 8.62 (t, 1H), 8.45 (s, 1H), 8.03 (d, 1H), 7.98 (dd, 1H), 7.75 (d, 1H), 7.63 (s (br), 1H), 7.32 (dd, 1H), 7.22 (s, 4H), 6.94 (dd, 1H), 6.92-6.85 (m, 1H), 4.61 (s, 2H), 4.28 (d, 2H), 4.25 (s, 2H), 4.12 (d, 2H), 4.00-3.80 (m, 3H), 3.44-3.37 (m, 2H), 1.93-1.78 (m, 2H), 1.62-1.45 (m, 2H). | 588 |

| Example | Structure | Name | ¹H NMR (400 MHz) | MS: [M + H]⁺ |
|---|---|---|---|---|
| 557 | 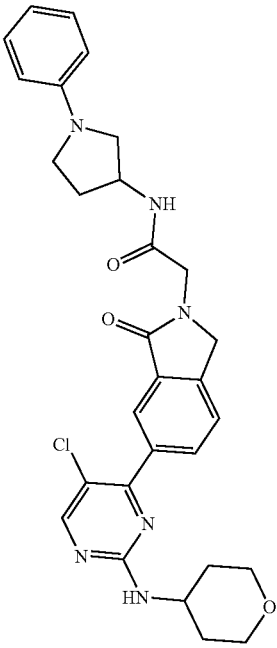 [SMILES: O=C(CN1Cc2ccc(-c3nc(NC4CCOCC4)ncc3Cl)cc2C1=O)NC1CCN(c2ccccc2)C1] | 2-(6-{5-chloro-2-[(oxan-4-yl)amino]pyrimidin-4-yl}-1-oxo-2,3-dihydro-1H-isoindol-2-yl)-N-(1-phenylpyrrolidin-3-yl)acetamide | 1H NMR (DMSO-d6) δ: 8.49 (d, 1H), 8.45 (s (br), 1H), 8.03 (d, 1H), 7.98 (dd, 1H), 7.75 (d, 1H), 7.63 (s (br), 1H), 7.17 (dd, 2H), 6.66-6.58 (m, 1H), 6.58-6.49 (m, 2H), 4.61 (s, 2H), 4.49-4.37 (m, 1H), 4.22 (s, 2H), 3.99-3.81 (m, 3H), 3.49 (dd, 1H), 3.45-3.35 (m, 3H), 3.31-3.22 (m, 1H), 3.10 (dd, 1H), 2.26-2.15 (m, 1H), 1.99-1.89 (m, 1H), 1.89-1.79 (m, 2H), 1.63-1.46 (m, 2H). | 547 |
| 558 | 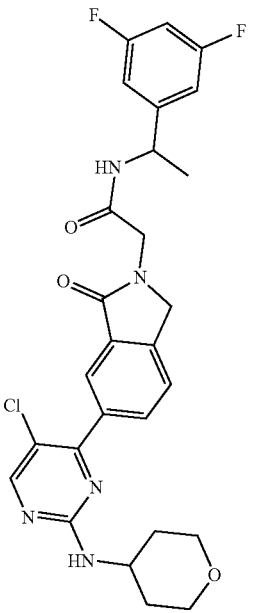 [SMILES: CC(NC(=O)CN1Cc2ccc(-c3nc(NC4CCOCC4)ncc3Cl)cc2C1=O)c1cc(F)cc(F)c1] | 2-(6-{5-chloro-2-[(oxan-4-yl)amino]pyrimidin-4-yl}-1-oxo-2,3-dihydro-1H-isoindol-2-yl)-N-[1-(3,5-difluorophenyl)ethyl]acetamide | 1H NMR (DMSO-d6) δ: 8.65 (d, 1H), 8.45 (s, 1H), 8.03 (d, 1H), 7.98 (dd, 1H), 7.75 (d, 1H), 7.62 (s (br), 1H), 7.13-7.03 (m, 3H), 4.97 (dq, 1H), 4.60 (s, 2H), 4.28 (s, 2H), 4.01-3.80 (m, 3H), 3.44-3.35 (m, 2H), 1.85 (m 2H), 1.53 (m 2H), 1.38 (d, 3H). | 542 |

| Example | Structure | Name | ¹H NMR (400 MHz) | MS: [M + H]⁺ |
|---|---|---|---|---|
| 559 | 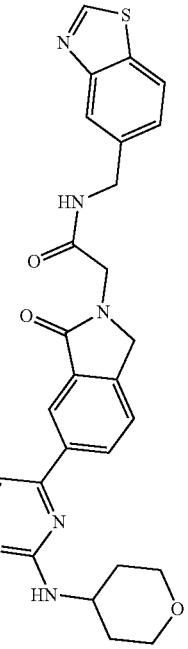 | N-[(1,3-benzothiazol-5-yl)methyl]-2-(6-{5-chloro-2-[(oxan-4-yl)amino]pyrimidin-4-yl}-1-oxo-2,3-dihydro-1H-isoindol-2-yl)acetamide | 1H NMR (DMSO-d6) δ: 9.37 (s, 1H), 8.75 (t, 1H), 8.45 (s (br), 1H), 8.09-8.01 (m, 3H), 7.98 (dd, 1H), 7.76 (d, 1H), 7.63 (s (br), 1H), 7.47 (dd, 1H), 4.63 (s, 2H), 4.47 (d, 2H), 4.30 (s, 2H), 3.98-3.81 (m, 3H), 3.43-3.35 (m, 2H), 1.90-1.79 (m, 2H), 1.58-1.46 (m, 2H). | 549 |
| 560 | 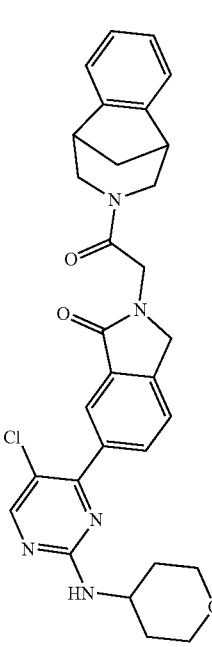 | 2-(2-{10-azatricyclo[6.3.1.02,7]dodeca-2,4,6-trien-10-yl}-2-oxoethyl)-6-{5-chloro-2-[(oxan-4-yl)amino]pyrimidin-4-yl}-2,3-dihydro-1H-isoindol-1-one | 1H NMR (DMSO-d6) δ: 8.44 (s, 1H), 8.00-7.97 (m, 1H), 7.95 (dd, 1H), 7.66 (d, 1H), 7.62 (s (br), 1H), 7.22 (d, 1H), 7.19-7.11 (m, 2H), 7.05-6.96 (m, 1H), 4.28-3.98 (m, 5H), 3.97-3.81 (m, 3H), 3.78-3.72 (m, 1H), 3.58-3.50 (m, 1H), 3.44-3.35 (m, 2H), 3.26-3.19 (m, 2H), 3.03 (dd, 1H), 2.27-2.16 (m, 1H), 1.94 (d, 1H), 1.88-1.79 (m, 2H), 1.59-1.45 (m, 2H) | 544 |

| Example | Structure | Name | ¹H NMR (400 MHz) | MS: [M + H]⁺ |
|---|---|---|---|---|
| 561 | 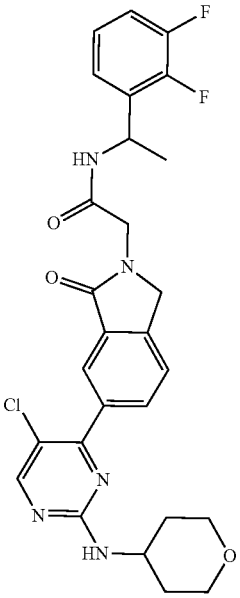 [SMILES: CC(NC(=O)CN1Cc2ccc(-c3nc(NC4CCOCC4)ncc3Cl)cc2C1=O)c1cccc(F)c1F] | 2-(6-{5-chloro-2-[(oxan-4-yl)amino]pyrimidin-4-yl}-1-oxo-2,3-dihydro-1H-isoindol-2-yl)-N-[1-(2,3-difluorophenyl)ethyl]acetamide | 1H NMR (DMSO-d6) δ: 8.77 (d, 1H), 8.45 (s, 1H), 8.02 (dd, 1H), 7.97 (d, 1H), 7.74 (d, 1H), 7.62 (s (br), 1H), 7.38-7.16 (m, 3H), 5.18 (qd, 1H), 4.58 (s, 2H), 4.26 (s, 2H), 3.95-3.83 (m, 3H), 3.39 (m, 2H), 1.84 (d, 2H), 1.60-1.48 (m, 2H), 1.40 (d, 3H). | 542 |
| 562 | 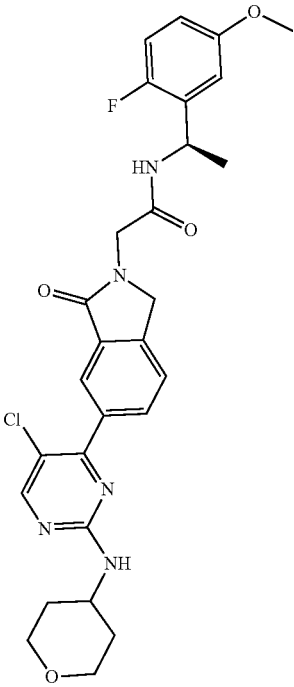 [SMILES: COc1ccc(F)c([C@@H](C)NC(=O)CN2Cc3ccc(-c4nc(NC5CCOCC5)ncc4Cl)cc3C2=O)c1] | 2-(6-{5-chloro-2-[(oxan-4-yl)amino]pyrimidin-4-yl}-1-oxo-2,3-dihydro-1H-isoindol-2-yl)-N-[(1R)-1-(2-fluoro-5-methoxyphenyl)-ethyl]acetamide | 1H NMR (DMSO-d6) δ: 8.68 (d, 1H), 8.45 (s, 1H), 8.03 (d, 1H), 7.98 (dd, 1H), 7.74 (d, 1H), 7.62 (s (br), 1H), 7.08 (dd, 1H), 6.95 (dd, 1H), 6.86-6.79 (m, 1H), 5.22-5.08 (m, 1H), 4.59 (s, 2H), 4.27 (s, 1H), 4.27 (d, 1H), 3.99-3.81 (m, 3H), 3.75 (s, 3H), 3.46-3.35 (m, 2H), 1.91-1.78 (m, 2H), 1.60-1.46 (m, 2H), 1.37 (d, 3H). | 554 |

Example 563-564

Prepared using an analogous procedure to Example 547, from 2-(6-{5-chloro-2-[(oxan-4-yl)amino]pyrimidin-4-yl}-1-oxo-2,3-dihydro-1H-isoindol-2-yl)acetic acid (Example 1) and the corresponding amine. The products were further purified by preparative HPLC (acidic) in these cases.

| Example | Structure | Name | ¹H NMR (400 MHz) | MS: [M + H]⁺ |
|---|---|---|---|---|
| 563 | 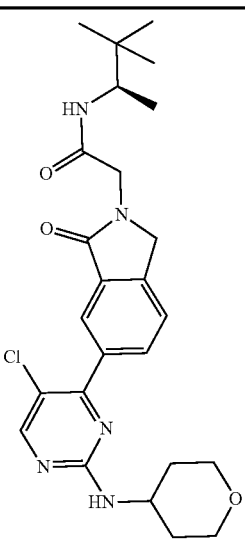 | 2-(6-{5-chloro-2-[(oxan-4-yl)amino]pyrimidin-4-yl}-1-oxo-2,3-dihydro-1H-isoindol-2-yl)-N-[(2R)-3,3-dimethylbutan-2-yl]acetamide | 1H NMR (400 MHz, DMSO-d6) δ: 8.44 (s, 1H), 8.02-8.01 (m, 1H), 7.97 (dd, 1H), 7.82 (d, 1H), 7.74 (d, 1H), 7.61 (s (br), 1H), 4.59 (s, 2H), 4.26-4.17 (m, 2H), 3.97-3.85 (m, 3H), 3.75-3.67 (m, 1H), 3.37 (t, 2H), 1.86-1.83 (br m, 2H), 1.57-1.47 (m, 2H), 1.00 (d, 3H), 0.85 (s, 9H). | 486 |
| 564 | 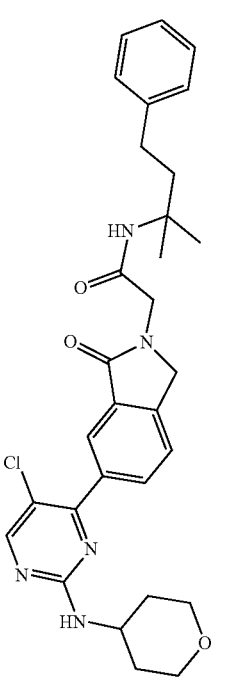 [SMILES: CC(C)(CCc1ccccc1)NC(=O)CN1Cc2ccc(-c3nc(NC4CCOCC4)ncc3Cl)cc2C1=O] | 2-(6-{5-chloro-2-[(oxan-4-yl)amino]pyrimidin-4-yl}-1-oxo-2,3-dihydro-1H-isoindol-2-yl)-N-(2-methyl-4-phenylbutan-2-yl)acetamide | 1H NMR (CDCl3, 400 MHz) δ 8.36-8.32 (2H, m), 8.03 (1H, dd), 7.60 (1H, dd), 7.25 (2H, dt), 7.20-7.13 (3H, m), 6.04 (1H, s), 5.18 (1H, d), 4.63 (2H, s), 4.17 (2H, s), 4.14-3.97 (3H, m), 3.61-3.52 (2H, m), 2.60-2.53 (2H, m), 2.12-2.00 (4H, m), 1.39 (6H, s). (2 protons overlapped with water peak) | 548 |

Example 565-568

Prepared using an analogous procedure to Example 547, from 2-(6-{5-chloro-2-[(oxan-4-yl)amino]pyrimidin-4-yl}-1-oxo-2,3-dihydro-1H-isoindol-2-yl)acetic acid (Example 1) and the corresponding amine. The products were further purified by chromatography (SiO₂, gradients of MeOH in DCM) in these cases.

| Example | Structure | Name | ¹H NMR (400 MHz) | MS: [M+ H]⁺ |
|---|---|---|---|---|
| 565 | 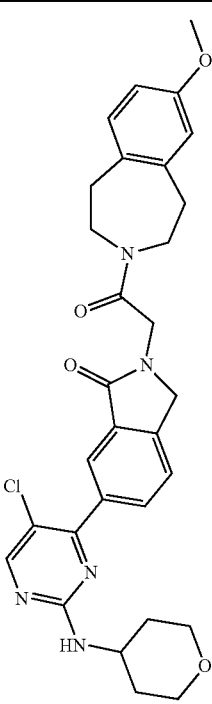 | 6-{5-chloro-2-[(oxan-4-yl)amino]pyrimidin-4-yl}-2-[2-(7-methoxy-2,3,4,5-tetrahydro-1H-3-benzazepin-3-yl)-2-oxoethyl]-2,3-dihydro-1H-isoindol-1-one | 1H NMR (DMSO-d6) δ: 8.46 (s, 1H), 8.08-8.01 (m, 1H), 7.99 (dd, 1H), 7.75 (d, 1H), 7.63 (s, 1H), 7.08 (t, 1H), 6.78 (dd, 1H), 6.69 (ddd, 1H), 4.61-4.50 (m, 4H), 3.85-3.98 (m, 3H), 3.72 (s, 3H), 3.67-3.52 (m, 4H), 3.43-3.35 (m, 2H), 2.90-2.95 (m, 2H), 2.76-2.84 (m, 2H), 1.81-1.88 (m, 2H), 1.53 (m, 2H). | 562 |
| 566 | 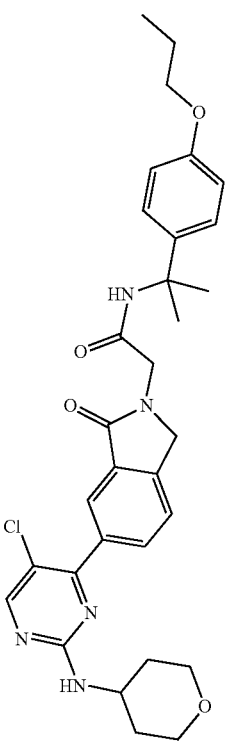 [SMILES: CCCOc1ccc(C(C)(C)NC(=O)CN2Cc3ccc(-c4nc(NC5CCOCC5)ncc4Cl)cc3C2=O)cc1] | 2-(6-{5-chloro-2-[(oxan-4-yl)amino]pyrimidin-4-yl}-1-oxo-2,3-dihydro-1H-isoindol-2-yl)-N-[2-(4-propoxyphenyl)propan-2-yl]acetamide | 1H NMR (DMSO) δ: 8.45 (s, 1H), 8.31 (s, 1H), 8.02 (d, 1H), 7.96 (dd, 1H), 7.72 (d, 1H), 7.62 (s (br), 1H), 7.25 (d, 2H), 6.83 (d, 2H), 4.55 (s, 2H), 4.24 (s, 2H), 3.82-3.98 (m, 5H), 3.44-3.35 (m, 2H), 1.79-1.89 (m, 2H), 1.77-1.64 (m, 2H), 1.56 (s, 6H), 1.57-1.47 (m, 2H), 0.97 (t, 3H). | 578 |

| Example | Structure | Name | ¹H NMR (400 MHz) | MS: [M+ H]⁺ |
|---|---|---|---|---|
| 567 | 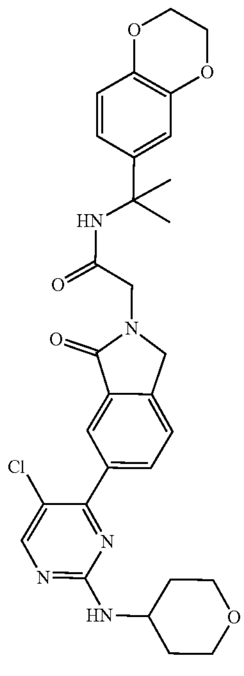 [SMILES: CC(C)(NC(=O)CN1Cc2ccc(-c3nc(NC4CCOCC4)ncc3Cl)cc2C1=O)c1ccc2c(c1)OCCO2] | 2-(6-{5-chloro-2-[(oxan-4-yl)amino]pyrimidin-4-yl}-1-oxo-2,3-dihydro-1H-isoindol-2-yl)-N-[2-(2,3-dihydro-1,4-benzodioxin-6-yl)propan-2-yl]acetamide | 1H NMR (DMSO-d6) δ: 8.45 (s, 1H), 8.29 (s, 1H), 8.01 (d, 1H), 7.96 (dd, 1H), 7.73 (d, 1H), 7.62 (s (br), 1H), 6.83-6.70 (m, 3H), 4.56(s, 2H), 4.26-4.17 (m, 6H), 3.98-3.82 (m, 3H), 3.45-3.34 (m, 2H), 1.85 (m, 2H), 1.53 (s, 6H), 1.56-1.48 (m, 2H). | 578 |
| 568 | 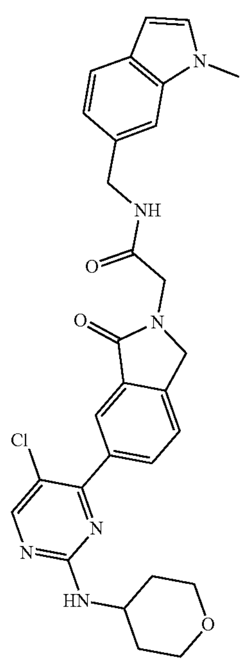 [SMILES: Cn1ccc2ccc(CNC(=O)CN3Cc4ccc(-c5nc(NC6CCOCC6)ncc5Cl)cc4C3=O)cc21] | 2-(6-{5-chloro-2-[(oxan-4-yl)amino]pyrimidin-4-yl}-1-oxo-2,3-dihydro-1H-isoindol-2-yl)-N-[(1-methyl-1H-indol-6-yl)methyl]acetamide | 1H NMR (DMSO-d6) δ: 8.64 (t, 1H), 8.45 (s, 1H), 8.04 (d, 1H), 7.99 (dd, 1H), 7.76 (d, 1H), 7.62 (s (br), 1H), 7.49 (d, 1H), 7.34 (s, 1H), 7.29 (d, 1H), 6.97 (dd, 1H), 6.39 (dd, 1H), 4.64 (s, 2H), 4.42 (d, 2H), 4.27 (s, 2H), 4.01-3.82 (m, 3H), 3.78 (s, 3H), 3.45-3.37 (m, 2H), 1.94-1.78 (m, 2H), 1.63-1.43 (m, 2H). | 545 |

Example 569-572

Prepared using an analogous procedure to Example 194, from 2-(6-{5-chloro-2-[(oxan-4-yl)amino]pyrimidin-4-yl}-1-oxo-2,3-dihydro-1H-isoindol-2-yl)acetic acid (Example 1) and the corresponding amine. The products were further purified by chromatography (SiO₂, gradients of MeOH in DCM) in these cases.

| Example | Structure | Name | ¹H NMR (400 MHz) | MS: [M + H]⁺ |
|---|---|---|---|---|
| 569 | 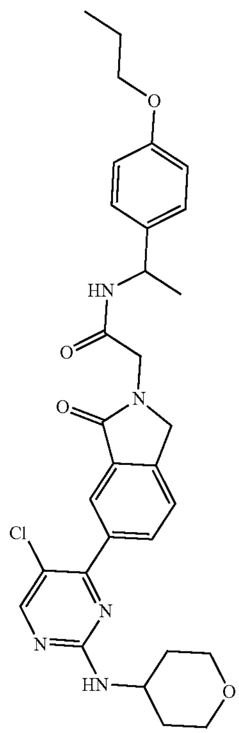 [SMILES: CCCOc1ccc(C(C)NC(=O)CN2Cc3ccc(-c4nc(NC5CCOCC5)ncc4Cl)cc3C2=O)cc1] | 2-(6-{5-chloro-2-[(oxan-4-yl)amino]pyrimidin-4-yl}-1-oxo-2,3-dihydro-1H-isoindol-2-yl)-N-[1-(4-propoxyphenyl)ethyl]acetamide | 1H NMR (DMSO-d6) δ: 8.53 (d, 1H), 8.45 (s, 1H), 8.02 (s, 1H), 7.98 (dd, 1H), 7.74 (d, 1H), 7.62 (s (br), 1H), 7.23 (d, 2H), 6.88 (d, 2H), 4.96-4.85 (m, 1H), 4.59 (s, 2H), 4.25 (d, 1H), 4.20 (s, 1H), 3.90 (t, 2H), 4.00-3.80 (m, 3H), 3.44-3.36 (m, 2H), 1.91-1.80 (m, 2H), 1.72 (qt, 2H), 1.60-1.46 (m, 2H), 1.36 (d, 3H), 0.97 (t, 3H). | 564 |
| 570 | 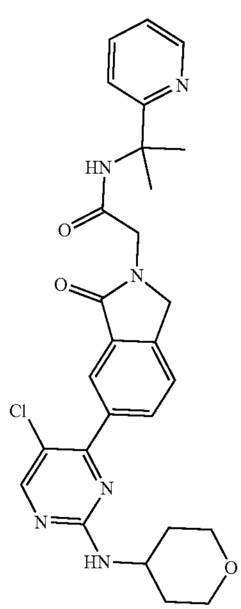 [SMILES: CC(C)(NC(=O)CN1Cc2ccc(-c3nc(NC4CCOCC4)ncc3Cl)cc2C1=O)c1ccccn1] | (2-(6-{5-chloro-2-[(oxan-4-yl)amino]pyrimidin-4-yl}-1-oxo-2,3-dihydro-1H-isoindol-2-yl)-N-[2-(pyridin-2-yl)propan-2-yl]acetamide | 1H NMR (DMSO-d6) δ: 8.55-8.39 (m, 3H), 8.02 (d, 1H), 7.96 (dd, 1H), 7.77-7.70 (m, 2H), 7.62 (s (br), 1H), 7.46-7.38 (m, 1H), 7.20 (ddd, 1H), 4.57 (d, 2H), 4.28 (d, 2H), 4.02-3.79 (m, 3H), 3.45-3.36 (m, 2H), 1.91-1.79 (m, 2H), 1.59 (s, 6H), 1.57-1.46 (m, 2H). | 521 |

| Example | Structure | Name | ¹H NMR (400 MHz) | MS: [M + H]⁺ |
|---|---|---|---|---|
| 571 | 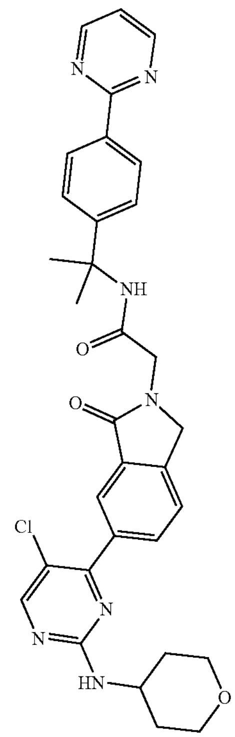 [SMILES: CC(C)(NC(=O)CN1Cc2ccc(-c3nc(NC4CCOCC4)ncc3Cl)cc2C1=O)c1ccc(-c2ncccn2)cc1] | 2-(6-{5-chloro-2-[(oxan-4-yl)amino]pyrimidin-4-yl}-1-oxo-2,3-dihydro-1H-isoindol-2-yl)-N-{2-[4-(pyrimidin-2-yl)phenyl]propan-2-yl}acetamide | 1H NMR (DMSO-d6, 400 MHz) δ 8.88 (2H, d), 8.50 (1H, s), 8.43 (1H, s), 8.35-8.25 (2H, m), 8.01 (1H, dd), 7.94 (1H, dd), 7.75-7.68 (1H, m), 7.60 (1H, s), 7.54-7.47 (2H, m), 7.41 (1H, t), 4.55 (2H, s), 4.28 (2H, s), 4.00-3.77 (3H, m), 3.43-3.34 (2H, m), 1.90-1.77 (2H, m), 1.62 (6H, s), 1.58-1.43 (2H, m). | 598 |
| 572 | 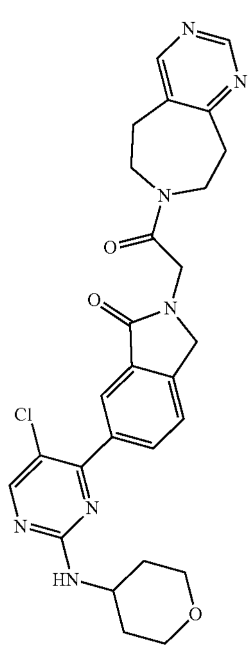 [SMILES: O=C(CN1Cc2ccc(-c3nc(NC4CCOCC4)ncc3Cl)cc2C1=O)N1CCc2cncnc2CC1] | 6-{5-chloro-2-[(oxan-4-yl)amino]pyrimidin-4-yl}-2-(2-oxo-2-{5H,6H,7H,8H,9H-pyrimido[4,5-d]azepin-7-yl}ethyl)-2,3-dihydro-1H-isoindol-1-one | 1H NMR (DMSO-d6) δ: 8.93 (d, 1H), 8.59 (d, 1H), 8.46 (s, 1H), 8.04 (d, 1H), 8.00 (dd, 1H), 7.76 (d, 1H), 7.63 (s (br), 1H), 4.64-4.52 (m, 4H), 4.01-3.82 (m, 3H), 3.81-3.62 (m, 4H), 3.44-3.37 (m, 2H), 3.25-3.15 (m, 1H), 3.10-2.98 (m, 2H), 2.94-2.85 (m, 1H), 1.92-1.76 (m, 2H), 1.60-1.45 (m, 2H). | 534 |

Example 573: 2-(6-{5-chloro-2-[(oxan-4-yl)amino]pyrimidin-4-yl}-1-oxo-2,3-dihydro-1H-isoindol-2-yl)-N-{[3-(pyrimidin-2-yl)phenyl]methyl}acetamide

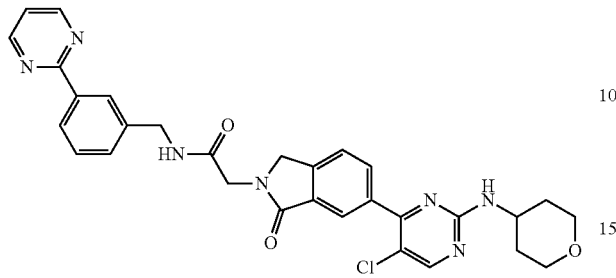

A stirred mixture of 2-(6-{5-chloro-2-[(oxan-4-yl)amino]pyrimidin-4-yl}-1-oxo-2,3-dihydro-1H-isoindol-2-yl)acetic acid (Example 1, 80 mg, 0.195 mmol), (3-(pyrimidin-2-yl)phenyl)methanamine (32.6 mg, 0.176 mmol) and triethylamine (73.6 μL, 0.528 mmol) in DMF (1 mL) was cooled in an ice bath. T3P (50% wt in EtOAc) (175 μL, 0.294 mmol) was added, the ice bath was removed and the reaction mixture allowed to warm to room temperature and stirred for 2 h. Water (5 mL) was added, and the resulting white precipitate was filtered, washed with water (5 mL). Trituration with MeOH and Et$_2$O afforded the title compound (79 mg, 77%) as a colourless powder. 1H NMR (DMSO, 400 MHz) δ 8.92 (1H, s), 8.91 (1H, s), 8.76 (1H, t), 8.44 (1H, s), 8.34 (1H, d), 8.28 (1H, dt), 8.03 (1H, d), 7.98 (1H, dd), 7.75 (1H, d), 7.62 (1H, bs), 7.53-7.42 (3H, m), 4.63 (2H, s), 4.41 (2H, d), 4.28 (2H, s), 3.88-3.84 (3H, m), 3.39-3.35 (2H, m), 1.89-1.79 (2H, m), 1.62-1.45 (2H, m). LC-MS: [M+H]+= 570.

Example 574: 2-(6-{5-chloro-2-[(oxan-4-yl)amino]pyrimidin-4-yl}-1-oxo-2,3-dihydro-1H-isoindol-2-yl)-N-[2-(4-methyl-1,3-thiazol-2-yl)propan-2-yl]acetamide

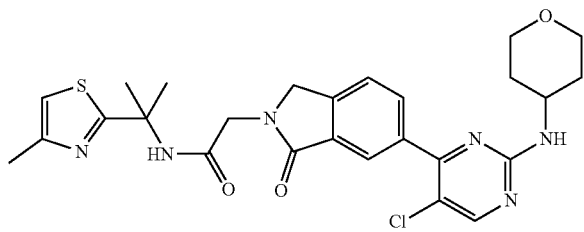 [SMILES: Cc1csc(C(C)(C)NC(=O)CN2Cc3ccc(-c4nc(NC5CCOCC5)ncc4Cl)cc3C2=O)n1]

Prepared using a similar procedure to Example 573. 1H NMR (DMSO, 400 MHz) δ 8.71 (1H, s), 8.44 (1H, s), 8.01 (1H, d), 7.96 (1H, dd), 7.73 (1H, d), 7.61 (1H, s), 7.08 (1H, s), 4.56 (2H, s), 4.24 (2H, s), 3.98-3.81 (3H, m), 3.38 (2H, m), 2.29 (3H, d), 1.90-1.80 (2H, m), 1.64 (6H, s), 1.58-1.44 (2H, m). LC-MS: [M+H]+=541.

Example 575: 2-(6-{5-chloro-2-[(oxan-4-yl)amino]pyrimidin-4-yl}-1-oxo-2,3-dihydro-1H-isoindol-2-yl)-N-[(naphthalen-2-yl)methyl]acetamide

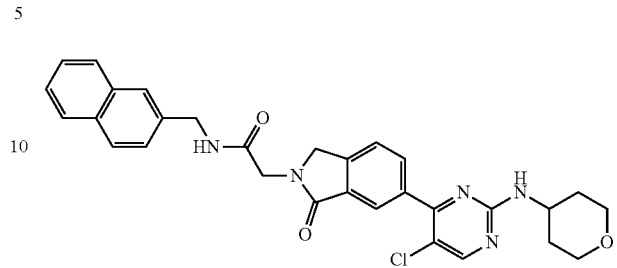

Prepared using a similar procedure to Example 573. 1H NMR (DMSO, 400 MHz) δ 8.75 (1H, t), 8.44 (1H, s), 8.04 (1H, d), 7.98 (1H, dd), 7.88 (3H, td), 7.79-7.73 (2H, m), 7.62 (1H, bs), 7.54-7.46 (2H, m), 7.44 (1H, dd), 4.64 (2H, s), 4.48 (2H, d), 4.30 (2H, s), 3.89-3.87 (3H, m), 3.39-3.35 (2H, m), 1.86-1.82 (2H, m), 1.57-1.47 (2H, m). LC-MS: [M+H]+= 542.

Example 576: 4-{[2-(6-{5-chloro-2-[(oxan-4-yl)amino]pyrimidin-4-yl}-1-oxo-2,3-dihydro-1H-isoindol-2-yl)acetamido]methyl}-N-cyclopropylbenzamide

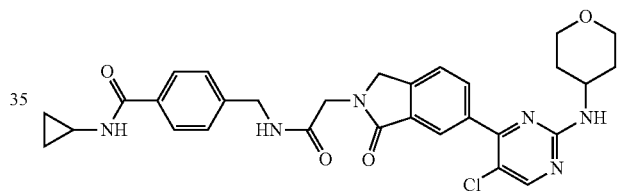

T3P (50% in EtOAc) (0.177 ml, 0.298 mmol) was added to a mixture of 2-(6-{5-chloro-2-[(oxan-4-yl)amino]pyrimidin-4-yl}-1-oxo-2,3-dihydro-1H-isoindol-2-yl)acetic acid (Example 1, 0.08 g, 0.199 mmol), 4-(aminomethyl)-N-cyclopropylbenzamide hydrochloride (0.045 g, 0.199 mmol) and triethylamine (0.111 ml, 0.794 mmol)) in DMF (1 mL) and the mixture was stirred for 3 h. Further 4-(aminomethyl)-N-cyclopropylbenzamide hydrochloride (0.019 g, 0.099 mmol), triethylamine (0.028 ml, 0.199 mmol) and T3P (50% in EtOAc) (0.059 ml, 0.099 mmol) were added and the mixture was stirred overnight. Water was added and the resulting precipitate was filtered, washed with water and dried under suction. The resulting solid was dissolved in DCM:MeOH and the mixture was concentrated under vacuum. The residue was triturated with EtOAc and the resulting precipitate was filtered, washed with EtOAc and Et$_2$O. The product was dried in a vacuum oven at 40° C. overnight to afford the title compound (0.072 g, 61.8%) as a white solid. 1H NMR (DMSO-d6) δ: 8.70 (t, 1H), 8.45 (s, 1H), 8.40 (d, 1H), 8.04 (d, 1H), 7.98 (dd, 1H), 7.77 (m, 3H), 7.63 (s (br), 1H), 7.34 (d, 2H), 4.62 (s, 2H), 4.35 (d, 2H), 4.28 (s, 2H), 3.99-3.82 (m, 3H), 3.35-3.45 (m, 2H), 2.87-2.80 (m, 1H), 1.90-1.78 (m, 2H), 1.60-1.45 (m, 2H), 0.72-0.67 (m, 2H), 0.58-0.54 (m, 2H). LC-MS: [M+H]+=575.

Example 577: N-{[4-(azetidine-1-carbonyl)phenyl]methyl}-2-(6-{5-chloro-2-[(oxan-4-yl)amino]pyrimidin-4-yl}-1-oxo-2,3-dihydro-1H-isoindol-2-yl)acetamide

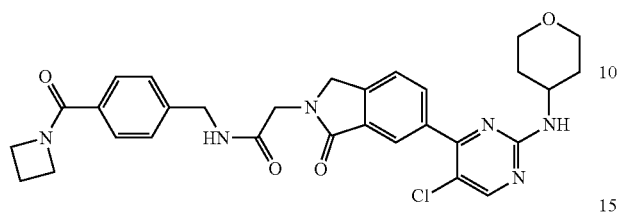

T3P (50% in EtOAc) (0.177 ml, 0.298 mmol) was added to a mixture of 2-(6-{5-chloro-2-[(oxan-4-yl)amino]pyrimidin-4-yl}-1-oxo-2,3-dihydro-1H-isoindol-2-yl)acetic acid (Example 1, 0.08 g, 0.199 mmol), (4-(aminomethyl)phenyl)(azetidin-1-yl)methanone (0.038 g, 0.199 mmol) and triethylamine (0.111 ml, 0.794 mmol) in DMF (1 mL) and the mixture was stirred for 4.5 h. (4-(aminomethyl)phenyl)(azetidin-1-yl)methanone (0.038 g, 0.199 mmol), triethylamine (0.083 ml, 0.596 mmol) and T3P (50% in EtOAc) (0.118 ml, 0.199 mmol) were added and the mixture was stirred overnight. Water followed by DCM were added and the layers were separated through a phase separating cartridge. The organic extract was dried (MgSO$_4$), filtered, and adsorbed on to silica. The crude product was purified by chromatography (SiO$_2$, 12 g column, 0-5% MeOH in DCM) to afford the title compound (0.015 g, 12.87%) as a white solid after trituration and evaporation from Et$_2$O. 1H NMR (DMSO-d6) δ: 8.71 (t, 1H), 8.45 (s, 1H), 8.07-8.02 (m, 1H), 7.99 (dd, 1H), 7.76 (d, 1H), 7.63 (s (br), 1H), 7.59 (d, 2H), 7.34 (d, 2H), 4.62 (s, 2H), 4.35 (d, 2H), 4.33-4.23 (m, 4H), 4.04 (t, 2H), 3.98-3.83 (m, 3H), 3.42-3.34 (m, 2H), 2.25 (quint, 2H), 1.89-1.80 (m, 2H), 1.60-1.47 (m, 2H). LCMS: [M+H]+=575.

Example 578: 2-(6-{5-chloro-2-[(oxan-4-yl)amino]pyrimidin-4-yl}-1-oxo-2,3-dihydro-1H-isoindol-2-yl)-N-(3,3,3-trifluoro-1-phenylpropyl)acetamide

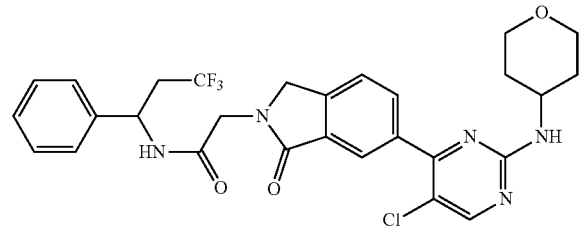 [SMILES: O=C(CN1Cc2ccc(-c3nc(NC4CCOCC4)ncc3Cl)cc2C1=O)NC(CC(F)(F)F)c1ccccc1]

A stirred mixture of 2-(6-{5-chloro-2-[(oxan-4-yl)amino]pyrimidin-4-yl}-1-oxo-2,3-dihydro-1H-isoindol-2-yl)acetic acid (Example 1, 75 mg, 0.182 mmol), 3,3,3-trifluoro-1-phenylpropan-1-amine (34.5 mg, 0.182 mmol) and triethylamine (76 µl, 0.547 mmol) in DMF (1 mL) was cooled with an ice bath. T3P (50% in EtOAc, 163 µl, 0.274 mmol) was added, the ice bath was removed and the reaction mixture allowed to warm to room temperature and stirred overnight. Water was added and the mixture was extracted with EtOAc (20 mL). The combined organic extracts were washed with water (15 mL) and brine (15 mL), dried (MgSO$_4$), filtered, and concentrated in vacuo to give the crude product. Purification by chromatography (SiO$_2$, 24 g column, 0-10% MeOH in EtOAc) afforded the title compound (48 mg, 44.9%) as a white solid. 1H NMR (400 MHz, DMSO-d6) δ 8.77 (d, 1H), 8.44 (s, 1H), 8.03 (dd, 1H), 7.98 (dd, 1H), 7.75 (d, 1H), 7.62 (s (br), 1H), 7.43-7.33 (m, 4H), 7.33-7.25 (m, 1H), 5.27-5.21 (m, 1H), 4.57 (s, 2H), 4.28-4.20 (m, 2H), 3.98-3.80 (m, 3H), 3.36 (t, 2H), 2.91-2.71 (m, 2H), 1.85-1.82 (m (br), 2H), 1.52 (qd, 2H). LCMS: [M+H]+=574.

Example 579: 2-(6-{5-chloro-2-[(oxan-4-yl)amino]pyrimidin-4-yl}-1-oxo-2,3-dihydro-1H-isoindol-2-yl)-N-[(1S)-2,2,2-trifluoro-1-phenylethyl]acetamide

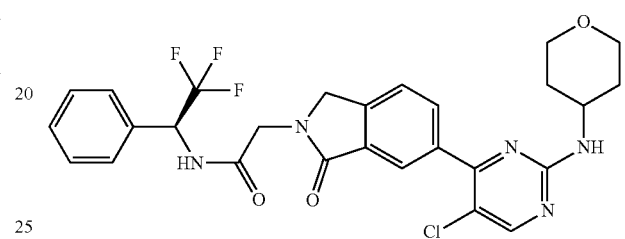

A stirred mixture of 2-(6-{5-chloro-2-[(oxan-4-yl)amino]pyrimidin-4-yl}-1-oxo-2,3-dihydro-1H-isoindol-2-yl)acetic acid (Example 1, 75 mg, 0.182 mmol), (S)-2,2,2-trifluoro-1-phenylethanamine (26.1 µl, 0.182 mmol) and triethylamine (76 µl, 0.547 mmol) in DMF (1 mL) was cooled in an ice bath. T3P (163 µl, 0.274 mmol) was added, the ice bath was removed and the reaction mixture allowed to warm to rt overnight. Water was added and the resulting precipitate collected by filtration and washed with water. The solid was triturated with diethyl ether/isohexane (1:1), filtered and dried to afford the title compound (70 mg, 67.8%) as a white solid. 1H NMR (400 MHz, DMSO-d6) δ 9.48 (d, 1H), 8.44 (s, 1H), 8.02 (dd, 1H), 7.98 (dd, 1H), 7.74 (d, 1H), 7.70-7.53 (m, 3H), 7.51-7.38 (m, 3H), 5.81 (p, 1H), 4.60 (s, 2H), 4.46-4.32 (m, 2H), 3.98-3.80 (m, 3H), 3.37 (t, 2H), 1.85-1.82 (m (br), 2H), 1.57-1.47 (m, 2H). LCMS: [M+H]+=560.

Example 580: 2-(6-{5-chloro-2-[(oxan-4-yl)amino]pyrimidin-4-yl}-1-oxo-2,3-dihydro-1H-isoindol-2-yl)-N-[2-(pyridin-3-yl)propan-2-yl]acetamide

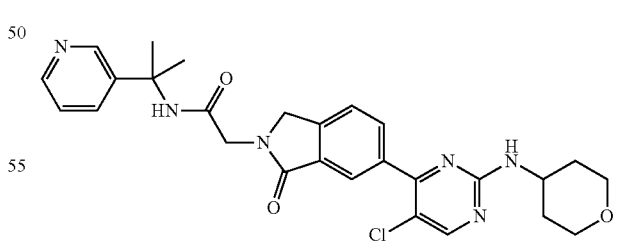

Triethylamine (0.090 mL, 0.646 mmol) followed by T3P (50 wt % in EtOAc) (0.200 mL, 0.336 mmol) were added to a stirred solution of 2-(6-{5-chloro-2-[(oxan-4-yl)amino]pyrimidin-4-yl}-1-oxo-2,3-dihydro-1H-isoindol-2-yl)acetic acid (Example 1, 0.085 g, 0.209 mmol) and 2-(pyridin-3-yl)propan-2-amine (0.043 g, 0.316 mmol) in DMF (2.5 mL, 32.3 mmol). The resulting pale yellow solution was stirred at room temperature for 75 minutes, then diluted with water (5 mL). The mixture was partitioned between saturated aqueous NH₄Cl (10 mL) and EtOAc (20 mL). The layers were separated and the aqueous layer was extracted with EtOAc (20 mL). The combined organic extracts were washed with water (10 mL), saturated aqueous NaHCO₃ (10 mL) and brine (3×10 mL), then dried (MgSO₄), filtered, and concentrated under reduced pressure to afford a white solid (63 mg). The solid was dissolved in EtOAc (20 mL) and washed with brine (5×20 mL), dried (MgSO₄), filtered, concentrated under reduced pressure and then dried in a desiccator at 50° C. overnight to afford the title compound (0.053 g, 46.8%) as a white solid. 1H NMR (DMSO-d6, 400 MHz) δ 8.60-8.55 (m, 1H), 8.52 (s, 1H), 8.44 (s, 1H), 8.38 (dd, 1H), 8.00 (dd, 1H), 7.95 (dd, 1H), 7.72 (dq, 2H), 7.61 (s (br), 1H), 7.31 (ddd, 1H), 4.55 (s, 2H), 4.27 (s, 2H), 3.95-3.83 (m, 3H), 3.39-3.33 (m, 2H), 1.84 (d (br), 2H), 1.59 (s, 6H), 1.51 (qd, 2H). LCMS: [M+H]+=521.

Example 581: 6-{5-chloro-2-[(oxan-4-yl)amino]pyrimidin-4-yl}-2-(2-oxo-2-{4-oxo-3H,4H,5H,6H,7H,8H,9H-pyrimido[4,5-d]azepin-7-yl}ethyl)-2,3-dihydro-1H-isoindol-1-one

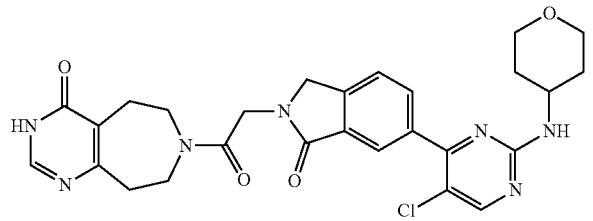 [SMILES: O=C(CN1Cc2ccc(-c3nc(NC4CCOCC4)ncc3Cl)cc2C1=O)N1CCc2nc[nH]c(=O)c2CC1]

Prepared using a similar procedure to Example 580. The product was purified by chromatography (SiO₂, 24 g column, 0-10% MeOH in DCM) in this case. 1H NMR (DMSO-d6, 400 MHz) δ 12.42 (s (br), 1H), 8.45 (s, 1H), 8.03 (d, 1H), 8.00-7.95 (m, 2H), 7.74 (d, 1H), 7.62 (s, 1H), 4.58 (s, 2H), 4.53 (d, 2H), 3.93-3.81 (m, 3H), 3.77-3.56 (m, 4H), 3.38-3.35 (m, 2H), 3.02-2.72 (m, 4H), 1.84 (d, 2H), 1.52 (qd, 2H). LCMS: [M+H]+=550.

Example 582: 2-(6-{5-chloro-2-[(oxan-4-yl)amino]pyrimidin-4-yl}-1-oxo-2,3-dihydro-1H-isoindol-2-yl)-N-[2-(1-methyl-1H-pyrazol-4-yl)propan-2-yl]acetamide

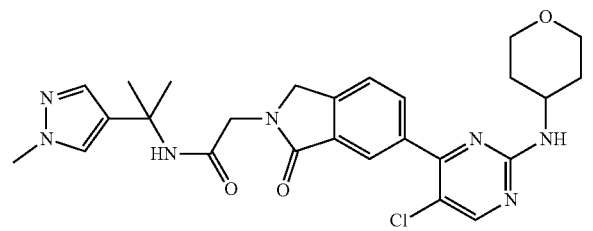 [SMILES: Cn1cc(C(C)(C)NC(=O)CN2Cc3ccc(-c4nc(NC5CCOCC5)ncc4Cl)cc3C2=O)cn1]

Prepared using a similar procedure to Example 580. The product was further purified by chromatography (SiO₂, 4 g column, 0-5% MeOH in DCM) in this case. 1H NMR (DMSO-d6) δ: 8.45 (s, 1H), 8.08 (s, 1H), 8.02 (dd, 1H), 7.97 (dd, 1H), 7.74 (d, 1H), 7.62 (s (br), 1H), 7.56 (d, 1H), 7.33 (d, 1H), 4.57 (s, 2H), 4.17 (s, 2H), 3.82-3.98 (m, 3H), 3.77 (s, 3H), 3.42-3.33 (m, 2H), 1.90-1.80 (m, 2H), 1.57 (s, 6H), 1.57-1.47 (m, 2H). LCMS: [M+H]+=524.

Example 583: 2-(6-{5-chloro-2-[(oxan-4-yl)amino]pyrimidin-4-yl}-1-oxo-2,3-dihydro-1H-isoindol-2-yl)-N-[(1S,2S)-2-hydroxy-1-(3-methylphenyl)propyl]acetamide

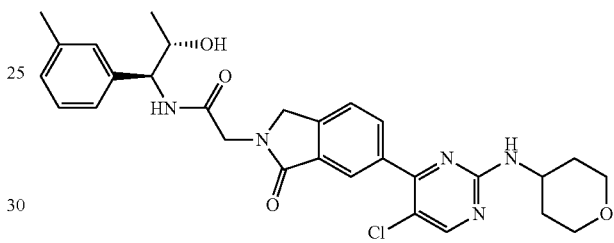

TBTU (96 mg, 0.298 mmol) was added to an ice-cooled stirred solution of 2-(6-{5-chloro-2-[(oxan-4-yl)amino]pyrimidin-4-yl}-1-oxo-2,3-dihydro-1H-isoindol-2-yl)acetic acid (Example 1, 80 mg, 0.199 mmol), (1S,2S)-1-amino-1-(m-tolyl)propan-2-ol hydrochloride (44.1 mg, 0.218 mmol) and triethylamine (111 μl, 0.794 mmol) in DMF (2 mL). The mixture was stirred at room temperature for 1 h, then diluted with EtOAc (30 mL). The organic phase was washed with water (30 mL) 1 M HCl (aq.) (30 mL) and brine (3×30 mL), dried (MgSO₄), filtered, and concentrated in vacuo to give a white semi-solid (150 mg). The crude product was purified by chromatography (SiO₂, 24 g column, 0-10% MeOH in DCM) to afford the title compound (95 mg, 86%) as a white solid. 1H NMR (DMSO-d6, 400 MHz) δ 8.54-8.35 (m, 2H), 8.02 (d, 1H), 7.96 (dd, 1H), 7.73 (d, 1H), 7.62 (s, 1H), 7.19 (t, 1H), 7.15-7.08 (m, 2H), 7.03 (d, 1H), 4.80 (d, 1H), 4.67 (dd, 1H), 4.57 (s, 2H), 4.35 (d, 1H), 4.28 (d, 1H), 4.01-3.77 (m, 4H), 3.42-3.31 (m, 2H), 2.29 (s, 3H), 1.93-1.77 (m, 2H), 1.62-1.44 (m, 2H), 0.98 (d, 3H). LCMS: [M+H]+=550.

Example 584-589

Prepared using an analogous procedure to Example 583, from 2-(6-{5-chloro-2-[(oxan-4-yl)amino]pyrimidin-4-yl}-1-oxo-2,3-dihydro-1H-isoindol-2-yl)acetic acid (Example 1) and the corresponding amine.

| Example | Structure | Name | ¹H NMR (400 MHz) | MS: [M + H]⁺ |
|---|---|---|---|---|
| 584 | 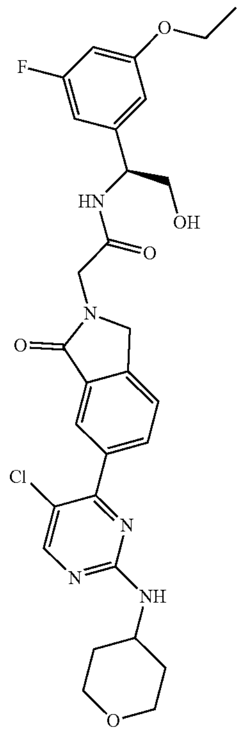 [SMILES: CCOc1cc(F)cc([C@@H](CO)NC(=O)CN2Cc3ccc(-c4nc(NC5CCOCC5)ncc4Cl)cc3C2=O)c1] | 2-(6-{5-chloro-2-[(oxan-4-yl)amino]pyrimidin-4-yl}-1-oxo-2,3-dihydro-1H-isoindol-2-yl)-N-[(1S)-1-(3-ethoxy-5-fluorophenyl)-2-hydroxyethyl]acetamide | 1H NMR (DMSO-d6, 400 MHz) δ 8.54 (d, 1H), 8.45 (s, 1H), 8.07-8.02 (m, 1H), 7.98 (dd, 1H), 7.74 (d, 1H), 7.63 (s (br), 1H), 6.76-6.65 (m, 3H), 4.96 (t, 1H), 4.89-4.82 (m, 1H), 4.60 (s, 2H), 4.35-4.26 (m, 2H), 4.03 (q, 2H), 3.98-3.83 (m, 3H), 3.59-3.54 (m, 2H), 3.42-3.36 (m, 2H), 1.90-1.82 (m, 2H), 1.61-1.47 (m, 2H), 1.32 (t, 3H). | 584 |
| 585 | 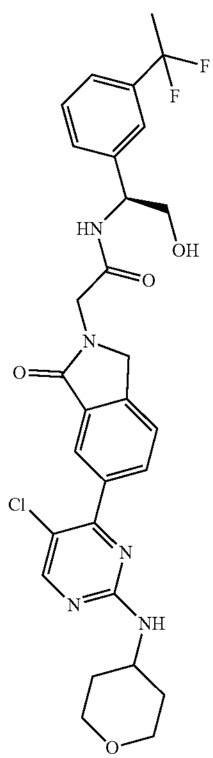 [SMILES: CC(F)(F)c1cccc([C@@H](CO)NC(=O)CN2Cc3ccc(-c4nc(NC5CCOCC5)ncc4Cl)cc3C2=O)c1] | 2-(6-{5-chloro-2-[(oxan-4-yl)amino]pyrimidin-4-yl}-1-oxo-2,3-dihydro-1H-isoindol-2-yl)-N-[(1S)-1-[3-(1,1-difluoroethyl)phenyl]-2-hydroxyethyl]acetamide | 1H NMR (DMSO-d6, 400 MHz) δ 8.65 (d, 1H), 8.45 (s, 1H), 8.05-8.01 (m, 1H), 7.98 (dd, 1H), 7.74 (d, 1H), 7.63 (s (br), 1H), 7.57-7.51 (m, 1H), 7.47-7.42 (m, 3H), 5.01-4.90 (m, 2H), 4.59 (s, 2H), 4.36-4.24 (m, 2H), 3.98-3.82 (m, 3H), 3.60 (t, 2H), 3.42-3.35 (m, 2H), 1.97 (t, 3H), 1.89-1.80 (m, 2H), 1.60-1.46 (m, 2H). | 586 |

| Example | Structure | Name | ¹H NMR (400 MHz) | MS: [M + H]⁺ |
|---|---|---|---|---|
| 586 | 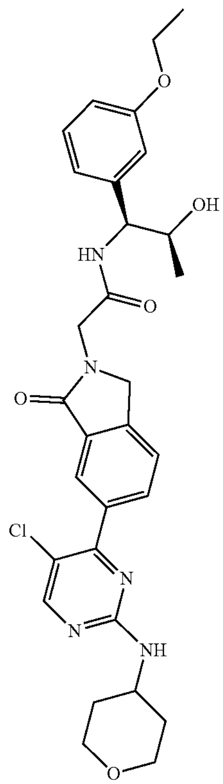 [SMILES: CCOc1cccc([C@H](NC(=O)CN2Cc3ccc(-c4nc(NC5CCOCC5)ncc4Cl)cc3C2=O)[C@H](C)O)c1] | 2-(6-{5-chloro-2-[(oxan-4-yl)amino]pyrimidin-4-yl}-1-oxo-2,3-dihydro-1H-isoindol-2-yl)-N-[(1S,2S)-1-(3-ethoxyphenyl)-2-hydroxypropyl]acetamide | 1H NMR (DMSO-d6, 400 MHz) δ 8.54-8.37 (2H, m), 8.02 (1H, dd), 7.97 (1H, dd), 7.73 (1H, d), 7.62 (1H, s), 7.20 (1H, dd), 6.94-6.84 (2H, m), 6.77 (1H, ddd), 4.80 (1H, d), 4.68 (1H, dd), 4.57 (2H, s), 4.35 (1H, d), 4.28 (1H, d), 4.00 (2H, q), 3.96-3.78 (4H, m), 3.45-3.35 (2H, m), 1.92-1.76 (2H, m), 1.61-1.44 (2H, m), 1.32 (3H, t), 0.98 (3H, d). | 580 |
| 587 | 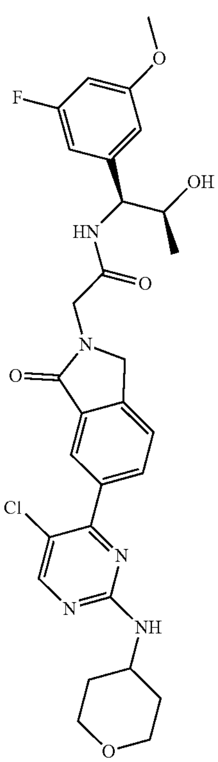 [SMILES: COc1cc(F)cc([C@H](NC(=O)CN2Cc3ccc(-c4nc(NC5CCOCC5)ncc4Cl)cc3C2=O)[C@H](C)O)c1] | 2-(6-{5-chloro-2-[(oxan-4-yl)amino]pyrimidin-4-yl}-1-oxo-2,3-dihydro-1H-isoindol-2-yl)-N-[(1S,2S)-1-(3-fluoro-5-methoxyphenyl)-2-hydroxypropyl]acetamide | 1H NMR (DMSO-d6, 400 MHz) δ 8.54-8.36 (m, 2H), 8.02 (dd, 1H), 7.97 (dd, 1H), 7.73 (d, 1H), 7.61 (s, 1H), 6.83-6.72 (m, 2H), 6.68 (dt, 1H), 4.85 (d, 1H), 4.72 (dd, 1H), 4.58 (s, 2H), 4.37 (d, 1H), 4.31 (d, 1H), 3.98-3.81 (m, 4H), 3.76 (s, 3H), 3.43-3.32 (m, 2H), 1.89-1.78 (m, 2H), 1.59-1.44 (m, 2H), 1.02 (d, 3H). | 584 |

| Example | Structure | Name | ¹H NMR (400 MHz) | MS: [M + H]⁺ |
|---|---|---|---|---|
| 588 | 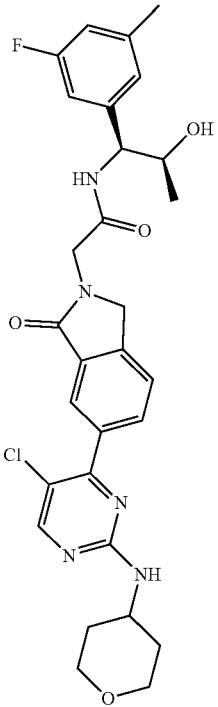 [SMILES: Cc1cc(F)cc([C@H](NC(=O)CN2Cc3ccc(-c4nc(NC5CCOCC5)ncc4Cl)cc3C2=O)[C@H](C)O)c1] | 2-(6-{5-chloro-2-[(oxan-4-yl)amino]pyrimidin-4-yl}-1-oxo-2,3-dihydro-1H-isoindol-2-yl)-N-[(1S,2S)-1-(3-fluoro-5-methylphenyl)-2-hydroxypropyl]acetamide | 1H NMR (DMSO-d6, 400 MHz) δ 8.54-8.38 (2H, m), 8.03 (1H, dd), 7.97 (1H, dd), 7.74 (1H, d), 7.62 (1H, s (br)), 7.05-6.94 (2H, m), 6.93-6.85 (1H, m), 4.86 (1H, d), 4.72 (1H, dd), 4.59 (2H, s), 4.37 (1H, d), 4.31 (1H, d), 4.04-3.80 (4H, m), 3.47-3.34 (2H, m), 2.31 (3H, s), 1.89-1.80 (2H, m), 1.62-1.45 (2H, m), 1.02 (3H, d). | 568 |
| 589 | 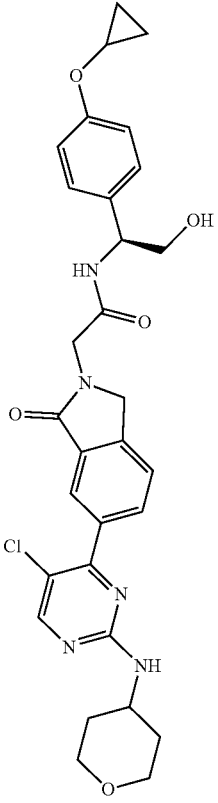 [SMILES: O=C(CN1Cc2ccc(-c3nc(NC4CCOCC4)ncc3Cl)cc2C1=O)N[C@H](CO)c1ccc(OC2CC2)cc1] | 2-(6-{5-chloro-2-[(oxan-4-yl)amino]pyrimidin-4-yl}-1-oxo-2,3-dihydro-1H-isoindol-2-yl)-N-[(1S)-1-(4-cyclopropoxyphenyl)-2-hydroxyethyl]acetamide | 1H NMR (DMSO-d6, 400 MHz) δ 8.50 (1H, d), 8.44 (1H, s), 8.02 (1H, d), 7.97 (1H, dd), 7.73 (1H, d), 7.62 (1H, s (br)), 7.31-7.14 (2H, m), 7.06-6.91 (2H, m), 4.88 (1H, s), 4.82 (1H, ddd), 4.58 (2H, s), 4.30 (1H, d), 4.24 (1H, d), 3.97-3.82 (3H, m), 3.83-3.75 (1H, m), 3.54 (2H, d), 3.46-3.35 (2H, m), 1.89-1.77 (2H, m), 1.60-1.43 (2H, m), 0.83-0.72 (2H, m), 0.67-0.58 (2H, m). | 578 |

Example 590: 2-(6-{5-chloro-2-[(oxan-4-yl)amino]pyrimidin-4-yl}-1-oxo-2,3-dihydro-1H-isoindol-2-yl)-N-[2-(hydroxymethyl)-2,3-dihydro-1H-inden-1-yl]acetamide (relative cis stereochemistry)

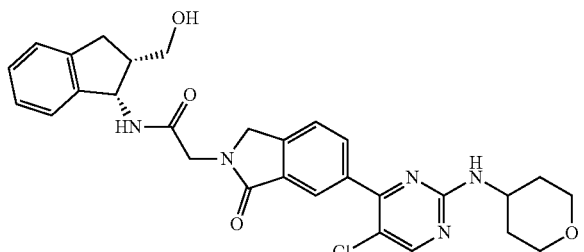

TBTU (0.067 g, 0.209 mmol) was added to a mixture of 2-(6-{5-chloro-2-[(oxan-4-yl)amino]pyrimidin-4-yl}-1-oxo-2,3-dihydro-1H-isoindol-2-yl)acetic acid (Example 1, 0.08 g, 0.199 mmol), (trans-1-amino-2,3-dihydro-1H-inden-2-yl)methanol (0.034 g, 0.209 mmol), and DIPEA (0.036 ml, 0.209 mmol) in DMF (1 mL) and the mixture was stirred for 1 h. The mixture was diluted with EtOAc and transferred into a separating funnel. 1 N aq. HCl was added and the product was extracted with EtOAc. The combined organic extracts were washed with water, saturated aqueous NaHCO$_3$, brine, dried (MgSO$_4$), filtered, and adsorbed on to silica. The crude product was purified by chromatography (SiO$_2$, 12 g column, 0-6% MeOH in DCM) to afford the title compound (0.07 g, 62.4%) as a white solid, after trituration and evaporation from Et$_2$O. 1H NMR (DMSO-d6) δ: 8.46 (s, 1H), 8.36 (d, 1H), 8.04 (d, 1H), 7.99 (dd, 1H), 7.76 (d, 1H), 7.63 (s (br), 1H), 7.30-7.16 (m, 4H), 5.38 (t, 1H), 4.65 (d, 1H), 4.60 (s, 1H), 4.46 (dd, 1H), 4.27 (s, 2H), 3.98-3.81 (m, 3H), 3.58-3.49 (m, 1H), 3.44-3.35 (m, 2H), 3.29 (ddd, 1H), 2.88 (ddd, 2H), 2.70-2.59 (m, 1H), 1.90-1.79 (m, 2H), 1.59-1.47 (m, 2H). LCMS: [M+H]+=548.

Example 591: 2-(6-{5-chloro-2-[(oxan-4-yl)amino]pyrimidin-4-yl}-1-oxo-2,3-dihydro-1H-isoindol-2-yl)-N-[(1S)-1-(4-fluoro-3-methylphenyl)-2-hydroxyethyl]acetamide

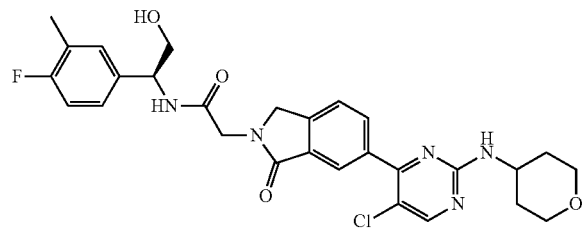 [SMILES: Cc1cc([C@@H](CO)NC(=O)CN2Cc3ccc(-c4nc(NC5CCOCC5)ncc4Cl)cc3C2=O)ccc1F]

Prepared using a similar procedure to Example 590. 1H NMR (DMSO-d6) δ: 8.54 (d, 1H), 8.45 (s, 1H), 8.03 (d, 1H), 7.98 (dd, 1H), 7.74 (d, 1H), 7.63 (s (br), 1H), 7.23 (dd, 1H), 7.17 (ddd, 1H), 7.08 (dd, 1H), 4.94 (t, 1H), 4.84 (td, 1H), 4.59 (s, 2H), 4.31 (d, 1H), 4.26 (d, 1H), 4.00-3.80 (m, 3H), 3.56 (dd, 2H), 3.42-3.35 (m, 2H), 2.23 (d, 3H), 1.89-1.79 (m, 2H), 1.60-1.46 (m, 2H). LCMS: [M+H]+=554.

Example 592: 2-(6-{5-chloro-2-[(oxan-4-yl)amino]pyrimidin-4-yl}-1-oxo-2,3-dihydro-1H-isoindol-2-yl)-N-[(1S,2S)-2-hydroxy-1-[3-(trifluoromethyl)phenyl]propyl]acetamide

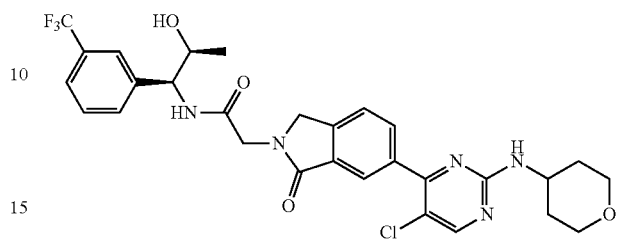

A stirred solution of 2-(6-{5-chloro-2-[(oxan-4-yl)amino]pyrimidin-4-yl}-1-oxo-2,3-dihydro-1H-isoindol-2-yl)acetic acid (Example 1, 70 mg, 0.170 mmol), (1S,2S)-1-amino-1-(3-(trifluoromethyl)phenyl)propan-2-ol, HCl (48 mg, 0.188 mmol), and triethylamine (95 µl, 0.681 mmol) in DMF (1 ml) was treated with TBTU (66 mg, 0.206 mmol) and stirred at room temperature overnight. The mixture was diluted with EtOAc (20 ml), washed with 1 M aq. KHSO$_4$ (10 ml) followed by saturated aqueous NaHCO$_3$ (10 ml), brine (2×10 ml), then dried (MgSO$_4$), filtered, and evaporated. The residue was purified by chromatography (SiO$_2$, 12 g column, 0-6% EtOH in EtOAc), to give a glassy semi-solid. the product was purified by reversed phase preparative HPLC on a Waters XBridge BEH C18 OBD, 130 A, 5 µm, 19 mm×50 mm column, using a gradient of 20 to 50% of acetonitrile in 10 mM aqueous ammonium bicarbonate solution at 28 ml/min as eluent. The clean fractions were pooled and concentrated to remove most of the acetonitrile. The residue was freeze-dried to give the title compound (41 mg, 39.5%) as a white powder. 1H NMR (DMSO-d6, 400 MHz) δ 8.62 (d, 1H), 8.44 (s, 1H), 8.04-8.00 (m, 1H), 7.96 (dd, 1H), 7.76-7.67 (m, 2H), 7.69-7.50 (m, 4H), 5.01-4.82 (m, 2H), 4.57 (s, 2H), 4.44-4.25 (m, 2H), 3.99-3.78 (m, 4H), 3.42-3.36 (m, 2H), 1.91-1.77 (m, 2H), 1.61-1.43 (m, 2H), 1.04 (d, 3H). LCMS: [M+H]+=604.

Example 593: 2-(6-{5-chloro-2-[(oxan-4-yl)amino]pyrimidin-4-yl}-1-oxo-2,3-dihydro-1H-isoindol-2-yl)-N-[(1S)-1-(2-fluoro-3-methylphenyl)-2-hydroxyethyl]acetamide

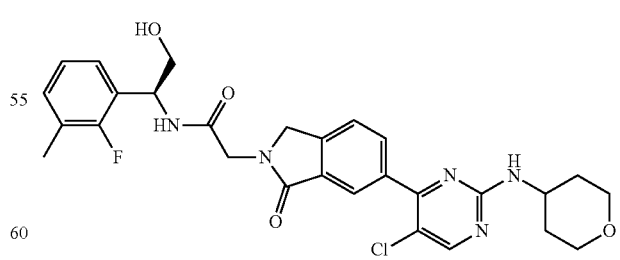

Prepared using a similar procedure to Example 590. 1H NMR (DMSO-d6) δ: 8.68 (d, 1H), 8.50 (s, 1H), 8.08 (d, 1H), 8.03 (dd, 1H), 7.79 (d, 1H), 7.67 (s (br), 1H), 7.32-7.19 (m, 2H), 7.13 (dd, 1H), 5.23 (td, 1H), 5.09 (t, 1H), 4.64 (s, 2H), 4.38 (d, 1H), 4.32 (d, 1H), 4.06-3.87 (m, 3H), 3.69-3.56 (m, 2H), 3.48-3.41 (m, 2H), 2.28 (d, 3H), 1.98-1.84 (m, 2H), 1.68-1.50 (m, 2H). LCMS: [M+H]+=554.

Example 594: 6-{5-chloro-2-[(oxan-4-yl)amino]pyrimidin-4-yl}-2-{2-[3-(hydroxymethyl)-3-methylazetidin-1-yl]-2-oxoethyl}-2,3-dihydro-1H-isoindol-1-one

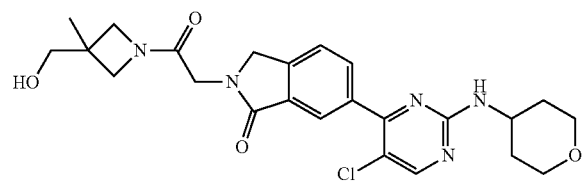 [SMILES: CC1(CO)CN(C(=O)CN2Cc3ccc(-c4nc(NC5CCOCC5)ncc4Cl)cc3C2=O)C1]

DIPEA (0.073 ml, 0.417 mmol) was added to a mixture of 2-(6-{5-chloro-2-[(oxan-4-yl)amino]pyrimidin-4-yl}-1-oxo-2,3-dihydro-1H-isoindol-2-yl)acetic acid (Example 1, 0.08 g, 0.199 mmol), (3-methylazetidin-3-yl)methanol hydrochloride (0.029 g, 0.209 mmol), and TBTU (0.032 g, 0.099 mmol) in DMF (1 mL) and the mixture was stirred for 45 minutes at room temperature. TBTU (0.067 g, 0.209 mmol), DIPEA (0.017 ml, 0.099 mmol) and (3-methylazetidin-3-yl)methanol hydrochloride (0.014 g, 0.099 mmol) were added and the mixture was stirred for 1.75 h. The mixture was diluted with EtOAc (vol?) and transferred into a separating funnel. 1 N aq. HCl was added and the product was extracted with EtOAc. The acidic aqueous layer was neutralized by the addition of 2 N aq. NaOH and was extracted with DCM. The combined organic extracts were dried (MgSO₄), adsorbed on to silica and purified by chromatography (SiO₂, 12 g column, 0-100% MeOH in DCM) to the title compound (0.034 g, 34.5%) as a white solid after trituration and evaporation from Et₂O. 1H NMR (DMSO-d6) δ: 8.45 (s, 1H), 8.03 (d, 1H), 7.98 (dd, 1H), 7.75 (d, 1H), 7.63 (s (br), 1H), 5.00 (s (br), 1H), 4.57 (s, 2H), 4.23 (s, 2H), 4.02 (d, 1H), 3.99-3.81 (m, 3H), 3.79 (d, 1H), 3.74 (d, 1H), 3.46 (d, 1H), 3.43-3.31 (m, 4H), 1.85 (d, 2H), 1.61-1.45 (m, 2H), 1.21 (s, 3H). LCMS: [M+H]+=486.

Example 595: 2-(6-{5-chloro-2-[(oxan-4-yl)amino]pyrimidin-4-yl}-1-oxo-2,3-dihydro-1H-isoindol-2-yl)-N-[(1S)-2-hydroxy-1-phenylethyl]-N-methylacetamide

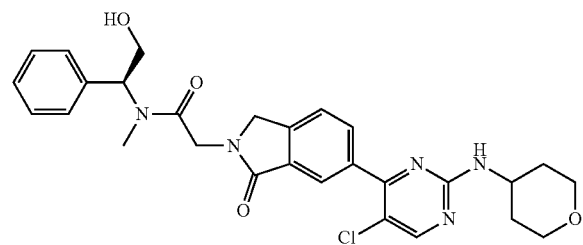 [SMILES: CN(C(=O)CN1Cc2ccc(-c3nc(NC4CCOCC4)ncc3Cl)cc2C1=O)[C@H](CO)c1ccccc1]

TBTU (67.0 mg, 0.209 mmol) was added to a mixture of 2-(6-{5-chloro-2-[(oxan-4-yl)amino]pyrimidin-4-yl}-1-oxo-2,3-dihydro-1H-isoindol-2-yl)acetic acid (Example 1, 80 mg, 0.199 mmol), (S)-2-(methylamino)-2-phenylethanol, HCl (41.0 mg, 0.218 mmol), and DIPEA (72.8 µl, 0.417 mmol) in DMF (2 mL) and the reaction was stirred at room temperature overnight. An aqueous solution of KHSO₄ (1 M, 10 mL) was added, and the crude product was extracted with EtOAc (15 mL). The organic extracts was successively washed with saturated aq. NaHCO₃ (10 mL) and brine (10 mL), dried (MgSO₄), filtered, and concentrated in vacuo. Purification by chromatography (SiO₂, 0-100% EtOAc in iso-hexanes) followed by preparative HPLC (acidic) gave the title compound (20 mg, 18.6%) as a colourless powder. 1H NMR (DMSO, 400 MHz) δ 8.46 (s, 1H), 8.06-7.96 (m, 2H), 7.76 (dd, 1H), 7.63 (s (br), 1H), 7.44-7.26 (m, 5H), 5.61 (t, 0.6H), 5.24 (s (br), 0.4H), 5.12 (t, 0.4H), 4.97 (s (br), 0.6H), 4.69-4.52 (m, 4H), 3.99-3.83 (m, 5H), 3.41 (m, 2H), 2.89 (s, 1.8H), 2.65 (s, 1.2H), 1.85 (m, 2H), 1.61-1.46 (m, 2H). LCMS: [M+H]+=536.

Example 596: 2-(6-{5-chloro-2-[(oxan-4-yl)amino]pyrimidin-4-yl}-1-oxo-2,3-dihydro-1H-isoindol-2-yl)-N-[(1S,2S)-2-hydroxy-1-phenylbutyl]acetamide

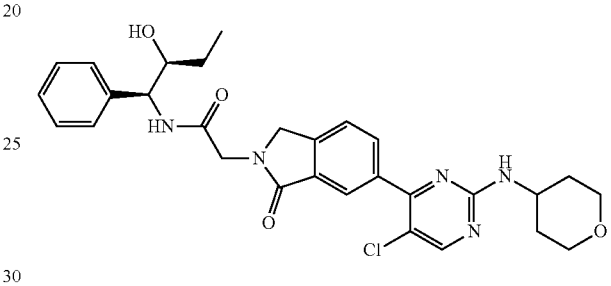

Prepared using a similar procedure to Example 583. In this case, the product was further purified by preparative HPLC (Waters, Basic (0.1% Ammonium Bicarbonate), Basic, Waters X-Bridge Prep-C18, 5 µm, 19×50 mm column, 35-65% MeCN in Water). The fractions were combined and the organics removed in vacuo. The aqueous was extracted with EtOAc (3×50 mL) and the combined organic phases were washed with brine (100 mL), dried (MgSO₄), filtered, and concentrated to give the title compound (78 mg, 44.5%) as a white solid. 1H NMR (DMSO-d6, 400 MHz) δ 8.55-8.49 (2H, m), 8.10-8.05 (1H, m), 8.03 (1H, dd), 7.79 (1H, d), 7.68 (1H, br. s), 7.43-7.34 (4H, m), 7.32-7.25 (1H, m), 4.88 (1H, dd), 4.85 (1H, d), 4.63 (2H, s), 4.43 (1H, d), 4.35 (1H, d), 4.04-3.87 (3H, m), 3.70-3.57 (1H, m), 3.47-3.41 (2H, m), 1.97-1.76 (2H, m), 1.65-1.52 (2H, m), 1.47-1.28 (2H, m), 0.93 (3H, t). LCMS: [M+H]+=550.

Example 597: 2-(6-(5-chloro-2-((oxan-4-yl)amino)pyrimidin-4-yl)-1-oxoisoindolin-2-yl)-N-((1S,2S)-1-(3-ethoxy-5-fluorophenyl)-2-hydroxypropyl)acetamide

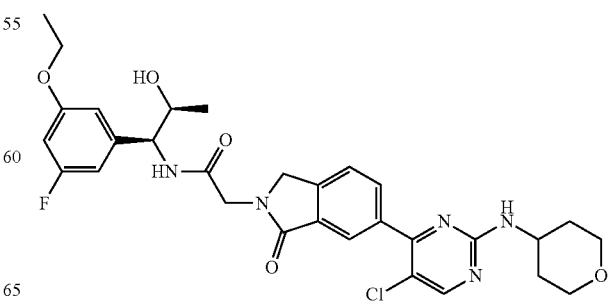

A stirred solution of 2-(6-{5-chloro-2-[(oxan-4-yl)amino]pyrimidin-4-yl}-1-oxo-2,3-dihydro-1H-isoindol-2-yl)acetic acid (Example 1, 70 mg, 0.170 mmol), (1S,2S)-1-amino-1-(3-ethoxy-5-fluorophenyl)propan-2-ol hydrochloride (47 mg, 0.188 mmol), and triethylamine (95 µl, 0.681 mmol) in DMF (1 ml) was treated with TBTU (66 mg, 0.206 mmol) and stirred at rt overnight. The mixture was diluted with EtOAc (20 ml), was washed successively with 1 M aq. KHSO₄ (10 ml), saturated aq. NaHCO₃ (10 ml), brine (2×10 ml), and then water (4×10 ml), dried (MgSO₄), filtered, and evaporated. The residue was purified on a 12 g graceresolv silica cartridge, using a gradient of 0-5% of EtOH/EtOAc as the eluent to give a glass, which was triturated with ether (2 ml) to give a solid. The solid was collected by filtration, washed with ether (2×1 ml) and dried under vacuum at 50° C. overnight to give a white powder (61 mg). LCMS showed this material to contain 5.7% of the dimeric ester product, so it was further purified by reversed phase preparative HPLC on a Waters XSelect CSH C18 OBD, 130 A, 5 µm, 19 mm×50 mm column, using a gradient of 20-50% of acetonitrile in water with 0.1% formic acid in both at 28 ml/min as the eluent. The clean fractions were pooled and concentrated to remove most of the acetonitrile. The residue was freeze-dried to give the title compound (34 mg, 33.0%) as a cream solid. 1H NMR (DMSO, 400 MHz) δ 8.51-8.40 (m, 2H), 8.04-8.00 (m, 1H), 8.00-7.93 (m, 1H), 7.73 (d, 1H), 7.62 (s, 1H), 6.79-6.70 (m, 2H), 6.70-6.61 (m, 1H), 4.88 (s, 1H), 4.76-4.65 (m, 1H), 4.58 (s, 2H), 4.42-4.27 (m, 2H), 4.01 (q, 2H), 3.97-3.76 (m, 4H), 3.44-3.37 (m, 2H), 1.84 (d, 2H), 1.59-1.43 (m, 2H), 1.31 (t, 3H), 1.01 (d, 3H). LCMS: [M+H]+=598.

Example 598: 2-(6-{5-chloro-2-[(oxan-4-yl)amino]pyrimidin-4-yl}-1-oxo-2,3-dihydro-1H-isoindol-2-yl)-N-[(1S)-2-hydroxy-1-[3-(methoxymethyl)phenyl]ethyl]acetamide

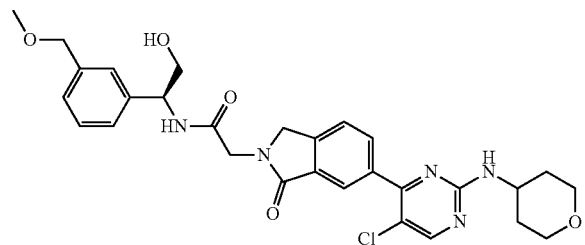 [SMILES: COCc1cccc([C@@H](CO)NC(=O)CN2Cc3ccc(-c4nc(NC5CCOCC5)ncc4Cl)cc3C2=O)c1]

Prepared using a similar procedure to Example 583. In this case, the product was further purified by preparative HPLC (Waters, Acidic (0.1% Formic acid), Acidic, Waters X-Select Prep-C18, 5 µm, 19×50 mm column, 20-50% MeCN in Water). 1H NMR (DMSO-d6, 400 MHz) δ 8.61 (d, 1H), 8.44 (s, 1H), 8.06-7.99 (m, 1H), 7.97 (dd, 1H), 7.73 (d, 1H), 7.64 (s, 1H), 7.33-7.22 (m, 3H), 7.20-7.16 (m, 1H), 5.04-4.93 (m, 1H), 4.87 (ddd, 1H), 4.58 (s, 2H), 4.39 (s, 2H), 4.31 (d, 1H), 4.26 (d, 1H), 4.00-3.79 (m, 3H), 3.64-3.51 (m, 2H), 3.44-3.35 (m, 2H), 3.29 (s, 3H), 1.92-1.77 (m, 2H), 1.60-1.44 (m, 2H). LCMS: [M+H]+=566.

Example 599: 6-{5-chloro-2-[(oxan-4-yl)amino]pyrimidin-4-yl}-2,3-bis(2-methoxyethyl)-2,3-dihydro-1H-isoindol-1-one

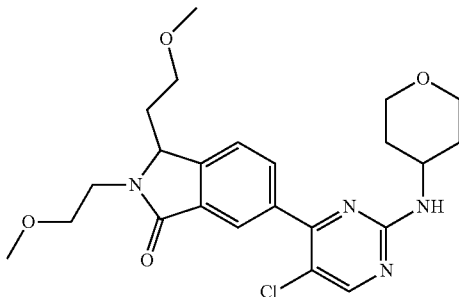 [SMILES: COCCC1c2ccc(-c3nc(NC4CCOCC4)ncc3Cl)cc2C(=O)N1CCOC]

Prepared from 6-{5-chloro-2-[(oxan-4-yl)amino]pyrimidin-4-yl}-2,3-dihydro-1H-isoindol-1-one (Example 128) using a similar procedure to Preparation 48. The product was separated from 6-{5-chloro-2-[(oxan-4-yl)amino]pyrimidin-4-yl}-2-(2-methoxyethyl)-2,3-dihydro-1H-isoindol-1-one (Example 103) by preparative HPLC (Waters, Acidic (0.1% Formic acid), Acidic, Waters X-Select Prep-C18, 5 µm, 19×50 mm column, 20-50% MeCN in Water). The product (36 mg, 25.8%) was obtained as a white solid. 1H NMR (400 MHz, CDCl₃) 8.38-8.23 (m, 2H), 7.98 (dd, 1H), 7.55 (dt, 1H), 5.17 (d, 1H), 4.93 (dd, 1H), 4.21 (dt, 1H), 4.12-4.02 (m, 1H), 3.99 (dt, 2H), 3.70-3.59 (m, 2H), 3.54 (td, 2H), 3.39 (ddd, 1H), 3.34 (s, 3H), 3.27-3.15 (m, 2H), 3.23 (s, 3H), 2.37 (dtd, 1H), 2.26-2.14 (m, 1H), 2.10-2.00 (m, 2H), 1.56 (dtd, 2H). LCMS: [M+H]+=461.

Example 600: N-tert-butyl-2-(5-{5-chloro-2-[(oxan-4-yl)amino]pyrimidin-4-yl}-1-(2-hydroxyethyl)-3-oxo-2,3-dihydro-1H-isoindol-2-yl)-N-methylacetamide

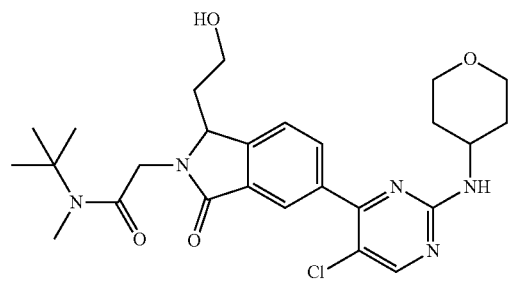 [SMILES: CN(C(=O)CN1C(=O)c2cc(-c3nc(NC4CCOCC4)ncc3Cl)ccc2C1CCO)C(C)(C)C]

Ethyl chloroformate (15.9 µl, 0.166 mmol) followed by isobutyl chloroformate (19.6 µl, 0.151 mmol) were added to a stirred solution of 2-(2-(2-(tert-butyl(methyl)amino)-2-oxoethyl)-5-(5-chloro-2-((oxan-4-yl)amino)pyrimidin-4-yl)-3-oxoisoindolin-1-yl)acetic acid (Preparation 331, 80 mg, 0.151 mmol) and N-methyl morpholine (17.4 µL, 0.158 mmL) in THF (5 mL). After 1 h the reaction mixture was filtered and the solid was washed with additional THF (10 mL). The combined filtrate and washings were cooled to 0° C. in an ice bath and then MeOH (5 mL) was added followed by addition of NaBH₄ (6.00 mg, 0.158 mmol). The resulting mixture was stirred at 0° C. for 2 h. The reaction mixture was concentrated, diluted with EtOAc (50 ml) and transferred into a separating funnel. The mixture was washed with NH₄Cl (20 ml), brine (20 ml), dried (MgSO₄), and concentrated to give a colourless oil. The crude product was purified by chromatography (SiO₂, 24 g column, 0-10% MeOH in DCM) to afford the title compound (56 mg, 71.2%) as a colourless solid. 1H NMR (DMSO-d6, 400 MHz) δ 8.45 (1H, s), 8.06-7.94 (2H, m), 7.78 (1H, d), 7.60 (1H, s), 4.81 (1H, t), 4.68-4.54 (2H, m), 4.10 (1H, d), 4.00-3.81 (3H, m), 3.39 (3H, dd), 2.95 (3H, s), 2.20 (1H, ddd), 1.99 (1H, dq), 1.85 (2H, d), 1.53 (2H, qd), 1.35 (9H, s). LC-MS: [M+H]+=516

Example 601:2-(5-{5-chloro-2-[(oxan-4-yl)amino]pyrimidin-4-yl}-1-(2-hydroxyethyl)-3-oxo-2,3-dihydro-1H-isoindol-2-yl)-N-(1-phenylcyclopropyl)acetamide

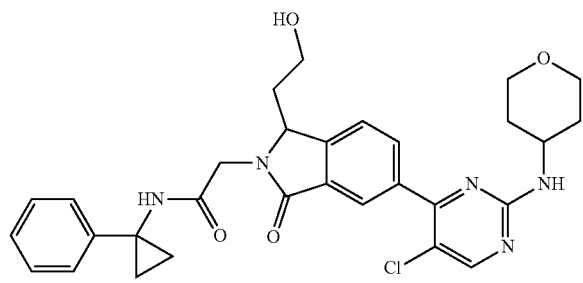 [SMILES: O=C(CN1C(=O)c2cc(-c3nc(NC4CCOCC4)ncc3Cl)ccc2C1CCO)NC1(c2ccccc2)CC1]

Isobutyl chloroformate (0.108 mL, 0.825 mmol) was added to a stirred solution of 2-(5-(5-chloro-2-((oxan-4-yl)amino)pyrimidin-4-yl)-3-oxo-2-(2-oxo-2-((1-phenylcyclopropyl)amino)ethyl)isoindolin-1-yl)acetic acid (Preparation 332, 480 mg, 0.750 mmol) and 4-methylmorpholine (0.091 mL, 0.825 mmol) in THF (25 mL) under nitrogen. The reaction was stirred at room temperature for 2.5 h. The reaction mixture was filtered and the solids were washed with THF (30 mL). MeOH (25 mL) was added to the filtrate, the solution was ice-cooled and sodium borohydride (31.2 mg, 0.825 mmol) was added. The reaction was allowed to warm slowly to room temperature and stirred overnight. A further portion of sodium borohydride (31.2 mg, 0.825 mmol) was added and the mixture stirred for a further 1 h. The reaction mixture was concentrated and diluted with EtOAc (100 ml). The organic phase was washed with NH₄Cl (100 ml), brine (100 ml) and dried (MgSO₄), and concentrated to give a yellow solid (470 mg). The crude product was purified by chromatography (40 g column, 0-5% MeOH in EtOAc) to afford the title compound (224 mg, 51.0%) as an off white solid. 1H NMR (DMSO-d6, 400 MHz) δ 8.88 (1H, s), 8.44 (1H, s), 8.03 (1H, dd), 7.99 (1H, dd), 7.77 (1H, d), 7.60 (1H, d), 7.31-7.22 (2H, m), 7.21-7.11 (3H, m), 4.86 (1H, dd), 4.67 (1H, t), 4.43 (1H, d), 3.99 (1H, d), 3.96-3.79 (3H, m), 3.46-3.33 (4H, m), 2.29-2.14 (1H, m), 2.06-1.94 (1H, m), 1.92-1.78 (2H, m), 1.59-1.45 (2H, m), 1.26-1.12 (4H, m). LC-MS: [M+H]+=562.

Example 602-604

Prepared using an analogous procedure to Example 601, from the appropriate carboxylic acid

| Example | Structure | Name | ¹H NMR (400 MHz) | MS: [M +H]⁺ |
|---|---|---|---|---|
| 602 | 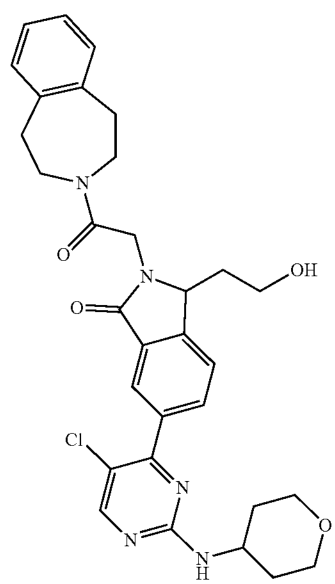 [SMILES: O=C(CN1C(=O)c2cc(-c3nc(NC4CCOCC4)ncc3Cl)ccc2C1CCO)N1CCc2ccccc2CC1] | 6-{5-chloro-2-[(oxan-4-yl)amino]pyrimidin-4-yl}-3-(2-hydroxyethyl)-2-[2-oxo-2-(2,3,4,5-tetrahydro-1H-3-benzazepin-3-yl)ethyl]-2,3-dihydro-1H-isoindol-1-one | 1H NMR (DMSO-d6, 400 MHz) δ 8.45 (1H, s), 8.06-7.96 (2H, m), 7.78 (1H, d, J = 7.9 Hz), 7.60 (1H, d, J = 7.7 Hz), 7.25-7.10 (4H, m), 4.88-4.76 (2H, m), 4.62 (1H, t, J = 4.8, 4.8 Hz), 4.23 (1H, d, J = 16.8 Hz), 4.00-3.80 (3H, m), 3.75-3.54 (4H, m), 3.44-3.34 (3H, m), 3.09-2.90 (2H, m), 2.84 (2H, q, J = 4.2, 4.0, 4.0 Hz), 2.19 (1H, ddd, J = 14.0, 11.2, 6.7 Hz), 2.09-1.95 (1H, m), 1.85 (2H, d, J = 12.6 Hz), 1.61-1.45 (2H, m). | 576 |

-continued

| Example | Structure | Name | ¹H NMR (400 MHz) | MS: [M +H]⁺ |
|---------|-----------|------|------------------|-------------|
| 603 | 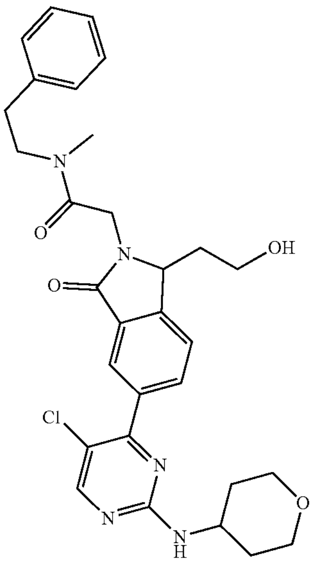 [SMILES: CN(CCc1ccccc1)C(=O)CN1C(=O)c2cc(-c3nc(NC4CCOCC4)ncc3Cl)ccc2C1CCO] | 2-(5-{5-chloro-2-[(oxan-4-yl)amino]pyrimidin-4-yl}-1-(2-hydroxyethyl)-3-oxo-2,3-dihydro-1H-isoindol-2-yl)-N-methyl-N-(2-phenylethyl)acetamide | 1H NMR (DMSO-d6, 400 MHz, 373 K) δ 8.40 (1H, s), 8.07 (1H, d), 8.02 (1H, dd), 7.79-7.71 (1H, m), 7.36-7.19 (5H, m), 7.11 (1H, d), 4.87-4.82 (1H, m), 4.67 (1H, d), 4.25-4.19 (1H, m), 4.12-3.93 (2H, m), 3.93-3.86 (2H, m), 3.67-3.56 (2H, m), 3.48-3.39 (4H, m), 2.24-2.11 (1H, m), 2.04-1.86 (4H, m), 1.66-1.54 (2H, m) (4 protons obscured by solvent peak). | 564 |
| 604 | 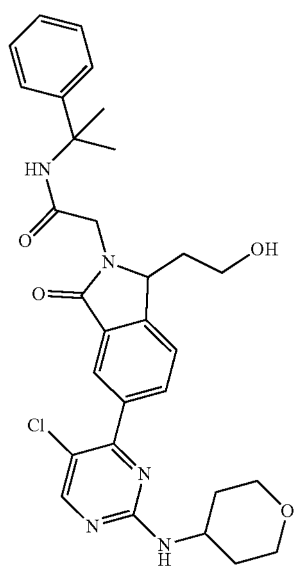 [SMILES: CC(C)(NC(=O)CN1C(=O)c2cc(-c3nc(NC4CCOCC4)ncc3Cl)ccc2C1CCO)c1ccccc1] | 2-(5-{5-chloro-2-[(oxan-4-yl)amino]pyrimidin-4-yl}-1-(2-hydroxyethyl)-3-oxo-2,3-dihydro-1H-isoindol-2-yl)-N-(2-phenylpropan-2-yl)acetamide | 1H NMR (DMSO-d6, 400 MHz) δ 8.44 (1H, s), 8.37 (1H, s), 8.01 (1H, dd), 7.98 (1H, dd), 7.75 (1H, d), 7.58 (1H, d), 7.37 (2H, dd), 7.29 (2H, dd), 7.22-7.12 (1H, m), 4.78 (1H, dd), 4.64 (1H, t), 4.50 (1H, d), 3.98 (1H, d), 3.90 (3H, dd), 3.46-3.34 (4H, m), 2.22 (1H, ddd), 1.99 (1H, dq), 1.85 (2H, d), 1.58 (6H, d), 1.57-1.47 (2H, m). | 564 |

Example 605: 2-[1-(2-aminoethyl)-5-{5-chloro-2-[(oxan-4-yl)amino]pyrimidin-4-yl}-3-oxo-2,3-dihydro-1H-isoindol-2-yl]-N-tert-butyl-N-methylacetamide

Example 606: 3-(2-aminoethyl)-6-{5-chloro-2-[(oxan-4-yl)amino]pyrimidin-4-yl}-2-[2-oxo-2-(2,3,4,5-tetrahydro-1H-3-benzazepin-3-yl)ethyl]-2,3-dihydro-1H-isoindol-1-one

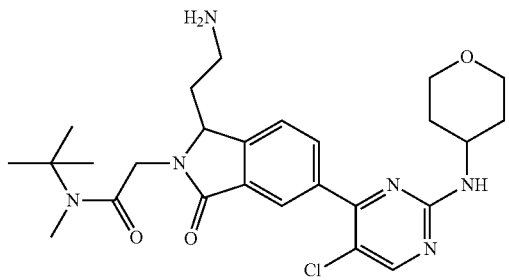 [SMILES: CN(C(=O)CN1C(=O)c2cc(-c3nc(NC4CCOCC4)ncc3Cl)ccc2C1CCN)C(C)(C)C]

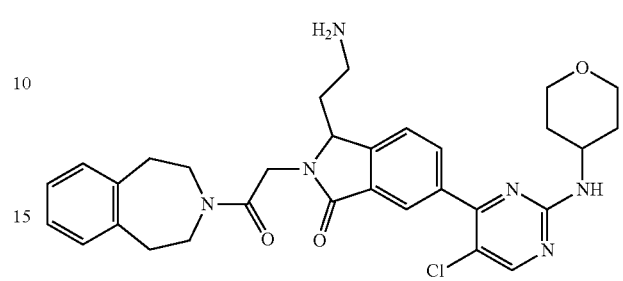

A stirred solution of N-(tert-butyl)-2-(5-(5-chloro-2-((oxan-4-yl)amino)pyrimidin-4-yl)-1-(2-(1,3-dioxoisoindolin-2-yl)ethyl)-3-oxoindolin-2-yl)-N-methylacetamide (Preparation 340, 20 mg, 0.031 mmol) in ethanol (1 ml) was treated with hydrazine hydrate (6.08 µl, 0.124 mmol) and the resulting white suspension was refluxed 1 h. The reaction mixture was cooled to room temperature and diluted with DCM (0.5 ml). The resulting homogenous solution was refluxed 5 h and the resulting white suspension was cooled to room temperature, then diluted further with DCM (0.5 ml). Further hydrazine hydrate (6.08 µl, 0.124 mmol) was added and the resulting homogenous solution refluxed overnight. The reaction mixture was concentrated under vacuum and the residue was purified by chromatography (SiO$_2$, 12 g column, 0 to 10% of MeOH in DCM) to afford the title compound (8 mg, 49.6%) as a colourless solid. 1H NMR (DMSO-d6, 400 MHz) δ 8.41 (1H, s), 8.06 (1H, dd), 8.02 (1H, dd), 7.75 (1H, dt), 7.22 (1H, d), 4.88 (1H, t), 4.67 (1H, d), 4.06 (1H, d), 4.02-3.93 (1H, m), 3.89 (2H, dt), 3.42 (2H, td), 2.98 (3H, s), 2.44-2.38 (1H, m), 2.20-2.08 (1H, m), 2.04-1.94 (1H, m), 1.90 (2H, d), 1.59 (2H, qd), 1.39 (9H, s). (3 protons overlapped with water peak). LC-MS: [M+H]+= 515

Hydrazine hydrate (60.1 µl, 0.741 mmol) was added to a stirred solution of 2-(2-(5-(5-chloro-2-((oxan-4-yl)amino)pyrimidin-4-yl)-2-(2-(4,5-dihydro-1H-benzo[d]azepin-3(2H)-yl)-2-oxoethyl)-3-oxoisoindolin-1-yl)ethyl)isoindoline-1,3-dione (Preparation 341, 55 mg, 0.074 mmol) in THF (1.5 mL) under nitrogen and the mixture heated to 65° C. and stirred overnight. The solvent was removed in vacuo and the crude product was adsorbed onto silica and purified by chromatography (SiO$_2$, 12 g column, 0-10% (0.7 M Ammonia/MeOH) in DCM) to afford the title compound (40 mg, 92%) as a white solid. 1H NMR (DMSO-d6, 400 MHz) δ 8.45 (1H, s), 8.05-7.97 (2H, m), 7.76 (1H, d), 7.61 (1H, d), 7.24-7.10 (4H, m), 4.91-4.73 (2H, m), 4.19 (1H, d), 3.91 (3H, dddd), 3.75-3.51 (4H, m), 3.43-3.35 (2H, m), 3.07-2.90 (2H, m), 2.89-2.77 (2H, m), 2.46 (1H, s), 2.27 (1H, s), 2.16-2.05 (1H, m), 2.04-1.91 (1H, m), 1.91-1.78 (2H, m), 1.60-1.45 (2H, m). LC-MS: [M+H]+=575.

Example 607-608

Prepared using an analogous procedure to Example 606, from the appropriate carboxylic acid

| Example | Structure | Name | $^1$H NMR (400 MHz) | MS: [M + H]$^+$ |
|---|---|---|---|---|
| 607 | 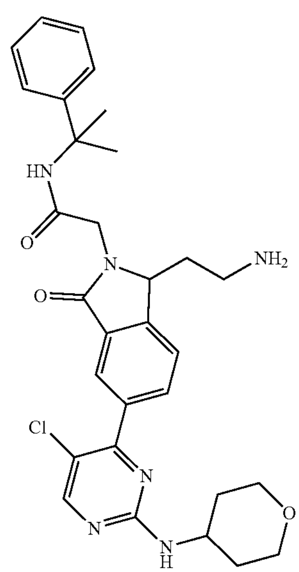 [SMILES: CC(C)(NC(=O)CN1C(=O)c2cc(-c3nc(NC4CCOCC4)ncc3Cl)ccc2C1CCN)c1ccccc1] | 2-[1-(2-aminoethyl)-5-{5-chloro-2-[(oxan-4-yl)amino]pyrimidin-4-yl}-3-oxo-2,3-dihydro-1H-isoindol-2-yl]-N-(2-phenylpropan-2-yl)acetamide | 1H NMR (DMSO-d6) δ: 8.43 (2H, d), 8.00 (1H, d), 7.97 (1H, dd), 7.74 (1H, d), 7.61 (1H, brs), 7.43-7.34 (2H, m), 7.33-7.24 (2H. m), 7.22-7.12 (1H, m), 4.84-4.72 (1H, m), 4.51 (1H, d), 4.02-3.80 (5H, m), 3.43-3.38 (1H, m), 2.47-2.42 (2H, m), 2.36-2.25 (2H, m), 2.17-2.08 (1H, m), 2.02-1.90 (1H, m), 1.90-1.78 (2H, m), 1.58 (6H, s), 1.56-1.46 (2H, m | 563 |

-continued

| Example | Structure | Name | ¹H NMR (400 MHz) | MS: [M + H]⁺ |
|---|---|---|---|---|
| 608 | 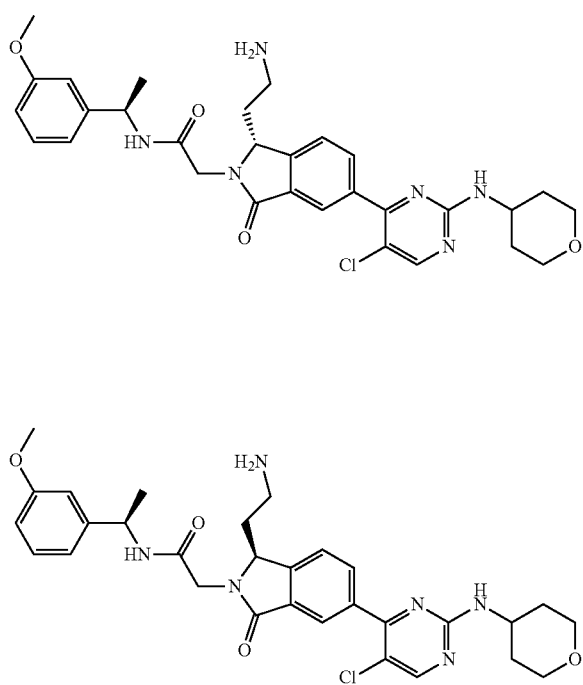 | 2[1-(2-aminoethyl)-5-{5-chloro-2-[(oxan-4-yl)amino]pyrimidin-4-yl}-3-oxo-2,3-dihydro-1H-isoindol-2-yl]-N-[(1S,2R)-2-hydroxy-2,3-dihydro-1H-inden-1-yl]acetamide | 1H NMR (DMSO-d6, 400 MHz) δ 8.46 (1H, s), 8.37-8.25 (1H, m), 8.12-7.94 (2H, m), 7.88-7.73 (1H, m), 7.62 (1H, s), 7.33-7.13 (4H, m), 5.29-5.14 (1H, m), 5.03-4.91 (1H, m), 4.60 (1H, d), 4.53-4.35 (1H, m), 4.23-4.03 (1H, m), 4.01-3.79 (3H, m), 3.45-3.38 (3H, m), 3.07 (1H, dd), 2.92-2.76 (1H, m), 2.42-2.15 (2H, m), 2.14-1.99(1H, m), 1.94-1.79 (2H, m), 1.62-1.43 (2H, m). 3 protons not observed, probably OH and NH2 under water or DMSO peak. | 577 |

Example 609 and 610: 2-[(1S)-1-(2-aminoethyl)-5-{5-chloro-2-[(oxan-4-yl)amino]pyrimidin-4-yl}-3-oxo-2,3-dihydro-1H-isoindol-2-yl]-N-[(1R)-1-(3-methoxyphenyl)ethyl]acetamide and 2-[(1R)-1-(2-aminoethyl)-5-{5-chloro-2-[(oxan-4-yl)amino]pyrimidin-4-yl}-3-oxo-2,3-dihydro-1H-isoindol-2-yl]-N-[(1R)-1-(3-methoxyphenyl)ethyl]acetamide The racemic mixture was prepared using a similar procedure to Example 606.

The diastereoisomers were separated by chiral preparative HPLC (Gilson, Diacel Chiralpak IA, 5 um, 20×250 mm 72:10:18 iso-hexane+0.2% TFA/EtOH/DCM) and each set of fractions (peak A and peak B) were combined separately and neutralised with NaHCO₃ (~40 mL). Most of the organic solvent was removed in vacuo and the residues were diluted with water (100 ml) and extracted with ethyl acetate (3×50 ml). The combined extracts were washed with brine (100 ml), dried (Na₂SO₄) and concentrated in vacuo. Each diastereoisomers were then further purified by chromatography (4 g column, 0-10% (0.7 M Ammonia/MeOH) in DCM) to afford 2-[(1S)-1-(2-aminoethyl)-5-{5-chloro-2-[(oxan-4-yl)amino]pyrimidin-4-yl}-3-oxo-2,3-dihydro-1H-isoindol-2-yl]-N-[(1R)-1-(3-methoxyphenyl)ethyl]acetamide (17 mg, 4.34%) (A) and 2-[(1R)-1-(2-aminoethyl)-5-{5-chloro-2-[(oxan-4-yl)amino]pyrimidin-4-yl}-3-oxo-2,3-dihydro-1H-isoindol-2-yl]-N-[(1R)-1-(3-methoxyphenyl)ethyl]acetamide (20 mg, 5.10%) (B) as white solids. (A): 1H NMR (DMSO-d6, 400 MHz) δ 8.60 (1H, d), 8.44 (1H, s), 8.06-7.92 (2H, m), 7.74 (1H, d), 7.61 (1H, s (br)), 7.24 (1H, t), 6.98-6.85 (2H, m), 6.80 (1H, ddd), 5.01-4.86 (1H, m), 4.82 (1H, dd), 4.48 (1H, d), 4.02-3.80 (4H, m), 3.76 (3H, s), 3.43-3.33 (2H, m), 2.46-2.35 (1H, m), 2.27 (1H, s), 2.17-2.02 (1H, m), 1.94 (1H, dt), 1.89-1.77 (2H, m), 1.63-1.43 (2H, m), 1.36 (3H, d) (NH2 signal was not observed and assumed to overlap with water or DMSO peaks). LCMS: [M+H]+=579. (B): 1H NMR (DMSO-d6, 400 MHz) δ 8.60 (1H, d), 8.44 (1H, s), 8.09-7.92 (2H, m), 7.75 (1H, d), 7.60 (1H, s (br)), 7.23 (1H, t), 6.97-6.84 (2H, m), 6.79 (1H, ddd), 5.00-4.81 (2H, m), 4.46 (1H, d), 4.03-3.80 (4H, m), 3.74 (3H, s), 3.48-3.34 (2H, m), 2.47-2.37 (1H, m), 2.36-2.21 (1H, m), 2.19-2.05 (1H, m), 2.03-1.89 (1H, m), 1.90-1.74 (2H, m), 1.61-1.43 (2H, m), 1.37 (3H, d) (NH2 signal was not observed and assumed to overlap with water or DMSO peaks). LCMS: [M+H]+=579.

Example 611, 612 and 613: 2-(5-{5-chloro-2-[(oxan-4-yl)amino]pyrimidin-4-yl}-1-methyl-3-oxo-2,3-dihydro-1H-isoindol-2-yl)-N-[(1S)-2-hydroxy-1-(3-methoxyphenyl)ethyl]acetamide

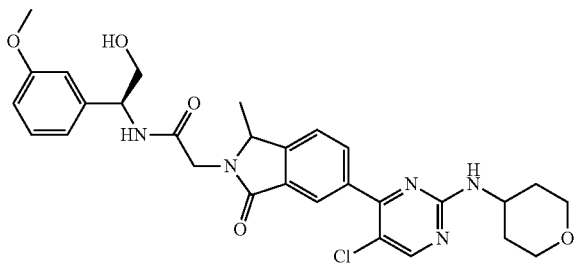

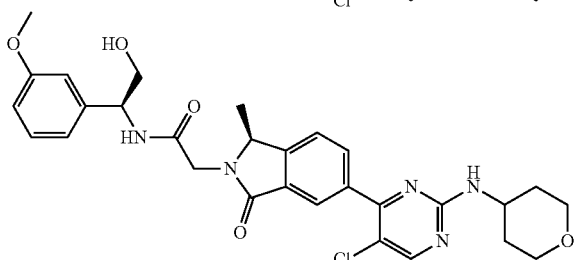

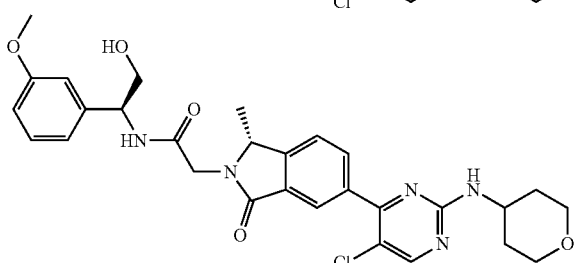

Prepared using a similar procedure to Example 590. 1H NMR (DMSO-d6) δ: 8.53 (d, 0.5H), 8.51 (d, 0.5H), 8.45 (s, 1H), 8.05-7.95 (m, 2H), 7.82-7.72 (m, 1H), 7.62 (s (br), 0.5H), 7.61 (s (br), 0.5H), 7.24 (m, 1H), 6.92-6.83 (m, 2H), 6.84-6.77 (m, 1H), 4.94-4.90 (m, 1H), 4.88-4.80 (m, 1H), 4.78 (q, 0.5H), 4.73 (q, 0.5H), 4.49 (d, 0.5H), 4.46 (d, 0.5H), 4.04 (d, 0.5H), 4.03 (d, 0.5H), 3.97-3.82 (m, 3H), 3.76 (s, 1.5H), 3.75 (s, 1.5H), 3.63-3.52 (m, 2H), 3.44-3.36 (m, 2H), 1.90-1.80 (m, 2H), 1.5-1.47 (m, 2H), 1.46 (d, 1.5H), 1.44 (d, 1.5H). LCMS: [M+H]+=566. The diastereoisomers were separated by preparative HPLC (Acquity, Basic, Waters X-Bridge Prep-C18, 5 μm, 19×50 mm column, 25% MeCN in 10 mM NH4HCO3). The fractions containing each stereoisomers were separately pooled and concentrated under vacuum. The residues were dissolved in DCM and water was added. The layers were separated through a phase separating cartridge and the organic layer was dried (MgSO4) and concentrated under vacuum to afford: 2-((S)-5-(5-chloro-2-((oxan-4-yl)amino)pyrimidin-4-yl)-1-methyl-3-oxoisoindolin-2-yl)-N—((S)-2-hydroxy-1-(3-methoxyphenyl)ethyl)acetamide (0.0073 g, 0.013 mmol, 6.72% yield) as a white solid. 1H NMR (DMSO-d6) δ: 8.51 (d, 1H), 8.45 (s, 1H), 8.03-7.96 (m, 2H), 7.78 (d, 1H), 7.61 (s (br), 1H), 7.23 (dd, 1H), 6.94-6.86 (m, 2H), 6.80 (ddd, 1H), 4.90 (t, 1H), 4.87-4.81 (m, 1H), 4.78 (q, 1H), 4.46 (d, 1H), 4.04 (d, 1H), 3.98-3.81 (m, 3H), 3.75 (s, 3H), 3.61-3.53 (m, 2H), 3.41-3.35 (m, 2H), 1.90-1.79 (m, 2H), 1.59-1.47 (m, 2H), 1.45 (d, 3H). LCMS: [M+H]+=566 and 2-((R)-5-(5-chloro-2-((oxan-4-yl)amino)pyrimidin-4-yl)-1-methyl-3-oxoisoindolin-2-yl)-N—((S)-2-hydroxy-1-(3-methoxyphenyl)ethyl)acetamide (0.0082 g, 0.014 mmol, 7.55% yield) as a white solid. 1H NMR (DMSO-d6) 5:8.54 (d, 1H), 8.45 (s, 1H), 8.03-8.01 (m, 1H), 7.99 (dd, 1H), 7.76 (d, 1H), 7.62 (s, 1H), 7.24 (dd, 1H), 6.94-6.87 (m, 2H), 6.86-6.78 (m, 1H), 4.92 (t, 1H), 4.90-4.79 (m, 1H), 4.72 (q, 1H), 4.49 (d, 1H), 4.03 (d, 1H), 3.97-3.83 (m, 3H), 3.76 (s, 3H), 3.62-3.53 (m, 2H), 3.44-3.35 (m, 2H), 1.90-1.77 (m, 2H), 1.60-1.47 (m, 2H), 1.44 (d, 3H). LCMS: [M+H]+=566

Example 614, 615 and 616: 2-(5-{5-chloro-2-[(oxan-4-yl)amino]pyrimidin-4-yl}-1-methyl-3-oxo-2,3-dihydro-1H-isoindol-2-yl)-N-[(1S)-2-hydroxy-1-(6-methoxypyridin-2-yl)ethyl]acetamide

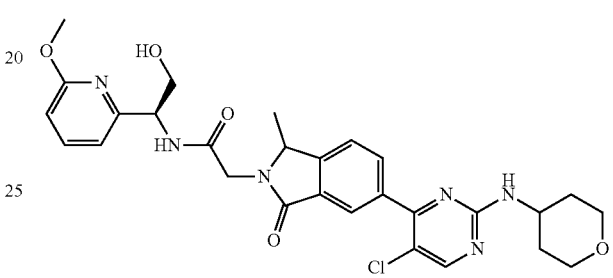

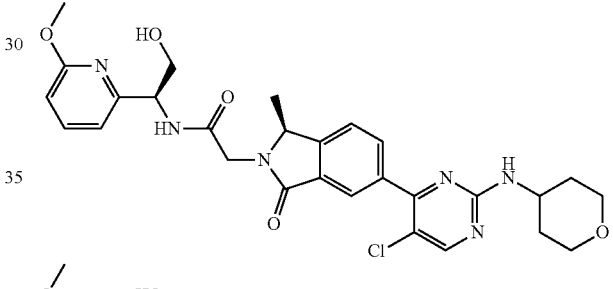

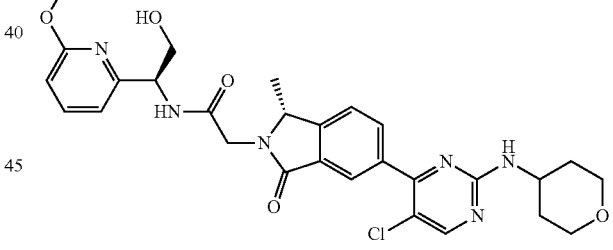

Prepared using a similar procedure to Example 590. 1H NMR (DMF-d7) δ: 8.47-8.35 (m, 2H), 8.04-7.95 (m, 2H), 7.77 (d, 0.5H), 7.76 (d, 0.5H), 7.66 (dd, 0.5H), 7.65 (dd, 0.5H), 7.61 (s (br), 0.5H), 7.60 (s (br), 0.5H), 6.95 (d, 0.5H), 6.94 (d, 0.5H), 6.68 (d, 0.5H), 6.67 (d, 0.5H), 4.91-4.70 (m, 3H), 4.52 (d, 0.5H), 4.49 (d, 0.5H), 4.13-4.05 (m, 1H), 3.97-3.83 (m, 3H), 3.82 (s, 1.5H), 3.81 (s, 1.5H), 3.78-3.62 (m, 2H), 3.42-3.33 (m, 2H), 1.88-1.79 (m, 2H), 1.58-1.42 (m, 5H). LCMS: [M+H]+=567.

The diastereoisomers were separated by preparative HPLC (Acquity, Basic, Waters X-Bridge Prep-C18, 5 μm, 19×50 mm column, 25% MeCN in 10 mM NH4HCO3). The fractions containing each stereoisomers were separately pooled and concentrated under vacuum. The residues were dissolved in DCM and water was added. The layers were separated through a phase separating cartridge and the organic layer was dried (MgSO4) and concentrated under vacuum to afford:

2-(5-{5-chloro-2-[(oxan-4-yl)amino]pyrimidin-4-yl}-1-methyl-3-oxo-2,3-dihydro-1H-isoindol-2-yl)-N-[(1S)-2-hydroxy-1-(6-methoxypyridin-2-yl)ethyl]acetamide (0.0089 g, 0.016 mmol, 7.79% yield). 1H NMR (DMSO-d6) δ: 8.45 (s, 1H), 8.41 (d, 1H), 8.03-7.97 (m, 2H), 7.79 (d, 1H), 7.66 (dd, 1H), 7.62 (s (br), 1H), 6.95 (d, 1H), 6.68 (d, 1H), 4.91-4.77 (m, 3H), 4.50 (d, 1H), 4.10 (d, 1H), 3.98-3.84 (m, 3H), 3.82 (s, 3H), 3.80-3.65 (m, 2H), 3.43-3.35 (m, 2H), 1.89-1.80 (m, 2H), 1.58-1.49 (m, 2H), 1.47 (d, 3H). LCMS: [M+H]+=567.

And 2-(5-{5-chloro-2-[(oxan-4-yl)amino]pyrimidin-4-yl}-1-methyl-3-oxo-2,3-dihydro-1H-isoindol-2-yl)-N-[(1S)-2-hydroxy-1-(6-methoxypyridin-2-yl)ethyl]acetamide (0.0108 g, 0.019 mmol, 9.45% yield). 1H NMR (DMSO-d6) δ: 8.45 (s, 1H), 8.43 (d, 1H), 8.02 (s, 1H), 7.99 (dd, 1H), 7.77 (d, 1H), 7.67 (dd, 1H), 7.62 (s, 1H), 6.97 (d, 1H), 6.69 (d, 1H), 4.90 (t, 1H), 4.88-4.82 (m, 1H), 4.76 (q, 1H), 4.52 (d, 1H), 4.10 (d, 1H), 3.98-3.84 (m, 3H), 3.83 (s, 3H), 3.79-3.62 (m, 2H), 3.42-3.34 (m, 2H), 1.92-1.78 (m, 2H), 1.60-1.47 (m, 2H), 1.45 (d, 3H). LCMS: [M+H]+=567.

Example 617: 6-(5-chloro-2-{[4-(dimethylamino)cyclohexyl]amino}pyrimidin-4-yl)-2-[2-oxo-2-(1,2,3,4-tetrahydroisoquinolin-2-yl)ethyl]-2,3-dihydro-1H-isoindol-1-one

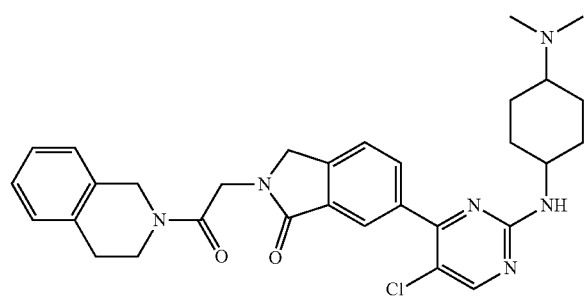 [SMILES: CN(C)C1CCC(Nc2ncc(Cl)c(-c3ccc4c(c3)C(=O)N(CC(=O)N3CCc5ccccc5C3)C4)n2)CC1]

A mixture of 6-(2,5-dichloropyrimidin-4-yl)-2-[2-oxo-2-(1,2,3,4-tetrahydroisoquinolin-2-yl)ethyl]-2,3-dihydro-1H-isoindol-1-one (Preparation 128, 0.1 g, 0.221 mmol), N1,N1-dimethylcyclohexane-1,4-diamine (0.047 g, 0.331 mmol) and DIPEA (0.077 ml, 0.441 mmol) in 1:1 dioxane:EtOH (1.5 mL) was heated at 80° C. overnight. The mixture was allowed to cool to room temperature and was concentrated under vacuum. The residue was diluted with EtOAc and transferred into a separating funnel. NaHCO3 was added and the crude product was extracted with EtOAc. The combined organic extracts were washed with brine, dried (MgSO4) and absorbed on silica. The crude product was purified by chromatography (SiO2, 12 g column, 0-10% of 1% NH3:MeOH in DCM) to afford the title compound (0.048 g, 38.5%) as a pale tan solid. 1H NMR (400 MHz, DMSO-d6, VT T=350K) δ: 8.39 (m, 1H), 8.08 (m, 1H), 8.01 (ddd, 1H), 7.73 (d, 1H), 7.21 (m, 4H), 7.13 (m, 1H), 4.69 (s (br), 2H), 4.61 (s, 2H), 4.57 (s, 2H), 3.95 (m, 0.7H), 3.63-3.81 (m, 2.5H), 2.91 (m (br), 2H), 2.23 (s, 3H), 2.22 (s, 3H), 2.13-2.21 (m, 1H), 2.00-2.07 (m, 1H), 1.72-1.89 (m, 3.5H), 1.48-1.66 (m, 2.5H), 1.24-1.39 (m, 2H). (note: rotamers were only partially resolved by VT as well as presence of stereoisomers, which made the assignment difficult: some signals may have been overintegrated/or overlapped with H2O/HDO signal resulting in higher hydrogen count.). LC-MS: [M+H]+=559.1.

Example 618: 6-(5-chloro-2-{[3-(hydroxymethyl)cyclohexyl]amino}pyrimidin-4-yl)-2-[2-oxo-2-(1,2,3,4-tetrahydroisoquinolin-2-yl)ethyl]-2,3-dihydro-1H-isoindol-1-one

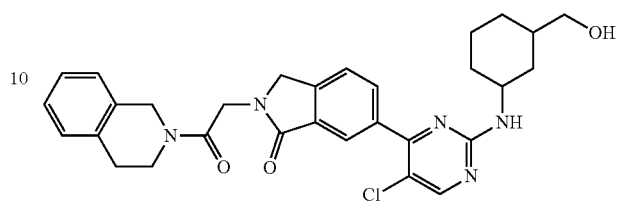

A mixture of 6-(2,5-dichloropyrimidin-4-yl)-2-[2-oxo-2-(1,2,3,4-tetrahydroisoquinolin-2-yl)ethyl]-2,3-dihydro-1H-isoindol-1-one (Preparation 128, 0.2 g, 0.441 mmol), (3-aminocyclohexyl)methanol (0.086 g, 0.662 mmol) and DIPEA (0.154 ml, 0.882 mmol) in 1:1 dioxane:EtOH (2 mL) was heated at 80° C. overnight. The mixture was allowed to cool to room temperature, then concentrated under vacuum. The residue was diluted with EtOAc and transferred into a separating funnel. Water was added and the crude product was extracted with EtOAc. The combined organic extracts were washed with brine, dried (MgSO4). The crude product obtained in experiment 1360-53 was combined and the mixture was absorbed on silica. The crude product was purified by chromatography on the Companion (24 g Grace column, DCM:MeOH gradient 100%-95%) to afford the title compound (0.078 g, 25.1%) as a pale tan solid. 1H NMR (400 MHz, DMSO-d6, VT T=350K) δ: 8.39 (s, 1H), 8.08 (d, 1H), 8.01 (dd, 1H), 7.73 (dd, 1H), 7.20 (m, 4H), 7.12 (d (br), 1H), 4.69 (m (br), 2H), 4.61 (s, 2H), 4.57 (s, 2H), 4.11 (t, 1H), 3.69-3.82 (m, 3H), 3.21-3.34 (m, 2H), 3.06 (s, 6H), 3.06 (m (br), 1H), 2.91 (m, (br), 2H), 1.93-2.08 (m, 2H), 1.67-1.82 (m, 2H), 1.45-1.56 (m, 1H), 1.16-1.39 (m, 3H), 0.93-1.04 (dd, 1H), 0.86 (ddd, 1H) (note: rotamers were only partially resolved by VT as well as presence of stereoisomers made the assignment difficult and some signals may have been overintegrated/or overlapped with H2O/HDO signal resulting in higher hydrogen count). LC-MS: [M+H]+=546

Example 619: (Trans) 6-(5-chloro-2-{[(3R,4S)-3-hydroxyoxan-4-yl]amino}pyrimidin-4-yl)-2-[2-oxo-2-(1,2,3,4-tetrahydroisoquinolin-2-yl)ethyl]-2,3-dihydro-1H-isoindol-1-one

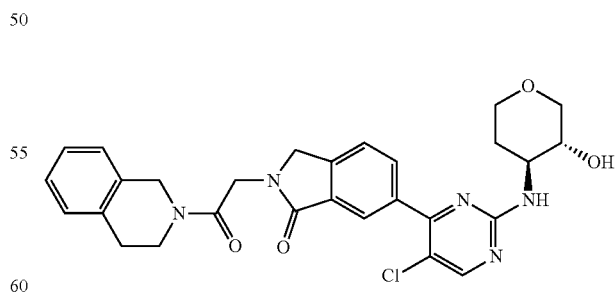

DIPEA (128 μl, 0.731 mmol) was added to a stirred suspension of 6-(2,5-dichloropyrimidin-4-yl)-2-[2-oxo-2-(1,2,3,4-tetrahydroisoquinolin-2-yl)ethyl]-2,3-dihydro-1H-isoindol-1-one (Preparation 128, 120 mg, 0.244 mmol) and (trans)-4-aminooxan-3-ol (racemic) (73.5 mg, 0.609 mmol) in dioxane/EtOH (1:1) (2.7 mL, 0.1 M). The reaction was heated to 80° C. and the resulting brown solution stirred overnight. A further portion of (trans)-4-aminooxan-3-ol (racemic) (14.26 mg, 0.122 mmol) was added and the reaction re-heated to 80° C. for 4 h. After cooling to room temperature, the solvent was removed in vacuo. The crude residue was partitioned between EtOAc (20 ml) and water (20 mL). The layers were separated and the aqueous phase was extracted with EtOAc (2×20 mL). The organic extracts were combined and washed with The 1M HCl (1×100 mL), brine (1×100 mL), dried (MgSO₄), filtered and concentrated in vacuo to afford a yellow/brown gum. The crude product was purified by chromatography (SiO₂, 12 g column, 0-5% MeOH in DCM) to afford the title compound (79 mg, 58.9%) as a pale yellow solid. 1H NMR (DMSO-d6, 400 MHz) δ 8.43 (1H, s), 8.07-8.02 (1H, m), 7.99 (1H, dd), 7.75 (1H, d), 7.50 (1H, s (br)), 7.26-7.17 (4H, m), 4.93 (1H, d), 4.76 (1H, s), 4.62 (1H, s), 4.59 (4H, m), 3.79 (4H, dq), 3.69 (1H, t), 3.49 (1H, tt), 3.29 (1H, s (br)), 3.04 (1H, dd), 2.93 (1H, t), 2.81 (1H, t), 1.94 (1H, br d), 1.49 (1H, qd). LC-MS: [M+H]+=534.

Example 620: (Cis) 6-(5-chloro-2-{[(3S,4S)-3-hydroxyoxan-4-yl]amino}pyrimidin-4-yl)-2-[2-oxo-2-(1,2,3,4-tetrahydroisoquinolin-2-yl)ethyl]-2,3-dihydro-1H-isoindol-1-one

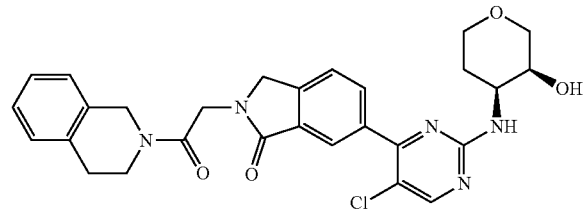 [SMILES: O=C(CN1Cc2ccc(-c3nc(N[C@H]4CCOC[C@H]4O)ncc3Cl)cc2C1=O)N1CCc2ccccc2C1]

Prepared using a similar procedure to Example 619 (HCl). 1H NMR (DMSO-d6, 400 MHz) δ 8.46 (1H, s), 8.08-8.01 (1H, m), 7.99 (1H, dd), 7.75 (1H, d), 7.29-7.13 (4H, m), 7.00 (1H, s), 4.89 (1H, d), 4.76 (1H, s), 4.64-4.55 (5H, m), 3.99 (1H, dddd), 3.85-3.65 (5H, m), 3.51-3.35 (2H, m), 2.93 (1H, t), 2.81 (1H, t), 1.98-1.84 (1H, m), 1.67-1.55 (1H, m). LC-MS: [M+H]+=534.

Example 621: (2R)-2-[6-(5-chloro-2-{[(2S)-1-hydroxypropan-2-yl]amino}pyrimidin-4-yl)-1-oxo-2,3-dihydro-1H-isoindol-2-yl]-N-[(1S)-2-hydroxy-1-(3-methoxyphenyl)ethyl]propanamide

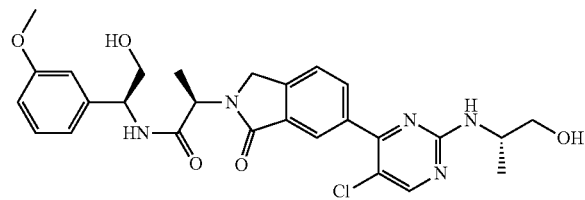 [SMILES: COc1cccc([C@@H](CO)NC(=O)[C@@H](C)N2Cc3ccc(-c4nc(N[C@@H](C)CO)ncc4Cl)cc3C2=O)c1]

A mixture of (R)-2-(6-(2,5-dichloropyrimidin-4-yl)-1-oxoisoindolin-2-yl)-N—((S)-2-hydroxy-1-(3-methoxyphenyl)ethyl)propanamide (Preparation 352, 120 mg, 0.215 mmol), DIPEA (94 μl, 0.539 mmol) and (S)-2-aminopropan-1-ol (24.27 mg, 0.323 mmol), in 1,4-dioxane (2 ml) was stirred and heated at 70° C. for 24 h, and then left at ambient temperature for 4 days. The solvent was removed under reduced pressure and the residue purified by chromatography (SiO₂, 4 g column, 100% EtOAc). Pure fractions were collected and the residue triturated diethyl ether affording a solid, which was collected by filtration (90 mg). The solid was dissolved in MeOH and loaded on a column packed with SCX. The column was washed with MeOH and the compound eluted with 1% NH3/MeOH. The resulting solution was concentrated under vacuum and the residue again triturated with ether. The resulting precipitate was filtered, dried, to afford the title compound (69 mg, 59.3%) as a colourless solid. 1H NMR (DMSO-d6) δ: 8.18 (1H, s), 8.06 (1H, s), 7.84 (1H, d), 7.7 (1H, d), 7.33 (1H, d), 7.15 (1H, d), 6.83 (2H, m), 6.72 (1H, d), 5.69 (1H, s), 5.06 (1H, m), 4.99 (1H, m), 4.72 (1H, d), 4.42 (1H, d), 4.09 (1H, m), 3.75-3.55 (7H, m), 1.44 (3H, d), 1.19 (3H, d). LC-MS: [M+H]+=540

Example 622: 2-[6-(5-chloro-2-{[(2S)-1-hydroxypropan-2-yl]amino}pyrimidin-4-yl)-1-oxo-2,3-dihydro-1H-isoindol-2-yl]-N-[(1S)-2-hydroxy-1-(3-methylphenyl)ethyl]acetamide

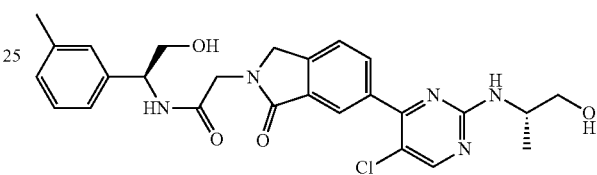

A mixture of (S)-2-(6-(2,5-dichloropyrimidin-4-yl)-1-oxoisoindolin-2-yl)-N-(2-hydroxy-1-(m-tolyl)ethyl)acetamide (Preparation 353, 0.18 g, 0.382 mmol), DIPEA (0.133 ml, 0.764 mmol), and (S)-2-aminopropan-1-ol (0.041 g, 0.542 mmol) in 1:1 EtOH:dioxane (3 mL) was heated at 80° C. under nitrogen overnight. The mixture was allowed to cool to room temperature and was concentrated under vacuum. The residue was partioned between DCM and water and the layers were separated through a phase separating cartridge. The organic layer was dried (MgSO4) and absorbed on silica. The crude product was purified by chromatography (SiO₂, 12 g column, 0-7% MeOH in DCM) to afford the title compound (0.016 g, 8.05%) as a white solid after trituration and evaporation from Et₂O. 1H NMR (DMSO-d6) δ: 8.53 (d, 1H), 8.43 (s, 1H), 8.04 (s, 1H), 7.99 (d, 1H), 7.74 (d, 1H), 7.29 (s, 1H), 7.21 (t, 1H), 7.16-7.02 (m, 3H), 4.91 (t, 1H), 4.84 (q, 1H), 4.69 (t, 1H), 4.59 (s, 2H), 4.32 (d, 1H), 4.26 (d, 1H), 3.98 (p, 1H), 3.56 (t, 2H), 3.52-3.43 (m, 1H), 3.34-3.29 (m, 1H), 2.30 (s, 3H), 1.14 (d, 3H). LC-MS: [M+H]+=510.

Example 623: 2-[6-(5-chloro-2-{[(2S)-1-hydroxypropan-2-yl]amino}pyrimidin-4-yl)-1-oxo-2,3-dihydro-1H-isoindol-2-yl]-N-[(1S)-1-(2-fluoro-5-methoxyphenyl)-2-hydroxyethyl]acetamide

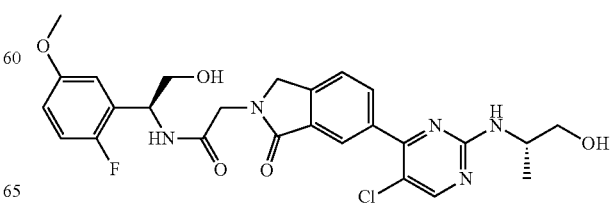

Prepared using a similar procedure to Example 617. 1H NMR (DMSO-d6) δ: 8.61 (d, 1H), 8.43 (s, 1H), 8.04 (s, 1H), 7.99 (d, 1H), 7.74 (d, 1H), 7.29 (s (br), 1H), 7.08 (dd, 1H), 6.97 (dd, 1H), 6.89-6.79 (m, 1H), 5.15 (td, 1H), 5.05 (t, 1H), 4.69 (t, 1H), 4.60 (s, 2H), 4.31 (s, 2H), 4.02-3.91 (m, 1H), 3.75 (s, 3H), 3.62-3.44 (m, 3H), 3.34-3.28 (m, 1H), 1.14 (d, 3H). LC-MS: [M+H]+=544.

Example 624:2-(6-{5-chloro-2-[(oxetan-3-yl)amino]pyrimidin-4-yl}-1-oxo-2,3-dihydro-1H-isoindol-2-yl)-N-[(1S)-2-hydroxy-1-(3-methylphenyl)ethyl]acetamide

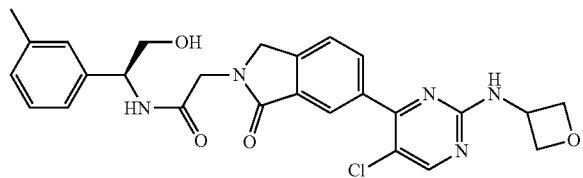 [SMILES: Cc1cccc([C@@H](CO)NC(=O)CN2Cc3ccc(-c4nc(NC5COC5)ncc4Cl)cc3C2=O)c1]

A mixture of (S)-2-(6-(2,5-dichloropyrimidin-4-yl)-1-oxoisoindolin-2-yl)-N-(2-hydroxy-1-(m-tolyl)ethyl)acetamide (Preparation 353, 0.17 g, 0.361 mmol), DIPEA (0.133 ml, 0.764 mmol), oxetan-3-amine (0.038 ml, 0.382 mmol) and DMF (0.2 mL) in 1:1 EtOH:dioxane (3 mL) was heated at 80° C. under nitrogen overnight. oxetan-3-amine (0.038 ml, 0.382 mmol) and DIPEA (0.067 ml, 0.382 mmol) were added and the mixture was stirred at 80° C. under nitrogen overnight. The mixture was diluted with EtOAc and transferred into a separating funnel. 1N HCl was added and the crude product was extracted with EtOAc, then DCM. Both extracts were washed with NaHCO₃, brine, then combined and concentrated under vacuum. The residue was suspended in DCM:MeOH and absorbed on silica. The crude product was purified by chromatography (SiO₂, 12 g column, 0-5% MeOH in DCM) to afford a white solid. The product was suspended in DCM and transferred into a separating funnel. 1N HCl was added and the product was extracted with DCM. The combined organic extracts were washed with NaHCO₃, then brine. The resulting fine suspension was heated, dried (MgSO₄) and concentrated under vacuum to afford the title compound (0.026 g, 13.27%) as a white solid. 1H NMR (DMSO-d6) δ: 8.53 (d, 1H), 8.48 (s, 1H), 8.34 (s (br), 1H), 8.04 (d, 1H), 7.98 (dd, 1H), 7.74 (d, 1H), 7.21 (dd, 1H), 7.15-7.01 (m, 3H), 4.97-4.88 (m, 2H), 4.83 (td, 1H), 4.76 (dd, 2H), 4.59 (s, 2H), 4.54 (dd, 2H), 4.32 (d, 1H), 4.26 (d, 1H), 3.61-3.51 (m, 2H), 2.29 (s, 3H). LC-MS: [M+H]+= 508.

Example 625: (2R)-2-[6-(5-chloro-2-{[trans-4-methoxycyclohexyl]amino}pyrimidin-4-yl)-1-oxo-2,3-dihydro-1H-isoindol-2-yl]-N-[(1S)-2-hydroxy-1-(3-methoxyphenyl)ethyl]propanamide

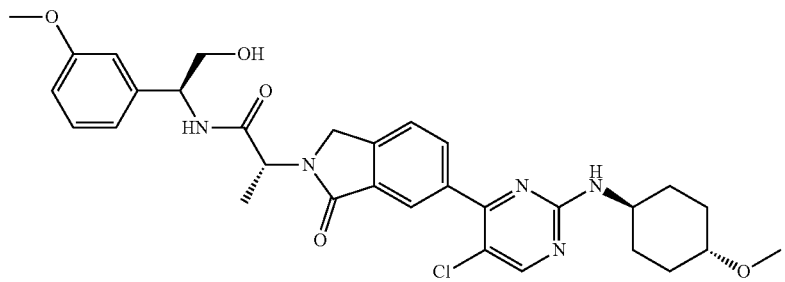

A mixture of (R)-2-(6-(2,5-dichloropyrimidin-4-yl)-1-oxoisoindolin-2-yl)-N—((S)-2-hydroxy-1-(3-methoxyphenyl)ethyl)propanamide (Preparation 352, 0.1 g, 0.199 mmol), DIPEA (0.070 ml, 0.399 mmol) and trans 4-methoxycyclohexanamine (0.039 g, 0.299 mmol) (0.024 ml, 0.232 mmol) in 1:1 EtOH:dioxane (1 mL) was heated at 80° C. under nitrogen overnight. The mixture was allowed to cool to room temperature and was concentrated under vacuum. The residue was dissolved in EtOAc and transferred into a separating funnel. 1N HCl was added and the crude product was extracted with EtOAc. The combined organic extracts were washed with NaHCO₃, brine, dried (MgSO4) and absorbed on silica. The crude product was purified by chromatography on the Companion (12 g column, 0-5% MeOH in DCM) to afford the title compound (0.06 g, 050.1%) as a white solid after trituration and evaporation from Et₂O. 1H NMR (DMSO-d6) δ: 8.56 (d, 1H), 8.44 (s (br), 1H), 8.07-8.01 (m, 1H), 7.97 (d, 1H), 7.75 (d, 1H), 7.52 (s (br), 1H), 7.28-7.19 (m, 1H), 6.93-6.85 (m, 2H), 6.83-6.76 (m, 1H), 5.06-4.96 (m, 1H), 4.89 (t, 1H), 4.85-4.80 (m, 1H), 4.77 (d, 1H), 4.60 (d, 1H), 3.75 (s, 3H), 3.73-3.63 (m, 1H), 3.57-3.52 (m, 2H), 3.23 (s, 3H), 3.16-3.06 (m, 1H), 2.05-1.91 (m, 4H), 1.45 (d, 3H), 1.39-1.13 (m, 4H). LCMS: [M+H]+=594.

Prepared using an analogous procedure to Example 625, from the appropriate dichloropyrimidine

| Example | Structure | Name | ¹H NMR (400 MHz) | MS: [M + H]⁺ |
|---|---|---|---|---|
| 626 | 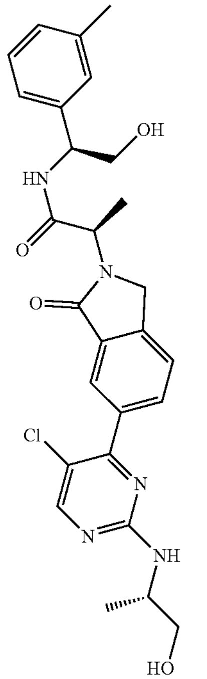 [SMILES: Cc1cccc([C@@H](CO)NC(=O)[C@@H](C)N2Cc3ccc(-c4nc(N[C@@H](C)CO)ncc4Cl)cc3C2=O)c1] | (2R)-2-[6-(5-chloro-2-{[(2S)-1-hydroxypropan-2-yl]amino}pyrimidin-4-yl)-1-oxo-2,3-dihydro-1H-isoindol-2-yl]-N-[(S)-2-hydroxy-1-(3-methylphenyl)ethyl]propanamide | 1H NMR (DMSO-d6) δ: 8.55 (d, 1H), 8.43 (s, 1H), 8.05 (s, 1H), 7.99 (d, 1H), 7.75 (d, 1H), 7.29 (s (br), 1H), 7.21 (dd, 1H), 7.14-7.00 (m, 3H), 5.01 (td, 1H), 4.88 (t, 1H), 4.84-4.67 (m, 3H), 4.60 (d, 1H), 4.04- 3.92 (m, 1H), 3.58-3.44 (m, 3H), 3.35-3.29 (m, 1H-overlapped with water peak), 2.30 (s, 3H), 1.43 (d, 3H), 1.14 (d, 3H). | 524 |
| 627 a) | 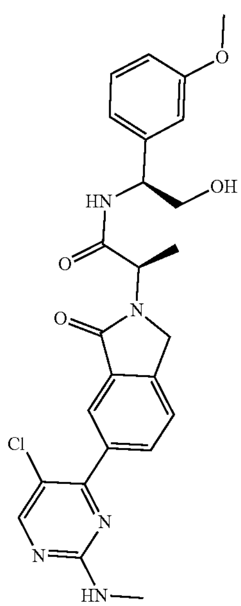 [SMILES: CNc1ncc(Cl)c(-c2ccc3c(c2)C(=O)N([C@H](C)C(=O)N[C@H](CO)c2cccc(OC)c2)C3)n1] | (2R)-2-{6-[5-chloro-2-(methylamino)pyrimidin-4-yl]-1-oxo-2,3-dihydro-1H-isoindol-2-yl}-N-[(1S)-2-hydroxy-1-(3-methoxyphenyl)ethyl]propanamide | 1H NMR (DMSO-d6) δ: 8.57 (d, 1H), 8.44 (s (br), 1H), 8.05 (s (br), 1H), 7.99 (s (br), 1H), 7.75 (d, 1H), 7.51 (s (br), 1H), 7.30-7.19 (m, 1H), 6.92-6.85 (m, 2H), 6.84-6.76 (m, 1H), 5.01 (td, 1H), 4.89 (t, 1H), 4.85-4.80 (m, 1H), 4.78 (d, 1H), 4.61 (d, 1H), 3.75 (s, 3H), 3.61-3.49 (m, 2H), 2.84 (d, 3H), 1.45 (d, 3H). | 496 |

| Example | Structure | Name | ¹H NMR (400 MHz) | MS: [M + H]⁺ |
|---|---|---|---|---|
| 628 | 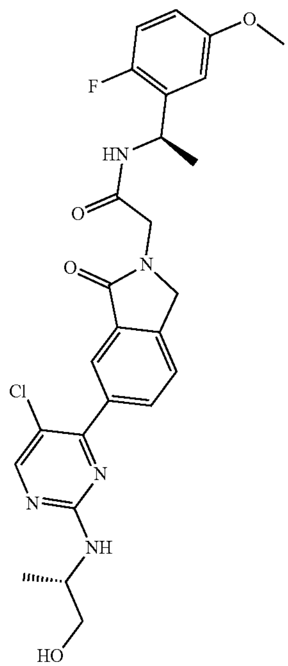 [SMILES: COc1ccc(F)c([C@@H](C)NC(=O)CN2Cc3ccc(-c4nc(N[C@@H](C)CO)ncc4Cl)cc3C2=O)c1] | 2-[6-(5-chloro-2-{[(2S)-1-hydroxypropan-2-yl]amino}pyrimidin-4-yl)-1-oxo-2,3-dihydro-1H-isoindol-2-yl]-N-[(R)-1-(2-fluoro-5-methoxyphenyl)ethyl]acetamide | 1H NMR (400 MHz, DMSO-d6) δ 8.67 (d, 1H), 8.43 (s, 1H), 8.06-7.98 (m, 2H), 7.74 (d, 1H), 7.29 (br. s, 1H), 7.09 (t, 1H), 6.95 (dd, 1H), 6.87-6.77 (m, 1H), 5.15 (p, 1H), 4.69 (t, 1H), 4.60 (s, 2H), 4.27 (s, 2H), 3.99 (td, 1H), 3.75 (s, 3H), 3.48 (dt, 1H), 3.34-3.30 (m, 1H), 1.36 (d, 3H), 1.14 (d, 3H). | 528 |
| 629 b) | | (2R)-2-[6-(5-chloro-2-{[trans-4-methoxycyclohexyl]amino}pyrimidin-4-yl)-1-oxo-2,3-dihydro-1H-isoindol-2-yl]-N-[(1S)-2-hydroxy-1-(3-methylphenyl)ethyl]propanamide | 1H NMR (DMSO, 400 MHz) δ 8.55 (1H, d), 8.44 (1H, s), 8.09-8.02 (1H, m), 7.74 (1H, d), 7.52 (1H, s), 7.21 (1H, t), 7.14-6.99 (3H, m), 5.00 (1H, q), 4.88 (1H, t), 4.84-4.72 (3H, m), 4.60 (1H, d), 3.77-3.60 (1H, m), 3.58-3.49 (2H, m), 3.23 (3H, s), 3.16-3.03 (1H, m), 2.30 (3H, s), 2.06-1.88 (4H, m), 1.43 (3H, d), 1.39-1.26 (2H, m), 1.26-1.13 (2H, m). | 578 | a) a sealed Biotage microwave tube was used in this case b) The reaction was carried out in dioxane at 80° C. in this case Example 630: (2R)-2-{6-[5-chloro-2-(methylamino)pyrimidin-4-yl]-1-oxo-2,3-dihydro-1H-isoindol-2-yl}-N-[(1S)-2-hydroxy-1-(3-methylphenyl)ethyl]propanamide

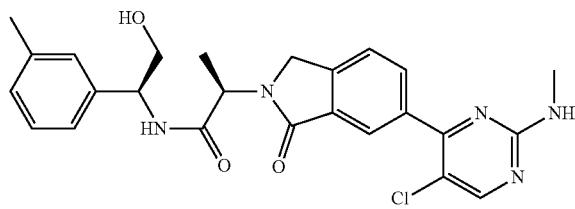 [SMILES: CNc1ncc(Cl)c(-c2ccc3c(c2)C(=O)N([C@H](C)C(=O)N[C@H](CO)c2cccc(C)c2)C3)n1]

A mixture of (R)-2-(6-(2,5-dichloropyrimidin-4-yl)-1-oxoisoindolin-2-yl)-N—((S)-2-hydroxy-1-(m-tolyl)ethyl) propanamide (2:1 mixture with (R)-2-(6-(2-((1H-benzo[d][1,2,3]triazol-1-yl)oxy)-5-chloropyrimidin-4-yl)-1-oxoisoindolin-2-yl)-N—((S)-2-hydroxy-1-(m-tolyl)ethyl) propanamid) (Preparation 355, 0.147 g, 0.284 mmol), DIPEA (0.198 ml, 1.136 mmol) and methylamine hydrochloride (38 mg, 0.568 mmol) in 1:1 EtOH:dioxane (1 mL) was heated at 80° C. in a sealed Biotage microwave vial for 3 days. The mixture were allowed to cool to room temperature and concentrated under vacuum. The residue was partioned between DCM and water and the layers were separated through a phase separating cartridge. The organic layer was dried (MgSO$_4$) and absorbed on silica. The crude products were purified by chromatography (SiO$_2$, 4 g column, 0-4% MeOH in DCM to afford the title compound (0.039 g, 28.3%) as a white solid after trituration and evaporation from Et$_2$O. 1H NMR (DMSO-d6) δ: 8.55 (d, 1H), 8.45 (s (br), 1H), 8.05 (s (br), 1H), 7.99 (s (br), 1H), 7.75 (d, 1H), 7.51 (s (br), 1H), 7.21 (dd, 1H), 7.14-7.01 (m, 3H), 5.01 (td, 1H), 4.88 (t, 1H), 4.83-4.76 (m, 1H), 4.77 (d, 1H), 4.60 (d, 1H), 3.66-3.47 (m, 2H), 2.84 (d, 3H), 2.30 (s, 3H), 1.43 (d, 3H). LC-MS: [M+H]+=480.

Example 631: (2R)-2-{6-[5-chloro-2-(methylamino)pyrimidin-4-yl]-1-oxo-2,3-dihydro-1H-isoindol-2-yl}-N-[(1S)-1-(3-fluoro-5-methylphenyl)-2-hydroxyethyl]propanamide

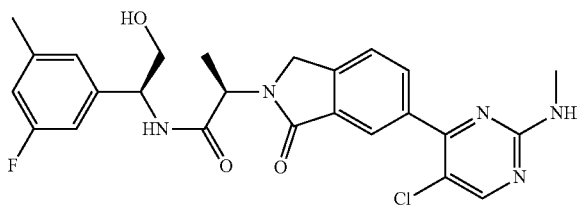 [SMILES: CNc1ncc(Cl)c(-c2ccc3c(c2)C(=O)N([C@H](C)C(=O)N[C@H](CO)c2cc(C)cc(F)c2)C3)n1]

Prepared using a similar procedure to Example 630. 1H NMR (DMSO-d6) δ: 8.57 (d, 1H), 8.45 (s (br), 1H), 8.05 (s (br), 1H), 7.99 (s (br), 1H), 7.75 (d, 1H), 7.51 (s (br), 1H), 6.93 (dd, 3H), 5.00 (td, 1H), 4.94 (t, 1H), 4.86-4.79 (m, 1H), 4.76 (d, 1H), 4.61 (d, 1H), 3.61-3.51 (m, 2H), 2.84 (d, 3H), 2.31 (s, 3H), 1.44 (d, 3H). LC-MS: [M+H]+=498.

Example 632:2-{6-[5-chloro-2-(methylamino)pyrimidin-4-yl]-1-oxo-2,3-dihydro-1H-isoindol-2-yl}-N-[(1S)-2-hydroxy-1-(3-methylphenyl)ethyl]acetamide

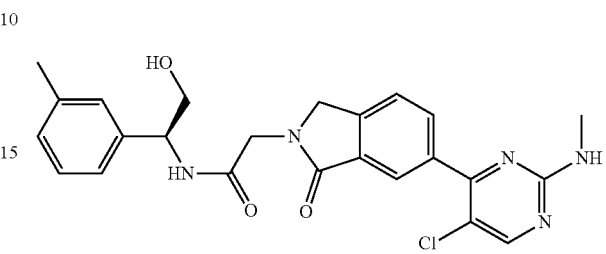

TBTU (96 mg, 0.300 mmol) was added to an ice-cooled stirred solution of 2-(6-(5-chloro-2-(methylamino)pyrimidin-4-yl)-1-oxoisoindolin-2-yl)acetic acid (Preparation 351, 70 mg, 0.200 mmol), (S)-2-amino-2-(m-tolyl)ethanol hydrochloride (41.3 mg, 0.220 mmol) and triethylamine (111 μl, 0.799 mmol) in DMF (2 mL). The mixture was stirred at room temperature for 16 h, then diluted with EtOAc (30 mL). The organic phase was washed with water (30 mL), NH$_4$Cl (30 mL) and brine (3×30 mL), dried (MgSO$_4$), filtered and concentrated in vacuo to give a white solid (100 mg). The crude product was purified by chromatography (SiO$_2$, 12 g column, 0-6% MeOH in DCM) to afford the title compound (31 mg, 32.1%) as a white solid. 1H NMR (DMSO-d6) δ 8.52 (1H, d), 8.44 (1H, s (br)), 8.12-7.88 (2H, m), 7.73 (1H, d), 7.50 (1H, s (br)), 7.20 (1H, t), 7.16-7.08 (2H, m), 7.08-7.02 (1H, m), 4.90 (1H, dd), 4.83 (1H, ddd), 4.59 (2H, s), 4.31 (1H, d), 4.26 (1H, d), 3.62-3.50 (2H, m), 2.83 (3H, d), 2.29 (3H, s). LC-MS: [M+H]+=466.

Example 633: 2-{6-[5-chloro-2-(methylamino)pyrimidin-4-yl]-1-oxo-2,3-dihydro-1H-isoindol-2-yl}-N-[(1S)-1-(3-fluoro-5-methylphenyl)-2-hydroxyethyl]acetamide

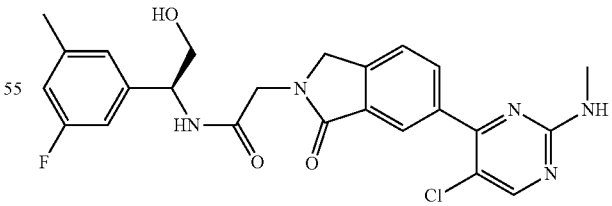

Prepared using a similar procedure to Example 632. 1H NMR (DMSO-d6) δ: 8.54 (1H, d), 8.44 (1H, s (br)), 8.11-7.91 (2H, m), 7.74 (1H, d), 7.50 (1H, s (br)), 7.05-6.81 (3H, m), 4.95 (1H, dd), 4.85 (1H, ddd), 4.59 (2H, s), 4.32 (1H, d), 4.27 (1H, d), 3.63-3.48 (2H, m), 2.83 (3H, d), 2.30 (3H, s). LC-MS: [M+H]+=484.

Example 634: (2R)-2-(6-{5-chloro-2-[(1-hydroxy-2-methylpropan-2-yl)amino]pyrimidin-4-yl}-1-oxo-2,3-dihydro-1H-isoindol-2-yl)-N-[(1S)-2-hydroxy-1-(3-methylphenyl)ethyl]propanamide

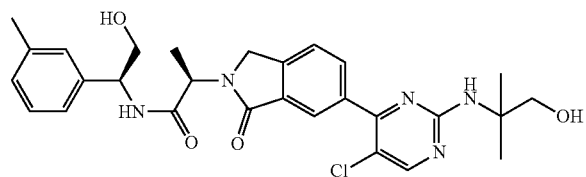 [SMILES: Cc1cccc([C@@H](CO)NC(=O)[C@@H](C)N2Cc3ccc(-c4nc(NC(C)(C)CO)ncc4Cl)cc3C2=O)c1]

A mixture of (R)-2-(6-(2,5-dichloropyrimidin-4-yl)-1-oxoisoindolin-2-yl)-N—((S)-2-hydroxy-1-(m-tolyl)ethyl)propanamide compound with (R)-2-(6-(2-((1H-benzo[d][1,2,3]triazol-1-yl)oxy)-5-chloropyrimidin-4-yl)-1-oxoisoindolin-2-yl)-N—((S)-2-hydroxy-1-(m-tolyl)ethyl)propanamide (5:1) (Preparation 355, 0.1 g, 0.206 mmol), DIPEA (0.108 ml, 0.618 mmol), and 2-amino-2-methylpropan-1-ol (0.037 g, 0.412 mmol) in 1:1 EtOH:dioxane (2 mL) was heated at 80° C. under nitrogen overnight. A further portion of 2-amino-2-methylpropan-1-ol (0.037 g, 0.412 mmol) and DIPEA (0.144 ml, 0.824 mmol) were added and the mixture was stirred at 80° C. overnight. The mixture was allowed to cool to room temperature and was concentrated under vacuum. The residue was partioned between EtOAc and NH4Cl and the layers were separated. The crude product was extracted with EtOAc and the combined organic extracts were washed with water, NaHCO₃, brine, dried (MgSO4) and absorbed on silica. The crude product was purified by chromatography on the Companion (12 g column, DCM:MeOH gradient 100%-95%) to afford the title compound (0.036 g, 32.5%) as a colourless solid after trituration and evaporation from Et₂O. 1H NMR (DMSO-d6) δ: 8.56 (d, 1H), 8.44 (s, 1H), 8.06 (d, 1H), 7.99 (dd, 1H), 7.76 (d, 1H), 7.21 (dd, 1H), 7.14-7.01 (m, 3H), 6.86 (s, 1H), 5.01 (q, 1H), 4.92-4.72 (m, 4H), 4.60 (d, 1H), 3.59-3.48 (m, 4H), 2.30 (s, 3H), 1.43 (d, 3H), 1.33 (s, 6H). LC-MS: [M+H]+=538.

Example 635: (2R)-2-[6-(5-chloro-2-{[trans-3-(hydroxymethyl)cyclobutyl]amino}pyrimidin-4-yl)-1-oxo-2,3-dihydro-1H-isoindol-2-yl]-N-[(1S)-2-hydroxy-1-(3-methylphenyl)ethyl]propanamide

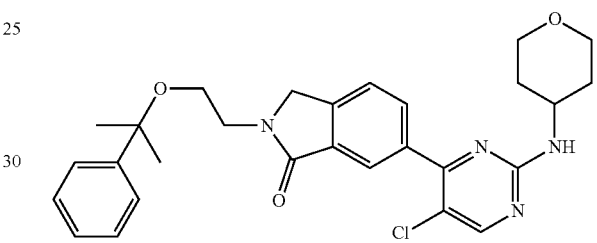

A mixture of (R)-2-(6-(2,5-dichloropyrimidin-4-yl)-1-oxoisoindolin-2-yl)-N—((S)-2-hydroxy-1-(m-tolyl)ethyl)propanamide compound with (R)-2-(6-(2-((1H-benzo[d][1,2,3]triazol-1-yl)oxy)-5-chloropyrimidin-4-yl)-1-oxoisoindolin-2-yl)-N—((S)-2-hydroxy-1-(m-tolyl)ethyl)propanamide (5:1) (Preparation 355, 0.1 g, 0.206 mmol), DIPEA (0.108 ml, 0.618 mmol), and trans-3-aminocyclobutyl)methanol hydrochloride (0.057 g, 0.412 mmol) in 1:1 EtOH:dioxane (2 mL) was heated at 80° C. under nitrogen overnight. The mixture was allowed to cool to room temperature and was concentrated under vacuum. The residue was partioned between EtOAc and NH4Cl and the layers were separated. The crude product was extracted with EtOAc and the combined organic extracts were washed with water, NaHCO₃, brine, dried (MgSO4) and absorbed on silica. The crude product was purified by chromatography on the Companion (12 g column, DCM:MeOH gradient 100%-95%) to afford the title compound (0.061 g, 0.111 mmol, 53.8% yield) as a colourless solid after trituration and evaporation from Et20. 1H NMR (DMSO-d6) δ: 8.56 (d, 1H), 8.43 (s, 1H), 8.04 (d, 1H), 7.97 (d, 1H), 7.91 (s (br), 1H), 7.75 (d, 1H), 7.21 (dd, 1H), 7.14-7.01 (m, 3H), 5.01 (q, 1H), 4.89 (t, 1H), 4.85-4.70 (m, 2H), 4.64-4.54 (m, 2H), 4.35 (m (br), 1H), 3.58-3.49 (m, 2H), 3.50-3.39 (m, 2H), 2.30 (s, 3H), 2.29-2.18 (m, 1H), 2.17-2.00 (m, 4H), 1.43 (d, 3H). LC-MS: [M+H]+=550.

Example 636: 6-{5-chloro-2-[(oxan-4-yl)amino]pyrimidin-4-yl}-2-{2-[(2-phenylpropan-2-yl)oxy]ethyl}-2,3-dihydro-1H-isoindol-1-one

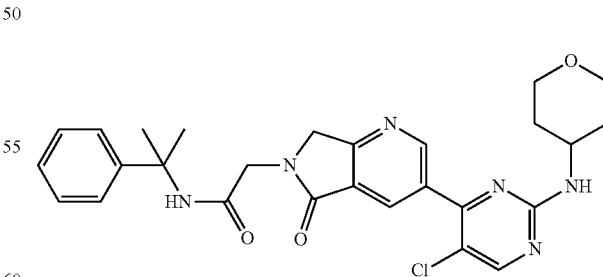

Prepared according to the procedure for Example 102. The reaction was carried out in refluxing EtOH:dioxane at 90° C. overnight. Further oxan-4-amine (0.050 mL, 0.483 mmol) and DIPEA (0.100 mL, 0.573 mmol) were added and the mixture was refluxed overnight. 1H NMR (DMSO-d6, 400 MHz) δ 8.45 (1H, s), 8.02-7.93 (2H, m), 7.74 (1H, d), 7.65-7.57 (1H, m), 7.35-7.27 (2H, m), 7.22-7.16 (3H, m), 4.61 (2H, s), 3.99-3.90 (1H, m), 3.86 (2H, d), 3.66 (2H, t), 3.42-3.33 (4H, m), 1.85 (2H, d), 1.58-1.49 (2H, m), 1.45 (6H, s). LC-MS: [M+H]+=507.

Example 637:2-(3-{5-chloro-2-[(oxan-4-yl)amino]pyrimidin-4-yl}-5-oxo-5H,6H,7H-pyrrolo[3,4-b]pyridin-6-yl)-N-(2-phenylpropan-2-yl)acetamide Triethylamine (0.075 mL, 0.538 mmol), 2-phenylpropan-2-amine (0.030 mL, 0.209 mmol) and T3P (50 wt % in EtOAc) (0.160 mL, 0.269 mmol) were added to a stirred solution of 2-(3-{5-chloro-2-[(oxan-4-yl)amino]pyrimidin-4-yl}-5-oxo-5H,6H,7H-pyrrolo[3,4-b]pyridin-6-yl)acetic acid (Preparation 9, 0.080 g, 0.178 mmol) in DMF (2.0 mL, 25.8 mmol) at room temperature. After 4.5 h further 2-phenylpropan-2-amine (15 µL), Triethylamine (35 µL) and T3P (50 wt % in EtOAc) (80 µL) were added. After a total of 6 h 45 min the reaction mixture was partitioned between DCM (20 mL) and water (20 mL). The layers were separated. NaHCO$_3$ (c.a. 5 mL) was added to the aqueous fraction and then the aqueous fraction was extracted with DCM (2×20 mL). The combined organic extracts were filtered through a phase separating cartridge and then concentrated under reduced pressure. The residue was purified by column chromatography (SiO2, 0-5% MeOH in DCM) to afford the crude product. The crude product was dissolved in DCM (5 mL) and washed with NH$_4$Cl (2×5 mL) and brine (2×5 mL). The organic fraction was filtered through a phase separating cartridge and concentrated under reduced pressure to afford the title compound as a white solid (13 mg, 13%). 1H NMR (DMSO-d6, 400 MHz) δ 9.10-9.02 (1H, m), 8.48 (1H, s), 8.42-8.36 (2H, m), 7.70 (1H, s (br)), 7.38-7.33 (2H, m), 7.29 (2H, dd), 7.22-7.11 (1H, m), 4.60 (2H, s), 4.29 (2H, s), 3.98-3.80 (3H, m), 3.38 (2H, t), 1.84 (2H, br. d), 1.58 (6H, s), 1.55-1.44 (2H, m). LC-MS: [M+H]+=521.

Example 638:3-{5-chloro-2-[(oxan-4-yl)amino]pyrimidin-4-yl}-6-[2-oxo-2-(2,3,4,5-tetrahydro-1H-3-benzazepin-3-yl)ethyl]-5H,6H,7H-pyrrolo[3,4-b]pyridin-5-one

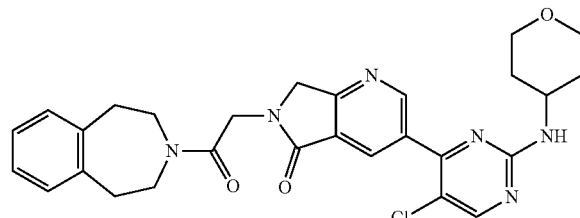

Triethylamine (0.080 mL, 0.574 mmol) followed by T3P (50 wt % in EtOAc) (0.180 mL, 0.302 mmol) were added to a stirred solution of 2-(3-{5-chloro-2-[(oxan-4-yl)amino]pyrimidin-4-yl}-5-oxo-5H,6H,7H-pyrrolo[3,4-b]pyridin-6-yl)acetic acid (Preparation 9, 0.081 g, 0.181 mmol) and 2,3,4,5-tetrahydro-1H-benzo[d]azepine (0.041 g, 0.279 mmol) in DMF (2.0 mL, 25.8 mmol) and the mixture was stirred for 1 h. Water (5 mL) was added and the mixture stirred at room temperature for 10 minutes. The resulting solid was filtered and washed with water (3×10 mL). The solid was dissolved in DCM (30 mL) and then washed with NH$_4$Cl (10 mL) and brine (3×10 mL). The organic fraction was filtered through a phase separating cartridge and concentrated under reduced pressure. The residue was dissolved in EtOAc (20 mL) and washed with brine (4×20 mL). The organic fraction was dried (MgSO$_4$), filtered and concentrated under reduced pressure to afford the title compound one (0.052 g, 51.9%) as a beige solid. 1H NMR (DMSO-d6, 400 MHz) δ 9.10 (1H, d), 8.49 (1H, s), 8.42 (1H, d), 7.72 (1H, br. s), 7.23-7.10 (4H, m), 4.60 (4H, d), 3.99-3.81 (3H, m), 3.70-3.55 (4H, m), 3.39 (2H, t), 3.02-2.93 (2H, m), 2.90-2.82 (2H, m), 1.85 (2H, br. d), 1.53 (2H, qd). LC-MS: [M+H]+=533

Example 639:2-(3-{5-chloro-2-[(oxan-4-yl)amino]pyrimidin-4-yl}-5-oxo-5H,6H,7H-pyrrolo[3,4-b]pyridin-6-yl)-N-[(1R)-1-(3-methoxyphenyl)ethyl]acetamide

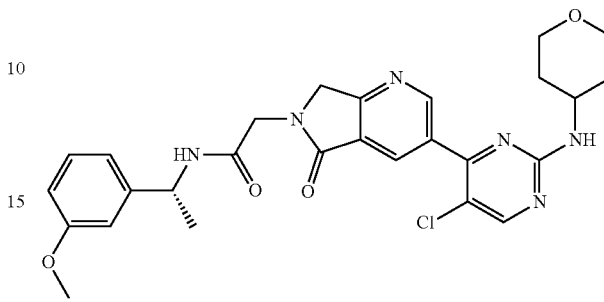

Prepared using a similar procedure to Example 638.
1H NMR (DMSO-d6, 400 MHz) δ 9.09 (1H, s), 8.58 (1H, d), 8.49 (1H, s), 8.40 (1H, d), 7.70 (1H, s), 7.27-7.20 (1H, m), 6.92-6.85 (2H, m), 6.83-6.74 (1H, m), 4.94 (1H, p), 4.64 (2H, s), 4.28 (2H, s), 3.93 (1H, br. s), 3.86 (2H, br. d), 3.75 (3H, s), 3.39-3.32 (2H, m), 1.84 (2H, br. d), 1.52 (2H, qd), 1.37 (3H, d).). LC-MS: [M+H]+=537.

Example 640:3-{5-chloro-2-[(oxan-4-yl)amino]pyrimidin-4-yl}-6-[2-(1-methyl-2,3,4,5-tetrahydro-1H-3-benzazepin-3-yl)-2-oxoethyl]-5H,6H,7H-pyrrolo[3,4-b]pyridin-5-one

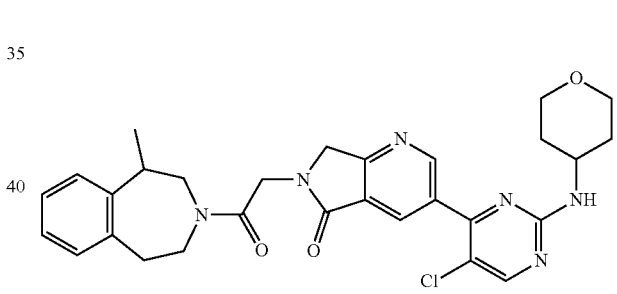

Triethylamine (0.080 mL, 0.574 mmol) followed by T3P (50 wt % in EtOAc) (0.180 mL, 0.302 mmol) were added to a stirred solution of 2-(3-{5-chloro-2-[(oxan-4-yl)amino]pyrimidin-4-yl}-5-oxo-5H,6H,7H-pyrrolo[3,4-b]pyridin-6-yl)acetic acid (Preparation 9, 0.085 g, 0.189 mmol) and 1-methyl-2,3,4,5-tetrahydro-1H-benzo[d]azepine (0.056 g, 0.278 mmol) in DMF (2.0 mL, 25.8 mmol) and the mixture was stirred for 2 h. Water (5 mL) was added and the mixture was stirred at room temperature for 5 minutes and then filtered and washed with water (3×10 mL). The filtrate was acidified with NH$_4$Cl and extracted with DCM (3×50 mL). The solid was dissolved with DCM and combined with the other DCM extracts. The combined DCM fractions were washed with brine (3×50 mL), filtered through a phase separating cartridge and then concentrated under reduced pressure. The residue was dissolved in EtOAc (30 mL) and washed with brine (5×20 mL) then dried (MgSO$_4$), filtered and concentrated under reduced pressure to leave a yellow gum (78 mg). The product was purified by chromatography (SiO$_2$, 12 g column, 0-100% (3% MeOH in DCM) in DCM), then further purified by reversed phase preparative HPLC (Waters XSelect CSH C18 OBD, 130A, 5 µm, 19 mm×50 mm column, using a gradient of 25 to 55% of acetonitrile in water with 0.1% formic acid in both at 28 ml/min as eluent). The clean fractions were pooled and concentrated to remove most of the acetonitrile. The residue was freeze-dried to give the title compound (32.3 mg, 70.3%) as a white solid. 1H NMR (DMSO-d6, 400 MHz, 90° C.) δ 9.12 (1H, d), 8.44 (1H, s), 8.40 (1H, d), 7.29 (1H, d), 7.19-7.08 (4H, m), 4.60-4.40 (4H, m), 4.03-3.48 (8H, m), 3.42 (2H, td), 3.24 (2H, s (br)), 1.93-1.86 (2H, m), 1.67-1.53 (2H, m), 1.29 (3H, s (br)). LC-MS: [M+H]+=547.

Example 641: 2-(3-{5-chloro-2-[(oxan-4-yl)amino]pyrimidin-4-yl}-5-oxo-5H,6H,7H-pyrrolo[3,4-b]pyridin-6-yl)-N-[(1S)-2-hydroxy-1-(3-methoxyphenyl)ethyl]acetamide

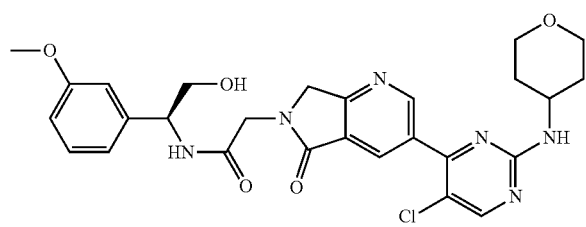 [SMILES: COc1cccc([C@@H](CO)NC(=O)CN2Cc3ncc(-c4nc(NC5CCOCC5)ncc4Cl)cc3C2=O)c1]

Prepared using a similar procedure to Example 95. 1H NMR (DMSO-d6, 400 MHz) δ 9.09 (1H, s), 8.55 (1H, d), 8.49 (1H, s), 8.41 (1H, d), 7.71 (1H, s (br)), 7.23 (1H, t), 6.93-6.85 (2H, m), 6.81 (1H, ddd), 4.92 (1H, t), 4.86 (1H, q), 4.64 (2H, s), 4.39-4.23 (2H, m), 3.99-3.80 (3H, m), 3.74 (3H, s), 3.62-3.51 (2H, m), 3.39-3.34 (2H, m), 1.84 (2H, d), 1.52 (2H, qd). LC-MS: [M+H]+=553.

Example 642: 2-(3-{5-chloro-2-[(oxan-4-yl)amino]pyrimidin-4-yl}-5-oxo-5H,6H,7H-pyrrolo[3,4-b]pyridin-6-yl)-N-[(1S)-1-[3-(difluoromethoxy)phenyl]-2-hydroxyethyl]acetamide

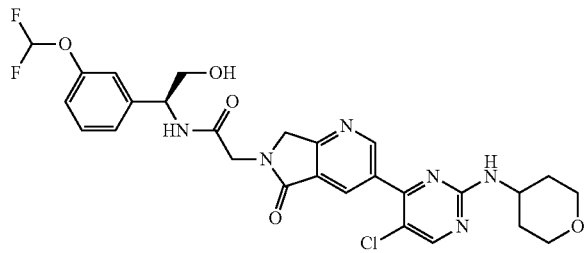

Prepared using a similar procedure to Example 95. 1H NMR (DMSO-d6, 400 MHz) δ 9.09 (1H, s), 8.61 (1H, d), 8.49 (1H, s), 8.41 (1H, d), 7.71 (1H, br. s), 7.43-7.33 (1H, m), 7.26-7.16 (2H, m), 7.14 (1H, d), 7.08-7.01 (1H, m), 4.98 (1H, t), 4.90 (1H, q), 4.64 (2H, s), 4.40-4.22 (2H, m), 3.99-3.80 (3H, m), 3.64-3.53 (2H, m), 3.39-3.34 (2H, m), 1.84 (2H, br d), 1.52 (2H, qd). LCMS: [M+H]+=589.

Example 643: 2-(3-{5-chloro-2-[(oxan-4-yl)amino]pyrimidin-4-yl}-5-oxo-5H,6H,7H-pyrrolo[3,4-b]pyridin-6-yl)-N-[(1S,2R)-2-hydroxy-6-methoxy-2,3-dihydro-1H-inden-1-yl]acetamide

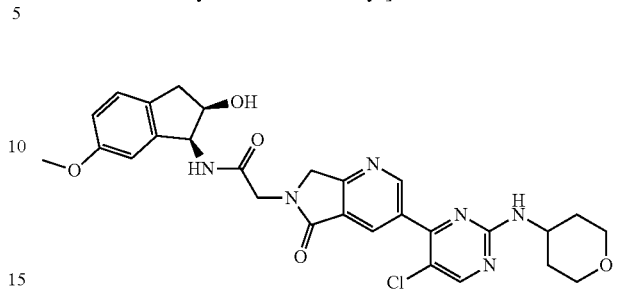

Prepared using a similar procedure to Example 407. 1H NMR (DMSO, 400 MHz) δ 9.11 (1H, d), 8.50 (1H, s), 8.43 (1H, d), 8.29 (1H, d), 7.72 (1H, s), 7.14 (1H, d), 6.81-6.75 (2H, m), 5.19 (1H, dd), 5.04 (1H, d), 4.72 (2H, s), 4.47-4.40 (3H, m), 3.99-3.83 (3H, m), 3.74 (3H, s), 3.43-3.35 (2H, m), 2.98 (1H, dd), 2.74 (1H, d), 1.90-1.80 (2H, m), 1.60-1.47 (2H, m). LCMS: [M+H]+=603.

Example 644: 2-(3-{5-chloro-2-[(oxan-4-yl)amino]pyrimidin-4-yl}-5-oxo-5H,6H,7H-pyrrolo[3,4-b]pyridin-6-yl)-N-[(1S)-2-hydroxy-1-(3-methylphenyl)ethyl]acetamide

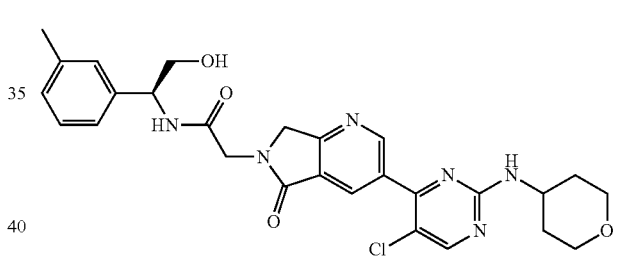

HATU (77 mg, 0.202 mmol) was added to an ice-cooled solution of 2-(3-{5-chloro-2-[(oxan-4-yl)amino]pyrimidin-4-yl}-5-oxo-5H,6H,7H-pyrrolo[3,4-b]pyridin-6-yl)acetic acid (Preparation 9, 68 mg, 0.135 mmol), (S)-2-amino-2-(m-tolyl)ethanol hydrochloride (27.8 mg, 0.148 mmol) and triethylamine (56.3 μl, 0.404 mmol) in DMF (1.4 mL) under nitrogen. The mixture was stirred at room temperature for 1.5 h, then diluted with EtOAc (30 mL). The organic phase was washed with water (30 mL) and brine (3×30 mL), dried (MgSO4), filtered and concentrated in vacuo to give a yellow residue. The crude product was purified by chromatography (SiO2, 24 g column, 0-10% MeOH in DCM) to afford a beige solid (58 mg). The product was loaded onto a column packed with SCX (0.5 g) in MeOH/DCM. The column was washed with MeOH and then the product was eluted with 0.7 M ammonia in MeOH. The resulting mixture was concentrated in vacuo to afford the title compound (50 mg, 68.4%) as a beige solid (1458-13-5c). 1H NMR (DMSO-d6, 400 MHz) δ 9.09 (1H, s), 8.54 (1H, d), 8.49 (1H, s), 8.41 (1H, d), 7.71 (1H, s (br)), 7.21 (1H, t), 7.15-7.08 (2H, m), 7.08-7.03 (1H, m), 4.91 (1H, t), 4.88-4.80 (1H, m), 4.64 (2H, s), 4.34 (1H, d), 4.29 (1H, d), 4.02-3.77 (3H, m), 3.63-3.49 (2H, m), 3.44-3.33 (2H, m), 2.29 (3H, s), 1.90-1.78 (2H, m), 1.61-1.45 (2H, m). LCMS: [M+H]+=537.

Example 645: (2R)-2-(3-{5-chloro-2-[(oxan-4-yl)amino]pyrimidin-4-yl}-5-oxo-5H,6H,7H-pyrrolo[3,4-b]pyridin-6-yl)-N-[(1S)-1-(3-ethylphenyl)-2-hydroxyethyl]propanamide

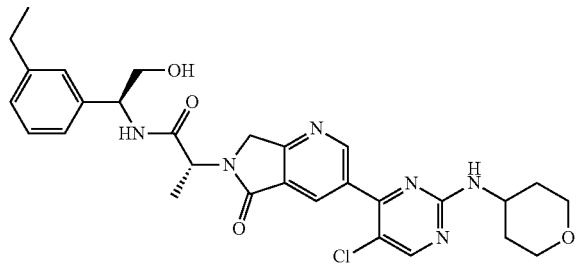 [SMILES: CCc1cccc([C@@H](CO)NC(=O)[C@@H](C)N2Cc3ncc(-c4nc(NC5CCOCC5)ncc4Cl)cc3C2=O)c1]

TBTU (0.056 g, 0.176 mmol) was added to a mixture of (R)-2-(3-(5-chloro-2-((oxan-4-yl)amino)pyrimidin-4-yl)-5-oxo-5H-pyrrolo[3,4-b]pyridin-6(7H)-yl)propanoic acid (Preparation 416, 0.07 g, 0.168 mmol), (S)-2-amino-2-(3-ethylphenyl)ethanol hydrochloride (0.035 g, 0.176 mmol) and DIPEA (0.091 ml, 0.519 mmol) in DMF (1 mL) and the mixture was stirred for 45 minutes. The mixture was diluted with EtOAc and transferred into a separating funnel. NH₄C was added and the product was extracted with EtOAc. The combined organic extracts were washed with water, NaHCO₃, brine, dried (MgSO₄) and absorbed on silica. The crude product was purified by chromatography (SiO₂, 12 g column, 0-5% MeOH in DCM) to afford the title compound (0.046 g, 0.078 mmol, 46.6%) as a white solid after trituation and evaporation from Et₂O. 1H NMR (DMSO-d6) δ: 9.09 (s, 1H), 8.56 (d, 1H), 8.49 (s (br), 1H), 8.41 (d, 1H), 7.71 (s (br), 1H), 7.22 (dd, 1H), 7.17-7.03 (m, 3H), 5.04 (td, 1H), 4.89 (t, 1H), 4.86-4.79 (m, 1H), 4.79 (d, 1H), 4.67 (d, 1H), 4.01-3.80 (m, 3H), 3.61-3.47 (m, 2H), 3.42-3.35 (m, 2H), 2.59 (q, 2H), 1.92-1.77 (m, 2H), 1.64-1.49 (m, 2H), 1.46 (d, 3H), 1.18 (t, 3H). LCMS: [M+H]+=565.

Examples 646-649

Prepared using an analogous procedure to Example 645

| Example | Structure | Name | ¹H NMR (400 MHz) | MS: [M + H]⁺ |
|---|---|---|---|---|
| 646 | 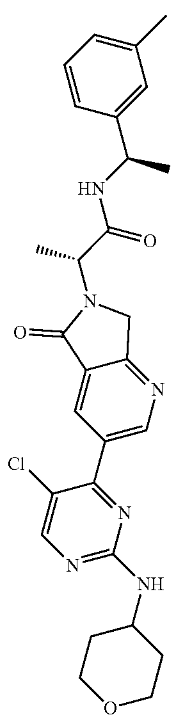 [SMILES: Cc1cccc([C@@H](C)NC(=O)[C@@H](C)N2Cc3ncc(-c4nc(NC5CCOCC5)ncc4Cl)cc3C2=O)c1] | (2R)-2-(3-{5-chloro-2-[(oxan-4-yl)amino]pyrimidin-4-yl}-5-oxo-5H,6H,7H-pyrrolo[3,4-b]pyridin-6-yl)-N-[(1R)-1-(3-methylphenyl)ethyl] propanamide | 1H NMR (400 MHz, DMSO-d6) δ 9.10 (s, 1H), 8.60 (d, 1H), 8.50 (s, 1H), 8.41 (d, 1H), 7.72 (br. s, 1H), 7.22 (t, 1H), 7.14-6.98 (m, 3H), 4.96 (q, 1H), 4.88 (t, 1H), 4.78-4.67 (m, 2H), 4.04-3.75 (m, 3H), 3.43-3.35 (m, 2H), 2.30 (s, 3H), 1.85 (d, 2H), 1.61-1.43 (d, 4H), 1.35 (d, 3H) (1 proton was not observed and was possibly overlapped with water or DMSO peaks). | 535 |

| Example | Structure | Name | ¹H NMR (400 MHz) | MS: [M + H]⁺ |
|---|---|---|---|---|
| 647 | 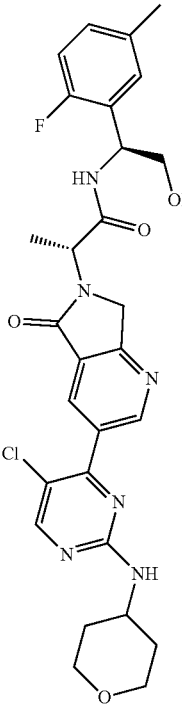 | (2R)-2-(3-{5-chloro-2-[(oxan-4-yl)amino]pyrimidin-4-yl}-5-oxo-5H,6H,7H-pyrrolo[3,4-b]pyridin-6-yl)-N-[(1S)-1-(2-fluoro-5-methylphenyl)-2-hydroxyethyl] propanamide | 1H NMR (400 MHz, DMSO-d6) δ 9.10 (s, 1H), 8.62 (d, 1H), 8.50 (s, 1H), 8.42 (d, 1H), 7.72 (br. s, 1H), 7.17 (d, 1H), 7.14-6.98 (m, 2H), 5.17-4.97 (m, 3H), 4.73 (q, 2H), 4.03-3.79 (m, 3H), 3.62-3.44 (m, 2H), 3.44-3.34 (m, 2H), 2.28 (s, 3H), 1.85 (d, 2H), 1.62-1.39 (m, 5H). LCMS: [M + H]⁺ = 569. | 569 |
| 648 | 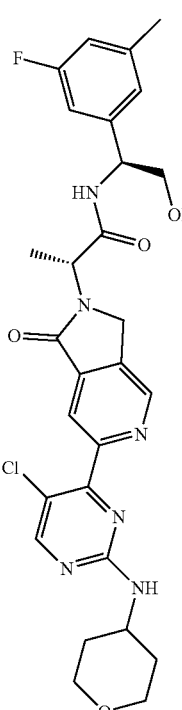 | (2R)-2-(3-{5-chloro-2-[(oxan-4-yl)amino]pyrimidin-4-yl}-5-oxo-5H,6H,7H-pyrrolo[3,4-b]pyridin-6-yl)-N-[(1S)-1-(3-fluoro-5-methylphenyl)-2-hydroxyethyl] propanamide | 1H NMR (400 MHz, DMSO-d6) δ 9.10 (s, 1H), 8.56 (d, 1H), 8.50 (s, 1H), 8.42 (d, 1H), 7.72 (br. s, 1H), 7.01-6.84 (m, 3H), 5.03 (q, 1H), 4.94 (t, 1H), 4.89-4.61 (m, 3H), 3.96-3.86 (m, 3H), 3.58-3.53 (m, 2H), 3.41-3.35 (m, 2H), 2.31 (s, 3H), 1.85 (d, 2H), 1.63-1.39 (m, 5H). | 569 |

| Example | Structure | Name | ¹H NMR (400 MHz) | MS: [M + H]⁺ |
|---|---|---|---|---|
| 649 | 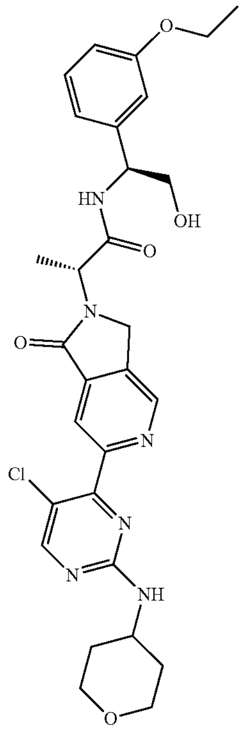 [SMILES: CCOc1cccc([C@@H](CO)NC(=O)[C@@H](C)N2Cc3cnc(-c4nc(NC5CCOCC5)ncc4Cl)cc3C2=O)c1] | (2R)-2-(3-{5-chloro-2-[(oxan-4-yl)amino]pyrimidin-4-yl}-5-oxo-5H,6H,7H-pyrrolo[3,4-b]pyridin-6-yl)-N-[(1S)-1-(3-ethoxyphenyl)-2-hydroxyethyl]propanamide | 1H NMR (400 MHz, DMSO-d6) δ 9.10 (s, 1H), 8.55 (d, 1H), 8.50 (s, 1H), 8.42 (d, 1H), 7.72 (br. s, 1H), 7.22 (t, 1H), 6.90 -6.82 (m, 2H), 6.82-6.76 (m, 1H), 5.04 (q, 1H), 4.90 (t, 1H), 4.87-4.62 (m, 3H), 4.01 (q, 2H), 3.97-3.81 (m, 3H), 3.61-3.47 (m, 2H), 3.41-3.34 (m, 2H), 1.85 (d, 2H), 1.62-1.43 (m, 5H), 1.33 (t, 3H). | 581 |

Example 650: (2R)-2-(3-{5-chloro-2-[(oxan-4-yl)amino]pyrimidin-4-yl}-5-oxo-5H,6H,7H-pyrrolo[3,4-b]pyridin-6-yl)-N-[(1S)-1-(2-fluoro-3-methylphenyl)-2-hydroxyethyl]propanamide Prepared using an analogous procedure to Example 645. In this case, the product was further purified by preparative HPLC (Varian, Basic (0.1% Ammonium Bicarbonate), Basic, Waters X-Bridge Prep-C18, 5 µm, 19×50 mm column, 20-50% MeCN in Water) 1H NMR (400 MHz, DMSO-d6) δ 9.09 (s, 1H), 8.64 (d, 1H), 8.49 (s, 1H), 8.41 (d, 1H), 7.71 (br. s, 1H), 7.17 (q, 2H), 7.06 (t, 1H), 5.14 (q, 1H), 5.09-4.96 (m, 2H), 4.72 (q, 2H), 3.95-3.85 (m, 3H), 3.61-3.44 (m, 2H), 3.40-3.34 (m, 2H), 2.22 (s, 3H), 1.84 (d, 2H), 1.53 (qd, 2H), 1.44 (d, 3H). LCMS: [M+H]+=569.

Example 651: (2R)-2-(3-{5-chloro-2-[(oxan-4-yl)amino]pyrimidin-4-yl}-5-oxo-5H,6H,7H-pyrrolo[3,4-b]pyridin-6-yl)-N-[(1S)-2-hydroxy-1-(6-methoxypyridin-2-yl)ethyl]propanamide TBTU (67.6 mg, 0.211 mmol) was added to a mixture of (R)-2-(3-(5-chloro-2-((oxan-4-yl)amino)pyrimidin-4-yl)-5-oxo-5H-pyrrolo[3,4-b]pyridin-6(7H)-yl)propanoic acid (Preparation 416, 80 mg, 0.191 mmol), (S)-2-amino-2-(6-methoxypyridin-2-yl)ethanol, HCl (43.1 mg, 0.211 mmol) and triethylamine (107 µl, 0.766 mmol) in DMF (1 mL) and the mixture was stirred at room temperature overnight. The reaction mixture was diluted with EtOAc (10 mL), washed successively with KHSO₄ (1M, 10 mL), NaHCO₃ (10 mL) and brine (10 mL), dried (MgSO₄) and concentrated in vacuo. Purification by chromatography (SiO₂, 0-100% EtOAc in iso-hexanes) gave the title compound (56 mg, 50.5%) as a colourless glass. 1H NMR (DMSO-D6, 400 MHz) δ 9.06 (1H, s), 8.50-8.44 (2H, m), 8.38 (1H, s), 7.69

(1H, s), 7.63 (1H, dd), 6.88 (1H, d), 6.64 (1H, d), 5.07 (1H, dt), 4.86 (1H, t), 4.83-4.77 (1H, m), 4.74 (1H, d), 4.66 (1H, d), 3.95-3.80 (3H, m), 3.80 (3H, s), 3.74-3.67 (1H, m), 3.63-3.56 (1H, m), 3.39-3.32 (2H, m), 1.86-1.76 (2H, m), 1.55-1.43 (5H, m). LCMS: [M+H]+=568.

Example 652: (2R)-2-(3-{5-chloro-2-[(oxan-4-yl)amino]pyrimidin-4-yl}-5-oxo-5H,6H,7H-pyrrolo[3,4-b]pyridin-6-yl)-N-[(1S)-2-hydroxy-1-(3-methoxyphenyl)ethyl]propanamide

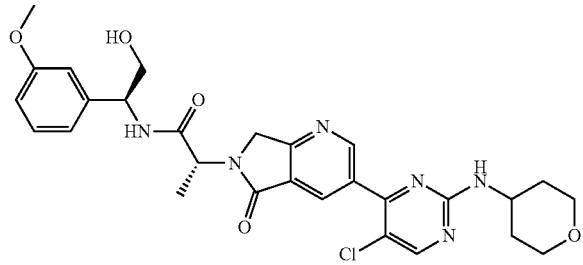 [SMILES: COc1cccc([C@@H](CO)NC(=O)[C@@H](C)N2Cc3ncc(-c4nc(NC5CCOCC5)ncc4Cl)cc3C2=O)c1]

A mixture of (R)-2-(3-(2,5-dichloropyrimidin-4-yl)-5-oxo-5H-pyrrolo[3,4-b]pyridin-6(7H)-yl)-N—((S)-2-hydroxy-1-(3-methoxyphenyl)ethyl)propanamide (0.08 g, 0.159 mmol), DIPEA (0.056 ml, 0.319 mmol) and oxan-4-amine (0.025 ml, 0.239 mmol) in 1:1 EtOH:dioxane (1 mL) was heated at 80° C. under nitrogen overnight. The mixture was allowed to cool to room temperature was diluted with EtOAc, then transferred into a separating funnel. Saturated aqueous NH₄Cl was added and the crude product was extracted with EtOAc. The combined organic extracts were washed with NaHCO₃, brine, dried (MgSO₄) and absorbed on silica. The crude product was purified by chromatography (12 g column, 0-6% MeOH in DCM), then re-purified by chromatography (12 g column, 5-10% EtOAc in MeOH) to afford the title compound (0.033 g, 35.8%) as a pale yellow solid after trituration and evaporation from Et₂O. 1H NMR (DMSO-d6) δ: 9.10 (s, 1H), 8.58 (d, 1H), 8.50 (s, 1H), 8.42 (d, 1H), 7.72 (s (br), 1H), 7.29-7.18 (m, 1H), 6.92-6.84 (m, 2H), 6.81 (dd, 1H), 5.11-4.98 (m, 1H), 4.92 (t, 1H), 4.87-4.74 (m, 2H), 4.68 (d, 1H), 4.01-3.82 (m, 3H), 3.75 (s, 3H), 3.61-3.48 (m, 2H), 3.44-3.36 (m, 2H), 1.92-1.77 (m, 2H), 1.60-1.50 (m, 2H), 1.48 (d, 3H). LCMS: [M+H]+=567.

Examples 653-657

Prepared using an analogous procedure to Example 652.

| Example | Structure | Name | ¹H NMR (400 MHz) | MS: [M + H]⁺ |
|---|---|---|---|---|
| 653 | 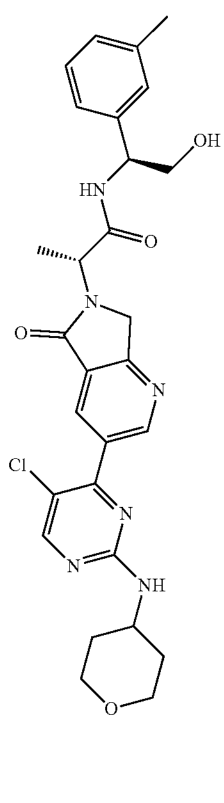 [SMILES: Cc1cccc([C@@H](CO)NC(=O)[C@@H](C)N2Cc3ncc(-c4nc(NC5CCOCC5)ncc4Cl)cc3C2=O)c1] | ((2R)-2-(3-{5-chloro-2-[(oxan-4-yl)amino]pyrimidin-4-yl}-5-oxo-5H,6H,7H-pyrrolo[3,4-b]pyridin-6-yl)-N-[(1S)-2-hydroxy-1-(3-methylphenyl)ethyl]propanamide | 1H NMR (DMSO-d6) δ: 9.10 (s, 1H), 8.55 (d, 1H), 8.50 (s, 1H), 8.42 (d, 1H), 7.72 (s (br), 1H), 7.21 (dd, 1H), 7.15-6.99 (m, 3H), 5.09-4.99 (m, 1H), 4.89 (t, 1H), 4.86-4.73 (m, 2H), 4.67 (d, 1H), 4.01-3.82 (m, 3H), 3.61-3.49 (m, 2H), 3.44-3.35 (m, 2H), 2.30 (s, 3H), 1.91-1.80 (m, 2H), 1.61-1.48 (m, 2H), 1.46 (d, 3H). | 551 |

-continued

| Example | Structure | Name | ¹H NMR (400 MHz) | MS: [M + H]⁺ |
|---|---|---|---|---|
| 654 | 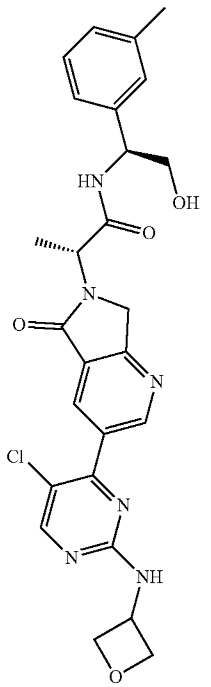 [SMILES: Cc1cccc([C@@H](CO)NC(=O)[C@@H](C)N2Cc3ncc(-c4nc(NC5COC5)ncc4Cl)cc3C2=O)c1] | (2R)-2-(3-{5-chloro-2-[(oxetan-3-yl)amino]pyrimidin-4-yl}-5-oxo-5H,6H,7H-pyrrolo[3,4-b]pyridin-6-yl)-N-[(1S)-2-hydroxy-1-(3-methylphenyl)ethyl]propanamide | 1H NMR (DMSO-d6) δ: 9.11 (d, 1H), 8.59-8.50 (m, 2H), 8.43 (d, 1H), 8.43 (s (br), 1H), 7.21 (dd, 1H), 7.15-7.01 (m, 3H), 5.04 (td, 1H), 4.98-4.86 (m, 2H), 4.86-4.73 (m, 4H), 4.68 (d, 1H), 4.56 (t, 2H), 3.60-3.48 (m, 2H), 2.30 , (s, 3H) 1.46 (d, 3H). | 523 |
| 655 | 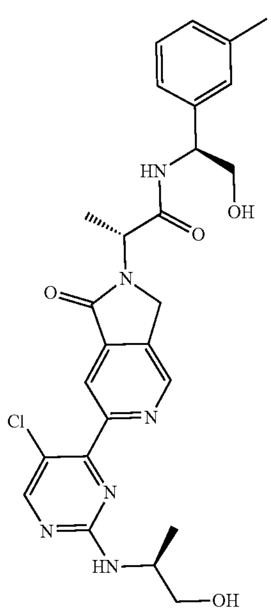 [SMILES: Cc1cccc([C@@H](CO)NC(=O)[C@@H](C)N2Cc3cnc(-c4nc(N[C@@H](C)CO)ncc4Cl)cc3C2=O)c1] | (2R)-2-[3-(5-chloro-2-{[(2S)-1-hydroxypropan-2-yl]amino}pyrimidin-4-yl)-5-oxo-5H,6H,7H-pyrrolo[3,4-b]pyridin-6-yl]-N-[(1S)-2-hydroxy-1-(3-methylphenyl)ethyl]propanamide | 1H NMR (DMSO-d6) δ: 9.11 (s (br), 1H), 8.55 (d, 1H), 8.48 (s (br), 1H), 8.42 (d, 1H), 7.39 (s (br), 1H), 7.21 (dd, 1H), 7.15-7.01 (m, 3H), 5.04 (td, 1H), 4.89 (t, 1H), 4.86-4.74 (m, 2H), 4.74-4.62 (m, 2H), 4.04-3.93 (m, 1H), 3.60-3.44 (m, 3H), 2.30 (s, 3H), 1.46 (d, 3H), 1.15 (d, 3H) (One proton overlapped with water peak). | 525 |

| Example | Structure | Name | ¹H NMR (400 MHz) | MS: [M + H]⁺ |
|---|---|---|---|---|
| 656 | 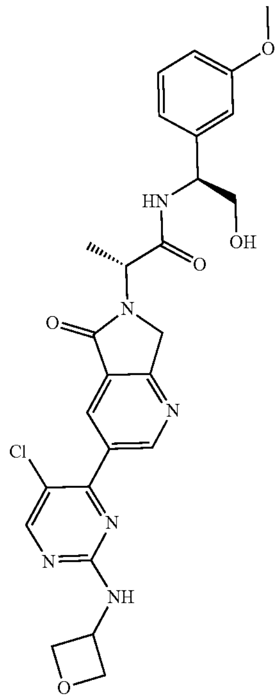 [SMILES: COc1cccc([C@@H](CO)NC(=O)[C@@H](C)N2Cc3ncc(-c4nc(NC5COC5)ncc4Cl)cc3C2=O)c1] | (2R)-2-(3-{5-chloro-2-[(oxetan-3-yl)amino]pyrimidin-4-yl}-5-oxo-5H,6H,7H-pyrrolo[3,4-b]pyridin-6-yl)-N-[(1S)-2-hydroxy-1-(3-methoxyphenyl)ethyl]propanamide | 1H NMR (DMSO-d6) δ: 9.11 (d, 1H), 8.57 (d, 1H), 8.53 (s, 1H), 8.43 (d, 1H), 8.43 (s (br), 1H), 7.24 (dd, 1H), 6.92-6.85 (m, 2H), 6.81 (ddd, 1H), 5.04 (td, 1H), 4.98-4.88 (m, 2H), 4.88-4.73 (m, 4H), 4.69 (d, 1H), 4.56 (t, 2H), 3.75 (s, 3H), 3.61-3.49 (m, 2H), 1.48 (d, 3H). | 539 |
| 657 | 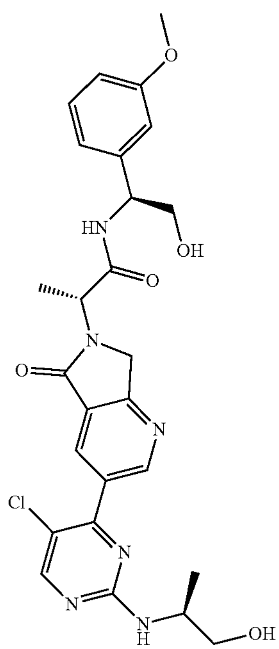 [SMILES: COc1cccc([C@@H](CO)NC(=O)[C@@H](C)N2Cc3ncc(-c4nc(N[C@@H](C)CO)ncc4Cl)cc3C2=O)c1] | (2R)-2-[3-(5-chloro-2-{[(2S)-1-hydroxypropan-2-yl]amino}pyrimidin-4-yl)-5-oxo-5H,6H,7H-pyrrolo[3,4-b]pyridin-6-yl]-N-[(1S)-2-hydroxy-1-(3-methoxyphenyl)ethyl]propanamide | 1H NMR (DMSO-d6) δ: 9.11 (s (br), 1H), 8.56 (d, 1H), 8.51-8.35 (m, 2H), 7.39 (s (br), 1H), 7.24 (dd, 1H), 6.92-6.84 (m, 2H), 6.84-6.76 (m, 1H), 5.04 (td, 1H), 4.90 (t, 1H), 4.87-4.61 (m, 4H), 4.05-3.91 (m, 1H), 3.75 (s, 3H), 3.61-3.42 (m, 3H), 1.48 (d, 3H), 1.15 (d, 3H). One proton overlapped with water peak. | 541 |

Example 658: (2R)-2-(3-{5-chloro-2-[(propan-2-yl)amino]pyrimidin-4-yl}-5-oxo-5H,6H,7H-pyrrolo[3,4-b]pyridin-6-yl)-N-[(1S)-2-hydroxy-1-(3-methoxyphenyl)ethyl]propanamide

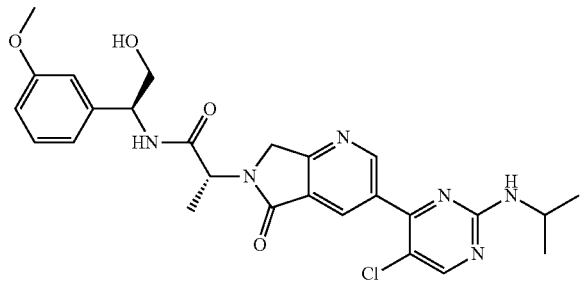 [SMILES: COc1cccc([C@@H](CO)NC(=O)[C@@H](C)N2Cc3ncc(-c4nc(NC(C)C)ncc4Cl)cc3C2=O)c1]

A mixture of (R)-2-(3-(2,5-dichloropyrimidin-4-yl)-5-oxo-5H-pyrrolo[3,4-b]pyridin-6(7H)-yl)-N—((S)-2-hydroxy-1-(3-methoxyphenyl)ethyl)propanamide (Preparation 370, 0.08 g, 0.159 mmol), DIPEA (0.056 ml, 0.319 mmol) and propan-2-amine (0.041 ml, 0.478 mmol) in 1:1 EtOH:dioxane (1 mL) was heated at 80° C. in a sealed Biotage microwave vial overnight. The mixture was allowed to cool to room temperature was diluted with EtOAc, then transferred into a separating funnel. Saturated aqueous $NH_4Cl$ was added and the crude product was extracted with EtOAc. The combined organic extracts were washed with $NaHCO_3$, brine, dried ($MgSO_4$) and absorbed on silica. The crude product was purified by chromatography ($SiO_2$, 4 g column, 0-4% MeOH in DCM) to afford the title compound (0.01 g, 11.84%) as a pale yellow solid after trituration and evaporation from $Et_2O$. 1H NMR (DMSO-d6) δ: 9.11 (s (br), 1H), 8.56 (d, 1H), 8.48 (s (br), 1H), 8.42 (d, 1H), 7.57 (d, 1H), 7.24 (dd, 1H), 6.93-6.84 (m, 2H), 6.81 (ddd, 1H), 5.11-4.98 (m, 1H), 4.91 (t, 1H), 4.87-4.73 (m, 2H), 4.68 (d, 1H), 4.09-3.97 (m, 1H), 3.75 (s, 3H), 3.59-3.49 (m, 2H), 1.47 (d, 3H), 1.18 (d, 6H). LCMS: [M+H]+=525.

Example 659: (2R)-2-(3-{5-chloro-2-[(oxan-4-yl)amino]pyrimidin-4-yl}-5-oxo-5H,6H,7H-pyrrolo[3,4-b]pyridin-6-yl)-N-[(1S)-1-[3-(difluoromethoxy)phenyl]-2-hydroxyethyl]propanamide

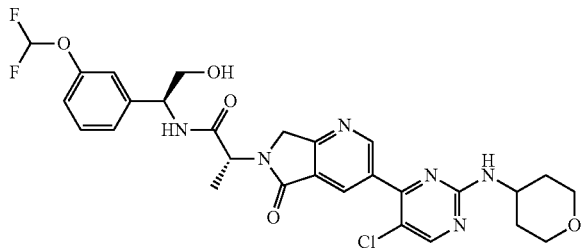 [SMILES: C[C@H](C(=O)N[C@H](CO)c1cccc(OC(F)F)c1)N1Cc2ncc(-c3nc(NC4CCOCC4)ncc3Cl)cc2C1=O]

DIPEA (0.060 mL, 0.344 mmol) followed by oxan-4-amine (0.020 mL, 0.193 mmol) were added to a stirred solution of (R)-2-(3-(2,5-dichloropyrimidin-4-yl)-5-oxo-5H-pyrrolo[3,4-b]pyridin-6(7H)-yl)-N—((S)-1-(3-(difluoromethoxy)phenyl)-2-hydroxyethyl)propanamide (0.057 g, 0.093 mmol) in 1,4-dioxane (1.0 mL, 11.69 mmol) and the mixture was heated to 90° C. for 3.5 h. After 4 h, further oxan-4-amine (0.020 mL, 0.193 mmol), DIPEA (0.060 mL, 0.344 mmol) and EtOH (1 mL) were added and the reaction mixture was left to heat for a further 2 h then cooled to room temperature and stirred overnight. The mixture was partitioned between EtOAc (50 mL) and water (50 mL). The layers were separated and the aqueous layer extracted with EtOAc (50 mL). The combined organic extracts were washed with brine (3×50 mL), dried ($MgSO_4$), filtered and concentrated. Purification by chromatography ($SiO_2$, 12 g column, 0-100% (10% MeOH in DCM) in DCM) afforded the title compound (16 mg, 27.9%) as a pale yellow solid. 1H NMR (DMSO-d6, 400 MHz) δ 9.10 (1H, d), 8.61 (1H, d), 8.49 (1H, s), 8.41 (1H, d), 7.71 (1H, br. s), 7.44-7.32 (1H, m), 7.24-7.14 (2H, m), 7.11 (1H, t), 7.07-7.01 (1H, m), 5.03 (1H, q), 4.95 (1H, t), 4.86 (1H, q), 4.81-4.60 (2H, m), 3.96-3.85 (3H, m), 3.63-3.49 (2H, m), 3.43-3.33 (2H, m), 1.89-1.78 (2H, m), 1.54 (2H, td), 1.47 (3H, d). LCMS: [M+H]+=603.

Example 660: 2-[3-(5-chloro-2-{[trans-4-methoxycyclohexyl]amino}pyrimidin-4-yl)-5-oxo-5H,6H,7H-pyrrolo[3,4-b]pyridin-6-yl]-N-[(1S)-2-hydroxy-1-(3-methylphenyl)ethyl]acetamide

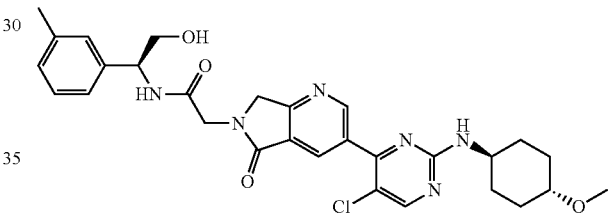

DIPEA (59.9 µl, 0.343 mmol) was added to a stirred solution of (S)-2-(3-(2,5-dichloropyrimidin-4-yl)-5-oxo-5H-pyrrolo[3,4-b]pyridin-6(7H)-yl)-N-(2-hydroxy-1-(m-tolyl)ethyl)acetamide (80 mg, 0.137 mmol) and (1r,4r)-4-methoxycyclohexanamine (26.6 mg, 0.206 mmol) in dioxane (1 mL) under nitrogen. The mixture was heated to 90° C. and stirred for 16 h. The mixture was allowed to cool to room temperature and was diluted with EtOAc (20 mL) and water (20 mL). The phases were separated and the aqueous layer was extracted with EtOAc (2×20 mL). The combined organic extracts were washed with brine (60 mL), dried ($MgSO_4$) and concentrated. The crude product was purified by chromatography ($SiO_2$, 24 g column, 0-10% MeOH in DCM) to afford a beige solid. The product was loaded onto a column packed with SCX (0.5 g) in MeOH. The column was washed with MeOH and the product eluted with 0.7 M ammonia in MeOH. The resulting mixture was concentrated in vacuo to afford the title compound (52 mg, 66.4%) as a beige solid. 1H NMR (DMSO-d6, 400 MHz) δ 9.09 (1H, s), 8.54 (1H, d), 8.48 (1H, s (br)), 8.40 (1H, d), 7.62 (1H, s (br)), 7.21 (1H, t), 7.15-7.08 (2H, m), 7.07-7.03 (1H, m), 4.91 (1H, t), 4.88-4.80 (1H, m), 4.64 (2H, s), 4.34 (1H, d), 4.29 (1H, d), 3.77-3.62 (1H, m), 3.61-3.50 (2H, m), 3.22 (3H, s), 3.17-3.05 (1H, m), 2.29 (3H, s), 2.10-1.84 (4H, m), 1.41-1.24 (2H, m), 1.24-1.11 (2H, m). LCMS: [M+H]+=565.

Example 661: 2-(3-{5-chloro-2-[(oxan-4-yl)amino]pyrimidin-4-yl}-5-oxo-5H,6H,7H-pyrrolo[3,4-b]pyridin-6-yl)-N-[(1R)-1-(6-methoxypyridin-2-yl)ethyl]acetamide

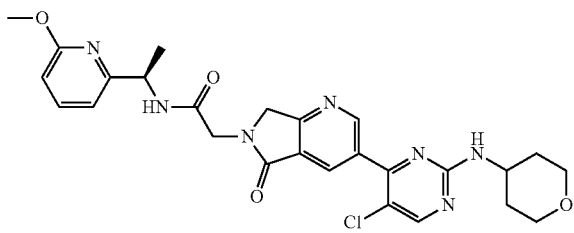 [SMILES: COc1cccc([C@@H](C)NC(=O)CN2Cc3ncc(-c4nc(NC5CCOCC5)ncc4Cl)cc3C2=O)n1]

A mixture of (R)-2-(3-(2,5-dichloropyrimidin-4-yl)-5-oxo-5H-pyrrolo[3,4-b]pyridin-6(7H)-yl)-N-(1-(6-methoxypyridin-2-yl)ethyl)acetamide (0.115 g, 0.243 mmol), DIPEA (0.085 ml, 0.486 mmol) and oxan-4-amine (0.038 ml, 0.364 mmol) in 1:1 EtOH:dioxane (1.5 mL) was heated at 80° C. under nitrogen overnight. The mixture was allowed to cool to room temperature was diluted with EtOAc, then transferred into a separating funnel. Water was added and the crude product was extracted with EtOAc. The combined organic extracts were washed with NaHCO$_3$, brine, dried (MgSO$_4$) and absorbed on silica. The crude product was purified by chromatography (SiO$_2$, 12 g column, 0-5% MOH in DCM) to afford the title compound (0.085 g, 64.4%) as a pale yellow solid after trituration and evaporation from Et$_2$O.1H NMR (DMSO-d6) δ: 9.10 (d, 1H), 8.57 (d, 1H), 8.49 (s, 1H), 8.42 (d, 1H), 7.72 (s (br), 1H), 7.67 (dd, 1H), 6.95 (d, 1H), 6.68 (d, 1H), 4.92 (dq, 1H), 4.70 (d, 1H), 4.64 (d, 1H), 4.34 (s, 2H), 3.98-3.86 (m, 3H), 3.86 (s, 3H), 3.43-3.35 (m, 2H), 1.91-1.78 (m, 2H), 1.61-1.46 (m, 2H), 1.42 (d, 3H). LCMS: [M+H]+=538.

Example 5260:2-(3-{5-chloro-2-[(oxan-4-yl)amino]pyrimidin-4-yl}-5-oxo-5H,6H,7H-pyrrolo[3,4-b]pyridin-6-yl)-N-[(1R)-1-(3-methylphenyl)ethyl]acetamide

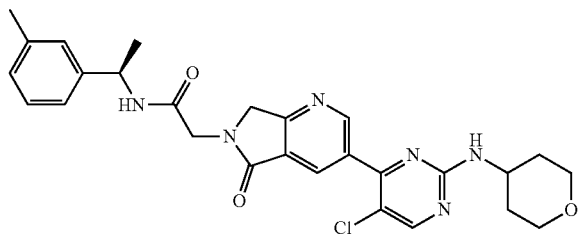 [SMILES: Cc1cccc([C@@H](C)NC(=O)CN2Cc3ncc(-c4nc(NC5CCOCC5)ncc4Cl)cc3C2=O)c1]

Oxan-4-amine (108 mg, 1.063 mmol) was added to a solution of crude (R)-2-(3-(2,5-dichloropyrimidin-4-yl)-5-oxo-5H-pyrrolo[3,4-b]pyridin-6(7H)-yl)-N-(1-(m-tolyl)ethyl)acetamide (97 mg, 0.213 mmol) (containing (R)-2-(3-(2-((1H-benzo[d][1,2,3]triazol-1-yl)oxy)-5-chloropyrimidin-4-yl)-5-oxo-5H-pyrrolo[3,4-b]pyridin-6(7H)-yl)-N-(1-(m-tolyl)ethyl)acetamide as impurity) in dioxane (2 ml) and the mixture heated at 90° C. overnight. The reaction mixture was cooled to room temperature and partitioned between water (50 ml) and 1N HCl (50 ml) and the organic phase collected. The DCM solution was washed with aq 10% NaHCO$_3$ (50 ml) and dried (MgSO$_4$). Concentration of the extract afforded a glass which was purified by chromatography (SiO$_2$, 4 g column, 100% EtOAc). The pure fractions were concentrated to dryness and the residue crystallised using diethyl ether to afford the title compound (70 mg, 63.2%) as a cream coloured solid. 1H NMR (DMSO-d6, 400 MHz) δ 9.10 (1H, d), 8.58 (1H, d), 8.50 (1H, s), 8.41 (1H, d), 7.72 (1H, s), 7.26-6.90 (4H, m), 5.02-4.85 (1H, m), 4.64 (2H, s), 4.28 (2H, s), 3.98-3.80 (3H, m), 3.41-3.36 (2H, m), 2.30 (3H, s), 1.90-1.79 (2H, m), 1.62-1.42 (2H, m), 1.37 (3H, d). LCMS: [M+H]+=521.

Example 663:2-(6-{5-chloro-2-[(oxan-4-yl)amino]pyrimidin-4-yl}-4-fluoro-1-oxo-2,3-dihydro-1H-isoindol-2-yl)-N-[(1S)-2-hydroxy-1-(3-methoxyphenyl)ethyl]acetamide

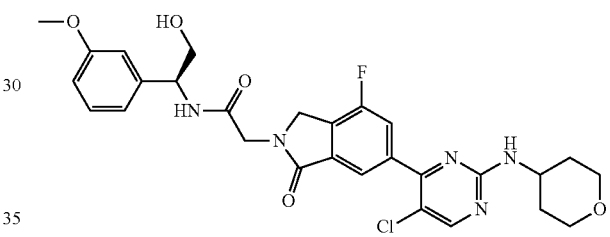

HATU (115 mg, 0.303 mmol) was added to a suspension of 2-(6-{5-chloro-2-[(oxan-4-yl)amino]pyrimidin-4-yl}-4-fluoro-1-oxo-2,3-dihydro-1H-isoindol-2-yl)acetic acid (118 mg, 0.275 mmol), (S)-2-amino-2-(3-methoxyphenyl)ethanol hydrochloride (61.6 mg, 0.303 mmol) and triethylamine (0.153 mL, 1.100 mmol) in DMF (1.5 mL, 19.37 mmol) at room temperature. The reaction was stirred for 1 h, then diluted with water (10 mL) and 1 M HCl (5 mL). The resulting precipitate was isolated by filtration, then dissolved in EtOAc (10 mL), dried (MgSO$_4$) and concentrated to give a pale yellow solid, which was redissolved in EtOAc (15 mL) and washed with 1 M HCl (2×15 mL), brine (2×15 mL), dried (MgSO4) and concentrated to give a pale yellow solid. The crude product was loaded onto a column of SCX (5 g) in MeOH. The column was washed with MeOH and then the product was eluted with 0.7 M ammonia in MeOH. The resulting mixture was concentrated in vacuo to afford the title compound (49 mg, 30.0%) as a white powder. 1H NMR (DMSO-d6, 400 MHz) δ 8.55 (1H, d), 8.48 (1H, s), 7.96-7.89 (1H, m), 7.83 (1H, dd), 7.68 (1H, br. s), 7.27-7.20 (1H, m), 6.92-6.88 (2H, m), 6.85-6.79 (1H, m), 4.93 (1H, t), 4.89-4.83 (1H, m), 4.68 (2H, s), 4.33 (1H, d), 4.28 (1H, d), 3.98-3.82 (3H, m), 3.75 (3H, s), 3.62-3.53 (2H, m), 3.42-3.35 (2H, m), 1.84 (2H, d), 1.59-1.47 (2H, m). LCMS: [M+H]+=570.

Example 664:2-(6-{5-chloro-2-[(oxan-4-yl)amino]pyrimidin-4-yl}-4-fluoro-1-oxo-2,3-dihydro-1H-isoindol-2-yl)-N-[(1S,2S)-2-hydroxy-1-phenylpropyl]acetamide

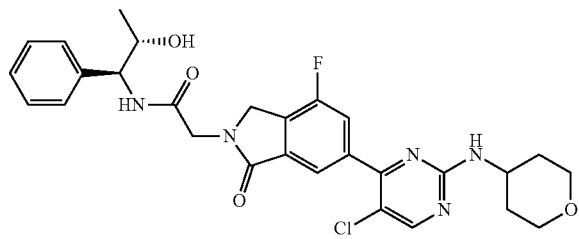 [SMILES: C[C@H](O)[C@@H](NC(=O)CN1Cc2c(F)cc(-c3nc(NC4CCOCC4)ncc3Cl)cc2C1=O)c1ccccc1]

DIPEA (0.110 ml, 0.631 mmol) and HATU (120 mg, 0.315 mmol) were added to a stirred solution of 2-(6-{5-chloro-2-[(oxan-4-yl)amino]pyrimidin-4-yl}-4-fluoro-1-oxo-2,3-dihydro-1H-isoindol-2-yl)acetic acid (Preparation 16, 90 mg, 0.214 mmol), and (1S,2S)-1-amino-1-phenylpropan-2-ol hydrochloride (40.1 mg, 0.214 mmol) in acetonitrile (2 ml, 0.214 mmol) and the resulting solution was stirred at room temperature for 48 h. The solution was concentrated and the residue dissolved in a small quantity of DCM purified by chromatography (SiO₂, 12 g column, 100% EtOAc) to give a colourless solid (75 mg). The solid was dissolved in methanol (2 ml) and the solution loaded on a column packed with SCX. The column was washed with MeOH and the product eluted with 1% ammonia in methanol. The resulting solution was concentrated to dryness and the residual glass triturated with Et₂O (2 ml). The resulting precipitate was filtered to afford the title compound (53 mg, 44.2%) as a colourless solid. 1H NMR (DMSO-d6, 400 MHz) δ 8.53 (1H, d), 8.48 (1H, s), 7.91 (1H, d), 7.82 (1H, dd), 7.68 (1H, s), 7.36-7.21 (5H, m), 4.83 (1H, d), 4.72 (1H, dd), 4.66 (2H, s), 4.38 (1H, d), 4.30 (1H, d), 3.99-3.80 (3H, m), 3.42-3.35 (2H, m), 1.84 (2H, d), 1.58-1.46 (2H, m), 1.00 (3H, d). (One exchangable proton was not observed and may have overlapped with DMSO or water peaks). LCMS: [M+H]+=554.

Example 665:2-(6-{5-chloro-2-[(oxan-4-yl)amino]pyrimidin-4-yl}-4-fluoro-1-oxo-2,3-dihydro-1H-isoindol-2-yl)-N-[(1S)-1-[3-(difluoromethoxy)phenyl]-2-hydroxyethyl]acetamide

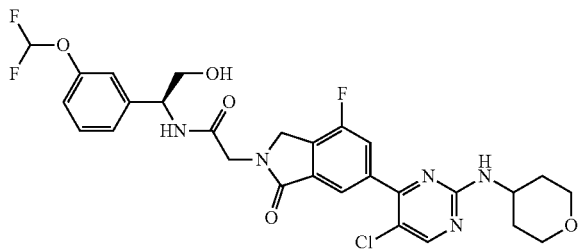 [SMILES: O=C(CN1Cc2c(F)cc(-c3nc(NC4CCOCC4)ncc3Cl)cc2C1=O)N[C@H](CO)c1cccc(OC(F)F)c1]

DIPEA (110 μl, 0.631 mmol) and HATU (120 mg, 0.315 mmol) were added to a stirred solution of 2-(6-{5-chloro-2-[(oxan-4-yl)amino]pyrimidin-4-yl}-4-fluoro-1-oxo-2,3-dihydro-1H-isoindol-2-yl)acetic acid (Preparation 16, 90 mg, 0.214 mmol) and (S)-2-amino-2-(3-(difluoromethoxy)phenyl)ethanol hydrochloride (51.3 mg, 0.214 mmol) in acetonitrile (8.78 mg, 0.214 mmol). The resulting solution was stirred at room temperature for 48 h. The solution was concentrated to dryness and the residue dissolved in a small quantity of DCM, then purified by chromatography (SiO₂, 12 g column, 100% EtOAc) to afford a colourless solid (89 mg). The solid was dissolved in methanol (2 ml) and the solution loaded on a column packed with SCX. The column was washed with MeOH and the product eluted with 1% ammonia in methanol. The resulting solution was concentrated to dryness and the residual glass triturated with Et₂O (2 ml). The resulting precipitate was filtered to afford afford a colourless solid (60 mg). The solid was dissolved in DCM (30 ml) and the solution washed with 1N HCl (20 ml). The organic phase was dried (MgSO₄) and concentrated to dryness, then purified by preparative HPLC (acidic) to afford the title compound acetamide (15 mg, 11.57%) as a colourless solid. 1H NMR (DMSO, 400 MHz) δ 8.62 (1H, d), 8.48 (1H, s), 7.92 (1H, s), 7.83 (1H, d), 7.68 (1H, s (br)), 7.45-6.97 (5H, m), 4.99 (1H, t), 4.96-4.80 (1H, m), 4.67 (2H, s), 4.42-4.20 (2H, m), 4.06-3.72 (3H, m), 3.41-3.47 (2H, m), 3.69-3.49 (2H, m), 1.93-1.72 (2H, m), 1.64-1.42 (2H, m). LCMS: [M+H]+=606.

Example 666: 2-[6-(5-chloro-2-{[(2S)-1-hydroxypropan-2-yl]amino}pyrimidin-4-yl)-4-fluoro-1-oxo-2,3-dihydro-1H-isoindol-2-yl]-N-[(1R)-1-(3-methoxyphenyl)ethyl]acetamide

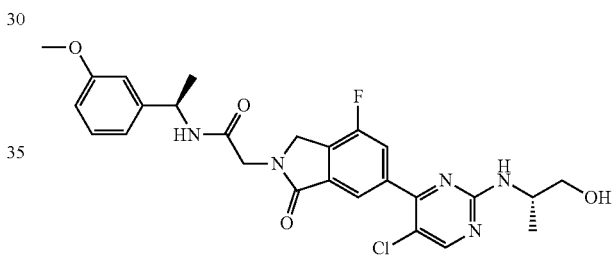

Prepared using a similar procedure to Example 102. 1H NMR (DMSO, 400 MHz) δ 8.58 (1H, d), 8.45 (1H, s), 7.92 (1H, d), 7.83 (1H, d), 7.34 (1H, s), 7.24 (1H, t), 6.92-6.86 (2H, m), 6.83-6.76 (1H, m), 4.93 (1H, p), 4.73-4.61 (3H, m), 4.25 (2H, s), 4.00-3.90 (1H, m), 3.75 (3H, s), 3.53-3.44 (1H, m), 3.32-3.26 (1H, m), 1.36 (3H, d), 1.13 (3H, d). LCMS: [M+H]+=528.

Example 667:2-(6-{5-chloro-2-[(oxan-4-yl)amino]pyrimidin-4-yl}-4-fluoro-1-oxo-2,3-dihydro-1H-isoindol-2-yl)-N-[(1S)-2-hydroxy-1-(3-methylphenyl)ethyl]acetamide

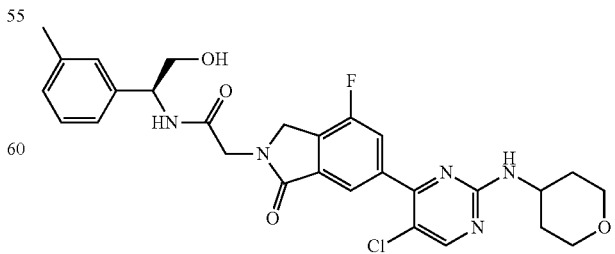

Prepared using a similar procedure to Example 583. 1H NMR (DMSO-d6, 400 MHz) δ 8.54 (1H, d), 8.47 (1H, s), 7.91 (1H, d), 7.82 (1H, dd), 7.67 (1H, s), 7.21 (1H, t), 7.17-7.08 (2H, m), 7.07-7.02 (1H, m), 4.92 (1H, t), 4.88-4.79 (1H, m), 4.66 (2H, s), 4.32 (1H, d), 4.26 (1H, d), 4.00-3.80 (3H, m), 3.66-3.49 (2H, m), 3.38 (2H, d), 2.29 (3H, s), 1.90-1.78 (2H, m), 1.58-1.46 (2H, m). LCMS: [M+H]+=554.

Example 668:2-(6-{5-chloro-2-[(oxan-4-yl)amino]
pyrimidin-4-yl}-4-fluoro-1-oxo-2,3-dihydro-1H-
isoindol-2-yl)-N-[(1S)-2-hydroxy-1-(6-methoxypyri-
din-2-yl)ethyl]acetamide

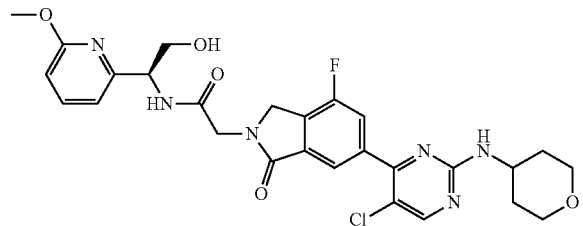 [SMILES: COc1cccc([C@@H](CO)NC(=O)CN2Cc3c(F)cc(-c4nc(NC5CCOCC5)ncc4Cl)cc3C2=O)n1]

TBTU (47.8 mg, 0.149 mmol) was added to an ice-cooled stirred solution of 2-(6-{5-chloro-2-[(oxan-4-yl)amino]pyrimidin-4-yl}-4-fluoro-1-oxo-2,3-dihydro-1H-isoindol-2-yl)acetic acid (Preparation 16.44 mg, 0.099 mmol), (S)-2-amino-2-(6-methoxypyridin-2-yl)ethanol hydrochloride (22.36 mg, 0.109 mmol) and triethylamine (55.41, 0.397 mmol) in DMF (1 m. The mixture was stirred at room temperature for 16 h, then diluted with EtOAc (30 mL). The organic phase was washed with water (30 mL), NH$_4$Cl (30 mL), brine (3×30 mL), dried (MgSO$_4$), filtered and concentrated in vacuo. The crude product was purified by chromatography (SiO$_2$, 12 g column, 0-6% MeOH in DCM) to afford the title compound (39 mg, 68.1%) as an off white solid. 1H NMR (DMSO-d6,400 MHz), 8.58-8.40 (2H, m), 7.91 (1H, d), 7.82 (1H, dd), 7.75-7.59 (2H, m), 7.03-6.88 (1H, m), 6.68 (1H, 4.95-4.81 (2H, m), 4.69 (2H, s), 4.34 (2H, s), 4.00-3.85 (3H, m), 3.84 (3H, s), 3.81-3.73 (1H, m), 3.72-3.63 (1H, m), 3.42-3.36 (2H, m), 1.88-1.78 (2H, m), 1.60-1.45 (2H, m). MS: [M+H]+=571.

Examples 669-670

Prepared using an analogous procedure to Example 668

| Example | Structure | Name | $^1$H NMR (400 MHz) | MS: [M + H]$^+$ |
|---|---|---|---|---|
| 669 | 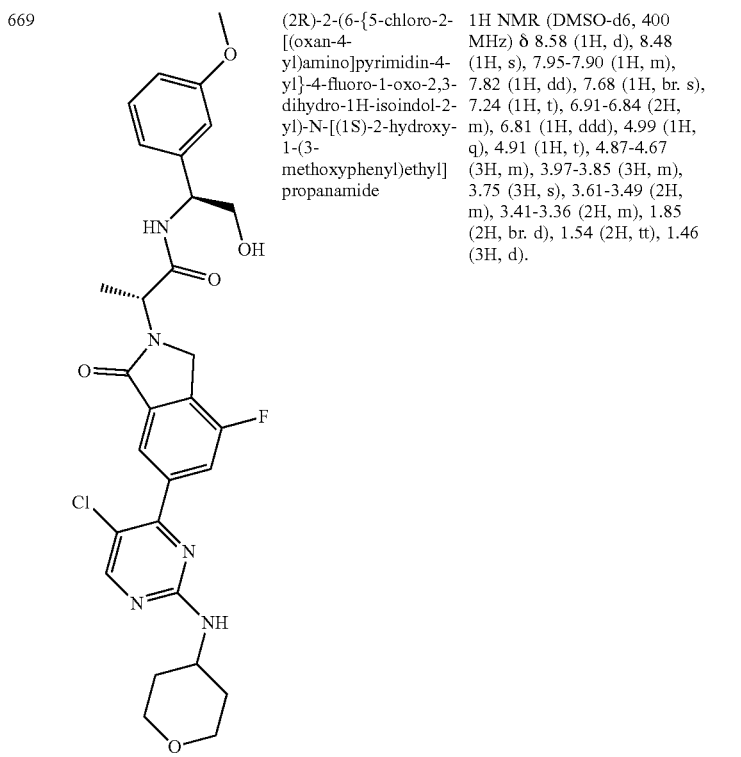 | (2R)-2-(6-{5-chloro-2-[(oxan-4-yl)amino]pyrimidin-4-yl}-4-fluoro-1-oxo-2,3-dihydro-1H-isoindol-2-yl)-N-[(1S)-2-hydroxy-1-(3-methoxyphenyl)ethyl]propanamide | 1H NMR (DMSO-d6, 400 MHz) δ 8.58 (1H, d), 8.48 (1H, s), 7.95-7.90 (1H, m), 7.82 (1H, dd), 7.68 (1H, br. s), 7.24 (1H, t), 6.91-6.84 (2H, m), 6.81 (1H, ddd), 4.99 (1H, q), 4.91 (1H, t), 4.87-4.67 (3H, m), 3.97-3.85 (3H, m), 3.75 (3H, s), 3.61-3.49 (2H, m), 3.41-3.36 (2H, m), 1.85 (2H, br. d), 1.54 (2H, tt), 1.46 (3H, d). | 584 |

| Example | Structure | Name | ¹H NMR (400 MHz) | MS: [M + H]⁺ |
|---|---|---|---|---|
| 670 | 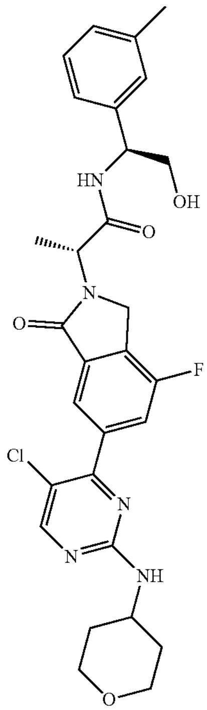 [SMILES: Cc1cccc([C@@H](CO)NC(=O)[C@@H](C)N2Cc3c(F)cc(-c4nc(NC5CCOCC5)ncc4Cl)cc3C2=O)c1] | (2R)-2-(6-{5-chloro-2-[(oxan-4-yl)amino]pyrimidin-4-yl}-4-fluoro-1-oxo-2,3-dihydro-1H-isoindol-2-yl)-N-[(1S)-2-hydroxy-1-(3-methylphenyl)ethyl]propanamide | 1H NMR (DMSO-d6, 400 MHz) δ 8.56 (1H, d), 8.48 (1H, s), 7.93 (1H, d), 7.82 (1H, dd), 7.68 (1H, br. s), 7.21 (1H, t), 7.12-7.01 (3H, m), 4.99 (1H, q), 4.89 (1H, t), 4.86-4.67 (3H, m), 4.01-3.81 (3H, m), 3.59-3.49 (2H, m), 3.40-3.34 (2H, m), 2.30 (3H, s), 1.85 (2H, br. d), 1.53 (2H, qd), 1.45 (3H, d). | 568 |

Example 671: (2R)-2-(6-{5-chloro-2-[(oxan-4-yl)amino]pyrimidin-4-yl}-4-fluoro-1-oxo-2,3-dihydro-1H-isoindol-2-yl)-N-[(1S)-2-hydroxy-1-(6-methylpyridin-2-yl)ethyl]propanamide Example 672: (2R)-2-[6-(5-chloro-2-{[(2S)-1-hydroxypropan-2-yl]amino}pyrimidin-4-yl)-4-fluoro-1-oxo-2,3-dihydro-1H-isoindol-2-yl]-N-[(1S)-2-hydroxy-1-(3-methylphenyl)ethyl]propanamide

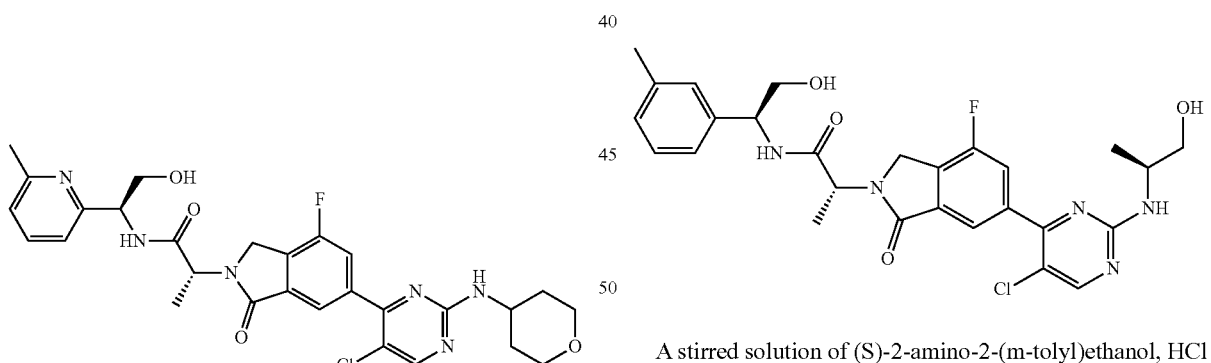

Prepared using an analogous procedure to Example 668. In this case, the product was further purified by preparative HPLC (Varian, Acidic, 15-35%, 10 min run), then freeze-dried. 1H NMR (DMSO-d6, 400 MHz) δ 8.55 (1H, d), 8.48 (1H, s), 7.93 (1H, s), 7.83 (1H, dd), 7.72-7.63 (2H, m), 7.13 (2H, m), 5.03 (1H, q), 4.93-4.69 (4H, m), 3.97-3.85 (3H, m), 3.74-3.68 (1H, m), 3.67-3.57 (1H, m), 3.41-3.34 (2H, m), 2.43 (3H, s), 1.85 (2H, br. d), 1.57-1.47 (5H, m). LCMS: [M+H]+=569.

A stirred solution of (S)-2-amino-2-(m-tolyl)ethanol, HCl (32 mg, 0.171 mmol), (R)-2-(6-(5-chloro-2-(((S)-1-hydroxypropan-2-yl)amino)pyrimidin-4-yl)-4-fluoro-1-oxoisoindolin-2-yl)propanoic acid (91 mg, 0.140 mmol) and triethylamine (78 μl, 0.561 mmol) in DMF (2 ml) was treated with TBTU (50 mg, 0.156 mmol) and stirred at room temperature overnight. The mixture was diluted with ethyl acetate (10 ml), was washed successively with 1M KHSO₄ (5 ml), NaHCO₃ (5 ml), brine (2×5 ml), water (4×5 ml), then dried (MgSO₄) and evaporated. The residue was purified on a 12 g graceresolv silica cartridge, using a gradient of 0 to 5% of ethanol in ethyl acetate as a eluent to give a colourless glass which was further purified by reversed phase preparative HPLC (Waters XSelect CSH C18 OBD, 130A, 5 μm, 19 mm×50 mm column, using a gradient of 20 to 50% of acetonitrile in water with 0.1% formic acid in both at 28 ml/min as eluent). The clean fractions were pooled and concentrated to remove most of the acetonitrile. The residue was freeze-dried to the title compound (21 mg, 27.4%) as a fluffy white solid. 1H NMR (DMSO-d6, 400 MHz) δ 8.56 (1H, d), 8.45 (1H, s), 7.97-7.88 (1H, m), 7.83 (1H, d), 7.34 (1H, s), 7.20 (1H, t), 7.13-7.00 (3H, m), 4.98 (1H, q), 4.89 (1H, t), 4.85-4.76 (2H, m), 4.74-4.67 (2H, m), 4.05-3.90 (1H, m), 3.59-3.41 (3H, m), 2.29 (3H, s), 1.44 (3H, d), 1.13 (3H, d). (One proton was not observed and overlapped with water peak). LCMS: [M+H]+=542.

Example 673: 2-(6-{5-chloro-2-[(propan-2-yl)amino]pyrimidin-4-yl}-4-fluoro-1-oxo-2,3-dihydro-1H-isoindol-2-yl)-N-[(1S)-2-hydroxy-1-(3-methoxyphenyl)ethyl]acetamide

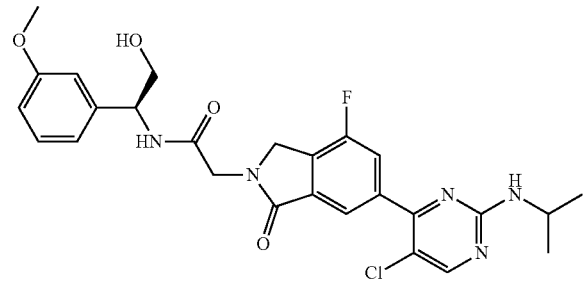 [SMILES: COc1cccc([C@@H](CO)NC(=O)CN2Cc3c(F)cc(-c4nc(NC(C)C)ncc4Cl)cc3C2=O)c1]

A solution of (S)-2-(6-(2-((3H-[1,2,3]triazolo[4,5-b]pyridin-3-yl)oxy)-5-chloropyrimidin-4-yl)-4-fluoro-1-oxoisoindolin-2-yl)-N-(2-hydroxy-1-(3-methoxyphenyl)ethyl)acetamide (62 mg, 0.102 mmol), isopropylamine (0.018 ml, 0.205 mmol) and DIPEA (0.054 ml, 0.307 mmol) in dioxane (2 mL) was sealed in a microwave vial and stirred at 85° C. (bath) overnight. The mixture was combined with the reaction mixture from a separate experiment (37 mg scale), diluted with ethyl acetate (20 ml), was washed with water (10 ml) followed by brine (20 ml), dried (Na2SO4) and evaporated. The residue was purified by chromatography (SiO2, 24 g column, 0 to 5% EtOH in EtOAc) to afford the title compound (42 mg, 44.5%) as a white powder. 1H NMR (DMSO-d6, 400 MHz) δ 8.54 (1H, d), 8.45 (1H, s), 7.92 (1H, s), 7.83 (1H, d), 7.53 (1H, d), 7.23 (1H, t), 6.92-6.85 (2H, m), 6.84-6.77 (1H, m), 4.92 (1H, t), 4.89-4.79 (1H, m), 4.67 (2H, s), 4.37-4.23 (2H, m), 4.08-3.95 (1H, m), 3.74 (3H, s), 3.64-3.48 (2H, m), 1.16 (6H, d). LCMS: [M+H]+=528.

Example 674: (2R)-2-(6-{5-chloro-2-[(oxan-4-yl)amino]pyrimidin-4-yl}-1-oxo-2,3-dihydro-1H-isoindol-2-yl)-N-[(1S)-2-hydroxy-1-phenylethyl]propanamide

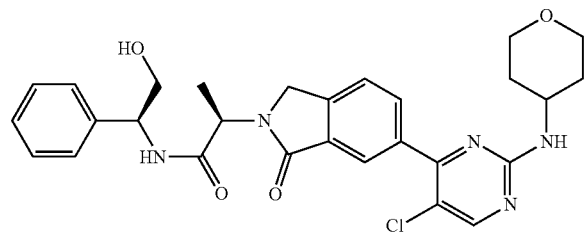 [SMILES: C[C@H](C(=O)N[C@H](CO)c1ccccc1)N1Cc2ccc(-c3nc(NC4CCOCC4)ncc3Cl)cc2C1=O]

Prepared using a similar procedure to Example 406. 1H NMR (DMSO-d6) δ: 8.59 (d, 1H), 8.45 (s, 1H), 8.04 (d, 1H), 7.98 (dd, 1H), 7.75 (d, 1H), 7.62 (s (br), 1H), 7.36-7.28 (m, 4H), 7.28-7.20 (m, 1H), 5.01 (q, 1H), 4.90 (t, 1H), 4.84 (td, 1H), 4.76 (d, 1H), 4.60 (d, 1H), 4.01-3.81 (m, 3H), 3.61-3.50 (m, 2H), 3.45-3.36 (m, 2H), 1.91-1.79 (m, 2H), 1.62-1.47 (m, 2H), 1.44 (d, 3H). LC-MS: [M+H]+=536.

Example 675: (2R)-2-(6-{5-chloro-2-[(oxan-4-yl)amino]pyrimidin-4-yl}-1-oxo-2,3-dihydro-1H-isoindol-2-yl)-N-[(1S)-2-hydroxy-1-(3-methoxyphenyl)ethyl]propanamide

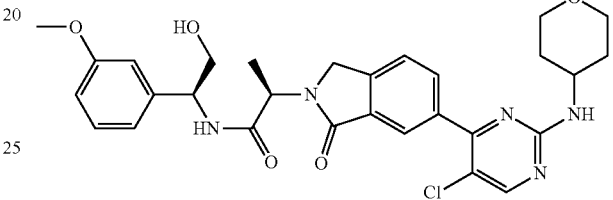

Prepared using a similar procedure to Example 451. 1H NMR (DMSO-d6, 400 MHz) δ 8.56 (1H, d), 8.45 (1H, s), 8.05-8.03 (1H, m), 7.98 (1H, dd), 7.75 (1H, d), 7.63 (1H, br. S), 7.27-7.20 (1H, m), 6.90-6.86 (2H, m), 6.85-6.76 (1H, m), 5.01 (1H, q), 4.89 (1H, t), 4.84-4.80 (1H, m), 4.77 (1H, d), 4.60 (1H, d), 3.99-3.83 (3H, m), 3.75 (3H, s), 3.57-3.52 (2H, m), 3.42-3.35 (2H, m), 1.88-1.80 (2H, m), 1.59-1.48 (2H, m), 1.45 (3H, d). LC-MS: [M+H]+=566.

Example 676: (2R)-2-(6-{5-chloro-2-[(oxan-4-yl)amino]pyrimidin-4-yl}-1-oxo-2,3-dihydro-1H-isoindol-2-yl)-N-[1-(hydroxymethyl)-2,3-dihydro-1H-inden-1-yl]propanamide

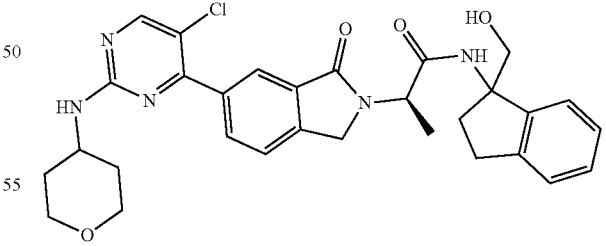

Prepared using a similar procedure to Example 95. 1H NMR (DMSO-d6) δ: 8.45 (s, 1H), 8.15-8.00 (m, 2H), 7.99-7.88 (m, 1H), 7.73 (dd, 1H), 7.63 (s, 1H), 7.26-7.05 (m, 4H), 5.05-4.91 (m, 2H), 4.70 (dd, 1H), 4.58 (dd, 1H), 3.96-3.83 (m, 3H), 3.61 (dt, 1H), 3.54-3.45 (m, 1H), 3.43-3.35 (m, 2H), 2.95-2.79 (m, 2H), 2.42-2.19 (m, 2H), 1.89-1.81 (m, 2H), 1.60-1.48 (m, 2H), 1.51-1.34 (m, 3H). LCMS: [M+H]+=562.

Example 677 (2R)-2-(6-{5-chloro-2-[(oxan-4-yl)amino]pyrimidin-4-yl}-1-oxo-2,3-dihydro-1H-isoindol-2-yl)-N-[(1S)-2-hydroxy-1-(3-methylphenyl)ethyl]butanamide

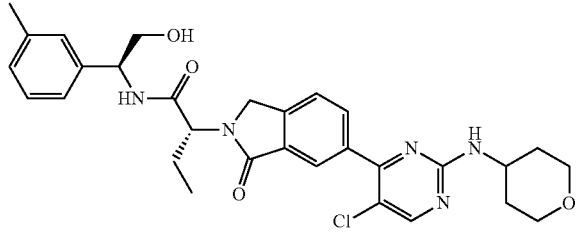 [SMILES: CC[C@H](C(=O)N[C@H](CO)c1cccc(C)c1)N1Cc2ccc(-c3nc(NC4CCOCC4)ncc3Cl)cc2C1=O]

Prepared using a similar procedure to Example 406. 1H NMR (DMSO, 400 MHz) δ 8.69 (1H, d), 8.45 (1H, s), 8.04 (1H, d), 7.97 (1H, dd), 7.74 (1H, d), 7.62 (1H, s), 7.20 (1H, dd), 7.12-7.07 (2H, m), 7.04 (1H, d), 4.90-4.81 (3H, m), 4.78 (1H, dt), 4.54 (1H, d), 3.97-3.82 (3H, m), 3.52 (2H, dd), 3.41-3.35 (2H, m), 2.29 (3H, s), 1.96-1.88 (1H, m), 1.88-1.80 (2H, m), 1.78-1.68 (1H, m), 1.58-1.46 (2H, m), 0.80 (3H, t). LCMS: [M+H]+=564.

Example 678 ((2R)-2-(6-{5-chloro-2-[(oxan-4-yl)amino]pyrimidin-4-yl}-1-oxo-2,3-dihydro-1H-isoindol-2-yl)-N-[(1S,2S)-2-hydroxy-1-phenylpropyl]butanamide

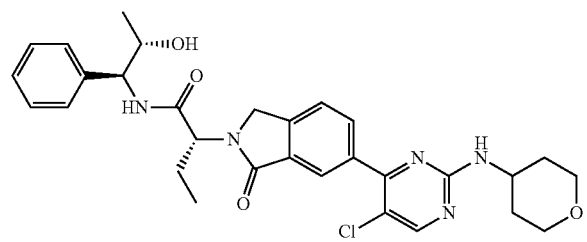

Prepared using a similar procedure to Example 406. 1H NMR (DMSO, 400 MHz) δ 8.62 (1H, d), 8.45 (1H, s), 8.05 (1H, d), 7.97 (1H, dd), 7.74 (1H, d), 7.62 (1H, s), 7.34-7.28 (4H, m), 7.24-7.19 (1H, m), 4.95 (1H, dd), 4.85 (1H, d), 4.75 (1H, d), 4.67 (1H, dd), 4.54 (1H, d), 3.97-3.80 (4H, m), 3.41-3.36 (2H, m), 1.95-1.81 (3H, m), 1.77-1.67 (1H, m), 1.58-1.47 (2H, m), 0.93 (3H, d), 0.80 (3H, t). LCMS: [M+H]+=564.

Example 679: (2R)-2-(6-{5-chloro-2-[(oxan-4-yl)amino]pyrimidin-4-yl}-1-oxo-2,3-dihydro-1H-isoindol-2-yl)-N-[(1S,2R)-2-hydroxy-2,3-dihydro-1H-inden-1-yl]propanamide

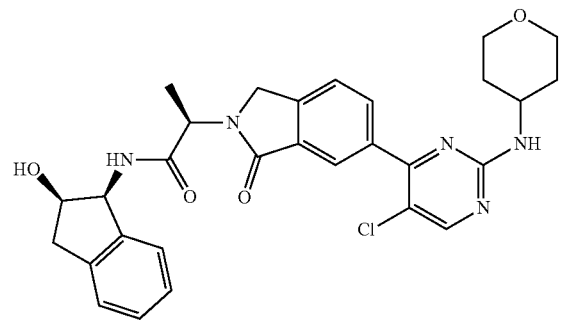 [SMILES: C[C@H](C(=O)N[C@H]1c2ccccc2C[C@H]1O)N1Cc2ccc(-c3nc(NC4CCOCC4)ncc3Cl)cc2C1=O]

Prepared using a similar procedure to Example 95. In this case, the product was further purified by preparative HPLC (acidic). 1H NMR (DMSO-d6) δ: 8.42 (s, 1H), 8.15 (d, 1H), 8.03 (d, 1H), 7.97 (dd, 1H), 7.77 (d, 1H), 7.55 (s, 1H), 7.25-7.10 (m, 4H), 5.19 (dd, 1H), 5.11-4.99 (m, 1H), 4.85 (d, 1H), 4.67 (d, 1H), 4.46-4.36 (m, 1H), 3.95-3.77 (m, 3H), 3.45-3.28 (m, 2H), 3.03 (dd, 1H), 2.79 (d, 1H), 1.94-1.74 (m, 2H), 1.56 (d, 4H), 1.55-1.43 (m, 2H). LC-MS: [M+H]+= 548.

Example 680: (2S)-2-(6-{5-chloro-2-[(oxan-4-yl)amino]pyrimidin-4-yl}-1-oxo-2,3-dihydro-1H-isoindol-2-yl)-N-[(1S)-2-hydroxy-1-phenylethyl]propanamide DIPEA (0.075 ml, 0.427 mmol) and HATU (121 mg, 0.318 mmol) were added to a stirred solution of (S)-2-(6-(5-chloro-2-((oxan-4-yl)amino)pyrimidin-4-yl)-1-oxoisoindolin-2-yl)propanoic acid (90 mg, 0.216 mmol), and (S)-2-amino-2-phenylethanol (29.6 mg, 0.216 mmol) in DCM (2 ml, 0.216 mmol). The resulting suspension was treated with MeCN (2 ml) and the resulting solution was stirred for 1 h, then concentrated under vacuum. The residue was dissolved in DCM and purified by chromatography (SiO2, 12 g column, 0-10% MeCN in EtOAc) to afford the title compound (90 mg, 78%) as a cream coloured solid. 1H NMR (DMSO-d6, 400 MHz) δ 8.5 (d, 1H), 8.44 (s, 1H), 8.02 (s, 1H), 7.97 (d, 1H) 7.73 (d, 1H), 7.61 (s (br), 1H), 7.3-.7.18 (m, 5H), 4.98 (q, 1H) 4.89 (t, 1H), 4.83 (q, 1H), 4.63 (q, 2H), 4-3.8 (m, 3H), 3.57 (t, 2H), 3.4-3.3 (m, 2H), 1.87-1.83 (m, 2H), 1.56-1.5 (m, 5H). LCMS: [M+H]+=534.

Example 681: (2R)-2-(6-{5-chloro-2-[(oxan-4-yl) amino]pyrimidin-4-yl}-1-oxo-2,3-dihydro-1H-isoindol-2-yl)-N-[(1R)-1-[3-(hydroxymethyl)phenyl] ethyl]propanamide

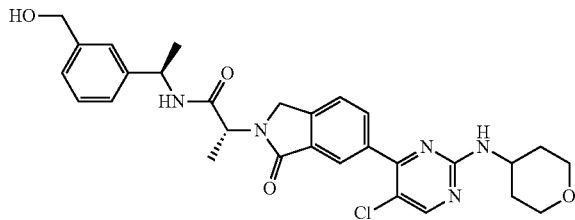 [SMILES: C[C@H](C(=O)N[C@H](C)c1cccc(CO)c1)N1Cc2ccc(-c3nc(NC4CCOCC4)ncc3Cl)cc2C1=O]

DIPEA (0.079 ml, 0.452 mmol) and HATU (127 mg, 0.333 mmol) were added to a stirred solution of (R)-2-(6-(5-chloro-2-((oxan-4-yl)amino)pyrimidin-4-yl)-1-oxoisoindolin-2-yl)propanoic acid. TFA (120 mg, 0.226 mmol), and (R)-(3-(1-aminoethyl)phenyl)methanol (68.4 mg, 0.452 mmol) in acetonitrile (5 ml, 0.226 mmol) and the resulting solution was stirred at ambient temperature for 1 h. The solution was concentrated and the residue was dissolved in a small quantity of DCM, then purified by chromatography (SiO$_2$, 4 g column, 100% EtOAc). Concentration of the pure fractions gave a colourless solid (107 mg), which was dissolved in MeOH and loaded on a column packed with SCX. The SCX was washed with methanol until no longer acidic to test paper, then the product was eluted with 1% ammonia in methanol. The resulting solution was concentrated to dryness under vacuum and the residue triturated with diethyl ether (1 ml) to afford the title compound (60 mg, 0.106 mmol, 46.8% yield) as a colourless solid. 1H NMR (400 MHz, DMSO-d6) δ 8.64 (d, 1H), 8.45 (s, 1H), 8.03 (s, 1H), 7.97 (d, 1H), 7.75 (d, 1H), 7.62 (s (br), 1H), 7.27 (m, 2H), 7.17 (d, 2H), 5.19 (t, 1H), 4.93 (m, 2H), 4.75 (d, 1H), 4.61 (d, 1H), 4.49 (d, 2H), 3.99-3.82 (m, 3H), 3.43-3.34 (m, 2H), 1.85 (d, 2H), 1.52 (m, 2H), 1.45 (d, 3H), 1.36 (d, 3H). LCMS: [M+H]+=550.

Example 682: (2R)-(2R)-2-(6-{5-chloro-2-[(oxan-4-yl)amino]pyrimidin-4-yl}-1-oxo-2,3-dihydro-1H-isoindol-2-yl)-N-[(1S,2S)-2-hydroxy-1-phenylpropyl]propanamide

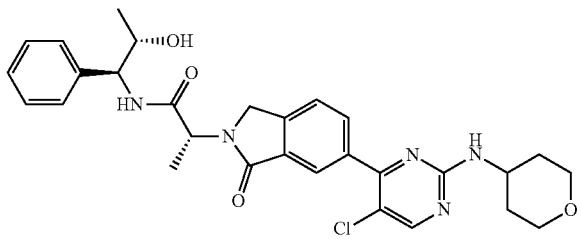 [SMILES: C[C@H](O)[C@@H](NC(=O)[C@@H](C)N1Cc2ccc(-c3nc(NC4CCOCC4)ncc3Cl)cc2C1=O)c1ccccc1]

Prepared using a similar procedure to Example 539. 1H NMR (DMSO-d6, 400 MHz) δ 8.49 (1H, d), 8.45 (1H, s), 8.05 (1H, s), 8.00-7.95 (1H, m), 7.74 (1H, d), 7.63 (1H, s), 7.37-7.19 (5H, m), 5.07 (1H, q), 4.78 (1H, d), 4.69 (1H, m), 4.61 (1H, d), 3.99-3.80 (4H, m), 3.35 (2H, m+water) 1.92-1.78 (2H, m), 1.53 (2H, m), 1.42 (3H, d), 0.96 (3H, d) (note: exchangeable OH signal was not observed and may have been overlapped with water or DMSO peaks). LCMS: [M+H]+=550.

Example 683: (2R)-2-(6-{5-chloro-2-[(oxan-4-yl)amino]pyrimidin-4-yl}-1-oxo-2,3-dihydro-1H-isoindol-2-yl)-N-[(1S)-2-hydroxy-1-(3-methylphenyl) ethyl]propanamide

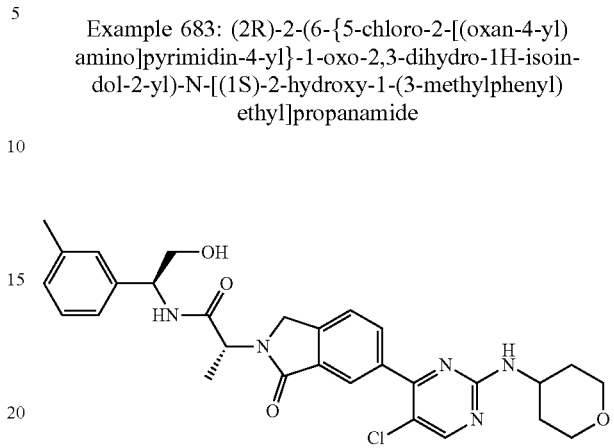

Method A:

A mixture of (R)-2-(6-(2,5-dichloropyrimidin-4-yl)-1-oxoisoindolin-2-yl)-N—((S)-2-hydroxy-1-(m-tolyl)ethyl) propanamide (200 mg, 0.330 mmol), oxan-4-amine (50.0 mg, 0.494 mmol) and N-ethyl-N-isopropylpropan-2-amine (144 µl, 0.824 mmol) in dry Dioxane (3 ml) was stirred and heated at 85° C. overnight. The reaction mixture was cooled to room temperature and partitioned between 1M HCl (50 ml) and dichloromethane (100 ml). The organic phase was collected and washed with NaHCO$_3$ (25 ml), dried (MgSO$_4$), filtered and concentrating to dryness. The residual oil was purified by chromatography (SiO$_2$, 4 g column, 100% EtOAc). The pure fractions were combined and concentrated to give a foam (95 mg) which upon trituration with diethyl ether (15 ml) afforded the title compound (75 mg, 41.4%) as a cream coloured solid.

Method B:

triethylamine (2.060 mL, 14.78 mmol) was added to a suspension of (R)-2-(6-(5-chloro-2-((oxan-4-yl)amino)pyrimidin-4-yl)-1-oxoisoindolin-2-yl)propanoic acid (1.54 g, 3.69 mmol) and (S)-2-amino-2-(m-tolyl)ethanol hydrochloride (0.763 g, 4.06 mmol) in DMF (15 mL, 194 mmol). After 15 minutes, TBTU (1.305 g, 4.06 mmol) was added and the mixture was stirred for 2 h at room temperature. The reaction was diluted with EtOAc (30 mL) and water (100 mL). The phases were separated and the aqueous phase was extracted with EtOAc (2×30 mL). The combined organic extracts were washed with NH$_4$Cl (100 mL), NaHCO$_3$ (100 mL), brine (2×100 mL), dried (MgSO$_4$) and concentrated. The crude product was purified by chromatography (SiO$_2$, 40 g column, 0-7% MeOH in DCM) to afford the product as a colourless gum. The gum was triturated with diethyl ether (100 mL) to give the title compound (1.409 g, 68.0%) as a white solid.

1H NMR (DMSO, 400 MHz) δ 8.56 (1H, d), 8.45 (1H, s), 8.08-8.02 (1H, m), 7.98 (1H, dd), 7.75 (1H, d), 7.63 (1H, s), 7.21 (1H, t), 7.13-6.96 (3H, m), 5.01 (1H, q), 4.93-4.84 (1H, m), 4.83-4.72 (2H, m), 4.60 (1H, d), 4.01-3.80 (3H, m), 3.59-3.50 (2H, m), 3.43-3.36 (2H, m), 2.30 (3H, s), 1.90-1.79 (2H, m), 1.60-1.46 (2H, m), 1.43 (3H, d). LCMS: [M+H]+=550.

Example 684: (2R)-2-(6-{5-chloro-2-[(oxan-4-yl)amino]pyrimidin-4-yl}-1-oxo-2,3-dihydro-1H-isoindol-2-yl)-N-[(1S)-1-(3-ethoxyphenyl)-2-hydroxyethyl]propanamide

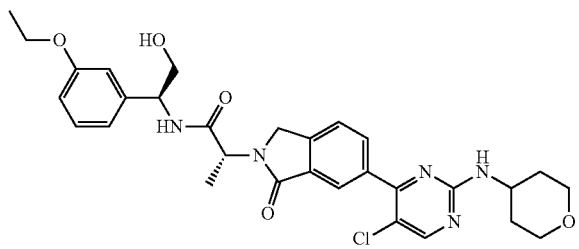 [SMILES: CCOc1cccc([C@@H](CO)NC(=O)[C@@H](C)N2Cc3ccc(-c4nc(NC5CCOCC5)ncc4Cl)cc3C2=O)c1]

Prepared using a similar procedure to Example 592. 1H NMR (DMSO, 400 MHz) δ 8.57 (1H, d), 8.44 (1H, s), 8.06-8.01 (1H, m), 7.97 (1H, dd), 7.74 (1H, d), 7.61 (1H, s), 7.25-7.16 (1H, m), 6.89-6.82 (2H, m), 6.81-6.74 (1H, m), 5.05-4.85 (2H, m), 4.85-4.71 (2H, m), 4.59 (1H, d), 4.07-3.80 (5H, m), 3.60-3.48 (2H, m), 3.43-3.36 (2H, m), 1.91-1.77 (2H, m), 1.60-1.37 (5H, m), 1.32 (3H, t). LCMS: [M+H]+=580.

Example 685: (2R)-2-(6-{5-chloro-2-[(oxan-4-yl)amino]pyrimidin-4-yl}-1-oxo-2,3-dihydro-1H-isoindol-2-yl)-N-[(1S)-1-(3-fluoro-5-methoxyphenyl)-2-hydroxyethyl]propanamide

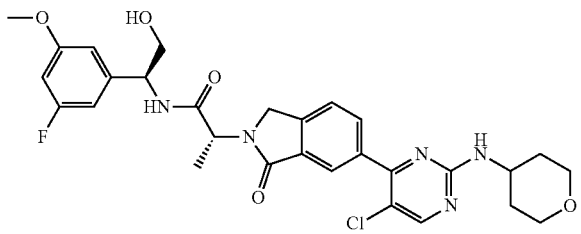 [SMILES: COc1cc(F)cc([C@@H](CO)NC(=O)[C@@H](C)N2Cc3ccc(-c4nc(NC5CCOCC5)ncc4Cl)cc3C2=O)c1]

A stirred solution of (R)-2-(6-(5-chloro-2-((oxan-4-yl)amino)pyrimidin-4-yl)-1-oxoisoindolin-2-yl)propanoic acid (70 mg, 0.168 mmol), (S)-2-amino-2-(3-fluoro-5-methoxyphenyl)ethanol, HCl (41 mg, 0.185 mmol) and triethylamine (0.094 ml, 0.672 mmol) in DMF (1 ml) was treated with TBTU (65 mg, 0.202 mmol) and stirred at room temperature overnight. The mixture was diluted with ethyl acetate (20 ml), was washed successively with 1M KHSO$_4$ (10 ml), NaHCO$_3$ (10 ml), brine (2×10 ml) and then water (4×10 ml), was dried (MgSO$_4$) and evaporated. The residue was purified by chromatography (SiO$_2$, 12 g column, 0-5% EtOOH in EtOAc) to give a glass, which was triturated with ether (2 ml) to give a solid. The solid was collected by filtration, washed with ether (2×1 ml) and dried under vacuum at 50° C. overnight to give the title compound (64.3 mg, 64.3%) as a cream solid. 1H NMR (DMSO, 400 MHz) δ 8.56 (1H, d), 8.44 (1H, s), 8.07-8.00 (1H, m), 7.97 (1H, dd), 7.74 (1H, d), 7.61 (1H, s), 6.76-6.64 (3H, m), 4.99 (1H, q), 4.91 (1H, t), 4.86-4.70 (2H, m), 4.60 (1H, d), 4.00-3.80 (3H, m), 3.76 (3H, s), 3.60-3.47 (2H, m), 3.40-3.33 (2H, m), 1.84 (2H, d), 1.59-1.39 (5H, m).). LCMS: [M+H]+=584.

Example 686: (2R)-2-(6-{5-chloro-2-[(oxan-4-yl)amino]pyrimidin-4-yl}-1-oxo-2,3-dihydro-1H-isoindol-2-yl)-N-[(1S)-1-(3-fluoro-5-methylphenyl)-2-hydroxyethyl]propanamide

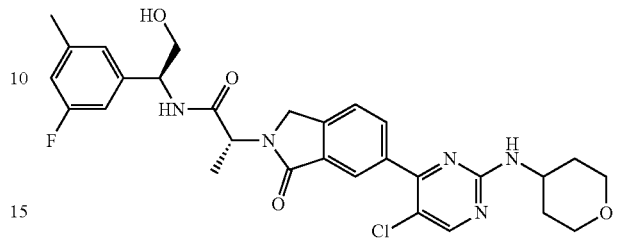

Prepared using a similar procedure to Example 685. 1H NMR (DMSO, 400 MHz) δ 8.55 (1H, d), 8.44 (1H, s), 8.06-8.01 (1H, m), 7.97 (1H, dd), 7.74 (1H, d), 7.61 (1H, s), 6.99-6.84 (3H, m), 4.99 (1H, q), 4.91 (1H, t), 4.86-4.74 (1H, m), 4.72 (1H, s), 4.60 (1H, d), 4.00-3.79 (3H, m), 3.60-3.46 (2H, m), 3.41-3.34 (2H, m), 2.35-2.24 (3H, m), 1.84 (2H, d), 1.61-1.37 (5H, m). LCMS: [M+H]+=568.

Example 687: (2R)-2-(6-{5-chloro-2-[(oxan-4-yl)amino]pyrimidin-4-yl}-1-oxo-2,3-dihydro-1H-isoindol-2-yl)-N-[(1S)-1-(4-fluoro-3-methylphenyl)-2-hydroxyethyl]propanamide

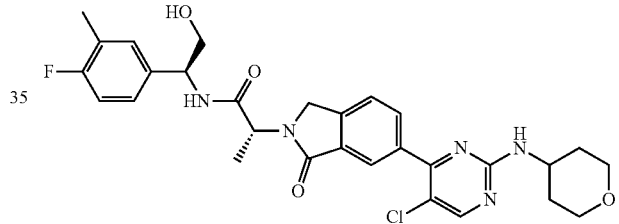

Prepared using a similar procedure to Example 590. 1H NMR (400 MHz, DMSO-d6) δ 8.54 (d, 1H), 8.45 (s, 1H), 8.03 (s, 1H), 7.97 (dd, 1H), 7.74 (d, 1H), 7.61 (br. S, 1H), 7.19 (d, 1H), 7.14 (td, 1H), 7.07 (dd, 1H), 4.98 (q, 1H), 4.89 (t, 1H), 4.83-4.53 (m, 3H), 3.92-3.85 (m, 3H), 3.52 (t, 2H), 3.33-3.40 (m, 2H), 2.22 (d, 3H), 1.84 (d, 2H), 1.52 (qd, 2H), 1.42 (d, 3H). LCMS: [M+H]+=568.

Example 688: (2R)-2-(6-{5-chloro-2-[(oxan-4-yl)amino]pyrimidin-4-yl}-1-oxo-2,3-dihydro-1H-isoindol-2-yl)-N-[(1S)-2-hydroxy-1-(6-methoxypyridin-2-yl)ethyl]propanamide

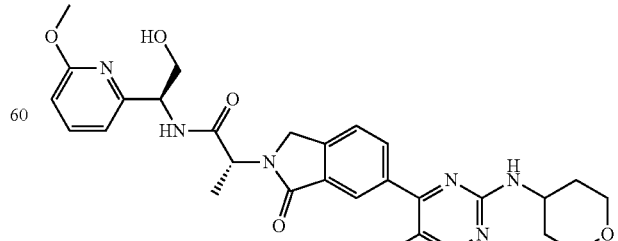

TBTU (0.057 g, 0.176 mmol) was added to a mixture of (R)-2-(6-(5-chloro-2-((oxan-4-yl)amino)pyrimidin-4-yl)-1-oxoisoindolin-2-yl)propanoic acid (0.07 g, 0.168 mmol), (S)-2-amino-2-(6-methoxypyridin-2-yl)ethanol hydrochloride (0.036 g, 0.176 mmol) and DIPEA (0.062 ml, 0.353 mmol) in DMF (1 mL) and the mixture was stirred for 45 minutes. DIPEA (0.032 ml, 0.185 mmol) was added and the mixture was stirred for a further 45 minutes. The mixture was diluted with EtOAc and transferred into a separating funnel. NH₄Cl was added and the product was extracted with EtOAc. The combined organic extracts were washed with water, NaHCO₃, brine, dried (MgSO₄) and absorbed on silica. The crude product was purified by chromatography (SiO₂, 12 g column, 0-5% MeOH in DCM) to afford a colourless glass (64 mg). The product was re-purified by chromatography (SiO₂, 12 g column, 0-2% MeOH in EtOAc), then by preparative HPLC (Varian, Acidic (0.1% Formic acid), Acidic, Waters X-Select Prep-C18, 5 μm, 19×50 mm column, 20-50% MeCN in Water). Fractions were pooled and reduced to a small volume under vacuum. The residue was partitioned between EtOAc and NaHCO₃ and the product was extracted with EtOAc. The combined organic extracts were washed with brine, dried (MgSO₄) and concentrated under vacuum to the title compound (0.028 g, 28.8%) as a white solid after trituration and evaporation from Et₂O. 1H NMR (DMSO-d6) δ: 8.55-8.47 (m, 2H), 8.10 (d, 1H), 8.04 (dd, 1H), 7.81 (d, 1H), 7.72 (dd, 1H), 7.69 (s (br), 1H), 6.98 (d, 1H), 6.74 (d, 1H), 5.13 (td, 1H), 4.93 (t, 1H), 4.90-4.87 (m, 1H), 4.84 (d, 1H), 4.68 (d, 1H), 4.04-3.89 (m, 3H), 3.88 (s, 3H), 3.84-3.75 (m, 1H), 3.74-3.66 (m, 1H), 3.48-3.41 (m, 2H), 1.96-1.85 (m, 2H), 1.65-1.57 (m, 2H), 1.55 (d, 3H). LCMS: [M+H]+=567.

Example 689: (2R)-2-(6-{5-chloro-2-[(oxan-4-yl)amino]pyrimidin-4-yl}-1-oxo-2,3-dihydro-1H-isoindol-2-yl)-N-[(1S)-1-(2-fluoro-3-methylphenyl)-2-hydroxyethyl]propanamide

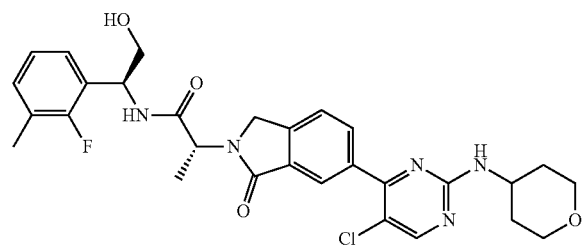 [SMILES: Cc1cccc([C@@H](CO)NC(=O)[C@@H](C)N2Cc3ccc(-c4nc(NC5CCOCC5)ncc4Cl)cc3C2=O)c1F]

Prepared using a similar procedure to Example 685. 1H NMR (DMSO-d6, 400 MHz) δ 8.64 (1H, d), 8.45 (1H, s), 8.05-8.00 (1H, m), 7.97 (1H, dd), 7.74 (1H, d), 7.62 (1H, s), 7.23-7.11 (2H, m), 7.06 (1H, t), 5.18-5.06 (1H, m), 5.06-4.94 (2H, m), 4.80-4.52 (2H, m), 3.98-3.80 (3H, m), 3.59-3.45 (2H, m), 3.43-3.33 (2H, m), 2.22 (3H, d), 1.84 (2H, d), 1.60-1.46 (2H, m), 1.41 (3H, d). LCMS: [M+H]+=568.

Example 690: (2R)-2-(6-{5-chloro-2-[(oxan-4-yl)amino]pyrimidin-4-yl}-1-oxo-2,3-dihydro-1H-isoindol-2-yl)-N-[(1S)-1-(2-fluoro-5-methylphenyl)-2-hydroxyethyl]propanamide

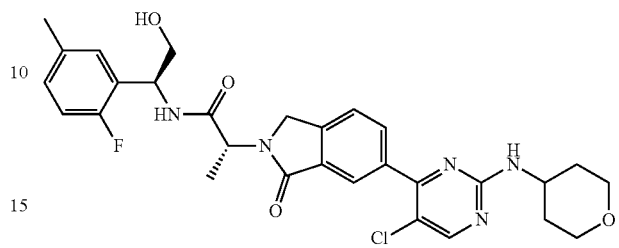

Prepared using a similar procedure to Example 590. 1H NMR (400 MHz, DMSO-d6) δ 8.61 (d, 1H), 8.45 (s, 1H), 8.04 (s, 1H), 7.98 (dd, 1H), 7.75 (d, 1H), 7.62 (br. S, 1H), 7.18 (d, 1H), 7.13-6.98 (m, 2H), 5.09 (q, 1H), 5.05-4.99 (m, 2H), 4.81-4.54 (m, 2H), 4.01-3.80 (m, 3H), 3.54 (q, 2H), 3.39 (t, 2H), 2.28 (s, 3H), 1.85 (d, 2H), 1.61-1.47 (m, 2H), 1.43 (d, 3H). LCMS: [M+H]+=568.

Example 691: (2R,3S)-2-(6-{5-chloro-2-[(oxan-4-yl)amino]pyrimidin-4-yl}-1-oxo-2,3-dihydro-1H-isoindol-2-yl)-3-hydroxy-N-[(1R)-1-(3-methoxyphenyl)ethyl]butanamide

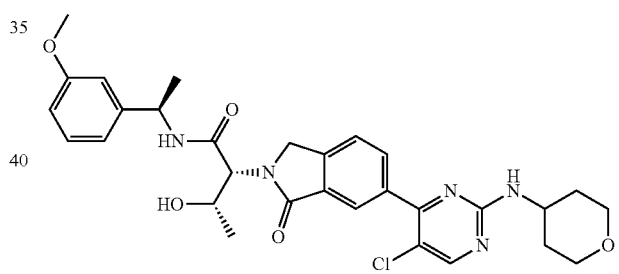

A solution of (2R,3S)-2-(6-(2,5-dichloropyrimidin-4-yl)-1-oxoisoindolin-2-yl)-3-hydroxy-N—((R)-1-(3-methoxyphenyl)ethyl)butanamide (150 mg, 0.239 mmol), oxan-4-amine (49.4 μl, 0.477 mmol) and DIPEA (108 μl, 0.621 mmol) in 1,4-dioxane (5 mL) was stirred at 80 C overnight. The reaction mixture was cooled to room temperature, diluted with EtOAc (10 mL), washed successively with KHSO4 (1M, 10 mL), NaHCO₃ (10 mL) and brine (10 mL), dried (MgSO₄) and concentrated in vacuo. Purification by chromatography (SiO₂, 0-100% EtOAc in iso-hexanes) gave the title compound (58 mg, 40.6%) as a colourless glass. 1H NMR (DMSO, 400 MHz) δ 8.88 (1H, d), 8.45 (1H, s), 8.07-8.03 (1H, m), 7.97 (1H, dd), 7.77 (1H, d), 7.62 (1H, s), 7.22 (1H, dd), 6.95-6.88 (2H, m), 6.78 (1H, ddd), 5.03 (1H, d), 4.96-4.84 (2H, m), 4.77-4.69 (2H, m), 4.14 (1H, q), 3.97-3.83 (3H, m), 3.74 (3H, s), 3.42-3.35 (2H, m), 1.89-1.81 (2H, m), 1.60-1.49 (21H, m), 1.34 (3H, d), 1.03 (3H, d). LCMS: [M+H]+=580.

Example 692: (2R)-2-(6-{5-chloro-2-[(oxan-4-yl)amino]pyrimidin-4-yl}-1-oxo-2,3-dihydro-1H-isoindol-2-yl)-N-[(1S)-2-hydroxy-1-(6-methylpyridin-2-yl)ethyl]propanamide

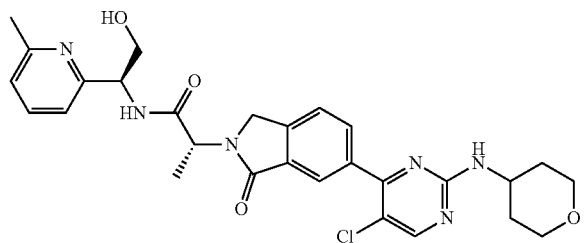 [SMILES: Cc1cccc([C@@H](CO)NC(=O)[C@@H](C)N2Cc3ccc(-c4nc(NC5CCOCC5)ncc4Cl)cc3C2=O)n1]

TBTU (0.065 g, 0.202 mmol) was added to a mixture of (R)-2-(6-(5-chloro-2-((oxan-4-yl)amino)pyrimidin-4-yl)-1-oxoisoindolin-2-yl)propanoic acid (0.08 g, 0.192 mmol), ((S)-2-amino-2-(6-methylpyridin-2-yl)ethanol dihydrochloride (0.045 g, 0.202 mmol) and DIPEA (0.134 ml, 0.768 mmol) in DMF (1 mL) and the mixture was stirred for 45 minutes. The mixture was diluted with EtOAc and transferred into a separating funnel. NH4Cl was added and the product was extracted with EtOAc. The combined organic extracts were washed with water, NaHCO₃, brine, dried (MgSO₄) and absorbed on silica. The crude product was purified by chromatography (SiO₂, 12 g column, DCM: MeOH gradient 100%-95%) to afford (R)-2-(6-(5-chloro-2-((oxan-4-yl)amino)pyrimidin-4-yl)-1-oxoisoindolin-2-yl)-N—((S)-2-hydroxy-1-(6-methylpyridin-2-yl)ethyl)propanamide a white solid (32 mg). The product was repurified by preparative HPLC (Waters, Acidic (0.1% Formic acid), Acidic, Waters X-Select Prep-C18, 5 µm, 19×50 mm column, 10-40% MeCN in Water). The fractions were pooled, concentrated under vacuum and the residue was diluted with EtOAc and NaHCO₃. The product was extracted with EtOAc and the combined organic extracts were washed with brine, dried (MgSO4) and concentrated under vacuum to afford the title compound (0.032 g, 30.0%) as a white solid after trituration and evaporation from Et2O. 1H NMR (DMSO-d6) δ: 8.52 (d, 1H), 8.45 (s, 1H), 8.04 (s (br), 1H), 7.98 (dd, 1H), 7.79-7.58 (m, 3H), 7.13 (dd, 2H), 5.05 (td, 1H), 4.91-4.80 (m, 2H), 4.77 (d, 1H), 4.62 (d, 1H), 4.00-3.82 (m, 3H), 3.77-3.58 (m, 2H), 3.44-3.36 (m, 2H), 2.43 (s, 3H), 1.89-1.80 (m, 2H), 1.59-1.50 (m, 2H), 1.48 (d, 3H). LCMS: [M+H]+=551.

Example 693: 2-(6-{5-chloro-2-[(oxan-4-yl)amino]pyrimidin-4-yl}-1-oxo-2,3-dihydro-1H-isoindol-2-yl)-3-hydroxy-N-[(1R)-1-phenylethyl]propanamide

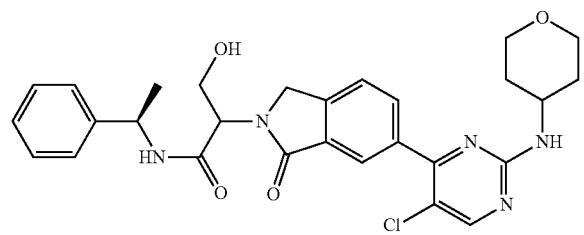 [SMILES: C[C@@H](NC(=O)C(CO)N1Cc2ccc(-c3nc(NC4CCOCC4)ncc3Cl)cc2C1=O)c1ccccc1]

Prepared using a similar procedure to Example 120 In this case, the product was purified by preparative HPLC (acidic). The product was obtained as a 3:2 mixture of diastereoisomers. 1H NMR (CDCl₃, 400 MHz) δ 8.33 (1H, s), 8.28 (1H, d), 8.00 (1H, m), 7.58 (0.6H, d), 7.51 (0.4H, d), 7.36-7.28 (2H, m), 7.16-7.09 (2.6H, m), 7.04 (0.4H, d), 5.23 (1H, d), 5.05 (1H, p), 4.93 (0.4H, t), 4.90 (0.6H, t), 4.84-4.66 (1.6H, m), 4.42 (0.4H, d), 4.29-4.18 (1H, m), 4.11-3.95 (4H, m), 3.77 (1H, bs), 3.54 (2H, td), 2.04 (2H, m), 1.57 (2H, m), 1.47 (1H, d), 1.43 (2H, d). (exchangeable OH not observed). LC-MS: [M+H]+=536.

Examples 694 and 695: (2R)-2-(6-{5-chloro-2-[(oxan-4-yl)amino]pyrimidin-4-yl}-1-oxo-2,3-dihydro-1H-isoindol-2-yl)-3-hydroxy-N-[(1R)-1-(3-methoxyphenyl)ethyl]propanamide and (2S)-2-(6-{5-chloro-2-[(oxan-4-yl)amino]pyrimidin-4-yl}-1-oxo-2,3-dihydro-1H-isoindol-2-yl)-3-hydroxy-N-[(1R)-1-(3-methoxyphenyl)ethyl]propanamide

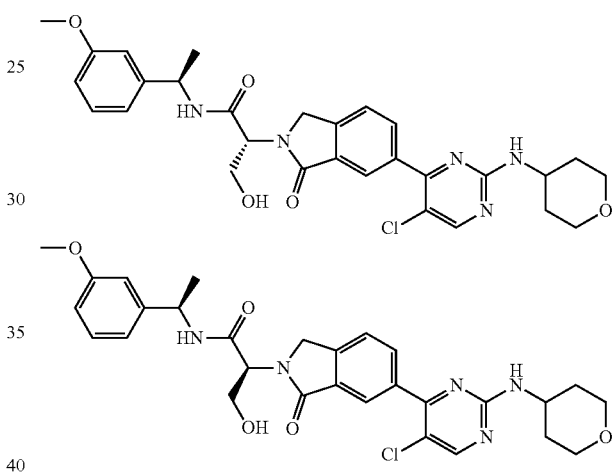

3-((tert-butyldimethylsilyl)oxy)-2-(6-(5-chloro-2-((oxan-4-yl)amino)pyrimidin-4-yl)-1-oxoisoindolin-2-yl)-N—((R)-1-(3-methoxyphenyl)ethyl)propanamide (Preparation 413, 260 mg, 0.382 mmol) was taken up in TFA (2 ml), allowed to stand for 2 minutes and evaporated. The residue was basified with NaHCO₃ (10 ml) and extracted with ethyl acetate (3×10 ml). The combined organic extracts were washed with brine (10 ml), dried (Na₂SO₄) and evaporated to give a viscous yellow oil. Purification by chromatography (SiO₂, 12 g column, 50-100% EtOAc in isohexane) afforded (2R)-2-(6-{5-chloro-2-[(oxan-4-yl)amino]pyrimidin-4-yl}-1-oxo-2,3-dihydro-1H-isoindol-2-yl)-3-hydroxy-N-[(1R)-1-(3-methoxyphenyl)ethyl]propanamide (55 mg, 25.4%) (A) and (2S)-2-(6-{5-chloro-2-[(oxan-4-yl)amino]pyrimidin-4-yl}-1-oxo-2,3-dihydro-1H-isoindol-2-yl)-3-hydroxy-N-[(1R)-1-(3-methoxyphenyl)ethyl]propanamide (19 mg, 8.78%) (B) as white powders. A: 1H NMR (DMSO-d6) δ: 8.69 (d, 1H), 8.45 (s, 1H), 8.03 (d, 1H), 7.97 (dd, 1H), 7.76 (d, 1H), 7.62 (s (br), 1H), 7.23 (dd, 1H), 6.91-6.83 (m, 2H), 6.78 (ddd, 1H), 5.13 (t, 1H), 4.98-4.86 (m, 2H), 4.81 (d, 1H), 4.64 (d, 1H), 3.97-3.77 (m, 5H), 3.75 (s, 3H), 3.41-3.34 (m, 2H), 1.91-1.77 (m, 2H), 1.60-1.43 (m, 2H), 1.34 (d, 3H). LCMS: [M+H]+=566. B: 1H NMR (DMSO-d6) δ: 8.68 (d, 1H), 8.44 (s, 1H), 8.01 (d, 1H), 7.96 (dd, 1H), 7.74 (d, 1H), 7.61 (s (br), 1H), 7.18 (dd, 1H), 6.88-6.82 (m, 2H), 6.75 (ddd, 1H), 5.13 (s (br), 1H), 4.96-4.83 (m, 2H), 4.75 (d, 1H), 4.64 (d, 1H), 3.98-3.78 (m, 5H), 3.68 (s, 3H), 3.49-3.38 (m, 2H), 1.90-1.76 (m, 2H), 1.60-1.43 (m, 2H), 1.34 (d, 3H). LCMS: [M+H]⁺=566.

Example 696: (2R)-2-(6-{5-chloro-2-[(oxan-4-yl)amino]pyrimidin-4-yl}-1-oxo-2,3-dihydro-1H-isoindol-2-yl)-4-hydroxy-N-[(1R)-1-(3-methoxyphenyl)ethyl]butanamide

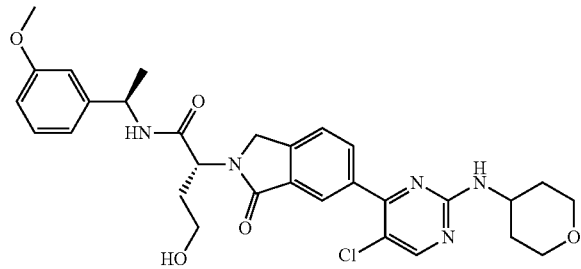 [SMILES: COc1cccc([C@@H](C)NC(=O)[C@@H](CCO)N2Cc3ccc(-c4nc(NC5CCOCC5)ncc4Cl)cc3C2=O)c1]

A mixture of (R)-2-(6-(2,5-dichloropyrimidin-4-yl)-1-oxoisoindolin-2-yl)-4-hydroxy-N—((R)-1-(3-methoxyphenyl)ethyl)butanamide (Preparation 403, 0.023 g, 0.043 mmol), oxan-4-amine (0.010 mL, 0.097 mmol) and DIPEA (0.020 mL, 0.115 mmol) in 1,4-dioxane (2.0 mL, 23.38 mmol) was heated to 90° C. overnight. After 16.5 h further oxan-4-amine (0.010 mL, 0.097 mmol) and DIPEA (0.020 mL, 0.115 mmol) were added and the mixture was heated to 90° C. for 41 h. The reaction mixture was cooled to room temperature and then partitioned between EtOAc (30 mL) and NH₄Cl (20 mL), The layers were separated and the organic fraction was washed with NH₄Cl (20 mL), water (20 mL) and brine (3×20 mL), then dried (MgSO₄), filtered and concentrated under reduced pressure to afford the crude product (26 mg) as a pale yellow solid. The crude product was purified by chromatography (SiO₂, 4 g column, 0-10% MeOH in DCM) to afford the title compound butanamide (0.015 g, 58.5%) as a white solid. 1H NMR (DMSO-d6, 400 MHz) δ 8.70 (1H, d), 8.45 (1H, s), 8.03 (1H, t), 7.97 (1H, dd), 7.75 (1H, d), 7.62 (1H, br. s), 7.24 (1H, t), 6.91-6.87 (2H, m), 6.80 (1H, ddd), 4.99 (1H, dd), 4.88 (1H, p), 4.81 (1H, d), 4.65-4.51 (2H, m), 3.90 (3H, dd), 3.96-3.85 (3H, m), 3.44-3.34 (4H, m), 2.06 (1H, dq), 2.01-1.88 (1H, m), 1.85 (2H, br. d), 1.53 (2H, qd), 1.34 (3H, d). LCMS: [M+H]⁺=580.

Example 697: (2R)-2-(6-{5-chloro-2-[(2-methyl-2H-1,2,3-triazol-4-yl)amino]pyrimidin-4-yl}-1-oxo-2,3-dihydro-1H-isoindol-2-yl)-N-[(1S)-1-(3-fluoro-5-methoxyphenyl)-2-hydroxyethyl]propanamide

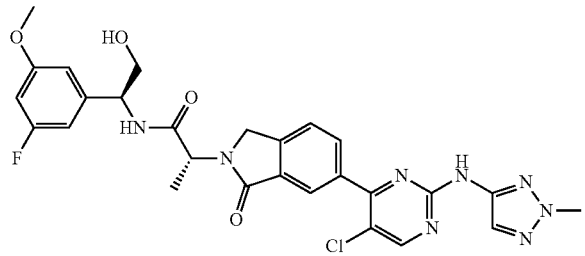 [SMILES: COc1cc(F)cc([C@@H](CO)NC(=O)[C@@H](C)N2Cc3ccc(-c4nc(Nc5cnn(C)n5)ncc4Cl)cc3C2=O)c1]

Method A:

A stirred solution of (R)-2-(6-(5-chloro-2-((2-methyl-2H-1,2,3-triazol-4-yl)amino)pyrimidin-4-yl)-1-oxoisoindolin-2-yl)propanoic acid (Preparation 417, 2.2 g, 4.78 mmol), (S)-2-amino-2-(3-fluoro-5-methoxyphenyl)ethanol hydrochloride (1.167 g, 5.26 mmol) and DIPEA (2.76 ml, 15.79 mmol) in dry DMF (5 ml) was treated with TBTU (1.997 g, 6.22 mmol). The solution was stirred at room temperature for 30 minutes and the resulting yellow solution was partitioned between DCM ((200 ml) and water (200 ml). The organic phase was collected and was successively washed with 10% aqueous NaHCO₃ (100 ml), 1M HCl (100 ml) and water (2×100 ml), dried (MgSO₄) and concentrated under vacuum. The residue was dissolved in DCM and purified by chromatography (SiO₂, 80 g column, 0-100% EtOAc in heptane). The product was then triturated with diethyl ether/heptane and the resulting precipitate was filtered, then dried in a dessicator at 56° C. overnight. The solid was dissolved in a mixture of DCM, ethyl acetate and acetonitrile and the solution concentrated to dryness. The residue was triturated with diethyl ether and the resulting precipitate was filtered and dried under vacuum at 60° C. to afford the title compound (2.2 g, 79%) as a yellow solid. 1H NMR (400 MHz, DMSO-d6) δ 10.64 (s, 1H), 8.69 (s, 1H), 8.58 (d, 1H), 8.16-8.09 (m, 1H), 8.07 (dd, 1H), 7.92 (s, 1H), 7.81 (d, 1H), 6.78-6.66 (m, 3H), 5.02 (q, 1H), 4.93 (t, 1H), 4.88-4.74 (m, 2H), 4.64 (d, 1H), 4.07 (s, 3H), 3.77 (s, 3H), 3.59-3.51 (m, 2H), 1.46 (d, 3H). LCMS: [M+H]⁺=581.

Procedure B:

A mixture of (R)-2-(6-(2,5-dichloropyrimidin-4-yl)-1-oxoisoindolin-2-yl)propanoic acid (Preparation 349) (185 mg, 0.525 mmol), 2-methyl-2H-1,2,3-triazol-4-amine hydrochloride (85 mg, 0.630 mmol) and cesium carbonate (455 mg, 1.397 mmol) was suspended in dry DMF and the suspension degassed by bubbling a stream of nitrogen through for 5 minutes. t-BuBrettPhos Allyl (Pd-175) (24.62 mg, 0.032 mmol) was added and the mixture heated at 70° C. under microwave radiation for 2 h. The mixture was cooled to room temperature and treated with DIPEA (0.212 ml, 1.211 mmol) and (S)-2-amino-2-(3-fluoro-5-methoxyphenyl)ethanol hydrochloride (163 mg, 0.734 mmol). After stirring for 5 minutes at room temperature, TBTU (177 mg, 0.551 mmol) was added and the mixture stirred a further 1.5 h. The suspension was diluted with DCM (50 ml) and the mixture washed with 2M NaHCO₃ (20 ml), 10% aqueous citric acid (20 ml) and water (20 ml). The organic phase was collected, dried (MgSO₄) and concentrated under vacuum. The crude product was purified purified by chromatography (SiO₂, 12 g column, 0-100% EtOAc in isohexane) to afford the title compound (55 mg, 25.8%) as a cream coloured solid.

Example 698: (2R)-2-(6-{5-Chloro-2-[(oxan-4-yl)amino]pyrimidin-4-yl}-1-oxo-2,3-dihydro-1H-isoindol-2-yl)-N-[(1S)-2-hydroxy-1-(2-methoxypyridin-4-yl)ethyl]propanamide

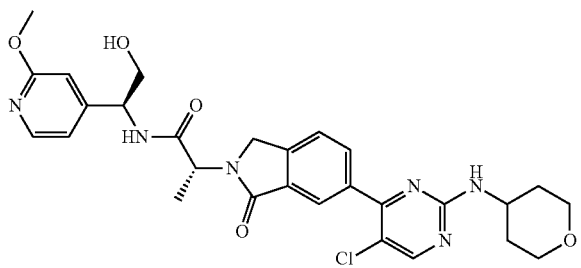 [SMILES: COc1cc([C@@H](CO)NC(=O)[C@@H](C)N2Cc3ccc(-c4nc(NC5CCOCC5)ncc4Cl)cc3C2=O)ccn1]

TBTU (0.095 g, 0.29 mmol) was added to a mixture of (2S)-2-amino-2-(2-methoxypyridin-4-yl)ethanol HCl (0.047 g, 0.23 mmol), (2R)-2-(6-{5-chloro-2-[(oxan-4-yl)amino]pyrimidin-4-yl}-1-oxo-2,3-dihydro-1H-isoindol-2-yl)propanoic acid (Preparation 99, 0.080 g, 0.19 mmol) and DIPEA (0.0101 mL, 0.58 mmol) in DCM (1.9 mL). The mixture was stirred for 2 hours. The reaction was quenched by diluting with water and extracting with EtOAc (×3). The combined organic layers were washed with brine, dried over MgSO$_4$, filtered, and concentrated to dryness. The residue was purified by biotage (EtOAc/0-15% MeOH) to yield the title compound as a colourless solid. 1H NMR (400 MHz, Me-d3-OD): 8.67-8.51 (1H, m), 8.36 (1H, s), 8.24 (1H, s), 8.12-8.03 (2H, m), 7.73 (1H, d), 6.96 (1H, dd), 6.80 (1H, s), 5.11 (1H, q), 4.98-4.91 (1H, m), 4.85 (1H, d), 4.71 (1H, d), 4.11-4.03 (1H, m), 4.02-3.96 (2H, m), 3.92 (3H, s), 3.84-3.72 (2H, m), 3.55 (2H, td), 2.02 (3H, d), 1.72-1.55 (5H, m). [M+H]$^+$=567.

Example 699: (2R)-2-(6-{5-chloro-2-[(oxan-4-yl)amino]pyrimidin-4-yl}-1-oxo-2,3-dihydro-1H-isoindol-2-yl)-N-[(1R)-1-[6-(4-methylpiperazin-1-yl)pyridin-2-yl]ethyl]propanamide

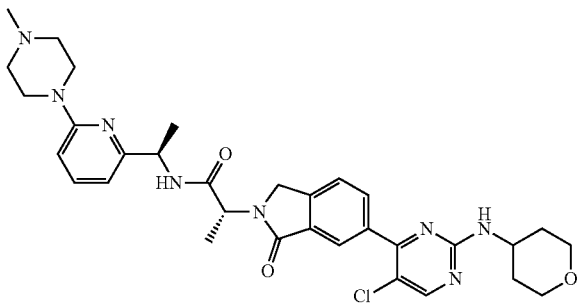 [SMILES: C[C@H](C(=O)N[C@H](C)c1cccc(N2CCN(C)CC2)n1)N1Cc2ccc(-c3nc(NC4CCOCC4)ncc3Cl)cc2C1=O]

Prepared from (1R)-1-[6-(4-Methylpiperazin-1-yl)pyridin-2-yl]ethan-1-amine (Preparation 418) and (2R)-2-(6-{5-chloro-2-[(oxan-4-yl)amino]pyrimidin-4-yl}-1-oxo-2,3-dihydro-1H-isoindol-2-yl)propanoic acid (Preparation 99) using a similar procedure to Example 2. 1H NMR (400 MHz, DMSO-d6) δ 8.45 (1H, s), 8.36 (1H, d), 8.05 (1H, s), 7.99 (1H, dd), 7.76 (1H, d), 7.58 (1H, d), 7.49 (1H, dd), 6.66 (1H, d), 6.59 (1H, d), 4.98 (1H, q), 4.84-4.70 (2H, m), 4.63 (1H, d), 3.99-3.83 (3H, m), 3.46 (4H, t), 2.39-2.33 (4H, m), 2.20 (3H, s), 1.85 (2H, d), 1.61-1.43 (5H, m), 1.34 (3H, d). LCMS: [M+H]$^+$=619.

Example 700: 2-(5-(5-chloro-2-((oxan-4-yl)amino)pyrimidin-4-yl)-1-(2-hydroxyethyl)-3-oxoisoindolin-2-yl)-N—((R)-1-(3-methoxyphenyl)ethyl)acetamide

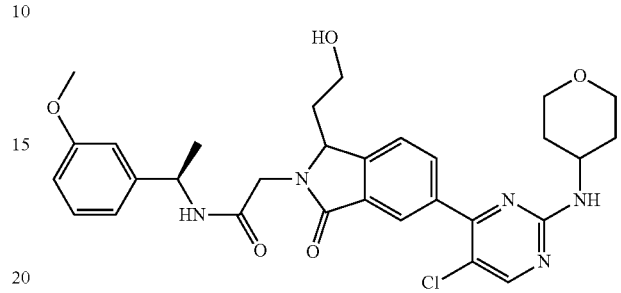

Prepared using a similar procedure to Example 601. LC-MS: [M+H]$^+$=580 (see also Preparation 338).

Example 701: (R)-2-(6-(5-chloro-2-((2-methoxypyridin-4-yl)amino)pyrimidin-4-yl)-1-oxoisoindolin-2-yl)-N—((S)-1-(3-fluoro-5-methoxyphenyl)-2-hydroxyethyl)propanamide

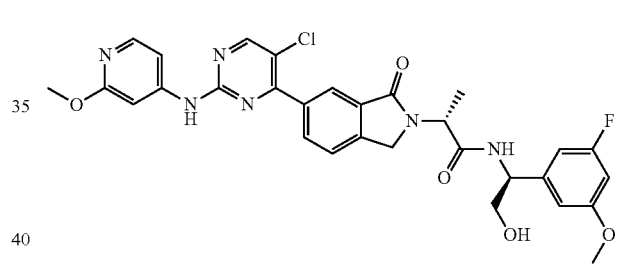

Procedure A:
TBTU (3.19 g, 9.95 mmol) was added to a solution of (R)-2-(6-(5-chloro-2-((2-methoxypyridin-4-yl)amino)pyrimidin-4-yl)-1-oxoisoindolin-2-yl)propanoic acid (3.4 g, 7.65 mmol), (S)-2-amino-2-(3-fluoro-5-methoxyphenyl)ethanol hydrochloride (2.035 g, 9.18 mmol), and DIPEA (4.14 ml, 23.72 mmol) in anhydrous DMF (30 mL) at room temperature and the mixture was stirred for 1 h. Saturated aqueous NH$_4$Cl (200 mL) was added and the mixture was stirred until formation of a cream coloured precipitate. The resulting suspension was diluted with water (100 mL) and the precipitate filtered, washed with water and semi-dried in a vacuum oven to give a cream coloured solid. The solid was taken up in EtOAc and the mixture washed with NaHCO$_3$ (200 mL). The phases were separated and the aqueous layer extracted with EtOAc (2×100 mL). The combined organic extracts were washed with brine (3×100 mL), dried (MgSO$_4$), filtered and evaporated to give a pale yellow foam, which was dried in a vacuum oven at 50° C. overnight. The solid was triturated with Et$_2$O and the resulting precipitate was collected by filtration to give a light brown solid which was dried in the desiccator at 45° C. overnight to give 4.5 g of a light brown solid (93%). A second batch (3 g) prepared following the same procedure was combined and the mixture was taken up in EtOAc (600 mL), washed with brine (4×200 mL), dried (MgSO$_4$), filtered and evaporated at 45° C. to give a solid (7.75 g). The solid was triturated with Et$_2$O (200 mL) and the resulting precipitate was filtered, washed with excess Et$_2$O and left to dry under reduced pressure to give a wet solid, which was further dried in the desiccator at 45° C. overnight. The product was then suspended in MeCN (3×50 mL) and the mixture was concentrated under vacuum. The resulting solid was then left to dry in the desiccator at 45° C. to give the title compound (6.55 g, 82%). 1H NMR (400 MHz, DMSO-d6) δ 10.40 (br s, 1H), 8.79 (s, 1H), 8.58 (d, 1H), 8.13 (dd, 1H), 8.05 (dd, 1H), 7.97 (d, 1H), 7.82 (dd, 1H), 7.40-7.34 (m, 1H), 7.26 (dd, 1H), 6.78-6.65 (m, 3H), 5.01 (q, 1H), 4.93 (t, 1H), 4.87-4.78 (m, 1H), 4.79 (d, 1H), 4.64 (d, 1H), 3.80 (s, 3H), 3.76 (s, 3H), 3.59-3.52 (m, 2H), 1.46 (d, 3H). LCMS: [M+H]$^+$=607.

Procedure B:

Pd(PPh$_3$)$_4$ (48.9 mg, 0.042 mmol) was added to a degassed (3× using nitrogen) suspension of (R)—N—((S)-1-(3-fluoro-5-methoxyphenyl)-2-hydroxyethyl)-2-(1-oxo-6-(4,4,5,5-tetramethyl-1,3,2-dioxaborolan-2-yl)isoindolin-2-yl)propanamide (422 mg, 0.847 mmol), 4,5-dichloro-N-(2-methoxypyridin-4-yl)pyrimidin-2-amine (270 mg, 0.847 mmol) and 2M Na$_2$CO$_3$ (0.847 mL, 1.693 mmol) in 1,4-dioxane (5 mL, 58.5 mmol). The reaction was further degassed, then stirred at 85° C. for 1.5 h under nitrogen. The mixture was allowed to cool to room temperature and was diluted with water (30 mL). The crude product was extracted with EtOAc (2×30 mL) and the combined organic extracts were washed with 1:1 water:brine (40 mL), brine (30 mL), dried (MgSO$_4$), filtered then concentrated in vacuo to leave a brown foam (505 mg). The crude product was purified by chromatography (SiO$_2$, 10-100% EtOAc in iso-hexane) to afford a pale yellow solid (195 mg). The product was re-purified by chromatography (SiO$_2$, 0-4% MeOH in DCM), then re-purified by chromatography (SiO$_2$, 0-100% THF in DCM) to afford a white solid (39 mg). The mixed fractions were further purified by chromatography (RP Flash C18, 10-80% solution of 0.1% formic acid in MeCN:0.1% formic acid in water) to afford a pale brown solid. The batches were combined and re-purified by chromatography (SiO$_2$, 0-50% (10% MeOH in DCM) in DCM) to afford the tile compound (72 mg, 13.59%) as a white solid.

Example 702: (R)-2-(6-(5-chloro-2-((2-methylpyrimidin-4-yl)amino)pyrimidin-4-yl)-1-oxoisoindolin-2-yl)-N—((S)-1-(6-(dimethylamino)pyridin-2-yl)-2-hydroxyethyl)propanamide

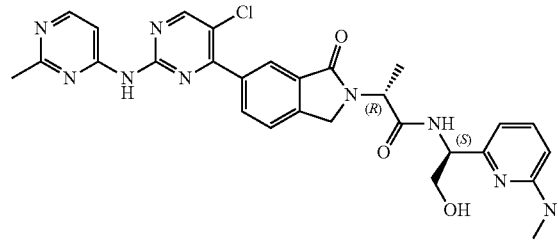

Procedure A:

DMF (109 mL) was added to a 500 mL round bottom flask containing (R)-2-(6-(2,5-dichloropyrimidin-4-yl)-1-oxoisoindolin-2-yl)propanoic acid (4.4 g, 10.87 mmol), 2-methylpyrimidin-4-amine (1.542 g, 14.13 mmol) and cesium carbonate (7.44 g, 22.83 mmol). The system was evacuated and back-filled with nitrogen (×3), heated to 75° C. and stirred for 10 minutes. XantPhos Allyl (Pd-177) (0.414 g, 0.543 mmol) was added and the system evacuated and back-filled with nitrogen (×3), The mixture was stirred at 75° C. for 2.5 h. After cooling to room temperature, (S)-2-amino-2-(6-(dimethylamino)pyridin-2-yl)ethanol (2.257 g, 11.96 mmol) was added in DMF (27 mL) followed by N-methylmorpholine (5.38 ml, 48.9 mmol). The mixture was ice-cooled and TBTU (5.76 g, 17.93 mmol) was added. The mixture was allowed to warm to room temperature and stirred for 1 h. The mixture was diluted with Et$_2$O (350 mL) and the resulting precipitate filtered in vacuo, washed with Et$_2$O (4×100 mL) to give a dark yellow solid (16.5 g). The solid was suspended in water (50 mL) and filtered in vacuo, then washed with water (4×50 mL) and dried to give a lighter yellow solid (14.05 g). The solid was partially dissolved in 10% MeOH/DCM (150 mL) and the resulting suspension filtered and washed with 10% MeOH/DCM (2×100 mL). The filtrate was adsorbed onto silica and purified by chromatography (SiO$_2$, 0-10% (0.7 M NH/MeOH) in DCM) to afford the title compound (3.63 g, 56.2% yield) as a pale yellow solid. 1H NMR (400 MHz, DMSO-d6) δ 10.77 (br s, 1H), 8.83 (s, 1H), 8.47 (d, 1H), 8.38 (d, 1H), 8.19-8.10 (m, 1H), 8.12-8.00 (m, 2H), 7.82 (d, 1H), 7.51-7.39 (m, 1H), 6.50 (dd, 2H), 5.06 (q, 1H), 4.95-4.58 (m, 4H), 3.77-3.64 (m, 1H), 3.64-3.54 (m, 1H), 2.97 (s, 6H), 2.51 (s, 3H), 1.49 (d, 3H). LCMS: [M+H]$^+$=588.

Note: Alternative catalysts systems (Xanpthos/Pd(OAc)$_2$, Xantphos Pd G3) can be used in first step.

Procedure B:

A microwave tube was charged with 4,5-dichloro-N-(2-methylpyrimidin-4-yl)pyrimidin-2-amine (124 mg, 0.485 mmol) and (R)—N—((S)-1-(6-(dimethylamino)pyridin-2-yl)-2-hydroxyethyl)-2-(1-oxo-6-(4,4,5,5-tetramethyl-1,3,2-dioxaborolan-2-yl)isoindolin-2-yl)propanamide (200 mg, 0.405 mmol). 1,4-dioxane (2 mL) and sodium carbonate (2 M aqueous) (0.405 mL, 0.809 mmol) were added and the mixture was degassed for 5 minutes before addition of Pd(dppf)Cl$_2$.CH$_2$Cl$_2$ (16.52 mg, 0.020 mmol). The mixture was heated to 80° C. for 1.5 h under nitrogen, then cooled to room temperature and diluted with water (10 mL). The precipitate was isolated by filtration and washed with water (30 mL). The solid was dissolved in DCM/MeOH (9:1, 100 mL) and passed through a phase separator then absorbed on silica gel. The crude product was purified by chromatography (SiO$_2$, 0-10% (0.7 M Ammonia/MeOH) in DCM) to afford the title compound (168 mg, 68.5%) as an off-white solid.

Example 702a: (R)-2-(6-(5-chloro-2-((2-methylpyrimidin-4-yl)amino)pyrimidin-4-yl)-1-oxoisoindolin-2-yl)-N—((S)-1-(6-(dimethylamino)pyridin-2-yl)-2-hydroxyethyl)propanamide hydrochloride salt

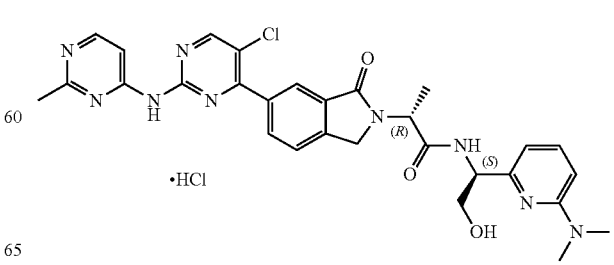

To a stirred solution of the product from Example 702 (154 mg) in THF (8 mL), was added HCl (2N in Et$_2$O, 127 µL, 1 mol. eq.). The resulting precipitate was collected by filtration and washed successively with THF and EtOAc. The title compound was obtained as a white solid (55 mg). 1H NMR (400 MHz, DMSO-d6): 11.72 (1H, br s), 8.95 (1H, s), 8.64 (1H, d), 8.48 (1H, br s), 8.24 (1H, d), 8.17 (1H, s), 8.10 (1H, dd), 7.84 (1H, d), 7.58 (1H, br s), 6.63 (2H, m), 5.06 (1H, q), 4.94-4.75 (2H, m), 4.68 (1H, d), 3.76-3.58 (3H, m), 3.05 (6H, s), 2.63 (3H, s), 1.51 (3H, d). LCMS: [M+H]$^+$=588.

Example 702b: (R)-2-(6-(5-chloro-2-((2-methylpyrimidin-4-yl)amino)pyrimidin-4-yl)-1-oxoisoindolin-2-yl)-N—((S)-1-(6-(dimethylamino)pyridin-2-yl)-2-hydroxyethyl)propanamide methanesulfonate salt To a stirred solution of the product from Example 702 (152 mg) in THF (8 mL), was added methanesulfonic acid (24.8 mg, 1 mol. eq.). The resulting precipitate was collected by filtration and washed successively with THF and EtOAc. The title compound was obtained as a white solid (106 mg). 1H NMR (400 MHz, DMSO-d6): 12.06 (1H, br s), 9.00 (1H, s), 8.71 (1H, d), 8.59 (1H, br s), 8.31 (1H, d), 8.18 (1H, s), 8.11 (1H, dd), 7.85 (1H, d), 7.72 (1H, br s), 6.83 (1H, br s), 6.70 (1H, d), 5.11-4.94 (2H, m), 4.79 (1H, d), 4.68 (1H, d), 3.79-3.63 (2H, m), 3.12 (6H, s), 2.66 (3H, s), 2.33 (5H, s), 1.51 (3H, d). LCMS: [M+H]$^+$=588.

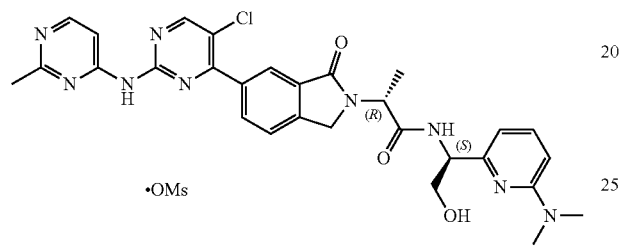

Examples 703-1123

The following Examples were prepared using procedures analogous to those described herein for Examples 1-702.

| Example | Structure | Name | MS Data [M+H]$^+$ unless specified |
|---|---|---|---|
| 703 | 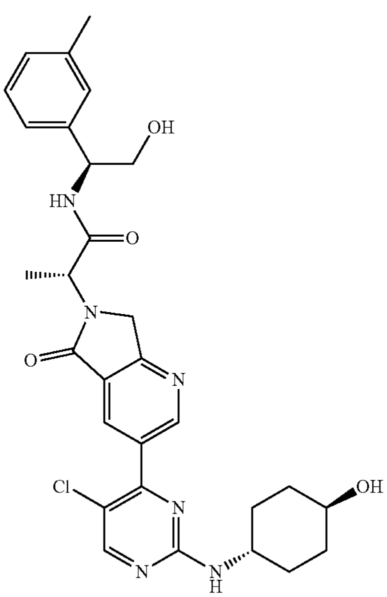 [SMILES: Cc1cccc([C@@H](CO)NC(=O)[C@@H](C)N2Cc3ncc(-c4nc(N[C@H]5CC[C@H](O)CC5)ncc4Cl)cc3C2=O)c1] | (2R)-2-[3-(5-chloro-2-{[trans-4-hydroxycyclohexyl]amino}pyrimidin-4-yl)-5-oxo-5H,6H,7H-pyrrolo[3,4-b]pyridin-6-yl]-N-[(1S)-2-hydroxy-1-(3-methylphenyl)ethyl]propanamide | 565 |

No Example 704

-continued

| Example | Structure | Name | MS Data [M +H]+ unless specified |
|---|---|---|---|
| 705 | 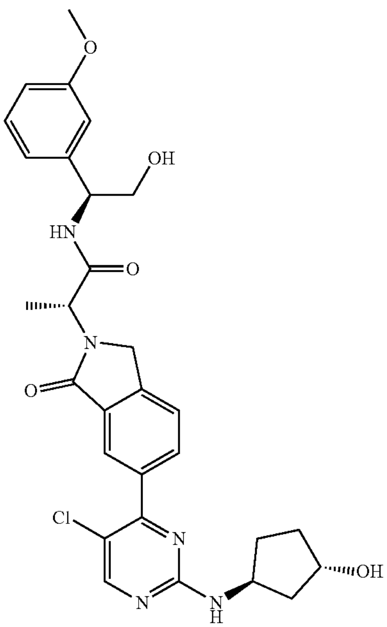 [SMILES: COc1cccc([C@@H](CO)NC(=O)[C@@H](C)N2Cc3ccc(-c4nc(N[C@H]5CC[C@H](O)C5)ncc4Cl)cc3C2=O)c1] | (2R)-2-[6-(5-chloro-2-{[(1S,3S)-3-hydroxycyclopentyl]amino}pyrimidin-4-yl)-1-oxo-2,3-dihydro-1H-isoindol-2-yl]-N-[(1S)-2-hydroxy-1-(3-methoxyphenyl)ethyl]propanamide | 566 |
| 706 | 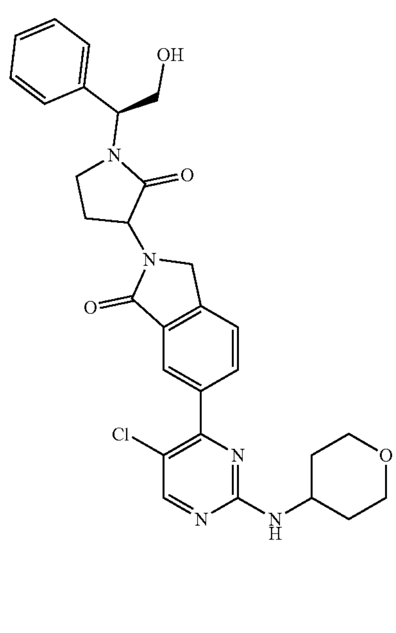 [SMILES: O=C1c2cc(-c3nc(NC4CCOCC4)ncc3Cl)ccc2CN1C1CCN([C@H](CO)c2ccccc2)C1=O] | 6-{5-chloro-2-[(oxan-4-yl)amino]pyrimidin-4-yl}-2-{1-[(1S)-2-hydroxy-1-phenylethyl]-2-oxopyrrolidin-3-yl}-2,3-dihydro-1H-isoindol-1-one | 548 |

| Example | Structure | Name | MS Data [M +H]+ unless specified |
|---|---|---|---|
| 707 | 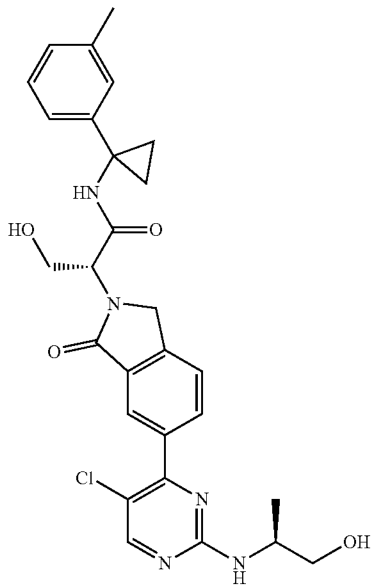 [SMILES: Cc1cccc(C2(NC(=O)[C@@H](CO)N3Cc4ccc(-c5nc(N[C@@H](C)CO)ncc5Cl)cc4C3=O)CC2)c1] | (2R)-2-[6-(5-chloro-2-{[(2S)-1-hydroxypropan-2-yl]amino}pyrimidin-4-yl)-1-oxo-2,3-dihydro-1H-isoindol-2-yl]-3-hydroxy-N-[1-(3-methylphenyl)cyclopropyl]propanamide | 536 |
| 708 | 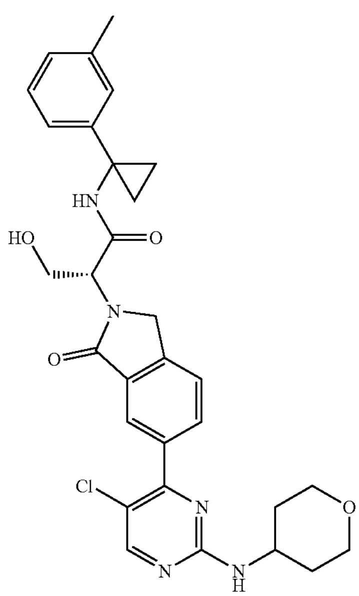 [SMILES: Cc1cccc(C2(NC(=O)[C@@H](CO)N3Cc4ccc(-c5nc(NC6CCOCC6)ncc5Cl)cc4C3=O)CC2)c1] | (2R)-2-(6-{5-chloro-2-[(oxan-4-yl)amino]pyrimidin-4-yl}-1-oxo-2,3-dihydro-1H-isoindol-2-yl)-3-hydroxy-N-[1-(3-methylphenyl)cyclopropyl]-propanamide | 562 |

| Example | Structure | Name | MS Data [M +H]+ unless specified |
|---|---|---|---|
| 709 | 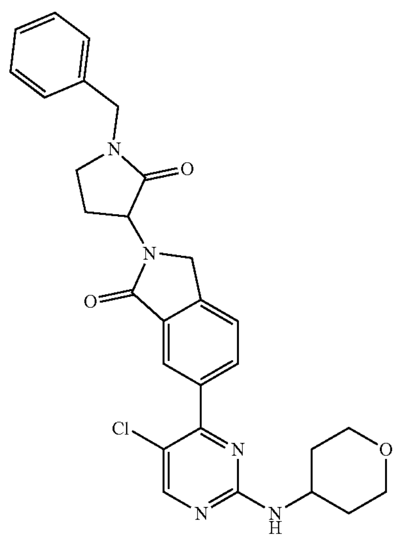 [SMILES: O=C1C(N2Cc3ccc(-c4nc(NC5CCOCC5)ncc4Cl)cc3C2=O)CCN1Cc1ccccc1] | 2-(1-benzyl-2-oxopyrrolidin-3-yl)-6-{5-chloro-2-[(oxan-4-yl)amino]pyrimidin-4-yl}-2,3-dihydro-1H-isoindol-1-one | 518 |
| 710 | | There is no Example 710 | |
| 711 | 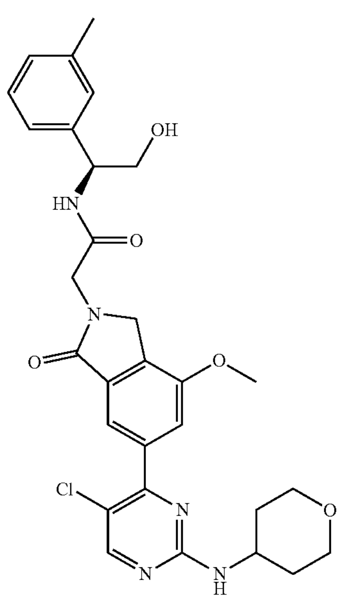 [SMILES: COc1cc(-c2nc(NC3CCOCC3)ncc2Cl)cc2c1CN(CC(=O)N[C@H](CO)c1cccc(C)c1)C2=O] | 2-(6-{5-chloro-2-[(oxan-4-yl)amino]pyrimidin-4-yl}-4-methoxy-1-oxo-2,3-dihydro-1H-isoindol-2-yl)-N-[(1S)-2-hydroxy-1-(3-methylphenyl)ethyl]acetamide | 566 |

-continued

| Example | Structure | Name | MS Data [M +H]+ unless specified |
|---|---|---|---|
| 712 | 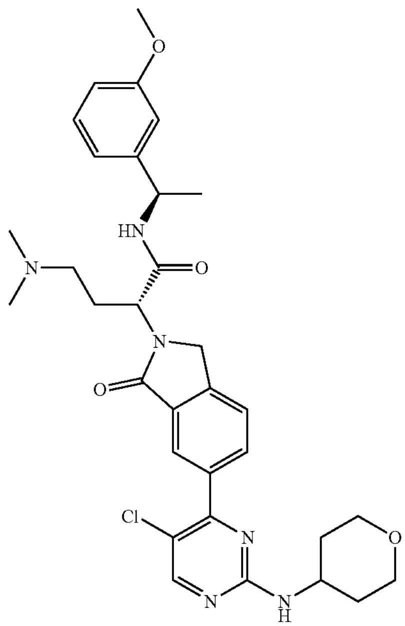 [SMILES: COc1cccc([C@@H](C)NC(=O)[C@@H](CCN(C)C)N2Cc3ccc(-c4nc(NC5CCOCC5)ncc4Cl)cc3C2=O)c1] | (2R)-2-(6-{5-chloro-2-[(oxan-4-yl)amino]pyrimidin-4-yl}-1-oxo-2,3-dihydro-1H-isoindol-2-yl)-4-(dimethylamino)-N-[(1R)-1-(3-methoxyphenyl)ethyl]butanamide | 607 |
| 713 | 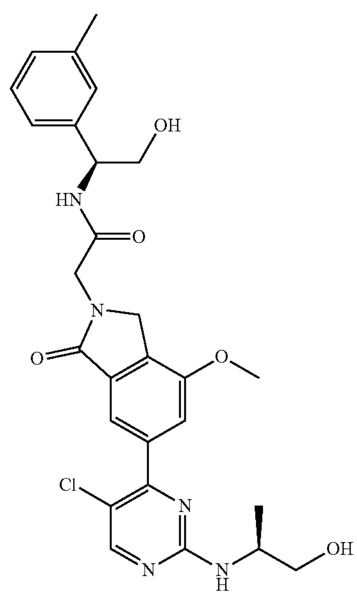 [SMILES: COc1cc(-c2nc(N[C@@H](C)CO)ncc2Cl)cc2c1CN(CC(=O)N[C@H](CO)c1cccc(C)c1)C2=O] | 2-[6-(5-chloro-2-{[(2S)-1-hydroxypropan-2-yl]amino}pyrimidin-4-yl)-4-methoxy-1-oxo-2,3-dihydro-1H-isoindol-2-yl]-N-[(1S)-2-hydroxy-1-(3-methylphenyl)ethyl]acetamide | 540 |
| 714 | 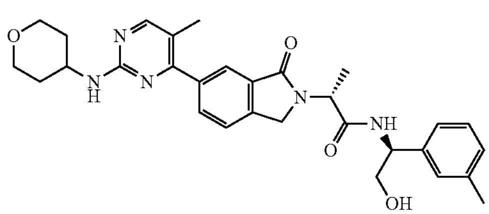 [SMILES: Cc1cccc([C@@H](CO)NC(=O)[C@@H](C)N2Cc3ccc(-c4nc(NC5CCOCC5)ncc4C)cc3C2=O)c1] | N-[(1S)-2-hydroxy-1-(3-methylphenyl)ethyl]-2-(6-{5-methyl-2-[(oxan-4-yl)amino]pyrimidin-4-yl}-1-oxo-2,3-dihydro-1H-isoindol-2-yl)acetamide | 530 |

| Example | Structure | Name | MS Data [M +H]+ unless specified |
|---|---|---|---|
| 715 | 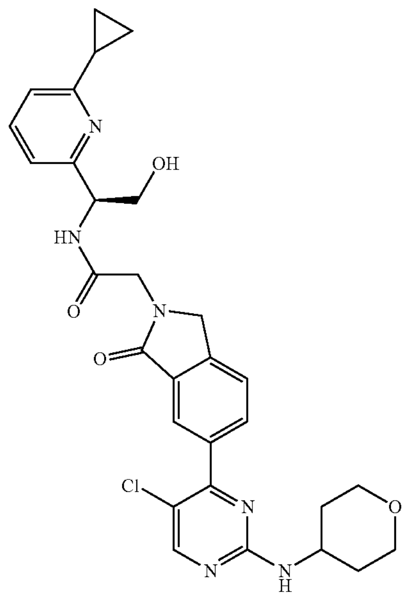 [SMILES: O=C(CN1Cc2ccc(-c3nc(NC4CCOCC4)ncc3Cl)cc2C1=O)N[C@H](CO)c1cccc(C2CC2)n1] | 2-(6-{5-chloro-2-[(oxan-4-yl)amino]pyrimidin-4-yl}-1-oxo-2,3-dihydro-1H-isoindol-2-yl)-N-[(1S)-1-(6-cyclopropylpyridin-2-yl)-2-hydroxyethyl]acetamide | 563 |
| 716 | 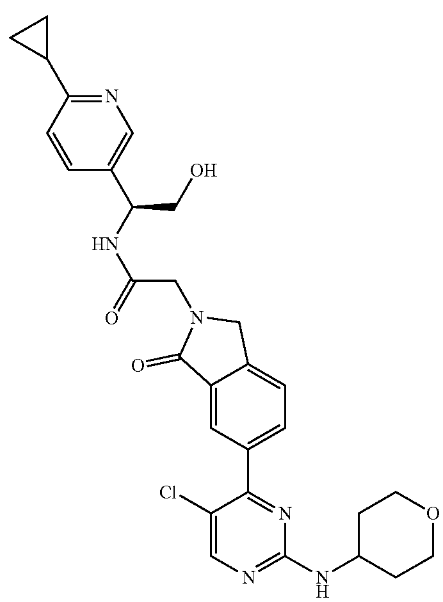 [SMILES: O=C(CN1Cc2ccc(-c3nc(NC4CCOCC4)ncc3Cl)cc2C1=O)N[C@H](CO)c1ccc(C2CC2)nc1] | 2-(6-{5-chloro-2-[(oxan-4-yl)amino]pyrimidin-4-yl}-1-oxo-2,3-dihydro-1H-isoindol-2-yl)-N-[(1S)-1-(6-cyclopropylpyridin-3-yl)-2-hydroxyethyl]acetamide | 561 [M −H]− |

| Example | Structure | Name | MS Data [M +H]+ unless specified |
|---|---|---|---|
| 717 | 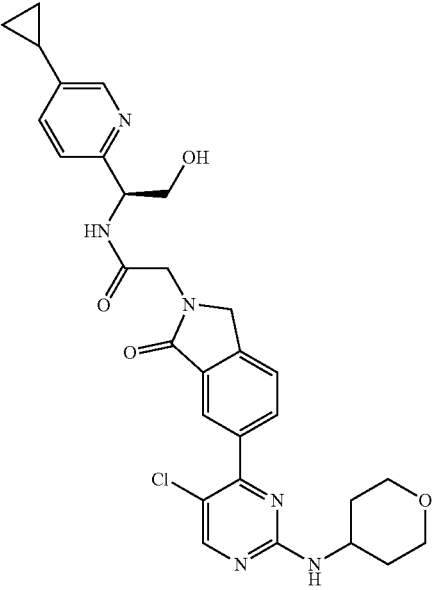 [SMILES: O=C(CN1Cc2ccc(-c3nc(NC4CCOCC4)ncc3Cl)cc2C1=O)N[C@H](CO)c1ccc(C2CC2)cn1] | 2-(6-{5-chloro-2-[(oxan-4-yl)amino]pyrimidin-4-yl}-1-oxo-2,3-dihydro-1H-isoindol-2-yl)-N-[(1S)-1-(5-cyclopropylpyridin-2-yl)-2-hydroxyethyl]acetamide | 563 |
| 718 | 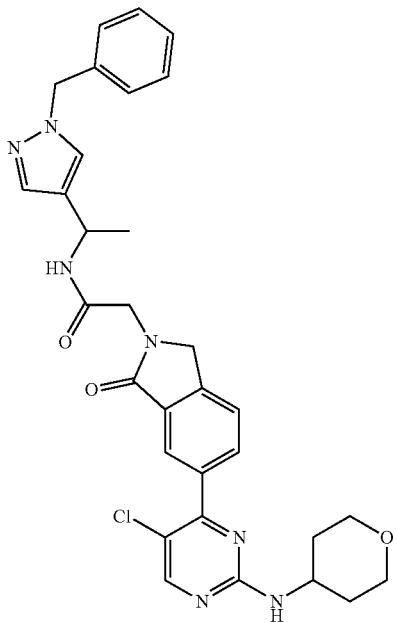 [SMILES: CC(NC(=O)CN1Cc2ccc(-c3nc(NC4CCOCC4)ncc3Cl)cc2C1=O)c1cnn(Cc2ccccc2)c1] | N-[1-(1-benzyl-1H-pyrazol-4-yl)ethyl]-2-(6-{5-chloro-2-[(oxan-4-yl)amino]pyrimidin-4-yl}-1-oxo-2,3-dihydro-1H-isoindol-2-yl)acetamide | 586 |

-continued

| Example | Structure | Name | MS Data [M +H]+ unless specified |
|---|---|---|---|
| 719 | 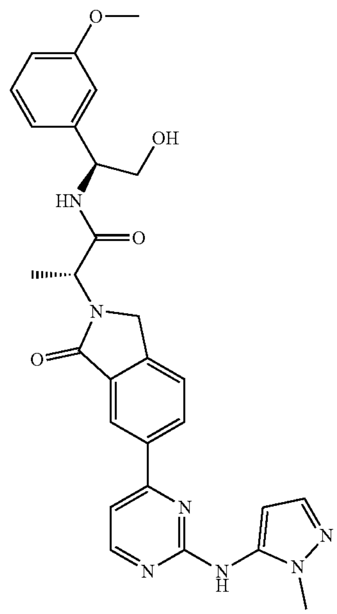 [SMILES: COc1cccc([C@@H](CO)NC(=O)[C@@H](C)N2Cc3ccc(-c4ccnc(Nc5ccnn5C)n4)cc3C2=O)c1] | (2R)-N-[(1S)-2-hydroxy-1-(3-methoxyphenyl)ethyl]-2-(6-{2-[(1-methyl-1H-pyrazol-5-yl)amino]pyrimidin-4-yl}-1-oxo-2,3-dihydro-1H-isoindol-2-yl)propanamide | 528 |
| 720 | 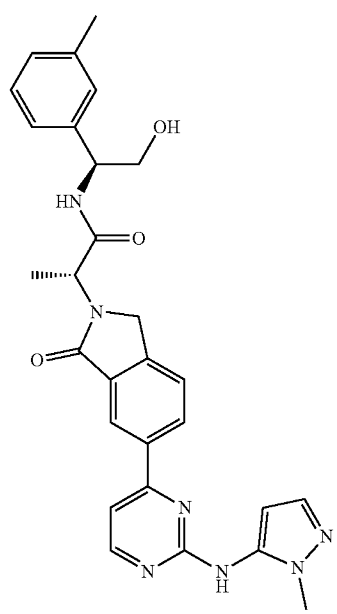 [SMILES: Cc1cccc([C@@H](CO)NC(=O)[C@@H](C)N2Cc3ccc(-c4ccnc(Nc5ccnn5C)n4)cc3C2=O)c1] | (2R)-N-[(1S)-2-hydroxy-1-(3-methylphenyl)ethyl]-2-(6-{2-[(1-methyl-1H-pyrazol-5-yl)amino]pyrimidin-4-yl}-1-oxo-2,3-dihydro-1H-isoindol-2-yl)propanamide | 510 [M −H]− |

-continued

| Example | Structure | Name | MS Data [M +H]+ unless specified |
|---|---|---|---|
| 721 | 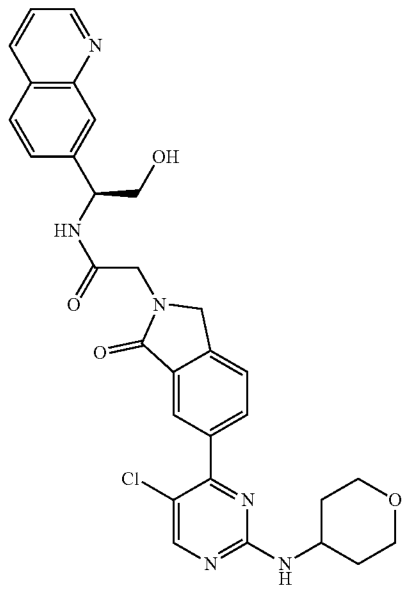 [SMILES: O=C(CN1Cc2ccc(-c3nc(NC4CCOCC4)ncc3Cl)cc2C1=O)N[C@H](CO)c1ccc2cccnc2c1] | 2-(6-{5-chloro-2-[(oxan-4-yl)amino]pyrimidin-4-yl}-1-oxo-2,3-dihydro-1H-isoindol-2-yl)-N-[(1S)-2-hydroxy-1-(quinolin-7-yl)ethyl]acetamide | 573 |
| 722 | 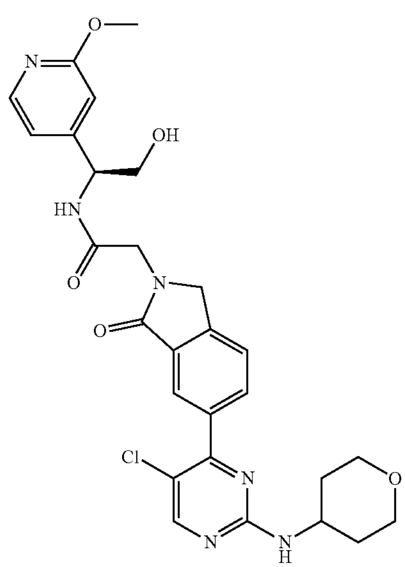 [SMILES: COc1cc([C@@H](CO)NC(=O)CN2Cc3ccc(-c4nc(NC5CCOCC5)ncc4Cl)cc3C2=O)ccn1] | 2-(6-{5-chloro-2-[(oxan-4-yl)amino]pyrimidin-4-yl}-1-oxo-2,3-dihydro-1H-isoindol-2-yl)-N-[(1S)-2-hydroxy-1-(2-methoxypyridin-4-yl)ethyl]acetamide | 553 |

| Example | Structure | Name | MS Data [M+H]+ unless specified |
|---|---|---|---|
| 723 | 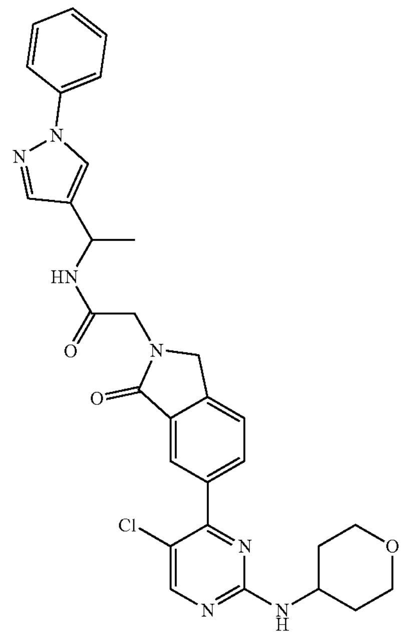 [SMILES: CC(NC(=O)CN1Cc2ccc(-c3nc(NC4CCOCC4)ncc3Cl)cc2C1=O)c1cnn(-c2ccccc2)c1] | 2-(6-{5-chloro-2-[(oxan-4-yl)amino]pyrimidin-4-yl}-1-oxo-2,3-dihydro-1H-isoindol-2-yl)-N-[1-(1-phenyl-1H-pyrazol-4-yl)ethyl]acetamide | 572 |
| 724 | 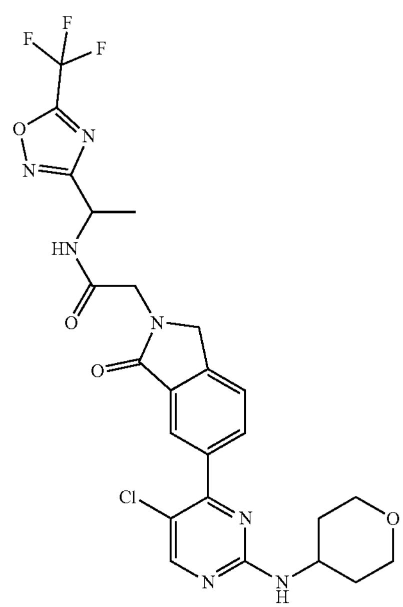 [SMILES: CC(NC(=O)CN1Cc2ccc(-c3nc(NC4CCOCC4)ncc3Cl)cc2C1=O)c1noc(C(F)(F)F)n1] | 2-(6-{5-chloro-2-[(oxan-4-yl)amino]pyrimidin-4-yl}-1-oxo-2,3-dihydro-1H-isoindol-2-yl)-N-{1-[5-(trifluoromethyl)-1,2,4-oxadiazol-3-yl]ethyl}acetamide | 566 |

-continued

| Example | Structure | Name | MS Data [M +H]+ unless specified |
|---|---|---|---|
| 725 | 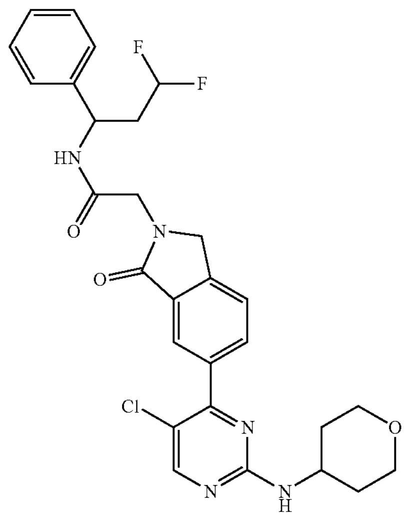 [SMILES: O=C(CN1Cc2ccc(-c3nc(NC4CCOCC4)ncc3Cl)cc2C1=O)NC(CC(F)F)c1ccccc1] | 2-(6-{5-chloro-2-[(oxan-4-yl)amino]pyrimidin-4-yl}-1-oxo-2,3-dihydro-1H-isoindol-2-yl)-N-(3,3-difluoro-1-phenylpropyl)acetamide | 556 |
| 726 | 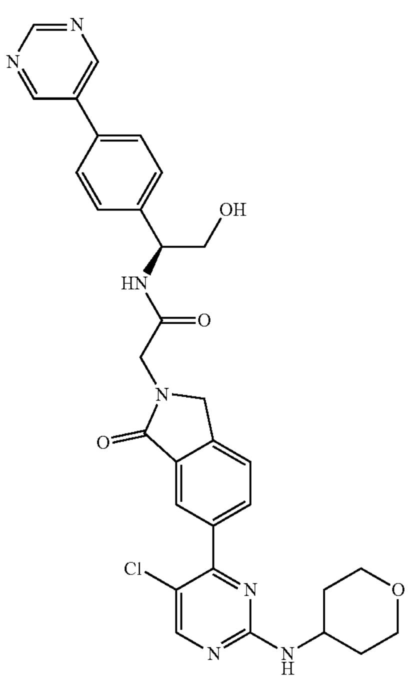 [SMILES: O=C(CN1Cc2ccc(-c3nc(NC4CCOCC4)ncc3Cl)cc2C1=O)N[C@H](CO)c1ccc(-c2cncnc2)cc1] | 2-(6-{5-chloro-2-[(oxan-4-yl)amino]pyrimidin-4-yl}-1-oxo-2,3-dihydro-1H-isoindol-2-yl)-N-[(1S)-2-hydroxy-1-[4-(pyrimidin-5-yl)phenyl]ethyl]acetamide | 600 |

| Example | Structure | Name | MS Data [M +H]+ unless specified |
|---|---|---|---|
| 727 | 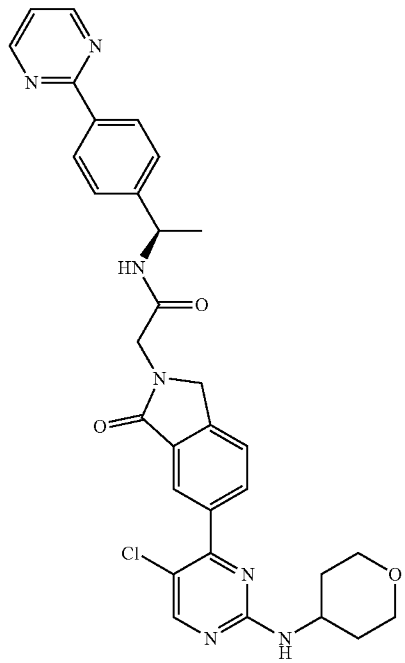 [SMILES: C[C@@H](NC(=O)CN1Cc2ccc(-c3nc(NC4CCOCC4)ncc3Cl)cc2C1=O)c1ccc(-c2ncccn2)cc1] | 2-(6-{5-chloro-2-[(oxan-4-yl)amino]pyrimidin-4-yl}-1-oxo-2,3-dihydro-1H-isoindol-2-yl)-N-[(1R)-1[4-(pyrimidin-2-yl)phenyl]ethyl]acetamide | 584 |
| 728 | 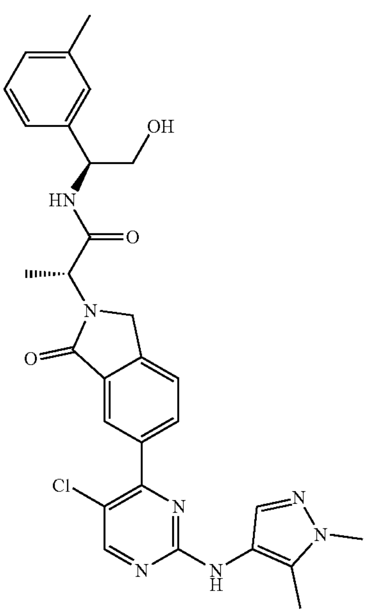 [SMILES: Cc1cccc([C@@H](CO)NC(=O)[C@@H](C)N2Cc3ccc(-c4nc(Nc5cnn(C)c5C)ncc4Cl)cc3C2=O)c1] | (2R)-2-(6-{5-chloro-2-[(1,5-dimethyl-1H-pyrazol-4-yl)amino]pyrimid in-4-yl}-1-oxo-2,3-dihydro-1H-isoindol-2-yl)-N-[(1S)-2-hydroxy-1-(3-methylphenyl)ethyl]propanamide | 560 |

-continued

| Example | Structure | Name | MS Data [M +H]+ unless specified |
|---|---|---|---|
| 729 | | No Example 729 | |
| 730 | 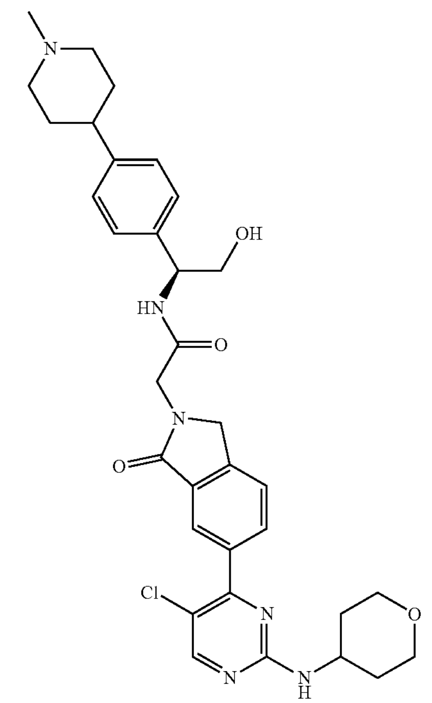 [SMILES: CN1CCC(c2ccc([C@@H](CO)NC(=O)CN3Cc4ccc(-c5nc(NC6CCOCC6)ncc5Cl)cc4C3=O)cc2)CC1] | 2-(6-{5-chloro-2-[(oxan-4-yl)amino]pyrimidin-4-yl}-1-oxo-2,3-dihydro-1H-isoindol-2-yl)-N-[(1S)-2-hydroxy-1-[4-(1-methylpiperidin-4-yl)phenyl]ethyl]acetamide | 619 |
| 731 | 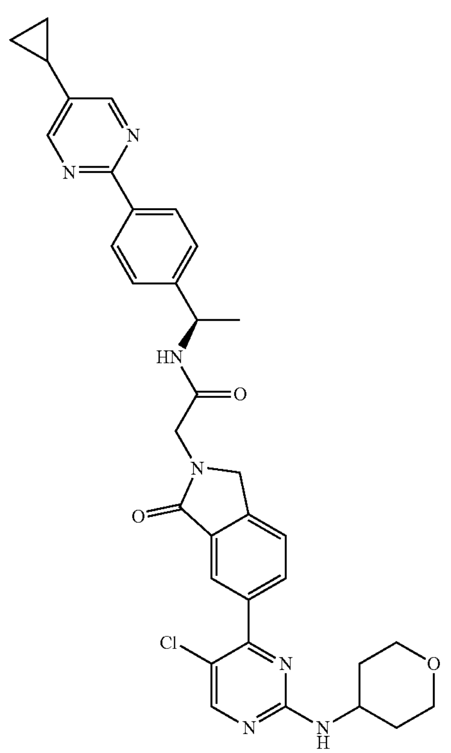 [SMILES: C[C@@H](NC(=O)CN1Cc2ccc(-c3nc(NC4CCOCC4)ncc3Cl)cc2C1=O)c1ccc(-c2ncc(C3CC3)cn2)cc1] | 2-(6-{5-chloro-2-[(oxan-4-yl)amino]pyrimidin-4-yl}-1-oxo-2,3-dihydro-1H-isoindol-2-yl)-N-[(1R)-1-[4-(5-cyclopropylpyrimidin-2-yl)phenyl]ethyl]acetamide | 624 |

-continued

| Example | Structure | Name | MS Data [M +H]+ unless specified |
|---|---|---|---|
| 732 | 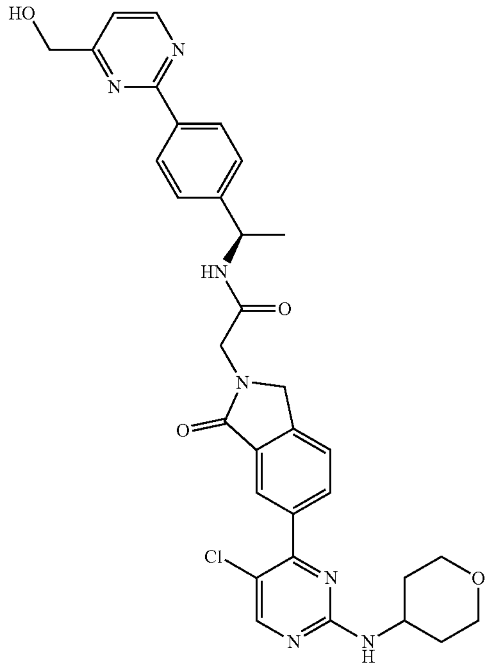 [SMILES: C[C@@H](NC(=O)CN1Cc2ccc(-c3nc(NC4CCOCC4)ncc3Cl)cc2C1=O)c1ccc(-c2nccc(CO)n2)cc1] | 2-(6-{5-chloro-2-[(oxan-4-yl)amino]pyrimidin-4-yl}-1-oxo-2,3-dihydro-1H-isoindol-2-yl)-N-[(1R)-1-{4[4-(hydroxymethyl)pyrimidin-2-yl]phenyl}ethyl]acetamide | 614 |
| 733 | 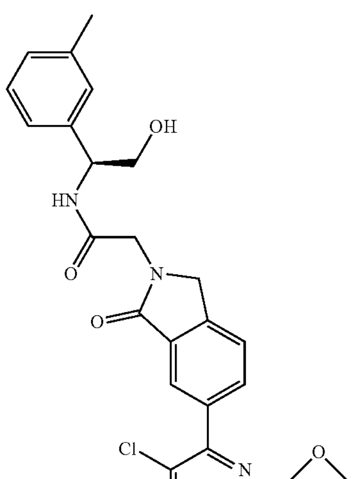 | 2-(6-{5-chloro-2-[(3-methyloxetan-3-yl)amino]pyrimidin-4-yl}-1-oxo-2,3-dihydro-1H-isoindol-2-yl)-N-[(1S)-2-hydroxy-1-(3-methylphenyl)ethyl]acetamide | 521 [M −H]− |

-continued

| Example | Structure | Name | MS Data [M +H]+ unless specified |
|---|---|---|---|
| 734 | 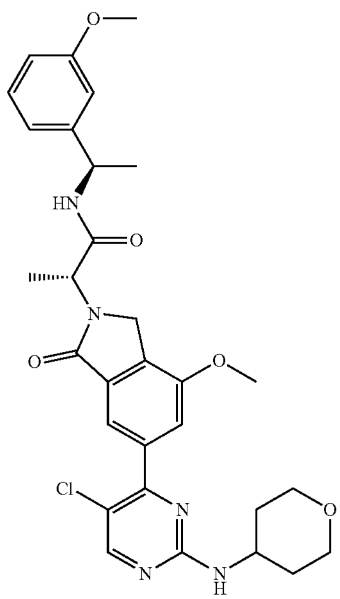 [SMILES: COc1cccc([C@@H](C)NC(=O)[C@@H](C)N2Cc3c(OC)cc(-c4nc(NC5CCOCC5)ncc4Cl)cc3C2=O)c1] | (2R)-2-(6-{5-chloro-2-[(oxan-4-yl)amino]pyrimidin-4-yl}-4-methoxy-1-oxo-2,3-dihydro-1H-isoindol-2-yl)-N-[(1 R)-1-(3-methoxyphenyl)ethyl]propanamide | 580 |
| 735 | 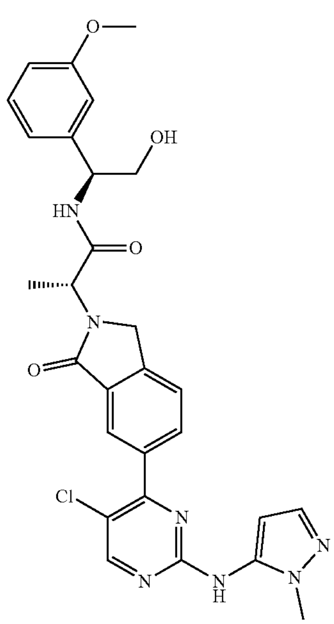 [SMILES: COc1cccc([C@@H](CO)NC(=O)[C@@H](C)N2Cc3ccc(-c4nc(Nc5ccnn5C)ncc4Cl)cc3C2=O)c1] | (2R)-2-(6-{5-chloro-2-[(1-methyl-1H-pyrazol-5-yl)amino]pyrimidin-4-yl}-1-oxo-2,3-dihydro-1H-isoindol-2-yl)-N-[(1S)-2-hydroxy-1-(3-methoxyphenyl)ethyl]propanamide | 562 |

| Example | Structure | Name | MS Data [M +H]+ unless specified |
|---|---|---|---|
| 736 | | No Example 736 | |
| 737 | 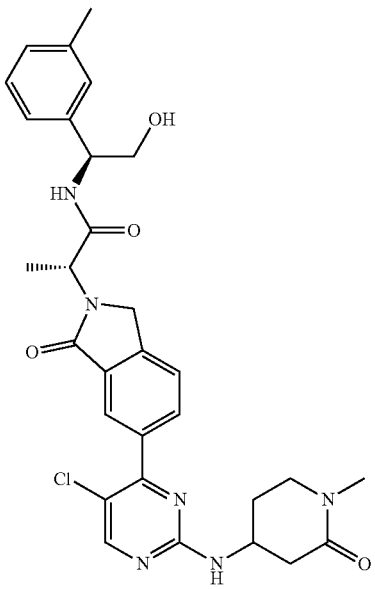 [SMILES: Cc1cccc([C@@H](CO)NC(=O)[C@@H](C)N2Cc3ccc(-c4nc(NC5CCN(C)C(=O)C5)ncc4Cl)cc3C2=O)c1] | (2R)-2-(6-{5-chloro-2-[(1-methyl-2-oxopiperidin-4-yl)amino]pyrimidin-4-yl}-1-oxo-2,3-dihydro-1H-isoindol-2-yl)-N-[(1S)-2-hydroxy-1-(3-methylphenyl)ethyl]propanamide | 577 |
| 738 | 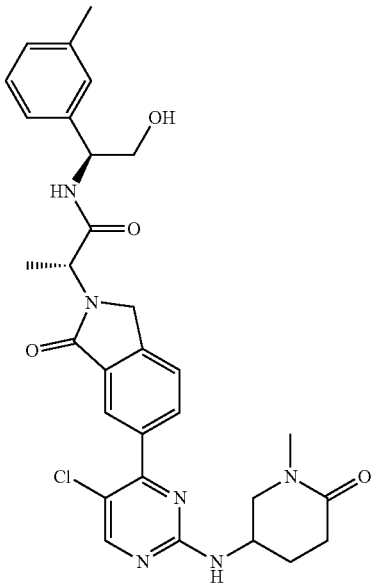 [SMILES: Cc1cccc([C@@H](CO)NC(=O)[C@@H](C)N2Cc3ccc(-c4nc(NC5CCC(=O)N(C)C5)ncc4Cl)cc3C2=O)c1] | (2R)-2-(6-{5-chloro-2-[(1-methyl-6-oxopiperidin-3-yl)amino]pyrimidin-4-yl}-1-oxo-2,3-dihydro-1H-isoindol-2-yl)-N-[(1S)-2-hydroxy-1-(3-methylphenyl)ethyl]propanamide | 577 |

| Example | Structure | Name | MS Data [M +H]+ unless specified |
|---|---|---|---|
| 739 | | No Example 739 | |
| 740 | 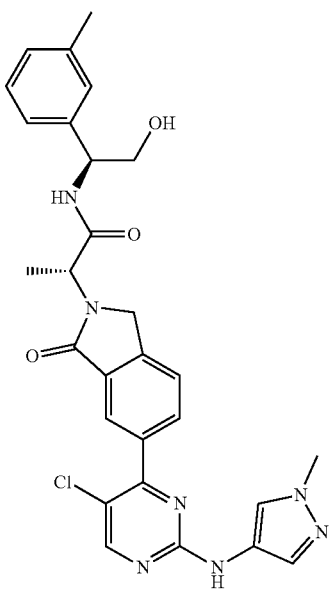 [SMILES: Cc1cccc([C@@H](CO)NC(=O)[C@@H](C)N2Cc3ccc(-c4nc(Nc5cnn(C)c5)ncc4Cl)cc3C2=O)c1] | (2R)-2-(6-{5-chloro-2-[(1-methyl-1H-pyrazol-4-yl)amino]pyrimidin-4-yl}-1-oxo-2,3-dihydro-1H-isoindol-2-yl)-N-[(1S)-2-hydroxy-1-(3-methylphenyl)ethyl]propanamide | 546 |
| 741 | 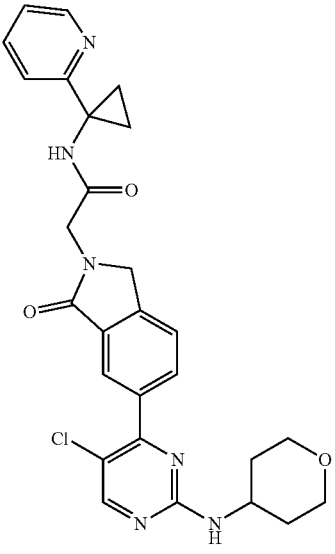 [SMILES: O=C(CN1Cc2ccc(-c3nc(NC4CCOCC4)ncc3Cl)cc2C1=O)NC1(c2ccccn2)CC1] | 2-(6-{5-chloro-2-[(oxan-4-yl)amino]pyrimidin-4-yl}-1-oxo-2,3-dihydro-1H-isoindol-2-yl)-N-[1-(pyridin-2-yl)cyclopropyl]acetamide | 519 |

-continued

| Example | Structure | Name | MS Data [M +H]+ unless specified |
|---|---|---|---|
| 742 | 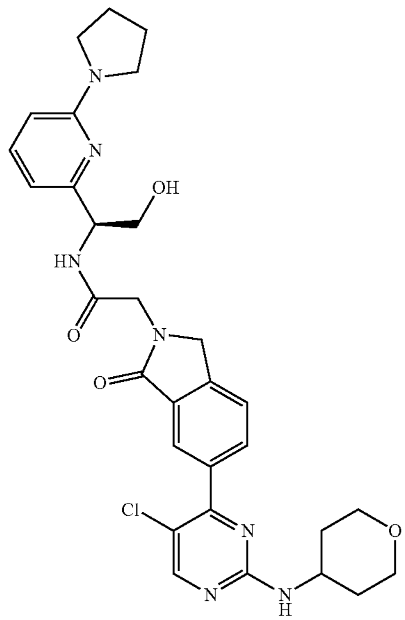 [SMILES: O=C(CN1Cc2ccc(-c3nc(NC4CCOCC4)ncc3Cl)cc2C1=O)N[C@H](CO)c1cccc(N2CCCC2)n1] | 2-(6-{5-chloro-2-[(oxan-4-yl)amino]pyrimidin-4-yl}-1-oxo-2,3-dihydro-1H-isoindol-2-yl)-N-[(1S)-2-hydroxy-1-[6-(pyrrolidin-1-yl)pyridin-2-yl]ethyl]acetamide | 592 |
| 743 | 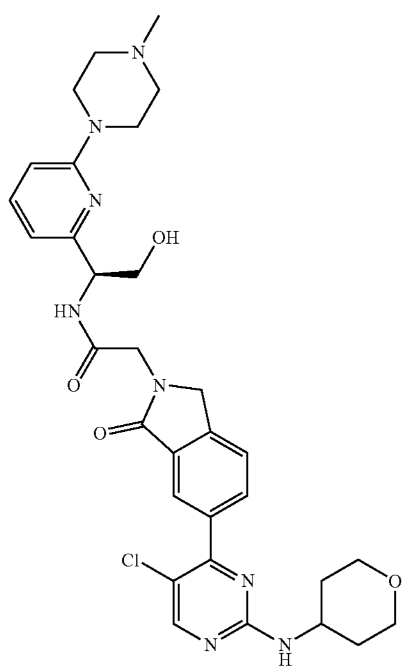 [SMILES: CN1CCN(c2cccc([C@@H](CO)NC(=O)CN3Cc4ccc(-c5nc(NC6CCOCC6)ncc5Cl)cc4C3=O)n2)CC1] | 2-(6-{5-chloro-2-[(oxan-4-yl)amino]pyrimidin-4-yl}-1-oxo-2,3-dihydro-1H-isoindol-2-yl)-N-[(1S)-2-hydroxy-1-[6-(4-methylpiperazin-1-yl)pyridin-2-yl]ethyl]acetamide | 621 |

-continued

| Example | Structure | Name | MS Data [M +H]+ unless specified |
|---|---|---|---|
| 744 | 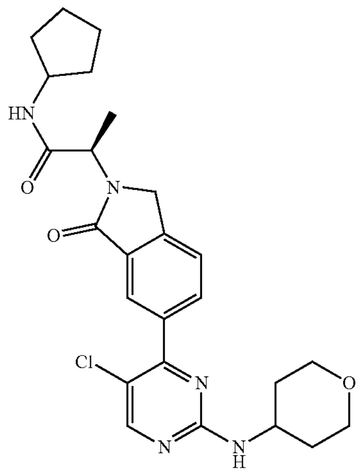 [SMILES: C[C@H](C(=O)NC1CCCC1)N1Cc2ccc(-c3nc(NC4CCOCC4)ncc3Cl)cc2C1=O] | (2R)-2-(6-{5-chloro-2-[(oxan-4-yl)amino]pyrimidin-4-yl}-1-oxo-2,3-dihydro-1H-isoindol-2-yl)-N-cyclopentylpropanamide | 484 |
| 745 | 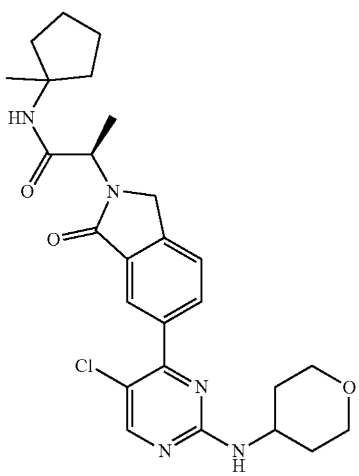 [SMILES: C[C@H](C(=O)NC1(C)CCCC1)N1Cc2ccc(-c3nc(NC4CCOCC4)ncc3Cl)cc2C1=O] | (2R)-2-(6-{5-chloro-2-[(oxan-4-yl)amino]pyrimidin-4-yl}-1-oxo-2,3-dihydro-1H-isoindol-2-yl)-N-(1-methylcyclopentyl)propanamide | 498 |
| 746 | 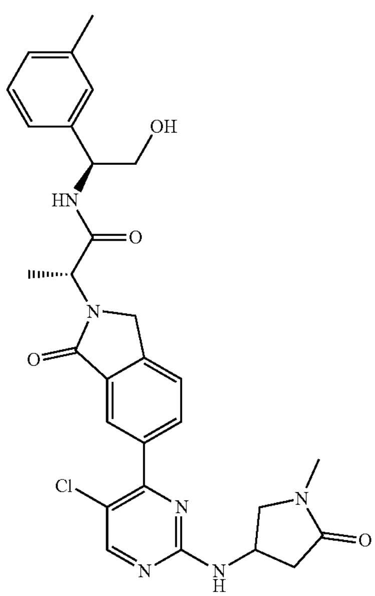 [SMILES: Cc1cccc([C@@H](CO)NC(=O)[C@@H](C)N2Cc3ccc(-c4nc(NC5CC(=O)N(C)C5)ncc4Cl)cc3C2=O)c1] | (2R)-2-(6-{5-chloro-2-[(1-methyl-5-oxopyrrolidin-3-yl)amino]pyrimidin-4-yl}-1-oxo-2,3-dihydro-1H-isoindol-2-yl)-N-[(1S)-2-hydroxy-1-(3-methylphenyl)ethyl]propanamide | 563 |

-continued

| Example | Structure | Name | MS Data [M +H]+ unless specified |
|---|---|---|---|
| 747 | 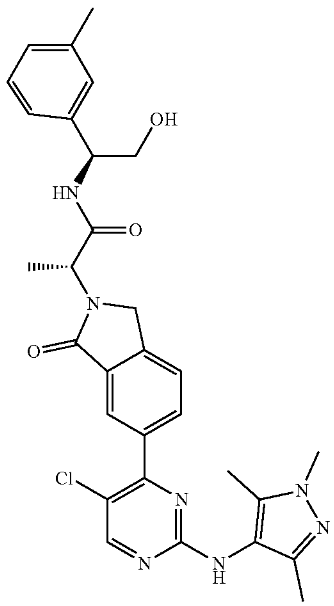 [SMILES: Cc1cccc([C@@H](CO)NC(=O)[C@@H](C)N2Cc3ccc(-c4nc(Nc5c(C)nn(C)c5C)ncc4Cl)cc3C2=O)c1] | (2R)-2-(6-{5-chloro-2-[(1,3,5-trimethyl-1H-pyrazol-4-yl)amino]pyrimidin-4-yl}-1-oxo-2,3-dihydro-1H-isoindol-2-yl)-N-[(1S)-2-hydroxy-1-(3-methylphenyl)ethyl]propanamide | 574 |
| 748 | 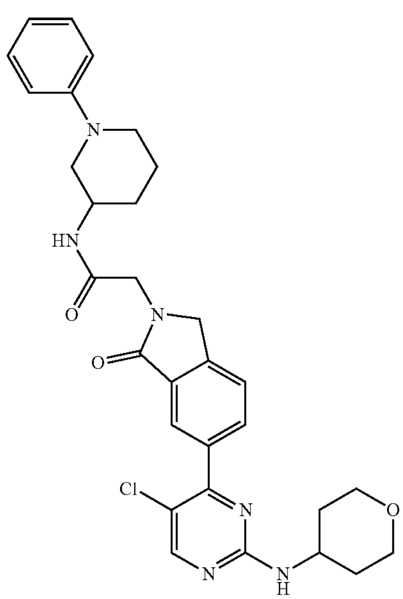 [SMILES: O=C(CN1Cc2ccc(-c3nc(NC4CCOCC4)ncc3Cl)cc2C1=O)NC1CCCN(c2ccccc2)C1] | 2-(6-{5-chloro-2-[(oxan-4-yl)amino]pyrimidin-4-yl}-1-oxo-2,3-dihydro-1H-isoindol-2-yl)-N-(1-phenylpiperidin-3-yl)acetamide | 561 |

-continued

| Example | Structure | Name | MS Data [M +H]+ unless specified |
|---|---|---|---|
| 749 | 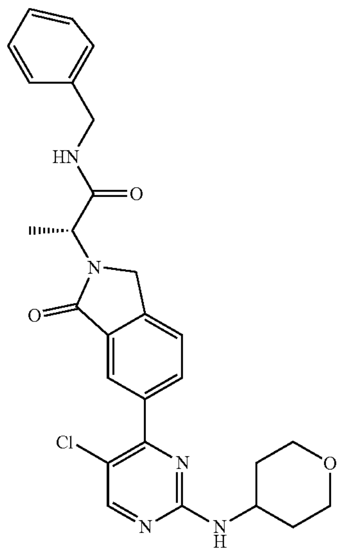 [SMILES: C[C@H](C(=O)NCc1ccccc1)N1Cc2ccc(-c3nc(NC4CCOCC4)ncc3Cl)cc2C1=O] | (2R)-N-benzyl-2-(6-{5-chloro-2-[(oxan-4-yl)amino]pyrimidin-4-yl}-1-oxo-2,3-dihydro-1H-isoindol-2-yl)propanamide | 506 |
| 750 | 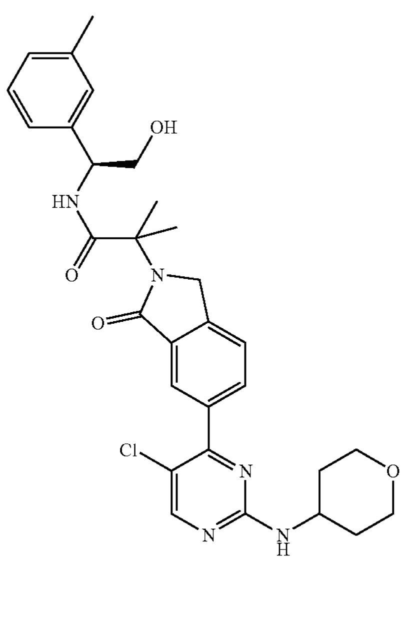 [SMILES: Cc1cccc([C@@H](CO)NC(=O)C(C)(C)N2Cc3ccc(-c4nc(NC5CCOCC5)ncc4Cl)cc3C2=O)c1] | 2-(6-{5-chloro-2-[(oxan-4-yl)amino]pyrimidin-4-yl}-1-oxo-2,3-dihydro-1H-isoindol-2-yl)-N-[(1S)-2-hydroxy-1-(3-methylphenyl)ethyl]-2-methylpropanamide | 564 |

| Example | Structure | Name | MS Data [M +H]+ unless specified |
|---|---|---|---|
| 751 | 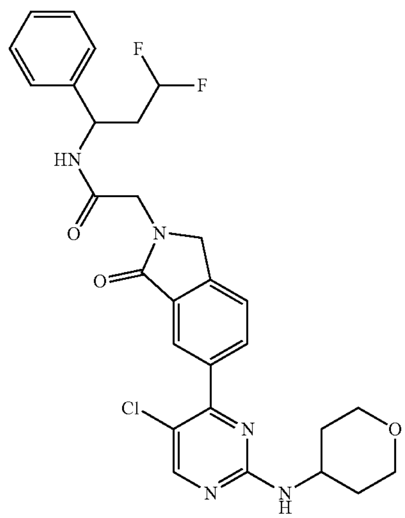 [SMILES: O=C(CN1Cc2ccc(-c3nc(NC4CCOCC4)ncc3Cl)cc2C1=O)NC(CC(F)F)c1ccccc1] | 2-(6-{5-chloro-2-[(oxan-4-yl)amino]pyrimidin-4-yl}-1-oxo-2,3-dihydro-1H-isoindol-2-yl)-N-(3,3-difluoro-1-phenylpropyl)acetamide Stereoisomer 1 | 556 |
| 752 | 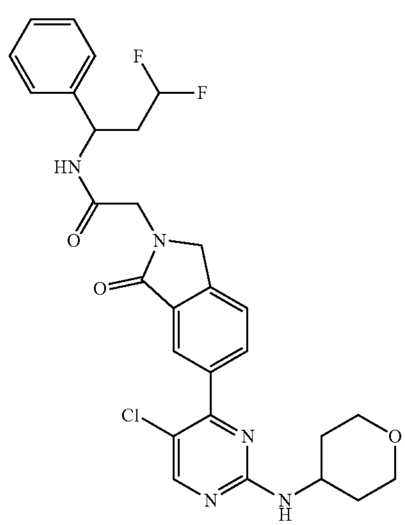 [SMILES: O=C(CN1Cc2ccc(-c3nc(NC4CCOCC4)ncc3Cl)cc2C1=O)NC(CC(F)F)c1ccccc1] | 2-(6-{5-chloro-2-[(oxan-4-yl)amino]pyrimidin-4-yl}-1-oxo-2,3-dihydro-1H-isoindol-2-yl)-N-(3,3-difluoro-1-phenylpropyl)acetamide Stereoisomer 2 | 556 |

| Example | Structure | Name | MS Data [M+H]+ unless specified |
|---|---|---|---|
| 753 | 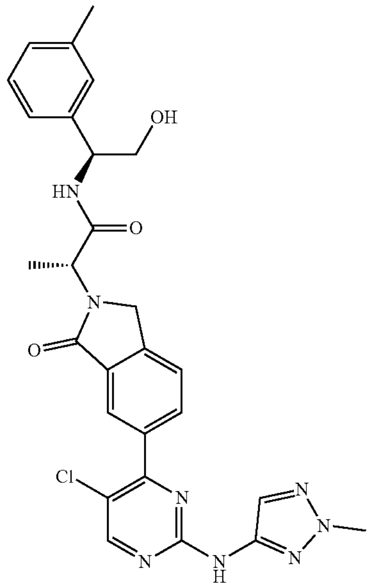 [SMILES: Cc1cccc([C@@H](CO)NC(=O)[C@@H](C)N2Cc3ccc(-c4nc(Nc5cnn(C)n5)ncc4Cl)cc3C2=O)c1] | (2R)-2-(6-{5-chloro-2-[(2-methyl-2H-1,2,3-triazol-4-yl)amino]pyrimidin-4-yl}-1-oxo-2,3-dihydro-1H-isoindol-2-yl)-N-[(1S)-2-hydroxy-1-(3-methylphenyl)ethyl]propanamide | 547 |
| 754 | 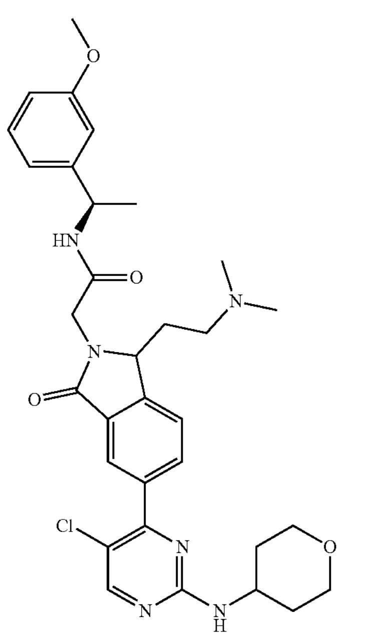 [SMILES: COc1cccc([C@@H](C)NC(=O)CN2C(=O)c3cc(-c4nc(NC5CCOCC5)ncc4Cl)ccc3C2CCN(C)C)c1] | 2-(5-{5-chloro-2-[(oxan-4-yl)amino]pyrimidin-4-yl}-1-[2-(dimethylamino)ethyl]-3-oxo-2,3-dihydro-1H-isoindol-2-yl)-N-[(1R)-1-(3-methoxyphenyl)ethyl]acetamide | 607 |

-continued

| Example | Structure | Name | MS Data [M +H]+ unless specified |
|---------|-----------|------|-----------------------------------|
| 755 | 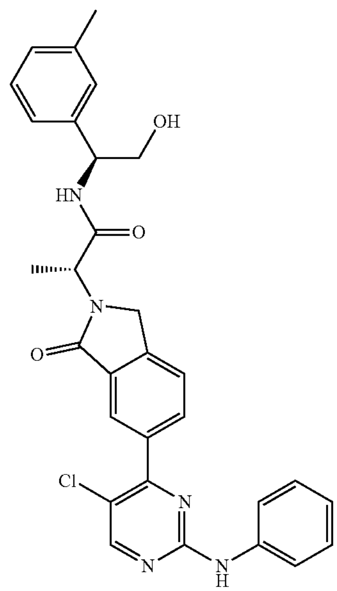 [SMILES: Cc1cccc([C@@H](CO)NC(=O)[C@@H](C)N2Cc3ccc(-c4nc(Nc5ccccc5)ncc4Cl)cc3C2=O)c1] | (2R)-2-{6-[5-chloro-2-(phenylamino)pyrimidin-4-yl]-1-oxo-2,3-dihydro-1H-isoindol-2-yl}-N-[(1S)-2-hydroxy-1-(3-methylphenyl)ethyl]propanamide | 542 |
| 756 | 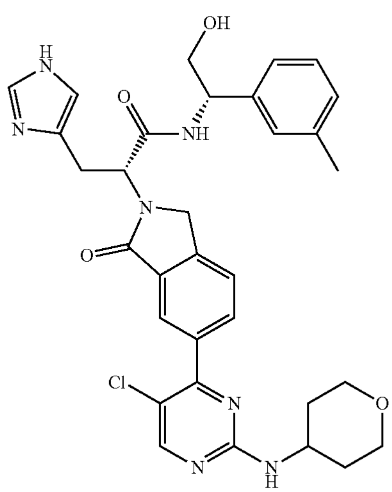 [SMILES: Cc1cccc([C@@H](CO)NC(=O)[C@@H](Cc2c[nH]cn2)N2Cc3ccc(-c4nc(NC5CCOCC5)ncc4Cl)cc3C2=O)c1] | (2R)-2-(6-{5-chloro-2-[(oxan-4-yl)amino]pyrimidin-4-yl}-1-oxo-2,3-dihydro-1H-isoindol-2-yl)-N-[(1S)-2-hydroxy-1-(3-methylphenyl)ethyl]-3-(1H-imidazol-4-yl)propanamide | 616 |

| Example | Structure | Name | MS Data [M +H]+ unless specified |
|---|---|---|---|
| 757 | 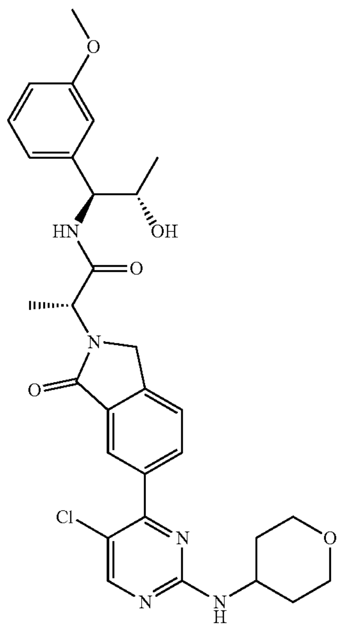 [SMILES: COc1cccc([C@H](NC(=O)[C@@H](C)N2Cc3ccc(-c4nc(NC5CCOCC5)ncc4Cl)cc3C2=O)[C@H](C)O)c1] | (2R)-2-(6-{5-chloro-2-[(oxan-4-yl)amino]pyrimidin-4-yl}-1-oxo-2,3-dihydro-1H-isoindol-2-yl)-N-[(1S,2S)-2-hydroxy-1-(3-methoxyphenyl)propyl]propanamide | 580 |
| 758 | 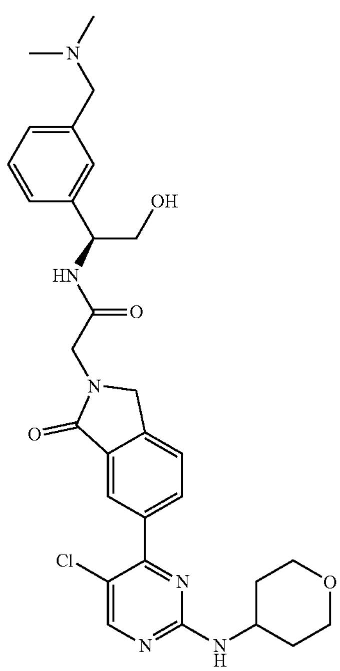 [SMILES: CN(C)Cc1cccc([C@@H](CO)NC(=O)CN2Cc3ccc(-c4nc(NC5CCOCC5)ncc4Cl)cc3C2=O)c1] | 2-(6-{5-chloro-2-[(oxan-4-yl)amino]pyrimidin-4-yl}-1-oxo-2,3-dihydro-1H-isoindol-2-yl)-N-[(1S)-1-{3-[(dimethylamino)methyl]phenyl}-2-hydroxyethyl]acetamide | 579 |

-continued

| Example | Structure | Name | MS Data [M +H]+ unless specified |
|---|---|---|---|
| 759 | 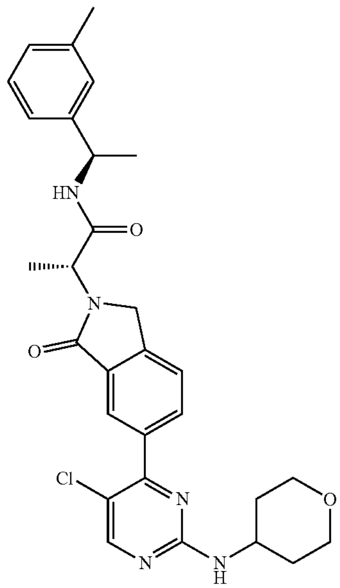 [SMILES: Cc1cccc([C@@H](C)NC(=O)[C@@H](C)N2Cc3ccc(-c4nc(NC5CCOCC5)ncc4Cl)cc3C2=O)c1] | (2R)-2-(6-{5-chloro-2-[(oxan-4-yl)amino]pyrimidin-4-yl}-1-oxo-2,3-dihydro-1H-isoindol-2-yl)-N-[(1R)-1-(3-methylphenyl)ethyl]propanamide | 534 |
| 760 | | No Example 760 | |
| 761 | 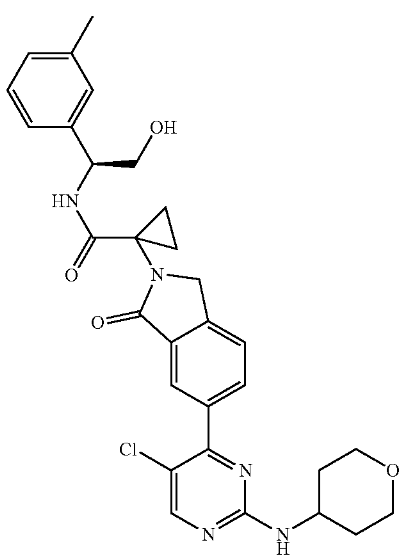 [SMILES: Cc1cccc([C@@H](CO)NC(=O)C2(N3Cc4ccc(-c5nc(NC6CCOCC6)ncc5Cl)cc4C3=O)CC2)c1] | 1-(6-{5-chloro-2-[(oxan-4-yl)amino]pyrimidin-4-yl}-1-oxo-2,3-dihydro-1H-isoindol-2-yl)-N-[(1S)-2-hydroxy-1-(3-methylphenyl)ethyl]cyclopropane-1-carboxamide | 562 |

-continued

| Example | Structure | Name | MS Data [M +H]+ unless specified |
|---|---|---|---|
| 762 | 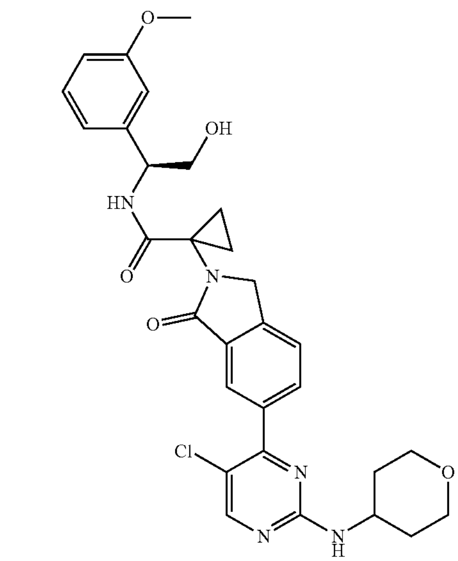 [SMILES: COc1cccc([C@@H](CO)NC(=O)C2(N3Cc4ccc(-c5nc(NC6CCOCC6)ncc5Cl)cc4C3=O)CC2)c1] | 1-(6-{5-chloro-2-[(oxan-4-yl)amino]pyrimidin-4-yl}-1-oxo-2,3-dihydro-1H-isoindol-2-yl)-N-[(1R)-1-(3-methoxyphenyl)ethyl]cyclopropane-1-carboxamide | 562 |
| 763 | 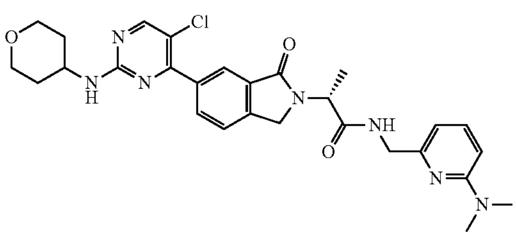 [SMILES: C[C@H](C(=O)NCc1cccc(N(C)C)n1)N1Cc2ccc(-c3nc(NC4CCOCC4)ncc3Cl)cc2C1=O] | 2-(6-{5-chloro-2-[(oxan-4-yl)amino]pyrimidin-4-yl}-1-oxo-2,3-dihydro-1H-isoindol-2-yl)-N-{[6-(dimethylamino)pyridin-2-yl]methyl}acetamide | 550 |
| 764 | 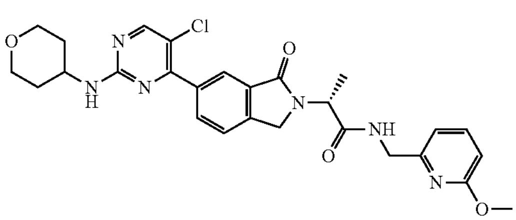 [SMILES: COc1cccc(CNC(=O)[C@@H](C)N2Cc3ccc(-c4nc(NC5CCOCC5)ncc4Cl)cc3C2=O)n1] | 2-(6-{5-chloro-2-[(oxan-4-yl)amino]pyrimidin-4-yl}-1-oxo-2,3-dihydro-1H-isoindol-2-yl)-N-[(6-methoxypyridin-2-yl)methyl]acetamide | 537 |

| Example | Structure | Name | MS Data [M +H]+ unless specified |
|---|---|---|---|
| 765 | 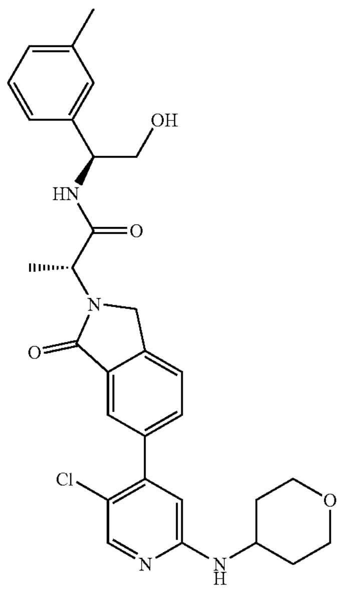 [SMILES: Cc1cccc([C@@H](CO)NC(=O)[C@@H](C)N2Cc3ccc(-c4cc(NC5CCOCC5)ncc4Cl)cc3C2=O)c1] | (2R)-2-(6-{5-chloro-2-[(oxan-4-yl)amino]pyridin-4-yl}-1-oxo-2,3-dihydro-1H-isoindol-2-yl)-N-[(1S)-2-hydroxy-1-(3-methylphenyl)ethyl]propanamide | 549 |
| 766 | 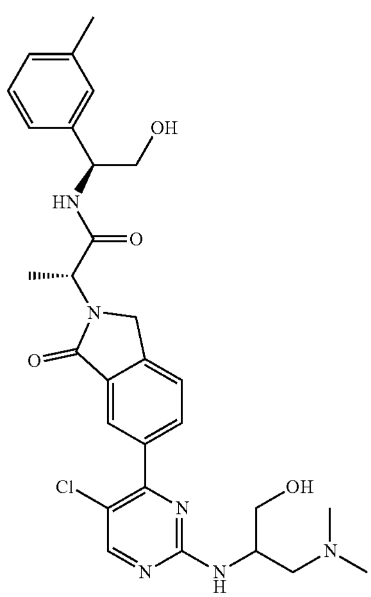 [SMILES: Cc1cccc([C@@H](CO)NC(=O)[C@@H](C)N2Cc3ccc(-c4nc(NC(CO)CN(C)C)ncc4Cl)cc3C2=O)c1] | (2R)-2-[6-(5-chloro-2-{[1-(dimethylamino)-3-hydroxypropan-2-yl]amino}pyrimidin-4-yl)-1-oxo-2,3-dihydro-1H-isoindol-2-yl]-N-[(1S)-2-hydroxy-1-(3-methylphenyl)ethyl]propanamide | 567 |

-continued

| Example | Structure | Name | MS Data [M +H]+ unless specified |
|---|---|---|---|
| 767 | 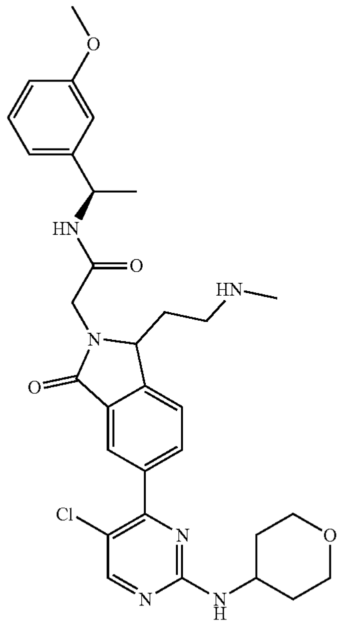 [SMILES: CNCCC1c2ccc(-c3nc(NC4CCOCC4)ncc3Cl)cc2C(=O)N1CC(=O)N[C@H](C)c1cccc(OC)c1] | 2-(5-{5-chloro-2-[(oxan-4-yl)amino]pyrimidin-4-yl}-1[2-(methylamino)ethyl]-3-oxo-2,3-dihydro-1H-isoindol-2-yl)-N-[(1R)-1-(3-methoxyphenyl)ethyl]acetamide | 593 |
| 768 | 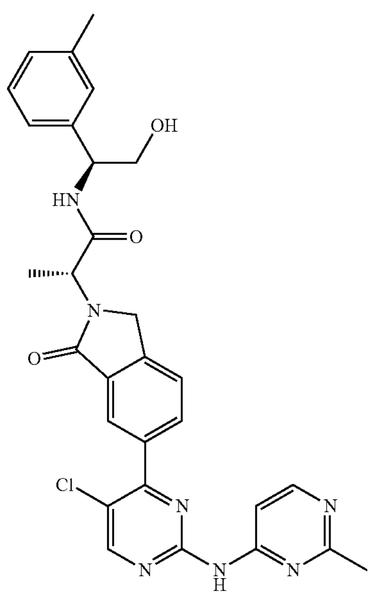 [SMILES: Cc1cccc([C@@H](CO)NC(=O)[C@@H](C)N2Cc3ccc(-c4nc(Nc5ccnc(C)n5)ncc4Cl)cc3C2=O)c1] | (2R)-2-(6-{5-chloro-2-[(2-methylpyrimidin-4-yl)amino]pyrimidin-4-yl}-1-oxo-2,3-dihydro-1H-isoindol-2-yl)-N-[(1S)-2-hydroxy-1-(3-methylphenyl)ethyl]propanamide | 558 |

-continued

| Example | Structure | Name | MS Data [M +H]+ unless specified |
|---|---|---|---|
| 769 | 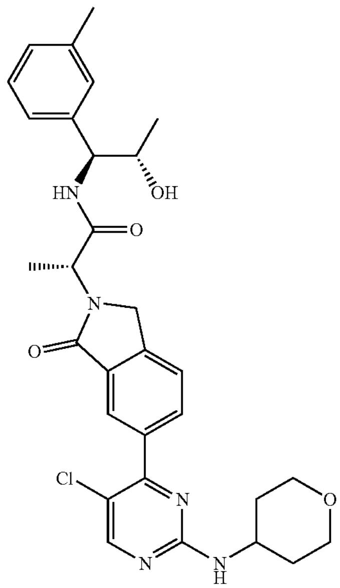 [SMILES: Cc1cccc([C@H](NC(=O)[C@@H](C)N2Cc3ccc(-c4nc(NC5CCOCC5)ncc4Cl)cc3C2=O)[C@H](C)O)c1] | (2R)-2-(6-{5-chloro-2-[(oxan-4-yl)amino]pyrimidin-4-yl}-1-oxo-2,3-dihydro-1H-isoindol-2-yl)-N-[(1S,2S)-2-hydroxy-1-(3-methylphenyl)propyl]propanamide | 564 |
| 770 | 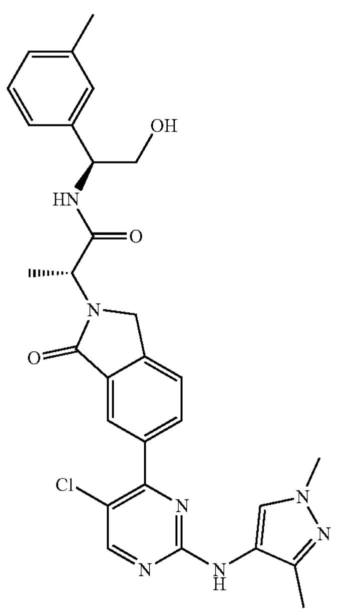 [SMILES: Cc1cccc([C@@H](CO)NC(=O)[C@@H](C)N2Cc3ccc(-c4nc(Nc5cn(C)nc5C)ncc4Cl)cc3C2=O)c1] | (2R)-2-(6-{5-chloro-2-[(1,3-dimethyl-1H-pyrazol-4-yl)amino]pyrimidin-4-yl}-1-oxo-2,3-dihydro-1H-isoindol-2-yl)-N-[(1S)-2-hydroxy-1-(3-methylphenyl)ethyl]propanamide | 560 |

-continued

| Example | Structure | Name | MS Data [M +H]+ unless specified |
|---|---|---|---|
| 771 | 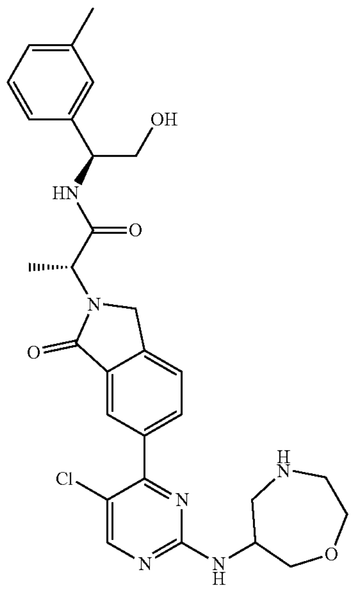 [SMILES: Cc1cccc([C@@H](CO)NC(=O)[C@@H](C)N2Cc3ccc(-c4nc(NC5CNCCOC5)ncc4Cl)cc3C2=O)c1] | (2R)-2-(6-{5-chloro-2-[(1,4-oxazepan-6-yl)amino]pyrimidin-4-yl}-1-oxo-2,3-dihydro-1H-isoindol-2-yl)-N-[(1S)-2-hydroxy-1-(3-methylphenyl)ethyl]propanamide | 565 |
| 772 | | No Example 772 | |
| 773 | 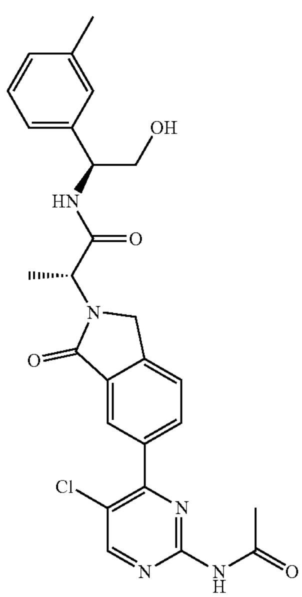 [SMILES: CC(=O)Nc1ncc(Cl)c(-c2ccc3c(c2)C(=O)N([C@H](C)C(=O)N[C@H](CO)c2cccc(C)c2)C3)n1] | (2R)-2-[6-(5-chloro-2-acetamidopyrimidin-4-yl)-1-oxo-2,3-dihydro-1H-isoindol-2-yl]-N-[(1S)-2-hydroxy-1-(3-methylphenyl)ethyl]propanamide | 508 |

| Example | Structure | Name | MS Data [M +H]+ unless specified |
|---|---|---|---|
| 774 | 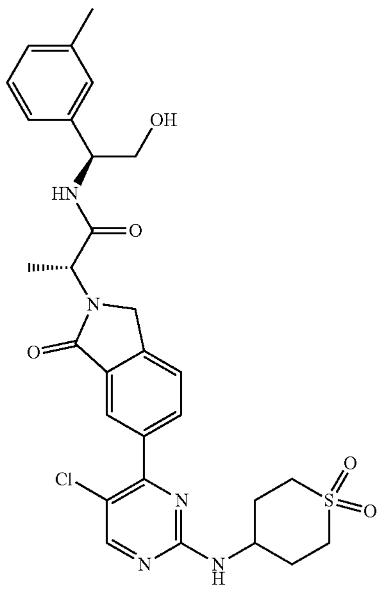 [SMILES: Cc1cccc([C@@H](CO)NC(=O)[C@@H](C)N2Cc3ccc(-c4nc(NC5CCS(=O)(=O)CC5)ncc4Cl)cc3C2=O)c1] | (2R)-2-(6-{5-chloro-2-[(1,1-dioxo-1λ⁶-thian-4-yl)amino]pyrimidin-4-yl}-1-oxo-2,3-dihydro-1H-isoindol-2-yl)-N-[(1S)-2-hydroxy-1-(3-methylphenyl)ethyl]propanamide | 598 |
| 775 | 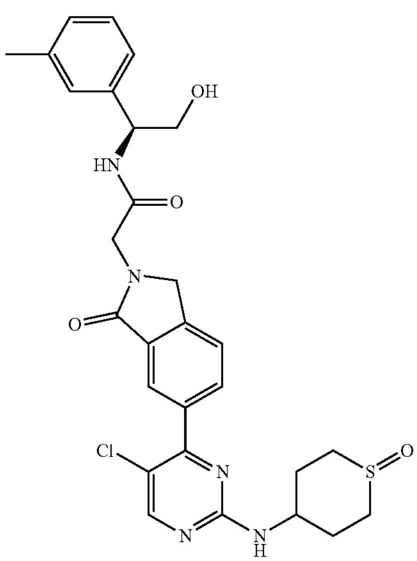 [SMILES: Cc1cccc([C@@H](CO)NC(=O)CN2Cc3ccc(-c4nc(NC5CCS(=O)CC5)ncc4Cl)cc3C2=O)c1] | 2-(6-}5-chloro-2-[(1-oxo-1λ⁴-thian-4-yl)amino]pyrimidin-4-yl}-1-oxo-2,3-dihydro-1H-isoindol-2-yl)-N-[(1S)-2-hydroxy-1-(3-methylphenyl)ethyl]acetamide | 568 |

-continued

| Example | Structure | Name | MS Data [M +H]+ unless specified |
|---|---|---|---|
| 776 | 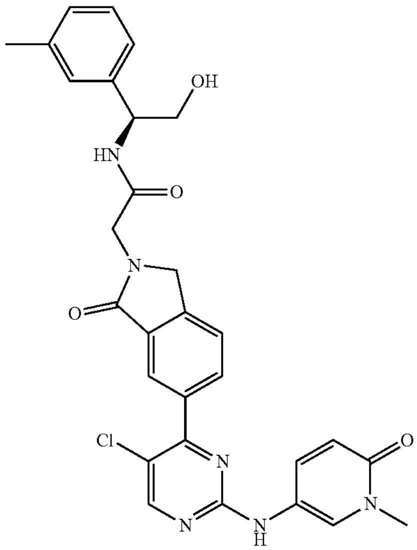 | 2-(6-{5-chloro-2-[(1-methyl-6-oxo-1,6-dihydropyridin-3-yl)amino]pyrimidin-4-yl}-1-oxo-2,3-dihydro-1H-isoindol-2-yl)-N-[(1S)-2-hydroxy-1-(3-methylphenyl)ethyl]acetamide | 559 |
| 777 | 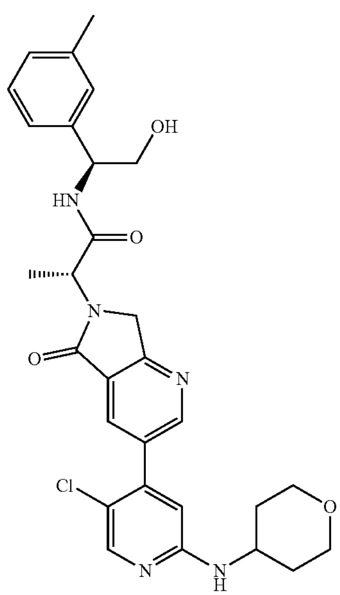 [SMILES: Cc1cccc([C@@H](CO)NC(=O)[C@@H](C)N2Cc3ncc(-c4cc(NC5CCOCC5)ncc4Cl)cc3C2=O)c1] | (2R)-2-(3-{5-chloro-2-[(oxan-4-yl)amino]pyridin-4-yl}-5-oxo-5H,6H,7H-pyrrolo[3,4-b]pyridin-6-yl)-N-[(1S)-2-hydroxy-1-(3-methylphenyl)ethyl]propanamide | 550 |

-continued

| Example | Structure | Name | MS Data [M +H]+ unless specified |
|---|---|---|---|
| 778 | 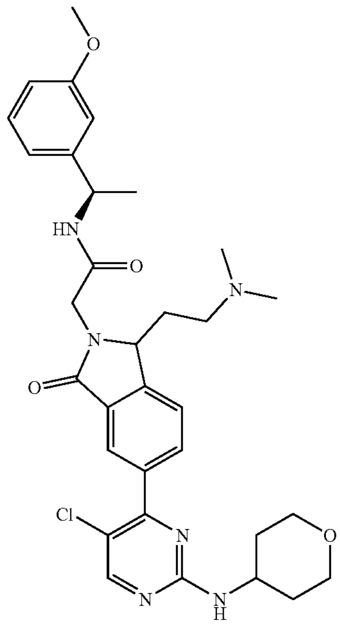 [SMILES: COc1cccc([C@@H](C)NC(=O)CN2C(=O)c3cc(-c4nc(NC5CCOCC5)ncc4Cl)ccc3C2CCN(C)C)c1] | 2-(5-{5-chloro-2-[(oxan-4-yl)amino]pyrimidin-4-yl}-1-[2-(dimethylamino)ethyl]-3-oxo-2,3-dihydro-1H-isoindol-2-yl)-N-[(1R)-1-(3-methoxyphenyl)ethyl]acetamide Stereoisomer 1 | 607 |
| 779 | 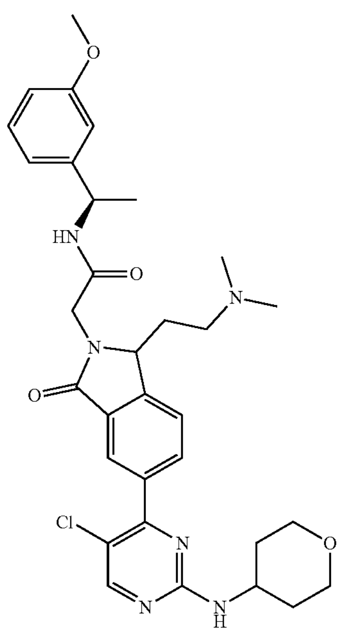 [SMILES: COc1cccc([C@@H](C)NC(=O)CN2C(=O)c3cc(-c4nc(NC5CCOCC5)ncc4Cl)ccc3C2CCN(C)C)c1] | 2-(5-{5-chloro-2-[(oxan-4-yl)amino]pyrimidin-4-yl}-1-[2-(dimethylamino)ethyl]-3-oxo-2,3-dihydro-1H-isoindol-2-yl)-N-[(1R)-1-(3-methoxyphenyl)ethyl]acetamide Stereoisomer 2 | 607 |

| Example | Structure | Name | MS Data [M +H]+ unless specified |
|---|---|---|---|
| 780 | 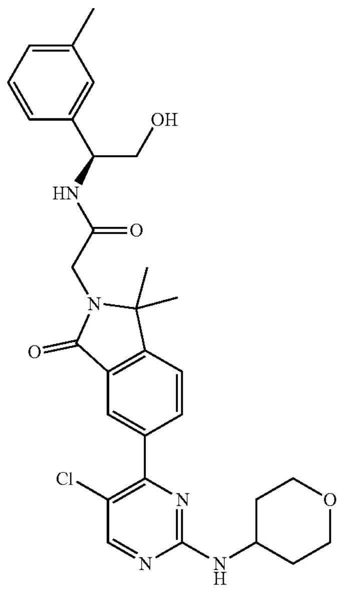 [SMILES: Cc1cccc([C@@H](CO)NC(=O)CN2C(=O)c3cc(-c4nc(NC5CCOCC5)ncc4Cl)ccc3C2(C)C)c1] | 2-(5-{5-chloro-2-[(oxan-4-yl)amino]pyrimidin-4-yl}-1,1-dimethyl-3-oxo-2,3-dihydro-1H-isoindol-2-yl)-N-[(1S)-2-hydroxy-1-(3-methylphenyl)ethyl]acetamide | 564 |
| 781 | 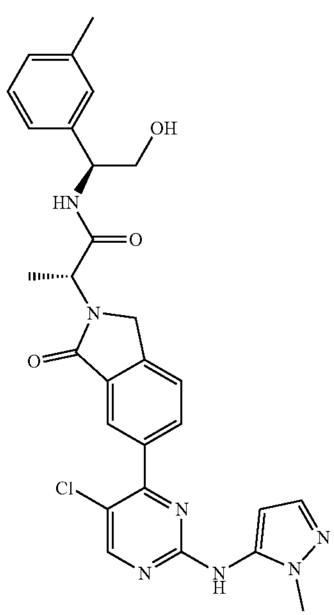 [SMILES: Cc1cccc([C@@H](CO)NC(=O)[C@@H](C)N2Cc3ccc(-c4nc(Nc5ccnn5C)ncc4Cl)cc3C2=O)c1] | (2R)-2-(6-}5-chloro-2-[(1-methyl-1H-pyrazol-5-yl)amino]pyrimidin-4-yl}-1-oxo-2,3-dihydro-1H-isoindol-2-yl)-N-[(1S)-2-hydroxy-1-(3-methylphenyl)ethyl]propanamide | 546 |

-continued

| Example | Structure | Name | MS Data [M +H]+ unless specified |
|---|---|---|---|
| 782 | 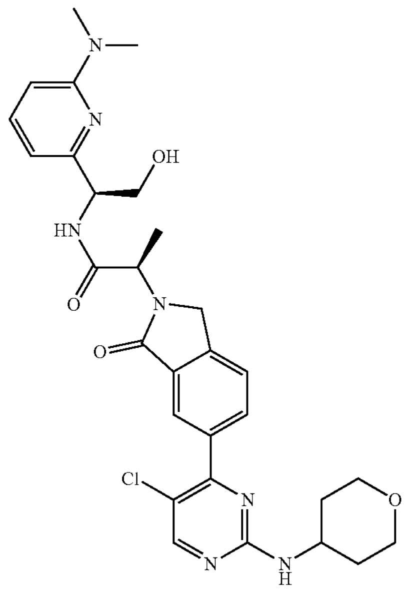 [SMILES: C[C@H](C(=O)N[C@H](CO)c1cccc(N(C)C)n1)N1Cc2ccc(-c3nc(NC4CCOCC4)ncc3Cl)cc2C1=O] | (2R)-2-(6-{5-chloro-2-[(oxan-4-yl)amino]pyrimidin-4-yl}-1-oxo-2,3-dihydro-1H-isoindol-2-yl)-N-[(1S)-1[6-(dimethylamino)pyridin-2-yl]-2-hydroxyethyl]propanamide | 580 |
| 783 | 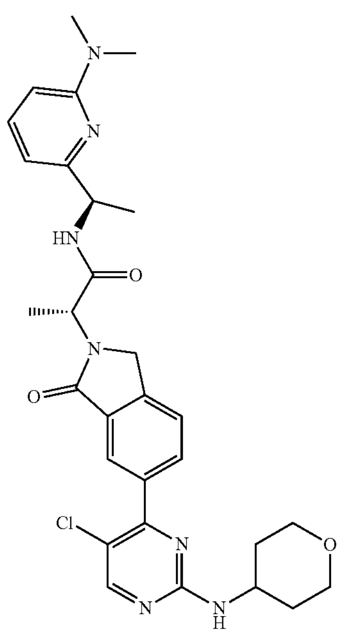 [SMILES: C[C@H](C(=O)N[C@H](C)c1cccc(N(C)C)n1)N1Cc2ccc(-c3nc(NC4CCOCC4)ncc3Cl)cc2C1=O] | (2R)-2-(6-{5-chloro-2-[(oxan-4-yl)amino]pyrimidin-4-yl}-1-oxo-2,3-dihydro-1H-isoindol-2-yl)-N-[(1R)-1[6-(dimethylamino)pyridin-2-yl]ethyl]propanamide | 564 |

-continued

| Example | Structure | Name | MS Data [M +H]+ unless specified |
|---|---|---|---|
| 784 | 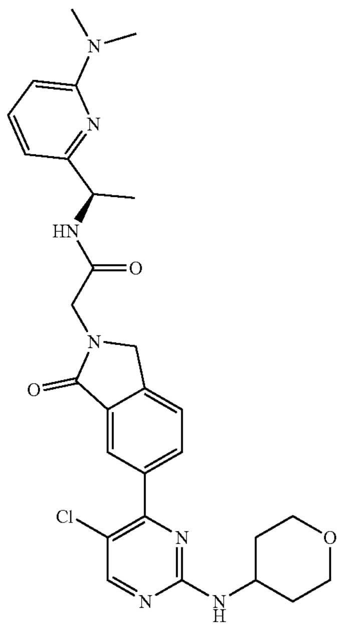 [SMILES: C[C@@H](NC(=O)CN1Cc2ccc(-c3nc(NC4CCOCC4)ncc3Cl)cc2C1=O)c1cccc(N(C)C)n1] | 2-(6-{5-chloro-2-[(oxan-4-yl)amino]pyrimidin-4-yl}-1-oxo-2,3-dihydro-1H-isoindol-2-yl)-N-[(1R)-1-[6-(dimethylamino)pyridin-2-yl]ethyl]acetamide | 550 [M −H]+ |
| 785 | 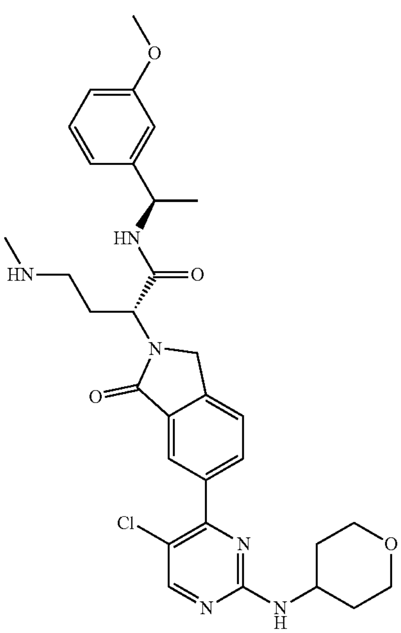 [SMILES: CNCC[C@H](C(=O)N[C@H](C)c1cccc(OC)c1)N1Cc2ccc(-c3nc(NC4CCOCC4)ncc3Cl)cc2C1=O] | (2R)-2-(6-{5-chloro-2-[(oxan-4-yl)amino]pyrimidin-4-yl}-1-oxo-2,3-dihydro-1H-isoindol-2-yl)-N-[(1R)-1-(3-methoxyphenyl)ethyl]-4-(methylamino)butanamide | 593 |

| Example | Structure | Name | MS Data [M +H]+ unless specified |
|---|---|---|---|
| 786 | 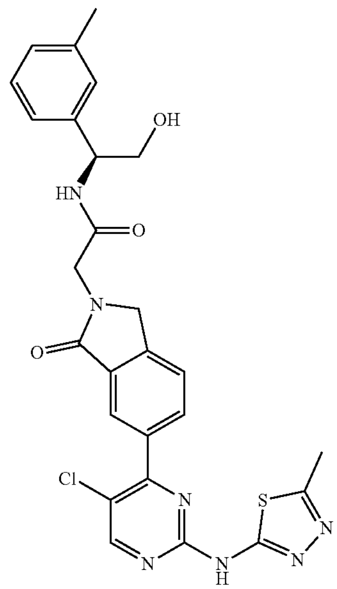 [SMILES: Cc1cccc([C@@H](CO)NC(=O)CN2Cc3ccc(-c4nc(Nc5nnc(C)s5)ncc4Cl)cc3C2=O)c1] | 2-(6-{5-chloro-2-[(5-methyl-1,3,4-thiadiazol-2-yl)amino]pyrimidin-4-yl}-1-oxo-2,3-dihydro-1H-isoindol-2-yl)-N-[(1S)-2-hydroxy-1-(3-methylphenyl)ethyl]acetamide | 550 |
| 787 | 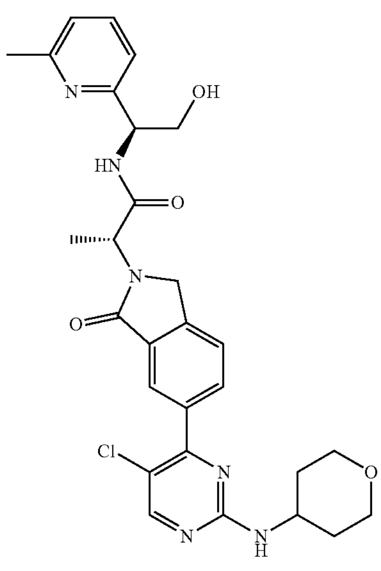 [SMILES: Cc1cccc([C@@H](CO)NC(=O)[C@@H](C)N2Cc3ccc(-c4nc(NC5CCOCC5)ncc4Cl)cc3C2=O)n1] | (2R)-2-(6-{5-chloro-2-[(oxan-4-yl)amino]pyridin-4-yl}-1-oxo-2,3-dihydro-1H-isoindol-2-yl)-N-[(1S)-2-hydroxy-1-(6-methylpyridin-2-yl)ethyl]propanamide | 550 |

| Example | Structure | Name | MS Data [M+H]+ unless specified |
|---------|-----------|------|--------------------------------|
| 788 | 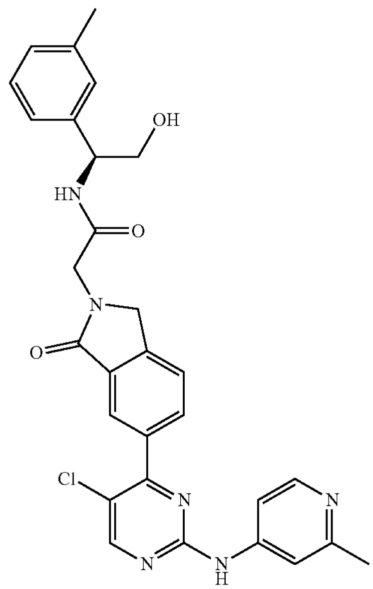 [SMILES: Cc1cccc([C@@H](CO)NC(=O)CN2Cc3ccc(-c4nc(Nc5ccnc(C)c5)ncc4Cl)cc3C2=O)c1] | 2-(6-{5-chloro-2-[(2-methylpyridin-4-yl)amino]pyrimidin-4-yl}-1-oxo-2,3-dihydro-1H-isoindol-2-yl)-N-[(1S)-2-hydroxy-1-(3-methylphenyl)ethyl]acetamide | 543 |
| 789 | 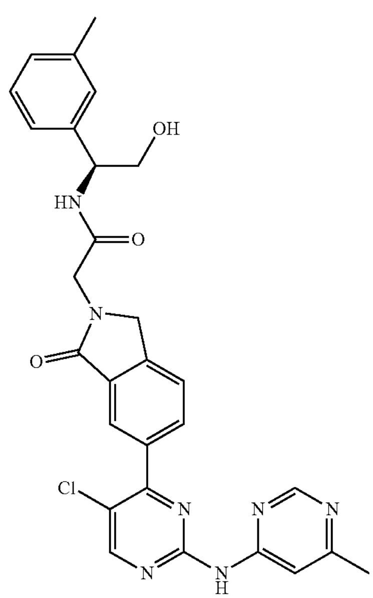 [SMILES: Cc1cccc([C@@H](CO)NC(=O)CN2Cc3ccc(-c4nc(Nc5cc(C)ncn5)ncc4Cl)cc3C2=O)c1] | 2-(6-{5-chloro-2-[(6-methylpyrimidin-4-yl)amino]pyrimidin-4-yl}-1-oxo-2,3-dihydro-1H-isoindol-2-yl)-N-[(1S)-2-hydroxy-1-(3-methylphenyl)ethyl]acetamide | 544 |

-continued

| Example | Structure | Name | MS Data [M +H]+ unless specified |
|---|---|---|---|
| 790 | 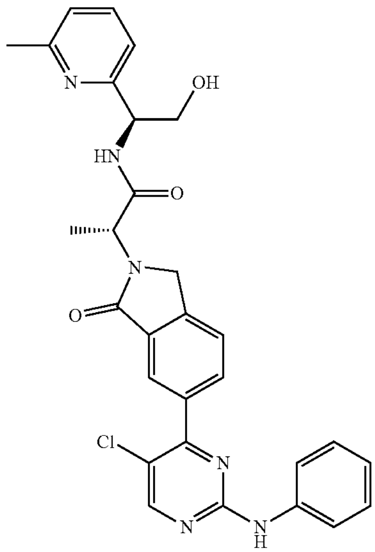 [SMILES: Cc1cccc([C@@H](CO)NC(=O)[C@@H](C)N2Cc3ccc(-c4nc(Nc5ccccc5)ncc4Cl)cc3C2=O)n1] | (2R)-2-{6-[5-chloro-2-(phenylamino)pyrimidin-4-yl]-1-oxo-2,3-dihydro-1H-isoindol-2-yl}-N-[(1S)-2-hydroxy-1-(6-methylpyridin-2-yl)ethyl]propanamide | 543 |
| 791 | 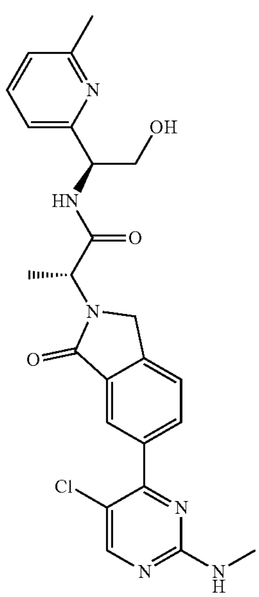 [SMILES: CNc1ncc(Cl)c(-c2ccc3c(c2)C(=O)N([C@H](C)C(=O)N[C@H](CO)c2cccc(C)n2)C3)n1] | (2R)-2-{6-[5-chloro-2-(methylamino)pyrimidin-4-yl]-1-oxo-2,3-dihydro-1H-isoindol-2-yl}-N-[(1S)-2-hydroxy-1-(6-methylpyridin-2-yl)ethyl]propanamide | 481 |

-continued

| Example | Structure | Name | MS Data [M +H]+ unless specified |
|---|---|---|---|
| 792 | 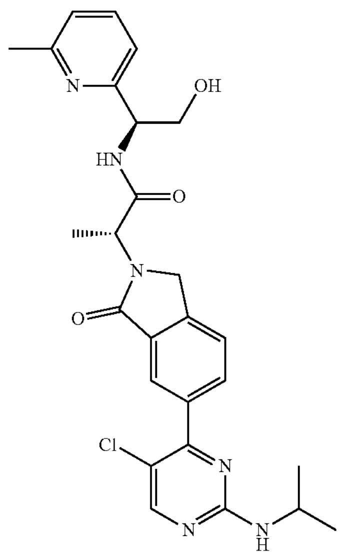 [SMILES: Cc1cccc([C@@H](CO)NC(=O)[C@@H](C)N2Cc3ccc(-c4nc(NC(C)C)ncc4Cl)cc3C2=O)n1] | (2R)-2-(6-{5-chloro-2-[(propan-2-yl)amino]pyrimidin-4-yl}-1-oxo-2,3-dihydro-1H-isoindol-2-yl)-N-[(1S)-2 hydroxy-1-(6-methylpyridin-2-yl)ethyl]propanamide | 509 |
| 793 | 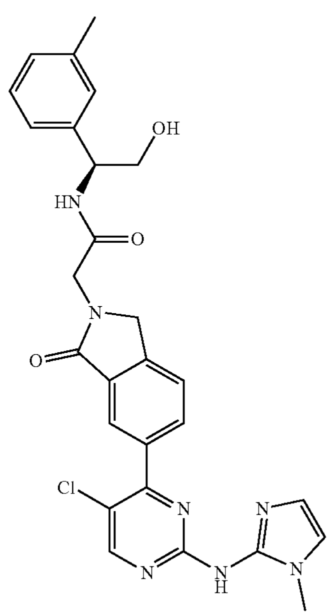 [SMILES: Cc1cccc([C@@H](CO)NC(=O)CN2Cc3ccc(-c4nc(Nc5nccn5C)ncc4Cl)cc3C2=O)c1] | 2-(6-{5-chloro-2-[(1-methyl-1H-imidazol-2-yl)amino]pyrimidin-4-yl}-1-oxo-2,3-dihydro-1H-isoindol-2-yl)-N-[(1S)-2-hydroxy-1-(3-methylphenyl)ethyl]acetamide | 532 |

-continued

| Example | Structure | Name | MS Data [M+H]+ unless specified |
|---|---|---|---|
| 794 | 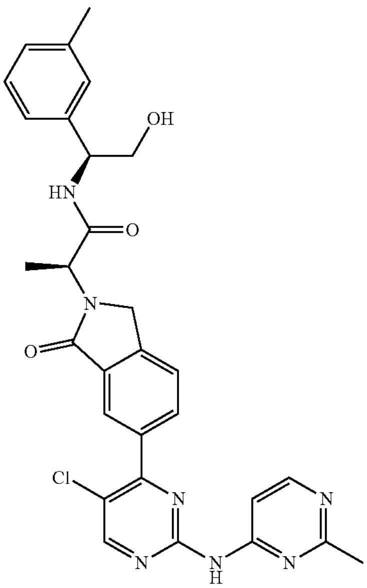 [SMILES: Cc1cccc([C@@H](CO)NC(=O)[C@H](C)N2Cc3ccc(-c4nc(Nc5ccnc(C)n5)ncc4Cl)cc3C2=O)c1] | (2S)-2-(6-{5-chloro-2-[(2-methylpyrimidin-4-yl)amino]pyrimidin-4-yl}-1-oxo-2,3-dihydro-1H-isoindol-2-yl)-N-[(1S)-2-hydroxy-1-(3-methylphenyl)ethyl]propanamide | 558 |
| 795 | 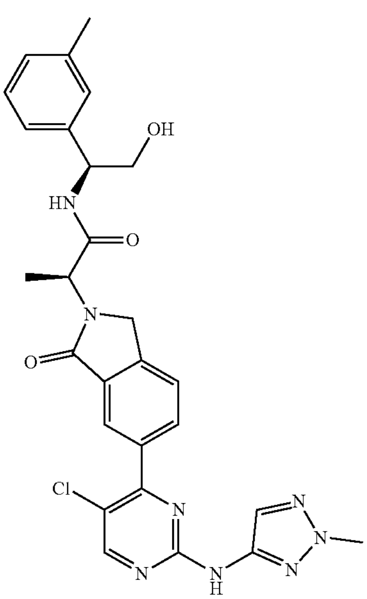 [SMILES: Cc1cccc([C@@H](CO)NC(=O)[C@H](C)N2Cc3ccc(-c4nc(Nc5cnn(C)n5)ncc4Cl)cc3C2=O)c1] | (2S)-2-(6-{5-chloro-2-[(2-methyl-2H-1,2,3-triazol-4-yl)amino]pyrimidin-4-yl}-1-oxo-2,3-dihydro-1H-isoindol-2-yl)-N-[(1S)-2-hydroxy-1-(3-methylphenyl)ethyl]propanamide | 547 |

-continued

| Example | Structure | Name | MS Data [M +H]+ unless specified |
|---|---|---|---|
| 796 | 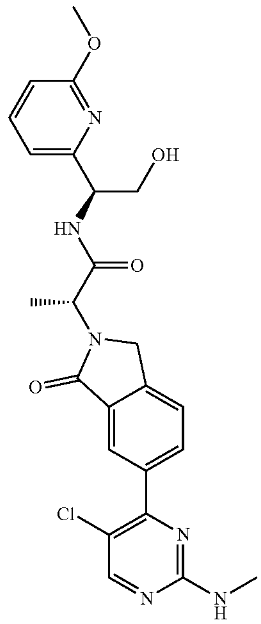 [SMILES: CNc1ncc(Cl)c(-c2ccc3c(c2)C(=O)N([C@H](C)C(=O)N[C@H](CO)c2cccc(OC)n2)C3)n1] | (2R)-2-{6-[5-chloro-2-(methylamino)pyrimidin-4-yl]-1-oxo-2,3-dihydro-1H-isoindol-2-yl}-N-[(1S)-2-hydroxy-1-(6-methoxypyridin-2-yl)ethyl]propanamide | 497 |
| 797 | 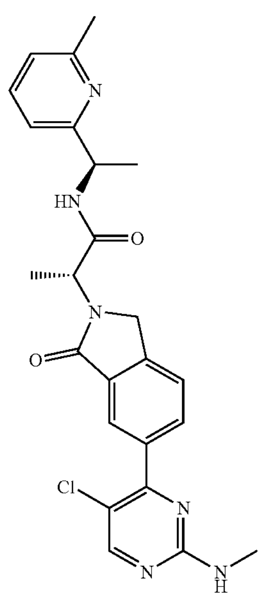 [SMILES: CNc1ncc(Cl)c(-c2ccc3c(c2)C(=O)N([C@H](C)C(=O)N[C@H](C)c2cccc(C)n2)C3)n1] | (2R)-2-{6-[5-chloro-2-(methylamino)pyrimidin-4-yl]-1-oxo-2,3-dihydro-1H-isoindol-2-yl}-N-[(1R)-1-(6-methylpyridin-2-yl)ethyl]propanamide | 465 |

-continued

| Example | Structure | Name | MS Data [M +H]+ unless specified |
|---|---|---|---|
| 798 | 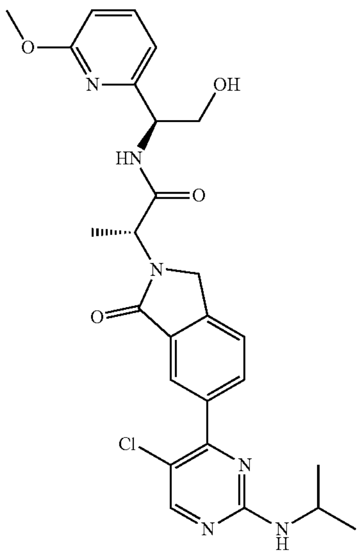 [SMILES: COc1cccc([C@@H](CO)NC(=O)[C@@H](C)N2Cc3ccc(-c4nc(NC(C)C)ncc4Cl)cc3C2=O)n1] | (2R)-2-(6-{5-chloro-2-[(propan-2-yl)amino]pyrimidin-4-yl}-1-oxo-2,3-dihydro-1H-isoindol-2-yl)-N-[(1S)-2-hydroxy-1-(6-methoxypyridin-2-yl)ethyl]propanamide | 525 |
| 799 | 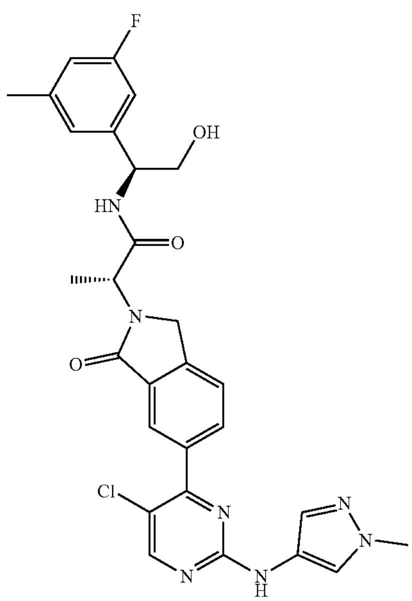 | (2R)-2-(6-{5-chloro-2-[(1-methyl-1H-pyrazol-4-yl)amino]pyrimidin-4-yl}-1-oxo-2,3-dihydro-1H-isoindol-2-yl)-N-[(1S)-1-(3-fluoro-5-methylphenyl)-2-hydroxyethyl]propanamide | 564 |

-continued

| Example | Structure | Name | MS Data [M +H]+ unless specified |
|---|---|---|---|
| 800 | 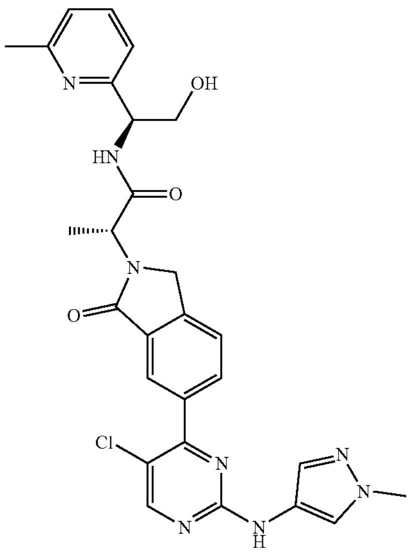 | (2R)-2-(6-{5-chloro-2-[(1-methyl-1H-pyrazol-4-yl)amino]pyrimidin-4-yl}-1-oxo-2,3-dihydro-1H-isoindol-2-yl)-N-[(1S)-2-hydroxy-1-(6-methylpyridin-2-yl)ethyl]propanamide | 547 |
| 801 | 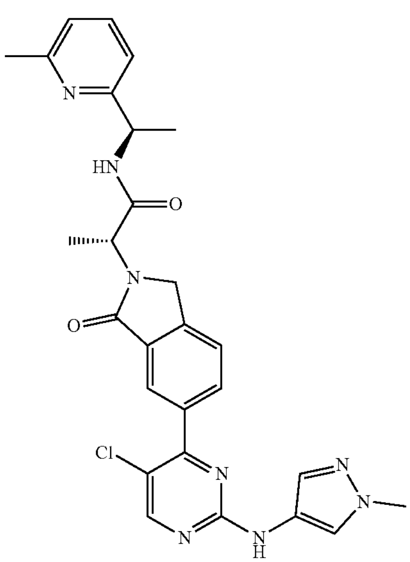 | (2R)-2-(6-{5-chloro-2-[(1-methyl-1H-pyrazol-4-yl)amino]pyrimidin-4-yl}-1-oxo-2,3-dihydro-1H-isoindol-2-yl)-N-[(1R)-1-(6-methylpyridin-2-yl)ethyl]propanamide | 531 |

-continued

| Example | Structure | Name | MS Data [M +H]+ unless specified |
|---|---|---|---|
| 802 | 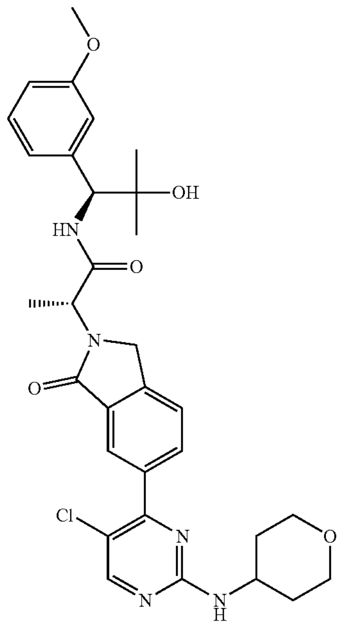 [SMILES: COc1cccc([C@H](NC(=O)[C@@H](C)N2Cc3ccc(-c4nc(NC5CCOCC5)ncc4Cl)cc3C2=O)C(C)(C)O)c1] | 2-(6-{5-chloro-2-[(oxan-4-yl)amino]pyrimidin-4-yl}-1-oxo-2,3-dihydro-1H-isoindol-2-yl)-N-[(1S)-2-hydroxy-1-(3-methoxyphenyl)-2-methylpropyl]acetamide | 580 |
| 803 | 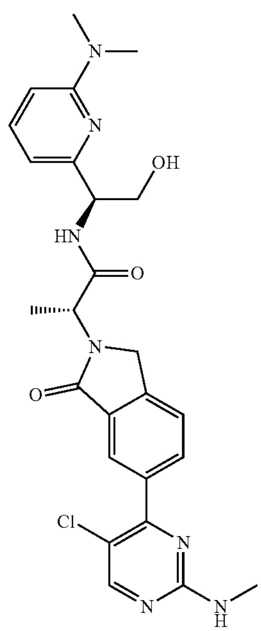 [SMILES: CNc1ncc(Cl)c(-c2ccc3c(c2)C(=O)N([C@H](C)C(=O)N[C@H](CO)c2cccc(N(C)C)n2)C3)n1] | (2R)-2-{6-[5-chloro-2-(methylamino)pyrimidin-4-yl]-1-oxo-2,3-dihydro-1H-isoindol-2-yl}-N-[(1S)-1-[6-(dimethylamino)pyridin-2-yl]-2-hydroxyethyl]propanamide | 510 |

-continued
| Example | Structure | Name | MS Data [M+H]+ unless specified |
|---|---|---|---|
| 804 | 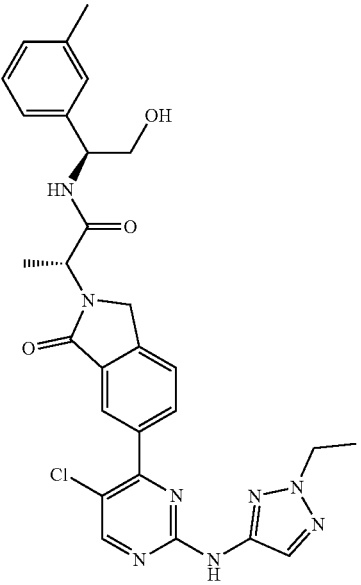 [SMILES: CCn1ncc(Nc2ncc(Cl)c(-c3ccc4c(c3)C(=O)N([C@H](C)C(=O)N[C@H](CO)c3cccc(C)c3)C4)n2)n1] | (2R)-2-(6-{5-chloro-2-[(2-ethyl-2H-1,2,3-triazol-4-yl)amino]pyrimidin-4-yl}-1-oxo-2,3-dihydro-1H-isoindol-2-yl)-N-[(1S)-2-hydroxy-1-(3-methylphenyl)ethyl]propanamide | 561 |
| 805 | 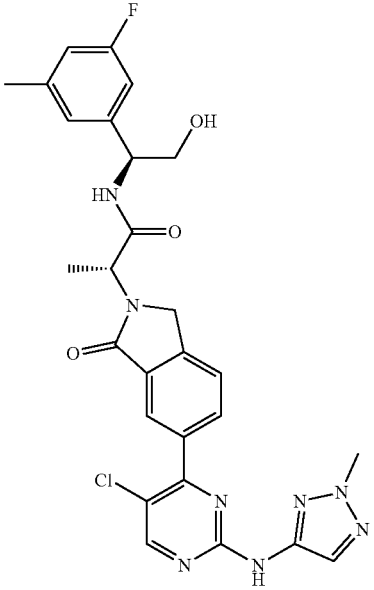 [SMILES: Cc1cc(F)cc([C@@H](CO)NC(=O)[C@@H](C)N2Cc3ccc(-c4nc(Nc5cnn(C)n5)ncc4Cl)cc3C2=O)c1] | (2R)-2-(6-{5-chloro-2-[(2-methyl-2H-1,2,3-triazol-4-yl)amino]pyrimidin-4-yl}-1-oxo-2,3-dihydro-1H-isoindol-2-yl)-N-[(1S)-1-(3-fluoro-5-methylphenyl)-2-hydroxyethyl]propanamide | 565 |

-continued

| Example | Structure | Name | MS Data [M +H]+ unless specified |
|---|---|---|---|
| 806 | 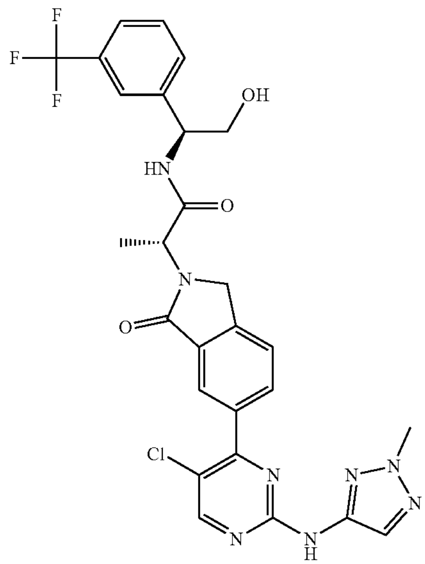 [SMILES: C[C@H](C(=O)N[C@H](CO)c1cccc(C(F)(F)F)c1)N1Cc2ccc(-c3nc(Nc4cnn(C)n4)ncc3Cl)cc2C1=O] | (2R)-2-(6-{5-chloro-2-[(2-methyl-2H-1,2,3-triazol-4-yl)amino]pyrimidin-4-yl}-1-oxo-2,3-dihydro-1H-isoindol-2-yl)-N-[(1S)-2-hydroxy-1-[3-(trifluoromethyl)phenyl]ethyl]propanamide | 599 |
| 807 | | No Example 807 | |
| 808 | 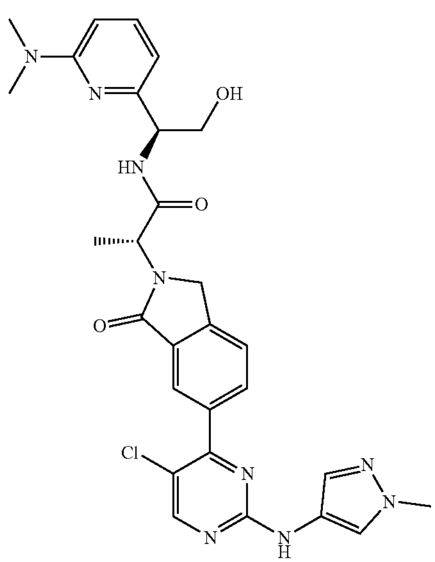 | (2R)-2-(6-{5-chloro-2-[(1-methyl-1H-pyrazol-4-yl)amino]pyrimidin-4-yl}-1-oxo-2,3-dihydro-1H-isoindol-2-yl)-N-[(1S)-1-[6-(dimethylamino)pyridin-2-yl]-2-hydroxyethyl]propanamide | 576 |

-continued

| Example | Structure | Name | MS Data [M +H]+ unless specified |
|---|---|---|---|
| 809 | 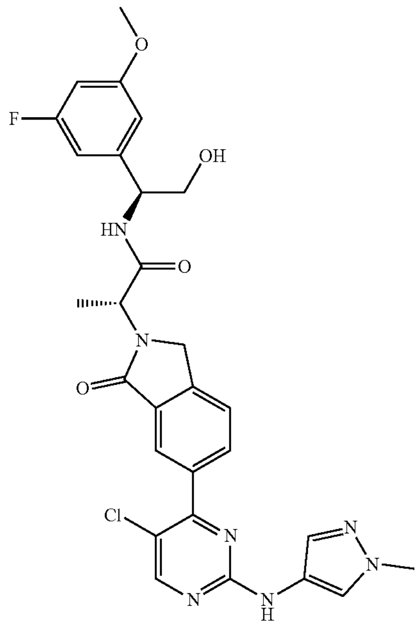 [SMILES: COc1cc(F)cc([C@@H](CO)NC(=O)[C@@H](C)N2Cc3ccc(-c4nc(Nc5cnn(C)c5)ncc4Cl)cc3C2=O)c1] | (2R)-2-(6-{5-chloro-2-[(1-methyl-1H-pyrazol-4-yl)amino]pyrimidin-4-yl}-1-oxo-2,3-dihydro-1H-isoindol-2-yl)-N-[(1S)-1-(3-fluoro-5-methoxyphenyl)-2-hydroxyethyl]propanamide | 580 |
| 810 | 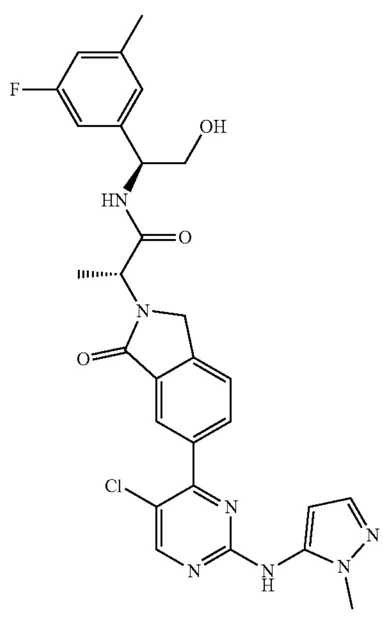 [SMILES: Cc1cc(F)cc([C@@H](CO)NC(=O)[C@@H](C)N2Cc3ccc(-c4nc(Nc5ccnn5C)ncc4Cl)cc3C2=O)c1] | (2R)-2-(6-{5-chloro-2-[(1-methyl-1H-pyrazol-5-yl)amino]pyrimidin-4-yl}-1-oxo-2,3-dihydro-1H-isoindol-2-yl)-N-[(1S)-1-(3-fluoro-5-methylphenyl)-2-hydroxyethyl]propanamide | 564 |

| Example | Structure | Name | MS Data [M +H]+ unless specified |
|---|---|---|---|
| 811 | 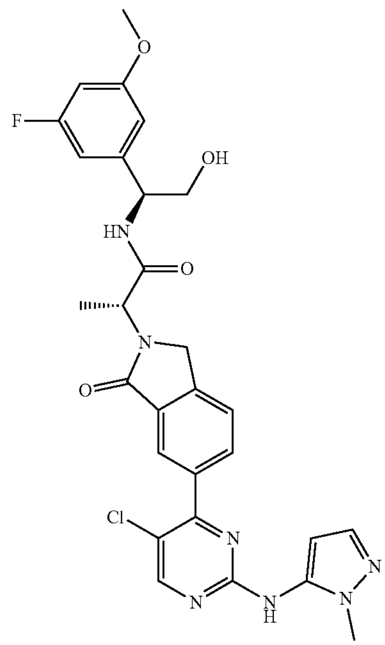 [SMILES: COc1cc(F)cc([C@@H](CO)NC(=O)[C@@H](C)N2Cc3ccc(-c4nc(Nc5ccnn5C)ncc4Cl)cc3C2=O)c1] | (2R)-2-(6-{5-chloro-2-[(1-methyl-1H-pyrazol-5-yl)amino]pyrimidin-4-yl}-1-oxo-2,3-dihydro-1H-isoindol-2-yl)-N-[(1S)-1-(3-fluoro-5-methoxyphenyl)-2-hydroxyethyl]propanamide | 580 |
| 812 | 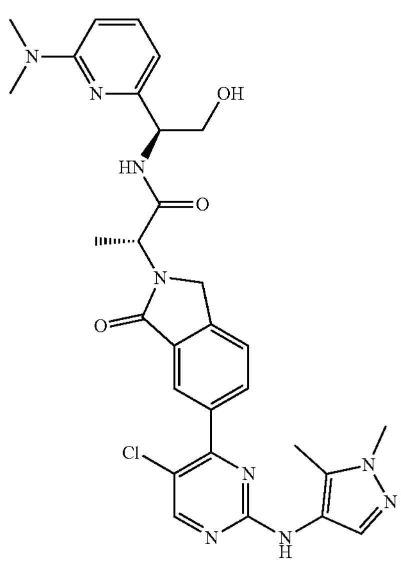 [SMILES: Cc1c(Nc2ncc(Cl)c(-c3ccc4c(c3)C(=O)N([C@H](C)C(=O)N[C@H](CO)c3cccc(N(C)C)n3)C4)n2)cnn1C] | (2R)-2-(6-{5-chloro-2-[(1,5-dimethyl-1H-pyrazol-4-yl)amino]pyrimidin-4-yl}-1-oxo-2,3-dihydro-1H-isoindol-2-yl)-N-[(1S)-1-[6-(dimethylamino)pyridin-2-yl]-2-hydroxyethyl]propanamide | 590 |

-continued

| Example | Structure | Name | MS Data [M +H]+ unless specified |
|---|---|---|---|
| 813 | 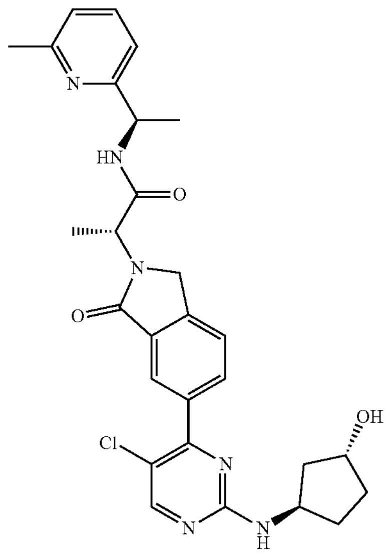 [SMILES: Cc1cccc([C@@H](C)NC(=O)[C@@H](C)N2Cc3ccc(-c4nc(N[C@@H]5CC[C@@H](O)C5)ncc4Cl)cc3C2=O)n1] | (2R)-2-[6-(5-chloro-2-{[(1R,3R)-3-hydroxycyclopentyl]amino}pyrimidin-4-yl)-1-oxo-2,3-dihydro-1H-isoindol-2-yl]N-[(1R)-1-(6-methylpyridin-2-yl)ethyl]propanamide | 535 |
| 814 | 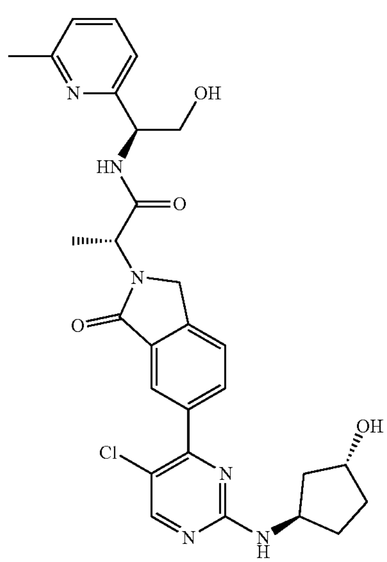 [SMILES: Cc1cccc([C@@H](CO)NC(=O)[C@@H](C)N2Cc3ccc(-c4nc(N[C@@H]5CC[C@@H](O)C5)ncc4Cl)cc3C2=O)n1] | (2R)-2-[6-(5-chloro-2-{[(1R,3R)-3-hydroxycyclopentyl]amino}pyrimidin-4-yl)-1-oxo-2,3-dihydro-1H-isoindol-2-yl]-N-(1S)-2-hydroxy-1-(6-methylpyridin-2-yl)ethyl]propanamide | 551 |

-continued

| Example | Structure | Name | MS Data [M +H]+ unless specified |
|---|---|---|---|
| 815 | 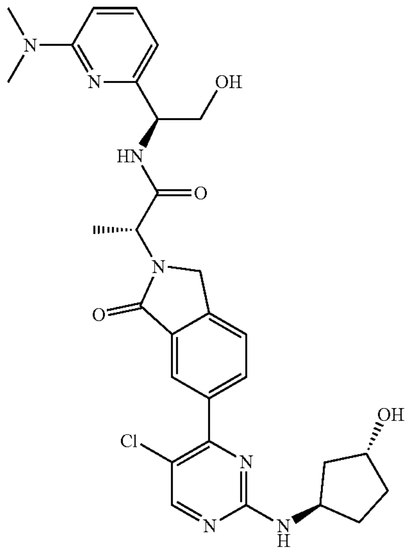 [SMILES: C[C@H](C(=O)N[C@H](CO)c1cccc(N(C)C)n1)N1Cc2ccc(-c3nc(N[C@@H]4CC[C@@H](O)C4)ncc3Cl)cc2C1=O] | (2R)-2-[6-(5-chloro-2-{[(1R,3R)-3-hydroxycyclopentyl]amino}pyrimidin-4-yl)-1-oxo-2,3-dihydro-1H-isoindol-2-yl]-N-[(1S)-1[6-(dimethylamino)pyridin-2-yl]-2-hydroxyethyl]propanamide | 580 |
| 816 | 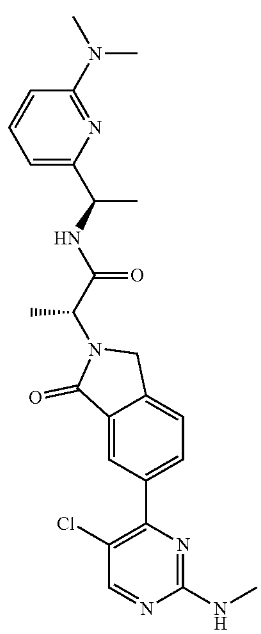 [SMILES: CNc1ncc(Cl)c(-c2ccc3c(c2)C(=O)N([C@H](C)C(=O)N[C@H](C)c2cccc(N(C)C)n2)C3)n1] | (2R)-2-{6[5-chloro-2-(methylamino)pyrimidin-4-yl]-1-oxo-2,3-dihydro-1H-isoindol-2-yl}-N-[(1R)-1-[6-(dimethylamino)pyridin-2-yl]ethyl]propanamide | 494 |

| Example | Structure | Name | MS Data [M+H]+ unless specified |
|---|---|---|---|
| 817 | 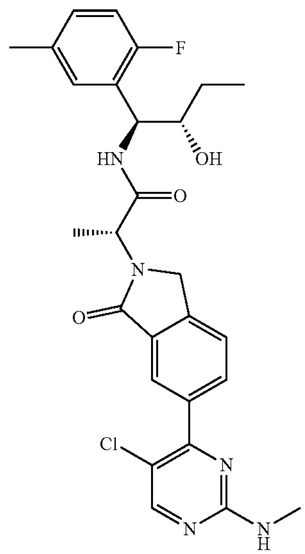 | (2R)-2-{6-[5-chloro-2-(methylamino)pyrimidin-4-yl]-1-oxo-2,3-dihydro-1H-isoindol-2-yl}-N-[(1S,2S)-1-(2-fluoro-5-methylphenyl)-2-hydroxybutyl]propanamide | 526 |
| 818 | 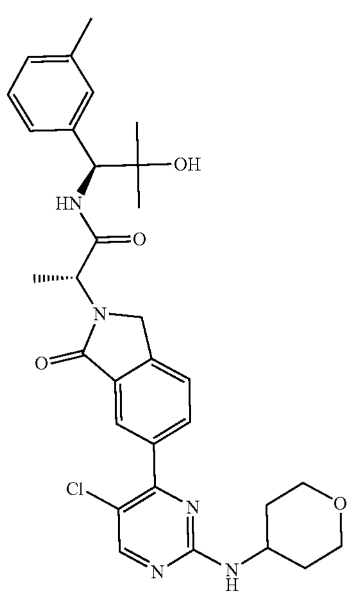 [SMILES: Cc1cccc([C@H](NC(=O)[C@@H](C)N2Cc3ccc(-c4nc(NC5CCOCC5)ncc4Cl)cc3C2=O)C(C)(C)O)c1] | (2R)-2-(6-{5-chloro-2-[(oxan-4-yl)amino]pyrimidin-4-yl}-1-oxo-2,3-dihydro-1H-isoindol-2-yl)-N-[(1S)-2-hydroxy-2-methyl-1-(3-methylphenyl)propyl]propanamide | 578 |

-continued

| Example | Structure | Name | MS Data [M +H]+ unless specified |
|---|---|---|---|
| 819 | 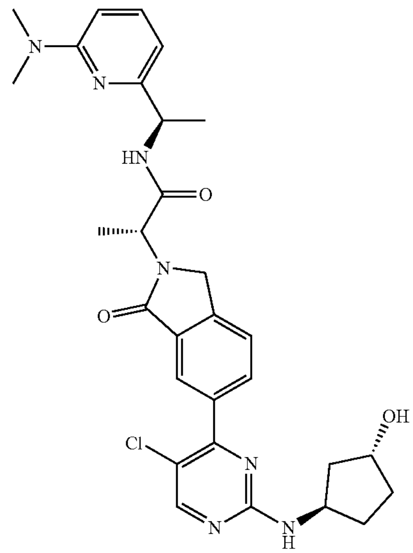 [SMILES: C[C@H](C(=O)N[C@H](C)c1cccc(N(C)C)n1)N1Cc2ccc(-c3nc(N[C@@H]4CC[C@@H](O)C4)ncc3Cl)cc2C1=O] | (2R)-2-[6-(5-chloro-2-{[(1R,3R)-3-hydroxycyclopentyl]amino}pyrimidin-4-yl)-1-oxo-2,3-dihydro-1H-isoindol-2-yl]-N-[(1R)-1-[6-(dimethylamino)pyridin-2-yl]ethyl]propanamide | 564 |
| 820 | 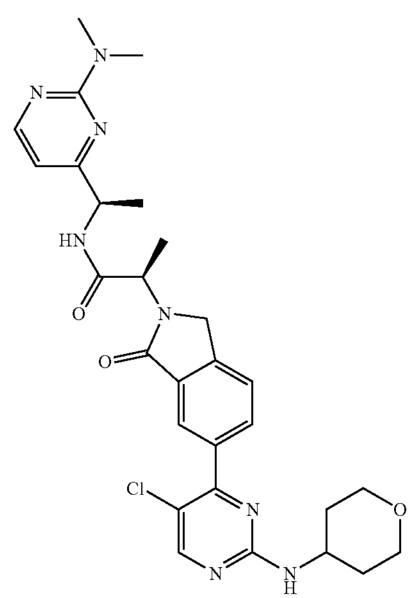 [SMILES: C[C@H](C(=O)N[C@H](C)c1ccnc(N(C)C)n1)N1Cc2ccc(-c3nc(NC4CCOCC4)ncc3Cl)cc2C1=O] | (2R)-2-(6-{5-chloro-2-[(oxan-4-yl)amino]pyrimidin-4-yl}-1-oxo-2,3-dihydro-1H-isoindol-2-yl)-N-[(1R)-1[2-(dimethylamino)pyrimidin-4-yl]ethyl]propanamide | 565 |

-continued

| Example | Structure | Name | MS Data [M+H]+ unless specified |
|---|---|---|---|
| 821 | 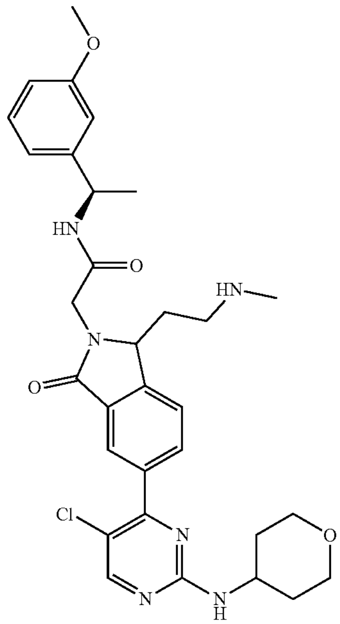 [SMILES: CNCCC1c2ccc(-c3nc(NC4CCOCC4)ncc3Cl)cc2C(=O)N1CC(=O)N[C@H](C)c1cccc(OC)c1] | 2-(5-{5-chloro-2-[(oxan-4-yl)amino]pyrimidin-4-yl}-1-[2-(methylamino)ethyl]-3-oxo-2,3-dihydro-1H-isoindol-2-yl)-N-[(1R)-1-(3-methoxyphenyl)ethyl]acetamide Stereoisomer 1 | 593 |
| 822 | 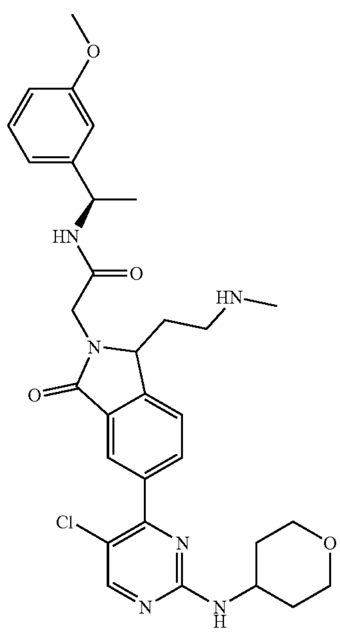 [SMILES: CNCCC1c2ccc(-c3nc(NC4CCOCC4)ncc3Cl)cc2C(=O)N1CC(=O)N[C@H](C)c1cccc(OC)c1] | 2-(5-{5-chloro-2-[(oxan-4-yl)amino]pyrimidin-4-yl}-1-[2-(methylamino)ethyl]-3-oxo-2,3-dihydro-1H-isoindol-2-yl)-N-[(1R)-1-(3-methoxyphenyl)ethyl]acetamide Stereoisomer 2 | 593 |

| Example | Structure | Name | MS Data [M +H]+ unless specified |
|---------|-----------|------|------|
| 823 | 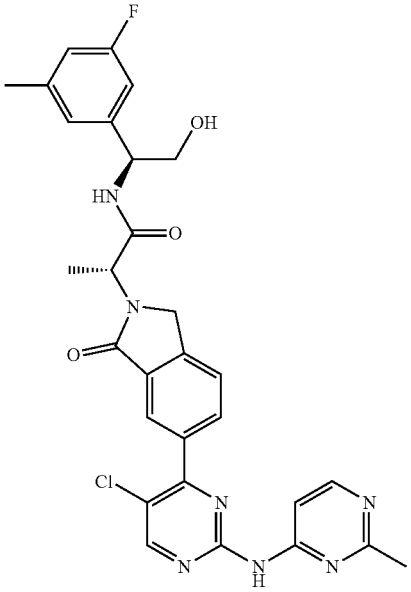 | (2R)-2-(6-{5-chloro-2-[(2-methylpyrimidin-4-yl)amino]pyrimidin-4-yl}-1-oxo-2,3-dihydro-1H-isoindol-2-yl)-N-[(1S)-1-(3-fluoro-5-methylphenyl)-2-hydroxyethyl]propanamide | 576 |
| 824 | 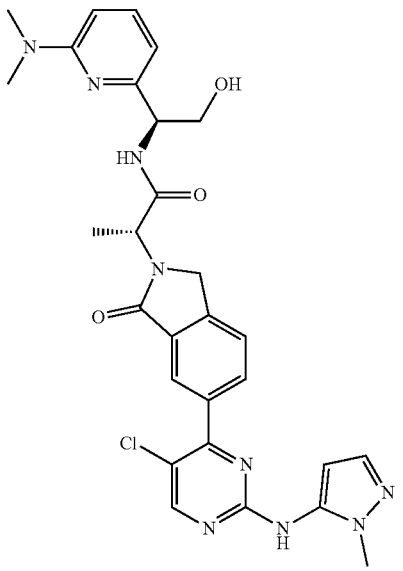 [SMILES: C[C@H](C(=O)N[C@H](CO)c1cccc(N(C)C)n1)N1Cc2ccc(-c3nc(Nc4ccnn4C)ncc3Cl)cc2C1=O] | (2R)-2-(6-{5-chloro-2-[(1-methyl-1H-pyrazol-5-yl)amino]pyrimidin-4-yl}-1-oxo-2,3-dihydro-1H-isoindol-2-yl)-N-[(1S)-1-[6-(dimethylamino)pyridin-2-yl]-2-hydroxyethyl]propanamide | 576 |

-continued

| Example | Structure | Name | MS Data [M +H]+ unless specified |
|---|---|---|---|
| 825 | | (2R)-2-(6-{5-chloro-2-[(1-methyl-1H-pyrazol-4-yl)amino]pyrimidin-4-yl}-1-oxo-2,3-dihydro-1H-isoindol-2-yl)-N-[(1R)-1-[6-(dimethylamino)pyridin-2-yl]ethyl]propanamide | 560 |
| 826 | 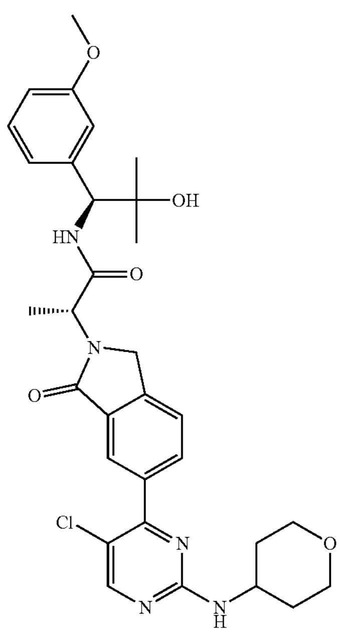 [SMILES: COc1cccc([C@H](NC(=O)[C@@H](C)N2Cc3ccc(-c4nc(NC5CCOCC5)ncc4Cl)cc3C2=O)C(C)(C)O)c1] | (2R)-2-(6-{5-chloro-2-[(oxan-4-yl)amino]pyrimidin-4-yl}-1-oxo-2,3-dihydro-1H-isoindol-2-yl)-N-[(1S)-2-hydroxy-1-(3-methoxyphenyl)-2-methylpropyl]propanamide | 594 |

-continued

| Example | Structure | Name | MS Data [M +H]+ unless specified |
|---|---|---|---|
| 827 | 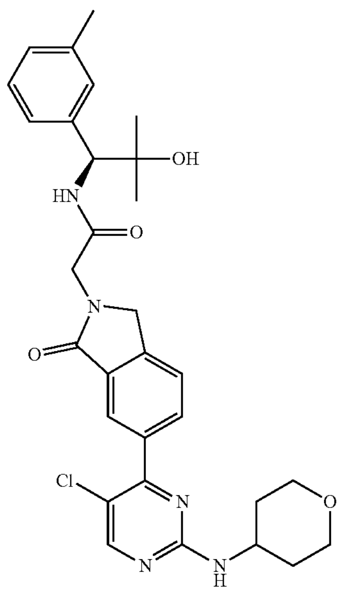 [SMILES: Cc1cccc([C@H](NC(=O)CN2Cc3ccc(-c4nc(NC5CCOCC5)ncc4Cl)cc3C2=O)C(C)(C)O)c1] | 2-(6-{5-chloro-2-[(oxan-4-yl)amino]pyrimidin-4-yl}-1-oxo-2,3-dihydro-1H-isoindol-2-yl)-N-[(1S)-2-hydroxy-2-methyl-1-(3-methylphenyl)propyl]acetamide | 564 |
| 828 | 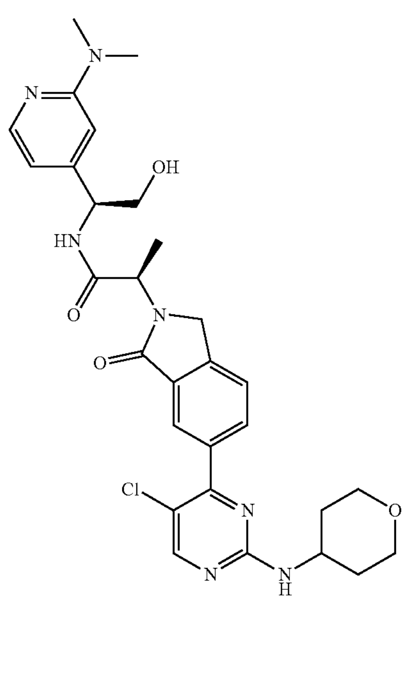 [SMILES: C[C@H](C(=O)N[C@H](CO)c1ccnc(N(C)C)c1)N1Cc2ccc(-c3nc(NC4CCOCC4)ncc3Cl)cc2C1=O] | (2R)-2-(6-{5-chloro-2-[(oxan-4-yl)amino]pyrimidin-4-yl}-1-oxo-2,3-dihydro-1H-isoindol-2-yl)-N-[(1S)-1-[2-(dimethylamino)pyridin-4-yl]-2-hydroxyethyl]propanamide | 580 |

| Example | Structure | Name | MS Data [M +H]+ unless specified |
|---|---|---|---|
| 829 | 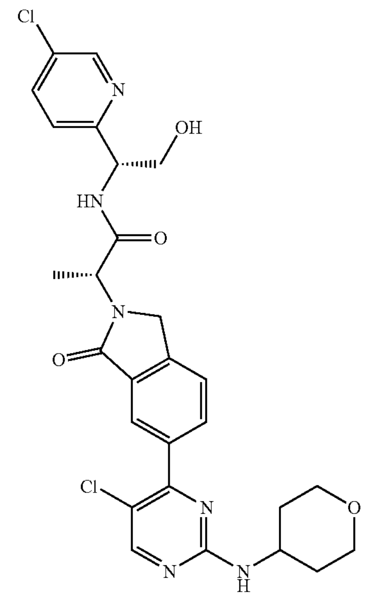 [SMILES: C[C@H](C(=O)N[C@@H](CO)c1ccc(Cl)cn1)N1Cc2ccc(-c3nc(NC4CCOCC4)ncc3Cl)cc2C1=O] | (2R)-2-(6-{5-chloro-2-[(oxan-4-yl)amino]pyrimidin-4-yl}-1-oxo-2,3-dihydro-1H-isoindol-2-yl)-N-[(1R)-1-(5-chloropyridin-2-yl)-2-hydroxyethyl]propanamide | 571 |
| 830 | 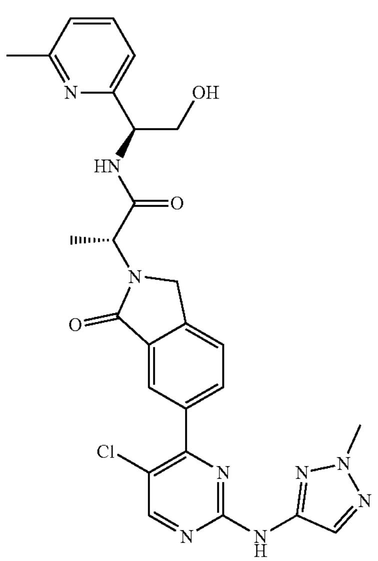 [SMILES: Cc1cccc([C@@H](CO)NC(=O)[C@@H](C)N2Cc3ccc(-c4nc(Nc5cnn(C)n5)ncc4Cl)cc3C2=O)n1] | (2R)-2-(6-{5-chloro-2-[(2-methyl-2H-1,2,3-triazol-4-yl)amino]pyrimidin-4-yl}-1-oxo-2,3-dihydro-1H-isoindol-2-yl)-N-[(1S)-2-hydroxy-1-(6-methylpyridin-2-yl)ethyl]propanamide | 548 |

-continued

| Example | Structure | Name | MS Data [M +H]+ unless specified |
|---|---|---|---|
| 831 | 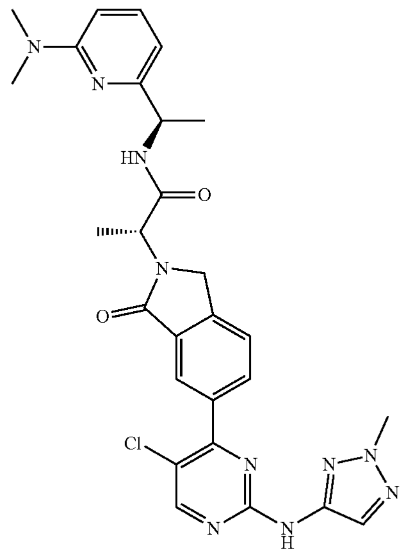 [SMILES: C[C@H](C(=O)N[C@H](C)c1cccc(N(C)C)n1)N1Cc2ccc(-c3nc(Nc4cnn(C)n4)ncc3Cl)cc2C1=O] | (2R)-2-(6-{5-chloro-2-[(2-methyl-2H-1,2,3-triazol-4-yl)amino]pyrimidin-4-yl}-1-oxo-2,3-dihydro-1H-isoindol-2-yl)-N-[(1R)-1-[6-(dimethylamino)pyridin-2-yl]ethyl]propanamide | 561 |
| 832 | 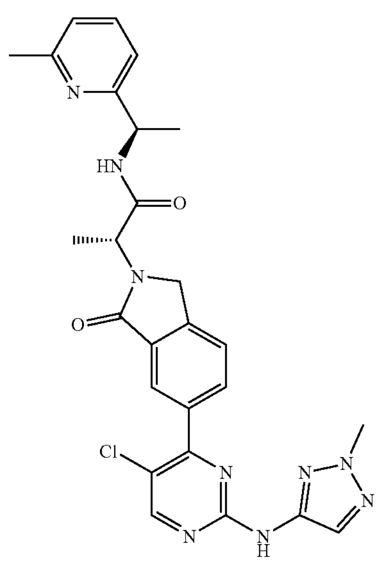 [SMILES: Cc1cccc([C@@H](C)NC(=O)[C@@H](C)N2Cc3ccc(-c4nc(Nc5cnn(C)n5)ncc4Cl)cc3C2=O)n1] | (2R)-2-(6-{5-chloro-2-[(2-methyl-2H-1,2,3-triazol-4-yl)amino]pyrimidin-4-yl}-1-oxo-2,3-dihydro-1H-isoindol-2-yl)-N-[(1R)-1-(6-methylpyridin-2-yl)ethyl]propanamide | 532 |

| Example | Structure | Name | MS Data [M +H]+ unless specified |
|---|---|---|---|
| 833 | 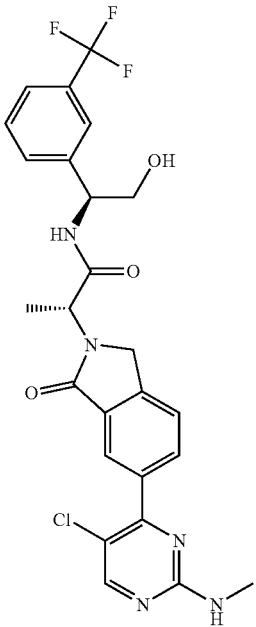 [SMILES: CNc1ncc(Cl)c(-c2ccc3c(c2)C(=O)N([C@H](C)C(=O)N[C@H](CO)c2cccc(C(F)(F)F)c2)C3)n1] | (2R)-2-{6-[5-chloro-2-(methylamino)pyrimidin-4-yl]-1-oxo-2,3-dihydro-1H-isoindol-2-yl}-N-[(1S)-2-hydroxy-1-[3-(trifluoromethyl)phenyl]ethyl]propanamide | 534 |
| 834 | 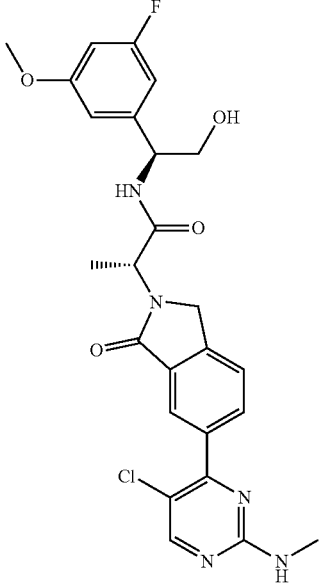 | (2R)-2-{6-[5-chloro-2-(methylamino)pyrimidin-4-yl]-1-oxo-2,3-dihydro-1H-isoindol-2-yl}-N-[(1S)-1-(3-fluoro-5-methoxyphenyl)-2-hydroxyethyl]propanamide | 514 |

-continued

| Example | Structure | Name | MS Data [M +H]+ unless specified |
|---|---|---|---|
| 835 | 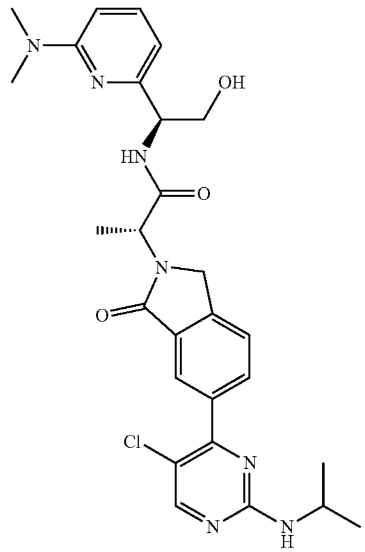 [SMILES: CC(C)Nc1ncc(Cl)c(-c2ccc3c(c2)C(=O)N([C@H](C)C(=O)N[C@H](CO)c2cccc(N(C)C)n2)C3)n1] | (2R)-2-(6-{5-chloro-2-[(propan-2-yl)amino]pyrimidin-4-yl}-1-oxo-2,3-dihydro-1H-isoindol-2-yl)-N-[(1S)-1-[6-(dimethylamino)pyridin-2-yl]-2-hydroxyethyl]propanamide | 538 |
| 836 | 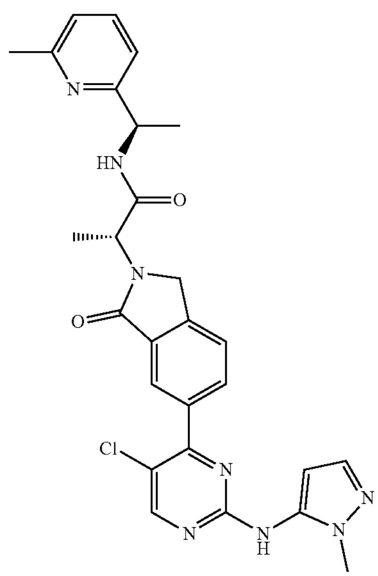 [SMILES: Cc1cccc([C@@H](C)NC(=O)[C@@H](C)N2Cc3ccc(-c4nc(Nc5ccnn5C)ncc4Cl)cc3C2=O)n1] | (2R)-2-(6-{5-chloro-2-[(1-methyl-1H-pyrazol-5-yl)amino]pyrimidin-4-yl}-1-oxo-2,3-dihydro-1H-isoindol-2-yl)-N-[(1R)-1-(6-methylpyridin-2-yl)ethyl]propanamide | 531 |

-continued

| Example | Structure | Name | MS Data [M +H]+ unless specified |
|---|---|---|---|
| 837 | 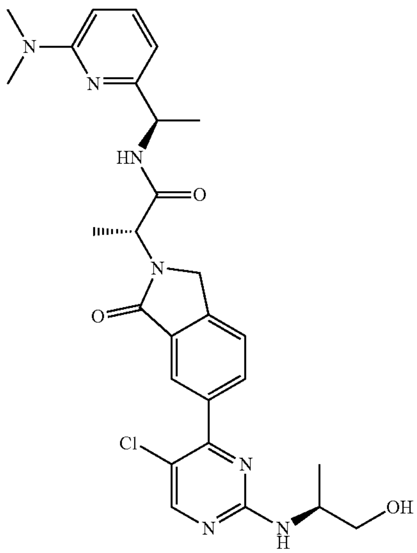 [SMILES: C[C@H](C(=O)N[C@H](C)c1cccc(N(C)C)n1)N1Cc2ccc(-c3nc(N[C@@H](C)CO)ncc3Cl)cc2C1=O] | (2R)-2-[6-(5-chloro-2-{[(2S)-1-hydroxypropan-2-yl]amino}pyrimidin-4-yl)-1-oxo-2,3-dihydro-1H-isoindol-2-yl]-N-[(1R)-1-[6-(dimethylamino)pyridin-2-yl]ethyl]propanamide | 538 |
| 838 | 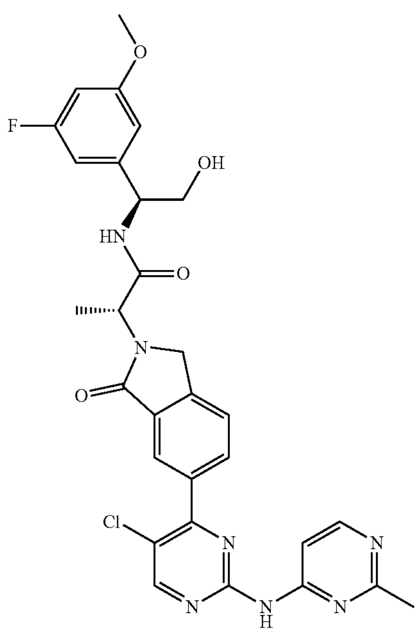 [SMILES: COc1cc(F)cc([C@@H](CO)NC(=O)[C@@H](C)N2Cc3ccc(-c4nc(Nc5ccnc(C)n5)ncc4Cl)cc3C2=O)c1] | (2R)-2-(6-{5-chloro-2-[(2-methylpyrimidin-4-yl)amino]pyrimidin-4-yl}-1-oxo-2,3-dihydro-1H-isoindol-2-yl)-N-[(1S)-1-(3-fluoro-5-methoxyphenyl)-2-hydroxyethyl]propanamide | 592 |

| Example | Structure | Name | MS Data [M +H]+ unless specified |
|---|---|---|---|
| 839 | 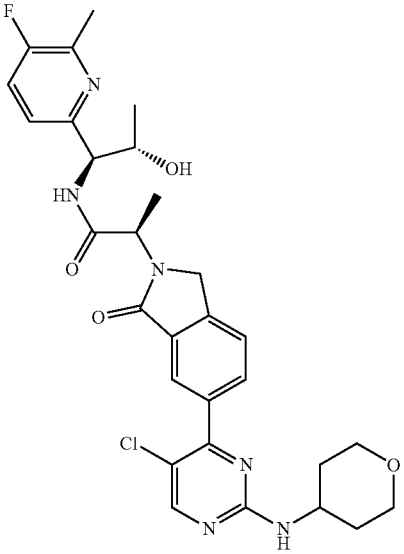 [SMILES: Cc1nc([C@H](NC(=O)[C@@H](C)N2Cc3ccc(-c4nc(NC5CCOCC5)ncc4Cl)cc3C2=O)[C@H](C)O)ccc1F] | (2R)-2-(6-{5-chloro-2-[(oxan-4-yl)amino]pyrimidin-4-yl}-1-oxo-2,3-dihydro-1H-isoindol-2-yl)-N-[(1S,2S)-1-(5-fluoro-6-methylpyridin-2-yl)-2-hydroxypropyl]propanamide | 583 |
| 840 | 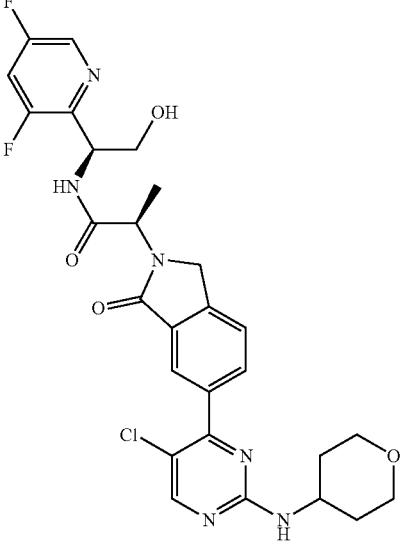 | (2R)-2-(6-{5-chloro-2-[(oxan-4-yl)amino]pyrimidin-4-yl}-1-oxo-2,3-dihydro-1H-isoindol-2-yl)-N-[(1S)-1-(3,5-difluoropyridin-2-yl)-2-hydroxyethyl]propanamide | 573 |

| Example | Structure | Name | MS Data [M+H]+ unless specified |
|---|---|---|---|
| 841 | 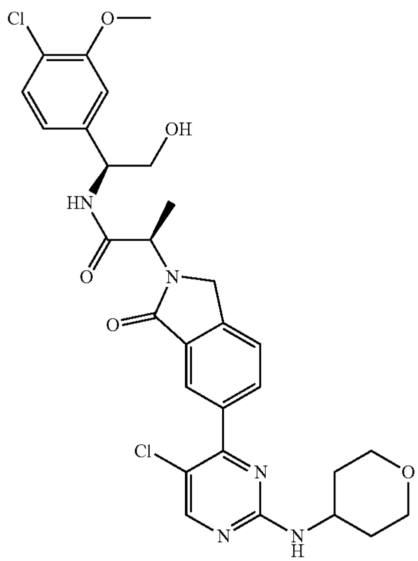 [SMILES: COc1cc([C@@H](CO)NC(=O)[C@@H](C)N2Cc3ccc(-c4nc(NC5CCOCC5)ncc4Cl)cc3C2=O)ccc1Cl] | (2R)-2-(6-{5-chloro-2-[(oxan-4-yl)amino]pyrimidin-4-yl}-1-oxo-2,3-dihydro-1H-isoindol-2-yl)-N-[(1S)-1-(4-chloro-3-methoxyphenyl)-2-hydroxyethyl]propanamide | 600 |
| 842 | 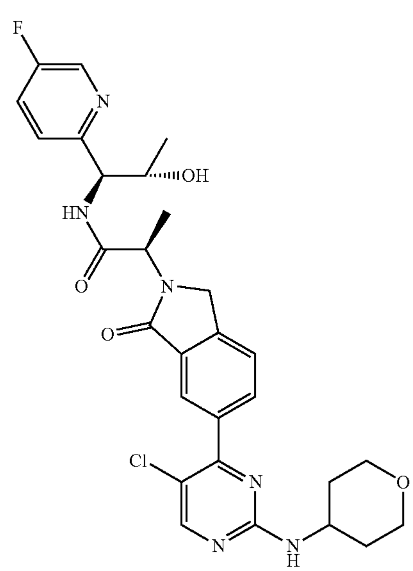 [SMILES: C[C@H](O)[C@@H](NC(=O)[C@@H](C)N1Cc2ccc(-c3nc(NC4CCOCC4)ncc3Cl)cc2C1=O)c1ccc(F)cn1] | (2R)-2-(6-{5-chloro-2-[(oxan-4-yl)amino]pyrimidin-4-yl}-1-oxo-2,3-dihydro-1H-isoindol-2-yl)-N-[(1S,2S)-1-(5-fluoropyridin-2-yl)-2-hydroxypropyl]propanamide | 567 [M−H]− |

| Example | Structure | Name | MS Data [M +H]+ unless specified |
|---|---|---|---|
| 843 | 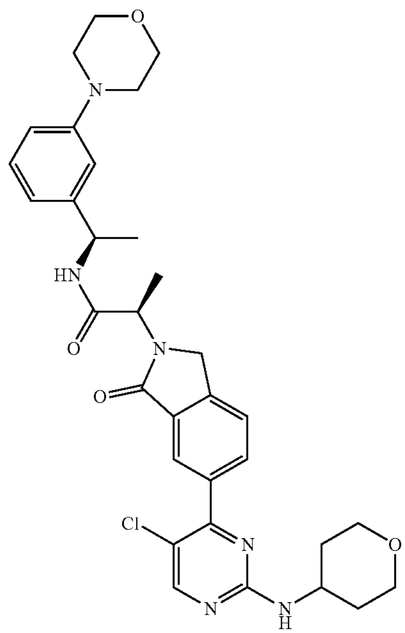 [SMILES: C[C@H](C(=O)N[C@H](C)c1cccc(N2CCOCC2)c1)N1Cc2ccc(-c3nc(NC4CCOCC4)ncc3Cl)cc2C1=O] | (2R)-2-(6-{5-chloro-2-[(oxan-4-yl)amino]pyrimidin-4-yl}-1-oxo-2,3-dihydro-1H-isoindol-2-yl)-N-[(1R)-1[3-(morpholin-4-yl)phenyl]ethyl]propanamide | 605 |
| 844 | 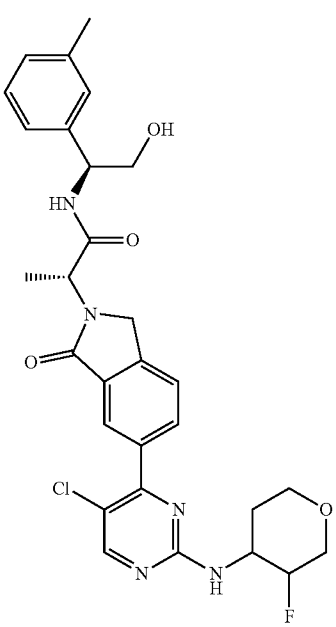 [SMILES: Cc1cccc([C@@H](CO)NC(=O)[C@@H](C)N2Cc3ccc(-c4nc(NC5CCOCC5F)ncc4Cl)cc3C2=O)c1] | (2R)-2-(6-{5-chloro-2-[(3-fluorooxan-4-yl)amino]pyrimidin-4-yl}-1-oxo-2,3-dihydro-1H-isoindol-2-yl)-N-[(1S)-2-hydroxy-1-(3-methylphenyl)ethyl]propanamide | 568 |

-continued

| Example | Structure | Name | MS Data [M +H]+ unless specified |
|---|---|---|---|
| 845 | | No Example 845 | |
| 846 | 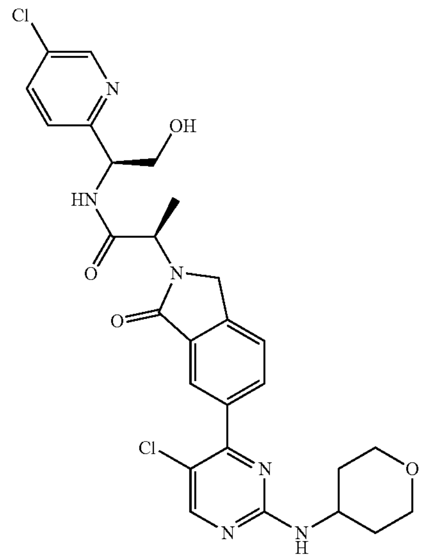 [SMILES: C[C@H](C(=O)N[C@H](CO)c1ccc(Cl)cn1)N1Cc2ccc(-c3nc(NC4CCOCC4)ncc3Cl)cc2C1=O] | (2R)-2-(6-{5-chloro-2-[(oxan-4-yl)amino]pyrimidin-4-yl}-1-oxo-2,3-dihydro-1H-isoindol-2-yl)-N-[(1S)-1-(5-chloropyridin-2-yl)-2-hydroxyethyl]propanamide | 569 [M −H]− |
| 847 | 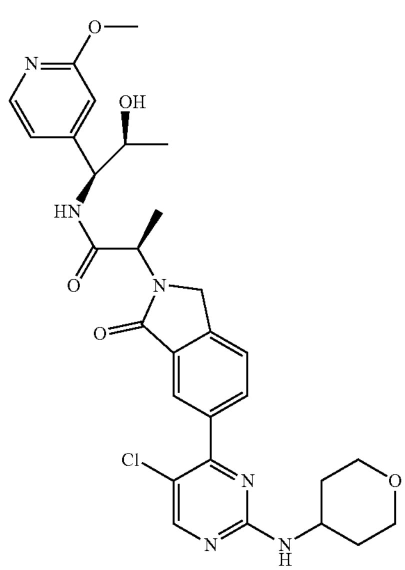 [SMILES: COc1cc([C@H](NC(=O)[C@@H](C)N2Cc3ccc(-c4nc(NC5CCOCC5)ncc4Cl)cc3C2=O)[C@H](C)O)ccn1] | (2R)-2-(6-{5-chloro-2-[(oxan-4-yl)amino]pyrimidin-4-yl}-1-oxo-2,3-dihydro-1H-isoindol-2-yl)-N-[(1S,2S)-2-hydroxy-1-(2-methoxypyridin-4-yl)propyl]propanamide | 581 |

-continued

| Example | Structure | Name | MS Data [M +H]+ unless specified |
|---------|-----------|------|----------------------------------|
| 848 | 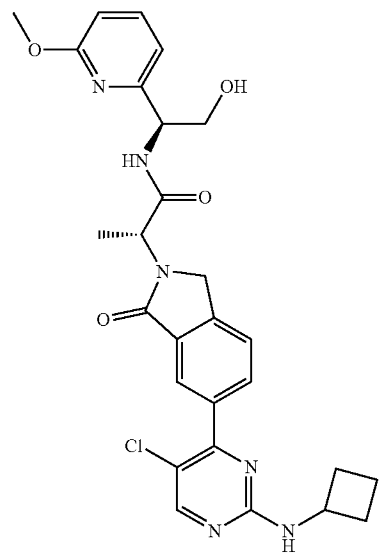 [SMILES: COc1cccc([C@@H](CO)NC(=O)[C@@H](C)N2Cc3ccc(-c4nc(NC5CCC5)ncc4Cl)cc3C2=O)n1] | (2R)-2-{6-[5-chloro-2-(cyclobutylamino)pyrimidin-4-yl]-1-oxo-2,3-dihydro-1H-isoindol-2-yl}-N-[(1S)-2-hydroxy-1-(6-methoxypyridin-2-yl)ethyl]propanamide | 537 |
| 849 | 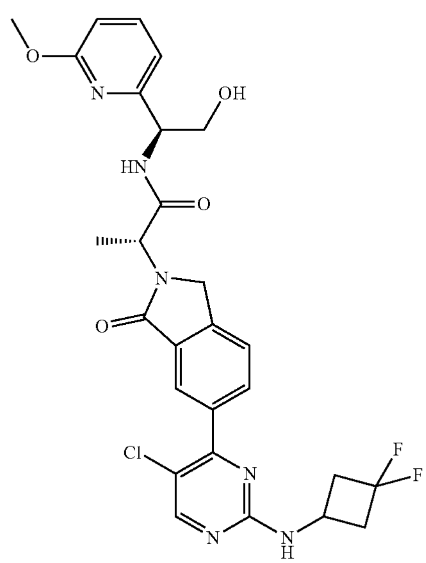 [SMILES: COc1cccc([C@@H](CO)NC(=O)[C@@H](C)N2Cc3ccc(-c4nc(NC5CC(F)(F)C5)ncc4Cl)cc3C2=O)n1] | (2R)-2-(6-{5-chloro-2-[(3,3-difluorocyclobutyl)amino]pyrimidin-4-yl}-1-oxo-2,3-dihydro-1H-isoindol-2-yl)-N-[(1S)-2-hydroxy-1-(6-methoxypyridin-2-yl)ethyl]propanamide | 573 |

-continued
| Example | Structure | Name | MS Data [M +H]+ unless specified |
|---|---|---|---|
| 850 | 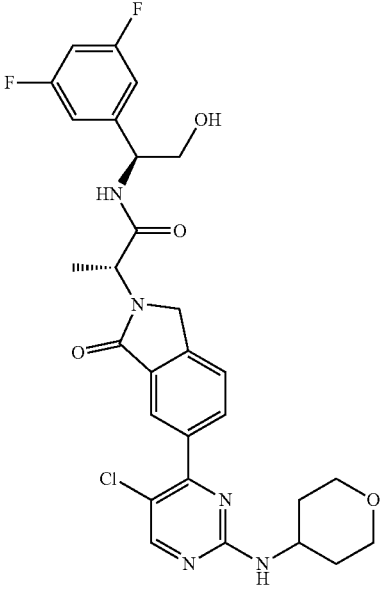 [SMILES: C[C@H](C(=O)N[C@H](CO)c1cc(F)cc(F)c1)N1Cc2ccc(-c3nc(NC4CCOCC4)ncc3Cl)cc2C1=O] | (2R)-2-(6-{5-chloro-2-[(oxan-4-yl)amino]pyrimidin-4-yl}-1-oxo-2,3-dihydro-1H-isoindol-2-yl)-N-[(1S)-1-(3,5-difluorophenyl)-2-hydroxyethyl]propanamide | 572 |
| 851 | 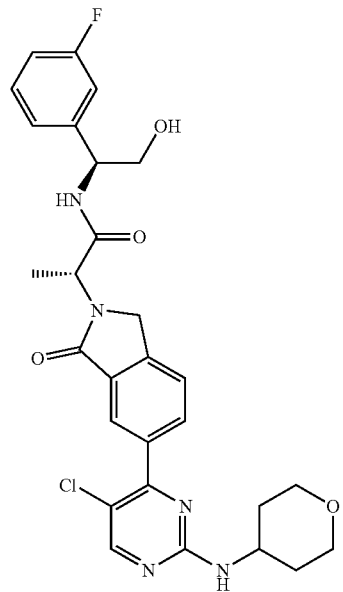 [SMILES: C[C@H](C(=O)N[C@H](CO)c1cccc(F)c1)N1Cc2ccc(-c3nc(NC4CCOCC4)ncc3Cl)cc2C1=O] | (2R)-2-(6-{5-chloro-2-[(oxan-4-yl)amino]pyrimidin-4-yl}-1-oxo-2,3-dihydro-1H-isoindol-2-yl)-N-[(1S)-1-(3-fluorophenyl)-2-hydroxyethyl]propanamide | 554 |

| Example | Structure | Name | MS Data [M+H]+ unless specified |
|---|---|---|---|
| 852 | 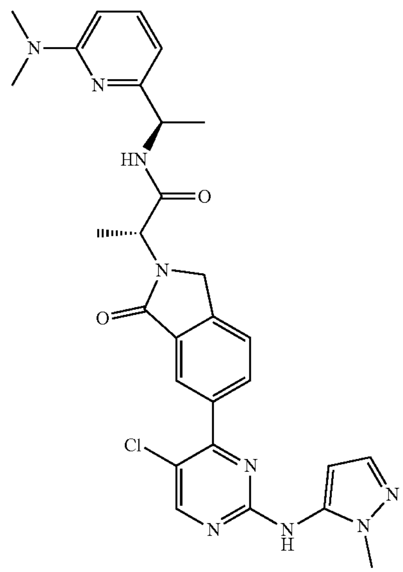 [SMILES: C[C@H](C(=O)N[C@H](C)c1cccc(N(C)C)n1)N1Cc2ccc(-c3nc(Nc4ccnn4C)ncc3Cl)cc2C1=O] | (2R)-2-(6-{5-chloro-2-[(1-methyl-1H-pyrazol-5-yl)amino]pyrimidin-4-yl}-1-oxo-2,3-dihydro-1H-isoindol-2-yl)-N-[(1R)-1-[6-(dimethylamino)pyridin-2-yl]ethyl]propanamide | 560 |
| 853 | 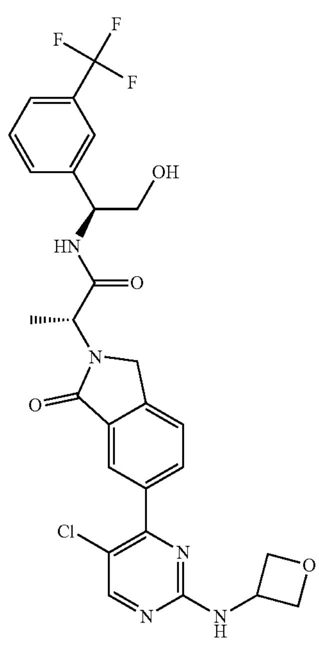 [SMILES: C[C@H](C(=O)N[C@H](CO)c1cccc(C(F)(F)F)c1)N1Cc2ccc(-c3nc(NC4COC4)ncc3Cl)cc2C1=O] | (2R)-2-(6-{5-chloro-2-[(oxetan-3-yl)amino]pyrimidin-4-yl}-1-oxo-2,3-dihydro-1H-isoindol-2-yl)-N-[(1S)-2-hydroxy-1-[3-(trifluoromethyl)phenyl]ethyl]propanamide | 576 |

-continued

| Example | Structure | Name | MS Data [M+H]+ unless specified |
|---|---|---|---|
| 854 | 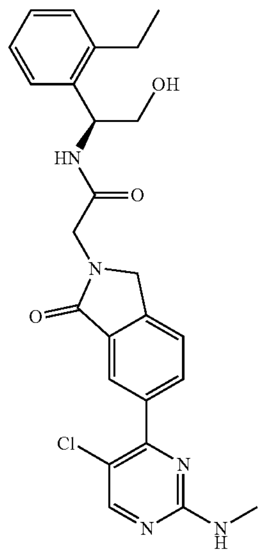 [SMILES: CCc1ccccc1[C@@H](CO)NC(=O)CN1Cc2ccc(-c3nc(NC)ncc3Cl)cc2C1=O] | 2-{6-[5-chloro-2-(methylamino)pyrimidin-4-yl]-1-oxo-2,3-dihydro-1H-isoindol-2-yl}-N-[(1S)-1-(2-ethylphenyl)-2-hydroxyethyl]acetamide | 480 |
| 855 | 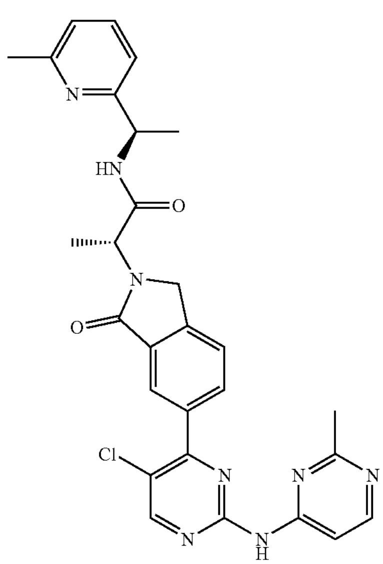 [SMILES: Cc1cccc([C@@H](C)NC(=O)[C@@H](C)N2Cc3ccc(-c4nc(Nc5ccnc(C)n5)ncc4Cl)cc3C2=O)n1] | (2R)-2-(6-{5-chloro-2-[(2-methylpyrimidin-4-yl)amino]pyrimidin-4-yl}-1-oxo-2,3-dihydro-1H-isoindol-2-yl)-N-[(1R)-1-(6-methylpyridin-2-yl)ethyl]propanamide | 543 |

| Example | Structure | Name | MS Data [M+H]+ unless specified |
|---|---|---|---|
| 856 | 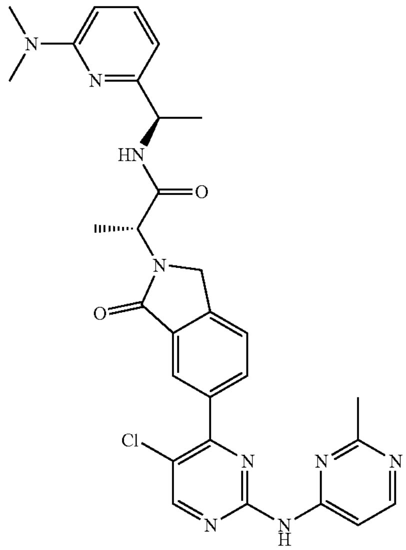 [SMILES: Cc1nccc(Nc2ncc(Cl)c(-c3ccc4c(c3)C(=O)N([C@H](C)C(=O)N[C@H](C)c3cccc(N(C)C)n3)C4)n2)n1] | (2R)-2-(6-{5-chloro-2-[(2-methylpyrimidin-4-yl)amino]pyrimidin-4-yl}-1-oxo-2,3-dihydro-1H-isoindol-2-yl)-N-[(1R)-1-[6-(dimethylamino)pyridin-2-yl]ethyl]propanamide | 572 |
| 857 | 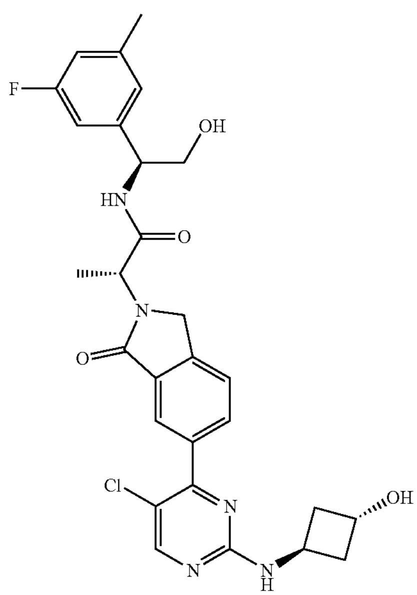 [SMILES: Cc1cc(F)cc([C@@H](CO)NC(=O)[C@@H](C)N2Cc3ccc(-c4nc(N[C@H]5C[C@H](O)C5)ncc4Cl)cc3C2=O)c1] | (2R)-2-[6-(5-chloro-2-{[trans-3-hydroxycyclobutyl]amino}pyrimidin-4-yl)-1-oxo-2,3-dihydro-1H-isoindol-2-yl]-N-[(1S)-1-(3-fluoro-5-methylphenyl)-2-hydroxyethyl]propanamide | 554 |

-continued

| Example | Structure | Name | MS Data [M +H]+ unless specified |
|---|---|---|---|
| 858 | 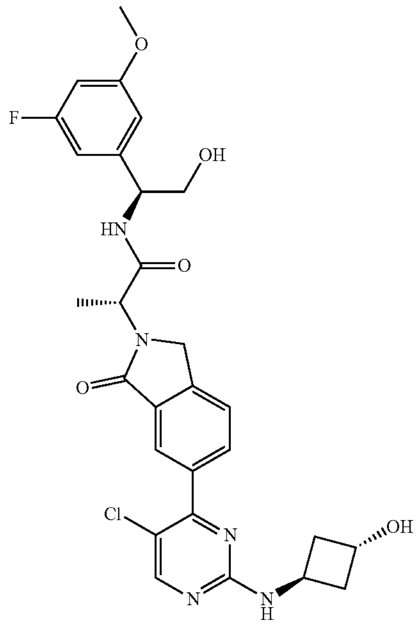 [SMILES: COc1cc(F)cc([C@@H](CO)NC(=O)[C@@H](C)N2Cc3ccc(-c4nc(N[C@H]5C[C@H](O)C5)ncc4Cl)cc3C2=O)c1] | (2R)-2-[6-(5-chloro-2-{[trans-3-hydroxycyclobutyl]amino}pyrimidin-4-yl)-1-oxo-2,3-dihydro-1H-isoindol-2-yl]-N-[(1S)-1-(3-fluoro-5-methoxyphenyl)-2-hydroxyethyl]propanamide | 570 |
| 859 | 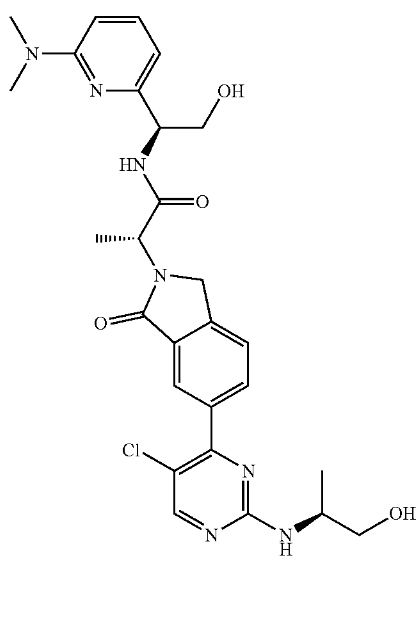 [SMILES: C[C@H](C(=O)N[C@H](CO)c1cccc(N(C)C)n1)N1Cc2ccc(-c3nc(N[C@@H](C)CO)ncc3Cl)cc2C1=O] | (2R)-2-[6-(5-chloro-2-{[(2S)-1-hydroxypropan-2-yl]amino}pyrimidin-4-yl)-1-oxo-2,3-dihydro-1H-isoindol-2-yl]N-[(1S)-1-[6-(dimethylamino)pyridin-2-yl]-2-hydroxyethyl]propanamide | 554 |

| Example | Structure | Name | MS Data [M +H]+ unless specified |
|---|---|---|---|
| 860 | 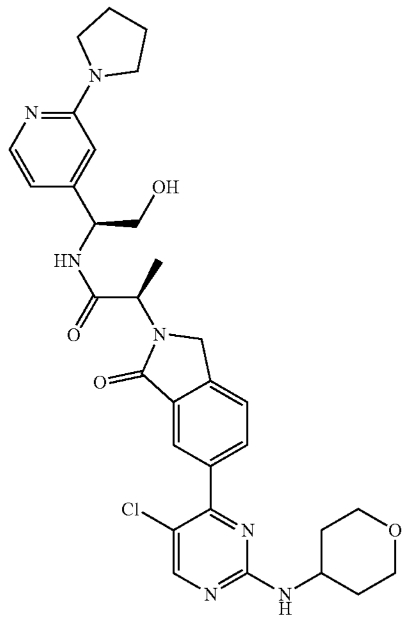 [SMILES: C[C@H](C(=O)N[C@H](CO)c1ccnc(N2CCCC2)c1)N1Cc2ccc(-c3nc(NC4CCOCC4)ncc3Cl)cc2C1=O] | (2R)-2-(6-{5-chloro-2-[(oxan-4-yl)amino]pyrimidin-4-yl}-1-oxo-2,3-dihydro-1H-isoindol-2-yl)-N-[(1S)-2-hydroxy-1-[2-(pyrrolidin-1-yl)pyridin-4-yl]ethyl]propanamide | 606 |
| 861 | 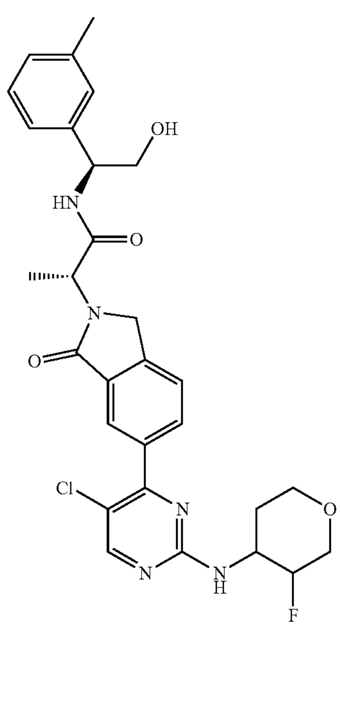 [SMILES: Cc1cccc([C@@H](CO)NC(=O)[C@@H](C)N2Cc3ccc(-c4nc(NC5CCOCC5F)ncc4Cl)cc3C2=O)c1] | (2R)-2-(6-{5-chloro-2-[(3-fluorooxan-4-yl)amino]pyrimidin-4-yl}-1-oxo-2,3-dihydro-1H-isoindol-2-yl)-N-[(1S)-2-hydroxy-1-(3-methylphenyl)ethyl]propanamide Stereoisomer 1 | 568 |

-continued

| Example | Structure | Name | MS Data [M +H]+ unless specified |
|---|---|---|---|
| 862 | 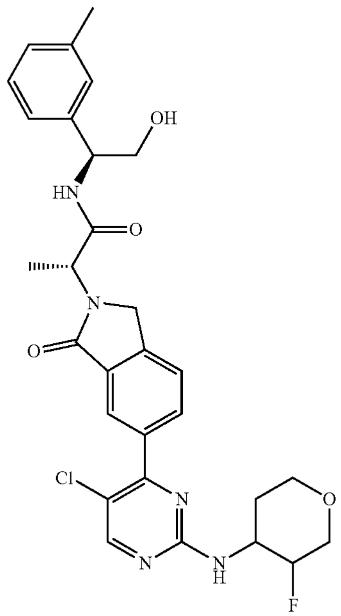 [SMILES: Cc1cccc([C@@H](CO)NC(=O)[C@@H](C)N2Cc3ccc(-c4nc(NC5CCOCC5F)ncc4Cl)cc3C2=O)c1] | (2R)-2-(6-{5-chloro-2-[(3-fluorooxan-4-yl)amino]pyrimidin-4-yl}-1-oxo-2,3-dihydro-1H-isoindol-2-yl)-N-[(1S)-2-hydroxy-1-(3-methylphenyl)ethyl]propanamide Stereoisomer 2 | 568 |
| 863 | 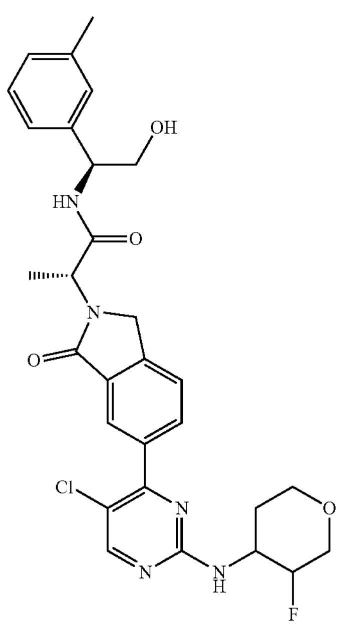 [SMILES: Cc1cccc([C@@H](CO)NC(=O)[C@@H](C)N2Cc3ccc(-c4nc(NC5CCOCC5F)ncc4Cl)cc3C2=O)c1] | (2R)-2-(6-{5-chloro-2-[(3-fluorooxan-4-yl)amino]pyrimidin-4-yl}-1-oxo-2,3-dihydro-1H-isoindol-2-yl)-N-[(1S)-2-hydroxy-1-(3-methylphenyl)ethyl]propanamide Stereoisomer 3 | 568 |

-continued

| Example | Structure | Name | MS Data [M +H]+ unless specified |
|---|---|---|---|
| 864 | 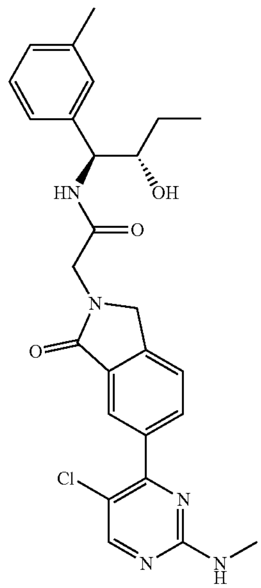 [SMILES: CC[C@H](O)[C@@H](NC(=O)CN1Cc2ccc(-c3nc(NC)ncc3Cl)cc2C1=O)c1cccc(C)c1] | 2-{6-[5-chloro-2-(methylamino)pyrimidin-4-yl]-1-oxo-2,3-dihydro-1H-isoindol-2-yl}-N-[(1S,2S)-2-hydroxy-1-(3-methylphenyl)butyl]acetamide | 494 |
| 865 | 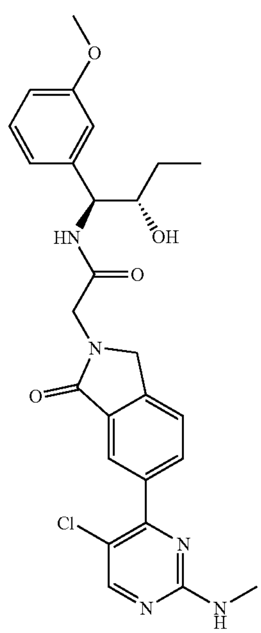 [SMILES: CC[C@H](O)[C@@H](NC(=O)CN1Cc2ccc(-c3nc(NC)ncc3Cl)cc2C1=O)c1cccc(OC)c1] | 2-{6-[5-chloro-2-(methylamino)pyrimidin-4-yl]-1-oxo-2,3-dihydro-1H-isoindol-2-yl}-N-[(1S,2S)-2-hydroxy-1-(3-methoxyphenyl)butyl]acetamide | 510 |

| Example | Structure | Name | MS Data [M +H]+ unless specified |
|---|---|---|---|
| 866 | 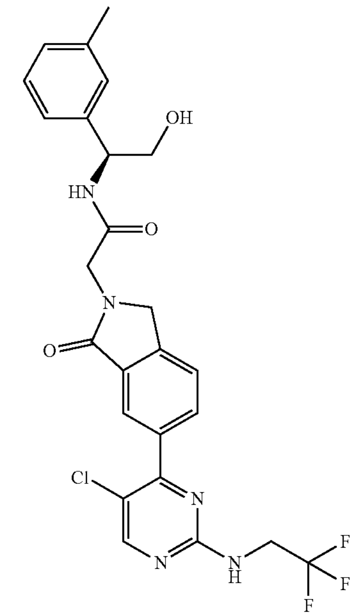 [SMILES: Cc1cccc([C@@H](CO)NC(=O)CN2Cc3ccc(-c4nc(NCC(F)(F)F)ncc4Cl)cc3C2=O)c1] | 2-(6-{5-chloro-2-[(2,2,2-trifluoroethyl)amino]pyrimidin-4-yl}-1-oxo-2,3-dihydro-1H-isoindol-2-yl)-N-[(1S)-2-hydroxy-1-(3-methylphenyl)ethyl]acetamide | 534 |
| 867 | 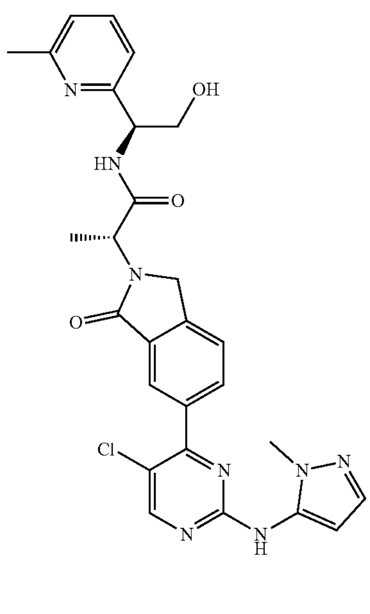 [SMILES: Cc1cccc([C@@H](CO)NC(=O)[C@@H](C)N2Cc3ccc(-c4nc(Nc5ccnn5C)ncc4Cl)cc3C2=O)n1] | (2R)-2-(6-{5-chloro-2-[(1-methyl-1H-pyrazol-5-yl)amino]pyrimidin-4-yl}-1-oxo-2,3-dihydro-1H-isoindol-2-yl)-N-[(1S)-2-hydroxy-1-(6-methylpyridin-2-yl)ethyl]propanamide | 547 |

-continued

| Example | Structure | Name | MS Data [M +H]+ unless specified |
|---|---|---|---|
| 868 | 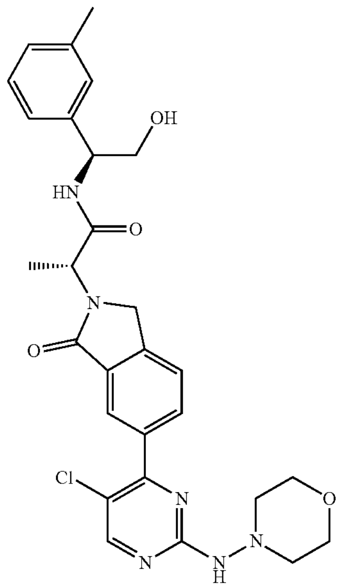 [SMILES: Cc1cccc([C@@H](CO)NC(=O)[C@@H](C)N2Cc3ccc(-c4nc(NN5CCOCC5)ncc4Cl)cc3C2=O)c1] | (2R)-2-(6-{5-chloro-2-[(morpholin-4-yl)amino]pyrimidin-4-yl}-1-oxo-2,3-dihydro-1H-isoindol-2-yl)-N-[(1S)-2-hydroxy-1-(3-methylphenyl)ethyl]propanamide | 551 |
| 869 | 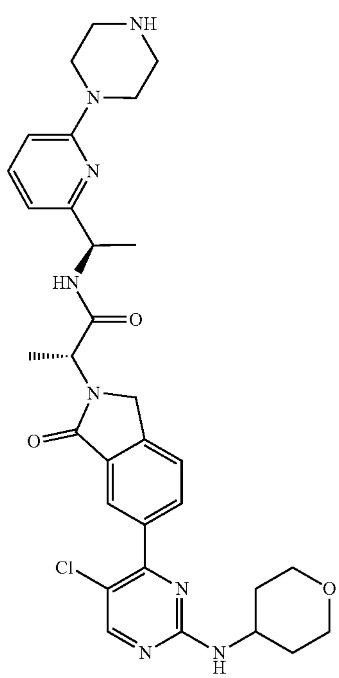 [SMILES: C[C@H](C(=O)N[C@H](C)c1cccc(N2CCNCC2)n1)N1Cc2ccc(-c3nc(NC4CCOCC4)ncc3Cl)cc2C1=O] | (2R)-2-(6-{5-chloro-2-[(oxan-4-yl)amino]pyrimidin-4-yl}-1-oxo-2,3-dihydro-1H-isoindol-2-yl)-N-[(1R)-1-[6-(piperazin-1-yl)pyridin-2-yl]ethyl]propanamide | 605 |

| Example | Structure | Name | MS Data [M +H]+ unless specified |
|---|---|---|---|
| 870 | 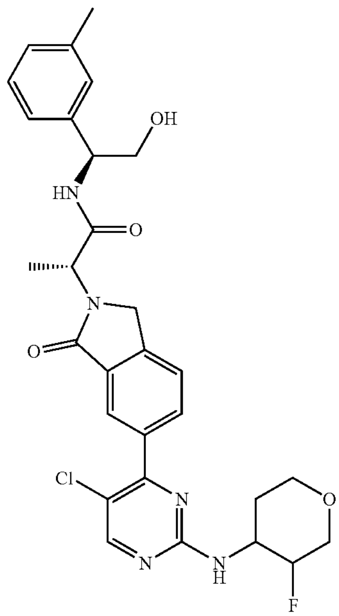 [SMILES: Cc1cccc([C@@H](CO)NC(=O)[C@@H](C)N2Cc3ccc(-c4nc(NC5CCOCC5F)ncc4Cl)cc3C2=O)c1] | (2R)-2-(6-{5-chloro-2-[(3-fluorooxan-4-yl)amino]pyrimidin-4-yl}-1-oxo-2,3-dihydro-1H-isoindol-2-yl)-N-[(1S)-2-hydroxy-1-(3-methylphenyl)ethyl]propanamide Stereoisomer 1 | 566 [M −H]− |
| 871 | 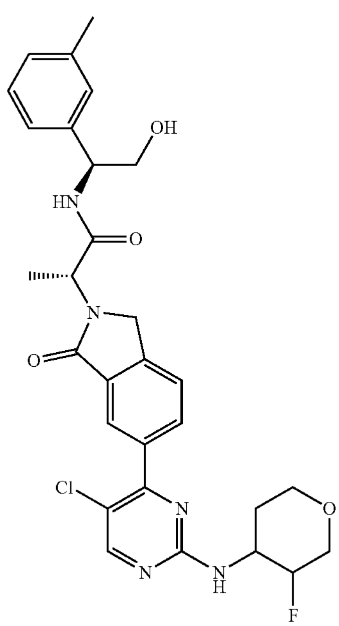 [SMILES: Cc1cccc([C@@H](CO)NC(=O)[C@@H](C)N2Cc3ccc(-c4nc(NC5CCOCC5F)ncc4Cl)cc3C2=O)c1] | (2R)-2-(6-{5-chloro-2-[(3-fluorooxan-4-yl)amino]pyrimidin-4-yl}-1-oxo-2,3-dihydro-1H-isoindol-2-yl)-N-[(1S)-2-hydroxy-1-(3-methylphenyl)ethyl]propanamide Stereoisomer 2 | 566 [M −H]− |

-continued

| Example | Structure | Name | MS Data [M +H]+ unless specified |
|---|---|---|---|
| 872 | 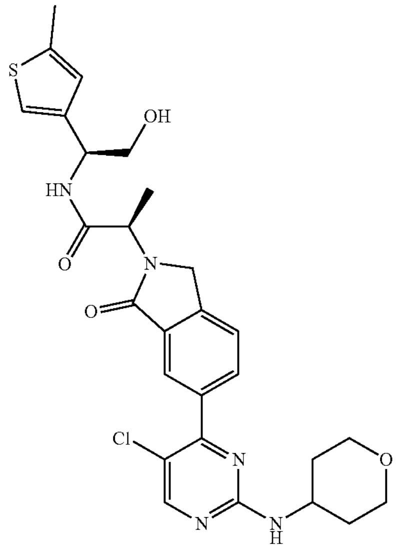 [SMILES: Cc1cc([C@@H](CO)NC(=O)[C@@H](C)N2Cc3ccc(-c4nc(NC5CCOCC5)ncc4Cl)cc3C2=O)cs1] | (2R)-2-(6-{5-chloro-2-[(oxan-4-yl)amino]pyrimidin-4-yl}-1-oxo-2,3-dihydro-1H-isoindol-2-yl)-N-[(1S)-2-hydroxy-1-(5-methylthiophen-3-yl)ethyl]propanamide | 554 [M −H]− |
| 873 | 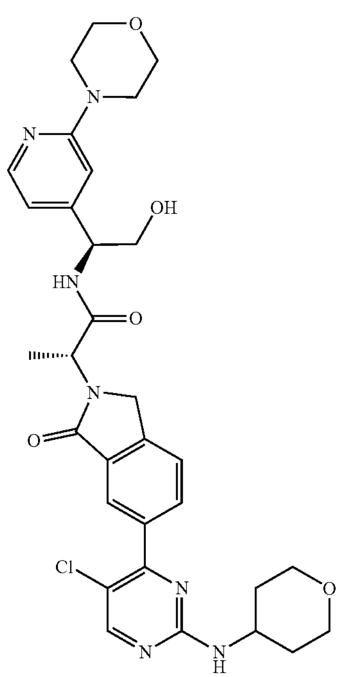 [SMILES: C[C@H](C(=O)N[C@H](CO)c1ccnc(N2CCOCC2)c1)N1Cc2ccc(-c3nc(NC4CCOCC4)ncc3Cl)cc2C1=O] | (2R)-2-(6-{5-chloro-2-[(oxan-4-yl)amino]pyrimidin-4-yl}-1-oxo-2,3-dihydro-1H-isoindol-2-yl)-N-[(1S)-2-hydroxy-1-[2-(morpholin-4-yl)pyridin-4-yl]ethyl]propanamide | 622 |

-continued
| Example | Structure | Name | MS Data [M +H]+ unless specified |
|---|---|---|---|
| 874 | 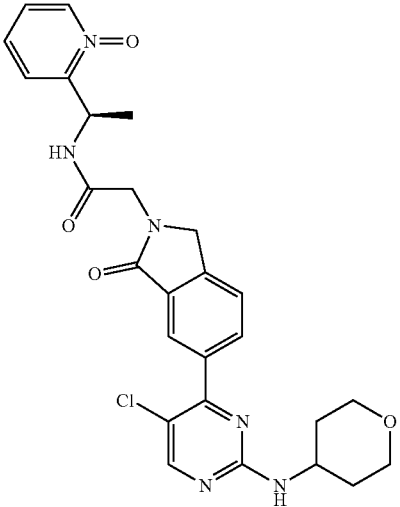 [SMILES: C[C@@H](NC(=O)CN1Cc2ccc(-c3nc(NC4CCOCC4)ncc3Cl)cc2C1=O)c1cccc[n+]1[O-]] | 2-(6-{5-chloro-2-[(oxan-4-yl)amino]pyrimidin-4-yl}-1-oxo-2,3-dihydro-1H-isoindol-2-yl)-N-[(1R)-1-(1-oxo-1$\lambda^5$-pyridin-2-yl)ethyl]acetamide | 523 |
| 875 | 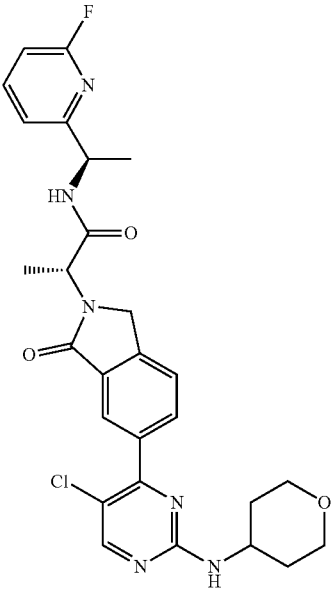 [SMILES: C[C@H](C(=O)N[C@H](C)c1cccc(F)n1)N1Cc2ccc(-c3nc(NC4CCOCC4)ncc3Cl)cc2C1=O] | (2R)-2-(6-{5-chloro-2-[(oxan-4-yl)amino]pyrimidin-4-yl}-1-oxo-2,3-dihydro-1H-isoindol-2-yl)-N-[(1R)-1-(6-fluoropyridin-2-yl)ethyl]propanamide | 539 |

-continued

| Example | Structure | Name | MS Data [M +H]+ unless specified |
|---|---|---|---|
| 876 | 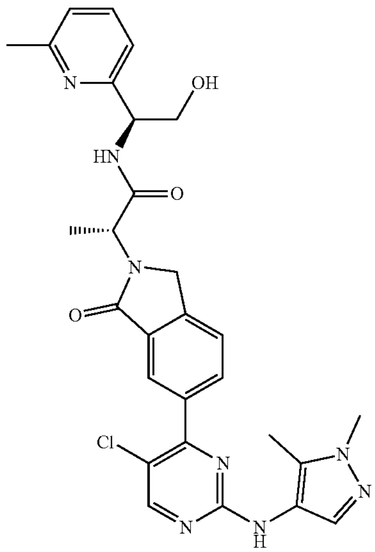 [SMILES: Cc1cccc([C@@H](CO)NC(=O)[C@@H](C)N2Cc3ccc(-c4nc(Nc5cnn(C)c5C)ncc4Cl)cc3C2=O)n1] | (2R)-2-(6-{5-chloro-2-[(1,5-dimethyl-1H-pyrazol-4-yl)amino]pyrimidin-4-yl}-1-oxo-2,3-dihydro-1H-isoindol-2-yl)-N-[(1S)-2-hydroxy-1-(6-methylpyridin-2-yl)ethyl]propanamide | 561 |
| 877 | 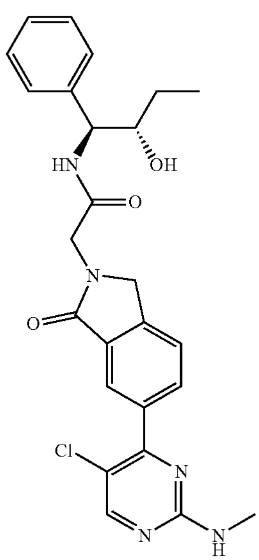 [SMILES: CC[C@H](O)[C@@H](NC(=O)CN1Cc2ccc(-c3nc(NC)ncc3Cl)cc2C1=O)c1ccccc1] | 2-{6-[5-chloro-2-(methylamino)pyrimidin-4-yl]-1-oxo-2,3-dihydro-1H-isoindol-2-yl}-N-[(1S,2S)-2-hydroxy-1-phenylbutyl]acetamide | 480 |

-continued

| Example | Structure | Name | MS Data [M +H]+ unless specified |
|---|---|---|---|
| 878 | 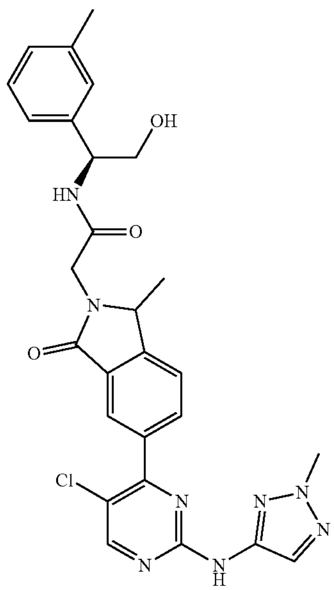 [SMILES: Cc1cccc([C@@H](CO)NC(=O)CN2C(=O)c3cc(-c4nc(Nc5cnn(C)n5)ncc4Cl)ccc3C2C)c1] | 2-(5-{5-chloro-2-[(2-methyl-2H-1,2,3-triazol-4-yl)amino]pyrimidin-4-yl}-1-methyl-3-oxo-2,3-dihydro-1H-isoindol-2-yl)-N-[(1S)-2-hydroxy-1-(3-methylphenyl)ethyl]acetamide Stereoisomer 1 | 547 |
| 879 | 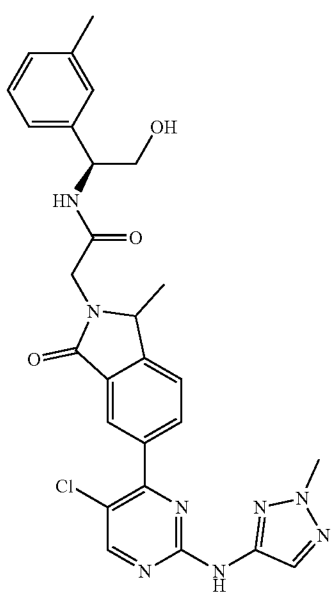 [SMILES: Cc1cccc([C@@H](CO)NC(=O)CN2C(=O)c3cc(-c4nc(Nc5cnn(C)n5)ncc4Cl)ccc3C2C)c1] | 2-(5-{5-chloro-2-[(2-methyl-2H-1,2,3-triazol-4-yl)amino]pyrimidin-4-yl}-1-methyl-3-oxo-2,3-dihydro-1H-isoindol-2-yl)-N-[(1S)-2-hydroxy-1-(3-methylphenyl)ethyl]acetamide Stereoisomer 2 | 547 |

-continued

| Example | Structure | Name | MS Data [M +H]+ unless specified |
|---------|-----------|------|------|
| 880 | 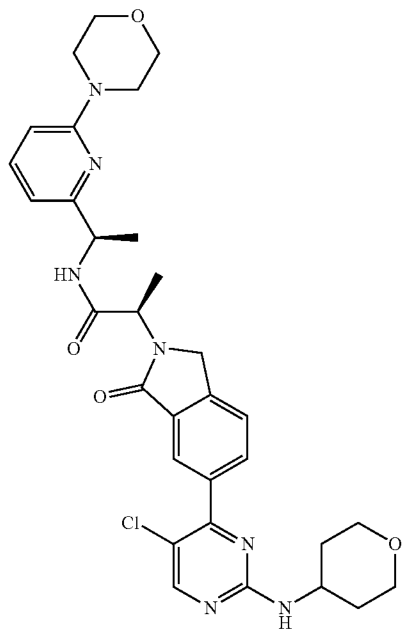 [SMILES: C[C@H](C(=O)N[C@H](C)c1cccc(N2CCOCC2)n1)N1Cc2ccc(-c3nc(NC4CCOCC4)ncc3Cl)cc2C1=O] | (2R)-2-(6-{5-chloro-2-[(oxan-4-yl)amino]pyrimidin-4-yl}-1-oxo-2,3-dihydro-1H-isoindol-2-yl)-N-[(1R)-1[6-(morpholin-4-yl)pyridin-2-yl]ethyl]propanamide | 606 |
| 881 | 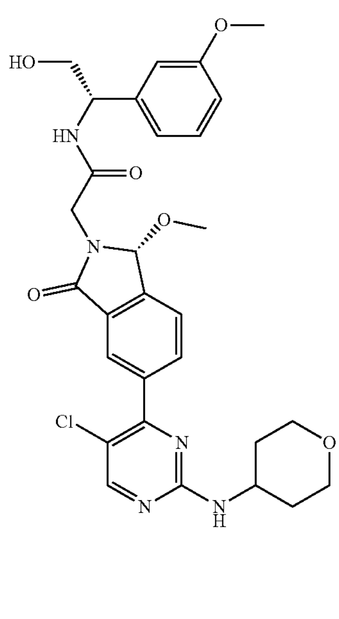 [SMILES: COc1cccc([C@@H](CO)NC(=O)CN2C(=O)c3cc(-c4nc(NC5CCOCC5)ncc4Cl)ccc3[C@H]2OC)c1] | 2-[(1R)-5-{5-chloro-2-[(oxan-4-yl)amino]pyrimidin-4-yl}-1-methoxy-3-oxo-2,3-dihydro-1H-isoindol-2-yl]-N-[(1S)-2-hydroxy-1-(3-methoxyphenyl)ethyl]acetamide | 580 [M −H]− |

| Example | Structure | Name | MS Data [M +H]+ unless specified |
|---|---|---|---|
| 882 | 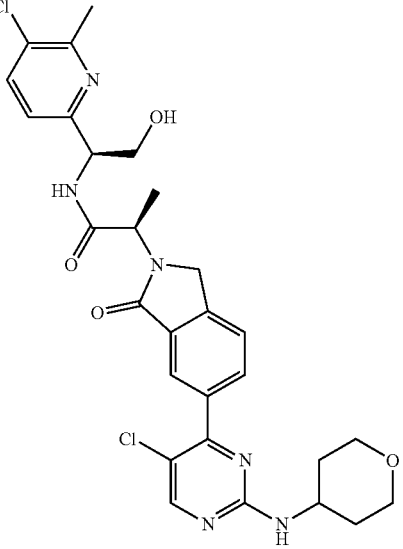 | (2R)-2-(6-{5-chloro-2-[(oxan-4-yl)amino]pyrimidin-4-yl}-1-oxo-2,3-dihydro-1H-isoindol-2-yl)-N-[(1S)-1-(5-chloro-6-methylpyridin-2-yl)-2-hydroxyethyl]propanamide | 585 |
| 883 | 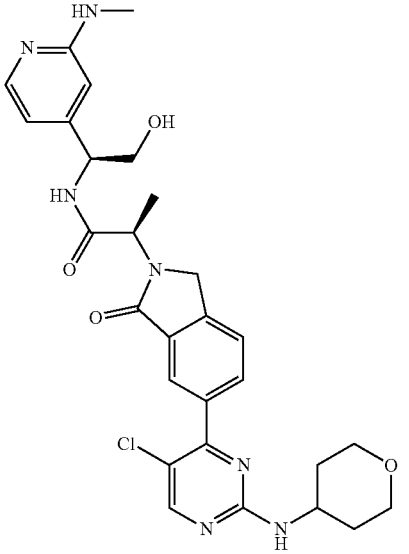 [SMILES: CNc1cc([C@@H](CO)NC(=O)[C@@H](C)N2Cc3ccc(-c4nc(NC5CCOCC5)ncc4Cl)cc3C2=O)ccn1] | (2R)-2-(6-{5-chloro-2-[(oxan-4-yl)amino]pyrimidin-4-yl}-1-oxo-2,3-dihydro-1H-isoindol-2-yl)-N-[(1S)-2-hydroxy-1-[2-(methylamino)pyridin-4-yl]ethyl]propanamide | 566 |

-continued

| Example | Structure | Name | MS Data [M +H]+ unless specified |
|---|---|---|---|
| 884 | 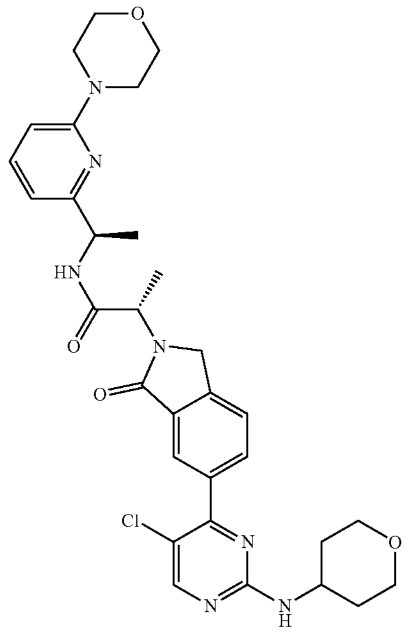 [SMILES: C[C@@H](NC(=O)[C@H](C)N1Cc2ccc(-c3nc(NC4CCOCC4)ncc3Cl)cc2C1=O)c1cccc(N2CCOCC2)n1] | (2S)-2-(6-{5-chloro-2-[(oxan-4-yl)amino]pyrimidin-4-yl}-1-oxo-2,3-dihydro-1H-isoindol-2-yl)-N-[(1R)-1-[6-(morpholin-4-yl)pyridin-2-yl]ethyl]propanamide | 606 |
| 885 | 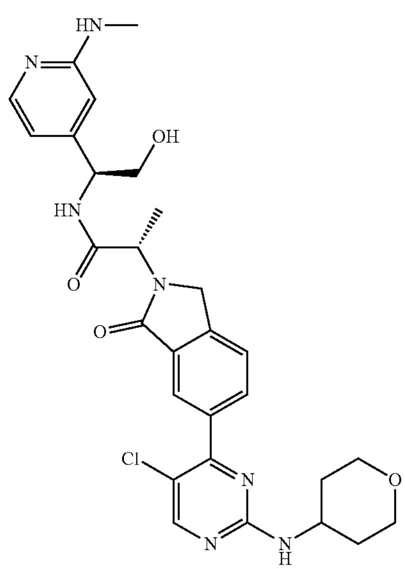 [SMILES: CNc1cc([C@@H](CO)NC(=O)[C@H](C)N2Cc3ccc(-c4nc(NC5CCOCC5)ncc4Cl)cc3C2=O)ccn1] | (2S)-2-(6-{5-chloro-2-[(oxan-4-yl)amino]pyrimidin-4-yl}-1-oxo-2,3-dihydro-1H-isoindol-2-yl)-N-[(1S)-2-hydroxy-1-[2-(methylamino)pyridin-4-yl]ethyl]propanamide | 566 |

-continued

| Example | Structure | Name | MS Data [M +H]+ unless specified |
|---|---|---|---|
| 886 | 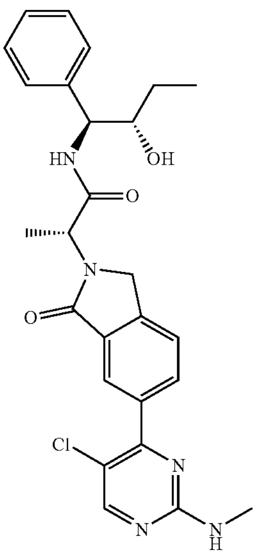 [SMILES: CC[C@H](O)[C@@H](NC(=O)[C@@H](C)N1Cc2ccc(-c3nc(NC)ncc3Cl)cc2C1=O)c1ccccc1] | (2R)-2-{6-[5-chloro-2 (methylamino)pyrimidin-4-yl]-1-oxo-2,3-dihydro-1H-isoindol-2-yl}-N-[(1S,2S)-2-hydroxy-1-phenylbutyl]propanamide | 494 |
| 887 | 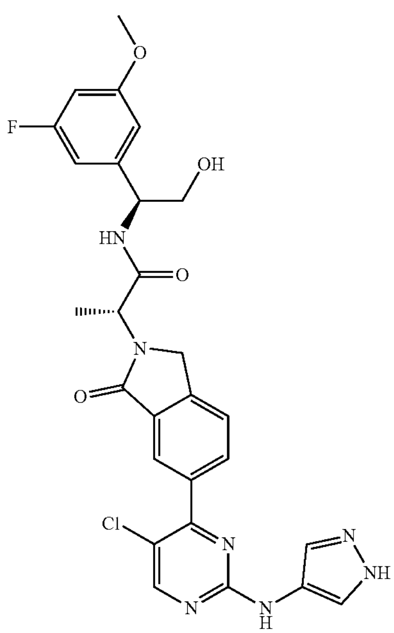 [SMILES: COc1cc(F)cc([C@@H](CO)NC(=O)[C@@H](C)N2Cc3ccc(-c4nc(Nc5cn[nH]c5)ncc4Cl)cc3C2=O)c1] | (2R)-2-(6-{5-chloro-2-[(1H-pyrazol-4-yl)amino]pyrimidin-4-yl}-1-oxo-2,3-dihydro-1H-isoindol-2-yl)-N-[(1S)-1-(3-fluoro-5-methoxyphenyl)-2-hydroxyethyl]propanamide | 566 |

-continued

| Example | Structure | Name | MS Data [M +H]+ unless specified |
|---|---|---|---|
| 888 | 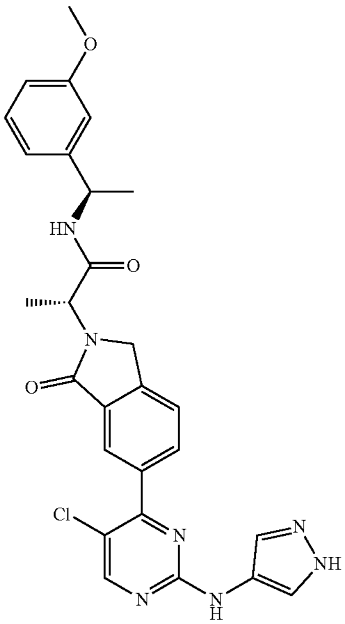 [SMILES: COc1cccc([C@@H](C)NC(=O)[C@@H](C)N2Cc3ccc(-c4nc(Nc5cn[nH]c5)ncc4Cl)cc3C2=O)c1] | (2R)-2-(6-{5-chloro-2-[(1H-pyrazol-4-yl)amino]pyrimidin-4-yl}-1-oxo-2,3-dihydro-1H-isoindol-2-yl)-N-[(1R)-1-(3-methoxyphenyl)ethyl]propanamide | 532 |
| 889 | 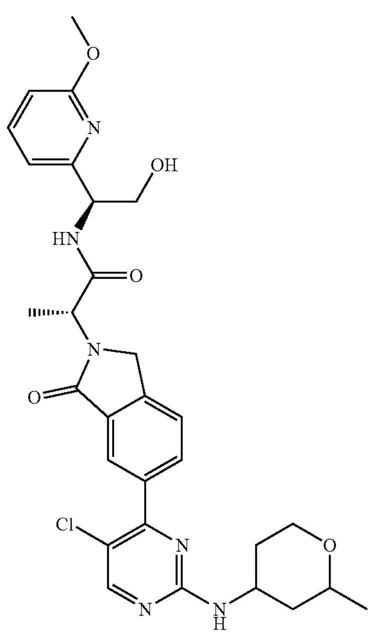 [SMILES: COc1cccc([C@@H](CO)NC(=O)[C@@H](C)N2Cc3ccc(-c4nc(NC5CCOC(C)C5)ncc4Cl)cc3C2=O)n1] | (2R)-2-(6-{5-chloro-2-[(2-methyloxan-4-yl)amino]pyrimidin-4-yl}-1-oxo-2,3-dihydro-1H-isoindol-2-yl)-N-[(1S)-2-hydroxy-1-(6-methoxypyridin-2-yl)ethyl]propanamide | 581 |

-continued

| Example | Structure | Name | MS Data [M +H]+ unless specified |
|---|---|---|---|
| 890 | 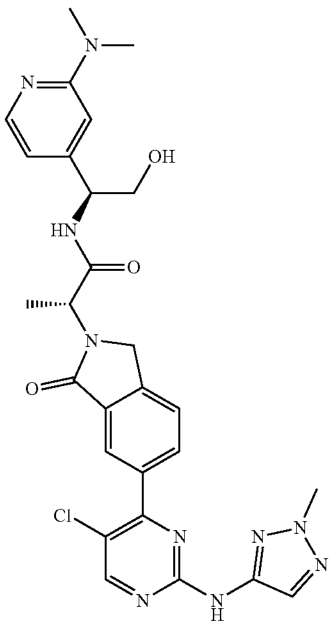 [SMILES: C[C@H](C(=O)N[C@H](CO)c1ccnc(N(C)C)c1)N1Cc2ccc(-c3nc(Nc4cnn(C)n4)ncc3Cl)cc2C1=O] | (2R)-2-(6-{5-chloro-2-[(2-methyl-2H-1,2,3-triazol-4-yl)amino]pyrimidin-4-yl}-1-oxo-2,3-dihydro-1H-isoindol-2-yl)-N-[(1S)-1-[2-(dimethylamino)pyridin-4-yl]-2-hydroxyethyl]propanamide | 577 |
| 891 | 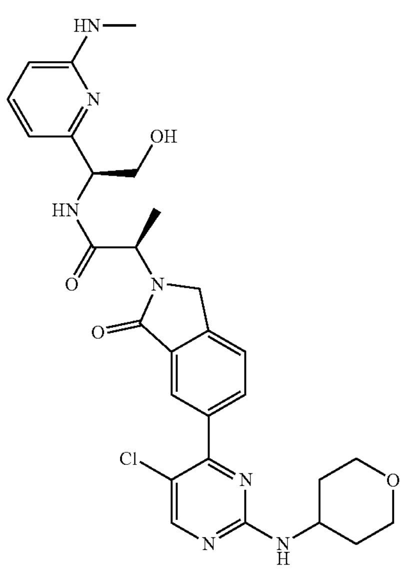 [SMILES: CNc1cccc([C@@H](CO)NC(=O)[C@@H](C)N2Cc3ccc(-c4nc(NC5CCOCC5)ncc4Cl)cc3C2=O)n1] | (2R)-2-(6-{5-chloro-2-[(oxan-4-yl)amino]pyrimidin-4-yl}-1-oxo-2,3-dihydro-1H-isoindol-2-yl)-N-[(1S)-2-hydroxy-1-[6-(methylamino)pyridin-2-yl]ethyl]propanamide | 566 |

-continued

| Example | Structure | Name | MS Data [M+H]+ unless specified |
|---|---|---|---|
| 892 | 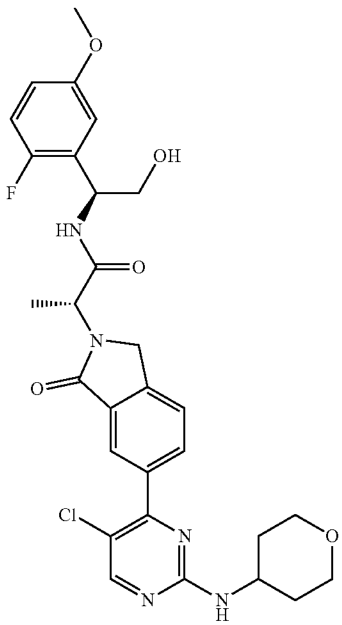 [SMILES: COc1ccc(F)c([C@@H](CO)NC(=O)[C@@H](C)N2Cc3ccc(-c4nc(NC5CCOCC5)ncc4Cl)cc3C2=O)c1] | (2R)-2-(6-{5-chloro-2-[(oxan-4-yl)amino]pyrimidin-4-yl}-1-oxo-2,3-dihydro-1H-isoindol-2-yl)-N-[(1S)-1-(2-fluoro-5-methoxyphenyl)-2-hydroxyethyl]propanamide | 584 |
| 893 | 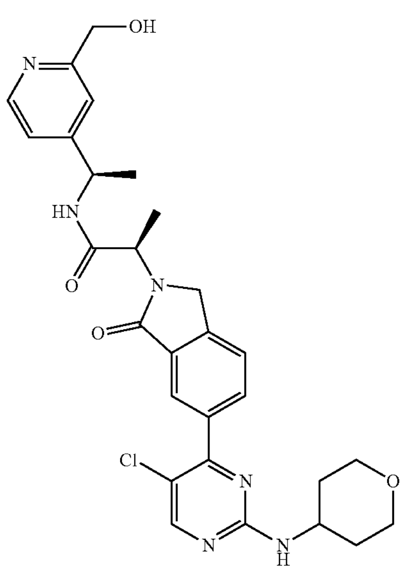 [SMILES: C[C@H](C(=O)N[C@H](C)c1ccnc(CO)c1)N1Cc2ccc(-c3nc(NC4CCOCC4)ncc3Cl)cc2C1=O] | (2R)-2-(6-{5-chloro-2-[(oxan-4-yl)amino]pyrimidin-4-yl}-1-oxo-2,3-dihydro-1H-isoindol-2-yl)-N-[(1R)-1-[2-(hydroxymethyl)pyridin-4-yl]ethyl]propanamide | 551 |

-continued

| Example | Structure | Name | MS Data [M +H]+ unless specified |
|---|---|---|---|
| 894 | 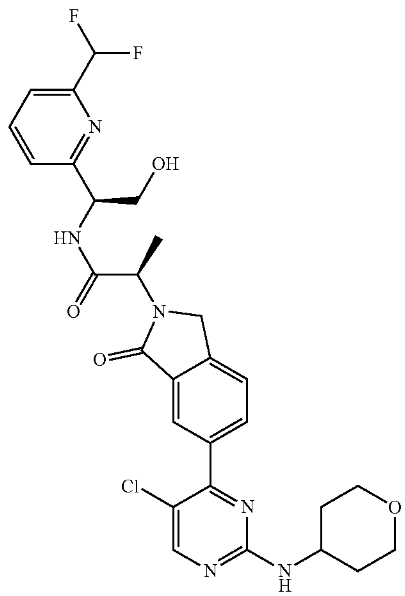 [SMILES: C[C@H](C(=O)N[C@H](CO)c1cccc(C(F)F)n1)N1Cc2ccc(-c3nc(NC4CCOCC4)ncc3Cl)cc2C1=O] | (2R)-2-(6-{5-chloro-2-[(oxan-4-yl)amino]pyrimidin-4-yl}-1-oxo-2,3-dihydro-1H-isoindol-2-yl)-N-[(1S)-1[6-(difluoromethyl)pyridin-2-yl]-2-hydroxyethyl]propanamide | 587 |
| 895 | 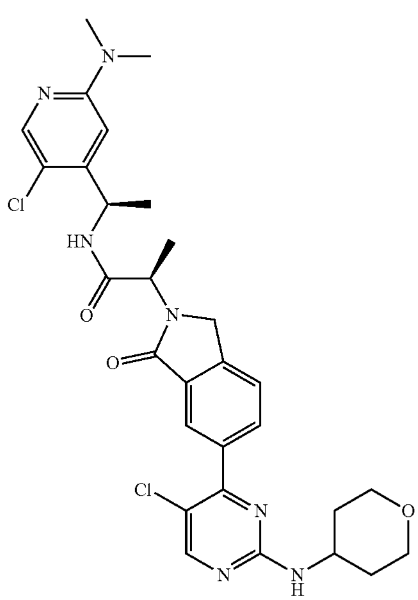 [SMILES: C[C@H](C(=O)N[C@H](C)c1cc(N(C)C)ncc1Cl)N1Cc2ccc(-c3nc(NC4CCOCC4)ncc3Cl)cc2C1=O] | (2R)-N-[(1R)-1-[5-chloro-2-(dimethylamino)pyridin-4-yl]ethyl]-2-(6-{5-chloro-2-[(oxan-4-yl)amino]pyrimidin-4-yl}-1-oxo-2,3-dihydro-1H-isoindol-2-yl)propanamide | 598 |

| Example | Structure | Name | MS Data [M+H]+ unless specified |
|---------|-----------|------|-----|
| 896 | 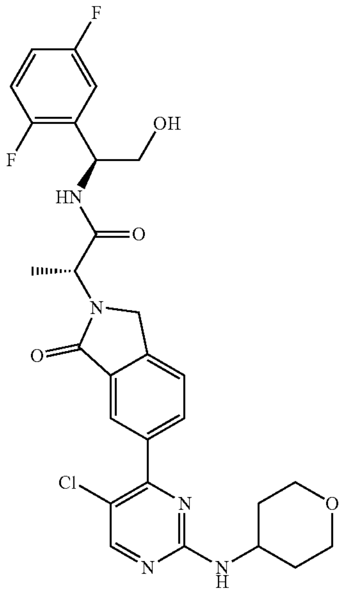 [SMILES: C[C@H](C(=O)N[C@H](CO)c1cc(F)ccc1F)N1Cc2ccc(-c3nc(NC4CCOCC4)ncc3Cl)cc2C1=O] | (2R)-2-(6-{5-chloro-2-[(oxan-4-yl)amino]pyrimidin-4-yl}-1-oxo-2,3-dihydro-1H-isoindol-2-yl)-N-[(1S)-1-(2,5-difluorophenyl)-2-hydroxyethyl]propanamide | 572 |
| 897 | 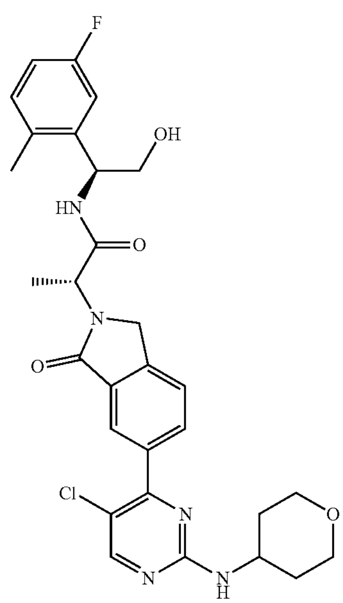 [SMILES: Cc1ccc(F)cc1[C@@H](CO)NC(=O)[C@@H](C)N1Cc2ccc(-c3nc(NC4CCOCC4)ncc3Cl)cc2C1=O] | (2R)-2-(6-{5-chloro-2-[(oxan-4-yl)amino]pyrimidin-4-yl}-1-oxo-2,3-dihydro-1H-isoindol-2-yl)-N-[(1S)-1-(5-fluoro-2-methylphenyl)-2-hydroxyethyl]propanamide | 568 |

-continued
| Example | Structure | Name | MS Data [M +H]+ unless specified |
|---|---|---|---|
| 898 | 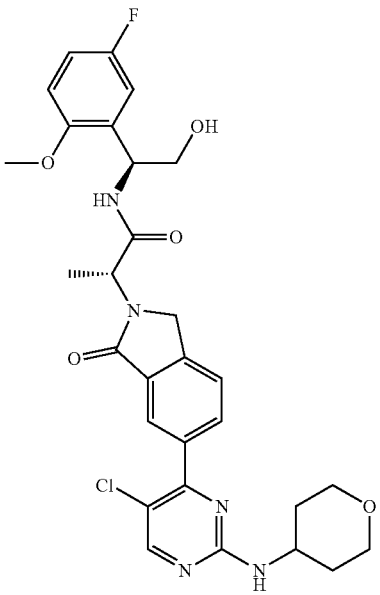 [SMILES: COc1ccc(F)cc1[C@@H](CO)NC(=O)[C@@H](C)N1Cc2ccc(-c3nc(NC4CCOCC4)ncc3Cl)cc2C1=O] | (2R)-2-(6-{5-chloro-2-[(oxan-4-yl)amino]pyrimidin-4-yl}-1-oxo-2,3-dihydro-1H-isoindol-2-yl)-N-[(1S)-1-(5-fluoro-2-methoxyphenyl)-2-hydroxyethyl]propanamide | 584 |
| 899 | 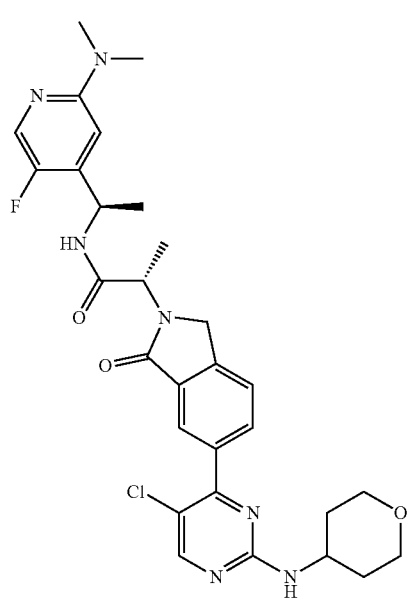 [SMILES: C[C@@H](NC(=O)[C@H](C)N1Cc2ccc(-c3nc(NC4CCOCC4)ncc3Cl)cc2C1=O)c1cc(N(C)C)ncc1F] | (2S)-2-(6-{5-chloro-2-[(oxan-4-yl)amino]pyrimidin-4-yl}-1-oxo-2,3-dihydro-1H-isoindol-2-yl)-N-[(1R)-1[2-(dimethylamino)-5-fluoropyridin-4-yl]ethyl]propanamide | 582 |

-continued

| Example | Structure | Name | MS Data [M+H]+ unless specified |
|---|---|---|---|
| 900 | 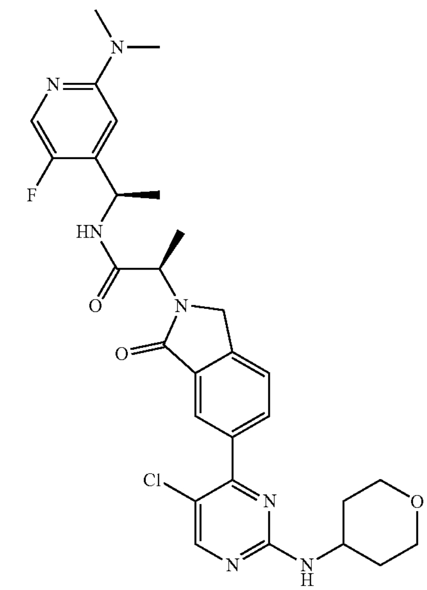 [SMILES: C[C@H](C(=O)N[C@H](C)c1cc(N(C)C)ncc1F)N1Cc2ccc(-c3nc(NC4CCOCC4)ncc3Cl)cc2C1=O] | (2R)-2-(6-{5-chloro-2-[(oxan-4-yl)amino]pyrimidin-4-yl}-1-oxo-2,3-dihydro-1H-isoindol-2-yl)-N-[(1R)-1[2-(dimethylamino)-5-fluoropyridin-4-yl]ethyl]propanamide | 582 |
| 901 | 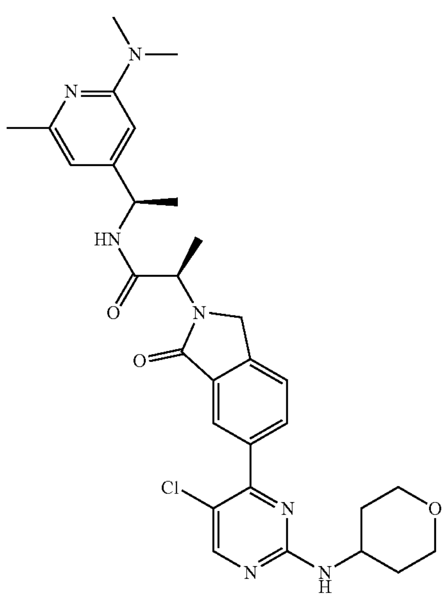 [SMILES: Cc1cc([C@@H](C)NC(=O)[C@@H](C)N2Cc3ccc(-c4nc(NC5CCOCC5)ncc4Cl)cc3C2=O)cc(N(C)C)n1] | (2R)-2-(6-{5-chloro-2-[(oxan-4-yl)amino]pyrimidin-4-yl}-1-oxo-2,3-dihydro-1H-isoindol-2-yl)-N-[(1R)-1-[2-(dimethylamino)-6-methylpyridin-4-yl]ethyl]propanamide | 578 |

-continued

| Example | Structure | Name | MS Data [M +H]+ unless specified |
|---|---|---|---|
| 902 | 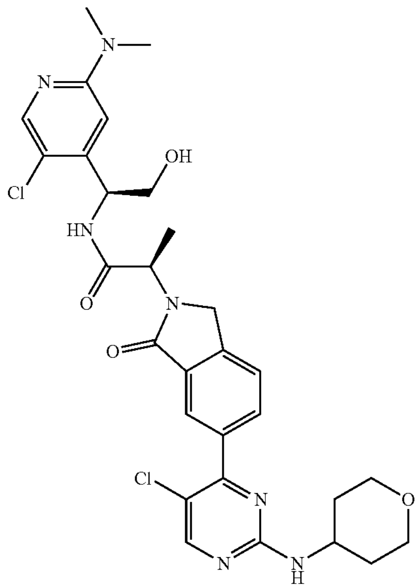 [SMILES: C[C@H](C(=O)N[C@H](CO)c1cc(N(C)C)ncc1Cl)N1Cc2ccc(-c3nc(NC4CCOCC4)ncc3Cl)cc2C1=O] | (2R)-N-[(1S)-1-[5-chloro-2-(dimethylamino)pyridin-4-yl]-2-hydroxyethyl]-2-(6-{5-chloro-2-[(oxan-4-yl)amino]pyrimidin-4-yl}-1-oxo-2,3-dihydro-1H-isoindol-2-yl)propanamide | 614 |
| 903 | 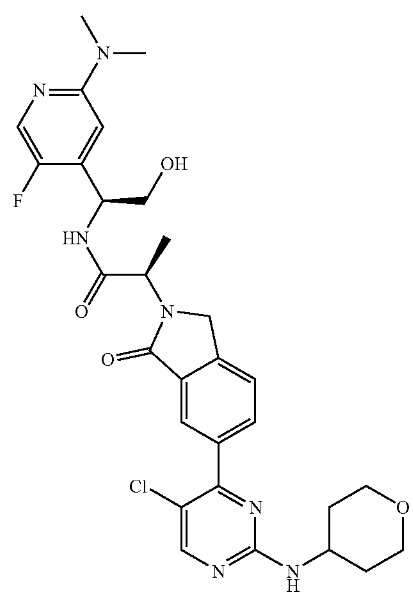 [SMILES: C[C@H](C(=O)N[C@H](CO)c1cc(N(C)C)ncc1F)N1Cc2ccc(-c3nc(NC4CCOCC4)ncc3Cl)cc2C1=O] | (2R)-2-(6-{5-chloro-2-[(oxan-4-yl)amino]pyrimidin-4-yl}-1-oxo-2,3-dihydro-1H-isoindol-2-yl)-N-[(1S)-1-[2-(dimethylamino)-5-fluoropyridin-4-yl]2-hydroxyethyl]propanamide | 598 |

-continued

| Example | Structure | Name | MS Data [M +H]+ unless specified |
|---|---|---|---|
| 904 | 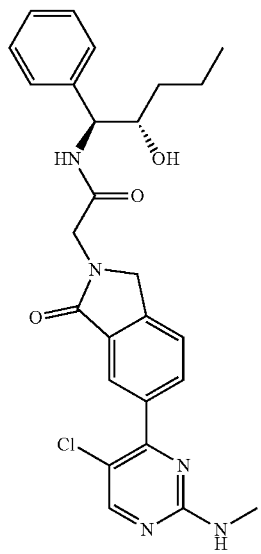 [SMILES: CCC[C@H](O)[C@@H](NC(=O)CN1Cc2ccc(-c3nc(NC)ncc3Cl)cc2C1=O)c1ccccc1] | 2-{6-[5-chloro-2-(methylamino)pyrimidin-4-yl]-1-oxo-2,3-dihydro-1H-isoindol-2-yl}-N-[(1S,2S)-2-hydroxy-1-phenylpentyl]acetamide | 494 |
| 905 | 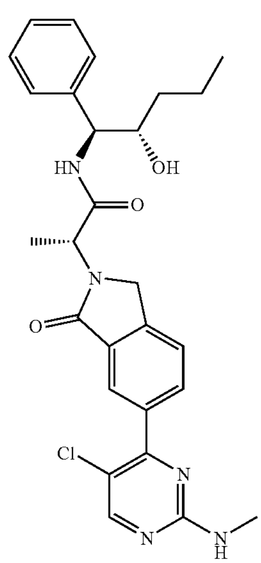 [SMILES: CCC[C@H](O)[C@@H](NC(=O)[C@@H](C)N1Cc2ccc(-c3nc(NC)ncc3Cl)cc2C1=O)c1ccccc1] | (2R)-2-{6-[5-chloro-2-(methylamino)pyrimidin-4-yl]-1-oxo-2,3-dihydro-1H-isoindol-2-yl}-N-[(1S,2S)-2-hydroxy-1-phenylpentyl]propanamide | 508 |

-continued

| Example | Structure | Name | MS Data [M +H]+ unless specified |
|---|---|---|---|
| 906 | 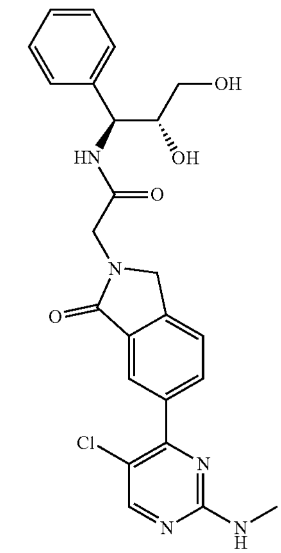 [SMILES: CNc1ncc(Cl)c(-c2ccc3c(c2)C(=O)N(CC(=O)N[C@@H](c2ccccc2)[C@@H](O)CO)C3)n1] | 2-{6-[5-chloro-2-(methylamino)pyrimidin-4-yl]-1-oxo-2,3-dihydro-1H-isoindol-2-yl}-N-[(1S,2R)-2,3-dihydroxy-1-phenylpropyl]acetamide | 482 |
| 907 | 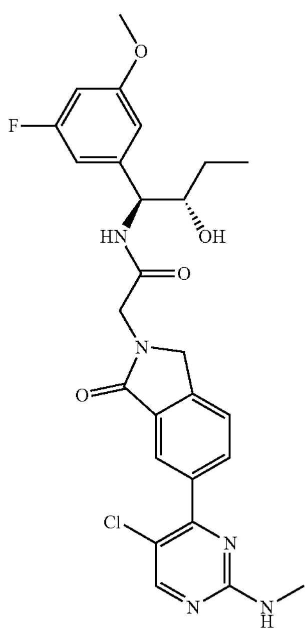 [SMILES: CC[C@H](O)[C@@H](NC(=O)CN1Cc2ccc(-c3nc(NC)ncc3Cl)cc2C1=O)c1cc(F)cc(OC)c1] | 2-{6-[5-chloro-2-(methylamino)pyrimidin-4-yl]-1-oxo-2,3-dihydro-1H-isoindol-2-yl}-N-[(1S,2S)-1-(3-fluoro-5-methoxyphenyl)-2-hydroxybutyl]acetamide | 528 |

-continued

| Example | Structure | Name | MS Data [M +H]+ unless specified |
|---|---|---|---|
| 908 | 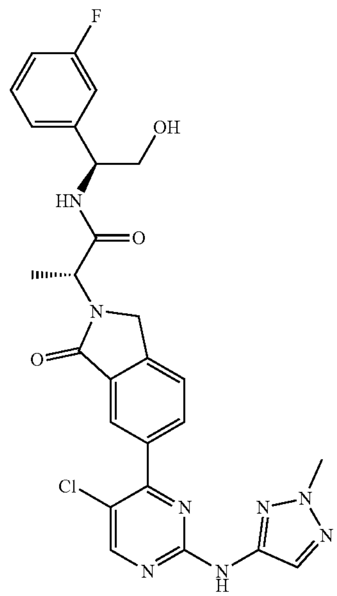 [SMILES: C[C@H](C(=O)N[C@H](CO)c1cccc(F)c1)N1Cc2ccc(-c3nc(Nc4cnn(C)n4)ncc3Cl)cc2C1=O] | (2R)-2-(6-}5-chloro-2-[(2-methyl-2H-1,2,3-triazol-4-yl)amino]pyrimidin-4-yl}-1-oxo-2,3-dihydro-1H-isoindol-2-yl)-N-[(1S)-1-(3-fluorophenyl)-2-hydroxyethyl]propanamide | 551 |
| 909 | 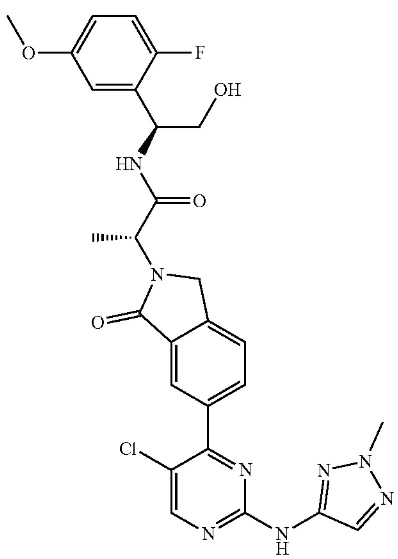 [SMILES: COc1ccc(F)c([C@@H](CO)NC(=O)[C@@H](C)N2Cc3ccc(-c4nc(Nc5cnn(C)n5)ncc4Cl)cc3C2=O)c1] | (2R)-2-(6-{5-chloro-2-[(2-methyl-2H-1,2,3-triazol-4-yl)amino]pyrimidin-4-yl}-1-oxo-2,3-dihydro-1H-isoindol-2-yl)-N-[(1S)-1-(2-fluoro-5-methoxyphenyl)-2-hydroxyethyl]propanamide | 581 |

| Example | Structure | Name | MS Data [M +H]+ unless specified |
|---|---|---|---|
| 910 | 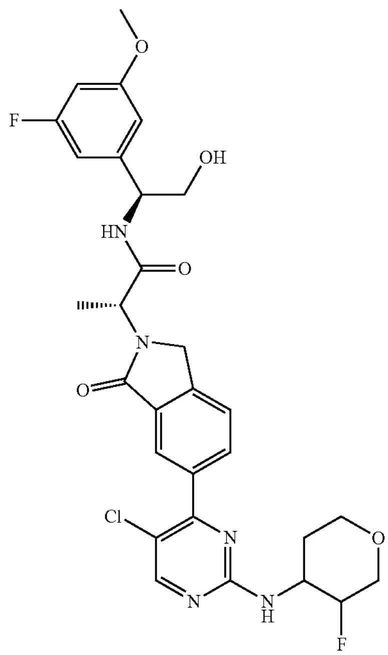 [SMILES: COc1cc(F)cc([C@@H](CO)NC(=O)[C@@H](C)N2Cc3ccc(-c4nc(NC5CCOCC5F)ncc4Cl)cc3C2=O)c1] | (2R)-2-(6-{5-chloro-2-[(3-fluorooxan-4-yl)amino]pyrimidin-4-yl}-1-oxo-2,3-dihydro-1H-isoindol-2-yl)-N-[(1S)-1-(3-fluoro-5-methoxyphenyl)-2-hydroxyethyl]propanamide | 600 [M −H]− |
| 911 | 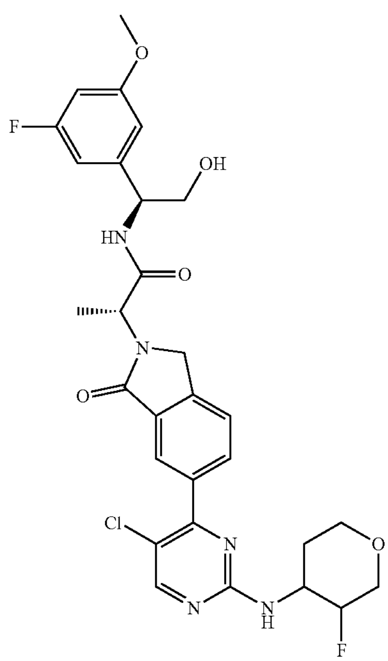 [SMILES: COc1cc(F)cc([C@@H](CO)NC(=O)[C@@H](C)N2Cc3ccc(-c4nc(NC5CCOCC5F)ncc4Cl)cc3C2=O)c1] | (2R)-2-(6-{5-chloro-2-[(3-fluorooxan-4-yl)amino]pyrimidin-4-yl}-1-oxo-2,3-dihydro-1H-isoindol-2-yl)-N-[(1S)-1-(3-fluoro-5-methoxyphenyl)-2-hydroxyethyl]propanamide Stereoisomer 1 | 602 [M +H]+ |

-continued
| Example | Structure | Name | MS Data [M +H]+ unless specified |
|---|---|---|---|
| 912 | 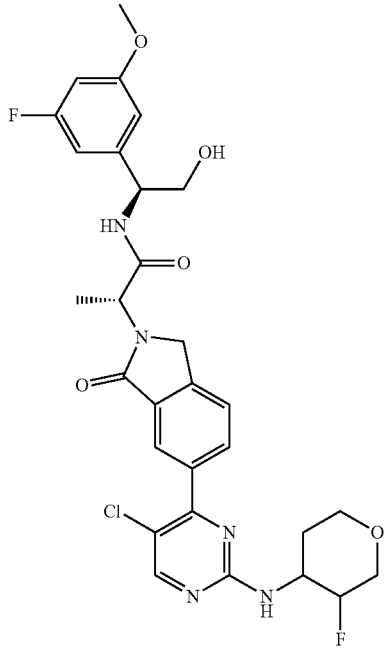 | (2R)-2-(6-{5-chloro-2-[(3-fluorooxan-4-yl)amino]pyrimidin-4-yl}-1-oxo-2,3-dihydro-1H-isoindol-2-yl)-N-[(1S)-1-(3-fluoro-5-methoxyphenyl)-2-hydroxyethyl]propanamide Stereoisomer 2 | 600 [M −H]− |
| 913 | 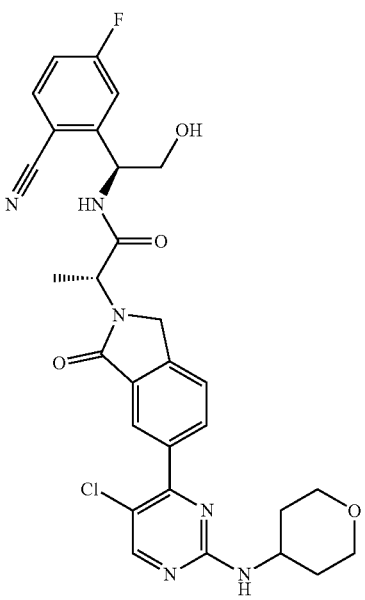 [SMILES: C[C@H](C(=O)N[C@H](CO)c1cc(F)ccc1C#N)N1Cc2ccc(-c3nc(NC4CCOCC4)ncc3Cl)cc2C1=O] | (2R)-2-(6-{5-chloro-2-[(oxan-4-yl)amino]pyrimidin-4-yl}-1-oxo-2,3-dihydro-1H-isoindol-2-yl)-N-[(1S)-1-(2-cyano-5-fluorophenyl)-2-hydroxyethyl]propanamide | 577 [M −H]− |

-continued

| Example | Structure | Name | MS Data [M +H]+ unless specified |
|---|---|---|---|
| 914 | 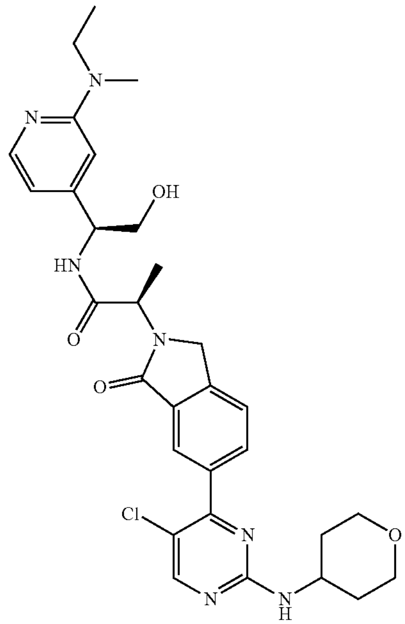 [SMILES: CCN(C)c1cc([C@@H](CO)NC(=O)[C@@H](C)N2Cc3ccc(-c4nc(NC5CCOCC5)ncc4Cl)cc3C2=O)ccn1] | (2R)-2-(6-{5-chloro-2-[(oxan-4-yl)amino]pyrimidin-4-yl}-1-oxo-2,3-dihydro-1H-isoindol-2-yl)-N-[(1S)-1-{2-[ethyl(methyl)amino]pyridin-4-yl{-2-hydroxyethyl]propanamide | 594 |
| 915 | 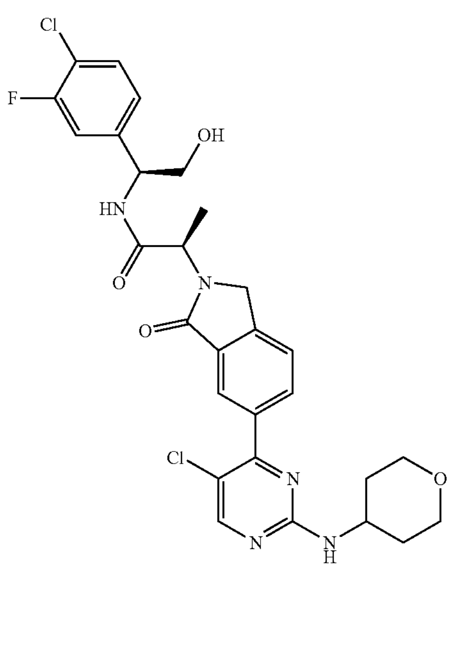 [SMILES: C[C@H](C(=O)N[C@H](CO)c1ccc(Cl)c(F)c1)N1Cc2ccc(-c3nc(NC4CCOCC4)ncc3Cl)cc2C1=O] | (2R)-2-(6-{5-chloro-2-[(oxan-4-yl)amino]pyrimidin-4-yl}-1-oxo-2,3-dihydro-1H-isoindol-2-yl)-N-[(1S)-1-(4-chloro-3-fluorophenyl)-2-hydroxyethyl]propanamide | 588 |

| Example | Structure | Name | MS Data [M+H]+ unless specified |
|---|---|---|---|
| 916 | 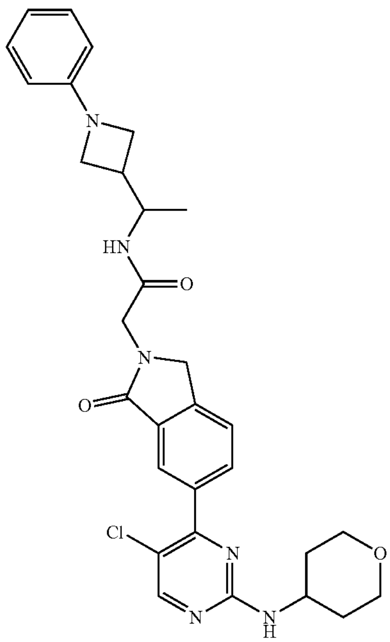 [SMILES: CC(NC(=O)CN1Cc2ccc(-c3nc(NC4CCOCC4)ncc3Cl)cc2C1=O)C1CN(c2ccccc2)C1] | 2-(6-{5-chloro-2-[(oxan-4-yl)amino]pyrimidin-4-yl}-1-oxo-2,3-dihydro-1H-isoindol-2-yl)-N-[1-(1-phenylazetidin-3-yl)ethyl]acetamide | 561 |
| 917 | 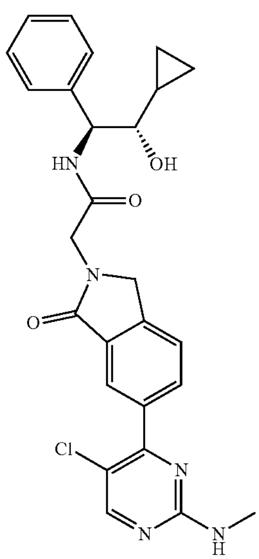 [SMILES: CNc1ncc(Cl)c(-c2ccc3c(c2)C(=O)N(CC(=O)N[C@@H](c2ccccc2)[C@@H](O)C2CC2)C3)n1] | 2-{6-[5-chloro-2-(methylamino)pyrimidin-4-yl]-1-oxo-2,3-dihydro-1H-isoindol-2-yl}-N-[(1S,2S)-2-cyclopropyl-2-hydroxy-1-phenylethyl]acetamide | 492 |

There is no Example 918

-continued

| Example | Structure | Name | MS Data [M +H]+ unless specified |
|---|---|---|---|
| 919 | 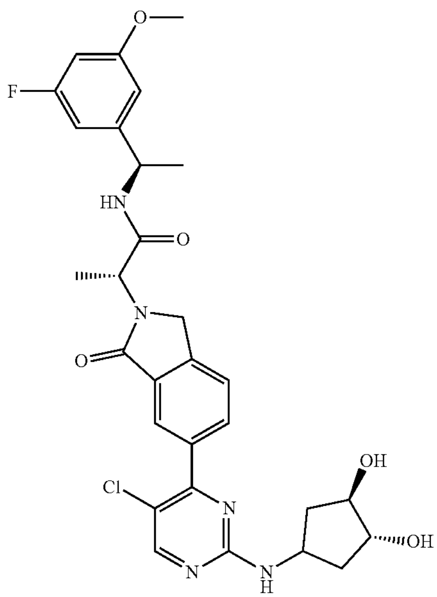 [SMILES: COc1cc(F)cc([C@@H](C)NC(=O)[C@@H](C)N2Cc3ccc(-c4nc(NC5C[C@@H](O)[C@H](O)C5)ncc4Cl)cc3C2=O)c1] | (2R)-2-[6-(5-chloro-2-{[(3R,4R)-3,4-dihydroxycyclopentyl]amino}pyrimidin-4-yl)-1-oxo-2,3-dihydro-1H-isoindol-2-yl]-N-[(1R)-1-(3-fluoro-5-methoxyphenyl)ethyl]propanamide | 584 |
| 920 | 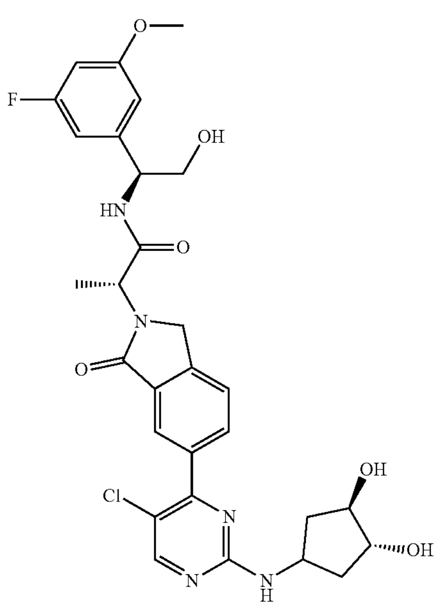 [SMILES: COc1cc(F)cc([C@@H](CO)NC(=O)[C@@H](C)N2Cc3ccc(-c4nc(NC5C[C@@H](O)[C@H](O)C5)ncc4Cl)cc3C2=O)c1] | (2R)-2-[6-(5-chloro-2-{[(3R,4R)-3,4-dihydroxycyclopentyl]amino}pyrimidin-4-yl)-1-oxo-2,3-dihydro-1H-isoindol-2-yl]N-[(1S)-1-(3-fluoro-5-methoxyphenyl)-2-hydroxyethyl]propanamide | 598 [M −H]− |

-continued

| Example | Structure | Name | MS Data [M+H]+ unless specified |
|---|---|---|---|
| 921 | 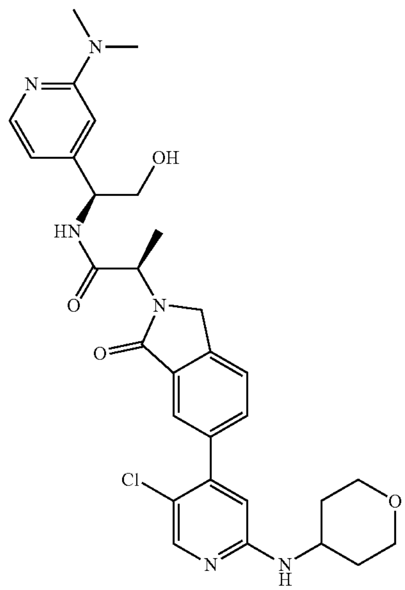 [SMILES: C[C@H](C(=O)N[C@H](CO)c1ccnc(N(C)C)c1)N1Cc2ccc(-c3cc(NC4CCOCC4)ncc3Cl)cc2C1=O] | (2R)-2-(6-{5-chloro-2-[(oxan-4-yl)amino]pyridin-4-yl}-1-oxo-2,3-dihydro-1H-isoindol-2-yl)-N-[(1S)-1[2-(dimethylamino)pyridin-4-yl]-2-hydroxyethyl]propanamide | 579 |
| 922 | 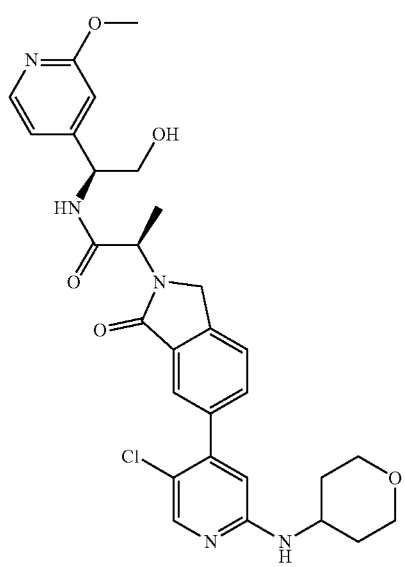 [SMILES: COc1cc([C@@H](CO)NC(=O)[C@@H](C)N2Cc3ccc(-c4cc(NC5CCOCC5)ncc4Cl)cc3C2=O)ccn1] | (2R)-2-(6-{5-chloro-2-[(oxan-4-yl)amino]pyridin-4-yl}-1-oxo-2,3-dihydro-1H-isoindol-2-yl)-N-[(1S)-2-hydroxy-1-(2-methoxypyridin-4-yl)ethyl]propanamide | 566 |

|  |  |  | MS Data [M+H]+ unless |
|---|---|---|---|
| Example | Structure | Name | specified |

923 — No Example 923

924 — (2R)-2-(6-{5-chloro-2-[(morpholin-4-yl)amino]pyrimidin-4-yl}-1-oxo-2,3-dihydro-1H-isoindol-2-yl)-N-[(1S)-1-(3-fluoro-5-methoxyphenyl)-2-hydroxyethyl]propanamide — 585

925 — (2R)-2-(6-{5-chloro-2-[(oxan-4-yl)amino]pyrimidin-4-yl}-1-oxo-2,3-dihydro-1H-isoindol-2-yl)-N-[(1R)-1-[2-(morpholin-4-yl)pyrimidin-4-yl]ethyl]propanamide — 607

There is no Example 926

| Example | Structure | Name | MS Data [M +H]+ unless specified |
|---------|-----------|------|-----|
| 927 | 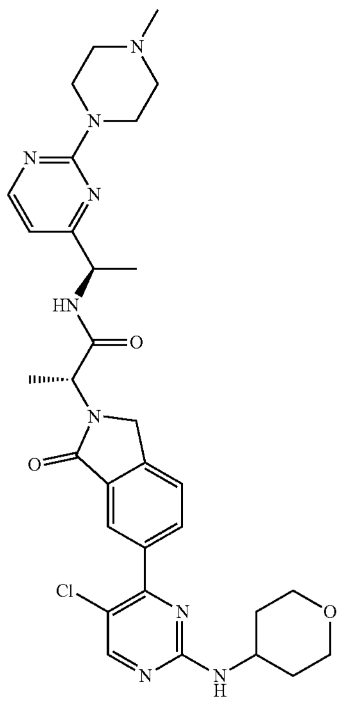 [SMILES: C[C@H](C(=O)N[C@H](C)c1ccnc(N2CCN(C)CC2)n1)N1Cc2ccc(-c3nc(NC4CCOCC4)ncc3Cl)cc2C1=O] | (2R)-2-(6-{5-chloro-2-[(oxan-4-yl)amino]pyrimidin-4-yl}-1-oxo-2,3-dihydro-1H-isoindol-2-yl)-N-[(1R)-1-[2-(4-methylpiperazin-1-yl)pyrimidin-4-yl]ethyl]propanamide | 620 |
| 928 | 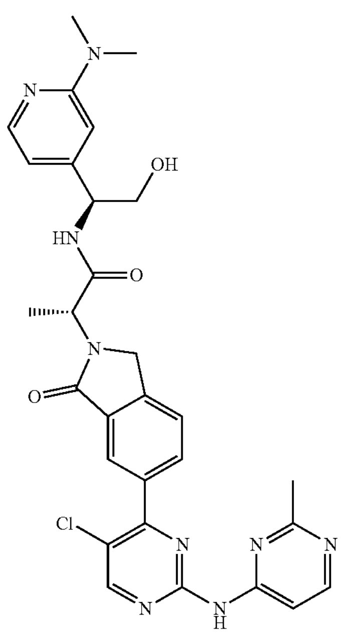 [SMILES: Cc1nccc(Nc2ncc(Cl)c(-c3ccc4c(c3)C(=O)N([C@H](C)C(=O)N[C@H](CO)c3ccnc(N(C)C)c3)C4)n2)n1] | (2R)-2-(6-{5-chloro-2-[(2-methylpyrimidin-4-yl)amino]pyrimidin-4-yl}-1-oxo-2,3-dihydro-1H-isoindol-2-yl)-N-[(1S)-1-[2-(dimethylamino)pyridin-4-yl]-2-hydroxyethyl]propanamide | 588 |

-continued

| Example | Structure | Name | MS Data [M +H]+ unless specified |
|---|---|---|---|
| 929 | 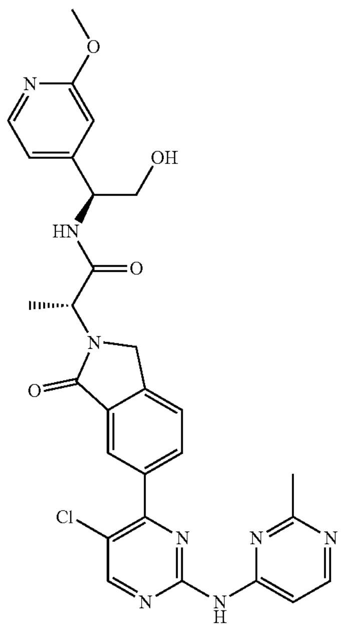 [SMILES: COc1cc([C@@H](CO)NC(=O)[C@@H](C)N2Cc3ccc(-c4nc(Nc5ccnc(C)n5)ncc4Cl)cc3C2=O)ccn1] | (2R)-2-(6-{5-chloro-2-[(2-methylpyrimidin-4-yl)amino]pyrimidin-4-yl}-1-oxo-2,3-dihydro-1H-isoindol-2-yl)-N-[(1S)-2-hydroxy-1-(2-methoxypyridin-4-yl)ethyl]propanamide | 575 |
| 930 | 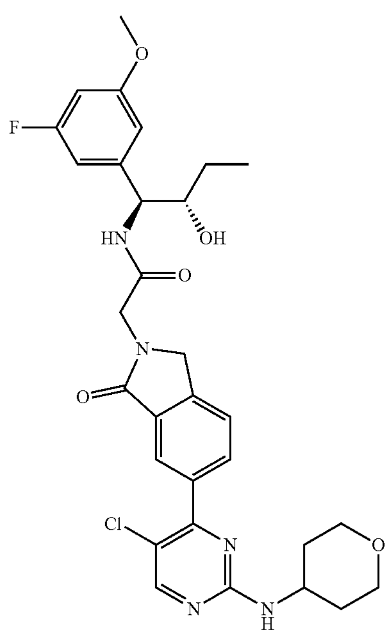 [SMILES: CC[C@H](O)[C@@H](NC(=O)CN1Cc2ccc(-c3nc(NC4CCOCC4)ncc3Cl)cc2C1=O)c1cc(F)cc(OC)c1] | 2-(6-{5-chloro-2-[(oxan-4-yl)amino]pyrimidin-4-yl}-1-oxo-2,3-dihydro-1H-isoindol-2-yl)-N-[(1S,2S)-1-(3-fluoro-5-methoxyphenyl)-2-hydroxybutyl]acetamide | 598 |

-continued

| Example | Structure | Name | MS Data [M +H]+ unless specified |
|---|---|---|---|
| 931 | 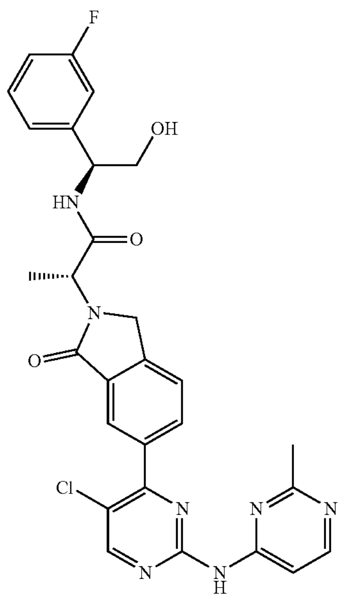 [SMILES: Cc1nccc(Nc2ncc(Cl)c(-c3ccc4c(c3)C(=O)N([C@H](C)C(=O)N[C@H](CO)c3cccc(F)c3)C4)n2)n1] | (2R)-2-(6-{5-chloro-2-[(2-methylpyrimidin-4-yl)amino]pyrimidin-4-yl}-1-oxo-2,3-dihydro-1H-isoindol-2-yl)-N-[(1S)-1-(3-fluorophenyl)-2-hydroxyethyl]propanamide | 562 |
| 932 | 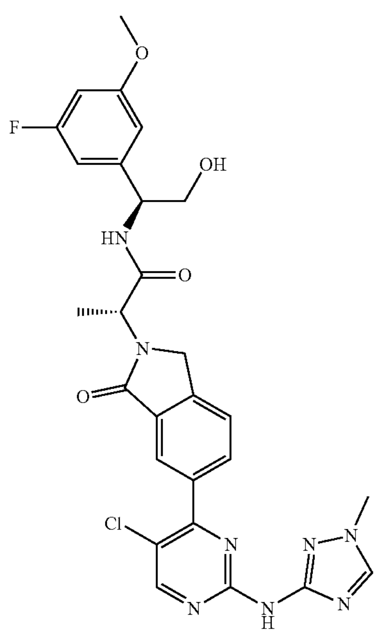 [SMILES: COc1cc(F)cc([C@@H](CO)NC(=O)[C@@H](C)N2Cc3ccc(-c4nc(Nc5ncn(C)n5)ncc4Cl)cc3C2=O)c1] | (2R)-2-(6-{5-chloro-2-[(1-methyl-1H-1,2,4-triazol-3-yl)amino]pyrimidin-4-yl}-1-oxo-2,3-dihydro-1H-isoindol-2-yl)-N-[(1S)-1-(3-fluoro-5-methoxyphenyl)-2-hydroxyethyl]propanamide | 581 |

-continued

| Example | Structure | Name | MS Data [M +H]+ unless specified |
|---|---|---|---|
| 933 | 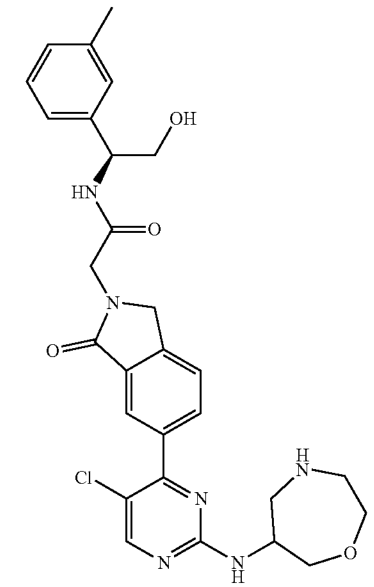 [SMILES: Cc1cccc([C@@H](CO)NC(=O)CN2Cc3ccc(-c4nc(NC5CNCCOC5)ncc4Cl)cc3C2=O)c1] | 2-(6-{5-chloro-2-[(1,4-oxazepan-6-yl)amino]pyrimidin-4-yl}-1-oxo-2,3-dihydro-1H-isoindol-2-yl)-N-[(1S)-2-hydroxy-1-(3-methylphenyl)ethyl]acetamide | 551 |
| 934 | 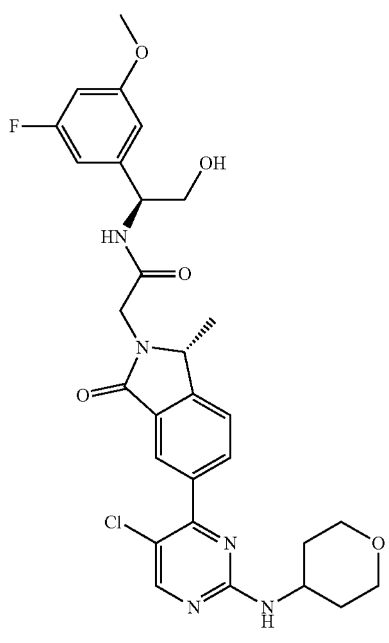 [SMILES: COc1cc(F)cc([C@@H](CO)NC(=O)CN2C(=O)c3cc(-c4nc(NC5CCOCC5)ncc4Cl)ccc3[C@H]2C)c1] | 2-[(1R)-5-{5-chloro-2-[(oxan-4-yl)amino]pyrimidin-4-yl}-1-methyl-3-oxo-2,3-dihydro-1H-isoindol-2-yl]-N-[(1S)-1-(3-fluoro-5-methoxyphenyl)-2-hydroxyethyl]acetamide | 584 |

-continued

| Example | Structure | Name | MS Data [M +H]+ unless specified |
|---|---|---|---|
| 935 | 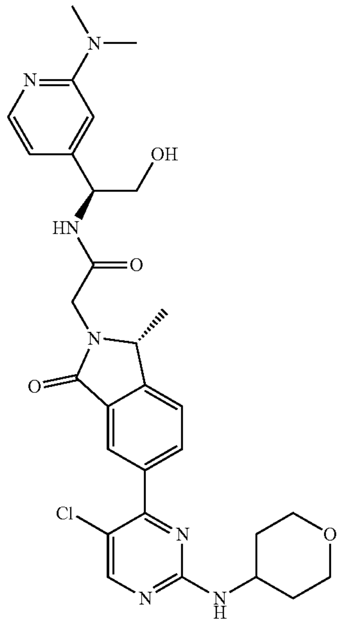 [SMILES: C[C@@H]1c2ccc(-c3nc(NC4CCOCC4)ncc3Cl)cc2C(=O)N1CC(=O)N[C@H](CO)c1ccnc(N(C)C)c1] | 2-[(1R)-5-{5-chloro-2-[(oxan-4-yl)amino]pyrimidin-4-yl}-1-methyl-3-oxo-2,3-dihydro-1H-isoindol-2-yl]-N-[(1S)-1[2-(dimethylamino)pyridin-4-yl]-2-hydroxyethyl]acetamide | 580 |
| 936 | 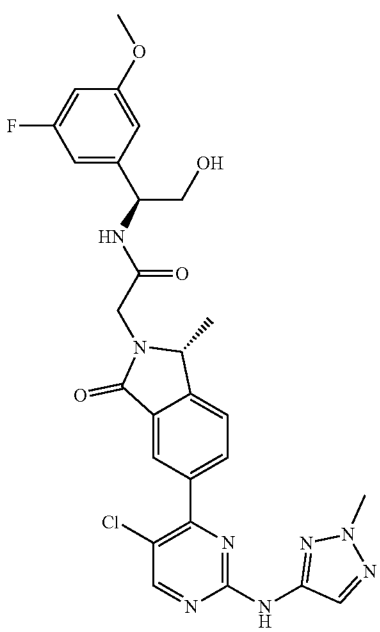 [SMILES: COc1cc(F)cc([C@@H](CO)NC(=O)CN2C(=O)c3cc(-c4nc(Nc5cnn(C)n5)ncc4Cl)ccc3[C@H]2C)c1] | 2-[(1R)-5-{5-chloro-2-[(2-methyl-2H-1,2,3-triazol-4-yl)amino]pyrimidin-4-yl}-1-methyl-3-oxo-2,3-dihydro-1H-isoindol-2-yl]N-[(1S)-1-(3-fluoro-5-methoxyphenyl)-2-hydroxyethyl]acetamide | 581 |

-continued
| Example | Structure | Name | MS Data [M +H]+ unless specified |
|---|---|---|---|
| 937 | 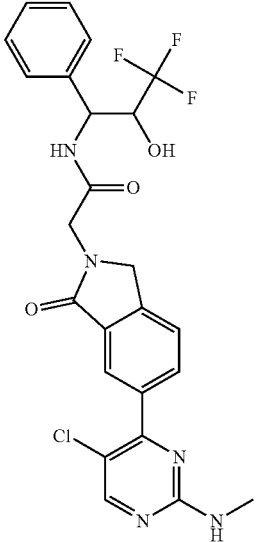 [SMILES: CNc1ncc(Cl)c(-c2ccc3c(c2)C(=O)N(CC(=O)NC(c2ccccc2)C(O)C(F)(F)F)C3)n1] | 2-{6-[5-chloro-2-(methylamino)pyrimidin-4-yl]-1-oxo-2,3-dihydro-1H-isoindol-2-yl}-N-(3,3,3-trifluoro-2-hydroxy-1-phenylpropyl)acetamide | 520 |
| 938 | 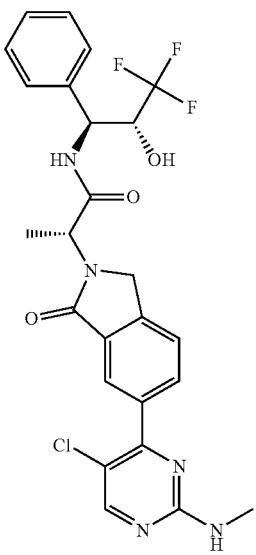 [SMILES: CNc1ncc(Cl)c(-c2ccc3c(c2)C(=O)N([C@H](C)C(=O)N[C@@H](c2ccccc2)[C@@H](O)C(F)(F)F)C3)n1] | (2R)-2-{6-[5-chloro-2-(methylamino)pyrimidin-4-yl]-1-oxo-2,3-dihydro-1H-isoindol-2-yl}-N-[(1S,2R)-3,3,3-trifluoro-2-hydroxy-1-phenylpropyl]propanamide | 534 |

| Example | Structure | Name | MS Data [M +H]+ unless specified |
|---|---|---|---|
| 939 | 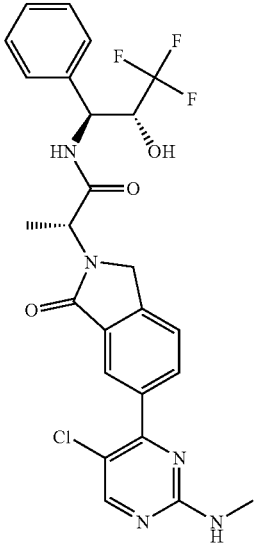 [SMILES: CNc1ncc(Cl)c(-c2ccc3c(c2)C(=O)N([C@H](C)C(=O)N[C@@H](c2ccccc2)[C@@H](O)C(F)(F)F)C3)n1] | (2R)-2-{6-[5-chloro-2-(methylamino)pyrimidin-4-yl]-1-oxo-2,3-dihydro-1H-isoindol-2-yl}-N-[(1R,2S)-3,3,3-trifluoro-2-hydroxy-1-phenylpropyl]propanamide | 534 |
| 940 | 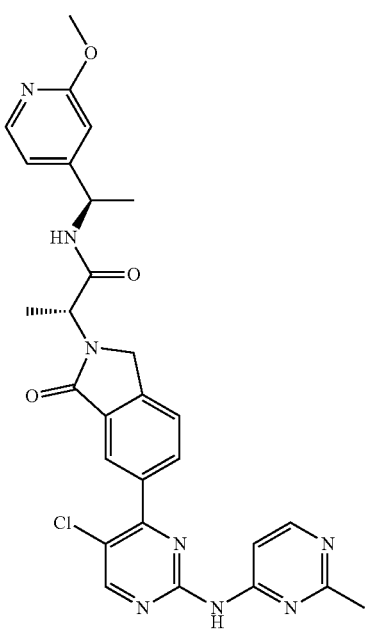 [SMILES: COc1cc([C@@H](C)NC(=O)[C@@H](C)N2Cc3ccc(-c4nc(Nc5ccnc(C)n5)ncc4Cl)cc3C2=O)ccn1] | (2R)-2-(6-{5-chloro-2-[(2-methylpyrimidin-4-yl)amino]pyrimidin-4-yl}-1-oxo-2,3-dihydro-1H-isoindol-2-yl)-N-[(1R)-1-(2-methoxypyridin-4-yl)ethyl]propanamide | 559 |

-continued

| Example | Structure | Name | MS Data [M +H]+ unless specified |
|---|---|---|---|
| 941 | 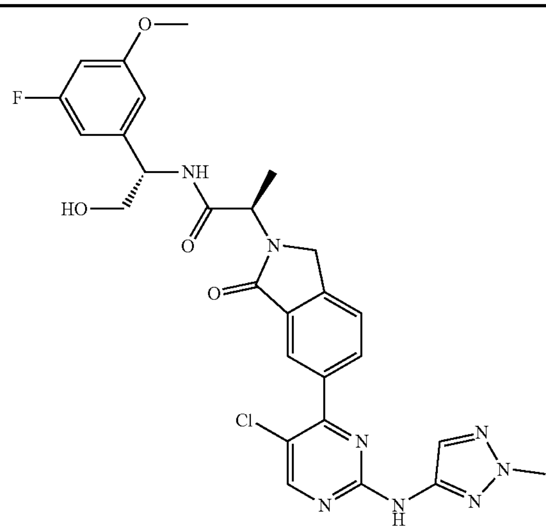 | (2R)-2-(6-{5-chloro-2-[(2-methyl-2H-1,2,3-triazol-4-yl)amino]pyridin-4-yl}-1-oxo-2,3-dihydro-1H-isoindol-2-yl)-N-[(1S)-1-(3-fluoro-5-methoxyphenyl)-2-hydroxyethyl]propanamide | 580 |
| 942 | 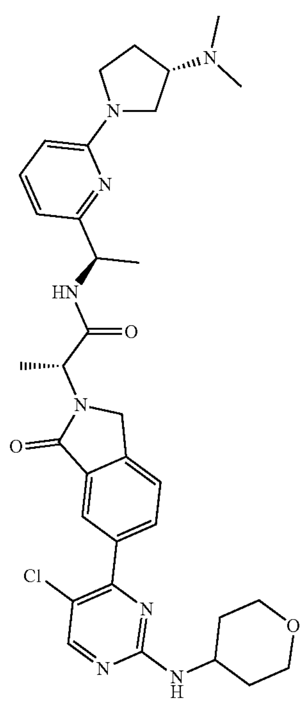 [SMILES: C[C@H](C(=O)N[C@H](C)c1cccc(N2CC[C@H](N(C)C)C2)n1)N1Cc2ccc(-c3nc(NC4CCOCC4)ncc3Cl)cc2C1=O] | (2R)-2-(6-{5-chloro-2-[(oxan-4-yl)amino]pyrimidin-4-yl}-1-oxo-2,3-dihydro-1H-isoindol-2-yl)-N-[(1R)-1-{6-[(3S)-3-(dimethylamino)pyrrolidin-1-yl]pyridin-2-yl}ethyl]propanamide | 633 |

-continued
| Example | Structure | Name | MS Data [M +H]+ unless specified |
|---|---|---|---|
| 943 | 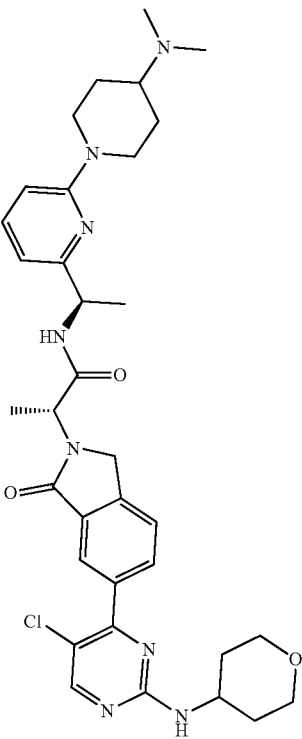 [SMILES: C[C@H](C(=O)N[C@H](C)c1cccc(N2CCC(N(C)C)CC2)n1)N1Cc2ccc(-c3nc(NC4CCOCC4)ncc3Cl)cc2C1=O] | (2R)-2-(6-{5-chloro-2-[(oxan-4-yl)amino]pyrimidin-4-yl}-1-oxo-2,3-dihydro-1H-isoindol-2-yl)-N-[(1R)-1-{6-[4-(dimethylamino)piperidin-1-yl]pyridin-2-yl}ethyl]propanamide | 647 |
| 944 | 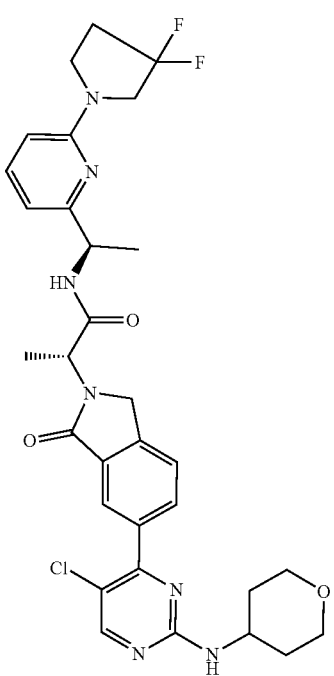 [SMILES: C[C@H](C(=O)N[C@H](C)c1cccc(N2CCC(F)(F)C2)n1)N1Cc2ccc(-c3nc(NC4CCOCC4)ncc3Cl)cc2C1=O] | (2R)-2-(6-{5-chloro-2-[(oxan-4-yl)amino]pyrimidin-4-yl}-1-oxo-2,3-dihydro-1H-isoindol-2-yl)-N-[(1R)-1-[6-(3,3-difluoropyrrolidin-1-yl)pyridin-2-yl]ethyl]propanamide | 626 |

-continued

| Example | Structure | Name | MS Data [M +H]+ unless specified |
|---|---|---|---|
| 945 | 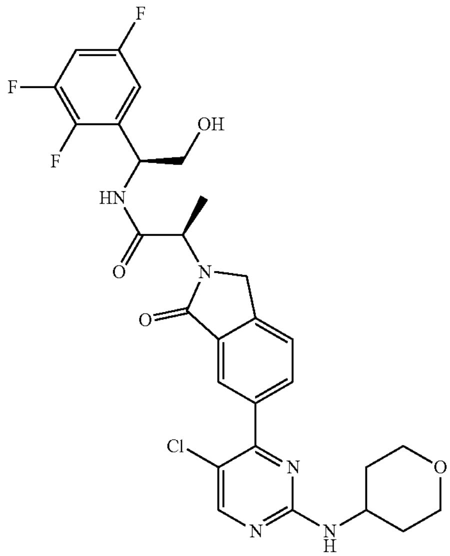 [SMILES: C[C@H](C(=O)N[C@H](CO)c1cc(F)cc(F)c1F)N1Cc2ccc(-c3nc(NC4CCOCC4)ncc3Cl)cc2C1=O] | (2R)-2-(6-{5-chloro-2-[(oxan-4-yl)amino]pyrimidin-4-yl}-1-oxo-2,3-dihydro-1H-isoindol-2-yl)-N-[(1S)-2-hydroxy-1-(2,3,5-trifluorophenyl)ethyl]propanamide | 590 |
| 946 | 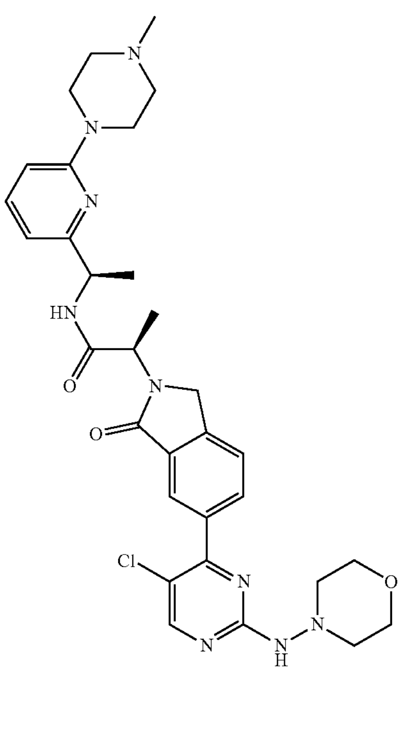 [SMILES: C[C@H](C(=O)N[C@H](C)c1cccc(N2CCN(C)CC2)n1)N1Cc2ccc(-c3nc(NN4CCOCC4)ncc3Cl)cc2C1=O] | (2R)-2-(6-{5-chloro-2-[(morpholin-4-yl)amino]pyrimidin-4-yl}-1-oxo-2,3-dihydro-1H-isoindol-2-yl)-N-[(1R)-1-[6-(4-methylpiperazin-1-yl)pyridin-2-yl]ethyl]propanamide | 620 |

-continued

| Example | Structure | Name | MS Data [M +H]+ unless specified |
|---|---|---|---|
| 947 | 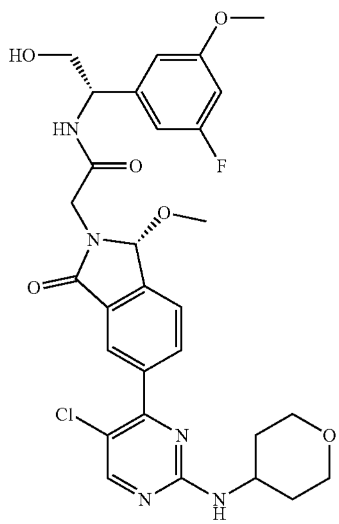 [SMILES: COc1cc(F)cc([C@@H](CO)NC(=O)CN2C(=O)c3cc(-c4nc(NC5CCOCC5)ncc4Cl)ccc3[C@H]2OC)c1] | 2-[(1R)-5-{5-chloro-2-[(oxan-4-yl)amino]pyrimidin-4-yl}-1-methoxy-3-oxo-2,3-dihydro-1H-isoindol-2-yl]-N-[(1S)-1-(3-fluoro-5-methoxyphenyl)-2-hydroxyethyl]acetamide | 598 [M −H]+ |
| 948 | 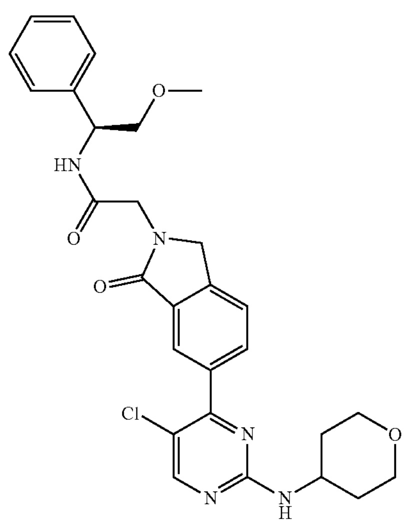 [SMILES: COC[C@@H](NC(=O)CN1Cc2ccc(-c3nc(NC4CCOCC4)ncc3Cl)cc2C1=O)c1ccccc1] | 2-(6-{5-chloro-2-[(oxan-4-yl)amino]pyrimidin-4-yl}-1-oxo-2,3-dihydro-1H-isoindol-2-yl)-N-[(1S)-2-methoxy-1-phenylethyl]acetamide | 536 |

-continued

| Example | Structure | Name | MS Data [M +H]+ unless specified |
|---|---|---|---|
| 949 | 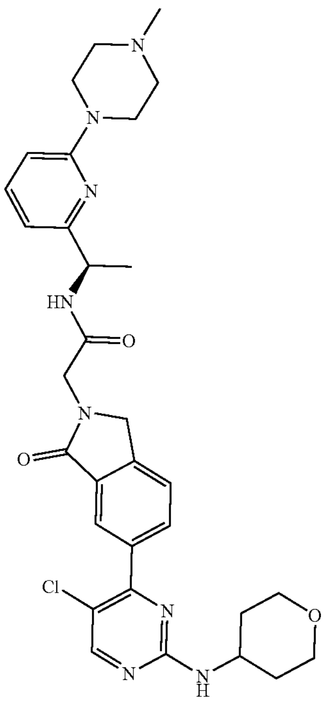 [SMILES: C[C@@H](NC(=O)CN1Cc2ccc(-c3nc(NC4CCOCC4)ncc3Cl)cc2C1=O)c1cccc(N2CCN(C)CC2)n1] | 2-(6-{5-chloro-2-[(oxan-4-yl)amino]pyrimidin-4-yl}-1-oxo-2,3-dihydro-1H-isoindol-2-yl)-N-[(1R)-1[6-(4-methylpiperazin-1-yl)pyridin-2-yl]ethyl]acetamide | 605 |
| 950 | 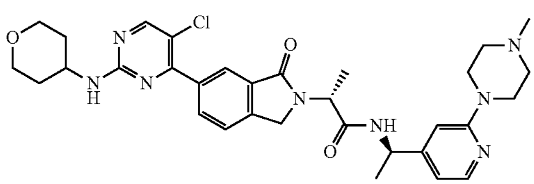 [SMILES: C[C@H](C(=O)N[C@H](C)c1ccnc(N2CCN(C)CC2)c1)N1Cc2ccc(-c3nc(NC4CCOCC4)ncc3Cl)cc2C1=O] | (2R)-2-(6-{5-chloro-2-[(oxan-4-yl)amino]pyrimidin-4-yl}-1-oxo-2,3-dihydro-1H-isoindol-2-yl)-N-[(1S)-1-[2-(4-methylpiperazin-1-yl)pyridin-4-yl]ethyl]propanamide | 617 [M −H]+ |
| 951 | 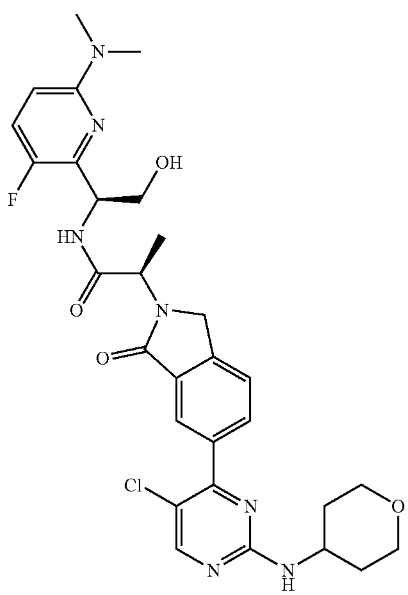 [SMILES: C[C@H](C(=O)N[C@H](CO)c1nc(N(C)C)ccc1F)N1Cc2ccc(-c3nc(NC4CCOCC4)ncc3Cl)cc2C1=O] | (2R)-2-(6-}5-chloro-2-[(oxan-4-yl)amino]pyrimidin-4-yl}-1-oxo-2,3-dihydro-1H-isoindol-2-yl)-N-[(1S)-1[6-(dimethylamino)-3-fluoropyridin-2-yl]-2-hydroxyethyl]propanamide | 596 [M −H]− |

-continued

| Example | Structure | Name | MS Data [M +H]+ unless specified |
|---|---|---|---|
| 952 | 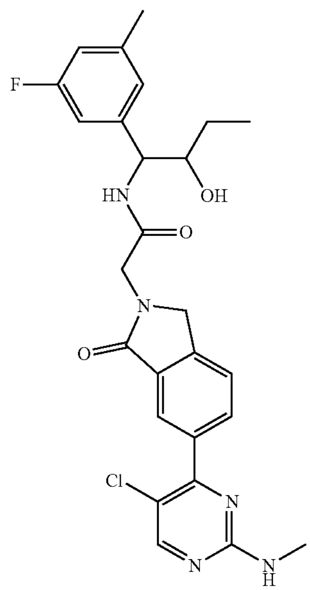 [SMILES: CCC(O)C(NC(=O)CN1Cc2ccc(-c3nc(NC)ncc3Cl)cc2C1=O)c1cc(C)cc(F)c1] | 2-{6-[5-chloro-2-(methylamino)pyrimidin-4-yl]-1-oxo-2,3-dihydro-1H-isoindol-2-yl}-N-[1-(3-fluoro-5-methylphenyl)-2-hydroxybutyl]acetamide | 512 |
| 953 | 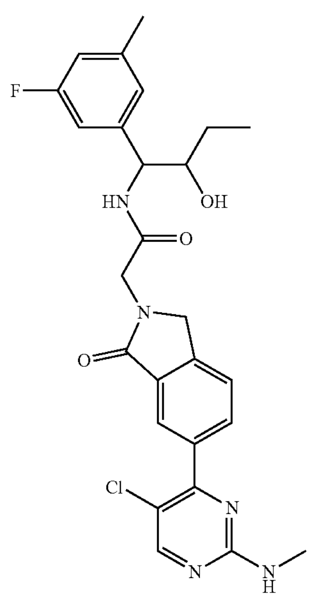 [SMILES: CCC(O)C(NC(=O)CN1Cc2ccc(-c3nc(NC)ncc3Cl)cc2C1=O)c1cc(C)cc(F)c1] | 2-{6-[5-chloro-2-(methylamino)pyrimidin-4-yl]-1-oxo-2,3-dihydro-1H-isoindol-2-yl}-N-[1-(3-fluoro-5-methylphenyl)-2-hydroxybutyl]acetamide | 512 |

-continued
| Example | Structure | Name | MS Data [M +H]+ unless specified |
|---|---|---|---|
| 954 | 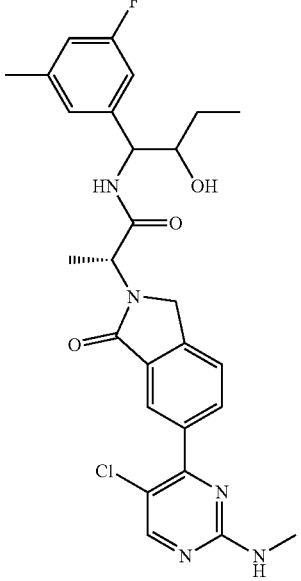 | (2R)-2-{6-[5-chloro-2-(methylamino)pyrimidin-4-yl]-1-oxo-2,3-dihydro-1H-isoindol-2-yl}-N-[1-(3-fluoro-5-methylphenyl)-2-hydroxybutyl]propanamide | 526 |
| 955 | 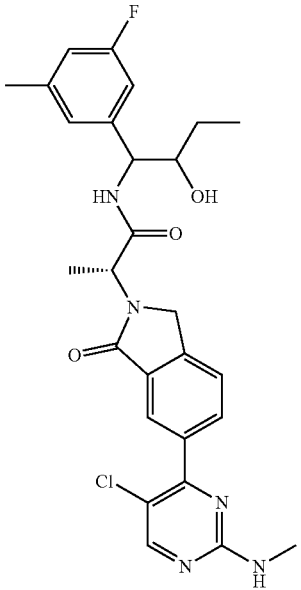 | (2R)-2-{6-[5-chloro-2-(methylamino)pyrimidin-4-yl]-1-oxo-2,3-dihydro-1H-isoindol-2-yl}-N-[1-(3-fluoro-5-methylphenyl)-2-hydroxybutyl]propanamide | 526 |

-continued

| Example | Structure | Name | MS Data [M +H]+ unless specified |
|---|---|---|---|
| 956 | 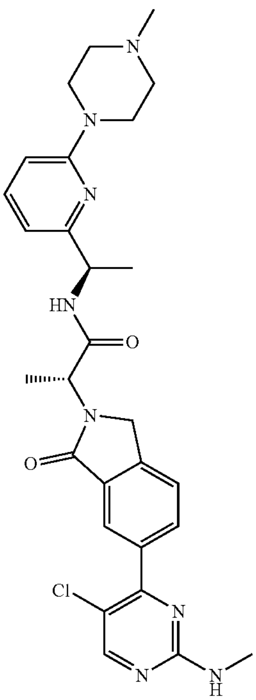 [SMILES: CNc1ncc(Cl)c(-c2ccc3c(c2)C(=O)N([C@H](C)C(=O)N[C@H](C)c2cccc(N4CCN(C)CC4)n2)C3)n1] | (2R)-2-{6-[5-chloro-2-(methylamino)pyrimidin-4-yl]-1-oxo-2,3-dihydro-1H-isoindol-2-yl}-N-[(1R)-1-[6-(4-methylpiperazin-1-yl)pyridin-2-yl]ethyl]propanamide | 607 |
| 957 | 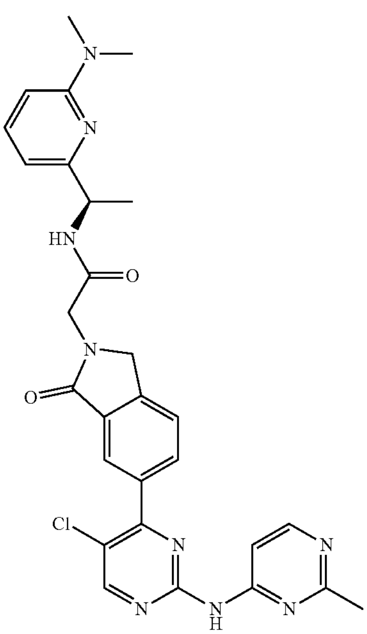 [SMILES: Cc1nccc(Nc2ncc(Cl)c(-c3ccc4c(c3)C(=O)N(CC(=O)N[C@H](C)c3cccc(N(C)C)n3)C4)n2)n1] | 2-(6-{5-chloro-2-[(2-methylpyrimidin-4-yl)amino]pyrimidin-4-yl}-1-oxo-2,3-dihydro-1H-isoindol-2-yl)-N-[(1R)-1[6-(dimethylamino)pyridin-2-yl]ethyl]acetamide | 558 |

-continued

| Example | Structure | Name | MS Data [M +H]+ unless specified |
|---|---|---|---|
| 958 | 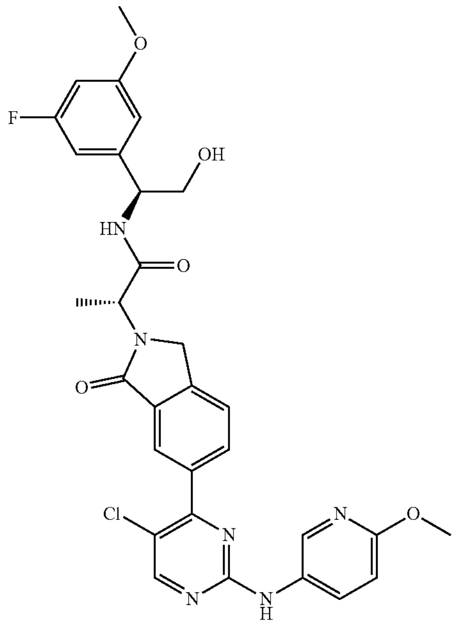 [SMILES: COc1cc(F)cc([C@@H](CO)NC(=O)[C@@H](C)N2Cc3ccc(-c4nc(Nc5ccc(OC)nc5)ncc4Cl)cc3C2=O)c1] | (2R)-2-(6-{5-chloro-2-[(6-methoxypyridin-3-yl)amino]pyrimidin-4-yl}-1-oxo-2,3-dihydro-1H-isoindol-2-yl)-N-[(1S)-1-(3-fluoro-5-methoxyphenyl)-2-hydroxyethyl]propanamide | 607 |
| 959 | 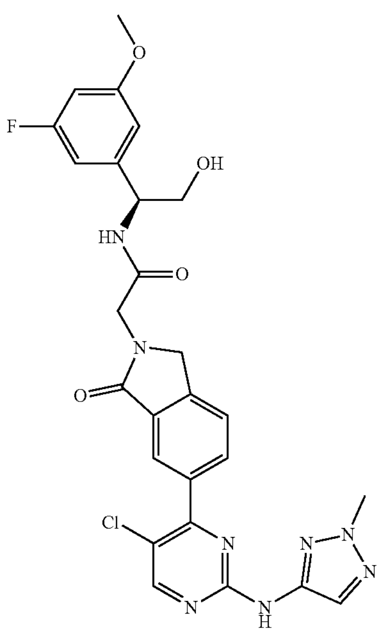 [SMILES: COc1cc(F)cc([C@@H](CO)NC(=O)CN2Cc3ccc(-c4nc(Nc5cnn(C)n5)ncc4Cl)cc3C2=O)c1] | 2-(6-{5-chloro-2-[(2-methyl-2H-1,2,3-triazol-4-yl)amino]pyrimidin-4-yl}-1-oxo-2,3-dihydro-1H-isoindol-2-yl)-N-[(1S)-1-(3-fluoro-5-methoxyphenyl)-2-hydroxyethyl]acetamide | 567 |

| Example | Structure | Name | MS Data [M +H]+ unless specified |
|---|---|---|---|
| 960 | 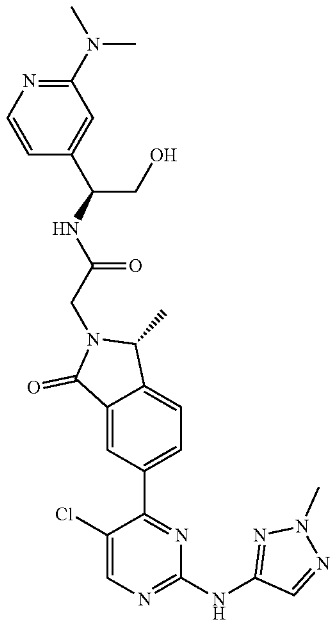 [SMILES: C[C@@H]1c2ccc(-c3nc(Nc4cnn(C)n4)ncc3Cl)cc2C(=O)N1CC(=O)N[C@H](CO)c1ccnc(N(C)C)c1] | 2-[(1R)-5-{5-chloro-2-[(2-methyl-2H-1,2,3-triazol-4-yl)amino]pyrimidin-4-yl}-1-methyl-3-oxo-2,3-dihydro-1H-isoindol-2-yl]-N-(1S)-1-[2-(dimethylamino)pyridin-4-yl]-2-hydroxyethyl]acetamide | 577 |
| 961 | 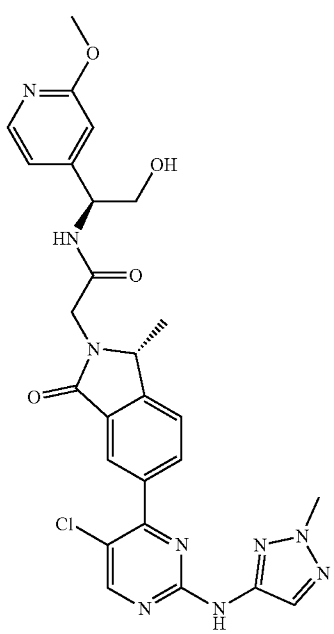 [SMILES: COc1cc([C@@H](CO)NC(=O)CN2C(=O)c3cc(-c4nc(Nc5cnn(C)n5)ncc4Cl)ccc3[C@H]2C)ccn1] | 2-[(1R)-5-{5-chloro-2-[(2-methyl-2H-1,2,3-triazol-4-yl)amino]pyrimidin-4-yl}-1-methyl-3-oxo-2,3-dihydro-1H-isoindol-2-yl]-N-[(1S)-2-hydroxy-1-(2-methoxypyridin-4-yl)ethyl]acetamide | 564 |

-continued

| Example | Structure | Name | MS Data [M +H]+ unless specified |
|---|---|---|---|
| 962 | 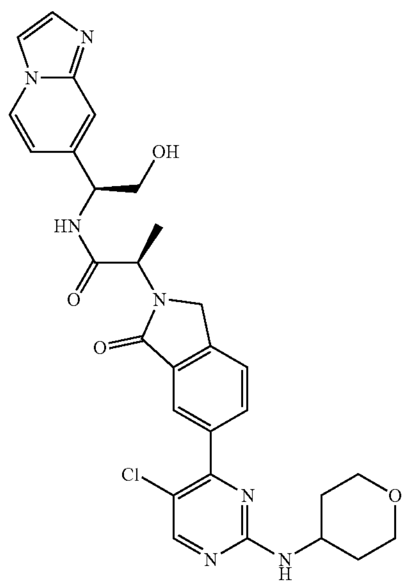 [SMILES: C[C@H](C(=O)N[C@H](CO)c1ccn2ccnc2c1)N1Cc2ccc(-c3nc(NC4CCOCC4)ncc3Cl)cc2C1=O] | (2R)-2-(6-{5-chloro-2-[(oxan-4-yl)amino]pyrimidin-4-yl}-1-oxo-2,3-dihydro-1H-isoindol-2-yl)-N-[(1S)-2-hydroxy-1-{imidazo[1,2-a]pyridin-7-yl}ethyl]propanamide | 574 [M −H]− |
| 963 | 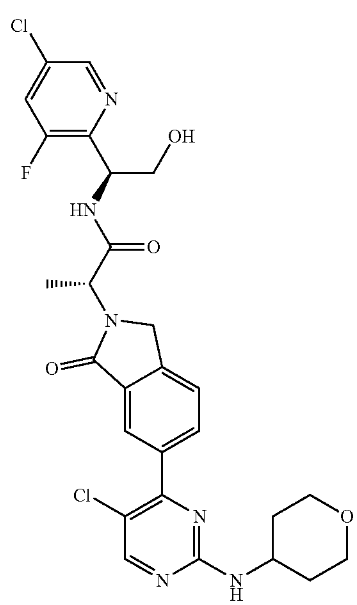 [SMILES: C[C@H](C(=O)N[C@H](CO)c1ncc(Cl)cc1F)N1Cc2ccc(-c3nc(NC4CCOCC4)ncc3Cl)cc2C1=O] | (2R)-2-(6-{5-chloro-2-[(oxan-4-yl)amino]pyrimidin-4-yl}-1-oxo-2,3-dihydro-1H-isoindol-2-yl)-N-[(1S)-1-(5-chloro-3-fluoropyridin-2-yl)-2-hydroxyethyl]propanamide | 587 [M −H]+ |

| Example | Structure | Name | MS Data [M +H]+ unless specified |
|---|---|---|---|
| 964 | 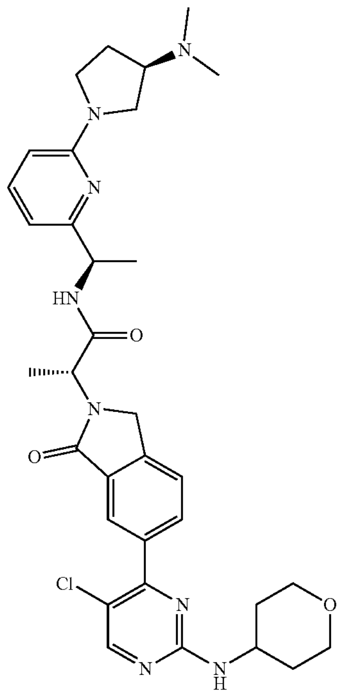 [SMILES: C[C@H](C(=O)N[C@H](C)c1cccc(N2CC[C@@H](N(C)C)C2)n1)N1Cc2ccc(-c3nc(NC4CCOCC4)ncc3Cl)cc2C1=O] | (2R)-2-(6-{5-chloro-2-[(oxan-4-yl)amino]pyrimidin-4-yl}-1-oxo-2,3-dihydro-1H-isoindol-2-yl)-N-[(1R)-1-{6-[(3R)-3-(dimethylamino)pyrrolidin-1-yl]pyridin-2-yl}ethyl]propanamide | 633 |
| 965 | 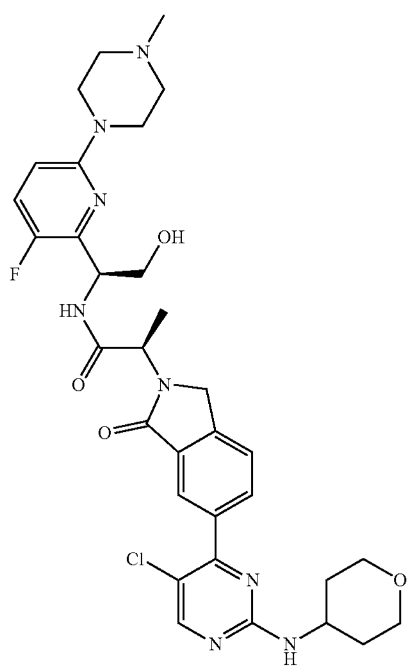 [SMILES: C[C@H](C(=O)N[C@H](CO)c1nc(N2CCN(C)CC2)ccc1F)N1Cc2ccc(-c3nc(NC4CCOCC4)ncc3Cl)cc2C1=O] | (2R)-2-(6-{5-chloro-2-[(oxan-4-yl)amino]pyrimidin-4-yl}-1-oxo-2,3-dihydro-1H-isoindol-2-yl)-N-[(1S)-1-[3-fluoro-6-(4-methylpiperazin-1-yl)pyridin-2-yl]-2-hydroxyethyl]propanamide | 651 [M −H]− |

-continued
| Example | Structure | Name | MS Data [M +H]+ unless specified |
|---|---|---|---|
| 966 | 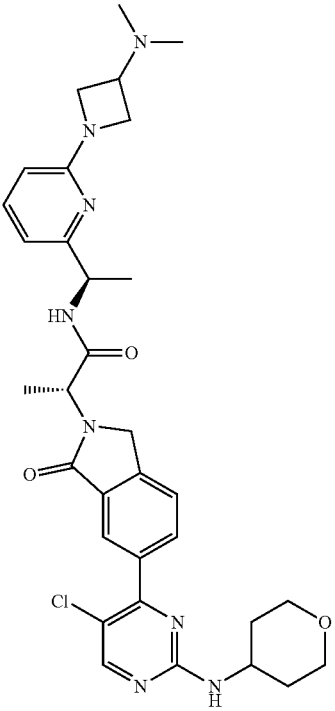 [SMILES: C[C@H](C(=O)N[C@H](C)c1cccc(N2CC(N(C)C)C2)n1)N1Cc2ccc(-c3nc(NC4CCOCC4)ncc3Cl)cc2C1=O] | (2R)-2-(6-{5-chloro-2-[(oxan-4-yl)amino]pyrimidin-4-yl}-1-oxo-2,3-dihydro-1H-isoindol-2-yl)-N-[(1R)-1-{6-[3-(dimethylamino)azetidin-1-yl]pyridin-2-yl}ethyl]propanamide | 619 |
| 967 | 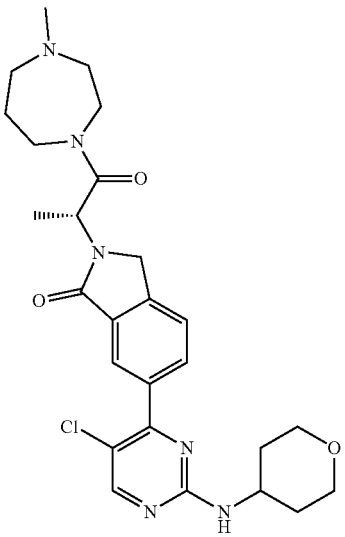 [SMILES: C[C@H](C(=O)N1CCCN(C)CC1)N1Cc2ccc(-c3nc(NC4CCOCC4)ncc3Cl)cc2C1=O] | 6-{5-chloro-2-[(oxan-4-yl)amino]pyrimidin-4-yl}-2-[(2R)-1-(4-methyl-1,4-diazepan-1-yl)-1-oxopropan-2-yl]-2,3-dihydro-1H-isoindol-1-one | 513 |

| Example | Structure | Name | MS Data [M+H]+ unless specified |
|---|---|---|---|
| 968 | 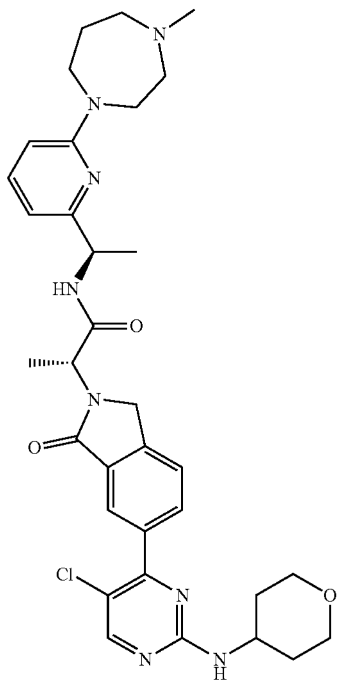 [SMILES: C[C@H](C(=O)N[C@H](C)c1cccc(N2CCCN(C)CC2)n1)N1Cc2ccc(-c3nc(NC4CCOCC4)ncc3Cl)cc2C1=O] | (2R)-2-(6-{5-chloro-2-[(oxan-4-yl)amino]pyrimidin-4-yl}-1-oxo-2,3-dihydro-1H-isoindol-2-yl)-N-[(1R)-1[6-(4-methyl-1,4-diazepan-1-1)pyridin-2-yl]ethyl]propanamide | 633 |
| 969 | 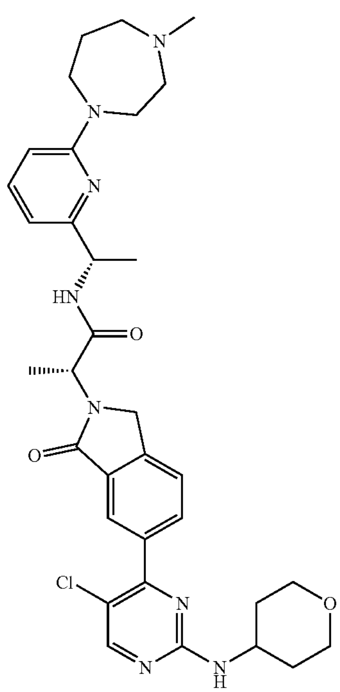 [SMILES: C[C@H](NC(=O)[C@@H](C)N1Cc2ccc(-c3nc(NC4CCOCC4)ncc3Cl)cc2C1=O)c1cccc(N2CCCN(C)CC2)n1] | (2R)-2-(6-{5-chloro-2-[(oxan-4-yl)amino]pyrimidin-4-yl}-1-oxo-2,3-dihydro-1H-isoindol-2-yl)-N-[(1S)-1-[6-(4-methyl-1,4-diazepan-1-yl)pyridin-2-yl]ethyl]propanamide | 633 |

-continued

| Example | Structure | Name | MS Data [M +H]+ unless specified |
|---|---|---|---|
| 970 | 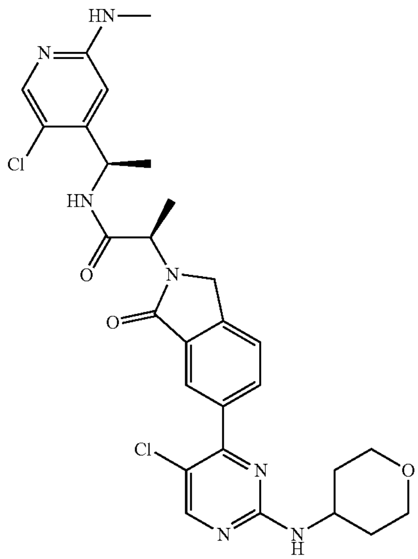 [SMILES: CNc1cc([C@@H](C)NC(=O)[C@@H](C)N2Cc3ccc(-c4nc(NC5CCOCC5)ncc4Cl)cc3C2=O)c(Cl)cn1] | (2R)-N-[(1R)-1-[5-chloro-2-(methylamino)pyridin-4-yl]ethyl]-2-(6-{5-chloro-2-[(oxan-4-yl)amino]pyrimidin-4-yl}-1-oxo-2,3-dihydro-1H-isoindol-2-yl)propanamide | 584 |
| 971 | 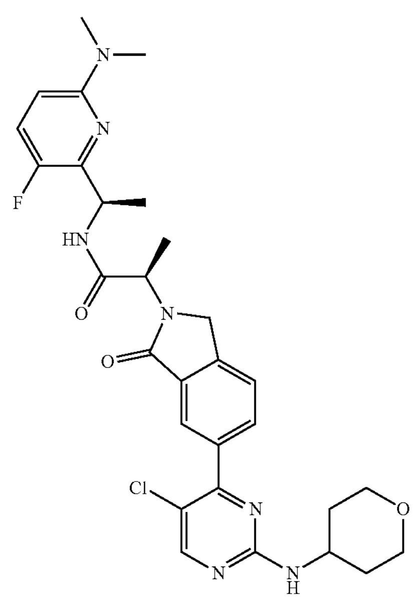 [SMILES: C[C@H](C(=O)N[C@H](C)c1nc(N(C)C)ccc1F)N1Cc2ccc(-c3nc(NC4CCOCC4)ncc3Cl)cc2C1=O] | (2R)-2-(6-{5-chloro-2-[(oxan-4-yl)amino]pyrimidin-4-yl}-1-oxo-2,3-dihydro-1H-isoindol-2-yl)-N-[(1R)-1[6-(dimethylamino)-3-fluoropyridin-2-yl]ethyl]propanamide | 582 |

-continued

| Example | Structure | Name | MS Data [M +H]+ unless specified |
|---|---|---|---|
| 972 | 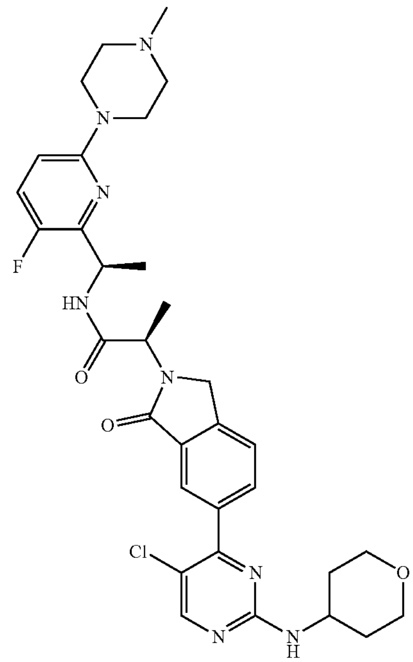 [SMILES: C[C@H](C(=O)N[C@H](C)c1nc(N2CCN(C)CC2)ccc1F)N1Cc2ccc(-c3nc(NC4CCOCC4)ncc3Cl)cc2C1=O] | (2R)-2-(6-{5-chloro-2-[(oxan-4-yl)amino]pyrimidin-4-yl}-1-oxo-2,3-dihydro-1H-isoindol-2-yl)-N-[(1R)-1[3-fluoro-6-(4-methylpiperazin-1-yl)pyridin-2-yl]ethyl]propanamide | 637 |
| 973 | 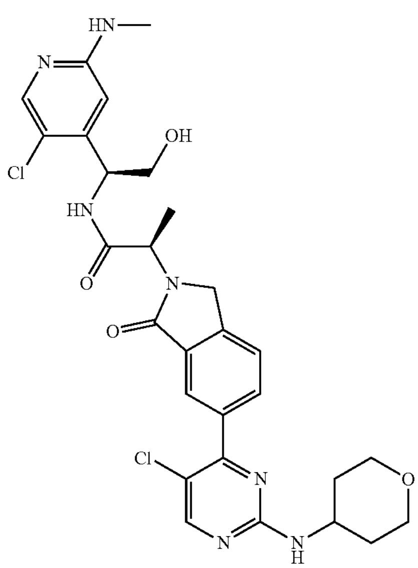 [SMILES: CNc1cc([C@@H](CO)NC(=O)[C@@H](C)N2Cc3ccc(-c4nc(NC5CCOCC5)ncc4Cl)cc3C2=O)c(Cl)cn1] | (2R)-N-[(1S)-1-[5-chloro-2-(methylamino)pyridin-4-yl]-2-hydroxyethyl]-2-(6-{5-chloro-2-[(oxan-4-yl)amino]pyrimidin-4-yl}-1-oxo-2,3-dihydro-1H-isoindol-2-yl)propanamide- | 598 [M −H]− |

-continued
| Example | Structure | Name | MS Data [M +H]+ unless specified |
|---|---|---|---|
| 974 | 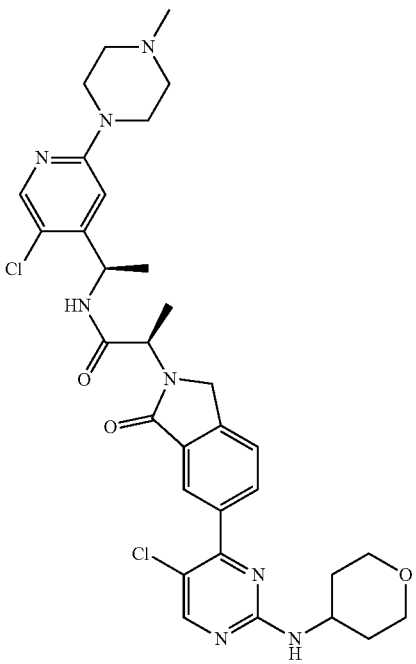 [SMILES: C[C@H](C(=O)N[C@H](C)c1cc(N2CCN(C)CC2)ncc1Cl)N1Cc2ccc(-c3nc(NC4CCOCC4)ncc3Cl)cc2C1=O] | (2R)-N-[(1R)-1-[5-chloro-2-(4-methylpiperazin-1-yl)pyridin-4-yl]ethyl]-2-(6-{5-chloro-2-[(oxan-4-yl)amino]pyrimidin-4-yl}-1-oxo-2,3-dihydro-1H-isoindol-2-yl)propanamide | 651 [M −H]− |
| 975 | 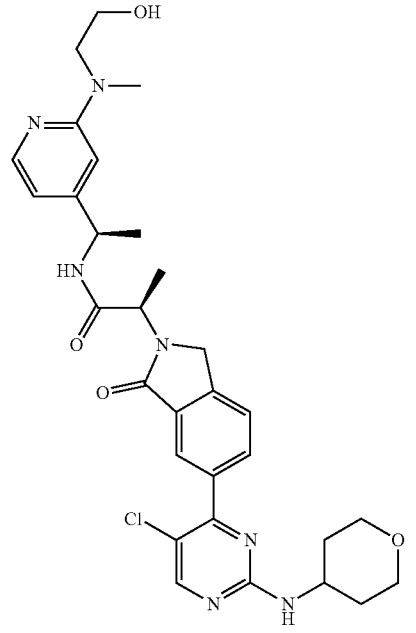 [SMILES: C[C@H](C(=O)N[C@H](C)c1ccnc(N(C)CCO)c1)N1Cc2ccc(-c3nc(NC4CCOCC4)ncc3Cl)cc2C1=O] | (2R)-2-(6-{5-chloro-2-[(oxan-4-yl)amino]pyrimidin-4-yl{-1-oxo-2,3-dihydro-1H-isoindol-2-yl)-N-[(1R)-1-{2[(2-hydroxyethyl)(methyl)amino]pyridin-4-yl}ethyl]propanamide | 592 [M −H]− |

| Example | Structure | Name | MS Data [M+H]+ unless specified |
|---|---|---|---|
| 976 | 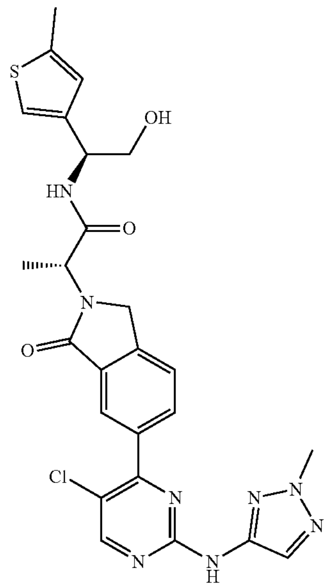 [SMILES: Cc1cc([C@@H](CO)NC(=O)[C@@H](C)N2Cc3ccc(-c4nc(Nc5cnn(C)n5)ncc4Cl)cc3C2=O)cs1] | (2R)-2-(6-{5-chloro-2-[(2-methyl-2H-1,2,3-triazol-4-yl)amino]pyrimidin-4-yl}-1-oxo-2,3-dihydro-1H-isoindol-2-yl)-N-[(1S)-2-hydroxy-1-(5-methylthiophen-3-yl)ethyl]propanamide | 553 |
| 977 | 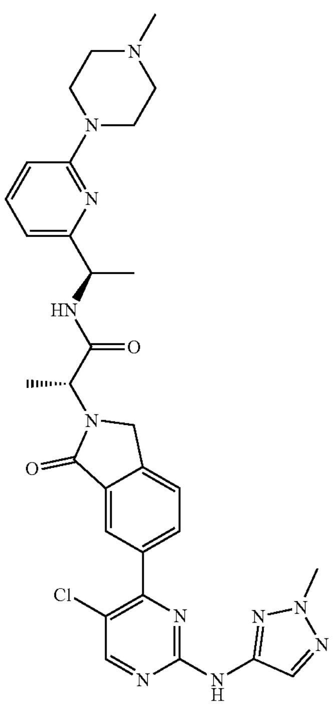 [SMILES: C[C@H](C(=O)N[C@H](C)c1cccc(N2CCN(C)CC2)n1)N1Cc2ccc(-c3nc(Nc4cnn(C)n4)ncc3Cl)cc2C1=O] | (2R)-2-(6-{5-chloro-2-[(2-methyl-2H-1,2,3-triazol-4-yl)amino]pyrimidin-4-yl}-1-oxo-2,3-dihydro-1H-isoindol-2-yl)-N-[(1R)-1-[6-(4-methylpiperazin-1-yl)pyridin-2-yl]ethyl]propanamide Stereoisomer 1 | 616 |

-continued

| Example | Structure | Name | MS Data [M +H]+ unless specified |
|---|---|---|---|
| 978 | 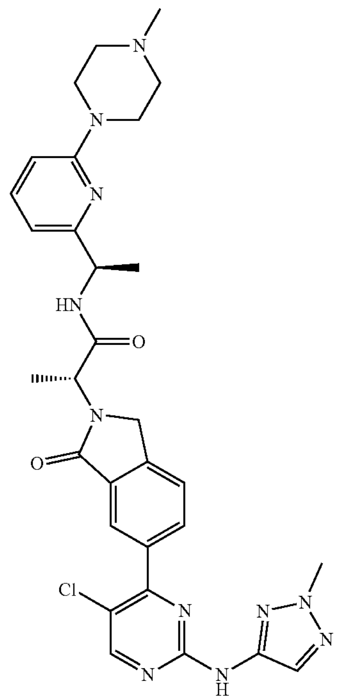 [SMILES: C[C@H](C(=O)N[C@H](C)c1cccc(N2CCN(C)CC2)n1)N1Cc2ccc(-c3nc(Nc4cnn(C)n4)ncc3Cl)cc2C1=O] | (2R)-2-(6-{5-chloro-2-[(2-methyl-2H-1,2,3-triazol-4-yl)amino]pyrimidin-4-yl}-1-oxo-2,3-dihydro-1H-isoindol-2-yl)-N-[(1R)-1-[6-(4-methylpiperazin-1-yl)pyridin-2-yl]ethyl]propanamide Stereoisomer 2 | 616 |
| 979 | 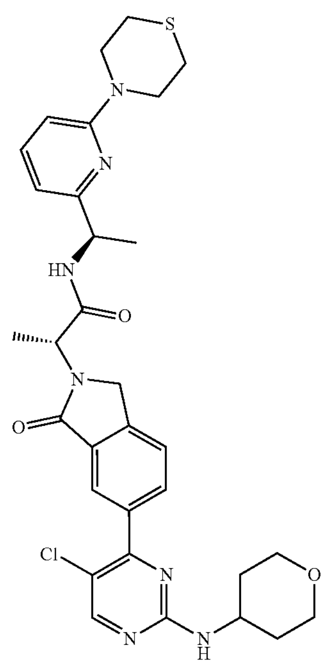 [SMILES: C[C@H](C(=O)N[C@H](C)c1cccc(N2CCSCC2)n1)N1Cc2ccc(-c3nc(NC4CCOCC4)ncc3Cl)cc2C1=O] | (2R)-2-(6-{5-chloro-2-[(oxan-4-yl)amino]pyrimidin-4-yl}-1-oxo-2,3-dihydro-1H-isoindol-2-yl)-N-[(1R)-1-[6-(thiomorpholin-4-yl)pyridin-2-yl]ethyl]propanamide | 622 |

| Example | Structure | Name | MS Data [M +H]+ unless specified |
|---|---|---|---|
| 980 | 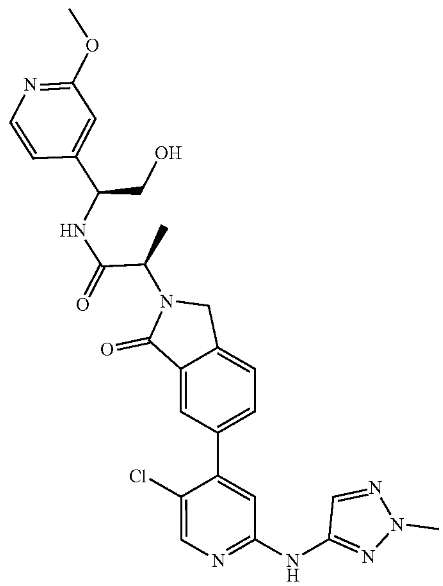 [SMILES: COc1cc([C@@H](CO)NC(=O)[C@@H](C)N2Cc3ccc(-c4cc(Nc5cnn(C)n5)ncc4Cl)cc3C2=O)ccn1] | (2R)-2-(6-{5-chloro-2-[(2-methyl-2H-1,2,3-triazol-4-yl)amino]pyridin-4-yl}-1-oxo-2,3-dihydro-1H-isoindol-2-yl)-N-[(1S)-2-hydroxy-1-(2-methoxypyridin-4-yl)ethyl]propanamide | 561 [M −H]+ |
| 981 | 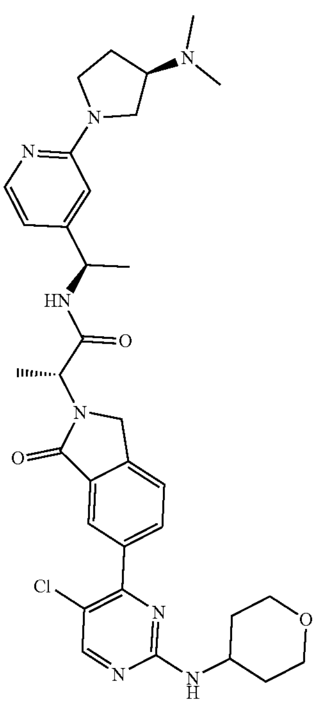 [SMILES: C[C@H](C(=O)N[C@H](C)c1ccnc(N2CC[C@@H](N(C)C)C2)c1)N1Cc2ccc(-c3nc(NC4CCOCC4)ncc3Cl)cc2C1=O] | (2R)-2-(6-{5-chloro-2-[(oxan-4-yl)amino]pyrimidin-4-yl}-1-oxo-2,3-dihydro-1H-isoindol-2-yl)-N-[(1R)-1-{2-[(3R)-3-(dimethylamino)pyrrolidin-1-yl]pyridin-4-yl}ethyl]propanamide | 633 |

-continued

| Example | Structure | Name | MS Data [M +H]+ unless specified |
|---|---|---|---|
| 982 | 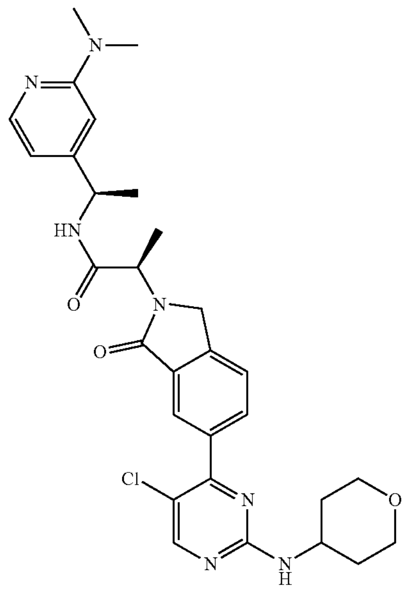 [SMILES: C[C@H](C(=O)N[C@H](C)c1ccnc(N(C)C)c1)N1Cc2ccc(-c3nc(NC4CCOCC4)ncc3Cl)cc2C1=O] | (2R)-2-(6-{5-chloro-2-[(oxan-4-yl)amino]pyrimidin-4-yl}-1-oxo-2,3-dihydro-1H-isoindol-2-yl)-N-[(1R)-1-[2-(dimethylamino)pyridin-4-yl]ethyl]propanamide | 564 |
| 983 | 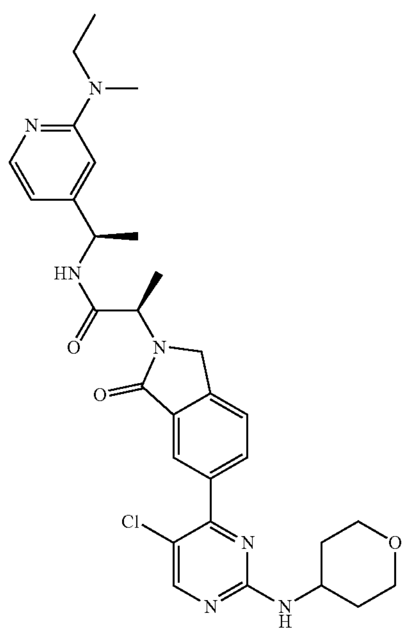 [SMILES: CCN(C)c1cc([C@@H](C)NC(=O)[C@@H](C)N2Cc3ccc(-c4nc(NC5CCOCC5)ncc4Cl)cc3C2=O)ccn1] | (2R)-2-(6-{5-chloro-2-[(oxan-4-yl)amino]pyrimidin-4-yl}-1-oxo-2,3-dihydro-1H-isoindol-2-yl)-N-[(1R)-1-{2-[ethyl(methyl)amino]pyridin-4-yl}ethyl]propanamide | 578 |

| Example | Structure | Name | MS Data [M +H]+ unless specified |
|---|---|---|---|
| 984 | 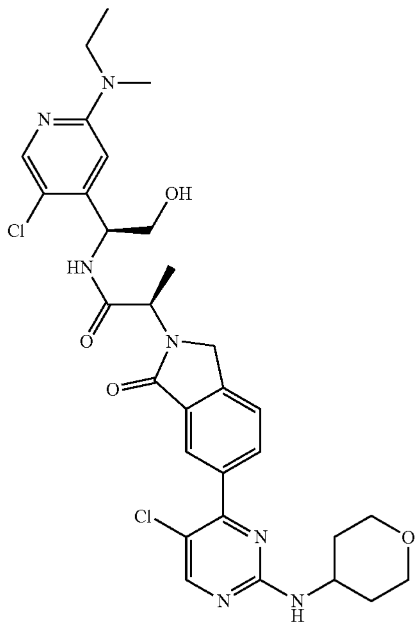 [SMILES: CCN(C)c1cc([C@@H](CO)NC(=O)[C@@H](C)N2Cc3ccc(-c4nc(NC5CCOCC5)ncc4Cl)cc3C2=O)c(Cl)cn1] | (2R)-2-(6-{5-chloro-2-[(oxan-4-yl)amino]pyrimidin-4-yl}-1-oxo-2,3-dihydro-1H-isoindol-2-yl)-N-[(1S)-1-{5-chloro-2-[ethyl(methyl)amino]pyridin-4-yl}-2-hydroxyethyl]propanamide | 626 [M −H]− |
| 985 | 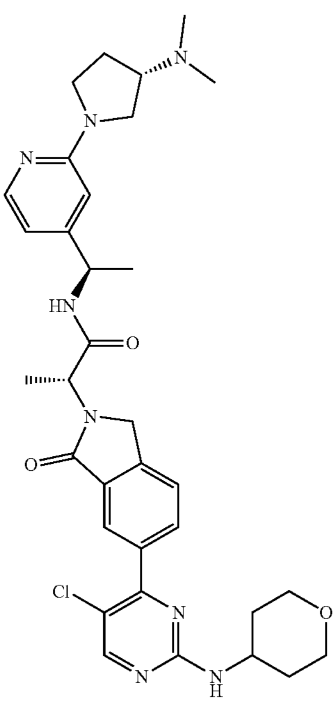 [SMILES: C[C@H](C(=O)N[C@H](C)c1ccnc(N2CC[C@H](N(C)C)C2)c1)N1Cc2ccc(-c3nc(NC4CCOCC4)ncc3Cl)cc2C1=O] | (2R)-2-(6-{5-chloro-2-[(oxan-4-yl)amino]pyrimidin-4-yl}-1-oxo-2,3-dihydro-1H-isoindol-2-yl)-N-[(1R)-1-{2-[(3S)-3-(dimethylamino)pyrrolidin-1-yl]pyridin-4-yl}ethyl]propanamide | 633 |

-continued

| Example | Structure | Name | MS Data [M +H]+ unless specified |
|---|---|---|---|
| 986 | 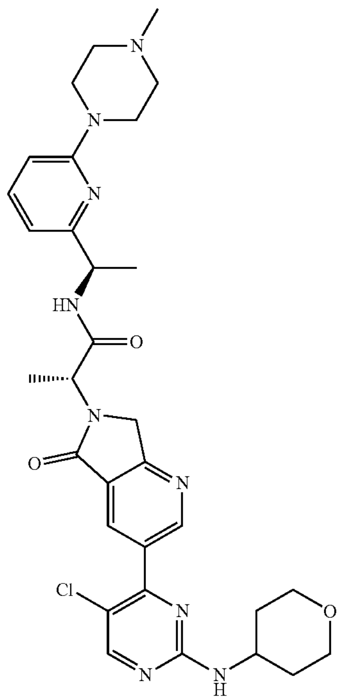 [SMILES: C[C@H](C(=O)N[C@H](C)c1cccc(N2CCN(C)CC2)n1)N1Cc2ncc(-c3nc(NC4CCOCC4)ncc3Cl)cc2C1=O] | (2R)-2-(3-{5-chloro-2-[(oxan-4-yl)amino]pyrimidin-4-yl}-5-oxo-5H,6H,7H-pyrrolo[3,4-b]pyridin-6-yl)-N-[(1R)-1-[6-(4-methylpiperazin-1-yl)pyridin-2-yl]ethyl]propanamide | 620 |
| 987 | 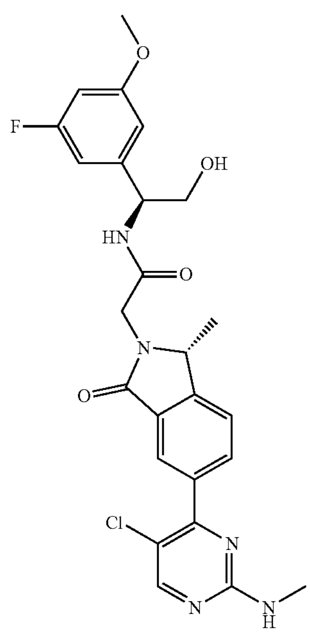 [SMILES: CNc1ncc(Cl)c(-c2ccc3c(c2)C(=O)N(CC(=O)N[C@H](CO)c2cc(F)cc(OC)c2)[C@@H]3C)n1] | 2-[(1R)-5-[5-chloro-2-(methylamino)pyrimidin-4-yl]-1-methyl-3-oxo-2,3-dihydro-1H-isoindol-2-yl]-N-[(1S)-1-(3-fluoro-5-methoxyphenyl)-2-hydroxyethyl]acetamide | 514 |

| Example | Structure | Name | MS Data [M +H]+ unless specified |
|---|---|---|---|
| 988 | 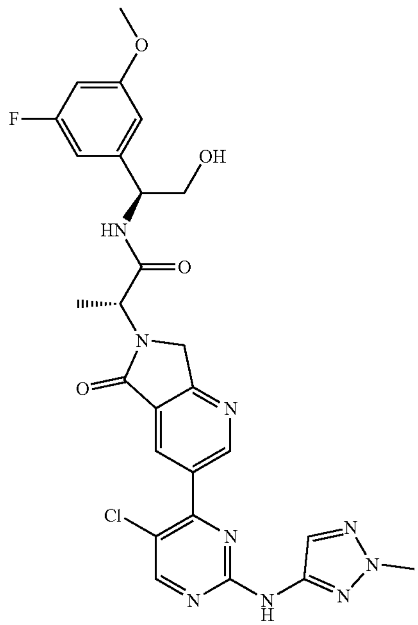 [SMILES: COc1cc(F)cc([C@@H](CO)NC(=O)[C@@H](C)N2Cc3ncc(-c4nc(Nc5cnn(C)n5)ncc4Cl)cc3C2=O)c1] | (2R)-2-(3-{5-chloro-2-[(2-methyl-2H-1,2,3-triazol-4-yl)amino]pyrimidin-4-yl}-5-oxo-5H,6H,7H-pyrrolo[3,4-b]pyridin-6-yl)-N-[(1S)-1-(3-fluoro-5-methoxyphenyl)-2-hydroxyethyl]propanamide | 582 |
| 989 | 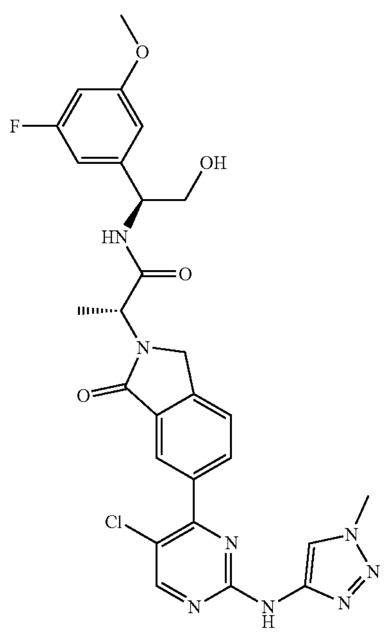 [SMILES: COc1cc(F)cc([C@@H](CO)NC(=O)[C@@H](C)N2Cc3ccc(-c4nc(Nc5cn(C)nn5)ncc4Cl)cc3C2=O)c1] | (2R)-2-(6-{5-chloro-2-[(1-methyl-1H-1,2,3-triazol-4-yl)amino]pyrimidin-4-yl}-1-oxo-2,3-dihydro-1H-isoindol-2-yl)-N-[(1S)-1-(3-fluoro-5-methoxyphenyl)-2-hydroxyethyl]propanamide | 581 |

| Example | Structure | Name | MS Data [M +H]+ unless specified |
|---|---|---|---|
| 990 | 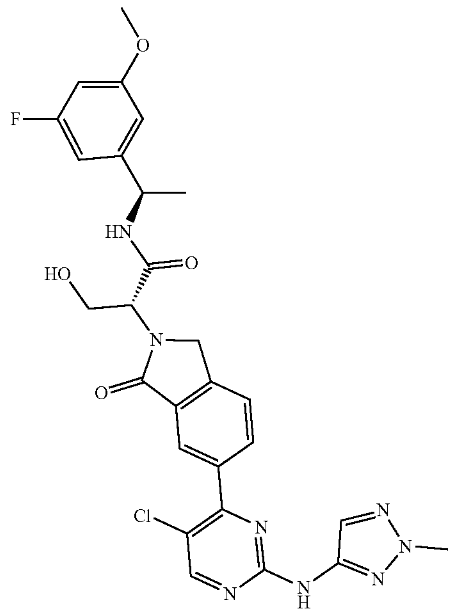 [SMILES: COc1cc(F)cc([C@@H](C)NC(=O)[C@@H](CO)N2Cc3ccc(-c4nc(Nc5cnn(C)n5)ncc4Cl)cc3C2=O)c1] | (2R)-2-(6-{5-chloro-2-[(2-methyl-2H-1,2,3-triazol-4-yl)amino]pyrimidin-4-yl}-1-oxo-2,3-dihydro-1H-isoindol-2-yl)-N-[(1R)-1-(3-fluoro-5-methoxyphenyl)ethyl]-3-hydroxypropanamide | 581 |
| 991 | 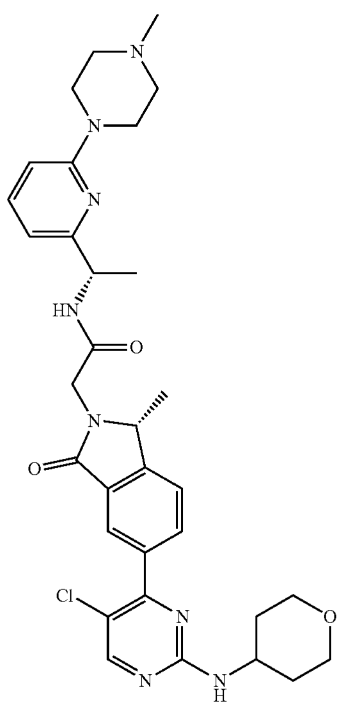 [SMILES: C[C@H](NC(=O)CN1C(=O)c2cc(-c3nc(NC4CCOCC4)ncc3Cl)ccc2[C@H]1C)c1cccc(N2CCN(C)CC2)n1] | 2-[(1R)-5-{5-chloro-2-[(oxan-4-yl)amino]pyrimidin-4-yl}-1-methyl-3-oxo-2,3-dihydro-1H-isoindol-2-yl]-N-[(1S)-1-[6-(4-methylpiperazin-1-yl)pyridin-2-yl]ethyl]acetamide | 619 |

-continued
| Example | Structure | Name | MS Data [M +H]+ unless specified |
|---|---|---|---|
| 992 | 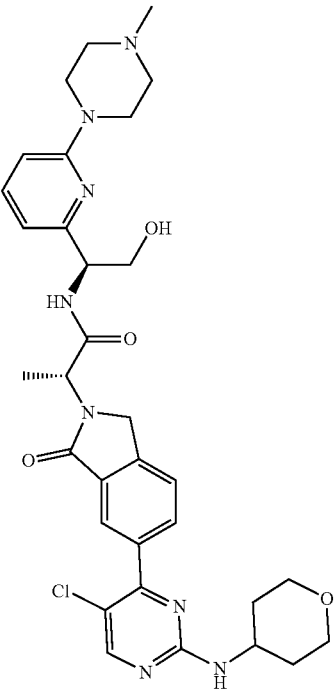 [SMILES: C[C@H](C(=O)N[C@H](CO)c1cccc(N2CCN(C)CC2)n1)N1Cc2ccc(-c3nc(NC4CCOCC4)ncc3Cl)cc2C1=O] | (2R)-2-(6-{5-chloro-2-[(oxan-4-yl)amino]pyrimidin-4-yl}-1-oxo-2,3-dihydro-1H-isoindol-2-yl)-N-[(1S)-2-hydroxy-1-[6-(4-methylpiperazin-1-yl)pyridin-2-yl]ethyl]propanamide | 635 |
| 993 | 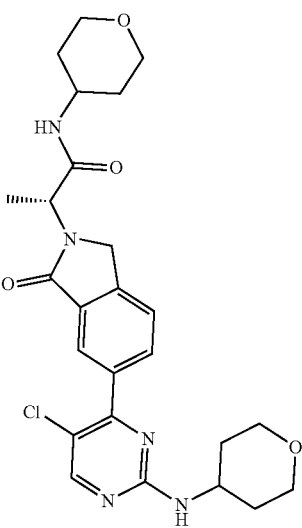 [SMILES: C[C@H](C(=O)NC1CCOCC1)N1Cc2ccc(-c3nc(NC4CCOCC4)ncc3Cl)cc2C1=O] | (2R)-2-(6-{5-chloro-2-[(oxan-4-yl)amino]pyrimidin-4-yl}-1-oxo-2,3-dihydro-1H-isoindol-2-yl)-N-(oxan-4-yl)propanamide | 499 |

| Example | Structure | Name | MS Data [M +H]+ unless specified |
|---|---|---|---|
| 994 | 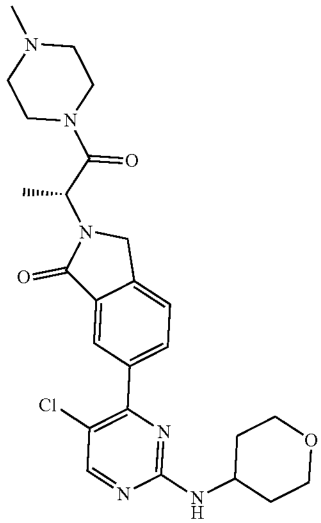 [SMILES: C[C@H](C(=O)N1CCN(C)CC1)N1Cc2ccc(-c3nc(NC4CCOCC4)ncc3Cl)cc2C1=O] | 6-{5-chloro-2-[(oxan-4-yl)amino]pyrimidin-4-yl}-2-[(2R)-1-(4-methylpiperazin-1-yl)-1-oxopropan-2-yl]-2,3-dihydro-1H-isoindol-1-one | 500 |
| 995 | 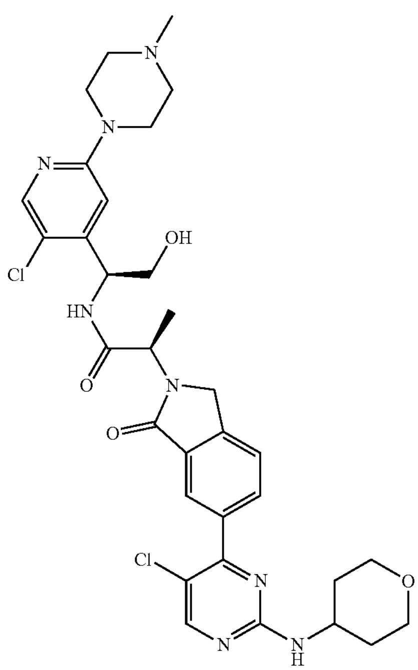 [SMILES: C[C@H](C(=O)N[C@H](CO)c1cc(N2CCN(C)CC2)ncc1Cl)N1Cc2ccc(-c3nc(NC4CCOCC4)ncc3Cl)cc2C1=O] | (2R)-N-[(1S)-1-[5-chloro-2-(4-methylpiperazin-1-yl)pyridin-4-yl]-2-hydroxyethyl]-2-(6-{5-chloro-2-[(oxan-4-yl)amino]pyrimidin-4-yl}-1-oxo-2,3-dihydro-1H-isoindol-2-yl)propanamide | 669 |

-continued

| Example | Structure | Name | MS Data [M +H]+ unless specified |
|---|---|---|---|
| 996 | 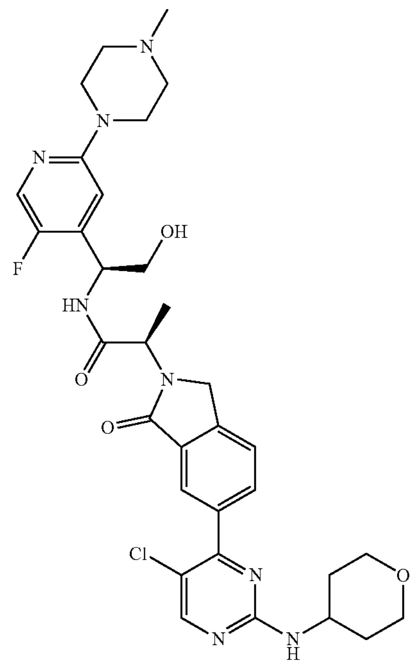 [SMILES: C[C@H](C(=O)N[C@H](CO)c1cc(N2CCN(C)CC2)ncc1F)N1Cc2ccc(-c3nc(NC4CCOCC4)ncc3Cl)cc2C1=O] | (2R)-2-(6-{5-chloro-2-[(oxan-4-yl)amino]pyrimidin-4-yl{-1-oxo-2,3-dihydro-1H-isoindol-2-yl)-N-[(1S)-1-[5-fluoro-2-(4-methylpiperazin-1-yl)pyridin-4-yl]-2-hydroxyethyl]propanamide | 653 |
| 997 | 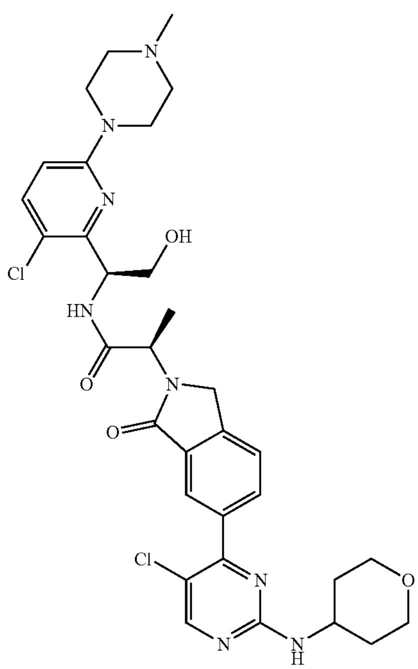 [SMILES: C[C@H](C(=O)N[C@H](CO)c1nc(N2CCN(C)CC2)ccc1Cl)N1Cc2ccc(-c3nc(NC4CCOCC4)ncc3Cl)cc2C1=O] | (2R)-2-(6-{5-chloro-2-[(oxan-4-yl)amino]pyrimidin-4-yl}-1-oxo-2,3-dihydro-1H-isoindol-2-yl)-N-[(1S)-1-[3-chloro-6-(4-methylpiperazin-1-yl)pyridin-2-yl]-2-hydroxyethyl]propanamide | 669 |

| Example | Structure | Name | MS Data [M +H]+ unless specified |
|---|---|---|---|
| 998 | 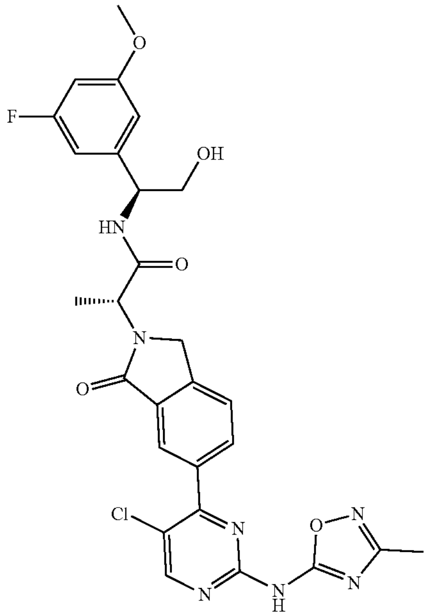 [SMILES: COc1cc(F)cc([C@@H](CO)NC(=O)[C@@H](C)N2Cc3ccc(-c4nc(Nc5nc(C)no5)ncc4Cl)cc3C2=O)c1] | (2R)-2-(6-{5-chloro-2-[(3-methyl-1,2,4-oxadiazol-5-yl)amino]pyrimidin-4-yl}-1-oxo-2,3-dihydro-1H-isoindol-2-yl)-N-[(1S)-1-(3-fluoro-5-methoxyphenyl)-2-hydroxyethyl]propanamide | 582 |
| 999 | 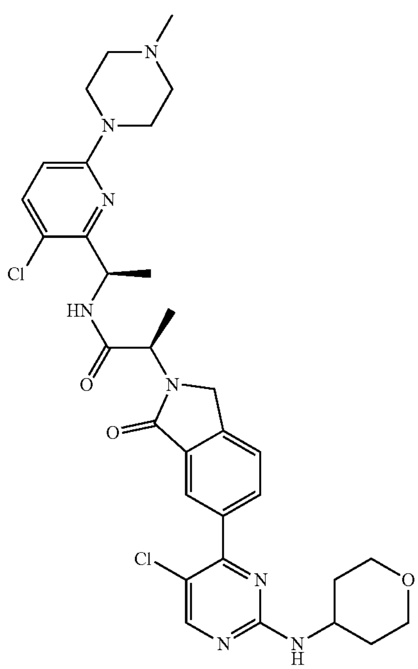 [SMILES: C[C@H](C(=O)N[C@H](C)c1nc(N2CCN(C)CC2)ccc1Cl)N1Cc2ccc(-c3nc(NC4CCOCC4)ncc3Cl)cc2C1=O] | (2R)-2-(6-{5-chloro-2-[(oxan-4-yl)amino]pyrimidin-4-yl}-1-oxo-2,3-dihydro-1H-isoindol-2-yl)-N-[(1R)-1-[3-chloro-6-(4-methylpiperazin-1-yl)pyridin-2-yl]ethyl]propanamide | 653 |

| Example | Structure | Name | MS Data [M +H]+ unless specified |
|---|---|---|---|
| 1000 | 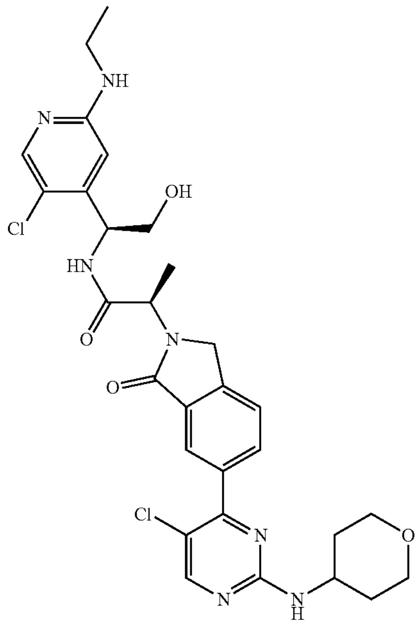 [SMILES: CCNc1cc([C@@H](CO)NC(=O)[C@@H](C)N2Cc3ccc(-c4nc(NC5CCOCC5)ncc4Cl)cc3C2=O)c(Cl)cn1] | (2R)-N-[(1S)-1-[5-chloro-2-(ethylamino)pyridin-4-yl]-2-hydroxyethyl]-2-(6-{5-chloro-2-[(oxan-4-yl)amino]pyrimidin-4-yl}-1-oxo-2,3-dihydro-1H-isoindol-2-yl)propanamide | 612 [M −H]− |
| 1001 | 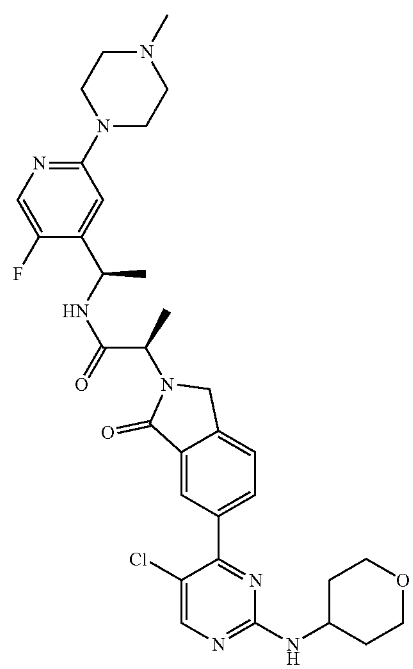 [SMILES: C[C@H](C(=O)N[C@H](C)c1cc(N2CCN(C)CC2)ncc1F)N1Cc2ccc(-c3nc(NC4CCOCC4)ncc3Cl)cc2C1=O] | (2R)-2-(6-{5-chloro-2-[(oxan-4-yl)amino]pyrimidin-4-yl}-1-oxo-2,3-dihydro-1H-isoindol-2-yl)-N-[(1R)-1-[5-fluoro-2-(4-methylpiperazin-1-yl)pyridin-4-yl]ethyl]propanamide | 637 |

| Example | Structure | Name | MS Data [M +H]+ unless specified |
|---|---|---|---|
| 1002 | 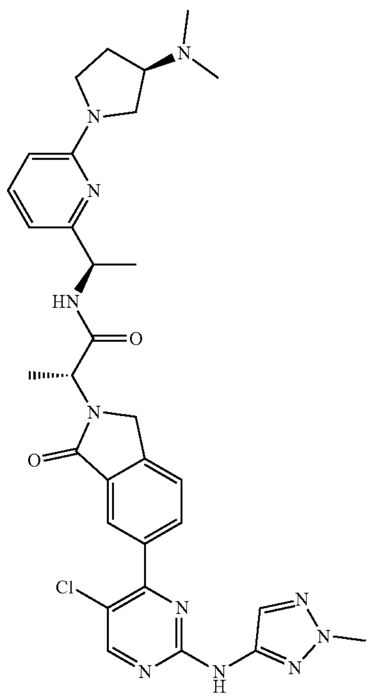 [SMILES: C[C@H](C(=O)N[C@H](C)c1cccc(N2CC[C@@H](N(C)C)C2)n1)N1Cc2ccc(-c3nc(Nc4cnn(C)n4)ncc3Cl)cc2C1=O] | (2R)-2-(6-{5-chloro-2-[(2-methyl-2H-1,2,3-triazol-4-yl)amino]pyrimidin-4-yl{-1-oxo-2,3-dihydro-1H-isoindol-2-yl)-N-[(1R)-1-{6-[(3R)-3-(dimethylamino)pyrrolidin-1-yl]pyridin-2-yl}ethyl]propanamide | 630 |
| 1003 | 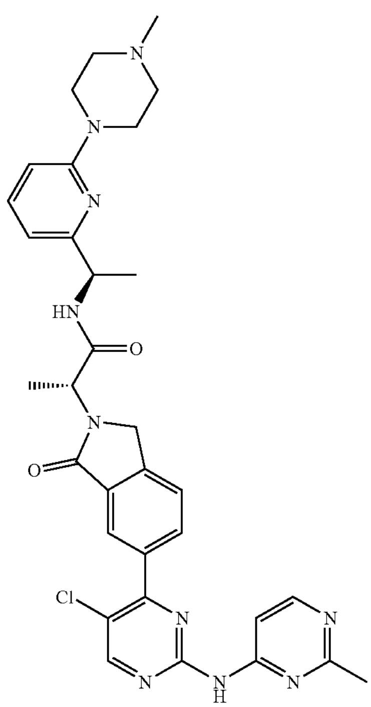 [SMILES: Cc1nccc(Nc2ncc(Cl)c(-c3ccc4c(c3)C(=O)N([C@H](C)C(=O)N[C@H](C)c3cccc(N5CCN(C)CC5)n3)C4)n2)n1] | (2R)-2-(6-{5-chloro-2-[(2-methylpyrimidin-4-yl)amino]pyrimidin-4-yl}-1-oxo-2,3-dihydro-1H-isoindol-2-yl)-N-[(1R)-1-[6-(4-methylpiperazin-1-yl)pyridin-2-yl]ethyl]propanamide | 627 |

| Example | Structure | Name | MS Data [M +H]+ unless specified |
|---|---|---|---|
| 1004 | 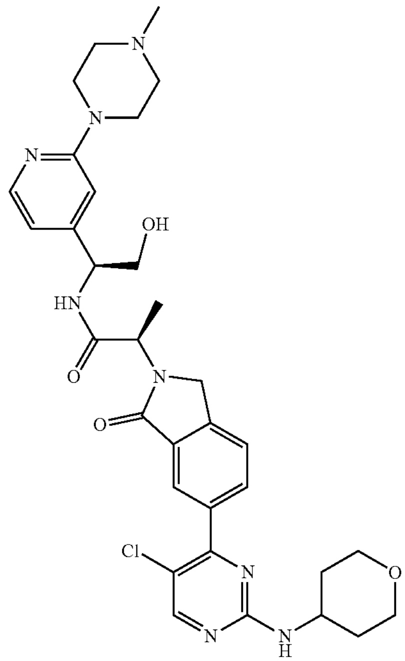 [SMILES: C[C@H](C(=O)N[C@H](CO)c1ccnc(N2CCN(C)CC2)c1)N1Cc2ccc(-c3nc(NC4CCOCC4)ncc3Cl)cc2C1=O] | (2R)-2-(6-{5-chloro-2-[(oxan-4-yl)amino]pyrimidin-4-yl}-1-oxo-2,3-dihydro-1H-isoindol-2-yl)-N-[(1S)-2-hydroxy-1-[2-(4-methylpiperazin-1-yl)pyridin-4-yl]ethyl]propanamide | 635 |
| 1005 | 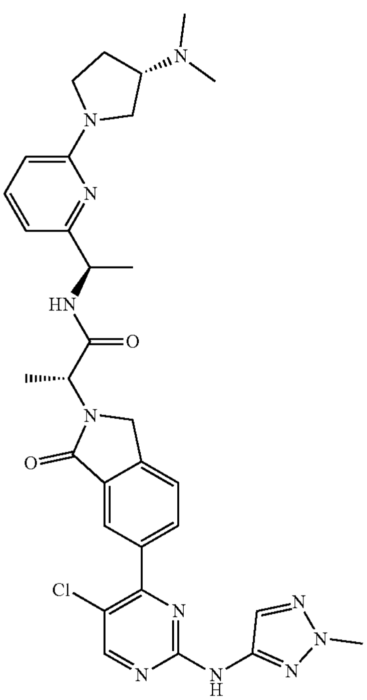 [SMILES: C[C@H](C(=O)N[C@H](C)c1cccc(N2CC[C@H](N(C)C)C2)n1)N1Cc2ccc(-c3nc(Nc4cnn(C)n4)ncc3Cl)cc2C1=O] | (2R)-2-(6-{5-chloro-2-[(2-methyl-2H-1,2,3-triazol-4-yl)amino]pyrimidin-4-yl}-1-oxo-2,3-dihydro-1H-isoindol-2-yl)-N-[(1R)-1-{6-[(3S)-3-(dimethylamino)pyrrolidin-1-yl]pyridin-2-yl}ethyl]propanamide | 630 |

-continued

| Example | Structure | Name | MS Data [M+H]+ unless specified |
|---|---|---|---|
| 1006 | 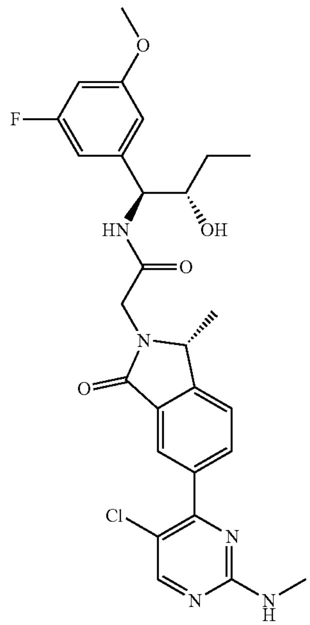 [SMILES: CC[C@H](O)[C@@H](NC(=O)CN1C(=O)c2cc(-c3nc(NC)ncc3Cl)ccc2[C@H]1C)c1cc(F)cc(OC)c1] | 2-[(1R)-5-[5-chloro-2-(methylamino)pyrimidin-4-yl]-1-methyl-3-oxo-2,3-dihydro-1H-isoindol-2-yl]-N-[(1S,2S)-1-(3-fluoro-5-methoxyphenyl)-2-hydroxybutyl]acetamide | 542 |
| 1007 | 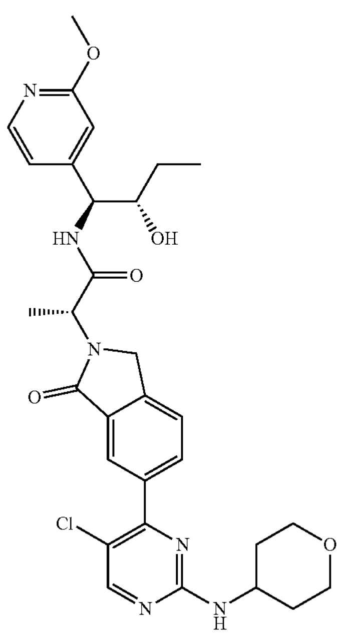 [SMILES: CC[C@H](O)[C@@H](NC(=O)[C@@H](C)N1Cc2ccc(-c3nc(NC4CCOCC4)ncc3Cl)cc2C1=O)c1ccnc(OC)c1] | (2R)-2-(6-{5-chloro-2-[(oxan-4-yl)amino]pyrimidin-4-yl}-1-oxo-2,3-dihydro-1H-isoindol-2-yl)-N-[(1S,2S)-2-hydroxy-1-(2-methoxypyridin-4-yl)butyl]propanamide | 595 |

| Example | Structure | Name | MS Data [M+H]+ unless specified |
|---|---|---|---|
| 1008 | 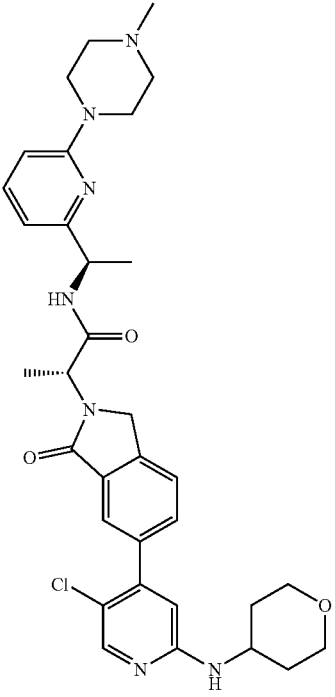 [SMILES: C[C@H](C(=O)N[C@H](C)c1cccc(N2CCN(C)CC2)n1)N1Cc2ccc(-c3cc(NC4CCOCC4)ncc3Cl)cc2C1=O] | (2R)-2-(6-{5-chloro-2-[(oxan-4-yl)amino]pyridin-4-yl}-1-oxo-2,3-dihydro-1H-isoindol-2-yl)-N-[(1R)-1-[6-(4-methylpiperazin-1-yl)pyridin-2-yl]ethyl]propanamide | 618 |
| 1009 | 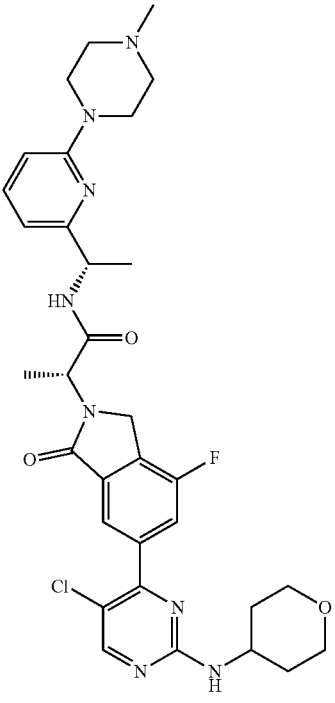 [SMILES: C[C@H](NC(=O)[C@@H](C)N1Cc2c(F)cc(-c3nc(NC4CCOCC4)ncc3Cl)cc2C1=O)c1cccc(N2CCN(C)CC2)n1] | (2R)-2-(6-{5-chloro-2-[(oxan-4-yl)amino]pyrimidin-4-yl}-4-fluoro-1-oxo-2,3-dihydro-1H-isoindol-2-yl)-N-[(1S)-1-[6-(4-methylpiperazin-1-yl)pyridin-2-yl]ethyl]propanamide | 637 |

-continued

| Example | Structure | Name | MS Data [M +H]+ unless specified |
|---|---|---|---|
| 1010 | 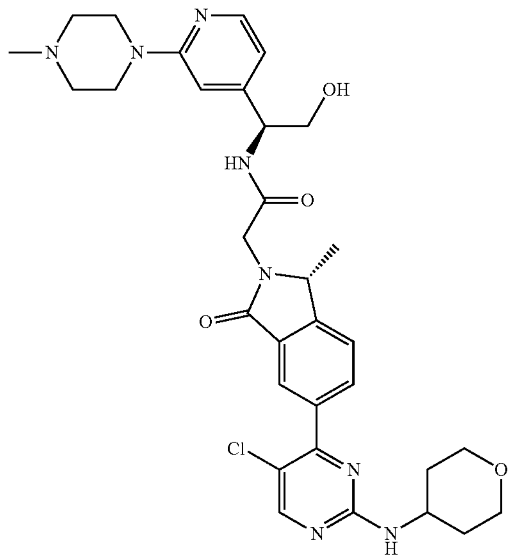 [SMILES: C[C@@H]1c2ccc(-c3nc(NC4CCOCC4)ncc3Cl)cc2C(=O)N1CC(=O)N[C@H](CO)c1ccnc(N2CCN(C)CC2)c1] | 2-[(1R)-5-{5-chloro-2-[(oxan-4-yl)amino]pyrimidin-4-yl}-1-methyl-3-oxo-2,3-dihydro-1H-isoindol-2-yl]-N-[(1S)-2-hydroxy-1-[2-(4-methylpiperazin-1-yl)pyridin-4-yl]ethyl]acetamide | 635 |
| 1011 | 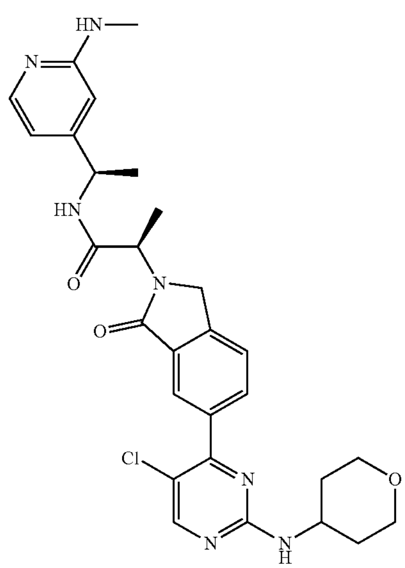 [SMILES: CNc1cc([C@@H](C)NC(=O)[C@@H](C)N2Cc3ccc(-c4nc(NC5CCOCC5)ncc4Cl)cc3C2=O)ccn1] | (2R)-2-(6-{5-chloro-2-[(oxan-4-yl)amino]pyrimidin-4-yl}-1-oxo-2,3-dihydro-1H-isoindol-2-yl)-N-[(1R)-1-[2-(methylamino)pyridin-4-yl]ethyl]propanamide | 550 |

| Example | Structure | Name | MS Data [M +H]+ unless specified |
|---|---|---|---|
| 1012 | 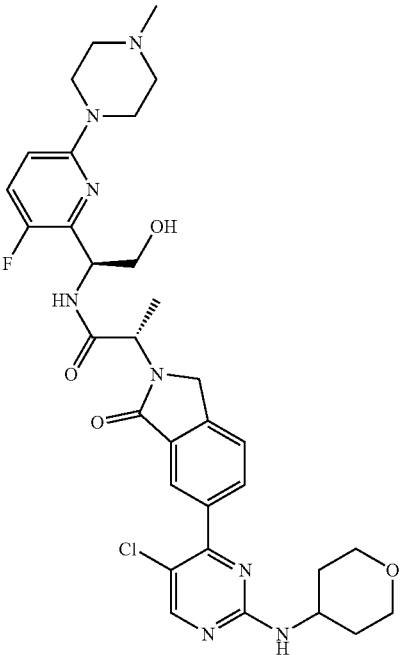 [SMILES: C[C@@H](C(=O)N[C@H](CO)c1nc(N2CCN(C)CC2)ccc1F)N1Cc2ccc(-c3nc(NC4CCOCC4)ncc3Cl)cc2C1=O] | (2S)-2-(6-{5-chloro-2-[(oxan-4-yl)amino]pyrimidin-4-yl}-1-oxo-2,3-dihydro-1H-isoindol-2-yl)-N-[(1S)-1-[3-fluoro-6-(4-methylpiperazin-1-yl)pyridin-2-yl]-2-hydroxyethyl]propanamide | 651 [M −H]+ |
| 1013 | 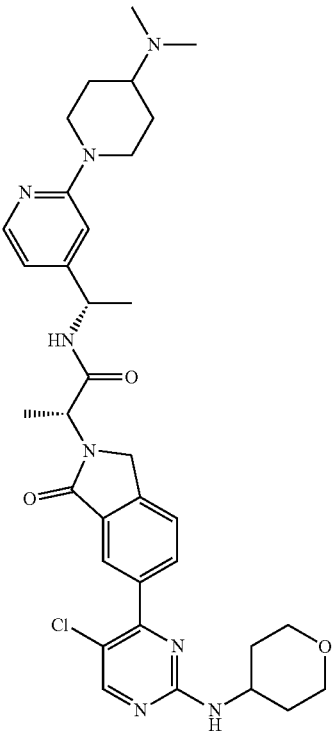 [SMILES: C[C@H](NC(=O)[C@@H](C)N1Cc2ccc(-c3nc(NC4CCOCC4)ncc3Cl)cc2C1=O)c1ccnc(N2CCC(N(C)C)CC2)c1] | (2R)-2-(6-{5-chloro-2-[(oxan-4-yl)amino]pyrimidin-4-yl}-1-oxo-2,3-dihydro-1H-isoindol-2-yl)-N-[(1S)-1-{2-[4-(dimethylamino)piperidin-1-yl]pyridin-4-yl}ethyl]propanamide | 647 |

| Example | Structure | Name | MS Data [M +H]+ unless specified |
|---|---|---|---|
| 1014 | 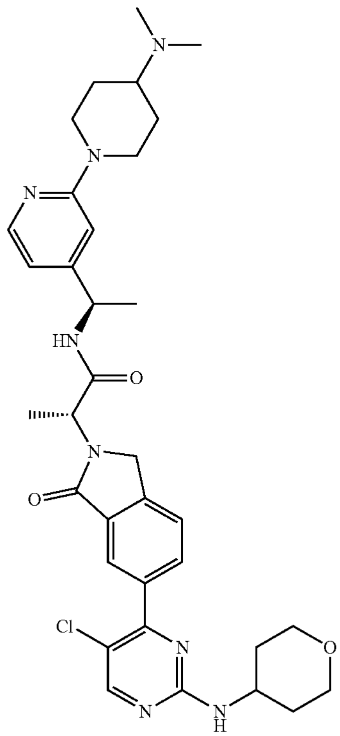 [SMILES: C[C@H](C(=O)N[C@H](C)c1ccnc(N2CCC(N(C)C)CC2)c1)N1Cc2ccc(-c3nc(NC4CCOCC4)ncc3Cl)cc2C1=O] | (2R)-2-(6-{5-chloro-2-[(oxan-4-yl)amino]pyrimidin-4-yl}-1-oxo-2,3-dihydro-1H-isoindol-2-yl)-N-[(1R)-1-{2-[4-(dimethylamino)piperidin-1-yl]pyridin-4-yl}ethyl]propanamide | 647 |
| 1015 | 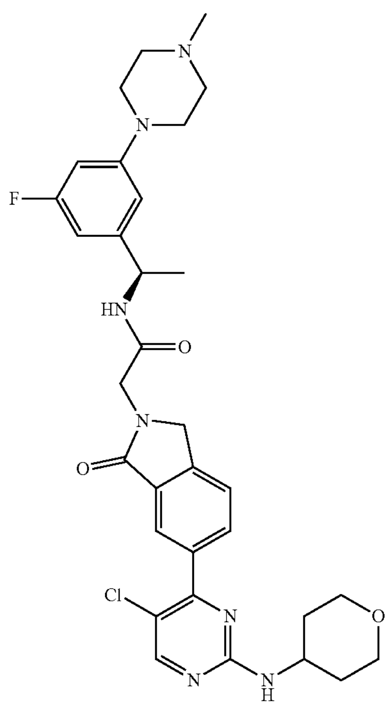 [SMILES: C[C@@H](NC(=O)CN1Cc2ccc(-c3nc(NC4CCOCC4)ncc3Cl)cc2C1=O)c1cc(F)cc(N2CCN(C)CC2)c1] | 2-(6-{5-chloro-2-[(oxan-4-yl)amino]pyrimidin-4-yl}-1-oxo-2,3-dihydro-1H-isoindol-2-yl)-N-[(1R)-1-[3-fluoro-5-(4-methylpiperazin-1-yl)phenyl]ethyl]acetamide | 622 |

-continued

| Example | Structure | Name | MS Data [M +H]+ unless specified |
|---|---|---|---|
| 1016 | 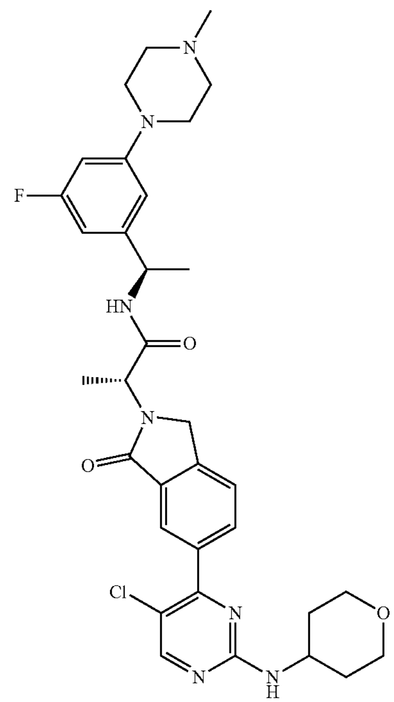 [SMILES: C[C@H](C(=O)N[C@H](C)c1cc(F)cc(N2CCN(C)CC2)c1)N1Cc2ccc(-c3nc(NC4CCOCC4)ncc3Cl)cc2C1=O] | (2R)-2-(6-{5-chloro-2-[(oxan-4-yl)amino]pyrimidin-4-yl}-1-oxo-2,3-dihydro-1H-isoindol-2-yl)-N-[(1R)-1-[3-fluoro-5-(4-methylpiperazin-1-yl)phenyl]ethyl]propanamide | 634 [M −H]+ |
| 1017 | 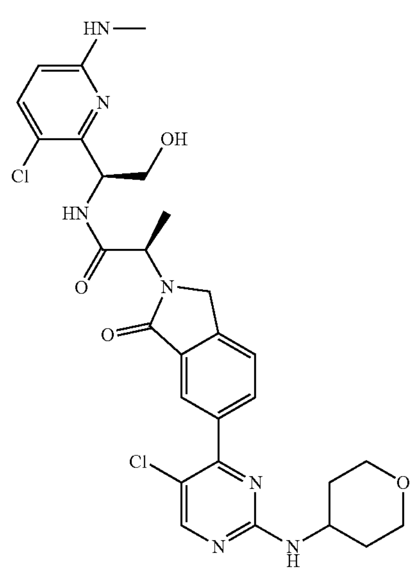 [SMILES: CNc1ccc(Cl)c([C@@H](CO)NC(=O)[C@@H](C)N2Cc3ccc(-c4nc(NC5CCOCC5)ncc4Cl)cc3C2=O)n1] | (2R)-2-(6-{5-chloro-2-[(oxan-4-yl)amino]pyrimidin-4-yl}-1-oxo-2,3-dihydro-1H-isoindol-2-yl)-N-[(1S)-1[3-chloro-6-(methylamino)pyridin-2-yl]-2-hydroxyethyl]propanamide | 600 |

-continued

| Example | Structure | Name | MS Data [M +H]+ unless specified |
|---|---|---|---|
| 1018 | 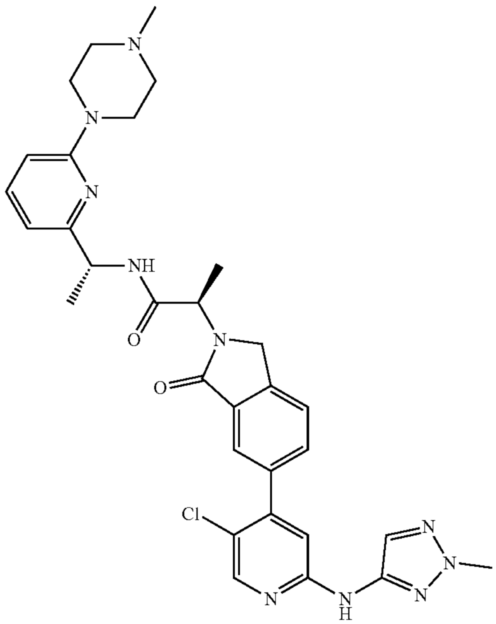 [SMILES: C[C@H](C(=O)N[C@H](C)c1cccc(N2CCN(C)CC2)n1)N1Cc2ccc(-c3cc(Nc4cnn(C)n4)ncc3Cl)cc2C1=O] | (2R)-2-(6-{5-chloro-2-[(2-methyl-2H-1,2,3-triazol-4-yl)amino]pyridin-4-yl}-1-oxo-2,3-dihydro-1H-isoindol-2-yl)-N-[(1R)-1-[6-(4-methylpiperazin-1-yl)pyridin-2-yl]ethyl]propanamide | 615 |
| 1019 | 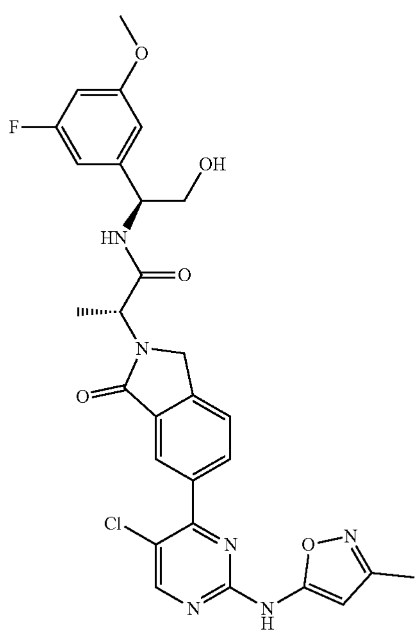 [SMILES: COc1cc(F)cc([C@@H](CO)NC(=O)[C@@H](C)N2Cc3ccc(-c4nc(Nc5cc(C)no5)ncc4Cl)cc3C2=O)c1] | (2R)-2-(6-{5-chloro-2-[(3-methyl-1,2-oxazol-5-yl)amino]pyrimidin-4-yl}-1-oxo-2,3-dihydro-1H-isoindol-2-yl)-N-[(1S)-1-(3-fluoro-5-methoxyphenyl)-2-hydroxyethyl]propanamide | 579 [M −H]− |

| Example | Structure | Name | MS Data [M +H]+ unless specified |
|---|---|---|---|
| 1020 | 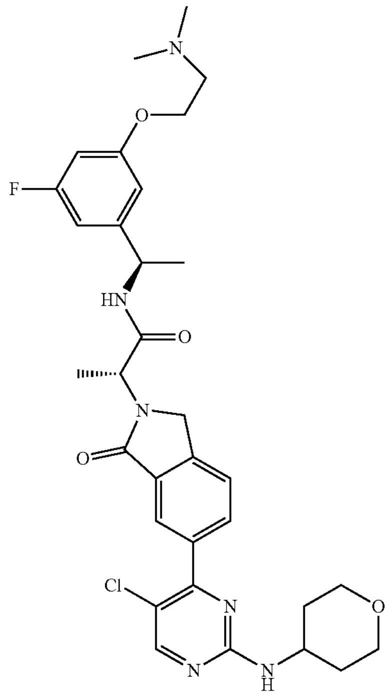 [SMILES: C[C@H](C(=O)N[C@H](C)c1cc(F)cc(OCCN(C)C)c1)N1Cc2ccc(-c3nc(NC4CCOCC4)ncc3Cl)cc2C1=O] | (2R)-2-(6-{5-chloro-2-[(oxan-4-yl)amino]pyrimidin-4-yl}-1-oxo-2,3-dihydro-1H-isoindol-2-yl)-N-[(1R)-1-{3-[2-(dimethylamino)ethoxy]-5-fluorophenyl}ethyl]propanamide | 625 |
| 1021 | 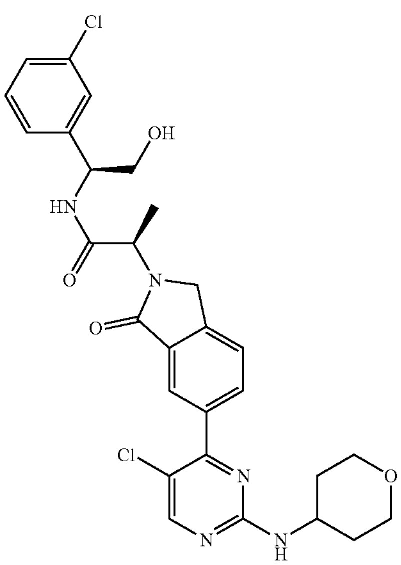 [SMILES: C[C@H](C(=O)N[C@H](CO)c1cccc(Cl)c1)N1Cc2ccc(-c3nc(NC4CCOCC4)ncc3Cl)cc2C1=O] | (2R)-2-(6-{5-chloro-2-[(oxan-4-yl)amino]pyrimidin-4-yl}-1-oxo-2,3-dihydro-1H-isoindol-2-yl)-N-[(1S)-1-(3-chlorophenyl)-2-hydroxyethyl]propanamide | 570 |

-continued

| Example | Structure | Name | MS Data [M +H]+ unless specified |
|---|---|---|---|
| 1022 | 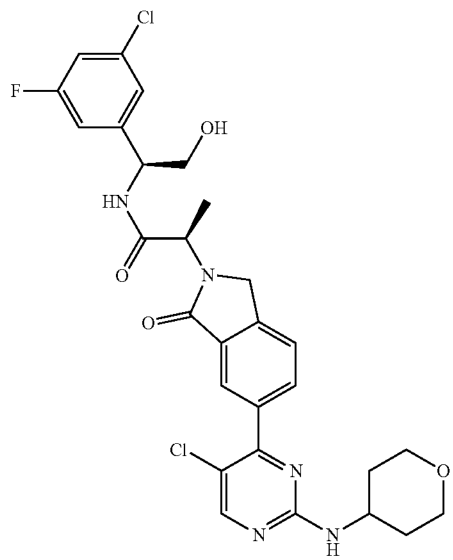 [SMILES: C[C@H](C(=O)N[C@H](CO)c1cc(F)cc(Cl)c1)N1Cc2ccc(-c3nc(NC4CCOCC4)ncc3Cl)cc2C1=O] | (2R)-2-(6-{5-chloro-2-[(oxan-4-yl)amino]pyrimidin-4-yl}-1-oxo-2,3-dihydro-1H-isoindol-2-yl)-N-[(1S)-1-(3-chloro-5-fluorophenyl)-2-hydroxyethyl]propanamide | 588 |
| 1023 | 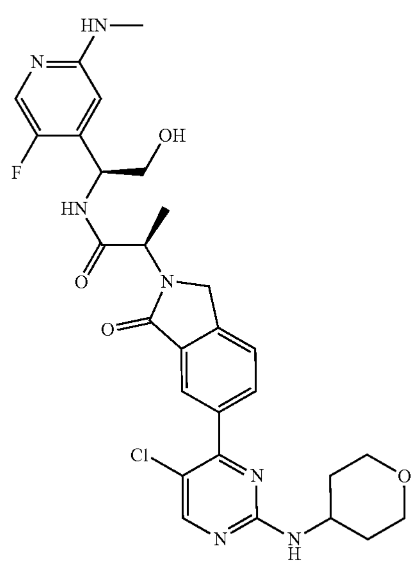 | (2R)-2-(6-{5-chloro-2-[(oxan-4-yl)amino]pyrimidin-4-yl}-1-oxo-2,3-dihydro-1H-isoindol-2-yl)-N-[(1S)-1-[5-fluoro-2-(methylamino)pyridin-4-yl]-2-hydroxyethyl]propanamide | 582 [M −H]− |

-continued

| Example | Structure | Name | MS Data [M +H]+ unless specified |
|---------|-----------|------|------|
| 1024 | 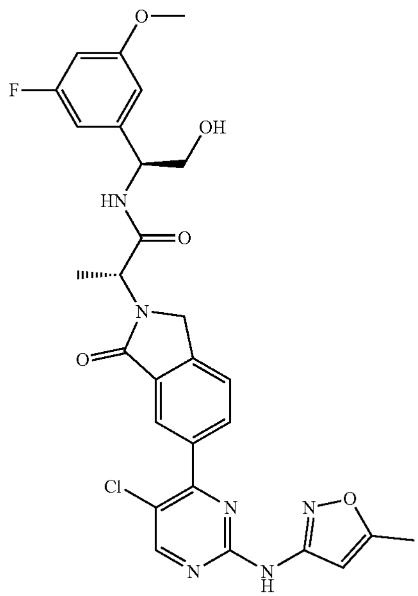 [SMILES: COc1cc(F)cc([C@@H](CO)NC(=O)[C@@H](C)N2Cc3ccc(-c4nc(Nc5cc(C)on5)ncc4Cl)cc3C2=O)c1] | (2R)-2-(6-{5-chloro-2-[(5-methyl-1,2-oxazol-3-l)amino]pyrimidin-4-yl}-1-oxo-2,3-dihydro-1H-isoindol-2-yl)-N-[(1S)-1-(3-fluoro-5-methoxyphenyl)-2-hydroxyethyl]propanamide | 579 [M −H]− |
| 1025 | 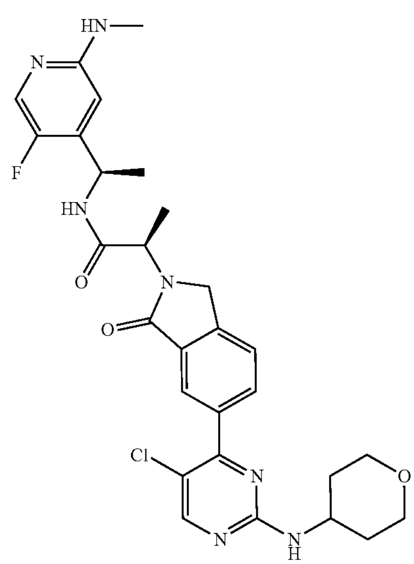 | (2R)-2-(6-{5-chloro-2-[(oxan-4-yl)amino]pyrimidin-4-yl}-1-oxo-2,3-dihydro-1H-isoindol-2-yl)-N-[(1R)-1[5-fluoro-2-(methylamino)pyridin-4-yl]ethyl]propanamide | 568 |

| Example | Structure | Name | MS Data [M +H]+ unless specified |
|---|---|---|---|
| 1026 | 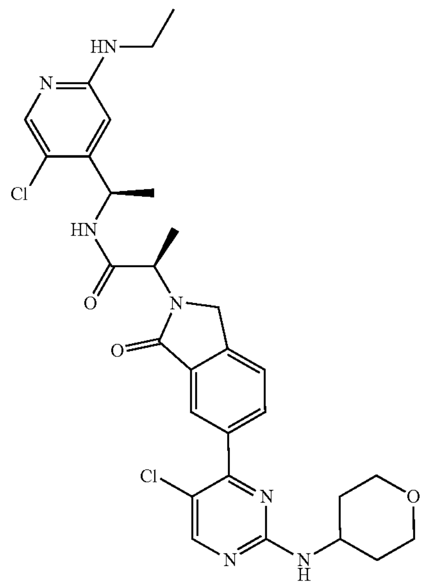 | (2R)-N-[(1R)-1-[5-chloro-2-(ethylamino)pyridin-4-yl]ethyl]-2-(6-{5-chloro-2-[(oxan-4-yl)amino]pyrimidin-4-yl}-1-oxo-2,3-dihydro-1H-isoindol-2-yl)propanamide | 598 |
| 1027 | 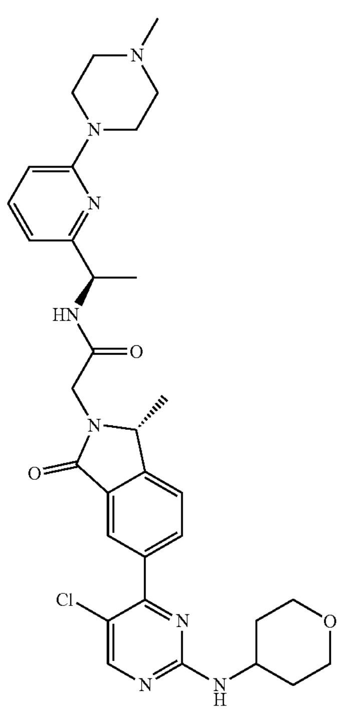 [SMILES: C[C@@H]1c2ccc(-c3nc(NC4CCOCC4)ncc3Cl)cc2C(=O)N1CC(=O)N[C@H](C)c1cccc(N2CCN(C)CC2)n1] | 2-[(1R)-5-{5-chloro-2-[(oxan-4-yl)amino]pyrimidin-4-yl}-1-methyl-3-oxo-2,3-dihydro-1H-isoindol-2-yl]-N-[(1R)-1-[6-(4-methylpiperazin-1-yl)pyridin-2-yl]ethyl]acetamide | 619 |

| Example | Structure | Name | MS Data [M +H]+ unless specified |
|---|---|---|---|
| 1028 | 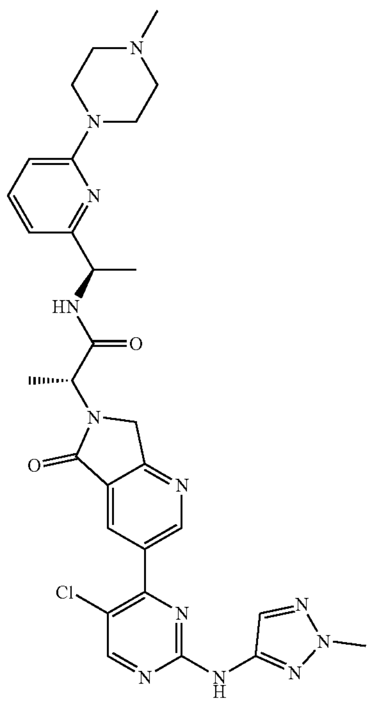 [SMILES: C[C@H](C(=O)N[C@H](C)c1cccc(N2CCN(C)CC2)n1)N1Cc2ncc(-c3nc(Nc4cnn(C)n4)ncc3Cl)cc2C1=O] | (2R)-2-(3-{5-chloro-2-[(2-methyl-2H-1,2,3-triazol-4-yl)amino]pyrimidin-4-yl}-5-oxo-5H,6H,7H-pyrrolo[3,4-b]pyridin-6-yl)-N-[(1R)-1-[6-(4-methylpiperazin-1-yl)pyridin-2-yl]ethyl]propanamide | 617 |
| 1029 | 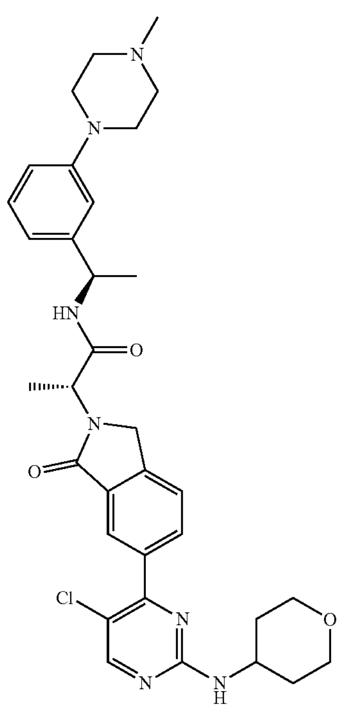 [SMILES: C[C@H](C(=O)N[C@H](C)c1cccc(N2CCN(C)CC2)c1)N1Cc2ccc(-c3nc(NC4CCOCC4)ncc3Cl)cc2C1=O] | (2R)-2-(6-{5-chloro-2-[(oxan-4-yl)amino]pyrimidin-4-yl}-1-oxo-2,3-dihydro-1H-isoindol-2-yl)-N-[(1R)-1-[3-(4-methylpiperazin-1-yl)phenyl]ethyl]propanamide | 618 |

-continued
| Example | Structure | Name | MS Data [M+H]+ unless specified |
|---|---|---|---|
| 1030 | 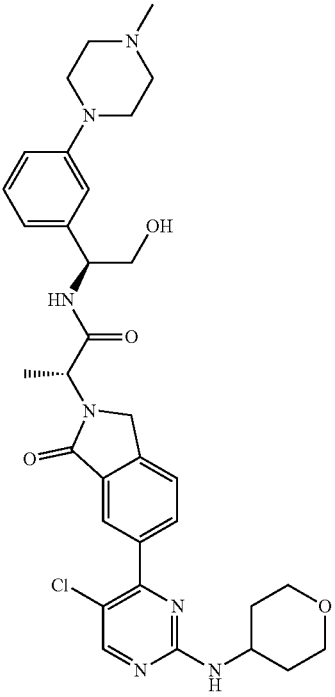 [SMILES: C[C@H](C(=O)N[C@H](CO)c1cccc(N2CCN(C)CC2)c1)N1Cc2ccc(-c3nc(NC4CCOCC4)ncc3Cl)cc2C1=O] | (2R)-2-(6-{5-chloro-2-[(oxan-4-yl)amino]pyrimidin-4-yl}-1-oxo-2,3-dihydro-1H-isoindol-2-yl)-N-[(1S)-2-hydroxy-1-[3-(4-methylpiperazin-1-yl)phenyl]ethyl]propanamide | 634 |
| 1031 | 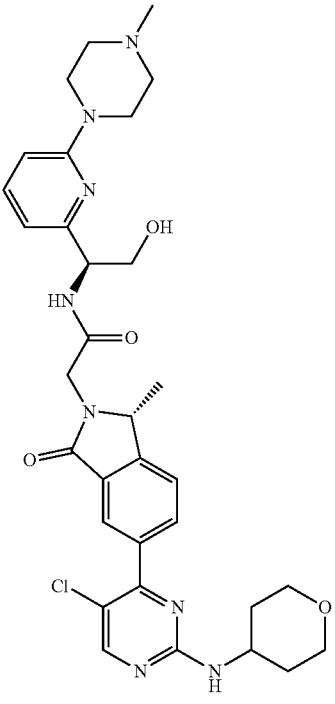 [SMILES: C[C@@H]1c2ccc(-c3nc(NC4CCOCC4)ncc3Cl)cc2C(=O)N1CC(=O)N[C@H](CO)c1cccc(N2CCN(C)CC2)n1] | 2-[(1R)-{5-chloro-2-[(oxan-4-yl)amino]pyrimidin-4-yl}-1-methyl-3-oxo-2,3-dihydro-1H-isoindol-2-ylFN-[(1S)-2-hydroxy-1-[6-(4-methyl piperazin-1-yl)pyridin-2-yl]ethyl]acetamide | 635 |

-continued

| Example | Structure | Name | MS Data [M +H]+ unless specified |
|---|---|---|---|
| 1032 | 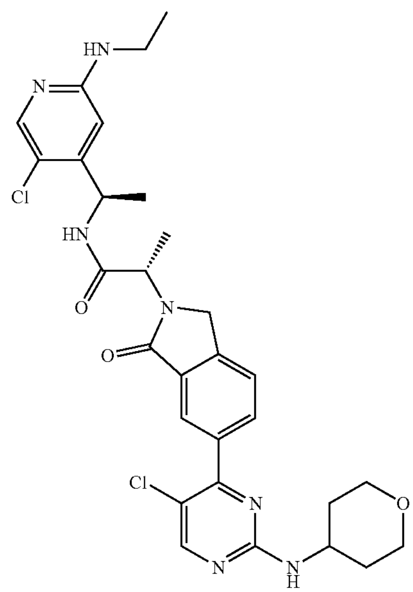 [SMILES: CCNc1cc([C@@H](C)NC(=O)[C@H](C)N2Cc3ccc(-c4nc(NC5CCOCC5)ncc4Cl)cc3C2=O)c(Cl)cn1] | (2S)-N-[(1R)-1-[5-chloro-2-(ethylamino)pyridin-4-yl]ethyl]-2-(6-{5-chloro-2-[(oxan-4-yl)amino]pyrimidin-4-yl}-1-oxo-2,3-dihydro-1H-isoindol-2-yl)propanamide | 598 |
| 1033 | 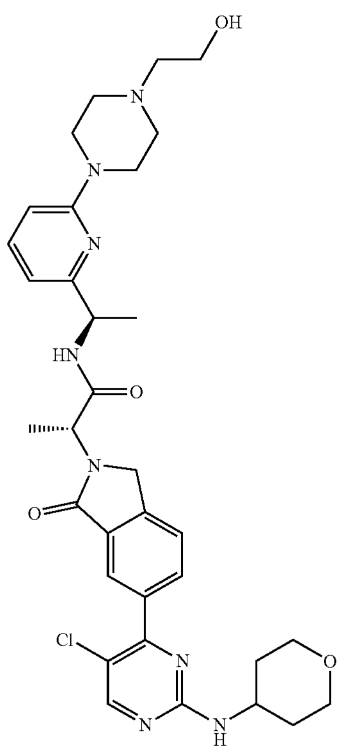 [SMILES: C[C@H](C(=O)N[C@H](C)c1cccc(N2CCN(CCO)CC2)n1)N1Cc2ccc(-c3nc(NC4CCOCC4)ncc3Cl)cc2C1=O] | (2R)-2-(6-{5-chloro-2-[(oxan-4-yl)amino]pyrimidin-4-yl{-1-oxo-2,3-dihydro-1H-isoindol-2-yl)-N-[(1R)-1-{6-[4-(2-hydroxyethyl)piperazin-1-yl]pyridin-2-yl}ethyl]propanamide | 649 |

-continued

| Example | Structure | Name | MS Data [M +H]+ unless specified |
|---|---|---|---|
| 1034 | 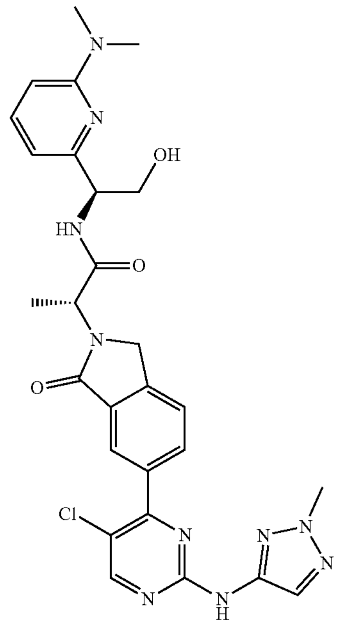 [SMILES: C[C@H](C(=O)N[C@H](CO)c1cccc(N(C)C)n1)N1Cc2ccc(-c3nc(Nc4cnn(C)n4)ncc3Cl)cc2C1=O] | (2R)-2-(6-{5-chloro-2-[(2-methyl-2H-1,2,3-triazol-4-yl)amino]pyrimidin-4-yl}-1-oxo-2,3-dihydro-1H-isoindol-2-yl)-N-[(1S)-1-[6-(dimethylamino)pyridin-2-yl]-2-hydroxyethyl]propanamide | 575 [M −H]+ |
| 1035 | 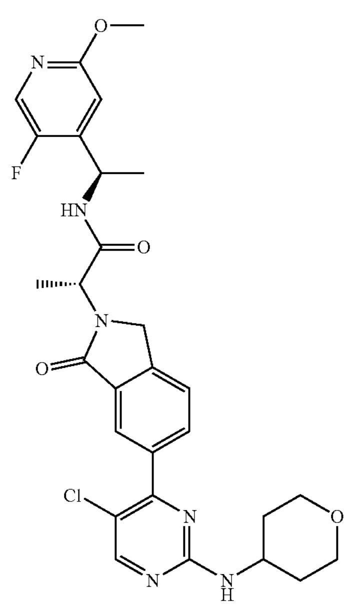 [SMILES: COc1cc([C@@H](C)NC(=O)[C@@H](C)N2Cc3ccc(-c4nc(NC5CCOCC5)ncc4Cl)cc3C2=O)c(F)cn1] | (2R)-2-(6-{5-chloro-2-[(oxan-4-yl)amino]pyrimidin-4-yl}-1-oxo-2,3-dihydro-1H-isoindol-2-yl)-N-[(1R)-1-(5-fluoro-2-methoxypyridin-4-yl)ethyl]propanamide | 569 |

-continued

| Example | Structure | Name | MS Data [M +H]+ unless specified |
|---|---|---|---|
| 1036 | 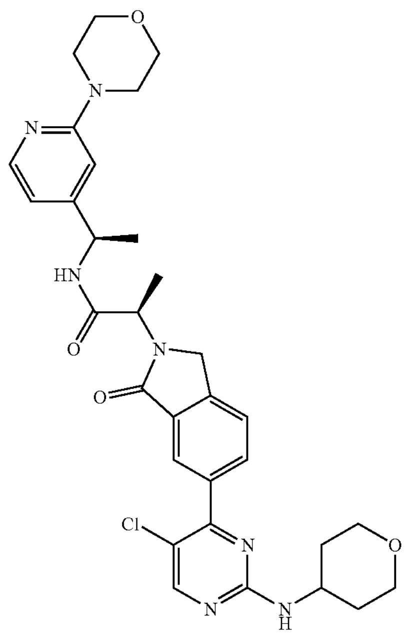 [SMILES: C[C@H](C(=O)N[C@H](C)c1ccnc(N2CCOCC2)c1)N1Cc2ccc(-c3nc(NC4CCOCC4)ncc3Cl)cc2C1=O] | (2R)-2-(6-{5-chloro-2-[(oxan-4-yl)amino]pyrimidin-4-yl}-1-oxo-2,3-dihydro-1H-isoindol-2-yl)-N-[(1R)-1[2-(morpholin-4-yl)pyridin-4-yl]ethyl]propanamide | 606 |
| 1037 | 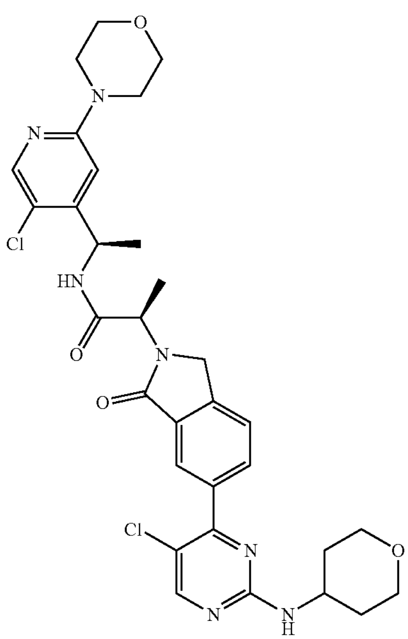 [SMILES: C[C@H](C(=O)N[C@H](C)c1cc(N2CCOCC2)ncc1Cl)N1Cc2ccc(-c3nc(NC4CCOCC4)ncc3Cl)cc2C1=O] | (2R)-N-[(1R)-1-[5-chloro-2-(morpholin-4-yl)pyridin-4-yl]ethyl]-2-(6-{5-chloro-2-[(oxan-4-yl)amino]pyrimidin-4-yl}-1-oxo-2,3-dihydro-1H-isoindol-2-yl)propanamide | 638 [M −H]− |

| Example | Structure | Name | MS Data [M +H]+ unless specified |
|---|---|---|---|
| 1038 | 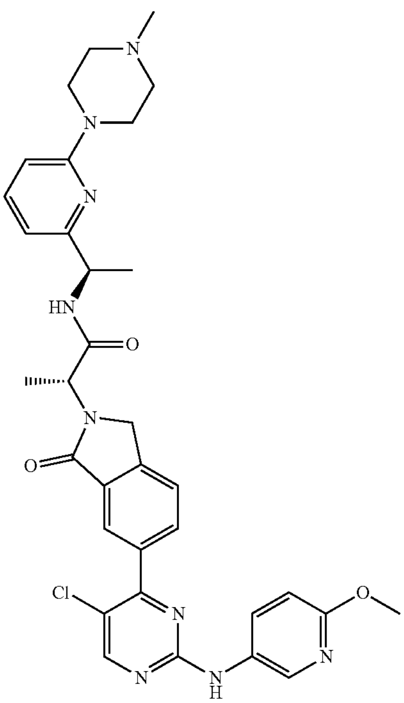 [SMILES: COc1ccc(Nc2ncc(Cl)c(-c3ccc4c(c3)C(=O)N([C@H](C)C(=O)N[C@H](C)c3cccc(N5CCN(C)CC5)n3)C4)n2)cn1] | (2R)-2-(6-{5-chloro-2-[(6-methoxypyridin-3-yl)amino]pyrimidin-4-yl}-1-oxo-2,3-dihydro-1H-isoindol-2-yl)-N-[(1R)-1-[6-(4-methylpiperazin-1-yl)pyridin-2-yl]ethyl]propanamide | 642 |
| 1039 | 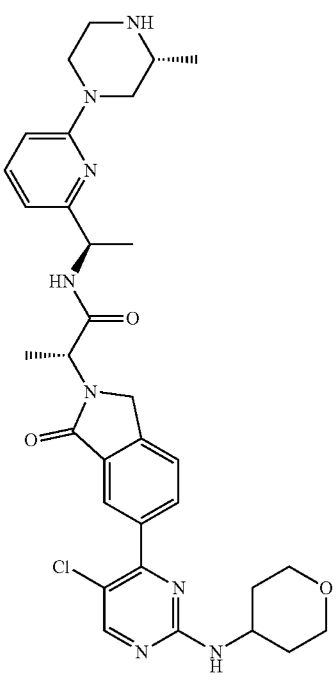 [SMILES: C[C@@H]1CN(c2cccc([C@@H](C)NC(=O)[C@@H](C)N3Cc4ccc(-c5nc(NC6CCOCC6)ncc5Cl)cc4C3=O)n2)CCN1] | (2R)-2-(6-{5-chloro-2-[(oxan-4-yl)amino]pyrimidin-4-yl}-1-oxo-2,3-dihydro-1H-isoindol-2-yl)-N-[(1R)-1-{6-[(3R)-3-methylpiperazin-1-yl]pyridin-2-yl}ethyl]propanamide | 619 |

-continued

| Example | Structure | Name | MS Data [M +H]+ unless specified |
|---|---|---|---|
| 1040 | 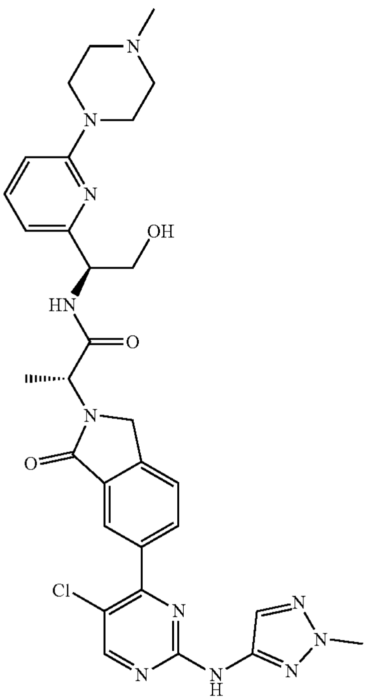 [SMILES: C[C@H](C(=O)N[C@H](CO)c1cccc(N2CCN(C)CC2)n1)N1Cc2ccc(-c3nc(Nc4cnn(C)n4)ncc3Cl)cc2C1=O] | (2R)-2-(6-{5-chloro-2-[(2-methyl-2H-1,2,3-triazol-4-yl)amino]pyrimidin-4-yl}-1-oxo-2,3-dihydro-1H-isoindol-2-yl)-N-[(1S)-2-hydroxy-1-[6-(4-methylpiperazin-1-yl)pyridin-2-yl]ethyl]propanamide | 632 |
| 1041 | 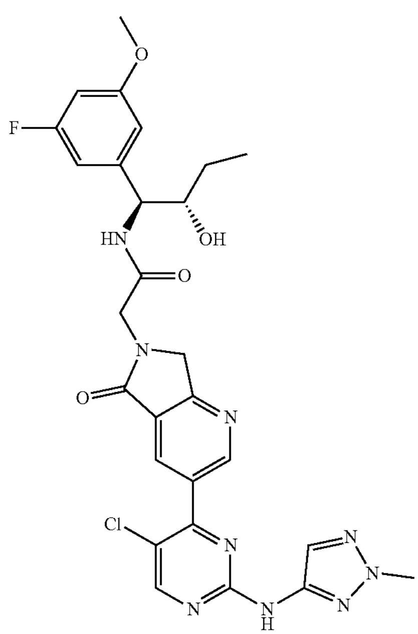 [SMILES: CC[C@H](O)[C@@H](NC(=O)CN1Cc2ncc(-c3nc(Nc4cnn(C)n4)ncc3Cl)cc2C1=O)c1cc(F)cc(OC)c1] | 2-(3-{5-chloro-2-[(2-methyl-2H-1 2,3-triazol-4-yl)amino]pyrimidin-4-yl}-5-oxo-5H,6H,7H-pyrrolo[3,4-b]pyridin-6-yl)-N-[(1S,2S)-1-(3-fluoro-5-methoxyphenyl)-2-hydroxybutyl]acetamide | 596 |

-continued

| Example | Structure | Name | MS Data [M +H]+ unless specified |
|---|---|---|---|
| 1042 | 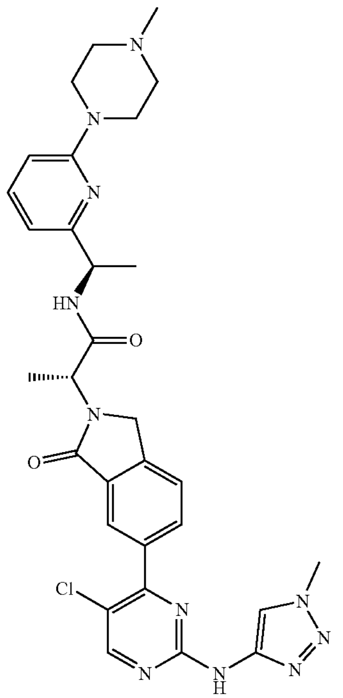 [SMILES: C[C@H](C(=O)N[C@H](C)c1cccc(N2CCN(C)CC2)n1)N1Cc2ccc(-c3nc(Nc4cn(C)nn4)ncc3Cl)cc2C1=O] | (2R)-2-(6-{5-chloro-2-[(1-methyl-1H-1,2,3-triazol-4-yl)amino]pyrimidin-4-yl}-1-oxo-2,3-dihydro-1H-isoindol-2-yl)-N-[(1R)-1-[6-(4-methylpiperazin-1-yl)pyridin-2-yl]ethyl]propanamide | 616 |
| 1043 | 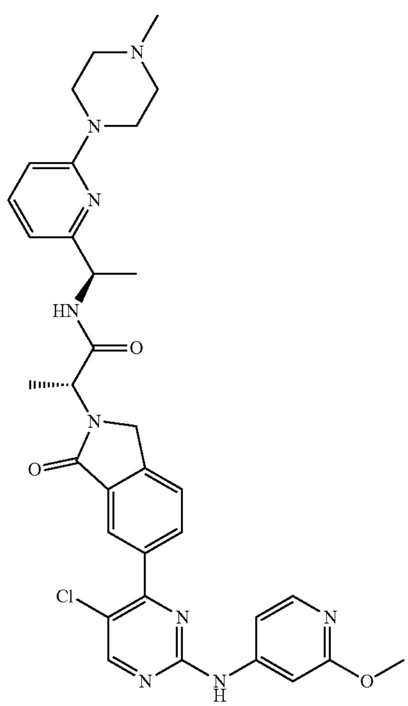 [SMILES: COc1cc(Nc2ncc(Cl)c(-c3ccc4c(c3)C(=O)N([C@H](C)C(=O)N[C@H](C)c3cccc(N5CCN(C)CC5)n3)C4)n2)ccn1] | (2R)-2-(6-{5-chloro-2-[(2-methoxypyridin-4-yl)amino]pyrimidin-4-yl}-1-oxo-2,3-dihydro-1H-isoindol-2-yl)-N-[(1R)-1-[6-(4-methylpiperazin-1-yl)pyridin-2-yl]ethyl]propanamide | 642 |

-continued

| Example | Structure | Name | MS Data [M +H]+ unless specified |
|---|---|---|---|
| 1044 | 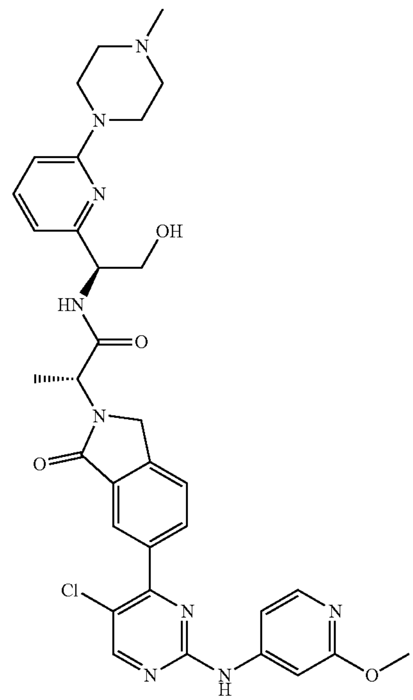 [SMILES: COc1cc(Nc2ncc(Cl)c(-c3ccc4c(c3)C(=O)N([C@H](C)C(=O)N[C@H](CO)c3cccc(N5CCN(C)CC5)n3)C4)n2)ccn1] | (2R)-2-(6-{5-chloro-2-[(2-methoxypyridin-4-yl)amino]pyrimidin-4-yl}-1-oxo-2,3-dihydro-1H-isoindol-2-yl)-N-[(1S)-2-hydroxy-1-[6-(4-methylpiperazin-1-yl)pyridin-2-yl]ethyl]propanamide | 658 |
| 1045 | 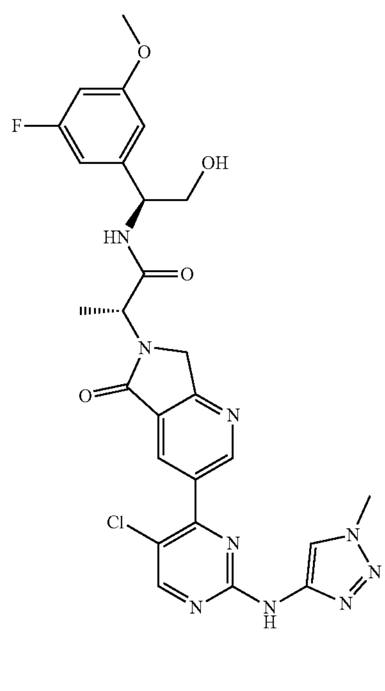 [SMILES: COc1cc(F)cc([C@@H](CO)NC(=O)[C@@H](C)N2Cc3ncc(-c4nc(Nc5cn(C)nn5)ncc4Cl)cc3C2=O)c1] | (2R)-2-(3-{5-chloro-2-[(1-methyl-1H-1,2,3-triazol-4-yl)amino]pyrimidin-4-yl}-5-oxo-5H,6H,7H-pyrrolo[3,4-b]pyridin-6-yl)-N-[(1S)-1-(3-fluoro-5-methoxyphenyl)-2-hydroxyethyl]propanamide | 582 |

-continued

| Example | Structure | Name | MS Data [M +H]+ unless specified |
|---|---|---|---|
| 1046 | 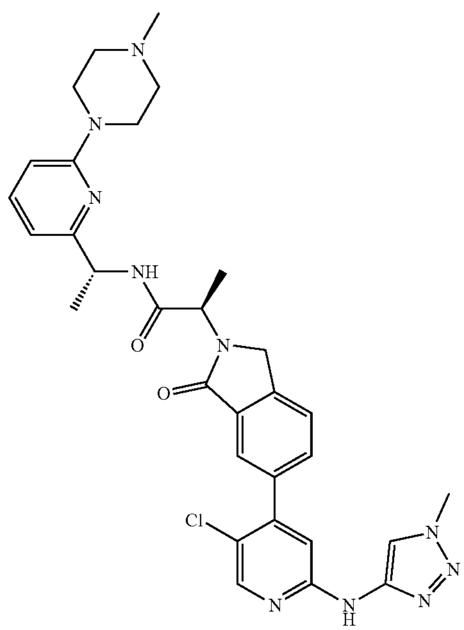 [SMILES: C[C@H](C(=O)N[C@H](C)c1cccc(N2CCN(C)CC2)n1)N1Cc2ccc(-c3cc(Nc4cn(C)nn4)ncc3Cl)cc2C1=O] | (2R)-2-(6-{5-chloro-2-[(1-methyl-1H-1,2,3-triazol-4-yl)amino]pyridin-4-yl}-1-oxo-2,3-dihydro-1H-isoindol-2-yl)-N-[(1R)-1-[6-(4-methylpiperazin-1-yl)pyridin-2-yl]ethyl]propanamide | 613 [M −H]+ |
| 1047 | 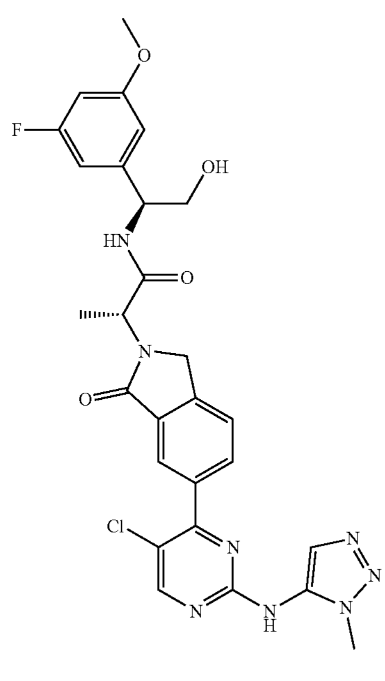 | (2R)-2-(6-{5-chloro-2-[(1-methyl-1H-1,2,3-triazol-5-yl)amino]pyrimidin-4-yl}-1-oxo-2,3-dihydro-1H-isoindol-2-yl)-N-[(1S)-1-(3-fluoro-5-methoxyphenyl)-2-hydroxyethyl]propanamide | 581 |

-continued

| Example | Structure | Name | MS Data [M +H]+ unless specified |
|---|---|---|---|
| 1048 | 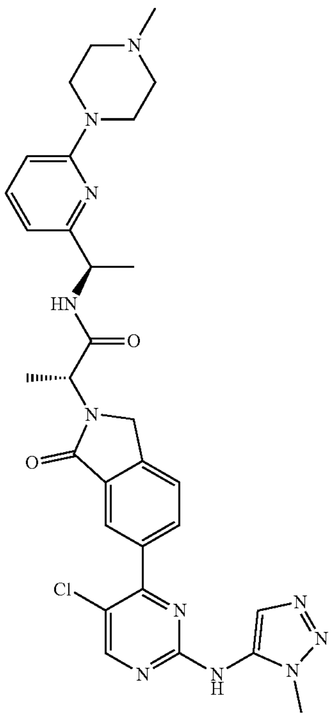 [SMILES: C[C@H](C(=O)N[C@H](C)c1cccc(N2CCN(C)CC2)n1)N1Cc2ccc(-c3nc(Nc4cnnn4C)ncc3Cl)cc2C1=O] | (2R)-2-(6-{5-chloro-2-[(1-methyl-1H-1,2,3-triazol-5-yl)amino]pyrimidin-4-yl}-1-oxo-2,3-dihydro-1H-isoindol-2-yl)-N-[(1R)-1-[6-(4-methylpiperazin-1-yl)pyridin-2-yl]ethyl]propanamide | 616 |
| 1049 | 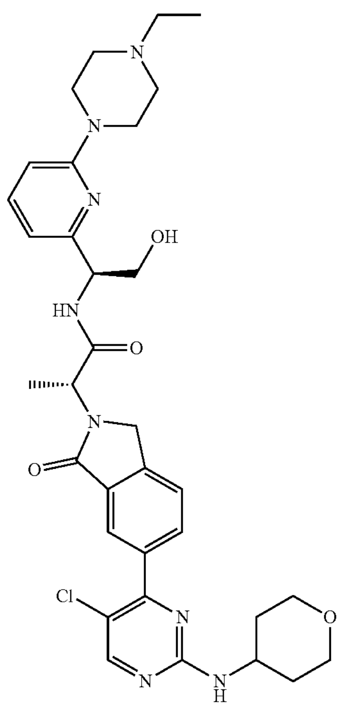 [SMILES: CCN1CCN(c2cccc([C@@H](CO)NC(=O)[C@@H](C)N3Cc4ccc(-c5nc(NC6CCOCC6)ncc5Cl)cc4C3=O)n2)CC1] | (2R)-2-(6-{5-chloro-2-[(oxan-4-yl)amino]pyrimidin-4-yl}-1-oxo-2,3-dihydro-1H-isoindol-2-yl)-N-[(1S)-1[6-(4-ethylpiperazin-1-yl)pyridin-2-yl]-2-hydroxyethyl]propanamide | 649 |

-continued

| Example | Structure | Name | MS Data [M +H]+ unless specified |
|---|---|---|---|
| 1050 | 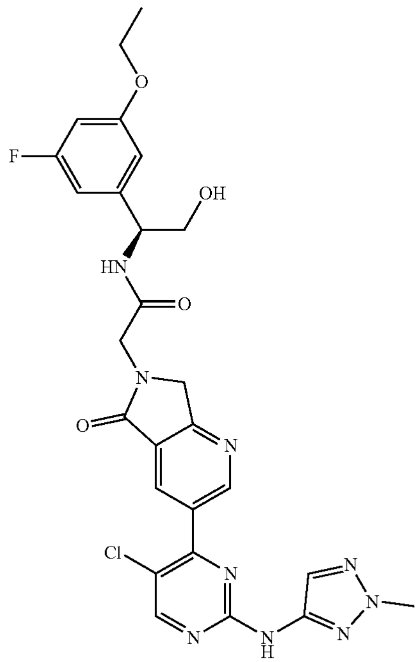 [SMILES: CCOc1cc(F)cc([C@@H](CO)NC(=O)CN2Cc3ncc(-c4nc(Nc5cnn(C)n5)ncc4Cl)cc3C2=O)c1] | 2-(3-{5-chloro-2-[(2-methyl-2H-1,2,3-triazol-4-yl)amino]pyrimidin-4-yl}-5-oxo-5H,6H,7H-pyrrolo[3,4-b]pyridin-6-yl)-N-[(1S)-1-(3-ethoxy-5-fluorophenyl)-2-hydroxyethyl]acetamide | 582 |
| 1051 | 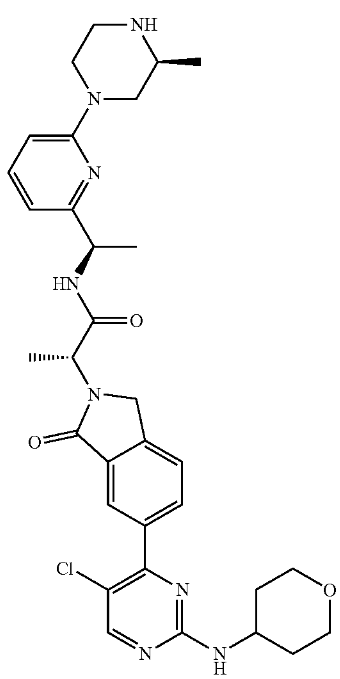 [SMILES: C[C@H](C(=O)N[C@H](C)c1cccc(N2CCN[C@@H](C)C2)n1)N1Cc2ccc(-c3nc(NC4CCOCC4)ncc3Cl)cc2C1=O] | (2R)-2-(6-{5-chloro-2-[(oxan-4-yl)amino]pyrimidin-4-yl}-1-oxo-2,3-dihydro-1H-isoindol-2-yl)-N-[(1R)-1-{6-[(3S)-3-methylpiperazin-1-yl]pyridin-2-yl}ethyl]propanamide | 619 |

-continued

| Example | Structure | Name | MS Data [M +H]+ unless specified |
|---|---|---|---|
| 1052 | 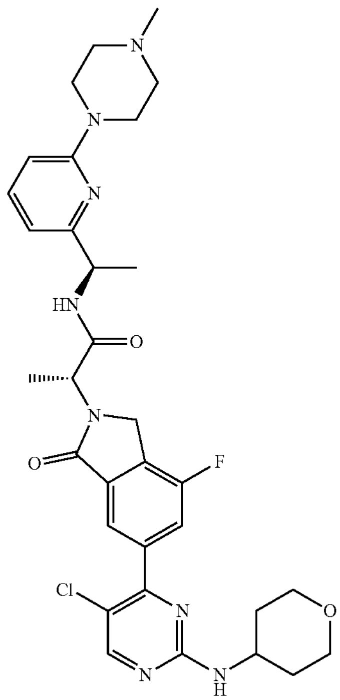 [SMILES: C[C@H](C(=O)N[C@H](C)c1cccc(N2CCN(C)CC2)n1)N1Cc2c(F)cc(-c3nc(NC4CCOCC4)ncc3Cl)cc2C1=O] | (2R)-2-(6-{5-chloro-2-[(oxan-4-yl)amino]pyrimidin-4-yl}-4-fluoro-1-oxo-2,3-dihydro-1H-isoindol-2-yl)-N-[(1R)-1-[6-(4-methylpiperazin-1-yl)pyridin-2-yl]ethyl]propanamide | 637 |
| 1053 | 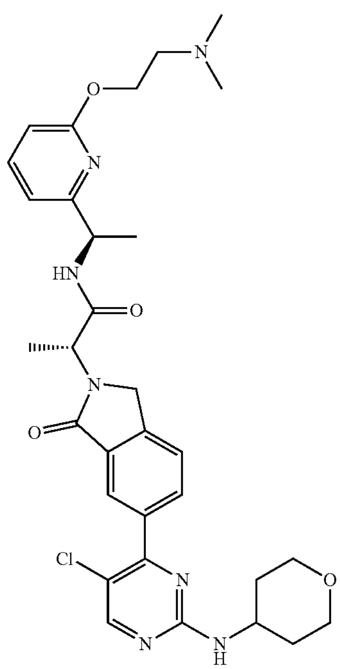 [SMILES: C[C@H](C(=O)N[C@H](C)c1cccc(OCCN(C)C)n1)N1Cc2ccc(-c3nc(NC4CCOCC4)ncc3Cl)cc2C1=O] | (2R)-2-(6-{5-chloro-2-[(oxan-4-yl)amino]pyrimidin-4-yl}-1-oxo-2,3-dihydro-1H-isoindol-2-yl)-N-[(1R)-1-{6-[2-(dimethylamino)ethoxy]pyridin-2-yl}ethyl]propanamide | 608 |

-continued

| Example | Structure | Name | MS Data [M +H]+ unless specified |
|---|---|---|---|
| 1054 | 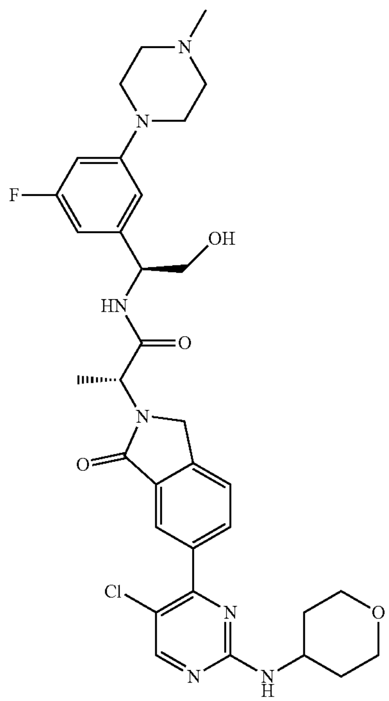 [SMILES: C[C@H](C(=O)N[C@H](CO)c1cc(F)cc(N2CCN(C)CC2)c1)N1Cc2ccc(-c3nc(NC4CCOCC4)ncc3Cl)cc2C1=O] | (2R)-2-(6-{5-chloro-2-[(oxan-4-yl)amino]pyrimidin-4-yl}-1-oxo-2,3-dihydro-1H-isoindol-2-yl)-N-[(1S)-1-[3-fluoro-5-(4-methylpiperazin-1-yl)phenyl]-2-hydroxyethyl]propanamide | 650 |
| 1055 | 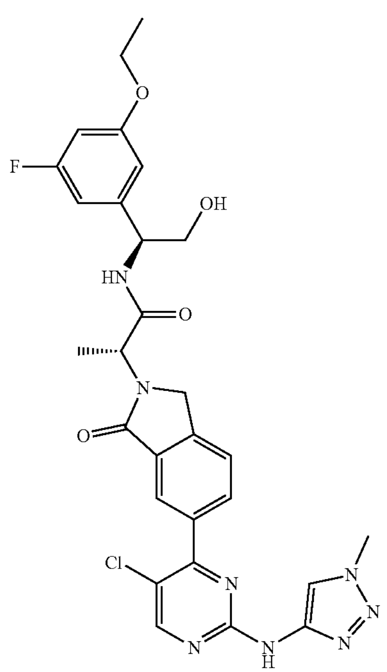 [SMILES: CCOc1cc(F)cc([C@@H](CO)NC(=O)[C@@H](C)N2Cc3ccc(-c4nc(Nc5cn(C)nn5)ncc4Cl)cc3C2=O)c1] | (2R)-2-(6-{5-chloro-2-[(1-methyl-1H-1,2,3-triazol-4-yl)amino]pyrimidin-4-yl}-1-oxo-2,3-dihydro-1H-isoindol-2-yl)-N-[(1S)-1-(3-ethoxy-5-fluorophenyl)-2-hydroxyethyl]propanamide | 595 |

-continued

| Example | Structure | Name | MS Data [M +H]+ unless specified |
|---|---|---|---|
| 1056 | 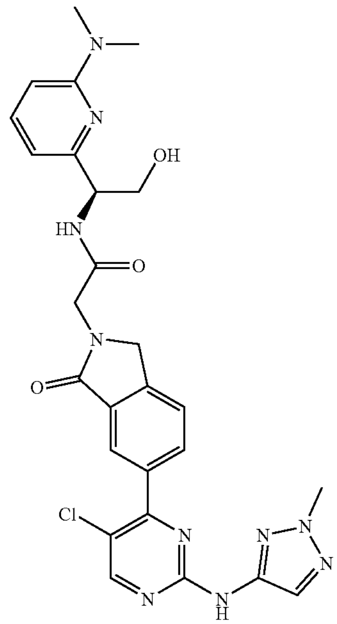 [SMILES: CN(C)c1cccc([C@@H](CO)NC(=O)CN2Cc3ccc(-c4nc(Nc5cnn(C)n5)ncc4Cl)cc3C2=O)n1] | 2-(6-{5-chloro-2-[(2-methyl-2H-1,2,3-triazol-4-yl)amino]pyrimidin-4-yl}-1-oxo-2,3-dihydro-1H-isoindol-2-yl)-N-[(1S)-1-[6-(dimethylamino)pyridin-2-yl]-2-hydroxyethyl]acetamide | 561 [M −H]+ |
| 1057 | 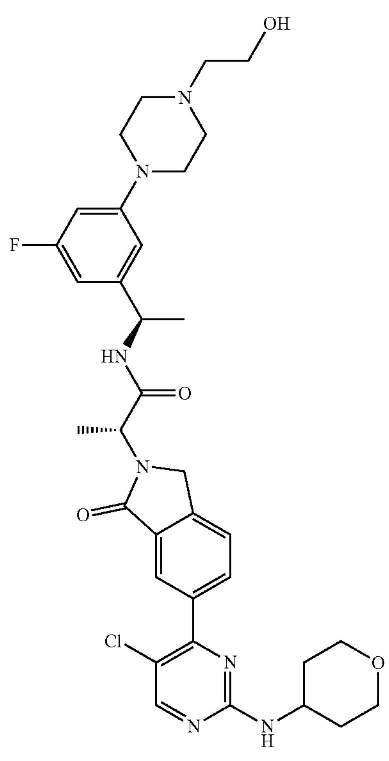 [SMILES: C[C@H](C(=O)N[C@H](C)c1cc(F)cc(N2CCN(CCO)CC2)c1)N1Cc2ccc(-c3nc(NC4CCOCC4)ncc3Cl)cc2C1=O] | (2R)-2-(6-{5-chloro-2-[(oxan-4-yl)amino]pyrimidin-4-yl}-1-oxo-2,3-dihydro-1H-isoindol-2-yl)-N-[(1R)-1-{3-fluoro-5-[4-(2-hydroxyethyl)piperazin-1-yl]phenyl}ethyl]propanamide | 664 [M −H]+ |

-continued

| Example | Structure | Name | MS Data [M +H]+ unless specified |
|---------|-----------|------|-----|
| 1058 | 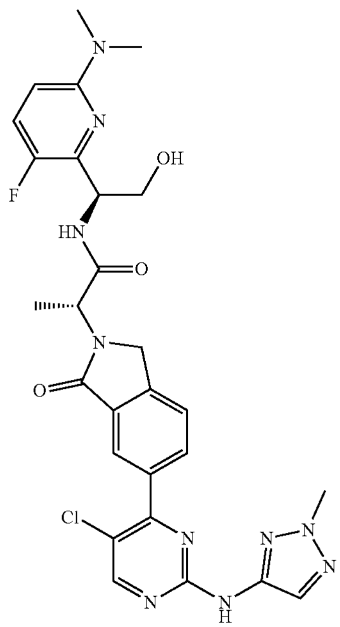 [SMILES: C[C@H](C(=O)N[C@H](CO)c1nc(N(C)C)ccc1F)N1Cc2ccc(-c3nc(Nc4cnn(C)n4)ncc3Cl)cc2C1=O] | (2R)-2-(6-{5-chloro-2-[(2-methyl-2H-1,2,3-triazol-4-yl)amino]pyrimidin-4-yl}-1-oxo-2,3-dihydro-1H-isoindol-2-yl)-N-[(1S)-146-(dimethylamino)-3-fluoropyridin-2-yl]-2-hydroxyethyl]propanamide | [M −H]+ 593 |
| 1059 | 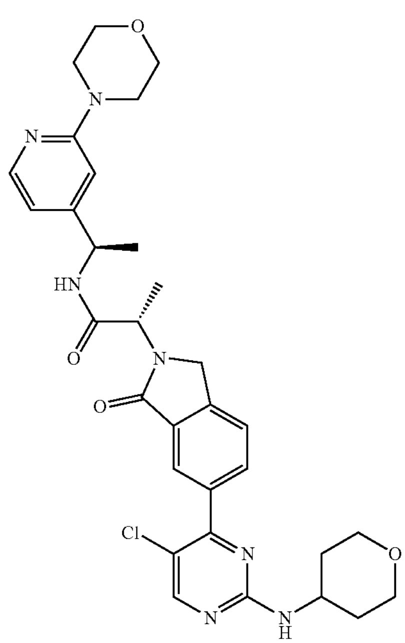 [SMILES: C[C@@H](NC(=O)[C@H](C)N1Cc2ccc(-c3nc(NC4CCOCC4)ncc3Cl)cc2C1=O)c1ccnc(N2CCOCC2)c1] | (2S)-2-(6-{5-chloro-2-[(oxan-4-yl)amino]pyrimidin-4-yl}-1-oxo-2,3-dihydro-1H-isoindol-2-yl)-N-[(1R)-1-[2-(morpholin-4-yl)pyridin-4-yl]ethyl]propanamide | 606 |

-continued

| Example | Structure | Name | MS Data [M +H]+ unless specified |
|---|---|---|---|
| 1060 | 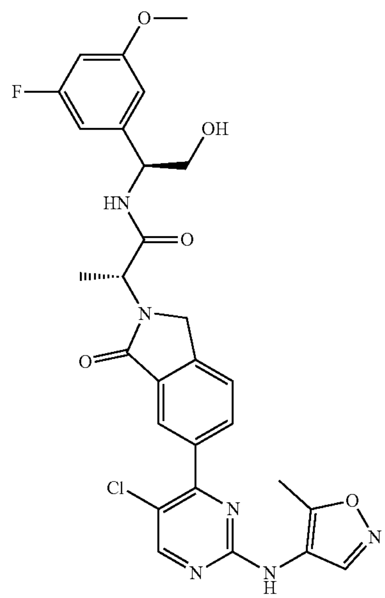 [SMILES: COc1cc(F)cc([C@@H](CO)NC(=O)[C@@H](C)N2Cc3ccc(-c4nc(Nc5cnoc5C)ncc4Cl)cc3C2=O)c1] | (2R)-2-(6-{5-chloro-2-[(5-methyl-1-2-oxazol-4-yl)amino]pyrimidin-4-yl}-1-oxo-2,3-dihydro-1H-isoindol-2-yl)-N-[(1S)-1-(3-fluoro-5-methoxyphenyl)-2-hydroxyethyl]propanamide | 581 |
| 1061 | 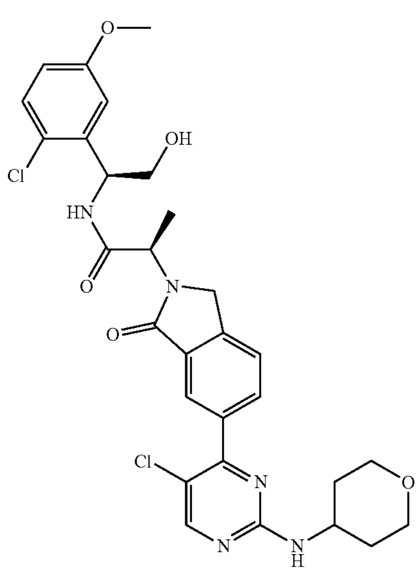 [SMILES: COc1ccc(Cl)c([C@@H](CO)NC(=O)[C@@H](C)N2Cc3ccc(-c4nc(NC5CCOCC5)ncc4Cl)cc3C2=O)c1] | (2R)-2-(6-{5-chloro-2-[(oxan-4-yl)amino]pyrimidin-4-yl}-1-oxo-2,3-dihydro-1H-isoindol-2-yl)-N-[(1S)-1-(2-chloro-5-methoxyphenyl)-2-hydroxyethyl]propanamide | M −H ion 598 |

-continued
| Example | Structure | Name | MS Data [M +H]+ unless specified |
|---|---|---|---|
| 1062 | 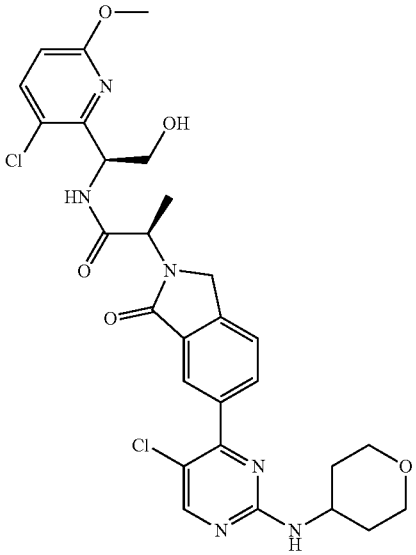 [SMILES: COc1ccc(Cl)c([C@@H](CO)NC(=O)[C@@H](C)N2Cc3ccc(-c4nc(NC5CCOCC5)ncc4Cl)cc3C2=O)n1] | (2R)-2-(6-{5-chloro-2-[(oxan-4-yl)amino]pyrimidin-4-yl}-1-oxo-2,3-dihydro-1H-isoindol-2-yl)-N-[(1S)-1-(3-chloro-6-methoxypyridin-2-yl)-2-hydroxyethyl]propanamide | M −H ion 599 |
| 1063 | 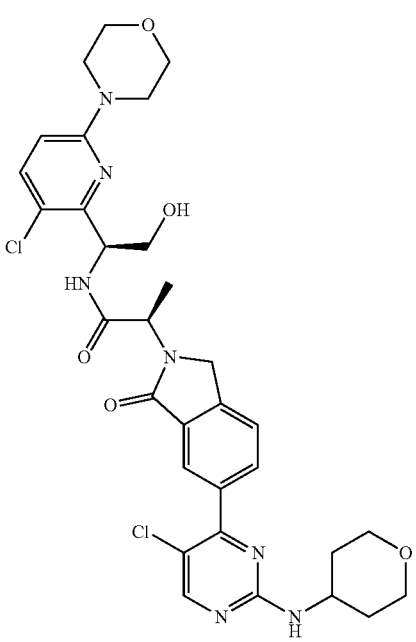 | (2R)-2-(6-{5-chloro-2-[(oxan-4-yl)amino]pyrimidin-4-yl}-1-oxo-2,3-dihydro-1H-isoindol-2-yl)-N-[(1S)-1-[3-chloro-6-(morpholin-4-yl)pyridin-2-yl]-2-hydroxyethyl]propanamide | M −H ion 654 |

| Example | Structure | Name | MS Data [M +H]+ unless specified |
|---|---|---|---|
| 1064 | 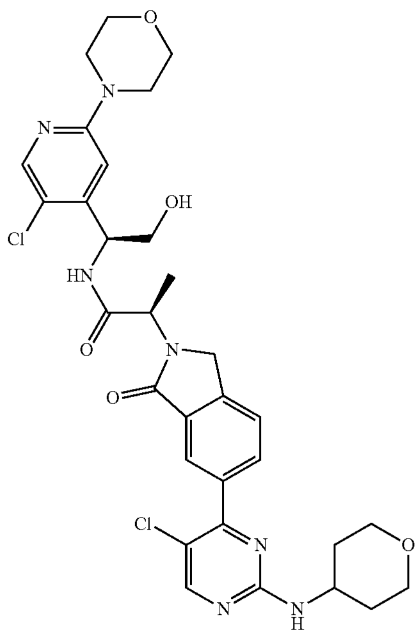 [SMILES: C[C@H](C(=O)N[C@H](CO)c1cc(N2CCOCC2)ncc1Cl)N1Cc2ccc(-c3nc(NC4CCOCC4)ncc3Cl)cc2C1=O] | (2R)-N-[(1S)-1-[5-chloro-2-(morpholin-4-yl)pyridin-4-yl]-2-hydroxyethyl]-2-(6-{5-chloro-2-[(oxan-4-yl)amino]pyrimidin-4-yl{-1-oxo-2,3-dihydro-1H-isoindol-2-yl)propanamide | M −H 645 |
| 1065 | 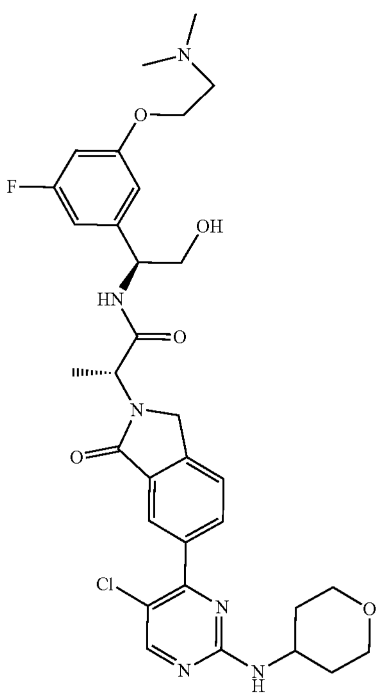 [SMILES: C[C@H](C(=O)N[C@H](CO)c1cc(F)cc(OCCN(C)C)c1)N1Cc2ccc(-c3nc(NC4CCOCC4)ncc3Cl)cc2C1=O] | (2R)-2-(6-{5-chloro-2-[(oxan-4-yl)amino]pyrimidin-4-yl}-1-oxo-2,3-dihydro-1H-isoindol-2-yl)-N-[(1S)-1-{3-[2-(dimethylamino)ethoxy]-5-fluorophenyl}-2-hydroxyethyl]propanamide | M −H 639 |

| Example | Structure | Name | MS Data [M +H]+ unless specified |
|---|---|---|---|
| 1066 | 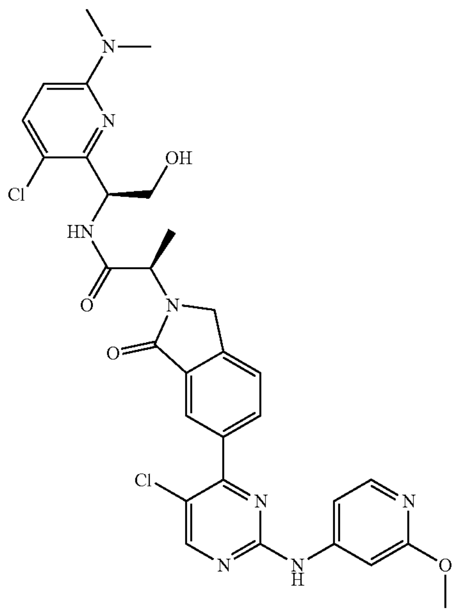 [SMILES: COc1cc(Nc2ncc(Cl)c(-c3ccc4c(c3)C(=O)N([C@H](C)C(=O)N[C@H](CO)c3nc(N(C)C)ccc3Cl)C4)n2)ccn1] | (2R)-2-(6-{5-chloro-2-[(2-methoxypyridin-4-yl)amino]pyrimidin-4-yl}-1-oxo-2,3-dihydro-1H-isoindol-2-yl)-N-[(1S)-1-[3-chloro-6-(dimethylamino)pyridin-2-yl]-2-hydroxyethyl]propanamide | M −H ion 635 |
| 1067 | 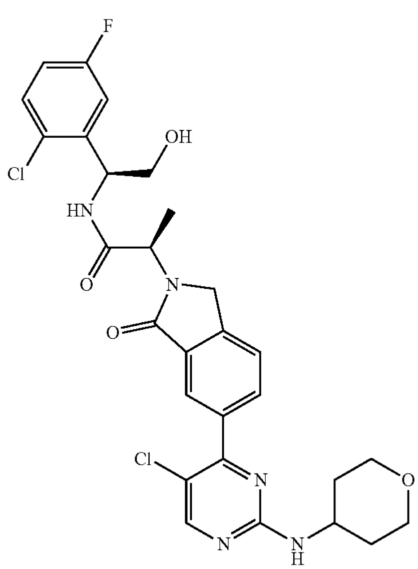 [SMILES: C[C@H](C(=O)N[C@H](CO)c1cc(F)ccc1Cl)N1Cc2ccc(-c3nc(NC4CCOCC4)ncc3Cl)cc2C1=O] | (2R)-2-(6-{5-chloro-2-[(oxan-4-yl)amino]pyrimidin-4-yl}-1-oxo-2,3-dihydro-1H-isoindol-2-yl)-N-[(1S)-1-(2-chloro-5-fluorophenyl)-2-hydroxyethyl]propanamide | 588 |

| Example | Structure | Name | MS Data [M +H]+ unless specified |
|---|---|---|---|
| 1068 | 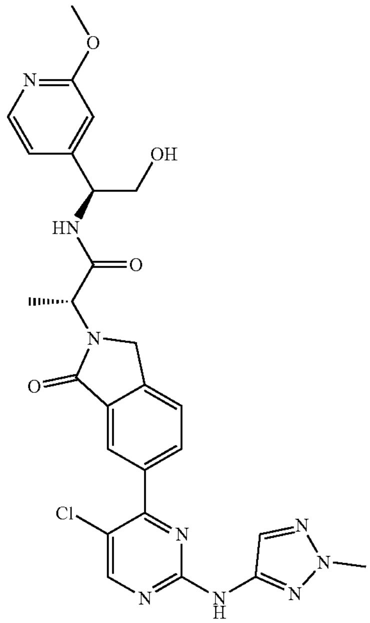 [SMILES: COc1cc([C@@H](CO)NC(=O)[C@@H](C)N2Cc3ccc(-c4nc(Nc5cnn(C)n5)ncc4Cl)cc3C2=O)ccn1] | (2R)-2-(6-{5-chloro-2-[(2-methyl-2H-1,2,3-triazol-4-yl)amino]pyrimidin-4-yl}-1-oxo-2,3-dihydro-1H-isoindol-2-yl)-N-[(1S)-2-hydroxy-1-(2-methoxypyridin-4-yl)ethyl]propanamide | 564 |
| 1069 | 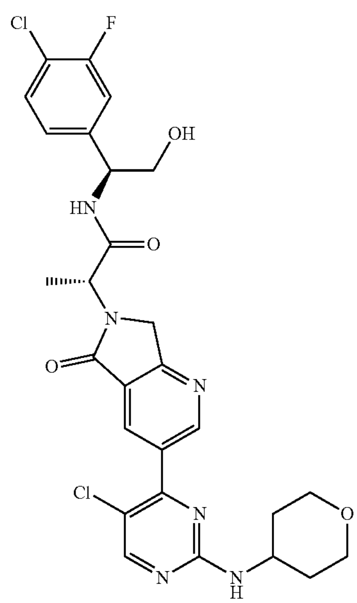 [SMILES: C[C@H](C(=O)N[C@H](CO)c1ccc(Cl)c(F)c1)N1Cc2ncc(-c3nc(NC4CCOCC4)ncc3Cl)cc2C1=O] | (2R)-2-(3-{5-chloro-2-[(oxan-4-yl)amino]pyrimidin-4-yl}-5-oxo-5H,6H,7H-pyrrolo[3,4-b]pyridin-6-yl)-N-[(1S)-1-(4-chloro-3-fluorophenyl)-2-hydroxyethyl]propanamide | 589 |

-continued

| Example | Structure | Name | MS Data [M +H]+ unless specified |
|---|---|---|---|
| 1070 | 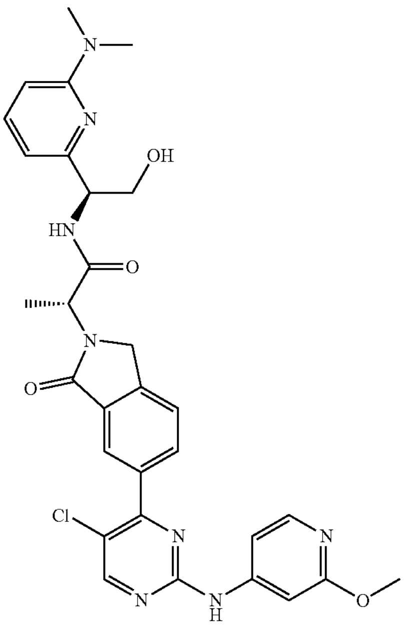 [SMILES: COc1cc(Nc2ncc(Cl)c(-c3ccc4c(c3)C(=O)N([C@H](C)C(=O)N[C@H](CO)c3cccc(N(C)C)n3)C4)n2)ccn1] | (2R)-2-(6-{5-chloro-2-[(2-methoxypyridin-4-yl)amino]pyrimidin-4-yl}-1-oxo-2,3-dihydro-1H-isoindol-2-yl)-N-[(1S)-1[6-(dimethylamino)pyridin-2-yl]-2-hydroxyethyl]propanamide | 603 |
| 1071 | 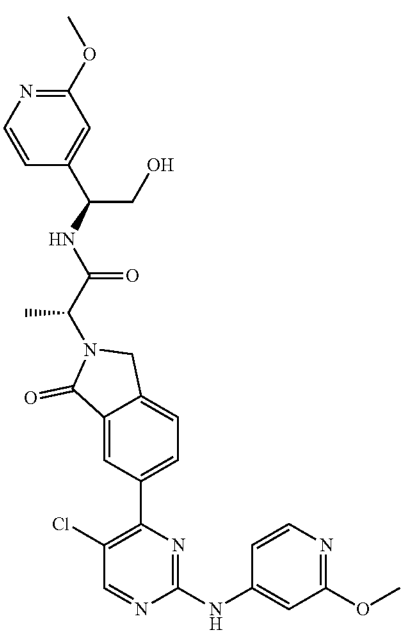 [SMILES: COc1cc(Nc2ncc(Cl)c(-c3ccc4c(c3)C(=O)N([C@H](C)C(=O)N[C@H](CO)c3ccnc(OC)c3)C4)n2)ccn1] | (2R)-2-(6-{5-chloro-2-[(2-methoxypyridin-4-yl)amino]pyrimidin-4-yl}-1-oxo-2,3-dihydro-1H-isoindol-2-yl)-N-[(1S)-2-hydroxy-1-(2-methoxypyridin-4-yl)ethyl]propanamide | 590 |

| Example | Structure | Name | MS Data [M+H]+ unless specified |
|---|---|---|---|
| 1072 | 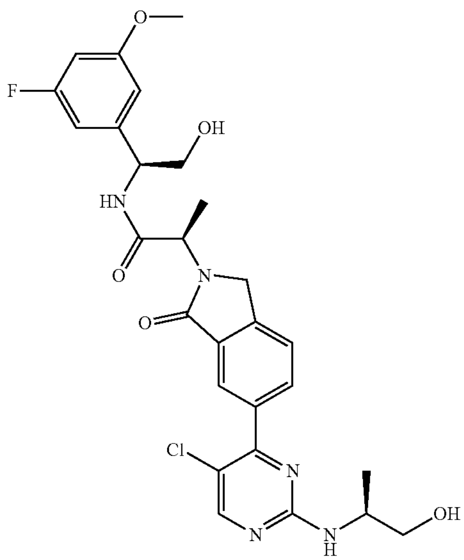 [SMILES: COc1cc(F)cc([C@@H](CO)NC(=O)[C@@H](C)N2Cc3ccc(-c4nc(N[C@@H](C)CO)ncc4Cl)cc3C2=O)c1] | (2R)-2-[6-(5-chloro-2-{[(2S)-1-hydroxypropan-2-yl]amino}pyrimidin-4-yl)-1-oxo-2,3-dihydro-1H-isoindol-2-yl]-N-[(1S)-1-(3-fluoro-5-methoxyphenyl)-2-hydroxyethyl]propanamide | 558 |
| 1073 | 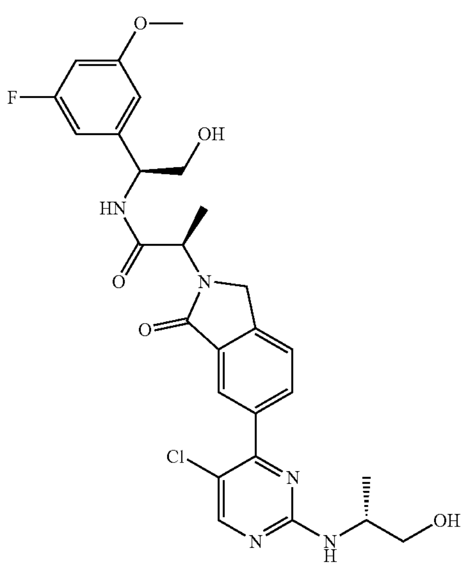 [SMILES: COc1cc(F)cc([C@@H](CO)NC(=O)[C@@H](C)N2Cc3ccc(-c4nc(N[C@H](C)CO)ncc4Cl)cc3C2=O)c1] | (2R)-2-[6-(5-chloro-2-{[(2R)-1-hydroxypropan-2-yl]amino}pyrimidin-4-yl)-1-oxo-2,3-dihydro-1H-isoindol-2-yl]-N-[(1S)-1-(3-fluoro-5-methoxyphenyl)-2-hydroxyethyl]propanamide | M−H ion 556 |

-continued

| Example | Structure | Name | MS Data [M+H]+ unless specified |
|---|---|---|---|
| 1074 | 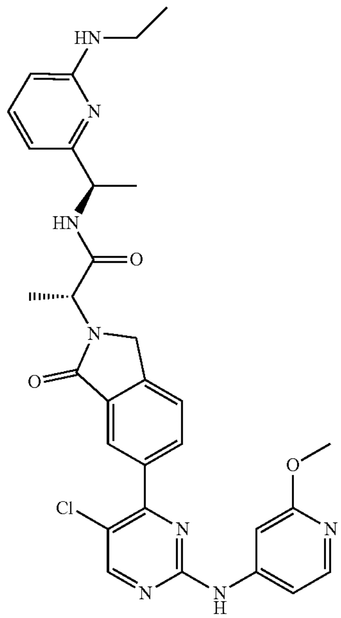 [SMILES: CCNc1cccc([C@@H](C)NC(=O)[C@@H](C)N2Cc3ccc(-c4nc(Nc5ccnc(OC)c5)ncc4Cl)cc3C2=O)n1] | (2R)-2-(6-{5-chloro-2-[(2-methoxypyridin-4-yl)amino]pyrimidin-4-yl}-1-oxo-2,3-dihydro-1H-isoindol-2-yl)-N-[(1R)-1-[6-(ethylamino)pyridin-2-yl]ethyl]propanamide | 587 |
| 1075 | 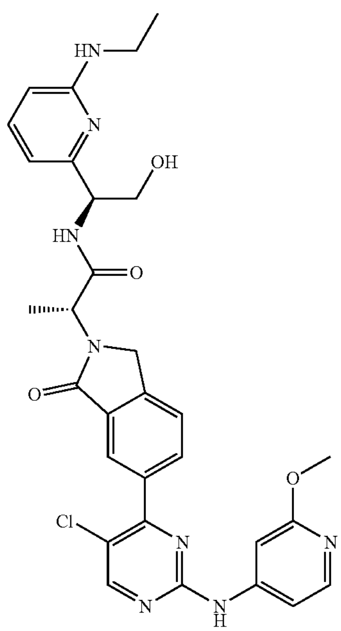 [SMILES: CCNc1cccc([C@@H](CO)NC(=O)[C@@H](C)N2Cc3ccc(-c4nc(Nc5ccnc(OC)c5)ncc4Cl)cc3C2=O)n1] | (2R)-2-(6-{5-chloro-2-[(2-methoxypyridin-4-yl)amino]pyrimidin-4-yl}-1-oxo-2,3-dihydro-1H-isoindol-2-yl)-N-[(1S)-1-[6-(ethylamino)pyridin-2-yl]-2-hydroxyethyl]propanamide | 603 |

-continued

| Example | Name | MS Data [M +H]+ unless specified |
|---|---|---|
| 1076 | (2R)-2-[6-(5-chloro-2-{[trans-4-hydroxycyclohexyl]amino}pyrimidin-4-yl)-1-oxo-2,3-dihydro-1H-isoindol-2-yl]N-[(1S)-1-(3-fluoro-5-methoxyphenyl)-2-hydroxyethyl]propanamide | M −H ion 596 |
| 1077 | (2R)-2-(6-{5-chloro-2-[(3-methyl-1,2-oxazol-5-yl)amino]pyrimidin-4-yl}-1-oxo-2,3-dihydro-1H-isoindol-2-yl)-N-[(1R)-1-[6-(4-methylpiperazin-1-yl)pyridin-2-yl]ethyl]propanamide | 616 |

-continued

| Example | Structure | Name | MS Data [M +H]+ unless specified |
|---|---|---|---|
| 1078 | 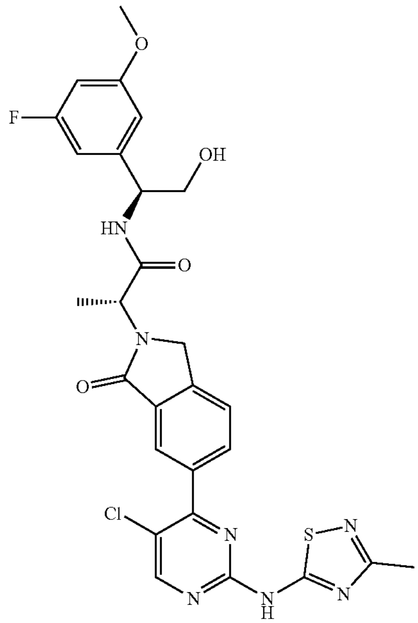 [SMILES: COc1cc(F)cc([C@@H](CO)NC(=O)[C@@H](C)N2Cc3ccc(-c4nc(Nc5nc(C)ns5)ncc4Cl)cc3C2=O)c1] | (2R)-2-(6-{5-chloro-2-[(3-methyl-1,2,4-thiadiazol-5-yl)amino]pyrimidin-4-yl}-1-oxo-2,3-dihydro-1H-isoindol-2-yl)-N-[(1S)-1-(3-fluoro-5-methoxyphenyl)-2-hydroxyethyl]propanamide | M −H 596 |
| 1079 | 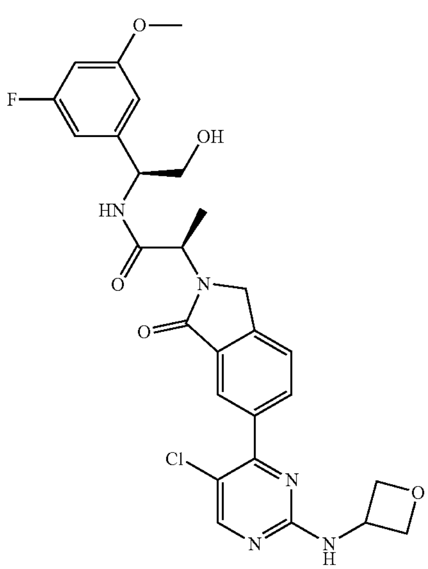 [SMILES: COc1cc(F)cc([C@@H](CO)NC(=O)[C@@H](C)N2Cc3ccc(-c4nc(NC5COC5)ncc4Cl)cc3C2=O)c1] | (2R)-2-(6-{5-chloro-2-[(oxetan-3-yl)amino]pyrimidin-4-yl}-1-oxo-2,3-dihydro-1H-isoindol-2-yl)-N-[(1S)-1-(3-fluoro-5-methoxyphenyl)-2-hydroxyethyl]propanamide | 556 |

-continued

| Example | Structure | Name | MS Data [M +H]+ unless specified |
|---|---|---|---|
| 1080 | 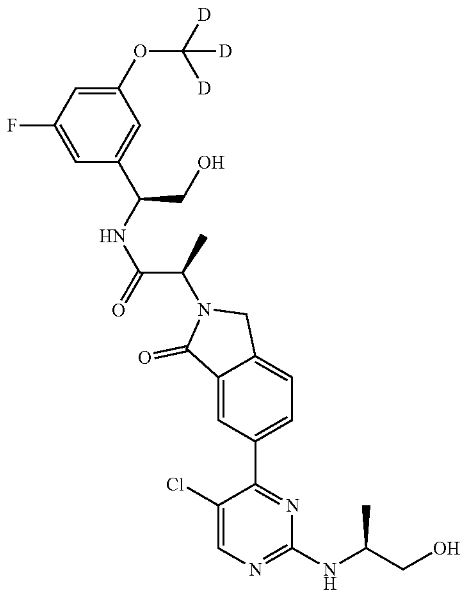 [SMILES: [2H]C([2H])([2H])Oc1cc(F)cc([C@@H](CO)NC(=O)[C@@H](C)N2Cc3ccc(-c4nc(N[C@@H](C)CO)ncc4Cl)cc3C2=O)c1] | (2R)-2-[6-(5-chloro-2-{[(2S)-1-hydroxypropan-2-yl]amino}pyrimidin-4-yl)-1-oxo-2,3-dihydro-1H-isoindol-2-yl]-N-[(1S)-1-[3-fluoro-5-trideuteromethoxyphenyl]-2-hydroxyethyl]propanamide | 561 |
| 1081 | 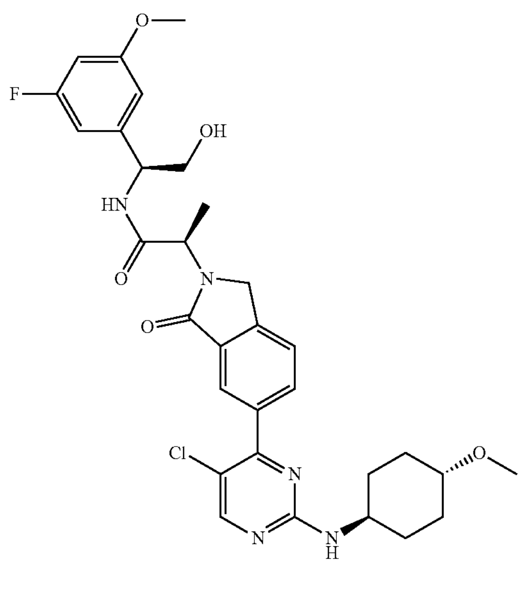 [SMILES: COc1cc(F)cc([C@@H](CO)NC(=O)[C@@H](C)N2Cc3ccc(-c4nc(N[C@H]5CC[C@H](OC)CC5)ncc4Cl)cc3C2=O)c1] | (2R)-2-[6-(5-chloro-2-{[trans-4-methoxycyclohexyl]amino}pyrimidin-4-yl)-1-oxo-2,3-dihydro-1H-isoindol-2-yl]-N-[(1S)-1-(3-fluoro-5-methoxyphenyl)-2-hydroxyethyl]propanamide | M −H 610 |

| Example | Structure | Name | MS Data [M +H]+ unless specified |
|---|---|---|---|
| 1082 | 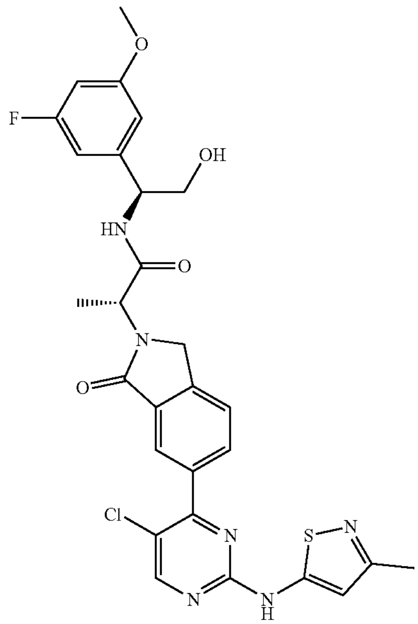 | (2R)-2-(6-{5-chloro-2-[(3-methyl-1,2-thiazol-5-yl)amino]pyrimidin-4-yl}-1-oxo-2,3-dihydro-1H-isoindol-2-yl)-N-[(1S)-1-(3-fluoro-5-methoxyphenyl)-2-hydroxyethyl]propanamide | 597 |
| 1083 | 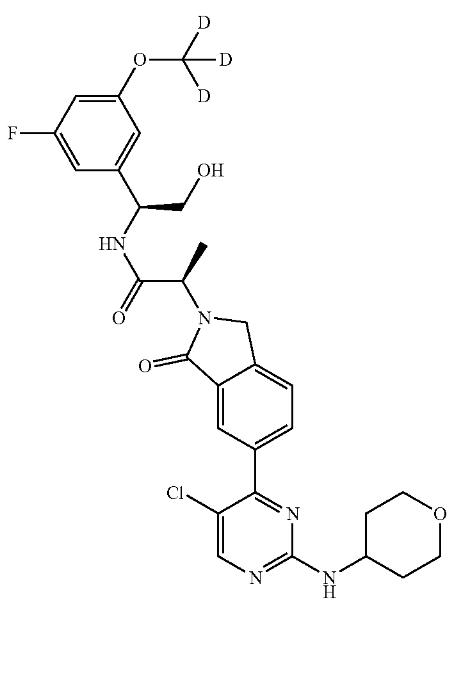 [SMILES: [2H]C([2H])([2H])Oc1cc(F)cc([C@@H](CO)NC(=O)[C@@H](C)N2Cc3ccc(-c4nc(NC5CCOCC5)ncc4Cl)cc3C2=O)c1] | (2R)-2-(6-{5-chloro-2-[(oxan-4-yl)amino]pyrimidin-4-yl}-1-oxo-2,3-dihydro-1H-isoindol-2-yl)-N-[(1S)-1-[3-fluoro-5-trideuteromethoxyphenyl]-2-hydroxyethyl]propanamide | M −H ion 585 |

| Example | Structure | Name | MS Data [M +H]+ unless specified |
|---|---|---|---|
| 1084 | 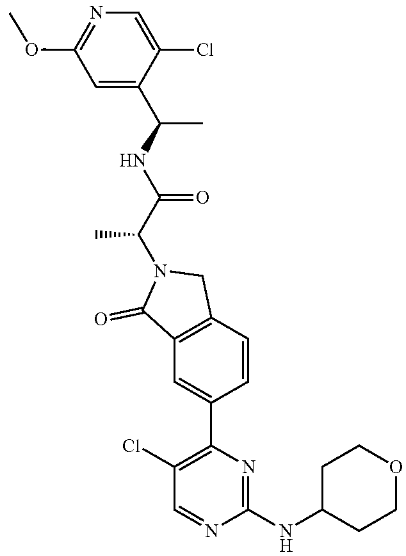 | (2R)-2-(6-{5-chloro-2-[(oxan-4-yl)amino]pyrimidin-4-yl}-1-oxo-2,3-dihydro-1H-isoindol-2-yl)-N-[(1R)-1-(5-chloro-2-methoxypyridin-4-yl)ethyl]propanamide | 585 |
| 1085 | 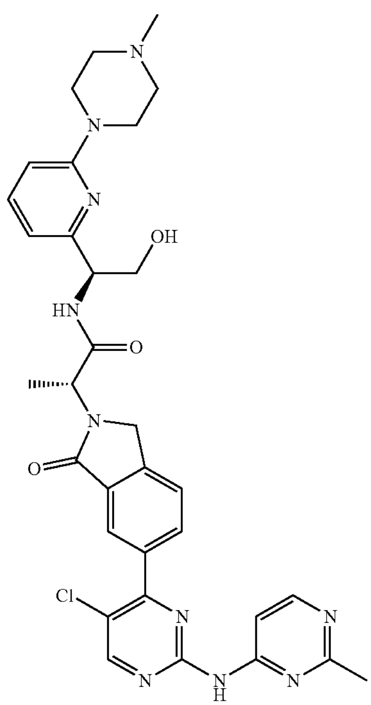 [SMILES: Cc1nccc(Nc2ncc(Cl)c(-c3ccc4c(c3)C(=O)N([C@H](C)C(=O)N[C@H](CO)c3cccc(N5CCN(C)CC5)n3)C4)n2)n1] | (2R)-2-(6-{5-chloro-2-[(2-methylpyrimidin-4-yl)amino]pyrimidin-4-yl}-1-oxo-2,3-dihydro-1H-isoindol-2-yl)-N-[(1S)-2-hydroxy-1-[6-(4-methylpiperazin-1-yl)pyridin-2-yl]ethyl]propanamide | 643 |

-continued

| Example | Structure | Name | MS Data [M +H]+ unless specified |
|---|---|---|---|
| 1086 | 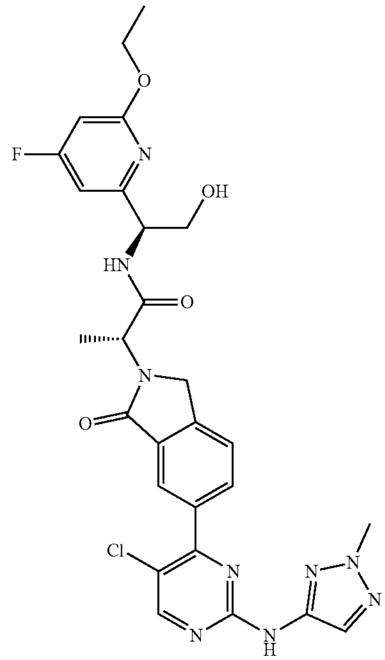 [SMILES: CCOc1cc(F)cc([C@@H](CO)NC(=O)[C@@H](C)N2Cc3ccc(-c4nc(Nc5cnn(C)n5)ncc4Cl)cc3C2=O)n1] | (2R)-2-(6-{5-chloro-2-[(2-methyl-2H-1,2,3-triazol-4-yl)amino]pyrimidin-4-yl}-1-oxo-2,3-dihydro-1H-isoindol-2-yl)-N-[(1S)-1-(3-ethoxy-5-fluorophenyl)-2-hydroxyethyl]propanamide | 595 |
| 1087 | 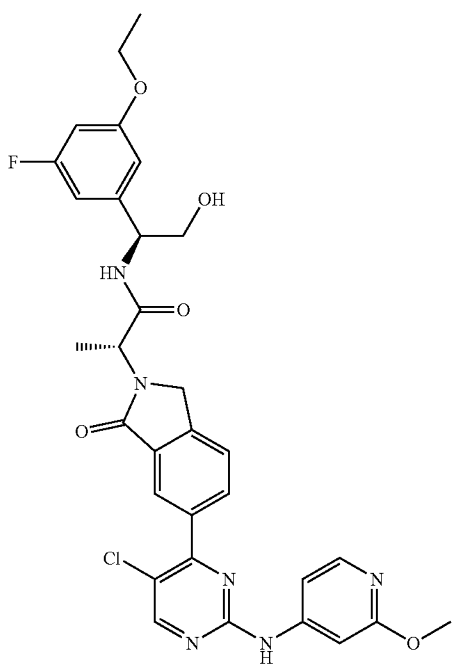 [SMILES: CCOc1cc(F)cc([C@@H](CO)NC(=O)[C@@H](C)N2Cc3ccc(-c4nc(Nc5ccnc(OC)c5)ncc4Cl)cc3C2=O)c1] | (2R)-2-(6-{5-chloro-2-[(2-methoxypyridin-4-yl)amino]pyrimidin-4-yl}-1-oxo-2,3-dihydro-1H-isoindol-2-yl)-N-[(1S)-1-(3-ethoxy-5-fluorophenyl)-2-hydroxyethyl]propanamide | 621 |

-continued

| Example | Structure | Name | MS Data [M +H]+ unless specified |
|---|---|---|---|
| 1088 | 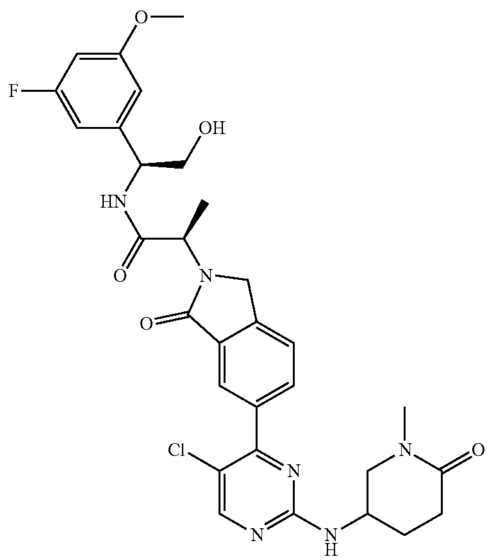 | (2R)-2-(6-{5-chloro-2-[(1-methyl-6-oxopiperidin-3-yl)amino]pyrimidin-4-yl}-1-oxo-2,3-dihydro-1H-isoindol-2-yl)-N-[(1S)-1-(3-fluoro-5-methoxyphenyl)-2-hydroxyethyl]propanamide | 609 [M −H]− |
| 1089 | 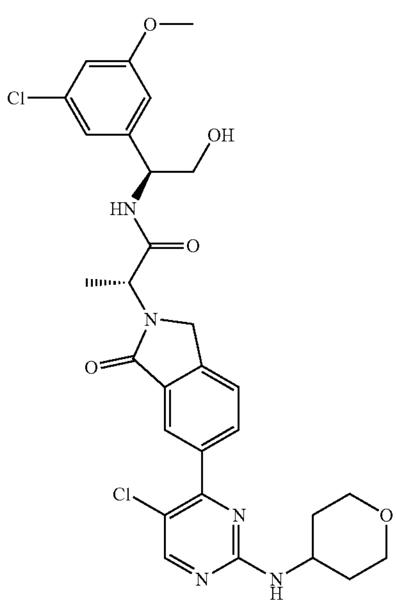 [SMILES: COc1cc(Cl)cc([C@@H](CO)NC(=O)[C@@H](C)N2Cc3ccc(-c4nc(NC5CCOCC5)ncc4Cl)cc3C2=O)c1] | (2R)-2-(6-{5-chloro-2-[(oxan-4-yl)amino]pyrimidin-4-yl}-1-oxo-2,3-dihydro-1H-isoindol-2-yl)-N-[(1S)-1-(3-chloro-5-methoxyphenyl)-2-hydroxyethyl]propanamide | 598 |

-continued

| Example | Structure | Name | MS Data [M +H]+ unless specified |
|---|---|---|---|
| 1090 | 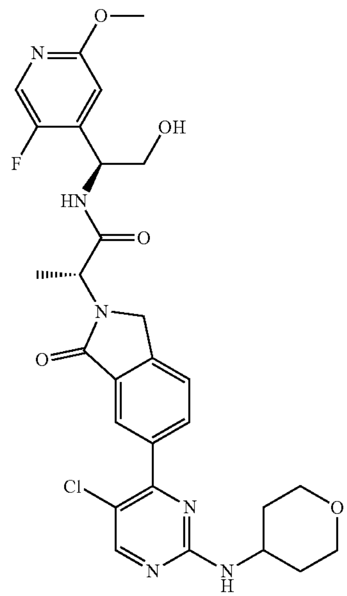 | (2R)-2-(6-{5-chloro-2-[(oxan-4-yl)amino]pyrimidin-4-yl}-1-oxo-2,3-dihydro-1H-isoindol-2-yl)-N-[(1S)-1-(5-fluoro-2-methoxypyridin-4-yl)-2-hydroxyethyl]propanamide | 585 |
| 1091 | 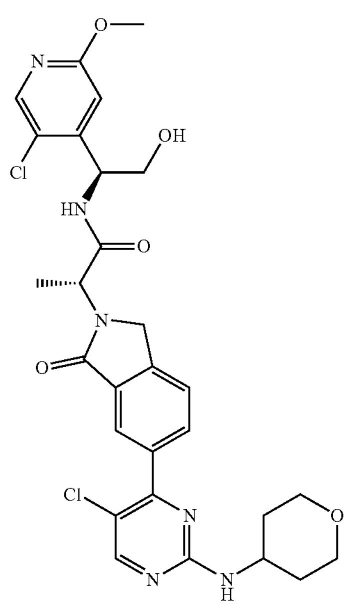 [SMILES: COc1cc([C@@H](CO)NC(=O)[C@@H](C)N2Cc3ccc(-c4nc(NC5CCOCC5)ncc4Cl)cc3C2=O)c(F)cn1] | (2R)-2-(6-{5-chloro-2-[(oxan-4-yl)amino]pyrimidin-4-yl}-1-oxo-2,3-dihydro-1H-isoindol-2-yl)-N-[(1S)-1-(5-chloro-2-methoxypyridin-4-yl)-2-hydroxyethyl]propanamide | M −H 599 |

-continued

| Example | Structure | Name | MS Data [M+H]+ unless specified |
|---|---|---|---|
| 1092 | 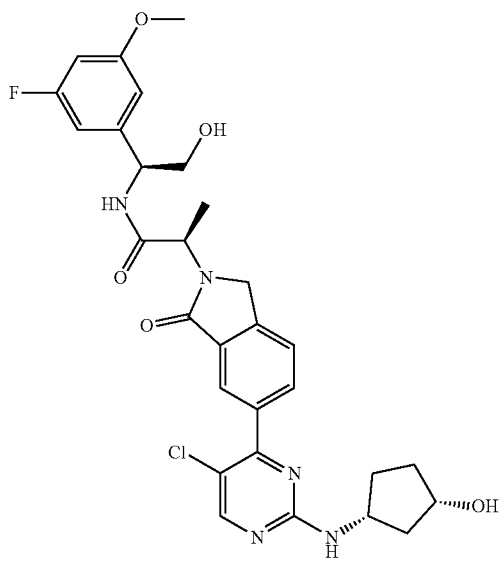 [SMILES: COc1cc(F)cc([C@@H](CO)NC(=O)[C@@H](C)N2Cc3ccc(-c4nc(N[C@@H]5CC[C@H](O)C5)ncc4Cl)cc3C2=O)c1] | (2R)-2-[6-(5-chloro-2-{[(1R,3S)-3-hydroxycyclopentyl]amino}pyrimidin-4-yl)-1-oxo-2,3-dihydro-1H-isoindol-2-yl]-N-[(1S)-1-(3-fluoro-5-methoxyphenyl)-2-hydroxyethyl]propanamide | M −H ion 582 |
| 1093 | 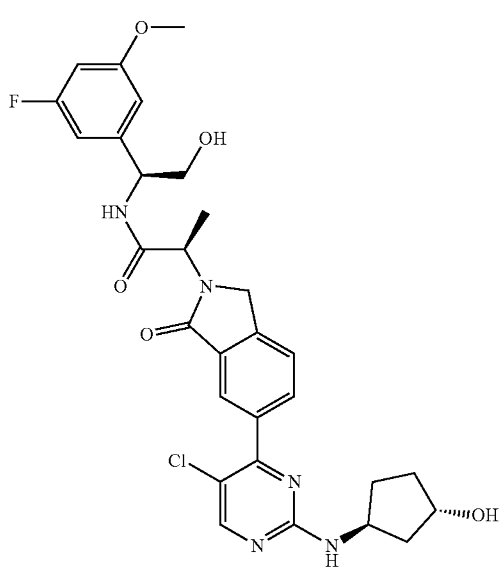 [SMILES: COc1cc(F)cc([C@@H](CO)NC(=O)[C@@H](C)N2Cc3ccc(-c4nc(N[C@H]5CC[C@H](O)C5)ncc4Cl)cc3C2=O)c1] | (2R)-2-[6-(5-chloro-2-{[(1S,3S)-3-hydroxycyclopentyl]amino}pyrimidin-4-yl)-1-oxo-2,3-dihydro-1H-isoindol-2-yl]-N-[(1S)-1-(3-fluoro-5-methoxyphenyl)-2-hydroxyethyl]propanamide | 582 |

-continued

| Example | Structure | Name | MS Data [M +H]+ unless specified |
|---|---|---|---|
| 1094 | 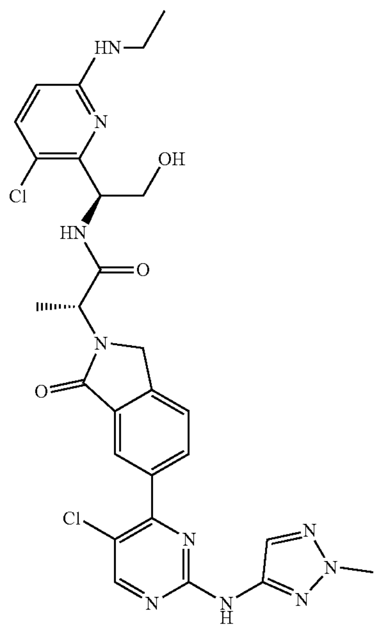 [SMILES: CCNc1ccc(Cl)c([C@@H](CO)NC(=O)[C@@H](C)N2Cc3ccc(-c4nc(Nc5cnn(C)n5)ncc4Cl)cc3C2=O)n1] | (2R)-2-(6-{5-chloro-2-[(2-methyl-2H-1,2,3-triazol-4-yl)amino]pyrimidin-4-yl}-1-oxo-2,3-dihydro-1H-isoindol-2-yl)-N-[(1S)-1-[3-chloro-6-(ethylamino)pyridin-2-yl]-2-hydroxyethyl]propanamide | 611 |
| 1095 | 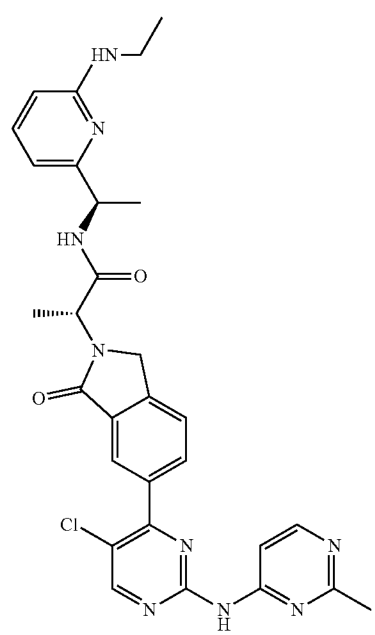 [SMILES: CCNc1cccc([C@@H](C)NC(=O)[C@@H](C)N2Cc3ccc(-c4nc(Nc5ccnc(C)n5)ncc4Cl)cc3C2=O)n1] | (2R)-2-(6-{5-chloro-2-[(2-methylpyrimidin-4-yl)amino]pyrimidin-4-yl}-1-oxo-2,3-dihydro-1H-isoindol-2-yl-N-[(1R)-1-[6-(ethylamino)pyridin-2-yl]ethyl]propanamide | 572 |

-continued

| Example | Structure | Name | MS Data [M+H]+ unless specified |
|---|---|---|---|
| 1096 | 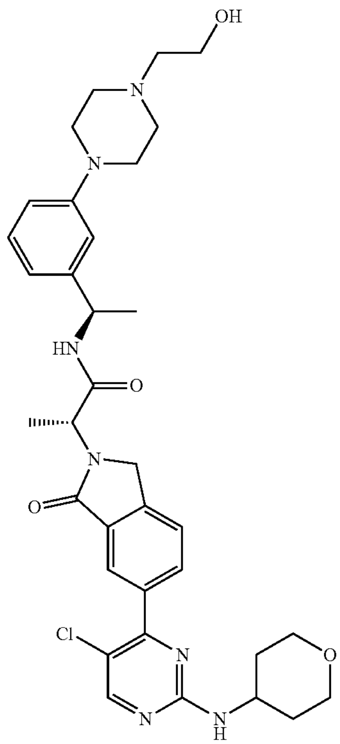 [SMILES: C[C@H](C(=O)N[C@H](C)c1cccc(N2CCN(CCO)CC2)c1)N1Cc2ccc(-c3nc(NC4CCOCC4)ncc3Cl)cc2C1=O] | (2R)-2-(6-{5-chloro-2-[(oxan-4-yl)amino]pyrimidin-4-yl}-1-oxo-2,3-dihydro-1H-isoindol-2-yl)-N-[(1R)-1-{3-[4-(2-hydroxyethyl)piperazin-1-yl]phenyl}ethyl]propanamide | 648 |
| 1097 | 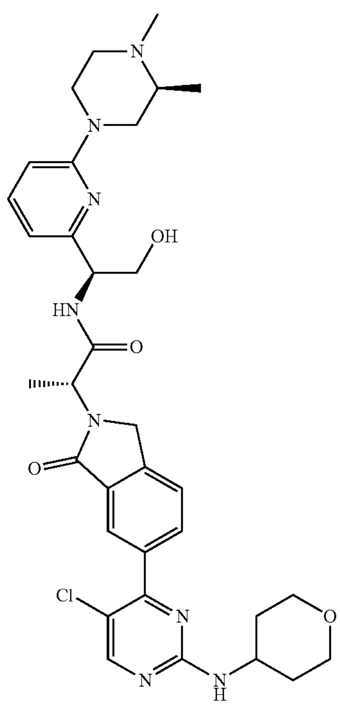 [SMILES: C[C@H](C(=O)N[C@H](CO)c1cccc(N2CCN(C)[C@@H](C)C2)n1)N1Cc2ccc(-c3nc(NC4CCOCC4)ncc3Cl)cc2C1=O] | (2R)-2-(6-{5-chloro-2-[(oxan-4-yl)amino]pyrimidin-4-yl}-1-oxo-2,3-dihydro-1H-isoindol-2-yl)-N-[(1S)-1-{6-[(3S)-3,4-dimethylpiperazin-1-yl]pyridin-2-yl}-2-hydroxyethyl]propanamide | M+H 649 |

-continued
| Example | Structure | Name | MS Data [M +H]+ unless specified |
|---|---|---|---|
| 1098 | 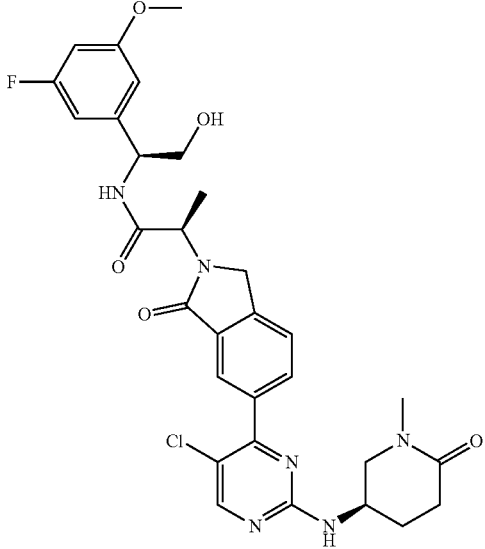 [SMILES: COc1cc(F)cc([C@@H](CO)NC(=O)[C@@H](C)N2Cc3ccc(-c4nc(N[C@@H]5CCC(=O)N(C)C5)ncc4Cl)cc3C2=O)c1] | (2R)-2-[6-(5-chloro-2-{[(3R)-1-methyl-6-oxopiperidin-3-yl]amino}pyrimidin-4-yl)-1-oxo-2,3-dihydro-1H-isoindol-2-yl]-N-[(1S)-1-(3-fluoro-5-methoxyphenyl)-2-hydroxyethyl]propanamide | M −H 609 |
| 1099 | 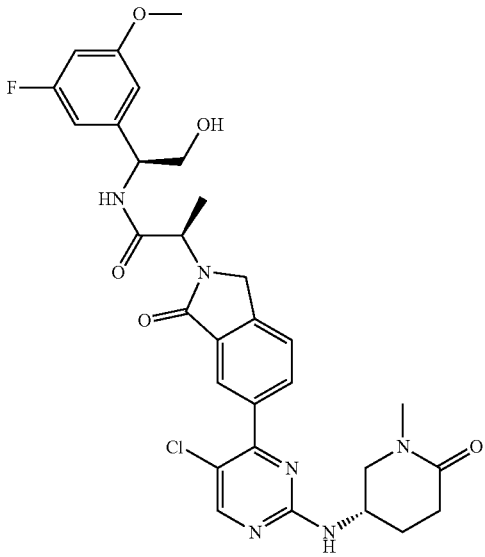 [SMILES: COc1cc(F)cc([C@@H](CO)NC(=O)[C@@H](C)N2Cc3ccc(-c4nc(N[C@H]5CCC(=O)N(C)C5)ncc4Cl)cc3C2=O)c1] | (2R)-2-[6-(5-chloro-2-{[(3S)-1-methyl-6-oxopiperidin-3-yl]amino}pyrimidin-4-yl)-1-oxo-2,3-dihydro-1H-isoindol-2-yl]-N-[(1S)-1-(3-fluoro-5-methoxyphenyl)-2-hydroxyethyl]propanamide | M −H 609 |

-continued
| Example | Structure | Name | MS Data [M +H]+ unless specified |
|---|---|---|---|
| 1100 | 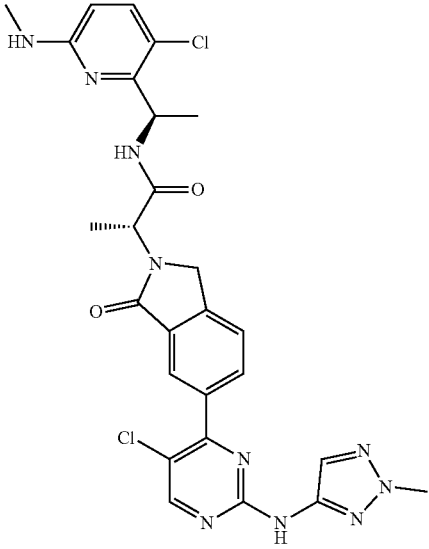 | (2R)-2-(6-{5-chloro-2-[(2-methyl-2H-1,2,3-triazol-4-yl)amino]pyrimidin-4-yl}-1-oxo-2,3-dihydro-1H-isoindol-2-yl)-N-[(1R)-1-[3-chloro-6-(methylamino)pyridin-2-yl]ethyl]propanamide | 581 |
| 1101 | 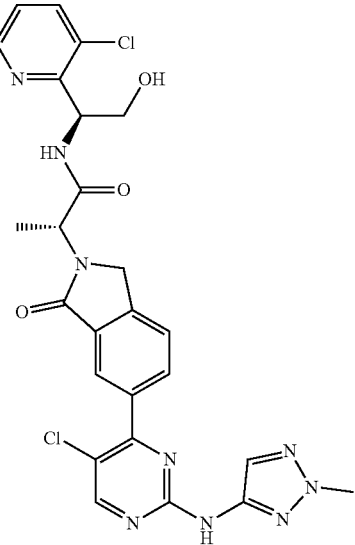 | (2R)-2-(6-{5-chloro-2-[(2-methyl-2H-1,2,3-triazol-4-yl)amino]pyrimidin-4-yl}-1-oxo-2,3-dihydro-1H-isoindol-2-yl)-N-[(1S)-1-[3-chloro-6-(methylamino)pyridin-2-yl]-2-hydroxyethyl]propanamide | 597 |

-continued

| Example | Structure | Name | MS Data [M +H]+ unless specified |
|---|---|---|---|
| 1102 | 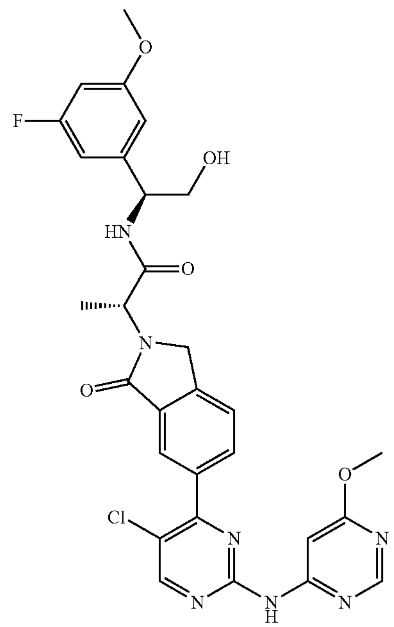 [SMILES: COc1cc(F)cc([C@@H](CO)NC(=O)[C@@H](C)N2Cc3ccc(-c4nc(Nc5cc(OC)ncn5)ncc4Cl)cc3C2=O)c1] | (2R)-2-(6-{5-chloro-2-[(6-methoxypyrimidin-4-yl)amino]pyrimidin-4-yl}-1-oxo-2,3-dihydro-1H-isoindol-2-yl)-N-[(1S)-1-(3-fluoro-5-methoxyphenyl)-2-hydroxyethyl]propanamide | 608 |
| 1103 | 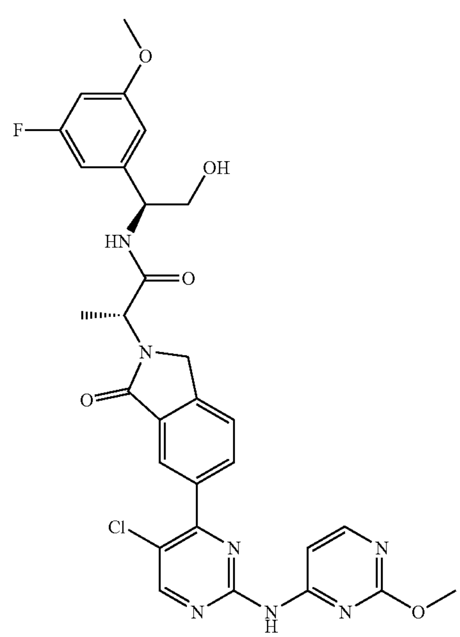 [SMILES: COc1cc(F)cc([C@@H](CO)NC(=O)[C@@H](C)N2Cc3ccc(-c4nc(Nc5ccnc(OC)n5)ncc4Cl)cc3C2=O)c1] | (2R)-2-(6-{5-chloro-2-[(2-methoxypyrimidin-4-yl)amino]pyrimidin-4-yl}-1-oxo-2,3-dihydro-1H-isoindol-2-yl)-N-[(1S)-1-(3-fluoro-5-methoxyphenyl)-2-hydroxyethyl]propanamide | 608 |

-continued

| Example | Structure | Name | MS Data [M +H]+ unless specified |
|---|---|---|---|
| 1104 | 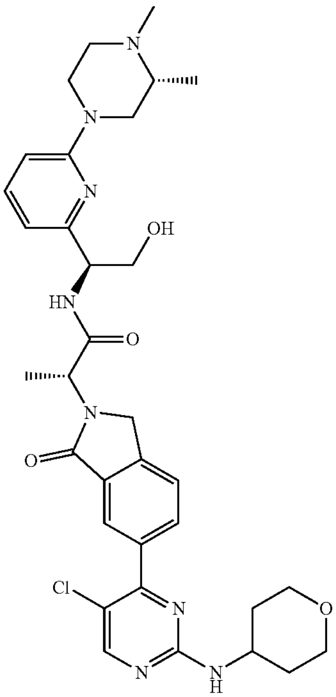 [SMILES: C[C@@H]1CN(c2cccc([C@@H](CO)NC(=O)[C@@H](C)N3Cc4ccc(-c5nc(NC6CCOCC6)ncc5Cl)cc4C3=O)n2)CCN1C] | (2R)-2-(6-}5-chloro-2-[(oxan-4-yl)amino]pyrimidin-4-yl}-1-oxo-2,3-dihydro-1H-isoindol-2-yl)-N-[(1S)-1-{6-[(3R)-3,4-dimethylpiperazin-1-yl]pyridin-2-yl}-2-hydroxyethyl]propanamide | M −H 647 |
| 1105 | 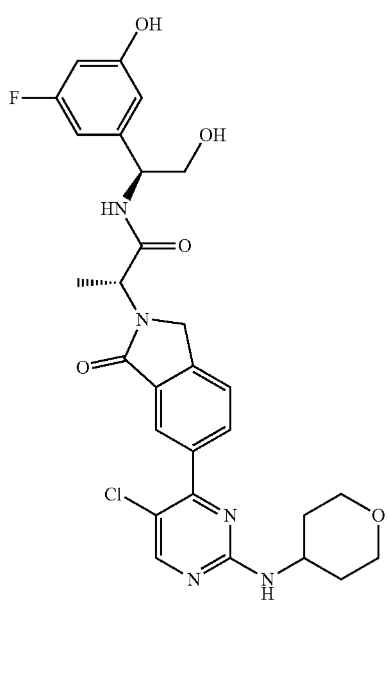 [SMILES: C[C@H](C(=O)N[C@H](CO)c1cc(O)cc(F)c1)N1Cc2ccc(-c3nc(NC4CCOCC4)ncc3Cl)cc2C1=O] | (2R)-2-(6-{5-chloro-2-[(oxan-4-yl)amino]pyrimidin-4-yl}-1-oxo-2,3-dihydro-1H-isoindol-2-yl)-N-[(1S)-1-(3-fluoro-5-hydroxyphenyl)-2-hydroxyethyl]propanamide | M −H 568 |

-continued

| Example | Structure | Name | MS Data [M +H]+ unless specified |
|---|---|---|---|
| 1106 | 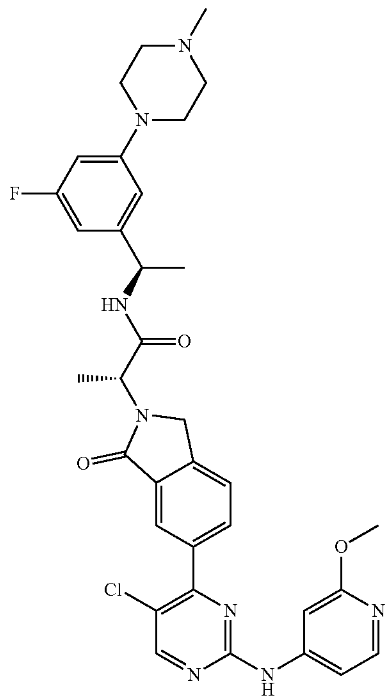 [SMILES: COc1cc(Nc2ncc(Cl)c(-c3ccc4c(c3)C(=O)N([C@H](C)C(=O)N[C@H](C)c3cc(F)cc(N5CCN(C)CC5)c3)C4)n2)ccn1] | (2R)-2-(6-{5-chloro-2-[(2-methoxypyridin-4-yl)amino]pyrimidin-4-yl}-1-oxo-2,3-dihydro-1H-isoindol-2-yl)-N-[(1R)-1-[3-fluoro-5-(4-methylpiperazin-1-yl)phenyl]ethyl]propanamide | 659 |
| 1107 | 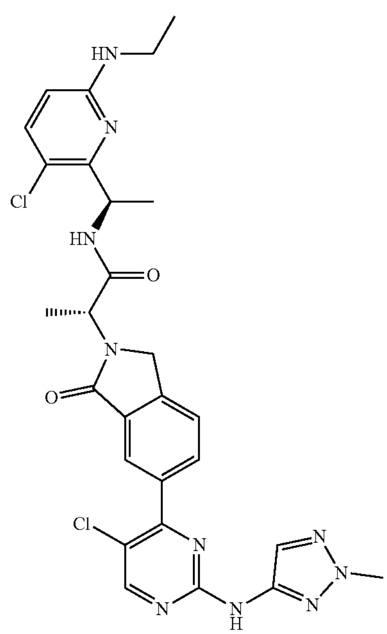 [SMILES: CCNc1ccc(Cl)c([C@@H](C)NC(=O)[C@@H](C)N2Cc3ccc(-c4nc(Nc5cnn(C)n5)ncc4Cl)cc3C2=O)n1] | (2R)-2-(6-{5-chloro-2-[(2-methyl-2H-1,2,3-triazol-4-yl)amino]pyrimidin-4-yl}-1-oxo-2,3-dihydro-1H-isoindol-2-yl)-N-[(1R)-1-[3-chloro-6-(ethylamino)pyridin-2-yl]ethyl]propanamide | 595 |

-continued
| Example | Structure | Name | MS Data [M +H]+ unless specified |
|---|---|---|---|
| 1108 | 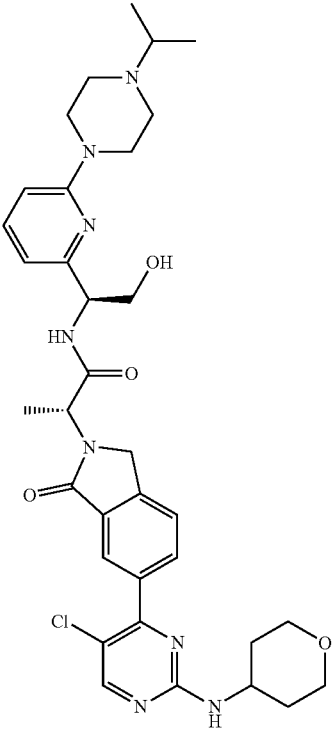 [SMILES: CC(C)N1CCN(c2cccc([C@@H](CO)NC(=O)[C@@H](C)N3Cc4ccc(-c5nc(NC6CCOCC6)ncc5Cl)cc4C3=O)n2)CC1] | (2R)-2-(6-{5-chloro-2-[(oxan-4-yl)amino]pyrimidin-4-yl}-1-oxo-2,3-dihydro-1H-isoindol-2-yl)-N-[(1S)-2-hydroxy-1-{6-[4-(propan-2-yl)piperazin-1-yl]pyridin-2-yl}ethyl]propanamide | M +H 663 |
| 1109 | 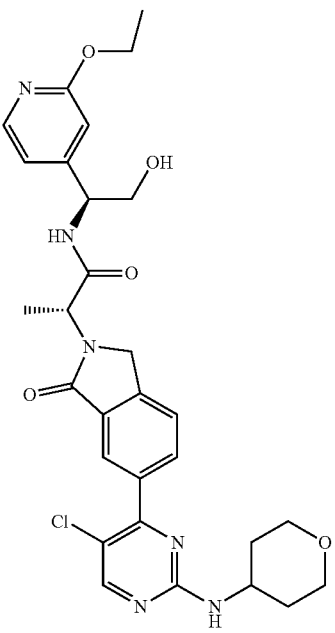 [SMILES: CCOc1cc([C@@H](CO)NC(=O)[C@@H](C)N2Cc3ccc(-c4nc(NC5CCOCC5)ncc4Cl)cc3C2=O)ccn1] | (2R)-2-(6-{5-chloro-2-[(oxan-4-yl)amino]pyrimidin-4-yl}-1-oxo-2,3-dihydro-1H-isoindol-2-yl)-N-[(1S)-1-(2-ethoxypyridin-4-yl)-2-hydroxyethyl]propanamide | 579 |

-continued

| Example | Structure | Name | MS Data [M +H]+ unless specified |
|---|---|---|---|
| 1110 | 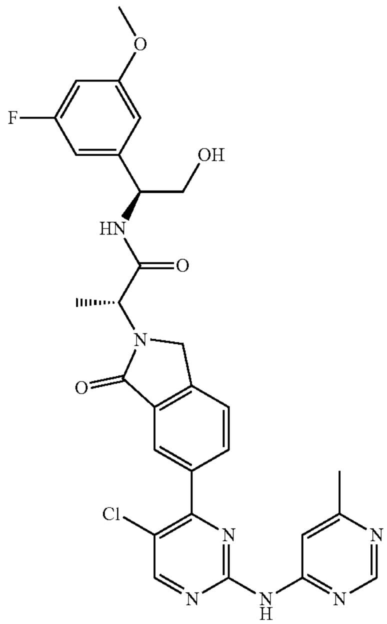 [SMILES: COc1cc(F)cc([C@@H](CO)NC(=O)[C@@H](C)N2Cc3ccc(-c4nc(Nc5cc(C)ncn5)ncc4Cl)cc3C2=O)c1] | (2R)-2-(6-{5-chloro-2-[(6-methylpyrimidin-4-yl)amino]pyrimidin-4-yl}-1-oxo-2,3-dihydro-1H-isoindol-2-yl)-N-[(1S)-1-(3-fluoro-5-methoxyphenyl)-2-hydroxyethyl]propanamide | 592 |
| 1111 | 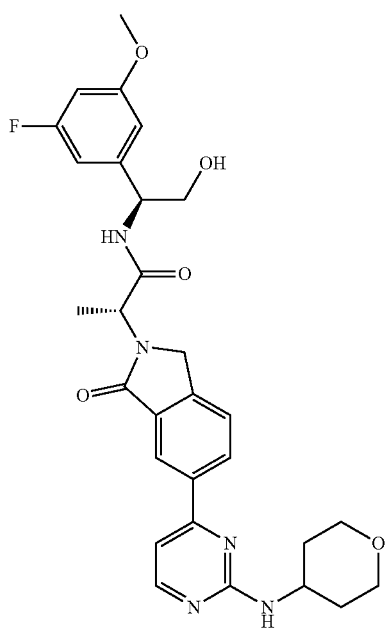 [SMILES: COc1cc(F)cc([C@@H](CO)NC(=O)[C@@H](C)N2Cc3ccc(-c4ccnc(NC5CCOCC5)n4)cc3C2=O)c1] | (2R)-N-[(1S)-1-(3-fluoro-5-methoxyphenyl)-2-hydroxyethyl]-2-(6-{2-[(oxan-4-yl)amino]pyrimidin-4-yl}-1-oxo-2,3-dihydro-1H-isoindol-2-yl)propanamide | 550 |

-continued

| Example | Structure | Name | MS Data [M +H]+ unless specified |
|---|---|---|---|
| 1112 | 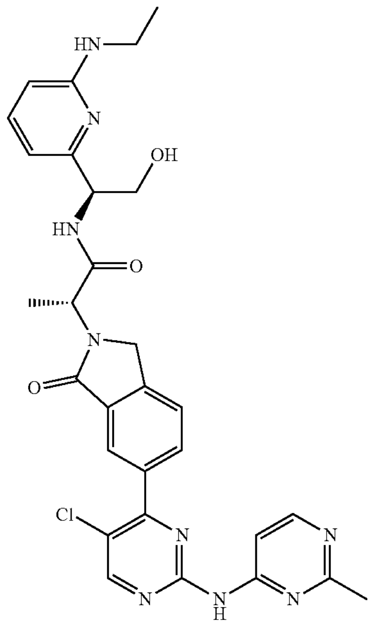 [SMILES: CCNc1cccc([C@@H](CO)NC(=O)[C@@H](C)N2Cc3ccc(-c4nc(Nc5ccnc(C)n5)ncc4Cl)cc3C2=O)n1] | (2R)-2-(6-{5-chloro-2-[(2-methylpyrimidin-4-yl)amino]pyrimidin-4-yl}-1-oxo-2,3-dihydro-1H-isoindol-2-yl)-N-[(1S)-1-[6-(ethylamino)pyridin-2-yl]-2-hydroxyethyl]propanamide | 588 |
| 1113 | 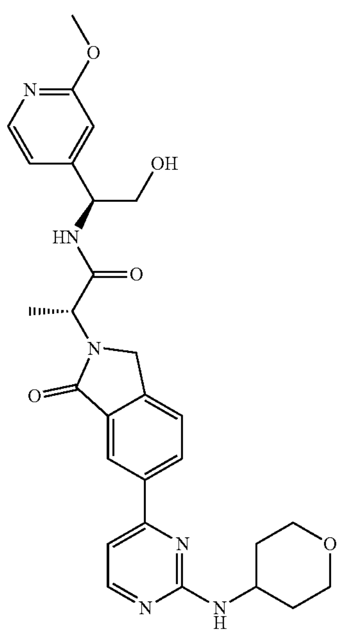 [SMILES: COc1cc([C@@H](CO)NC(=O)[C@@H](C)N2Cc3ccc(-c4ccnc(NC5CCOCC5)n4)cc3C2=O)ccn1] | (2R)-N-[(1S)-2-hydroxy-1-(2-methoxypyridin-4-yl)ethyl]-2-(6-{2-[(oxan-4-yl)amino]pyrimidin-4-yl}-1-oxo-2,3-dihydro-1H-isoindol-2-yl)propanamide | 533 |

-continued

| Example | Structure | Name | MS Data [M +H]+ unless specified |
|---|---|---|---|
| 1114 | 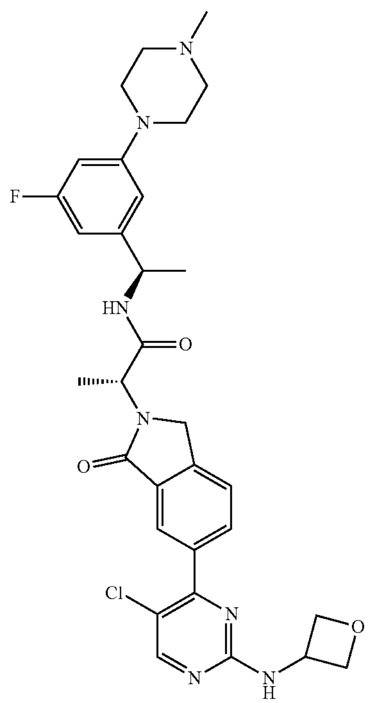 [SMILES: C[C@H](C(=O)N[C@H](C)c1cc(F)cc(N2CCN(C)CC2)c1)N1Cc2ccc(-c3nc(NC4COC4)ncc3Cl)cc2C1=O] | (2R)-2-(6-}5-chloro-2-[(oxetan-3-yl)amino]pyrimidin-4-yl}-1-oxo-2,3-dihydro-1H-isoindol-2-yl)-N-[(1R)-1-[3-fluoro-5-(4-methylpiperazin-1-yl)phenyl]ethyl]propanamide | 608 |
| 1115 | 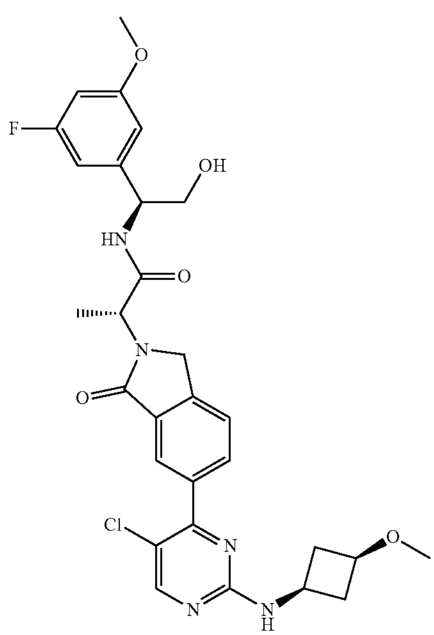 [SMILES: COc1cc(F)cc([C@@H](CO)NC(=O)[C@@H](C)N2Cc3ccc(-c4nc(N[C@H]5C[C@@H](OC)C5)ncc4Cl)cc3C2=O)c1] | (2R)-2-[6-(5-chloro-2-{[cis-3-methoxycyclobutyl]amino}pyrimidin-4-yl)-1-oxo-2,3-dihydro-1H-isoindol-2-yl]-N-[(1S)-1-(3-fluoro-5-methoxyphenyl)-2-hydroxyethyl]propanamide | [M −H]+ 582 |

-continued

| Example | Structure | Name | MS Data [M +H]+ unless specified |
|---|---|---|---|
| 1116 | 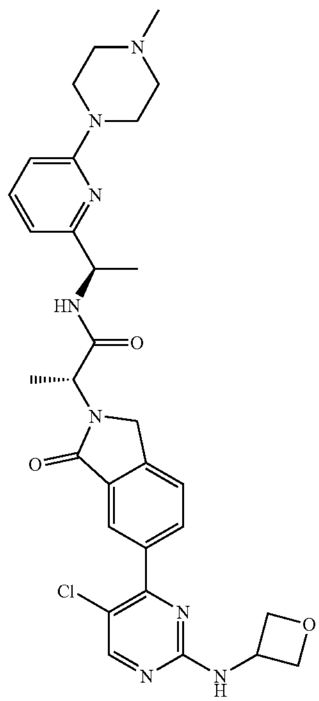 [SMILES: C[C@H](C(=O)N[C@H](C)c1cccc(N2CCN(C)CC2)n1)N1Cc2ccc(-c3nc(NC4COC4)ncc3Cl)cc2C1=O] | (2R)-2-(6-{5-chloro-2-[(oxetan-3-yl)amino]pyrimidin-4-yl}-1-oxo-2,3-dihydro-1H-isoindol-2-yl)-N-[(1R)-1-[6-(4-methylpiperazin-1-yl)pyridin-2-yl]ethyl]propanamide | 591 |
| 1117 | 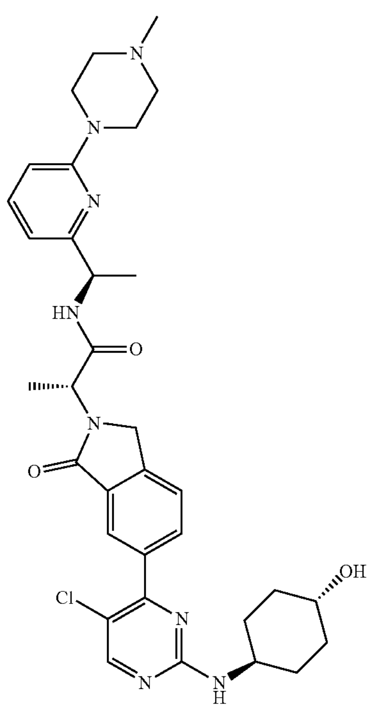 [SMILES: C[C@H](C(=O)N[C@H](C)c1cccc(N2CCN(C)CC2)n1)N1Cc2ccc(-c3nc(N[C@H]4CC[C@H](O)CC4)ncc3Cl)cc2C1=O] | (2R)-2-[6-(5-chloro-2-{[trans-4-hydroxycyclohexyl]amino}pyrimidin-4-yl)-1-oxo-2,3-dihydro-1H-isoindol-2-yl]-N-[(1R)-1-[6-(4-methylpiperazin-1-yl)pyridin-2-yl]ethyl]propanamide | 633 |

| Example | Structure | Name | MS Data [M+H]+ unless specified |
|---|---|---|---|
| 1118 | 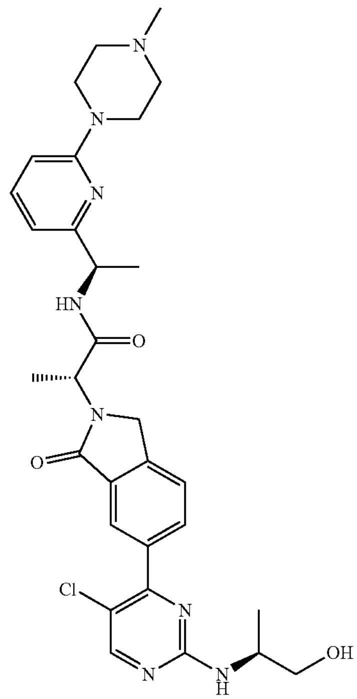 [SMILES: C[C@H](C(=O)N[C@H](C)c1cccc(N2CCN(C)CC2)n1)N1Cc2ccc(-c3nc(N[C@@H](C)CO)ncc3Cl)cc2C1=O] | (2R)-2-[6-(5-chloro-2-{[(2S)-1-hydroxypropan-2-yl]amino}pyrimidin-4-yl)-1-oxo-2,3-dihydro-1H-isoindol-2-yl]-N-[(1R)-1-[6-(4-methylpiperazin-1-yl)pyridin-2-yl]ethyl]propanamide | 593 |
| 1119 | 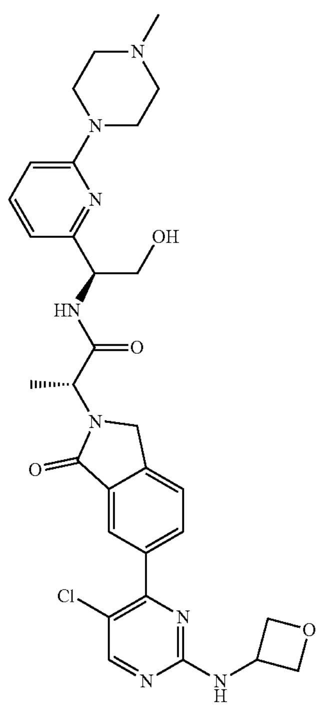 [SMILES: C[C@H](C(=O)N[C@H](CO)c1cccc(N2CCN(C)CC2)n1)N1Cc2ccc(-c3nc(NC4COC4)ncc3Cl)cc2C1=O] | (2R)-2-(6-{5-chloro-2-[(oxetan-3-yl)amino]pyrimidin-4-yl}-1-oxo-2,3-dihydro-1H-isoindol-2-yl)-N-[(1S)-2-hydroxy-1-[6-(4-methylpiperazin-1-yl)pyridin-2-yl]ethyl]propanamide | 607 |

-continued

| Example | Structure | Name | MS Data [M+H]+ unless specified |
|---|---|---|---|
| 1120 | 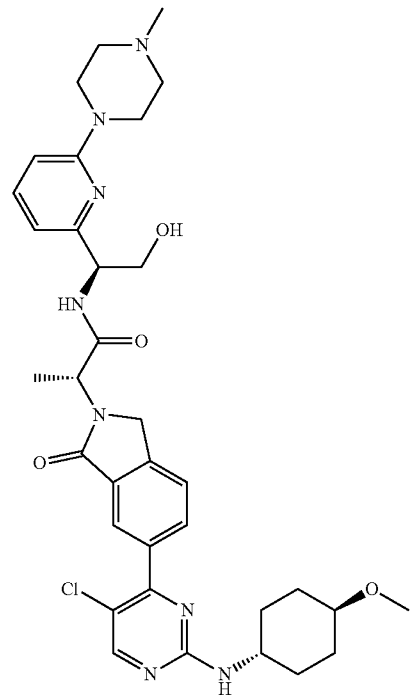 [SMILES: CO[C@H]1CC[C@H](Nc2ncc(Cl)c(-c3ccc4c(c3)C(=O)N([C@H](C)C(=O)N[C@H](CO)c3cccc(N5CCN(C)CC5)n3)C4)n2)CC1] | (2R)-2-[6-(5-chloro-2-{[trans-4-methoxycyclohexyl]amino}pyrimidin-4-yl)-1-oxo-2,3-dihydro-1H-isoindol-2-yl]-N-[(1S)-2-hydroxy-1-[6-(4-methylpiperazin-1-yl)pyridin-2-yl]ethyl]propanamide | 663 |
| 1121 | 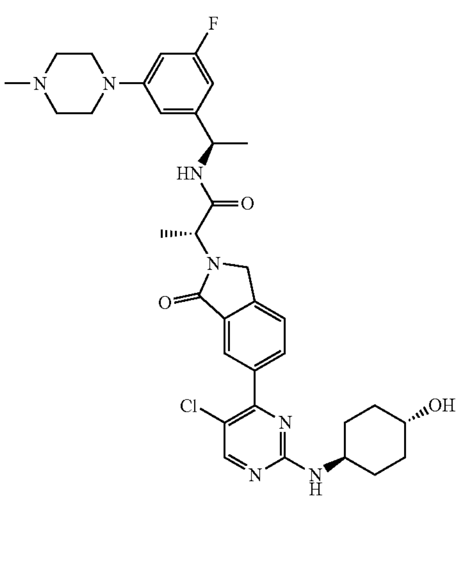 [SMILES: C[C@H](C(=O)N[C@H](C)c1cc(F)cc(N2CCN(C)CC2)c1)N1Cc2ccc(-c3nc(N[C@H]4CC[C@H](O)CC4)ncc3Cl)cc2C1=O] | (2R)-2-[6-(5-chloro-2-{[trans-4-hydroxycyclohexyl]amino}pyrimidin-4-yl)-1-oxo-2,3-dihydro-1H-isoindol-2-yl]-N-[(1R)-1-[3-fluoro-5-(4-methylpiperazin-1-yl)phenyl]ethyl]propanamide | 650 |

| Example | Structure | Name | MS Data [M +H]+ unless specified |
|---|---|---|---|
| 1122 | 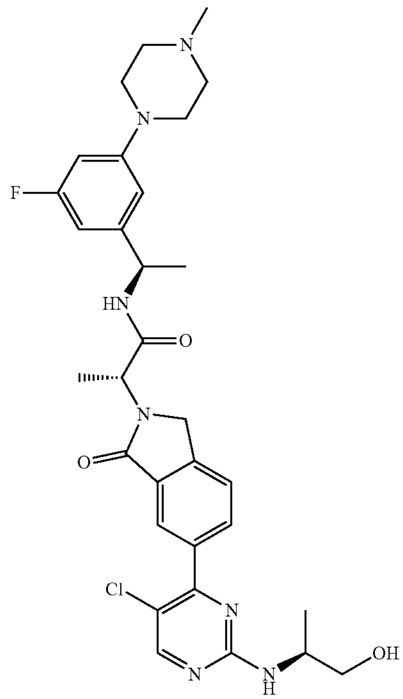 [SMILES: C[C@H](C(=O)N[C@H](C)c1cc(F)cc(N2CCN(C)CC2)c1)N1Cc2ccc(-c3nc(N[C@@H](C)CO)ncc3Cl)cc2C1=O] | (2R)-2-[6-(5-chloro-2-{[(2S)-1-hydroxypropan-2-yl]amino}pyrimidin-4-yl)-1-oxo-2,3-dihydro-1H-isoindol-2-yl]-N-[(1R)-1-[3-fluoro-5-(4-methylpiperazin-1-yl)phenyl]ethyl]propanamide | 610 |
| 1123 | 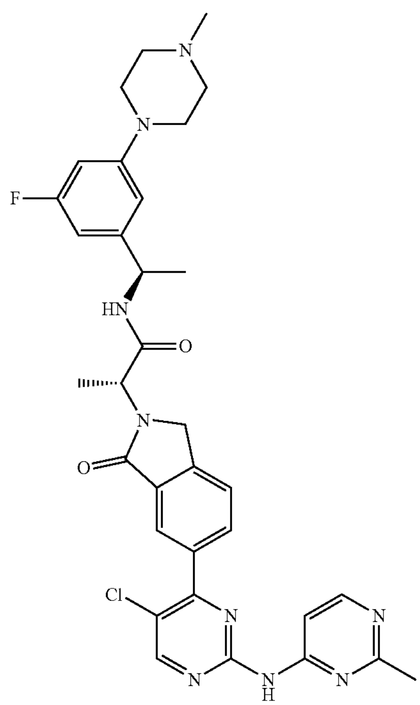 [SMILES: Cc1nccc(Nc2ncc(Cl)c(-c3ccc4c(c3)C(=O)N([C@H](C)C(=O)N[C@H](C)c3cc(F)cc(N5CCN(C)CC5)c3)C4)n2)n1] | (2R)-2-(6-{5-chloro-2-[(2-methylpyrimidin-4-yl)amino]pyrimidin-4-yl}-1-oxo-2,3-dihydro-1H-isoindol-2-yl)-N-[(1R)-1-[3-fluoro-5-(4-methylpiperazin-1-yl)phenyl]ethyl]propanamide | 644 |

| Example | Structure | Name | MS Data [M +H]+ unless specified |
|---|---|---|---|
| 1124 | 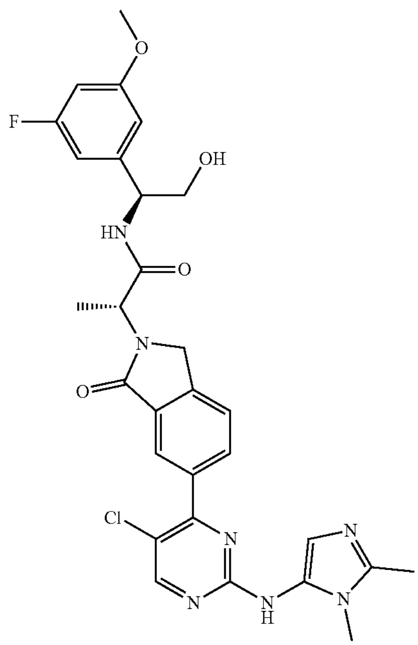 [SMILES: COc1cc(F)cc([C@@H](CO)NC(=O)[C@@H](C)N2Cc3ccc(-c4nc(Nc5cnc(C)n5C)ncc4Cl)cc3C2=O)c1] | (2R)-2-(6-{5-chloro-2-[(1,2-dimethyl-1H-imidazol-5-yl)amino]pyrimidin-4-yl}-1-oxo-2,3-dihydro-1H-isoindol-2-yl)-N-[(1S)-1-(3-fluoro-5-methoxyphenyl)-2-hydroxyethyl]propanamide | 594 |
| 1125 | 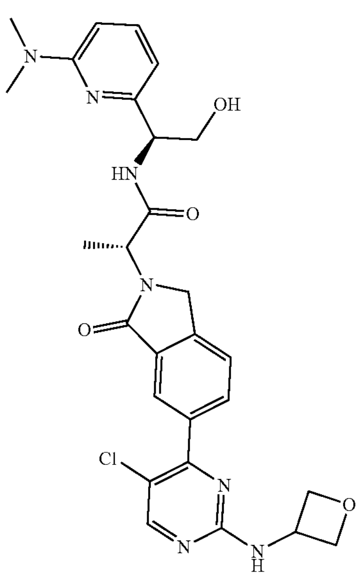 [SMILES: C[C@H](C(=O)N[C@H](CO)c1cccc(N(C)C)n1)N1Cc2ccc(-c3nc(NC4COC4)ncc3Cl)cc2C1=O] | (2R)-2-(6-{5-chloro-2-[(oxetan-3-yl)amino]pyrimidin-4-yl}-1-oxo-2,3-dihydro-1H-isoindol-2-yl)-N-[(1S)-1[6-(dimethylamino)pyridin-2-yl]-2-hydroxyethyl]propanamide | 552 |

-continued

| Example | Structure | Name | MS Data [M+H]+ unless specified |
|---|---|---|---|
| 1126 | 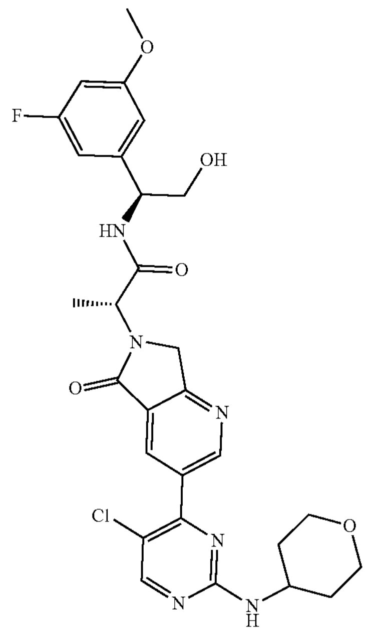 [SMILES: COc1cc(F)cc([C@@H](CO)NC(=O)[C@@H](C)N2Cc3ncc(-c4nc(NC5CCOCC5)ncc4Cl)cc3C2=O)c1] | (2R)-2-(3-{5-chloro-2-[(oxan-4-yl)amino]pyrimidin-4-yl}-5-oxo-5H,6H,7H-pyrrolo[3,4-b]pyridin-6-yl)-N-[(1S)-1-(3-fluoro-5-methoxyphenyl)-2-hydroxyethyl]propanamide | 585 |
| 1127 | 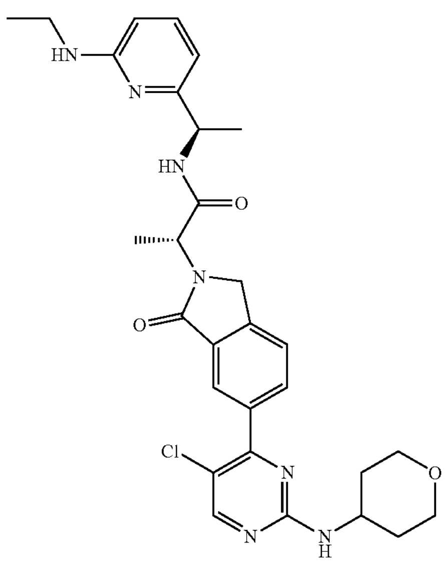 [SMILES: CCNc1cccc([C@@H](C)NC(=O)[C@@H](C)N2Cc3ccc(-c4nc(NC5CCOCC5)ncc4Cl)cc3C2=O)n1] | (2R)-2-(6-{5-chloro-2-[(oxan-4-yl)amino]pyrimidin-4-yl}-1-oxo-2,3-dihydro-1H-isoindol-2-yl)-N-[(1R)-1[6-(ethylamino)pyridin-2-yl]ethyl]propanamide | 564 |

-continued
| Example | Structure | Name | MS Data [M +H]+ unless specified |
|---|---|---|---|
| 1128 | 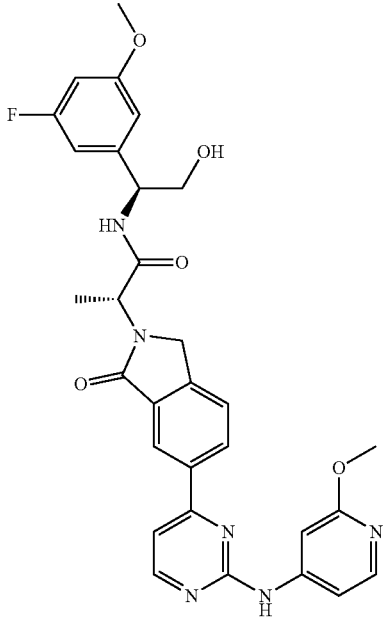 [SMILES: COc1cc(F)cc([C@@H](CO)NC(=O)[C@@H](C)N2Cc3ccc(-c4ccnc(Nc5ccnc(OC)c5)n4)cc3C2=O)c1] | (2R)-N-[(1S)-1-(3-fluoro-5-methoxyphenyl)-2-hydroxyethyl]-2-(6-{2-[(2-methoxypyridin-4-yl)amino]pyrimidin-4-yl}-1-oxo-2,3-dihydro-1H-isoindol-2-yl)propanamide | 573 |
| 1129 | 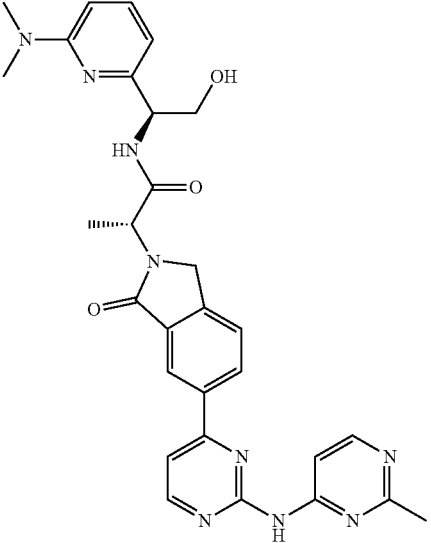 | (2R)-N-[(1S)-1-[6-(dimethylamino)pyridin-2-yl]-2-hydroxyethyl]-2-(6-{2-[(2-methylpyrimidin-4-yl)amino]pyrimidin-4-yl}-1-oxo-2,3-dihydro-1H-isoindol-2-yl)propanamide | 554 |

-continued

| Example | Structure | Name | MS Data [M +H]+ unless specified |
|---|---|---|---|
| 1130 | 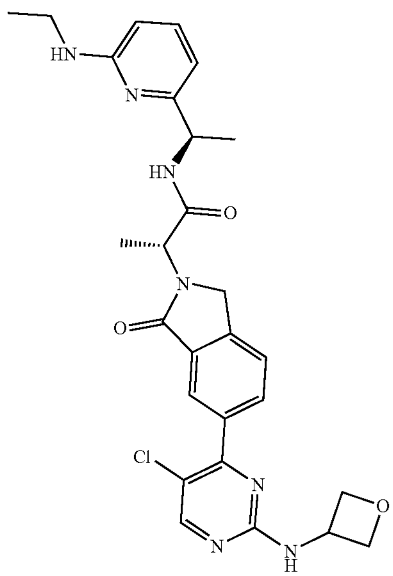 [SMILES: CCNc1cccc([C@@H](C)NC(=O)[C@@H](C)N2Cc3ccc(-c4nc(NC5COC5)ncc4Cl)cc3C2=O)n1] | (2R)-2-(6-{5-chloro-2-[(oxetan-3-yl)amino]pyrimidin-4-yl}-1-oxo-2,3-dihydro-1H-isoindol-2-yl)-N-[(1R)-1-[6-ethylamino)pyridin-2-yl]ethyl]propanamide | 536 |
| 1131 | 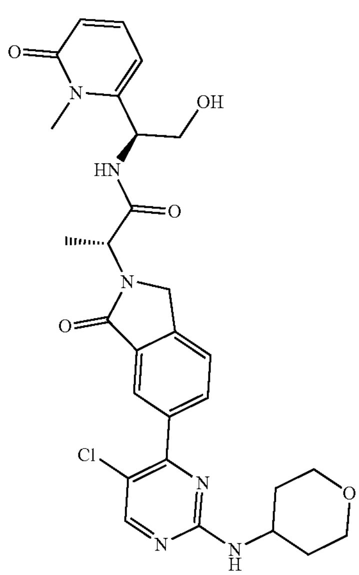 [SMILES: C[C@H](C(=O)N[C@H](CO)c1cccc(=O)n1C)N1Cc2ccc(-c3nc(NC4CCOCC4)ncc3Cl)cc2C1=O] | (2R)-2-(6-{5-chloro-2-[(oxan-4-yl)amino]pyrimidin-4-yl}-1-oxo-2,3-dihydro-1H-isoindol-2-yl)-N-[(1S)-2-hydroxy-1-(1-methyl-6-oxo-1,6-dihydropyridin-2-yl)ethyl]propanamide | 567 |

-continued

| Example | Structure | Name | MS Data [M +H]+ unless specified |
|---|---|---|---|
| 1132 | 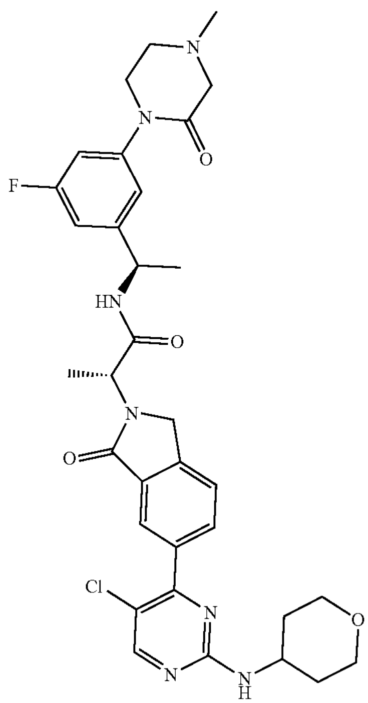 [SMILES: C[C@H](C(=O)N[C@H](C)c1cc(F)cc(N2CCN(C)CC2=O)c1)N1Cc2ccc(-c3nc(NC4CCOCC4)ncc3Cl)cc2C1=O] | (2R)-2-(6-{5-chloro-2-[(oxan-4-yl)amino]pyrimidin-4-yl}-1-oxo-2,3-dihydro-1H-isoindol-2-yl)-N-[(1R)-1-[3-fluoro-5-(4-methyl-2-oxopiperazin-1-yl)phenyl]ethyl]propanamide | 648 [M −H]+ |
| 1133 | 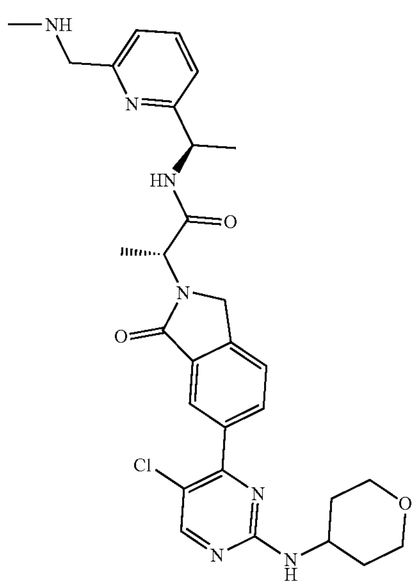 [SMILES: CNCc1cccc([C@@H](C)NC(=O)[C@@H](C)N2Cc3ccc(-c4nc(NC5CCOCC5)ncc4Cl)cc3C2=O)n1] | (2R)-2-(6-{5-chloro-2-[(oxan-4-yl)amino]pyrimidin-4-yl}-1-oxo-2,3-dihydro-1H-isoindol-2-yl)-N-[(1R)-1-{6-[(methylamino)methyl]pyridin-2-yl}ethyl]propanamide | 564 |

| Example | Structure | Name | MS Data [M +H]+ unless specified |
|---|---|---|---|
| 1134 | 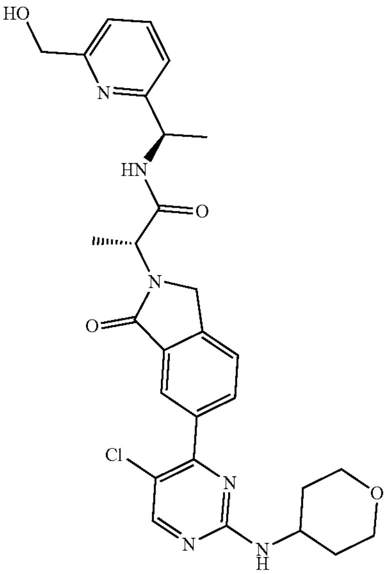 [SMILES: C[C@H](C(=O)N[C@H](C)c1cccc(CO)n1)N1Cc2ccc(-c3nc(NC4CCOCC4)ncc3Cl)cc2C1=O] | (2R)-2-(6-{5-chloro-2-[(oxan-4-yl)amino]pyrimidin-4-yl}-1-oxo-2,3-dihydro-1H-isoindol-2-yl)-N-[(1R)-1-[6-(hydroxymethyl)pyridin-2-yl]ethyl]propanamide | 551 |

Biological Activity

Example A

ERK2 In vitro Inhibition Assay

The inhibitory activity of the compounds of the invention was determined using the protocol set out below.

Activity of ERK2 enzyme (Life Technologies) was determined using a time-resolved fluorescence format measuring the phosphorylation of a truncated version of Activating transcription factor 2 labelled with green fluorescent protein (ATF2-GFP) (Life Technologies). Assay reactions containing 50 mM Tris pH 7.5, 10 mM $MgC_2$, 1 mM EGTA, 0.01% Triton X-100, 1 mM DTT, 2.5% DMSO, 0.4 μM ATF2-GFP, 20 μM ATP and 0.25 nM ERK2 were set up in the presence of compound and allowed to proceed for 30 min at room temperature. Reactions were then stopped using TR-FRET dilution buffer (Life Technologies), 25 mM EDTA and 2 nM Tb-Anti-pATF2 (Thr71) (Life Technologies). After a further incubation period of at least 30 minutes, fluorescence was read on a Pherastar reader (Lanthascreen optic module; excitation 340 nm, emission 520 nm (channel A), 495 nm (channel B)). The ratio between A and B counts was used to calculate signal. $IC_{50}$ values were calculated using a sigmoidal dose response equation (Prism GraphPad software, La Jolla, Calif., USA).

In the assays using ERK2, the compounds of Examples 125, 127, 162, 181, 183, 289, 299, 310 and 939 have $IC_{50}$ values in the range from 1 μM to 10 μM, provide at least 50% inhibition of the activity at a concentration of 10 μM in the assay against ERK2 or would be expected to provide at least 50% inhibition of the activity at a concentration of 10 μM (based on the level of inhibition of the activity at concentrations of 3 μM) in the assay against ERK2.

The compounds of Examples 1, 12, 24, 28, 30, 36, 37, 44, 45, 51, 61, 65, 69, 71, 73, 89, 92, 106, 109, 111, 113, 114, 118, 119, 121, 124, 126, 129, 133, 135, 138, 139, 140, 143, 156, 158, 159, 160, 161, 166, 167, 169, 170, 171, 172, 173, 174, 178, 180, 182, 184, 185, 187, 189, 191, 198, 199, 204, 215, 222, 223, 243, 251, 255, 258, 279, 285, 296, 297, 301, 302, 305, 306, 307, 308, 309, 314, 331, 363, 378, 382, 404, 411, 414, 483, 486, 492, 494, 496, 501, 503, 513, 515, 520, 521, 528, 530, 532, 534, 536, 541, 546, 551, 553, 556, 572, 576, 577, 581, 594, 617, 618, 620, 680, 706, 709, 719, 724, 737, 749, 750, 752, 762, 766, 793, 794, 821, 874, 893, 917, 937, 938, 967, 978, 991, 993, 994, 1006, 1013, 1014, 1059 and 1113 have $IC_{50}$ values in the range from 0.1 μM to 1 μM, provide at least 50% inhibition of the activity at a concentration of 1 μM or would be expected to provide at least 50% inhibition of the activity at a concentration of 1 μM (based on the level of inhibition of the activity at concentrations of 0.10 μM) in the assay against ERK2.

The compounds of Examples 5, 6, 8, 9, 10, 13, 14, 15, 17, 18, 20, 23, 29, 31, 32, 33, 39, 41, 43, 46, 47, 49, 50, 52, 53, 54, 58, 60, 62, 63, 64, 66, 68, 70, 75, 77, 81, 83, 88, 90, 91, 97, 98, 99, 100, 102, 104, 105, 107, 108, 110, 112, 115, 116, 117, 120, 122, 123, 128, 130, 131, 132, 134, 136, 142, 144, 145, 146, 147, 148, 149, 153, 154, 155, 157, 163, 164, 165, 168, 175, 176, 177, 179, 186, 188, 190, 200, 202, 203, 205, 206, 208, 211, 212, 213, 216, 217, 218, 220, 224, 225, 226, 227, 228, 229, 231, 233, 236, 238, 245, 246, 247, 248, 249, 250, 252, 253, 254, 256, 257, 259, 265, 267, 268, 269, 270, 272, 273, 274, 275, 276, 277, 278, 281, 286, 288, 292, 293, 295, 300, 304, 311, 312, 313, 315, 320, 329, 330, 334, 338, 339, 340, 343, 345, 346, 350, 353, 361, 362, 364, 368, 373, 374, 375, 376, 377, 379, 380, 387, 388, 389, 394, 401, 405, 407, 408, 409, 410, 412, 413, 416, 417, 418, 419, 420, 424, 426, 427, 438, 439, 440, 441, 446, 449, 464, 467, 470, 472, 473, 474, 479, 484, 485, 487, 489, 490, 491, 493, 497, 502, 505, 506, 507, 508, 516, 518, 519, 523, 524, 531, 533, 535, 537, 539, 544, 547, 550, 552, 557, 559, 561, 562, 564, 566, 568, 569, 570, 573, 578, 579, 580, 582, 584, 585, 586, 587, 589, 590, 592, 595, 599, 605, 607, 610, 611, 619, 622, 632, 636, 637, 638, 645, 646, 647, 648, 649, 655, 659, 662, 664, 667, 668, 670, 679, 682, 690, 691, 695, 714, 718, 723, 725, 726, 731, 733, 734, 741, 744, 745, 748, 751, 755, 758, 761, 764, 770, 771, 773, 775, 778, 790, 791, 792, 796, 797, 813, 829, 832, 833, 839, 842, 854, 866, 879, 884, 885, 889, 899, 901, 904, 905, 906, 916, 933, 946, 948, 955, 969, 998, 1009, 1012, 1028, 1032, 1055, 1082, 1084 and 1091 have $IC_{50}$ values in the range from 0.01 µM to 0.1 µM provide at least 50% inhibition of the activity at a concentration of 0.1 µM or would be expected to provide at least 50% inhibition of the activity at a concentration of 0.1 µM (based on the level of inhibition of the activity at concentrations of 0.0030 µM or 0.010 µM) in the assay against ERK2.

The compounds of Examples 2, 3, 4, 7, 11, 16, 19, 21, 22, 25, 26, 27, 34, 35, 38, 40, 42, 48, 55, 56, 57, 59, 67, 72, 74, 76, 78, 79, 80, 82, 84, 85, 86, 87, 93, 94, 95, 96, 101, 103, 137, 141, 150, 151, 152, 192, 193, 194, 195, 196, 197, 201, 207, 209, 210, 214, 219, 221, 230, 232, 234, 235, 237, 239, 240, 241, 242, 244, 260, 261, 262, 263, 264, 266, 271, 280, 282, 283, 284, 287, 289, 290, 291, 294, 303, 316, 317, 318, 319, 321, 322, 323, 324, 325, 326, 327, 328, 333, 335, 336, 337, 341, 342, 344, 347, 348, 349, 351, 352, 354, 355, 356, 357, 358, 359, 360, 365, 367, 369, 370, 371, 372, 381, 383, 384, 372, 386, 390, 391, 392, 393, 395, 396, 397, 398, 399, 400, 402, 403, 406, 415, 421, 422, 423, 425, 428, 429, 430, 431, 432, 433, 434, 435, 436, 437, 442, 443, 444, 445, 448, 450, 451, 452, 453, 454, 455, 456, 457, 458, 459, 460, 461, 462, 463, 465, 466, 469, 471, 475, 476, 477, 478, 480, 481, 482, 488, 495, 498, 499, 500, 504, 509, 510, 511, 512, 514, 517, 522, 525, 526, 529, 538, 540, 542, 543, 545, 548, 549, 554, 555, 558, 560, 563, 565, 567, 571, 574, 575, 583, 588, 591, 593, 596, 597, 598, 600, 601, 602, 603, 604, 606, 608, 609, 612, 613, 614, 615, 616, 621, 623, 624, 625, 626, 627, 628, 629, 630, 631, 633, 634, 635, 639, 640, 641, 642, 643, 644, 650, 651, 652, 653, 654, 656, 657, 658, 660, 661, 663, 665, 666, 669, 671, 672, 673, 674, 675, 676, 677, 678, 681, 683, 684, 685, 686, 687, 688, 689, 692, 693, 694, 696, 697, 698, 699, 701, 702, 703, 705, 707, 708, 711, 712, 713, 715, 716, 717, 719, 720, 721, 722, 727, 728, 730, 732, 735, 737, 738, 740, 742, 743, 746, 747, 753, 754, 756, 757, 759, 763, 765, 767, 768, 769, 774, 776, 777, 779, 780, 781, 782, 783, 784, 785, 786, 787, 788, 789, 798, 799, 800, 801, 802, 803, 804, 805, 806, 808, 809, 810, 811, 812, 814, 815, 816, 817, 818, 819, 820, 822, 823, 824, 825, 826, 827, 828, 830, 831, 834, 835, 836, 837, 838, 840, 841, 843, 844, 846, 847, 848, 849, 850, 851, 852, 853, 855, 856, 857, 858, 859, 864, 865, 867, 868, 869, 870, 871, 872, 873, 875, 876, 877, 878, 880, 881, 882, 883, 886, 887, 888, 890, 891, 892, 894, 895, 896, 897, 986, 900, 902, 903, 907, 908, 909, 910, 911, 912, 913, 914, 915, 918, 919, 920, 921, 922, 924, 925, 926, 927, 928, 929, 930, 931, 932, 934, 935, 936, 940, 941, 942, 943, 944, 945, 947, 949, 950, 951, 952, 953, 954, 956, 957, 958, 959, 960, 961, 962, 963, 964, 965, 966, 968, 970, 971, 972, 973, 974, 975, 976, 977, 979, 980, 981, 982, 983, 984, 985, 986, 987, 988, 989, 990, 992, 995, 996, 997, 999, 1000, 1001, 1002, 1003, 1004, 1005, 1007, 1008, 1010, 1011, 1014, 1015, 1016, 1017, 1018, 1019, 1020, 1021, 1022, 1023, 1024, 1025, 1026, 1027, 1029, 1030, 1031, 1033, 1034, 1035, 1036, 1038, 1039, 1040, 1041, 1042, 1043, 1044, 1045, 1046, 1047, 1048, 1049, 1050, 1051, 1052, 1053, 1054, 1056, 1057, 1058, 1060, 1061, 1062, 1063, 1064, 1065, 1066, 1067, 1068, 1069, 1070, 1071, 1072, 1073, 1074, 1075, 1076, 1077, 1078, 1079, 1080, 1081, 1083, 1085, 1086, 1087, 1088, 1089, 1092, 1093, 1094, 1095, 1096, 1097, 1098, 1099, 1100, 1101, 1102, 1103, 598, 1105, 1106, 1107, 1108, 1109, 1110, 1111, 1112, 1113, 1114, 609, 1116, 1117, 1118, 1119, 1120, 1121, 1122, 1123, 1124, 1125, 1126, 1127, 1128, 1129, 1130, 1131, 1132, 1133, 1134 have $IC_{50}$ values in the range from 0.001 µM to 0.01 µM, provide at least 50% inhibition of the activity at a concentration of 0.01 µM or would be expected to provide at least 50% inhibition of the activity at a concentration of 0.01 µM (based on the level of inhibition of the activity at concentrations of 0.00050 µM, 0.0010 µM or 0.0030 µM) in the assay against ERK2.

Example B

Anti-Proliferative Activity

The anti-proliferative activities of compounds of the invention were determined by measuring the ability of the compounds to inhibit growth in the Human melanoma cell line A375.

Cell proliferation was determined by measuring the conversion of rezasurin (Alamar Blue) to resorufin in reponse to mitochondrial activity (Nociari, M. M, Shalev, A., Benias, P., Russo, C. *Journal of Immunological Methods* 1998, 213, 157-167). A375 cells (American Type Culture Collection, Teddington, UK) were grown in Dulbecco's Modified Eagle Medium+10% FBS. Each well of a black 96-well flat-bottomed plate was seeded with $2 \times 10^3$ cells in 200 µl of complete culture medium one day before the compound treatment. Cells were incubated with compound in 0.1% (v/v) dimethyl sulfoxide (DMSO) for 4 days before addition of 20 µl Alamar blue. After a further 6 h incubation at 37° C. the plate was read on a Spectramax Gemini reader (Molecular Devices; excitation 535 nm, emission 590 nm). $GI_{50}$ values were calculated using a sigmoidal dose response equation (Prism GraphPad software, La Jolla, Calif., USA).

In the assays using A375, the compounds of Examples 5, 6, 7, 8, 9, 10, 15, 18, 20, 25, 29, 41, 42, 46, 49, 50, 51, 53, 58, 60, 62, 68, 78, 81, 88, 97, 98, 100, 102, 108, 110, 112, 115, 116, 120, 122, 124, 128, 130, 134, 137, 144, 145, 146, 147, 149, 154, 155, 157, 158, 163, 165, 168, 170, 174, 176, 177, 179, 184, 368, 405, 407, 410, 412, 417, 418, 426, 438, 439, 445, 449, 471, 481, 483, 485, 553, 564, 566, 569, 578, 582, 599, 619, 632, 636, 771, 776, 913, 920, 932 and 1055 have $GI_{50}$ values in the range from 1 µM to 10 µM, provide at least 50% inhibition of growth at a concentration of 10 µM or would be expected to provide at least 50% inhibition of the activity at a concentration of 10 µM (based on the level of inhibition of the activity at concentrations of 1 µM) in the assay against A375.

In the assays using A375, the compounds of Examples 2, 3, 4, 11, 13, 16, 17, 19, 21, 22, 23, 26, 27, 31, 33, 34, 35, 38, 39, 40, 43, 47, 48, 54, 55, 56, 57, 59, 63, 64, 66, 67, 70, 72, 74, 75, 76, 82, 83, 84, 85, 87, 90, 91, 93, 94, 95, 96, 101, 103, 107, 117, 141, 148, 150, 151, 152, 153, 164, 175, 186, 190, 193, 194, 195, 196, 197, 201, 221, 237, 287, 294, 317, 318, 319, 320, 322, 323, 328, 337, 369, 371, 381, 383, 386, 389, 398, 401, 406, 413, 415, 416, 419, 421, 423, 424, 426, 427, 428, 429, 430, 437, 440, 441, 442, 447, 453, 455, 469, 470, 473, 476, 477, 479, 480, 487, 488, 495, 497, 498, 500, 511, 538, 540, 547, 548, 549, 550, 552, 555, 558, 559, 560, 561, 563, 565, 567, 568, 570, 571, 573, 574, 575, 580, 600, 601, 602, 603, 605, 606, 607, 630, 637, 638, 639, 640, 643, 654, 655, 656, 657, 666, 693, 703, 712, 716, 717, 719, 720, 727, 731, 737, 738, 746, 747, 756, 774, 785, 786, 787, 790, 798, 800, 801, 813, 816, 830, 834, 836, 839, 840, 846, 848, 849, 855, 867, 875, 876, 883, 886, 889, 901, 918, 919, 921, 926, 927, 928, 929, 940, 946, 949, 950, 956, 960, 961, 962, 968, 975, 977, 981, 983, 985, 986, 987, 996, 1001, 1002, 1003, 1004, 1008, 1011, 1014, 1015, 1018, 1020, 1027, 1038, 1039, 1042, 1045, 1046, 1047, 1048, 1050, 1051, 1053, 1065, 1073, 1077, 1078, 1113, 1117, 1118, 1121, 1123, 1124, 1132 and 1134 have GI$_{50}$ values in the range from 0.1 μM to 1 μM or provide at least 50% inhibition of growth at a concentration of 1 μM or would be expected to provide at least 50% inhibition of the activity at a concentration of 1 μM (based on the level of inhibition of the activity at concentrations of 0.30 μM) in the assay against A375.

In the assays using A375, the compounds of Examples 52, 77, 79, 80, 86, 192, 209, 232, 240, 261, 264, 265, 271, 282, 283, 291, 292, 316, 324, 325, 326, 327, 334, 335, 336, 342, 347, 348, 349, 351, 354, 355, 356, 357, 359, 360, 367, 370, 372, 385, 390, 392, 393, 395, 399, 400, 402, 403, 422, 425, 431, 432, 444, 448, 451, 452, 459, 460, 467, 475, 478, 482, 499, 504, 508, 510, 517, 525, 539, 554, 562, 579, 591, 593, 598, 609, 611, 612, 613, 614, 616, 621, 622, 623, 624, 625, 626, 627, 628, 629, 631, 633, 634, 635, 641, 642, 644, 645, 648, 650, 653, 658, 659, 663, 664, 665, 668, 669, 670, 671, 672, 673, 674, 681, 682, 687, 688, 689, 692, 696, 697, 698, 699, 701, 702, 705, 708, 711, 713, 715, 721, 722, 728, 734, 735, 740, 743, 753, 754, 755, 759, 763, 765, 767, 768, 770, 777, 780, 781, 783, 784, 788, 789, 799, 802, 803, 804, 805, 806, 809, 810, 811, 817, 818, 819, 820, 822, 823, 824, 825, 826, 827, 828, 831, 835, 837, 838, 841, 843, 847, 850, 851, 852, 853, 856, 857, 858, 860, 861, 864, 865, 868, 869, 870, 871, 872, 873, 877, 878, 882, 887, 888, 890, 894, 895, 896, 897, 898, 900, 902, 903, 907, 908, 912, 914, 915, 922, 924, 925, 931, 935, 936, 941, 942, 943, 944, 945, 952, 953, 954, 957, 958, 959, 963, 964, 965, 966, 970, 971, 972, 973, 974, 976, 979, 980, 982, 984, 988, 989, 990, 992, 995, 999, 1000, 1005, 1007, 1016, 1019, 1023, 1024, 1025, 1026, 1029, 1030, 1031, 1033, 1034, 1035, 1036, 1037, 1040, 1041, 1043, 1044, 1049, 1052, 1054, 1056, 1057, 1058, 1060, 1064, 1066, 1067, 1068, 1069, 1071, 1072, 1074, 1075, 1076, 1079, 1080, 1081, 1082, 1084, 1085, 1086, 1087, 1088, 1089, 1090, 1092, 1093, 1094, 1095, 1096, 1097, 1098, 1099, 1100, 1101, 1102, 1103, 1104, 1105, 1106, 1107, 1108, 1109, 1110, 1111, 1112, 1114, 1115, 1116, 1119, 1120, 1122 and 1126 have GI$_{50}$ values in the range from 0.01 μM to 0.1 μM or provide at least 50% inhibition of growth at a concentration of 0.1 μM.

In the assays using A375, the compounds of Examples 262, 284, 303, 333, 345, 346, 434, 443, 446, 450, 456, 457, 458, 461, 462, 463, 465, 544, 545, 583, 584, 585, 586, 587, 588, 592, 596, 597, 598, 609, 647, 649, 652, 667, 675, 683, 684, 685, 686, 690, 694, 742, 757, 769, 782, 808, 812, 815, 859, 862, 880, 881, 891, 892, 909, 910, 911, 923, 930, 934, 947, 951, 997, 1017, 1021, 1022, 1061, 1062, 1063, 1070, 1083, 1125, 1127, 1128, 1129 and 1130 have GI$_{50}$ values in the range from 0.001 μM to 0.01 μM or provide at least 50% inhibition of growth at a concentration of 0.01 μM.

The individual IC$_{50}$ values for the compounds tested in Example A are set out in the table below.

| Example | ERK2 IC$_{50}$ (μM) | Example | ERK2 IC$_{50}$ (μM) | Example | ERK2 IC$_{50}$ (μM) |
|---|---|---|---|---|---|
| 1 | 0.21 | 2 | 0.0030 | 3 | 0.0039 |
| 4 | 0.0053 | 5 | 0.027 | 6 | 0.027 |
| 7 | 46% @ 0.0030 | 8 | 0.063 | 9 | 0.067 |
| 10 | 0.057 | 11 | 0.0019 | 12 | 0.27 |
| 13 | 0.014 | 14 | 0.016 | 15 | 0.023 |
| 16 | 0.0059 | 17 | 0.061 | 18 | 0.038 |
| 19 | 0.0068 | 20 | 0.035 | 21 | 0.0050 |
| 22 | 0.0028 | 23 | 0.025 | 24 | 0.11 |
| 25 | 0.0069 | 26 | 0.010 | 27 | 0.0039 |
| 28 | 0.29 | 29 | 0.014 | 30 | 0.19 |
| 31 | 0.044 | 32 | 0.10 | 33 | 0.031 |
| 34 | 0.0063 | 35 | 0.0079 | 36 | 0.77 |
| 37 | 0.13 | 38 | 0.0035 | 39 | 0.038 |
| 40 | 0.0064 | 41 | 0.035 | 42 | 0.0058 |
| 43 | 0.014 | 44 | 0.13 | 45 | 0.11 |
| 46 | 0.094 | 47 | 0.027 | 48 | 0.0088 |
| 49 | 0.045 | 50 | 0.020 | 51 | 0.17 |
| 52 | 0.062 | 53 | 0.027 | 54 | 0.027 |
| 55 | 0.0048 | 56 | 0.010 | 57 | 0.010 |
| 58 | 0.020 | 59 | 0.0034 | 60 | 0.083 |
| 61 | 0.160 | 62 | 0.032 | 63 | 0.019 |
| 64 | 0.015 | 65 | 0.15 | 66 | 0.034 |
| 67 | 48% @ 0.0030 | 68 | 0.061 | 69 | 0.11 |
| 70 | 0.041 | 71 | 0.18 | 72 | 0.0068 |
| 73 | 0.50 | 74 | 0.0065 | 75 | 0.02 |
| 76 | 0.0040 | 77 | 0.021 | 78 | 0.0052 |
| 79 | 49% @ 0.0010 | 80 | 0.0043 | 81 | 0.012 |
| 82 | 0.0099 | 83 | 0.032 | 84 | 0.0097 |
| 85 | 0.0060 | 86 | 0.0028 | 87 | 0.0040 |
| 88 | 0.016 | 89 | 0.20 | 90 | 0.043 |
| 91 | 0.056 | 92 | 0.14 | 93 | 53% @ 0.0030 |
| 94 | 0.0072 | 95 | 0.0065 | 96 | 0.0028 |
| 97 | 0.04 | 98 | 0.012 | 99 | 0.057 |
| 100 | 0.020 | 101 | 0.0046 | 102 | 0.074 |
| 103 | 0.0039 | 104 | 0.012 | 105 | 0.038 |
| 106 | 0.12 | 107 | 0.051 | 108 | 0.023 |
| 109 | 0.12 | 110 | 0.016 | 111 | 0.34 |
| 112 | 0.019 | 113 | 1.0 | 114 | 0.36 |
| 115 | 0.012 | 116 | 0.024 | 117 | 0.072 |
| 118 | 0.87 | 119 | 0.12 | 120 | 0.091 |
| 121 | 0.62 | 122 | 0.018 | 123 | 0.072 |
| 124 | 0.12 | 125 | 1.2 | 126 | 0.36 |
| 127 | 5.2 | 128 | 0.011 | 129 | 0.11 |
| 130 | 0.035 | 131 | 0.025 | 132 | 0.023 |
| 133 | 0.17 | 134 | 0.057 | 135 | 0.14 |
| 136 | 0.069 | 137 | 0.0087 | 138 | 0.16 |

-continued

| Example | ERK2 IC$_{50}$ (μM) | Example | ERK2 IC$_{50}$ (μM) | Example | ERK2 IC$_{50}$ (μM) |
|---|---|---|---|---|---|
| 139 | 0.16 | 140 | 0.12 | 141 | 0.009 |
| 142 | 0.033 | 143 | 0.17 | 144 | 0.023 |
| 145 | 0.032 | 146 | 0.034 | 147 | 0.09 |
| 148 | 0.029 | 149 | 0.032 | 150 | 0.010 |
| 151 | 0.0023 | 152 | 0.0044 | 153 | 0.011 |
| 154 | 0.014 | 155 | 0.098 | 156 | 0.11 |
| 157 | 0.030 | 158 | 0.13 | 159 | 40% @ 0.30 |
| 160 | 0.49 | 161 | 0.21 | 162 | 2.0 |
| 163 | 0.048 | 164 | 0.059 | 165 | 0.083 |
| 166 | 0.14 | 167 | 0.69 | 168 | 0.048 |
| 169 | 0.47 | 170 | 0.11 | 171 | 0.12 |
| 172 | 0.24 | 173 | 1.0 | 174 | 0.14 |
| 175 | 0.09 | 176 | 0.081 | 177 | 0.082 |
| 178 | 0.22 | 179 | 0.084 | 180 | 0.19 |
| 181 | 1.2 | 182 | 0.39 | 183 | 1.4 |
| 184 | 0.17 | 185 | 0.22 | 186 | 0.030 |
| 187 | 54% @ 1.0 | 188 | 41% @ 0.030 | 189 | 0.45 |
| 190 | 0.036 | 191 | 0.32 | 192 | 0.0068 |
| 193 | 0.0051 | 194 | 0.0094 | 195 | 0.0051 |
| 196 | 0.0034 | 197 | 0.004 | 198 | 0.11 |
| 199 | 0.3 | 202 | 0.041 | 205 | 0.012 |
| 200 | 0.053 | 203 | 0.014 | 206 | 0.014 |
| 201 | 0.01 | 204 | 0.21 | 207 | 0.0062 |
| 208 | 0.015 | 233 | 0.033 | 258 | 0.25 |
| 209 | 0.0033 | 234 | 0.01 | 259 | 0.06 |
| 210 | 0.01 | 235 | 0.0085 | 260 | 0.0065 |
| 211 | 0.019 | 236 | 0.022 | 261 | 54% @ 0.0010 μM |
| 212 | 0.013 | 237 | 0.0069 | 262 | 0.0021 |
| 213 | 0.095 | 238 | 0.015 | 263 | 0.0057 |
| 214 | 0.01 | 239 | 0.0097 | 264 | 0.0025 |
| 215 | 0.33 | 240 | 0.0061 | 265 | 57% @ 0.0030 μM |
| 216 | 0.022 | 241 | 0.0093 | 266 | 0.008 |
| 217 | 0.042 | 242 | 0.0086 | 267 | 0.058 |
| 218 | 0.014 | 243 | 0.65 | 268 | 0.1 |
| 219 | 0.01 | 244 | 0.0078 | 269 | 0.028 |
| 220 | 0.021 | 245 | 0.038 | 270 | 0.036 |
| 221 | 0.0047 | 246 | 0.033 | 271 | 0.0054 |
| 222 | 0.11 | 247 | 0.054 | 272 | 0.012 |
| 223 | 0.16 | 248 | 0.038 | 273 | 0.036 |
| 224 | 0.023 | 249 | 0.078 | 274 | 0.061 |
| 225 | 0.024 | 250 | 0.074 | 275 | 0.039 |
| 226 | 0.023 | 251 | 0.27 | 276 | 0.1 |
| 227 | 0.013 | 252 | 0.031 | 277 | 0.079 |
| 228 | 0.045 | 253 | 0.023 | 278 | 0.031 |
| 229 | 0.033 | 254 | 0.016 | 279 | 0.38 |
| 230 | 0.01 | 255 | 0.31 | 280 | 0.0048 |
| 231 | 0.048 | 256 | 0.06 | 281 | 0.044 |
| 232 | 0.0018 | 257 | 0.026 | 282 | 0.0024 |
| 283 | 0.0026 | 308 | 0.36 | 333 | 51% @ 0.00050 μM, 51% @ 0.0010 μM |
| 284 | 39% @ 0.0010 μM | 309 | 0.12 | 334 | 62% @ 0.0030 μM |
| 285 | 0.2 | 310 | 1.3 | 335 | 0.0029 |
| 286 | 0.032 | 311 | 0.023 | 336 | 0.0016 |
| 287 | 0.004 | 312 | 0.035 | 337 | 0.0071 |
| 288 | 0.016 | 313 | 0.088 | 338 | 0.022 |
| 289 | 0.0063 | 314 | 0.42 | 339 | 0.021 |
| 290 | 0.0085 | 315 | 0.014 | 340 | 0.1 |
| 291 | 0.0031 | 316 | 71% @ 0.0010 μM | 341 | 0.0038 |
| 292 | 48% @ 0.0030 μM | 317 | 0.0037 | 342 | 0.0028 |
| 293 | 0.019 | 318 | 0.0049 | 343 | 0.013 |
| 294 | 0.002 | 319 | 0.0059 | 344 | 0.0098 |
| 295 | 0.018 | 320 | 0.011 | 345 | 57% @ 0.0030 μM |
| 296 | 0.16 | 321 | 0.0078 | 346 | 45% @ 0.0030 μM |
| 297 | 0.2 | 322 | 0.0026 | 347 | 0.0032 |
| 298 | 1.8 | 323 | 0.0021 | 348 | 0.0031 |
| 299 | 1.2 | 324 | 0.0019 | 349 | 0.0047 |
| 300 | 0.053 | 325 | 48% @ 0.0010 μM | 350 | 0.054 |

-continued

| Example | ERK2 IC$_{50}$ (μM) | Example | ERK2 IC$_{50}$ (μM) | Example | ERK2 IC$_{50}$ (μM) |
|---|---|---|---|---|---|
| 301 | 0.18 | 326 | 40% @ 0.0010 μM | 351 | 0.0035 |
| 302 | 0.14 | 327 | 40% @ 0.0010 μM | 352 | 0.0067 |
| 303 | 0.002 | 328 | 0.0046 | 353 | 0.031 |
| 304 | 0.015 | 329 | 0.029 | 354 | 0.0052 |
| 305 | 0.45 | 330 | 0.092 | 355 | 0.0047 |
| 306 | 0.72 | 331 | 0.23 | 356 | 0.0044 |
| 307 | 0.21 | 332 | 59% @ 3.0 μM | 357 | 0.0038 |
| 358 | 0.0056 | 384 | 0.0084 | 409 | 0.032 |
| 359 | 0.0042 | 385 | 41% @ 0.0010 μM | 410 | 0.059 |
| 360 | 0.0039 | 386 | 0.00363 | 411 | 0.35 |
| 361 | 0.035 | 387 | 0.018 | 412 | 0.026 |
| 362 | 0.016 | 388 | 0.011 | 413 | 0.017 |
| 363 | 0.22 | 389 | 55% @ 0.0030 μM | 414 | 0.11 |
| 364 | 0.08 | 390 | 0.0036 | 415 | 0.007 |
| 365 | 0.0079 | 391 | 0.009 | 416 | 0.03 |
| 367 | 0.0043 | 392 | 0.003 | 417 | 0.024 |
| 368 | 0.011 | 393 | 0.0042 | 418 | 0.022 |
| 369 | 0.0056 | 394 | 0.034 | 419 | 0.011 |
| 370 | 0.0026 | 395 | 0.0029 | 420 | 0.062 |
| 371 | 45% @ 0.0010 μM | 396 | 0.0089 | 421 | 0.0079 |
| 372 | 44% @ 0.0010 μM | 397 | 0.0069 | 422 | 0.0042 |
| 373 | 0.015 | 398 | 0.0034 | 423 | 0.0053 |
| 374 | 0.035 | 399 | 0.0026 | 424 | 0.013 |
| 375 | 0.025 | 400 | 0.0024 | 425 | 0.0029 |
| 376 | 0.053 | 401 | 51% @ 0.0030 μM | 426 | 0.036 |
| 377 | 0.05 | 402 | 0.0036 | 427 | 0.027 |
| 378 | 0.14 | 403 | 49% @ 0.0030 μM | 428 | 0.0055 |
| 379 | 0.027 | 404 | 0.32 | 429 | 0.0045 |
| 380 | 0.011 | 405 | 0.033 | 430 | 0.0035 |
| 381 | 0.0052 | 406 | 0.0085 | 431 | 0.0037 |
| 382 | 0.13 | 407 | 0.027 | 432 | 42% @ 0.0010 μM |
| 383 | 0.0017 | 408 | 0.1 | 433 | 0.0069 |
| 434 | 57% @ 0.0010 μM | 460 | 0.0025 | 486 | 0.15 |
| 435 | 0.0064 | 461 | 43% @ 0.0010 μM | 487 | 0.021 |
| 436 | 0.0076 | 462 | 0.0021 | 488 | 0.0047 |
| 437 | 0.01 | 463 | 0.002 | 489 | 0.066 |
| 438 | 0.053 | 464 | 0.087 | 490 | 0.033 |
| 439 | 0.052 | 465 | 0.0032 | 491 | 0.062 |
| 440 | 0.042 | 466 | 0.007 | 492 | 0.15 |
| 441 | 0.016 | 467 | 52% @ 0.0030 μM | 493 | 0.03 |
| 442 | 0.0069 | 469 | 0.0054 | 494 | 0.11 |
| 443 | 0.0019 | 470 | 0.04 | 495 | 0.0094 |
| 444 | 0.0023 | 471 | 0.01 | 496 | 0.18 |
| 445 | 48% @ 0.0010 μM | 472 | 0.036 | 497 | 0.012 |
| 446 | 0.09 | 473 | 0.012 | 498 | 0.0022 |
| 448 | 0.0051 | 474 | 0.078 | 499 | 0.0035 |
| 449 | 0.055 | 475 | 0.0033 | 500 | 0.0073 |
| 450 | 0.0016 | 476 | 0.0052 | 501 | 0.24 |
| 451 | 0.0017 | 477 | 0.01 | 502 | 0.052 |
| 452 | 37% @ 0.0010 μM | 478 | 0.0024 | 503 | 0.17 |
| 453 | 0.0064 | 479 | 0.016 | 504 | 0.0024 |
| 454 | 0.009 | 480 | 0.0028 | 505 | 0.027 |
| 455 | 0.0033 | 481 | 0.0082 | 506 | 0.06 |
| 456 | 43% @ 0.0010 μM | 482 | 0.003 | 507 | 0.028 |
| 457 | 54% @ 0.0010 μM | 483 | 0.19 | 508 | 61% @ 0.0030 μM |
| 458 | 55% @ 0.0010 μM | 484 | 0.082 | 509 | 0.0029 |
| 459 | 51% @ 0.0010 μM | 485 | 0.021 | 510 | 0.0028 |
| 511 | 0.0036 | 537 | 0.02 | 562 | 61% @ 0.0030 μM |

-continued

| Example | ERK2 IC$_{50}$ (μM) | Example | ERK2 IC$_{50}$ (μM) | Example | ERK2 IC$_{50}$ (μM) |
|---|---|---|---|---|---|
| 512 | 0.0082 | 538 | 0.01 | 563 | 0.01 |
| 513 | 0.2 | 539 | 53% @ 0.0030 μM | 564 | 0.016 |
| 514 | 0.0065 | 540 | 0.0028 | 565 | 0.0048 |
| 515 | 0.25 | 541 | 0.15 | 566 | 0.03 |
| 516 | 0.014 | 542 | 0.0025 | 567 | 0.005 |
| 517 | 0.0034 | 543 | 0.009 | 568 | 0.031 |
| 518 | 0.051 | 544 | 60% @ 0.0030 μM | 569 | 0.045 |
| 519 | 0.016 | 545 | 0.0017 | 570 | 0.021 |
| 520 | 0.38 | 546 | 0.2 | 571 | 0.006 |
| 521 | 0.66 | 547 | 0.035 | 572 | 0.32 |
| 522 | 0.0054 | 548 | 0.005 | 573 | 0.015 |
| 523 | 0.023 | 549 | 0.0084 | 574 | 0.008 |
| 524 | 0.049 | 550 | 0.055 | 575 | 0.0086 |
| 525 | 0.0051 | 551 | 0.14 | 576 | 0.27 |
| 526 | 0.0069 | 552 | 0.031 | 577 | 0.15 |
| 528 | 0.15 | 553 | 0.12 | 578 | 0.046 |
| 529 | 0.0078 | 554 | 0.0021 | 579 | 0.051 |
| 530 | 0.48 | 555 | 0.0066 | 580 | 0.015 |
| 531 | 0.029 | 556 | 0.11 | 581 | 0.17 |
| 532 | 0.23 | 557 | 0.1 | 582 | 0.041 |
| 533 | 0.046 | 558 | 0.0085 | 583 | 40% @ 0.0010 μM, 55% @ 0.0030 μM |
| 534 | 0.29 | 559 | 0.017 | 584 | 48% @ 0.0030 μM |
| 535 | 0.014 | 560 | 0.0046 | 585 | 65% @ 0.0030 μM |
| 536 | 0.14 | 561 | 0.018 | 586 | 57% @ 0.0030 μM |
| 587 | 35% @ 0.0010 μM | 612 | 0.0034 | 637 | 0.021 |
| 588 | 0.002 | 613 | 0.0025 | 638 | 42% @ 0.0030 μM |
| 589 | 0.011 | 614 | 0.004 | 639 | 0.0055 |
| 590 | 0.035 | 615 | 0.0013 | 640 | 0.0038 |
| 591 | 0.0033 | 616 | 0.0023 | 641 | 42% @ 0.0010 μM |
| 592 | 38% @ 0.0030 μM | 617 | 0.38 | 642 | 0.0017 |
| 593 | 0.0029 | 618 | 0.13 | 643 | 0.0065 |
| 594 | 0.39 | 619 | 0.087 | 644 | 0.0021 |
| 595 | 0.097 | 620 | 0.52 | 645 | 55% @ 0.0030 μM |
| 596 | 0.0019 | 621 | 0.0017 | 646 | 0.016 |
| 597 | 0.0029 | 622 | 60% @ 0.0030 μM | 647 | 47% @ 0.0030 μM |
| 598 | 43% @ 0.0010 μM | 623 | 41% @ 0.0010μM | 648 | 45% @ 0.0030μM |
| 599 | 0.015 | 624 | 43% @ 0.0010 μM | 649 | 50% @ 0.0030μM |
| 600 | 0.0085 | 625 | 0.0027 | 650 | 0.0051 |
| 601 | 0.0089 | 626 | 41% @ 0.0010 μM | 651 | 0.0061 |
| 602 | 0.0036 | 627 | 0.0059 | 652 | 0.0032 |
| 603 | 0.0043 | 628 | 0.004 | 653 | 0.0026 |
| 604 | 0.008 | 629 | 0.0037 | 654 | 0.0026 |
| 605 | 0.011 | 630 | 0.0075 | 655 | 54% @ 0.0030 μM |
| 606 | 0.0048 | 631 | 0.0067 | 656 | 0.0024 |
| 607 | 32% @ 0.0030 μM | 632 | 0.013 | 657 | 0.0023 |
| 608 | 0.005 | 633 | 0.006 | 658 | 0.0044 |
| 609 | 47% @ 0.0010 μM, 50% @ 0.0030 μM | 634 | 0.0034 | 659 | 46% @ 0.0030 μM |
| 610 | 0.057 | 635 | 0.0021 | 660 | 0.0064 |
| 611 | 62% @ 0.0030 μM | 636 | 0.021 | 661 | 0.0099 |
| 662 | 0.015 | 687 | 0.0028 | 715 | 60% @ 0.0010 μM |
| 663 | 0.0024 | 688 | 0.0026 | 716 | 0.003 |
| 664 | 62% @ 0.0030 μM | 689 | 0.0026 | 717 | 0.0051 |

-continued

| Example | ERK2 IC$_{50}$ (μM) | Example | ERK2 IC$_{50}$ (μM) | Example | ERK2 IC$_{50}$ (μM) |
|---|---|---|---|---|---|
| 665 | 0.003 | 690 | 63% @ 0.0030 μM | 718 | 0.086 |
| 666 | 0.0094 | 691 | 0.031 | 719 | 0.005 |
| 667 | 0.029 | 692 | 0.0032 | 720 | 0.0067 |
| 668 | 0.035 | 693 | 0.0046 | 721 | 43% @ 0.0010 μM |
| 669 | 0.0028 | 694 | 0.0025 | 722 | 56% @ 0.0030 μM |
| 670 | 42% @ 0.0030 μM | 695 | 0.03 | 723 | 0.029 |
| 671 | 0.0046 | 696 | 0.0035 | 724 | 0.16 |
| 672 | 42% @ 0.0010 μM | 697 | 0.0020 | 725 | 0.036 |
| 673 | 0.0051 | 698 | 0.0023 | 726 | 0.011 |
| 674 | 0.0025 | 699 | 37% @ 0.0010 μM | 727 | 64% @ 0.010 μM |
| 675 | 0.0013 | 701 | 44% @ 0.0030 μM | 728 | 0.0038 |
| 676 | 0.0083 | 702 | 65% @ 0.0030 μM | 730 | 59% @ 0.030 μM |
| 677 | 0.0062 | 703 | 0.0074 | 731 | 45% @ 0.010 μM |
| 678 | 0.0092 | 705 | 37% @ 0.0010 μM | 732 | 72% @ 0.030 μM |
| 679 | 0.015 | 706 | 0.77 | 733 | 0.015 |
| 680 | 44% @ 0.10 μM | 707 | 0.01 | 734 | 0.012 |
| 681 | 0.0034 | 708 | 61% @ 0.0030 μM | 735 | 0.0023 |
| 682 | 60% @ 0.0030 μM | 709 | 0.37 | 737 | 0.0064 |
| 683 | 0.003 | 711 | 0.0024 | 738 | 45% @ 0.0030 μM |
| 684 | 0.003 | 712 | 0.009 | 740 | 0.0021 |
| 685 | 0.0025 | 713 | 55% @ 0.0030 μM | 741 | 0.035 |
| 686 | 0.0027 | 714 | 36% @ 0.010 μM | 742 | 64% @ 0.0030 μM |
| 743 | 49% @ 0.0030 μM | 769 | 40% @ 0.0030 μM | 796 | 0.031 |
| 744 | 0.04 | 770 | 33% @ 0.0030 μM | 797 | 0.098 |
| 745 | 0.022 | 771 | 53% @ 0.030 μM | 798 | 0.0061 |
| 746 | 0.0067 | 773 | 0.03 | 799 | 33% @ 0.0010 μM |
| 747 | 0.0082 | 774 | 0.0029 | 800 | 0.0027 |
| 748 | 0.055 | 775 | 0.016 | 801 | 0.0054 |
| 749 | 0.15 | 776 | 0.0026 | 802 | 0.002 |
| 750 | 0.18 | 777 | 0.0076 | 803 | 0.0017 |
| 751 | 0.025 | 778 | 0.062 | 804 | 0.002 |
| 752 | 0.11 | 779 | 0.0062 | 805 | 0.0018 |
| 753 | 66% @ 0.0030 μM | 780 | 0.0044 | 806 | 0.0033 |
| 754 | 0.0076 | 781 | 0.0026 | 808 | 71% @ 0.0030 μM |
| 755 | 0.021 | 782 | 0.0036 | 809 | 37% @ 0.0010 μM |
| 756 | 0.0028 | 783 | 0.0038 | 810 | 64% @ 0.0030 μM |
| 757 | 0.0028 | 784 | 0.002 | 811 | 68% @ 0.0030 μM |
| 758 | 0.051 | 785 | 0.0039 | 812 | 60% @ 0.0030 μM |
| 759 | 0.0055 | 786 | 58% @ 0.0030 μM | 813 | 0.013 |
| 761 | 0.037 | 787 | 0.0054 | 814 | 0.01 |
| 762 | 0.2 | 788 | 54% @ 0.0010 μM | 815 | 71% @ 0.0030 μM |
| 763 | 0.0029 | 789 | 42% @ 0.0010 μM | 816 | 0.0043 |
| 764 | 0.013 | 790 | 0.012 | 817 | 52% @ 0.0030 μM |
| 765 | 0.0031 | 791 | 0.062 | 818 | 0.0035 |
| 766 | 0.2 | 792 | 0.017 | 819 | 0.0019 |
| 767 | 0.006 | 793 | 0.5 | 820 | 0.0024 |
| 768 | 56% @ 0.0030 μM | 794 | 0.18 | 821 | 0.37 |
| 822 | 0.0032 | 848 | 0.0069 | 877 | 0.004 |
| 823 | 0.0019 | 849 | 0.0091 | 878 | 0.0023 |
| 824 | 0.0026 | 850 | 43% @ 0.0010 μM | 879 | 36% @ 0.010 μM |
| 825 | 0.0026 | 851 | 40% @ 0.0010 μM | 880 | 0.0033 |
| 826 | 0.0035 | 852 | 57% @ 0.0030 μM | 881 | 56% @ 0.0030 μM |
| 827 | 60% @ 0.0030 μM | 853 | 39% @ 0.0010 μM | 882 | 0.0038 |
| 828 | 0.0017 | 854 | 0.052 | 883 | 55% @ 0.0030 μM |
| 829 | 0.083 | 855 | 0.0065 | 884 | 0.019 |
| 830 | 0.0086 | 856 | 0.0028 | 885 | 0.054 |
| 831 | 0.0077 | 857 | 47% @ 0.0010 μM | 886 | 0.01 |
| 832 | 0.024 | 858 | 71% @ 0.0030 μM | 887 | 0.0018 |

-continued

| Example | ERK2 IC$_{50}$ (µM) | Example | ERK2 IC$_{50}$ (µM) | Example | ERK2 IC$_{50}$ (µM) |
|---|---|---|---|---|---|
| 833 | 0.027 | 859 | 35% @ 0.0010 µM | 888 | 63% @ 0.0030 µM |
| 834 | 0.0073 | 864 | 0.0031 | 889 | 0.011 |
| 835 | 0.0074 | 865 | 0.0024 | 890 | 0.0023 |
| 836 | 0.0097 | 866 | 54% @ 0.030 µM | 891 | 0.0018 |
| 837 | 64% @ 0.0030 µM | 867 | 0.0069 | 892 | 67% @ 0.0030 µM |
| 838 | 0.0028 | 868 | 0.0055 | 893 | 0.21 |
| 839 | 0.014 | 869 | 0.0025 | 894 | 0.002 |
| 840 | 0.0099 | 870 | 54% @ 0.0030 µM | 895 | 0.005 |
| 841 | 0.0043 | 871 | 0.0095 | 896 | 42% @ 0.0010 µM |
| 842 | 0.064 | 872 | 0.0016 | 897 | 47% @ 0.0010 µM |
| 843 | 49% @ 0.0030 µM | 873 | 64% @ 0.0030 µM | 898 | 55% @ 0.0030 µM |
| 844 | 0.0026 | 874 | 0.26 | 899 | 0.07 |
| 846 | 0.0088 | 875 | 0.0045 | 900 | 0.0036 |
| 847 | 0.0046 | 876 | 0.0067 | 901 | 0.012 |
| 902 | 0.0033 | 928 | 40% @ 0.0030 µM | 953 | 0.0015 |
| 903 | 56% @ 0.0030 µM | 929 | 0.0018 | 954 | 0.0044 |
| 904 | 0.024 | 930 | 35% @ 0.0010 µM | 955 | 0.03 |
| 905 | 0.1 | 931 | 0.0025 | 956 | 0.0061 |
| 906 | 0.047 | 932 | 0.009 | 957 | 38% @ 0.0010 µM |
| 907 | 0.002 | 933 | 0.054 | 958 | 0.0052 |
| 908 | 0.0039 | 934 | 0.0011 | 959 | 44% @ 0.0010 µM |
| 909 | 0.0018 | 935 | 47% @ 0.0030 µM | 960 | 0.0052 |
| 910 | 0.0024 | 936 | 0.0017 | 961 | 0.0039 |
| 911 | 42% @ 0.0030 µM | 937 | 0.15 | 962 | 0.0016 |
| 912 | 0.0058 | 938 | 0.3 | 963 | 0.004 |
| 913 | 0.0028 | 939 | 40% @ 3.0 µM | 964 | 0.0021 |
| 914 | 0.0033 | 940 | 0.0073 | 965 | 0.0024 |
| 915 | 0.0041 | 941 | 0.0041 | 966 | 0.0047 |
| 916 | 0.068 | 942 | 0.0021 | 967 | 0.57 |
| 917 | 0.31 | 943 | 0.0025 | 968 | 0.003 |
| 918 | 0.0023 | 944 | 0.0057 | 969 | 0.071 |
| 919 | 0.0021 | 945 | 0.0021 | 970 | 0.0031 |
| 920 | 64% @ 0.0030 µM | 946 | 0.011 | 971 | 0.004 |
| 921 | 0.0027 | 947 | 0.0013 | 972 | 0.0029 |
| 922 | 57% @ 0.0030 µM | 948 | 0.057 | 973 | 40% @ 0.0010 µM |
| 924 | 0.0035 | 949 | 0.0034 | 974 | 0.0029 |
| 925 | 43% @ 0.0010 µM | 950 | 0.0055 | 975 | 0.0051 |
| 926 | 42% @ 0.0030 µM | 951 | 65% @ 0.0030 µM | 976 | 0.0021 |
| 927 | 0.0037 | 952 | 0.0017 | 977 | 0.0023 |
| 978 | 62% @ 0.30 µM | 1003 | 0.0028 | 1028 | 0.014 |
| 979 | 52% @ 0.0030 µM | 1004 | 0.0037 | 1029 | 0.0035 |
| 980 | 0.0051 | 1005 | 0.0019 | 1030 | 0.0034 |
| 981 | 0.0073 | 1006 | 54% @ 1.0 µM | 1031 | 0.0023 |
| 982 | 0.0034 | 1007 | 0.0021 | 1032 | 0.07 |
| 983 | 0.0074 | 1008 | 0.0028 | 1033 | 0.003 |
| 984 | 0.0026 | 1009 | 0.07 | 1034 | 35% @ 0.0010 µM |
| 985 | 0.0035 | 1010 | 0.0055 | 1035 | 0.0039 |
| 986 | 0.0056 | 1011 | 0.0028 | 1036 | 0.0035 |
| 987 | 0.0041 | 1012 | 0.038 | 1038 | 0.0027 |
| 988 | 0.0014 | 1013 | 0.2 | 1039 | 0.0026 |
| 989 | 48% @ 0.0010 µM | 1014 | 0.0071 | 1040 | 69% @ 0.0030 µM |
| 990 | 0.003 | 1015 | 42% @ 0.0010 µM | 1041 | 38% @ 0.0010 µM |
| 991 | 0.19 | 1016 | 0.0021 | 1042 | 52% @ 0.0030 µM |
| 992 | 0.0031 | 1017 | 38% @ 0.0010 µM | 1043 | 65% @ 0.0030 µM |
| 993 | 0.43 | 1018 | 0.0056 | 1044 | 41% @ 0.0010 µM |
| 994 | 0.12 | 1019 | 43% @ 0.0010 µM | 1045 | 0.0017 |
| 995 | 66% @ 0.0030 µM | 1020 | 0.0044 | 1046 | 0.0037 |
| 996 | 0.0015 | 1021 | 60% @ 0.0030 µM | 1047 | 44% @ 0.0010 µM |

-continued

| Example | ERK2 IC$_{50}$ (µM) | Example | ERK2 IC$_{50}$ (µM) | Example | ERK2 IC$_{50}$ (µM) |
|---|---|---|---|---|---|
| 997 | 0.0014 | 1022 | 0.0027 | 1048 | 0.0015 |
| 998 | 0.027 | 1023 | 35% @ 0.0010 µM | 1049 | 50% @ 0.0030 µM |
| 999 | 0.0023 | 1024 | 0.0028 | 1050 | 42% @ 0.0010 µM |
| 1000 | 70% @ 0.0050 µM | 1025 | 0.0026 | 1051 | 0.0026 |
| 1001 | 0.0026 | 1026 | 0.0037 | 1052 | 0.0044 |
| 1002 | 0.0035 | 1027 | 0.0047 | 1053 | 0.0083 |
| 1054 | 0.0018 | 1079 | 48% @ 0.0010 µM | 1104 | 37% @ 0.0030 µM |
| 1055 | 0.041 | 1080 | 45% @ 0.0010 µM | 1105 | 0.0016 |
| 1056 | 54% @ 0.0010 µM | 1081 | 0.0054 | 1106 | 0.0022 |
| 1057 | 0.0022 | 1082 | 0.017 | 1107 | 0.0043 |
| 1058 | 0.0017 | 1083 | 0.0023 | 1108 | 0.0032 |
| 1059 | 0.11 | 1084 | 0.012 | 1109 | 0.0031 |
| 1060 | 51% @ 0.0030 µM | 1085 | 0.003 | 1110 | 46% @ 0.0010 µM |
| 1061 | 68% @ 0.0030 µM | 1086 | 0.0023 | 1111 | 51% @ 0.0030 µM |
| 1062 | 0.0022 | 1087 | 56% @ 0.010 µM | 1112 | 0.0015 |
| 1063 | 0.0016 | 1088 | 0.0094 | 1113 | 0.0075 |
| 1064 | 0.0024 | 1089 | 0.0029 | 1114 | 0.0015 |
| 1065 | 63% @ 0.0030 µM | 1090 | 0.0044 | 1115 | 0.0016 |
| 1066 | 0.0031 | 1091 | 0.059 | 1116 | 59% @ 0.0030 µM |
| 1067 | 38% @ 0.0010 µM | 1092 | 32% @ 0.0010 µM | 1117 | 0.0028 |
| 1068 | 0.0037 | 1093 | 45% @ 0.0010 µM | 1118 | 0.0029 |
| 1069 | 0.004 | 1094 | 38% @ 0.0010 µM | 1119 | 41% @ 0.0010 µM |
| 1070 | 51% @ 0.0030 µM | 1095 | 0.0016 | 1120 | 0.003 |
| 1071 | 65% @ 0.0030 µM | 1096 | 65% @ 0.0030 µM | 1121 | 45% @ 0.0030 µM |
| 1072 | 0.0012 | 1097 | 0.0026 | 1122 | 0.0024 |
| 1073 | 0.0021 | 1098 | 71% @ 0.0030 µM | 1123 | 0.0033 |
| 1074 | 0.01 | 1099 | 36% @ 0.0010 µM | 1124 | 0.0025 |
| 1075 | 0.0027 | 1100 | 70% @ 0.010 µM | 1125 | 50% @ 0.0010 µM |
| 1076 | 0.0028 | 1101 | 35% @ 0.0010 µM | 1126 | 0.0028 |
| 1077 | 0.004 | 1102 | 61% @ 0.0030 µM | 1127 | 60% @ 0.0030 µM |
| 1078 | 0.003 | 1103 | 67% @ 0.0030 µM | 1128 | 43% @ 0.0030 µM |
| 1129 | 0.0024 | 1131 | 0.0059 | 1133 | 0.071 |
| 1130 | 51% @ 0.0010 µM | 1132 | 0.0060 | 1134 | 47% @ 0.0030 µM |

Combination Protocol for Cell Proliferation

The effect of a compound of formula (0) (Compound I) in combination with an anticancer agent (Compound II) can be assessed using the following technique. Human cancer cell lines (e.g. A375) were seeded onto 96-well tissue culture plates at a concentration of $2 \times 10^3$-$4 \times 10^3$ cells/well. Cells were allowed to recover for 16-24 hours prior to addition of compound(s) or DMSO control (0.1-0.5% DMSO). Cells were incubated with compound in 0.1%-0.5% (v/v) dimethyl sulfoxide (DMSO) for 72-96 hours, before addition of 20 µl Alamar blue. After a further 6 h incubation at 37° C. the plate was read on a Spectramax Gemini reader (Molecular Devices; excitation 535 nm, emission 590 nm). GI$_{50}$ values were calculated using a sigmoidal dose response equation (Prism GraphPad software, La Jolla, Calif., USA). The GI$_{50}$ for Compound II in the presence of varying doses of Compound I was determined. Synergy was determined when the GI$_{50}$ shifted down in the presence of sub-effective doses of Compound I. Additivity was determined when the response to Compound and Compound I together resulted in an effect equivalent to the sum of the two compounds individually. Antagonistic effects were defined as those causing the GI$_{50}$ to shift upwards, i.e. those where the response to the two compounds was less than the sum of the effect of the two compounds Pharmaceutical Formulations (i) Tablet Formulation A tablet composition containing a compound of formulae (0), (1) and subformulae thereof as defined herein is prepared by mixing an appropriate amount of the compound (for example 50-250 mg) with an appropriate diluent, disintegrant, compression agent and/or glidant. One possible tablet comprises 50 mg of the compound with 197 mg of lactose (BP) as diluent, and 3 mg magnesium stearate as a lubricant and compressing to form a tablet in known manner. The compressed tablet may be optionally film coated.

(ii) Capsule Formulation

A capsule formulation is prepared by mixing 100-250 mg (e.g. 100 mg) of a compound of formulae (0), (1) and subformulae thereof as defined herein with an equivalent amount of lactose (e.g. 100 mg) and filling the resulting mixture into standard opaque hard gelatin capsules. An appropriate disintegrant and/or glidant can be included in appropriate amounts as required.

(iii) Injectable Formulation I

A parenteral composition for administration by injection can be prepared by dissolving a compound of formulae (0), (1) and subformulae thereof as defined herein (e.g. in a salt form) in water containing 10% propylene glycol to give a concentration of active compound of 1.5% by weight. The solution is then sterilised by filtration, filled into an ampoule and sealed. Optionally the solution can be made isotonic before sterilisation.

(iv) Injectable Formulation II

A parenteral composition for injection is prepared by dissolving in water a compound of formulae (0), (1) and subformulae thereof as defined herein (e.g. in salt form) (2 mg/ml) and mannitol (50 mg/ml), sterile filtering the solution and filling into sealable 1 ml vials or ampoules or pre-filled syringe.

(v) Injectable formulation III

A formulation for i.v. delivery by injection or infusion can be prepared by dissolving the compound of formulae (0), (1) and subformulae thereof (e.g. in a salt form) in water at 20 mg/ml and optionally then adjusted for isotonicity. The vial is then sealed and sterilised by autoclaving. Alternatively it may be filled into an ampoule or vial or pre-filled syringe, sterilised by filtration and sealed.

(vi) Injectable formulation IV

A formulation for i.v. delivery by injection or infusion can be prepared by dissolving the compound of formulae (0), (1) and subformulae thereof (e.g. in a salt form) in water containing a buffer (e.g. 0.2 M acetate pH 4.6) at 20 mg/ml. The vial is then sealed and sterilised by autoclaving. Alternatively a pre-filled syringe is then sealed and sterilised by autoclaving or sterilized by filtration and sealed.

(vii) Subcutaneous or Intramuscular Injection Formulation

A composition for sub-cutaneous (or intramuscular) administration is prepared by mixing a compound of formulae (0), (1) and subformulae thereof as defined herein with pharmaceutical grade corn oil to give a concentration of 5-50 mg/ml (e.g. 5 mg/ml). The composition is sterilised and filled into a suitable container.

(viii) Lyophilised Formulation

Aliquots of formulated compound of formulae (0), (1) and subformulae thereof are put into 50 ml vials and lyophilized. During lyophilisation, the compositions are frozen using a one-step freezing protocol at (−45° C.). The temperature is raised to −10° C. for annealing, then lowered to freezing at −45° C., followed by primary drying at +25° C. for approximately 3400 minutes, followed by a secondary drying with increased steps if temperature to 50° C. The pressure during primary and secondary drying is set at 80 millitor.

(ix) Lyophilised Formulation II

Aliquots of formulated compound of formulae (0), (1) and subformulae thereof or a salt thereof as defined herein are put into 50 mL vials and lyophilized. During lyophilisation, the compositions are frozen using a one-step freezing protocol at (−45° C.). The temperature is raised to −10° C. for annealing, then lowered to freezing at −45° C., followed by primary drying at +25° C. for approximately 3400 minutes, followed by a secondary drying with increased steps if temperature to 50° C. The pressure during primary and secondary drying is set at 80 millitor.

(x) Lyophilised Formulation for Use in i.v. Administration III

An aqueous buffered solution is prepared by dissolving a compound of formulae (0), (1) and subformulae thereof in a buffer. The buffered solution is filled, with filtration to remove particulate matter, into a container (such as a Type 1 glass vial) which is then partially sealed (e.g. by means of a Fluorotec stopper). If the compound and formulation are sufficiently stable, the formulation is sterilised by autoclaving at 121° C. for a suitable period of time. If the formulation is not stable to autoclaving, it can be sterilised using a suitable filter and filled under sterile conditions into sterile vials. The solution is freeze dried using a suitable cycle. On completion of the freeze drying cycle the vials are back filled with nitrogen to atmospheric pressure, stoppered and secured (e.g. with an aluminium crimp). For intravenous administration, the freeze dried solid can be reconstituted with a pharmaceutically acceptable diluent, such as 0.9% saline or 5% dextrose. The solution can be dosed as is, or can be diluted further into an infusion bag (containing a pharmaceutically acceptable diluent, such as 0.9% saline or 5% dextrose), before administration.

(xii) Powder in a Bottle

A composition for oral administration is prepared by filling a bottle or vial with a compound of formulae (0), (1) and subformulae thereof. The composition is then reconstituted with a suitable diluent for example water, fruit juice, or commercially available vehicle such as OraSweet or Syrspend. The reconstituted solution may be dispensed into dosing cups or oral syringes for administration.

The invention claimed is:

1. A pharmaceutical composition which is a unit dosage form comprising from approximately 1% (w/w) to approximately 95% active ingredient and from approximately 99% (w/w) to approximately 5% (w/w) of a pharmaceutically acceptable excipient or combination of excipients, wherein said active ingredient comprises a compound selected from:

(2R)-2-(6-{5-chloro-2-[(oxan-4-yl)amino]pyrimidin-4-yl}-1-oxo-2,3-dihydro-1H-isoindol-2-yl)-N-[(1S)-1-(3-fluoro-5-methoxyphenyl)-2-hydroxyethyl]propanamide;

(2R)-2-(6-{5-Chloro-2-[(oxan-4-yl)amino]pyrimidin-4-yl}-1-oxo-2,3-dihydro-1H-isoindol-2-yl)-N-[(1S)-2-hydroxy-1-(2-methoxypyridin-4-yl)ethyl]propanamide;

(R)-2-(6-(5-chloro-2-((2-methoxypyridin-4-yl)amino)pyrimidin-4-yl)-1-oxoisoindolin-2-yl)-N—((S)-1-(3-fluoro-5-methoxyphenyl)-2-hydroxyethyl)propanamide;

(R)-2-(6-(5-chloro-2-((2-methylpyrimidin-4-yl)amino)pyrimidin-4-yl)-1-oxoisoindolin-2-yl)-N—((S)-1-(6-(dimethylamino)pyridin-2-yl)-2-hydroxyethyl)propanamide;

(2R)-2-(6-{5-chloro-2-[(oxan-4-yl)amino]pyrimidin-4-yl}-1-oxo-2,3-dihydro-1H-isoindol-2-yl)-N-[(1S)-2-hydroxy-1-[6-(4-methylpiperazin-1-yl)pyridin-2-yl]ethyl]propanamide; and (2R)-2-(6-{5-chloro-2-[(oxan-4-yl)amino]pyrimidin-4-yl}-1-oxo-2,3-dihydro-1H-isoindol-2-yl)-N-[(1R)-1-[3-fluoro-5-(4-methylpiperazin-1-yl)phenyl]ethyl]propanamide; and pharmaceutically acceptable salts and tautomers thereof.

2. A pharmaceutical composition according to claim 1 wherein the unit dosage form comprises from 20% (w/w) to 90% active ingredient and from 80% (w/w) to 10% (w/w) of the pharmaceutically acceptable excipient or combination of excipients.

3. A method for the preparation of:
(i) a compound having the formula (2):

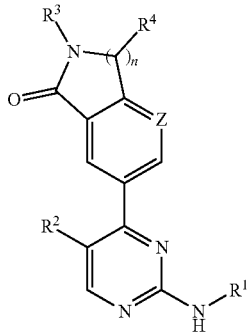

(2)

or a pharmaceutically acceptable salt or tautomer thereof; or
(ii) a compound having the formula (5):

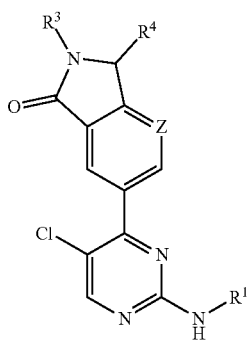

(5)

or a pharmaceutically acceptable salt or tautomer thereof;
wherein
n is 1 or 2;
Z is selected from C—$R^z$ and N;
$R^z$ is selected from hydrogen; halogen; methoxy; and $C_{1-3}$ alkyl optionally substituted with hydroxy or methoxy;
$R^1$ is selected from:
-(Alk$^1$)$_t$-Cyc$^1$; wherein t is 0 or 1; and Alk$^1$ is a $C_{1-4}$ straight chain or branched alkylene group optionally substituted with 1 or 2 hydroxy groups; and
$C_{1-6}$ acyclic hydrocarbon groups which are unsubstituted or substituted with 1, 2 or 3 substituents $R^5$ selected from hydroxy; oxo; fluorine; and cyano; and wherein 1 or 2 but not all of the carbon atoms of the hydrocarbon group can be replaced by O or N;
Cyc$^1$ is a cyclic group selected from (a) 3 to 9 membered non-aromatic monocyclic and bicyclic carbocyclic and heterocyclic groups containing 0, 1, 2, or 3 heteroatom ring members selected from O, N, S, S(O) and S(O)$_2$; (b) 5 to 6 membered monocyclic heteroaryl groups containing 1, 2 or 3 heteroatom ring members of which 1 is N and the others, when present, are selected from O, N and S; and (c) 3 to 7 membered monocyclic carbocyclic groups; wherein each cyclic group (a), (b) and (c) is unsubstituted or substituted with 1, 2 or 3 substituents $R^6$ selected from hydroxy; oxo; fluorine; amino; NH(Hyd$^1$); N(Hyd$^1$)$_2$; O-Hyd$^1$; —C(=O)-Hyd$^1$; —C(=O)—O-Hyd$^1$ and Hyd$^1$; where Hyd$^1$ is a $C_{1-4}$ non-aromatic hydrocarbon group optionally substituted with one or more substituents selected from fluorine, hydroxyl and methoxy;
$R^2$ is selected from hydrogen; halogen; and $C_{1-3}$ hydrocarbon groups optionally substituted with one or more fluorine atoms;
$R^3$ is hydrogen or a group L-$R^7$;
$R^4$ is selected from hydrogen; methoxy; and $C_{1-3}$ alkyl optionally substituted with hydroxy, amino, mono- or di-$C_{1-2}$ alkylamino, a cyclic amino group or methoxy; wherein the cyclic amino group is a saturated 4-7 membered heterocyclic group containing a nitrogen ring member and optionally a second heteroatom ring member selected from O, N and S, wherein the cyclic amino group is linked via a nitrogen ring member thereof to the $C_{1-3}$ alkyl, and wherein the cyclic amino group is optionally substituted with one or two methyl groups; provided that no more than one $R^4$ can be other than hydrogen or methyl;
$L^1$ is selected from a bond; Alk$^2$, Alk$^2$-O and Alk$^2$-C(=O) wherein Alk$^2$ is a $C_{1-4}$ straight chain or branched alkylene group which is optionally substituted with one or more substituents selected from hydroxy, methoxy, amino, methylamino, dimethylamino and fluorine;
$R^7$ is selected from:
  hydrogen;
  CO$_2$H;
  NR$^8$R$^9$;
  a carbocyclic or heterocyclic group having from 3 to 12 ring members, of which 0, 1, 2 or 3 are heteroatom ring members selected from O, N and S and oxidised forms of S, the carbocyclic or heterocyclic group being optionally substituted with one or more substituents $R^{10}$; and
  an acyclic $C_{1-8}$ hydrocarbon group optionally substituted with one or more substituents selected from hydroxy; oxo; halogen; cyano; carboxy; amino; mono- or di-$C_{1-4}$ alkylamino; and carbocyclic and heterocyclic groups having from 3 to 12 ring members, of which 0, 1, 2 or 3 are heteroatom ring members selected from O, N and S and oxidised forms of S, the carbocyclic or heterocyclic group being optionally substituted with one or more substituents $R^{10}$; wherein one or two but not all of the carbon atoms of the acyclic $C_{1-8}$ hydrocarbon group may optionally be replaced by O, S, SO, SO$_2$ or NR$^{11}$;
$R^8$ is selected from hydrogen and a $C_{1-4}$ hydrocarbon group, the $C_{1-4}$ hydrocarbon group being optionally substituted with 1-2 substituents selected from hydroxy, amino, mono-$C_{1-4}$ alkylamino, di-$C_{1-4}$ alkylamino, and 4-7 membered saturated heterocyclic rings containing 1-2 heteroatom ring members selected from O and N, wherein the mono-$C_{1-4}$ alkylamino, di-$C_{1-4}$ alkylamino, and 4-7 membered saturated heterocyclic rings are each optionally substituted with 1-2 hydroxy or $C_{1-3}$ alkyl substituents;
$R^9$ is selected from:
  hydrogen;
  a carbocyclic or heterocyclic group having from 3 to 12 ring members, of which 0, 1, 2 or 3 are heteroatom ring members selected from O, N and S and oxidised forms of S, the carbocyclic or heterocyclic group being optionally substituted with one or more substituents $R^{10}$; and
  an acyclic $C_{1-8}$ hydrocarbon group optionally substituted with one or more substituents selected from hydroxy; oxo; halogen; cyano; carboxy; amino; mono- or di-$C_{1-4}$ alkylamino; and carbocyclic and heterocyclic groups having from 3 to 12 ring members, of which 0, 1, 2 or 3 are heteroatom ring members selected from O, N and S and oxidised forms of S, the carbocyclic or heterocyclic group being optionally substituted with one or more substituents $R^{10}$; wherein one or two but not all of the carbon atoms of the acyclic $C_{1-8}$ hydrocarbon group may optionally be replaced by O, S, SO, $SO_2$ or $NR^{11}$;

or $NR^8R^9$ forms a heterocyclic group having from 4 to 12 ring members wherein, in addition to the nitrogen atom of $NR^8R^9$, the heterocyclic group optionally contains 1 or 2 further heteroatom ring members selected from O, N and S and oxidised forms of S; and wherein the heterocyclic group is optionally substituted with one or more substituents $R^{10}$;

$R^{10}$ is selected from:

halogen; hydroxy; oxo; cyano;

$OR^{12}$ wherein $R^{12}$ is $C_{1-6}$ alkyl or $C_{3-6}$ cycloalkyl, each being optionally substituted with halogen;

an acyclic $C_{1-8}$ hydrocarbon group optionally substituted with one or more substituents selected from hydroxy; oxo; halogen; cyano; carboxy; amino; mono- or di-$C_{1-4}$ alkylamino; and carbocyclic and heterocyclic groups having 3 to 7 ring members of which 0, 1, 2, 3 or 4 are heteroatom ring members selected from N, O and S, wherein the carbocyclic and heterocyclic groups are optionally substituted with one or more substituents $R^{13}$ selected from hydroxy; halogen; cyano; amino; —NH(Hyd$^1$); —N(Hyd$^1$)$_2$; and —(O)$_v$-Hyd$^1$ where v is 0 or 1; wherein one or two but not all of the carbon atoms of the acyclic $C_{1-8}$ hydrocarbon group may optionally be replaced by O, S, SO, $SO_2$ or $NR^{11}$; and carbocyclic and heterocyclic groups having 3 to 7 ring members of which 0, 1, 2, 3 or 4 are heteroatom ring members selected from N, O and S, wherein the carbocyclic and heterocyclic groups are optionally substituted with one or more substituents $R^{13}$; and $R^{11}$ is selected from hydrogen and a $C_{1-4}$ hydrocarbon group, which method comprises:

(a) (i) reacting a compound of formula (II):

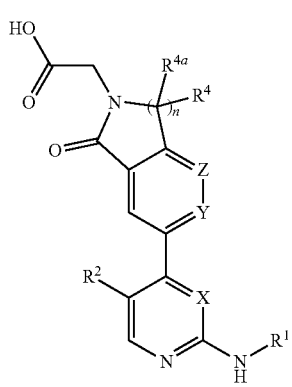

(II)

wherein $R^{4a}$ is hydrogen, X is N, and Y is CH, with a compound of formula $HNR^8R^9$ under amide forming conditions; or (ii) reacting a compound of formula (III):

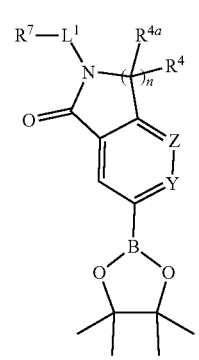

(III)

wherein $R^{4a}$ is hydrogen, and Y is CH, with a compound of formula (IV):

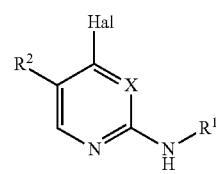

(IV)

wherein X is N, and Hal is a suitable leaving group, in the presence of a palladium catalyst; or (iii) reacting a compound of formula (V):

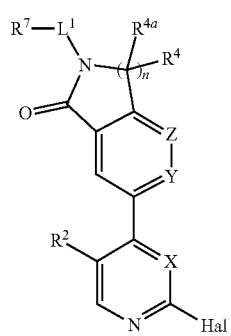

(V)

wherein $R^{4a}$ is hydrogen, X is N, Y is CH, and Hal is a suitable leaving group, with a compound of formula $R^1NH_2$; or (iv) reacting a compound of formula (VI):

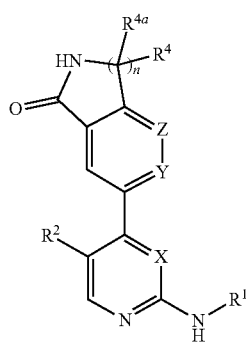

(VI)

wherein $R^{4a}$ is hydrogen, X is N, and Y is CH, with a compound of formula $R^7L^1$-J, wherein J is a suitable leaving group; and/or
(b) deprotecting a protected form of a compound of formulae (2) or (5); and/or
(c) interconverting a compound of formulae (2) or (5) or protected form thereof to a further compound of formulae (2), (5), or protected form thereof; and
(d) optionally forming a pharmaceutically acceptable salt of a compound of formulae (2) or (5).

4. The method of claim 3 wherein $R^1$ is a group AA:

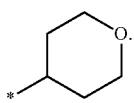

AA

5. The method of claim 3 wherein $R^2$ is chlorine.
6. The method of claim 3 wherein Z is C—$R^z$ where R is hydrogen.
7. The method of claim 3 wherein $R^4$ is hydrogen and $R^{4a}$ when present is also hydrogen.
8. The method of claim 3 wherein $R^3$ is $L^1$-$R^7$ wherein $L^1$ is $Alk^2$ or $Alk^2$-C(=O).
9. The method of claim 8 wherein $Alk^2$ is $CH(CH_3)$.
10. The method of claim 9 wherein $R^7$ is an acyclic $C_{1-8}$ hydrocarbon group optionally substituted with one or more substituents selected from hydroxy; oxo; halogen; cyano; carboxy; amino; mono- or di-$C_{1-4}$ alkylamino; and carbocyclic and heterocyclic groups having from 3 to 12 ring members, of which 0, 1, 2 or 3 are heteroatom ring members selected from O, N and S and oxidised forms of S, the carbocyclic or heterocyclic group being optionally substituted with one or more substituents $R^{10}$; wherein one or two but not all of the carbon atoms of the acyclic $C_{1-8}$ hydrocarbon group may optionally be replaced by O, S, SO, $SO_2$ or $NR^{11}$.
11. The method of claim 3 wherein process (a)(i) comprises reacting the compound of formula (II) with the compound of formula $HNR^8R^9$ in the presence of an amide coupling agent selected from HATU, TBTU, HBTU, and 1-propanephosphonic anhydride.
12. The method of claim 3 wherein process (a)(ii) comprises reacting the compound of formula (III) with the compound of formula (IV) in the presence of the palladium catalyst and a base in a solvent.

13. The method of claim 3 wherein:
in formula (IV), Hal is a halide; and
in formula (V), Hal is a halide.
14. The method of claim 13 wherein:
in formula (IV), Hal is chloro; and
in formula (V), Hal is chloro.
15. The method of claim 3 for the preparation of a compound selected from:
(a) a compound having the formula (6):

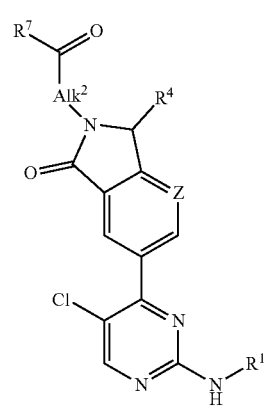

(6)

or a pharmaceutically acceptable salt or tautomer thereof;
(b) a compound having the formula (7):

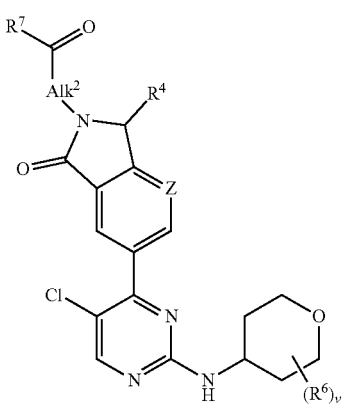

(7)

or a pharmaceutically acceptable salt or tautomer thereof, wherein v is 0, 1, 2 or 3; and (c) a compound having the formula (8):

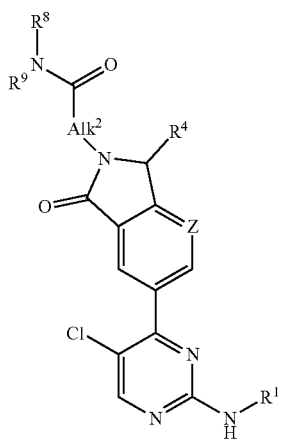

or a pharmaceutically acceptable salt or tautomer thereof.

16. The method of claim 15 wherein said method comprises the process (a)(ii), which comprises reacting the compound of formula (III) with the compound of formula (IV) in the presence of the palladium catalyst and a base in a solvent.

17. The method of claim 3 for the preparation of a compound wherein n is 1, said compound having the formula (3):

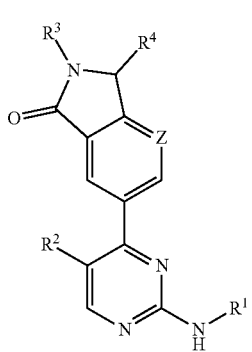

or a pharmaceutically acceptable salt or tautomer thereof.

18. The method of claim 3 for the preparation of a compound selected from:
(2R)-2-(6-{5-chloro-2-[(oxan-4-yl)amino]pyrimidin-4-yl}-1-oxo-2,3-dihydro-1H-isoindol-2-yl)-N-[(1S)-1-(3-fluoro-5-methoxyphenyl)-2-hydroxyethyl]propanamide;
(2R)-2-(6-{5-Chloro-2-[(oxan-4-yl)amino]pyrimidin-4-yl}-1-oxo-2,3-dihydro-1H-isoindol-2-yl)-N-[(1S)-2-hydroxy-1-(2-methoxypyridin-4-yl)ethyl]propanamide;
(R)-2-(6-(5-chloro-2-((2-methoxypyridin-4-yl)amino)pyrimidin-4-yl)-1-oxoisoindolin-2-yl)-N—((S)-1-(3-fluoro-5-methoxyphenyl)-2-hydroxyethyl)propanamide;
(R)-2-(6-(5-chloro-2-((2-methylpyrimidin-4-yl)amino)pyrimidin-4-yl)-1-oxoisoindolin-2-yl)-N—((S)-1-(6-(dimethylamino)pyridin-2-yl)-2-hydroxyethyl)propanamide;
(2R)-2-(6-{5-chloro-2-[(oxan-4-yl)amino]pyrimidin-4-yl}-1-oxo-2,3-dihydro-1H-isoindol-2-yl)-N-[(1S)-2-hydroxy-1-[6-(4-methylpiperazin-1-yl)pyridin-2-yl]ethyl]propanamide; and
(2R)-2-(6-{5-chloro-2-[(oxan-4-yl)amino]pyrimidin-4-yl}-1-oxo-2,3-dihydro-1H-isoindol-2-yl)-N-[(1R)-1-[3-fluoro-5-(4-methylpiperazin-1-yl)phenyl]ethyl]propanamide; and
pharmaceutically acceptable salts thereof.

19. The method of claim 18 for the preparation of (2R)-2-(6-{5-chloro-2-[(oxan-4-yl)amino]pyrimidin-4-yl}-1-oxo-2,3-dihydro-1H-isoindol-2-yl)-N-[(1S)-1-(3-fluoro-5-methoxyphenyl)-2-hydroxyethyl]propanamide or a pharmaceutically acceptable salt thereof.

20. The method of claim 18 for the preparation of (2R)-2-(6-{5-Chloro-2-[(oxan-4-yl)amino]pyrimidin-4-yl}-1-oxo-2,3-dihydro-1H-isoindol-2-yl)-N-[(1S)-2-hydroxy-1-(2-methoxypyridin-4-yl)ethyl]propanamide or a pharmaceutically acceptable salt thereof.

21. The method of claim 18 for the preparation of (R)-2-(6-(5-chloro-2-((2-methoxypyridin-4-yl)amino)pyrimidin-4-yl)-1-oxoisoindolin-2-yl)-N—((S)-1-(3-fluoro-5-methoxyphenyl)-2-hydroxyethyl)propanamide or a pharmaceutically acceptable salt thereof.

22. The method of claim 18 for the preparation of (R)-2-(6-(5-chloro-2-((2-methylpyrimidin-4-yl)amino)pyrimidin-4-yl)-1-oxoisoindolin-2-yl)-N—((S)-1-(6-(dimethylamino)pyridin-2-yl)-2-hydroxyethyl)propanamide or a pharmaceutically acceptable salt thereof.

23. The method of claim 18 for the preparation of (2R)-2-(6-{5-chloro-2-[(oxan-4-yl)amino]pyrimidin-4-yl}-1-oxo-2,3-dihydro-1H-isoindol-2-yl)-N-[(1S)-2-hydroxy-1-[6-(4-methylpiperazin-1-yl)pyridin-2-yl]ethyl]propanamide or a pharmaceutically acceptable salt thereof.

24. The method of claim 18 for the preparation of (2R)-2-(6-{5-chloro-2-[(oxan-4-yl)amino]pyrimidin-4-yl}-1-oxo-2,3-dihydro-1H-isoindol-2-yl)-N-[(1R)-1-[3-fluoro-5-(4-methylpiperazin-1-yl)phenyl]ethyl]propanamide or a pharmaceutically acceptable salt thereof.

25. A compound selected from:

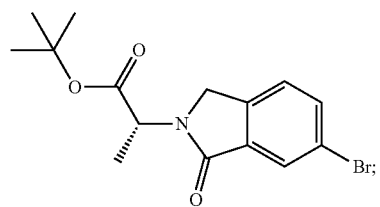

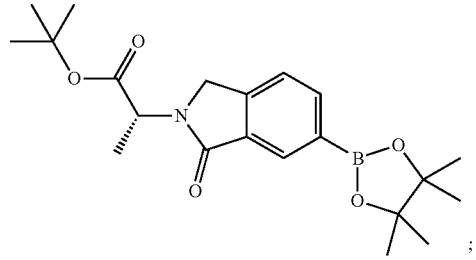

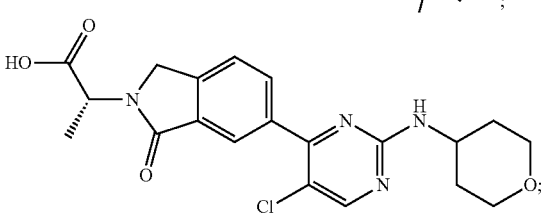

1391
-continued
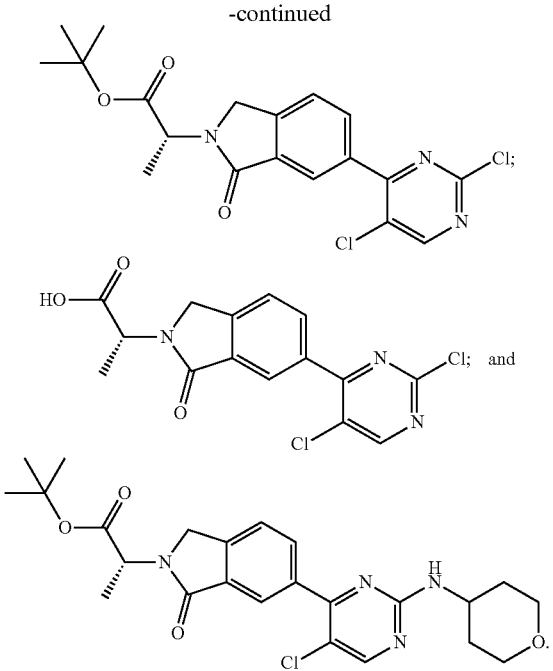
26. A compound according to claim 25 selected from:
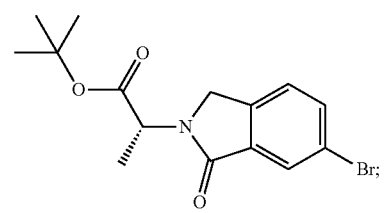
1392
-continued
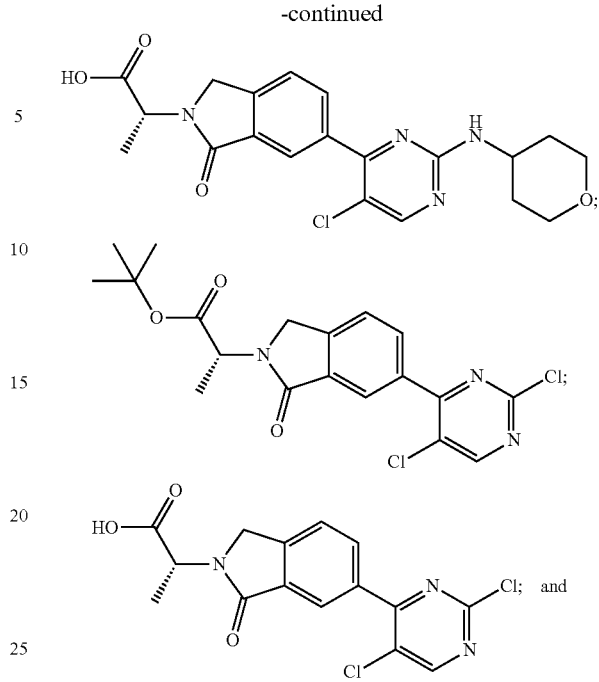
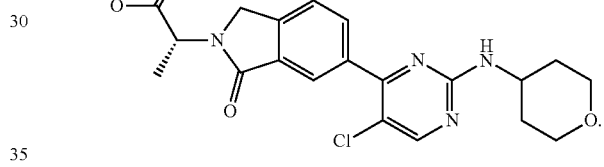
* * * * *